(12) United States Patent
Flohr et al.

(10) Patent No.: US 11,034,672 B1
(45) Date of Patent: Jun. 15, 2021

(54) TYROSINE KINASE INHIBITOR COMPOSITIONS, METHODS OF MAKING AND METHODS OF USE

(71) Applicant: Black Diamond Therapeutics, Inc., Cambridge, MA (US)

(72) Inventors: Alexander Flohr, Basel (CH); Alexander Mayweg, Stony Brook, NY (US); George Trainor, Stony Brook, NY (US); David M. Epstein, Philadelphia, PA (US); Matthew O'Connor, Massapequa Park, NY (US); Elizabeth Buck, Huntington, NY (US); Luca Arista, Riehen (CH)

(73) Assignee: Black Diamond Therapeutics, Inc., Cambridge, MA (US)

( * ) Notice: Subject to any disclaimer, the term of this patent is extended or adjusted under 35 U.S.C. 154(b) by 8 days.

(21) Appl. No.: 16/851,767

(22) Filed: Apr. 17, 2020

Related U.S. Application Data

(63) Continuation of application No. PCT/US2019/052784, filed on Sep. 24, 2019.

(60) Provisional application No. 62/903,592, filed on Sep. 20, 2019, provisional application No. 62/736,293, filed on Sep. 25, 2018.

(51) Int. Cl.

| | |
|---|---|
| *C07D 401/14* | (2006.01) |
| *C07D 403/14* | (2006.01) |
| *C07D 413/14* | (2006.01) |
| *C07D 487/04* | (2006.01) |
| *C07D 491/04* | (2006.01) |
| *C07D 491/08* | (2006.01) |
| *C07D 239/74* | (2006.01) |
| *C07D 401/12* | (2006.01) |
| *C07D 295/13* | (2006.01) |
| *C07D 295/088* | (2006.01) |
| *C07D 405/14* | (2006.01) |
| *C07D 487/08* | (2006.01) |
| *C07D 491/107* | (2006.01) |
| *C07D 471/08* | (2006.01) |
| *C07D 487/10* | (2006.01) |
| *C07D 491/048* | (2006.01) |
| *C07D 417/14* | (2006.01) |

(52) U.S. Cl.
CPC ......... *C07D 401/14* (2013.01); *C07D 239/74* (2013.01); *C07D 295/088* (2013.01); *C07D 295/13* (2013.01); *C07D 401/12* (2013.01); *C07D 405/14* (2013.01); *C07D 417/14* (2013.01); *C07D 471/08* (2013.01); *C07D 487/04* (2013.01); *C07D 487/08* (2013.01); *C07D 487/10* (2013.01); *C07D 491/048* (2013.01); *C07D 491/08* (2013.01); *C07D 491/107* (2013.01)

(58) Field of Classification Search
CPC .. C07D 487/04; C07D 487/10; C07D 401/12; C07D 401/14; C07D 403/10; C07D 403/14; C07D 413/14; C07D 491/04; C07D 491/08; A61K 31/517; A61P 35/00
USPC ............. 544/284; 514/266.2, 266.21, 266.22
See application file for complete search history.

(56) References Cited

U.S. PATENT DOCUMENTS

| | | | |
|---|---|---|---|
| 4,169,846 | A | 10/1979 | Kidani et al. |
| 4,261,989 | A | 4/1981 | Sasaki et al. |
| 5,266,573 | A | 11/1993 | Croci et al. |
| 5,621,002 | A | 4/1997 | Bosslet et al. |
| 5,763,263 | A | 6/1998 | Dehlinger |
| 6,780,996 | B2 | 8/2004 | Boschelli et al. |
| 6,867,201 | B2 | 3/2005 | Kath et al. |
| 8,735,409 | B2 | 5/2014 | Zhang et al. |

FOREIGN PATENT DOCUMENTS

| | | |
|---|---|---|
| CN | 101679384 A | 3/2010 |
| CN | 102382065 A | 3/2012 |
| CN | 102452989 A | 5/2012 |
| CN | 102731485 A | 10/2012 |
| CN | 103965120 A | 8/2014 |
| EP | 1 000 039 B1 | 6/2004 |

(Continued)

OTHER PUBLICATIONS

Cecil Textbook of Medicine, edited by Bennet, J.C., and Plum F., 20th edition, vol. 1, 1004-1010, 1996.*

(Continued)

*Primary Examiner* — Emily A Bernhardt
(74) *Attorney, Agent, or Firm* — Cooley LLP; Heidi A. Erlacher; Xixi Sun

(57) ABSTRACT

The present disclosure relates to new compounds or pharmaceutically acceptable salts or stereoisomers thereof of formula I

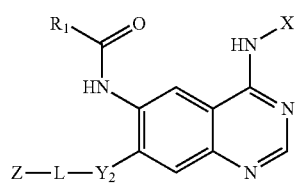

as inhibitors of receptor tyrosine kinases (RTK), in particular extracellular mutants of ErbB-receptors. The present disclosure also relates to methods of preparation these compounds, compositions comprising these compounds, and methods of using them in the treatment of cancer in mammals (e.g. humans).

29 Claims, 45 Drawing Sheets
(26 of 45 Drawing Sheet(s) Filed in Color)
Specification includes a Sequence Listing.

(56) References Cited

FOREIGN PATENT DOCUMENTS

| | | |
|---|---|---|
| EP | 1 506 962 A2 | 2/2005 |
| EP | 2 612 860 A1 | 7/2013 |
| JP | 5155391 B2 | 3/2013 |
| WO | WO 96/30347 A1 | 10/1996 |
| WO | WO 97/38983 A1 | 10/1997 |
| WO | WO 99/06378 A1 | 2/1999 |
| WO | WO 99/09016 A1 | 2/1999 |
| WO | WO 00/44728 A1 | 8/2000 |
| WO | WO 00/47212 A1 | 8/2000 |
| WO | WO 00/78735 A1 | 12/2000 |
| WO | WO 01/002369 A2 | 1/2001 |
| WO | WO 01/77104 A1 | 10/2001 |
| WO | WO 02/010192 A2 | 2/2002 |
| WO | WO 02/18370 A1 | 3/2002 |
| WO | WO 02/50043 A1 | 6/2002 |
| WO | WO 02/066470 A1 | 8/2002 |
| WO | WO 03/045939 A1 | 6/2003 |
| WO | WO 03/064383 A2 | 8/2003 |
| WO | WO 03/075836 A2 | 9/2003 |
| WO | WO 03/089439 A1 | 10/2003 |
| WO | WO 2004/069791 A2 | 8/2004 |
| WO | WO 2005/026157 A1 | 3/2005 |
| WO | WO 2005/028443 A2 | 3/2005 |
| WO | WO 2005/107758 A1 | 11/2005 |
| WO | WO 2006/028958 A2 | 3/2006 |
| WO | WO 2006/122806 A2 | 11/2006 |
| WO | WO 2007/013950 A2 | 2/2007 |
| WO | WO 2007/055513 A1 | 5/2007 |
| WO | WO 2008/033749 A2 | 3/2008 |
| WO | WO 2008/150118 A2 | 12/2008 |
| WO | WO 2009/036082 A2 | 3/2009 |
| WO | WO 2009/055730 A1 | 4/2009 |
| WO | WO 2009/155386 A1 | 12/2009 |
| WO | WO 2010/036629 A2 | 4/2010 |
| WO | WO 2012/122058 A2 | 9/2012 |
| WO | WO 2012/136099 A1 | 10/2012 |
| WO | WO 2013/013640 A1 | 1/2013 |
| WO | WO 2013/131424 A1 | 9/2013 |
| WO | WO 2013/173254 A1 | 11/2013 |
| WO | WO 2014/177038 A1 | 11/2014 |
| WO | WO 2015/043515 A1 | 4/2015 |
| WO | WO 2015/054572 A1 | 4/2015 |
| WO | WO 2016/023217 A1 | 2/2016 |
| WO | WO 2016/055982 A1 | 4/2016 |
| WO | WO 2020/068867 A1 | 4/2020 |

OTHER PUBLICATIONS

Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.Golub et al., Science, 286.*
Altschul, S. F. et al., "Basic Local Alignment Search Tool," J. Mol. Biol., 215:403-410 (1990).
Altschul, S. F. et al., "Gapped BLAST and PSI-BLAST: a new generation of protein database search programs," Nucleic Acids Research, 25(17):3389-3402 (1997).
Argiris, A. et al., "Phase III Randomized, Placebo-Controlled Trial of Docetaxel With or Without Gefitinib in Recurrent or Metastatic Head and Neck Cancer: An Eastern Cooperative Oncology Group Trial," Journal of Clinical Oncology, 31(11):1405-1414 (2013).
Asadollahi-Baboli, M., "In silico evaluation, molecular docking and QSAR analysis of quinazoline-based EGFR-T790M inhibitors," Mol Divers, 20:729-739 (2016).
Berge, S. M. et al., "Pharmaceutical Salts," Journal of Pharmaceutical Sciences 1977, 66(1), 19 pages.
Brennan, C. W. et al., "The Somatic Genomic Landscape of Glioblastoma," Cell, 155:462-477 (2013).
CAS Registry No. 183319-69-9, Nov. 22, 1996, 1 page.
CAS Registry No. 184475-35-2, Dec. 26, 1996, 1 page.
CAS Registry No. 187724-61-4, Mar. 28, 1997, 1 page.
CAS Registry No. 194423-15-9, Sep. 24, 1997, 1 page.
CAS Registry No. 196612-93-8, Oct. 31, 1997, 1 page.
CAS Registry No. 212141-54-3, Oct. 4, 1998, 1 page.
CAS Registry No. 231277-92-2, Aug. 7, 1999, 1 page.
CAS Registry No. 257933-82-7, Mar. 3, 2000, 1 page.
CAS Registry No. 267243-28-7, May 30, 2000, 1 page.
CAS Registry No. 439081-18-2, Jul. 17, 2002, 1 page.
CAS Registry No. 443913-73-3, Aug. 14, 2002, 1 page.
CAS Registry No. 451493-31-5, Sep. 16, 2002, 1 page.
CAS Registry No. 477202-00-9, Dec. 19, 2002, 1 page.
CAS Registry No. 497839-62-0, Mar. 11, 2003, 1 page.
CAS Registry No. 610798-31-7, Oct. 30, 2003, 1 page.
CAS Registry No. 692737-80-7, Jun. 14, 2004, 1 page.
CAS Registry No. 698387-09-6, Jun. 24, 2004, 1 page.
CAS Registry No. 714971-09-2, Jul. 23, 2004, 1 page.
CAS Registry No. 781613-23-8, Nov. 16, 2004, 1 page.
CAS Registry No. 848133-17-5, Apr. 8, 2005, 1 page.
CAS Registry No. 848942-61-0, Apr. 21, 2005, 1 page.
CAS Registry No. 871026-44-7, Jan. 3, 2006, 1 page.
CAS Registry No. 897383-62-9, Jul. 28, 2006, 1 page.
CAS Registry No. 915296-00-3, Dec. 13, 2006, 1 page.
CAS Registry No. 934235-44-6, May 3, 2007, 1 page.
CAS Registry No. 934660-93-2, May 13, 2007, 1 page.
CAS Registry No. 1012054-59-9, Apr. 4, 2008, 1 page.
CAS Registry No. 1092364-38-9, Dec. 31, 2008, 1 page.
CAS Registry No. 1110813-31-4, Feb. 23, 2009, 1 page.
CAS Registry No. 1131863-89-2, Apr. 3, 2009, 1 page.
CAS Registry No. 1197953-54-0, Dec. 17, 2009, 1 page.
CAS Registry No. 1213269-23-8, Mar. 23, 2010, 1 page.
CAS Registry No. 1214265-56-1, Mar. 24, 2010, 1 page.
CAS Registry No. 1214265-57-2, Mar. 24, 2010, 1 page.
CAS Registry No. 1374640-70-6, May 29, 2012, 1 page.
CAS Registry No. 1398833-56-1, Oct. 3, 2012, 1 page.
CAS Registry No. 1421373-65-0, Feb. 19, 2013, 1 page.
Dayoff, M. O. et al., Atlas of Protein Sequence and Structure, vol. 5, Supplement 3, a Model of Evolutionary Change, pp. 345-358 (1978).
Francis, J. M. et al., "EGFR Variant Heterogeneity in Glioblastoma Resolved through Single-Nucleus Sequencing," Cancer Discovery, 4:956-971 (2014); doi: 10.1158/2159-8290.CD-13-0879.
Furnari, F. B. et al., "Heterogeneity of epidermal growth factor receptor signalling networks in glioblastoma," Nature Reviews Cancer, 15:302-310 (2015).
GenBank Accession No. CAA25240.1, Oct. 7, 2008, 3 pages.
GenBank Accession No. NP_004439.2, May 3, 2020, 9 pages.
GenBank Accession No. NP_001005262.2, May 6, 2020, 2 pages.
GenBank Accession No. NP_001276865, Apr. 17, 2020, 4 pages.
GenBank Accession No. NP_001276866, May 3, 2020, 5 pages.
GenBank Accession No. NP_001276867, Apr. 17, 2020, 4 pages.
Hein, J., "Unified Approach to Alignment and Phylogenies," Methods in Enzymology, 183:626-645 (1990).
Henikoff, S. & Henikoff, J. G., "Amino acid substitution matrices from protein blocks," Proc. Natl. Acad. Sci. USA, 89:10915-10919 (1992).
Higgins, D. G. & Sharp, P. M., "Fast and sensitive multiple sequence alignments on a microcomputer," Comput Appl Biosci, 5(2):151-153 (1989).
Ji, H. et al., "Epidermal growth factor receptor variant III mutations in lung tumorigenesis and sensitivity to tyrosine kinase inhibitors," PNAS, 103(20):7817-7822 (2006).
Keller, J. et al., "Combination of Phosphorylated and Truncated EGFR Correlates With Higher Tumor and Nodal Stage in Head and Neck Cancer," Cancer Investigation, 28:1054-1062 (2010).
Martins, R. G. et al., "Cisplatin and Radiotherapy With or Without Erlotinib in Locally Advanced Squamous Cell Carcinoma of the Head and Neck: A Randomized Phase II Trial," Journal of Clinical Oncology, 31(11):1415-1421 (2013).
Myers, E. W. & Miller, W., "Optimal alignments in linear space," Comput Appl Biosci, 4(1):11-17 (1988).
Needleman, S. B. & Wunsch, C. D., "A General Method Applicable to the Search for Similarities in the Amino Acid Sequence of Two Proteins," J. Mol. Biol., 48:443-453 (1970).

(56) References Cited

OTHER PUBLICATIONS

Nishikawa, R. et al., "A mutant epidermal growth factor receptor common in human glioma confers enhanced tumorigenicity," Proc. Natl. Acad. Sci. USA, 91:7727-7731 (1994).

Pearson, W. R. & Lipman, D. J., "Improved tools for biological sequence comparison," Proc. Natl. Acad. Sci. USA, 85:2444-2448 (1988).

Peereboom, D. M. et al., "Phase II trial of erlotinib with temozolomide and radiation in patients with newly diagnosed glioblastoma multiforme," J Neurooncol, 98:93-99 (2010).

Petrylak, D. P. et al., "Results of the Southwest Oncology Group phase II evaluation (study S0031) of ZD1839 for advanced transitional cell carcinoma of the urothelium," Southwest Oncology Group, 105:317-321 (2009); doi:10.1111/j.1464-410X.2009.08799.x.

Philips, G. K. et al., "A phase II trial of cisplatin (C), gemcitabine (G) and gefitinib for advanced urothelial tract carcinoma: results of Cancer and Leukemia Group B (CALGB) 90102," Annals of Oncology, 20:1074-1079 (2009).

Reardon, D. A. et al., "Phase I/randomized phase II study of afatinib, an irreversible ErbB family blocker, with or without protracted temozolomide in adults with recurrent glioblastoma," Neuro-Oncology, 17(3) (2014), 10 pages; doi:10.1093/neuonc/nou160.

Robinson, D. F., "Comparison of Labeled Trees with Valency Three," Journal of Combinatorial Theory, 11:105-119 (1971).

Saitou, N. & Nei, M., "The Neighbor-joining Method: A New Method for Reconstructing Phylogenetic Trees," Mol. Biol. Evol., 4(4):406-425 (1987).

Sasaki, H. et al., "EGFRvIII mutation in lung cancer correlates with increased EGFR copy number," Oncology Reports, 17:319-323 (2007).

Smith, T. F. & Waterman, M. S., "Comparison of Biosequences," Advances in Applied Mathematics, 2:482-489 (1981).

Sok, J. C. et al., "Mutant Epidermal Growth Factor Receptor (EGFRvIII) Contributes to Head and Neck Cancer Growth and Resistance to EGFR Targeting," Clin Cancer Res, 12(17):5064-5073 (2006).

Sugawa, N. et al., "Identical splicing of aberrant epidermal growth factor receptor transcripts from amplified rearranged genes in human glioblastomas," Proc. Natl. Acad. Sci. USA, 87:8602-8606 (1990).

Tinhofer, I. et al., "Expression of Amphiregulin and EGFRvIII Affect Outcome of Patients with Squamous Cell Carcinoma of the Head and Neck Receiving Cetuximab—Docetaxel Treatment," Clin Cancer Res, 17(15): 5197-5204 (2011).

Van Den Bent, M. J. et al., "Randomized Phase II Trial of Erlotinib Versus Temozolomide or Carmustine in Recurrent Glioblastoma: EORTC Brain Tumor Group Study 26034," J Clin Oncol, 27:1268-1274 (2009).

Wheeler, S. E. et al., "Challenges in EGFRvIII Detection in Head and Neck Squamous Cell Carcinoma," PLoS One, 10(2):e0117781 (2015), 13 pages; doi:10.1371/journal.pone.0117781.

Wheeler, S. E. et al., "Epidermal growth factor receptor variant III mediates head and neck cancer cell invasion via STAT3 activation," Oncogene, 29:5135-5145 (2010).

Wilbur, W. J. & Lipman, D. J., "Rapid similarity searches of nucleic acid and protein data banks," Proc. Natl. Acad. Sci. USA, 80:726-730 (1983).

\* cited by examiner

| ErbB inhibitor | ErbB WT | | EGFR-ATP site mutants | | HER2 allosteric mutants | | | | | ErbB Exon 20 insertions | | | | EGFR Exon 20 del |
|---|---|---|---|---|---|---|---|---|---|---|---|---|---|---|
| | EGFR-HER2-wt wt | EGFR-HER2-wt | EGFR-19del | H4006 | HER2-S310F | HER2-R678Q | HER2-V777L | HER2-L755S | HER2-V842I | HER2-YVMA | HER2-NPH | EGFR-SVD | EGFR-Viii | |
| Erlotinib (Tarceva) | 144 | >1000 | 16 | 30 | >1000 | 592 | >1000 | >1000 | >1000 | >1000 | >1000 | >1000 | >1000 | |
| Afatinib (Gilotrif) | 7 | 6 | 1 | 0.6 | 14 | 14 | 5 | 14 | 14 | 45 | >1000 | 135 | 8 | |
| Neratinib (Nerlynx) | 33 | 1 | 67 | 43 | 6 | 1 | 1 | 3 | 4 | 13 | 585 | 278 | 38 | |
| Osimertinib (Tagrisso) | 134 | 36 | 3 | 5 | 93 | 12 | 24 | 33 | 122 | 527 | 110 | 115 | 109 | |

FIGURE 19

| ErbB inhibitor | ErbB WT | | EGFR-ATP site mutants | | ErbB Exon 20 insertions | | | | | | EGFR Exon 20 del |
|---|---|---|---|---|---|---|---|---|---|---|---|
| | EGFR-wt | HER2-wt | EGFR-19del | H4006 | HER2-YVMA | EGFR-GSP | EGFR-ASV | EGFR-NPH | EGFR-SVD | EGFR-FQEA | EGFR-Viii |
| Erlotinib (Tarceva) | 144 | >1000 | 16 | 30 | >1000 | >1000 | >1000 | >1000 | >1000 | 263 | >1000 |
| Afatinib (Gilotrif) | 7 | 6 | 1 | 0.6 | 45 | 9 | 97 | >1000 | 135 | 2 | 8 |
| Neratinib (Nerlynx) | 33 | 1 | 67 | 43 | 13 | 8 | 109 | 585 | 278 | 40 | 38 |
| Osimertinib (Tagrisso) | 134 | 36 | 3 | 5 | 527 | 188 | 267 | 110 | 115 | 42 | 109 |

FIGURE 20

SEQUENCE LISTING

```
<160> NUMBER OF SEQ ID NOS: 17

<210> SEQ ID NO 1
<211> LENGTH: 1210
<212> TYPE: PRT
<213> ORGANISM: Homo sapien

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45
```

```
Leu Ser Leu Gln Arg Met Phe Asn Asn Cys Glu Val Val Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460
```

-continued

```
Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
```

```
                        885             890             895
Val Trp Ser Tyr Gly Val Thr Val Trp Glu Leu Met Thr Phe Gly Ser
                    900             905             910

Lys Pro Tyr Asp Gly Ile Pro Ala Ser Glu Ile Ser Ser Ile Leu Glu
                915             920             925

Lys Gly Glu Arg Leu Pro Gln Pro Pro Ile Cys Thr Ile Asp Val Tyr
            930             935             940

Met Ile Met Val Lys Cys Trp Met Ile Asp Ala Asp Ser Arg Pro Lys
945             950             955             960

Phe Arg Glu Leu Ile Ile Glu Phe Ser Lys Met Ala Arg Asp Pro Gln
                965             970             975

Arg Tyr Leu Val Ile Gln Gly Asp Glu Arg Met His Leu Pro Ser Pro
            980             985             990

Thr Asp Ser Asn Phe Tyr Arg Ala Leu Met Asp Glu Glu Asp Met Asp
        995             1000            1005

Asp Val Val Asp Ala Asp Glu Tyr Leu Ile Pro Gln Gln Gly Phe
    1010            1015            1020

Phe Ser Ser Pro Ser Thr Ser Arg Thr Pro Leu Leu Ser Ser Leu
    1025            1030            1035

Ser Ala Thr Ser Asn Asn Ser Thr Val Ala Cys Ile Asp Arg Asn
    1040            1045            1050

Gly Leu Gln Ser Cys Pro Ile Lys Glu Asp Ser Phe Leu Gln Arg
    1055            1060            1065

Tyr Ser Ser Asp Pro Thr Gly Ala Leu Thr Glu Asp Ser Ile Asp
    1070            1075            1080

Asp Thr Phe Leu Pro Val Pro Glu Tyr Ile Asn Gln Ser Val Pro
    1085            1090            1095

Lys Arg Pro Ala Gly Ser Val Gln Asn Pro Val Tyr His Asn Gln
    1100            1105            1110

Pro Leu Asn Pro Ala Pro Ser Arg Asp Pro His Tyr Gln Asp Pro
    1115            1120            1125

His Ser Thr Ala Val Gly Asn Pro Glu Tyr Leu Asn Thr Val Gln
    1130            1135            1140

Pro Thr Cys Val Asn Ser Thr Phe Asp Ser Pro Ala His Trp Ala
    1145            1150            1155

Gln Lys Gly Ser His Gln Ile Ser Leu Asp Asn Pro Asp Tyr Gln
    1160            1165            1170

Gln Asp Phe Phe Pro Lys Glu Ala Lys Pro Asn Gly Ile Phe Lys
    1175            1180            1185

Gly Ser Thr Ala Glu Asn Ala Glu Tyr Leu Arg Val Ala Pro Gln
    1190            1195            1200

Ser Ser Glu Phe Ile Gly Ala
    1205            1210

<210> SEQ ID NO 2
<211> LENGTH: 1255
<212> TYPE: PRT
<213> ORGANISM: Homo sapien

<400> SEQUENCE: 2

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30
```

-continued

```
Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
65                   70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
             100                 105                 110

Ala Leu Ala Val Leu Asp Asn Gly Asp Pro Leu Asn Asn Thr Thr Pro
         115                 120                 125

Val Thr Gly Ala Ser Pro Gly Gly Leu Arg Glu Leu Gln Leu Arg Ser
 130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                 165                 170                 175

Asn Gln Leu Ala Leu Thr Leu Ile Asp Thr Asn Arg Ser Arg Ala Cys
             180                 185                 190

His Pro Cys Ser Pro Met Cys Lys Gly Ser Arg Cys Trp Gly Glu Ser
         195                 200                 205

Ser Glu Asp Cys Gln Ser Leu Thr Arg Thr Val Cys Ala Gly Gly Cys
 210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                 245                 250                 255

His Phe Asn His Ser Gly Ile Cys Glu Leu His Cys Pro Ala Leu Val
             260                 265                 270

Thr Tyr Asn Thr Asp Thr Phe Glu Ser Met Pro Asn Pro Glu Gly Arg
         275                 280                 285

Tyr Thr Phe Gly Ala Ser Cys Val Thr Ala Cys Pro Tyr Asn Tyr Leu
 290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                 325                 330                 335

Pro Cys Ala Arg Val Cys Tyr Gly Leu Gly Met Glu His Leu Arg Glu
             340                 345                 350

Val Arg Ala Val Thr Ser Ala Asn Ile Gln Glu Phe Ala Gly Cys Lys
         355                 360                 365

Lys Ile Phe Gly Ser Leu Ala Phe Leu Pro Glu Ser Phe Asp Gly Asp
 370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                 405                 410                 415

Asp Ser Leu Pro Asp Leu Ser Val Phe Gln Asn Leu Gln Val Ile Arg
             420                 425                 430

Gly Arg Ile Leu His Asn Gly Ala Tyr Ser Leu Thr Leu Gln Gly Leu
         435                 440                 445

Gly Ile Ser Trp Leu Gly Leu Arg Ser Leu Arg Glu Leu Gly Ser Gly
```

-continued

```
            450                 455                 460
Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                    485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Thr Gln Cys
            515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
                835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880
```

```
Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 3
<211> LENGTH: 1225
```

<212> TYPE: PRT
<213> ORGANISM: Homo sapien

<400> SEQUENCE: 3

```
Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400
```

-continued

```
Ile Arg Gly Arg Ile Leu His Asn Gly Ala Tyr Ser Leu Thr Leu Gln
            405                 410                 415
Gly Leu Gly Ile Ser Trp Leu Gly Leu Arg Ser Leu Arg Glu Leu Gly
        420                 425                 430
Ser Gly Leu Ala Leu Ile His His Asn Thr His Leu Cys Phe Val His
            435                 440                 445
Thr Val Pro Trp Asp Gln Leu Phe Arg Asn Pro His Gln Ala Leu Leu
450                 455                 460
His Thr Ala Asn Arg Pro Glu Asp Glu Cys Val Gly Glu Gly Leu Ala
465                 470                 475                 480
Cys His Gln Leu Cys Ala Arg Gly His Cys Trp Gly Pro Gly Pro Thr
            485                 490                 495
Gln Cys Val Asn Cys Ser Gln Phe Leu Arg Gly Gln Glu Cys Val Glu
        500                 505                 510
Glu Cys Arg Val Leu Gln Gly Leu Pro Arg Glu Tyr Val Asn Ala Arg
        515                 520                 525
His Cys Leu Pro Cys His Pro Glu Cys Gln Pro Gln Asn Gly Ser Val
        530                 535                 540
Thr Cys Phe Gly Pro Glu Ala Asp Gln Cys Val Ala Cys Ala His Tyr
545                 550                 555                 560
Lys Asp Pro Pro Phe Cys Val Ala Arg Cys Pro Ser Gly Val Lys Pro
            565                 570                 575
Asp Leu Ser Tyr Met Pro Ile Trp Lys Phe Pro Asp Glu Glu Gly Ala
        580                 585                 590
Cys Gln Pro Cys Pro Ile Asn Cys Thr His Ser Cys Val Asp Leu Asp
        595                 600                 605
Asp Lys Gly Cys Pro Ala Glu Gln Arg Ala Ser Pro Leu Thr Ser Ile
        610                 615                 620
Ile Ser Ala Val Val Gly Ile Leu Leu Val Val Leu Gly Val Val
625                 630                 635                 640
Phe Gly Ile Leu Ile Lys Arg Arg Gln Gln Lys Ile Arg Lys Tyr Thr
            645                 650                 655
Met Arg Arg Leu Leu Gln Glu Thr Glu Leu Val Glu Pro Leu Thr Pro
            660                 665                 670
Ser Gly Ala Met Pro Asn Gln Ala Gln Met Arg Ile Leu Lys Glu Thr
        675                 680                 685
Glu Leu Arg Lys Val Lys Val Leu Gly Ser Gly Ala Phe Gly Thr Val
        690                 695                 700
Tyr Lys Gly Ile Trp Ile Pro Asp Gly Glu Asn Val Lys Ile Pro Val
705                 710                 715                 720
Ala Ile Lys Val Leu Arg Glu Asn Thr Ser Pro Lys Ala Asn Lys Glu
            725                 730                 735
Ile Leu Asp Glu Ala Tyr Val Met Ala Gly Val Gly Ser Pro Tyr Val
            740                 745                 750
Ser Arg Leu Leu Gly Ile Cys Leu Thr Ser Thr Val Gln Leu Val Thr
        755                 760                 765
Gln Leu Met Pro Tyr Gly Cys Leu Leu Asp His Val Arg Glu Asn Arg
        770                 775                 780
Gly Arg Leu Gly Ser Gln Asp Leu Leu Asn Trp Cys Met Gln Ile Ala
785                 790                 795                 800
Lys Gly Met Ser Tyr Leu Glu Asp Val Arg Leu Val His Arg Asp Leu
            805                 810                 815
```

```
Ala Ala Arg Asn Val Leu Val Lys Ser Pro Asn His Val Lys Ile Thr
                820                 825                 830

Asp Phe Gly Leu Ala Arg Leu Leu Asp Ile Asp Glu Thr Glu Tyr His
            835                 840                 845

Ala Asp Gly Gly Lys Val Pro Ile Lys Trp Met Ala Leu Glu Ser Ile
    850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
                900                 905                 910

Gln Pro Pro Ile Cys Thr Ile Asp Val Tyr Met Ile Met Val Lys Cys
            915                 920                 925

Trp Met Ile Asp Ser Glu Cys Arg Pro Arg Phe Arg Glu Leu Val Ser
    930                 935                 940

Glu Phe Ser Arg Met Ala Arg Asp Pro Gln Arg Phe Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe Phe Cys Pro Asp Pro Ala Pro Gly
        995                 1000                1005

Ala Gly Gly Met Val His His Arg His Arg Ser Ser Ser Thr Arg
    1010                1015                1020

Ser Gly Gly Gly Asp Leu Thr Leu Gly Leu Glu Pro Ser Glu Glu
    1025                1030                1035

Glu Ala Pro Arg Ser Pro Leu Ala Pro Ser Glu Gly Ala Gly Ser
    1040                1045                1050

Asp Val Phe Asp Gly Asp Leu Gly Met Gly Ala Ala Lys Gly Leu
    1055                1060                1065

Gln Ser Leu Pro Thr His Asp Pro Ser Pro Leu Gln Arg Tyr Ser
    1070                1075                1080

Glu Asp Pro Thr Val Pro Leu Pro Ser Glu Thr Asp Gly Tyr Val
    1085                1090                1095

Ala Pro Leu Thr Cys Ser Pro Gln Pro Glu Tyr Val Asn Gln Pro
    1100                1105                1110

Asp Val Arg Pro Gln Pro Pro Ser Pro Arg Glu Gly Pro Leu Pro
    1115                1120                1125

Ala Ala Arg Pro Ala Gly Ala Thr Leu Glu Arg Pro Lys Thr Leu
    1130                1135                1140

Ser Pro Gly Lys Asn Gly Val Val Lys Asp Val Phe Ala Phe Gly
    1145                1150                1155

Gly Ala Val Glu Asn Pro Glu Tyr Leu Thr Pro Gln Gly Gly Ala
    1160                1165                1170

Ala Pro Gln Pro His Pro Pro Ala Phe Ser Pro Ala Phe Asp
    1175                1180                1185

Asn Leu Tyr Tyr Trp Asp Gln Asp Pro Pro Glu Arg Gly Ala Pro
    1190                1195                1200

Pro Ser Thr Phe Lys Gly Thr Pro Thr Ala Glu Asn Pro Glu Tyr
    1205                1210                1215

Leu Gly Leu Asp Val Pro Val
```

-continued

```
        1220            1225
```

<210> SEQ ID NO 4
<211> LENGTH: 1240
<212> TYPE: PRT
<213> ORGANISM: Homo sapien

<400> SEQUENCE: 4

```
Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
                20                  25                  30

His Leu Tyr Gln Gly Cys Gln Val Val Gln Gly Asn Leu Glu Leu Thr
            35                  40                  45

Tyr Leu Pro Thr Asn Ala Ser Leu Ser Phe Leu Gln Asp Ile Gln Glu
        50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
        195                 200                 205

Cys Ala Arg Cys Lys Gly Pro Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met Pro Asn Pro Glu Gly
            260                 265                 270

Arg Tyr Thr Phe Gly Ala Ser Cys Val Thr Ala Cys Pro Tyr Asn Tyr
        275                 280                 285

Leu Ser Thr Asp Val Gly Ser Cys Thr Leu Val Cys Pro Leu His Asn
    290                 295                 300

Gln Glu Val Thr Ala Glu Asp Gly Thr Gln Arg Cys Glu Lys Cys Ser
305                 310                 315                 320

Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
        355                 360                 365
```

```
Asp Pro Ala Ser Asn Thr Ala Pro Leu Gln Pro Glu Gln Leu Gln Val
    370             375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
        435                 440                 445

Gly Leu Ala Leu Ile His His Asn Thr His Leu Cys Phe Val His Thr
    450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
            500                 505                 510

Cys Val Asn Cys Ser Gln Phe Leu Arg Gly Gln Glu Cys Val Glu Glu
        515                 520                 525

Cys Arg Val Leu Gln Gly Leu Pro Arg Glu Tyr Val Asn Ala Arg His
530                 535                 540

Cys Leu Pro Cys His Pro Glu Cys Gln Pro Gln Asn Gly Ser Val Thr
545                 550                 555                 560

Cys Phe Gly Pro Glu Ala Asp Gln Cys Val Ala Cys Ala His Tyr Lys
                565                 570                 575

Asp Pro Pro Phe Cys Val Ala Arg Cys Pro Ser Gly Val Lys Pro Asp
            580                 585                 590

Leu Ser Tyr Met Pro Ile Trp Lys Phe Pro Asp Glu Glu Gly Ala Cys
        595                 600                 605

Gln Pro Cys Pro Ile Asn Cys Thr His Ser Cys Val Asp Leu Asp Asp
    610                 615                 620

Lys Gly Cys Pro Ala Glu Gln Arg Ala Ser Pro Leu Thr Ser Ile Ile
625                 630                 635                 640

Ser Ala Val Val Gly Ile Leu Leu Val Val Val Leu Gly Val Val Phe
                645                 650                 655

Gly Ile Leu Ile Lys Arg Arg Gln Gln Lys Ile Arg Lys Tyr Thr Met
            660                 665                 670

Arg Arg Leu Leu Gln Glu Thr Glu Leu Val Glu Pro Leu Thr Pro Ser
        675                 680                 685

Gly Ala Met Pro Asn Gln Ala Gln Met Arg Ile Leu Lys Glu Thr Glu
    690                 695                 700

Leu Arg Lys Val Lys Val Leu Gly Ser Gly Ala Phe Gly Thr Val Tyr
705                 710                 715                 720

Lys Gly Ile Trp Ile Pro Asp Gly Glu Asn Val Lys Ile Pro Val Ala
                725                 730                 735

Ile Lys Val Leu Arg Glu Asn Thr Ser Pro Lys Ala Asn Lys Glu Ile
            740                 745                 750

Leu Asp Glu Ala Tyr Val Met Ala Gly Val Gly Ser Pro Tyr Val Ser
        755                 760                 765

Arg Leu Leu Gly Ile Cys Leu Thr Ser Thr Val Gln Leu Val Thr Gln
    770                 775                 780

Leu Met Pro Tyr Gly Cys Leu Leu Asp His Val Arg Glu Asn Arg Gly
```

-continued

```
                785                 790                 795                 800
        Arg Leu Gly Ser Gln Asp Leu Leu Asn Trp Cys Met Gln Ile Ala Lys
                        805                 810                 815

Gly Met Ser Tyr Leu Glu Asp Val Arg Leu Val His Arg Asp Leu Ala
                        820                 825                 830

Ala Arg Asn Val Leu Val Lys Ser Pro Asn His Val Lys Ile Thr Asp
                        835                 840                 845

Phe Gly Leu Ala Arg Leu Leu Asp Ile Asp Glu Thr Glu Tyr His Ala
        850                 855                 860

Asp Gly Gly Lys Val Pro Ile Lys Trp Met Ala Leu Glu Ser Ile Leu
        865                 870                 875                 880

Arg Arg Arg Phe Thr His Gln Ser Asp Val Trp Ser Tyr Gly Val Thr
                        885                 890                 895

Val Trp Glu Leu Met Thr Phe Gly Ala Lys Pro Tyr Asp Gly Ile Pro
                        900                 905                 910

Ala Arg Glu Ile Pro Asp Leu Leu Glu Lys Gly Glu Arg Leu Pro Gln
                        915                 920                 925

Pro Pro Ile Cys Thr Ile Asp Val Tyr Met Ile Met Val Lys Cys Trp
                        930                 935                 940

Met Ile Asp Ser Glu Cys Arg Pro Arg Phe Arg Glu Leu Val Ser Glu
        945                 950                 955                 960

Phe Ser Arg Met Ala Arg Asp Pro Gln Arg Phe Val Val Ile Gln Asn
                        965                 970                 975

Glu Asp Leu Gly Pro Ala Ser Pro Leu Asp Ser Thr Phe Tyr Arg Ser
                        980                 985                 990

Leu Leu Glu Asp Asp Asp Met Gly Asp Leu Val Asp Ala Glu Glu Tyr
                        995                 1000                1005

Leu Val Pro Gln Gln Gly Phe Phe Cys Pro Asp Pro Ala Pro Gly
                1010                1015                1020

Ala Gly Gly Met Val His His Arg His Arg Ser Ser Ser Thr Arg
                1025                1030                1035

Ser Gly Gly Gly Asp Leu Thr Leu Gly Leu Glu Pro Ser Glu Glu
                1040                1045                1050

Glu Ala Pro Arg Ser Pro Leu Ala Pro Ser Glu Gly Ala Gly Ser
                1055                1060                1065

Asp Val Phe Asp Gly Asp Leu Gly Met Gly Ala Ala Lys Gly Leu
                1070                1075                1080

Gln Ser Leu Pro Thr His Asp Pro Ser Pro Leu Gln Arg Tyr Ser
                1085                1090                1095

Glu Asp Pro Thr Val Pro Leu Pro Ser Glu Thr Asp Gly Tyr Val
                1100                1105                1110

Ala Pro Leu Thr Cys Ser Pro Gln Pro Glu Tyr Val Asn Gln Pro
                1115                1120                1125

Asp Val Arg Pro Gln Pro Pro Ser Pro Arg Glu Gly Pro Leu Pro
                1130                1135                1140

Ala Ala Arg Pro Ala Gly Ala Thr Leu Glu Arg Pro Lys Thr Leu
                1145                1150                1155

Ser Pro Gly Lys Asn Gly Val Val Lys Asp Val Phe Ala Phe Gly
                1160                1165                1170

Gly Ala Val Glu Asn Pro Glu Tyr Leu Thr Pro Gln Gly Gly Ala
                1175                1180                1185

Ala Pro Gln Pro His Pro Pro Pro Ala Phe Ser Pro Ala Phe Asp
                1190                1195                1200
```

Asn Leu Tyr Tyr Trp Asp Gln Asp Pro Pro Glu Arg Gly Ala Pro
1205                1210                1215

Pro Ser Thr Phe Lys Gly Thr Pro Thr Ala Glu Asn Pro Glu Tyr
1220                1225                1230

Leu Gly Leu Asp Val Pro Val
1235                1240

<210> SEQ ID NO 5
<211> LENGTH: 1055
<212> TYPE: PRT
<213> ORGANISM: Homo sapien

<400> SEQUENCE: 5

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys

-continued

```
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
    370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
            405                 410                 415
Asp Ser Leu Pro Asp Leu Ser Val Phe Gln Asn Leu Gln Val Ile Arg
        420                 425                 430
Gly Arg Ile Leu His Asn Gly Ala Tyr Ser Leu Thr Leu Gln Gly Leu
    435                 440                 445
Gly Ile Ser Trp Leu Gly Leu Arg Ser Leu Arg Glu Leu Gly Ser Gly
450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
            485                 490                 495
Ala Asn Arg Pro Glu Asp Glu Cys Val Gly Glu Gly Leu Ala Cys His
        500                 505                 510
Gln Leu Cys Ala Arg Gly His Cys Trp Gly Pro Gly Pro Thr Gln Cys
    515                 520                 525
Val Asn Cys Ser Gln Phe Leu Arg Gly Gln Glu Cys Val Glu Glu Cys
530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
            565                 570                 575
Phe Gly Pro Glu Ala Asp Gln Cys Val Ala Cys Ala His Tyr Lys Asp
        580                 585                 590
Pro Pro Phe Cys Val Ala Arg Cys Pro Ser Gly Val Lys Pro Asp Leu
    595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
            645                 650                 655
Ala Val Val Gly Ile Leu Leu Val Val Leu Gly Val Val Phe Gly
        660                 665                 670
Ile Leu Ile Lys Arg Arg Gln Gln Lys Ile Arg Lys Tyr Thr Met Arg
    675                 680                 685
Arg Leu Leu Gln Glu Thr Glu Leu Val Glu Pro Leu Thr Pro Ser Gly
    690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
            725                 730                 735
Gly Ile Trp Ile Pro Asp Gly Glu Asn Val Lys Ile Pro Val Ala Ile
        740                 745                 750
```

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
                835                 840                 845

Arg Asn Val Leu Val Lys Ser Pro Asn His Val Lys Ile Thr Asp Phe
        850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Asn Met
    1055

<210> SEQ ID NO 6
<211> LENGTH: 603
<212> TYPE: PRT
<213> ORGANISM: Homo sapien

<400> SEQUENCE: 6

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val

-continued

```
            50                  55                  60
Pro Leu Gln Arg Leu Arg Ile Val Arg Gly Thr Gln Leu Phe Glu Asp
 65                      70                  75                  80

Asn Tyr Ala Leu Ala Val Leu Asp Asn Gly Asp Pro Leu Asn Asn Thr
                     85                  90                  95

Thr Pro Val Thr Gly Ala Ser Pro Gly Leu Arg Glu Leu Gln Leu
                100                 105                 110

Arg Ser Leu Thr Glu Ile Leu Lys Gly Gly Val Leu Ile Gln Arg Asn
            115                 120                 125

Pro Gln Leu Cys Tyr Gln Asp Thr Ile Leu Trp Lys Asp Ile Phe His
130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
                180                 185                 190

Gly Cys Ala Arg Cys Lys Gly Pro Leu Pro Thr Asp Cys Cys His Glu
            195                 200                 205

Gln Cys Ala Ala Gly Cys Thr Gly Pro Lys His Ser Asp Cys Leu Ala
210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
                260                 265                 270

Tyr Leu Ser Thr Asp Val Gly Ser Cys Thr Leu Val Cys Pro Leu His
            275                 280                 285

Asn Gln Glu Val Thr Ala Glu Asp Gly Thr Gln Arg Cys Glu Lys Cys
290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
            355                 360                 365

Val Phe Glu Thr Leu Glu Glu Ile Thr Gly Tyr Leu Tyr Ile Ser Ala
370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
            435                 440                 445

Thr Val Pro Trp Asp Gln Leu Phe Arg Asn Pro His Gln Ala Leu Leu
450                 455                 460

His Thr Ala Asn Arg Pro Glu Asp Glu Cys Val Gly Glu Gly Leu Ala
465                 470                 475                 480
```

```
Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525

His Cys Leu Pro Cys His Pro Glu Cys Gln Pro Gln Asn Gly Ser Val
530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser
        595                 600

<210> SEQ ID NO 7
<211> LENGTH: 21
<212> TYPE: PRT
<213> ORGANISM: Artificial sequence
<220> FEATURE:
<223> OTHER INFORMATION: EGFR insertion encoding exon 20

<400> SEQUENCE: 7

Lys Glu Ile Leu Asp Glu Ala Tyr Val Met Ala Ser Val Asp Asn Pro
1               5                   10                  15

His Val Cys Ala Arg
            20

<210> SEQ ID NO 8
<211> LENGTH: 20
<212> TYPE: PRT
<213> ORGANISM: Artificial sequence
<220> FEATURE:
<223> OTHER INFORMATION: HER2 receptor insertion encoding exon 20

<400> SEQUENCE: 8

Lys Glu Ile Leu Asp Glu Ala Tyr Val Met Ala Gly Val Gly Ser Pro
1               5                   10                  15

Tyr Val Ser Arg
            20

<210> SEQ ID NO 9
<211> LENGTH: 17
<212> TYPE: DNA
<213> ORGANISM: Artificial sequence
<220> FEATURE:
<223> OTHER INFORMATION: EGFRVIII forward

<400> SEQUENCE: 9
tcgggctctg gaggaaa                                                    17

<210> SEQ ID NO 10
<211> LENGTH: 24
<212> TYPE: DNA
<213> ORGANISM: Artificial sequence
<220> FEATURE:
<223> OTHER INFORMATION: EGFRVIII probe

<400> SEQUENCE: 10
```

```
atgtggtgac agatcacggc tcgt                                          24

<210> SEQ ID NO 11
<211> LENGTH: 21
<212> TYPE: DNA
<213> ORGANISM: Artificial sequence
<220> FEATURE:
<223> OTHER INFORMATION: EGFRVIII reverse

<400> SEQUENCE: 11
ccgtcttcct ccatctcata g                                             21

<210> SEQ ID NO 12
<211> LENGTH: 19
<212> TYPE: DNA
<213> ORGANISM: Artificial sequence
<220> FEATURE:
<223> OTHER INFORMATION: EGFRVii forward

<400> SEQUENCE: 12
cttctggagg gatgcactg                                                19

<210> SEQ ID NO 13
<211> LENGTH: 24
<212> TYPE: DNA
<213> ORGANISM: Artificial sequence
<220> FEATURE:
<223> OTHER INFORMATION: EGFRVii probe

<400> SEQUENCE: 13
caacgaatgg gcctaagatc ccgt                                          24

<210> SEQ ID NO 14
<211> LENGTH: 17
<212> TYPE: DNA
<213> ORGANISM: Artificial sequence
<220> FEATURE:
<223> OTHER INFORMATION: EGFRvii reverse

<400> SEQUENCE: 14
caccaccagc agcaaga                                                  17

<210> SEQ ID NO 15
<211> LENGTH: 22
<212> TYPE: DNA
<213> ORGANISM: Artificial sequence
<220> FEATURE:
<223> OTHER INFORMATION: EGFRVvi forward

<400> SEQUENCE: 15
ccatgccttt gagaacctag aa                                            22

<210> SEQ ID NO 16
<211> LENGTH: 24
<212> TYPE: DNA
<213> ORGANISM: Artificial sequence
<220> FEATURE:
<223> OTHER INFORMATION: EGFRVvi probe

<400> SEQUENCE: 16
acatgagcca agggagtttg tgga                                          24

<210> SEQ ID NO 17
<211> LENGTH: 19
<212> TYPE: DNA
<213> ORGANISM: Artificial sequence
```

```
<220> FEATURE:
<223> OTHER INFORMATION: EGFRVvi reverse

<400> SEQUENCE: 17
ctctgggtgg cactgtatg                                    19
```

TYROSINE KINASE INHIBITOR COMPOSITIONS, METHODS OF MAKING AND METHODS OF USE

RELATED APPLICATIONS

This application is a continuation of International Patent Application No. PCT/US2019/052784, filed Sep. 24, 2019, which claims priority to, and the benefit of, U.S. Application Nos. 62/903,592, filed Sep. 20, 2019, and 62/736,293, filed Sep. 25, 2018, the entire contents of each of which are incorporated herein by reference.

INCORPORATION OF THE SEQUENCE LISTING

The contents of the text file submitted electronically herewith are incorporated herein by reference in their entirety: a computer readable format copy of the Sequence Listing (filename: ASET-007C01US_SeqList, date recorded: Apr. 13, 2020, file size: 59 KB).

FIELD OF THE DISCLOSURE

The present disclosure relates to new compounds as inhibitors of receptor tyrosine kinases (RTK), in particular oncogenic mutants of ErbB-receptors. The present disclosure also relates to methods of preparation these compounds, compositions comprising these compounds, and methods of using them in the treatment of abnormal cell growth in mammals (e.g., humans).

BACKGROUND

Mutations affecting either the intracellular catalytic domain or extracellular ligand binding domain of an ErbB receptor can generate oncogenic activity (the ErbB protein family consists of 4 members including ErbB-1, also named epidermal growth factor receptor (EGFR) and Erb-2, also named HER2 in humans). ErbB inhibitors are a known treatment for a number of cancers. However, not every patient is responsive satisfactorily to this treatment. Thus, there is a long-felt need in the art for new therapies that are able to address the variable responsiveness of cancer patients to known therapies. The present disclosure provides compositions and methods for treating cancer in patients with these oncogenic mutations without the variable reponsivenss observed when patients having these ErbB mutants are treated using the existing standard of care.

SUMMARY

In some aspects, the present disclosure is directed towards a compound or pharmaceutically acceptable salts or stereoisomers thereof of formula I

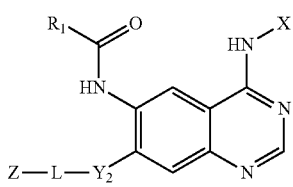

wherein L is a covalent bond, straight chain or branched $C_{1-4}$ alkyl or

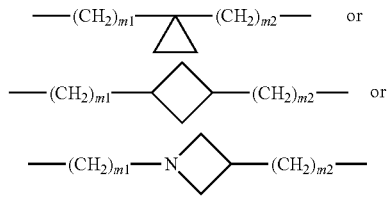

wherein m1, m2 are independently of each other 0, 1, 3, or 4;

$Y^2$ is a covalent bond, —O—, —NH—, —NCH$_3$—, or —C≡C—;

Z is —(NR$^4$R$^5$), wherein R$^4$ and R$^5$ are independently of each other H, $C_{1-6}$ alkyl, cyclopropyl, cylobutyl, 3-6-membered heterocycloalkyl, or —(NR$^6$R$^7$), —(CHR$^6$R$^7$), wherein R$^6$ and R$^7$ form together with the atom to which they are attached to 3-6-membered heteroaryl or 3-9-membered heterocycloalkyl, wherein the 3-9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl;

$R^1$ is —CR$_b$═CHR$_a$, —C≡CH or —C≡C—CH$_3$; wherein $R^a$, $R^b$ are independently of each other H, hal, —CH$_2$—O—CH$_3$ and X is a group of formula (i)a

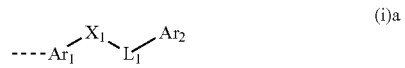

wherein $X^1$ is —O—, —CH$_2$—, —NH—, —S—; Ar$^1$ is 6 membered aryl or N-heteroaryl, which is unsubstituted or substituted with one or more of a group selected from hal, $C_{1-6}$alkyl or $C_{1-6}$alkoxy; Ar$^2$ is 6 membered aryl or N-heteroaryl, which is unsubstituted or substituted with one or more of a group selected from halogen, $C_{1-6}$alkyl, $C_{1-6}$alkoxy, —CF$_3$ or —OCF$_3$; $L^1$ is a covalent bond or straight or branched $C_{1-3}$alkyl, which is unsubstituted or substituted with hal.

In some embodiments substituent Z-L-Y$_2$ contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if Y$_2$ is not N(H) or (NMe) or L does not contain a nitrogen atom.

In some embodiments R$^a$ and R$^b$ are hydrogen.

In some embodiments, $L^1$ is selected from a covalent bond, —CH$_2$— or —CH(CH$_3$)—, CH(hal)-, —CH$_2$—CH$_2$— or —CH$_2$—CH(CH$_3$)—, —CH$_2$-CH(hal)-.

In some embodiments, $X^1$—$L^1$ is —O—, —NH—, —S—, —CH$_2$—, —O—CH$_2$—, —NH—CH$_2$—, —S—CH$_2$, —CH$_2$—CH$_2$—, —O—CH(CH$_3$)—, —CH$_2$—CH(CH$_3$)—, —NH—CH(CH$_3$)—, —S—CH(CH$_3$)—, —O—CH(hal)-, —CH$_2$—CH(hal)-, —NH—CH(hal)-, or —S—CH(hal)-.

In some embodiments, $L^1$ is straight chain or branched $C_{1-3}$alkyl, which is unsubstituted or substituted with hal. In some embodiments, $L^1$ is not a covalent bond.

In some embodiments, Ar$_1$ of the compound of formula (i)a or pharmaceutically acceptable salts or stereoisomers thereof is a group of formula (i)b

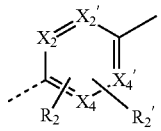
(i)b wherein $X^2$, $X^{2'}$, $X^4$, $X^{4'}$ are independently of each other —N= or —CH=; $R^2$, $R^{2'}$ are independently of each other H, $C_{1-6}$ alkyl, hal, —$CF_3$, with the proviso that at least two of $X^2$, $X^{2'}$, $X^4$, $X^{4'}$ are —CH=;

and/or wherein $Ar_2$ of the compound of formula (i)a or pharmaceutically acceptable salts or stereoisomers thereof is a group of formula (i)c

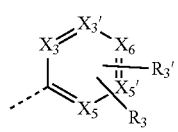
(i)c wherein $X^3$, $X^{3'}$, $X^5$, $X^{5'}$, $X^6$ are independently of each other —N=, —CH=; $R^3$, $R^{3'}$ are independently of each other H, $C_{1-6}$ alkyl, hal, —$CF_3$, —$OCF_3$, with the proviso that at least two of $X^3$, $X^{3'}$, $X^5$, $X^{5'}$, $X^6$ are —CH=.

In some embodiments, group X is a group of formula (ii)a,

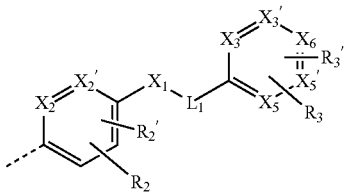
(ii)a wherein $X^1$ is —O—, —$CH_2$—, —NH—, —S—; $L^1$ is a covalent bond or $C_{1-3}$alkyl, which is unsubstituted or substituted with —$CH_3$, hal; $X^2$, $X^{2'}$, $X^3$, $X^{3'}$, $X^5$, $X^{5'}$, $X^6$ are independently of each other —N=, —CH=; and $R^2$, $R^{2'}$, $R^3$, $R^{3'}$ are independently of each other H, $C_{1-6}$ alkyl, hal, —$CF_3$, —$OCF_3$.

In some embodiments, group X is a group of formula (ii)b, (e.g. (ii)b-1 or (ii)b-2), or (ii)c, (e.g. (ii)c-1 or (ii)c-2):

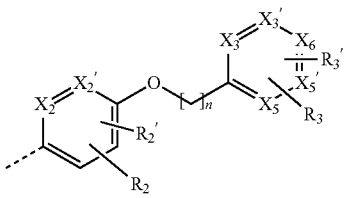
(ii)b

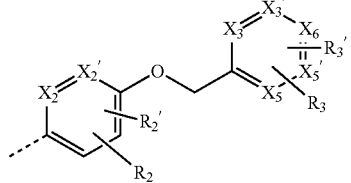
(ii)b-1

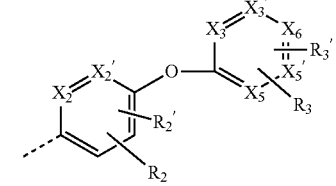
(ii)b-2

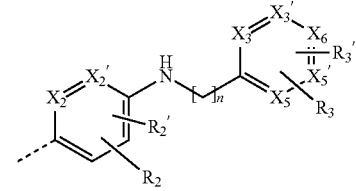
(ii)c

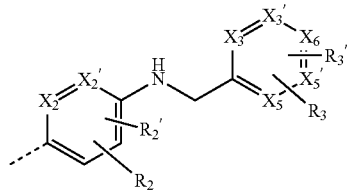
(ii)c-1

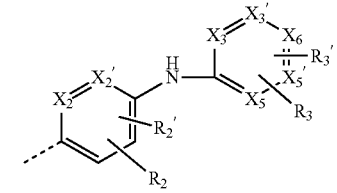
(ii)c-2 wherein $X^2$, $X^{2'}$, $X^3$, $X^{3'}$, $X^5$, $X^{5'}$, $X^6$ are independently of each other —N=, —CH=; $R^2$, $R^{2'}$, $R^3$, $R^{3'}$ are independently of each other H, $C_{1-6}$ alkyl, hal, —$CF_3$, —$OCF_3$, and n is 0, 1, 2, 3.

In some embodiments, (i) $X^2$ and $X^{2'}$ are —CH= or (ii) $X^2$ is —CH= and $X^{2'}$ is —N= or $X^{2'}$ is —CH= and $X^2$ is —N= or (iii) or $X^2$ and $X^{2'}$ are —N=.

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other H, $C_{1-6}$ alkyl, hal, (e.g., H, —$CH_3$, F, and Cl) and/or $R^3$ and $R^{3'}$ are independently of each other H, $C_{1-6}$ alkyl, hal, —$CF_3$, —$OCF_3$.

In some embodiments, —(NR⁶R⁷), —(CR⁶R⁷) are selected from

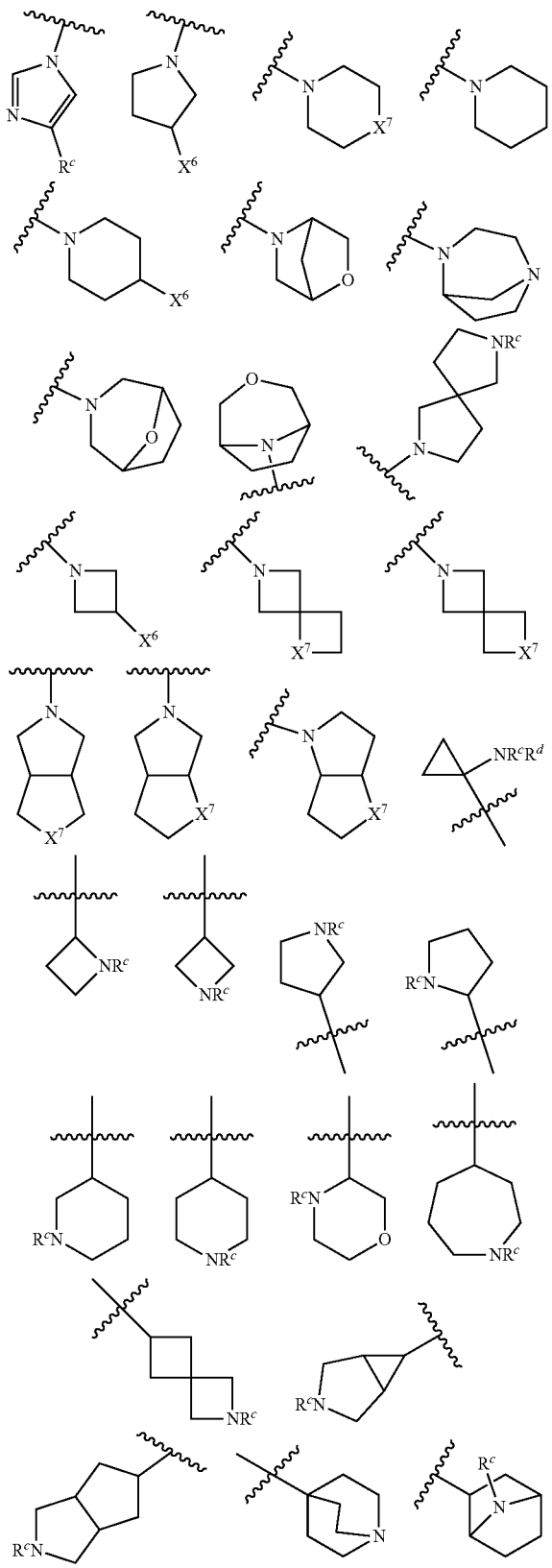

wherein $R^c$ is H, $C_{1-4}$ alkyl, oxetane, and $R^d$ is H, $C_{1-4}$ alkyl; $X^4$ is H, —CH₃, —OH, —OCH₃, —OCF₃, —N(CH₃)₂, F Cl; and $X^5$ is —O—, —NH— or —N(CH₃)—, —SO₂.

In some embodiments, the compound of formula I is not any of

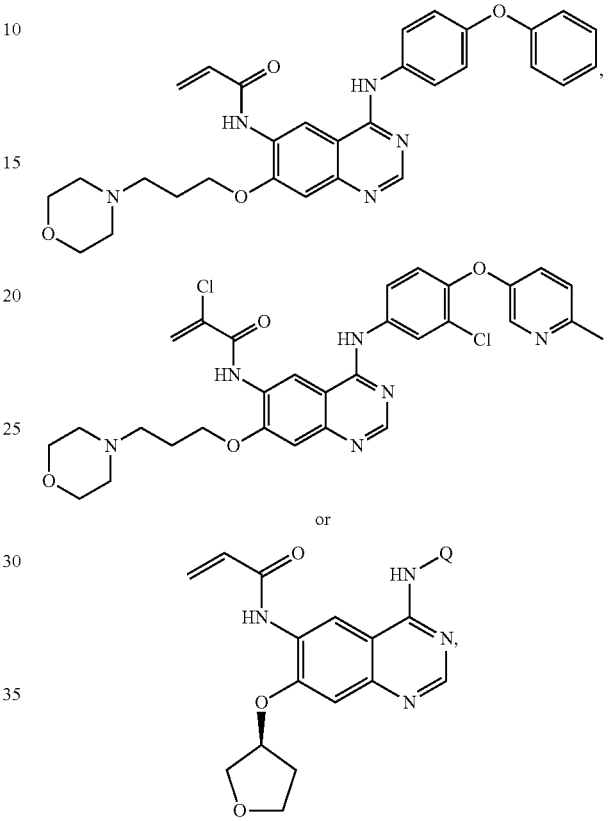

wherein Q is

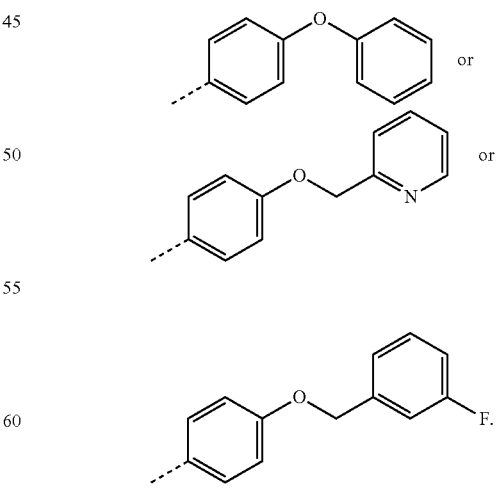

In some embodiments, the compound of the present disclosure or pharmaceutically acceptable salts or stereoisomers thereof has formula II or III

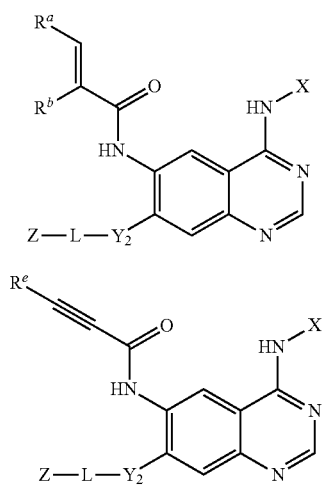

II

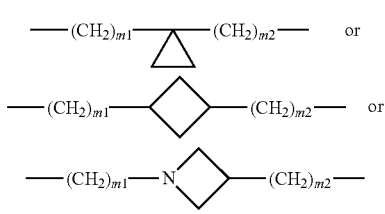

III wherein L is a covalent bond, straight chain or branched $C_{1-4}$ alkyl or

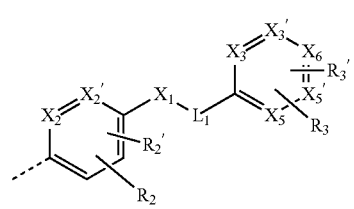

wherein m1, m2 are independently of each other 0, 1, 2, 3, or 4;

$Y^2$ is a covalent bond, —O—, —NH—, —NCH$_3$—, —C≡C—;

Z is —(NR$^4$R$^5$), wherein R$^4$ and R$^5$ are independently of each other H, $C_{1-6}$ alkyl, cyclopropyl, cylobutyl, 3-6-membered heterocycloalkyl, or —(NR$^6$R$^7$), —(CHR$^6$R$^7$), wherein R$^6$ and R$^7$ form together with the atom to which they are attached to 3-6-membered heteroaryl or 3-9-membered heterocycloalkyl, wherein the 3-9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl;

R$^a$, R$^b$ are independently of each other H, hal, or —CH$_2$—O—CH$_3$ (e.g. H) and R$_e$ is H or methyl; and X is a group of formula (ii)a (ii)a wherein X$^1$ is —O—, —CH$_2$—, —NH—, —S—; L$^1$ is a covalent bond or $C_{1-3}$alkyl, which is unsubstituted or substituted with —CH$_3$, hal; X$^2$, X$^{2'}$, X$^3$, X$^{3'}$, X$^5$, X$^{5'}$, X$^6$ are independently of each other —N═, —CH═; R$^2$, R$^{2'}$, R$^3$, R$^{3'}$ are independently of each other H, $C_{1-6}$ alkyl, hal, —CF$_3$, —OCF$_3$.

In some embodiments substituent Z-L-Y$_2$ contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if Y$_2$ is not N(H) or (NMe) or L does not contain a nitrogen atom.

In some embodiments R$^a$ and R$^b$ are hydrogen.

In some embodiments, the compound of formula II is not any of

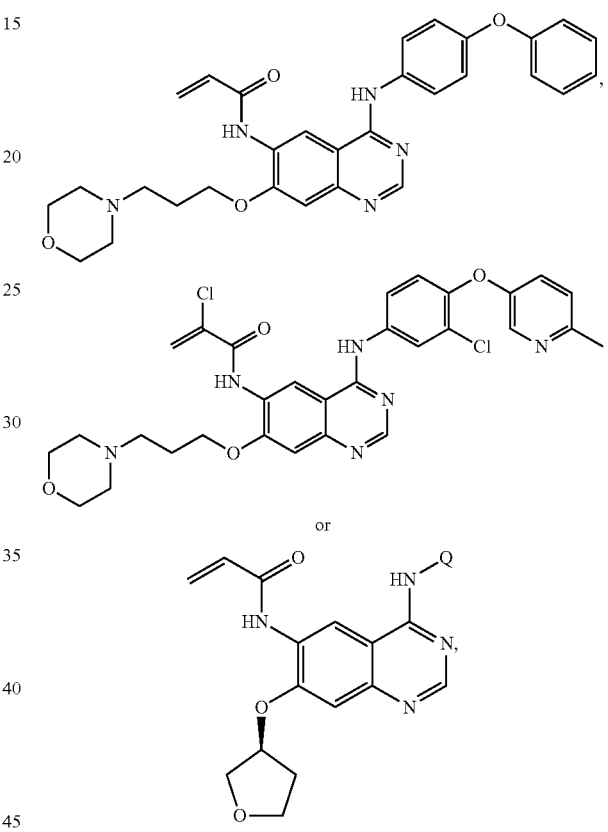

or wherein Q is

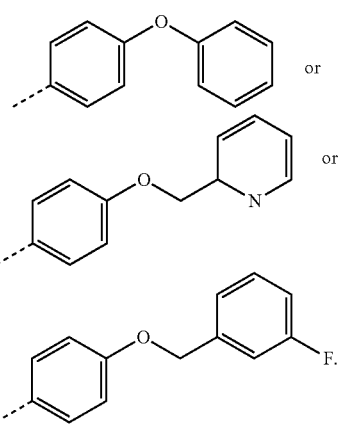

In some embodiments, the compound of the present disclosure or pharmaceutically acceptable salts or stereoisomers thereof has formula IV

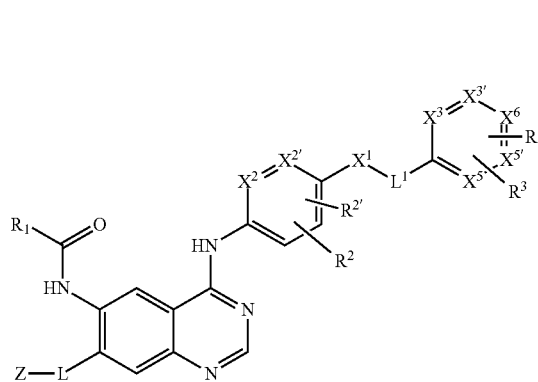

IV wherein $X^2$, $X^{2'}$, $X^3$, $X^{3'}$, $X^5$, $X^{5'}$, $X^6$ are independently of each other —N═, —CH═;

$X^1$ is —O—, —CH$_2$—, —NH—;

$L^1$ is a covalent bond or straight chain or branched $C_{1-3}$ alkyl, which is unsubstituted or substituted with hal, $R^1$ is —CR$_b$═CHR$_a$, —C≡CH or —C≡C—CH$_3$; wherein $R^a$, $R^b$ are independently of each other H, hal, —CH$_2$—O—CH$_3$; and $R^2$, $R^{2'}$, $R^3$, $R^{3'}$ are independently of each other H, $C_{1-6}$ alkyl, hal, —CF$_3$, —OCF$_3$;

L is a covalent bond, straight chain or branched $C_{1-4}$ alkyl or

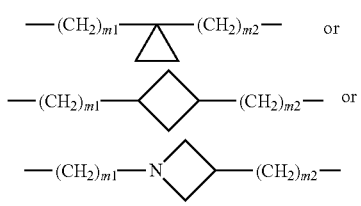

wherein m1, m2 are independently of each other 0, 1, 2, or 4;

Z is —(NR$^6$R$^7$)— or —(CHR$^6$R$^7$)—, wherein R$^6$ and R$^7$ form together with the atom to which they are attached to 3-6-membered heteroaryl or 3-9-membered heterocycloalkyl, wherein the 3-9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments substituent Z-L contains at least one nitrogen atom. Thus, the 3-6-membered heteroaryl or 3-9-membered heterocycloalkyl formed by R$^6$ and R$^7$ of (CHR$_6$R$_7$) includes a nitrogen atom if Y$_2$ is not N(H) or (NMe) or L does not contain a nitrogen atom.

In some embodiments R$^a$ and R$^b$ are hydrogen.

In some embodiments, the compound of the present disclosure or pharmaceutically acceptable salts or stereoisomers thereof has formula VII

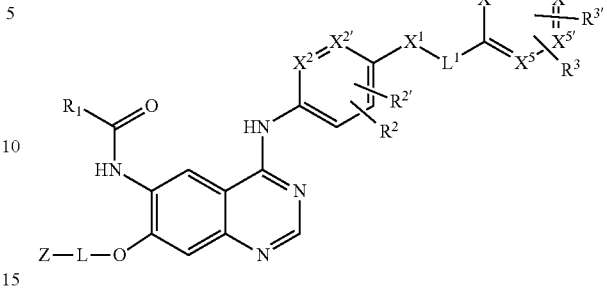

VII wherein $X^2$, $X^{2'}$, $X^3$, $X^{3'}$, $X^5$, $X^{5'}$, $X^6$ are independently of each other —N═, —CH═;

$X^1$ is —O—, —CH$_2$—, —NH—, —S—;

$L^1$ is a covalent bond or straight chain or branched $C_{1-3}$ alkyl, which is unsubstituted or substituted with hal, $R^1$ is —CR$_b$═CHR$_a$, —C≡CH or —C≡C—CH$_3$; wherein $R^a$, $R^b$ are independently of each other H, hal, —CH$_2$—O—CH$_3$;

$R^2$, $R^{2'}$, $R^3$, $R^{3'}$ are independently of each other H, $C_{1-6}$ alkyl, hal, —CF$_3$, —OCF$_3$;

L is a covalent bond, straight chain or branched $C_{1-4}$ alkyl or

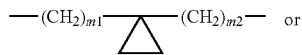

wherein m1, m2 are independently of each other 0, 1, 2, or 4;

Z is —(NR$^4$R$^5$), wherein R$^4$ and R$^5$ are independently of each other H, $C_{1-6}$ alkyl, cyclopropyl, cylobutyl, 3-6-membered heterocycloalkyl, or —(NR$^6$R$^7$), —(CHR$^6$R$^7$), wherein R$^6$ and R$^7$ form together with the atom to which they are attached to 3-6-membered heteroaryl or 3-9-membered heterocycloalkyl, wherein the 3-9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments substituent Z-L contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if Y$_2$ is not N(H) or (NMe) or L does not contain a nitrogen atom.

In some embodiments R$^a$ and R$^b$ are hydrogen.

In some embodiments, the compound of formula VII is not any of

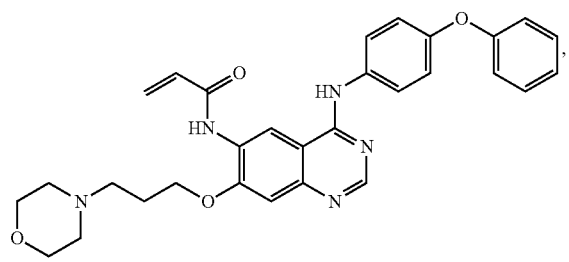

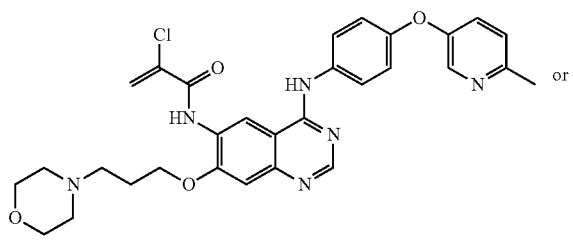

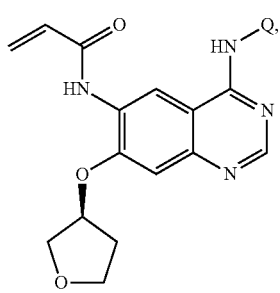

wherein Q is

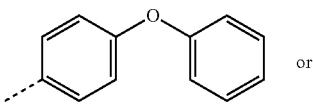

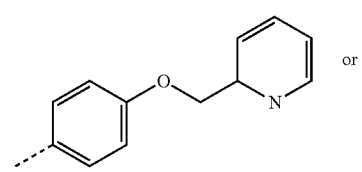

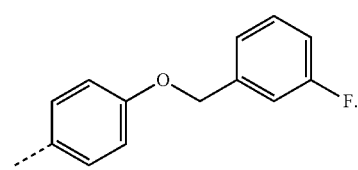

In some embodiments, the compound of the present disclosure or pharmaceutically acceptable salts or stereoisomers thereof has formula X

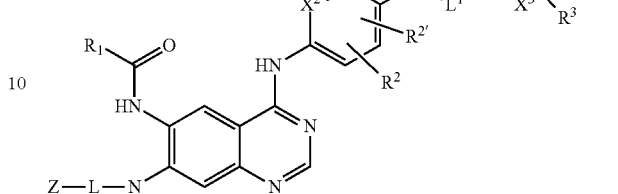

wherein $X^2$, $X^{2'}$, $X^3$, $X^{3'}$, $X^5$, $X^{5'}$, $X^6$ are independently of each other —N=, —CH=;

$X^1$ is —O—, —CH$_2$—, —NH—, —S—;

$L^1$ is a covalent bond or straight chain or branched $C_{1-3}$alkyl, which is unsubstituted or substituted with hal, $R^1$ is —CR$_b$=CHR$_a$, —C≡CH or —C≡C—CH$_3$; wherein $R^a$, $R^b$ are independently of each other H, hal, —CH$_2$—O—CH$_3$;

$R^2$, $R^{2'}$, $R^3$, $R^{3'}$ are independently of each other H, $C_{1-6}$ alkyl, hal, —CF$_3$, —OCF$_3$;

L is a covalent bond, straight chain or branched $C_{1-4}$ alkyl or

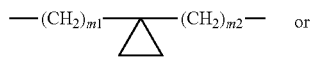

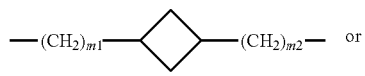

wherein m1, m2 are independently of each other 0, 1, 2, or 4;

R''' is H or —CH$_3$;

Z is —(NR$^4$R$^5$), wherein R$^4$ and R$^5$ are independently of each other H, $C_{1-6}$ alkyl, cyclopropyl, cylobutyl, 3-6-membered heterocycloalkyl, or —(NR$^6$R$^7$), —(CHR$^6$R$^7$), wherein R$^6$ and R$^7$ form together with the atom to which they are attached to 3-6-membered heteroaryl or 3-9-membered heterocycloalkyl, wherein the 3-9-membered heterocycloalkyl is a monocycle or a fused, bridged or spirobicycle or a combination thereof, and is unsubstituted or substituted with $C_{1-4}$ alkyl, hal, —OR', —NR'R'', wherein R', R'' are independently of each other H or -$C_{1-4}$ alkyl.

In some embodiments $R^a$ and $R^b$ are hydrogen.

In some embodiments, the compound of the present disclosure or pharmaceutically acceptable salts or stereoisomers thereof has formula XIII

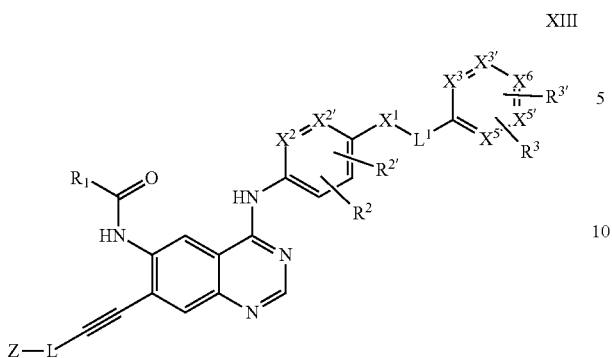

wherein
$X^2$, $X^{2'}$, $X^3$, $X^{3'}$, $X^5$, $X^{5'}$, $X^6$ are independently of each other —N—, —CH—;
$X^1$ is —O—, —CH$_2$—, —NH—, —S—;
$L^1$ is a covalent bond or straight chain or branched $C_{1-3}$ alkyl, which is unsubstituted or substituted with hal,
$R^1$ is —CH=CH$_2$, —C≡CH or —C≡C—CH$_3$; and
$R^2$, $R^{2'}$, $R^3$, $R^{3'}$ are independently of each other H, $C_{1-6}$ alkyl, hal, —CF$_3$, —OCF$_3$;
L is a covalent bond, straight chain or branched $C_{1-4}$ alkyl or

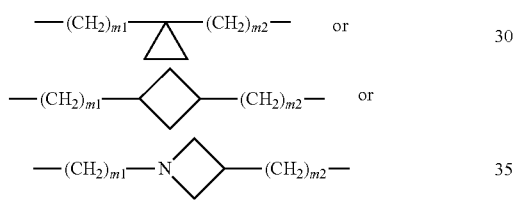

wherein m1, m2 are independently of each other 0, 1, 2, 3, or 4;
Z is —(NR$^4$R$^5$), wherein R$^4$ and R$^5$ are independently of each other H, $C_{1-6}$ alkyl, or —(NR$^6$R$^7$)— or —(CHR$^6$R$^7$)—, wherein R$^6$ and R$^7$ form together with the atom to which they are attached to 3-6-membered heteroaryl, or 3-9-membered heterocycloalkyl, wherein the 3-9-membered heterocycloalkyl is a monocycle, fused bicycle, spirobicycle or a combination thereof, or bridged bicycle, which is unsubstituted or substituted with $C_{1-4}$ alkyl, hal, —OR', —NR'R", wherein R', R" are independently of each other H or -$C_{1-4}$ alkyl.

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if $Y_2$ is not N(H) or (NMe) or L does not contain a nitrogen atom.

In some embodiments $R^a$ and $R^b$ are hydrogen.

In some embodiments, —(NR$^6$R$^7$), —(CHR$^6$R$^7$) are selected from

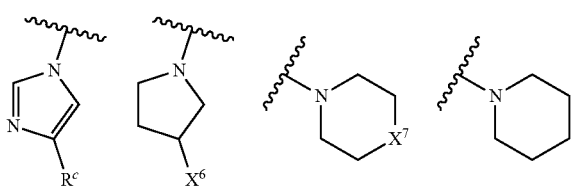

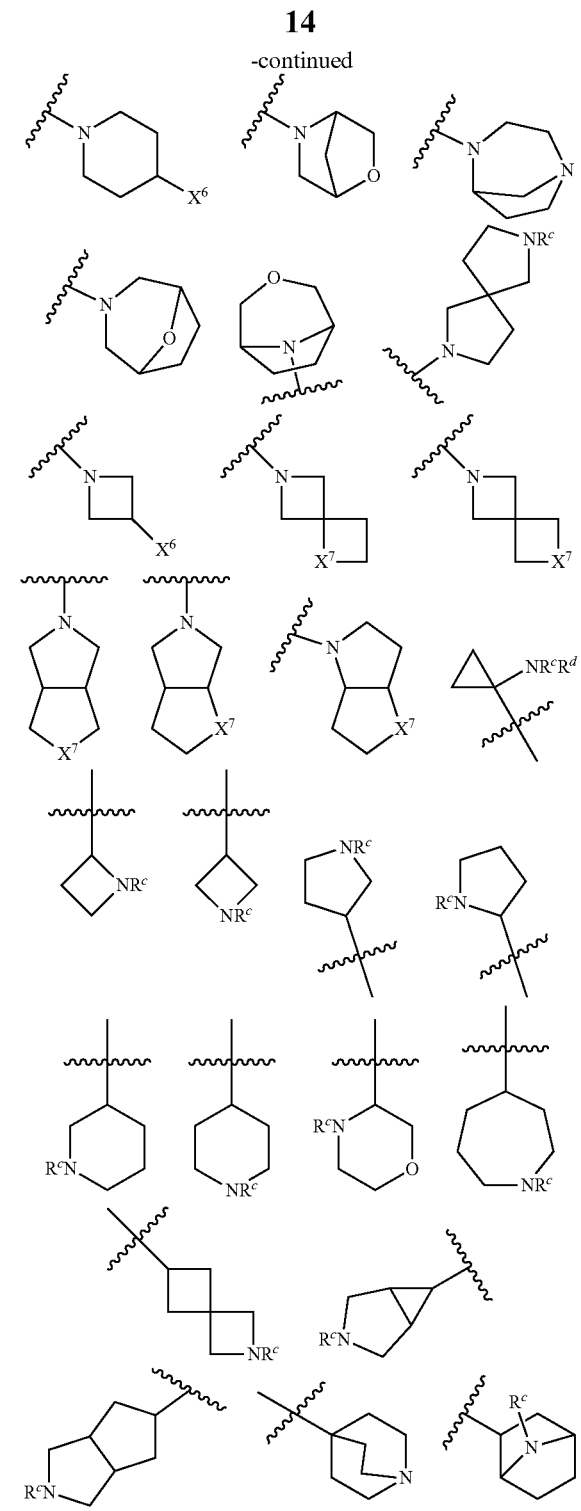

wherein $R^c$ is H, $C_{1-4}$ alkyl, oxetane; $X^6$ is H, —CH$_3$, —OH, —OCH$_3$, —OCF$_3$, —N(CH$_3$)$_2$, F, Cl; $X^7$ is —O—, —NH— or —N(CH$_3$)—, —SO$_2$; and $R^d$ is H, $C_{1-4}$ alkyl.

The disclosure provides a composition comprising a compound of the disclosure or pharmaceutically acceptable salts or stereoisomers thereof. In some embodiments, the composition further comprises a pharmaceutically acceptable carrier. In some embodiments, the composition further comprises a second therapeutically active agent. In some embodiments, the second therapeutically active agent comprises a non-Type I inhibitor. In some embodiments, the non-Type I inhibitor comprises a small molecule Type II inhibitor.

The disclosure provides a composition of the disclosure for use in the treatment of cancer.

The disclosure provides a use of a composition of the disclosure for treating cancer, comprising administering to a subject a therapeutically-effective amount of the composition.

The disclosure provides a method of treating cancer in a subject, comprising administering to a subject a therapeutically effective amount of a composition of the disclosure.

In some aspects, the present disclosure is directed to a method of inhibiting an oncogenic variant of an ErbB receptor (e.g., an oncogenic variant of an EGFR), comprising administering the subject in need thereof a therapeutically effective amount of a compound described herein.

In some aspects, the present disclosure is directed to a method of inhibiting an oncogenic variant of an ErbB receptor (e.g., an oncogenic variant of an EGFR), comprising administering the subject in need thereof a composition described herein.

In some aspects, the present disclosure is directed to a method of preventing or treating cancer, comprising administering the subject in need thereof a therapeutically effective amount of a compound described herein.

In some aspects, the present disclosure is directed to a method of preventing or treating cancer, comprising administering the subject in need thereof a composition described herein.

In some aspects, the present disclosure is directed to a method of preventing or treating cancer, comprising: i) identifying a subject candidate as the subject in need of the treatment when that at least one oncogenic variant of an ErbB receptor described herein is present in the subject; and ii) administering the subject in need of the treatment a therapeutically effective amount of a compound described herein.

In some aspects, the present disclosure is directed to a method of preventing or treating cancer, comprising: i) identifying a subject candidate as the subject in need of the treatment when that at least one oncogenic variant of an ErbB receptor described herein is present in the subject; and ii) administering the subject in need of the treatment a composition described herein.

In some aspects, the present disclosure is directed to a method of preventing or treating cancer, comprising: i) identifying a subject candidate as the subject in need of the treatment when that at least one oncogenic variant of an ErbB receptor described herein is present in a biological sample from the subject; and ii) administering the subject in need of the treatment a therapeutically effective amount of a compound described herein.

In some aspects, the present disclosure is directed to a method of preventing or treating cancer, comprising: i) identifying a subject candidate as the subject in need of the treatment when that at least one oncogenic variant of an ErbB receptor described herein is present in a biological sample from the subject; and ii) administering the subject in need of the treatment a composition described herein.

In some aspects, the present disclosure is directed to a method of preventing or treating cancer, comprising administering the subject in need thereof a therapeutically effective amount of a compound described herein when that at least one oncogenic variant of an ErbB receptor described herein is identified as being present in the subject.

In some aspects, the present disclosure is directed to a method of preventing or treating cancer, comprising administering the subject in need thereof a compound described herein when that at least one oncogenic variant of an ErbB receptor described herein is identified as being present in the subject.

In some aspects, the present disclosure is directed to a method of preventing or treating cancer, comprising administering the subject in need thereof a therapeutically effective amount of a compound described herein when that at least one oncogenic variant of an ErbB receptor described herein is identified as being present in a biological sample from the subject.

In some aspects, the present disclosure is directed to a method of preventing or treating cancer, comprising administering the subject in need thereof a composition described herein when that at least one oncogenic variant of an ErbB receptor described herein is identified as being present in a biological sample from the subject.

In some aspects, the present disclosure is directed to a compound described herein for use in the inhibition of an oncogenic variant of an ErbB receptor (e.g., an oncogenic variant of an EGFR).

In some aspects, the present disclosure is directed to a compound described herein for use in the prevention or treatment of cancer.

In some aspects, the present disclosure is directed to a composition described herein for use in the inhibition of an oncogenic variant of an ErbB receptor (e.g., an oncogenic variant of an EGFR).

In some aspects, the present disclosure is directed to a composition described herein for use in the prevention or treatment of cancer.

In some aspects, the present disclosure is directed to a compound described herein for use in the prevention or treatment of cancer in a subject, wherein at least one oncogenic variant of an ErbB receptor described herein is present in the subject.

In some aspects, the present disclosure is directed to a composition described herein for use in the prevention or treatment of cancer in a subject, wherein at least one oncogenic variant of an ErbB receptor described herein is present in the subject.

In some aspects, the present disclosure is directed to a compound described herein for use in the prevention or treatment of cancer in a subject, wherein at least one oncogenic variant of an ErbB receptor described herein is present in a biological sample from the subject.

In some aspects, the present disclosure is directed to a composition described herein for use in the prevention or treatment of cancer in a subject, wherein at least one oncogenic variant of an ErbB receptor described herein is present in a biological sample from the subject.

In some aspects, the present disclosure is directed to use of a compound described herein in the manufacture of a medicament for inhibiting an oncogenic variant of an ErbB receptor (e.g., an oncogenic variant of an EGFR).

In some aspects, the present disclosure is directed to use of a compound described herein in the manufacture of a medicament for preventing or treating cancer.

The disclosure provides a method of treating cancer in a subject, comprising administering to a subject a therapeutically effective amount of a composition of the disclosure, wherein the cancer is characterized by expression of an oncogenic variant of an epidermal growth factor receptor (EGFR). In some embodiments, the cancer, a tumor or a cell thereof expresses the oncogenic variant of an EGFR. In some embodiments, the oncogenic variant of EGFR is an allosteric variant of EGFR.

In some embodiments of the methods of treating cancer of the disclosure, including those wherein the cancer is characterized by expression of an oncogenic variant and the oncogenic variant of EGFR is an allosteric variant of EGFR, the oncogenic variant of an EGFR comprises an EGFR variant III (EGFR-Viii) mutation.

In some embodiments of the methods of treating cancer of the disclosure, including those wherein the cancer is characterized by expression of an oncogenic variant and the oncogenic variant of EGFR is an allosteric variant of EGFR, the oncogenic variant of an EGFR comprises a substitution of a valine (V) for an alanine (A) at position 289 of SEQ ID NO: 1.

In some embodiments of the methods of treating cancer of the disclosure, including those wherein the cancer is characterized by expression of an oncogenic variant and the oncogenic variant of EGFR is an allosteric variant of EGFR, the oncogenic variant of an EGFR comprises a modification of a structure of the EGFR, wherein the oncogenic variant of an EGFR is a capable of forming a covalently linked dimer, wherein the covalently linked dimer is constitutively active and wherein the covalently linked dimer enhances an activity of EGFR when contacted to a Type I ErbB inhibitor. In some embodiments, the modification of the structure of the EGFR comprises a modification of one or more of a nucleic acid sequence, an amino acid sequence, a secondary structure, a tertiary structure, and a quaternary structure. In some embodiments, the oncogenic variant comprises a mutation, a splicing event, a post-translational process, a conformational change or any combination thereof. In some embodiments, the modification of the structure of the EGFR occurs within a first cysteine rich (CR1) and/or second cysteine rich (CR2) region of EGFR. In some embodiments, the first cysteine rich (CR1) and/or second cysteine rich (CR2) region of EGFR comprises amino acid residues T211-R334 and/or C526-S645 of SEQ ID NO: 1, respectively. In some embodiments, the oncogenic variant of an EGFR generates a physical barrier to formation of a disulfide bond within the CR1 and/or the CR2 region. In some embodiments, the oncogenic variant of an EGFR removes a physical barrier to formation of a disulfide bond within the CR1 and/or the CR2 region. In some embodiments, the oncogenic variant of an EGFR comprises one or more free or unpaired Cysteine (C) residues located at a dimer interface of the EGFR. In some embodiments, the oncogenic variant of an EGFR comprises one or more free or unpaired Cysteine (C) residues at a site selected from the group consisting of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1. In some embodiments, the modification occurs within 10 angstroms or less of an intramolecular disulfide bond at a site selected from the group consisting of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1.

In some embodiments of the methods of treating cancer of the disclosure, including those wherein the cancer is characterized by expression of an oncogenic variant and the oncogenic variant of EGFR is mutation of EGFR, a nucleotide sequence encoding the oncogenic variant of an EGFR comprises a deletion or a substitution of a sequence encoding exon 19 or a portion thereof. In some embodiments, the deletion or the substitution comprises one or more amino acids that encode an adenosine triphosphate (ATP) binding site. In some embodiments, the ATP binding site comprises amino acids E746 to A750 of SEQ ID NO: 1. In some embodiments, the ATP binding site or the deletion or substitution thereof comprises K858 of SEQ ID NO: 1. In some embodiments, the deletion comprises K858 of SEQ ID NO: 1. In some embodiments, an arginine (R) is substituted for the lysine (K) at position 858 (K858R) of SEQ ID NO: 1. In some embodiments, an arginine (R) is substituted for the leucine (L) at position 858 (L858R) of SEQ ID NO: 1.

In some embodiments of the methods of treating cancer of the disclosure, including those wherein the cancer is characterized by expression of an oncogenic variant and the oncogenic variant of EGFR is an allosteric variant of EGFR, a nucleotide sequence encoding the oncogenic variant of an EGFR comprises an insertion within a sequence encoding exon 20 or a portion thereof. In some embodiments, the sequence encoding exon 20 or a portion thereof comprises a sequence encoding KEILDEAYVMASVDNPHVCAR (SEQ ID NO: 7). In some embodiments, the sequence encoding exon 20 or a portion thereof comprises a sequence encoding a C-helix, a terminal end of the C-helix or a loop following the C-helix. In some embodiments, the insertion comprises the amino acid sequence of ASV, SVD, NTH, or FQEA. In some embodiments, the sequence encoding exon 20 or a portion thereof comprises one or more of (a) an insertion of the amino acid sequence ASV between positions V769 and D770 of SEQ ID NO: 1; (b) an insertion of the amino acid sequence SVD between positions D770 and N771 of SEQ ID NO: 1; (c) an insertion of the amino acid sequence NPH between positions H773 and V774 of SEQ ID NO: 1; (d) an insertion of the amino acid sequence FQEA between positions A763 and Y764 of SEQ ID NO: 1; (e) an insertion of the amino acid sequence PH between positions H773 and V774 of SEQ ID NO: 1; (f) an insertion of the amino acid G between positions D770 and N771 of SEQ ID NO: 1; (g) an insertion of the amino acid H between positions H773 and V774 of SEQ ID NO: 1; (h) an insertion of the amino acid sequence HV between positions V774 and C775 of SEQ ID NO: 1; (i) an insertion of the amino acid sequence AH between positions H773 and V774 of SEQ ID NO: 1; (j) an insertion of the amino acid sequence SVA between positions A767 and S768 of SEQ ID NO: 1; (k) a substitution of the amino acid sequence GYN for the DN between positions 770 and 771 of SEQ ID NO: 1; (l) an insertion of the amino acid H between positions N771 and P772 of SEQ ID NO: 1; (m) an insertion of the amino acid Y between positions H773 and V774 of SEQ ID NO: 1; (n) an insertion of the amino acid sequence PHVC between positions C775 and R776 of SEQ ID NO: 1; (o) a substitution of the amino acid sequence YNPY for the H at position 773 of SEQ ID NO: 1; (p) an insertion of the amino acid sequence DNP between positions P772 and H773 of SEQ ID NO: 1; (q) an insertion of the amino acid sequence VDS between positions S768 and V769 of SEQ ID NO: 1; (r) an insertion of the amino acid H between positions D770 and N771 of SEQ ID NO: 1; (s) an insertion of the amino acid N between positions N771 and P772 of SEQ ID NO: 1; (t) an insertion of the amino acid sequence PNP between positions P772 and H773 of SEQ ID NO: 1; (u) a substitution of the amino acid sequence GSVDN for the DN between positions 770 and 771 of SEQ ID NO: 1; (v) a substitution of the amino acid sequence GYP for the NP between positions 771 and 772 of SEQ ID NO: 1; (w) an insertion of the amino acid G between positions N771 and P772 of SEQ ID NO: 1; (x) an insertion of the amino acid sequence GNP between positions P772 and H773 of SEQ ID NO: 1; (y) an insertion of the amino acid sequence GSV between positions V769 and D770 of SEQ ID NO: 1; (z) a substitution of the amino acid sequence GNPHVC for the VC between positions 774 and 775 of SEQ ID NO: 1; (aa) an insertion of the amino acid sequence LQEA between positions A763 and Y764 of SEQ ID NO: 1; (bb) an insertion of the amino acid sequence GL between positions D770 and N771 of SEQ ID NO: 1; (cc) an insertion of the amino acid Y between positions D770 and N771 of SEQ ID NO: 1; (dd) an insertion of the amino acid sequence NPY between positions H773 and V774 of SEQ ID NO: 1; (ee) an insertion of the amino acid sequence TH between positions H773 and V774 of SEQ ID NO: 1; (ff) a substitution of the amino acid sequence KGP for the NP between positions 771 and 772 of SEQ ID NO: 1; (gg) a substitution of the amino acid sequence SVDNP for the NP between positions 771 and 772 of SEQ ID NO: 1; (hh) an insertion of the amino acid sequence NN between positions N771 and P772 of SEQ ID NO: 1; (ii) an insertion of the amino acid T between positions N771 and P772 of SEQ ID NO: 1; and (jj) a substitution of the amino acid sequence STLASV for he SV between positions 768 and 769 of SEQ ID NO: 1.

In some embodiments of the methods of treating cancer of the disclosure, including those wherein the cancer is characterized by expression of an oncogenic variant and the oncogenic variant of EGFR is an allosteric variant of EGFR, the oncogenic variant of an EGFR comprises EGFR-Vii, EGFR-Vvi, EGFR-R222C, EGFR-R252C, EGFR-R252P, EGFR-R256Y, EGFR-T263P, EGFR-Y270C, EGFR-A289T, EGFR-A289V, EGFR-A289D, EGFR-H304Y, EGFR-G331R, EGFR-P5965, EGFR-P596L, EGFR-P596R, EGFR-G598V, EGFR-G598A, EGFR-G614D, EGFR-C620Y, EGFR-C614W, EGFR-C628F, EGFR-C628Y, EGFR-C636Y, EGFR-G645C, EGFR-Δ660, EGFR-Δ768 or any combination thereof.

The disclosure provides a method of treating cancer in a subject, comprising administering to a subject a therapeutically effective amount of a composition of the disclosure, wherein the cancer is characterized by expression of one or more of: (a) a wild type human epidermal growth factor receptor 2 (HER2) receptor or (b) an oncogenic variant of a HER-2 receptor. In some embodiments, the cancer, a tumor or a cell thereof expresses one or more of: (a) a wild type human epidermal growth factor receptor 2 (HER2) receptor or (b) an oncogenic variant of a HER-2 receptor. In some embodiments of the methods of treating cancer of the disclosure, including those wherein cancer is characterized by characterized by expression of a wild type HER2 receptor, the wild type HER2 receptor comprises the amino acid sequence of SEQ ID NO: 2, 3, 4, 5, or 6.

In some embodiments of the methods of treating cancer of the disclosure, including those wherein cancer is characterized by expression of an oncogenic variant of a HER2 receptor, the oncogenic variant of the HER2 receptor is an allosteric variant of the HER2 receptor.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, the oncogenic variant of a HER2 receptor comprises a substitution of a phenylalanine (F) for a serine (S) at position 310 of SEQ ID NO: 2 or 5.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, the oncogenic variant of a HER2 receptor comprises a substitution of a tyrosine (Y) for a serine (S) at position 310 of SEQ ID NO: 2 or 5.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, the oncogenic variant of a HER2 receptor comprises a substitution of a glutamine (Q) for an arginine (R) at position 678 of SEQ ID NO: 2 or 5.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, the oncogenic variant of a HER2 receptor comprises a substitution of a leucine (L) for a valine (V) at position 777 of SEQ ID NO: 2 or 5.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, the oncogenic variant of a HER2 receptor comprises a substitution of a methionine (M) for a valine (V) at position 777 of SEQ ID NO: 2 or 5.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, the oncogenic variant of a HER2 receptor comprises a substitution of an isoleucine (I) for a valine (V) at position 842 of SEQ ID NO: 2 or 5.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, the oncogenic variant of a HER2 receptor comprises a substitution of an alanine (A) for a leucine (L) at position 755 of SEQ ID NO: 2 or 5.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, the oncogenic variant of a HER2 receptor comprises a substitution of a proline (P) for a leucine (L) at position 755 of SEQ ID NO: 2 or 5.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, the oncogenic variant of a HER2 receptor comprises a substitution of a serine (S) for a leucine (L) at position 755 of SEQ ID NO: 2 or 5.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, a nucleotide sequence encoding the oncogenic variant of a HER2 receptor comprises an insertion within a sequence encoding exon 20 or a portion thereof. In some embodiments, the sequence encoding exon 20 or a portion thereof comprises a sequence encoding KEILDEAY-VMAGVGSPYVSR (SEQ ID NO: 8). In some embodiments, the sequence encoding exon 20 or a portion thereof comprises a sequence encoding a C-helix, a terminal end of the C-helix or a loop following the C-helix. In some embodiments, the insertion comprises the amino acid sequence of GSP or YVMA. In some embodiments, the sequence encoding exon 20 or a portion thereof comprises one or more of: (a) an insertion of the amino acid sequence YVMA between positions A775 and G776 of SEQ ID NO: 2; (b) an insertion of the amino acid sequence GSP between positions P780 and Y781 of SEQ ID NO: 2; (c) an insertion of the amino acid sequence YVMA between positions A771 and Y772 of SEQ ID NO: 2; (d) an insertion of the amino acid sequence YVMA between positions A775 and G776 of SEQ ID NO: 2; (e) an insertion of the amino acid V between positions V777 and G778 of SEQ ID NO: 2; (f) an insertion of the amino acid V between positions V777 and G778 of SEQ ID NO: 2; (g) a substitution of the amino acid sequence AVGCV for the GV between positions 776 and 777 of SEQ ID NO: 2; (h) a substitution of the amino acid sequence LC for the G between position 776 of SEQ ID NO: 2; (i) a substitution of the amino acid sequence LCV for the G between position 776 of SEQ ID NO: 2; (j) an insertion of the amino acid sequence GSP between positions V777 and G778 of SEQ ID NO: 2; (k) a substitution of the amino acid sequence PS for the LRE between positions 755 and 757 of SEQ ID NO: 2; (l) a substitution of the amino acid sequence CPGSP for the SP between positions 779 and 780 of SEQ ID NO: 2; (m) an insertion of the amino acid C between positions V777 and G778 of SEQ ID NO: 2; (n) a substitution of the amino acid sequence VVMA for the AG between positions 775 and 776 of SEQ ID NO: 2; (o) a substitution of the amino acid sequence VV for the G at position 776 of SEQ ID NO: 2; (p) a substitution of the amino acid sequence AVCV for the GV between positions 776 and 777 of SEQ ID NO: 2; (q) a substitution of the amino acid sequence VCV for the GV between positions 776 and 777 of SEQ ID NO: 2; (r) an insertion of the amino acid G between positions G778 and S779 of SEQ ID NO: 2; (s) a substitution of the amino acid sequence PK for the LRE between positions 755 and 757 of SEQ ID NO: 2; (t) an insertion of the amino acid V between positions A775 and G776 of SEQ ID NO: 2; (u) an insertion of the amino acid sequence YAMA between positions A775 and G776 of SEQ ID NO: 2; (v) a substitution of the amino acid sequence CV for the G at position 776 of SEQ ID NO: 2; (w) a substitution of the amino acid sequence AVCGG for the GVG between positions 776 and 778 of SEQ ID NO: 2; (x) a substitution of the amino acid sequence CVCG for the GVG between positions 776 and 778 of SEQ ID NO: 2; (y) a substitution of the amino acid sequence VVVG for the GVG between positions 776 and 778 of SEQ ID NO: 2; (z) a substitution of the amino acid sequence SVGG for the GVGS between positions 776 and 779 of SEQ ID NO: 2; (aa) a substitution of the amino acid sequence VVGES for the GVGS between positions 776 and 779 of SEQ ID NO: 2; (bb) a substitution of the amino acid sequence AVGSGV for the GV between positions 776 and 777 of SEQ ID NO: 2; (cc) a substitution of the amino acid sequence CVC for the GV between positions 776 and 777 of SEQ ID NO: 2; (dd) a substitution of the amino acid sequence HVC for the GV between positions 776 and 777 of SEQ ID NO: 2; (ee) a substitution of the amino acid sequence VAAGV for the GV between positions 776 and 777 of SEQ ID NO: 2; (ff) a substitution of the amino acid sequence VAGV for the GV between positions 776 and 777 of SEQ ID NO: 2; (gg) a substitution of the amino acid sequence VVV for the GV between positions 776 and 777 of SEQ ID NO: 2; (hh) an insertion of the amino acid sequence FPG between positions G778 and S779 of SEQ ID NO: 2; (ii) an insertion of the amino acid sequence GS between positions S779 and P780 of SEQ ID NO: 2; (jj) a substitution of the amino acid sequence VPS for the VLRE between positions 754 and 757 of SEQ ID NO: 2; (kk) an insertion of the amino acid E between positions V777 and G778 of SEQ ID NO: 2; (ll) an insertion of the amino acid sequence MAGV between positions V777 and G778 of SEQ ID NO: 2; (mm) an insertion of the amino acid S between positions V777 and G778 of SEQ ID NO: 2; (nn) an insertion of the amino acid sequence SCV between positions V777 and G778 of SEQ ID NO: 2; and (oo) an insertion of the amino acid sequence LMAY between positions Y772 and V773 of SEQ ID NO: 2.

In some embodiments of the methods of treating cancer of the disclosure, including those wherein cancer is characterized by expression of an oncogenic variant of a HER2 receptor and wherein the oncogenic variant of the HER2 receptor is an allosteric variant of the HER2 receptor, the oncogenic variant of a HER2 receptor comprises HER2-Δ16 (i.e. a HER2 variant that lacks Exon 16), HER2-C311R, HER2-S310F, p95-HER2-M611 (i.e. a HER2 variant wherein the amino acid encoding the protein begins at M611 of a wild type HER2 sequence, including SEQ ID NO: 2) or any combination thereof.

The disclosure provides a method of treating cancer in a subject, comprising administering to a subject a therapeutically effective amount of the composition of the disclosure, wherein the cancer is characterized by expression of an oncogenic variant of a HER-4 receptor. In some embodiments, the oncogenic variant of the HER-4 receptor is an allosteric variant of the HER4 receptor. In some embodiments, the oncogenic variant of a HER4 receptor comprises deletion of exon 16 (HER4-Δ16).

In some embodiments of the methods of treating cancer of the disclosure, the administration is systemic. In some embodiments, the administration oral. In some embodiments, the administration is intravenous.

In some embodiments of the methods of treating cancer of the disclosure, the administration is local. In some embodiments, the administration intratumoral, intraocular, intraosseus, intraspinal or intracerebroventricular.

In some embodiments of the methods of treating cancer of the disclosure, the subject or the cancer is insensitive or resistant to treatment with one or more of gefinitinib, erlotinib, afatinib, osimertinib, necitunumab, crizotinib, alectinib, ceritinib, dabrafenib, trametinib, afatinib, sapitinib, dacomitinib, canertinib, pelitinib, WZ4002, WZ8040, WZ3146, CO-1686 and AZD9291.

In some embodiments of the methods of treating cancer of the disclosure, the subject or the cancer has an adverse reaction to treatment with one or more of gefinitinib, erlotinib, afatinib, osimertinib, necitunumab, crizotinib. alectinib, ceritinib, dabrafenib, trametinib, afatinib, sapitinib, dacomitinib, canertinib, pelitinib, WZ4002, WZ8040, WZ3146, CO-1686 and AZD9291. In some embodiments, the adverse reaction is an activation of the oncogenic variant of an EGFR and wherein the oncogenic variant comprises a mutation in an extracellular domain of the receptor. In some embodiments, the adverse reaction is an activation of the oncogenic variant of a HER-2 Receptor and wherein the oncogenic variant comprises a mutation in an extracellular domain of the receptor.

In some embodiments of the methods of treating cancer of the disclosure, the cancer, a tumor or a cell thereof expresses an oncogenic variant of an EGFR, wherein the sequence encoding the oncogenic variant of the EGFR comprises a deletion of exon 20 or a portion thereof and wherein the cancer, the tumor or the cell thereof does not comprise a second oncogenic variation in a sequence other than exon 20 of EGFR. In some embodiments, the second oncogenic variation comprises a sequence encoding one or more of an EGFR kinase domain (KD), BRAF, NTRK, and KRAS.

In some embodiments of the methods of treating cancer of the disclosure, the cancer, a tumor or a cell thereof expresses an oncogenic variant of an EGFR, wherein the sequence encoding the oncogenic variant of the EGFR comprises a deletion of exon 20 or a portion thereof and wherein the cancer, the tumor or the cell thereof does not comprise a marker indicating responsiveness to immunotherapy.

In some embodiments of the methods of treating cancer of the disclosure, the cancer comprises a solid tumor. In some embodiments, the cancer is a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC) or any subtype thereof. In some embodiments, the cancer is a glioblastoma (GBM) or any subtype thereof. In some embodiments, the cancer is a breast cancer or any subtype thereof. In some embodiments, the cancer is a lung cancer or any subtype thereof.

In some embodiments of the methods of treating cancer of the disclosure, the therapeutically effective amount reduces a severity of a sign or symptom of the cancer. In some embodiments, the sign of the cancer comprises a tumor grade and wherein a reduction of the severity of the sign comprises a decrease of the tumor grade. In some embodiments, the sign of the cancer comprises a tumor metastasis and wherein a reduction of the severity of the sign comprises an elimination of the metastasis or a reduction in the rate or extent the metastasis. In some embodiments, the sign of the cancer comprises a tumor volume and wherein a reduction of the severity of the sign comprises an elimination of the tumor or a reduction in the volume. In some embodiments, the symptom of the cancer comprises pain and wherein a reduction of the severity of the sign comprises an elimination or a reduction in the pain.

In some embodiments of the methods of treating cancer of the disclosure, the therapeutically effective amount induces a period of remission.

In some embodiments of the methods of treating cancer of the disclosure, the therapeutically effective amount improves a prognosis of the subject.

In some embodiments of the methods of treating cancer of the disclosure, the subject is a participant or a candidate for participation in in a clinical trial or protocol thereof. In some embodiments, the subject is excluded from treatment with a Type I inhibitor. In some embodiments, the Type I inhibitor comprises gefinitinib, erlotinib, afatinib, osimertinib, necitunumab, crizotinib, alectinib, ceritinib, dabrafenib, trametinib, afatinib, sapitinib, dacomitinib, canertinib, pelitinib, W74002, W78040, WZ3146, CO-1686 or AZD9291.

In some embodiments of the methods of treating cancer of the disclosure, the method further comprises treating the subject with a Non-Type I inhibitor.

In some embodiments of the methods of treating cancer of the disclosure, the composition further comprises a Non-Type I inhibitor.

In some embodiments of the methods of treating cancer of the disclosure, the Non-Type I inhibitor comprises a Type II small molecule inhibitor. In some embodiments, the Type II small molecule inhibitor comprises neratinib, AST-1306, HKI-357, or lapatinib.

The disclosure provides a method of treating cancer in a subject comprising administering to the subject a Non-Type I inhibitor or a potent Type I inhibitor, wherein the subject comprises an allosteric variant of an EGFR or an allosteric variant of a HER2-receptor. In some embodiments, the Non-Type I ErbB inhibitor comprises a Type II small molecule inhibitor. In some embodiments, the Non-Type I ErbB inhibitor or potent Type I inhibitor comprises AMG-595, rindopepimut, sapitinib, afatinib, neratinib, AST-1306, HKI-357, or lapatinib. In some embodiments, the cancer comprises a solid cancer. In some embodiments, the cancer comprises a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC) or any subtype thereof. In some embodiments, the cancer comprises a glioblastoma (GBM) or any subtype thereof. In some embodiments, the cancer comprises a breast cancer or any subtype thereof. In some embodiments, the cancer comprises a lung cancer or any subtype thereof.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 19 is a table providing potency values for representative marketed ErbB inhibitors against EGFR and HER2 receptor variants. The data show that these cpds lack potency and selectivity against allo-HER2 mutations. These compounds also lack potency and selectivity against ErbB Exon 20 ins mutants and ErbB Exon 20 deletion mutants. Potency values reflect cellular anti-proliferative activity (IC50, nM). EGFR-WT=A431 (+H292); HER2-WT=BT474; H4006=EGFR19del; all mutants are BaF3 transformants. Green boxes depict greater than a 10-fold selective inhibition of oncogenic mutants versus WT-EGFR and red boxes depict less than a 10-fold selective inhibition of oncogenic mutants versus WT-EGFR.

FIG. 20 is a table providing potency values for representative marketed ErbB inhibitors against EGFR and HER2 receptor variants. The data show that these cpds lack potency and selectivity against ErbB Exon 20 ins mutants and ErbB Exon 20 deletion mutants. Potency values reflect cellular anti-proliferative activity (IC50, nM). EGFR-WT A431 (+H292); HER2-WT=BT474; H4006=EGFR19del; all mutants are BaF3 transformants. Green boxes depict greater than a 10-fold selective inhibition of oncogenic mutants versus WT-EGFR and red boxes depict less than a 10-fold selective inhibition of oncogenic mutants versus WT-EGFR.

DETAILED DESCRIPTION

Figure 1:
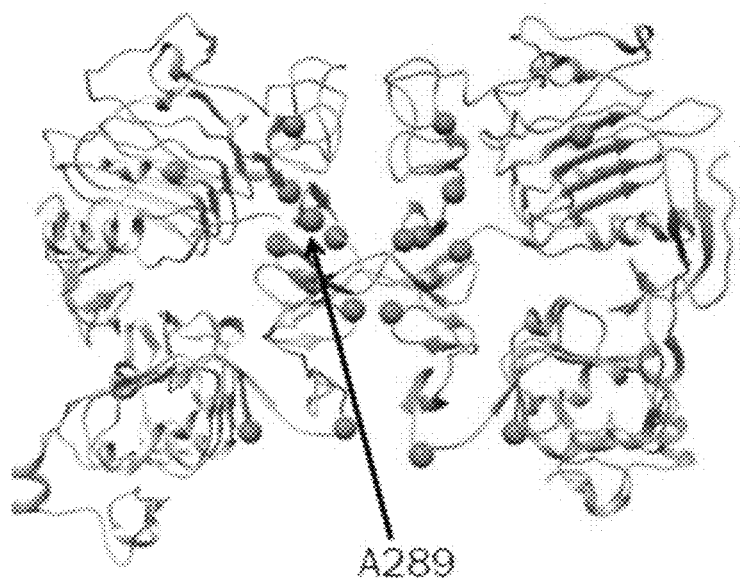
FIG. 1 is an illustration of the structure of EGFR and a group of 20 genomic mutations affecting the CR1 or CR2 regions of EGFR and which are expressed in GBM tumors. Mutations are highlighted within the crystal structure for the ectodomain of EGFR (1IVO). Mutations are noted as magenta spheres. EGF ligand is shown in green, and the EGFR protomers are shown in grey and orange. See also Table 2.

The present disclosure relates to new compounds useful as inhibitors of receptor tyrosine kinases (RTK), including oncogenic mutants of ErbB-receptors. In some embodiments of the present disclosure, oncogenic mutants of ErbB-receptors are also allosteric mutants of ErbB-receptors. In some embodiments of the present disclosure, allosteric mutants may comprise or consist of an ErbB receptor variant having a mutation in a sequence outside of an ATP-binding site. In some embodiments of the present disclosure, allosteric mutants may comprise or consist of an ErbB receptor variant having a mutation in a sequence within one or more of exon 19, exon 20 or a C1-C2 extracellular dimerization interface.

Mutations affecting either the intracellular catalytic domain or extracellular ligand binding domain of an ErbB receptor can generate oncogenic activity (the ErbB protein family consists of 4 members including ErbB-1, also named epidermal growth factor receptor (EGFR) and Erb-2, also named HER2 in humans). Extracellular mutants of ErbB receptors in cancer, including EGFR-Viii (also EGFR-V3) and HER2-S310F, are constitutively activated in the absence of ligand, exhibit sustained signaling that is resistant to downregulation, and are both transforming and tumorigenic (Nishikawa, Ji et al. 1994, 2013, Francis, Zhang et al. 2014). Their expression is associated with metastasis and with poor long term overall survival.

In glioblastoma (also glioblastoma multiforma or GBM), EGFR-Viii is expressed by 20% of tumors (Sugawa, Ekstrand et al. 1990, Brennan, Verhaak et al. 2013). Expression of EGFR-Viii in GBM tends to be mutually exclusive with expression of other RTK oncogenes, which are co-expressed with EGFR variants in only 7% of GBM tumors (Furnari, Cloughesy et al. 2015). These data demonstrate how EGFR-Viii in GBM has a dominant and mutually exclusive expression pattern compared with other oncogenic drivers. EGFR-Viii is also expressed by approximately 30% of SCCHN tumors (Sok, Coppelli et al. 2006, Keller, Shroyer et al. 2010, Wheeler, Suzuki et al. 2010, Tinhofer, Klinghammer et al. 2011, Wheeler, Egloff et al. 2015) and 10% of squamous NSCLC (Ji, Zhao et al. 2006, Sasaki, Kawano et al. 2007), and is associated with resistance to current therapeutics including the anti-EGFR antibody cetuximab (Sok, Coppelli et al. 2006, Tinhofer, Klinghammer et al. 2011). Normal tissues do not express this oncogenic receptor variant.

HER2-S310F is the most common mutation of HER2 expressed in human tumors, expressed by approximately 0.5% of all tumors. HER2-S310F expression is mutually exclusive with expression of HER2 amplification. HER2-S310F is highly oncogenic, transforming BaF3 cells (a murine interleukin-3 (IL-3) dependent pro-B cell line) to IL-3 independence and promoting tumor growth in vivo.

Short insertions of within Exon 20 of EGFR and HER2 are expressed by lung adenocarcinoma tumors and other tumor groups. ErbB Exon 20 insertion mutants are expressed by 4-5% of lung adenocarcinoma tumors. Examples include HER2-YVMA, EGFR-SVD, and EGFR-NPH.

These ErbB Exon 20 insertion mutants are highly oncogenic, transforming BaF3 cells to IL-3 independence and promoting tumor growth in vivo.

ErbB inhibitors are a known treatment for a number of cancers. However, not every patient is responsive satisfactorily to this treatment. Thus, there is a long-felt need in the art for new therapies that are able to address the variable responsiveness of cancer patients to known therapies. The present disclosure is able to overcome some of these drawbacks of the standard of care, as it existed prior to the development of the compositions and methods disclosed herein.

Definitions

Unless specified otherwise defined, the following general definitions apply to the compounds of the present disclosure according to the description.

The term "compound of the present disclosure," as used herein, refers to compounds represented by formulae I to XVI and any of the examples disclosed herein.

It is understood that "independently of each other" means that when a group is occurring more than one time in any compound, its definition on each occurrence is independent from any other occurrence.

It is understood that a dashed line (or a wave being transverse to a bond) depicts the site of attachment of a residue (i.e. a partial formula).

It is also understood that a group defined as being a "covalent bond" refers to a direct linkage between its two neighbouring groups.

The following definitions regarding group Z apply to each of the embodiments cited hereinafter: the term "3 to 6-membered heterocycloalkyl" in combination with —(NR$^4$R$^5$), refers to a non-aromatic or partially aromatic ring system having 3, 4, 5, or 6 ring atoms selected from C, N, O, or S, (e.g. C, N, or O), the number of N atoms being 0, 1, 2 and the number of O and S atoms each being 0, 1, 2. Examples of 3 to 6-membered heterocycloalkyl groups include oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3 dithianyl, piperazinyl, thiomorpholinyl, dioxothiomorpholinyl, piperidinyl, morpholinyl and the like. In some embodiments, 3 to 6-membered heterocycloalkyl include 5-membered heterocycloalkyl having 1 or 2 O-atoms, such as oxiranyl, oxetanyl, tetrahydrofuranyl, dioxanyl. In some embodiments, a 3 to 6-membered heterocycloalkyl is oxetanyl. In some embodiments, a 3 to 6-membered heterocycloalkyl is tetrahydrofuranyl. In some embodiments, a 3 to 6-membered heterocycloalkyl is (dioxo-)thiomorpholinyl.

A "partially aromatic" ring system is a ring system with one or more unsaturations, which are not fully conjugated over the whole ring system.

The term "3 to 6-membered heteroaryl" in combination with —(NR$^6$R$^7$) or —(CHR$^6$R$^7$), refers to a (fully) aromatic ring system having 3, 4, 5, or 6 ring atoms (e.g. 5 ring atoms), selected from C, N, O, or S (e.g. C, N, or O and C or N; with the number of N atoms being 0, 1, 2 or 3 and the number of O and S atoms each being 0, 1 or 2). Examples of "heteroaryl" include furyl, imidazolyl, isoxazolyl, oxazolyl, pyrazinyl, pyrazolyl (pyrazyl), pyridazinyl, pyridinyl, pyrimidinyl, pyrrolyl, thiazolyl, thienyl, and the like. In some embodiments, "heteroaryl" is pyrrolyl, imidazolyl.

The term "3 to 9-membered heterocycloalkyl" in combination with —(NR$^6$R$^7$) or —(CHR$^6$R$^7$), refers to a non-aromatic or partially aromatic ring system having 3, 4, 5, 6, 7, 8, or 9 ring atoms selected from C, N, O, or S (e.g. C, N, or O; the number of N atoms being 0, 1, 2 or 3 and the number of O and S atoms each being 0, 1 or 2). The term "monocycle" in connection with a 3 to 9-membered heterocycloalkyl refers to the 3 to 9 ring atoms forming a single ring. Examples of such monocycles include oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxatinanyl 1,4-dithianyl, 1,3-dioxane, piperazinyl, thiomorpholinyl, dioxothiomorpholinyl, piperidinyl, morpholinyl, oxepanyl, thiepanyl, azepanyl, diazepanyl, oxazepanyl and the like. In some embodiments, monocycles include azetidinyl, pyrrolidinyl, piperazinyl, morpholinyl, azepanyl.

The term "fused bicycle" in connection with a 3 to 9-membered heterocycloalkyl refers to the 3 to 9 ring atoms selected from C, N, O, or S, forming two or three rings (e.g. two rings) that are sharing two adjacent atoms (i.e. one bond) and at least one ring in the fused ring system contains one or more heteroatoms (e.g. 1, 2 or 3 heteroatoms selected from N, O, S). Some non-limiting examples of the fused heterobicyclyl group include 3-azabicyclo[3.1.0]hexyl, 3-azabicyclo[3.3.0]octyl, 3,7-diazabicyclo[3.3.0]octyl, 3-aza-7-oxabicyclo[3.3.0]octyl, 2,6-diazabicyclo[3.3.0]octyl, 2,7-diazabicyclo[3.3.0]octyl, 2,8-diazabicyclo[4.3.0]nonyl, 3-oxa-8-azabicyclo[4.3.0]nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4.3.0]nonyl, and the like.

The term "bridged bicycle" in connection with a 3 to 9-membered heterocycloalkyl refers to the 3 to 9 ring atoms forming a ring system that has a carbocyclyl or heterocyclyl, wherein two non-adjacent atoms of the ring are connected (bridged) by at least one (e.g. one or two) atoms selected from C, N, O, or S (e.g. C, N, or O), with the proviso that at least one heteroatom is present. Examples of such bridged ring systems include bicyclo[3.3.1]nonanyl, bicyclo[3.2.1]octanyl, bicyclo[2.2.2]octanyl, bicyclo[3.1.1]heptanyl, bicyclo[2.2.1]heptanyl (e.g. bicyclo[3.2.1]octanyl, bicyclo[2.2.1]heptanyl), having one or two heteroatoms selected from N and O.

The term "spirobicycle" connection with a 3 to 9-membered heterocycloalkyl refers to the 3 to 9 ring atoms forming a ring system that has two rings each of which are independently selected from a carbocyclyl or a heterocyclyl, wherein the two rings share one atom. Examples of such spiro ring systems include spiropentanyl, spiro[2.3]hexanyl spiro[3.3]heptanyl, spiro[3.4]octanyl, spiro[4.4]nonanyl, spiro[3.5]nonanyl, spiro[4.5]decanyl, (e.g. spiro[3.3]heptanyl, spiro[4.4]nonanyl), having one or two heteroatoms selected from N and O. In some embodiments, examples include diazaspiro[3.3]heptanyl, oxa-azaspiro[3.3]heptanyl, diazaspiro[4.4]nonanyl, oxa-azaspiro[4.4]nonanyl.

The term "halogen" or "hal" as used herein may be fluoro, chloro, bromo or iodo (e.g. fluoro or chloro).

The term "alkyl" as used herein refers to a fully saturated branched or unbranched hydrocarbon moiety. The term "$C_{1-4}$alkyl" refers to a fully saturated branched or unbranched hydrocarbon moiety having 1, 2, 3 or 4 carbon atoms. Representative examples of alkyl include, but are not limited to, methyl, ethyl, n-propyl, iso-propyl, n-butyl, sec-butyl, iso-butyl, tert-butyl. In connection with group L, the term "straight chain or branched $C_{1-4}$ alkyl" refers to —CH$_2$—, —(CH$_2$)$_2$—, —(CH$_2$)$_3$—, —(CH$_2$)$_4$—, —C(CH$_3$)$_2$— or —CH$_2$—C(CH$_3$)$_2$—.

According to the methods of the disclosure, exemplary subjects are mammals. In some embodiments, exemplary subjects are human. Exemplary subjects may be male or female. Exemplary subjects may be of any age (fetal, neonatal, child, adolescent, or adult) In some embodiments, the subject is an adult. Exemplary subjects may be healthy, for example, healthy subjects of the disclosure may participate in a clinical trial in which one or more steps of the methods of the disclosure are performed. In certain embodiments, exemplary subjects may have at least one benign or malignant tumor. In some embodiments, exemplary subjects have at least one form or type of cancer. Subjects of the methods of the disclosure may be patients diagnosed with cancer, patients undergoing treatment for cancer, potential participants in a research and/or clinical study, and/or participants selected for inclusion in or exclusion from a research and/or clinical study.

According to the methods of the disclosure, the term "mammal" refers to any mammal, including humans, domestic and farm animals, and zoo, sports, or pet animals, such as dogs, cats, cattle, horses, sheep, pigs, goats, rabbits, etc. (e.g. human).

The term "prevention" or "preventing" refers to reducing or eliminating the onset of the symptoms or complications of a disease (e.g., cancer). In some embodiments, such prevention comprises the step of administering a therapeutically effective amount of a compound disclosed herein (e.g., a compound of Formula I or a pharmaceutically acceptable salt thereof) or a pharmaceutical composition disclosed herein (e.g., a pharmaceutical composition containing a compound of Formula I or a pharmaceutically acceptable salt thereof) to a subject in need thereof (e.g., a mammal (e.g., a human).

The term "treatment" or "treating" is intended to encompass therapy and cure. In some embodiments, such treatment comprises the step of administering a therapeutically effective amount of a compound disclosed herein (e.g., a compound of Formula I or a pharmaceutically acceptable salt thereof) or a pharmaceutical composition disclosed herein (e.g., a pharmaceutical composition containing a compound of Formula I or a pharmaceutically acceptable salt thereof) to a subject in need thereof (e.g., a mammal (e.g., a human). In some embodiments, the term "treating" or "treatment" refers to therapeutic treatment measures; wherein the object is to slow down (lessen) the targeted pathologic condition or disorder. Those in need of treatment include those already with the disorder as well as those prone to have the disorder. For example, when treating cancer according to a method of the disclosure, a subject or mammal is successfully "treated" for cancer if, after receiving a therapeutic amount of an ErbB inhibitor according to the methods of the present disclosure, the patient shows observable and/or measurable reduction in or absence of one or more of the following: reduction in the number of cancer cells or absence of the cancer cells; reduction in the proliferation or survival of cancer cells; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician. According to the methods of the disclosure, subjects having a mutation of the disclosure may be treated for cancer by administering a therapeutically-effective amount of a composition of the disclosure, a Type II ErbB inhibitor, an EGFR-Viii selective agent/inhibitor or the NT-113 Type I inhibitor. The term "therapeutically effective amount" refers to an amount of a composition of the disclosure, a Type II ErbB inhibitor, an EGFR-Viii selective agent/inhibitor or the NT-113 Type I inhibitor effective to "treat" a disease or disorder (e.g. cancer) in a subject or mammal. See preceding definition of "treating."

According to the methods of the disclosure, a Type II ErbB inhibitor may include a small molecule. A "small molecule" is defined herein to have a molecular weight below about 1500 Daltons.

According to the methods of the disclosure, mutations may be detected by analyzing either nucleic acid or amino acid sequences from a subject. Nucleic acid and/or amino acid sequences may be isolated prior to sequence analysis.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. This refers to the nucleic acid as originally isolated and does not exclude genes or sequences later added to the isolated nucleic acid.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof.

An "isolated polypeptide" is one that has been identified and separated and/or recovered from a component of its natural environment. In some embodiments, the isolated polypeptide will be purified (1) to greater than 95% by weight of polypeptide as determined by the Lowry method (e.g. more than 99% by weight), (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or silver stain. Isolated polypeptide includes the polypeptide in situ within recombinant cells since at least one component of the polypeptide's natural environment will not be present. In some embodiments, the isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g. EGFR) derived from nature (e.g., from any species). Such native sequence polynucleotides and polypeptides can be isolated from nature or can be produced by recombinant or synthetic means.

A polynucleotide "variant," as the term is used herein, is a polynucleotide that differs from a disclosed polynucleotide herein in one or more substitutions, deletions, additions and/or insertions.

A polypeptide "variant," as the term is used herein, is a polypeptide that differs from a disclosed polypeptide herein in one or more substitutions, deletions, additions and/or insertions, or inversions. Such variants may be naturally occurring, non-naturally occurring, or may be synthetically generated.

EGFR mutations (or variants) of the disclosure may comprise one or more substitutions, deletions, additions and/or insertions, or inversions of the amino acid sequence that are alter the function of the resultant protein. Mutations may be detected, for example, by comparison or alignment of a nucleic or amino acid sequence with a wild type sequence.

When comparing polynucleotide and polypeptide sequences, two sequences are said to be "identical" if the sequence of nucleotides or amino acids in the two sequences is the same when aligned for maximum correspondence, as described below. Comparisons between two sequences are performed by comparing the sequences over a comparison window to identify and compare local regions of sequence similarity. A "comparison window" as used herein, refers to a segment of at least about 20 contiguous positions, (e.g. 30 to about 75 or 40 to about 50), in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example, with the parameters described herein, to determine percent sequence identity for the polynucleotides and polypeptides of the present disclosure. Software for performing BLAST analyses is publicly available through the National Center for Biotechnology Information.

In some embodiments, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Nall. Acad. Sci. USA* 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less (e.g. 5 to 15 percent, or 10 to 12 percent), as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Sequences

A wild type EGFR sequence of the disclosure may comprise or consist of the amino acid sequence of:

```
   1 mrpsgtagaa llallaalcp asraleekkv cqgtsnkltq lgtfedhfls lqrmfnncev
  61 vlgnleityv grnydlsflk tiqevagyvl ialntverip lenlqiirgn myyensyala
 121 vlsnydankt glkelpmrnl qeilhgavrf snnpalcnve siqwrdivss drlsnmsmdf
 181 qnhlgscqkc dpscpngscw gageencgkl tkiicaqqcs grcrgkspsd cchnqcaagc
 241 tgpresdclv crkfrdeatc kdtcpplmlv npttygmdvn pegkysfgat cvkkcprnvv
 301 vtdhgscvra cgadsyemee dgvrkckkce gporkvongi gigefkdsls inatnikhfk
 361 nctsisgdlh ilpvafrgds fthtppldpq eldilktvke itgflliqaw penrtdlhaf
 421 enleiirgrt kqhgqfslav vslnitslgl rslkeisdgd viisgnknlc vantinwkkl
 481 fgtsgqktki isnrgensck atgqvchalc spegcwgpep rdcvscrnvs rgrecvdkck
 541 llegeprefv enseciqchp eclpqamnit ctgrgpdnci qcahyidgph cvktcpagvm
 601 genntlvwky adaghvchlc hpnctygctg pglegcptng pkipsiatgm vgallllvv
 661 algiglfmrr rhlvrkrtlr rllqerelve pltpsgeapn qallrilket efkkikvlgs
 721 gafgtvvkgl wipegekvki pvaikelrea tspkankeil deavvmasvd nphvcrllgi
 781 cltstvglit qlmpfgclld yvrehkdhig sqyllnwcvq iakgmnyled rrlvhrdlaa
 841 rnvlvktpqh vkitdfglak llgaeekeyh aeggkvpikw malesilhri ythqsdvwsy
 901 gvtvwelmtf gskpydgipa seissilekg erlpqppict idvymimvkc wmidadsrpk
 961 freliiefsk mardpqrylv iqgdermhlp sptdsnfyra lmdeedmddv vdadeylipq
1021 qgffsspsts rtpllsslsa tsanstvaci drnglqscpi kedsflqrys sdptgalted
1081 siddtflpvp eyinqsvpkr pagsvqnpvy hnqplnpaps rdphyqdphs tavgnpeyln
1141 tvqptovnst fdspahwaqk gshqisldnp dyqqdffpke akpngifkgs taenaeylrv
1201 apqssefiga
```

(SEQ ID NO: 1, corresponding to epidermal growth factor receptor [*Homo sapiens*] and Genbank Accession No. CAA25240).

A wild type HER2 Receptor sequence of the disclosure may comprise or consist of the amino acid sequence of:

```
   1 melaalcrwg lllallppga astqvctgtd mklrlpaspe thldmlrhly qgcqvvqgnl
  61 eltylptnas lsflgdiqev qgyvliahnq vrqvplgrlr ivrgtqlfed nyalavldng
 121 dplnnttpvt gaspgglrel qlrslteilk ggvliqrnpq lcyqdtilwk difhknnqla
 181 ltlidtnrsr achpcspmck gsrcwgesse dcqsltrtvc aggcarckgp lptdccheqc
 241 aagctgpkhs dclaclhfnh sgicelhcpa lvtyntdtfe smpnpegryt fgascvtacp
 301 ynvlstdvgs ctlvcplhnq evtaedgtqr cekcskpcar vcyglgmehl revravtsan
 361 iqefagckki fgslaflpes fdgdpasnta plqpeqlqvf etleeitgyl yisawpdslp
 421 dlsvfqnlqv irgrilhnga ysltlqglgi swlglrslre lgsglalihh nthlcfvhtv
 481 pwdqlfrnph gallhtanrp edecvgegla chqlcarghc wgpgptqcvn csqflrgqec
 541 veecrvlqgl preyvnarhc lpchpecqpq ngsvtcfgpe adqcvacahy kdppfcvarc
 601 psgvkpdlsy mpiwkfpdee gacqpcpinc thscvdlddk gcpaeqrasp ltsiisavvg
 661 illvvvlgvv fgilikrrqg kirkytmrrl lqetelvepl tpsgampnqa qmrilketel
```

-continued

```
 721 rkvkvlgsga fgtvykgiwi pdgenvkipv aikvlrents pkankeilde ayvmagvgsp 781 yvsrllgicl tstvqlvtql mpygclldhv renrgrlgsq dllnwcmqia kgmsvledvr 841 lvhrdlaarn vlvkspnhvk itdtglarll dideteyhad ggkvpikwma lesilrrrft 901 hqsdvwsygv tvwelmtfga kpydgipare ipdllekger lpqppictid vymimvkcwm 961 idsecrprfr elvsefsrma rdpqrfvviq nedlgpaspl dstfyrslle dddmgdlvda 1021 eeylvpqqgf fcpdpapgag qmvhhrhrss strsgggdlt lglepseeea prsplapseg 1081 agsdvfdqdl gmgaakglqs lpthdpsplq rysedptypl psetdgyvap ltcspqpeyv 1141 nqpdvrpqpp spregplpaa rpagatlerp ktlspgkngv vkdvfafgga venpeyltpq 1201 ggaapqphpp pafspafdnl yywdqdpper gappstfkgt ptaenpeylg ldvpv
```

(SEQ ID NO: 2, corresponding to receptor tyrosine-protein kinase erbB-2 isoform a precursor [Homo sapiens] and GenBank Accession No. NP_004439).

A wild type HER2 Receptor sequence of the disclosure may comprise or consist of the amino acid sequence of:

```
   1 mklrlpaspe thldmlrhly qgcqvvqgnl eltylptnas lsflqdigev qgyvliahnq 61 vrqvplqrlr ivrgtqlfed nyalavldng dplnnttpvt gaspgglrel qlrslteilk 121 ggvliqrnpq lcyqdtilwk difhknnqla ltlidtnrsr achpcspmck gsrcwgesse 181 dcqsltrtvc aggcarckgp lptdccheqc aagctgpkhs dclaclhfnh sgicelhcpa 241 lvtyntdtfe smpnpegryt fgascvtacp ynylstdvgs ctlvcplhnq evtaedgtqr 301 cekcskpcar vcyglgmehl revravtsan iqefagckki fgslaflpes fdgdpasnta 361 plgpeqlqvf etleeitgyl yisawpdslp dlsvfqnlqv irgrilhnga ysltlqglgi 421 swlglrslre lgsglalihh nthlcfvhtv pwdglfrnph qallhtanrp edecvgegla 481 chqlcarghc wgpgptgcvn csgflrgqec veecrvlqgl preyvnarhc lpchpecqpg 541 ngsvtcfgpe adqcvacahy kdppfcvarc psgvkpdlsy mpiwktpdee gacqpcpinc 601 thscvdlddk gcpaeqrasp ltsiisavvg illvvvlgvv fgilikrrqq kirkytmrrl 661 lqetelvepl tpsgampnqa qmrilketel rkvkvlgsga fgtvykgiwi pdgenvkipv 721 aikvlrents pkankeilde ayvmagvgsp yvsrllgicl tstvqlvtql mpygclldhv 781 renrgrlgsq dllnwcmqia kgmsyledvr lvhrdlaarn vlvkspnhvk itdfglarll 841 dideteyhad ggkvpikwma lesilrrrft hgsdvwsygv tvwelmtfga kpydgipare 901 ipdllekger lpqppictid vymimvkcwr idsecrprfr elvsefsrma rdpqrfvvig 961 nedlgpaspl dstfyrslle dddmgdlvda eeylvpqqgf fcpdpapgag gmvhhrhrss 1021 strsgggdlt lglepseeea prsplapseg agsdvfdqdl gmgaakglqs lpthdpsplq 1081 rysedptvpl psetdgyvap ltcspqpeyv nqpdvrpqpp spregplpaa rpagatlerp 1141 ktlspgkngv vkdvfafgga venpeyltpq ggaapqphpp pafspafdnl yywdqdpper 1201 gappstfkgt ptaenpeylg ldvpv
```

(SEQ ID NO: 3, corresponding to receptor tyrosine-protein kinase erbB-2 isoform b [Homo sapiens] and GenBank Accession No. NP_001005862).

A wild type HER2 Receptor sequence of the disclosure may comprise or consist of the amino acid sequence of:

```
   1 mprqswkpqv ctgtdmklrl paspethldm lrhlyqgcqv vqgnleltyl ptnaslsflq
  61 diqevqgyvl iahnqvrqvp lqrlrivrgt qlfednyala vldngdplnn ttpvtgaspg
 121 glrelqlrsl teilkggvli qrnpqlcyqd tilwkdifhk nnqlaltlid tnrsrachpc
 181 spmckgsrcw gessedcqsl trtvcaggca rckgplptdc cheqcaagct gpkhsdclac
 241 lhfnhsgice lhcpalvtyn tdtfesmpnp egrytfgasc vtacpynyls tdvgsctlvc
 301 plhnqevtae dgtqrcekcs kpcarvcygl gmehlrevra vtsaniqefa gckkifgsla
 361 flpesfdgdp asntaplqpe qlqvfetlee itgylyisaw pdslpdlsvf qnlqvirgri
 421 lhngaysltl qglgiswlgl rslrelgsgl alihhnthlc fvhtvpwdql frnphqallh
 481 tanrpedecv geglachqlc arghcwgpgp tqcvncsqfl rgqecveecr vlqglpreyv
 541 narhclpchp ecqpqngsvt cfgpeadqcv acahykdppf cvarcpsyvk pdlsympiwk
 601 fpdeegacqp cpincthscv dlddkgcpae qraspltsii savvgillvv vlgvvfgili
 661 krrqkirky tmrrllqete lvepltpsga mpnqaqmril ketelrkvkv lgsgafgtvy
 721 kgiwipdgen vkipvaikvl rentspkank eildeayvma gvgspyvsrl lgicltstvq
 781 lvtqlmpygc lldhvrenrg rlgsqdllnw cmqiakgmsy ledvrlvhrd laarnvlvks
 841 pnhvkitdfg larlldidet eyhadggkvp ikwmalesil rrrfthqsdv wsygvtvwel
 901 mtfgakpydg ipareipdll ekgerlpqpp ictidvymim vkcwmidsec rprfrelvse
 961 fsrmardpqr fvvignedlg paspldstfy rslledddmg dlvdaeeylv pqqgffcpdp
1021 apgaggmvhh rhrssstrsg ggdltlglep seeeaprspl apsegagsdv fdgdlgmgaa
1081 kglqslpthd psplqrysed ptvplpsetd gyvapltcsp qpeyvnqpdv rpqppspreg
1141 plpaarpaga tlerpktlsp gkngvvkdvf afggavenpe yltpqggaap qphpppafsp
1201 afdnlyywdq dppergapps tflftptaen peylgldvpv
```
(SEQ ID NO: 4, corresponding to receptor tyrosine-protein kinase erbB-2 isoform c [*Homo sapiens*] and GenBank Accession No. NP_001276865).

A wild type HER2 Receptor sequence of the disclosure may comprise or consist of the amino acid sequence of:

```
   1 melaalcrwg lllallppga astqvdtgtd mklrlpaspe thldmlrhly qgcqvvqgnl
  61 eltylptnas lsflqdiqev qgyvliahnq vrqvplqrlr ivrgtqlfed nyalavldng
 121 dplnnttpvt gaspgglrel qlrslteilk ggvliqrnpq lcyqdtilwk difhknnqla
 181 ltlidtnrsr achpcspmdk gsrcwgesse dcqnltrtvc aggcarckgp lptdccheqc
 241 aagctgpkhs dclaclhfnh sgicelhdpa lvtyntdtfe smpnpegryt fgascvtacp
 301 ynylstdvgs ctlvdplhnq evtaedgtqr cekcskpcar vcyglgmehl revravtsan
 361 iqefagqkki fgnlaflpes fdgdpasnta plqpeqlqvf etleeitgya yisawpdslp
 421 dlsvfqnlqv irgrilhnga ysltlqglgi swlglrslre lgsglalhh nthlcfvhtv
 481 pwdqlfrnph qallhtanrp edecvgegla chqlcarghc wgpgptqcvn csqflrgqec
 541 veecrvlqgl preyvnarhc lpchpecqpq ngsvtcfgpe adqcvacahy kdppfcvarc
 601 psgvkpdlsy mpiwkfpdee gacqpcpinc thscvdlddk gdpaeqrasp ltsiisavvg
 661 illvvvlgvv fgilikrrqq kirkytmrrl lqetelvepl tpsgampnqa qmrilketel
 721 rkvkvlgsga fgtvykgiwi pdgenvkipv aikvlrents pkankeilde ayvmagvgsp
 781 yvsrllgicl tstvqlvtql mpygclldhv renrgrlgsq dllnwcmqia kgmsyledvr
```

```
841 lvhrdlaarn vlvkspnhvk itdfglarll dideteyhad ggkvpikwma lesilrrrft 901 hqsdvwsygv tvwelmtfga kpydgipare ipdllekger lpqppictid vymimvkcwm 961 idsecrprfr elvsefsrma rdpqrfvviq nedlgpaspl dstfyrslle dddmgdlvda 1021 eeylvpqqgf fcpdpapgag gmvhhrhrss strnm
```

(SEQ ID NO: 5, corresponding to receptor tyrosine-protein kinase erbB-2 isoform d precursor [Homo sapiens] and GenBank Accession No. NP_001276866).

A wild type HER2 Receptor sequence of the disclosure may comprise or consist of the amino acid sequence of:

```
  1 mklrlpaspe thldmlrhly qgcqvvqgnl eltylptnas lsflqdiqev qgyvliahnq 61 vrqvplqrlr ivrgtqlfed nyalavldng dplnnttpvt gaspgglrel qlrslteilk 121 ggvliqrnpg lcyqdtilwk difhknnqla ltlidtnrsr achpcspmck gsrcwgesse 181 dcqsltrtvc aggcarckgp lptdccheqc aagctgpkhs dclaclhfnh sgicelhcpa 241 lvtyntdtfe smpnpegryt fgascvtacp ynylstdvqs ctlvcplhnq evtaedgtqr 301 cekcskpcar vcyglgmehl revravtsan igefagckki fgslaflpes fdgdpasnta 361 plqpeqlqvf etleeitgyl yisawpdslp dlsvfqnlqv irgrilhnga ysltlqglgi 421 swlglrslre lgsglalihh nthlcfvhtv pwdglfrnph qallhtanrp edecvgegla 481 chqlcarghc wgpgptgcvn csgflrgqec veecrvlqgl preyvnarhc lpchpecqpg 541 ngsvtcfgpe adqcvacahy kdppfcvarc psgvkpdlsy mpiwkfpdee gacqpcpinc 601 ths
```

(SEQ ID NO: 6, corresponding to receptor tyrosine-protein kinase erbB-2 isoform e [Homo sapiens] and GenBank Accession No. NP_001276867).

Based on the definitions given throughout the application the skilled person knows which combinations are synthetically feasible and realistic, e.g. typically combinations of groups leading to heteroatoms directly linked to each other are not contemplated.

Compounds of the Present Disclosure

In some aspects, the present disclosure is directed towards a compound or pharmaceutically acceptable salts or stereoisomers thereof of formula I

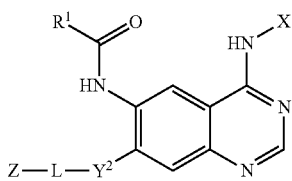

wherein L is a covalent bond, straight chain or branched $C_{1-4}$ alkyl or

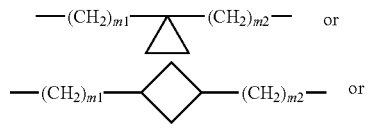

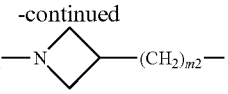

wherein m1, m2 are independently of each other 0, 1, 2, 3, or 4;

$Y^2$ is a covalent bond, —O—, —NH—, —NCH$_3$—, —C≡C—;

Z is —(NR$^4$R$^5$), wherein R$^4$ and R$^5$ are independently of each other H, $C_{1-6}$ alkyl, cyclopropyl, cylobutyl, 3 to 6-membered heterocycloalkyl, or —(NR$^6$R$^7$), —(CHR$^6$R$^7$), wherein R$^6$ and R$^7$ form together with the atom to which they are attached to 3 to 6-membered heteroaryl or 3 to 9-membered heterocycloalkyl, wherein the 3 to 9-membered heterocycloalkyl is a monocycle or a fused-, bridged- or spirobicycle or a combination thereof, and is unsubstituted or substituted with $C_{1-4}$ alkyl, hal, —OR', —NR'R", wherein R', R" are independently of each other H or -$C_{1-4}$ alkyl;

$R^1$ is —CR$_b$=CHR$_a$, —C≡CH or —C≡C—CH$_3$; wherein R$^a$, R$^b$ are independently of each other H, hal, —CH$_2$—O—CH$_3$; and X is a group of formula (i)a

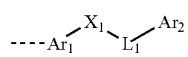

(i)a wherein $X^1$ is —O—, —CH$_2$—, —NH—, —S—;

Ar$^1$ is 6 membered aryl or N-heteroaryl, which is unsubstituted or substituted with one or more of a group selected from hal, $C_{1-6}$alkyl or $C_{1-6}$alkoxy;

Ar$^2$ is 6 membered aryl or N-heteroaryl, which is unsubstituted or substituted with one or more of a group selected from halogen, $C_{1-6}$alkyl, $C_{1-6}$alkoxy, —CF$_3$ or —OCF$_3$;

L$^1$ is a covalent bond or straight chain or branched $C_{1-3}$alkyl, which is unsubstituted or substituted with hal (e.g. a covalent bond or —CH$_2$—).

In some embodiments substituent Z-L-Y$_2$ contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if Y$_2$ is not N(H) or (NMe) or L does not contain a nitrogen atom.

In some embodiments R$^a$ and R$^b$ are hydrogen.

In some embodiments, the compound of formula I is not any of

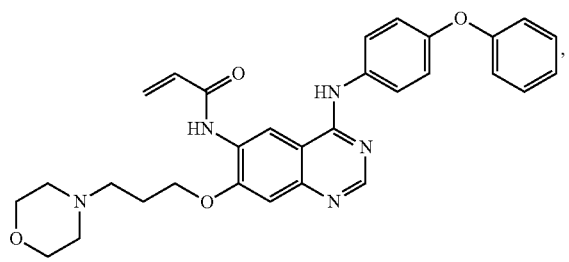

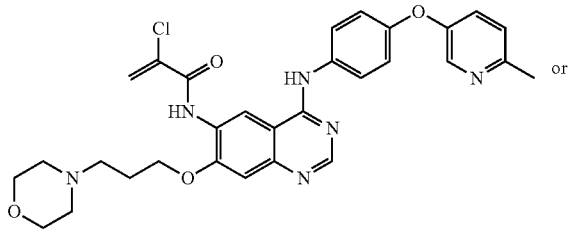 or

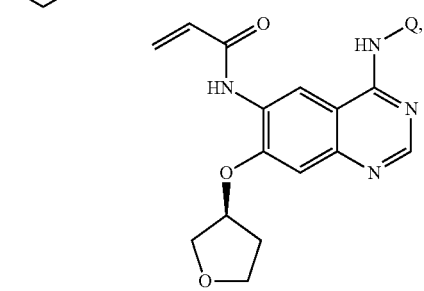

wherein Q is

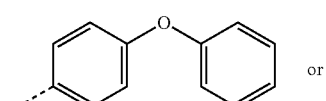 or

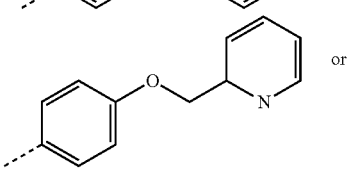 or

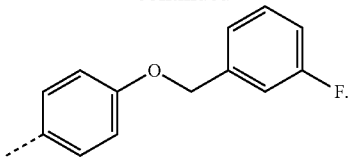

In some embodiments, Ar$_1$ of the compound of formula (i)a or pharmaceutically acceptable salts or stereoisomers thereof is a group of formula (i)b

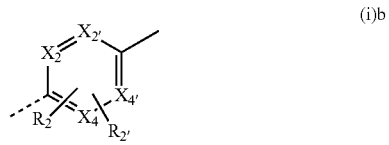

(i)b wherein $X^2$, $X^{2'}$, $X^4$, $X^{4'}$ are independently of each other —N= or —CH=; and wherein $R^2$, $R^{2'}$ are independently of each other H, $C_{1-6}$ alkyl, hal, —CF$_3$, —OCF$_3$, with the proviso that at least two of $X^2$, $X^{2'}$, $X^4$, $X^{4'}$ are —CH=;

It is understood that $R^2$, $R^{2'}$ can only be bound to X-groups being —CH=.

In some embodiments, 2, 3 or all of $X^2$, $X^{2'}$, $X^4$, $X^{4'}$ are —CH= and thus Ar$_1$ of formula (i)b is selected from phenyl, pyridine, pyridazine, pyrimidine and pyrazine ring system.

In some embodiments, Ar$_1$ of formula (i)b is a phenyl group a (e.g. a1)

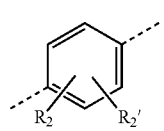

a preferably

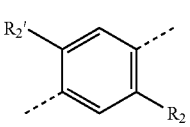

a1

In some embodiments, Ar$_1$ of formula (i)b is one of groups b or c (e.g., b1 or c1), wherein the pyridine is linked to the amino group in ortho- or meta-position to the ring nitrogen

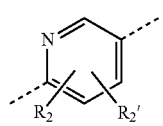

b

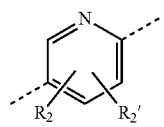

c

-continued

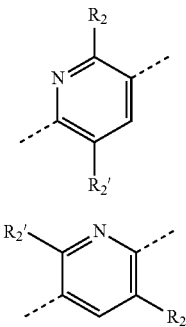

b1

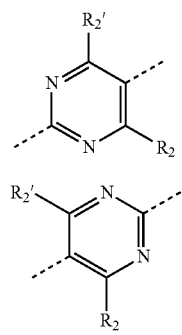

c1

In some embodiments, Ar$_1$ of formula (i)b is one of groups d or e, wherein the pyrimidine is linked to the amino group in ortho- or meta-position to the ring nitrogen

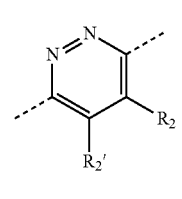

d

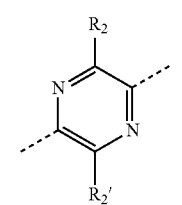

e

In some embodiments, Ar$_1$ of formula (i)b is a pyridazine group f. In some embodiments, Ar$_1$ of formula (i)b is the following pyrazine group g.

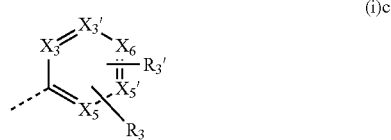

f g

In some embodiments of Ar$_1$, both X$^4$ and X$^{4'}$ are —CH=.

In some embodiments, Ar$_1$ is
ring a (or a1) wherein X$^2$, X$^{2'}$, X$^4$ and X$^{4'}$ are —CH=; or
ring b (or b1) wherein X$^2$ is —N= and X$^{2'}$, X$^4$, X$^{4'}$ are —CH=; or
ring c (or c1) wherein X$^{2'}$ is —N= and X$^2$, X$^4$, X$^{4'}$ are —CH=; or
ring f wherein X$^2$, X$^{2'}$ are —N= and X$^4$, X$^{4'}$ are —CH=.

In some embodiments, R$^2$ and R$^{2'}$ are independently of each other H, C$_{1-6}$ alkyl (e.g. methyl), halogen (e.g. Cl or F).

In some embodiments, Ar$_2$ of the compound of formula (i)a or pharmaceutically acceptable salts or stereoisomers thereof is a group of formula (i)c

(i)c wherein X$^3$, X$^{3'}$, X$^5$, X$^{5'}$, X$^6$ are independently of each other —N=, —CH=; and R$^3$, R$^{3'}$ are independently of each other H, C$_{1-6}$ alkyl, hal, —CF$_3$, —OCF$_3$, with the proviso that at least two of X$^3$, X$^{3'}$, X$^5$, X$^{5'}$, X$^6$ are —CH=.

In some embodiments, R$^3$, R$^{3'}$ can only be bound to X-groups being —CH=.

In some embodiments, 2, 3 or all of X$^3$, X$^{3'}$, X$^5$, X$^{5'}$, X$^6$ are —CH= and thus Ar$_2$ of formula (i)c is selected from phenyl, pyridine, pyridazine, pyrimidine and pyrazine.

In some embodiments, Ar$_2$ of formula (i)c is a phenyl group a' (e.g. a'1)

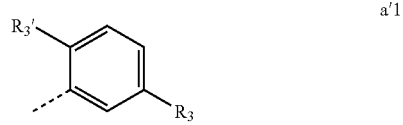

a' preferably

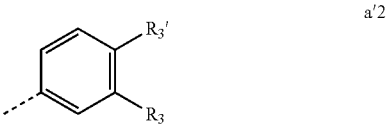

a'1

a'2

In some embodiments, Ar$_2$ of formula (i)c is one of groups b' or c' or d' (e.g. b'1 or c'1 or d'1), wherein the pyridine is linked in ortho- or meta- or para-position to the ring nitrogen

b'

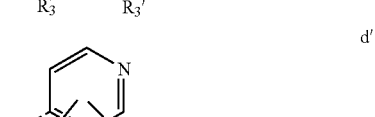

c' d'

-continued

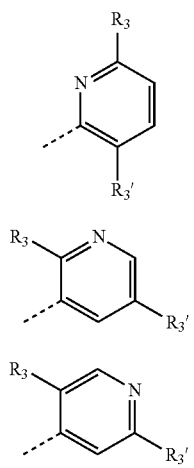

b'1 c'1 d'1

In some embodiments Ar₂ of formula (i)c is one of groups e' or f' (e.g. e'1 or f'1), wherein the pyrimidine is linked in ortho- or meta-position to the ring nitrogens

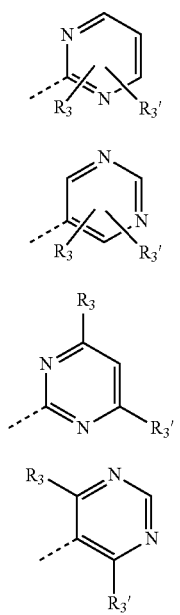

e' f' e'1 f'1

In some embodiments, Ar₂ of formula (i)c is group g' (e.g. g'1). In some embodiments, Ar₂ of formula (i)c is a pyrazine group h' (e.g. h'1)

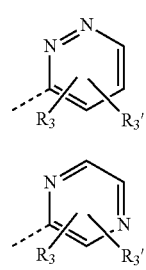

g' h'

-continued g'1 h'1

In some embodiments, Ar₂ of formula (i)c is group i' (e.g. i'1). In some embodiments, Ar₂ of formula (i)c is a pyrazine group k' (e.g. k'1).

i' k' i'1 k'1

In some embodiments of Ar₂, both $X^5$ and $X^{5'}$ are —CH=.

In some embodiments, Ar₂ is
ring a' wherein $X^3$, $X^{3'}$, $X^5$, $X^{5'}$ and $X^6$ are —CH=; or
ring b' wherein $X^3$ is —N= and $X^{3'}$, $X^5$, $X^{5'}$, $X^6$ are —CH=; or
ring c' wherein $X^{3'}$ is —N= and $X^3$, $X^5$, $X^{5'}$, $X^6$ are —CH=; or
ring d' wherein $X^6$ is —N= and $X^3$, $X^{3'}$, $X^5$, $X^{5'}$ are —CH=; or
ring g' wherein $X^3$, $X^{3'}$ are —N= and $X^5$, $X^{5'}$, $X^6$ are —CH=; or
ring i' wherein $X^3$, $X^6$ are —N= and $X^{3'}$, $X^5$, $X^{5'}$ are —CH=; or
ring k' wherein $X^{3'}$, $X^6$ are —N= and $X^3$, $X^5$, $X^{5'}$ are —CH=.

In some embodiments of Ar₂, both $X^{3'}$ and $X^6$ a —CH=.

In some embodiments, Ar₂ is
ring e' wherein $X^3$, $X^5$ are —N= and $X^{3'}$, $X^{5'}$, $X^6$ are —CH=; or ring h' wherein $X^3$, $X^{5'}$ are —N= and $X^{3'}$, $X^5$, $X^6$ are —CH.

In some embodiments of $Ar_2$, both $X^3$ and $X^6$ are —CH=.

In some embodiments, $Ar_2$ is
ring f' wherein $X^{3'}$, $X^{5'}$ are —N= and $X^3$, $X^5$, $X^6$ are —CH=

The present disclosure includes all possible combinations of group (i)b with group (i)c linked by the linker $-X^1-L^1-$, e.g., a combination of a with either group a'-k' (aa', ab', ac', ad', ae', af', ag', ah', ai', ak'); a combination of b with either group a'-k' (ba', bb', bc', bd', be', bf', bg', bh', bi', bk'); a combination of c with either group a'-k' (ca', cb', cc', cd', ce', cf', cg', ch', ci', ck'); a combination of d with either group a'-k' (da', db', dc', dd', de', df', dg', dh', di', dk'); a combination of e with either group a'-i' (ea', eb', cc', ed', ee', ef', eg', eh', ei', ek'); a combination of f with either group a'-k' (fa', fb', fc', fd', fe', ff', fg', fh', fi', fk'); or g with either group a'-k' (ga', gb', gc', gd', ge', gf', gg', gh', gi', gk').

In some embodiments, the ring combinations include
aa' or ab' or ac' or ad'
ae' or ag' or ah' or ai'
bb' or cb'.

In some embodiments of the compound of formula (i)a are directed to groups $X^1$ and $L^1$, which form together the linker between $Ar_1$ and $Ar_2$. In some embodiments, $X^1$ is —O—. In some embodiments, $X^1$ is —CH$_2$—. In some embodiments, $X^1$ is —NH—. In some embodiments, $X^1$ is —S—.

In some embodiments, $L^1$ is a covalent bond. In some embodiments, $L^1$ is —CH$_2$—, —CH(CH$_3$)—, or —CH(hal)-. In some embodiments, $L^1$ is —CH$_2$—CH$_2$—, —CH$_2$—CH(CH$_3$)—, or —CH$_2$—CH(hal)-.

In some embodiments, linker combinations $-X^1-L^1-$ for each of the combinations of (i)b and (i)c include —O—, —CH$_2$—, —O—CH$_2$—, —NH—CH$_2$—, —S—CH$_2$—, —CH$_2$—CH$_2$—, —O—CH(CH$_3$)—, —CH$_2$—CH(CH$_3$)—, —NH—CH(CH$_3$)—, —S—CH(CH$_3$)—, —O—CH(hal)-, —CH$_2$—CH(hal)-, —NH—CH(hal)-, —S—CH(hal)- (e.g., —O—, —CH$_2$—, —O—CH$_2$—, —NH—CH$_2$—, —CH$_2$—CH$_2$—, —O—CH(CH$_3$)—, —CH$_2$ CH(CH$_3$)—, —O—CH(hal)-, —CH$_2$—CH(hal)- (e.g., —O—, —CH$_2$—, —O—CH$_2$—, —NH—CH$_2$—, or —CH$_2$—CH$_2$—)).

In some embodiments, a group of formula (i)a is selected from the combinations (i) a—O-a', a—O—CH$_2$-a', a—O—CH(CH$_3$)-a', a—O—CH(hal)-a', and a—NH-a', a—NH—CH$_2$-a', a—NH—CH(CH$_3$)-a', a—NH—CH(hal)-a', (ii) a—O-b', a—O—CH$_2$-b', a—O—CH(CH$_3$)-b', a—O—CH(hal)-b', and a—NH-b', a—NH—CH$_2$-b', a—NH—CH(CH$_3$)-b', a—NH—CH(hal)-b', (iii) a—O-c', a—O—CH$_2$-c', a—O—CH(CH$_3$)-c', a—O—CH(hal)-c', and a—NH-c', a—NH—CH$_2$-c', a—NH—CH(CH$_3$)-c', a—NH—CH(hal)-c', (iv) a—O-d', a—O—CH$_2$-d', a—O—CH(CH$_3$)-d', a—O—CH(hal)-d', and a—NH-d', a—NH—CH$_2$-d', a—NH—CH(CH$_3$)-d', a—NH—CH(hal)-d', (v) a—O-e', a—O—CH$_2$-e', a—O—CH(CH$_3$)-e', a—O—CH(hal)-e', and a—NH-e', a—NH—CH$_2$-e', a—NH—CH(CH$_3$)-e', a—NH—CH(hal)-e', (vi) a—O-g', a—O—CH$_2$-g', a—O—CH(CH$_3$)-g', a—O—CH(hal)-g', and a—NH-g', a—NH—CH$_2$-g', a—NH—CH(CH$_3$)-g', a—NH—CH(hal)-g', (vii) a—O-h', a—O—CH$_2$-h', a—O—CH(CH$_3$)-h', a—O—CH(hal)-h', and a—NH-a', a—NH—CH$_2$-h', a—NH—CH(CH$_3$)-h', a—NH—CH(hal)-h', (viii) a—O-i', a—O—CH$_2$-i', a—O—CH(CH$_3$)-i', a—O—CH(hal)-i', and a—NH-a', a—NH—CH$_2$-i', a—NH—CH(CH$_3$)-i', a—NH—CH(hal)-i', (ix) b—O-b', b—O—CH$_2$-b', b—O—CH(CH$_3$)-b', b—O—CH(hal)-b', and b—NH-b', b—NH—CH$_2$-b', b—NH—CH(CH$_3$)-b', b—NH—CH(hal)-b', (x) c—O-b', c—O—CH$_2$-b', c—O—CH(CH$_3$)-b', c—O—CH(hal)-b', and c—NH-b', c—NH—CH$_2$-b', c—NH—CH(CH$_3$)-b', c—NH—CH(hal)-b'.

In some embodiments, $R^4$ and $R^5$ are independently of each other H, $C_{1-4}$ alkyl, cyclopropyl, or tetrahydrofuryl.

Group Z is as defined above. In some embodiments of a compound of formula I, a 3 to 6-membered heterocycloalkyl (in combination with —(NR$^4$R$^5$)) refers to a non-aromatic or partially aromatic ring system having 3, 4, 5, or 6 ring atoms selected from C, N, O, and/or S, (e.g., C, and/or O). In some embodiments, the number of N atoms is 0, 1, or 2. In some embodiments, the number of O and S atoms each is 0, 1, or 2. Examples of 3 to 6-membered heterocycloalkyl groups include oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, morpholinyl and the like. In some embodiments, 3 to 6-membered heterocycloalkyl include 5-membered heterocycloalkyl having 1 or 2 O-atoms, such as oxiranyl, oxetanyl, tetrahydrofuranyl, dioxanyl.

In some embodiments of a compound of formula I, a 3 to 6-membered heteroaryl (in combination with —(NR$^6$R$^7$) or —(CHR$^7$)) refers to a (fully) aromatic ring system having 3, 4, 5, or 6 ring atoms (e.g., 3, 4, or 5 ring atoms), selected from C, N, O and/or S, (e.g. C, N, and/or O, and C or N). In some embodiments, the number of N atoms is 0, 1, 2 or 3. In some embodiments, the number of O and S atoms each is 0, 1 or 2. Examples of "heteroaryl" include furyl, imidazolyl, isoxazolyl, oxazolyl, pyrazinyl, pyrazolyl (pyrazyl), pyridazinyl, pyridinyl, pyrimidinyl, pyrrolyl, thiazolyl, thienyl, and the like. Examples of "heteroaryl" include pyrrolyl, imidozolyl.

In some embodiments of a compound of formula I, a 3 to 9-membered heterocycloalkyl (in combination with —(NR$^6$R$^7$) or —(CHR$^7$)) refers to a non-aromatic or partially aromatic ring system having 3 to 9 ring atoms selected from C, N, O, and/or S (e.g., C, N, and/or O). In some embodiments, the number of N atoms is 0, 1, 2 or 3. In some embodiments, the number of O and S atoms each is 0, 1 or 2. Examples of a 3 to 9-membered heterocycloalkyl (in combination with —(NR$^6$R$^7$) or —(CHR$^6$R$^7$)) include monocycles such as oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl, oxepanyl, thiepanyl, azepanyl, diazepanyl, oxazepanyl (e.g. azetidinyl, pyrrolidinyl, piperidinyl, piperazinyl, morpholinyl, azepanyl); fused ring systems, such as 3-azabicyclo[3.1.0]hexyl, 3-azabicyclo[3.3.0]octyl, 3,7-diazabicyclo[3.3.0]octyl, 3-aza-7-oxabicyclo[3.3.0]octyl, 2,6-diazabicyclo[3.3.0]octyl, 2,7-diazabicyclo[3.3.0]octyl, 2,8-diazabicyclo[4.3.0]nonyl, 3-oxa-8-azabicyclo[4.3.0]nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4.3.0]nonyl, and the like; bridged ring systems such as bicyclo[3.3.1]nonanyl, bicyclo[3.2.1] octanyl, bicyclo[2.2.2]octanyl, bicyclo[3.1.1]heptanyl, bicyclo[2.2.1]heptanyl (e.g. bicyclo[3.2.1]octanyl, bicyclo [2.2.1]heptanyl), having one or two heteroatoms selected from N and O; spiro ring systems such as spiropentanyl, spiro[2.3]hexanyl spiro[3.3]heptanyl, spiro[3.4]octanyl, spiro[4.4]nonanyl, spiro[3.5]nonanyl, spiro[4.5]decanyl, (e.g. spiro[3.3]heptanyl, spiro[4.4]nonanyl, having one or two heteroatoms selected from N and O, (e.g. diazaspiro [3.3]heptanyl, oxa-azaspiro[3.3]heptlanyl, diazaspiro[4.4] nonanyl, oxa-azaspiro[4.4]nonanyl)).

In some embodiments, Z is —($NR^4R^5$), wherein $R^4$ and $R^5$ are independently of each other H, $C_{1-4}$ alkyl, cyclopropyl, cylobutyl, 3 to 6-membered heterocycloalkyl containing 0, 1, or 2 N-atoms and 0, 1, or 2 O-atoms, or —($NR^6R^7$), —($CHR^6R^7$), wherein $R^6$ and $R^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments, —($NR^6R^7$) ring systems include

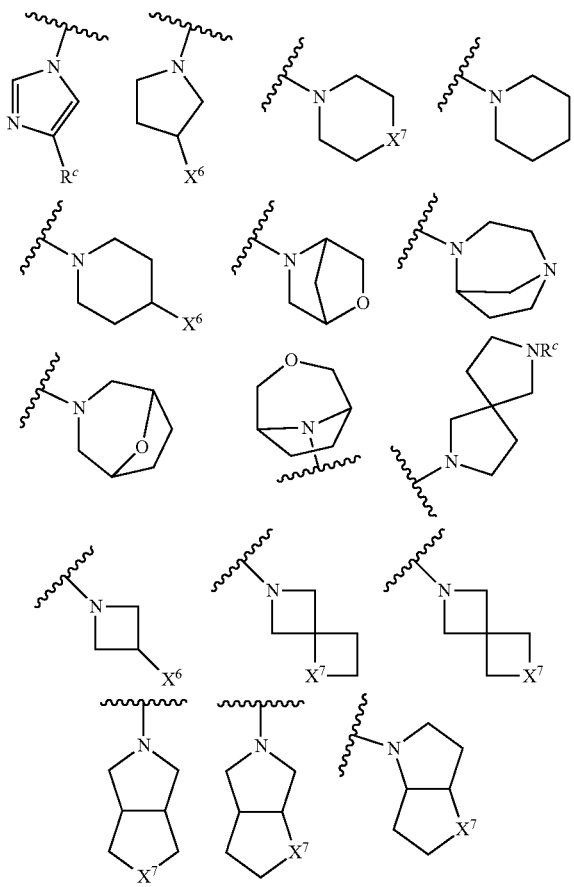

wherein $R^c$ is H, $C_{1-4}$ alkyl, oxetane; $X^6$ is H, —$CH_3$, —OH, —$OCH_3$, —$N(CH_3)_2$, F, Cl; $X^7$ is —O—, —NH— or —$N(CH_3)$—, —$SO_2$.

In some embodiments, —($CHR^6R^7$) ring systems include

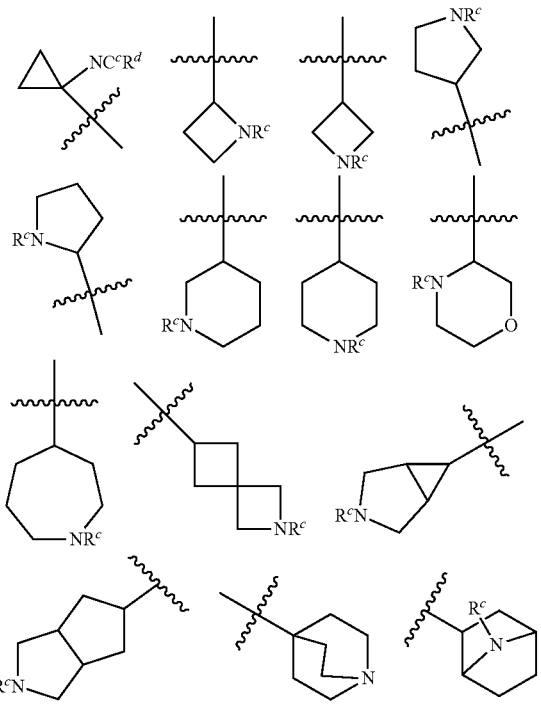

wherein $R^c$ is H, $C_{1-4}$ alkyl, oxetane, and $R^d$ is H, $C_{1-4}$ alkyl. In such embodiments, Z includes at least one nitrogen atom.

In some embodiments of a compound of formula I, the following variations of group $R^1$ are included, which apply to each of the embodiments cited above. In some embodiments, $R^1$ is —$CR_b$=$CHR_a$, wherein $R^a$, $R^b$ are independently of each other H, hal, —$CH_2$—O—$CH_3$. In some embodiments, $R^1$ is —CH=$CH_2$. In some embodiments, $R^1$ is —CH=CH-hal or —C(hal)=$CH_2$. In some embodiments, $R^1$ is —CH=CH—$CH_2$—O—$CH_3$. In some embodiments, $R^1$ is —C≡CH or —C≡C—$CH_3$.

In some embodiments, $Y^2$ is covalent bond. In some embodiments, $Y^2$ is —O—. In some embodiments, $Y^2$ is —NH— or $NCH_3$—. In some embodiments, $Y^2$ is —C≡C—.

In some embodiments, L is a covalent bond. In some embodiments, L is straight chain or branched $C_{1-4}$ alkyl (e.g., —$CH_2$—, —$(CH_2)_2$—, —$(CH_2)_3$—, —$(CH_2)_4$—, —$C(CH_3)_2$—, or —$CH_2$—$C(CH_3)_2$—). In some embodiments, L is

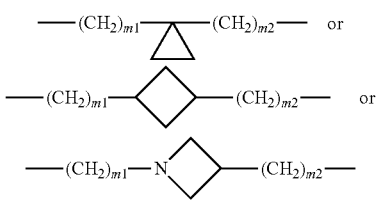

wherein m1, m2 are independently of each other 0, 2, 3, or 4 (e.g., 0, 1, or 2). In some embodiments, m2 is 0 and m1 is 0 or 1 or 2. In some embodiments, m1 and m2 are 1 or m1 and m2 are 2.

In some aspects, the present disclosure is directed towards a compound or pharmaceutically acceptable salts or stereoisomers thereof of formula

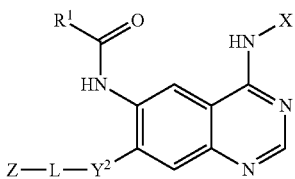

wherein L is a covalent bond, straight chain or branched $C_{1-4}$ alkyl or

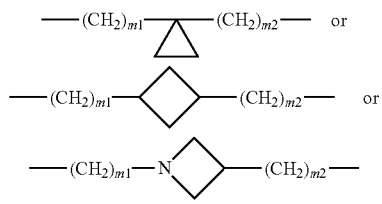

wherein m1, m2 are independently of each other 0, 1, 2, 3, or 4;

$Y^2$ is a covalent bond, —O—, —NH—, —NCH$_3$—, —C≡C—;

Z is —(NR$^4$R$^5$), wherein R$^4$ and R$^5$ are independently of each other H, $C_{1-6}$ alkyl, cyclopropyl, cylobutyl, 3-6-membered heterocycloalkyl, or —(NR$^6$R$^7$), —(CHR$^6$R$^7$), wherein R$^6$ and R$^7$ form together with the atom to which they are attached to 3-6-membered heteroaryl or 3-9-membered heterocycloalkyl, wherein the 3-9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl;

R$^1$ is —CR$_b$=CHR$_a$, —C≡CH or —C≡C—CH$_3$; wherein R$^a$, R$^b$ are independently of each other H, hal, —CH$_2$—O—CH$_3$; and X is a group of formula (ii)a

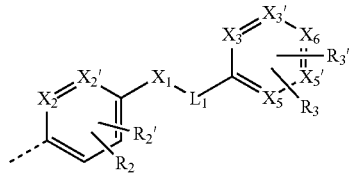

wherein X$^1$ is —O—, —CH$_2$—, —NH—, —S—; X$^2$, X$^{2'}$, X$^3$, X$^{3'}$, X$^5$, X$^{5'}$, X$^6$ are independently of each other —N=, —CH=;

L$^1$ is a covalent bond or straight chain branched $C_{1-3}$alkyl, which is unsubstituted or substituted with hal.

In some embodiments substituent Z-L-Y$^2$ contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if Y$^2$ is not N(H) or (NMe) or L does not contain a nitrogen atom.

In some embodiments R$^a$ and R$^b$ are hydrogen.

In some embodiments, L$^1$ is straight chain or branched $C_{1-3}$alkyl, which is unsubstituted or substituted with hal. In some embodiments, L$^1$ is not a covalent bond.

In some embodiments, R$^2$, R$^{2'}$, R$^3$, R$^{3'}$ are independently of each other H, $C_{1-6}$ alkyl, hal, —CF$_3$, —OCF$_3$.

In some embodiments of a compound of formula I, the following variations of group R$^1$ are included, which apply to each of the embodiments cited above. In some embodiments, R$^1$ is —CR$_b$=CHR$_a$, wherein R$^a$, R$^b$ are independently of each other H, hal, —CH$_2$—O—CH$_3$. In some embodiments, R$^1$ is —CH=CH$_2$. In some embodiments, R$^1$ is —CH=CH-hal or —C(hal)=CH$_2$. In some embodiments, R$^1$ is —CH=CH—CH$_2$—O—CH$_3$. In some embodiments, R$^1$ is —C≡CH or —C≡C—CH$_3$.

Each of the following definitions equally applies to a compound of formula I.

In some embodiments, X$^1$ is —O—. In some embodiments, X$^1$ is —CH$_2$—. In some embodiments, X$^1$ is —NH—. In some embodiments, X$^1$ is —S—. In some embodiments, L$^1$ is a covalent bond. In some embodiments, L$^1$ is —CH$_2$— or —CH(CH$_3$)— or —CH(hal)-. In some embodiments, L$^1$ is —CH$_2$—CH$_2$— or —CH$_2$—CH(CH$_3$)— or —CH$_2$—CH(hal)-.

In some embodiments, linker combinations -X$^1$-L$^1$- for (ii)a include —O—, —CH$_2$—, —O—CH$_2$—, —NH—CH$_2$—, —S—CH$_2$—, —CH$_2$—CH$_2$—, —O—CH(CH$_3$)—, —CH$_2$—CH(CH$_3$)—, —NH—CH(CH$_3$)—, —S—CH(CH$_3$)—, —O—CH(hal)-, —CH$_2$—CH(hal)-, —NH—CH(hal)-, —S—CH(hal)- (e.g., —O—, —CH$_2$—, —O—CH$_2$—, —NH—CH$_2$—, —CH$_2$—CH$_2$—, —O—CH(CH$_3$)—, —CH$_2$—CH(CH$_3$)—, —O—CH(hal)-, —CH$_2$—CH(hal)- (e.g., —O—, —CH$_2$—, —O—CH$_2$—, —NH—CH$_2$—, —CH$_2$—CH$_2$—)).

In some embodiments, -X$^1$-L$^1$ - is —O—. In some embodiments, -X$^1$-L$^1$- is —O—CH$_2$—. In some embodiments, group X has the following formula (ii)b, (e.g. (ii)b-1 or (ii)b-2):

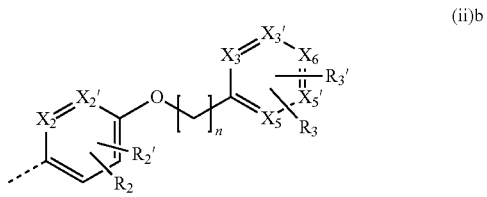

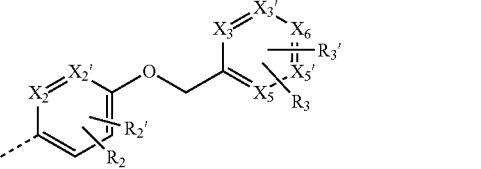

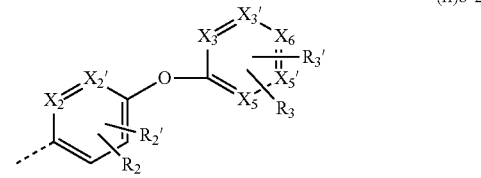

wherein X$^2$, X$^{2'}$ and X$^3$, X$^{3'}$, X$^5$, X$^{5'}$, X$^6$ are independently of each other —N= or —CH=; R$^2$, R$^{2'}$ and R$^3$, R$^{3'}$ are independently of each other H, $C_{1-6}$ alkyl, hal, —CF$_3$, or —OCF$_3$, and n is 0, 1, 2, 3.

In some embodiments, both X$^2$, X$^{2'}$ are —CH= (i.e. a phenyl ring). In some embodiments, X$^2$ is —N= and X$^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other H, $C_{1-6}$ alkyl, hal (e.g. H, —CH$_3$, F, Cl). In some embodiments, $R^3$ and $R^{3'}$ are independently of each other H, $C_{1-6}$ alkyl, hal, —CF$_3$, —OCF$_3$.

In some embodiments, group X has the following formula (ii)d-1, (ii)d-2, (ii)d-3, (ii)d-4, (ii)d-5 or (ii)d-6

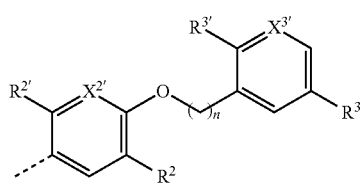
(ii)d-1

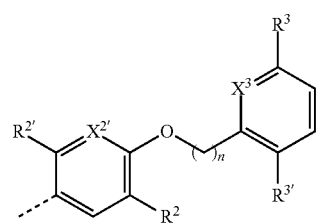
(ii)d-2

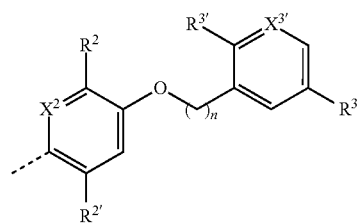
(ii)d-3

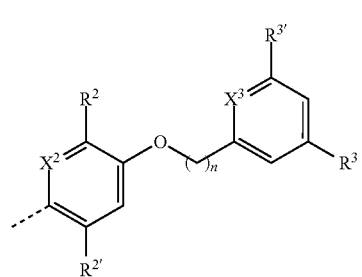
(ii)d-4

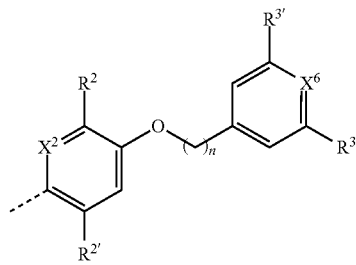
(ii)d-5

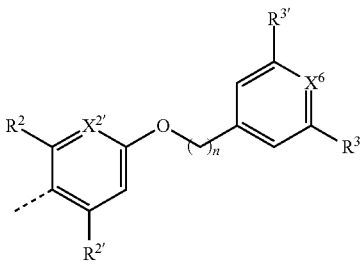
(ii)d-6 wherein $X^2$, $X^{2'}$, $X^3$, $X^{3'}$, $X^6$ are independently of each other —N= or —CH=; and $R^2$, $R^{2'}$, $R^3$, $R^{3'}$ are independently of each other H, $C_{1-6}$ alkyl, hal, —CF$_3$, or —OCF$_3$, n is 0 or 1.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, group X has the following formula (ii)e-1, (ii)e-2, (ii)e-3, (ii)e-4, (ii)e-5 or (ii)e-6

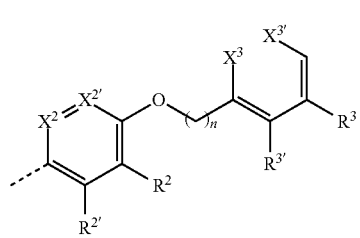
(ii)e-1

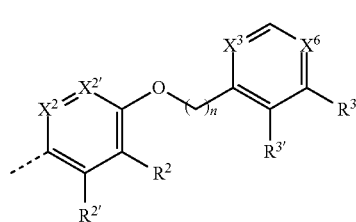
(ii)e-2

-continued

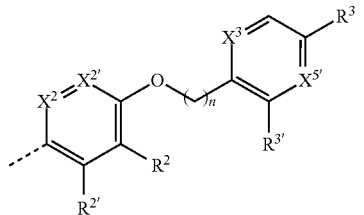
(ii)e-3

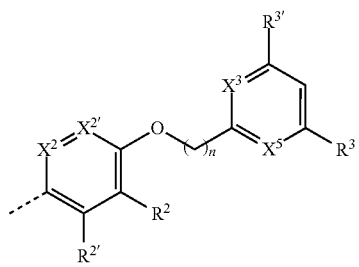
(ii)e-4

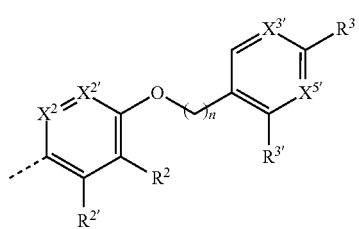
(ii)e-5

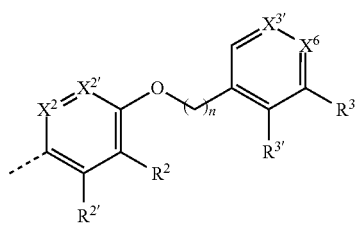
(ii)e-6 wherein $X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, -$X^1$-$L^1$- is —NH—. In some embodiments, -$X^1$-$L^1$- is —NH—$CH_2$—. In some embodiments, group X has the following formula (ii)c (e.g. (ii)c-1 or (ii)c-2):

(ii)c (ii)c-1

(ii)c-2 wherein $X^2$, $X^{2'}$ and $X^3$, $X^{3'}$, $X^5$, $X^{5'}$, $X^6$ are independently of each other —N= or —CH=; $R^2$, $R^{2'}$ and $R^3$, $R^{3'}$ are independently of each other H, $C_{1-6}$ alkyl, hal, —$CF_3$, or —$OCF_3$, and n is 0, 1, 2, 3.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other H, $C_{1-6}$ alkyl, or hal (e.g., H, —$CH_3$, F, or Cl). In some embodiments, $R^3$ and $R^{3'}$ are independently of each other H, $C_{1-6}$ alkyl, hal, —$CF_3$, or —$OCF_3$.

In some embodiments, group X has the following formula (ii)f-1, (ii)f-2, (ii)f-3, (ii)f-4, (ii)f-5 or (ii)f-6

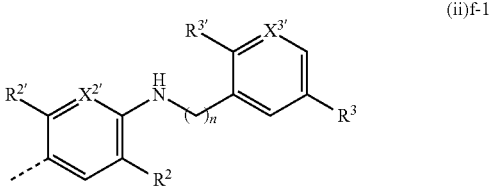
(ii)f-1

-continued

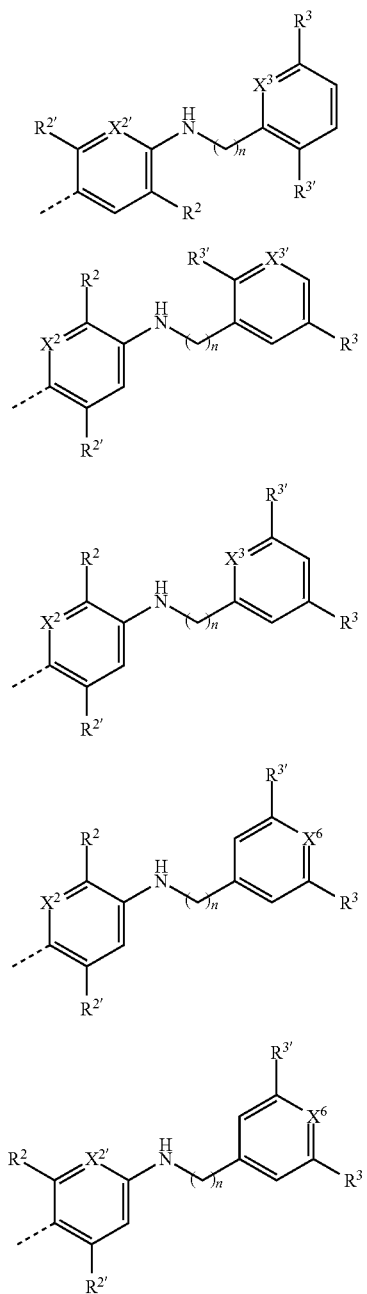

wherein $X^2$, $X^{2'}$, $X^3$, $X^{3'}$, $X^6$ are independently of each other —N═ or —CH═; and $R^2$, $R^{2'}$, $R^3$, $R^{3'}$ are independently of each other H, $C_{1-6}$ alkyl, hal, —$CF_3$, or —$OCF_3$, n is 0 or 1.

In some embodiments, $X^2$ and $X^{2'}$ are —CH═ (i.e. a phenyl ring) and $X^3$, $X^{3'}$ and $X^6$ are —CH═ (i.e. a phenyl ring).

In some embodiments, $X^2$ and $X^{2'}$ are —CH═ (i.e. a phenyl ring) and $X^3$, $X^{3'}$ and $X^6$ are —N═ (i.e. a pyridine ring).

In some embodiments, $X^2$ and $X^{2'}$ are —N═ (i.e. a pyridine ring) and $X^3$, $X^{3'}$ and $X^6$ are —CH═ (i.e. a phenyl ring).

In some embodiments, $X^2$ and $X^{2'}$ a —N═ (i.e. a pyridine ring) and $X^3$, $X^{3'}$ and $X^6$ are —N═ (i.e. a pyridine ring).

In some embodiments, group X has the following formula (ii)g-1, (ii)g-2, (ii)g-3, (ii)g-4, (ii)g-5 or (ii)g-6

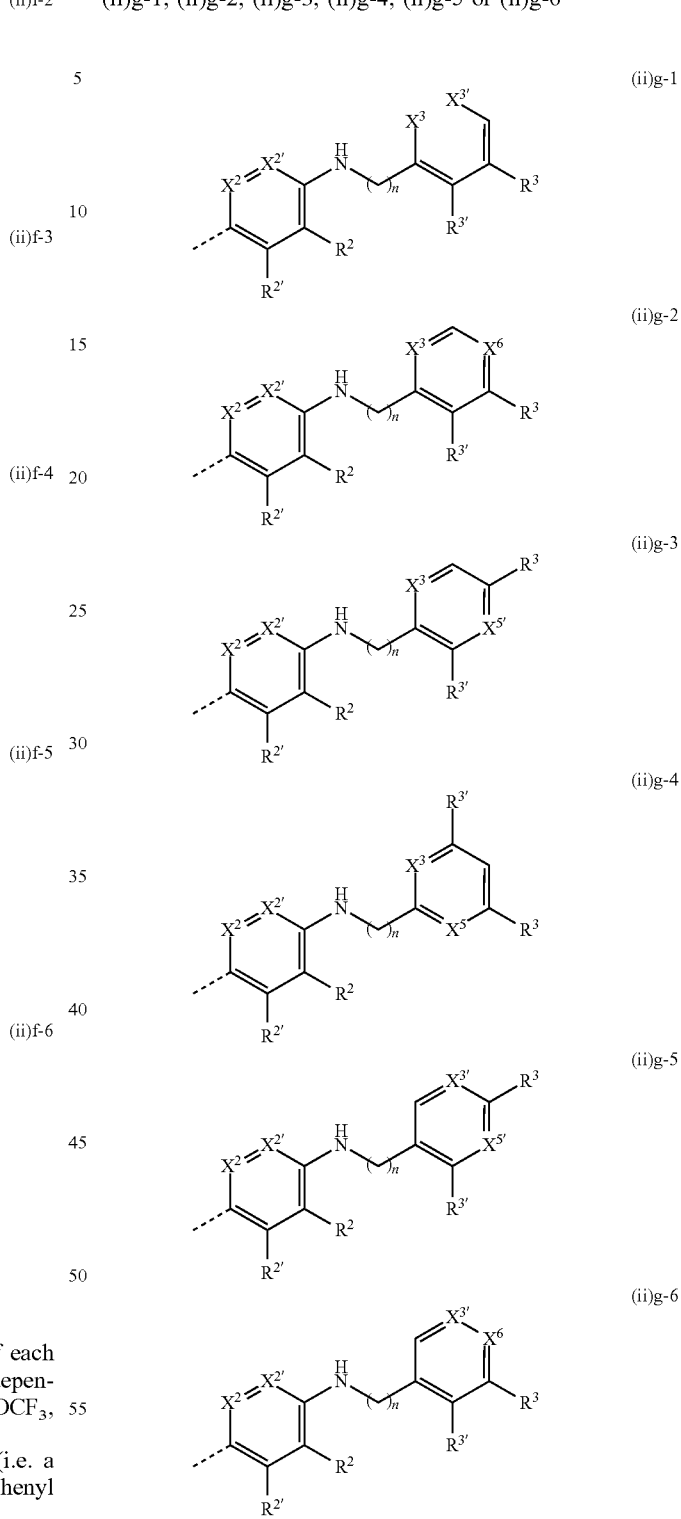

wherein $X^2$, $X^{2'}$, $X^3$, $X^{3'}$, $X^5$, $X^{5'}$, $X^6$ are independently of each other —N═ or —CH═; and $R^2$, $R^{2'}$, $R^3$, $R^{3'}$ are independently of each other H, $C_{1-6}$ alkyl, hal, —$CF_3$, or —$OCF_3$, n is 0 or 1.

In some embodiments, both $X^2$, $X^{2'}$ are —CH═ (i.e. a phenyl ring). In some embodiments, $X^2$ is —N═ and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other H, $C_{1-6}$ alkyl, or hal (e.g., H, —CH$_3$, F, or Cl). In some embodiments, $R^3$ and $R^{3'}$ are independently of each other H, $C_{1-6}$ alkyl, hal, —CF$_3$, or —OCF$_3$.

In some embodiments, $R^3$ is H, hal, —CF$_3$, or —OCF$_3$. In some embodiments, $R^{3'}$ is H, hal or $C_{1-6}$ alkyl (e.g., H, hal or —CH$_3$).

In some embodiments, $R^3$ and $R^{3'}$ are H. In some embodiments, $R^3$ and $R^{3'}$ are hal. In some embodiments, $R^3$ is hal, —CF$_3$, or —OCF$_3$ and $R^{3'}$ is H. In some embodiments, $R^3$ is H and $R^{3'}$ is hal, or $C_{1-6}$ alkyl.

In some embodiments, $R^2$ and $R^{2'}$ are H. In some embodiments, $R^2$ and $R^{2'}$ are hal. In some embodiments, $R^2$ is hal or $C_{1-6}$ alkyl and $R^{2'}$ is H. In some embodiments, $R^2$ is H and $R^{2'}$ is hal.

In some embodiments of a compound of the present disclosure, group X is

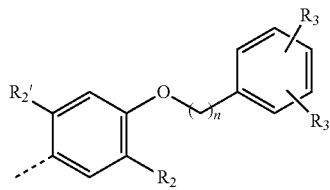
(ii)h-a

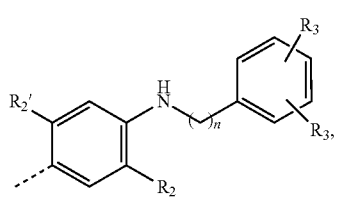
(ii)i-a

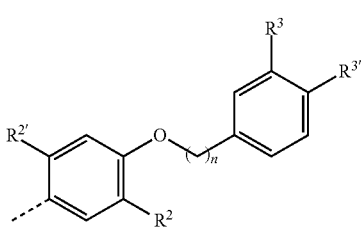
(ii)h-a-1

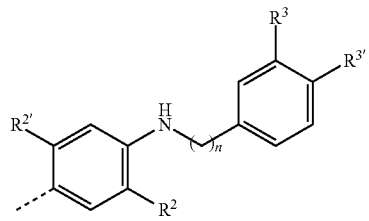
(ii)i-a-1 wherein $R^2$, $R^{2'}$ are independently of each other H, $C_{1-6}$ alkyl, hal, (e.g. H, —CH$_3$, F, Cl); $R^3$, $R^{3'}$ are is H, $C_{1-6}$ alkyl, hal, —CF$_3$, —OCF$_3$; and n is 0 or 1.

In some embodiments of a compound of formula I group X is

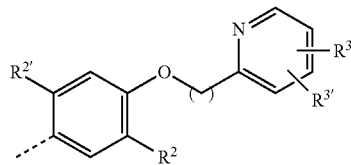
(ii)h-b

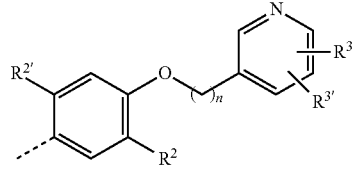
(ii)h-c

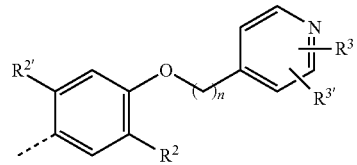
(ii)h-d (e.g.

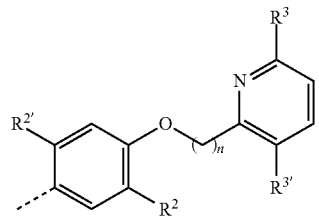
(ii)h-b-1

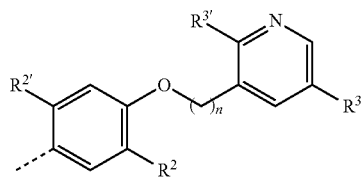
(ii)h-c-1

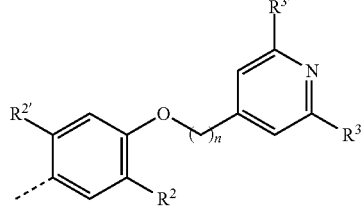
(ii)h-d-1 wherein $R^2$, $R^{2'}$ are independently of each other H, $C_{1-6}$ alkyl, hal, (e.g. H, —$CH_3$, F, Cl); $R^3$, $R^{3'}$ are H, $C_{1-6}$ alkyl, hal, —$CF_3$, —$OCF_3$; and n is 0 or 1.

In some embodiments of a compound of the present disclosure, group X is

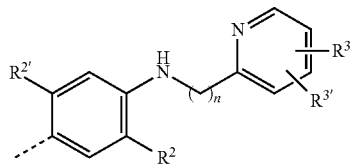
(ii)i-b

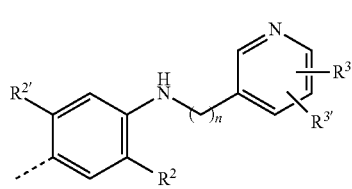
(ii)i-c

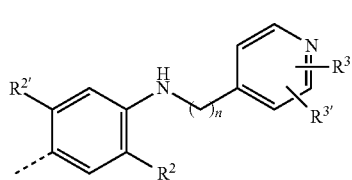
(ii)i-d

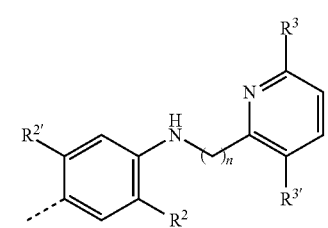
(ii)i-b-1

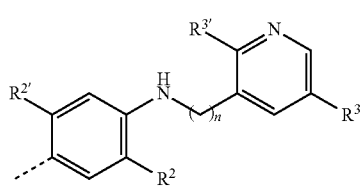
(ii)i-c-1

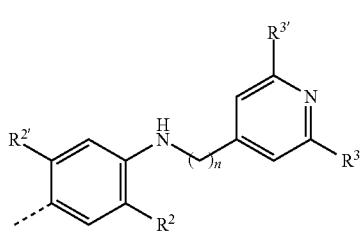
(ii)i-d-1 wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1.

In some embodiments of a compound of formula I, group X is

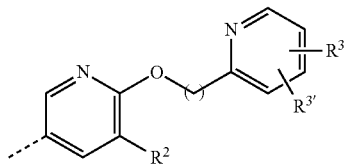
(ii)h-e

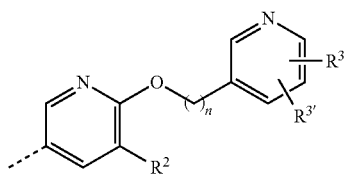
(ii)h-f

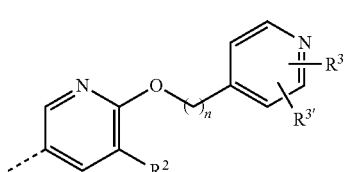
(ii)h-g

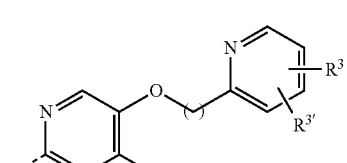
(ii)h-h

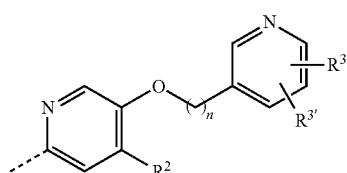
(ii)h-i

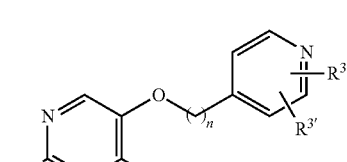
(ii)h-j

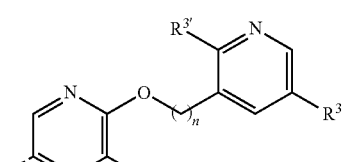
(ii)h-e-1

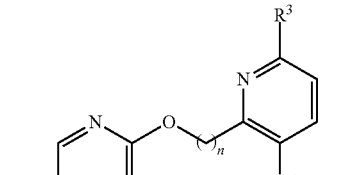
(ii)h-f-1

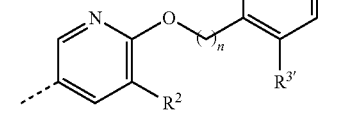

-continued
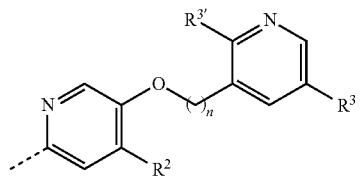
(ii)h-g-1
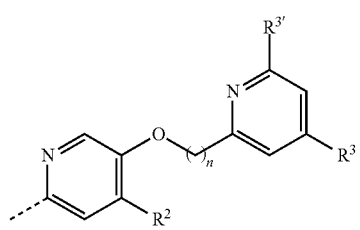
(ii)h-h-1
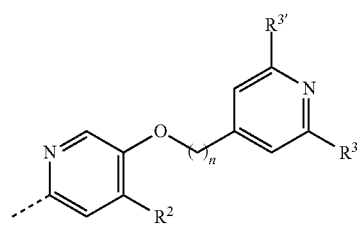
(ii)h-i-1
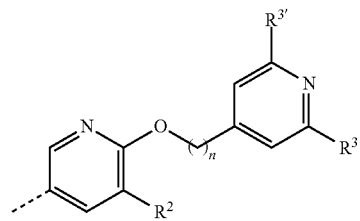
(ii)h-j-1
wherein $R^2$, $R^{2'}$ are independently of each other H, $C_{1-6}$ alkyl, hal, (e.g. H, —$CH_3$, F, Cl); $R^3$, $R^{3'}$ are H, $C_{1-6}$ alkyl, hal, —$CF_3$, —$OCF_3$; and n is 0 or 1.
In some embodiments of a compound of formula I, group X is
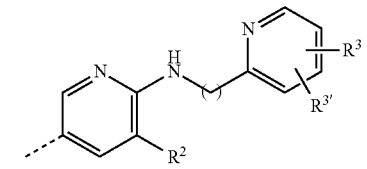
(ii)i-e
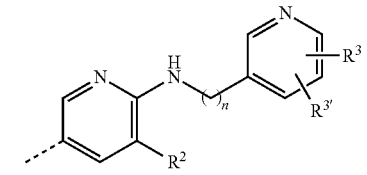
(ii)i-f
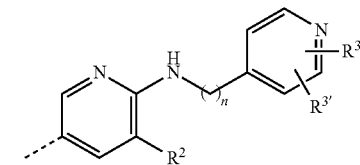
(ii)i-g
-continued
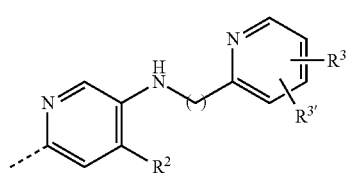
(ii)i-h
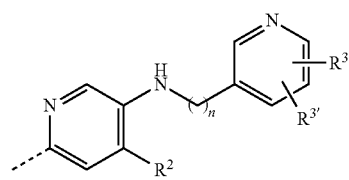
(ii)i-i
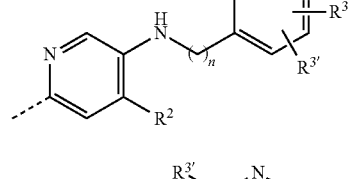
(ii)i-j
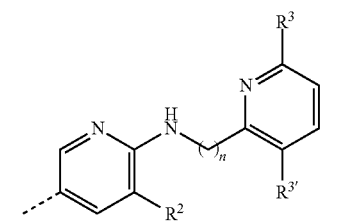
(ii)i-e-1
(ii)i-f-1
(ii)i-g-1
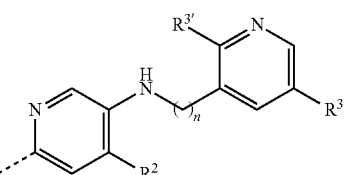
(ii)i-h-1
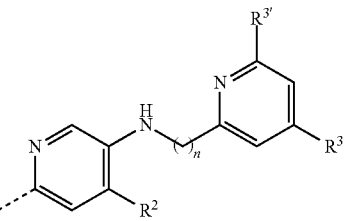
(ii)i-i-1
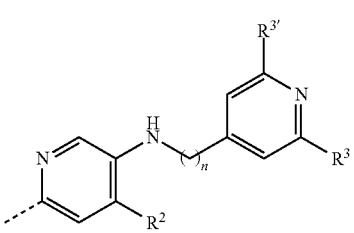

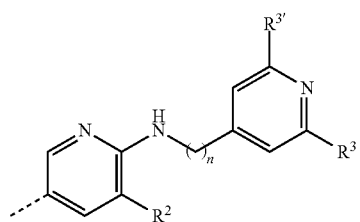
(ii)i-j-1 wherein R² is H, C₁₋₆ alkyl, hal (e.g. H, —CH₃, F, Cl); R³, R³' are H, C₁₋₆ alkyl, alkyl, hal, —CF₃, —OCF₃; and n is 0 or 1.

In some embodiments of a compound of formula I group X is

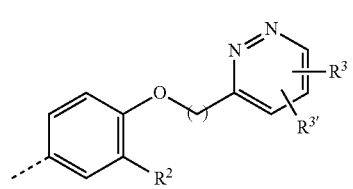
(ii)h-k

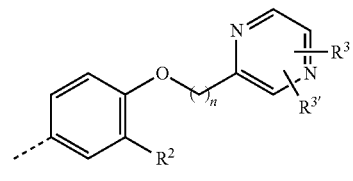
(ii)h-l

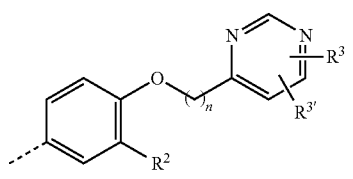
(ii)h-m

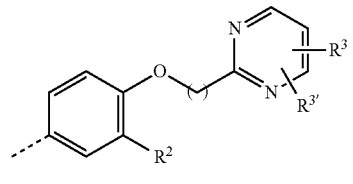
(ii)h-n

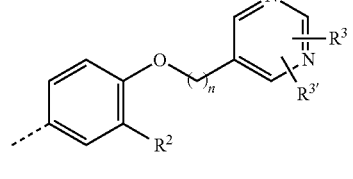
(ii)h-o

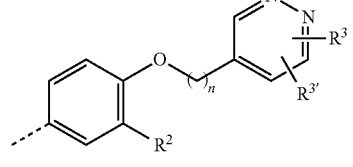
(ii)h-p

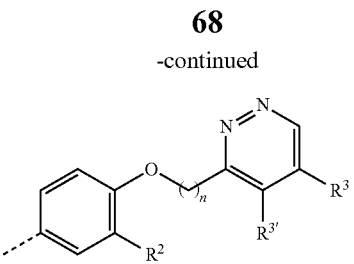
(ii)h-k-1

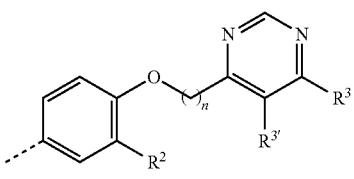
(ii)h-l-1

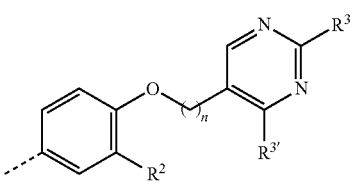
(ii)h-m-1

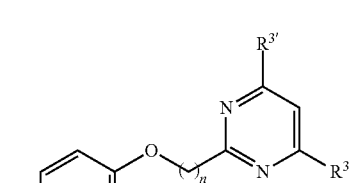
(ii)h-n-1

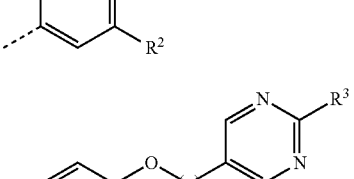
(ii)h-o-1

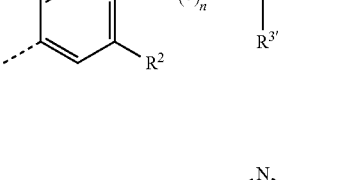
(ii)h-p-1 wherein R², R²' are independently of each other H, C₁₋₆ alkyl, hal (e.g. H, —CH₃, F, Cl); R³, R³' are H, C₁₋₆ alkyl, hal, —CF₃, —OCF₃; and n is 0 or 1.

In some embodiments of a compound of formula I group X is

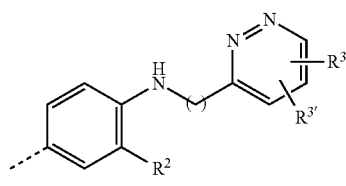
(ii)i-k

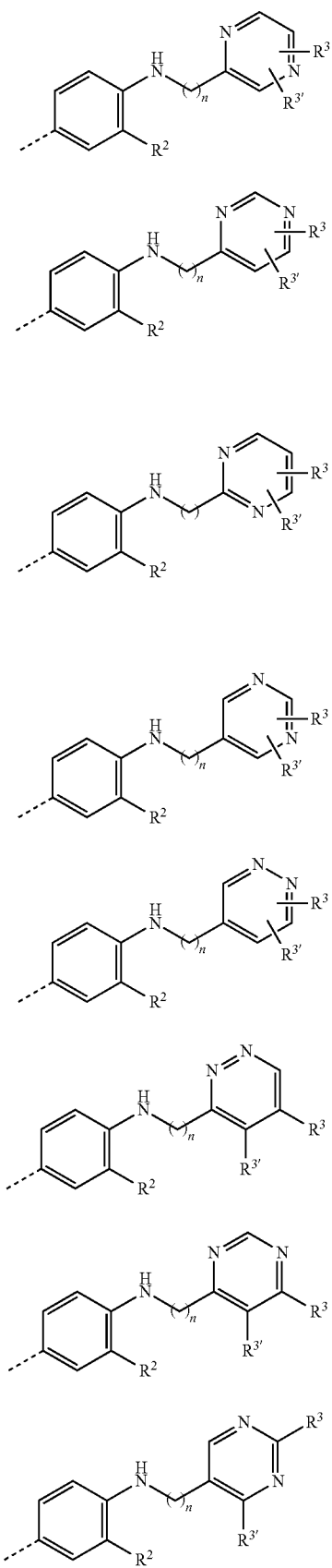

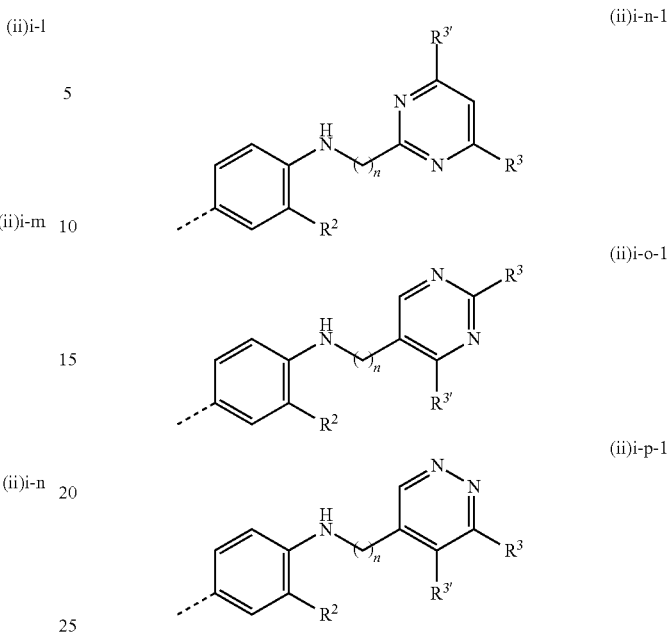

wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1.

In some embodiments, $R^4$ and $R^5$ are independently of each other H, $C_{1-4}$ alkyl, cyclopropyl, tetrahydrofuryl.

In some embodiments of a compound of formula I, a 3 to 6-membered heterocycloalkyl (in combination with —($NR^4R^5$)) refers to a non-aromatic or partially aromatic ring system having 3, 4, 5, or 6 ring atoms selected from C, N, O, or S (e.g. C, N, or O), the number of N atoms being 0, 1, 2 and the number of O and S atoms each being 0, 1, 2. Examples of 3 to 6-membered heterocycloalkyl groups include oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl, 1,4-dithianyl, 1,3-dioxane, 1,3-dithianyl, piperazinyl, thiomorpholinyl, dioxothiomorpholinyl, piperidinyl, morpholinyl and the like. In some embodiments, 3 to 6-membered heterocycloalkyl include 5-membered heterocycloalkyl having 1 or 2 O-atoms, (e.g. oxiranyl, oxetanyl, tetrahydrofuranyl, dioxanyl).

In some embodiments of a compound of formula I, a 3 to 6-membered heteroaryl (in combination with —($NR^6R^7$) or —($CHR^6R^7$)) refers to a (fully) aromatic ring system having 3, 4, 5, or 6 ring atoms, (e.g. 5 ring atoms), selected from C, N, O, or S (e.g. C, N, or O, and C or N, with the number of N atoms being 0, 1, 2 or 3 and the number of O and S atoms each being 0, 1 or 2). Examples of "heteroaryl" include furyl, imidazolyl, isoxazolyl, oxazolyl, pyrazinyl, pyrazolyl (pyrazyl), pyridazinyl, pyridinyl, pyrimidinyl, pyrrolyl, thiazolyl, thienyl, and the like. In some embodiments, "heteroaryl" include pyrrolyl, imidazolyl. Preferably, the aromatic ring system is a nitrogen containing heteroaryl.

In some embodiments of a compound of formula I, a 3 to 9-membered heterocycloalkyl (in combination with —($NR^6R^7$) or —($CHR^6R^7$)) refers to a non-aromatic or partially aromatic ring system having 3 to 9 ring atoms selected from C, N, O, or S, (e.g. C, N, or O), the number of N atoms being 0, 1, 2 or 3 and the number of O and S atoms each being 0, 1 or 2, Examples of a 3 to 9-membered heterocycloalkyl (in combination with —($NR^6R^7$) or —($CHR^6R^7$)) include monocycles such as oxiranyl, thiaranyl, aziradinyl, oxetanyl, thiatanyl, azetidinyl, pyrrolidinyl, tetrahydrofuranyl, tetrahrydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl, oxepanyl, thiepanyl, azepanyl, diazepanyl, oxazepanyl (e.g. azetidinyl, pyrrolidinyl, piperidinyl, piperazinyl, morpholinyl, azepanyl); fused ring systems, such as 3-azabicyclo[3.1.0]hexyl, 3-azabicyclo[3.3.0]octyl, 3,7-diazabicyclo[3.3.0]octyl, 3-aza-7-oxabicyclo[3.3.0]octyl, 2,6-diazabicyclo[3.3.0]octyl, 2,7-diazabicyclo[3.3.0]octyl, 2,8-diazabicyclo[4.3.0]nonyl, 3-oxa-8-azabicyclo[4.3.0]nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4,3.0]nonyl, and the like; bridged ring systems such as bicyclo[3.3.1]nonanyl, bicyclo[3.2.1]octanyl, bicyclo[2.2.2]octanyl, bicyclo[3.1.1]heptanyl, bicyclo[2.2.1]heptanyl (e.g. bicyclo[3.2.1]octanyl, bicyclo[2.2.1]heptanyl), having one or two heteroatoms selected from N and O; spino ring systems such as spiropentanyl, spiro[2.3]hexanyl spiro[3.3]heptanyl, spiro[3.4]octanyl, spiro[4.4]nonanyl, spiro[3.5]nonanyl, spiro[4.5]decanyl (e.g. spiro[3.3]heptanyl, spiro[4.4]nonanyl), having one or two heteroatoms selected from N and O, (e.g. diazaspiro[3.3]heptanyl, oxa-azaspiro[3.3]heptanyl, diazaspiro[4.4]nonanyl, oxa-azaspiro[4.4]nonanyl). Preferably, the 3 to 9-membered heterocycloalkyl contains at least one nitrogen atom.

In some embodiments, Z is —(NR$^4$R$^5$), wherein R$^4$ and R$^5$ are independently of each other H, C$_{1-6}$ alkyl cyclopropyl, cylobutyl, 3 to 6-membered heterocycloalkyl containing 0, 1, or 2 N-atoms and 0, 1, or 2 O-atoms, or —(NR$^6$R$^7$), —(CHR$^6$R$^7$), wherein R$^6$ and R$^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with C$_{1-4}$ alkyl, hal, —OR', —NR'R", wherein R', R" are independently of each other H or -C$_{1-4}$ alkyl.

In some embodiments, —(NR$^6$R$^7$) ring systems include

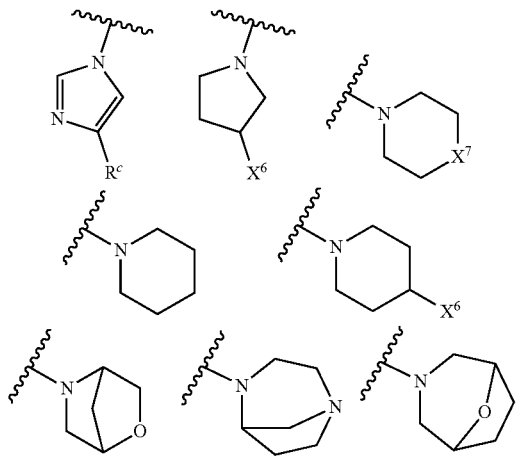

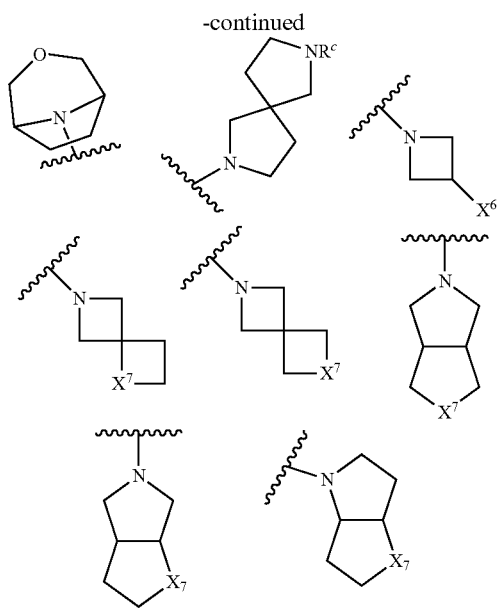

wherein R$^c$ is H, C$_{1-4}$ alkyl, oxetane; X$^6$ is H, —CH$_3$, —OH, —OCH$_3$, —OCF$_3$, —N(CH$_3$)$_2$, F, Cl; X$^7$ is —O—, —NH— or —N(CH$_3$)—, —SO$_2$.

In some embodiments, —(CHR$^6$R$^7$) ring systems include

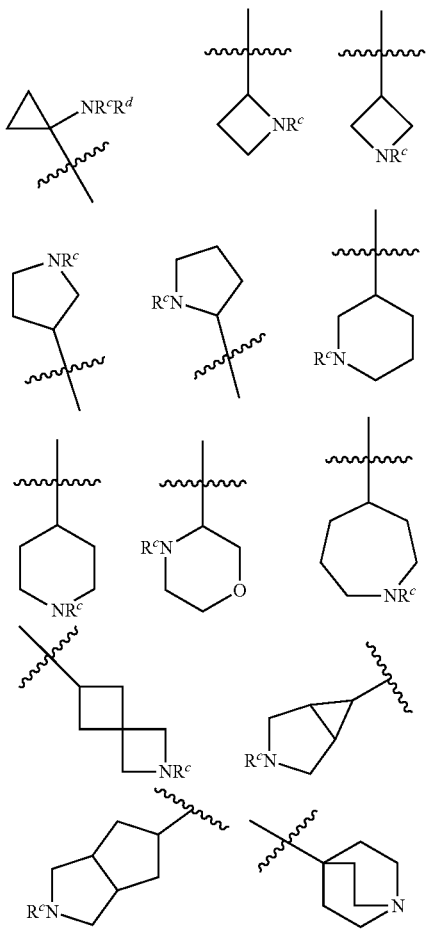

73
-continued

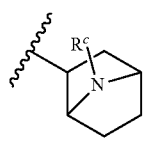

wherein $R^c$ is H, $C_{1-4}$ alkyl, oxetane, and $R^d$ is H, $C_{1-4}$ alkyl.

In some embodiments, $Y^2$ is covalent bond. In some embodiments, $Y^2$ is —O—. In some embodiments, $Y^2$ is —NH—, NCH$_3$—. In some embodiments, $Y^2$ is —C≡C—.

In some embodiments, L is a covalent bond. In some embodiments, L is straight chain or branched $C_{1-4}$ alkyl, (e.g. —CH$_2$—, —(CH$_2$)$_2$—, —(CH$_2$)$_3$—, —(CH$_2$)$_4$— or —C(CH$_3$)$_2$— or —CH$_2$—C(CH$_3$)$_2$—). In some embodiments, L is

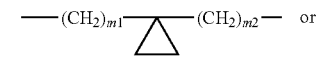

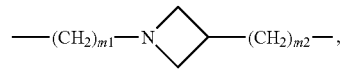

wherein m1, m2 are independently of each other 0, 1, 2, 3, 4, (e.g. 0 or 1 or 2). In some embodiments, m2 is 0 and m1 is 0 or 1 or 2. In some embodiments, m1 and m2 are 1 or m1 and m2 are 2.

In some embodiments, the compound of formula I is not any of

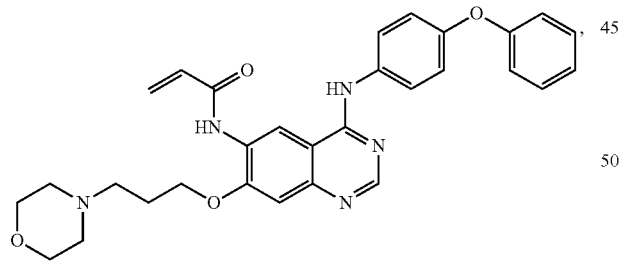

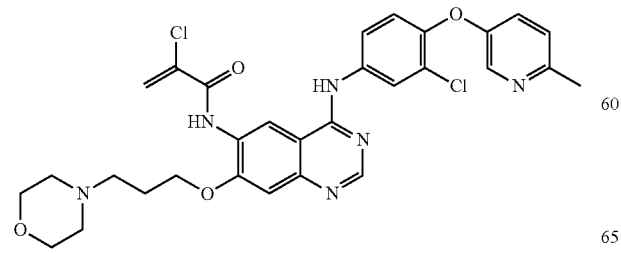

74
-continued
or

wherein Q is

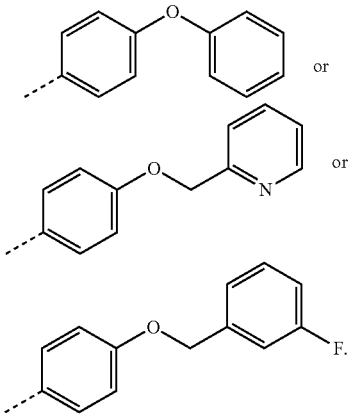

In some embodiments, the present disclosure is directed towards a compound or pharmaceutically acceptable salts or stereoisomers thereof of formula II or III

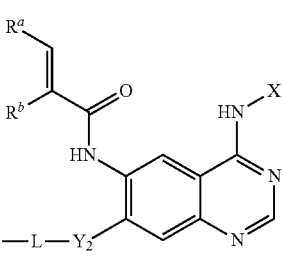

II

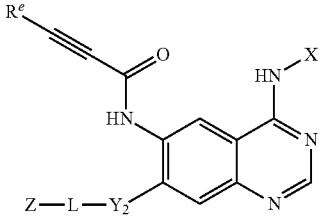

III wherein L is a covalent bond, straight chain or branched $C_{1-4}$ alkyl or

-continued

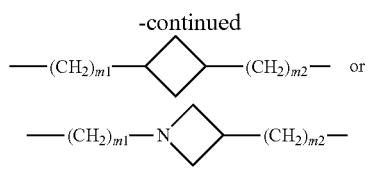

wherein m1, m2 are independently of each other 0, 1, 2, 3, or 4;

$Y^2$ is a covalent bond, —O—, —NH—, —NCH$_3$—, —C≡C—;

Z is —(NR$^4$R$^5$), wherein R$^4$ and R$^5$ are independently of each other H, C$_{1-6}$ alkyl, cyclopropyl, cylobutyl, 3 to 6-membered heterocycloalkyl, or —(NR$^6$R$^7$), —(CHR$^6$R$^7$), wherein R$^6$ and R$^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with C$_{1-4}$ alkyl, hal, —OR', —NR'R", wherein R', R" are independently of each other H or -C$_{1-4}$ alkyl; R$^a$, R$^b$ are independently of each other H, hal, or —CH$_2$—O—CH$_3$, (e.g. H), and R$_e$ is H or methyl; and X is a group of formula (ii)a

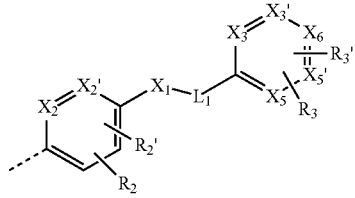

wherein X$^1$ is —O—, —CH$_2$—, —NH—, —S—;

L$^1$ is a covalent bond or straight chain or branched C$_{1-3}$ alkyl, which is unsubstituted or substituted with hal, X$^2$, X$^{2'}$, X$^3$X$^{3'}$, X$^5$, X$^{5'}$, X$^6$ are independently of each other —N=, —CH=;

R$^2$, R$^{2'}$, R$^3$, R$^{3'}$ are independently of each other H, C$_{1-6}$ alkyl, hal, —CF$_3$, —OCF$_3$;

In some embodiments substituent Z-L-Y$_2$ contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if Y$^2$ is not N(H) or (NMe) or L does not contain a nitrogen atom.

In some embodiments R$^a$ and R$^b$ are hydrogen.

In some embodiments, L$^1$ is straight chain or branched C$_{1-3}$alkyl, which is unsubstituted or substituted with hal. In some embodiments, L$^1$ is not a covalent bond.

In some embodiments, X$^1$ is —O—. In some embodiments, X$^1$ is —CH$_2$—. In some embodiments, X$^1$ is —NH—. In some embodiments, X$^1$ is —S—. In some embodiments, L$^1$ is a covalent bond. In some embodiments, L$^1$ is —CH$_2$— or —CH(CH$_3$)— or —CH(hal)-. In some embodiments, L$^1$ is —CH$_2$—CH$_2$— or —CH$_2$—CH(CH$_3$)— or —CH$_2$—CH(hal)-.

In some embodiments, linker combinations -X$^1$-L$^1$- for (ii)a include —O—, —CH$_2$—, —O—CH$_2$—, —NH—CH$_2$—, —S—CH$_2$—, —CH$_2$—CH$_2$—, —O—CH(CH$_3$)—, —CH$_2$—CH(CH$_3$)—, —NH—CH(CH$_3$)—, —S—CH(CH$_3$)—, —O—CH(hal)-, —CH$_2$—CH(hal)-, —NH—CH(hal)-, —S—CH(hal)-, (e.g. —O—, —CH$_2$—, —O—CH$_2$—, —NH—CH$_2$—, —CH$_2$—CH$_2$-, —O—CH(CH$_3$)—, —CH$_2$—CH(CH$_3$)—, —O—CH(hal)-, or —CH$_2$—CH(hal)- and —O—, —CH$_2$—, —O—CH$_2$—, —NH—CH$_2$—, or —CH$_2$—CH$_2$—).

In some embodiments, -X$^1$-L$^1$- is —O—, In some embodiments, -X$^1$-L$^1$- is —O—CH$_2$—. In some embodiments, group X has the following formula (ii)b (e.g. (ii)b-1 or (ii)b-2):

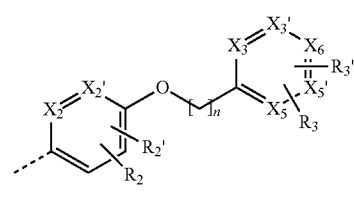

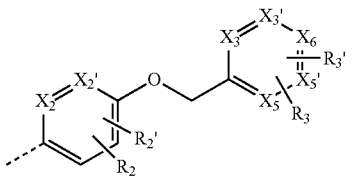

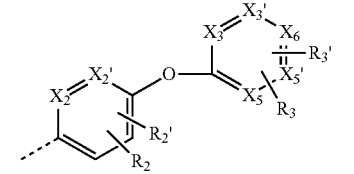

wherein X$^2$, X$^{2'}$ and X$^3$, X$^{3'}$, X$^5$, X$^{5'}$, X$^6$ are independently of each other —N= or —CH=; R$^2$, R$^{2'}$ and R$^3$, R$^{3'}$ are independently of each other H, C$_{1-6}$ alkyl, hal, —CF$_3$, or —OCF$_3$, and n is 0, 1, 2, 3.

In some embodiments, both X$^2$, X$^{2'}$ are —CH= (i.e. a phenyl ring). In some embodiments, X$^2$ is —N= and X$^{2'}$ is —CH= or X$^{2'}$ is —N= and X$^2$ is —CH= (i.e. a pyridine ring). In some embodiments, both X$^2$, X$^{2'}$ are —N= (i.e. a pyridazine ring).

In some embodiments, X$^3$, X$^{3'}$, X$^5$, X$^{5'}$, X$^6$ are —CH= (i.e. a phenyl ring). In some embodiments, X$^3$ is —N= and X$^{3'}$, X$^5$, X$^{5'}$, X$^6$ are —CH= or X$^{3'}$ is —N= and X$^3$, X$^5$, X$^{5'}$, X$^6$ are —CH= or X$^6$ is —N= and X$^3$, X$^{3'}$, X$^5$, X$^{5'}$ are —CH= (i.e. a pyridine ring).

In some embodiments, both X$^3$, X$^{3'}$ are —N= and X$^5$, X$^{5'}$, X$^6$ are —CH= or both X$^{3'}$, X$^6$ are —N= and X$^3$, X$^5$, X$^{5'}$ are —CH= (i.e. a pyridazine ring). In some embodiments, both X$^3$, X$^5$ are —N= and X$^{3'}$, X$^{5'}$, X$^6$ are —CH= or both X$^{3'}$, X$^{5'}$ are —N= and X$^3$, X$^5$, X$^6$ are —CH= or both X$^3$, X$^6$ are —N= and X$^{3'}$, X$^5$, X$^{5'}$ are —CH= (i.e. a pyrimidine ring). In some embodiments, both X$^3$, X$^{5'}$ are —N= and X$^{3'}$, X$^5$, X$^6$ are —CH= (i.e. a pyrazine ring).

In some embodiments, R$^2$ and R$^{2'}$ are independently of each other H, C$_{1-6}$ alkyl, hal (e.g. H, —CH$_3$, F, Cl). In some embodiments, R$^3$ and R$^{3'}$ are independently of each other H, C$_{1-6}$ alkyl, hal, —CF$_3$, —OCF$_3$.

In some embodiments, group X has the following formula (ii)d-1, (ii)d-2, (ii)d-3, (ii)d-4, (ii)d-5 or (ii)d-6

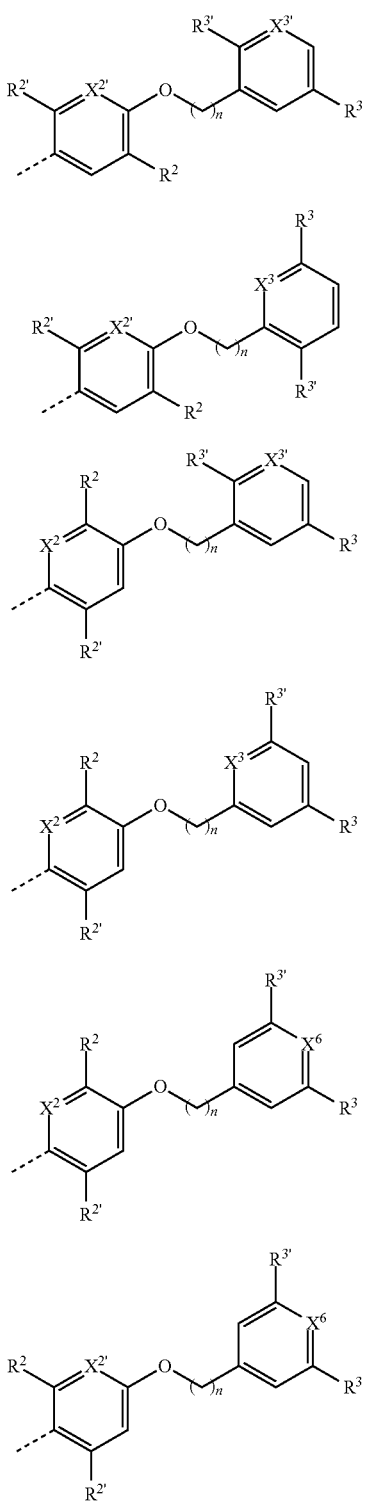

wherein $X^2$, $X^{2'}$, $X^3$, $X^{3'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, and n is 0 or 1.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, group X has the following formula (ii)e-1, (ii)e-2, (ii)e-3, (ii)e-4, (ii)e-5 or (ii)e-6

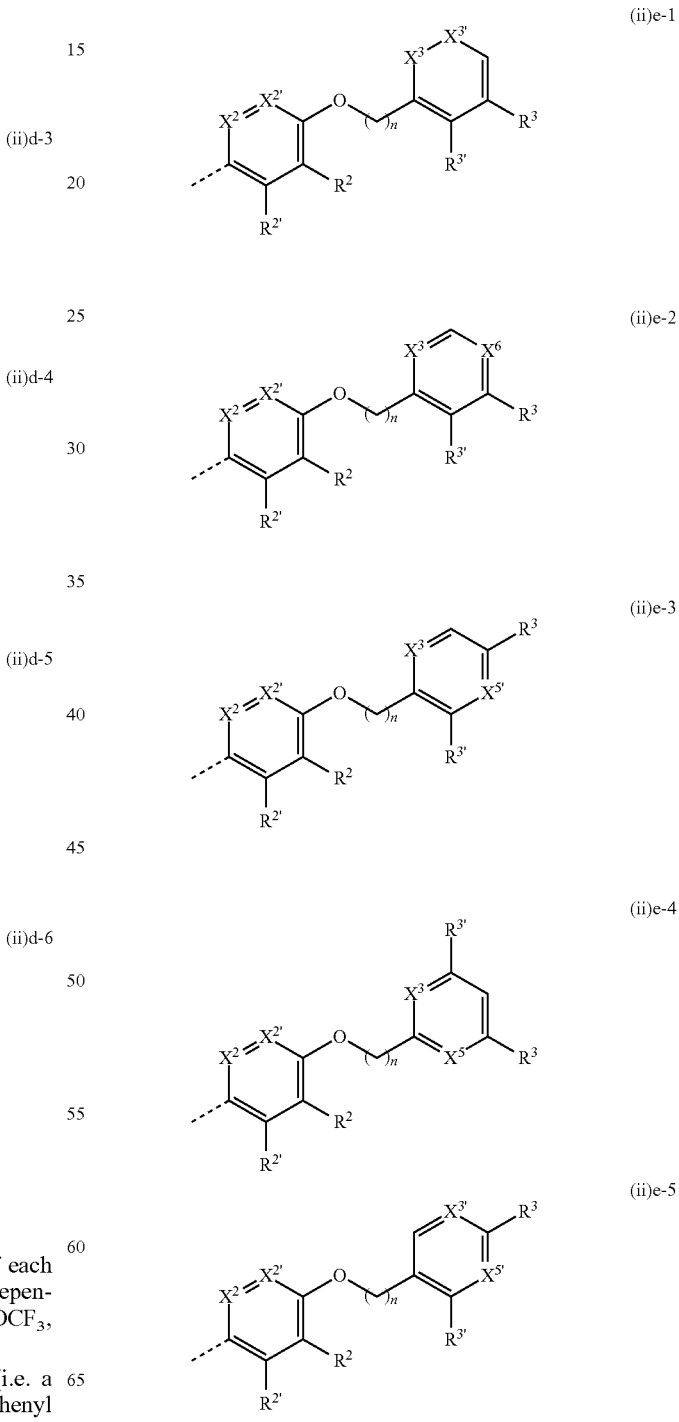

-continued

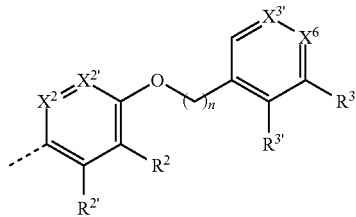

(ii)e-6 wherein $X^2$, $X^{2\prime}$, $X^3$, $X^{3\prime}$, $X^5$, $X^{5\prime}$, $X^6$ are independently of each other —N= or —CH=; and $R^2$, $R^{2\prime}$, $R^3$, $R^{3\prime}$ are independently of each other H, $C_{1-6}$ alkyl, hal, —$CF_3$, or —$OCF_3$, n is 0 or 1.

In some embodiments, both $X^2$, $X^{2\prime}$ are —CH= (i.e. a phenyl ring). In some embodiments, $X^2$ is —N= and $X^{2\prime}$ is —CH= or $X^{2\prime}$ is —N= and $X^2$ is —CH= (i.e. a pyridine ring). In some embodiments, both $X^2$, $X^{2\prime}$ are —N= (i.e. a pyridazine ring).

In some embodiments, $X^3$, $X^{3\prime}$, $X^5$, $X^{5\prime}$, $X^6$ are —CH= (i.e. a phenyl ring). In some embodiments, $X^3$ is —N= and $X^{3\prime}$, $X^5$, $X^{5\prime}$, $X^6$ are —CH= or $X^{3\prime}$ is —N= and $X^3$, $X^5$, $X^{5\prime}$, $X^6$ are —CH= or $X^6$ is —N= and $X^3$, $X^{3\prime}$, $X^5$, $X^{5\prime}$ are —CH= (i.e. a pyridine ring).

In some embodiments, both $X^3$, $X^{3\prime}$ are —N= and $X^5$, $X^{5\prime}$, $X^6$ are —CH= or both $X^{3\prime}$, $X^6$ are —N= and $X^3$, $X^5$, $X^{5\prime}$ are —CH= (i.e. a pyridazine ring). In some embodiments, both $X^3$, $X^5$ are —N= and $X^{3\prime}$, $X^{5\prime}$, $X^6$ are —CH= or both $X^{3\prime}$, $X^{5\prime}$ are —N= and $X^3$, $X^5$, $X^6$ are —CH= or both $X^3$, $X^6$ are —N= and $X^{3\prime}$, $X^5$, $X^{5\prime}$ are —CH= (i.e. a pyrimidine ring). In some embodiments, both $X^3$, $X^{5\prime}$ are —N= and $X^{3\prime}$, $X^5$, $X^6$ are —CH= (i.e. a pyrazine ring).

In some embodiments, -$X^1$-$L^1$- is —NH—. In some embodiments, -$X^1$-$L^1$- is —NH—$CH_2$—. In some embodiments, group X has the following formula (ii)c (e.g. (ii)c-1 or (ii)c-2):

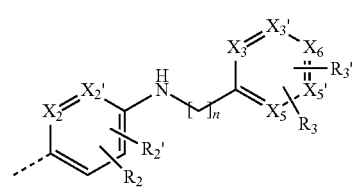

(ii)c

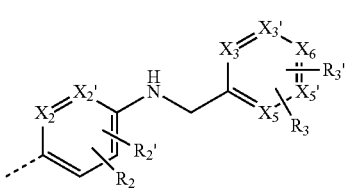

(ii)c-1

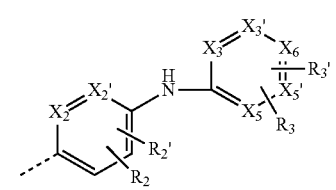

(ii)c-2 wherein $X^2$, $X^{2\prime}$ and $X^3$, $X^{3\prime}$, $X^5$, $X^{5\prime}$, $X^6$ are independently of each other —N= or —CH=; and $R^2$, $R^{2\prime}$ and $R^3$, $R^{3\prime}$ are independently of each other H, $C_{1-6}$ alkyl, hal, —$CF_3$, or —$OCF_3$, n is 0, 1, 2, 3.

In some embodiments, both $X^2$, $X^{2\prime}$ are —CH= (i.e. a phenyl ring). In some embodiments, $X^2$ is —N= and $X^{2\prime}$ is —CH= or $X^{2\prime}$ is —N= and $X^2$ is —CH= (i.e. a pyridine ring). In some embodiments, both $X^2$, $X^{2\prime}$ are —N= (i.e. a pyridazine ring).

In some embodiments, $X^3$, $X^{3\prime}$, $X^5$, $X^{5\prime}$, $X^6$ are —CH= (i.e. a phenyl ring). In some embodiments, $X^3$ is —N= and $X^{3\prime}$, $X^5$, $X^{5\prime}$, $X^6$ are —CH= or $X^{3\prime}$ is —N= and $X^3$, $X^5$, $X^{5\prime}$, $X^6$ are —CH= or $X^6$ is —N= and $X^3$, $X^{3\prime}$, $X^5$, $X^{5\prime}$ are —CH= (i.e. a pyridine ring).

In some embodiments, both $X^3$, $X^{3\prime}$ are —N= and $X^5$, $X^{5\prime}$, $X^6$ are —CH= or both $X^{3\prime}$, $X^6$ are —N= and $X^3$, $X^5$, $X^{5\prime}$ are —CH= (i.e. a pyridazine ring). In some embodiments, both $X^3$, $X^5$ are —N= and $X^{3\prime}$, $X^{5\prime}$, $X^6$ are —CH= or both $X^{3\prime}$, $X^{5\prime}$ are —N= and $X^3$, $X^5$, $X^6$ are —CH= or both $X^3$, $X^6$ are —N= and $X^{3\prime}$, $X^5$, $X^{5\prime}$ are —CH= (i.e. a pyrimidine ring). In some embodiments, both $X^3$, $X^{5\prime}$ are —N= and $X^{3\prime}$, $X^5$, $X^6$ are —CH= (i.e. a pyrazine ring).

$R^2$ and $R^{2\prime}$ are independently of each other H, $C_{1-6}$ alkyl, hal (e.g. H, —$CH_3$, F, Cl). In some embodiments, $R^3$ and $R^{3\prime}$ are independently of each other H, $C_{1-6}$ alkyl, hal, —$CF_3$, —$OCF_3$.

In some embodiments, group X has the following formula (ii)f-1, (ii)f-2, (ii)f-3, (ii)f-4, (ii)f-5 or (ii)f-6

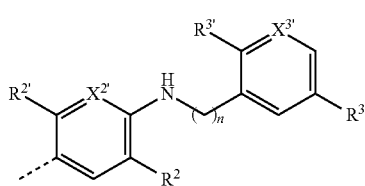

(ii)f-1

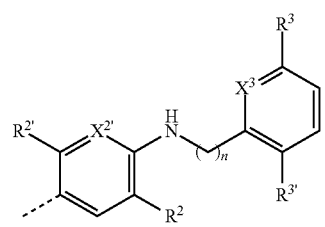

(ii)f-2

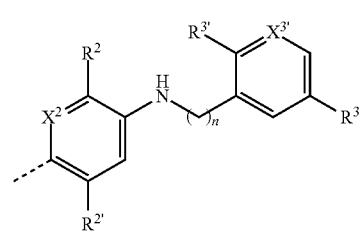

(ii)f-3

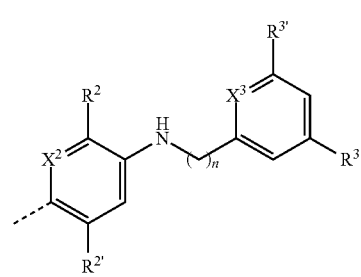

(ii)f-4

(ii)f-5

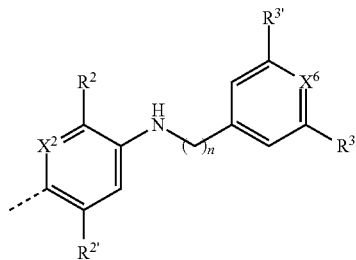

(ii)f-6

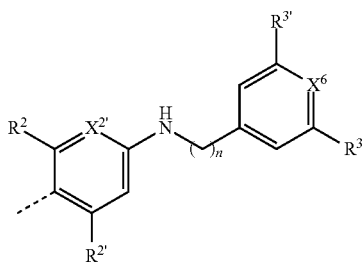

wherein $X^2$, $X^{2'}$, $X^3$, $X^{3'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, group X has the following formula (ii)g-1, (ii)g-2, (ii)g-3, (ii)g-4, (ii)g-5 or (ii)g-6

(ii)g-1

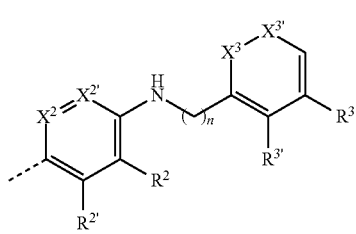

(ii)g-2

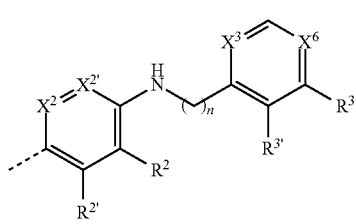

(ii)g-3

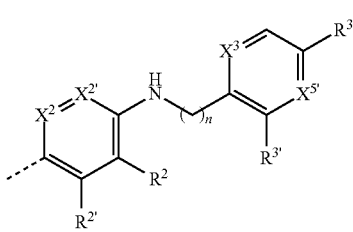

(ii)g-4

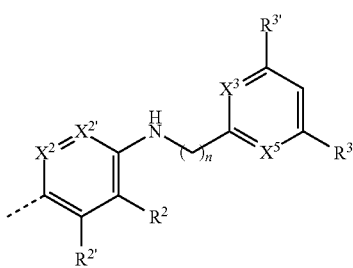

(ii)g-5

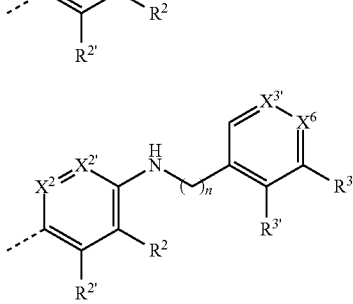

(ii)g-6 wherein $X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other H, $C_{1-6}$ alkyl, or hal (e.g., H, —$CH_3$, F, or Cl). In some embodiments, $R^3$ and $R^{3'}$ are independently of each other H, $C_{1-6}$ alkyl, hal, —$CF_3$, or —$OCF_3$.

In some embodiments, $R^3$ is H, hal, —$CF_3$, or —$OCF_3$.

In some embodiments, $R^{3'}$ is H, hal or $C_{1-6}$ alkyl (e.g., H, hal or —$CH_3$).

In some embodiments, the following combinations of $R^3$ and $R^{3'}$ and $R^2$ and $R^{2'}$ are included. In some embodiments, $R^3$ and $R^{3'}$ are H. In some embodiments, $R^3$ and $R^{3'}$ are hal. In some embodiments, $R^3$ is hal, —$CF_3$, or —$OCF_3$ and $R^{3'}$ is H. In some embodiments, $R^3$ is H and $R^{3'}$ is hal, or $C_{1-6}$ alkyl.

In some embodiments, $R^2$ and $R^{2'}$ are H. In some embodiments, $R^2$ and $R^{2'}$ are hal. In some embodiments, $R^2$ is hal or $C_{1-6}$ alkyl and $R^{2'}$ is H. In some embodiments, $R^2$ is H and $R^{2'}$ is hal.

In some embodiments of a compound of formula II or III, group X is

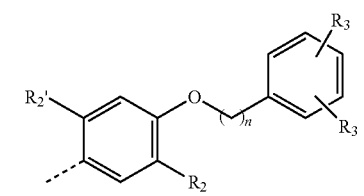
(ii)h-a

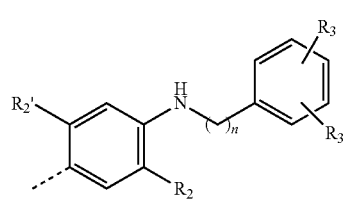
(ii)i-a

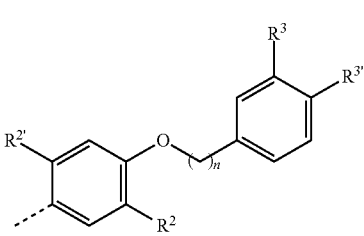
(ii)h-a-1

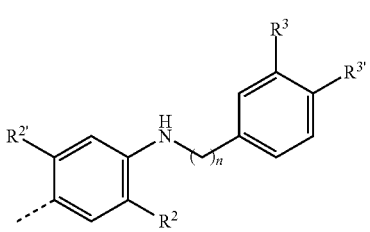
(ii)i-a-1 wherein $R^2$, $R^{2'}$ are independently of each other H, $C_{1-6}$ alkyl, hal (e.g. H, —$CH_3$, F, Cl); $R^3$, $R^{3'}$ are is H, $C_{1-6}$ alkyl, hal, —$CF_3$, —$OCF_3$; and n is 0 or 1.

In some embodiments of a compound of formula II or III, group X is

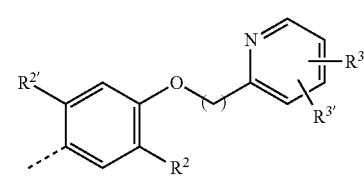
(ii)h-b

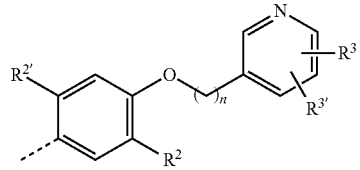
(ii)h-c

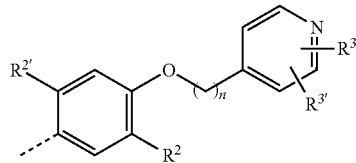
(ii)h-d

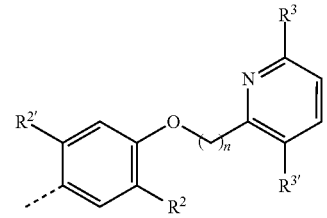
(ii)h-b-1

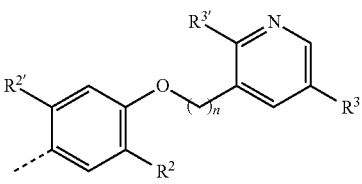
(ii)h-c-1

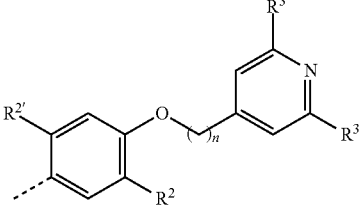
(ii)h-d-1 wherein $R^2$, $R^{2'}$ are independently of each other H, $C_{1-6}$ alkyl, hal, (e.g. H, —$CH_3$, F, Cl); $R^3$, $R^{3'}$ are H, $C_{1-6}$ alkyl, hal, —$CF_3$, —$OCF_3$; and n is 0 or 1.

In some embodiments of a compound of formula II or III, group X is

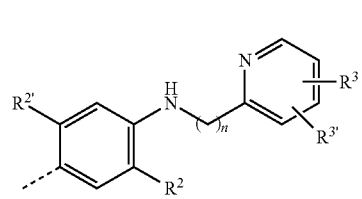
(ii)i-b

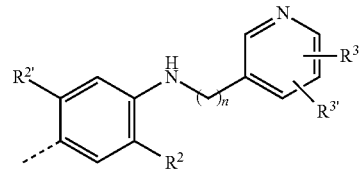
(ii)i-c

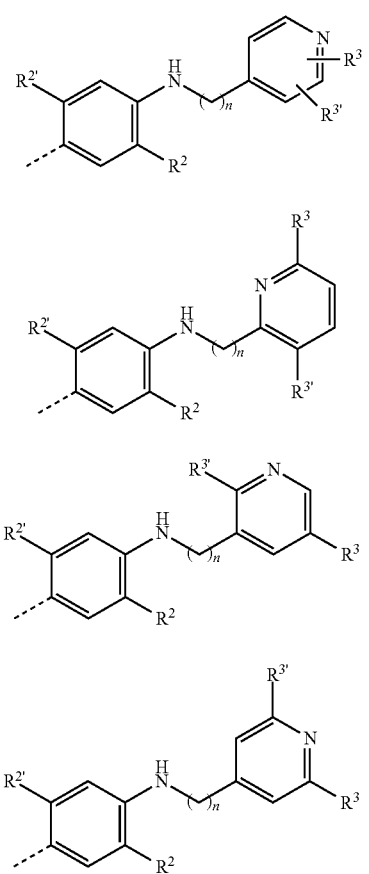
(ii)i-d
(ii)i-b-1
(ii)i-c-1
(ii)i-d-1
wherein $R^2$, $R^{2'}$ are independently of each other H, $C_{1-6}$ alkyl, hal, (e.g. H, —$CH_3$, F, Cl); $R^3$, $R^{3'}$ are H, $C_{1-6}$ alkyl, hal, —$CF_3$, —$OCF_3$; and n is 0 or 1.
In some embodiments of a compound of formula II or III, group X is
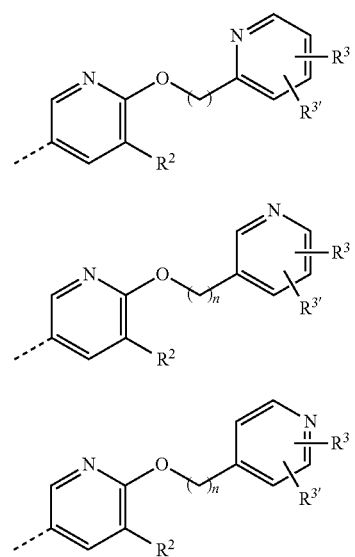
(ii)h-e
(ii)h-f
(ii)h-g
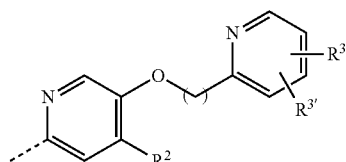
(ii)h-h
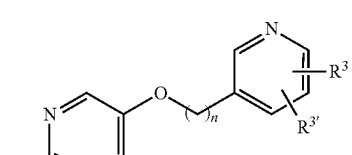
(ii)h-i
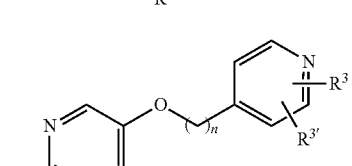
(ii)h-j
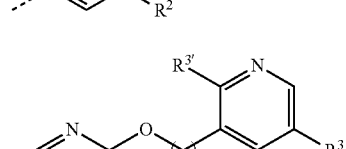
(ii)h-e-1
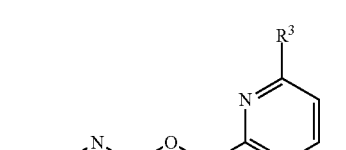
(ii)h-f-1
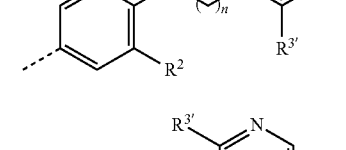
(ii)h-g-1
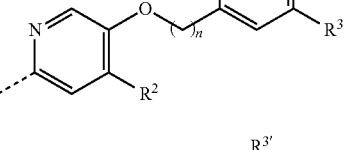
(ii)h-h-1
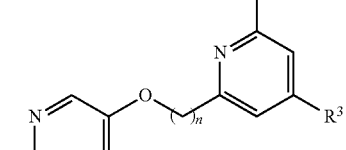
(ii)h-i-1
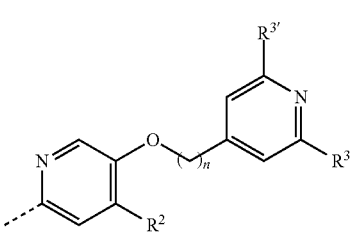

(ii)h-j-1

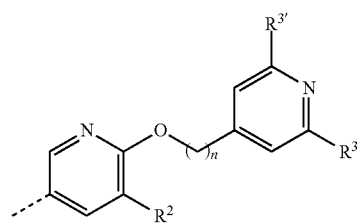

wherein R² is H, C₁₋₆ alkyl, hal (e.g. H, —CH₃, F, Cl); R³, R³' are H, C₁₋₆ alkyl, hal, —CF₃, —OCF₃; and n is 0 or 1.

In some embodiments of a compound of formula II or III, group X is (ii)h-k

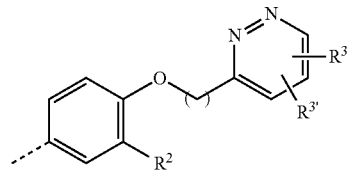

(ii)h-l

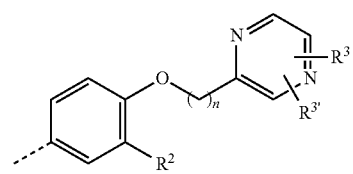

(ii)h-m

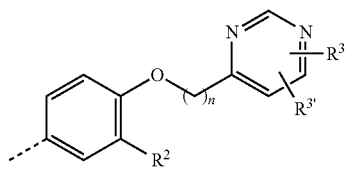

(ii)h-n

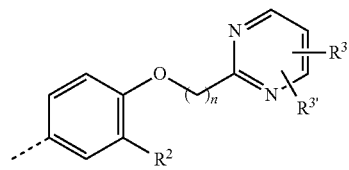

(ii)h-o

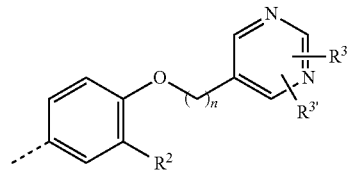

(ii)h-p

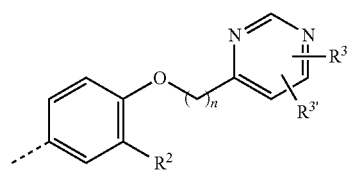

wherein R² is H, C₁₋₆ alkyl, hal (e.g. H, —CH₃, F, Cl); R³, R³' are H, C₁₋₆ alkyl, hal, —CF₃, —OCF₃; and n is 0 or 1.

In some embodiments of a compound of formula II or III, group X is (ii)i-e-1

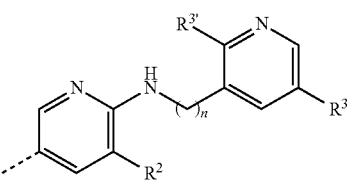

(ii)i-f-1

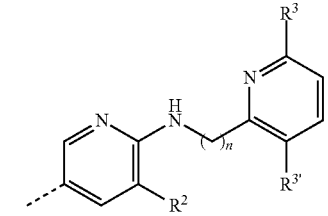

(ii)i-g-1

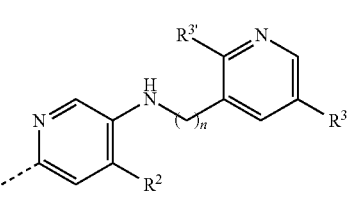

(ii)i-h-1

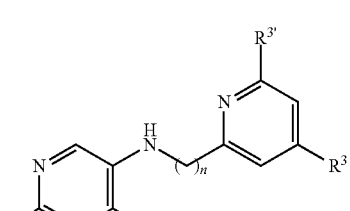

(ii)i-i-1

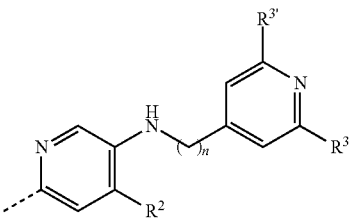

(ii)i-j-1

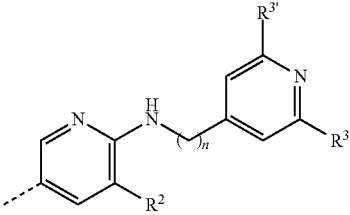

wherein R² is H, C₁₋₆ alkyl, hal (e.g. H, —CH₃, F, Cl); R³, R³' are H, C₁₋₆ alkyl, hal, —CF₃, —OCF₃; and n is 0 or 1.

In some embodiments of a compound of formula II or III, group X is

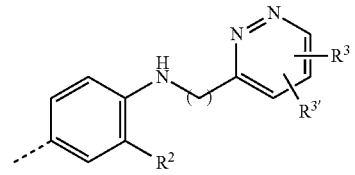
(ii)i-k

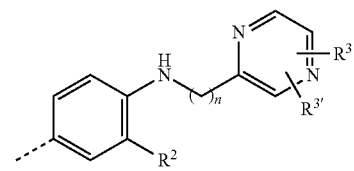
(ii)i-l

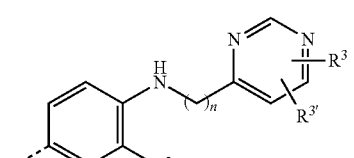
(ii)i-m

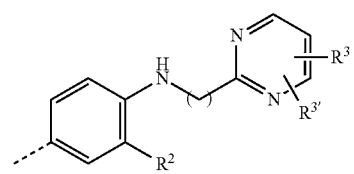
(ii)i-n

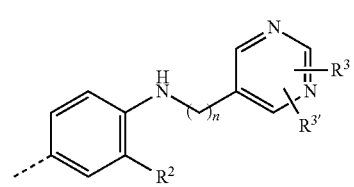
(ii)i-o

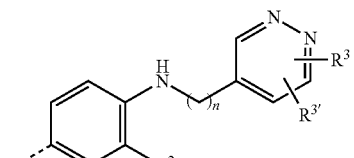
(ii)i-p

(ii)i-k-1

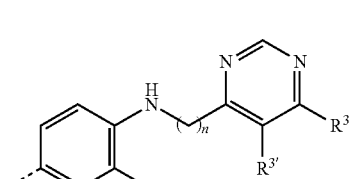
(ii)i-l-1

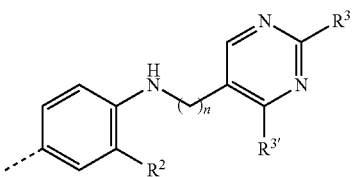
(ii)i-m-1

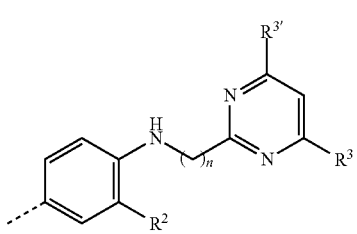
(ii)i-n-1

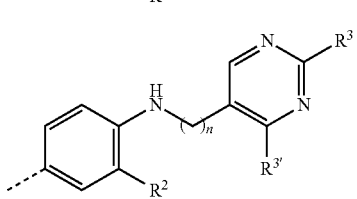
(ii)i-o-1

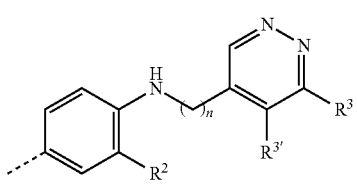
(ii)i-p-1 wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1.

In some embodiments, $R^4$ and $R^5$ are independently of each other H, $C_{1-4}$ alkyl, cyclopropyl, tetrahydrofuryl.

In some embodiments of a compound of formula II or III, a 3 to 6-membered heterocycloalkyl (in combination with —($NR^4R^5$)) refers to a non-aromatic or partially aromatic ring system having 3, 4, 5, or 6 ring atoms selected from C, N, O, or S (e.g. C, N, or O), the number of N atoms being 0, 1, 2 and the number of O and S atoms each being 0, 1, 2. Examples of 3 to 6-membered heterocycloalkyl groups include oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl, 1,4-dithianyl, 1,3-dioxane, 1,3-dithianyl, piperazinyl, thiomorpholinyl, dioxothiomorpholinyl, piperidinyl, morpholinyl and the like. In some embodiments, 3 to 6-membered heterocycloalkyl include 5-membered heterocycloalkyl having 1 or 2 O-atoms, such as oxiranyl, oxetanyl, tetrahydrofuranyl, dioxanyl.

In some embodiments of a compound of formula II or III, a 3 to 6-membered heteroaryl (in combination with —($NR^6R^7$) or —($CHR^6R^7$)) refers to a (fully) aromatic ring system having 3, 4, 5, or 6 ring atoms (e.g. 5 ring atoms), selected from C, N, O, or S (e.g. C, N, or O, and C or N, with the number of N atoms being 0, 1, 2 or 3 and the number of O and S atoms each being 0, 1 or 2). Examples of "heteroaryl" include furyl, imidazolyl, isoxazolyl, oxazolyl, pyrazinyl, pyrazolyl (pyrazyl), pyridazinyl, pyridinyl, pyrimidinyl, pyrrolyl, thiazolyl, thienyl, and the like.

In some embodiments, "heteroaryl" include pyrrolyl, imidazolyl. Preferably, the aromatic ring system is a nitrogen containing heteroaryl.

In some embodiments of a compound of formula II or III, a 3 to 9-membered heterocycloalkyl (in combination with —(NR⁶R⁷) or —(CHR⁶R⁷)) refers to a non-aromatic or partially aromatic ring system having 3 to 9 ring atoms selected from C, N, O, or S (e.g. C, N, or O), the number of N atoms being 0, 1, 2 or 3 and the number of O and S atoms each being 0, 1 or 2. Examples of a 3 to 9-membered heterocycloalkyl (in combination with —(NR⁶R⁷) or —(CHR⁶R⁷)) include monocycles such as oxiranyl, thiaranyl, aziradinyl, oxetanyl, thiatanyl, azetidinyl, pyrrolidinyl, tetrahydrofuranyl, tetrahrydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl, oxepanyl, thiepanyl, azepanyl, diazepanyl, oxazepanyl (e.g. azetidinyl, pyrrolidinyl, piperidinyl, piperazinyl, morpholinyl, azepanyl); fused ring systems, such as 3-azabicyclo[3.1.0]hexyl, 3-azabicyclo[3.3.0]octyl, 3,7-diazabicyclo[3.3.0]octyl, 3-aza-7-oxabicyclo[3.3.0]octyl, 2,6-diazabicyclo[3.3.0]octyl, 2,7-diazabicyclo[3.3.0]octyl, 2,8-diazabicyclo[4.3.0]nonyl, 3-oxa-8-azabicyclo[4.3.0]nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4.3.0]nonyl, and the like; bridged ring systems such as bicyclo[3.3.1]nonanyl, bicyclo[3.2.1]octanyl, bicyclo[2.2.2]octanyl, bicyclo[3.1.1]heptanyl, bicyclo[2.2.1]heptanyl (e.g. bicyclo[3.2.1]octanyl, bicyclo[2.2.1]heptanyl), having one or two heteroatoms selected from N and O; spino ring systems such as spiropentanyl, spiro[2.3]hexanyl spiro[3.3]heptanyl, spiro[3.4]octanyl, spiro[4.4]nonanyl, spiro[3.5]nonanyl, spiro[4.5]decanyl (e.g. spiro[3.3]heptanyl, spiro[4.4]nonanyl), having one or two heteroatoms selected from N and O, (e.g. diazaspiro[3.3]heptanyl, oxa-azaspiro[3.3]heptanyl, diazaspiro[4.4]nonanyl, oxa-azaspiro[4.4]nonanyl). Preferably, the 3 to 9-membered heterocycloalkyl contains at least one nitrogen atom.

In some embodiments, Z is —(NR⁴R⁵), wherein R⁴ and R⁵ are independently of each other H, C₁₋₆ alkyl cyclopropyl, cylobutyl, 3 to 6-membered heterocycloalkyl containing 0, 1, or 2 N-atoms and 0, 1, or 2 O-atoms, or —(NR⁶R⁷), —(CHR⁶R⁷), wherein R⁶ and R⁷ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with C₁₋₄ alkyl, hal, —OR', —NR'R", wherein R', R" are independently of each other H or -C₁₋₄ alkyl.

In some embodiments, —(NR⁶R⁷) ring systems include

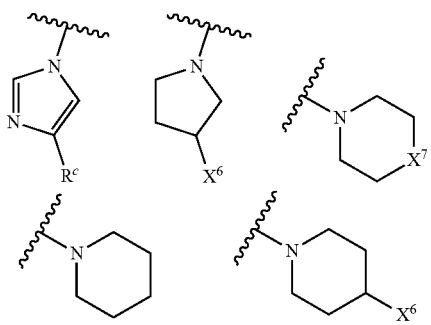

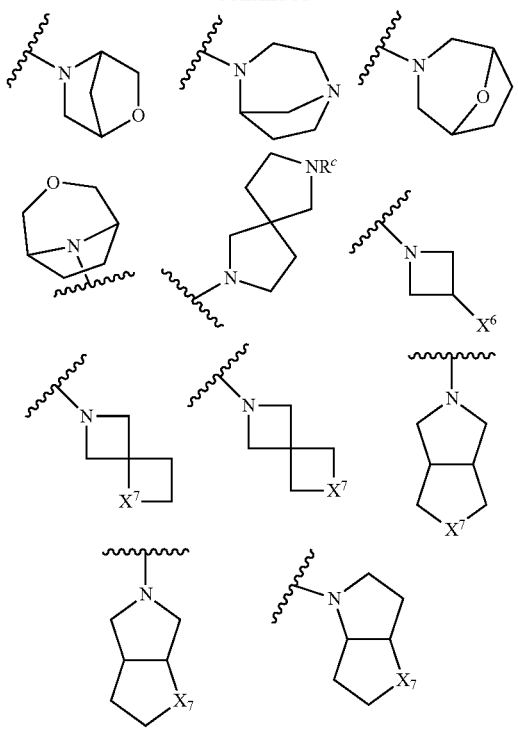

wherein R^c is H, C₁₋₄ alkyl, oxetane; X⁶ is H, —CH₃, —OH, —OCH₃, —OCF₃, —N(CH₃)₂, F, Cl; X⁷ is —O—, —NH— or —N(CH₃)—, —SO₂.

In some embodiments, —(CHR⁶R⁷) ring systems include

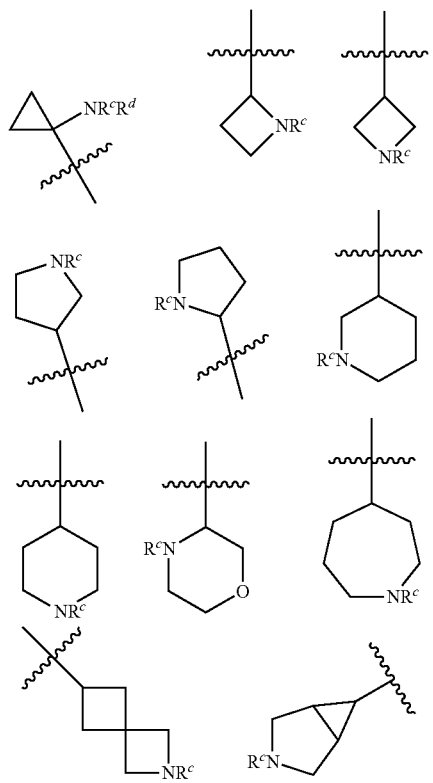

-continued

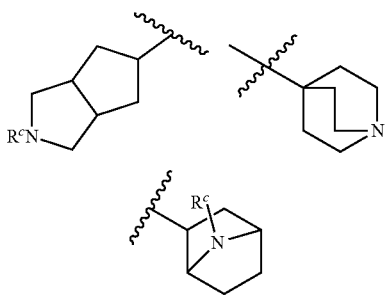

wherein $R^c$ is H, $C_{1-4}$ alkyl, oxetane, and $R^d$ is H, $C_{1-4}$ alkyl.

In some embodiments, $Y^2$ is covalent bond. In some embodiments, $Y^2$ is —O—. In some embodiments, $Y^2$ is —NH—, NCH$_3$—. In some embodiments, $Y^2$ is —C≡C—.

In some embodiments, L is a covalent bond. In some embodiments, L is straight chain or branched $C_{1-4}$ alkyl (e.g. —CH$_2$—, —(CH$_2$)$_2$—, —(CH$_2$)$_3$—, —(CH$_2$)$_4$— or —C(CH$_3$)$_2$— or —CH$_2$—C(CH$_3$)$_2$—). In some embodiments, L is

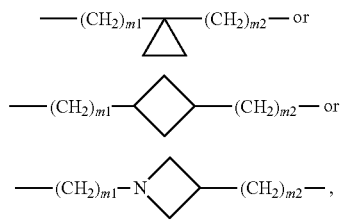

wherein m1, m2 are independently of each other 0, 1, 2, 3, 4, (e.g. 0 or 1 or 2). In some embodiments, m2 is 0 and m1 is 0 or 1 or 2. In some embodiments, m1 and m2 are 1 or m1 and m2 are 2.

In some embodiments, the compound of formula II is not any of

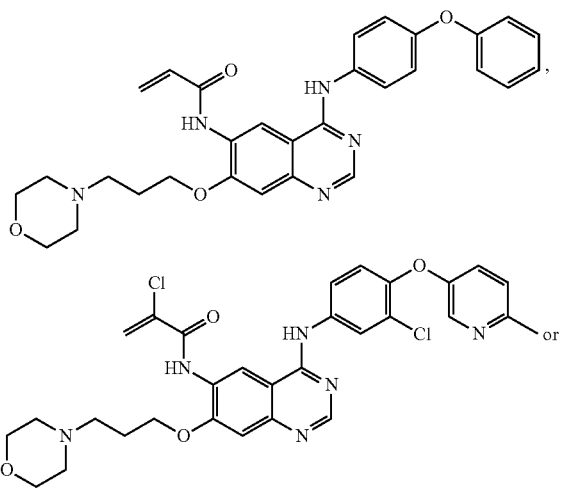

wherein Q is

In some embodiments, the present disclosure is directed towards a compound or pharmaceutically acceptable salts or stereoisomers thereof of formula I above wherein $Y^2$ is covalent bond, having the following formula IV

IV

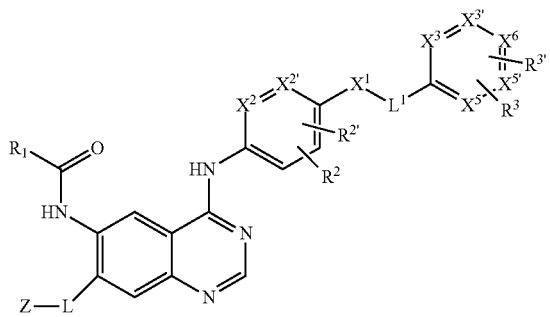

wherein $X^1$ is —O—, —CH$_2$—, —NH—; $X^2X^{2'}$, $X^3$, $X^{3'}$, $X^5$, $X^{5'}$, $X^6$ are independently of each other —N=, —CH=;

$L^1$ is a covalent bond or straight chain or branched $C_{1-3}$alkyl, which is unsubstituted or substituted with hal;

$R^1$ is —CR$_b$=CHR$_a$, —C≡CH or —C≡C—CH$_3$, wherein $R^a$, $R^b$ are independently of each other H, hal, —CH$_2$—O—CH$_3$;

$R^2$, $R^{2'}$, $R^3$, $R^{3'}$ are independently of each other H, $C_{1-6}$ alkyl, hal, —CF$_3$, —OCF$_3$;

L is a covalent bond, straight chain or branched $C_{1-4}$ alkyl or

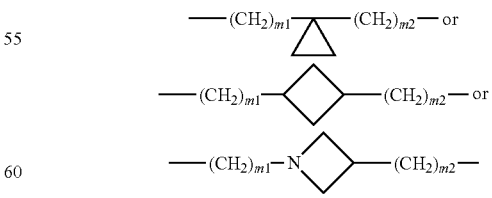

wherein m1, m2 are independently of each other 0, 1, 2, 3, or 4;

Z is —(NR$^4$R$^5$), wherein R$^4$ and R$^5$ are independently of each other H, $C_{1-6}$ alkyl, cyclopropyl, cylobutyl, 3 to 6-membered heterocycloalkyl, or —(NR$^6$R$^7$), —(CHR$^6$R$^7$), wherein $R^6$ and $R^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, $L^1$ is straight chain or branched $C_{1-3}$alkyl, which is unsubstituted or substituted with hal. In some embodiments, $L^1$ is not a covalent bond.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}X^5$, $X^{5'}$, $X^6$ are —CH= or $X^{3'}$ is —N= and $X^3$, $X^5$, $X^{5'}$, $X^6$ are is —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

The following embodiments apply for the compounds of formula IV.

In some embodiments, $X^2$, $X^{2'}$ are —CH= (i.e. a phenyl ring).

In some embodiments, $X^3$ is —N= and $X^{3'}$, $X^5$, $X^{5'}$, $X^6$ are —CH=.

In some embodiments, L is a covalent bond.
In some embodiments, L is

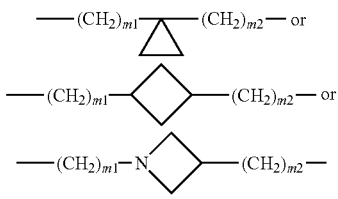

wherein m1, m2 are independently of each other 0, 1, 2, 3, or 4. $R^2$ and $R^{2'}$ are independently of each other H, $C_{1-6}$ alkyl, hal (e.g. H, —$CH_3$, F, Cl).

In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —$CF_3$, —$OCF_3$. In some embodiments, $R^3$ is H, $C_{1-6}$ alkyl, hal, —$CF_3$, —$OCF_3$ and $R^{3'}$ is H.

In some embodiments, $R^2$ and $R^{2'}$ are H and $R^3$ is H, $C_{1-6}$ alkyl, hal, —$CF_3$, —$OCF_3$and $R^{3'}$ is H, hal; or $R^2$ and $R^{2'}$ are hal and $R^3$ is H, $C_{1-6}$ alkyl, hal, —$CF_3$, —$OCF_3$ and $R^{3'}$ is H, hal; or $R^2$ is hal and $R^{2'}$ is H and $R^3$ is H, $C_{1-6}$ alkyl, hal, —$CF_3$, —$OCF_3$ and $R^{3'}$ is H.

In some embodiments, $X^1$ is —O—. In some embodiments, $X^1$ is —$CH_2$—. In some embodiments, $X^1$ is —NH—. In some embodiments, $X^1$ is —S—. In some embodiments, $L^1$ is a covalent bond. In some embodiments, $L^1$ is —$CH_2$— or —CH($CH_3$)— or —CH(hal)-. In some embodiments, $L^1$ is —$CH_2$—$CH_2$— or —$CH_2$—CH($CH_3$)— or —$CH_2$—CH(hal)-.

In some embodiments, linker combinations -$X^1$-$L^1$- —O—, —$CH_2$—, —O—$CH_2$—, —NH—$CH_2$—, —S—$CH_2$—, —$CH_2$—$CH_2$—, —O—CH($CH_3$)—, —$CH_2$—CH($CH_3$)—, —NH—CH($CH_3$)—, —S—CH($CH_3$)—, —O—CH(hal)-, —$CH_2$—CH(hal)-, —NH—CH(hal)-, —S—CH(hal)- (e.g., —O—, —$CH_2$—, —O—$CH_2$—, —NH—$CH_2$—, —$CH_2$—$CH_2$—, —O—CH($CH_3$)—, —$CH_2$—CH($CH_3$)—, —O—CH(hal)-, or —$CH_2$—CH(hal)- and —O—, —$CH_2$—, —O—$CH_2$—, —NH—$CH_2$—, or —$CH_2$—$CH_2$—).

In some embodiments, -$X^1$-$L^1$- is —O—. In some embodiments, -$X^1$-$L^1$- is —O—$CH_2$—. In some embodiments, compound IV has the following formula

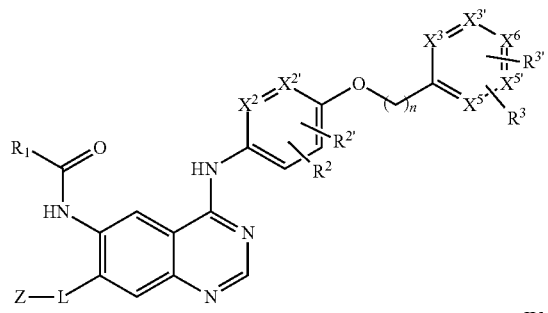

IV-1

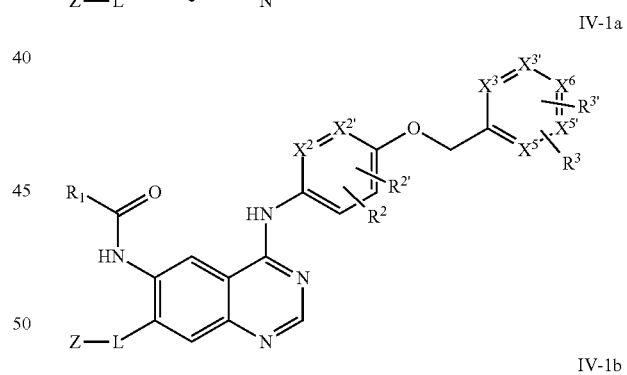

IV-1a

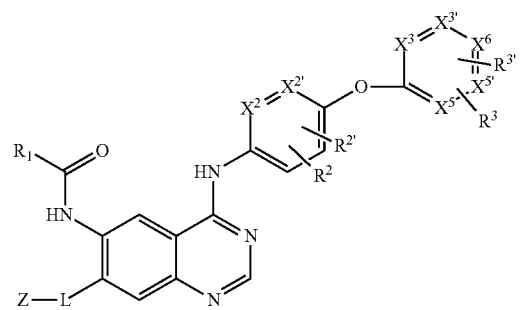

IV-1b wherein $X^2$, $X^{2'}$ and $X^3$, $X^{3'}$, $X^5$, $X^{5'}$, $X^6$ are independently of each other —N= or —CH=; $R^2$, $R^{2'}$ and $R^3$, $R^{3'}$ are independently of each other H, $C_{1-6}$ alkyl, hal, —$CF_3$, or —$OCF_3$, and n is 0, 1, 2, 3; and Z, L, $R^1$ are as defined above for a compound of formula IV.

In some embodiments of a compound of formula IV, IV-1, IV-1a or IV-1b substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring).

In some embodiments, $X^3$ is —N= and $X^{3'}$, $X^5$, $X^{5'}$, $X^6$ are —CH=.

In some embodiments, L is a covalent bond.

In some embodiments, L is

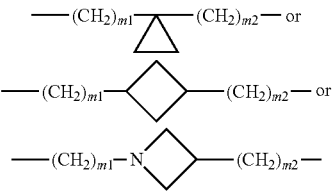

wherein m1, m2 are independently of each other 0, 1, 2, 3, or 4.

In some embodiments, $R^2$ and $R^{2'}$ are independently of each other H, $C_{1-6}$ alkyl, hal, (e.g. H, —$CH_3$, F, Cl).

In some embodiments, $R^2$ and $R^{2'}$ are independently of each other H, $C_{1-6}$ alkyl, hal (e.g. H, —$CH_3$, F, Cl). In some embodiments, $R^3$ and $R^{3'}$ are independently of each other H, $C_{1-6}$ alkyl, hal, —$CF_3$, —$OCF_3$.

In some embodiments, $R^2$ and $R^{2'}$ are H and $R^3$ is H, $C_{1-6}$ alkyl, hal, —$CF_3$, —$OCF_3$ and $R^{3'}$ is H, hal; or $R^2$ and $R^{2'}$ are hal and $R^3$ is H, $C_{1-6}$ alkyl, hal, —$CF_3$, —$OCF_3$ and $R^{3'}$ is H, hal; or $R^2$ is hal and $R^{2'}$ is H and $R^3$ is H, $C_{1-6}$ alkyl, hal, —$CF_3$, —$OCF_3$ and $R^{3'}$ is H.

In some embodiments, a compound of formula IV has one of the following formulas

IV-(ii)d-1

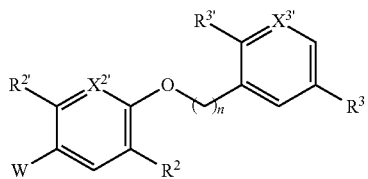

IV-(ii)d-2

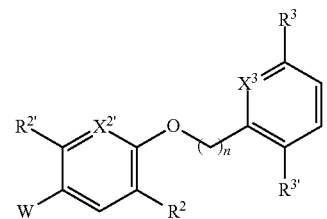

IV-(ii)d-3

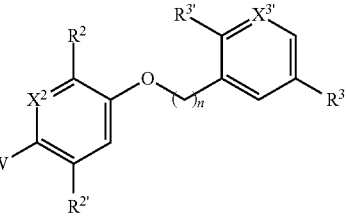

IV-(ii)d-4

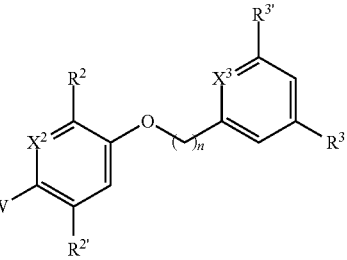

IV-(ii)d-5

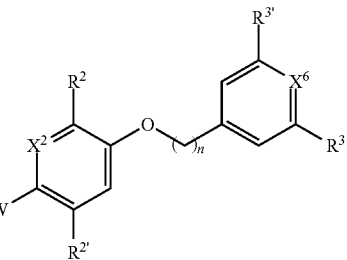

IV-(ii)d-6

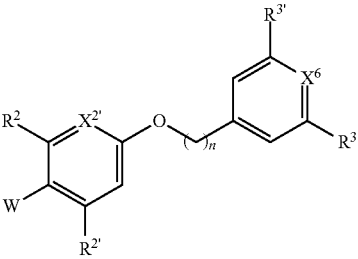

wherein W is

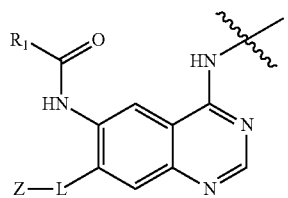

$X^2$, $X^{2'}$, $X^3$, $X^{3'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$; and n is 0 or 1; and Z, L, $R^1$ are as defined above for a compound of formula IV.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, a compound of formula IV has the following formula IVe-1, IVe-2, IVe-3, IVe-4, IVe-5 or IVe-6

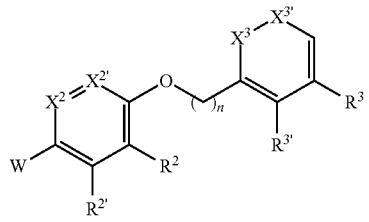
IVe-1

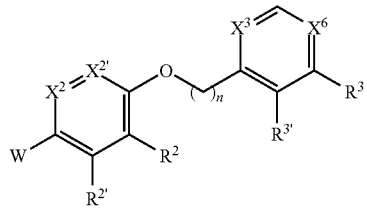
IVe-2

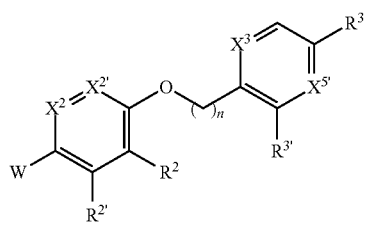
IVe-3

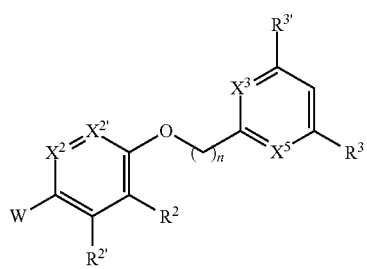
IVe-4

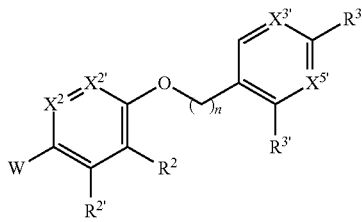
IVe-5

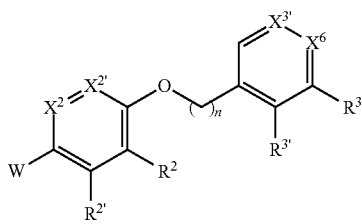
IVe-6 wherein W is

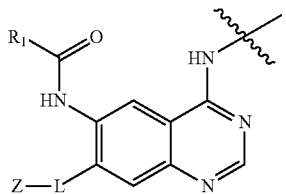

$X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are is —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, -$X^1$-$L^1$- is —NH—. In some embodiments, -$X^1$-$L^1$- is —NH—$CH_2$—.

In some embodiments, a compound of formula IV has the following formula.

IV-2

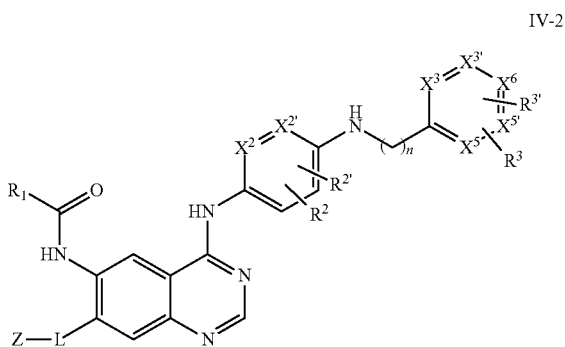

IV-2a

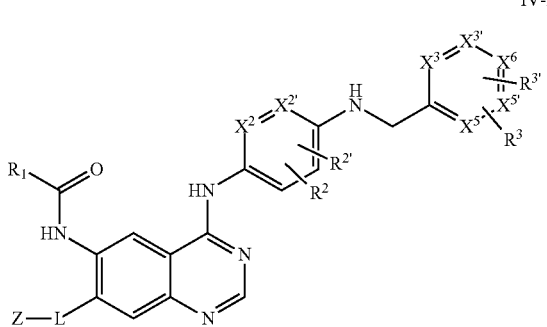

IV-2b

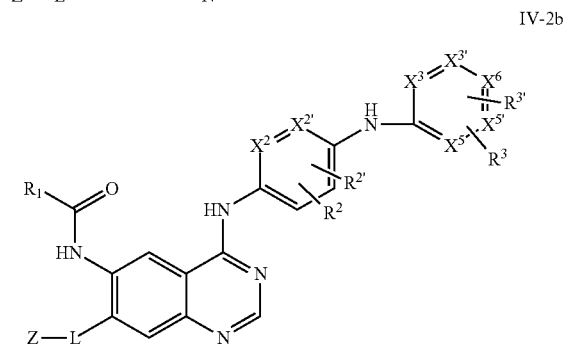

wherein $X^2$, $X^{2'}$ and $X^3$, $X^{3'}$, $X^5$, $X^{5'}$, $X^6$ are independently of each other —N= or —CH=; $R^2$, $R^{2'}$ and $R^3$, $R^{3'}$ are independently of each other H, $C_{1-6}$ alkyl, hal, —CF$_3$, or —OCF$_3$, and n is 0, 1, 2, 3; and Z, L, $R^1$ are as defined above for a compound of formula IV.

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring).

In some embodiments, $X^3$ is —N= and $X^{3'}$, $X^5$, $X^{5'}$, $X^6$ are —CH=.

In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —CF$_3$, —OCF$_3$. In some embodiments, $R^3$ is H, $C_{1-6}$ alkyl, hal, —CF$_3$, —OCF$_3$ and $R^{3'}$ is H.

In some embodiments, $R^2$ and $R^{2'}$ are H and $R^3$ is H, $C_{1-6}$ alkyl, hal, —CF$_3$, —OCF$_3$ and $R^{3'}$ is H, hal; or $R^2$ and $R^{2'}$ are hal and $R^3$ is H, $C_{1-6}$ alkyl, hal, —CF$_3$, —OCF$_3$ and $R^{3'}$ is H, hal; or $R^2$ is hal and $R^{2'}$ is H and $R^3$ is H, $C_{1-6}$ alkyl, hal, —CF$_3$, —OCF$_3$ and $R^{3'}$ is H.

In some embodiments, a compound of formula IV has one of the following formulas

IV-(ii)f-1

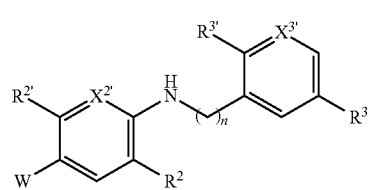

IV-(ii)f-2

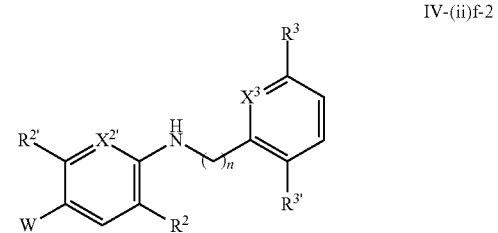

IV-(ii)f-3

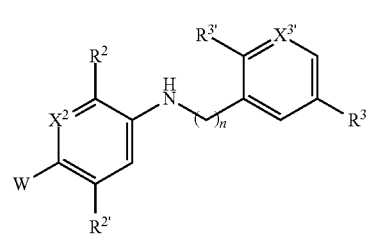

IV-(ii)f-4

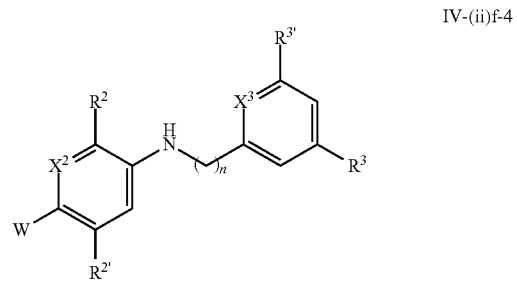

IV-(ii)f-5

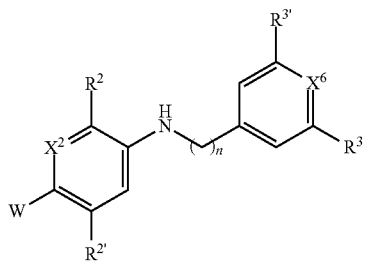

IV(ii)f-6

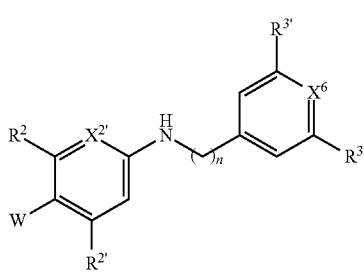

wherein W is

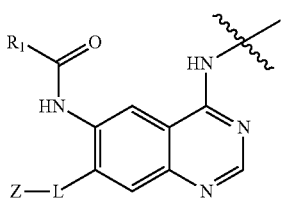

$X^2$, $X^{2'}$, $X^3$, $X^{3'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$; and n is 0 or 1; and Z, L, $R^1$ are as defined above for a compound of formula IV.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, a compound of formula IV has the following formula

IV-(ii)g-1

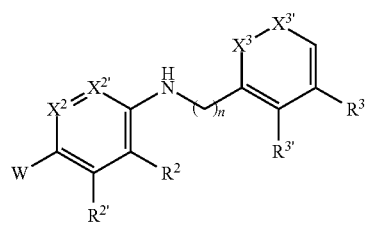

IV-(ii)g-2

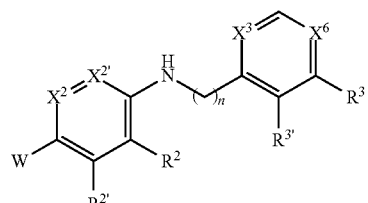

IV-(ii)g-3

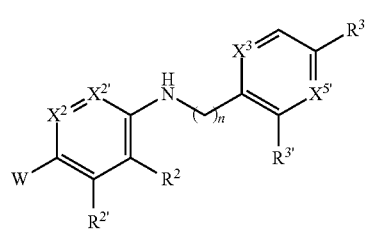

IV-(ii)g-4

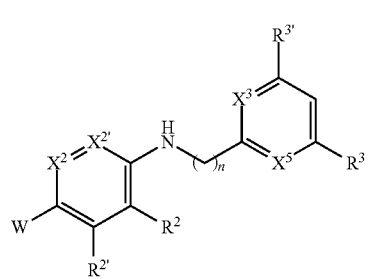

IV-(ii)g-5

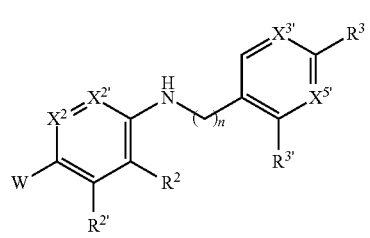

IV-(ii)g-6

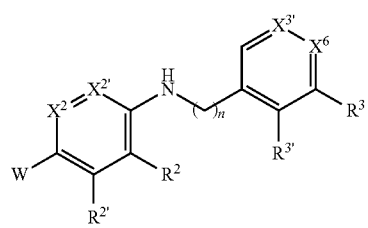

wherein W is

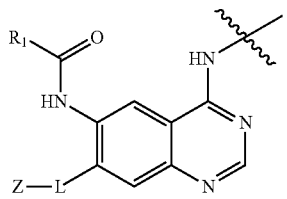

$X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH=(i.e. a phenyl ring).

In some embodiments, $X^3$ is —N= and $X^{3'}$, $X^5$, $X^{5'}$, $X^6$ are —CH=.

In some embodiments, $R^2$ and $R^{2'}$ are independently of each other (i.e. H, hal or $C_{1-6}$ alkyl and H, hal or —$CH_3$).

In some embodiments, $R^3$ is H, hal, —$CF_3$, or —$OCF_3$.

In some embodiments, $R^{3'}$ is H, hal or $C_{1-6}$ alkyl (e.g., H, hal or —$CH_3$).

In some embodiments, $R^3$ and $R^{3'}$ are H. In some embodiments, $R^3$ and $R^{3'}$ are hal. In some embodiments, $R^3$ is hal, —$CF_3$, or —$OCF_3$ and $R^{3'}$ is H. In some embodiments, $R^3$ is H and $R^{3'}$ is hal, or $C_{1-6}$ alkyl.

In some embodiments, $R^2$ and $R^{2'}$ are H. In some embodiments, $R^2$ and $R^{2'}$ are hal. In some embodiments, $R^2$ is hal or $C_{1-6}$ alkyl and $R^{2'}$ is H. In some embodiments, $R^2$ is H and $R^{2'}$ is hal.

In some embodiments, $R^2$ and $R^{2'}$ are H and $R^3$ is H, $C_{1-6}$ alkyl, hal, —$CF_3$, —$OCF_3$ and $R^{3'}$ is H, hal; or $R^2$ and $R^{2'}$ are hal and $R^3$ is H, $C_{1-6}$ alkyl, hal, —$CF_3$, —$OCF_3$ and $R^{3'}$ is H, hal; or $R^2$ is hal and $R^{2'}$ is H and $R^3$ is H, $C_{1-6}$ alkyl, hal, —$CF_3$, —$OCF_3$ and $R^{3'}$ is H.

In some embodiments, a compound of formula IV has the following formula

IV-(ii)h-a-1

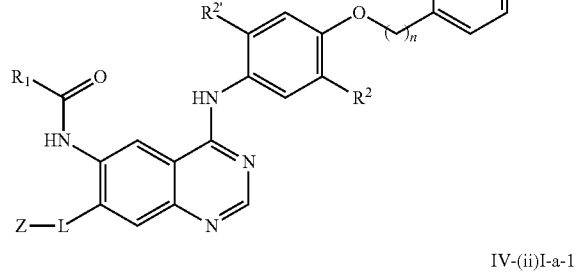

IV-(ii)I-a-1 wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$ are as defined above for a compound of formula IV. In some embodiments, n is 0. In some embodiments, n is 1.

In some embodiments of a compound of formula IV-(ii)h-a-1 or IV-(ii)i-a-1, substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, a compound of formula IV has the following formulas

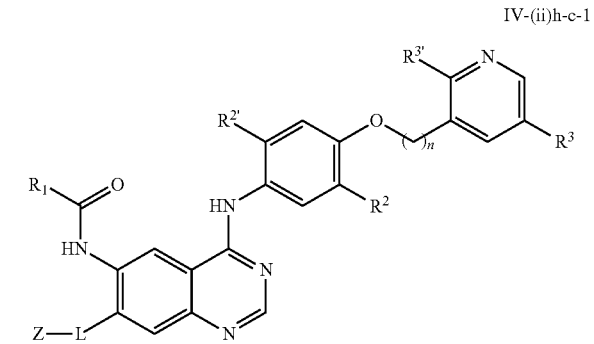

IV-(ii)h-c-1

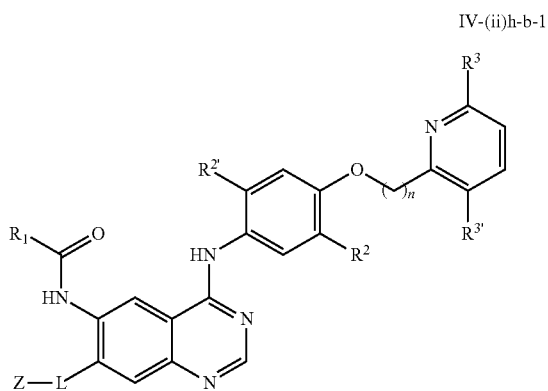

IV-(ii)h-b-1

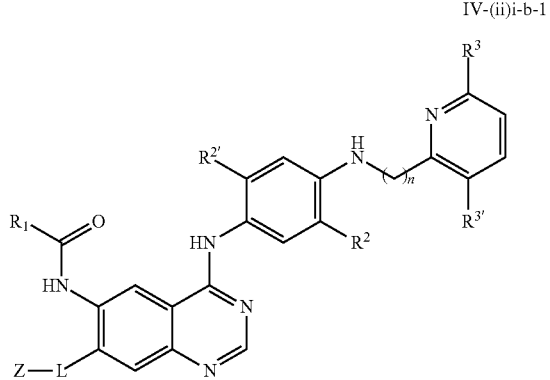

IV-(ii)i-b-1

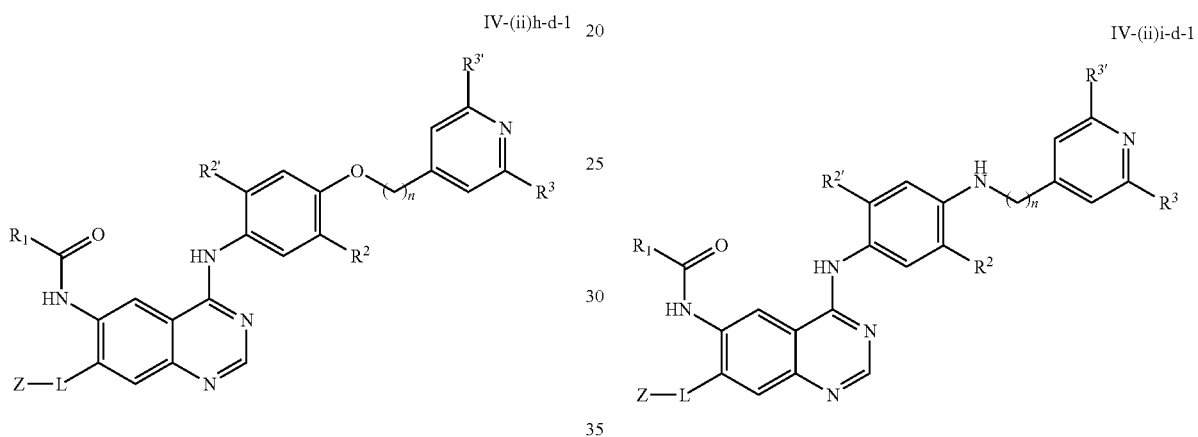

IV-(ii)h-d-1

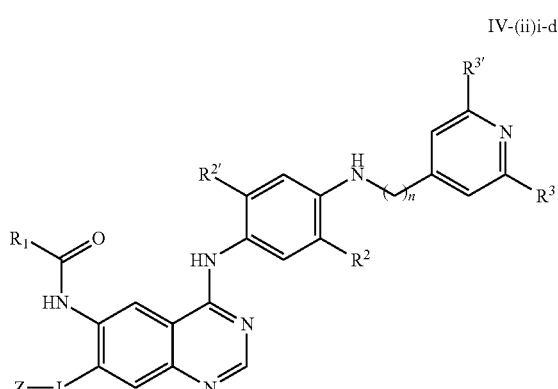

IV-(ii)i-d-1 wherein $R^2$, $R^{2'}$ are independently of each other H, $C_{1-6}$ alkyl, hal, (e.g. H, —$CH_3$, F, Cl); $R^3$, $R^{3'}$ are H, $C_{1-6}$ alkyl, hal, —$CF_3$, —$OCF_3$; and n is 0 or 1.

In some embodiments of a compound of formula IV-(ii)h-c-1, IV-(ii)h-b-1 or IV-(ii)h-d-1, substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, a compound of formula IV has the following formulas wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$ are as defined above for a compound of formula IV. In some embodiments, n is 0. in some embodiments, n is 1.

In some embodiments of a compound of formula IV-(ii)i-c-1, IV-(ii)i-b-1 or IV-(ii)i-d-1, substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, a compound of formula IV has the following formulas

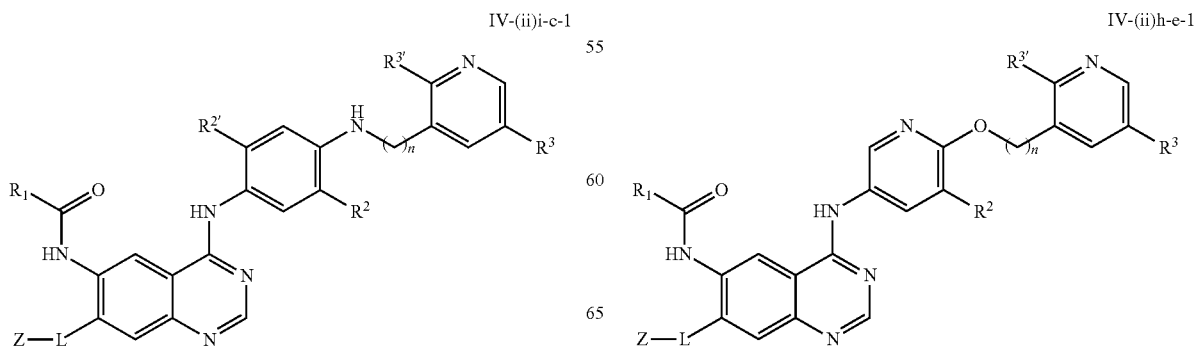

IV-(ii)i-c-1

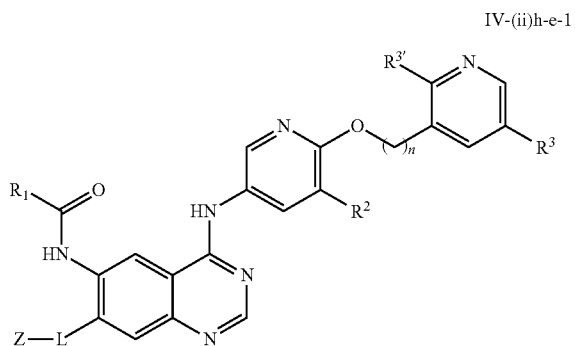

IV-(ii)h-e-1

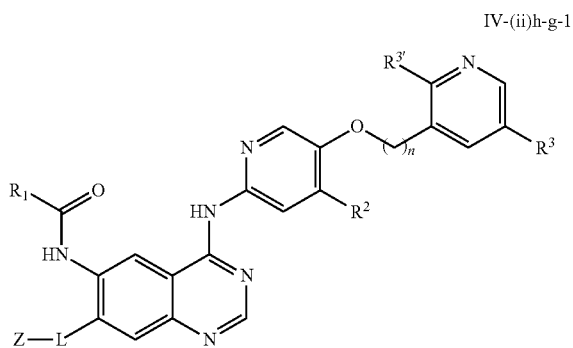

IV-(ii)h-g-1

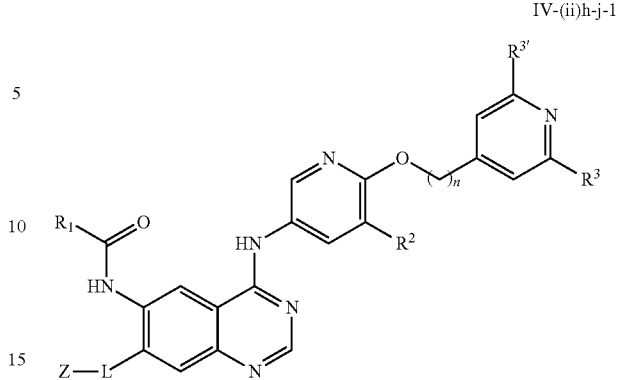

IV-(ii)h-j-1

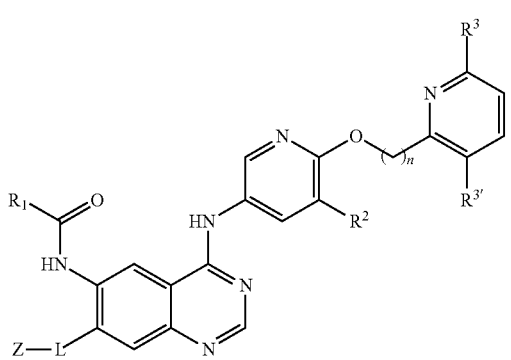

IV-(ii)h-f-1 wherein $R^2$ is H, $C_{1-6}$ alkyl, hal (e.g. H, —CH$_3$, F, Cl); $R^3$, $R^{3'}$ are H, $C_{1-6}$ alkyl, hal, —CF$_3$, —OCF$_3$; and n is 0 or 1; and Z, L, $R^1$ are as defined above for a compound of formula IV. In some embodiments, n is 0. In some embodiments, n is 1.

In some embodiments of a compound of formula IV-(ii)h-e-1, IV-(ii)-h-f-1, IV-(ii)h-g-1, IV-(ii)h-h-1, IV-(ii)h-i-1 or IV-(ii)h-j-1, substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, a compound of formula IV has the following formulas

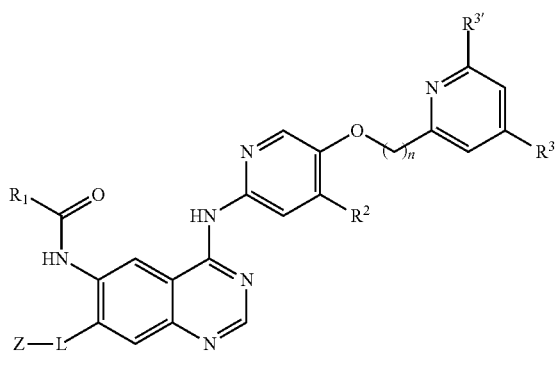

IV-(ii)h-h-1

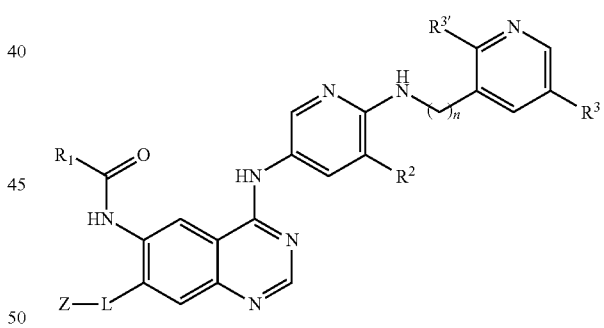

IV-(ii)i-e-1

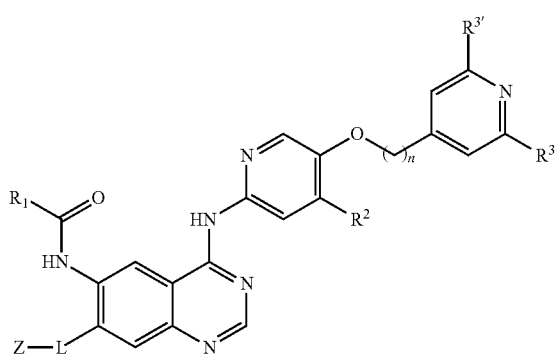

IV-(ii)h-i-1

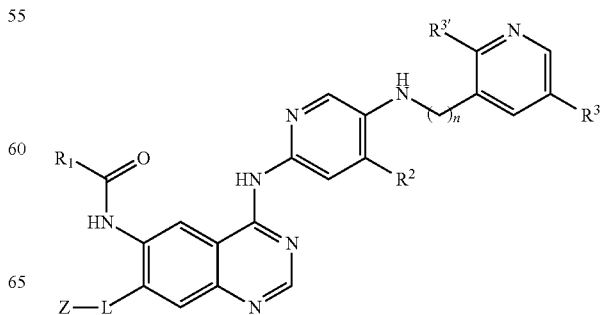

IV-(ii)i-g-1

-continued

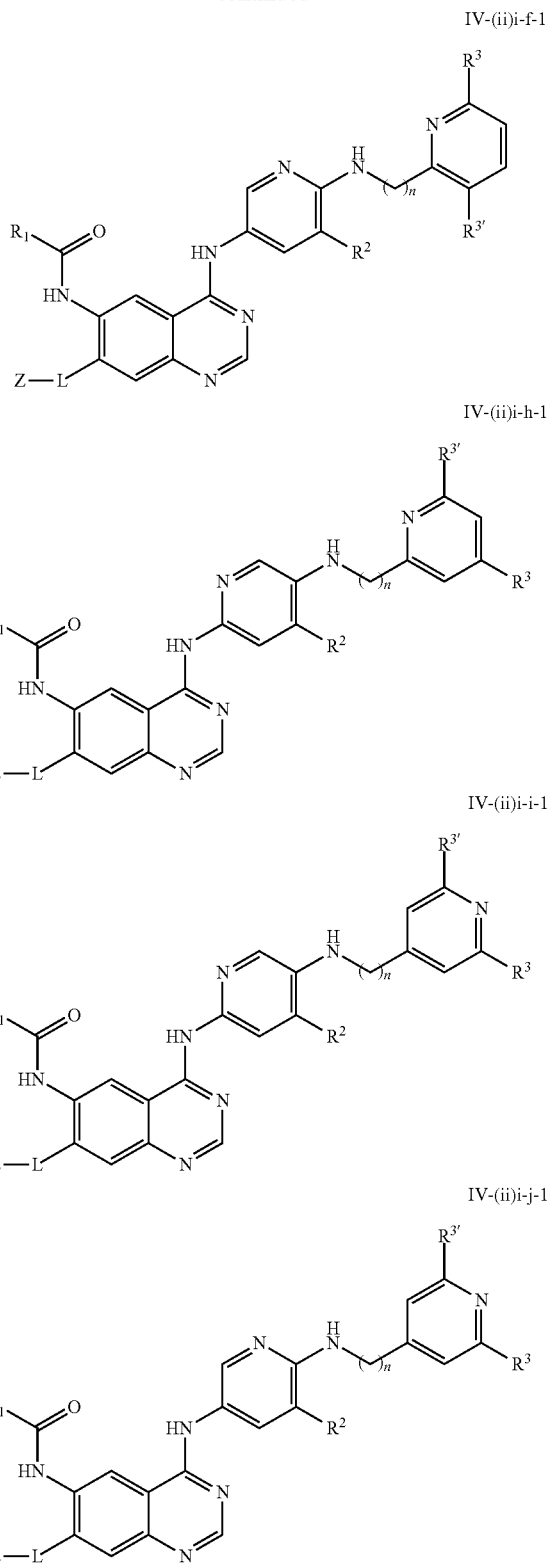

wherein R² is H, C₁₋₆ alkyl, hal (e.g. H, —CH₃, F, Cl); R³, R³' are H, C₁₋₆ alkyl, hal, —CF₃, —OCF₃; and n is 0 or 1; and Z, L, R¹ are as defined above for a compound of formula IV. In some embodiments, n is 0. In some embodiments, n is 1.

In some embodiments of a compound of formula IV-(ii) i-e-1, IV-(ii)i-f-1, IV-(ii)i-g-1, IV-(ii)i-h-1, IV-(ii)i-i-1 or IV-(ii)i-j-1, substituent Z-L contains at least one nitrogen atom. Thus, the 3-6-membered heteroaryl or 3-9-membered heterocycloalkyl formed by R₆ and R₇ of (CHR₆R₇) includes a nitrogen atom if L does not contain a nitrogen atom.

In some embodiments $R^a$ and $R^b$ are hydrogen.

In some embodiments, a compound of formula IV has the following formulas

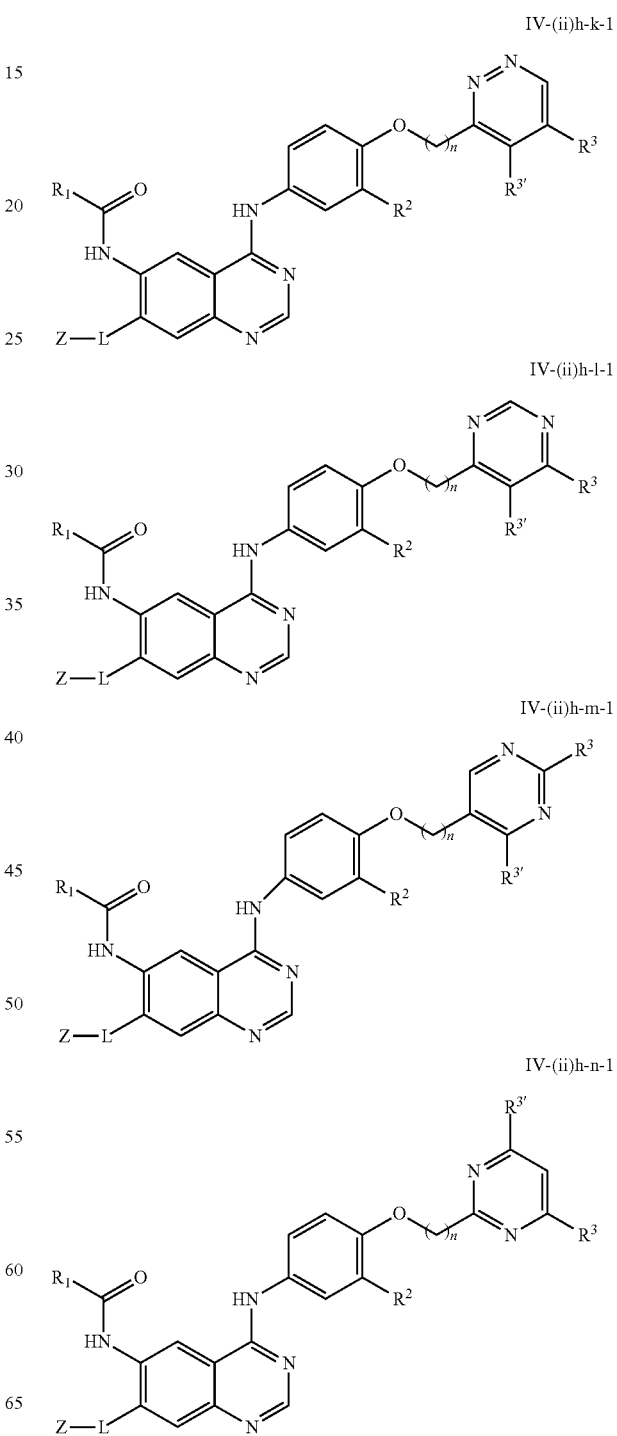

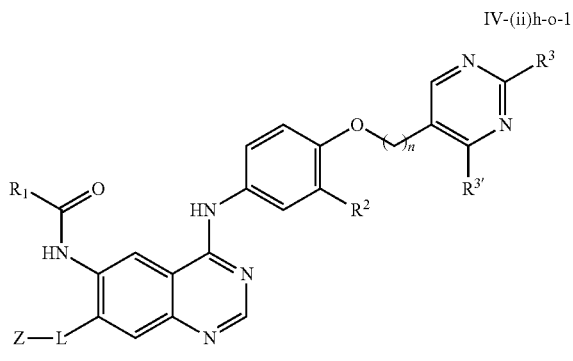
IV-(ii)h-o-1

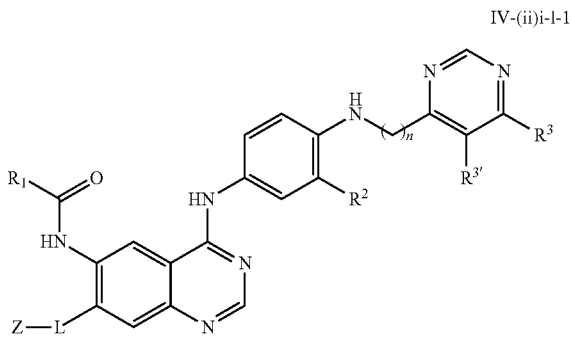
IV-(ii)i-l-1

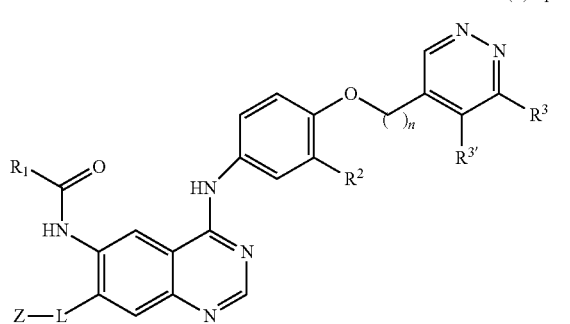
IV-(ii)h-p-1

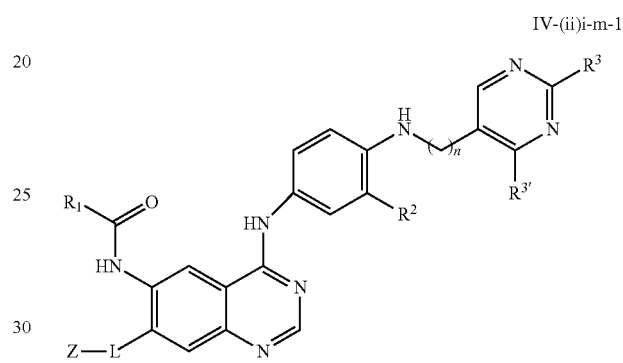
IV-(ii)i-m-1 wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$ are as defined above for a compound of formula IV. In some embodiments, n is 0. In some embodiments, n is 1.

In some embodiments of a compound of formula IV-(ii) h-k-1, IV-(ii)h-l-1, IV-(ii)h-m-1, IV-(ii)h-n-1, IV-(ii)h-o-1 or IV-(ii)h-p-1, substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, a compound of formula IV has the following formulas

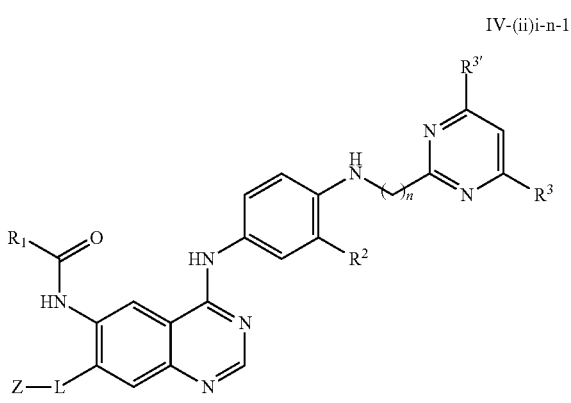
IV-(ii)i-n-1

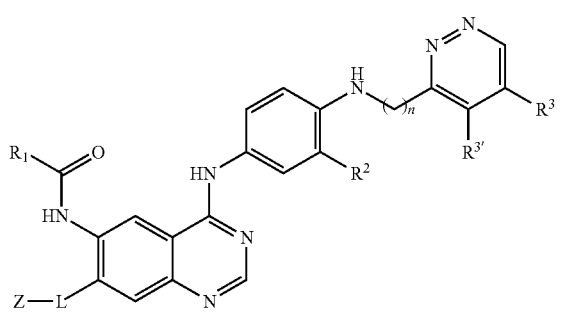
IV-(ii)i-k-1

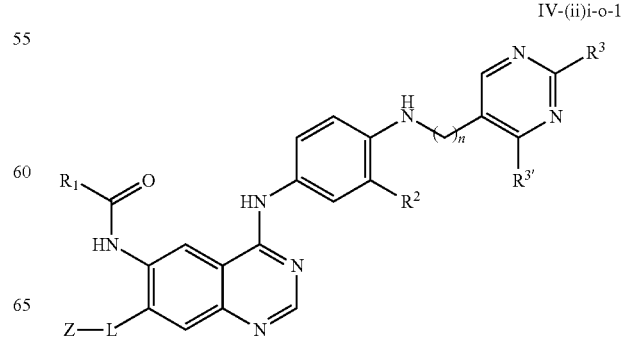
IV-(ii)i-o-1

-continued

IV-(ii)i-p-1

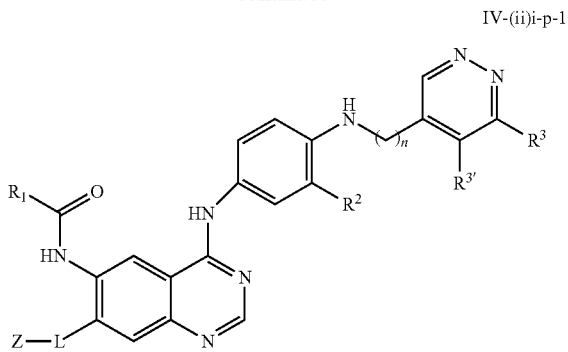

wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$ are as defined above for a compound of formula IV. In some embodiments, n is 0. In some embodiments, n is 1.

In some embodiments of a compound of formula IV-(ii) i-k-1, IV-(ii)i-l-1, IV-(ii)i-m-1, IV-(ii)i-n-1, IV-(ii)i-o-1 or IV-(ii)i-p-1 substituent Z-L contains at least one nitrogen atom. Thus, the 3-6-membered heteroaryl or 3-9-membered heterocycloalkyl formed by $R_6$ and $R_7$ of $(CHR_6R_7)$ includes a nitrogen atom if L does not contain a nitrogen atom.

In some embodiments $R^a$ and $R^b$ are hydrogen.

In some embodiments, $R^4$ and $R^5$ are independently of each other H, $C_{1-4}$ alkyl, cyclopropyl, or tetrahydrofuryl.

In some embodiments of a compound of formula IV, a 3 to 6-membered heterocycloalkyl (in combination with —$(NR^4R^5)$) refers to a non-aromatic or partially aromatic ring system having 3, 4, 5, or 6 ring atoms selected from C, N, O, or S (e.g. C, N, or O), the number of N atoms being 0, 1, 2 and the number of O and S atoms each being 0, 1, 2. Examples of 3 to 6-membered heterocycloalkyl groups include oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl and the like. In some embodiments, 3 to 6-membered heterocycloalkyl include 5-membered heterocycloalkyl having 1 or 2 O-atoms, such as oxiranyl, oxetanyl, tetrahydrofuranyl, dioxanyl.

In some embodiments of a compound of formula IV, a 3 to 6-membered heteroaryl (in combination with —$(NR^6R^7)$ or —$(CHR^6R^7)$) refers to a (fully) aromatic ring system having 3, 4, 5, or 6 ring atoms (e.g. 5 ring atoms), selected from C, N, O, or S (e.g. C, N, or O, and C or N, with the number of N atoms being 0, 1, 2 or 3 and the number of O and S atoms each being 0, 1 or 2). Examples of "heteroaryl" include furyl, imidazolyl, isoxazolyl, oxazolyl, pyrazinyl, pyrazolyl (pyrazyl), pyridazinyl, pyridinyl, pyrimidinyl, pyrrolyl, thiazolyl, thienyl, and the like. In some embodiments, examples of "heteroaryl" include pyrrolyl, imidazolyl. Preferably, the aromatic ring system is a nitrogen containing heteroaryl.

In some embodiments of a compound of formula IV, a 3 to 9-membered heterocycloalkyl (in combination with —$(NR^6R^7)$ or —$(CHR^6R^7)$) refers to a non-aromatic or partially aromatic ring system having 3 to 9 ring atoms selected from C, N, O, or S (e.g. C, N, or O), the number of N atoms being 0, 1, 2 or 3 and the number of O and S atoms each being 0, 1 or 2. Examples of a 3 to 9-membered heterocycloalkyl (in combination with —$(NR^6R^7)$ or —$(CHR^6R^7)$) include monocycles such as oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl, oxepanyl, thiepanyl, azepanyl, diazepanyl, oxazepanyl (e.g. azetidinyl, pyrrolidinyl, piperidinyl, piperazinyl, morpholinyl, azepanyl); fused ring systems, such as 3-azabicyclo[3.1.0]hexyl, 3-azabicyclo[3.3.0]octyl, 3,7-di-azabicyclo[3.3.0]octyl, 3-aza-7-oxabicyclo[3.3.0]octyl , 2,6-diazabicyclo[3.3.0]octyl, 2,7-diazabicyclo[3.3.0]octyl, 2,8-diazabicyclo[4.3.0]nonyl, 3-oxa-8-azabicyclo[4.3.0]nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4.3.0]nonyl, and the like; bridged ring systems such as bicyclo[3.3.1]nonanyl, bicyclo[3.2.1]octanyl, bicyclo[2.2.2]octanyl, bicyclo[3.1.1]heptanyl, bicyclo[2.2.1]heptanyl (e.g. bicyclo[3.2.1]octanyl, bicyclo[2.2.1]heptanyl), having one or two heteroatoms selected from N and O; spiro ring systems such as spiropentanyl, spiro[2.3]hexanyl spiro[3.3] heptanyl, spiro[3.4]octanyl, spiro[4.4]nonanyl, spiro[3.5] nonanyl, spiro[4.5]decanyl (e.g. spiro[3.3]heptanyl, spiro [4.4]nonanyl), having one or two heteroatoms selected from N and O (e.g. diazaspiro[3.3]heptanyl, oxa-azaspiro[3.3] heptanyl, diazaspiro[4.4]nonanyl, oxa-azaspiro[4.4] nonanyl). Preferably, the 3 to 9-membered heterocycloalkyl contains at least one nitrogen atom.

In some embodiments, Z is —$(NR^4R^5)$, wherein $R^4$ and $R^5$ are independently of each other H, $C_{1-6}$ alkyl, cyclopropyl, cylobutyl, 3 to 6-membered heterocycloalkyl containing 0, 1, or 2 N-atoms and 0, 1, or 2 O-atoms, or —$(NR^6R^7)$, —$(CHR^6R^7)$, wherein $R^6$ and $R^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments, —$(NR^6R^7)$ ring systems include

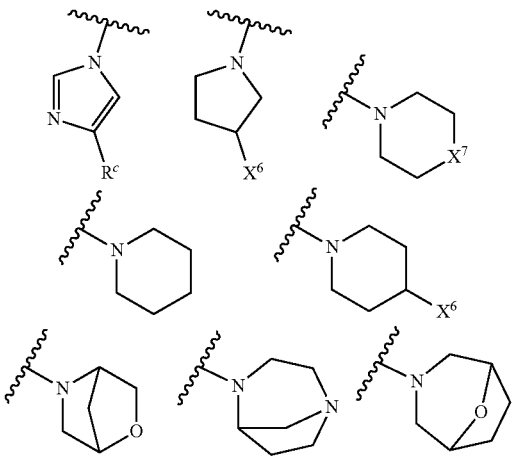

-continued

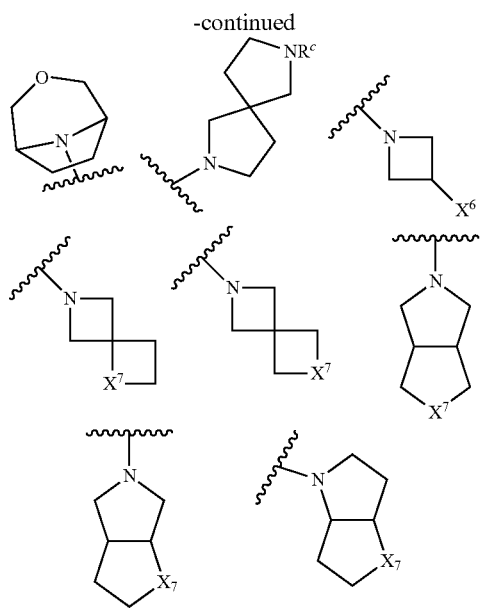

wherein $R^c$ is H, $C_{1-4}$ alkyl, oxetane; $X^6$ is H, —CH₃, —OH, —OCH₃, —OCF₃, —N(CH₃)₂, F, Cl; $X^7$ is —O—, —NH— or —N(CH₃)—, —SO₂.

In some embodiments, —(CHR⁶R⁷) ring systems include

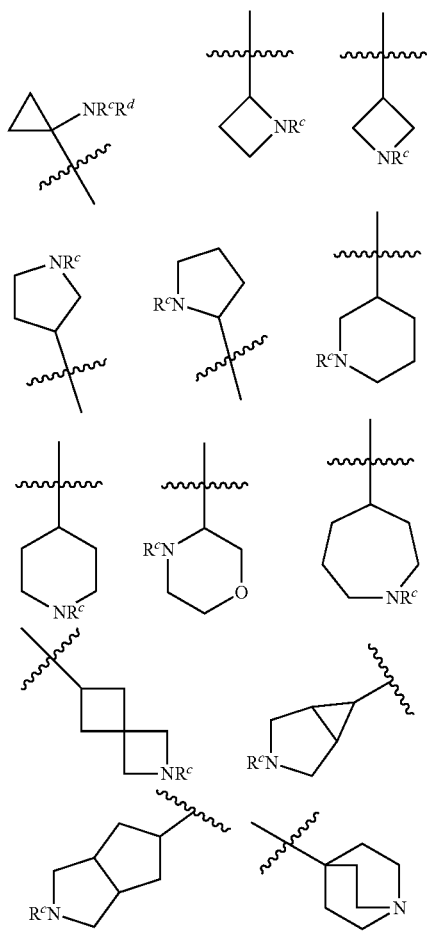

-continued

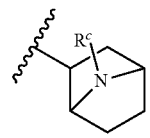

wherein $R^c$ is H, $C_{1-4}$ alkyl, oxetane, and $R^d$ is H, $C_{1-4}$ alkyl.

In some embodiments, ring systems for the compounds of formula IV include

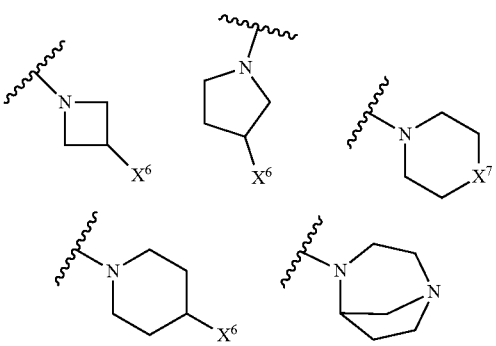

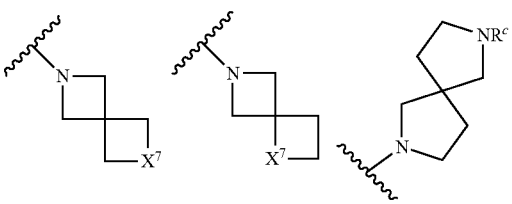

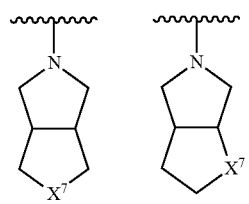

wherein $R^c$ is H, $C_{1-4}$ alkyl, oxetane, and $R^d$ is H, $C_{1-4}$ alkyl, $X^7$ is —O—, —NH— or —N(CH₃)—, —SO₂.

In some embodiments, compound of formula IV has the formula V or VI

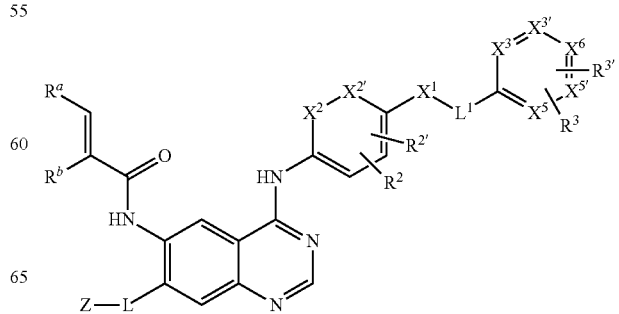

V

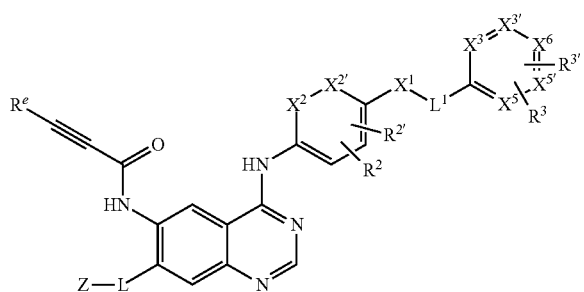

wherein $X^1$ is —O—, —CH$_2$—, —NH—, $X^2$, $X^{2'}$, $X^3$, $X^{3'}$, $X^5$, $X^{5'}$, $X^6$ are independently of each other —N=, —CH=;

$L^1$ is a covalent bond or straight chain or branched $C_{1-3}$alkyl, which is unsubstituted or substituted with hal.

$R^2$, $R^{2'}$, $R^3$, $R^{3'}$ are independently of each other H, $C_{1-6}$ alkyl, hal, —CF$_3$, —OCF$_3$;

L is a covalent bond, straight chain or branched $C_{1-4}$ alkyl or

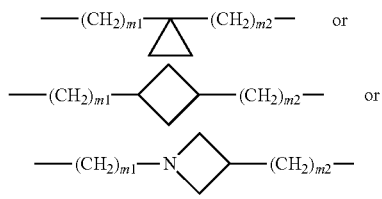

wherein m1, m2 are independently of each other 0, 1, 2, 3, or 4;

Z is —(NR$^6$R$^7$)- or —(CHR$^6$R$^7$)-, wherein R$^6$ and R$^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R''', wherein R', R''' are independently of each other H or -$C_{1-4}$ alkyl, $R^a$, $R^b$ are independently of each other H, hal, or —CH$_2$—O—CH$_3$ (e.g. H), and $R_e$ is H or methyl.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments substituent Z-L contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if L does not contain a nitrogen atom.

In some embodiments R$^a$ and R$^b$ are hydrogen.

In some embodiments, L$^1$ is straight chain or branched $C_{1-3}$alkyl, which is unsubstituted or substituted with hal. In some embodiments, L$^1$ is not a covalent bond.

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring). In some embodiments of the compounds of formula V or VI $X^2$, $X^{2'}$ are —CH=.

In some embodiments of the compounds of formula V or VI $X^3$ is —N= and $X^{3'}$, $X^5$, $X^{5'}$, $X^6$ are —CH=.

In some embodiments, $R^2$ and $R^{2'}$ are independently of each other H, $C_{1-6}$ alkyl, hal, (e.g. H, —CH$_3$, F, Cl). In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —CF$_3$, —OCF$_3$. In some embodiments, $R^3$ is H, $C_{1-6}$ alkyl, hal, —CF$_3$, —OCF$_3$ and $R^{3'}$ is H, hal.

In some embodiments of compounds of formula V or VI, $R^2$ and $R^{2'}$ are H and $R^3$ is H, $C_{1-6}$ alkyl, hal, —CF$_3$, —OCF$_3$ and $R^{3'}$ is H, hal; or $R^2$ and $R^{2'}$ are hal and $R^3$ is H, $C_{1-6}$ alkyl, hal, —CF$_3$, —OCF$_3$ and $R^{3'}$ is H, hal; or $R^2$ is hal and $R^{2'}$ is H and $R^3$ is H, $C_{1-6}$ alkyl, hal, —CF$_3$, —OCF$_3$ and $R^{3'}$ is H.

In some embodiments, Z is —(NR$^4$R$^5$), wherein R$^4$ and R$^5$ are independently of each other H, $C_{1-6}$ alkyl cyclopropyl, cylobutyl, 3 to 6-membered heterocycloalkyl containing 0, 1, or 2 N-atoms and 0, 1, or 2 O-atoms, or —(NR$^6$R$^7$), —(CHR$^6$R$^7$), wherein R$^6$ and R$^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R''', wherein R', R''' are independently of each other H or -$C_{1-4}$ alkyl.

In some embodiments, —(NR$^6$R$^7$) ring systems include

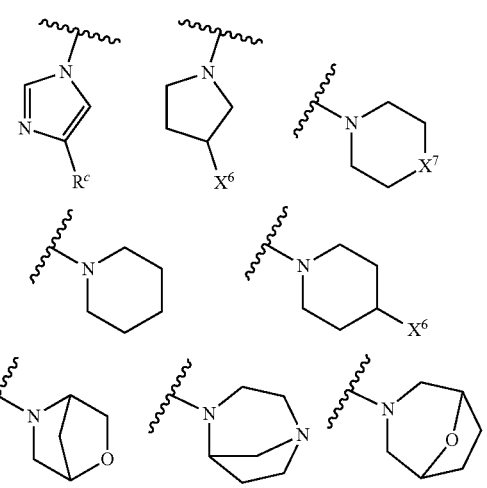

-continued

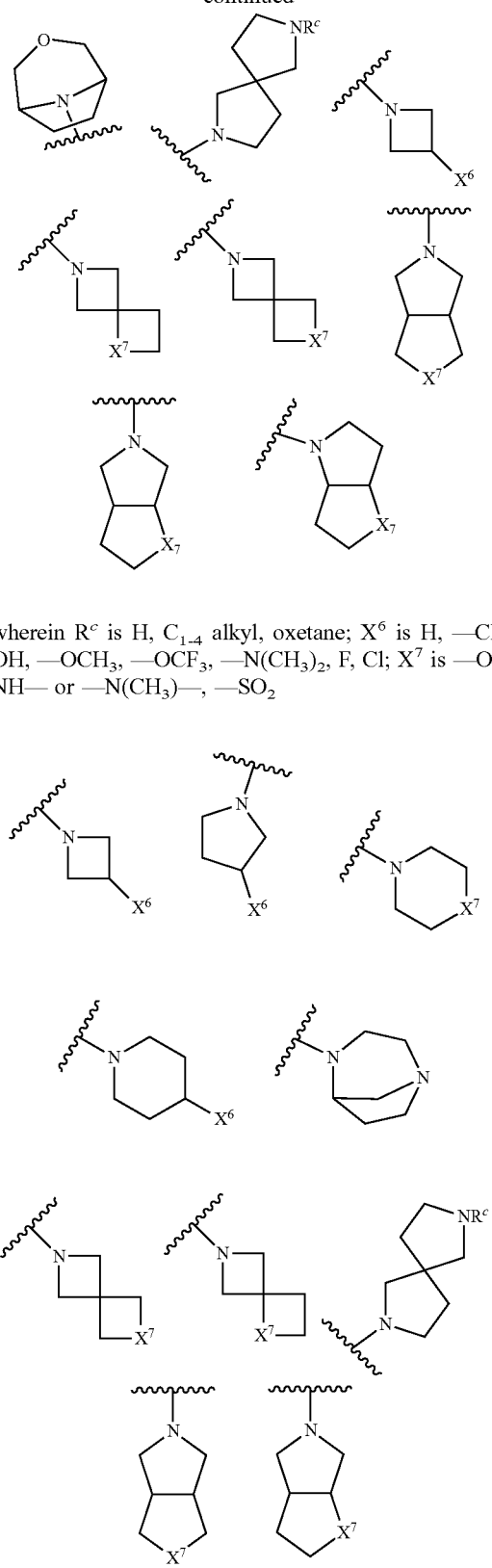

wherein $R^c$ is H, $C_{1-4}$ alkyl, oxetane; $X^6$ is H, —CH$_3$, —OH, —OCH$_3$, —OCF$_3$, —N(CH$_3$)$_2$, F, Cl; $X^7$ is —O—, —NH— or —N(CH$_3$)—, —SO$_2$ wherein $R^c$ is H, $C_{1-4}$ alkyl, oxetane (e.g. H, —CH$_3$); $X^6$ is H, —CH$_3$, —OH, —OCH$_3$, —OCF$_3$, —N(CH$_3$)$_2$, F, Cl, and $X^7$ is —O—, —NH— or —N(CH$_3$)—, —SO$_2$.

In some embodiments, —(CR$^6$R$^7$) ring systems include

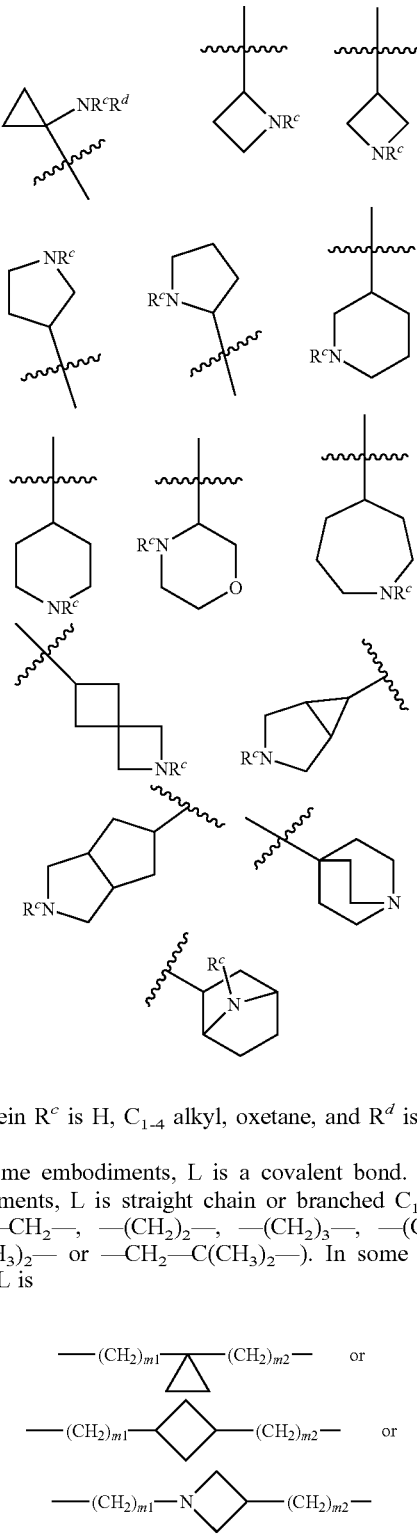

wherein $R^c$ is H, $C_{1-4}$ alkyl, oxetane, and $R^d$ is H, $C_{1-4}$ alkyl.

In some embodiments, L is a covalent bond. In some embodiments, L is straight chain or branched $C_{1-4}$ alkyl, (e.g. —CH$_2$—, —(CH$_2$)$_2$—, —(CH$_2$)$_3$—, —(CH$_2$)$_4$—, —C(CH$_3$)$_2$— or —CH$_2$—C(CH$_3$)$_2$—). In some embodiments, L is —(CH$_2$)$_{m1}$—⟨▷⟩—(CH$_2$)$_{m2}$—    or —(CH$_2$)$_{m1}$—⟨□⟩—(CH$_2$)$_{m2}$—    or —(CH$_2$)$_{m1}$—N⟨□⟩—(CH$_2$)$_{m2}$— wherein m1, m2 are independently of each other 0, 1 or 2.

In some embodiments, $X^1$ is —O—. In some embodiments, $X^1$ is —CH$_2$-. In some embodiments, $X^1$ is —NH—. In some embodiments, $X^1$ is —S—. In some embodiments, $L^1$ is a covalent bond. In some embodiments, $L^1$ is —CH$_2$— or —CH(CH₃)— or —CH(hal)-. In some embodiments, L¹ is —CH₂—CH₂— or —CH₂—CH(CH₃)— or —CH₂—CH(hal)-.

In some embodiments, the linker combinations -X¹-L¹- include —O—, —CH₂—, —O—CH₂—, —NH—CH₂—, —S—CH₂—, —CH₂—CH₂—, —O—CH(CH₃)—, —CH₂—CH(CH₃)—, —NH—CH(CH₃)—, —S—CH(CH₃)—, —O—CH(hal)-, —CH₂—CH(hal)-, —NH—CH(hal)-, —S—CH(hal)-, (e.g. —O—, —CH₂—, —O—CH₂—, —NH—CH₂—, —CH₂—CH₂—, —O—CH(CH₃)—, —CH₂—CH(CH₃)—, —O—CH(hal)-, or —CH₂—CH(hal)-, and —O—, —CH₂—, —O—CH₂—, —NH—CH₂—, or —CH₂—CH₂—).

In some embodiments, -X¹-L¹- is —O—. In some embodiments, -X¹-L¹- is —O—CH₂—. In some embodiments, -X¹-L¹- is —NH—. In some embodiments, -X¹-L¹- is —NH—CH₂—. In some embodiments, a compound of formula V or VI has the formula V-1, VI-1, or V-2, VI-2

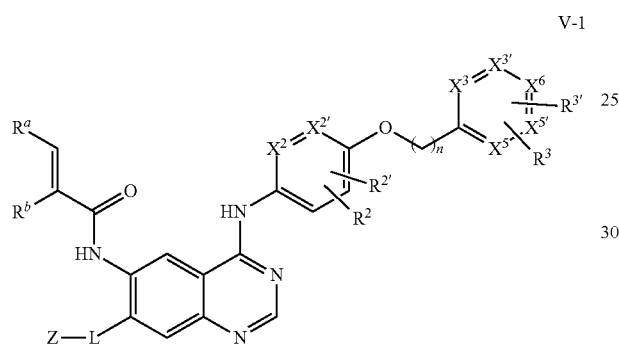

V-1

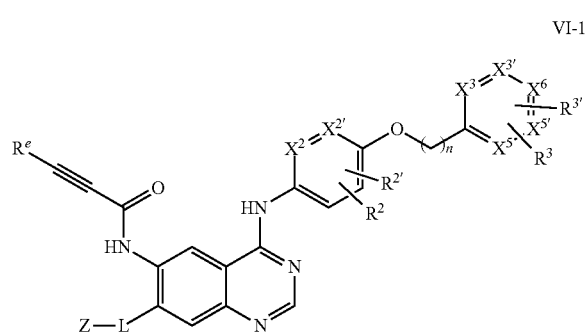

VI-1

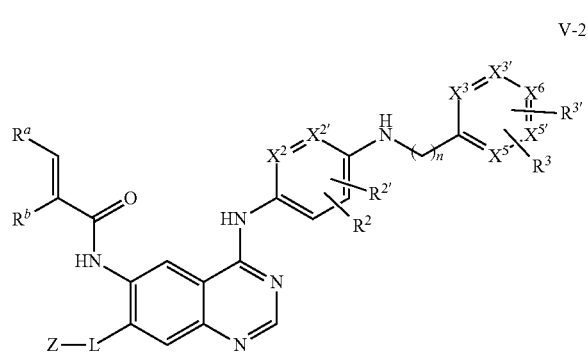

V-2

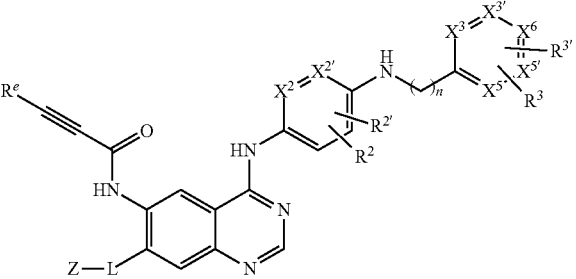

VI-2 wherein X², X²', X³, X³', X⁵, X⁵', X⁶ are independently of each other —N═, —CH═;

R², R²', R³, R³' are independently of each other H, $C_{1-6}$ alkyl, hal, —CF₃, —OCF₃;

L is a covalent bond, straight chain or branched $C_{1-4}$ alkyl or

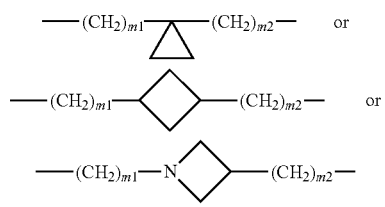

wherein m1, m2 are independently of each other 0, 1, 2, 3, or 4;

Z is —(NR⁶R⁷)- or —(CHR⁶R⁷)-, wherein R⁶ and R⁷ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R''', wherein R', R''' are independently of each other H or -$C_{1-4}$ alkyl, R$^a$, R$^b$ are independently of each other H, hal, or —CH₂—O—CH₃ (e.g. H); R$_e$ is H or methyl and n is 0 or 1.

In some embodiments substituent Z-L contains at least one nitrogen atom. Thus, the 3-6-membered heteroaryl or 3-9-membered heterocycloalkyl formed by R₆ and R₇ of (CHR₆R₇) includes a nitrogen atom if L does not contain a nitrogen atom.

In some embodiments R$^a$ and R$^b$ are hydrogen.

In some embodiments, n is 0. In some embodiments, n is 1.

In some embodiments, both X², X²' are —CH═ (i.e. a phenyl ring). In some embodiments, X² is —N═ and X²' is —CH═ or X²' is —N═ and X² is —CH═ (i.e. a pyridine ring). In some embodiments, both X², X²' are —N═ (i.e. a pyridazine ring).

In some embodiments, X³, X³', X⁵, X⁵', X⁶ are —CH═ (i.e. a phenyl ring). In some embodiments, X³ is —N═ and X³', X⁵, X⁵', X⁶ are —CH═ or X³' is —N═ and X³, X⁵, X⁵', X⁶ are —CH═ or X⁶ is —N═ and X³, X³', X⁵, X⁵' are —CH═ (i.e. a pyridine ring).

In some embodiments, both X³, X³' are —N═ and X⁵, X⁵', X⁶ are —CH═ or both X³', X⁶ are —N═ and X³, X⁵, X⁵' are —CH═ (i.e. a pyridazine ring). In some embodiments, both X³, X⁵ are —N═ and X³', X⁵', X⁶ are —CH═ or both X³', X⁵' are —N═ and X³, X⁵, X⁶ are —CH═ or both $X^3$, $X^6$ are —N= and $X^{3'}$, $X^5$, $X^{5'}$ are —CH= (i.e. pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other H, $C_{1-6}$ alkyl, hal, (e.g. H, —CH$_3$, F, Cl). In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —CF$_3$, —OCF$_3$. In some embodiments, $R^3$ is H, $C_{1-6}$ alkyl, hal, —CF$_3$, —OCF$_3$ and $R^{3'}$ is H, hal.

In some embodiments, a compound of formula V-1, VI-1 has one of the following formulas V-1-(ii)d-1
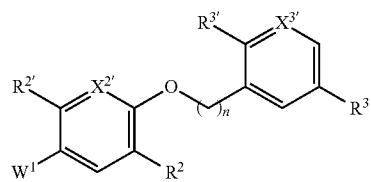

V-1-(ii)d-2
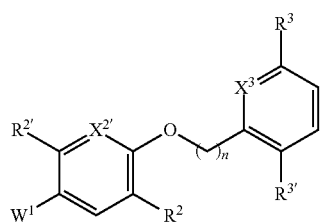

V-1-(ii)d-3
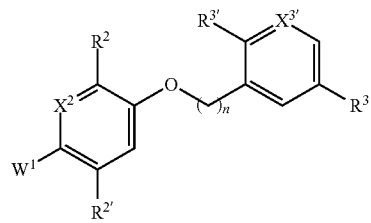

V-1-(ii)d-4
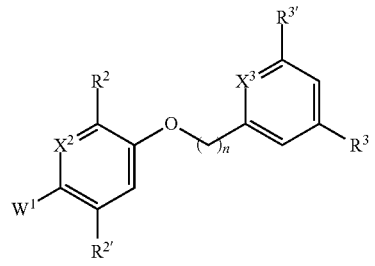

V-1-(ii)d-5
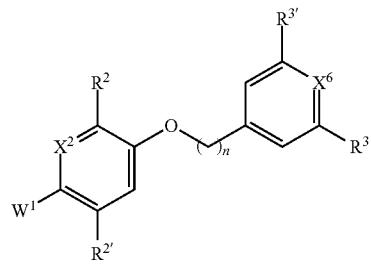

-continued

V-1-(ii)d-6
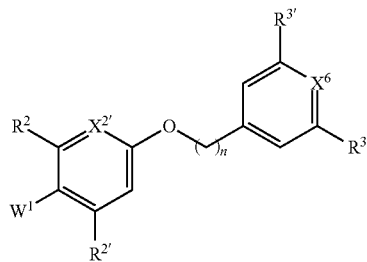

and W$_1$ is

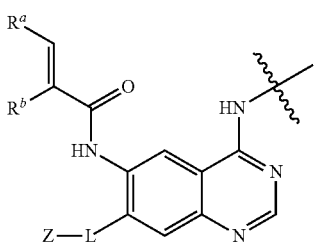

or

VI-1-(ii)d-1
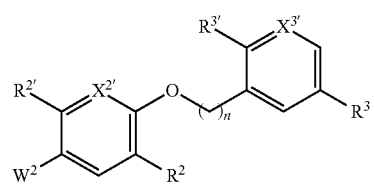

VI-1-(ii)d-2
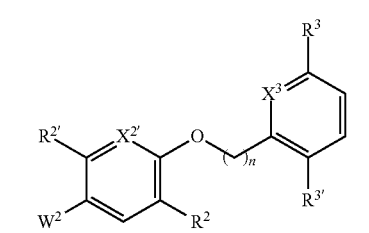

VI-1-(ii)d-3
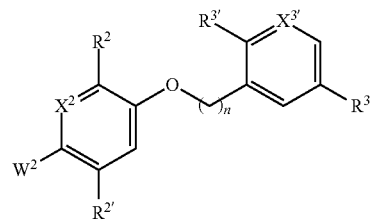

VI-1-(ii)d-4
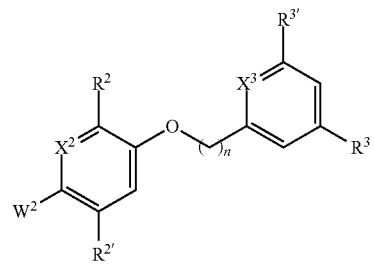

VI-1-(ii)d-5

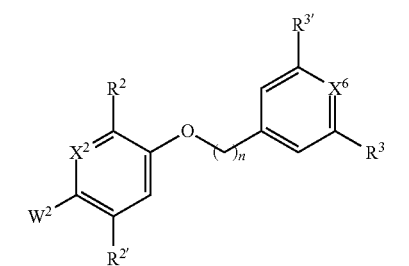

VI-1-(ii)d-6

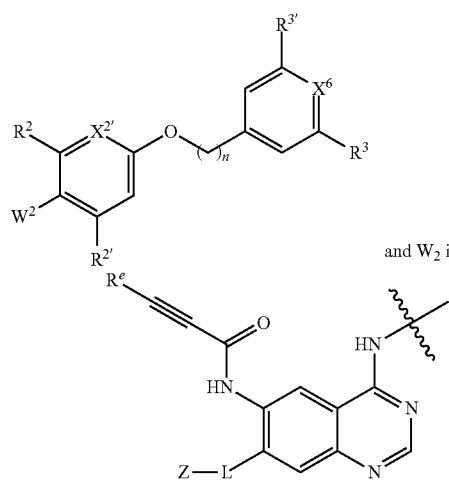

and W$_2$ is

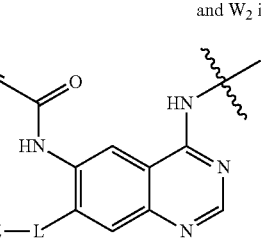

wherein X$^2$, X$^{2'}$, X$^3$, X$^{3'}$, X$^5$, X$^{5'}$, X$^6$ are independently of each other —N= or —CH=; and R$^2$, R$^{2'}$, R$^3$, R$^{3'}$ are independently of each other H, C$_{1-6}$ alkyl, hal, —CF$_3$, or —OCF$_3$; and Z, L, R$^e$a, R$^b$, R$^e$ are as defined above for a compound of formula V and VI (or V-1, VI-1).

In some embodiments substituent Z-L contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if L does not contain a nitrogen atom.

In some embodiments R$^a$ and R$^b$ are hydrogen.

In some embodiments, X$^2$ and X$^{2'}$ are —CH= (i.e. a phenyl ring) and X$^3$, X$^{3'}$ and X$^6$ are —CH= (i.e. a phenyl ring).

In some embodiments, X$^2$ and X$^{2'}$ are —CH= (i.e. a phenyl ring) and X$^3$, X$^{3'}$ and X$^6$ are —N= (i.e. a pyridine ring).

In some embodiments, X$^2$ and X$^{2'}$ are —N= (i.e. a pyridine ring) and X$^3$, X$^{3'}$ and X$^6$ are —CH= (i.e. a phenyl ring).

In some embodiments, X$^2$ and X$^{2'}$ a —N= (i.e. a pyridine ring) and X$^3$, X$^{3'}$ and X$^6$ are —N= (i.e. a pyridine ring).

In some embodiments, a compound of formula V-1, VI-1 has one of the following formulas V-1-(ii)e-1

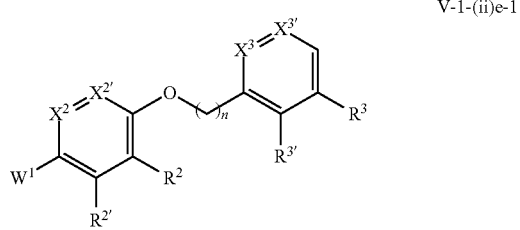

V-1-(ii)e-2

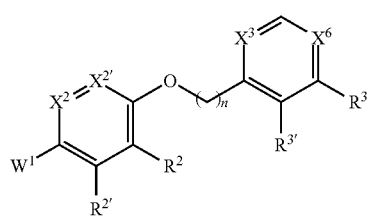

V-1-(ii)e-3

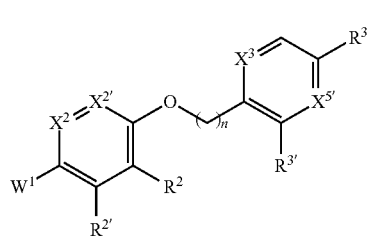

V-1-(ii)e-4

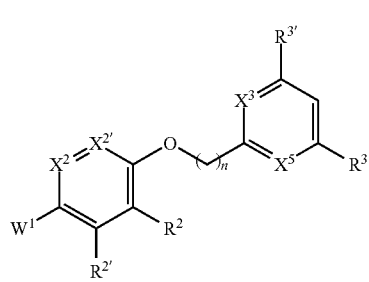

V-1-(ii)e-5

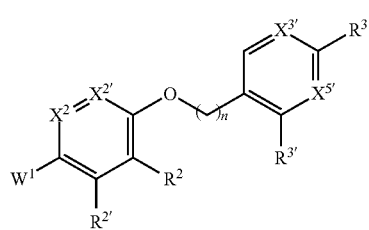

V-1-(ii)e-6

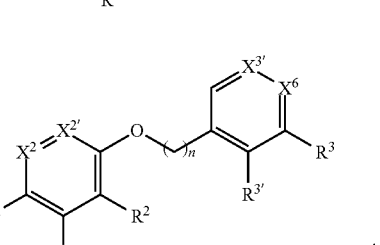

and W$_1$ is

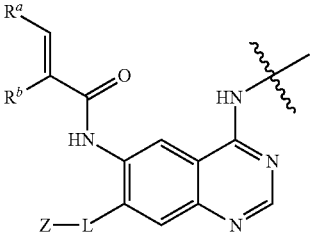

VI-1-(ii)e-1

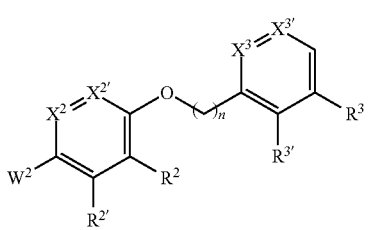

-continued

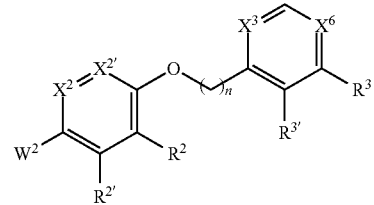
VI-1-(ii)e-2

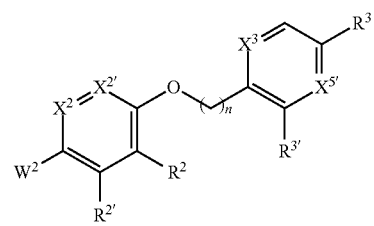
VI-1-(ii)e-3

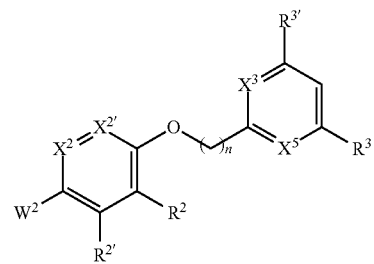
VI-1-(ii)e-4

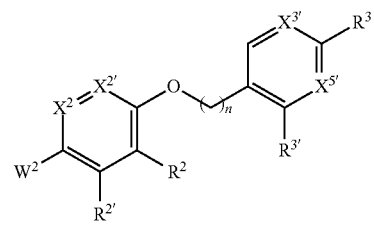
VI-1-(ii)e-5

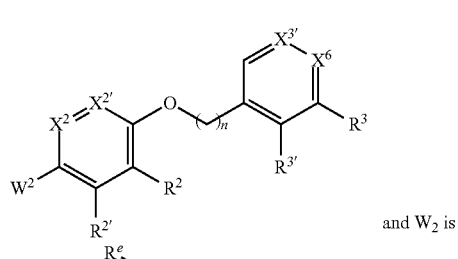
VI-1-(ii)e-6 and W₂ is

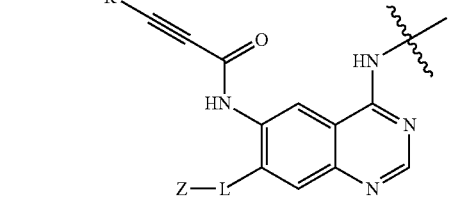

wherein $X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —CF$_3$, or —OCF$_3$, n is 0 or 1.

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^{5'}$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring). In some embodiments, a compound of formula V-2, VI-2 has one of the following formulas

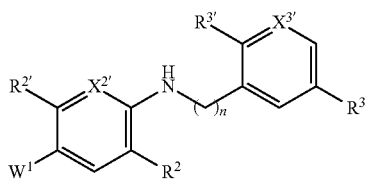
V-2-(ii)f-1

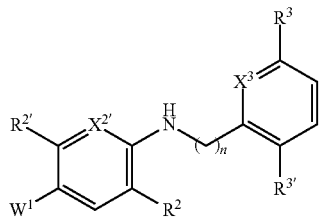
V-2-(ii)f-2

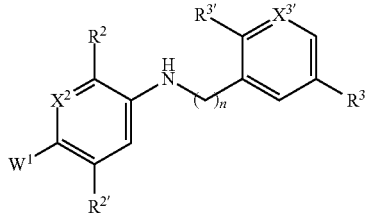
V-2-(ii)f-3

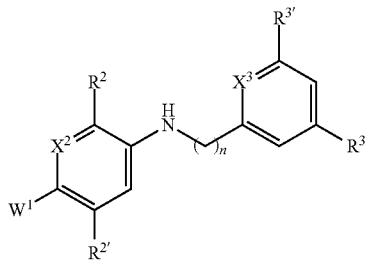
V-2-(ii)f-4

V-2-(ii)f-5

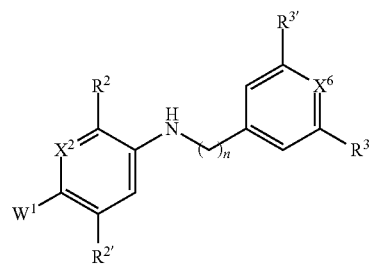

V-2-(ii)f-6

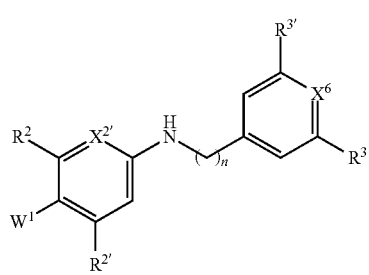

and W₁ is

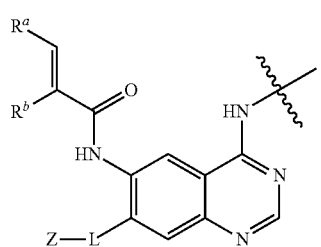

VI-2-(ii)f-1

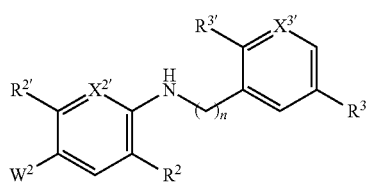

VI-2-(ii)f-2

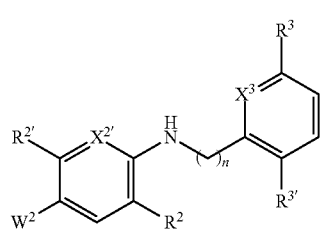

VI-2-(ii)f-3

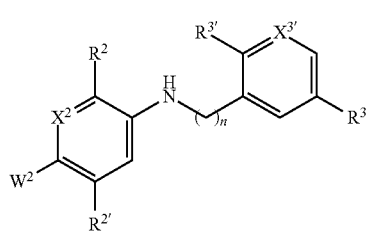

VI-2-(ii)f-4

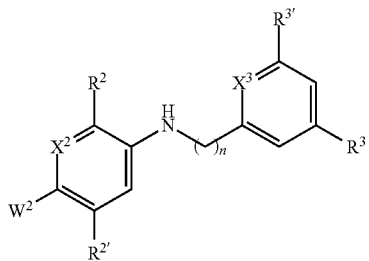

VI-2-(ii)f-5

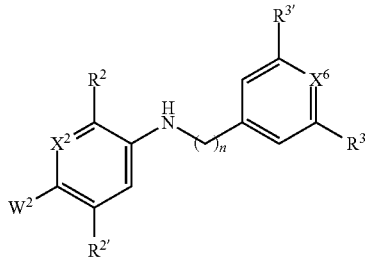

VI-2-(ii)f-6

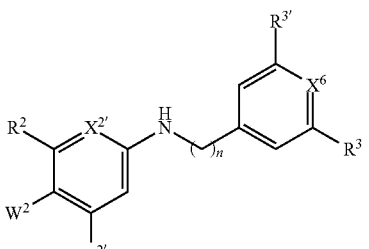

and W₂ is

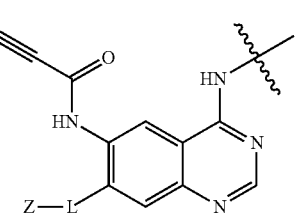

wherein $X^2$, $X^{2\prime}$, $X^3$, $X^{3\prime}$, $X^5$, $X^{5\prime}$, $X^6$ are independently of each other —N═ or —CH═; and $R^2$, $R^{2\prime}$, $R^3$, $R^{3\prime}$ are independently of each other H, $C_{1-6}$ alkyl, hal, —$CF_3$, or —$OCF_3$; and Z, L, $R^e$a, $R^b$, $R^e$ are as defined above for a compound of formula V and VI (or V-2, VI-2).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, $X^2$ and $X^{2\prime}$ are —CH═ (i.e. a phenyl ring) and $X^3$, $X^{3\prime}$ and $X^6$ are —CH═ (i.e. a phenyl ring).

In some embodiments, $X^2$ and $X^{2\prime}$ are —CH═ (i.e. a phenyl ring) and $X^3$, $X^{3\prime}$ and $X^6$ are —N═ (i.e. a pyridine ring).

In some embodiments, $X^2$ and $X^{2\prime}$ are —N═ (i.e. a pyridine ring) and $X^3$, $X^{3\prime}$ and $X^6$ are —CH═ (i.e. a phenyl ring).

In some embodiments, $X^2$ and $X^{2\prime}$ a —N═ (i.e. a pyridine ring) and $X^3$, $X^{3\prime}$ and $X^6$ are —N═ (i.e. a pyridine ring).

In some embodiments, a compound of formula V-2, VI-2 has one of the following formulas V-2-(ii)g-1
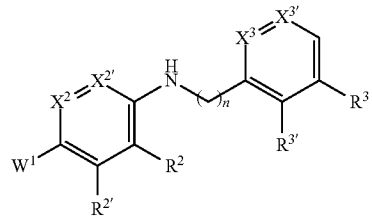
VI-2-(ii)g-1
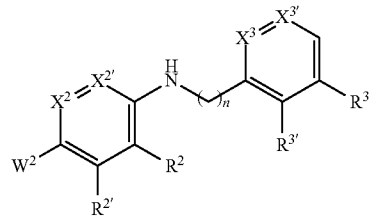
V-2-(ii)g-2
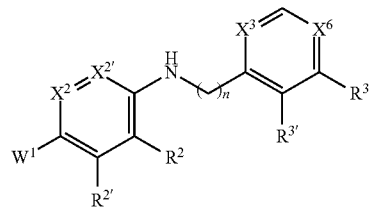
VI-2-(ii)g-2
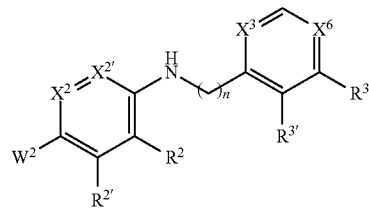
V-2-(ii)g-3
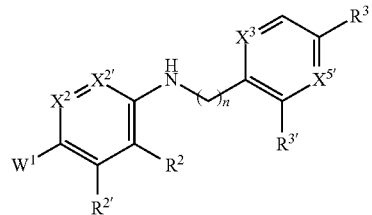
VI-2-(ii)g-3
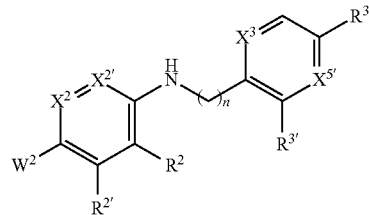
V-2-(ii)g-4
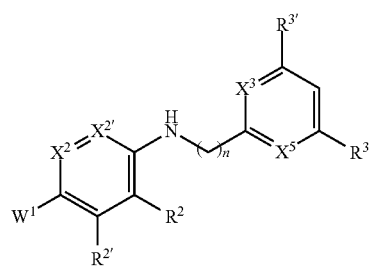
VI-2-(ii)g-4
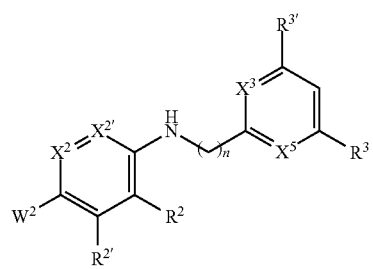
V-2-(ii)g-5
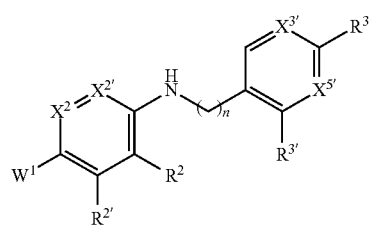
VI-2-(ii)g-5
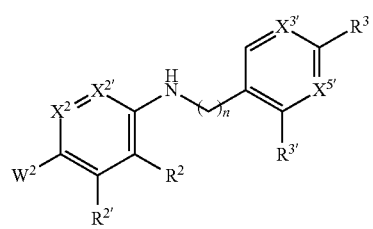
V-2-(ii)g-6
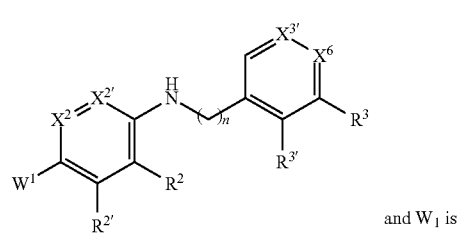
VI-2-(ii)g-6
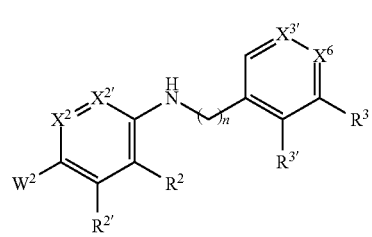
and $W_1$ is
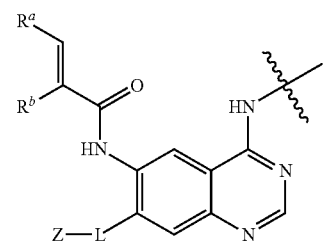
and $W_2$ is
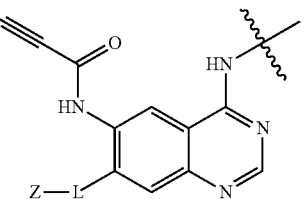

wherein $X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring) In some embodiments, both $X^2$, $X^{2'}$ are —N= (i.e. a pyridazine ring).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other H, hal or $C_{1-6}$ alkyl and H, hal or —$CH_3$).

In some embodiments, $R^3$ is H, hal, —$CF_3$, or —$OCF_3$.

In some embodiments, $R^{3'}$ is H, hal or $C_{1-6}$ alkyl (e.g. H, hal or —$CH_3$).

In some embodiments, $R^3$ and $R^{3'}$ are H. In some embodiments, $R^3$ and $R^{3'}$ are hal. In some embodiments, $R^3$ is hal, —$CF_3$, or —$OCF_3$ and $R^{3'}$ is H. In some embodiments, $R^3$ is H and $R^{3'}$ is is hal, or $C_{1-6}$ alkyl.

In some embodiments, $R^2$ and $R^{2'}$ are H. In some embodiments, $R^2$ and $R^{2'}$ are hal. In some embodiments, $R^2$ is hal or $C_{1-6}$ alkyl and $R^{2'}$ is H. In some embodiments, $R^2$ is H and $R^{2'}$ is hal.

In some embodiments, a compound of formula V-1, VI-1, or V-2, VI-2 has the formulas V-1-(ii)h-a

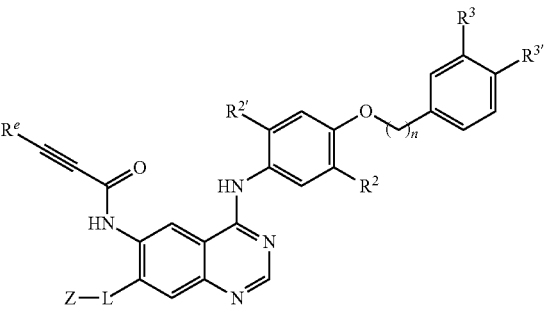

-continued

VI-1-(ii)h-a

V-2-(ii)h-a

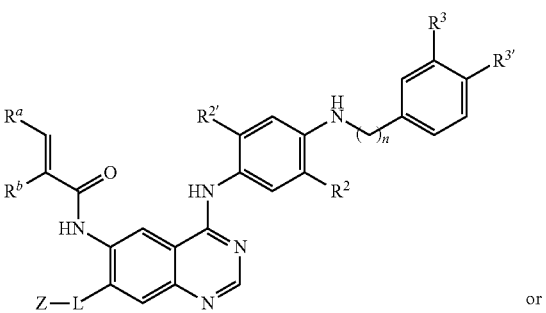

or

VI-2-(ii)h-a wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^a$, $R^b$ $R^e$ are as defined above for a compound of formula V and VI (or V-1, VI-1, or V-2, VI-2).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula V-1, VI-1 has the formulas

V-1-(ii)h-c-1
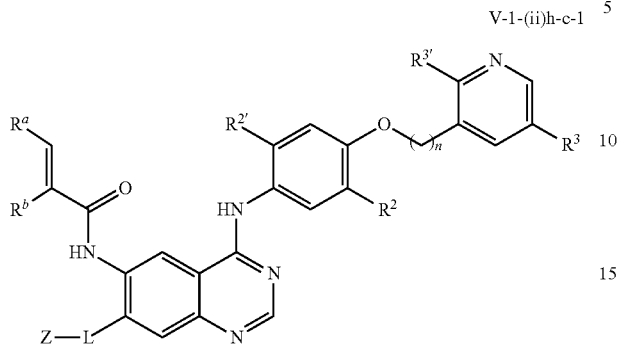

V-1-(ii)h-b-1
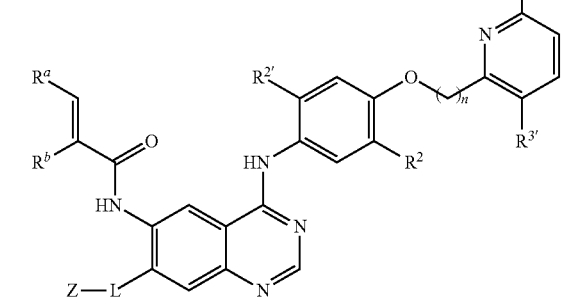

V-1-(ii)h-d-1
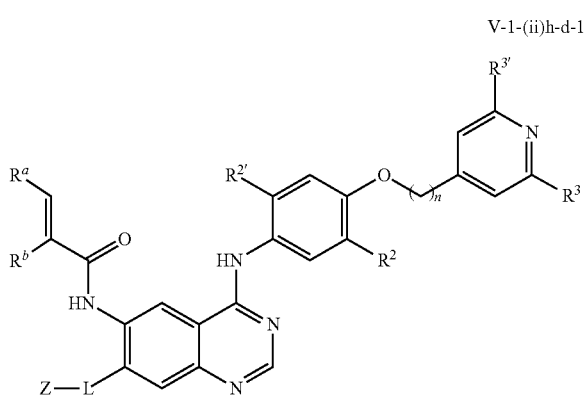

VI-1-(ii)h-d-1
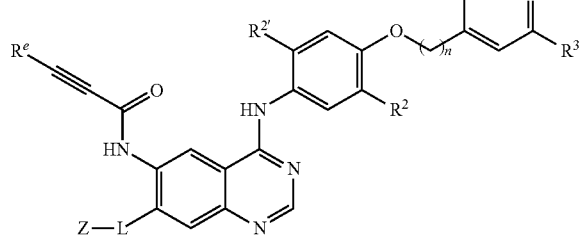

VI-1-(ii)h-c-1
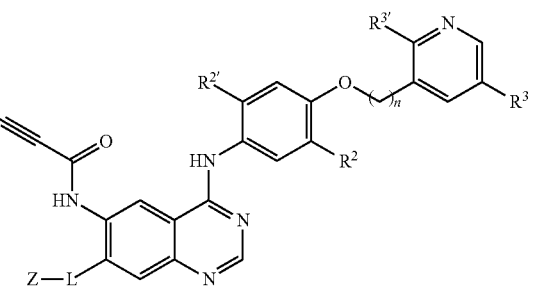

VI-1-(ii)h-b-1
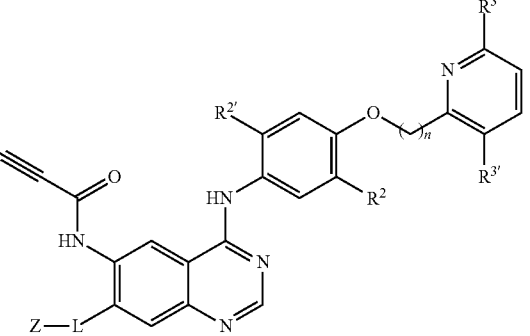

wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^a$, $R^b$, $R^e$ are as defined above for a compound of formula V and VI (or V-1, VI-1, or V-2, VI-2).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula V-I has the formula

V-1-(ii)h-b-2
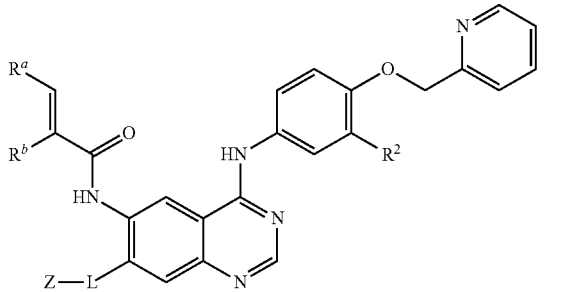

wherein $R^2$ is H, $C_{1-6}$ alkyl, hal (e.g. H, —$CH_3$, F, Cl); $R^3$, $R^{3'}$ are H, $C_{1-6}$ alkyl, hal, —$CH_3$, —$OCF_3$; and n is 0 or 1; and Z, L, $R^a$, $R^b$, $R^e$ are as defined above for a compound of formula V and VI (or V-1, VI-1, or V-2, VI-2).

In some embodiments, $R^2$ is halogen, such as Cl.

In some embodiments, $R^a$ and $R^b$ are hydrogen.

In some embodiments, a compound of formula V-2, VI-2 has the formulas

V-1-(ii)i-c-1
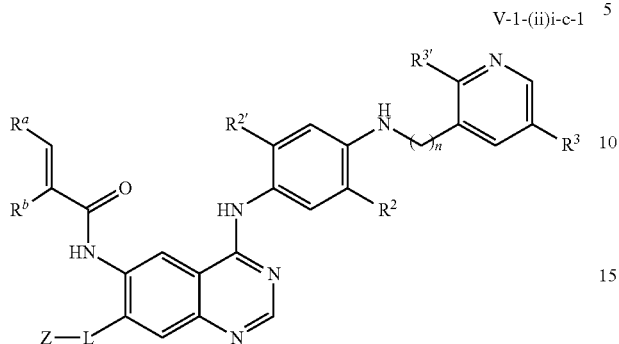

V-1-(ii)i-b-1
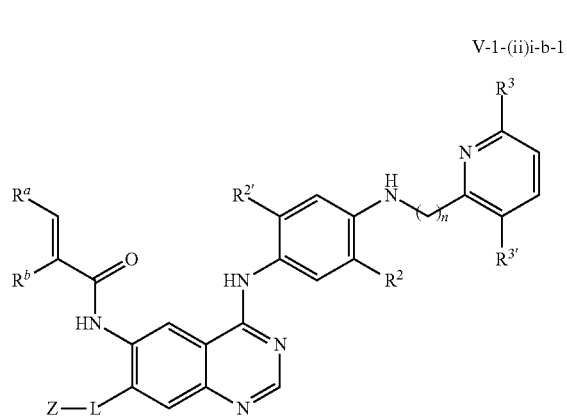

V-1-(ii)i-d-1
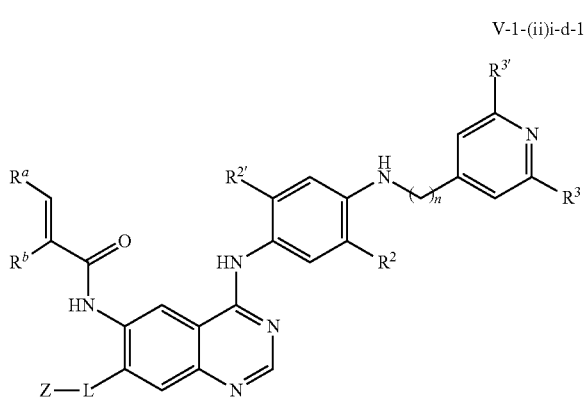

VI-1-(ii)i-d-1
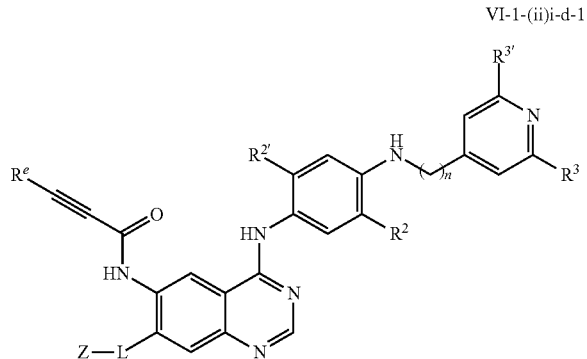

VI-1-(ii)i-c-1
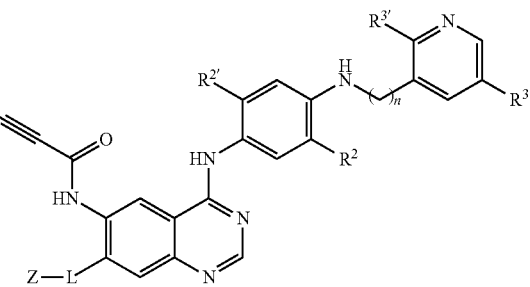

VI-1-(ii)i-b-1
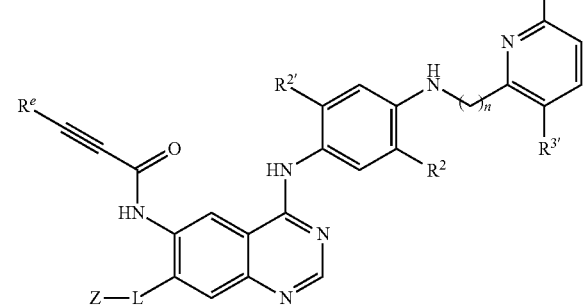

wherein $R^2$, $R^{2'}$ are independently of each other H, $C_{1-6}$ alkyl, hal, (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^a$, $R^b$, $R^e$ are as defined above for a compound of formula V and VI (or V-2, VI-2).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula V-1, VI-1 has the formulas

V-1-(ii)h-h-1
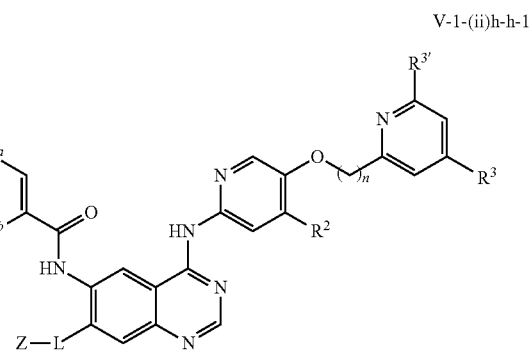

141
-continued
V-1-(ii)h-i-1
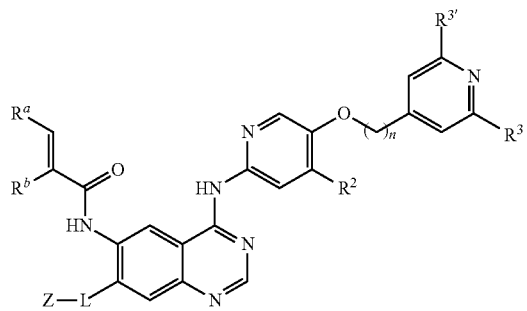
V-1-(ii)h-j-1
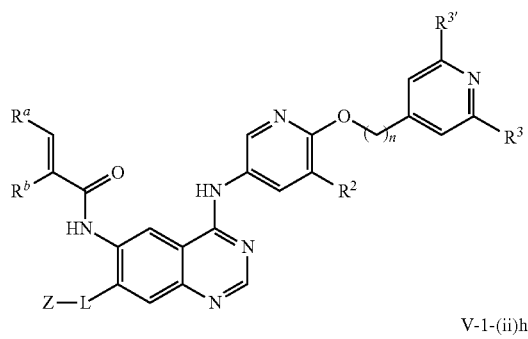
V-1-(ii)h-f-1
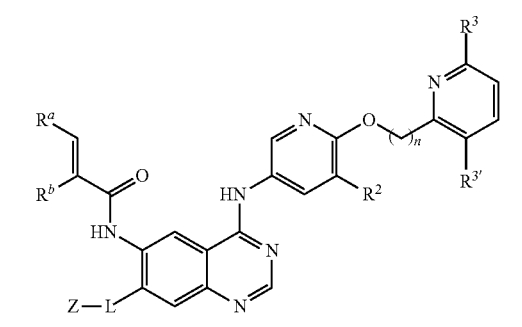
V-1-(ii)h-e-1
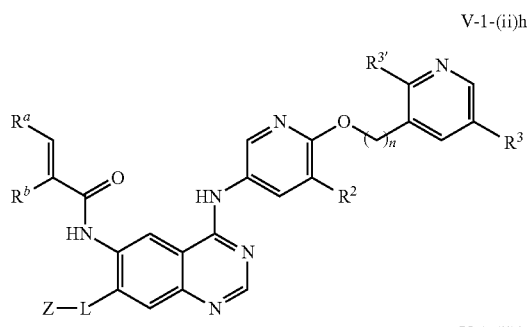
V-1-(ii)h-g-1
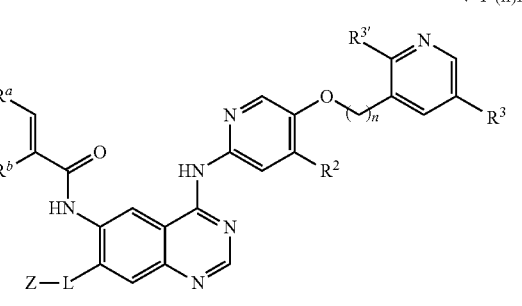
or
142
-continued
VI-1-(ii)h-h-1
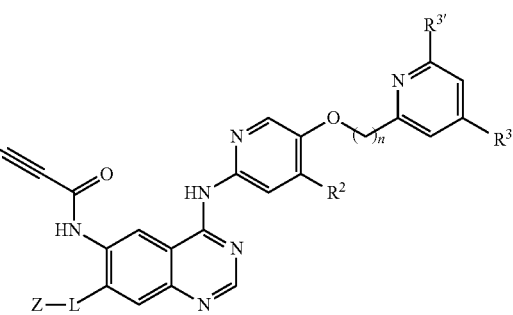
VI-1-(ii)h-i-1
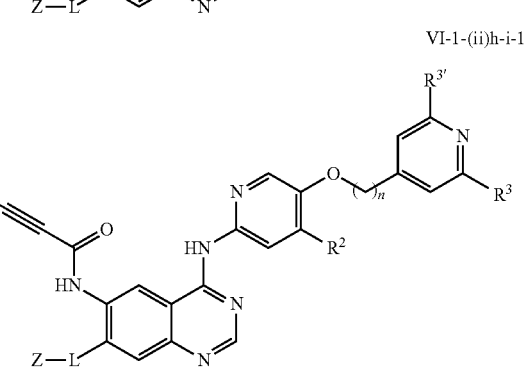
VI-1-(ii)h-j-1
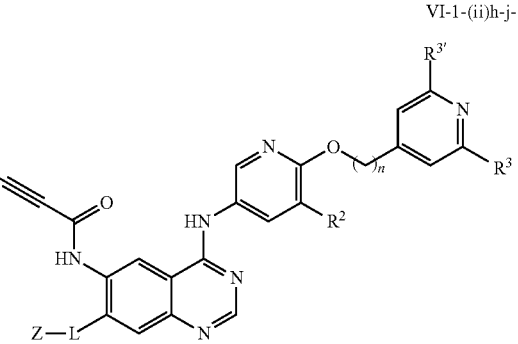
VI-1-(ii)h-f-1
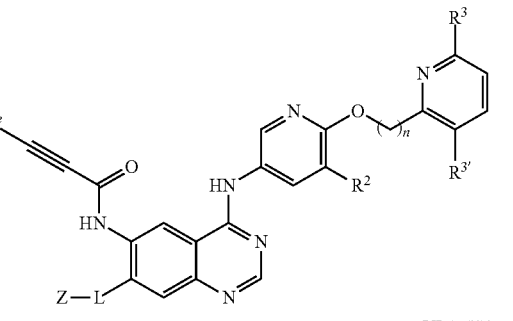
VI-1-(ii)h-e-1
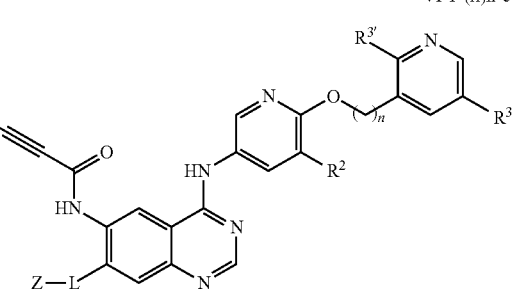

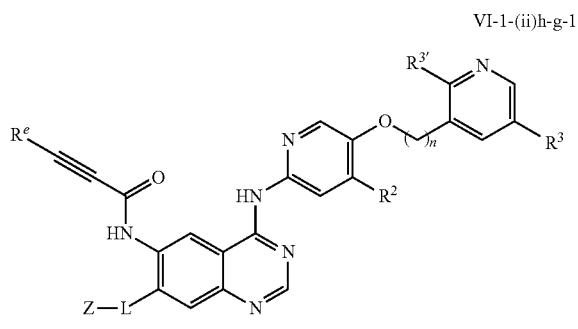

VI-1-(ii)h-g-1 wherein $R^2$ is H, $C_{1-6}$ alkyl, hal (e.g. H, —$CH_3$, F, Cl); $R^3$, $R^{3'}$ are is H, $C_{1-6}$ alkyl, hal, —$CF_3$, —$OCF_3$; and n is 0 or 1; and Z, L, $R^a$, $R^b$, $R^e$ are as defined above for a compound of formula V and VI (or V-1, VI-1).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula V-2, VI-2 has the formulas

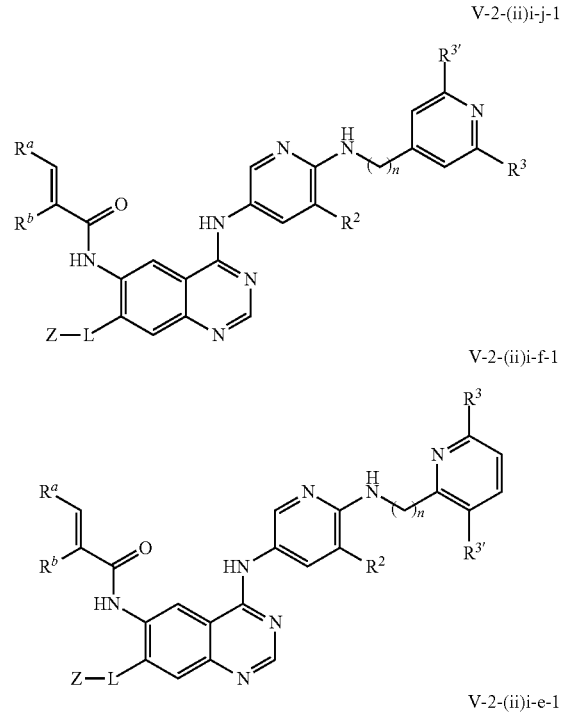

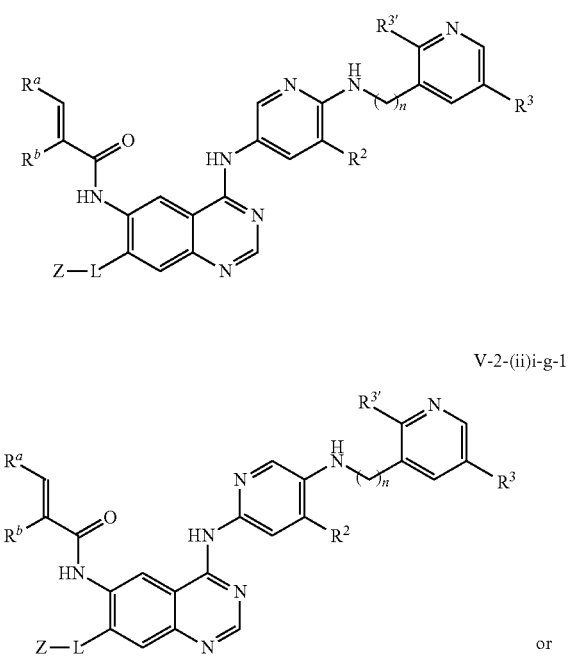

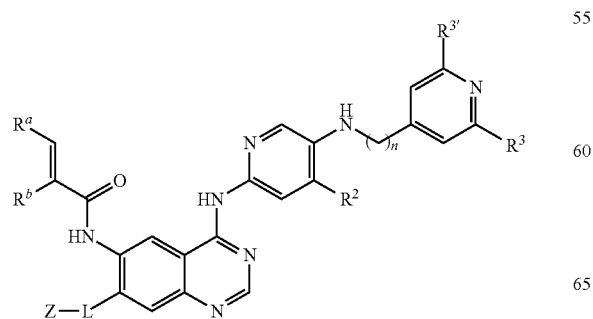

VI-2-(ii)i-i-1

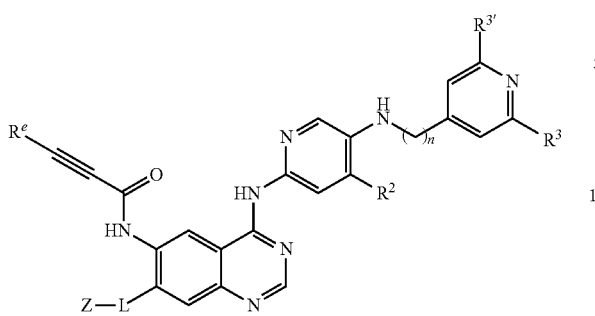

VI-2-(ii)i-j-1

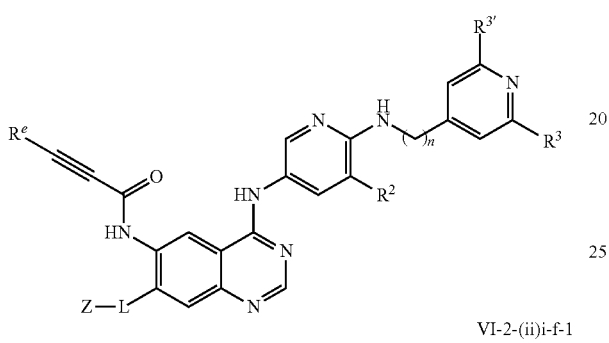

VI-2-(ii)i-f-1

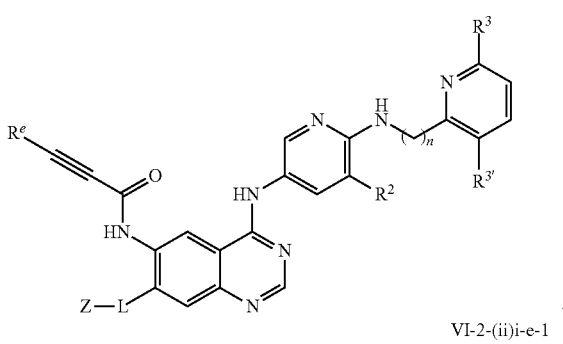

VI-2-(ii)i-e-1

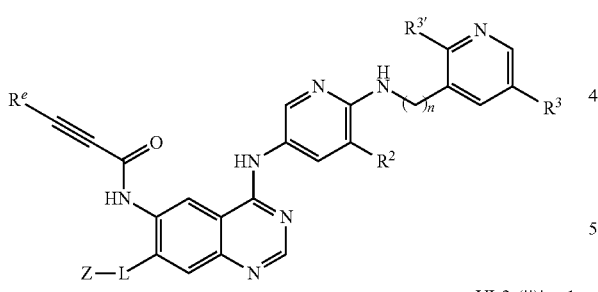

VI-2-(ii)i-g-1

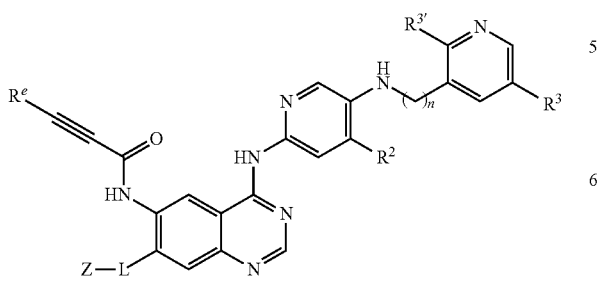

wherein $R^2$ is H, $C_{1-6}$ alkyl, hal (e.g. H, —CH$_3$, F, Cl); $R^3$, $R^{3'}$ are is H, $C_{1-6}$ alkyl, hal, —CF$_3$, —OCF$_3$; and n is 0 or 1; and Z, L, $R^a$, $R^b$, $R^e$ are as defined above for a compound of formula V and VI (or V-2, VI-2).

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula V-1, VI-1 has the formulas

V-1-(ii)h-k-1

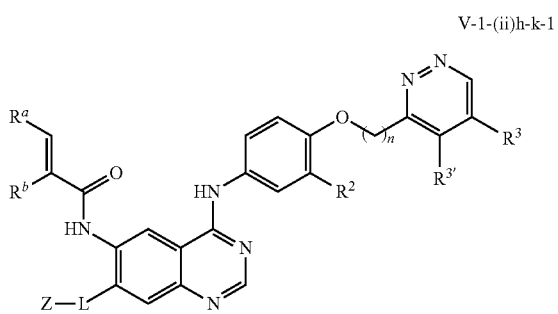

V-1-(ii)h-i-1

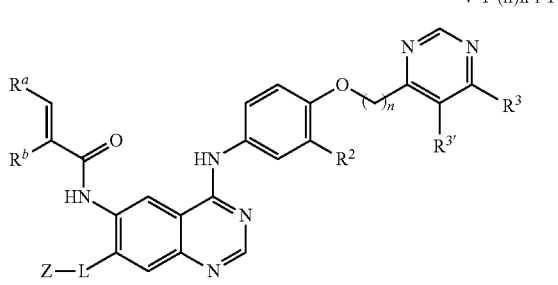

V-1-(ii)h-n-1

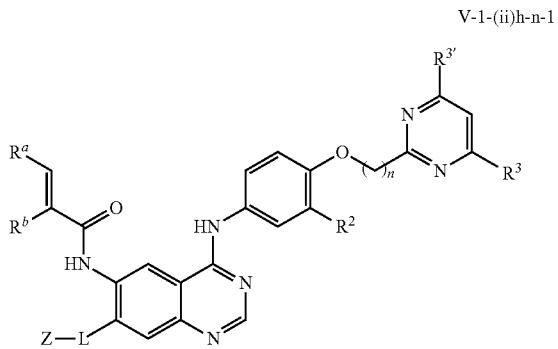

V-1-(ii)h-m-1

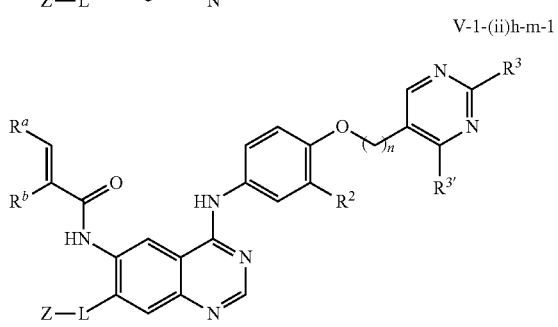

V-1-(ii)h-o-1

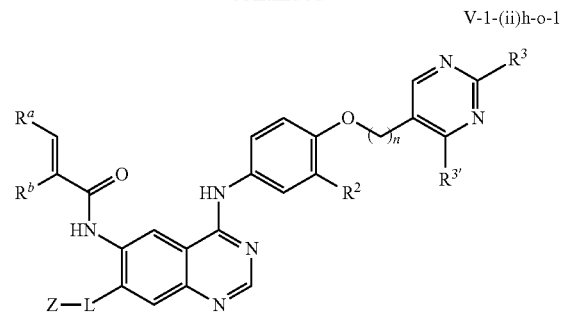

V-1-(ii)h-p-1

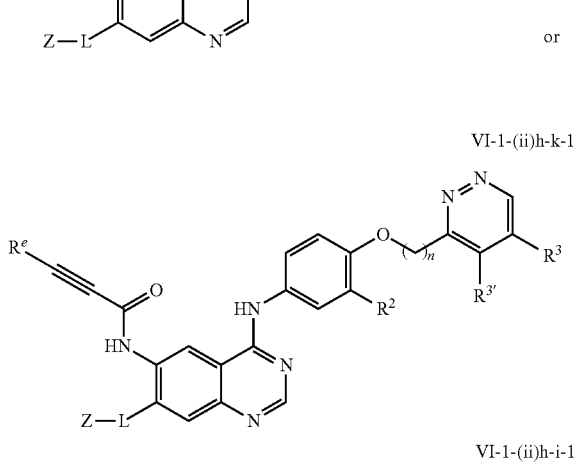

or

VI-1-(ii)h-k-1

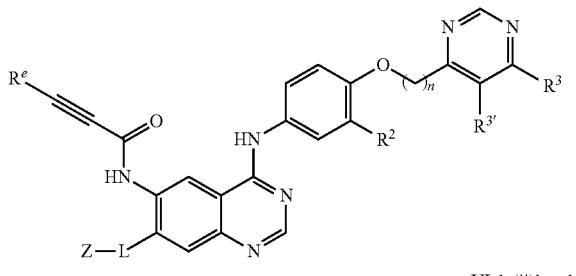

VI-1-(ii)h-i-1

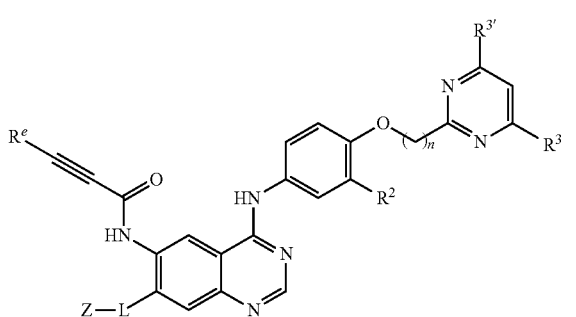

VI-1-(ii)h-n-1

VI-1-(ii)h-m-1

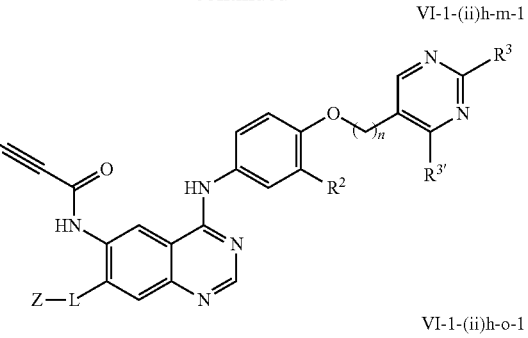

VI-1-(ii)h-o-1

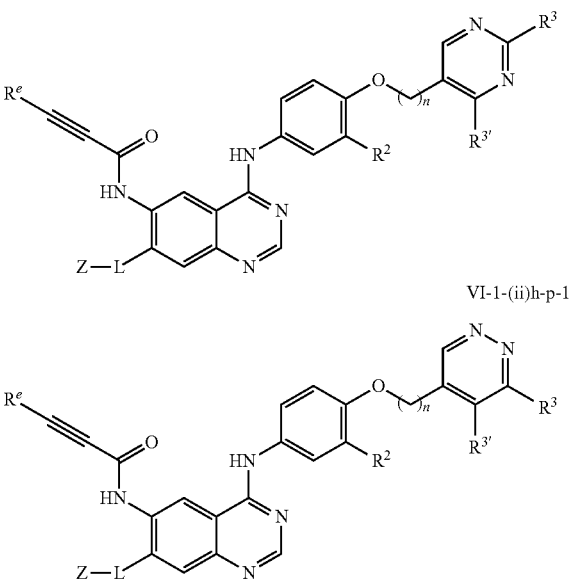

VI-1-(ii)h-p-1 wherein $R^2$ is H, $C_{1-6}$ alkyl, hal (e.g. H, —$CH_3$, F, Cl); $R^3$, $R^{3'}$ are is H, $C_{1-6}$ alkyl, hal, —$CF_3$, —$OCF_3$; and n is 0 or 1; and Z, L, $R^a$, $R^b$, $R^e$ are as defined above for a compound of formula V and VI (or V-1, VI-1).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula V-2, VI-2 has the formulas

V-2-(ii)i-k-1

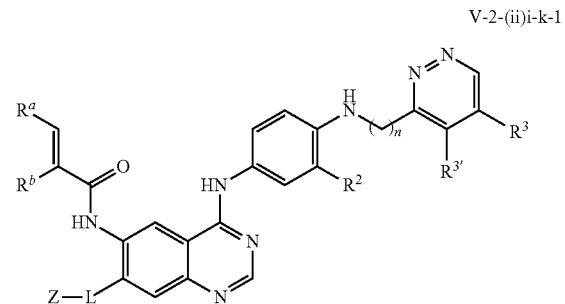

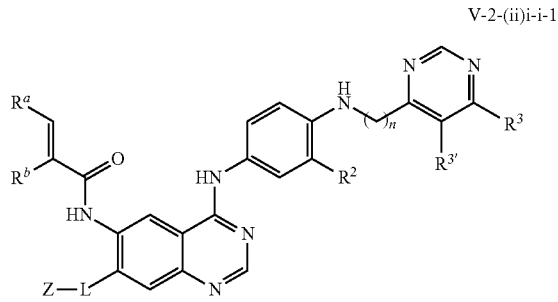
V-2-(ii)i-i-1
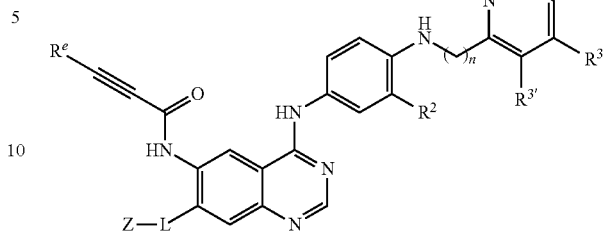
VI-2-(ii)i-k-1
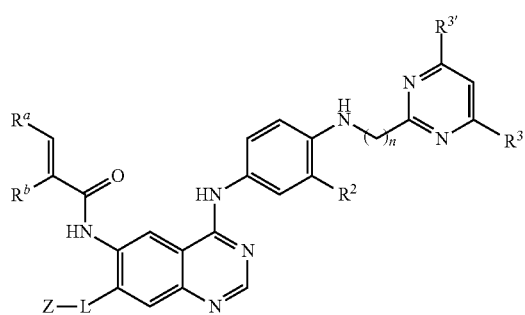
V-2-(ii)i-n-1
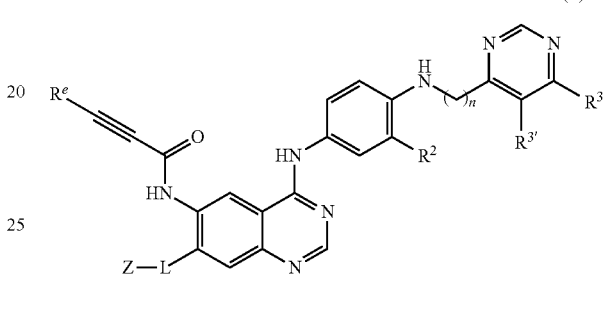
VI-2-(ii)i-l-1
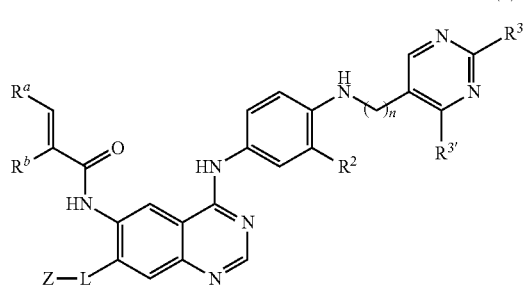
V-2-(ii)i-m-1
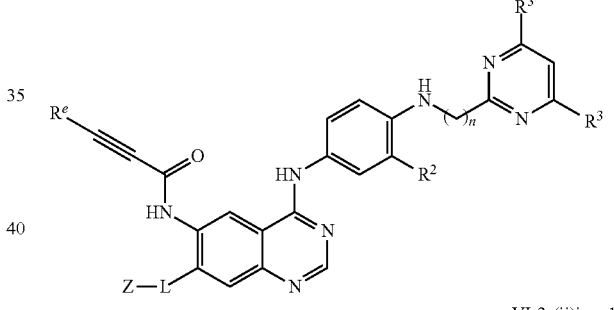
VI-2-(ii)i-n-1
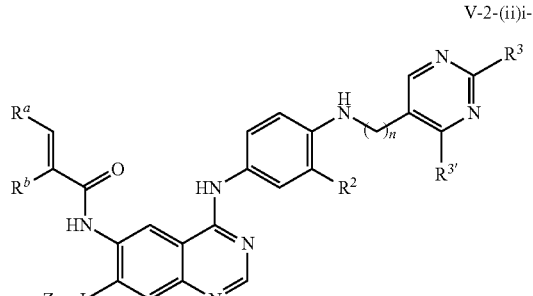
V-2-(ii)i-o-1
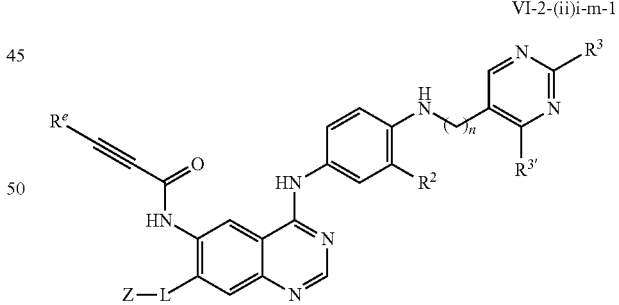
VI-2-(ii)i-m-1
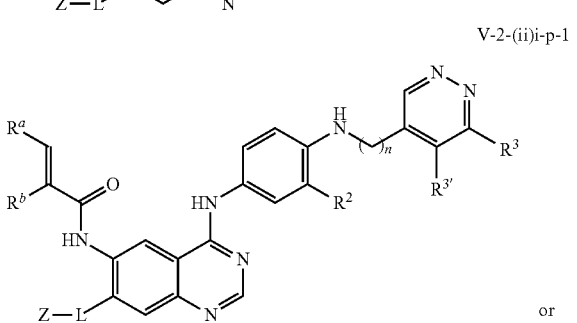
V-2-(ii)i-p-1
or
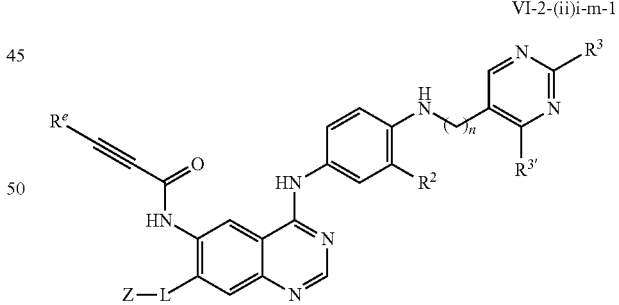
VI-2-(ii)i-o-1

-continued

VI-2-(ii)i-p-1

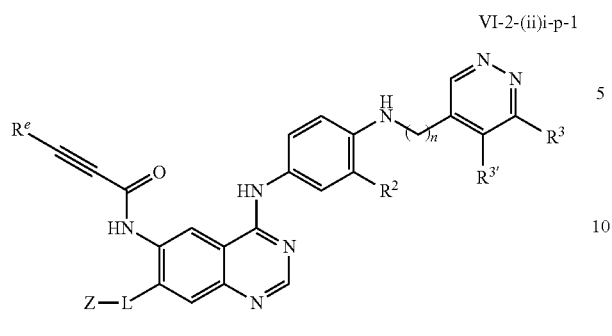

wherein $R^2$ is H, $C_{1-6}$ alkyl, hal (e.g. H, —CH$_3$, F, Cl); $R^3$, $R^{3'}$ are is H, $C_{1-6}$ alkyl, hal, —CF$_3$, —OCF$_3$; and n is 0 or 1; and Z, L, $R^a$, $R^b$, $R^e$ are as defined above for a compound of formula V and VI (or V-2, VI-2).

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, n is 0. In some embodiments, n is 1.

In some embodiments, group Z is defined as specified above. In some embodiments, Z is —(NR$^4$R$^5$), wherein $R^4$ and $R^5$ are independently of each other H, $C_{1-6}$ alkyl, cyclopropyl, cylobutyl, 3 to 6-membered heterocycloalkyl containing 0, 1, or 2 N-atoms and 0, 1, or 2 O-atoms, or —(NR$^6$R$^7$), —(CHR$^6$R$^7$), wherein $R^6$ and $R^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R" are independently of each other H or -$C_{1-4}$ alkyl.

In some embodiments, the —(CR$^6$R$^7$) and —(NR$^6$R$^7$) ring systems of Z is selected from

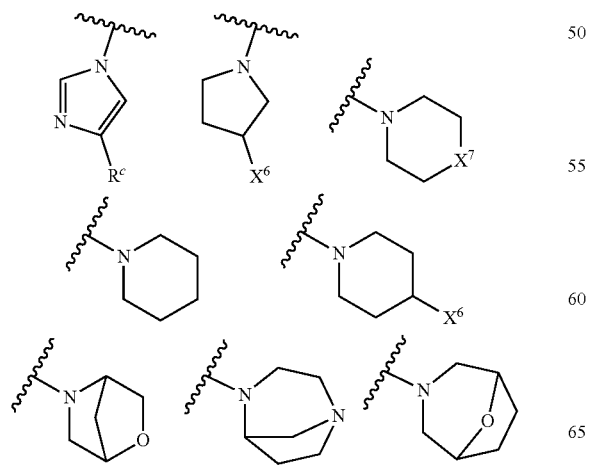

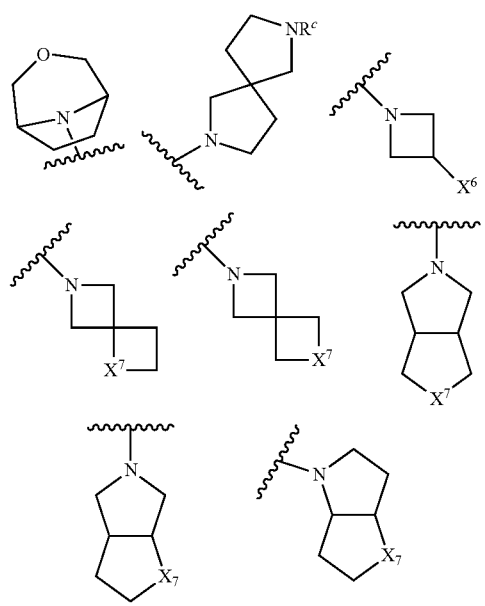

wherein $R^c$ is H, $C_{1-4}$ alkyl, oxetane; $X^6$ is H, —CH$_3$, —OH, —OCH$_3$, —OCF$_3$, —N(CH$_3$)$_2$, F, Cl; $X^7$ is —O—, —NH— or —N(CH$_3$)—, —SO$_2$, and

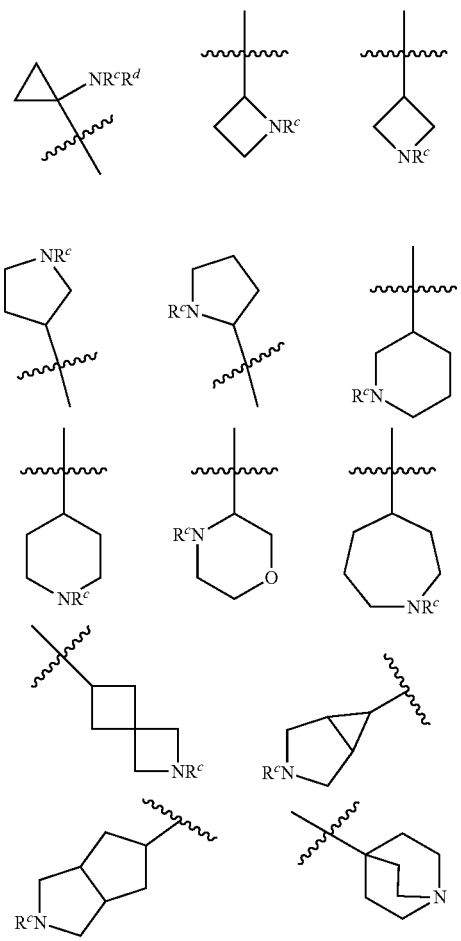

153

-continued

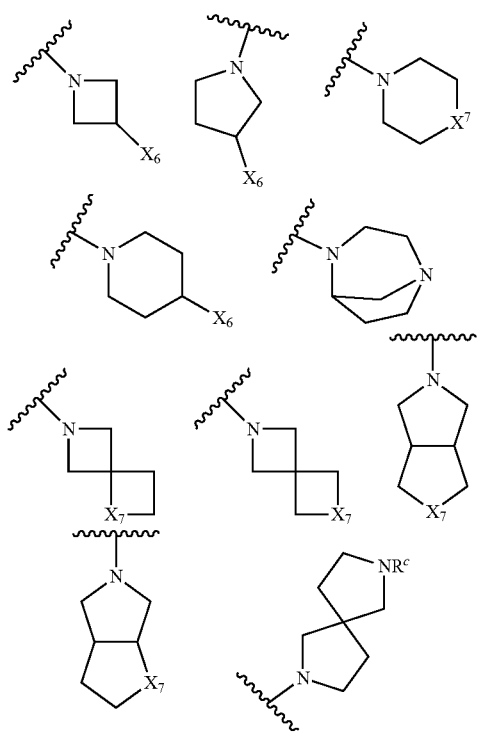

wherein $R^c$ is H, $C_{1-4}$ alkyl, oxetane, and $R^d$ is H, $C_{1-4}$ alkyl.

In some embodiments, the —(CR$^6$R$^7$) and —(NR$^6$R$^7$) ring systems of Z is selected from wherein $R^c$ is H, $C_{1-4}$ alkyl, oxetane (e.g. H, —CH$_3$); $X^6$ is H, —CH$_3$, —OH, —OCH$_3$, —OCF$_3$, —N(CH$_3$)$_2$, F, Cl, and $X^7$ is —O—, —NH— or —N(CH$_3$)—, —SO$_2$.

In some embodiments, L is a covalent bond. In some embodiments, L is straight chain or branched $C_{1-4}$ alkyl, (e.g. —CH$_2$—, —(CH$_2$)$_2$—, —(CH$_2$)$_3$—, —(CH$_2$)$_4$— or —C(CH$_3$)$_2$— or —CH$_2$—C(CH$_3$)$_2$—). In some embodiments, L is

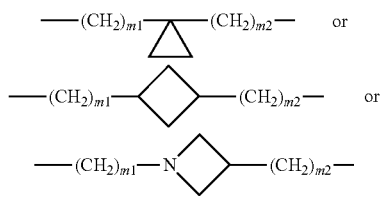

wherein m1, m2 are independently of each other 0, 1, 2, 3, 4, (e.g. 0, 1 or 2). In some embodiments, m2 is 0 and m1 is 0 or 1 or 2. In some embodiments, m1 and m2 are 1 or m1 and m2 are 2.

In some embodiments, the present disclosure is directed towards a compound or pharmaceutically acceptable salts or stereoisomers thereof of formula I above wherein $Y^2$ is —O—, having the following formula VII

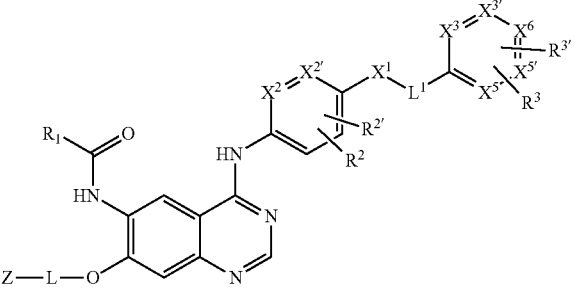

VII wherein $X^1$ is —O—, —CH$_2$—, —NH—, —S—;

$X^2$, $X^{2'}$, $X^3$, $X^{3'}$, $X^5$, $X^{5'}$, $X^6$ are independently of each other —N=, —CH=;

$L^1$ is a covalent bond or straight chain or branched $C_{1-3}$alkyl, which is unsubstituted or substituted with hal, $R^1$ is —CR$_b$=CHR$_a$, —C≡CH or —C≡C—CH$_3$; wherein $R^a$, $R^b$ are independently of each other H, hal, —CH$_2$—O—CH$_3$;

$R^2$, $R^{2'}$, $R^3$, $R^{3'}$ are independently of each other H, $C_{1-6}$ alkyl, hal, —CF$_3$, —OCF$_3$;

L is a covalent bond, straight chain or branched $C_{1-4}$ alkyl or

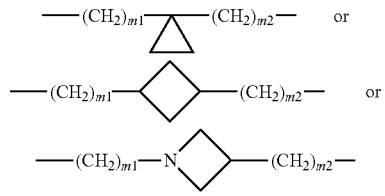

wherein m1, m2 are independently of each other 0, 1, 2, 3, or 4;

Z is —(NR$^4$R$^5$), wherein $R^4$ and $R^5$ are independently of each other H, $C_{1-6}$ alkyl, cyclopropyl, cylobutyl, 3 to 6-membered heterocycloalkyl, or —(NR$^6$R$^7$), —(CHR$^6$R$^7$), wherein $R^6$ and $R^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments substituent Z-L contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if L does not contain a nitrogen atom.

In some embodiments $R^a$ and $R^b$ are hydrogen.

In some embodiments, $L^1$ is straight chain or branched $C_{1-3}$alkyl, which is unsubstituted or substituted with hal. In some embodiments, $L^1$ is not a covalent bond.

In some embodiments, $X^3$, $X^{3'}$, $X^5$, $X^{5'}$, $X^6$ are —CH=
(i.e. a phenyl ring). In some embodiments, $X^3$ is —N= and
$X^{3'}$, $X^5$, $X^{5'}$, $X^6$ are —CH= or $X^{3'}$ is —N= and $X^3$, $X^5$, $X^{5'}$,
$X^6$ are is —CH= or $X^6$ is —N= and $X^3$, $X^{3'}$, $X^5$, $X^{5'}$ are
—CH= (i.e. a pyridine ring).

In some embodiments, both $X^3$, $X^{3'}$ are —N= and $X^5$,
$X^{5'}$, $X^6$ are —CH= or both $X^{3'}$, $X^6$ are —N= and $X^3$, $X^5$,
$X^{5'}$ are —CH= (i.e. a pyridazine ring). In some embodiments, both $X^3$, $X^5$ are —N= and $X^{3'}$, $X^{5'}$, $X^6$ are —CH=
or both $X^{3'}$, $X^{5'}$ are —N= and $X^3$, $X^5$, $X^{5'}$ are —CH= or
both $X^3$, $X^6$ are —N= and $X^{3'}$, $X^5$, $X^{5'}$ are —CH= (i.e. a
pyrimidine ring). In some embodiments, both $X^3$, $X^{5'}$ are
—N= and $X^{3'}$, $X^5$, $X^6$ are —CH= (i.e. a pyrazine ring).

In some embodiments, $R^2$ and $R^{2'}$ are independently of
each other H, $C_{1-6}$ alkyl, hal (e.g. H, —$CH_3$, F, Cl).

In some embodiments, $R^2$ and $R^{2'}$ are H. In some embodiments, $R^2$ and $R^{2'}$ are hal. In some embodiments, $R^2$ is hal
and $R^{2'}$ is H.

In some embodiments, $R^3$ and $R^{3'}$ are independently of
each other H, $C_{1-6}$ alkyl, hal, —$CF_3$, —$OCF_3$. In some
embodiments, $R^3$ is H, $C_{1-6}$ alkyl, hal, —$CF_3$, —$OCF_3$ and
$R^{3'}$ is H, hal.

In some embodiments, $R^2$ and $R^{2'}$ are H and $R^3$ is H, $C_{1-6}$
alkyl, hal, —$CF_3$, —$OCF_3$ and $R^{3'}$ is H, hal; or $R^2$ and $R^{2'}$
are hal and $R^3$ is H, $C_{1-6}$ alkyl, hal, —$CF_3$, —$OCF_3$ and $R^{3'}$
is H, hal; or $R^2$ is hal and $R^{2'}$ is H and $R^3$ is H, $C_{1-6}$ alkyl,
hal, —$CF_3$, —$OCF_3$ and $R^{3'}$ is H.

In some embodiments, $X^1$ is —O—. In some embodiments, $X^1$ is —$CH_2$—. In some embodiments, $X^1$ is
—NH—. In some embodiments, $X^1$ is —S—. In some
embodiments, $L^1$ is a covalent bond. In some embodiments,
$L^1$ is —$CH_2$— or —$CH(CH_3)$— or —CH(hal)-. In some
embodiments, $L^1$ is —$CH_2$—$CH_2$— or —$CH_2$—CH
($CH_3$)— or —$CH_2$—CH(hal)-.

In some embodiments, linker combinations -$X^1$-$L^1$-
—O—, —$CH_2$—, —O—$CH_2$—, —NH—$CH_2$—,
—S—$CH_2$—, —$CH_2$—$CH_2$—, —O—$CH(CH_3)$—,
—$CH_2$—$CH(CH_3)$—, —NH—$CH(CH_3)$—, —S—CH
($CH_3$)—, —O—CH(hal)-, —$CH_2$—CH(hal)-, —NH—CH
(hal)-, —S—CH(hal)- (e.g., —O—, —$CH_2$—,
—O—$CH_2$—, —NH—$CH_2$—, —$CH_2$—$CH_2$—, —O—CH
($CH_3$)—, —$CH_2$—$CH(CH_3)$—, —O—CH(hal)-, or
—$CH_2$—CH(hal)- and —O—, —$CH_2$—, —O—$CH_2$—,
—NH—$CH_2$—, or —$CH_2$—$CH_2$—).

In some embodiments, the compound of formula VII is
not any of

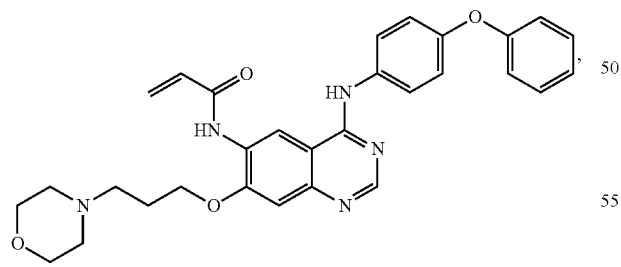

,

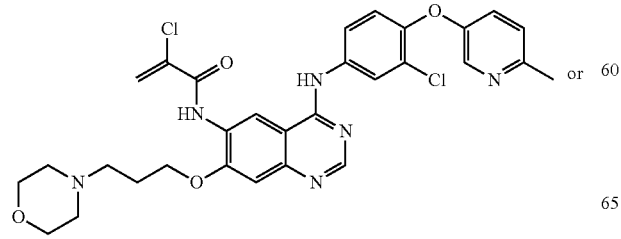

or

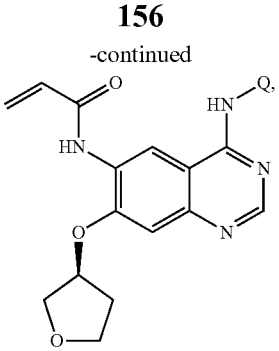

wherein Q is

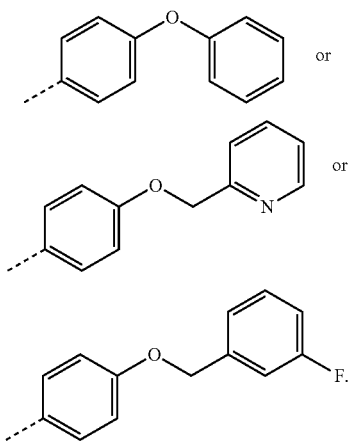

In some embodiments, -$X^1$-$L^1$- is —O—, In some
embodiments, -$X^1$-$L^1$- is —O—$CH_2$—. In some embodiments, compound VII has the following formula

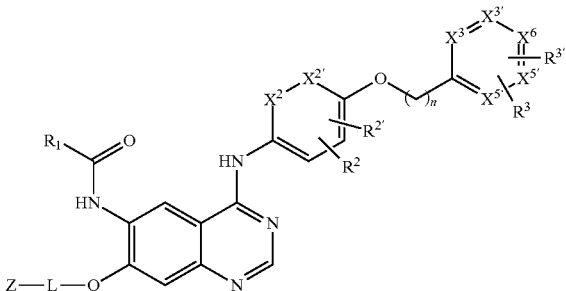

VII-1

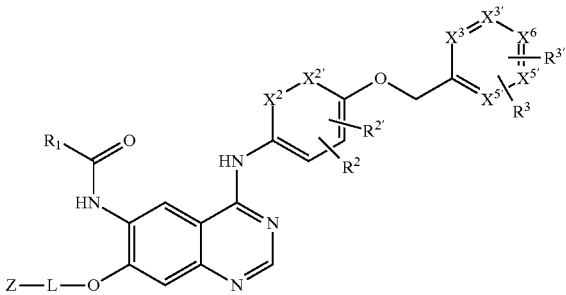

VII-1a

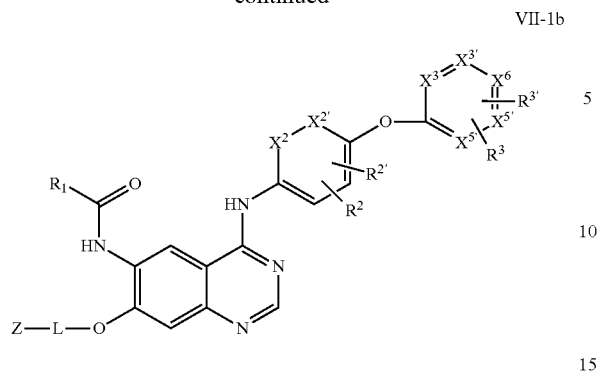
VII-1b wherein $X^2$, $X^{2'}$ and $X^3$, $X^{3'}$, $X^5$, $X^{5'}$, $X^6$ are independently of each other —N= or —CH=; $R^2$, $R^{2'}$ and $R^3$, $R^{3'}$ are independently of each other H, $C_{1-6}$ alkyl, hal, —$CF_3$, or —$OCF_3$, and n is 0, 1, 2, 3; and Z, L, $R^1$ are as defined above for a compound of formula VII.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other H, $C_{1-6}$ alkyl, hal (e.g. H, —$CH_3$, F, Cl). In some embodiments, $R^3$ and $R^{3'}$ are independently of each other H, $C_{1-6}$ alkyl, hal, —$CF_3$, —$OCF_3$.

In some embodiments, compound of formula VII has the following formulas

VII-(ii)d-1

VII-(ii)d-2

VII-(ii)d-3

VII-(ii)d-4

VII-(ii)d-5

VII-(ii)d-6 wherein W is

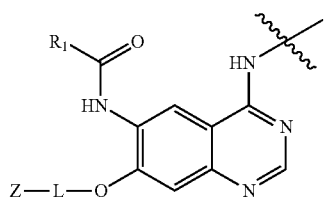

$X^2$, $X^{2'}$, $X^3$, $X^{3'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$; and n is 0 or 1; and Z, L, $R^1$ are as defined above for a compound of formula. VII.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, $X^2$ and $X^{2\prime}$ are —CH= (i.e. a phenyl ring) and $X^3$, $X^{3\prime}$ and $X^6$ are —CH= (i.e. a phenyl ring).

In some embodiments, $X^2$ and $X^{2\prime}$ are —CH= (i.e. a phenyl ring) and $X^3$, $X^{3\prime}$ and $X^6$ are —N= (i.e. a pyridine ring).

In some embodiments, $X^2$ and $X^{2\prime}$ are —N= (i.e. a pyridine ring) and $X^3$, $X^{3\prime}$ and $X^6$ are —CH= (i.e. a phenyl ring).

In some embodiments, $X^2$ and $X^{2\prime}$ a —N= (i.e. a pyridine ring) and $X^3$, $X^{3\prime}$ and $X^6$ are —N= (i.e. a pyridine ring).

In some embodiments, a compound of formula VII has the following formulas

VIIe-1
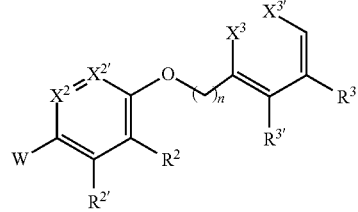

VIIe-2
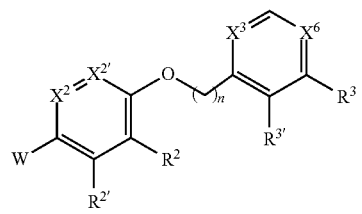

VIIe-3
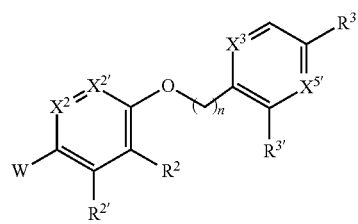

VIIe-4
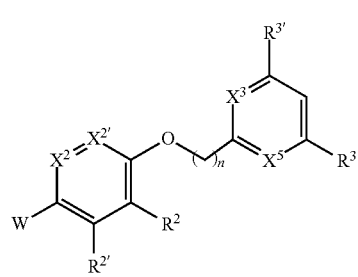

VIIe-5
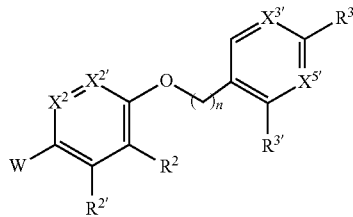

VIIe-6
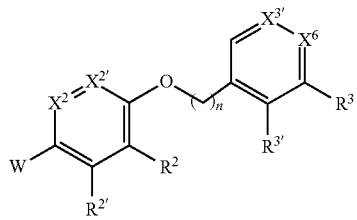

wherein W is

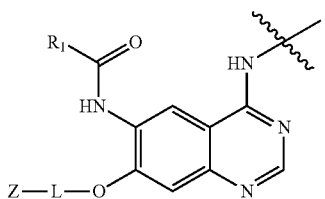

$X^2$, $X^{2\prime}$, $X^3$, $X^{3\prime}$, $X^5$, $X^{5\prime}$, $X^6$ are independently of each other —N= or —CH=; and $R^2$, $R^{2\prime}$, $R^3$, $R^{3\prime}$ are independently of each other H, $C_{1-6}$ alkyl, hal, —$CF_3$, or —$OCF_3$, n is 0 or 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, both $X^2$, $X^{2\prime}$ are —CH= (i.e. a phenyl ring). In some embodiments, $X^2$ is —N= and $X^{2\prime}$ is —CH= or $X^{2\prime}$ is —N= and $X^2$ is —CH= (i.e. a pyridine ring). In some embodiments, both $X^2$, $X^{2\prime}$ are —N= (i.e. a pyridazine ring).

In some embodiments, $X^3$, $X^{3\prime}$, $X^5$, $X^{5\prime}$, $X^6$ are —CH= (i.e. a phenyl ring). In some embodiments, $X^3$ is —N= and $X^{3\prime}$, $X^5$, $X^{5\prime}$, $X^6$ are —CH= or $X^{3\prime}$ is —N= and $X^3$, $X^5$, $X^{5\prime}$, $X^6$ are —CH= or $X^6$ is —N= and $X^3$, $X^{3\prime}$, $X^5$, $X^{5\prime}$ are —CH= (i.e. a pyridine ring).

In some embodiments, both $X^3$, $X^{3\prime}$ are —N= and $X^5$, $X^{5\prime}$, $X^6$ are —CH= or both $X^{3\prime}$, $X^6$ are —N= and $X^3$, $X^5$, $X^{5\prime}$ are —CH= (i.e. a pyridazine ring). In some embodiments, both $X^3$, $X^5$ are —N= and $X^{3\prime}$, $X^{5\prime}$, $X^6$ are —CH= or both $X^{3\prime}$, $X^{5\prime}$ are —N= and $X^3$, $X^5$, $X^6$ are —CH= or both $X^3$, $X^6$ are —N= and $X^{3\prime}$, $X^5$, $X^{5\prime}$ are —CH= (i.e. a pyrimidine ring). In some embodiments, both $X^3$, $X^{5\prime}$ are —N= and $X^{3\prime}$, $X^5$, $X^6$ are —CH= (i.e. a pyrazine ring).

In some embodiments, $R^2$ and $R^{2\prime}$ are H and $R^3$ is H, $C_{1-6}$ alkyl, hal, —$CF_3$, —$OCF_3$ and $R^{3\prime}$ is H, hal; or $R^2$ and $R^{2\prime}$ are hal and $R^3$ is H, $C_{1-6}$ alkyl, hal, —$CF_3$, —$OCF_3$ and $R^{3\prime}$ is H, hal; or $R^2$ is hal and $R^{2\prime}$ is H and $R^3$ is H, $C_{1-6}$ alkyl, hal, —$CF_3$, —$OCF_3$ and $R^{3\prime}$ is H.

In some embodiments, the compound of formula VII-1 is not any of

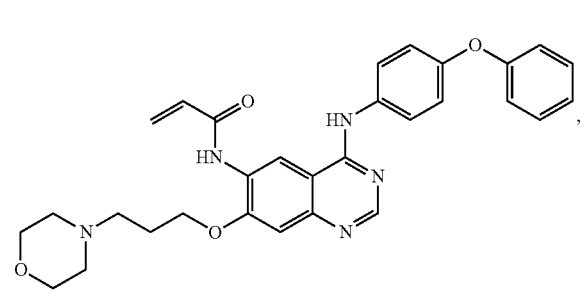

,

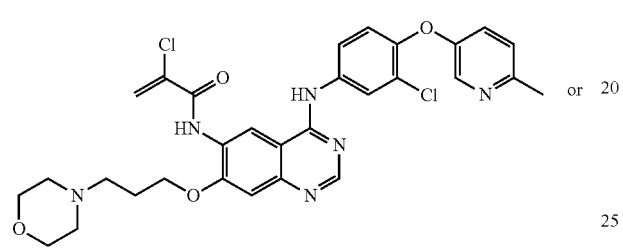

or

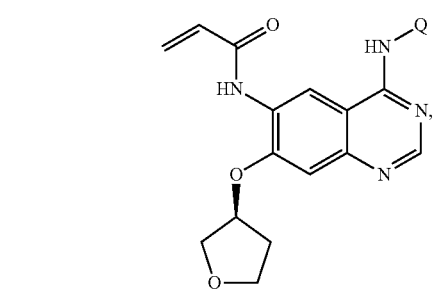

wherein Q is

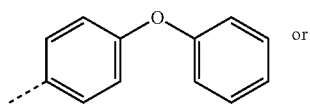

or

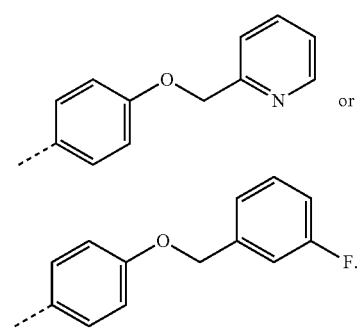

In some embodiments, -X$^1$-L$^1$- is —NH—. In some embodiments, -X$^1$-L$^1$- is —NH—CH$_2$—. In some embodiments, compound VII has the following formula

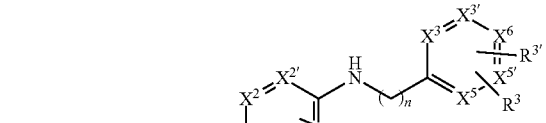
VII-2

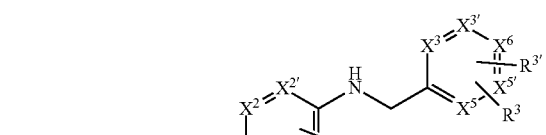
VII-2a

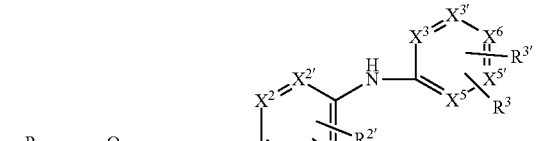
VII-2b wherein X$^2$, X$^{2'}$ and X$^3$, X$^{3'}$, X$^5$, X$^{5'}$, X$^6$ are independently of each other —N= or —CH=; R$^2$, R$^{2'}$ and R$^3$, R$^{3'}$ are independently of each other H, C$_{1-6}$ alkyl, hal, —CF$_3$, or —OCF$_3$, and n is 0, 1, 2, 3; and Z, L, R$^1$ are as defined above for a compound of formula VII.

In some embodiments substituent Z-L contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if L does not contain a nitrogen atom.

In some embodiments R$^a$ and R$^b$ are hydrogen.

In some embodiments, both X$^2$, X$^{2'}$ are —CH= (i.e. a phenyl ring). In some embodiments, X$^2$ is —N= and X$^{2'}$ is —CH= or X$^{2'}$ is —N= and X$^2$ is —CH= (i.e. a pyridine ring). In some embodiments, both X$^2$, X$^{2'}$ are —N= (i.e. a pyridazine ring).

In some embodiments, X$^3$, X$^{3'}$, X$^5$, X$^{5'}$, X$^6$ are —CH= (i.e. a phenyl ring). In some embodiments, X$^3$ is —N= and X$^{3'}$, X$^5$, X$^{5'}$, X$^6$ are —CH= or X$^{3'}$ is —N= and X$^3$, X$^5$, X$^{5'}$, X$^6$ are —CH= or X$^6$ is —N= and X$^3$, X$^{3'}$, X$^5$, X$^{5'}$ are —CH= (i.e. a pyridine ring).

In some embodiments, both X$^3$, X$^{3'}$ are —N= and X$^5$, X$^{5'}$, X$^6$ are —CH= or both X$^{3'}$, X$^6$ are —N= and X$^3$, X$^5$, X$^{5'}$ are —CH= (i.e. a pyridazine ring). In some embodiments, both X$^3$, X$^5$ are —N= and X$^{3'}$, X$^{5'}$, X$^6$ are —CH= or both X$^{3'}$, X$^{5'}$ are —N= and X$^3$, X$^5$, X$^6$ are —CH= or both $X^3$, $X^6$ are —N═ and $X^{3'}$, $X^5$, $X^{5'}$ are —CH═ (i.e. a pyrimidine ring). In some embodiments, both $X^3$, $X^{5'}$ are —N═ and $X^{3'}$, $X^5$, $X^6$ are —CH═ (i.e. a pyrazine ring).

In some embodiments, $R^2$ and $R^{2'}$ are independently of each other H, $C_{1-6}$ alkyl, hal (e.g. H, —$CH_3$, F, Cl). In some embodiments, $R^3$ and $R^{3'}$ are independently of each other H, $C_{1-6}$ alkyl, hal, —$CF_3$, —$OCF_3$.

In some embodiments, $R^2$ and $R^{2'}$ are H and $R^3$ is H, $C_{1-6}$ alkyl, hal, —$CF_3$, —$OCF_3$ and $R^{3'}$ is H, hal; or $R^2$ and $R^{2'}$ are hal and $R^3$ is H, $C_{1-6}$ alkyl, hal, —$CF_3$, —$OCF_3$ and $R^{3'}$ is H, hal; or $R^2$ is hal and $R^{2'}$ is H and $R^3$ is H, $C_{1-6}$ alkyl, hal, —$CF_3$, —$OCF_3$ and $R^{3'}$ is H.

In some embodiments, a compound of formula VII has one of the following formulas VII-(ii)f-1
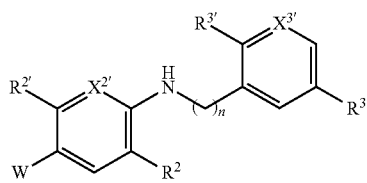

VII-(ii)f-2
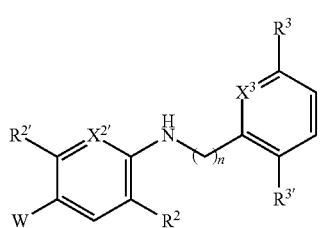

VII-(ii)f-3
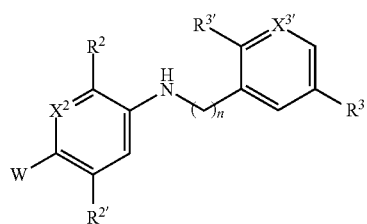

VII-(ii)f-4
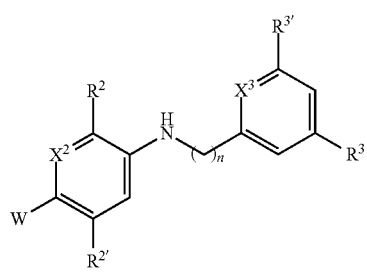

VII-(ii)f-5
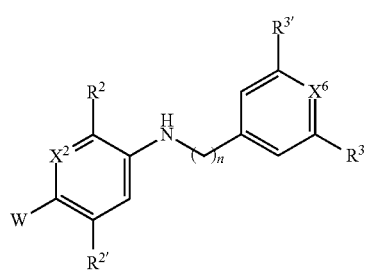

VII-(ii)f-6
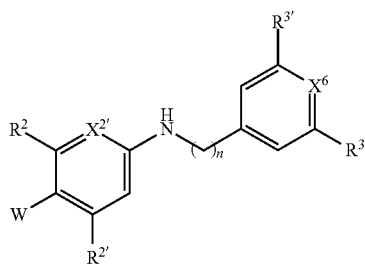

wherein W is

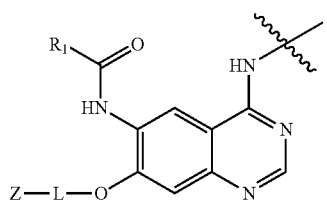

$X^2$, $X^{2'}$, $X^3$, $X^{3'}$, $X^6$ are independently of each other —N═ or —CH═; and $R^2$, $R^{2'}$, $R^3$, $R^{3'}$ are independently of each other H, $C_{1-6}$ alkyl, hal, —$CF_3$, or —$OCF_3$; and n is 0 or 1; and Z, L, $R^1$ are as defined above for a compound of formula VII.

In some embodiments, $X^2$ and $X^{2'}$ are —CH═ (i.e. a phenyl ring) and $X^3$, $X^{3'}$ and $X^6$ are —CH═ (i.e. a phenyl ring).

In some embodiments, $X^2$ and $X^{2'}$ are —CH═ (i.e. a phenyl ring) and $X^3$, $X^{3'}$ and $X^6$ are —N═ (i.e. a pyridine ring).

In some embodiments, $X^2$ and $X^{2'}$ are —N═ (i.e. a pyridine ring) and $X^3$, $X^{3'}$ and $X^6$ are —CH═ (i.e. a phenyl ring).

In some embodiments, $X^2$ and $X^{2'}$ a —N═ (i.e. a pyridine ring) and $X^3$, $X^{3'}$ and $X^6$ are —N═ (i.e. a pyridine ring).

In some embodiments, a compound of formula VII has the following formulas

VII-(ii)g-1
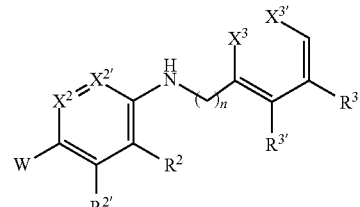

VII-(ii)g-2
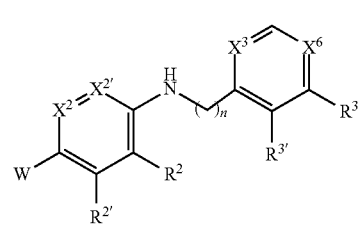

-continued

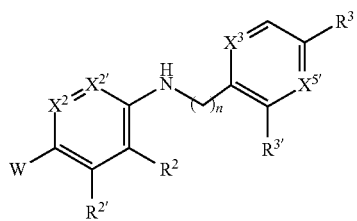
VII-(ii)g-3

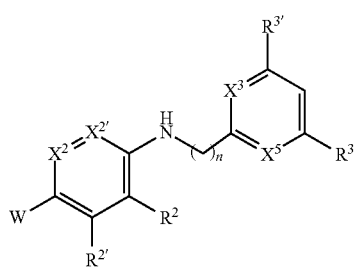
VII-(ii)g-4

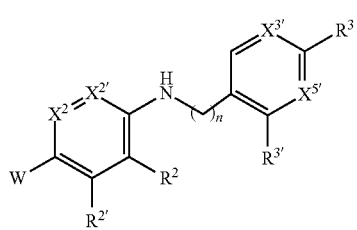
VII-(ii)g-5

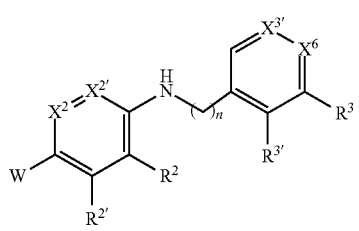
VII-(ii)g-6 wherein W is

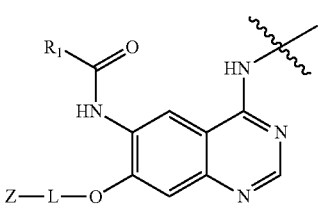

$X^2$, $X^{2\prime}$, $X^3$, $X^{3\prime}$, $X^5$, $X^{5\prime}$, $X^6$ are independently of each other —N= or —CH=; and $R^2$, $R^{2\prime}$, $R^3$, $R^{3\prime}$ are independently of each other H, $C_{1-6}$ alkyl, hal, —$CF_3$, or —$OCF_3$, n is 0 or 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, both $X^2$, $X^{2\prime}$ are —CH= (i.e. a phenyl ring). In some embodiments, $X^2$ is —N= and $X^{2\prime}$ is —CH= or $X^{2\prime}$ is —N= and $X^2$ is —CH= (i.e. a pyridine ring). In some embodiments, both $X^2$, $X^{2\prime}$ are —N= (i.e. a pyridazine ring).

In some embodiments, $X^3$, $X^{3\prime}$, $X^5$, $X^{5\prime}$, $X^6$ are —CH= (i.e. a phenyl ring). In some embodiments, $X^3$ is —N= and $X^{3\prime}$, $X^5$, $X^{5\prime}$, $X^6$ are —CH= or $X^{3\prime}$ is —N= and $X^3$, $X^5$, $X^{5\prime}$, $X^6$ are —CH= or $X^6$ is —N= and $X^3$, $X^{3\prime}$, $X^5$, $X^{5\prime}$ are —CH= (i.e. a pyridine ring).

In some embodiments, both $X^3$, $X^{3\prime}$ are —N= and $X^5$, $X^{5\prime}$, $X^6$ are —CH= or both $X^{3\prime}$, $X^6$ are —N= and $X^3$, $X^5$, $X^{5\prime}$ are —CH= (i.e. a pyridazine ring). In some embodiments, both $X^3$, $X^5$ are —N= and $X^{3\prime}$, $X^{5\prime}$, $X^6$ are —CH= or both $X^{3\prime}$, $X^{5\prime}$ are —N= and $X^3$, $X^5$, $X^6$ are —CH= or both $X^3$, $X^6$ are —N= and $X^{3\prime}$, $X^5$, $X^{5\prime}$ are —CH= (i.e. a pyrimidine ring). In some embodiments, both $X^3$, $X^{5\prime}$ are —N= and $X^{3\prime}$, $X^5$, $X^6$ are —CH= (i.e. a pyrazine ring).

$R^2$ and $R^{2\prime}$ are independently of each other H, hal or $C_{1-6}$ alkyl (e.g. H, hal or —$CH_3$).

In some embodiments, $R^3$ is H, hal, —$CF_3$, or —$OCF_3$.

In some embodiments, $R^{3\prime}$ is H, hal or $C_{1-6}$ alkyl (e.g. H, hal or —$CH_3$).

In some embodiments, $R^3$ and $R^{3\prime}$ are H. In some embodiments, $R^3$ and $R^{3\prime}$ are hal. In some embodiments, $R^3$ is hal, —$CF_3$, or —$OCF_3$ and $R^{3\prime}$ is H. In some embodiments, $R^3$ is H and $R^{3\prime}$ is hal, or $C_{1-6}$ alkyl.

In some embodiments, $R^2$ and $R^{2\prime}$ are H. In some embodiments, $R^2$ and $R^{2\prime}$ are hal. In some embodiments, $R^2$ is hal or $C_{1-6}$ alkyl, and $R^{2\prime}$ is H. In some embodiments, $R^2$ is H and $R^{2\prime}$ is hal.

In some embodiments, a compound of formula VII has the following formula

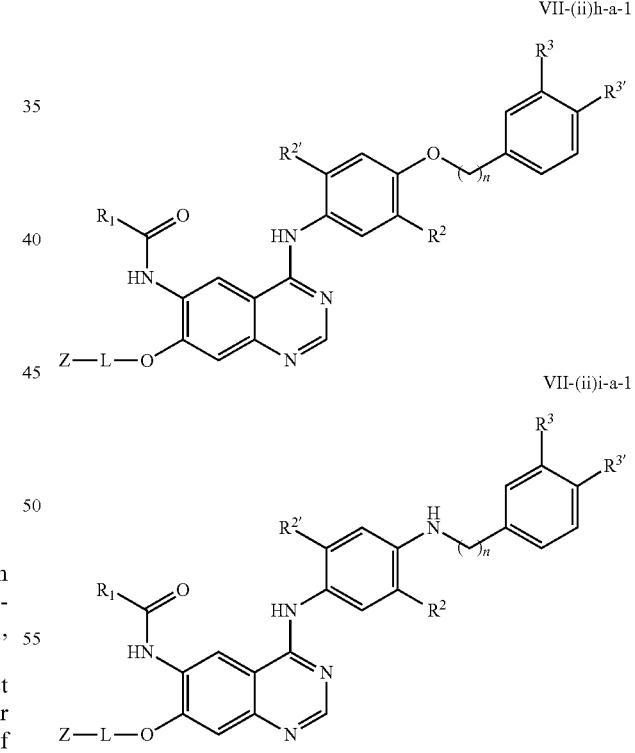

wherein $R^2$, $R^{2\prime}$ are independently of each other H, $C_{1-6}$ alkyl, hal (e.g. H, —$CH_3$, F, Cl); $R^3$ is H, $C_{1-6}$ alkyl, hal, —$CF_3$, —$OCF_3$; and n is 0 or 1; and Z, L, $R^1$ are as defined above for a compound of formula VII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, a compound of formula VII has the following formulas

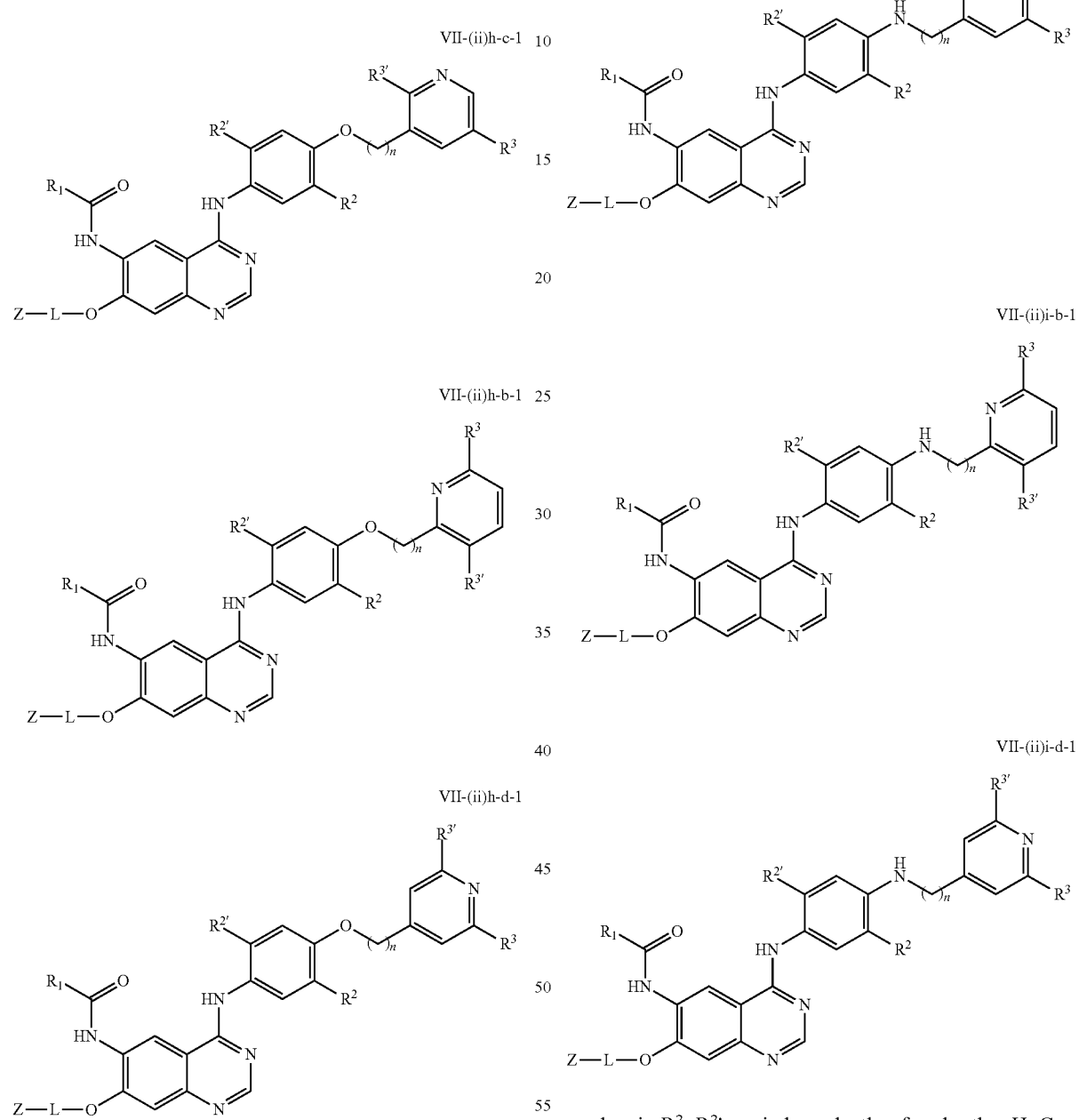

wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$ are as defined above for a compound of formula VII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, a compound of formula VII has the following formulas

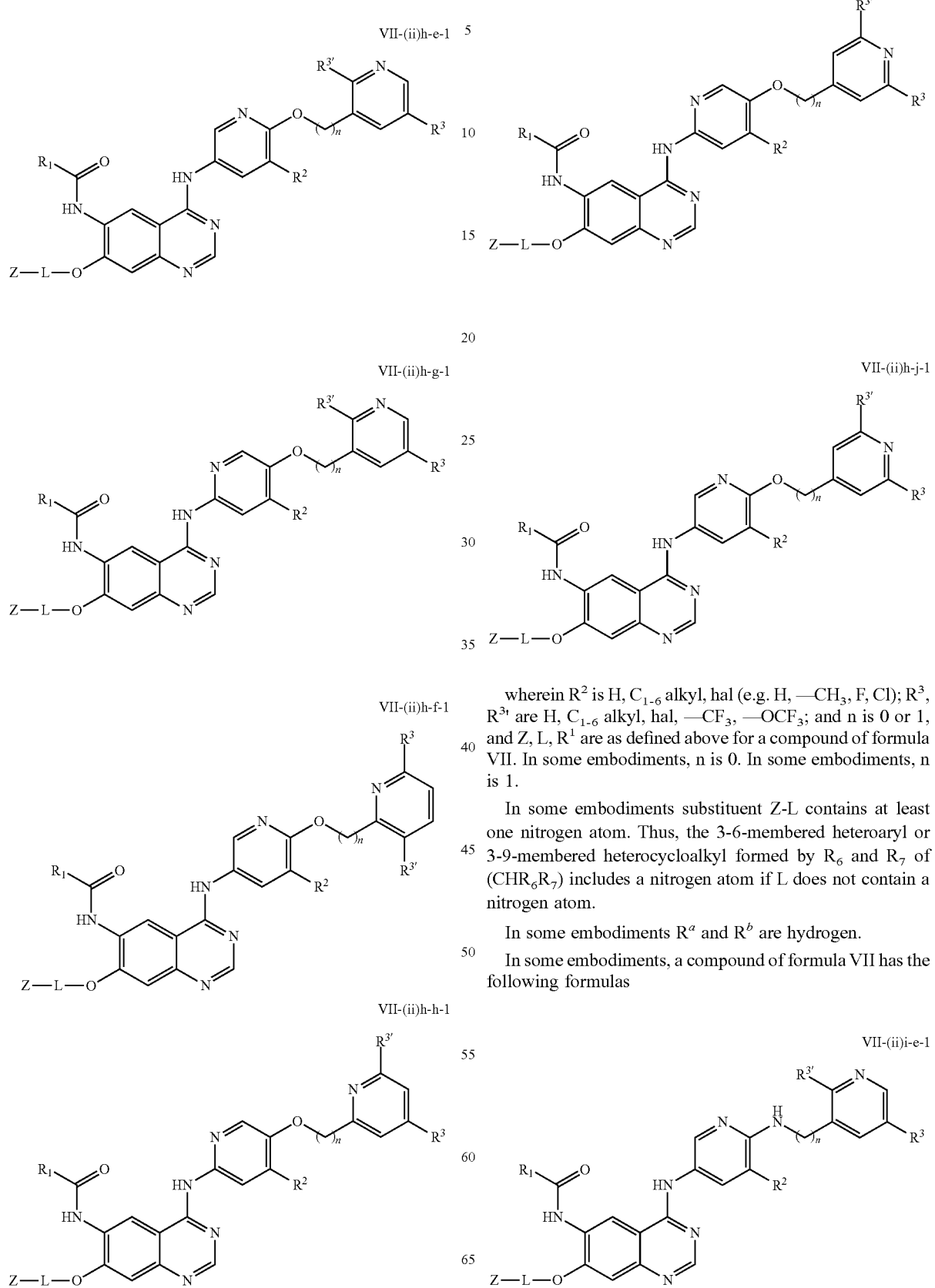

wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1, and Z, L, $R^1$ are as defined above for a compound of formula VII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, a compound of formula VII has the following formulas

VII-(ii)i-g-1
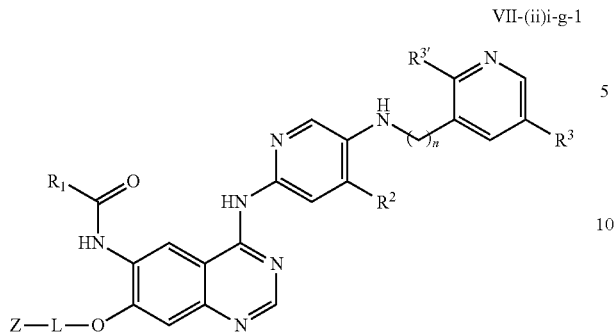

VII-(ii)i-f-1
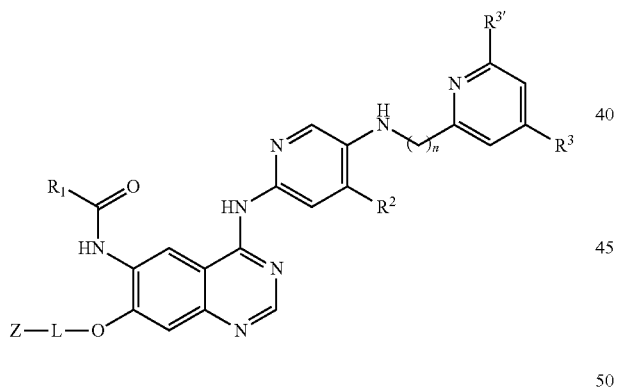

VII-(ii)i-h-1
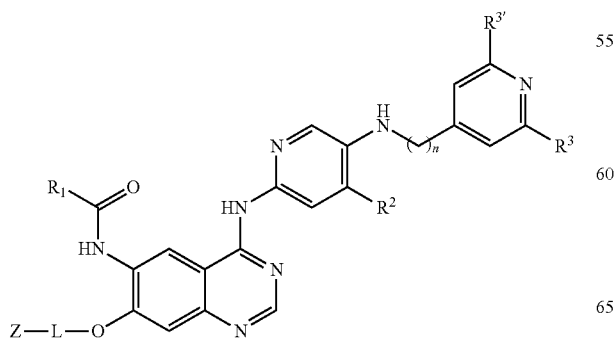

VII-(ii)i-i-1

VII-(ii)i-j-1
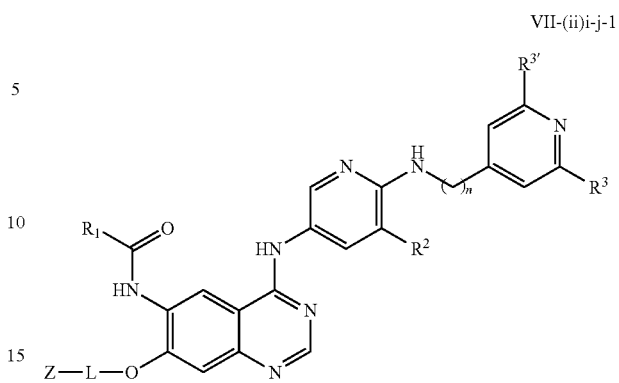

wherein $R^2$ is H, $C_{1-6}$ alkyl, hal (e.g. H, —CH$_3$, F, Cl); $R^3$, $R^{3'}$ are H, $C_{1-6}$ alkyl, hal, —CF$_3$, —OCF$_3$; and n is 0 or 1; and Z, L, $R^1$ are as defined above for a compound of formula VII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, a compound of formula VII has the following formulas

VII-(ii)h-k-1
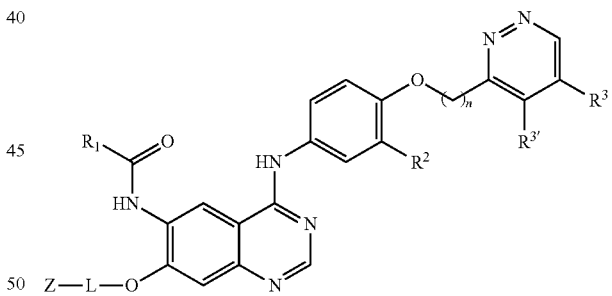

VII-(ii)h-i-1
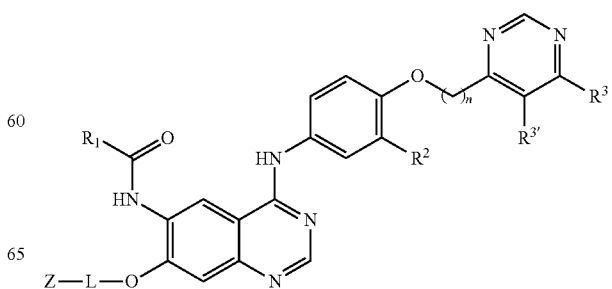

In some embodiments, a compound of formula VII has the following formulas

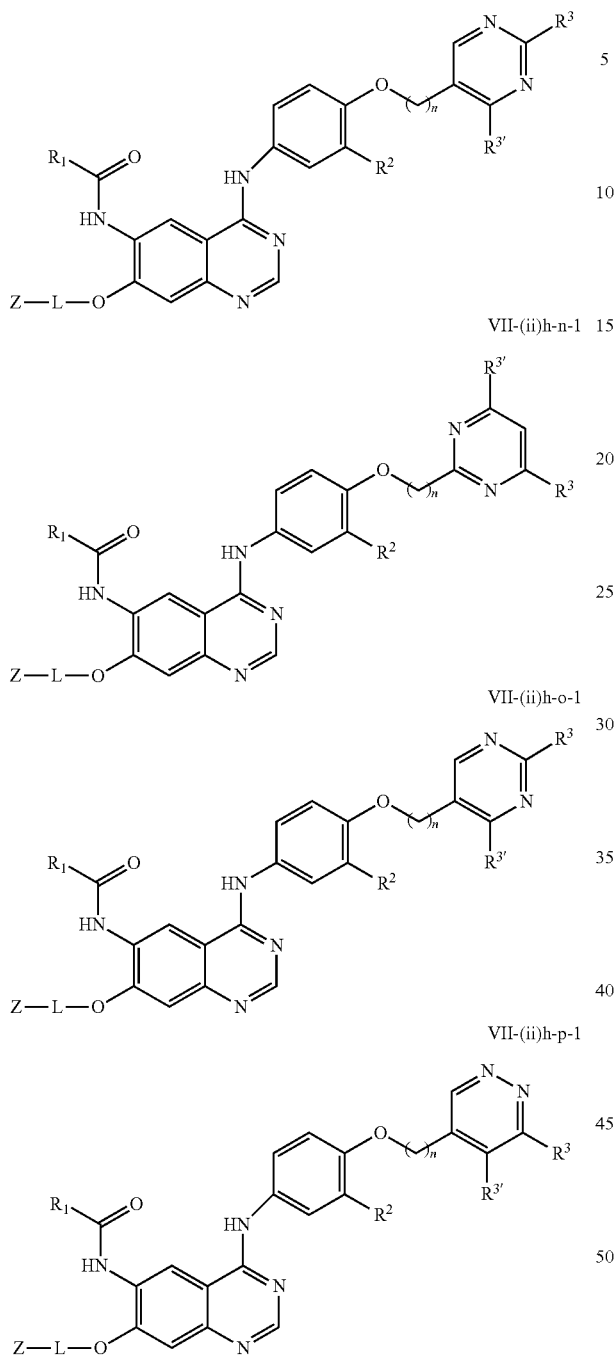

wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$ are as defined above for a compound of formula VII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

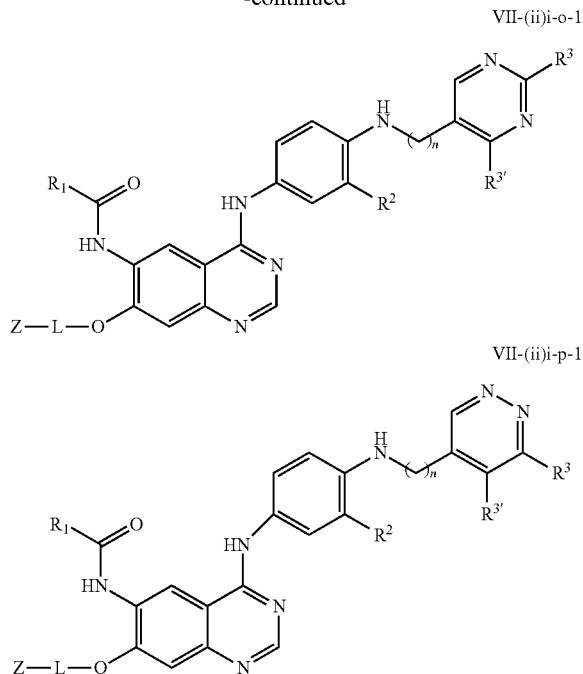

VII-(ii)i-o-1

VII-(ii)i-p-1 wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$ are as defined above for a compound of formula VII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R^6$ and $R^7$ of ($CHR_6R_7$) includes a nitrogen atom if L does not contain a nitrogen atom.

In some embodiments $R^a$ and $R^b$ are hydrogen.

In some embodiments, $R^4$ and $R^5$ are independently of each other H, $C_{1-4}$ alkyl, cyclopropyl, tetrahydrofuryl.

In some embodiments of a compound of formula VII, a 3 to 6-membered heterocycloalkyl (in combination with —($NR^4R^5$)) refers to a non-aromatic or partially aromatic ring system having 3, 4, 5, or 6 ring atoms selected from C, N, O, or S (e.g. C, N, or O), the number of N atoms being 0, 1, 2 and the number of O and S atoms each being 0, 1, 2. Examples of 3 to 6-membered heterocycloalkyl groups include oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl and the like. In some embodiments, 3 to 6-membered heterocycloalkyl include 5-membered heterocycloalkyl having 1 or 2 O-atoms, such as oxiranyl, oxetanyl, tetrahydrofuranyl, dioxanyl.

In some embodiments of a compound of formula VII, a 3 to 6-membered heteroaryl (in combination with —($NR^6R^7$) or —($CHR^6R^7$)) refers to a (fully) aromatic ring system having 3, 4, 5, or 6 ring atoms (e.g. 5 ring atoms), selected from C, N, O, or S (e.g. C, N, or O, and C or N, with the number of N atoms being 0, 1, 2 or 3 and the number of O and S atoms each being 0, 1 or 2). Examples of "heteroaryl" include furyl, imidazolyl, isoxazolyl, oxazinyl, pyrazinyl, pyrazolyl (pyrazyl), pyridazinyl, pyridinyl, pyrimidinyl, pyrrolyl, thiazolyl, thienyl, and the like. In some embodiments, examples of "heteroaryl" include pyrrolyl, imidazolyl. Preferably, the aromatic ring system is a nitrogen containing heteroaryl.

In some embodiments of a compound of formula VII, a 3 to 9-membered heterocycloalkyl (in combination with —($NR^6R^7$) or —($CHR^6R^7$)) refers to a non-aromatic or partially aromatic ring system having 3 to 9 ring atoms selected from C, N, O, or S (e.g. C, N, or O), the number of N atoms being 0, 1, 2 or 3 and the number of O and S atoms each being 0, 1 or 2. Examples of a 3 to 9-membered heterocycloalkyl (in combination with —($NR^6R^7$) or —($CHR^6R^7$)) include monocycles such as oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl, oxepanyl, thiepanyl, azepanyl, diazepanyl, oxazepanyl (e.g. azetidinyl, pyrrolidinyl, piperidinyl, piperazinyl, morpholinyl, azepanyl); fused ring systems, such as 3-azabicyclo[3.1.0]hexyl, 3-azabicyclo[3.3.0]octyl, 3,7-diazabicyclo[3.3.0]octyl, 3-aza-7-oxabicyclo[3.3.0]octyl, 2,6-diazabicyclo[3.3.0]octyl, 2,7-diazabicyclo[3.3.0]octyl, 2,8-diazabicyclo[4.3.0]nonyl, 3-oxa-8-azabicyclo[4.3.0] nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4.3.0] nonyl, and the like; bridged ring systems such as bicyclo [3.3.1]nonanyl, bicyclo[3.2.1]octanyl, bicyclo[2.2.2]octanyl, bicyclo[3.1.1]heptanyl, bicyclo[2.2.1]heptanyl (e.g. bicyclo[3.2.1]octanyl, bicyclo[2.2.1]heptanyl), having one or two heteroatoms selected from N and O; spiro ring systems such as spiropentanyl, spiro[2.3]hexanyl spiro[3.3]heptanyl, spiro[3.4]octanyl, spiro[4.4]nonanyl, spiro[3.5]nonanyl, spiro[4.5]decanyl (e.g. spiro[3.3]heptanyl, spiro[4.4]nonanyl), having one or two heteroatoms selected from N and O (e.g. diazaspiro[3.3]heptanyl, oxa-azaspiro[3.3]heptanyl, diazaspiro[4.4]nonanyl, oxa-azaspiro[4.4]nonanyl). Preferably, the 3 to 9-membered heterocycloalkyl contains at least one nitrogen atom.

In some embodiments, Z is —($NR^4R^5$), wherein $R^4$ and $R^5$ are independently of each other H, $C_{1-6}$ alkyl, cyclopropyl, cylobutyl, 3 to 6-membered heterocycloalkyl containing 0, 1, or 2 N-atoms and 0, 1, or 2 O-atoms, or —($NR^6R^7$), —($CHR^6R^7$), wherein $R^6$ and $R^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments, —($NR^6R^7$) ring systems include

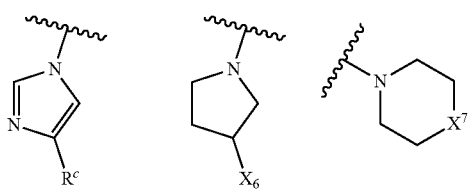

-continued

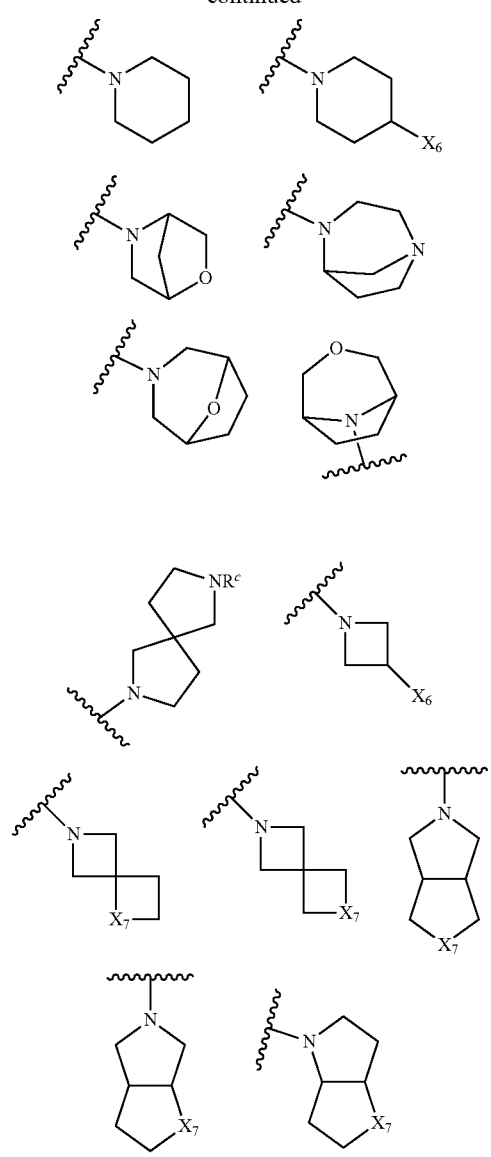

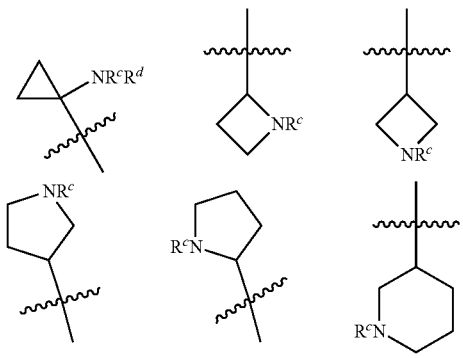

wherein $R^c$ is H, $C_{1-4}$ alkyl, oxetane; $X^6$ is H, —CH$_3$, —OH, —OCH$_3$, —OCF$_3$, —N(CH$_3$)$_2$, F, Cl; $X^7$ is —O—, —NH— or —N(CH$_3$)—, —SO$_2$.

In some embodiments, —(CHR$^6$R$^7$) ring systems include

-continued

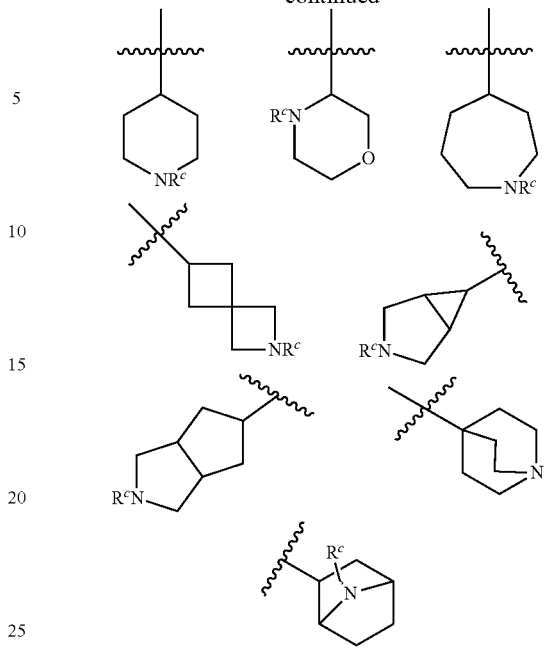

wherein $R^c$ is H, $C_{1-4}$ alkyl, oxetane, and $R^d$ is H, $C_{1-4}$ alkyl.

In some embodiments, the compound of formula VII has the formula VIII or IX

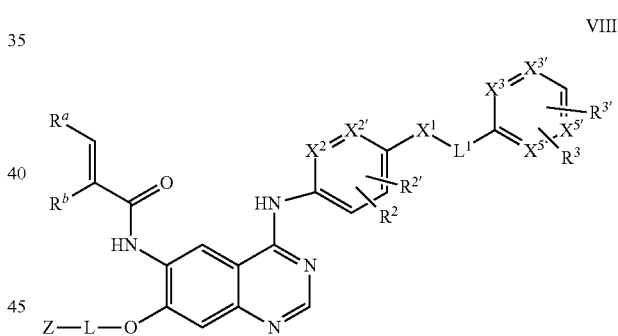

VIII

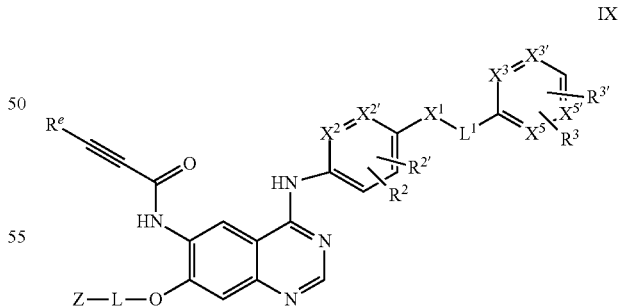

IX wherein $X^1$ is —O—, —CH$_2$—, —NH—, —S—; $X^2$, $X^{2'}$, $X^3$, $X^{3'}$, $X^5$, $X^{5'}$, $X^6$ are independently of each other —N=, —CH=;

$L^1$ is a covalent bond or straight chain or branched $C_{1-3}$ alkyl, which is unsubstituted or substituted with hal, $R^2$, $R^{2'}$, $R^3$, $R^{3'}$ are independently of each other H, $C_{1-6}$ alkyl, hal, —CF$_3$, —OCF$_3$;

L is a covalent bond, straight chain or branched $C_{1-4}$ alkyl or

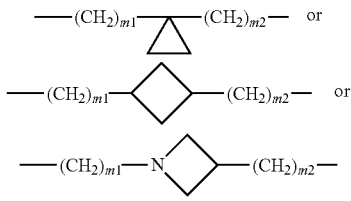

wherein m1, m2 are independently of each other 0, 1, 2, 3, or 4;

Z is —($NR^4R^5$), wherein $R^4$ and $R^5$ are independently of each other H, $C_{1-6}$ alkyl, cyclopropyl, cylobutyl, 3 to 6-membered heterocycloalkyl, or —($NR^6R^7$), —($CHR^6R^7$), wherein $R^6$ and $R^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

$R^a$, $R^b$ are independently of each other H, hal, or —$CH_2$—O—$CH_3$, (e.g. H), and $R_e$ is H or methyl.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, $L^1$ is straight chain or branched $C_{1-3}$alkyl, which is unsubstituted or substituted with hal. In some embodiments, $L^1$ is not a covalent bond.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other H, $C_{1-6}$ alkyl, hal, (e.g. H, —$CH_3$, F, Cl). In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —$CF_3$, —$OCF_3$. In some embodiments, $R^3$ is H, $C_{1-6}$ alkyl, hal, —$CF_3$, —$OCF_3$ and $R^{3'}$ is H, hal.

In some embodiments, $R^2$ and $R^{2'}$ are H and $R^3$ is H, $C_{1-6}$ alkyl, hal, —$CF_3$, —$OCF_3$ and $R^{3'}$ is H, hal; or $R^2$ and $R^{2'}$ are hal and $R^3$ is H, $C_{1-6}$ alkyl, hal, —$CF_3$, —$OCF_3$ and $R^{3'}$ is H, hal; or $R^2$ is hal and $R^{2'}$ is H and $R^3$ is H, $C_{1-6}$ alkyl, hal, —$CF_3$, —$OCF_3$ and $R^{3'}$ is H.

In some embodiments, Z is —($NR^4R^5$), wherein $R^4$ and $R^5$ are independently of each other H, $C_{1-6}$ alkyl, cyclopropyl, cylobutyl, 3 to 6-membered heterocycloalkyl containing 0, 1, or 2 N-atoms and 0, 1, or 2 O-atoms, or —($NR^6R^7$), —($CHR^6R^7$), wherein $R^6$ and $R^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments, $R^4$ and $R^5$ are independently of each other H, $C_{1-4}$ alkyl, cyclopropyl, tetrahydrofuryl (e.g. methyl).

In some embodiments, —($NR^6R^7$) ring systems include

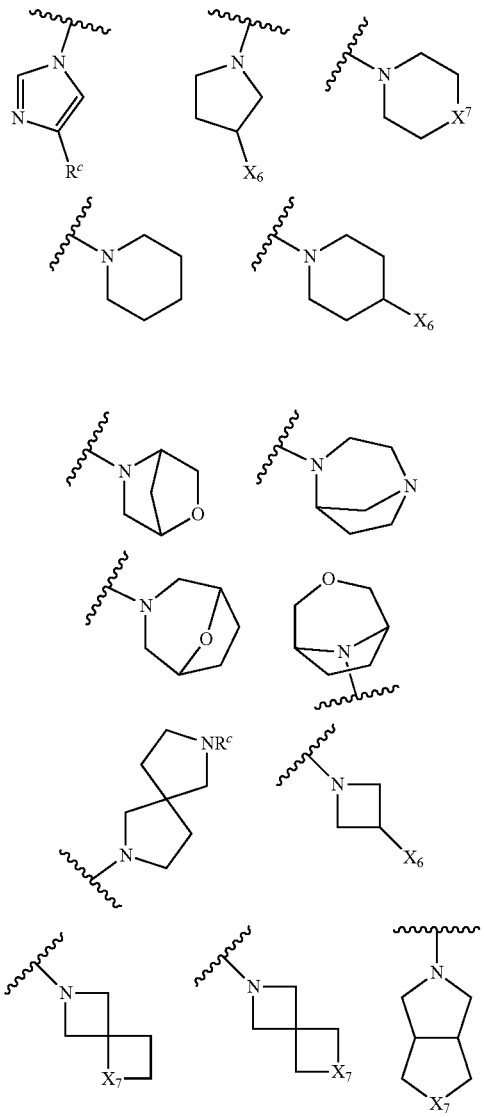

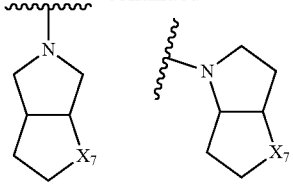

wherein $R^c$ is H, $C_{1-4}$ alkyl, oxetane; $X^6$ is H, —$CH_3$, —OH, —$OCH_3$, —$OCF_3$, —$N(CH_3)_2$, F, Cl; $X^7$ is —O—, —NH— or —$N(CH_3)$—, —$SO_2$.

In some embodiments, —$(CR^6R^7)$ ring systems include

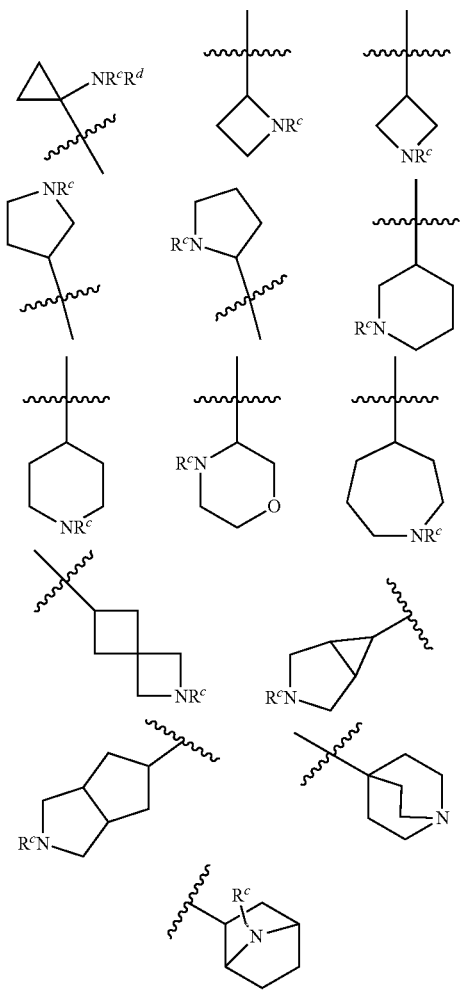

wherein $R^c$ is H, $C_{1-4}$ alkyl, oxetane, and $R^d$ is H, $C_{1-4}$ alkyl.

In some embodiments, L is a covalent bond. In some embodiments, L is straight chain or branched $C_{1-4}$ alkyl (e.g. —$CH_2$—, —$(CH_2)_2$—, —$(CH_2)_3$—, —$(CH_2)_4$—, —$C(CH_3)_2$— or —$CH_2$—$C(CH_3)_2$—). In some embodiments, L is

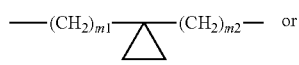

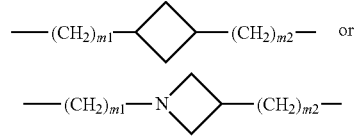

wherein m1, m2 are independently of each other 0, 1 or 2.

In some embodiments, $X^1$ is —O—. In some embodiments, $X^1$ is —$CH_2$—. In some embodiments, $X^1$ is —NH—. In some embodiments, $X^1$ is —S—. In some embodiments, $L^1$ is a covalent bond. In some embodiments, $L^1$ is —$CH_2$— or —$CH(CH_3)$— or —CH(hal)-. In some embodiments, $L^1$ is —$CH_2$—$CH_2$— or —$CH_2$—CH($CH_3$)— or —$CH_2$—CH(hal)-.

In some embodiments, linker combinations -$X^1$-$L^1$- include —O—, —$CH_2$—, —O—$CH_2$—, —NH—$CH_2$—, —S—$CH_2$—, —$CH_2$—$CH_2$—, —O—CH($CH_3$)—, —$CH_2$—CH($CH_3$)—, —NH—CH($CH_3$)—, —S—CH($CH_3$)—, —O—CH(hal)-, —$CH_2$—CH(hal)-, —NH—CH(hal)-, —S—CH(hal)- (e.g. —O—, —$CH_2$—, —O—$CH_2$—, —NH—$CH_2$—, —$CH_2$—$CH_2$—, —O—CH($CH_3$)—, —$CH_2$—CH($CH_3$)—, —O—CH(hal)-, or —$CH_2$—CH(hal)- and —O—, —$CH_2$—, —O—$CH_2$—, —NH—$CH_2$—, or —$CH_2$—$CH_2$—).

In some embodiments, -$X^1$-$L^1$- is —O—, In some embodiments, -$X^1$-$L^1$- is —O—$CH_2$—. In some embodiments, -$X^1$-$L^1$- is —NH—. In some embodiments, -$X^1$-$L^1$- is —NH—$CH_2$—.

In some embodiments, the compound of formula VIII is not any of

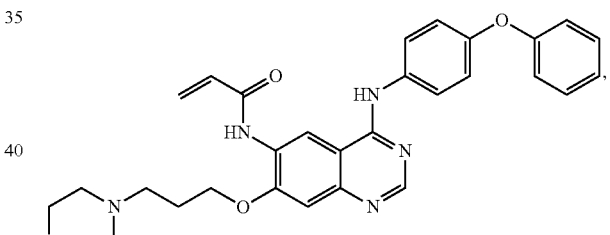

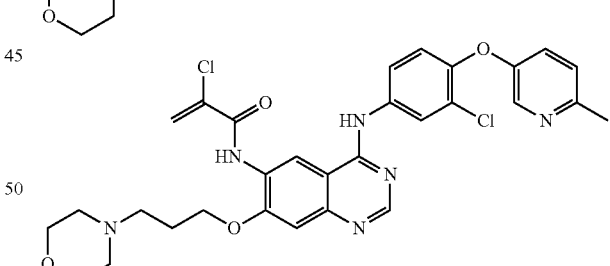

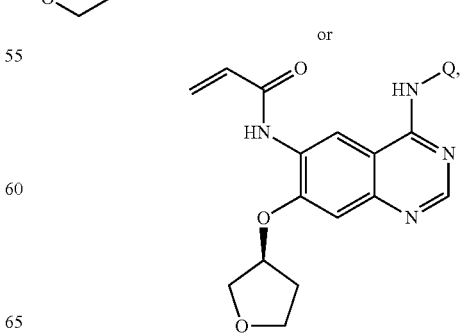

wherein Q is

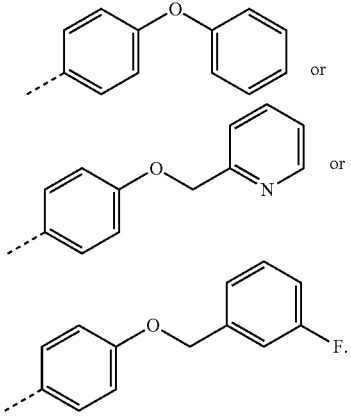

In some embodiments, the compound of formula VIII or IX has the formula VIII-1, VIII-2 or IX-1, IX-2

VIII-1

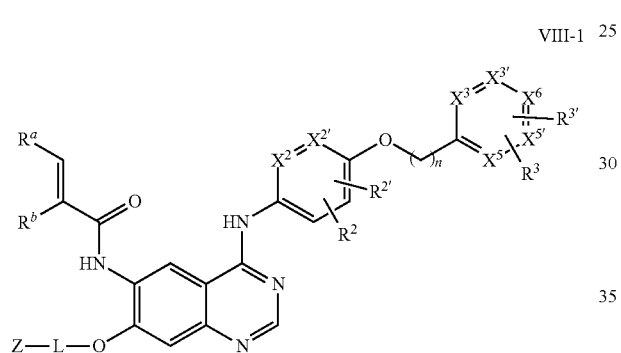

IX-1

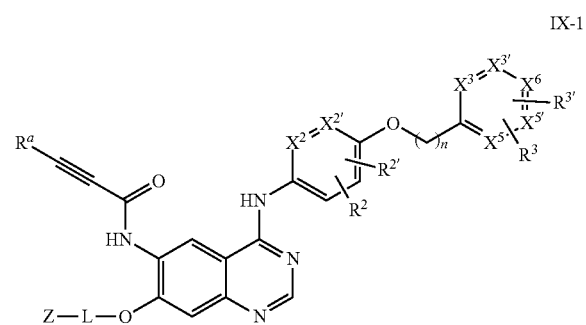

VIII-2

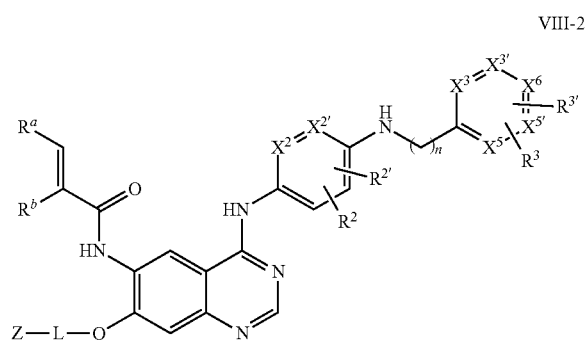

IX-2

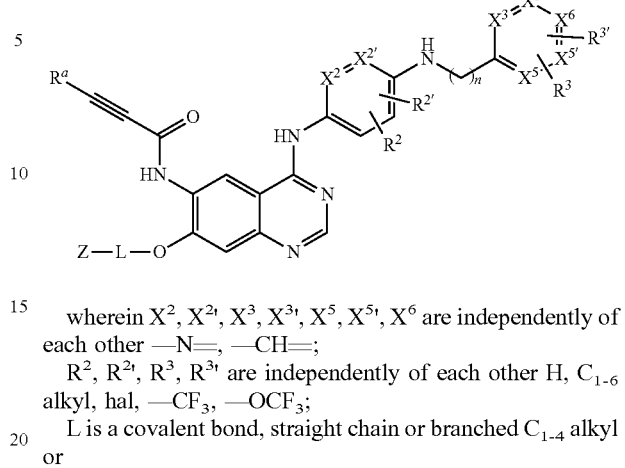

wherein $X^2$, $X^{2'}$, $X^3$, $X^{3'}$, $X^5$, $X^{5'}$, $X^6$ are independently of each other —N=, —CH=;

$R^2$, $R^{2'}$, $R^3$, $R^{3'}$ are independently of each other H, $C_{1-6}$ alkyl, hal, —$CF_3$, —$OCF_3$;

L is a covalent bond, straight chain or branched $C_{1-4}$ alkyl or

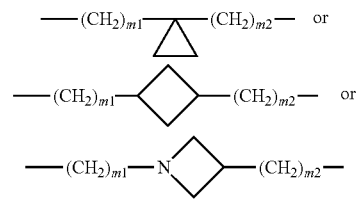

wherein m1, m2 are independently of each other 0, 1, 2, 3, or 4

Z is —($NR^4R^5$), wherein $R^4$ and $R^5$ are independently of each other H, $C_{1-6}$ alkyl, cyclopropyl, cylobutyl, 3 to 6-membered heterocycloalkyl, or —($NR^6R^7$), —($CHR^6R^7$), wherein $R^6$ and $R^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

$R^a$, $R^b$ are independently of each other H, hal, or —$CH_2$—O—$CH_3$ (e.g. H), and $R_e$ is H or methyl, and n is 0 or 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, n is 0. In some embodiments, n is 1.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. pyrimidine ring). In some embodiments, both $X^3$, $X^{5'}$ are —N= and $X^{3'}$, $X^5$, $X^6$ are —CH= (i.e. a pyrazine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring). $R^2$ and $R^{2'}$ are independently of each other H, $C_{1-6}$ alkyl, hal (e.g. H, —CH$_3$, F, Cl). In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —CF$_3$, —OCF$_3$. In some embodiments, $R^3$ is H, $C_{1-6}$ alkyl, hal, —CF$_3$, —OCF$_3$ and $R^{3'}$ is H, hal.

In some embodiments, $R^2$ and $R^{2'}$ are H and $R^3$ is H, $C_{1-6}$ alkyl, hal, —CF$_3$, —OCF$_3$ and $R^{3'}$ is H, hal; or $R^2$ and $R^{2'}$ are hal and $R^3$ is H, $C_{1-6}$ alkyl, hal, —CF$_3$, —OCF$_3$ and $R^{3'}$ is H, hal; or $R^2$ is hal and $R^{2'}$ is H and $R^3$ is H, $C_{1-6}$ alkyl, hal, —CF$_3$, —OCF$_3$ and $R^{3'}$ is H.

In some embodiments, a compound of formula VIII-1, IX-1 has one of the following formulas

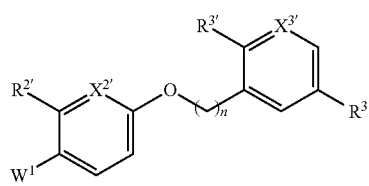
VIII-1-(ii)d-1

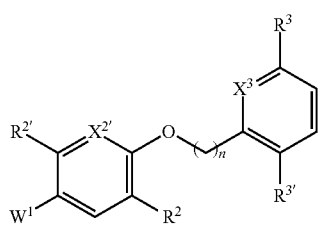
VIII-1-(ii)d-2

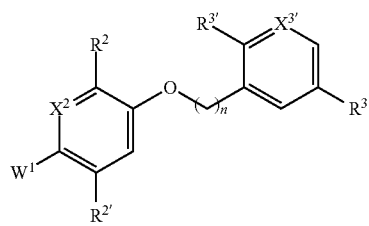
VIII-1-(ii)d-3

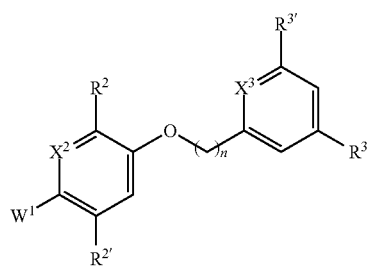
VIII-1-(ii)d-4

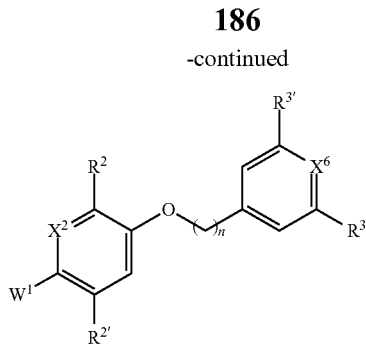
VIII-1-(ii)d-5

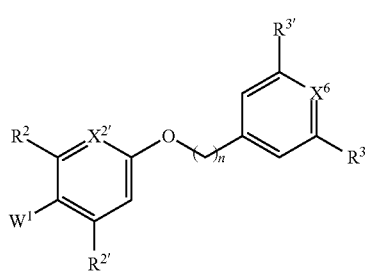
VIII-1-(ii)d-6 and $W_1$ is

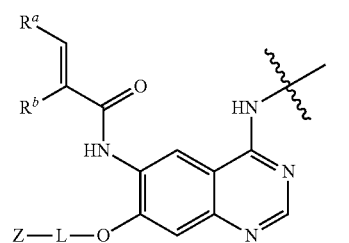

or

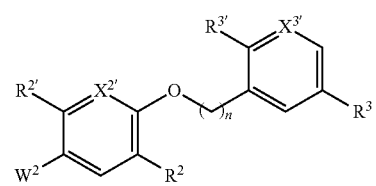
IX-1-(ii)d-1

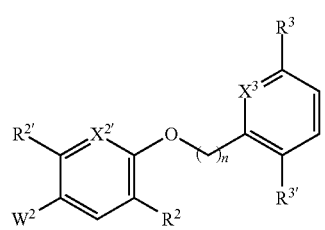
IX-1-(ii)d-2

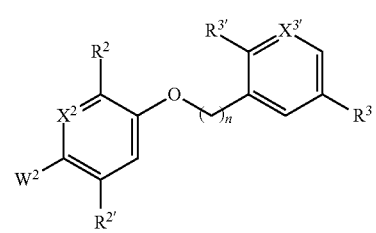
IX-1-(ii)d-3

-continued

IX-1-(ii)d-4

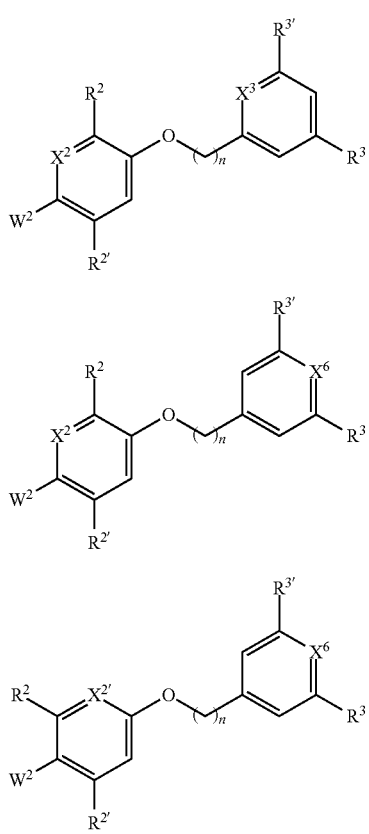

IX-1-(ii)d-5

IX-1-(ii)d-6 and W₂ is

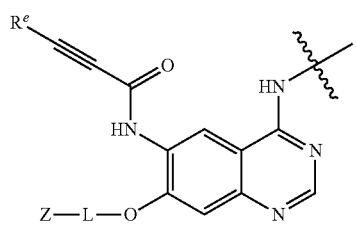

$X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$; and Z, L, $R^a$, $R^b$, $R^e$ and $R^1$ are as defined above for a compound of formula V III or IX (or VIII-1, IX-1).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $^{3'}$ and $X^6$ are —N= (i.e. a pyridine ring).

In some embodiments, a compound of formula VIII-1, IX-1 has one of the following formulas VIII-1-(ii)e-1

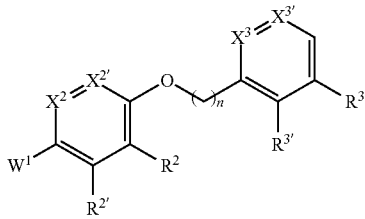

VIII-1-(ii)e-2

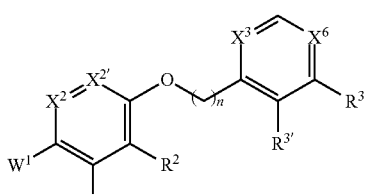

VIII-1-(ii)e-3

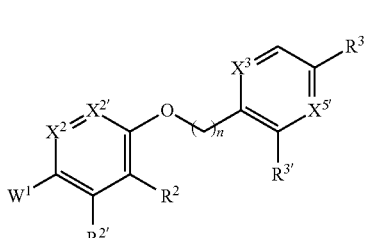

VIII-1-(ii)e-4

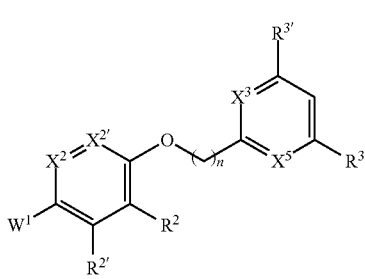

VIII-1-(ii)e-5

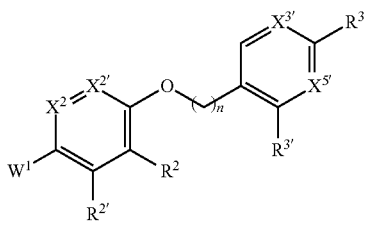

VIII-1-(ii)e-6

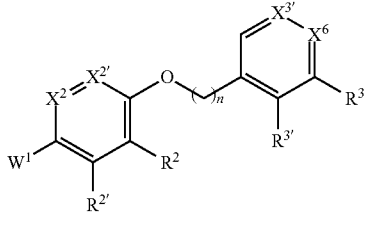

and W₁ is

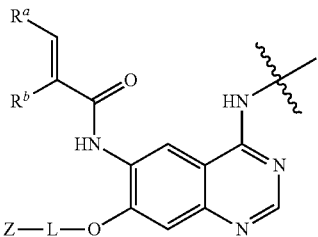

or

IX-1-(ii)e-1
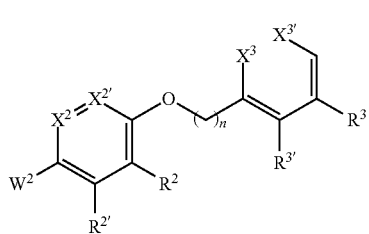

IX-1-(ii)e-2
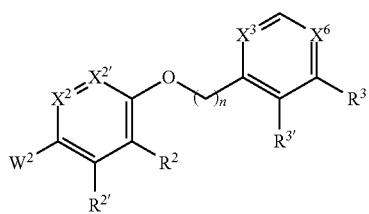

IX-1-(ii)e-3
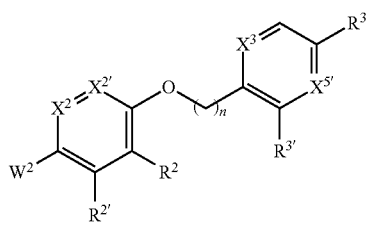

IX-1-(ii)e-4
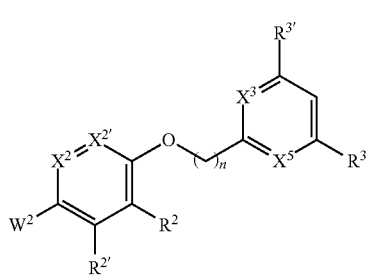

IX-1-(ii)e-5
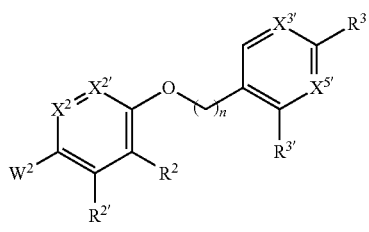

-continued

IX-1-(ii)e-6
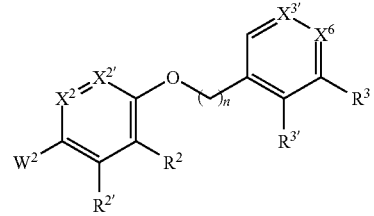

and W₂ is

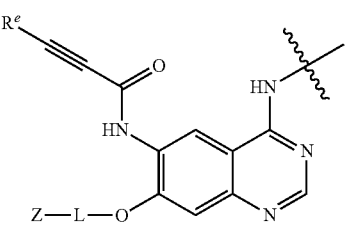

wherein $X^2, X^{2'}, X^3, X^{3'}, X^5, X^{5'}, X^6$ are independently of each other —N= or —CH=; and $R^2, R^{2'}, R^3, R^{3'}$ are independently of each other H, $C_{1-4}$ alkyl, hal, —CF₃, or —OCF₃, n is 0 or 1 and Z, L, $R^a, R^b, R^e$ and $R^1$ are as defined above for a compound of formula VIII or IX (or VIII-1, IX-1).

In some embodiments substituent Z-L contains at least one nitrogen atom. Thus, the 3-6-membered heteroaryl or 3-9-membered heterocycloalkyl formed by $R^6$ and $R^7$ of (CHR₆R₇) includes a nitrogen atom if L, does not contain a nitrogen atom.

In some embodiments $R^a$ and $R^b$ are hydrogen.

In some embodiments, both $X^2, X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring), In some embodiments, both $X^2, X^{2'}$ are —N= (i.e. a pyridazine ring).

In some embodiments, $X^3, X^{3'}, X^5, X^{5'}, X^6$ are —CH= (i.e. a phenyl ring). In some embodiments, $X^3$ is —N= and $X^{3'}, X^5, X^{5'}, X^6$ are —CH= or $X^{3'}$ is —N= and $X^3, X^5, X^{5'}, X^6$ are —CH= or $X^6$ is —N= and $X^3, X^{3'}, X^5, X^{5'}$ are —CH= (i.e. a pyridine ring).

In some embodiments, both $X^3, X^{3'}$ are —N= and $X^5, X^{5'}, X^6$ are —CH= or both $X^{3'}, X^6$ are —N= and $X^3, X^5, X^{5'}$ are —CH= (i.e. a pyridazine ring). In some embodiments, both $X^3, X^5$ are —N= and $X^{3'}, X^{5'}, X^6$ are —CH= or both $X^{3'}, X^{5'}$ are —N= and $X^3, X^5, X^6$ are —CH= or both $X^3, X^6$ are —N= and $X^{3'}, X^5, X^{5'}$ are —CH= (i.e. pyrimidine ring). In some embodiments, both $X^3, X^{5'}$ are —N= and $X^{3'}, X^5, X^6$ are —CH= (i.e. a pyrazine ring).

In some embodiments, a compound of formula VIII-2, IX-2 has one of the following formulas VIII-2-(ii)f-1
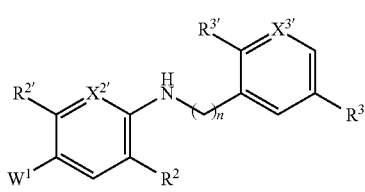

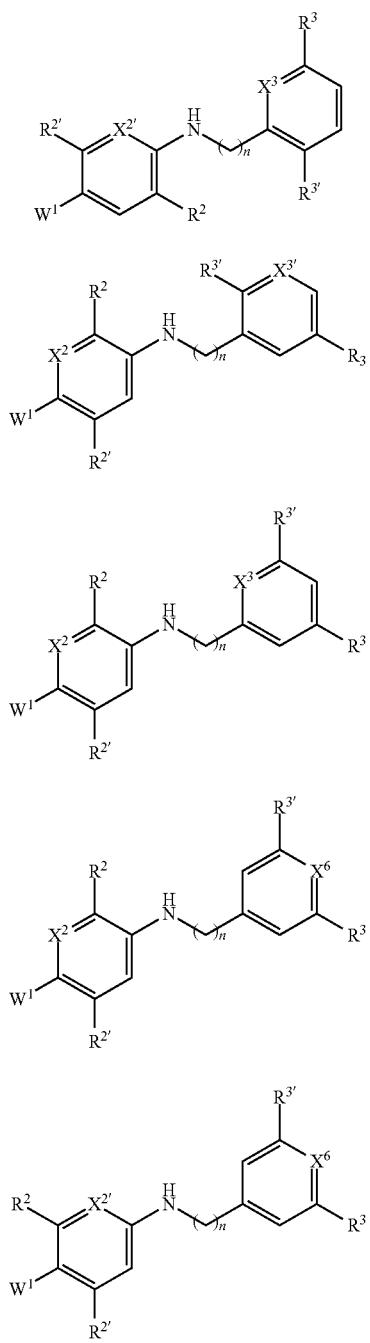
and W₁ is
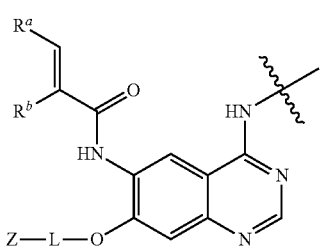
or
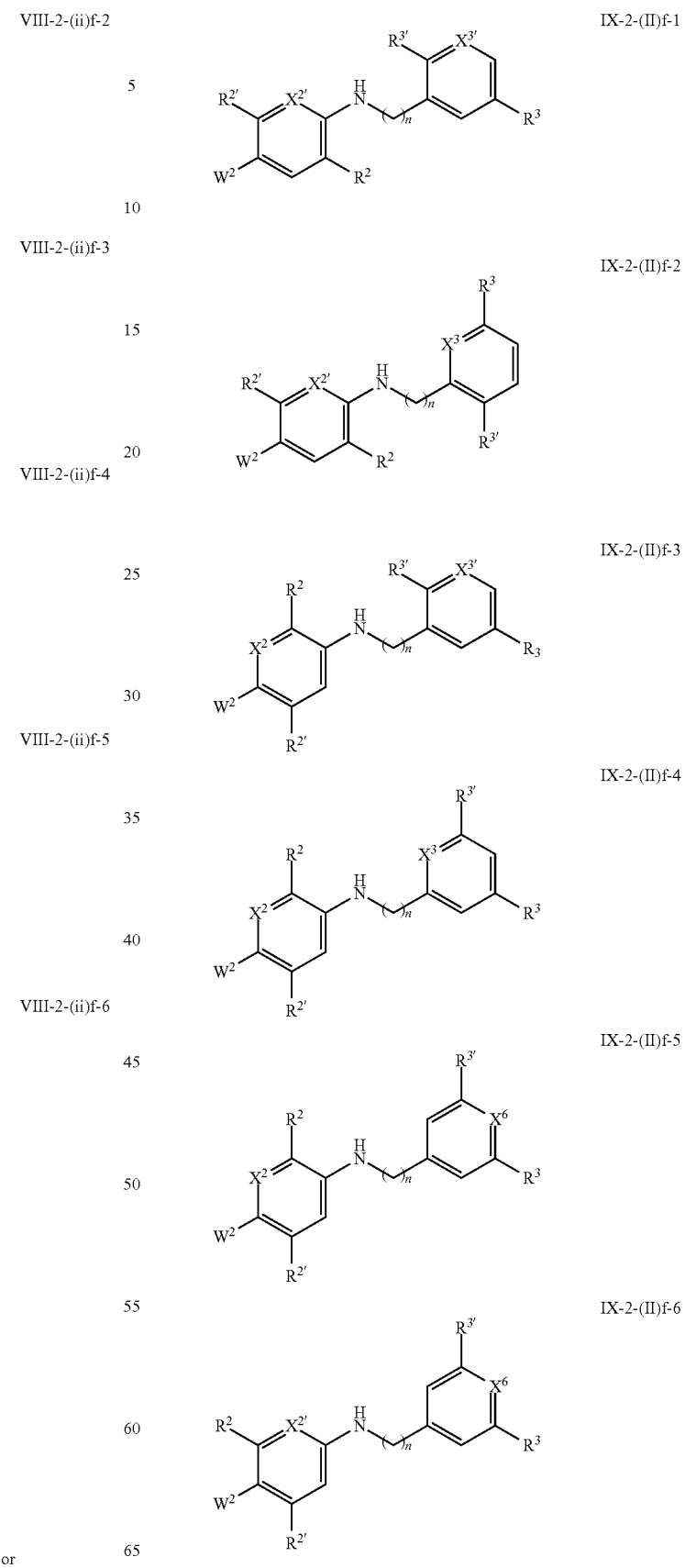

and W₂ is

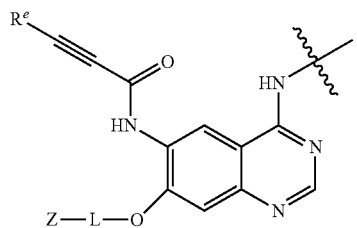

wherein $X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$; and Z, L, $R^a$, $R^b$, $R^e$ are as defined above for a compound of formula V and VI (or V-2, VI-2).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, a compound of formula VIII-2, IX-2 has one of the following formulas VIII-2-(ii)g-1

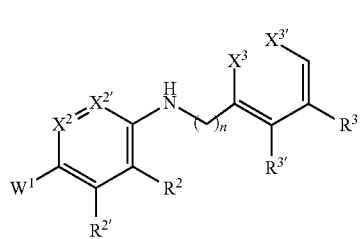

VIII-2-(ii)g-2

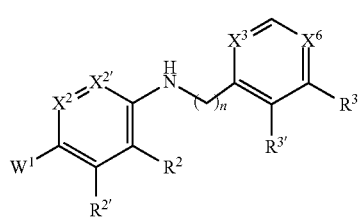

VIII-2-(ii)g-3

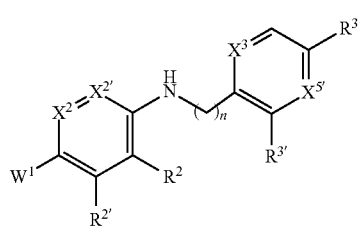

VIII-2-(ii)g-4

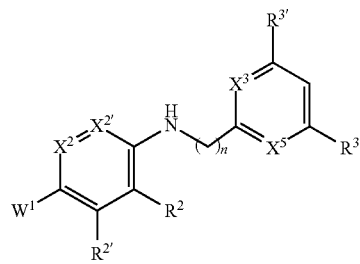

VIII-2-(ii)g-5

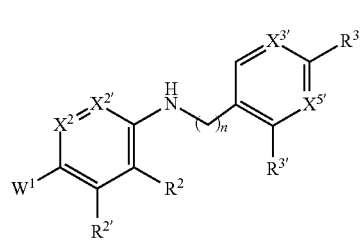

VIII-2-(ii)g-6

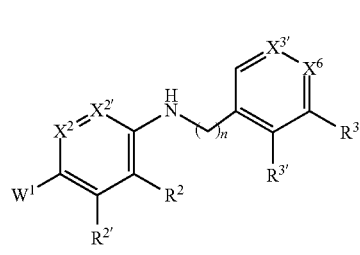

and W₁ is

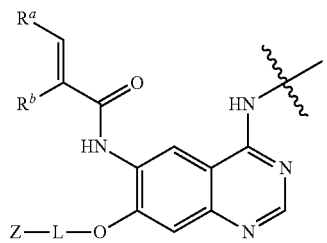

or

IX-2-(ii)g-1

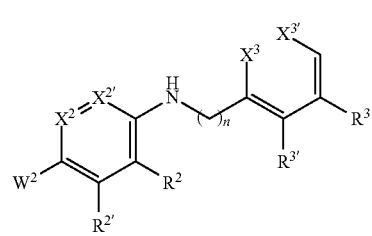

IX-2-(ii)g-2

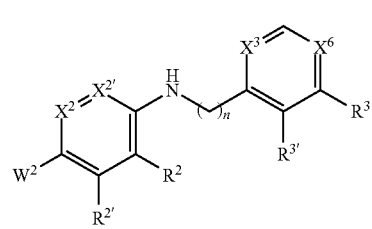

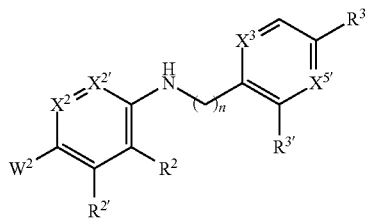

IX-2-(ii)g-3

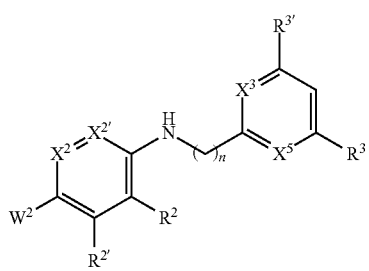

IX-2-(ii)g-4

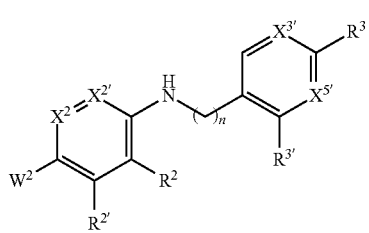

IX-2-(ii)g-5

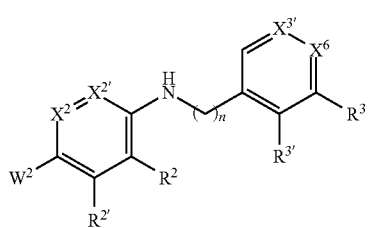

IX-2-(ii)g-6 and $W_2$ is

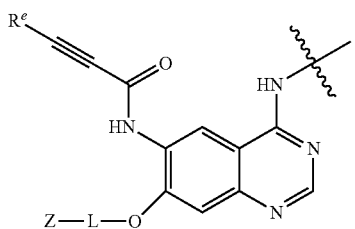

wherein $X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —CF$_3$, or —OCF$_3$, n is 0 or 1 and Z, L, $R^a$, $R^b$, $R^e$ and $R^1$ are as defined above for a compound of formula VIII or IX (or VIII-1, IX-1).

In some embodiments substituent Z-L contains at least one nitrogen atom. Thus, the 3-6-membered heteroaryl or 3-9-membered heterocycloalkyl formed by $R^6$ and $R^7$ of (CHR$_6$R$_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other H, hal or $C_{1-6}$ alkyl (e.g. H, hal or —CH$_3$).

In some embodiments, $R^3$ is H, hal, —CF$_3$, or —OCF$_3$.

In some embodiments, $R^{3'}$ is H, hal or $C_{1-6}$ alkyl (e.g. H, hal or —CH$_3$).

In some embodiments, $R^3$ and $R^{3'}$ are H. In some embodiments, $R^3$ and $R^{3'}$ are hal. In some embodiments, $R^3$ is hal, —CF$_3$, or —OCF$_3$ and $R^{3'}$ is H. In some embodiments, $R^3$ is H and $R^{3'}$ is is hal, or $C_{1-6}$ alkyl.

In some embodiments, $R^2$ and $R^{2'}$ are H. In some embodiments, $R^2$ and $R^{2'}$ are hal. In some embodiments, $R^2$ is hal or $C_{1-6}$ alkyl and $R^{2'}$ is H. In some embodiments, $R^2$ is H and $R^{2'}$ is hal.

In some embodiments, a compound of formula VIII-1, VIII-2 or IX-1, IX-2 has the formulas

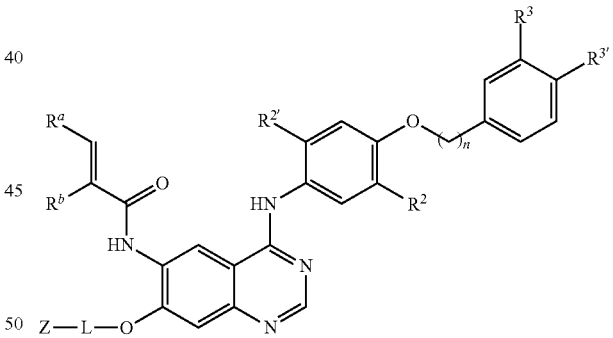

VIII-1-(ii)h-a

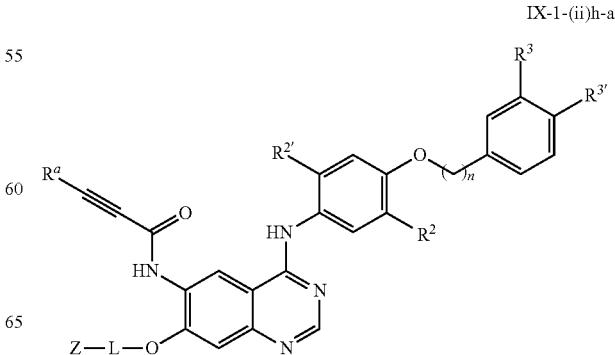

IX-1-(ii)h-a

VIII-2-(ii)h-a

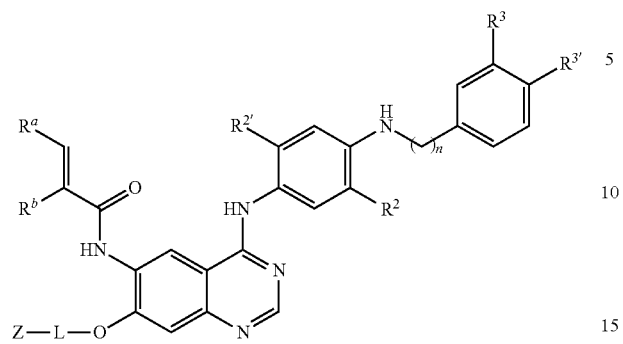

VIII-1-(ii)h-b-1

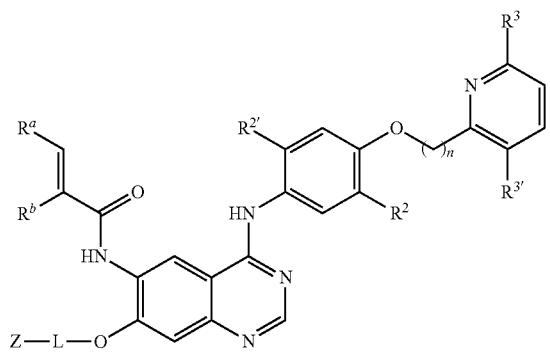

IX-2-(ii)h-a

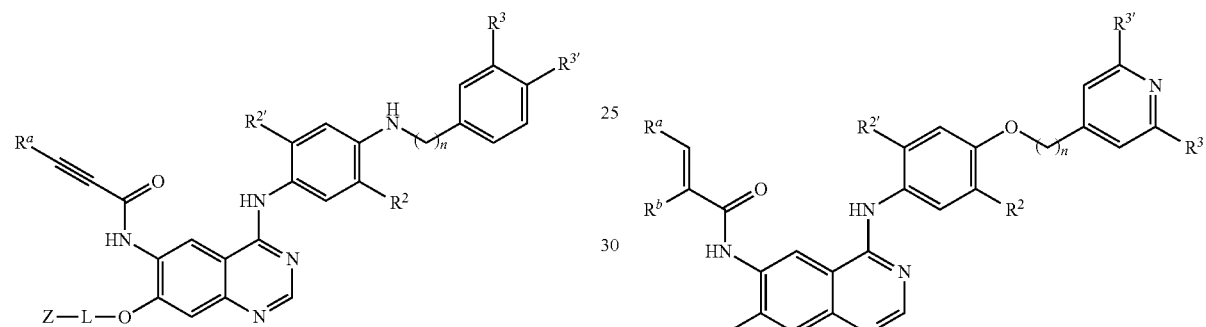

VIII-1-(ii)h-d-1 wherein $R^2$, $R^{2'}$ are independently of each other H, $C_{1-6}$ alkyl, hal (e.g. H, —CH$_3$, F, Cl); $R^3$, $R^{3'}$ are H, $C_{1-6}$ alkyl, hal, —CF$_3$, —OCF$_3$; and n is 0 or 1; and Z, L, $R^a$, $R^b$, $R^e$ are as defined above for a compound of formula VIII and IX (or VIII-1, IX-1 or VIII-2, IX-2).

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula VIII-1, IX-1 has the formulas

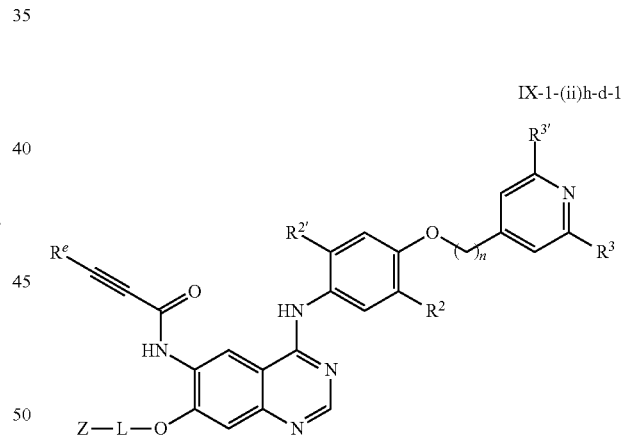

IX-1-(ii)h-d-1

VIII-1-(ii)h-c-1

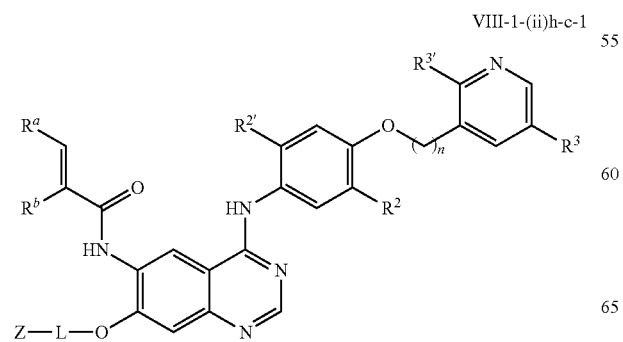

IX-1-(ii)h-c-1

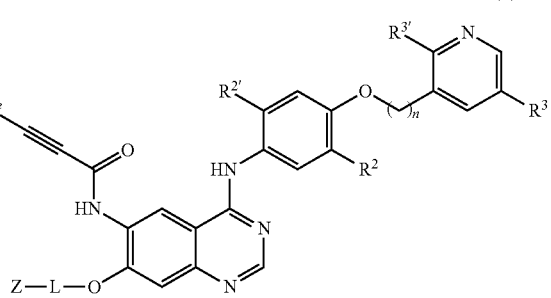

-continued

IX-1-(ii)h-b-1

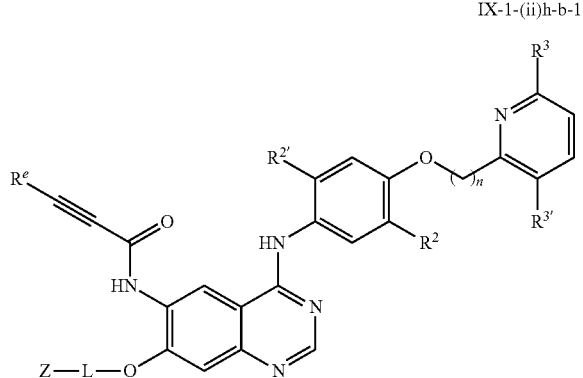

In some embodiments, a compound of formula VIII-2, IX-2 has the formulas

VIII-1-(ii)i-c-1

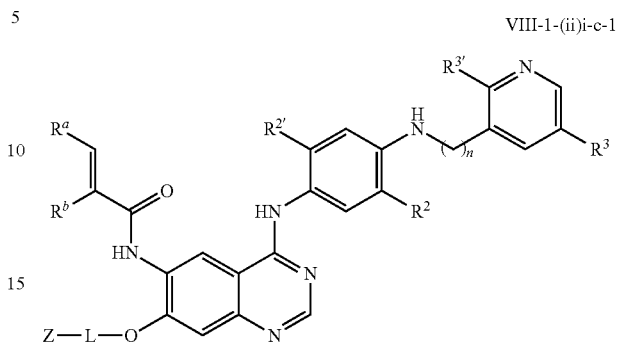

wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^a$, $R^b$, $R^e$ are as defined above for a compound of formula VIII and IX (or VIII-1, IX-1).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula IX-1 has the formula

VIII-1-(ii)i-b-1

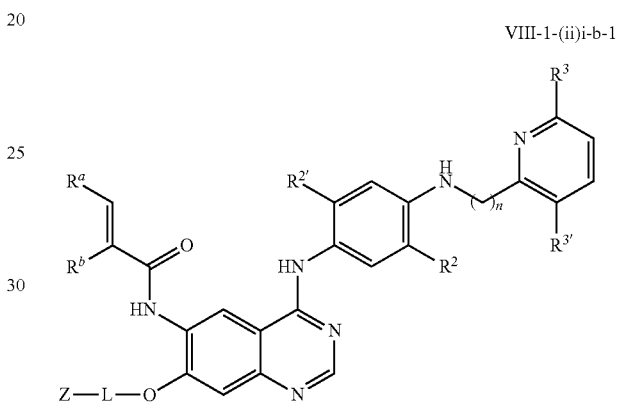

IX-1-(ii)h-b-2

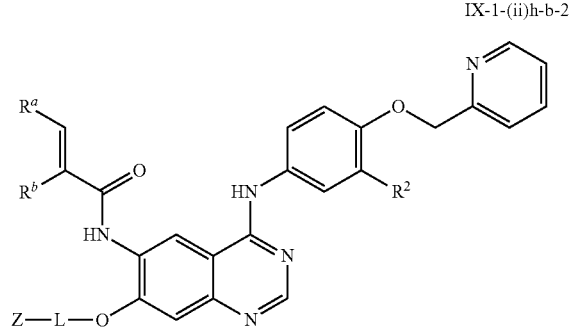

VIII-1-(ii)i-d-1

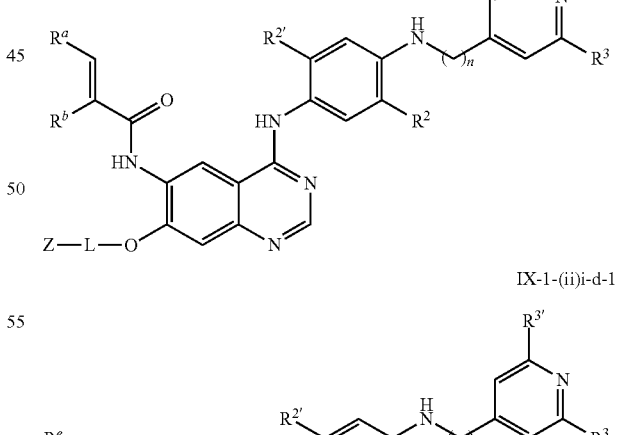

IX-1-(ii)i-d-1

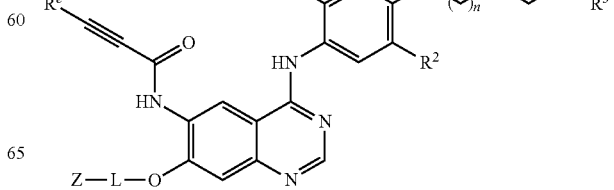

wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^a$, $R^b$, $R^e$ are as defined above for a compound of formula V and VI (or V-1, VI-1, or V-2, VI-2).

IX-1-(ii)i-c-1

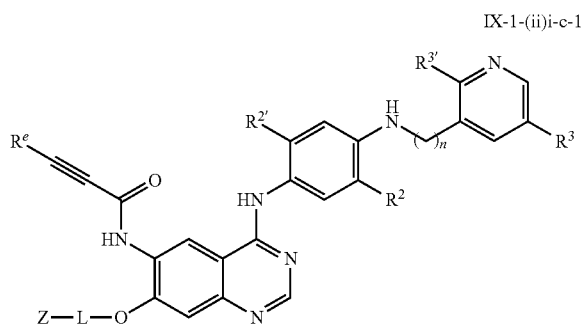

VIII-1-(ii)h-i-1

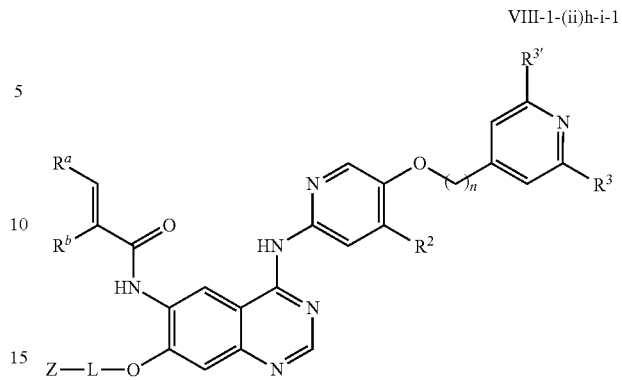

IX-1-(ii)i-b-1

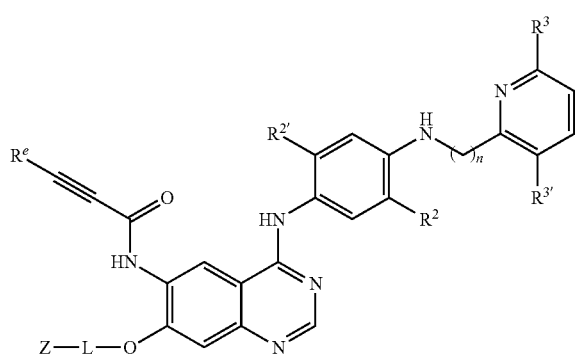

VIII-1-(ii)h-j-1

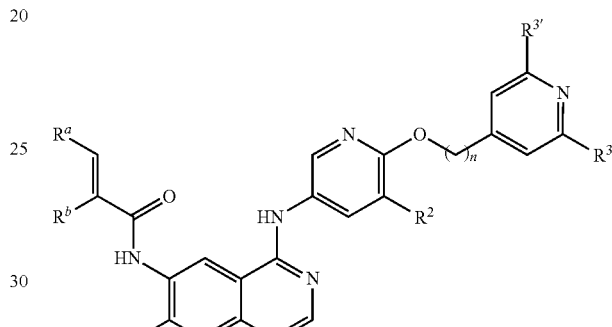

wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^a$, $R^b$ $R^e$ are as defined above for a compound of formula VIII or IX (or VIII-2, IX-2).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, a compound of formula VIII-1, IX-1 has the formulas

VIII-1-(ii)h-f-1

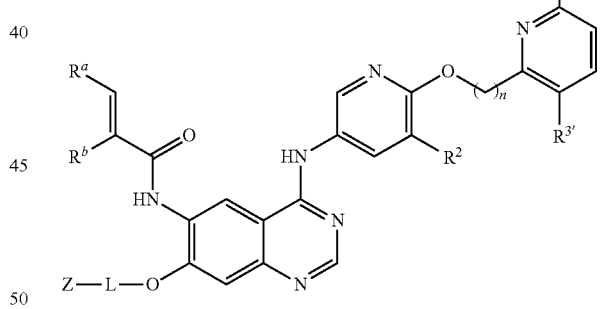

VIII-1-(ii)h-h-1

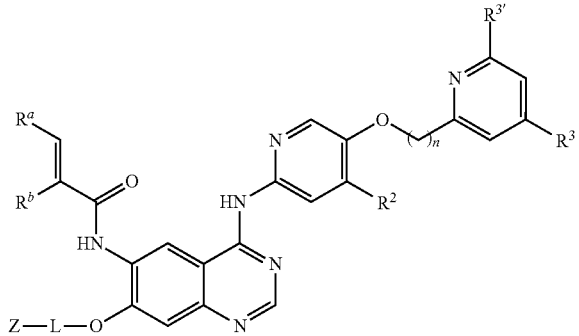

VIII-1-(ii)h-e-1

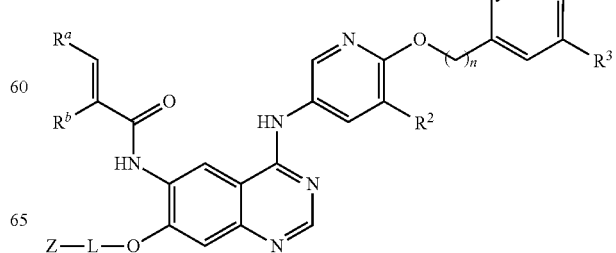

VIII-1-(ii)h-g-1

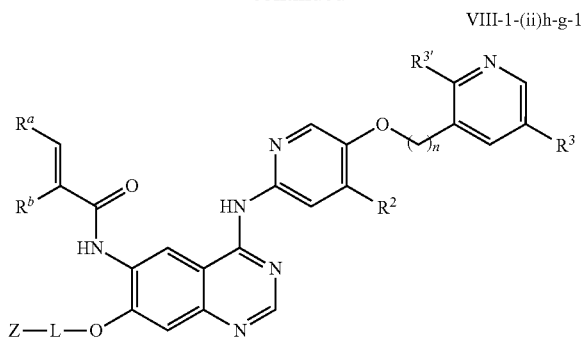

or

IX-1-(ii)h-h-1

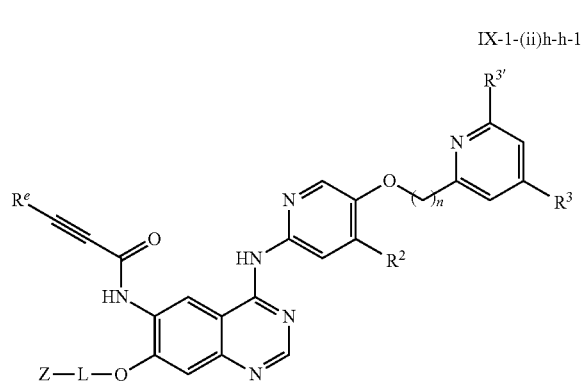

IX-1-(ii)h-i-1

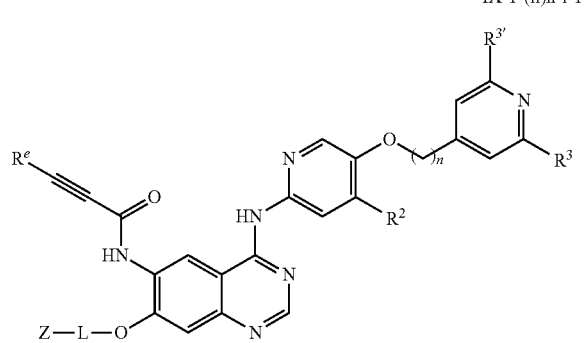

IX-1-(ii)h-j-1

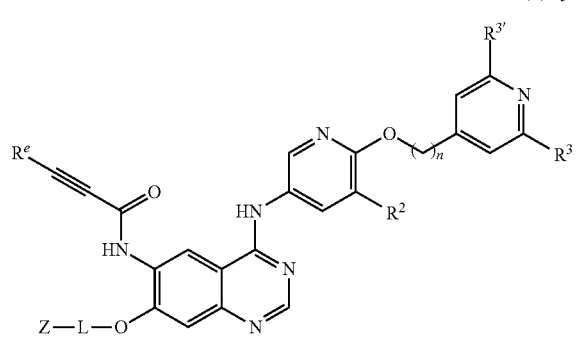

IX-1-(ii)h-f-1

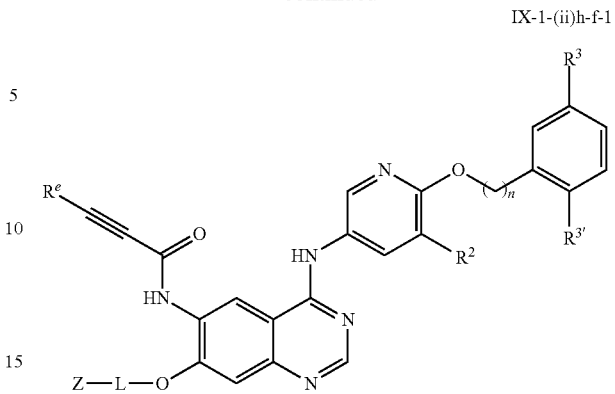

IX-1-(ii)h-e-1

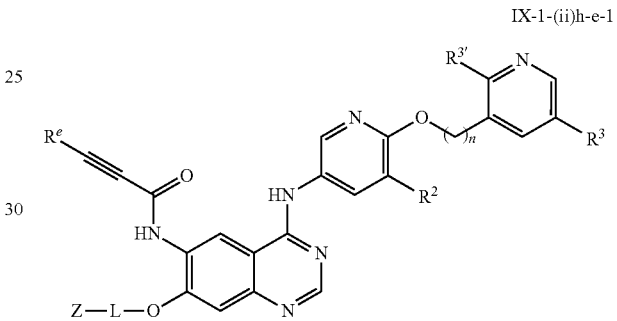

IX-1-(ii)h-g-1 wherein $R^2$ is H, $C_{1-6}$ alkyl, hal, (e.g. H, —CH$_3$, F, Cl); $R^3$, $R^{3'}$ are is H, $C_{1-6}$ alkyl, hal, —CF$_3$, —OCF$_3$; and n is 0 or 1; and Z, L, $R^a$, $R^b$ $R^e$ are as defined above for a compound of formula VIII and IX (or VIII-1, IX-1).

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula VIII-2, IX-2 has the formulas

VIII-2-(ii)i-h-1
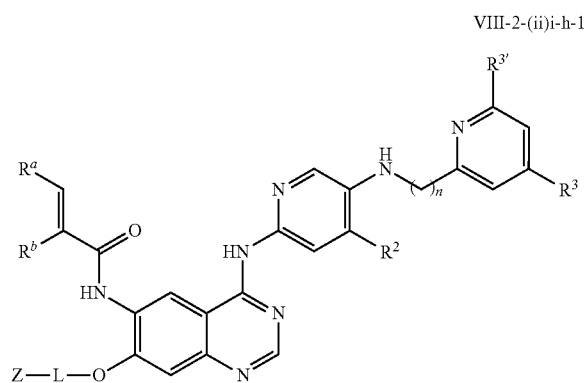
VIII-2-(ii)i-e-1
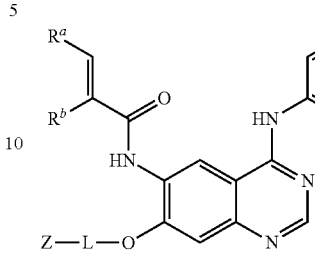
VIII-2-(ii)i-i-1
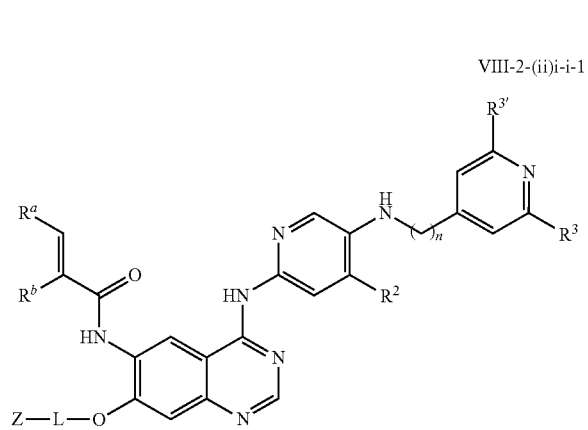
VIII-2-(ii)i-g-1
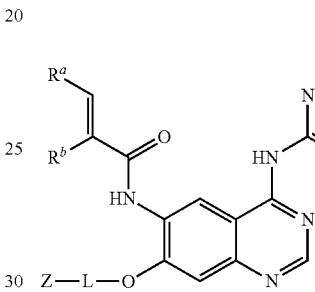
or
VIII-2-(ii)i-j-1
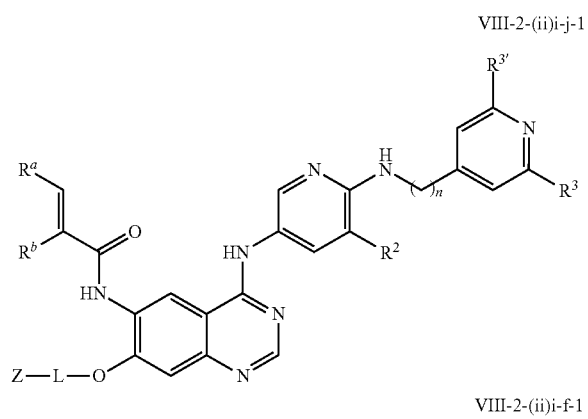
IX-2-(ii)i-h-1
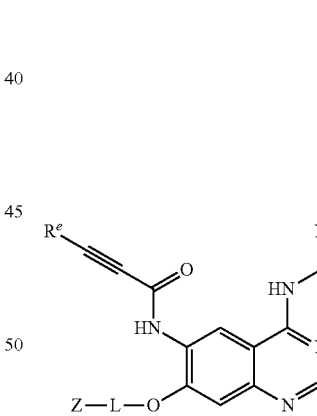
VIII-2-(ii)i-f-1
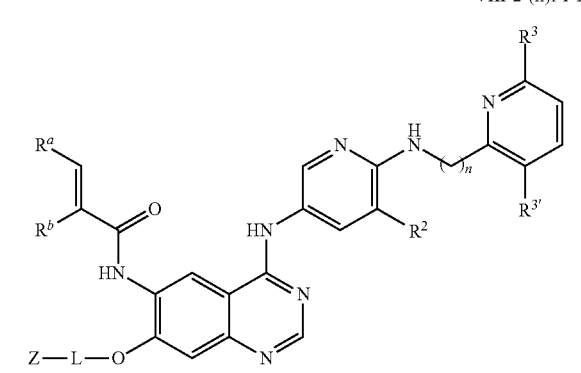
IX-2-(ii)i-i-1
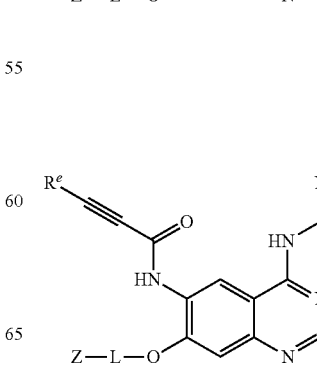

-continued

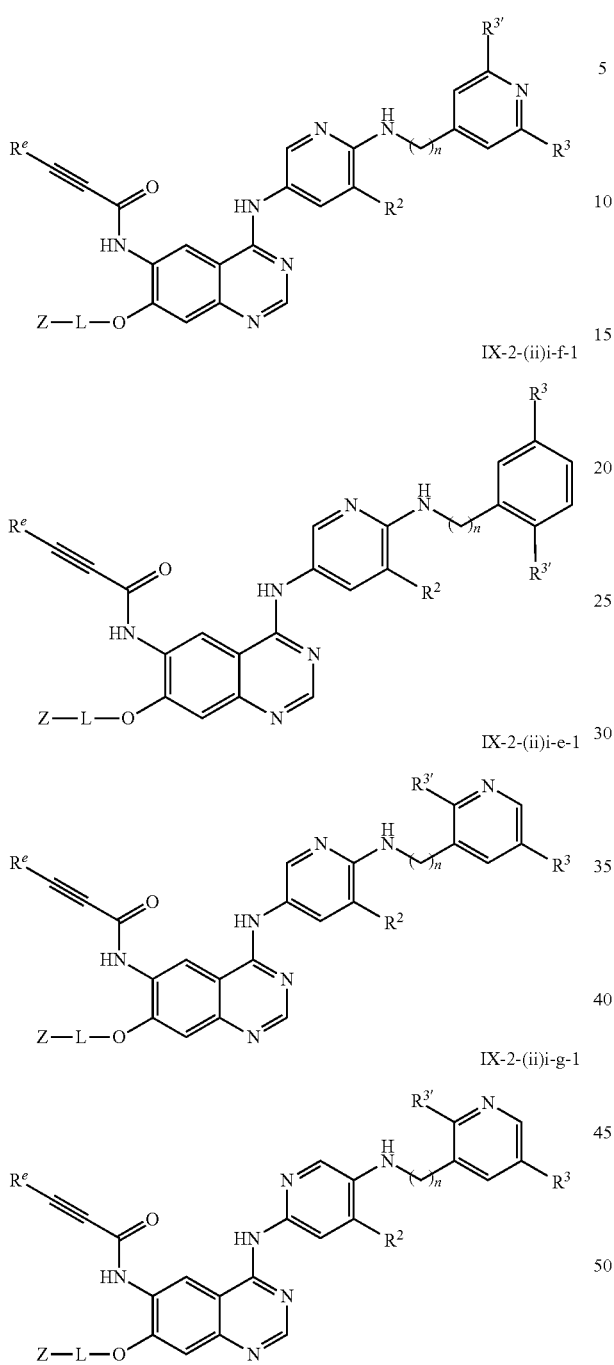

wherein R² is H, C₁₋₆ alkyl, hal (e.g. H, —CH₃, F, Cl); R³, R³' are H, C₁₋₆ alkyl, hal, —CF₃, —OCF₃; and n is 0 or 1; and Z, L, Rᵃ, Rᵇ, Rᵉ are as defined above for a compound of formula VIII or IX (or VIII-2, IX-2).

In some embodiments substituent Z-L contains at least one nitrogen atom. Thus, the 3-6-membered heteroaryl or 3-9-membered heterocycloalkyl formed by R₆ and R₇ of (CHR₆R₇) includes a nitrogen atom if L does not contain a nitrogen atom.

In some embodiments Rᵃ and Rᵇ are hydrogen.

In some embodiments, n is 0. In some embodiments, n is 1.

In some embodiments, a compound of formula VIII-1, IX-1 has the formulas

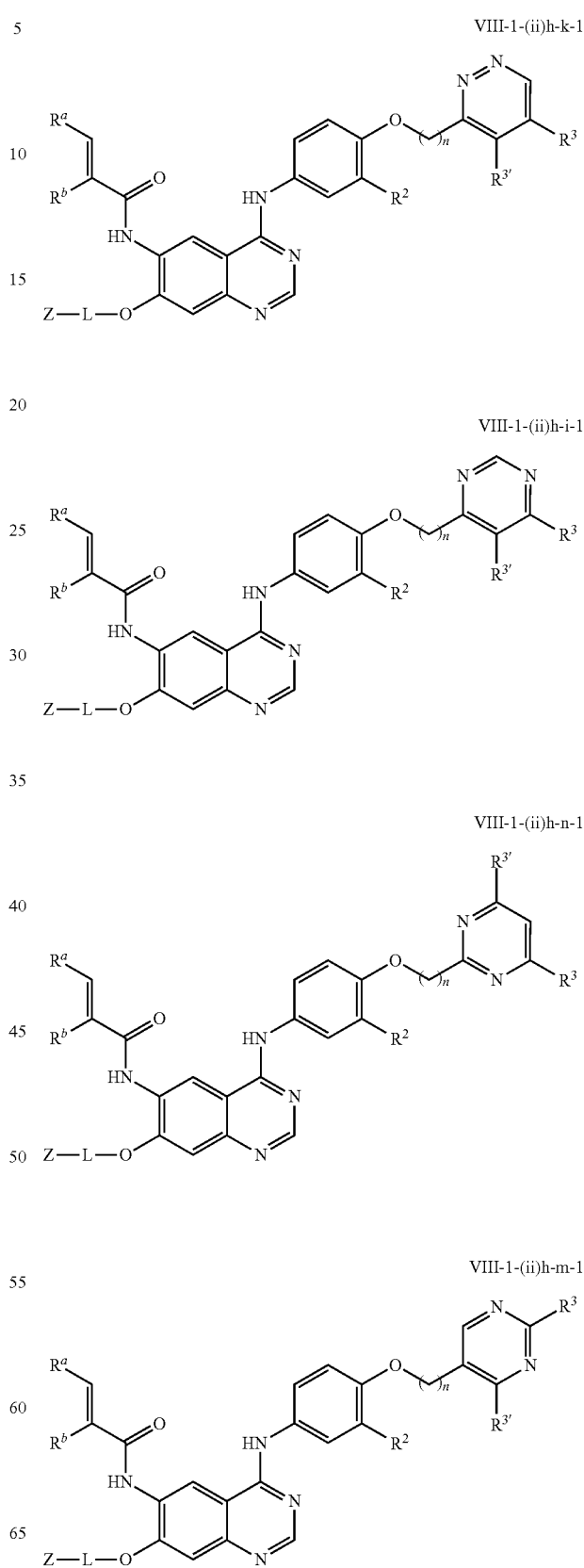

VIII-1-(ii)h-o-1

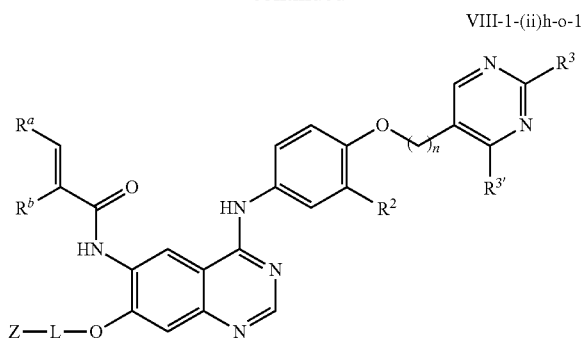

VIII-1-(ii)h-p-1

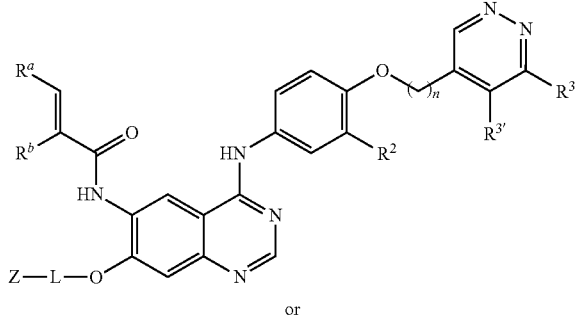

or

IX-1-(ii)h-k-1

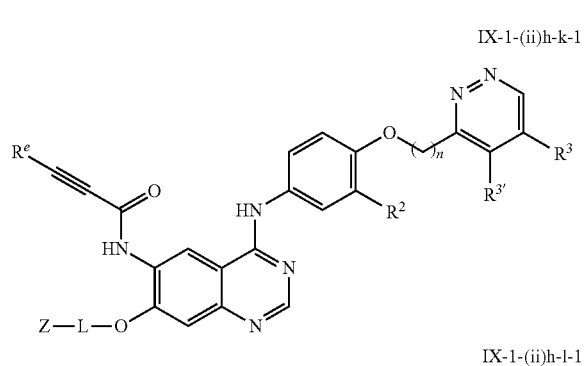

IX-1-(ii)h-l-1

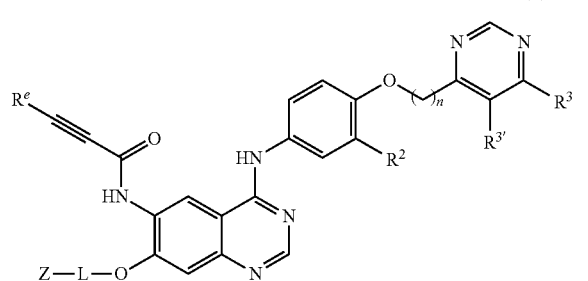

IX-1-(ii)h-n-1

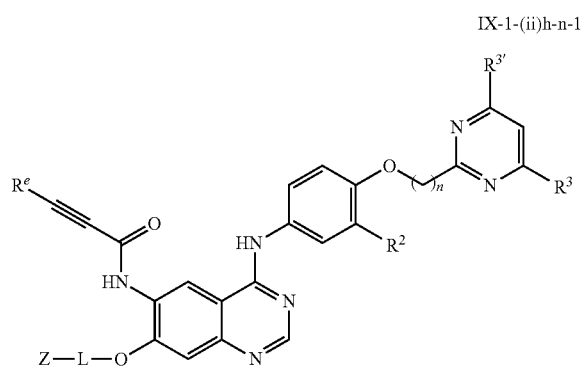

IX-1-(ii)h-m-1

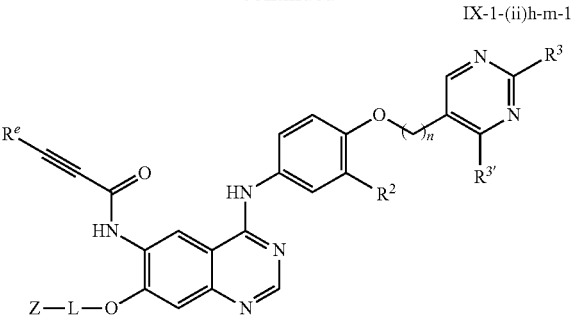

IX-1-(ii)h-o-1

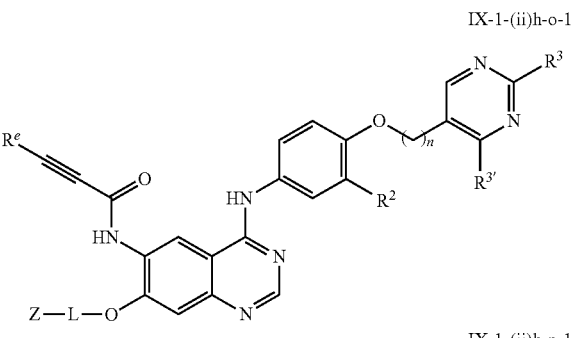

IX-1-(ii)h-p-1

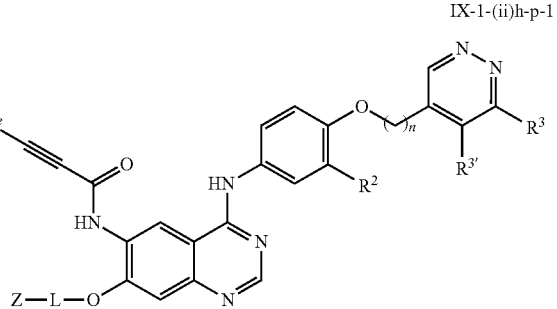

wherein $R^2$ is H, $C_{1-6}$ alkyl, hal (e.g. H, —CH$_3$, F, Cl); $R^3$, $R^{3'}$ are is H, $C_{1-6}$ alkyl, hal, —CF$_3$, —OCF$_3$; and n is 0 or 1; and Z, L, $R^a$, $R^b$, $R^e$ are as defined above for a compound of formula VIII and IX (or VIII-1, IX-1).

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula VIII-2, IX-2 has the formulas

VIII-2-(ii)i-k-1

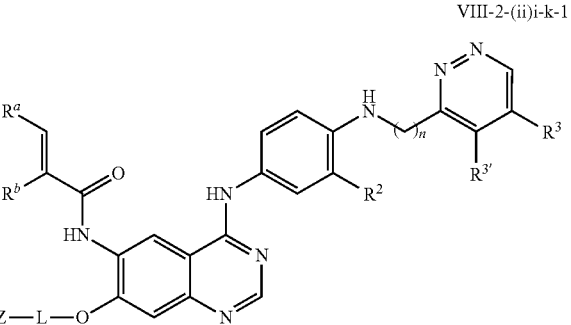

-continued
VIII-2-(ii)i-i-1
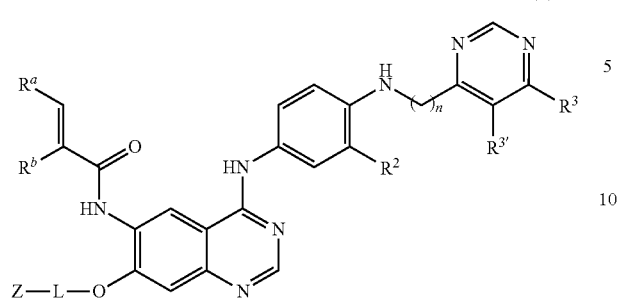
VIII-2-(ii)i-n-1
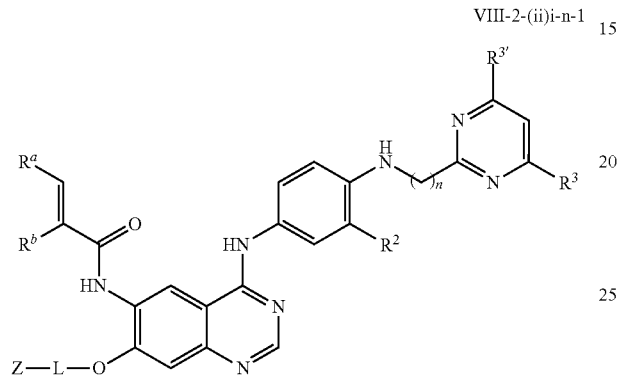
VIII-2-(ii)i-m-1
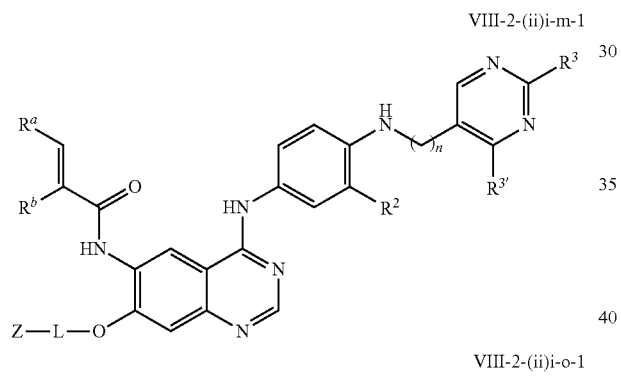
VIII-2-(ii)i-o-1
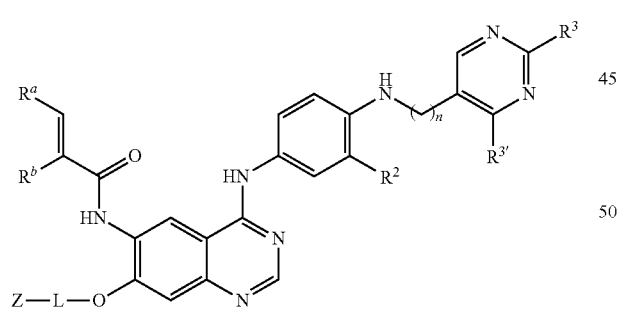
VIII-2-(ii)h-p-1
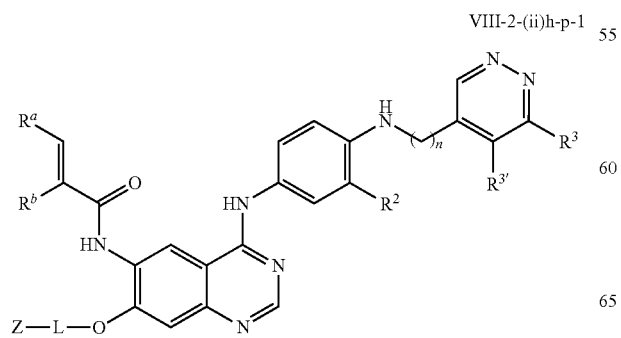
or
IX-2-(ii)i-k-1
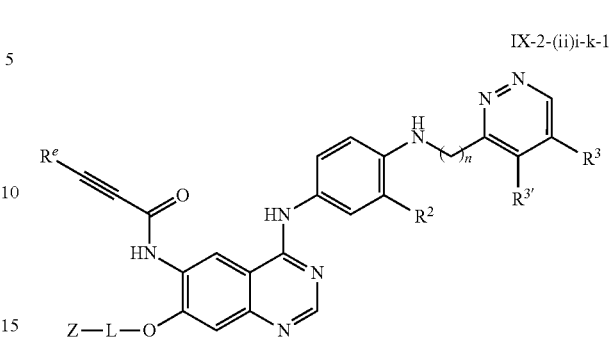
IX-2-(ii)i-l-1
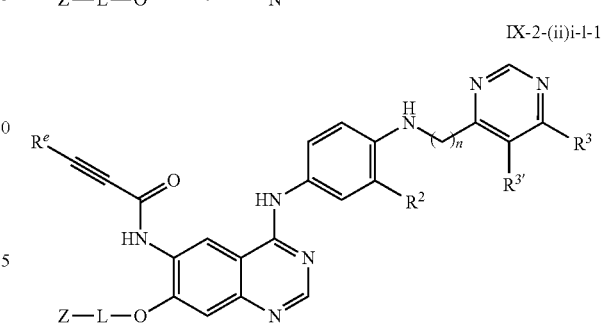
IX-2-(ii)i-n-1
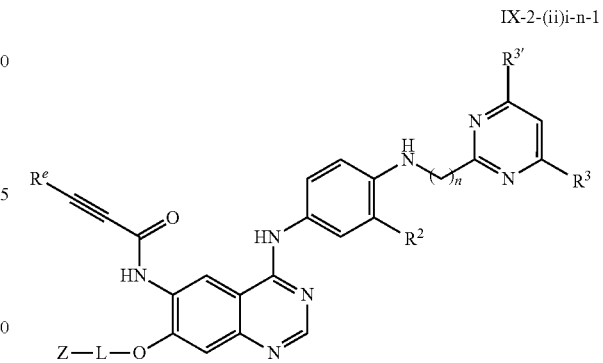
IX-2-(ii)i-m-1
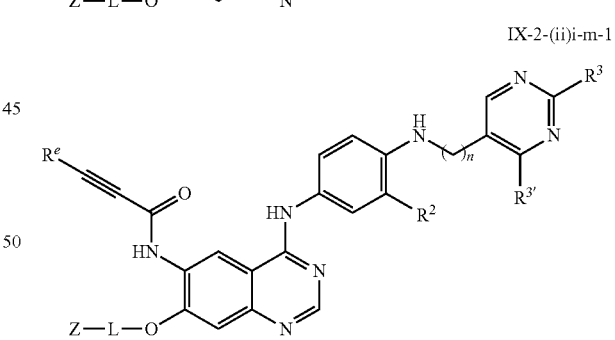
IX-1-(ii)i-o-1
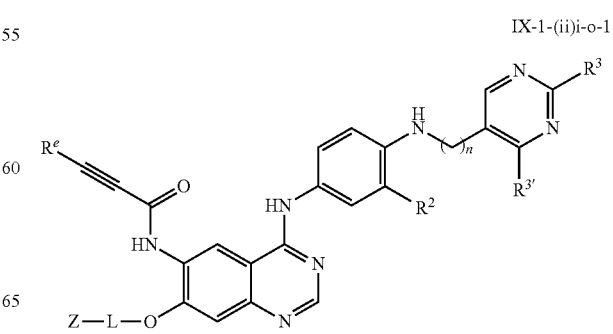

IX-1-(ii)i-p-1

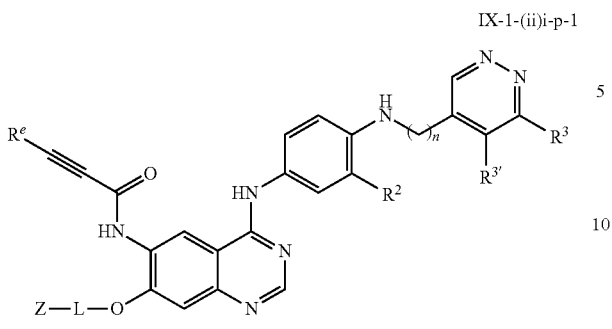

wherein R² is H, C₁₋₆ alkyl, hal (e.g. H, —CH₃, F, Cl); R³, R³' are is H, C₁₋₆ alkyl, hal, —CF₃, —OCF₃; and n is 0 or 1; and Z, L, R$^a$, R$^b$, R$^e$ are as defined above for a compound of formula VIII and IX (or VIII-2, IX-2).

In some embodiments substituent Z-L contains at least one nitrogen atom. Thus, the 3-6-membered heteroaryl or 3-9-membered heterocycloalkyl formed by R₆ and R₇ of (CHR₆R₇) includes a nitrogen atom if L does not contain a nitrogen atom.

In some embodiments R$^a$ and R$^b$ are hydrogen.

In some embodiments, n is 0. In some embodiments, n is 1.

In some embodiments, group Z is defined as specified above. In some embodiments, Z is —(NR⁴R⁵), wherein R⁴ and R⁵ are independently of each other H, C₁₋₆ alkyl, cyclopropyl, cylobutyl, 3 to 6-membered heterocycloalkyl containing 0, 1, or 2 N-atoms and 0, 1, or 2 O-atoms, or —(NR⁶R⁷), —(CHR⁶R⁷), wherein R⁶ and R⁷ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with C₁₋₄ alkyl, hal, —OR', —NR'R", wherein R', R" are independently of each other H or -C₁₋₄ alkyl.

In some embodiments, the —(CR⁶R⁷) and —NR⁶R⁷) ring systems of Z are selected from

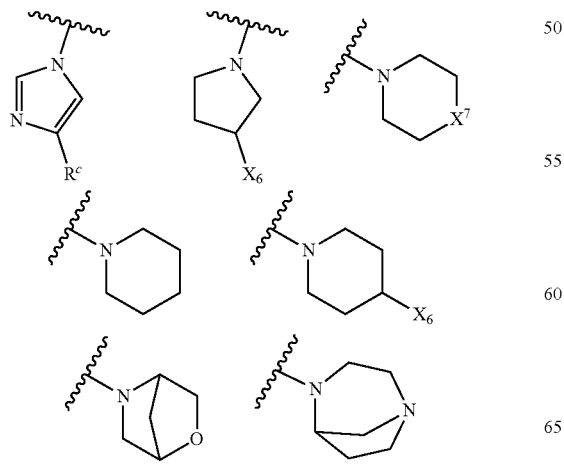

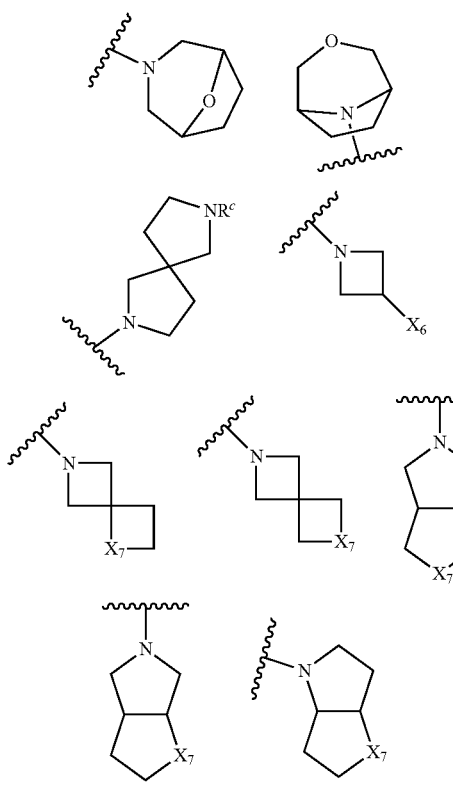

wherein R$^c$ is H, C₁₋₄ alkyl, oxetane; X⁶ is H, —CH₃, —OH, —OCH₃, —OCF₃, —N(CH₃)₂, F, Cl; X⁷ is —O—, —NH— or —N(CH₃)—, —SO₂, and

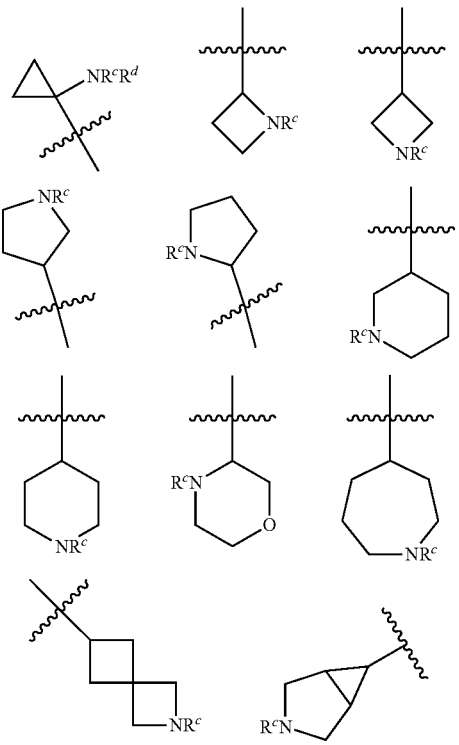

-continued

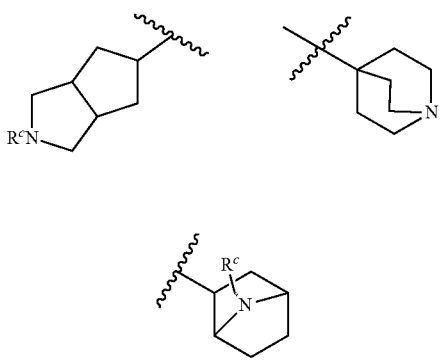

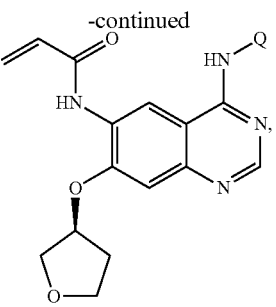

wherein $R^c$ is H, $C_{1-4}$ alkyl, oxetane, and $R^d$ is H, $C_{1-4}$ alkyl.

In some embodiments, L is a covalent bond or straight chain or branched $C_{1-4}$ alkyl (e.g. —CH$_2$—, —(CH$_2$)$_2$—, —(CH$_2$)$_3$—, —(CH$_2$)$_4$—, —(CH$_3$)$_2$— or —CH$_2$—C(CH$_3$)$_2$— and —(CH$_2$)$_2$— or —(CH$_2$)$_3$— or —CH$_2$—C(CH$_3$)$_2$—). In some embodiments, L is

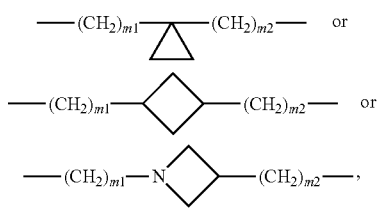

wherein m1, m2 are independently of each other 0, 1, 2, 3, 4 (e.g., 0 or 1 or 2). In some embodiments, m2 is 0 and m1 is 0 or 1 or 2, In some embodiments, m1 and m2 are 1 or m1 and m2 are 2.

In some embodiments, the compound of formula VIII-1 is not any of

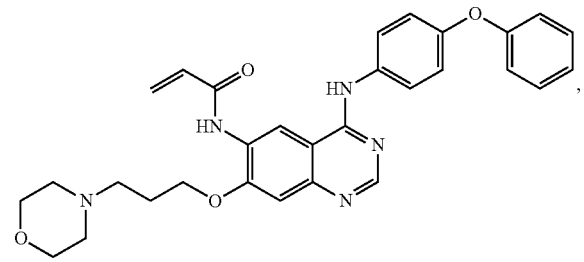

,

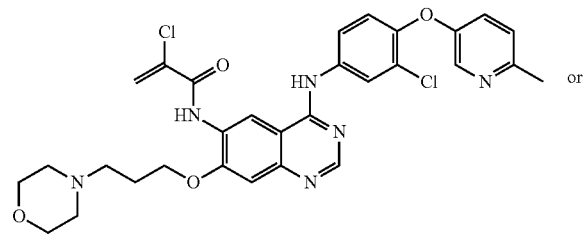

or

-continued

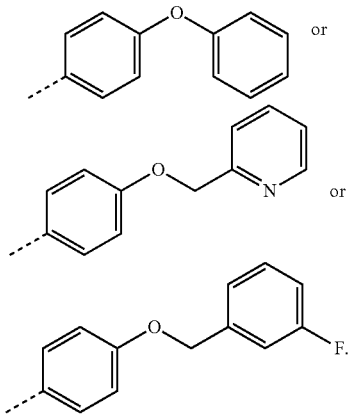

wherein Q is

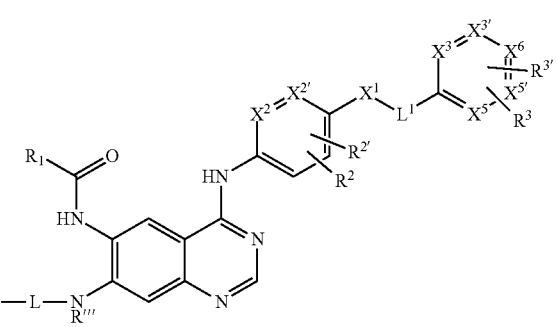

In some embodiments, the present disclosure is directed towards a compound or pharmaceutically acceptable salts or stereoisomers thereof of formula I above wherein $Y^2$ is —NR'''—, having the following formula X

X wherein $X^1$ is —O—, —CH$_2$—, —NH—, —S—; $X^2$, $X^{2'}$, $X^3$, $X^{3'}$, $X^5$, $X^{5'}$, $X^6$ are independently of each other —N=, —CH=;

$L^1$ is a covalent bond or straight chain or branched $C_{1-3}$alkyl, which is unsubstituted or substituted with hal, $R^1$ is —CR$_b$=CHR$_a$, —C≡CH or —C≡C—CH$_3$; wherein $R^a$, $R^b$ are independently of each other H, hal, —CH$_2$—O—CH$_3$;

$R^2$, $R^{2'}$, $R^3$, $R^{3'}$ are independently of each other H, $C_{1-6}$ alkyl, hal, —CF$_3$, —OCF$_3$;

L is a covalent bond, straight chain or branched $C_{1-4}$ alkyl or

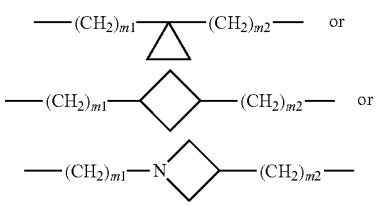

wherein m1, m2 are independently of each other 0, 1, 2, 3, or 4;

R''' is H or —CH$_3$;

Z is —(NR$^4$R$^5$), wherein R$^4$ and R$^5$ are independently of each other H, C$_{1-6}$ alkyl, cyclopropyl, cylobutyl, 3 to 6-membered heterocycloalkyl, or —(NR$^6$R$^7$), —(CHR$^6$R$^7$), wherein R$^6$ and R$^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with C$_{1-4}$ alkyl, hal, —OR', —NR'R'', wherein R', R'' are independently of each other H or -C$_{1-4}$ alkyl.

In some embodiments R$^a$ and R$^b$ are hydrogen.

In some embodiments, L$^1$ is straight chain or branched C$_{1-3}$alkyl, which is unsubstituted or substituted with hal. In some embodiments, L$^1$ is not a covalent bond.

In some embodiments, both X$^2$, X$^{2'}$ are —CH= (i.e. a phenyl ring). In some embodiments, X$^2$ is —N= and X$^{2'}$ is —CH= or X$^{2'}$ is —N= and X$^2$ is —CH= (i.e. a pyridine ring), In some embodiments, both X$^2$, X$^{2'}$ are —N= (i.e. a pyridazine ring).

In some embodiments, X$^3$, X$^{3'}$, X$^5$, X$^{5'}$, X$^6$ are —CH= (i.e. a phenyl ring). In some embodiments, X$^3$ is —N= and X$^{3'}$, X$^5$, X$^{5'}$, X$^6$ are —CH= or X$^{3'}$ is —N= and X$^3$, X$^5$, X$^{5'}$, X$^6$ are —CH= or X$^6$ is —N= and X$^3$, X$^{3'}$, X$^5$, X$^{5'}$ are —CH= (i.e. a pyridine ring).

In some embodiments, both X$^3$, X$^{3'}$ are —N= and X$^5$, X$^{5'}$, X$^6$ are —CH= or both X$^{3'}$, X$^6$ are —N= and X$^3$, X$^5$, X$^{5'}$ are —CH= (i.e. a pyridazine ring). In some embodiments, both X$^3$, X$^5$ are —N= and X$^{3'}$, X$^{5'}$, X$^6$ are —CH= or both X$^{3'}$, X$^{5'}$ are —N= and X$^3$, X$^5$, X$^6$ are —CH= or both X$^3$, X$^6$ are —N= and X$^{3'}$, X$^5$, X$^{5'}$ are —CH= (i.e. pyrimidine ring). In some embodiments, both X$^3$, X$^{5'}$ are —N= and X$^{3'}$, X$^5$, X$^6$ are —CH= (i.e. a pyrazine ring).

In some embodiments the compounds of formula X, groups X$^2$, X$^{2'}$ are —CH= (i.e. a phenyl ring).

In some embodiments of the compounds of formula X, groups X$^3$, X$^{3'}$, X$^5$, X$^{5'}$, X$^6$ are —CH= (i.e. a phenyl ring) or X$^3$ is —N= and X$^{3'}$, X$^5$, X$^{5'}$, X$^6$ are —CH= (i.e. a pyridine ring).

In some embodiments, R$^2$ and R$^{2'}$ are independently of each other H, C$_{1-6}$ alkyl, or hal (e.g., H, —CH$_3$, F, or Cl).

In some embodiments, R$^2$ and R$^{2'}$ are H. In some embodiments, R$^2$ and R$^{2'}$ are hal. In some embodiments, R$^2$ is hal and R$^{2'}$ is H.

In some embodiments, R$^3$ and R$^{3'}$ are independently of each other H, C$_{1-6}$ alkyl, hal, —CF$_3$, —OCF$_3$. In some embodiments, R$^3$ is H, C$_{1-6}$ alkyl, hal, —CF$_3$, —OCF$_3$ and R$^{3'}$ is H, hal.

In some embodiments, R$^2$ and R$^{2'}$ are H and R$^3$ is H, C$_{1-6}$ alkyl, hal, —CF$_3$, —OCF$_3$ and R$^{3'}$ is H, hal; or R$^2$ and R$^{2'}$ are hal and R$^3$ is H, C$_{1-6}$ alkyl, hal, —CF$_3$, —OCF$_3$ and R$^{3'}$ is H, hal; or R$^2$ is hal and R$^{2'}$ is H and R$^3$ is H, C$_{1-6}$ alkyl, hal, —CF$_3$, —OCF$_3$ and R$^{3'}$ is H.

In some embodiments, X$^2$, X$^{2'}$ are —CH= (i.e. a phenyl ring).

In some embodiments, X$^3$, X$^{3'}$, X$^5$, X$^{5'}$, X$^6$ are —CH= (i.e. a phenyl ring) or X$^3$ is —N= and X$^{3'}$, X$^5$, X$^{5'}$, X$^6$ are —CH= (i.e. a pyridine ring).

In some embodiments, L is a covalent bond, straight chain or branched C$_{1-4}$ alkyl (e.g. straight chain or branched C$_{1-4}$ alkyl).

In some embodiments, X$^1$ is —O—. In some embodiments, X$^1$ is —CH$_2$—. In some embodiments, X$^1$ is —NH—. In some embodiments, X$^1$ is —S—.

In some embodiments, L$^1$ is a covalent bond. In some embodiments, L$^1$ is —CH$_2$—, —CH(CH$_3$)—, or —CH(hal)-. In some embodiments, L$^1$ is —CH$_2$—CH$_2$— or —CH$_2$—CH(CH$_3$)— or —CH$_2$—CH(hal)-.

In some embodiments, linker combinations -X$^1$-L$^1$- include —O—, —CH$_2$—, —O—CH$_2$—, —NH—CH$_2$—, —S—CH$_2$—, —CH$_2$—CH$_2$—, —O—CH(CH$_3$)—, —CH$_2$—CH(CH$_3$)—, —NH—CH(CH$_3$)—, —S—CH(CH$_3$)—, —O—CH(hal)-, —CH$_2$—CH(hal)-, —NH—CH(hal)-, —S—CH(hal)- (e.g., —O—, —CH$_2$—, —O—CH$_2$—, —NH—CH$_2$—, —CH$_2$—CH$_2$—, —O—CH(CH$_3$)—, —CH$_2$CH(CH$_3$)—, —O—CH(hal)-, or —CH$_2$—CH(hal)- and —O—, —CH$_2$—, —O—CH$_2$—, —NH—CH$_2$—, —CH$_2$—CH$_2$—).

In some embodiments, -X$^1$-L$^1$- is —O—, In some embodiments, -X$^1$-L$^1$- is —O—CH$_2$—.

In some embodiments, compound of formula X has the following formula

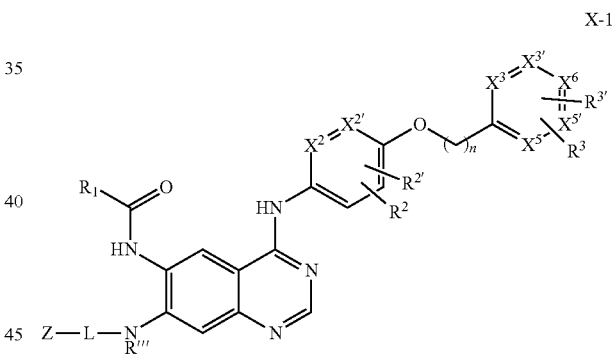

X-1

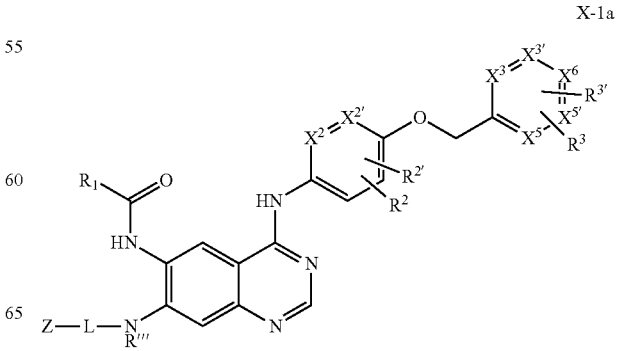

X-1a

-continued

X-1b

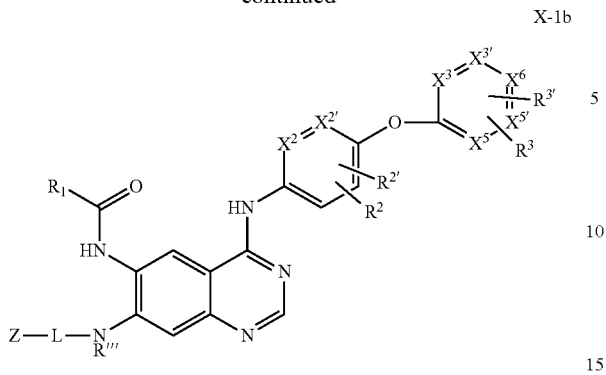

wherein $X^2$, $X^{2'}$ and $X^3$, $X^{3'}$, $X^5$, $X^{5'}$, $X^6$ are independently of each other —N= or —CH=; $R^2$, $R^{2'}$ and $R^3$, $R^{3'}$ are independently of each other H, $C_{1-6}$ alkyl, hal, —$CF_3$, or —$OCF_3$, and n is 0, 1, 2, 3; and Z, L, $R^1$, $R'''$ are as defined above for a compound of formula X.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments of the compounds of formula X, groups $X^2$, $X^{2'}$ are —CH= (i.e. a phenyl ring). In some embodiments of the compounds of formula X, groups $X^3$, $X^{3'}$, $X^5$, $X^{5'}$, $X^6$ are —CH= (i.e. a phenyl ring) or $X^3$ is —N= and $X^{3'}$, $X^5$, $X^{5'}$, $X^6$ are —CH= (a pyridine ring).

In some embodiments, $R^2$ and $R^{2'}$ are independently of each other H, $C_{1-6}$ alkyl, hal (e.g. H, —$CH_3$, F, Cl). In some embodiments, $R^3$ and $R^{3'}$ are independently of each other H, $C_{1-6}$ alkyl, hal, —$CF_3$, —$OCF_3$.

In some embodiments, $R^2$ and $R^{2'}$ are H and $R^3$ is H, $C_{1-6}$ alkyl, hal, —$CF_3$, —$OCF_3$ and $R^{3'}$ is H, hal; or $R^2$ and $R^{2'}$ are hal and $R^3$ is H, $C_{1-6}$ alkyl, hal, —$CF_3$, —$OCF_3$ and $R^3$ is H, hal; or $R^2$ is hal and $R^{2'}$ is H and $R^3$ is H, $C_{1-6}$ alkyl, hal, —$CF_3$, —$OCF_3$ and $R^{3'}$ is H.

In some embodiments, compound of formula X has the following formulas

X-(ii)d-1

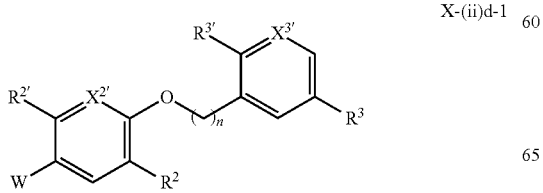

X-(ii)d-2

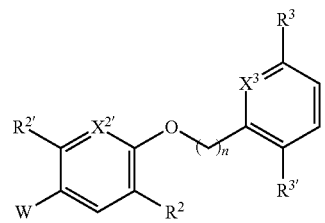

X-(ii)d-3

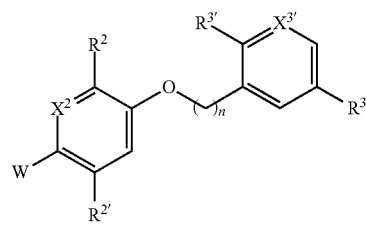

X-(ii)d-4

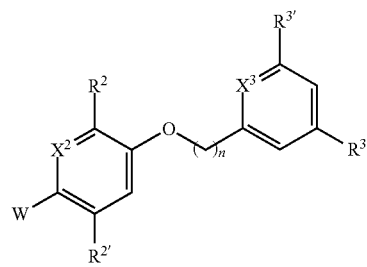

X-(ii)d-5

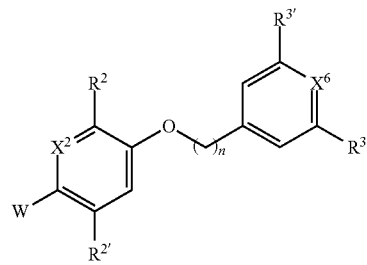

X-(ii)d-6

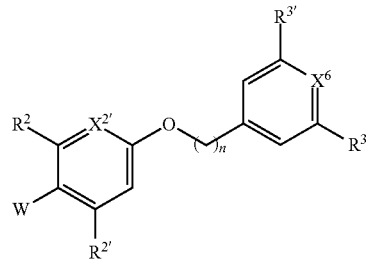

wherein W is

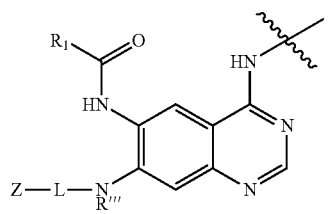

$X^2$, $X^{2'}$, $X^3$, $X^{3'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$; and n is 0 or 1; and Z, L, $R^1$, R''' are as defined above for a compound of formula X.

In some embodiments $R^a$ and $R^b$ are hydrogen.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, a compound of formula X has the following formulas

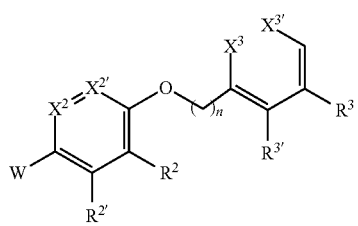
Xe-1

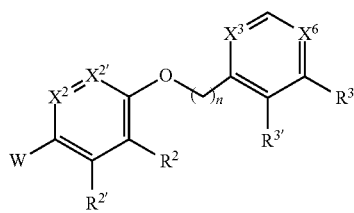
Xe-2

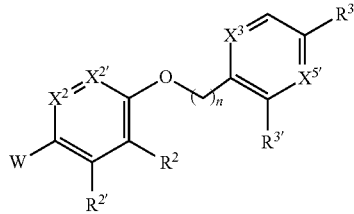
Xe-3

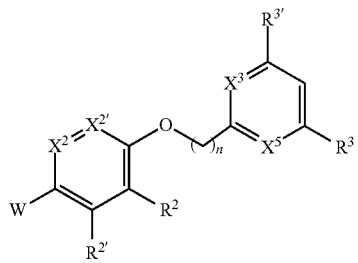
Xe-4

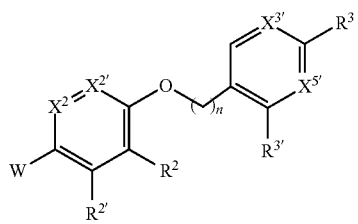
Xe-5

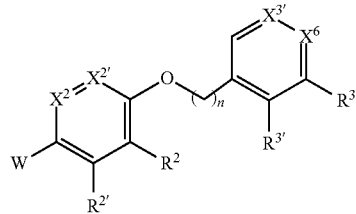
Xe-6 wherein W is

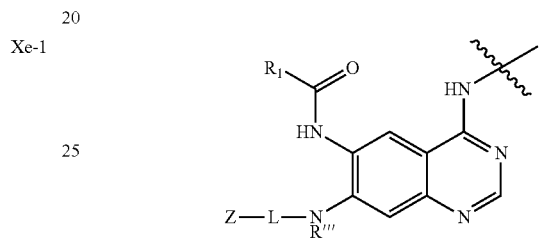

$X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a. pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring), $X^3$, $X^{3'}$, $X^5$, $X^{5'}$, $X^6$ are —CH= (i.e. a phenyl ring) or $X^3$ is —N= and $X^{3'}$, $X^5$, $X^{5'}$, $X^6$ are —CH= (i.e. a pyridine ring).

In some embodiments, L is a covalent bond, straight chain or branched $C_{1-4}$ alkyl (e.g. straight chain or branched $C_{1-4}$ alkyl).

In some embodiments, -$X^1$-$L^1$- is —NH—. In some embodiments, -$X^1$-$L^1$- is —NH—$CH_2$—. In some embodiments, compound X has the following formula

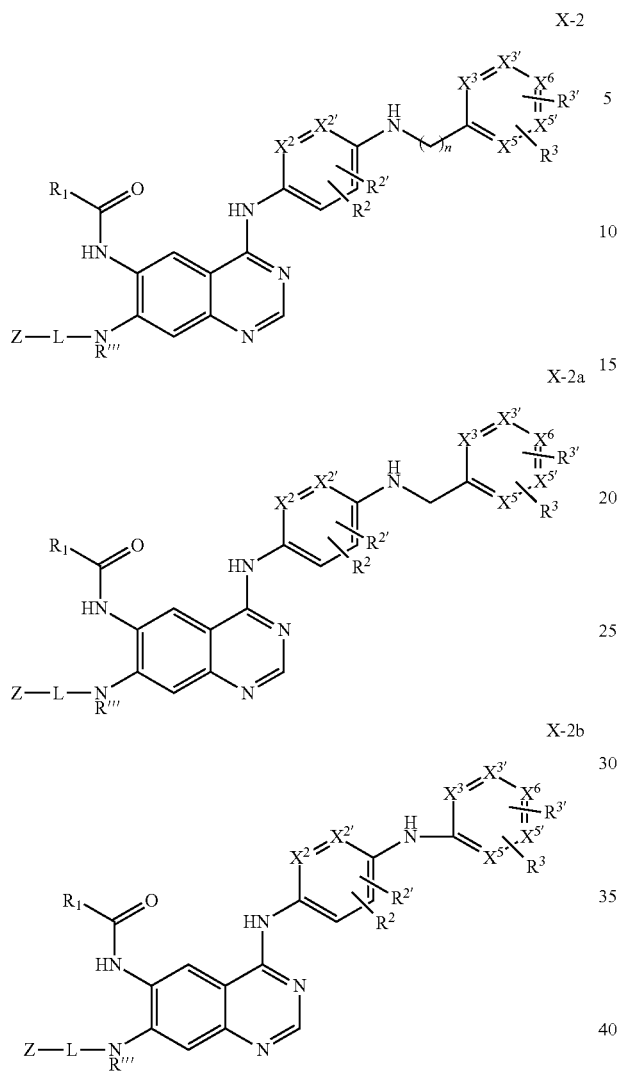

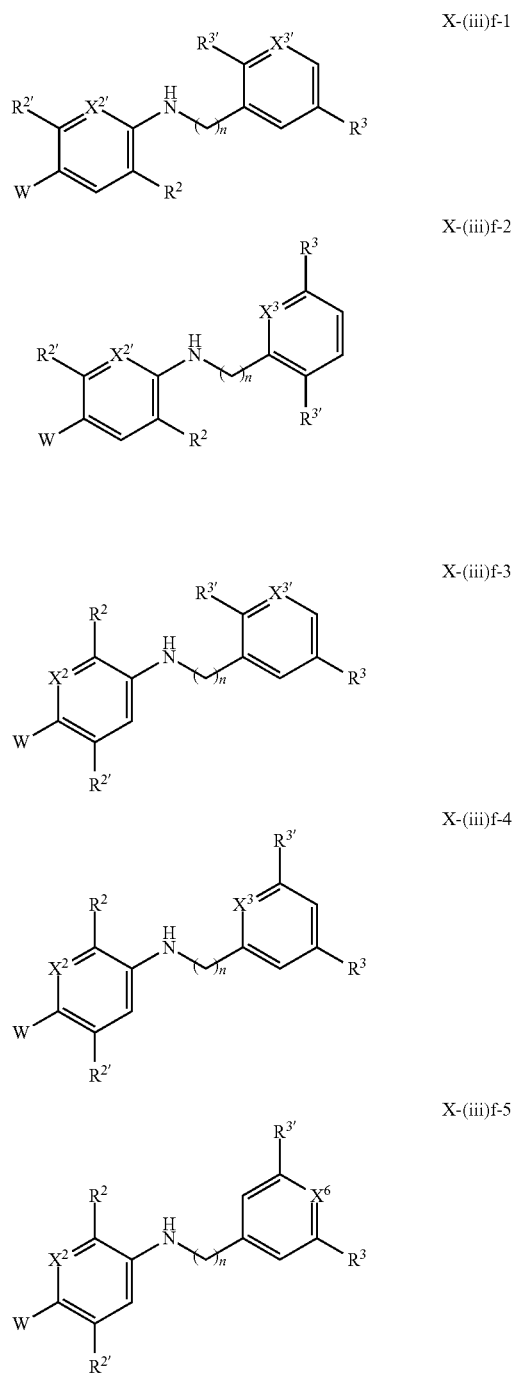

In some embodiments, $X^3$, $X^{3'}$, $X^5$, $X^{5'}$, $X^6$ are —CH═ (i.e. a phenyl ring) or $X^3$ is —N═ and $X^{3'}$, $X^5$, $X^{5'}$, $X^6$ are —CH═ (i.e. a pyridine ring). In some embodiments, L is a covalent bond, straight chain or branched $C_{1-4}$ alkyl (e.g. straight chain or branched $C_{1-4}$ alkyl).

In some embodiments, $R^2$ and $R^2$40 are independently of each other H, $C_{1-6}$ alkyl, hal (e.g. H, —$CH_3$, F, Cl). In some embodiments, $R^3$ and $R^{3'}$ are independently of each other H, $C_{1-6}$ alkyl, hal, —$CF_3$, —$OCF_3$.

In some embodiments, a compound of formula X has one of the following formulas wherein $X^2$, $X^{2'}$ and $X^3$, $X^{3'}$, $X^5$, $X^{5'}$, $X^6$ are independently of each other —N═ or —CH═; $R^2$, $R^{2'}$ and $R^3$, $R^{3'}$ are independently of each other H, $C_{1-6}$ alkyl, hal, —$CF_3$, or —$OCF_3$, and n is 0, 1, 2, 3; and Z, L, $R^1$, R''' are as defined above for a compound of formula X.

In some embodiments $R^a$ and $R^b$ are hydrogen.

In some embodiments, both $X^2$, $X^{2'}$ are —CH═ (i.e. a phenyl ring). In some embodiments, $X^2$ is —N═ and $X^{2'}$ is —CH═ or $X^{2'}$ is —N═ and $X^2$ is —CH═ (i.e. a pyridine ring). In some embodiments, both $X^2$, $X^{2'}$ are —N═ (i.e. a pyridazine ring).

In some embodiments, $X^3$, $X^{3'}$, $X^5$, $X^{5'}$, $X^6$ are —CH═ (i.e. a phenyl ring). In some embodiments, $X^3$ is —N═ and $X^{3'}$, $X^5$, $X^{5'}$, $X^6$ are —CH═ or $X^{3'}$ is —N═ and $X^3$, $X^5$, $X^{5'}$, $X^6$ are —CH═ or $X^6$ is —N═ and $X^3$, $X^{3'}$, $X^5$, $X^{5'}$ are —CH═ (i.e. a pyridine ring).

In some embodiments, both $X^3$, $X^{3'}$ are —N═ and $X^5$, $X^{5'}$, $X^6$ are —CH═ or both $X^{3'}$, $X^6$ are —N═ and $X^3$, $X^5$, $X^{5'}$ are —CH═ (i.e. a pyridazine ring). In some embodiments, both $X^3$, $X^5$ are —N═ and $X^{3'}$, $X^{5'}$, $X^6$ are —CH═ or both $X^{3'}$, $X^{5'}$ are —N═ and $X^3$, $X^5$, $X^6$ are —CH═ or both $X^3$, $X^6$ are —N═ and $X^{3'}$, $X^5$, $X^{5'}$ are —CH═ (i.e. a pyrimidine ring). In some embodiments, both $X^3$, $X^{5'}$ are —N═ and $X^{3'}$, $X^5$, $X^6$ are —CH═ (i.e. a pyrazine ring).

X-(iii)f-6

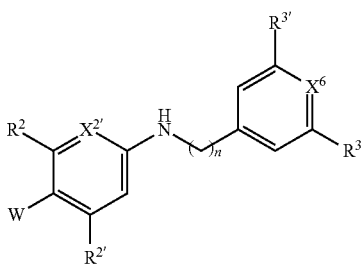

wherein W is

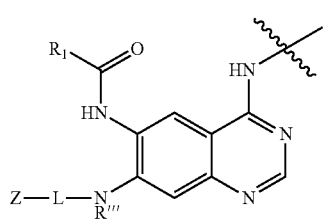

$X^2$, $X^{2'}$, $X^3$, $X^{3'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$; and n is 0 or 1; and Z, L, $R^1$, $R'''$ are as defined above for a compound of formula X.

In some embodiments $R^a$ and $R^b$ are hydrogen.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, a compound of formula X has the following formulas

X-(ii)g-1

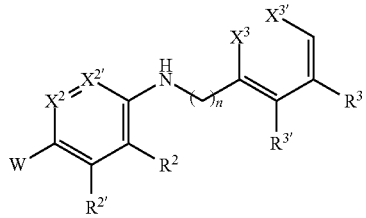

X-(ii)g-2

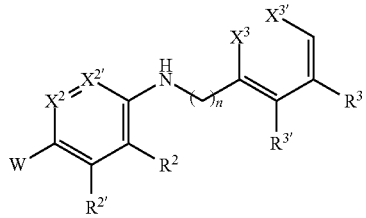

X-(ii)g-3

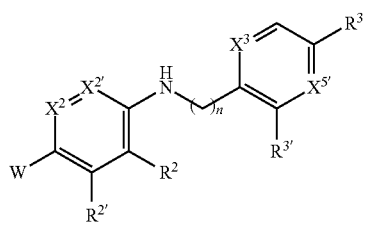

X-(ii)g-4

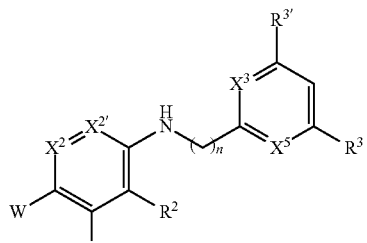

X-(ii)g-5

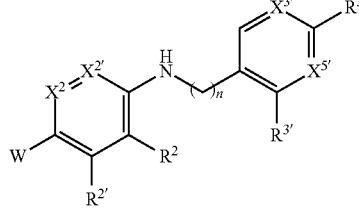

X-(ii)g-6

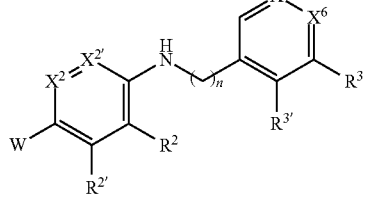

wherein W is

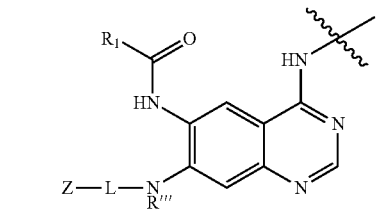

$X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1 and Z, L, $R^1$, $R'''$ are as defined above for a compound of formula X.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring). In some embodiments, $X^3$, $X^{3'}$, $X^5$, $X^{5'}$, $X^6$ are —CH= (i.e. a phenyl ring) or $X^3$ is —N= and $X^{3'}$, $X^5$, $X^{5'}$, $X^6$ are —CH= (i.e. a pyridine ring).

In some embodiments, L is a covalent bond, straight chain or branched $C_{1-4}$ alkyl (e.g. straight chain or branched $C_{1-4}$ alkyl).

In some embodiments, $R^2$ and $R^{2'}$ are independently of each other (e.g. H, hal or $C_{1-6}$ alkyl and H, hal or —$CH_3$).

In some embodiments, $R^3$ is H, hal, —$CF_3$, or —$OCF_3$.

In some embodiments, $R^{3'}$ is H, hal or $C_{1-6}$ alkyl (e.g. H, hal or —$CH_3$).

In some embodiments, $R^3$ and $R^{3'}$ are H. In some embodiments, $R^3$ and $R^{3'}$ are hal. In some embodiments, $R^3$ is hal, —$CF_3$, or —$OCF_3$ and $R^{3'}$ is H. In some embodiments, $R^3$ is H and $R^{3'}$ is hal, or $C_{1-6}$ alkyl.

In some embodiments, $R^2$ and $R^{2'}$ are H. In some embodiments, $R^2$ and $R^{2'}$ are hal. In some embodiments, $R^2$ is hal or $C_{1-6}$ alkyl and $R^{2'}$ is H. In some embodiments, $R^2$ is H and $R^{2'}$ is hal.

In some embodiments of a compound of formula X has the following formula

X-(ii)h-a-1

X-(ii)i-a-1 wherein $R^2$, $R^{2'}$ are independently of each other H, $C_{1-6}$ alkyl, hal (e.g. H, —$CH_3$, Cl); $R^3$ is H, $C_{1-6}$ alkyl, hal, —$CF_3$, —$OCF_3$; and n is 0 or 1; and Z, L, $R^1$, $R'''$ are as defined above for a compound of formula X in some embodiments, n is 0, in some embodiments, n is 1.

In some embodiments $R^a$ and $R^b$ are hydrogen.

In some embodiments, a compound of formula X has the following formulas

X-(ii)h-c-1

X-(ii)h-b-1

X-(ii)h-d-1 wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1 and Z, L, $R^1$, $R'''$ are as defined above for a compound of formula X.

In some embodiments of a compound of formula X has the following formulas

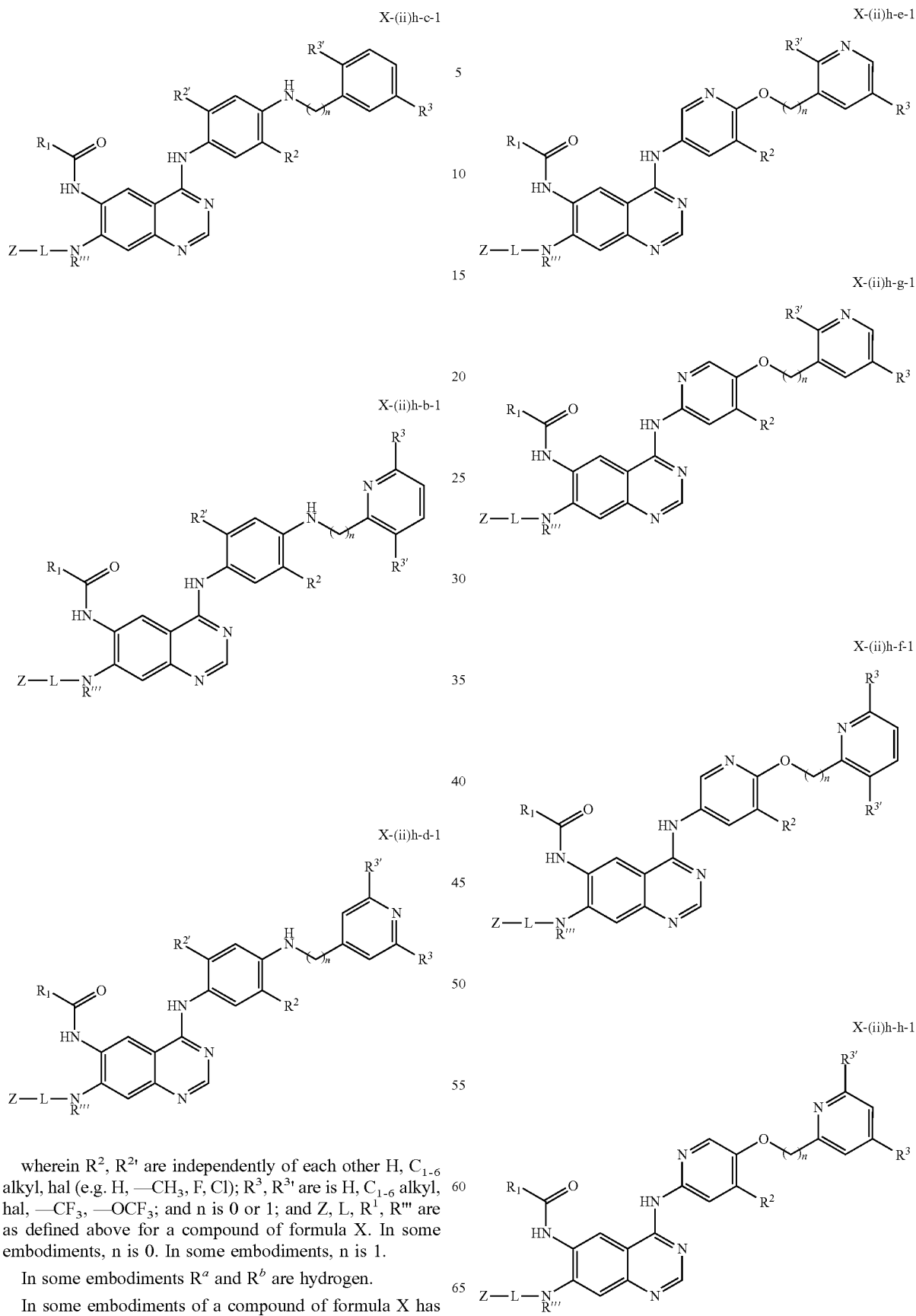

wherein $R^2$, $R^{2'}$ are independently of each other H, $C_{1-6}$ alkyl, hal (e.g. H, —$CH_3$, F, Cl); $R^3$, $R^{3'}$ are is H, $C_{1-6}$ alkyl, hal, —$CF_3$, —$OCF_3$; and n is 0 or 1; and Z, L, $R^1$, $R'''$ are as defined above for a compound of formula X. In some embodiments, n is 0. In some embodiments, n is 1.

In some embodiments $R^a$ and $R^b$ are hydrogen.

In some embodiments of a compound of formula X has the following formula

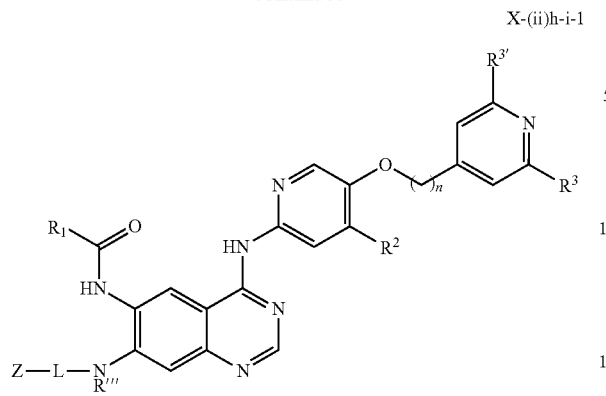

X-(ii)h-i-1

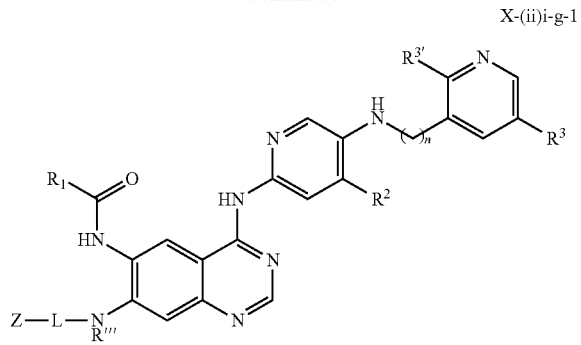

X-(ii)i-g-1

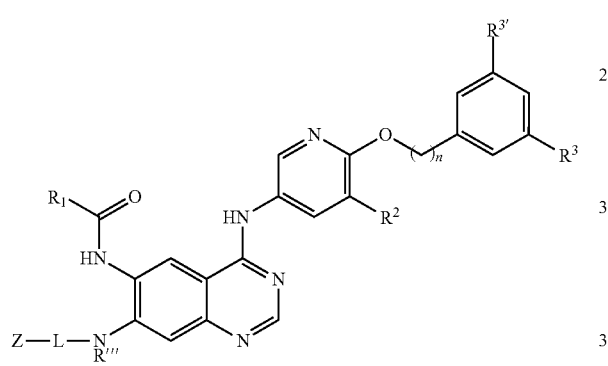

X-(ii)h-j-1

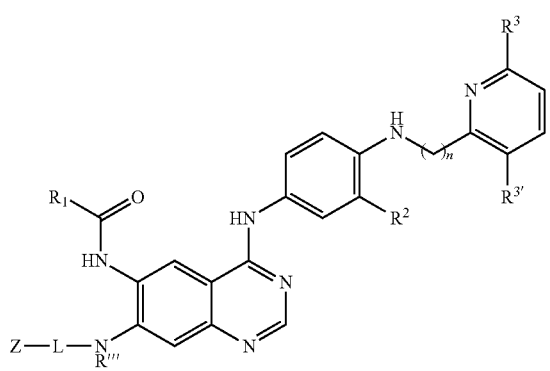

X-(ii)i-f-1 wherein $R^2$ is H, $C_{1-6}$ alkyl, hal (e.g. H, —CH$_3$, F, Cl); $R^3$, $R^{3'}$ are H, $C_{1-6}$ alkyl, hal, —CF$_3$, —OCF$_3$; and n is 0 or 1; and Z, L, $R^1$, $R'''$ are as defined above for a compound of formula X. In some embodiments $R^a$ and $R^b$ are hydrogen.

In some embodiments, n is 0. In some embodiments, n is 1.

In some embodiments of a compound of formula X has the following formulas

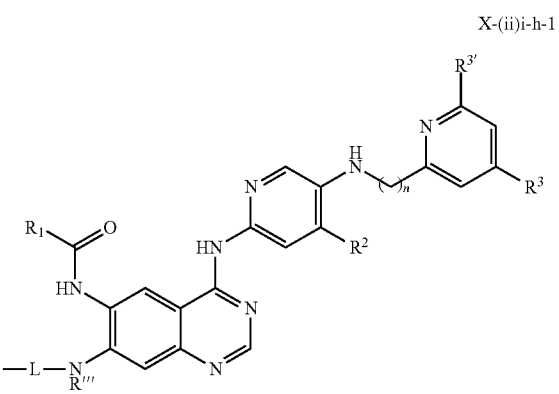

X-(ii)i-h-1

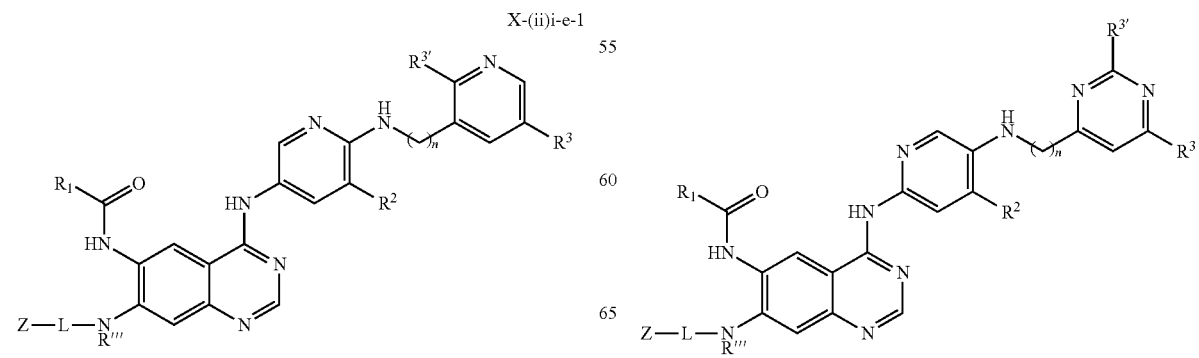

X-(ii)i-e-1

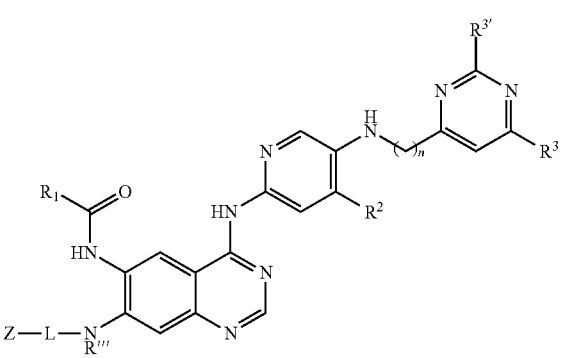

X-(ii)i-i-1

-continued

X-(ii)i-j-1

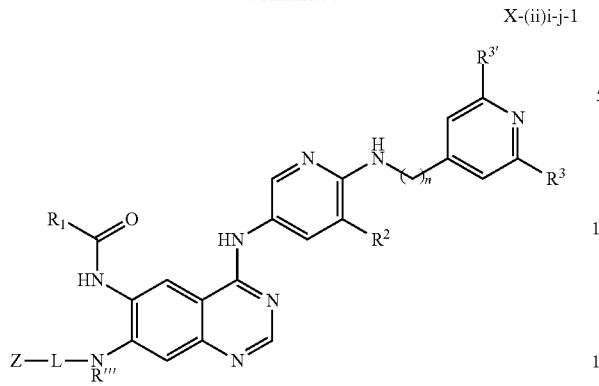

wherein R² is H, C$_{1-6}$ alkyl, hal (e.g. H, —CH$_3$, F, Cl); R³, R³' are H, C$_{1-6}$ alkyl, hal, —CF$_3$, —OCF$_3$; and n is 0 or 1; and Z, L, R¹, R''' are as defined above for a compound of formula X. In some embodiments, n is 0. In some embodiments, n is 1.

In some embodiments R$^a$ and R$^b$ are hydrogen.

In some embodiments, a compound of formula X has the following formulas

X-(ii)h-k-1

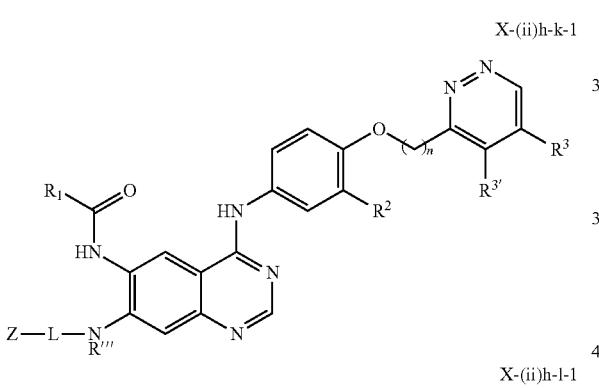

X-(ii)h-l-1

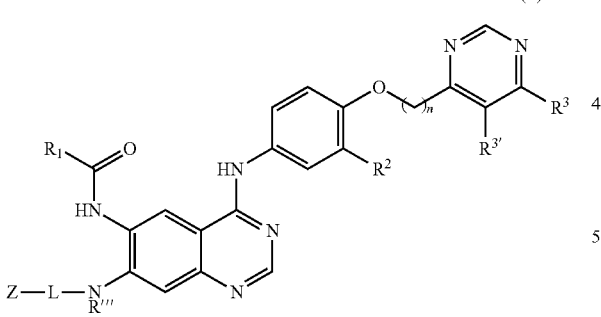

X-(ii)h-m-1

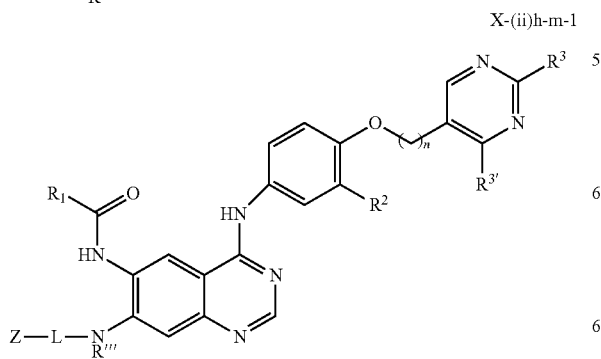

-continued

X-(ii)h-n-1

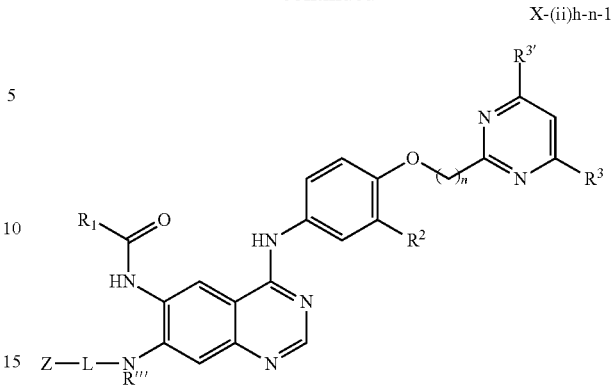

X-(ii)h-o-1

X-(ii)h-p-1

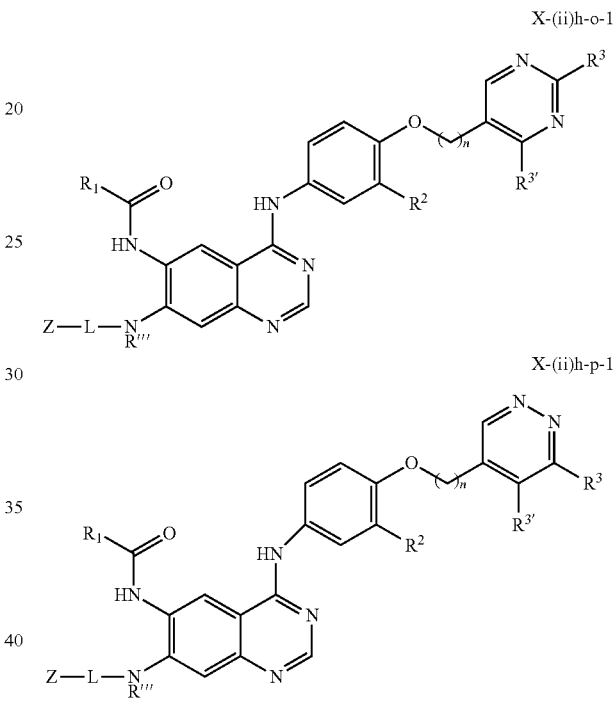

wherein R² is H, C$_{1-6}$ alkyl, hal (e.g. H, —CH$_3$, F, Cl); R³, R³' are H, C$_{1-6}$ alkyl, hal, —CF$_3$, —OCF$_3$; and n is 0 or 1; and Z, L, R¹, R''' are as defined above for a compound of formula X. In some embodiments, n is 0. In some embodiments, n is 1.

In some embodiments R$^a$ and R$^b$ are hydrogen.

In some embodiments of a compound of formula X has the following formulas

X-(ii)i-k-1

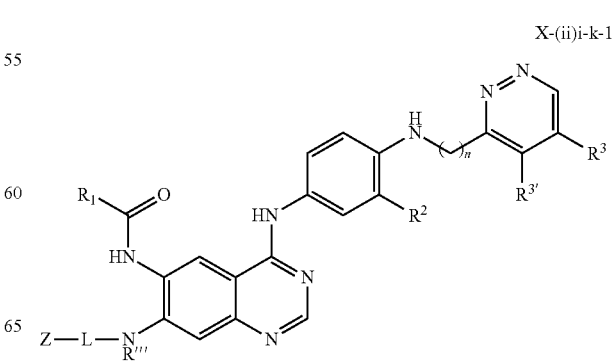

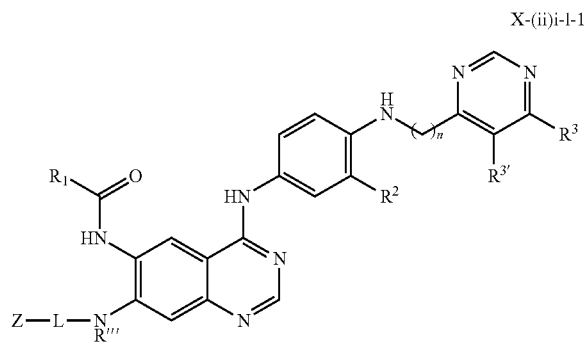

X-(ii)i-l-1

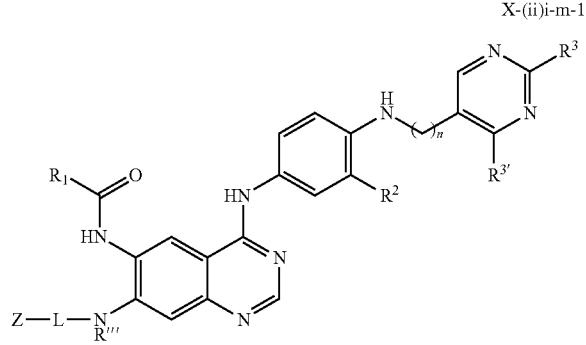

X-(ii)i-m-1

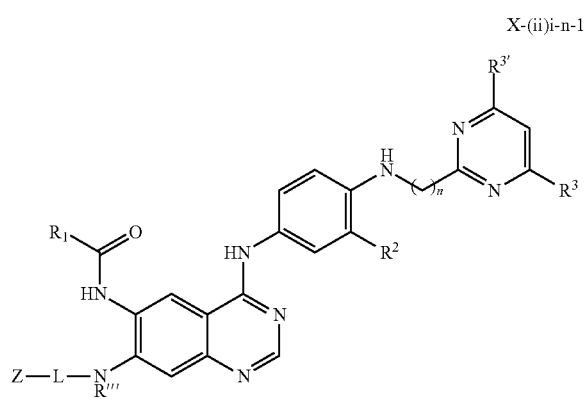

X-(ii)i-n-1

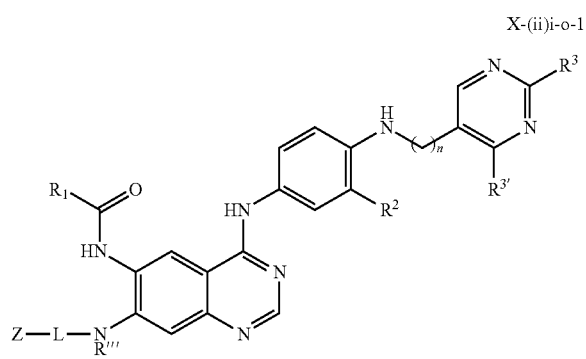

X-(ii)i-o-1

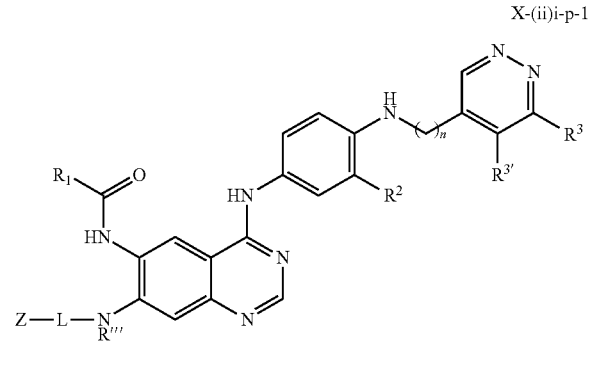

X-(ii)i-p-1 wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$, $R'''$ are as defined above for a compound of formula X. In some embodiments, n is 0. In some embodiments, n is 1.

In some embodiments $R^a$ and $R^b$ are hydrogen.

In some embodiments, $R^4$ and $R^5$ are independently of each other H, $C_{1-4}$ alkyl, cyclopropyl, or tetrahydrofuryl (e.g., $C_{1-4}$ alkyl).

In some embodiments, L is a covalent bond, straight chain or branched $C_{1-4}$ alkyl. In some embodiments, L is —$CH_2$—, —$(CH_2)_2$—, —$(CH_2)_3$—, —$(CH_2)_4$— or —$C(CH_3)_2$— or —$CH_2$—$C(CH_3)_2$—.

In some embodiments of a compound of formula X, a 3 to 6-membered heterocycloalkyl (in combination with —($NR^4R^5$)) refers to a non-aromatic or partially aromatic ring system having 3, 4, 5, or 6 ring atoms selected from C, N, O, or S (e.g. C, N, or O), the number of N atoms being 0, 1, 2 and the number of O and S atoms each being 0, 1, 2. Examples of 3 to 6-membered heterocycloalkyl groups include oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl and the like. In some embodiments, 3 to 6-membered heterocycloalkyl include 5-membered heterocycloalkyl having 1 or 2 O-atoms, such as oxiranyl, oxetanyl, tetrahydrofuranyl, dioxanyl.

In some embodiments of a compound of formula X, a 3 to 6-membered heteroaryl (in combination with —($NR^6R^7$) or —($CHR^6R^7$)) refers to a (fully) aromatic ring system having 3, 4, 5, or 6 ring atoms (e.g. 5 ring atoms), selected from C, N, O, or S (e.g. C, N, or O, and C or N, with the number of N atoms being 0, 1, 2 or 3 and the number of O and S atoms each being 0, 1 or 2). Examples of "heteroaryl" include furyl, imidazolyl, isoxazolyl, oxazolyl, pyrazinyl, pyrazolyl (pyrazyl), pyridazinyl, pyridinyl, pyrimidinyl, pyrrolyl, thiazolyl, thienyl, and the like. In some embodiments, examples of "heteroaryl" include pyrrolyl, imidazolyl.

In some embodiments of a compound of formula X, a 3 to 9-membered heterocycloalkyl (in combination with —($NR^6R^7$) or —($CHR^6R^7$)) refers to a non-aromatic or partially aromatic ring system having 3 to 9 ring atoms selected from C, N, O, or S (e.g. C, N, or O), the number of N atoms being 0, 1, 2 or 3 and the number of O and S atoms each being 0, 1 or 2. Examples of a 3 to 9-membered heterocycloalkyl (in combination with —($NR^6R^7$) or —($CHR^6R^7$)) include monocycles such as oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl, oxepanyl, thiepanyl, azepanyl, diazepanyl, oxazepanyl (e.g. azetidinyl, pyrrolidinyl, piperidinyl, piperazinyl, morpholinyl, azepanyl); fused ring systems, such as 3-azabicyclo[3.1.0]hexyl, 3-azabicyclo[3.3.0]octyl, 3,7-diazabicyclo[3.3.0]octyl, 3-aza-7-oxabicyclo[3.3.0]octyl, 2,6-diazabicyclo[3.3.0]octyl, 2,7-diazabicyclo[3.3.0]octyl, 2,8-diazabicyclo[4.3.0]nonyl, 3-oxa-8-azabicyclo[4.3.0]nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4.3.0]nonyl, and the like; bridged ring systems such as bicyclo[3.3.1]nonanyl, bicyclo[3.2.1]octanyl, bicyclo[2.2.2]octanyl, bicyclo[3.1.1]heptanyl, bicyclo[2.2.1]heptanyl (e.g. bicyclo[3.2.1]octanyl, bicyclo[2.2.1]heptanyl), having one or two heteroatoms selected from N and O; spiro ring systems such as spiropentanyl, spiro[2.3]hexanyl spiro[3.3]heptanyl, spiro[3.4]octanyl, spiro[4.4]nonanyl, spiro[3.5]nonanyl, spiro[4.5]decanyl (e.g. spiro[3.3]heptanyl, spiro[4.4]nonanyl), having one or two heteroatoms selected from N and O (e.g. diazaspiro[3.3]heptanyl, oxa-azaspiro[3.3]heptanyl, diazaspiro[4.4]nonanyl, oxa-azaspiro[4.4]nonanyl).

In some embodiments, Z is $-(NR^4R^5)$, wherein $R^4$ and $R^5$ are independently of each other H, $C_{1-6}$ alkyl, cylopropyl, cylobutyl, 3 to 6-membered heterocycloalkyl containing 0, 1, or 2 N-atoms and 0, 1, or 2 O-atoms, or $-(NR^6R^7)$, $-(CHR^6R^7)$, wherein $R^6$ and $R^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments, $-(NR^6R^7)$ ring systems include

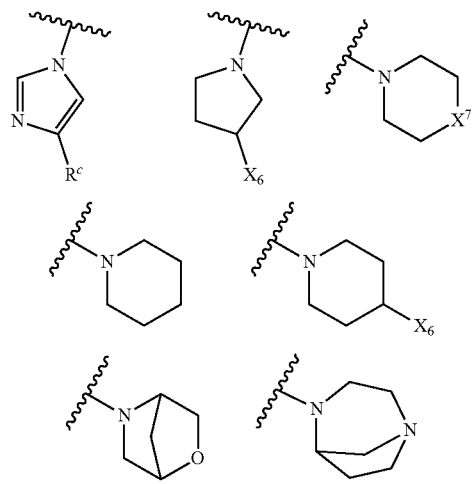

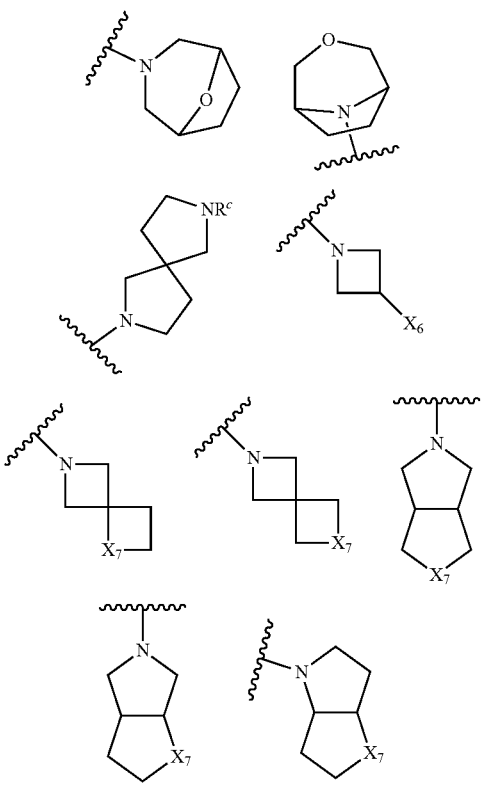

wherein $R^c$ is H, $C_{1-4}$ alkyl, oxetane; $X^6$ is H, —CH$_3$, —OH, —OCH$_3$, —OCF$_3$, —N(CH$_3$)$_2$, F, Cl; $X^7$ is —O—, —NH— or —N(CH$_3$)—, —SO$_2$.

In some embodiments, —(CHR$^6$R$^7$) ring systems include

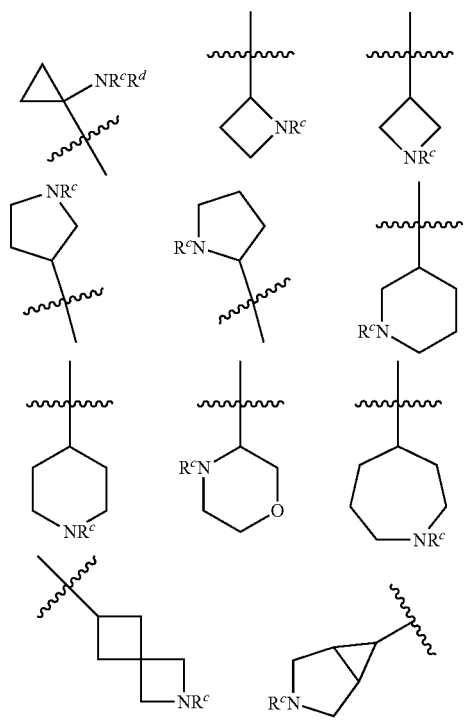

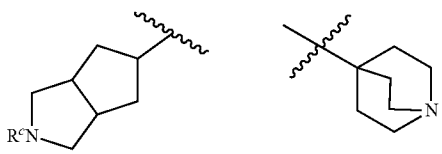

wherein $R^c$ is H, $C_{1-4}$ alkyl, oxetane, and $R^d$ is H, $C_{1-4}$ alkyl.

In some embodiments, examples of 3 to 9-membered heterocycloalkyl are

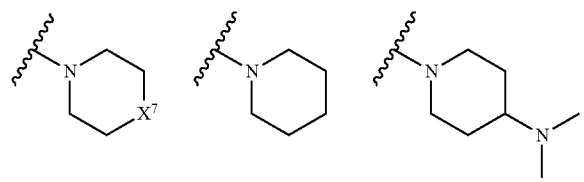

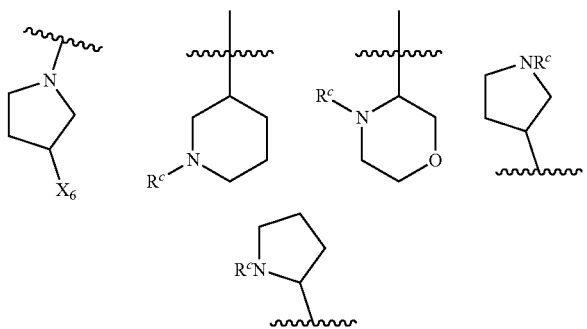

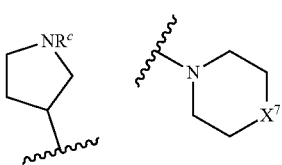

wherein $R^c$ is H, $C_{1-4}$ alkyl, oxetane (e.g. H, —CH$_3$); $X^6$ is H, —CH$_3$, —OH, —OCH$_3$, —N(CH$_3$)$_2$, F, Cl, and $X^7$ is —O—, —NH— or —N(CH$_3$)—, —SO$_2$ (e.g. O).

In some embodiments, the —(CR$^6$R$^7$) and —(NR$^6$R$^7$) ring systems of Z is selected from wherein $R^c$ is H, $C_{1-4}$ alkyl, oxetane (e.g. H, —CH$_3$), and $X^7$ is —O—, —NH— or —N((H$_3$)—, —SO$_2$ (e.g. —O—).

In some embodiments, compound of formula X has the formula XI or XII

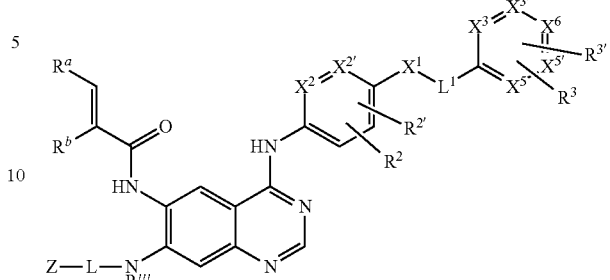

XI

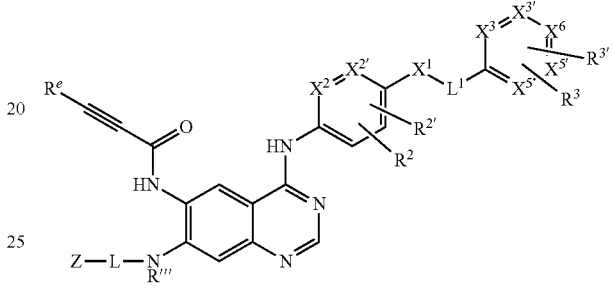

XII wherein $X^1$ is —O—, —CH$_2$—, —NH—, —S—; $X^2$, $X^{2'}$, $X^3$, $X^{3'}$, $X^5$, $X^{5'}$, $X^6$ are independently of each other —N=, —CH=;

$L^1$ is a covalent bond or straight chain or branched $C_{1-3}$alkyl, is unsubstituted or substituted with hal, $R^2$, $R^{2'}$, $R^3$, $R^{3'}$ are independently of each other H, $C_{1-6}$ alkyl, hal, —CF$_3$, —OCF$_3$;

L is a covalent bond, straight chain or branched $C_{1-4}$ alkyl or

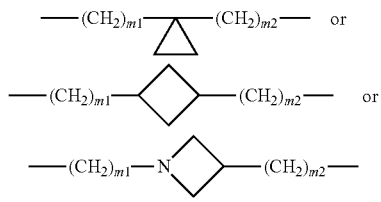

wherein m1, m2 are independently of each other 0, 1, 2, 3, or 4;

R''' is H or —CH$_3$;

Z is —(NR$^4$R$^5$), wherein R$^4$ and R$^5$ are independently of each other H, $C_{1-6}$ alkyl, cyclopropyl, cylobutyl, 3 to 6-membered heterocycloalkyl, or —(NR$^6$R$^7$), —(CHR$^6$R$^7$), wherein R$^6$ and R$^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl;

$R^a$, $R^b$ are independently of each other H, hal, or —CH$_2$—O—CH$_3$ (e.g. H), and $R_e$ is H or methyl.

In some embodiments $R^a$ and $R^b$ are hydrogen.

In some embodiments, $L^1$ is straight chain or branched $C_{1-3}$alkyl, which is unsubstituted or substituted with hal. In some embodiments, $L^1$ is not a covalent bond.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring). In some embodiments, $X^3$, $X^{3'}$, $X^5$, $X^{5'}$, $X^6$ are —CH= (i.e. a phenyl ring) or $X^3$ is —N= and $X^{3'}$, $X^5$, $X^{5'}$, $X^6$ are —CH= (i.e. a pyridine ring).

In some embodiments, L is a covalent bond, straight chain or branched $C_{1-4}$ alkyl (e.g. straight chain or branched $C_{1-4}$ alkyl).

In some embodiments, $R^2$ and $R^{2'}$ are independently of each other H, $C_{1-6}$ alkyl, hal, (e.g. H, —$CH_3$, F, Cl). In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —$CF_3$, —$OCF_3$. In some embodiments, $R^3$ is H, $C_{1-6}$ alkyl, hal, —$CF_3$, —$OCF_3$ and $R^{3'}$ is H, hal.

In some embodiments, $R^4$ and $R^5$ are independently of each other H, $C_{1-4}$ alkyl, cyclopropyl, tetrahydrofuryl (e.g. $C_{1-4}$ alkyl).

In some embodiments, L is a covalent bond, straight chain or branched $C_{1-4}$ alkyl. In some embodiments, L is —$CH_2$—, —$(CH_2)_2$—, —$(CH_2)_3$—, —$(CH_2)_4$— or —$C(CH_3)_2$— or —$CH_2$—$C(CH_3)_2$—.

In some embodiments, Z is —$(NR^4R^5)$, wherein $R^4$ and $R^5$ are independently of each other H, $C_{1-6}$ alkyl, cyclopropyl, cylobutyl, 3 to 6-membered heterocycloalkyl containing 0, 1, or 2 N-atoms and 0, 1, or 2 O-atoms, or —$(NR^6R^7)$, —$(CHR^6R^7)$, wherein $R^6$ and $R^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments, $R^4$ and $R^5$ are independently of each other H, $C_{1-4}$ alkyl, cyclopropyl, or tetrahydrofuryl (e.g., methyl).

In some embodiments, —$(NR^6R^7)$ ring systems include

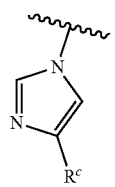 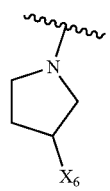 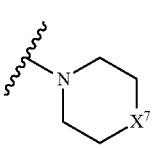

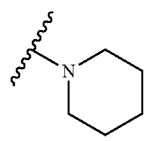 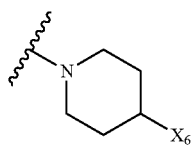

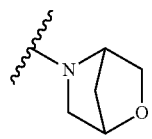 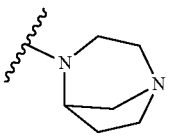

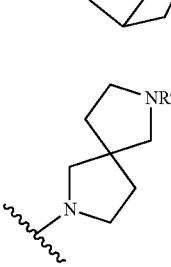 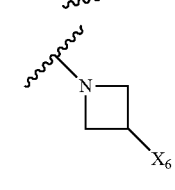

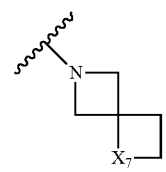 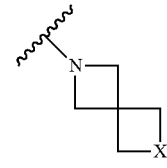 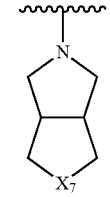

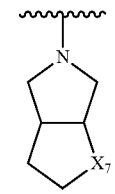 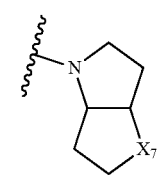

wherein $R^c$ is H, $C_{1-4}$ alkyl, oxetane; $X^6$ is H, —$CH_3$, —OH, —$OCH_3$, —$OCF_3$, —$N(CH_3)_2$, F, Cl; $X^7$ is —O—, —NH— or —$N(CH_3)$—, —$SO_2$,

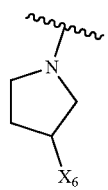 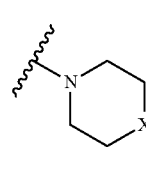 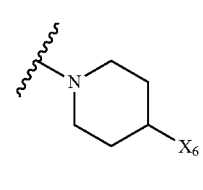

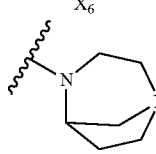 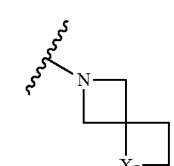 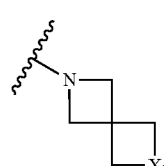

-continued

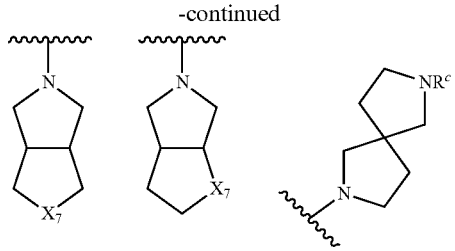

wherein $R^c$ is H, $C_{1-4}$ alkyl, oxetane (e.g. H, —CH$_3$); $X^6$ is H, —CH$_3$, —OH, —OCH$_2$, —OCF$_3$, —N(CH$_3$)$_2$, F, Cl, and $X^7$ is —O—, —NH— or —N(CH$_3$)—, —SO$_2$.

In some embodiments, —(CR$^6$R$^7$) ring systems include

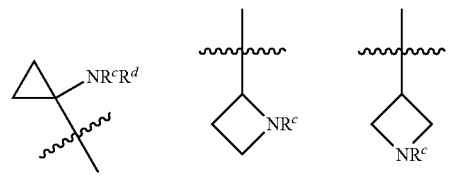

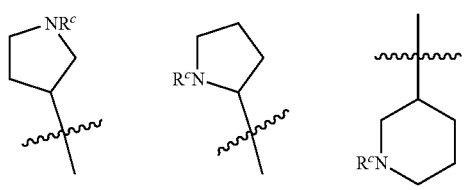

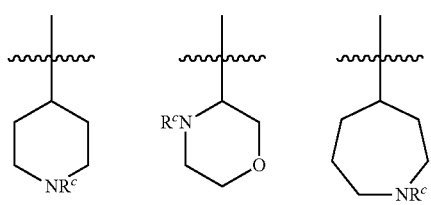

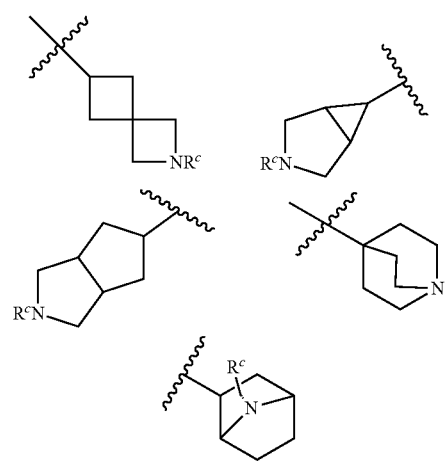

wherein $R^c$ is H, $C_{1-4}$ alkyl, oxetane, and $R^d$ is H, $C_{1-4}$ alkyl.

In some embodiments, 3 to 9-membered heterocycloalkyl are

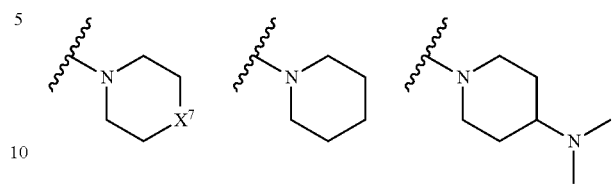

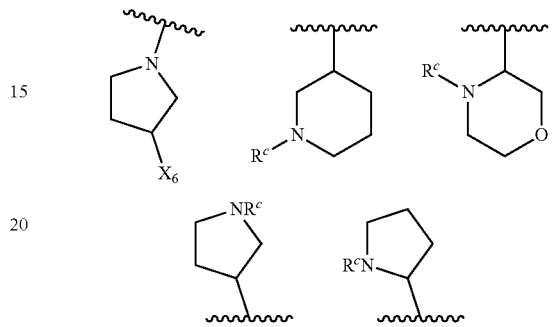

wherein $R^c$ is H, $C_{1-4}$ alkyl, oxetane (e.g. H, —CH$_3$); $X^6$ is H, —CH$_3$, —OH, —OCH$_3$, OCF$_3$, —N(CH$_3$)$_2$, F, Cl, and $X^7$ is —O—, —NH— or —N(CH$_3$)—, —SO$_2$ (e.g. —O—).

In some embodiments, the —(CR$^6$R$^7$) and —(NR$^6$R$^7$) ring systems of Z are selected from

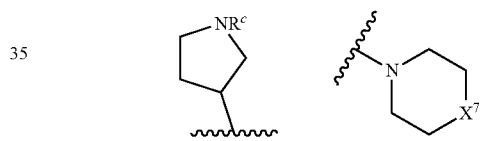

wherein $R^c$ is H, $C_{1-4}$ alkyl, oxetane (e.g. H, —CH$_3$), and $X^7$ is —O—, —NH— or —N(CH$_3$)—, —SO$_2$, (e.g. —O—).

In some embodiments, $X^1$ is —O—. In some embodiments, $X^1$ is —CH$_2$—. In some embodiments, $X^1$ is —NH—. In some embodiments, $X^1$ is —S—. In some embodiments, $L^1$ is a covalent bond. In some embodiments, $L^1$ is —CH$_2$— or —CH(CH$_3$)— or —CH(hal)-. In some embodiments, $L^1$ is —CH$_2$—CH$_2$— or —CH$_2$CH(CH$_3$)— or —CH$_2$—CH(hal)-.

In some embodiments, linker combinations -$X^1$-$L^1$- include —O—, —CH$_2$—, —O—CH$_2$—, —NH—CH$_2$—, —S—CH$_2$—, —CH$_2$—CH$_2$—, —O—CH(CH$_3$)—, —CH$_2$—CH(CH$_3$)—, —NH—CH(CH$_3$)—, —S—CH(CH$_3$)—, —O—CH(hal)-, CH$_2$—CH(hal)-, —NH—CH(hal)-, —S—CH(hal)- (e.g. —O—, —CH$_2$—, —O—CH$_2$—, —NH—CH$_2$—, —CH$_2$—CH$_2$—, —O—CH(CH$_3$)—, —CH$_2$—CH(CH$_3$)—, —O—CH(hal)-, or —CH$_2$—CH(hal)- and —O—, —CH$_2$—, —O—CH$_2$—, —NH—CH$_2$—, —CH$_2$—CH$_2$—).

In some embodiments, -$X^1$-$L^1$- is —O—, In some embodiments, -$X^1$-$L^1$- is —O—CH$_2$—. In some embodiments, -$X^1$-$L^1$- is —NH—. In some embodiments, -$X^1$-$L^1$- is —NH—CH$_2$—.

In some embodiments, the compound of formula XI or XII has the formula XI-1, XII-1, or XI-2, XII-2

XI-1

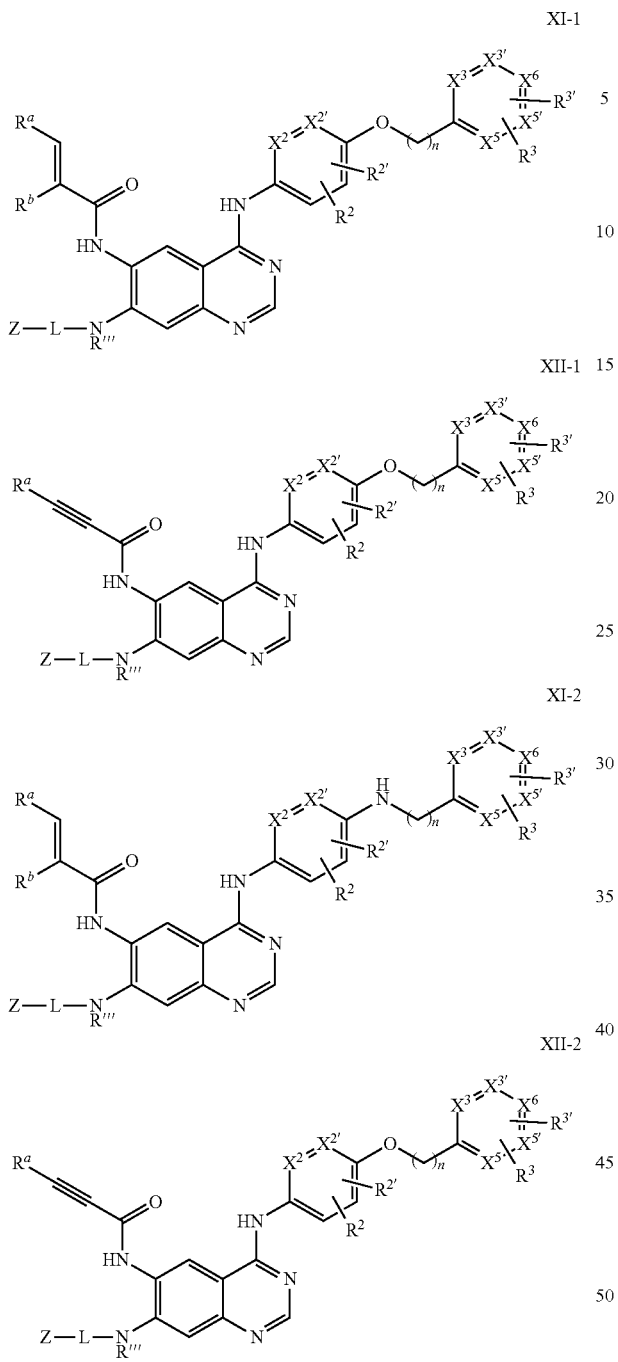

XII-1

XI-2

XII-2 wherein
$X^2$, $X^{2'}$, $X^3$, $X^{3'}$, $X^5$, $X^{5'}$, $X^6$ are independently of each other —N=, —CH=;

$R^2$, $R^{2'}$, $R^3$, $R^{3'}$ are independently of each other H, $C_{1-6}$ alkyl, hal, —$CF_3$, —$OCF_3$;

L is a covalent bond, straight chain or branched $C_{1-4}$ alkyl or

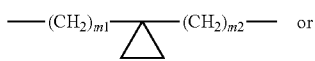 or

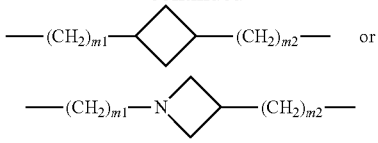

wherein m1, m2 are independently of each other 0, 1, 2, 3, or 4;

R''' is H or —$CH_3$;

Z is —($NR^4R^5$), wherein $R^4$ and $R^5$ are independently of each other H, $C_{1-6}$ alkyl, cyclopropyl, cylobutyl, 3 to 6-membered heterocycloalkyl, or —($NR^6R^7$), —($CHR^6R^7$), wherein $R^6$ and $R^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R'', wherein R', R'' are independently of each other H or -$C_{1-4}$;

$R^a$, $R^b$ are independently of each other H, hal, or —$CH_2$—O—$CH_3$ (e.g. H); $R_e$ is H or methyl and n is 0 or 1.

In some embodiments $R^a$ and $R^b$ are hydrogen.

In some embodiments, n is 0. In some embodiments, n is 1.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring). In some embodiments, $X^2$ and $X^{2'}$ are —CH= (i.e. a phenyl ring). In some embodiments $X^3$, $X^{3'}$, $X^5$, $X^{5'}$, $X^6$ are —CH= (i.e. a phenyl ring) or $X^3$ is —N= and $X^{3'}$, $X^5$, $X^{5'}$, $X^6$ are —CH= (i.e. a pyridine ring).

In some embodiments, L is a covalent bond, straight chain or branched $C_{1-4}$ alkyl (e.g. straight chain or branched $C_{1-4}$ alkyl).

In some embodiments, $R^2$ and $R^{2'}$ are independently of each other H, $C_{1-6}$ alkyl, hal, (e.g. H, —$CH_3$, F, Cl). In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —$CF_3$, —$OCF_3$. In some embodiments, $R^3$ is H, $C_{1-6}$ alkyl, hal, —$CF_3$, —$OCF_3$ and $R^{3'}$ is H.

In some embodiments, $R^2$ and $R^{2'}$ are H and $R^3$ is H, $C_{1-6}$ alkyl, hal, —$CF_3$, —$OCF_3$ and $R^{3'}$ is H, hal; or $R^2$ and $R^{2'}$ are hal and $R^3$ is H, $C_{1-6}$ alkyl, hal, —$CF_3$, —$OCF_3$ and $R^{3'}$ is H, hal; or $R^2$ is hal and $R^{2'}$ is H and $R^3$ is H, $C_{1-6}$ alkyl, hal, —$CF_3$, —$OCF_3$ and $R^{3'}$ is H.

In some embodiments, the compound of formula XI-1, XI-2 has one of the following formulas XI-1-(II)d-1
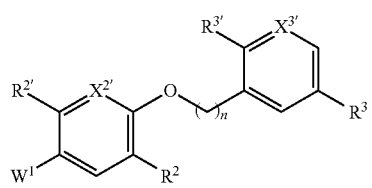
XI-1-(II)d-2
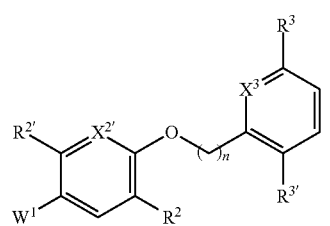
XI-1-(ii)d-3
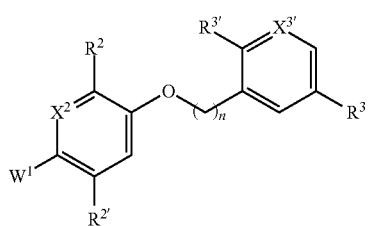
XI-1-(ii)d-4
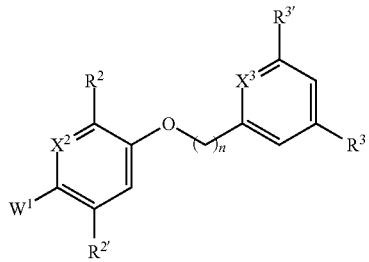
XI-1-(ii)d-5
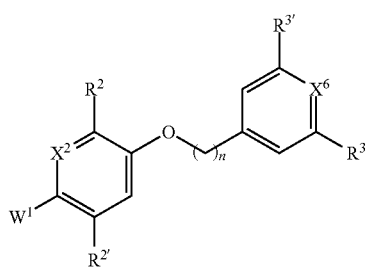
XI-1-(ii)d-6
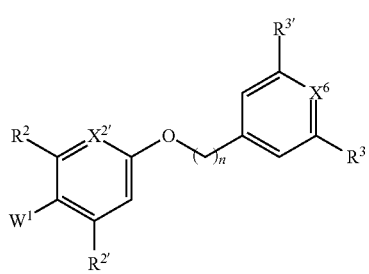
and $W^1$ is
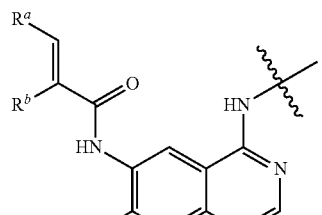
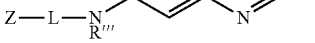
or
XII-1-(ii)d-1
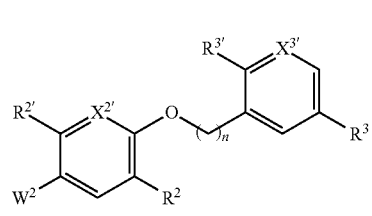
XII-1-(ii)d-2
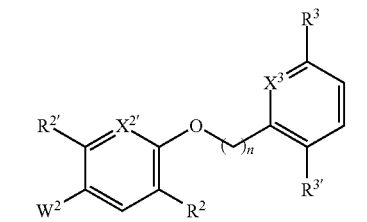
XII-1-(ii)d-3
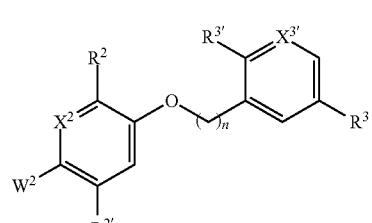
XII-1-(ii)d-4
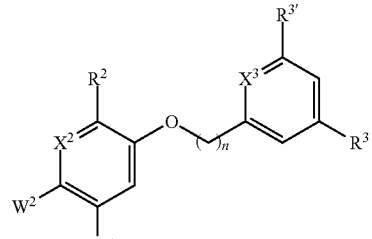
XII-1-(ii)d-5
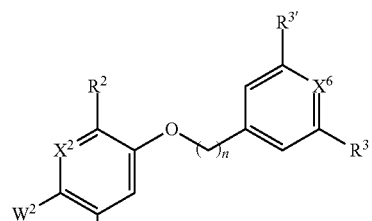

-continued

XII-1-(ii)d-6

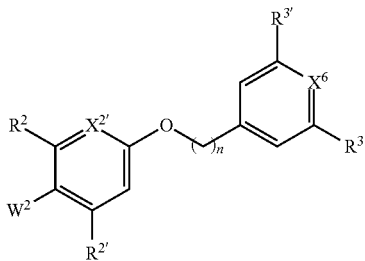

and W² is

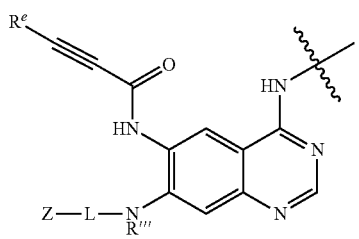

X², X²', X³, X³', X⁵, X⁵', X⁶ are independently of each other —N= or —CH=; and R², R²', R³, R³' are independently of each other H, $C_{1-6}$ alkyl, hal, —$CF_3$, or —$OCF_3$; and Z, L, R''', $R^a$, $R^b$, $R^e$ are as defined above for a compound of formula XI or XII (or XI-1, XII-1).

In some embodiments $R^a$ and $R^b$ are hydrogen.

In some embodiments, X² and X²' are —CH= (i.e. a phenyl ring) and X³, X³' and X⁶ are —CH= (i.e. a phenyl ring).

In some embodiments, X² and X²' are —CH= (i.e. a phenyl ring) and X³, X³' and X⁶ are —N= (i.e. a pyridine ring).

In some embodiments, X² and X²' are —N= (i.e. a pyridine ring) and X³, X³' and X⁶ are —CH= (i.e. a phenyl ring).

In some embodiments, X² and X²' a —N= (i.e. a pyridine ring) and X³, X³' and X⁶ are —N= (i.e. a pyridine ring), In some embodiments, a compound of formula XI-1, XII-1 has one of the following formulas XI-1-(ii)e-1

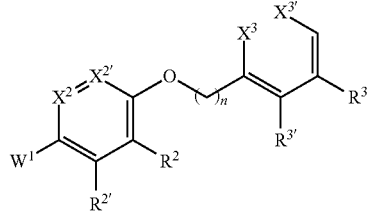

XI-1-(ii)e-2

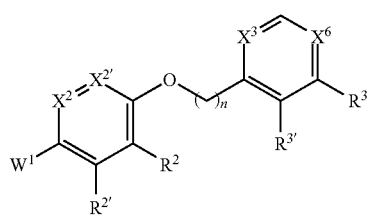

-continued

XI-1-(ii)e-3

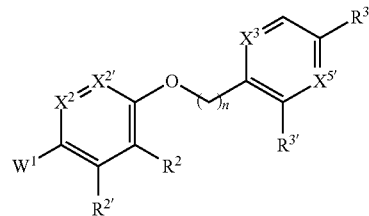

XI-1-(ii)e-4

XI-1-(ii)e-5

XI-1-(ii)e-6 and W¹ is

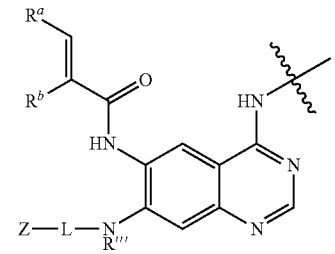

XII-1-(ii)e-1

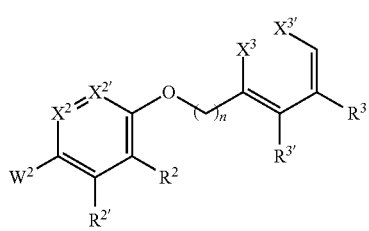

-continued

XII-1-(ii)e-2
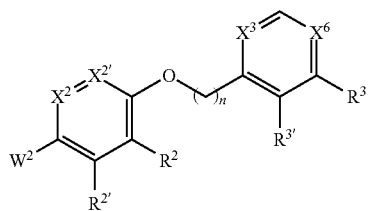

XII-1-(ii)e-3
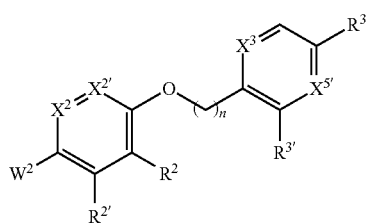

XII-1-(ii)e-4
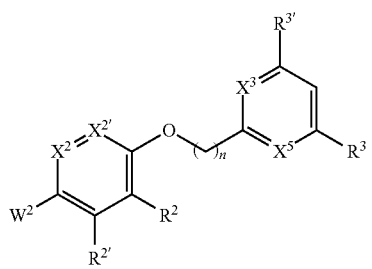

XII-1-(ii)e-5
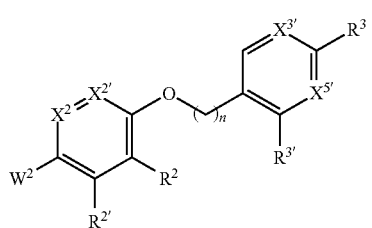

XII-1-(ii)e-6
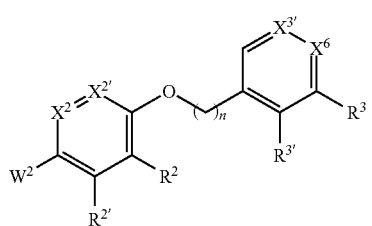

and $W^2$ is

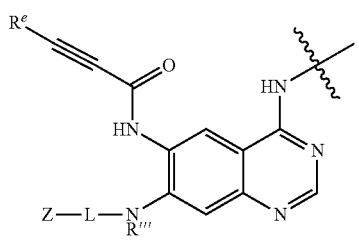

wherein $X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1, and Z, L, R''', $R^a$, $R^b$, $R^e$ are as defined above for a compound of formula XI or XII (or XI-1, XII-1).

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, a compound of formula XI-2, XII-2 has one of the following formulas XI-2-(ii)f-1
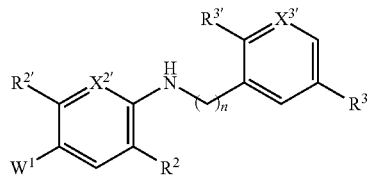

XI-2-(ii)f-2
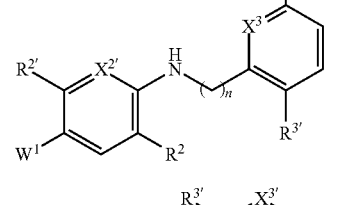

XI-2-(ii)f-3
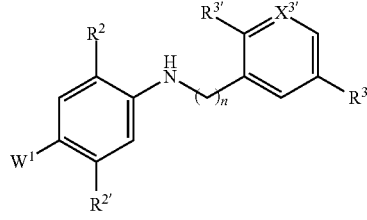

XI-2-(ii)f-4
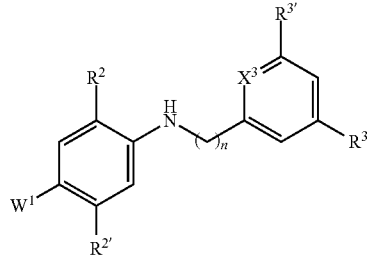

-continued

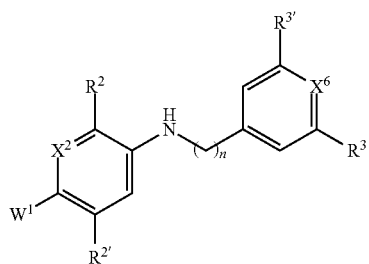
XI-2-(ii)f-5

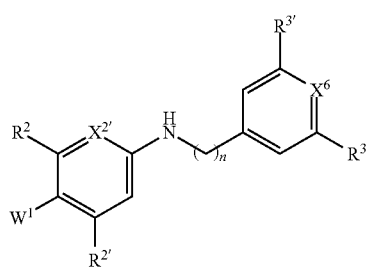
XI-2-(ii)f-6 and W¹ is

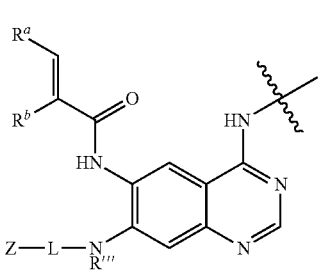

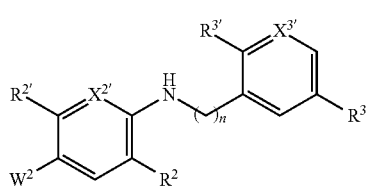
XII-2-(ii)f-1

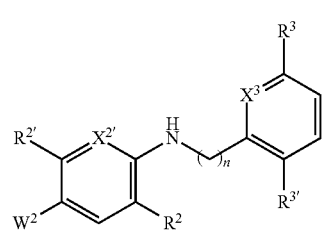
XII-2-(ii)f-2

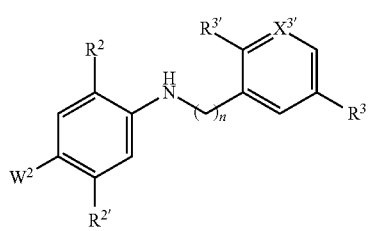
XII-2-(ii)f-3

-continued

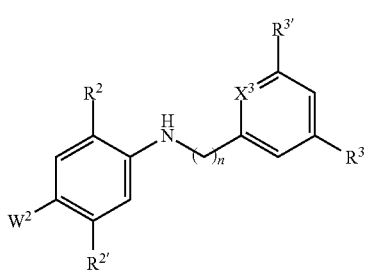
XII-2-(ii)f-4

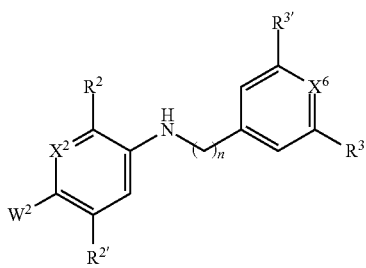
XII-2-(ii)f-5

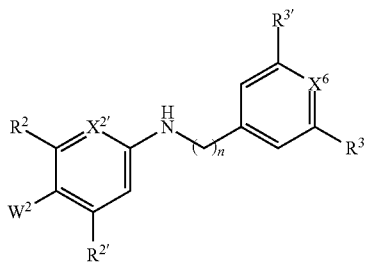
XII-2-(ii)f-6 and W² is

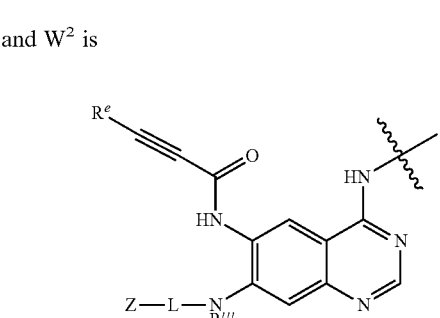

wherein $X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$; and Z, L, R''', $R^a$, $R^b$, $R^e$ are as defined above for a compound of formula XI or XII (or XI-1, XII-1).

In some embodiments $R^a$ and $R^b$ are hydrogen.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, a compound of formula XI-2, XII-2 has one of the following formulas XI-2-(ii)g-1
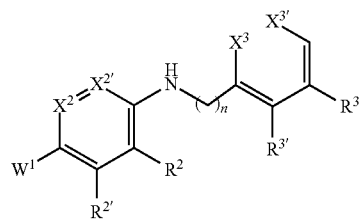
XI-2-(ii)g-2
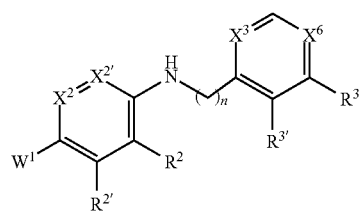
XI-2-(ii)g-3
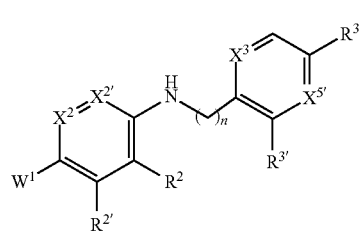
XI-2-(ii)g-4
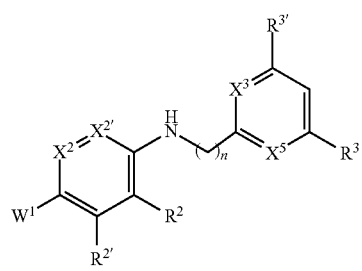
XI-2-(ii)g-5
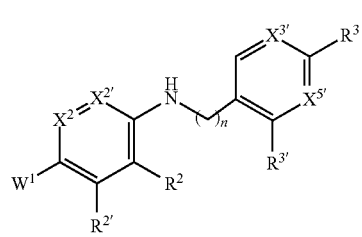
XI-2-(ii)g-6
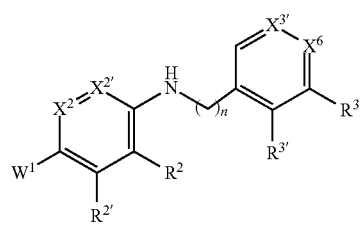
and $W^1$ is
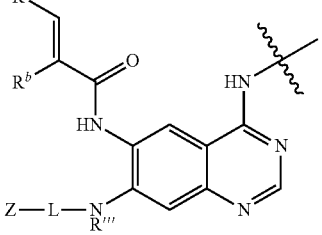
XII-2-(ii)g-1
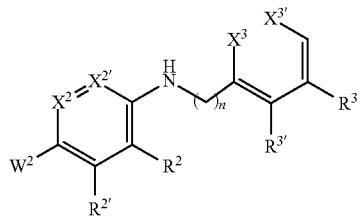
XII-2-(ii)g-2
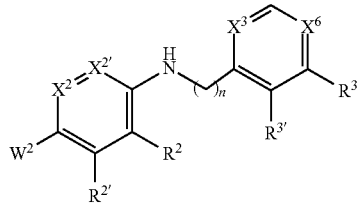
XII-2-(ii)g-3
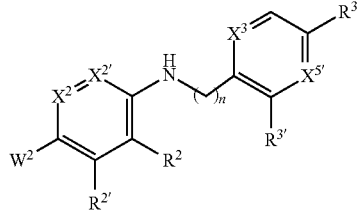
XII-2-(ii)g-4
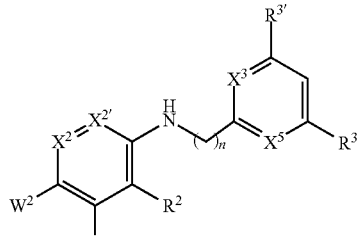
XII-2-(ii)g-5
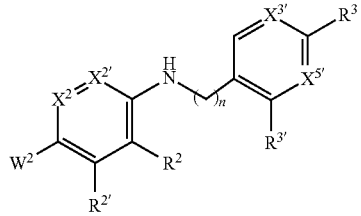
XII-2-(ii)g-6
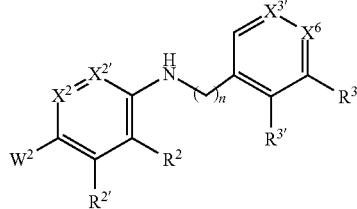

and W² is

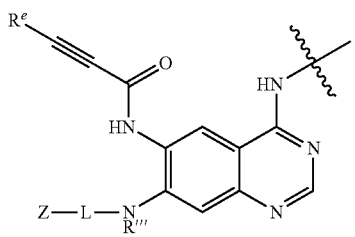

wherein $X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —CF₃, or —OCF₃, n is 0 or 1; and Z, L, R''', $R^a$, $R^b$, $R^e$ are as defined above for a compound of formula XI or XII (or XI-1, XII-1).

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $R^2$ and $R^{2'}$ are independently of each other (e.g. H, hal or $C_{1-6}$ alkyl and H, hal or —CH₃).

In some embodiments, $R^3$ is H, hal, —CF₃, or —OCF₃.

In some embodiments, $R^{3'}$ is H, hal or $C_{1-6}$ alkyl (e.g. H, hal or —CH₃).

In some embodiments, $R^3$ and $R^{3'}$ are H. In some embodiments, $R^3$ and $R^{3'}$ are hal. In some embodiments, $R^3$ is hal, —CF₃, or —OCF₃ and $R^{3'}$ is H. In some embodiments, $R^3$ is H and $R^{3'}$ is hal, or $C_{1-6}$ alkyl.

In some embodiments, $R^2$ and $R^{2'}$ are H. In some embodiments, $R^2$ and $R^{2'}$ are hal. In some embodiments, $R^2$ is hal or $C_{1-6}$ alkyl and $R^{2'}$ is H. In some embodiments, $R^2$ is H and $R^{2'}$ is hal.

In some embodiments, a compound of formula XI-1, XII-1, or XI-2, XII-2 has the formulas XI-1-(ii)h-a

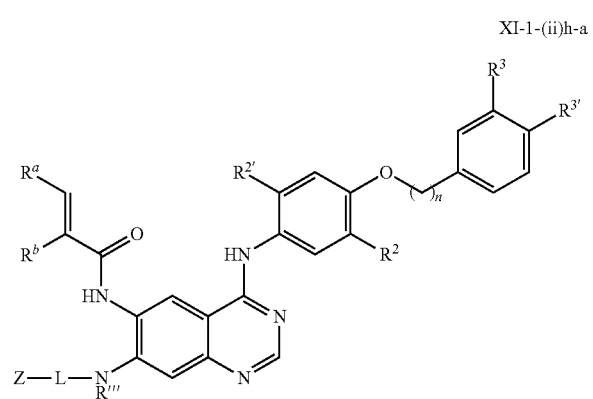

XI-1-(ii)h-a

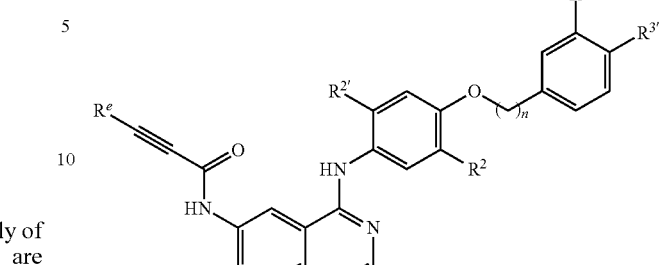

XI-2-(ii)h-a

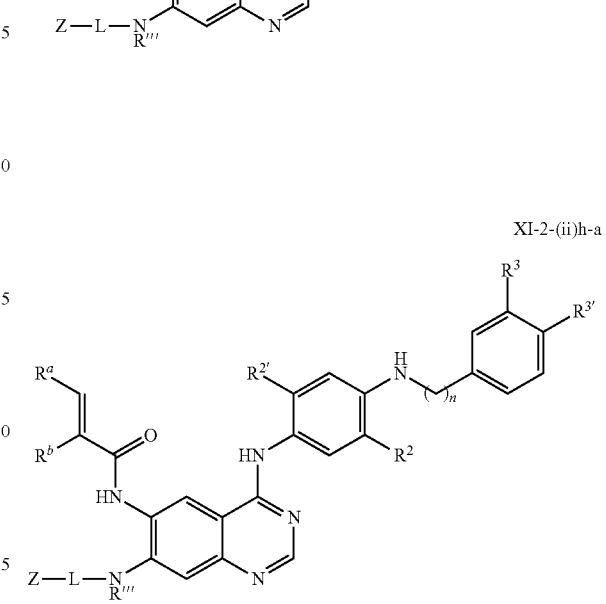

XII-2-(ii)h-a

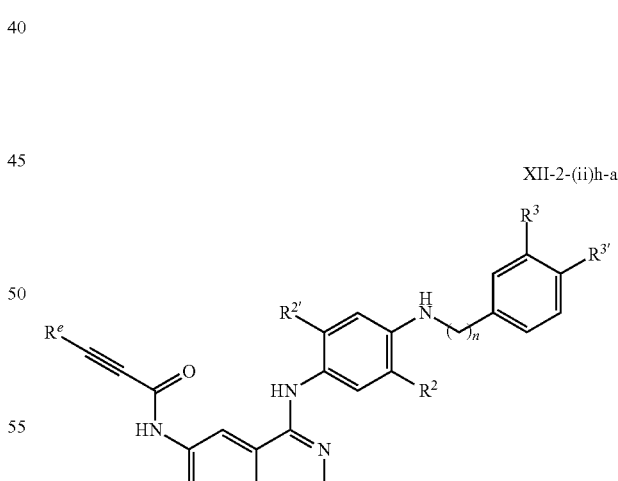

wherein $R^2$, $R^{2'}$ are independently of each other H, $C_{1-6}$ alkyl, hal (e.g. H, —CH₃, F, Cl); $R^3$, $R^{3'}$ are H, $C_{1-6}$ alkyl, hal, —CF₃, —OCF₃; and n is 0 or 1; and Z, L, R''', $R^a$, $R^b$, $R^e$ are as defined above for a compound of formula XI or XII (or XI-1, XII-1 or XI-2, XII-2).

In some embodiments $R^a$ and $R^b$ are hydrogen.

In some embodiments, n is 0. In some embodiments, n is 1.

In some embodiments, a compound of formula XI-1, XII-1 has the formulas

XI-1-(ii)h-c-1

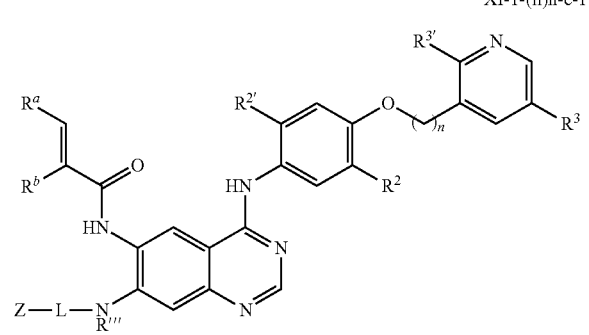

XI-1-(ii)h-b-1

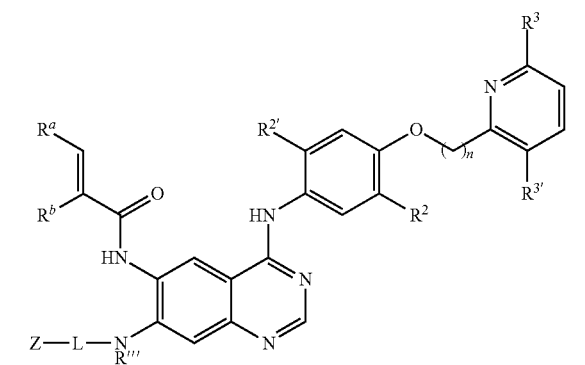

XI-1-(ii)h-d-1

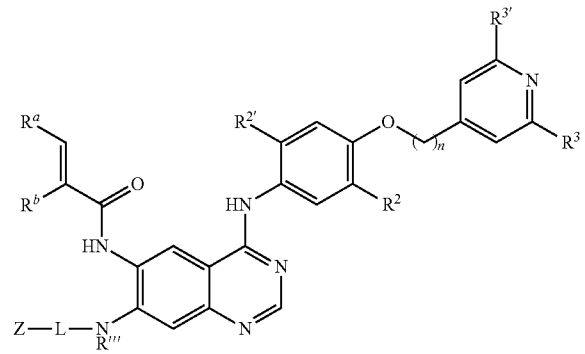

XII-1-(ii)h-d-1

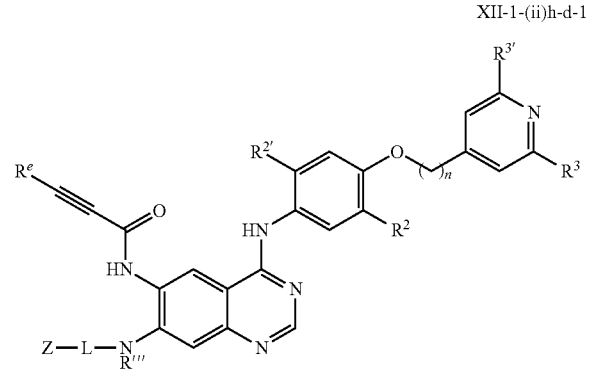

XII-1-(ii)h-c-1

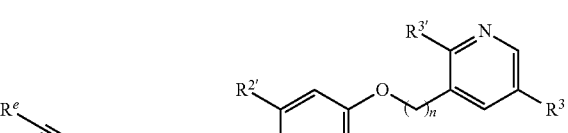

XII-1-(ii)h-b-1

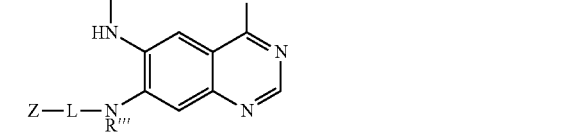

wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, R''', $R^a$, $R^b$, $R^e$ are as defined above for a compound of formula XI or XII (or XI-1, XII-1 or XI-2, XII-2).

In some embodiments $R^a$ and $R^b$ are hydrogen.

In some embodiments, n is 0. In some embodiments, n is 1.

In some embodiments, a compound of formula XI-2, XII-2 has the formulas

XI-1-(ii)i-c-1

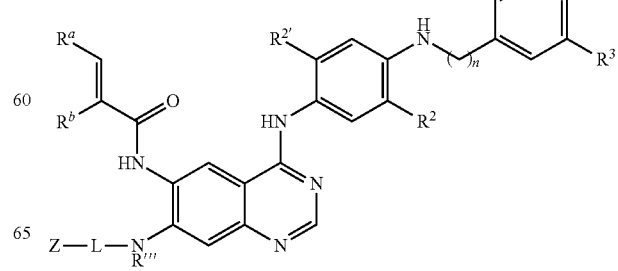

XI-1-(ii)i-b-1

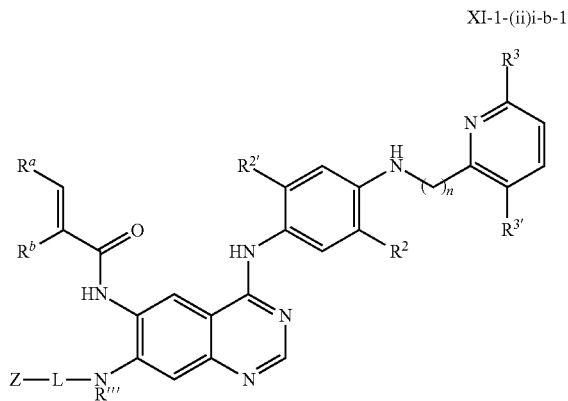

XI-1-(ii)i-d-1

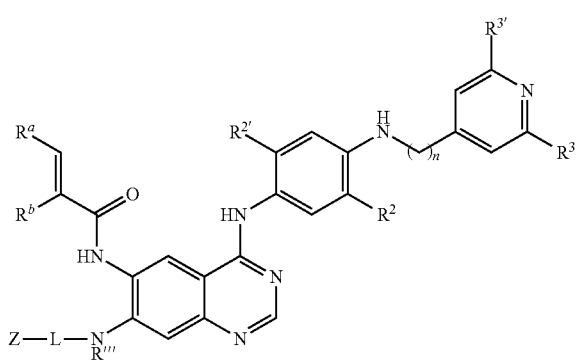

XII-1-(ii)i-d-1

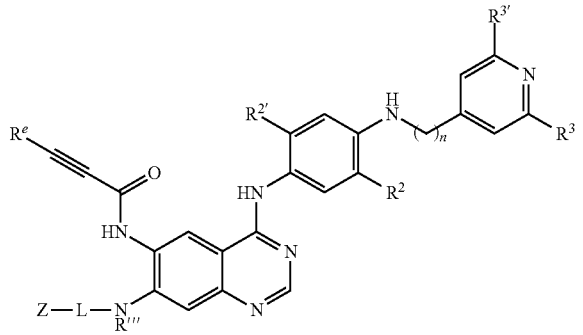

XII-1-(ii)i-c-1

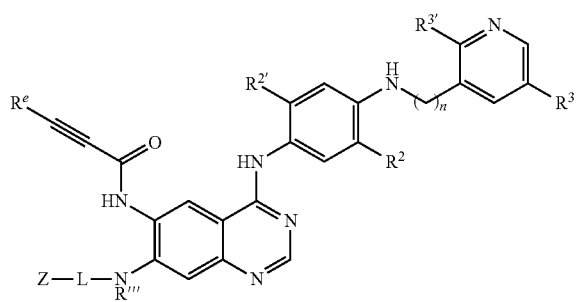

XII-1-(ii)i-b-1

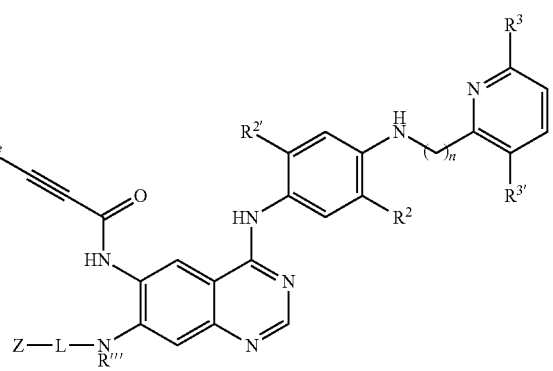

wherein $R^2$, $R^{2'}$ are independently of each other H, $C_{1-6}$ alkyl, hal (e.g. H, —CH$_3$, F, Cl); $R^3$, $R^{3'}$ are H, $C_{1-6}$ alkyl, hal, —CF$_3$, —OCF$_3$; and n is 0 or 1; and Z, L, R''', $R^a$, $R^b$, $R^e$ are as defined above for a compound of formula XI or XII (or XI-1, XII-1 or XI-2, XII-2) In some embodiments, n is 0. In some embodiments, n is 1.

In some embodiments $R^a$ and $R^b$ are hydrogen.

In some embodiments, a compound of formula XI-1 has the formula

XI-1-(ii)h-b-2

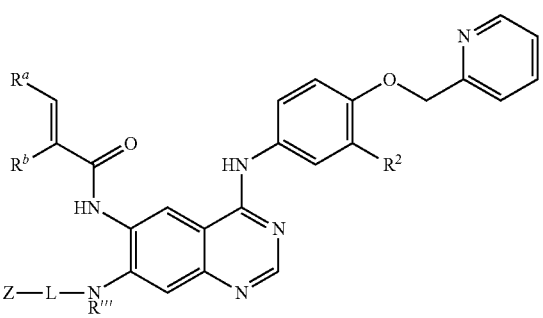

wherein $R^2$ is H, $C_{1-6}$ alkyl, hal (e.g. H, —CH$_3$, F, Cl); $R^3$, $R^{3'}$ are H, $C_{1-6}$ alkyl, hal, —CF$_3$, —OCF$_3$; and n is 0 or 1; and Z, L, $R^a$, $R^b$, $R^e$ are as defined above for a compound of formula V and VI (or V-1, V1-1, or V-2, VI-2).

In some embodiments, $R^2$ is halogen, such as Cl.

In some embodiments, $R^a$ and $R^b$ are hydrogen.

In some embodiments, a compound of formula XI-1, XII-1 has the formula

XI-1-(ii)h-h-1

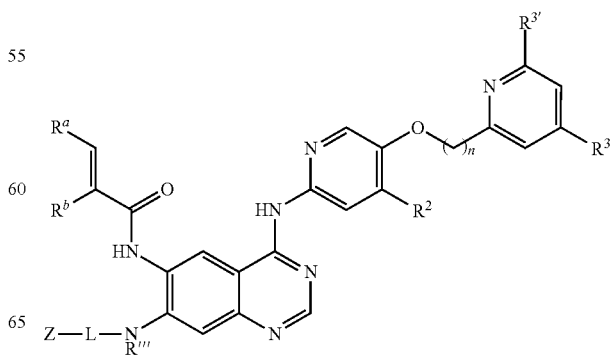

XI-1-(ii)h-i-1
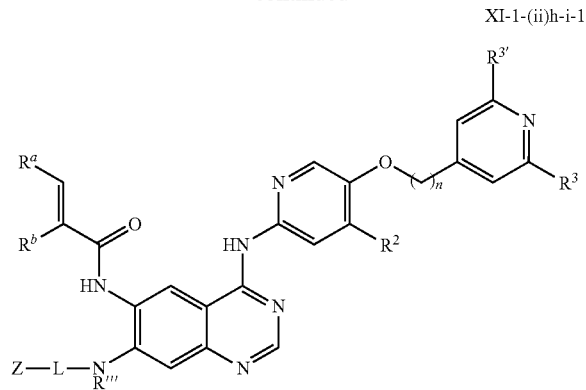
XI-1-(ii)h-g-1
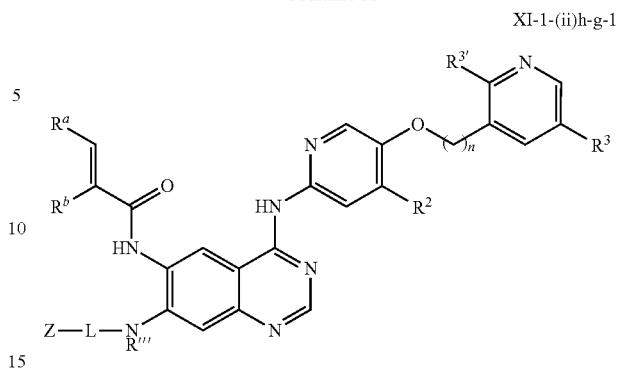
XI-1-(ii)h-j-1
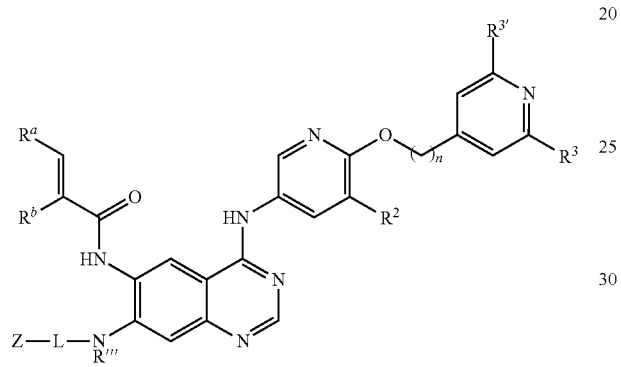
or
XII-1-(ii)h-h-1
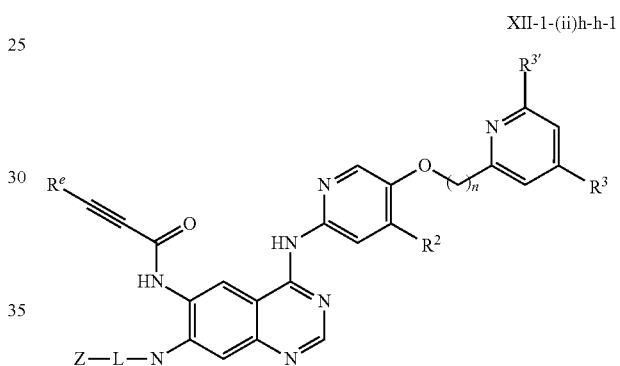
XI-1-(ii)h-f-1
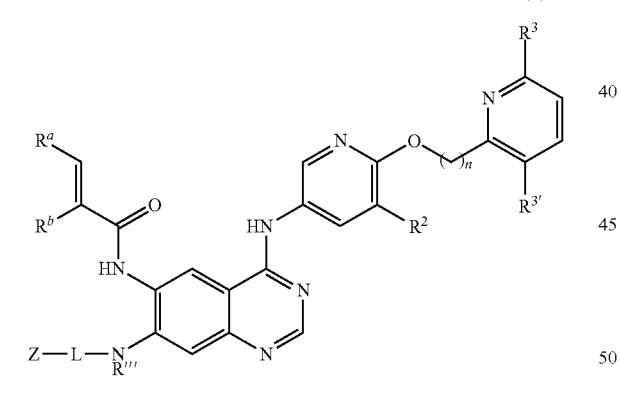
XII-1-(ii)h-i-1
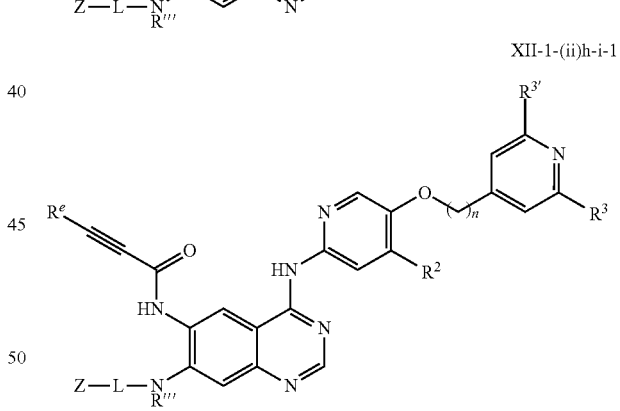
XI-1-(ii)h-e-1
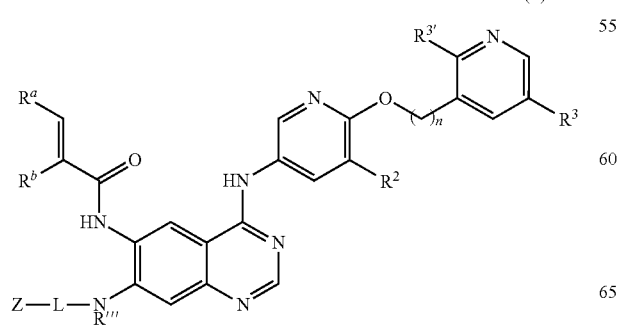
XII-1-(ii)h-j-1
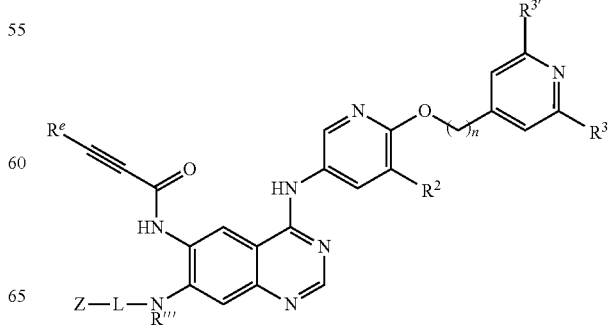

XII-1-(ii)h-f-1

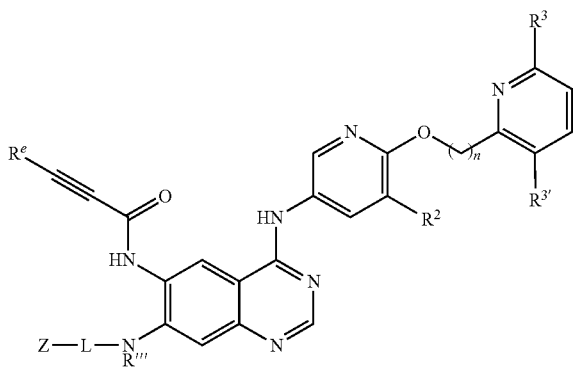

XII-1-(ii)h-e-1

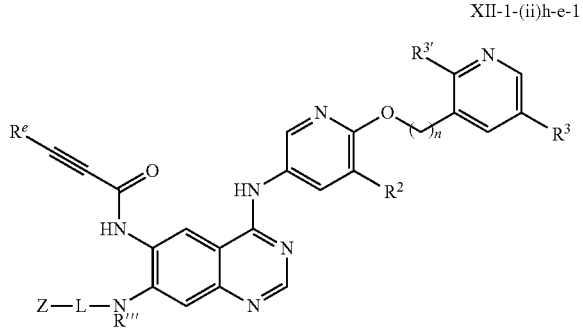

XII-1-(ii)h-g-1

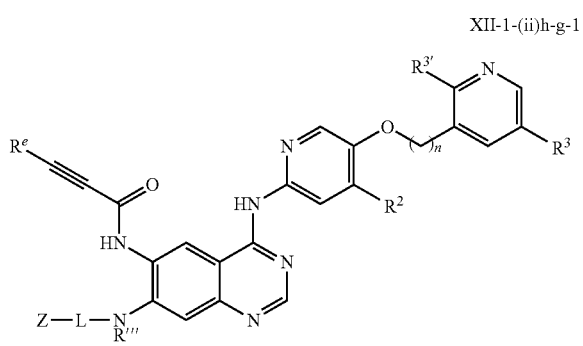

wherein R² is H, C₁₋₆ alkyl, hal (e.g. H, —CH₃, F, Cl); R³, R³' are H, C₁₋₆ alkyl, hal, —CF₃, —OCF₃; and n is 0 or 1; and Z, L, R''', R$^a$, R$^b$, R$^e$ are as defined above for a compound of formula XI or XII (or XI-1, XII-1 or XI-2, XII-2).

In some embodiments R$^a$ and R$^b$ are hydrogen.

In some embodiments, n is 0. In some embodiments, n is 1.

In some embodiments, a compound of formula XI-2, XII-2 has the formulas

XI-2-(ii)i-h-1

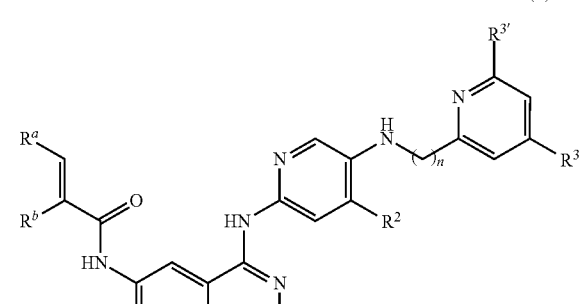

XI-2-(ii)i-i-1

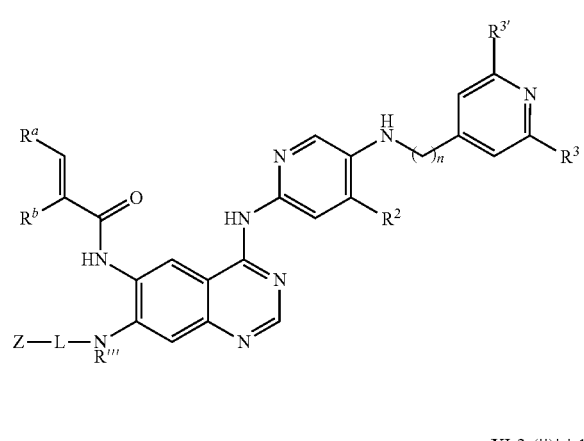

XI-2-(ii)i-j-1

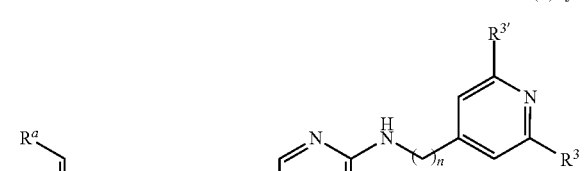

XI-2-(ii)i-f-1

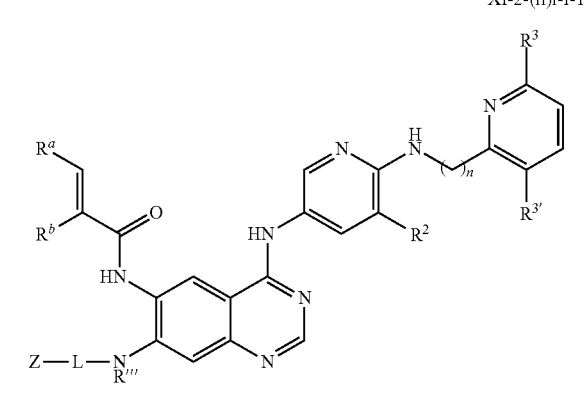

XI-2-(ii)i-e-1
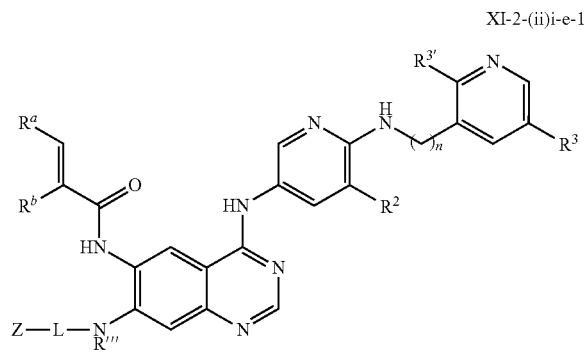
XI-2-(ii)i-g-1
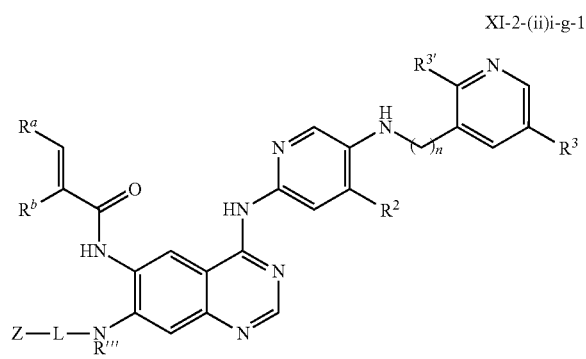
or
XII-2-(ii)i-h-1
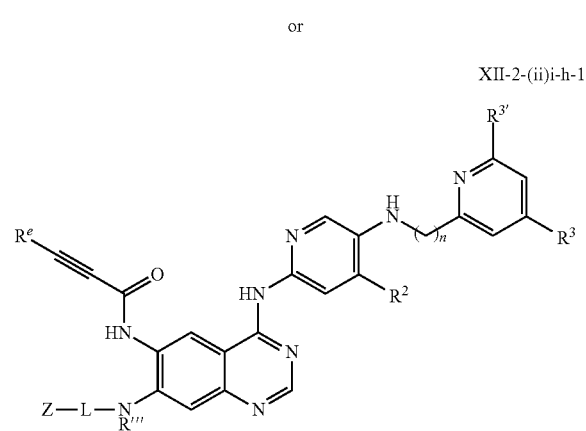
XII-2-(ii)i-i-1
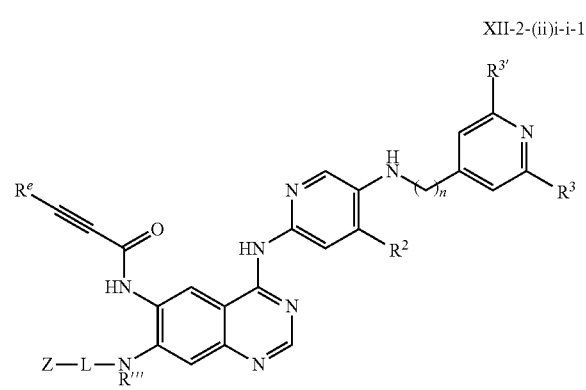
XII-2-(ii)i-j-1
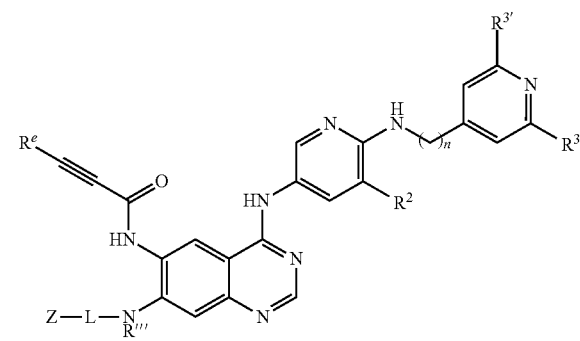
XII-2-(ii)i-f-1
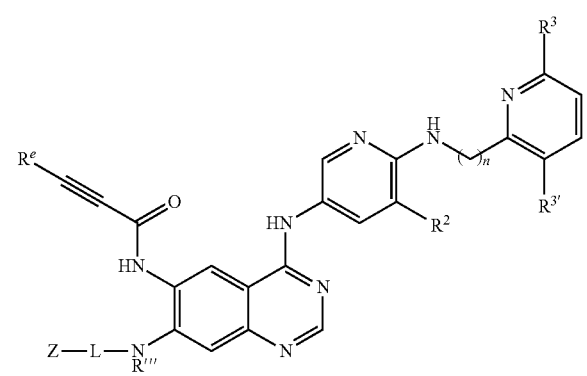
XII-2-(ii)i-e-1
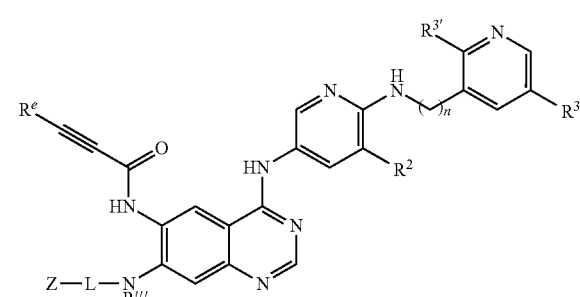
XII-2-(ii)i-g-1
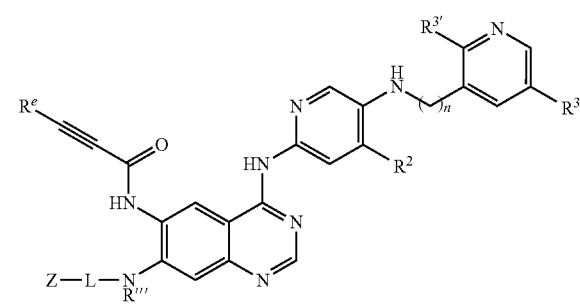
wherein $R^2$ is H, $C_{1-6}$ alkyl, hal (e.g. H, —CH$_3$, F, Cl); $R^3$, $R^{3'}$ are H, $C_{1-6}$ alkyl, hal, —CF$_3$, —OCF$_3$; and n is 0 or 1; and Z, L, R''', $R^a$, $R^b$, $R^e$ are as defined above for a compound of formula XI or XII (or XI-1, XII-1 or XI-2, XII-2).
In some embodiments $R^a$ and $R^b$ are hydrogen.
In some embodiments, n is 0. In some embodiments, n is 1.

In some embodiments, a compound of formula XI-2, XII-2 has the formulas
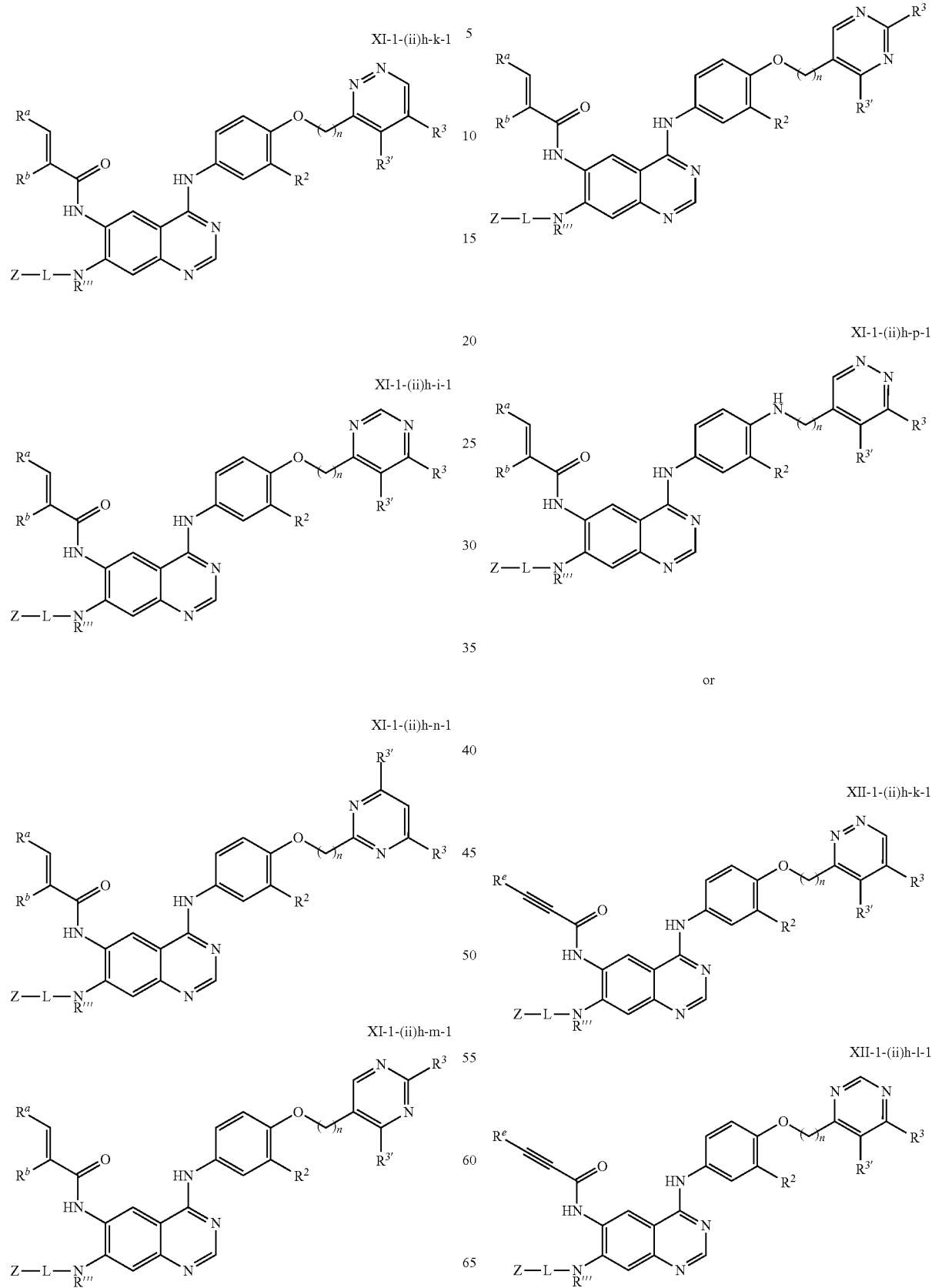

-continued

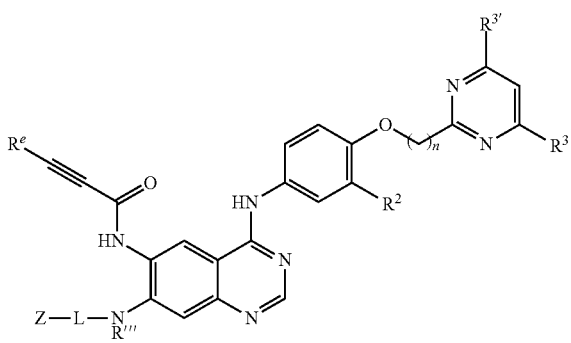

XII-1-(ii)h-n-1

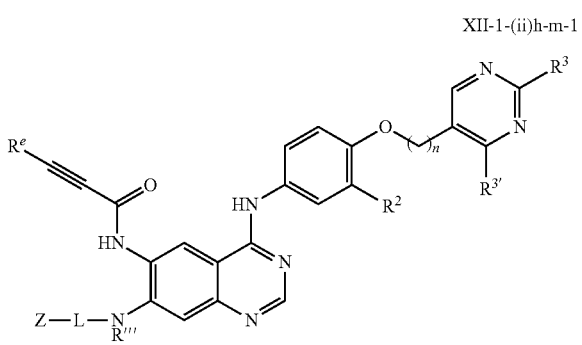

XII-1-(ii)h-m-1

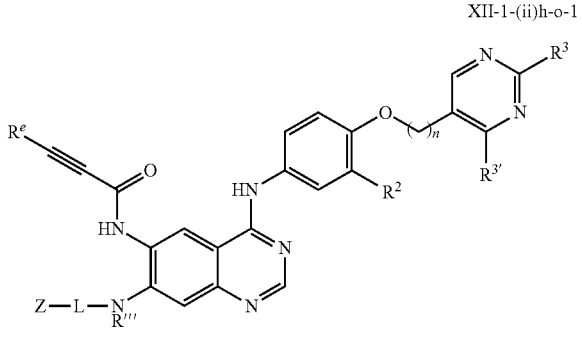

XII-1-(ii)h-o-1

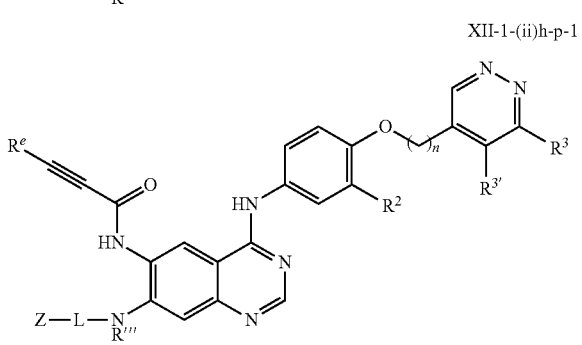

XII-1-(ii)h-p-1 wherein $R^2$ is H, $C_{1-6}$ alkyl, hal (e.g. H, —CH$_3$, F, Cl); $R^3$, $R^{3'}$ are H, $C_{1-6}$ alkyl, hal, —CF$_3$, —OCF$_3$; and n is 0 or 1; and Z, L, R''', $R^a$, $R^b$, $R^e$ are as defined above for a compound of formula XI or XII (or XI-1, XII-1 or XI-2, XII-2).

In some embodiments $R^a$ and $R^b$ are hydrogen.

In some embodiments, n is 0. In some embodiments, n is 1.

In some embodiments, a compound of formula XI-2, XII-2 has the formulas

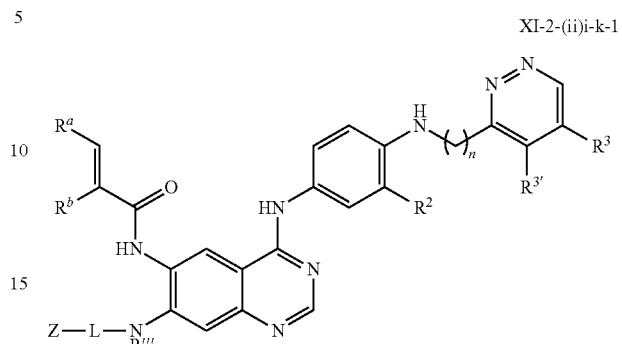

XI-2-(ii)i-k-1

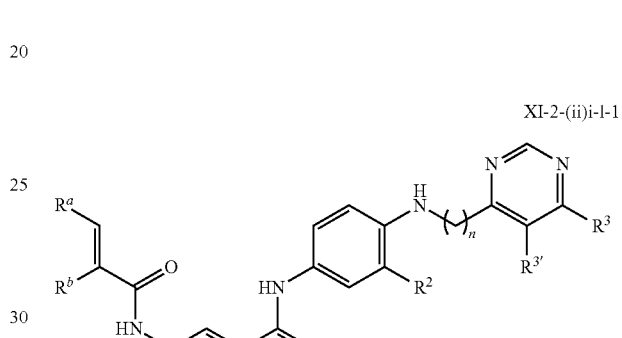

XI-2-(ii)i-l-1

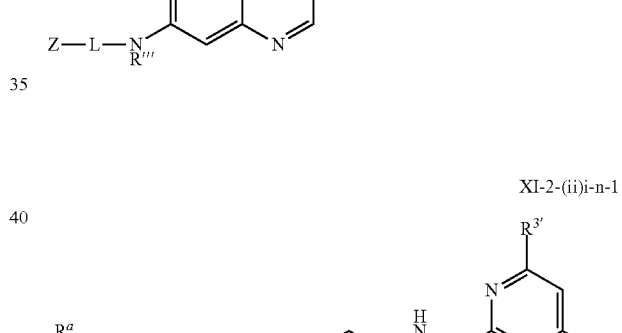

XI-2-(ii)i-n-1

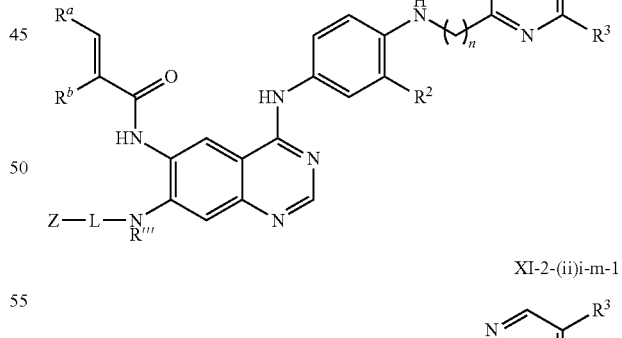

XI-2-(ii)i-m-1

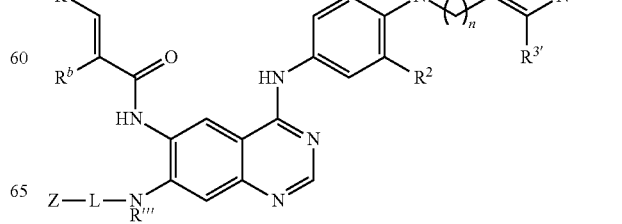

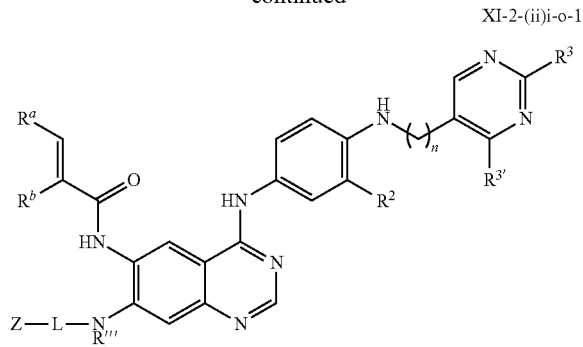

XI-2-(ii)i-o-1

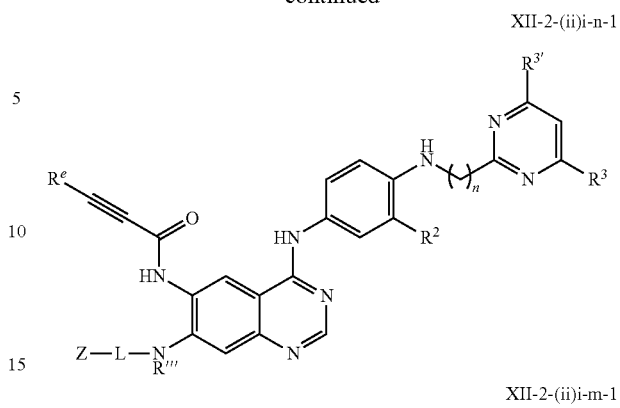

XII-2-(ii)i-n-1

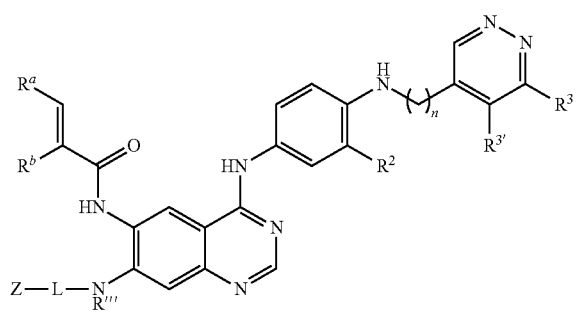

XI-2-(ii)i-p-1

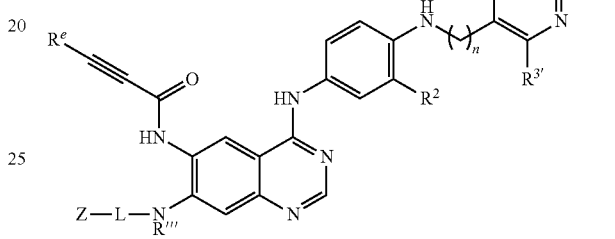

XII-2-(ii)i-m-1 or

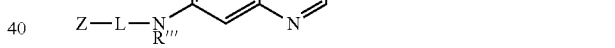

XII-2-(ii)i-o-1

XII-2-(ii)i-k-1

XII-2-(ii)i-p-1

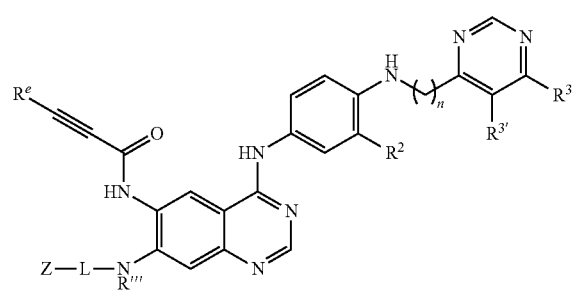

XII-2-(ii)i-l-1 wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, R''', $R^a$, $R^b$, $R^e$ are as defined above for a compound of formula XI or XII (or XI-1, XII-1 or XI-2, XII-2).

In some embodiments $R^a$ and $R^b$ are hydrogen.

In some embodiments, n is 0. In some embodiments, n is 1.

In some embodiments, $R^4$ and $R^5$ are independently of each other H, $C_{1-4}$ alkyl, cyclopropyl, tetrahydrofuryl (e.g. $C_{1-4}$ alkyl).

In some embodiments, L is a covalent bond, straight chain or branched $C_{1-4}$ alkyl. In some embodiments, L is —$CH_2$—, —$(CH_2)_2$—, —$(CH_2)_3$—, —$(CH_2)_4$— or —$C(CH_3)_2$—.

In some embodiments, group Z is defined as specified above. In some embodiments, Z is —$(NR^4R^5)$, wherein $R^4$ and $R^5$ are independently of each other H, $C_{1-6}$ alkyl, cyclopropyl, cylobutyl, 3 to 6-membered heterocycloalkyl containing 0, 1, or 2 N-atoms and 0, 1, or 2 O-atoms, or —$(NR^6R^7)$, —$(CHR^6R^7)$, wherein $R^6$ and $R^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments, the —$(CR^6R^7)$ and —$(NR^6R^7)$ ring systems of Z are selected from

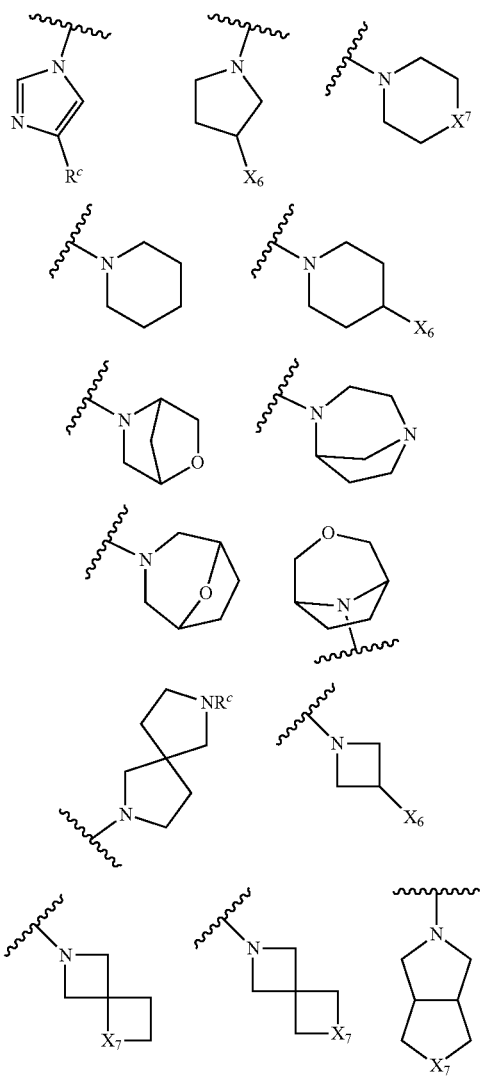

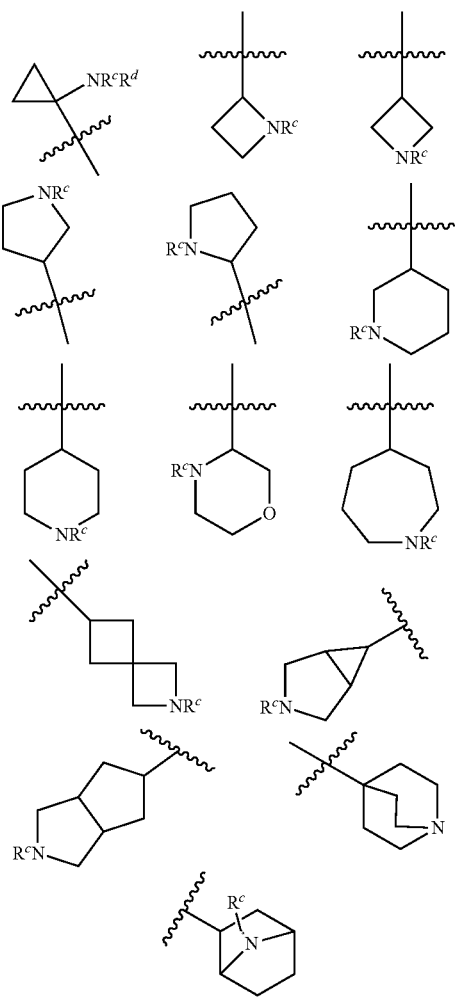

wherein $R^c$ is H, $C_{1-4}$ alkyl, oxetane; $X^6$ is H, —$CH_3$, —OH, —$OCH_3$, —$OCF_3$, —$N(CH_3)_2$, F, Cl; $X^7$ is —O—, —NH— or —$N(CH_3)$—, —$SO_2$, and wherein $R^c$ is H, $C_{1-4}$ alkyl, oxetane, and $R^d$ is H, $C_{1-4}$ alkyl.

In some embodiments, —$(CR^6R^7)$ and —$(NR^6R^7)$ ring systems of Z are selected from

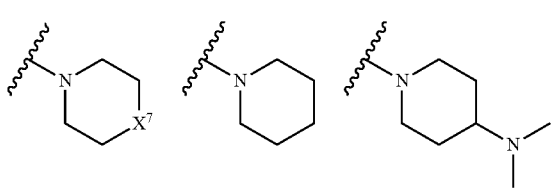

277

-continued

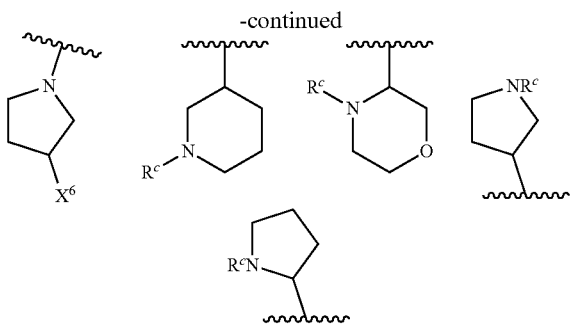

wherein $R^c$ is H, $C_{1-4}$ alkyl, oxetane (e.g. H, —CH$_3$); $X^6$ is H, —CH$_3$, —OH, —OCH$_3$, —OCF$_3$, —N(CH$_3$)$_2$, F, Cl, and $X^7$ is —O—, —NH— or —N(CH$_3$)—, —SO$_2$ (e.g. —O—).

In some embodiments, group Z is selected from

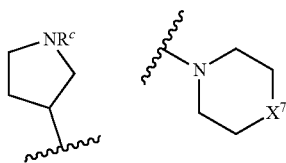

wherein $R^c$ is H, $C_{1-4}$ alkyl, oxetane (e.g. H, —CH$_3$), and $X^7$ is —O—, —NH— or —N(CH$_3$)—, —SO$_2$ (e.g. —O—).

In some embodiments, the present disclosure is directed towards a compound or pharmaceutically acceptable salts or stereoisomers thereof of formula I above wherein $Y^2$ is —C≡C— having the following formula XIII

XIII

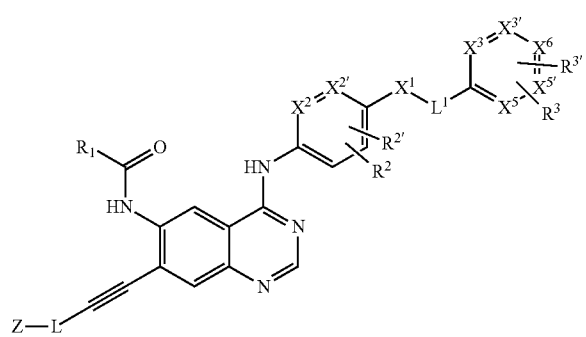

wherein $X^1$ is —O—, —CH$_2$—, —NH—, —S—; $X^2$, $X^{2'}$, $X^3$, $X^{3'}$, $X^5$, $X^{5'}$, $X^6$ are independently of each other —N—, —CH—;

$L^1$ is a covalent bond or straight chain or branched $C_{1-3}$alkyl, which is unsubstituted or substituted with hal, $R^1$ is —CH═CH$_2$, —C≡CH or —C≡C—CH$_3$;

$R^2$, $R^{2'}$, $R^3$, $R^{3'}$ are independently of each other H, $C_{1-6}$ alkyl, hal, —CF$_3$, —OCF$_3$;

wherein L is a covalent bond, straight chain or branched $C_{1-4}$ alkyl or

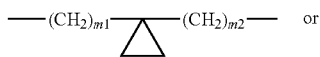

278

-continued

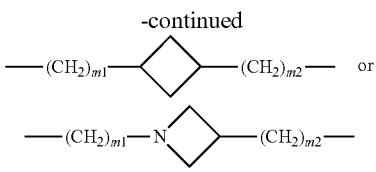

wherein m1, m2 are independently of each other 0, 1, 2, 3, or 4;

Z is —(NR$^4$R$^5$), wherein R$^4$ and R$^5$ are independently of each other H, $C_{1-6}$ alkyl, or —(NR$^6$R$^7$)- or —(CHR$^6$R$^7$), wherein R$^6$ and R$^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments substituent Z-L contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if L does not contain a nitrogen atom.

In some embodiments $R^a$ and $R^b$ are hydrogen.

In some embodiments, $L^1$ is straight chain or branched $C_{1-3}$alkyl, which is unsubstituted or substituted with hal. In some embodiments, $L^1$ is not a covalent bond.

In some embodiments, both $X^2$, $X^{2'}$ are —CH═ (i.e. a phenyl ring). In some embodiments, $X^2$ is —N═ and $X^{2'}$ is —CH═ or $X^{2'}$ is —N═ and $X^2$ is —CH═ (i.e. a pyridine ring). In some embodiments, both $X^2$, $X^{2'}$ are —N═ (i.e. a pyridazine ring).

In some embodiments, $X^3$, $X^{3'}$, $X^5$, $X^{5'}$, $X^6$ are —CH═ (i.e. a phenyl ring). In some embodiments, $X^3$ is —N═ and $X^{3'}$, $X^5$, $X^{5'}$, $X^6$ are —CH═ or $X^{3'}$ is —N═ and $X^3$, $X^5$, $X^{5'}$, $X^6$ are is —CH═ or $X^6$ is —N═ and $X^3$, $X^{3'}$, $X^5$, $X^{5'}$ are —CH═ (i.e. a pyridine ring).

In some embodiments, both $X^3$, $X^{3'}$ are —N═ and $X^5$, $X^{5'}$, $X^6$ are —CH═ or both $X^{3'}$, $X^6$ are —N═ and $X^3$, $X^5$, $X^{5'}$ are —CH═ (i.e. a pyridazine ring). In some embodiments, both $X^3$, $X^5$ are —N═ and $X^{3'}$, $X^{5'}$, $X^6$ are —CH═ or both $X^{3'}$, $X^{5'}$ are —N═ and $X^3$, $X^5$, $X^6$ are —CH═ or both $X^3$, $X^6$ are —N═ and $X^{3'}$, $X^5$, $X^{5'}$ are —CH═ (i.e. a pyrimidine ring). In some embodiments, both $X^3$, $X^{5'}$ are —N═ and $X^{3'}$, $X^5$, $X^6$ are —CH═ (i.e. a pyrazine ring).

In some embodiments, for the compounds of formula XIII, groups $X^2$, $X^{2'}$ are —CH═ (i.e. a phenyl ring). In some embodiments, $X^3$, $X^{3'}$, $X^5$, $X^{5'}$, $X^6$ are —CH═ (i.e. a phenyl ring). In some embodiments, $X^3$ is —N═ and $X^{3'}$, $X^5$, $X^{5'}$, $X^6$ are —CH═ or $X^{3'}$ is —N═ and $X^3$, $X^5$, $X^{5'}$, $X^6$ are —CH═ (i.e. a pyridine ring).

In some embodiments, for the compounds of formula XIII, group L is a covalent bond or straight chain or branched $C_{1-4}$ alkyl.

In some embodiments, $R^2$ and $R^{2'}$ are independently of each other H, $C_{1-6}$ alkyl, hal (e.g. H, —CH$_3$, F, Cl).

In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —CF$_3$, —OCF$_3$.

In some embodiments, for the compounds of formula XIII, groups $R^2$ and $R^{2'}$ are H and $R^3$ is H, $C_{1-6}$ alkyl, hal, —CF$_3$, —OCF$_3$ and $R^{3'}$ is H, hal; or $R^2$ and $R^{2'}$ are hal and $R^3$ is H, $C_{1-6}$ alkyl, hal, —CF$_3$, —OCF$_3$ and $R^{3'}$ is H, hal; or $R^2$ is hal or $C_{1-6}$ alkyl and $R^{2'}$ is H and $R^3$ is H, $C_{1-6}$ alkyl, hal, —$CF_3$, —$OCF_3$ and $R^{3'}$ is H; or $R^2$ is hal or $C_{1-6}$ alkyl and $R^{2'}$ is H and $R^{3'}$ is $C_{1-6}$ alkyl, hal and $R^3$ is H.

In some embodiments, $X^1$ is —O—. In some embodiments, $X^1$ is —$CH_2$—. In some embodiments, $X^1$ is —NH—. In some embodiments, $X^1$ is —S—. In some embodiments, $L^1$ is a covalent bond. In some embodiments, $L^1$ is —$CH_2$— or —$CH(CH_3)$— or —CH(hal)-. In some embodiments, $L^1$ is —$CH_2$—$CH_2$— or —$CH_2CH(CH_3)$— or —$CH_2$—CH(hal)-.

In some embodiments, linker combinations -$X^1$-$L^1$- include —O—, —$CH_2$—, —O—$CH_2$—, —NH—$CH_2$—, —S—$CH_2$—, —$CH_2$—$CH_2$—, —O—$CH(CH_3)$—, —$CH_2$—$CH(CH_3)$—, —NH—$CH(CH_3)$—, —S—CH($CH_3$)—, —O—CH(hal)-, $CH_2$—CH(hal)-, —NH—CH(hal)-, —S—CH(hal)- (e.g. —O—, —$CH_2$—, —O—$CH_2$—, —NH—$CH_2$—, —$CH_2$—$CH_2$—, —O—CH($CH_3$)—, —$CH_2$—$CH(CH_3)$—, —O—CH(hal)-, or —$CH_2$—CH(hal)- and —O—, —$CH_2$—, —O—$CH_2$—, —NH—$CH_2$—, —$CH_2$—$CH_2$—).

In some embodiments, -$X^1$-$L^1$- is —O—, In some embodiments, -$X^1$-$L^1$- is —O—$CH_2$—. In some embodiments, compound XIII has the following formula

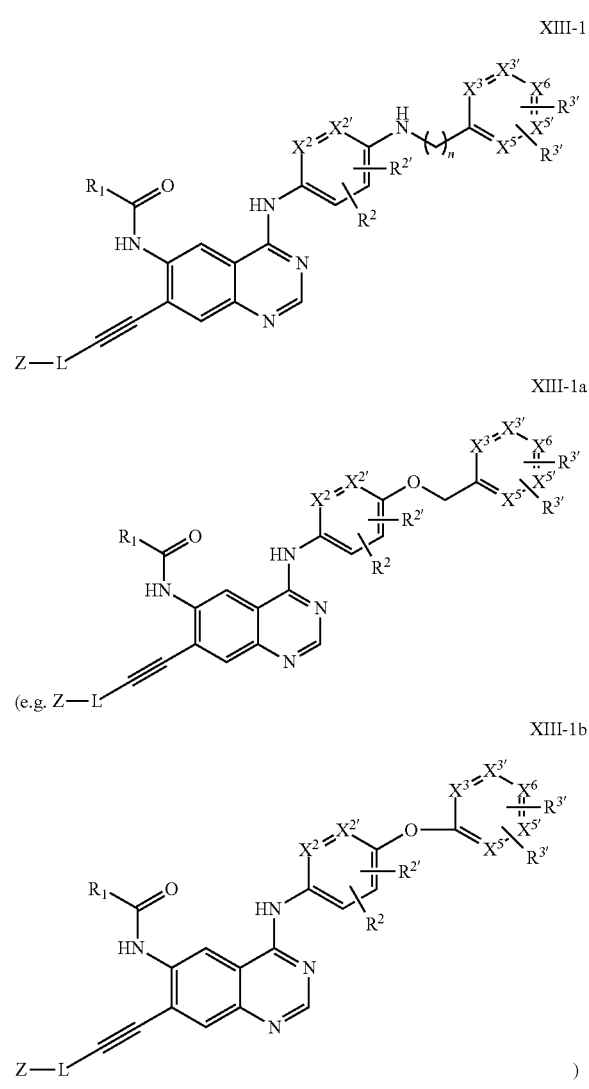

XIII-1a

XIII-1b (e.g. Z—L)

wherein $X^2$, $X^{2'}$ and $X^3$, $X^{3'}$, $X^5$, $X^{5'}$, $X^6$ are independently of each other —N= or —CH=; $R^2$, $R^{2'}$ and $R^3$, $R^{3'}$ are independently of each other H, $C_{1-6}$ alkyl, hal, —$CF_3$, or —$OCF_3$, and n is 0, 1, 2, 3; and Z, L, $R^1$, R'" are as defined above for a compound of formula XIII.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring) . In some embodiments, $X^3$, $X^{3'}$, $X^5$, $X^{5'}$, $X^6$ are —CH= (i.e. a pyridine ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= (i.e. a pyridine ring).

In some embodiments, $R^2$ and $R^2$40 are independently of each other H, $C_{1-6}$ alkyl, hal (e.g. H, —$CH_3$, F, Cl). In some embodiments, $R^3$ and $R^{3'}$ are independently of each other H, $C_{1-6}$ alkyl, hal, —$CF_3$, —$OCF_3$.

In some embodiments, $R^2$ and $R^{2'}$ are H and $R^3$ is H, $C_{1-6}$ alkyl, hal, —$CF_3$, —$OCF_3$ and $R^{3'}$ is H, hal; or $R^2$ and $R^{2'}$ are hal and $R^3$ is H, $C_{1-6}$ alkyl, hal, —$CF_3$, —$OCF_3$ and $R^{3'}$ is H, hal; or $R^2$ is hal or $C_{1-6}$ alkyl and $R^{2'}$ is H and $R^3$ is H, $C_{1-6}$ alkyl, hal, —$CF_3$, —$OCF_3$ and $R^{3'}$ is H; or $R^2$ is hal or $C_{1-6}$ alkyl and $R^{2'}$ is H and $R^{3'}$ is $C_{1-6}$ alkyl, hal and $R^3$ is H.

In some embodiments, L is a covalent bond or straight chain or branched $C_{1-4}$ alkyl.

In some embodiments, a compound of formula XIII has one of the following formulas

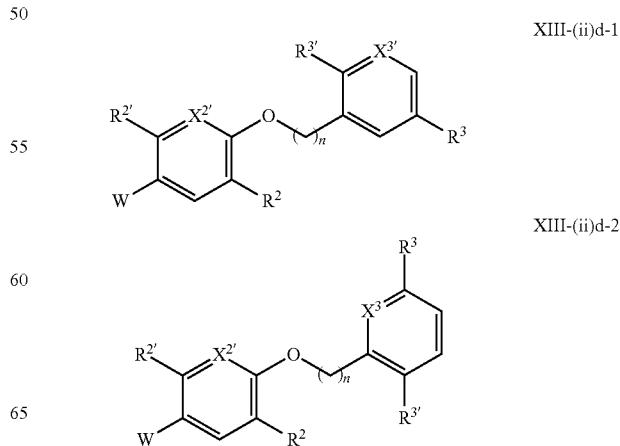

XIII-(ii)d-1

XIII-(ii)d-2

-continued

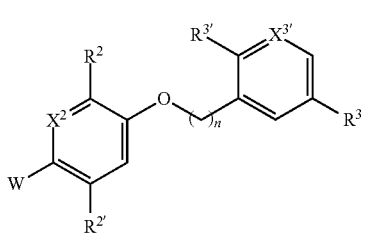
XIII-(ii)d-3

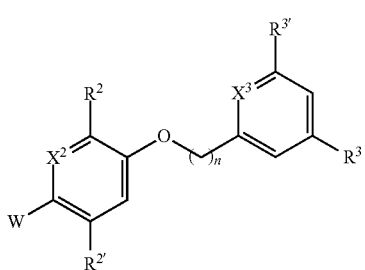
XIII-(ii)d-4

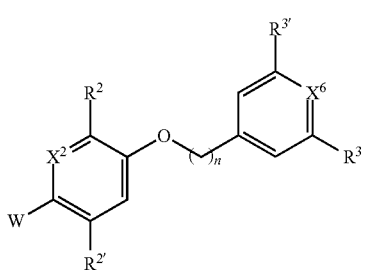
XIII-(ii)d-5

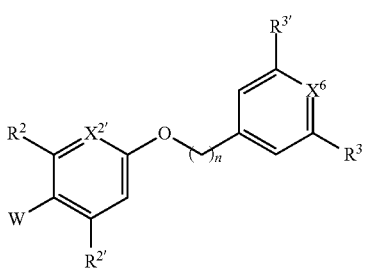
XIII-(ii)d-6 wherein W is

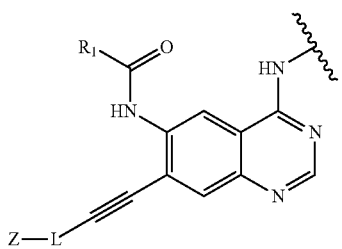

wherein $X^2$, $X^{2'}$ and $X^3$, $X^{3'}$, $X^6$ are independently of each other —N= or —CH=; $R^2$, $R^{2'}$ and $R^3$, $R^{3'}$ are independently of each other H, $C_{1-6}$ alkyl, hal, —$CF_3$, or —$OCF_3$, and n is 0, 1, 2, 3; and Z, L, $R^1$ are as defined above for a compound of formula XIII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, the compound of formula XIII has the following formulas

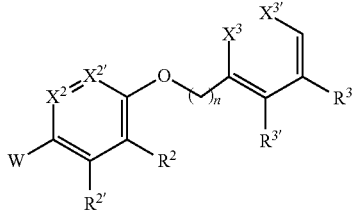
XIIIe-1

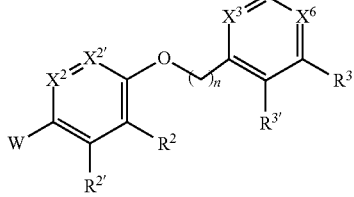
XIIIe-2

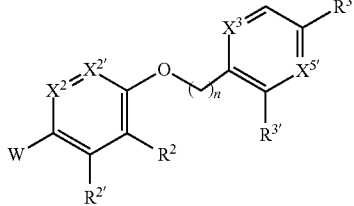
XIIIe-3

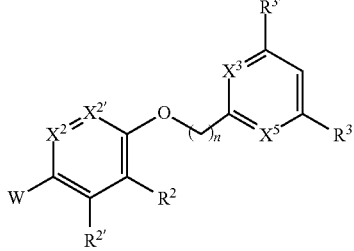
XIIIe-4

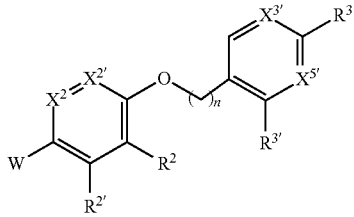
XIIIe-5

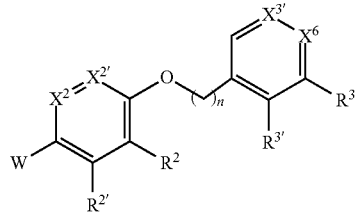

wherein W is

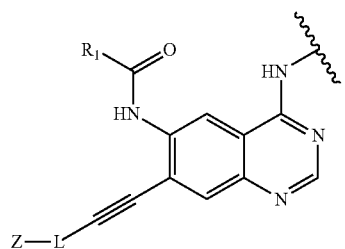

$X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1; and Z, L, $R^1$ are as defined above for a compound of formula XIII.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring). In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= (i.e. a pyridine ring).

In some embodiments, L is a covalent bond or straight chain or branched $C_{1-4}$ alkyl.

In some embodiments, -$X^1$-$L^1$- is —NH—. In some embodiments, -$X^1$-$L^1$- is —NH—$CH_2$—. In some embodiments, a compound of formula XIII has the following formula

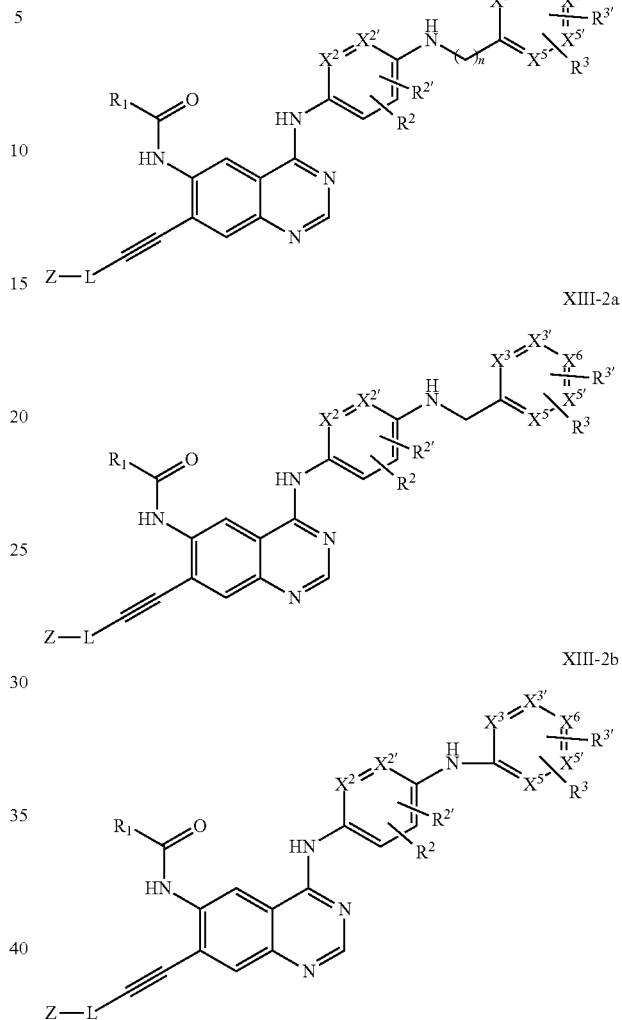

wherein $X^2$, $X^{2'}$ and $X^3$, $X^{3'}$, $X^5$, $X^{5'}$, $X^6$ are independently of each other —N= or —CH=; $R^2$, $R^{2'}$ and $R^3$, $R^{3'}$ are independently of each other H, $C_{1-6}$ alkyl, hal, —$CF_3$, or —$OCF_3$, and n is 0, 1, 2, 3; and Z, L, $R^1$ are as defined above for a compound of formula XIII.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring). In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= (i.e. a pyridine ring).

In some embodiments, L is a covalent bond or straight chain or branched $C_{1-4}$ alkyl.

$R^2$ and $R^{2'}$ are independently of each other H, $C_{1-6}$ alkyl, hal, (e.g. H, —CH$_3$, F, Cl). In some embodiments, $R^3$ and $R^{3'}$ are independently of each other H, $C_{1-6}$ alkyl, hal, —CF$_3$, —OCF$_3$.

In some embodiments, $R^2$ and $R^{2'}$ are H and $R^3$ is H, $C_{1-6}$ alkyl, hal, —CF$_3$, —OCF$_3$ and $R^{3'}$ is H, hal; or $R^2$ and $R^{2'}$ are hal and $R^3$ is H, $C_{1-6}$ alkyl, hal, —CF$_3$, —OCF$_3$ and $R^{3'}$ is H, hal; or $R^2$ is hal or $C_{1-6}$ alkyl and $R^{2'}$ is H and $R^3$ is H, $C_{1-6}$ alkyl, hal, —CF$_3$, —OCF$_3$ and $R^{3'}$ is H; or $R^2$ is hal or $C_{1-6}$ alkyl and $R^{2'}$ is H and $R^{3'}$ is $C_{1-6}$ alkyl, hal and $R^3$ is H.

In some embodiments, a compound of formula XIII has one of the following formulas

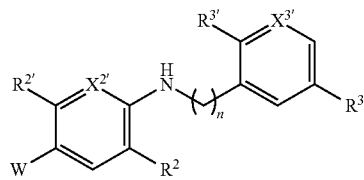
XIII-(ii)f-1

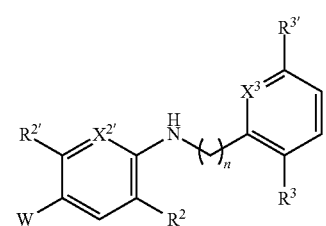
XIII-(ii)f-2

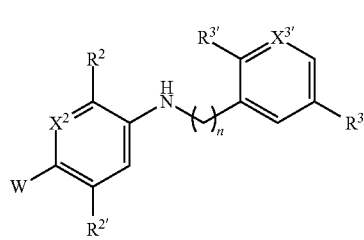
XIII-(ii)f-3

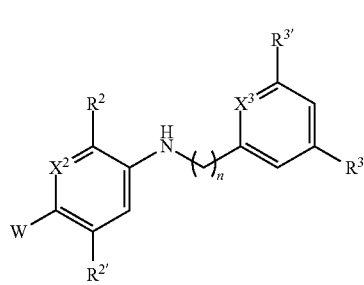
XIII-(ii)f-4

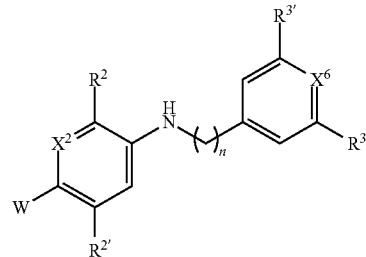
XIII-(ii)f-5

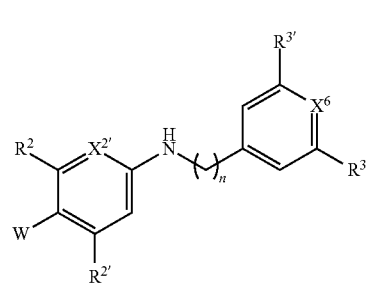
XIII-(ii)f-6 wherein W is

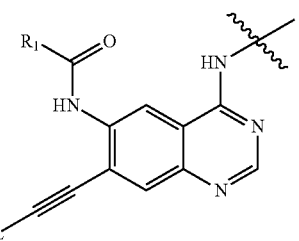

$X^2$, $X^{2'}$, $X^3$, $X^{3'}$, $X^6$ are independently of each other —N= or —CH=; and $R^2$, $R^{2'}$, $R^3$, $R^{3'}$ are independently of each other H, $C_{1-6}$ alkyl, hal, —CF$_3$, or —OCF$_3$; and n is 0 or 1; and Z, L, $R^1$ are as defined above for a compound of formula XIII.

In some embodiments substituent Z-L contains at least one nitrogen atom. Thus, the 3-6-membered heteroaryl or 3-9-membered heterocycloalkyl formed by $R^6$ and $R_7$ of (CHR$_6$R$^7$) includes a nitrogen atom if L does not contain a nitrogen atom.

In some embodiments $R^a$ and $R^b$ are hydrogen.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, a compound of formula XIII has the following formulas

XIII-(ii)g-1

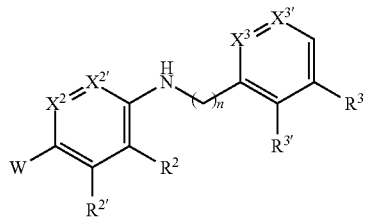

XIII-(ii)g-2

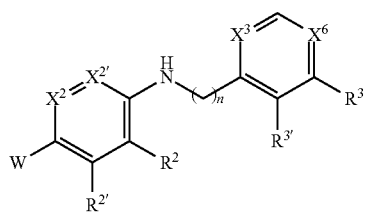

XIII-(ii)g-3

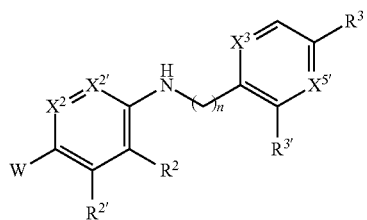

XIII-(ii)g-4

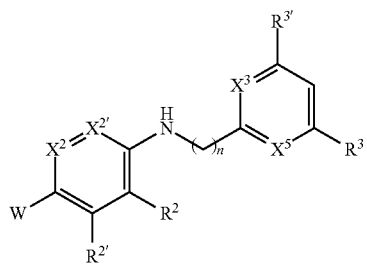

XIII-(ii)g-5

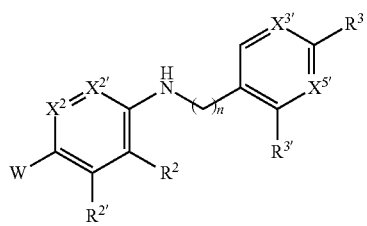

XIII-(ii)g-6

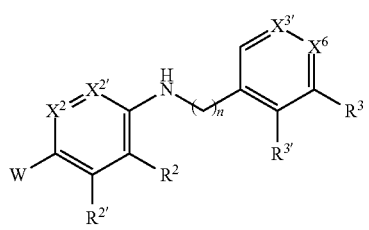

wherein W is

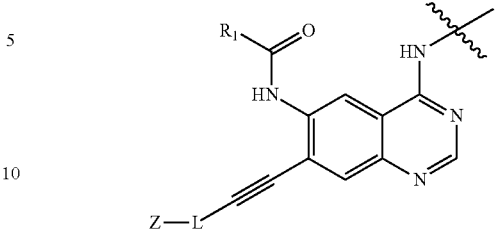

wherein $X^2$, $X^{2'}$, $X^3$, $X^{3'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$, n is 0 or 1; and Z, L, $R^1$ are as defined above for a compound of formula XIII.

In some embodiments substituent Z-L contains at least one nitrogen atom. Thus, the 3-6-membered heteroaryl or 3-9-membered heterocycloalkyl formed by $R^6$ and $R^7$ of (CHR$_6$R$_7$) includes a nitrogen atom if L does not contain a nitrogen atom.

In some embodiments $R^a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring). In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= (i.e. a pyridine ring).

In some embodiments, L is a covalent bond or straight chain or branched $C_{1-4}$ alkyl.

In some embodiments, $R^2$ and $R^{2'}$ are independently of each other H, hal or $C_{1-6}$ alkyl (e.g. H, hal or —$CH_3$).

In some embodiments, $R^3$ is H, hal, —$CF_3$, or —$OCF_3$.

In some embodiments, $R^{3'}$ is H, hal or $C_{1-6}$ alkyl, (e.g. H, hal or —$CH_3$).

In some embodiments, $R^3$ and $R^{3'}$ are H. In some embodiments, $R^3$ and $R^{3'}$ are hal. In some embodiments, $R^3$ is hal, —$CF_3$, or —$OCF_3$ and $R^{3'}$ is H. In some embodiments, $R^3$ is H and is hal, or $C_{1-6}$ alkyl.

In some embodiments, $R^2$ and $R^{2'}$ are H. In some embodiments, $R^2$ and $R^{2'}$ are hal. In some embodiments, $R^2$ is hal or $C_{1-6}$ alkyl and $R^{2'}$ is H. In some embodiments, $R^2$ is H and $R^{2'}$ is hal.

In some embodiments, a compound of formula XIII has the following formula

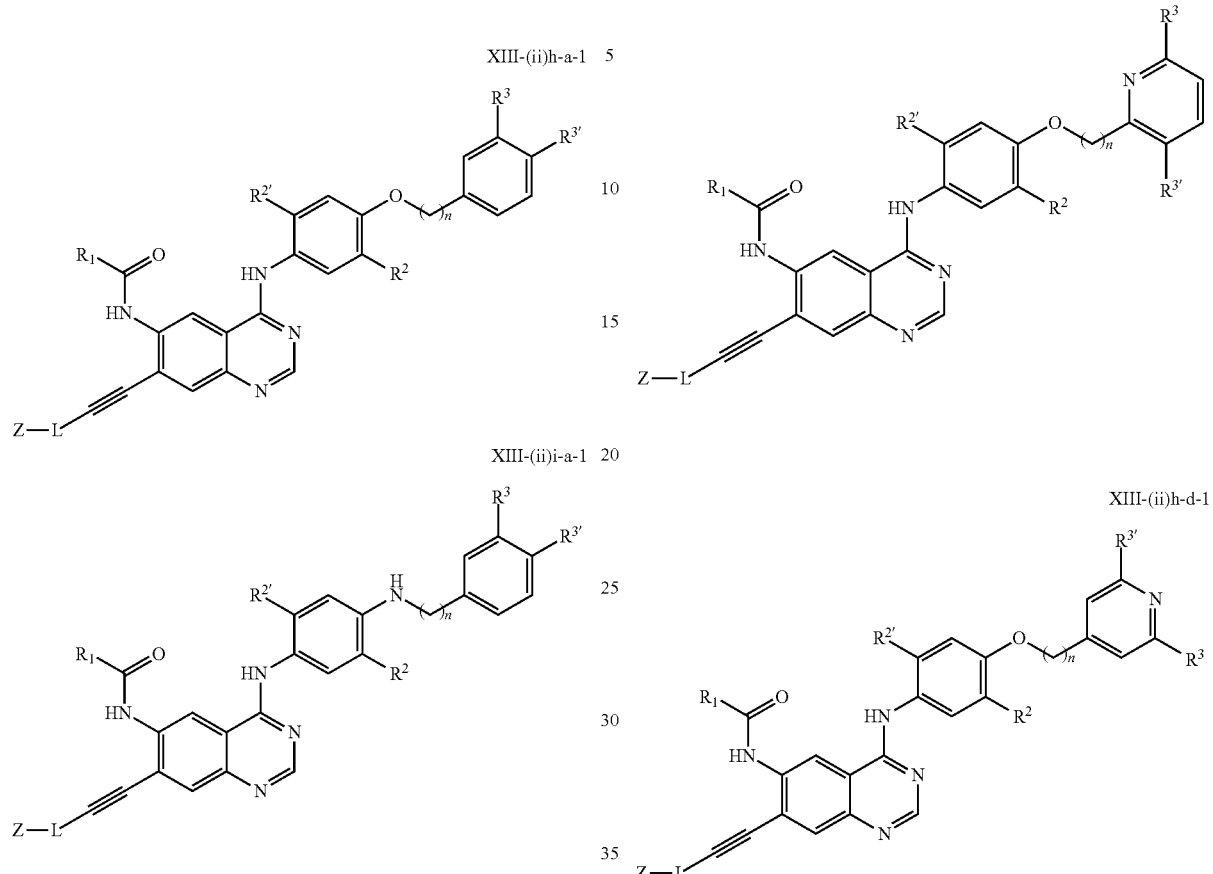

wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$ are as defined above for a compound of formula XIII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R^6$ and $R^7$ of ($CHR_6R_7$) includes a nitrogen atom if L does not contain a nitrogen atom.

In some embodiments $R^a$ and $R^b$ are hydrogen.

In some embodiments, a compound of formula XIII has the following formulas

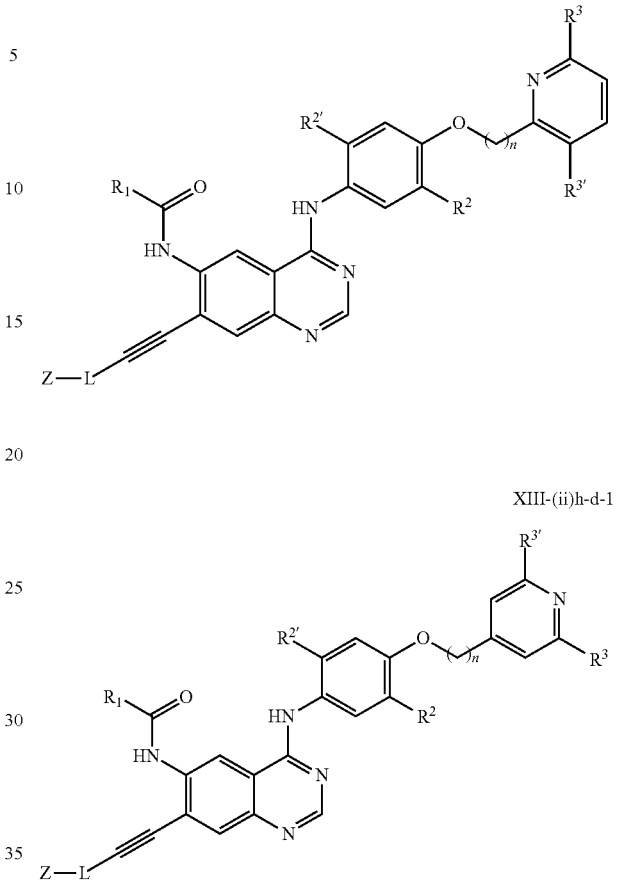

wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$ are as defined above for a compound of formula XIII.

In some embodiments substituent Z-L contains at least one nitrogen atom. Thus, the 3-6-membered heteroaryl or 3-9-membered heterocycloalkyl formed by $R^6$ and $R^7$ of ($CHR_6R_7$) includes a nitrogen atom if L does not contain a nitrogen atom.

In some embodiments $R^a$ and $R^b$ are hydrogen.

In some embodiments of a compound of formula XIII has the following formulas

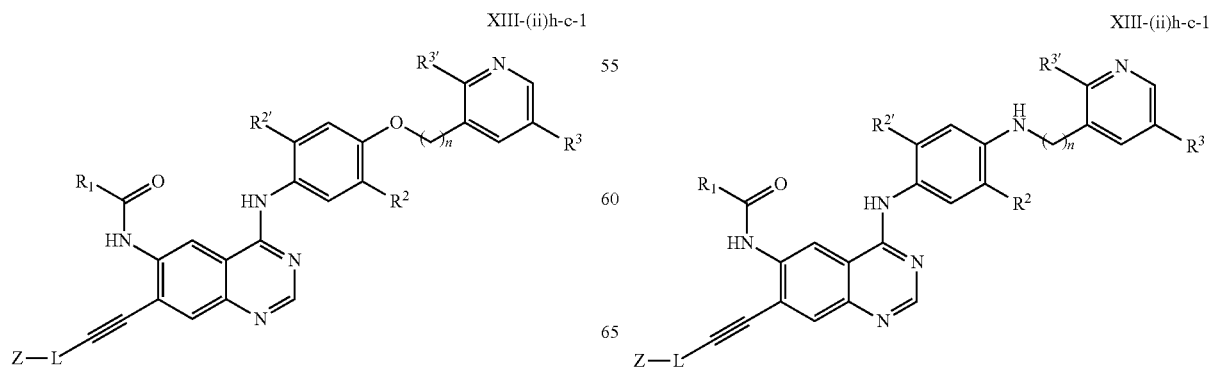

XIII-(ii)h-b-1

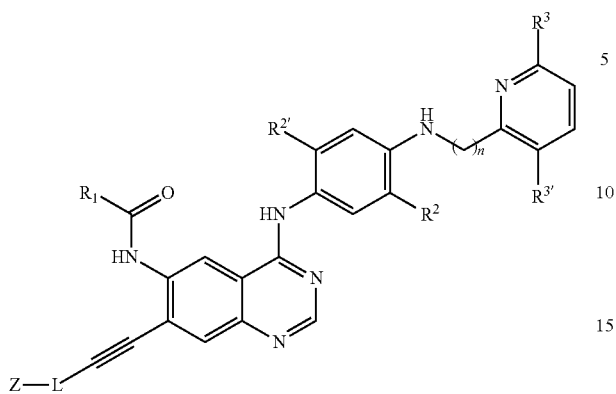

XIII-(ii)h-g-1

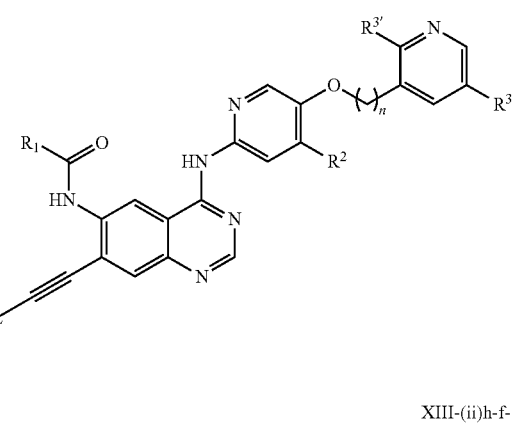

XIII-(ii)h-d-1

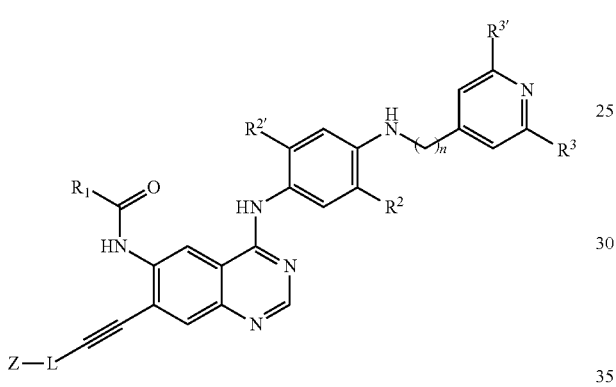

XIII-(ii)h-f-1

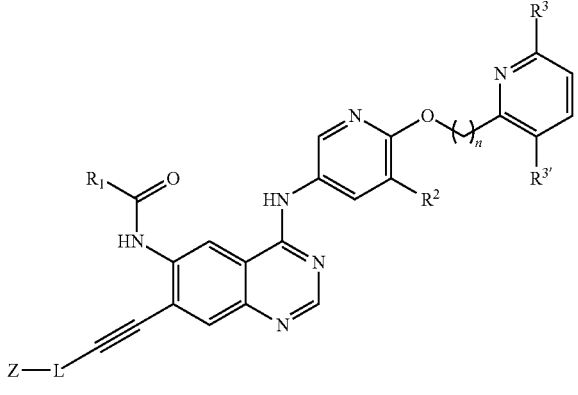

wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^1$ are as defined above for a compound of formula VI. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R^6$ and $R^7$ of ($CHR_6R_7$) includes a nitrogen atom if L does not contain a nitrogen atom.

In some embodiments $R^a$ and $R^b$ are hydrogen.

In some embodiments, a compound of formula XIII has the following formulas

XIII-(ii)h-h-1

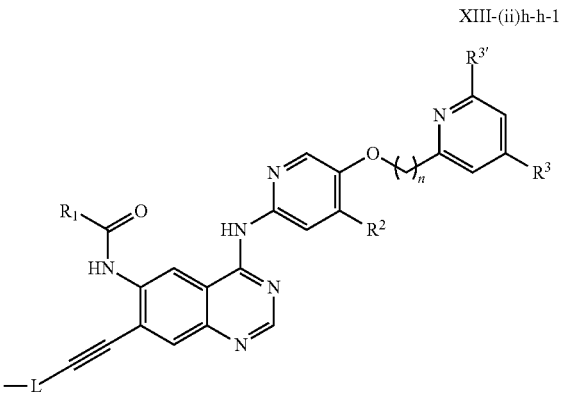

XIII-(ii)h-e-1

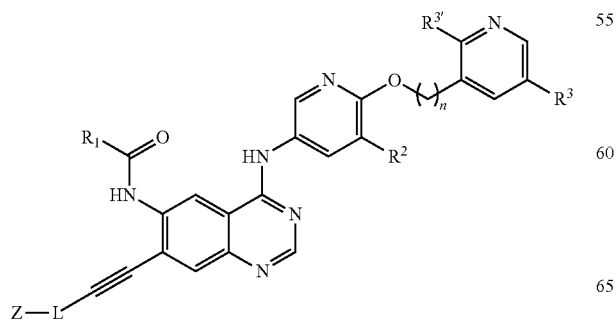

XIII-(ii)h-i-1

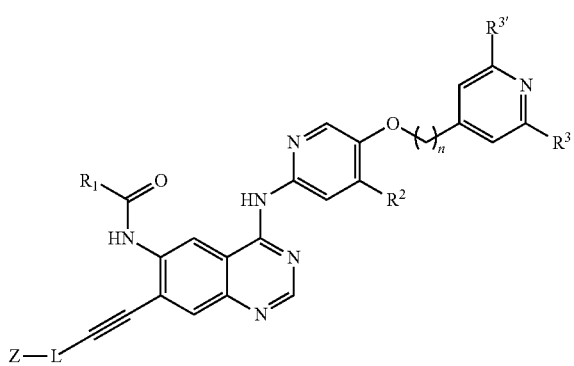

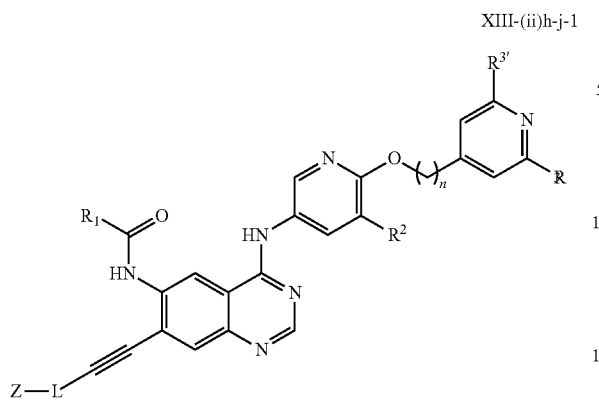

XIII-(ii)h-j-1

XIII-(ii)i-f-1 wherein R² is H, C$_{1-6}$ alkyl, hal (e.g. H, —CH$_3$, F, Cl); R³, R³' are H, C$_{1-6}$ alkyl, hal, —CF$_3$, —OCF$_3$; and n is 0 or 1; and Z, L, R¹ are as defined above for a compound of formula XIII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if L does not contain a nitrogen atom.

In some embodiments R$^a$ and R$^b$ are hydrogen.

In some embodiments of a compound of formula XIII has the following formulas

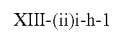

XIII-(ii)i-e-1

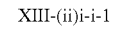

XIII-(ii)i-h-1

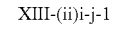

XIII-(ii)i-i-1

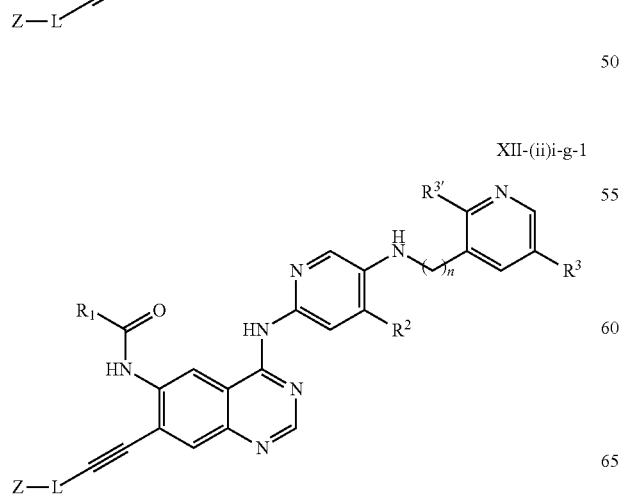

XII-(ii)i-g-1

XIII-(ii)i-j-1 wherein R² is H, C$_{1-6}$ alkyl, hal (e.g. H, —CH$_3$, F, Cl); R³, R³' are H, C$_{1-6}$ alkyl, hal, —CF$_3$, —OCF$_3$; and n is 0 or 1;

and Z, L, R¹ are as defined above for a compound of formula XIII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments of a compound of formula XIII has the following formulas

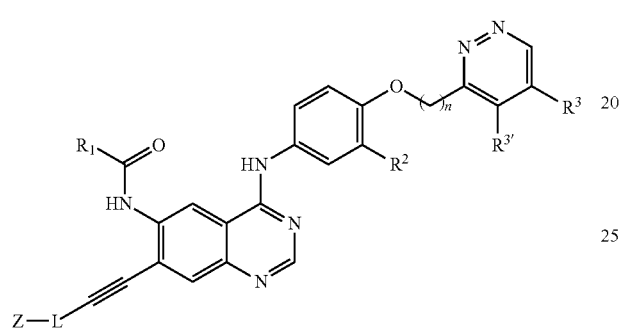

XIII-(ii)h-k-1

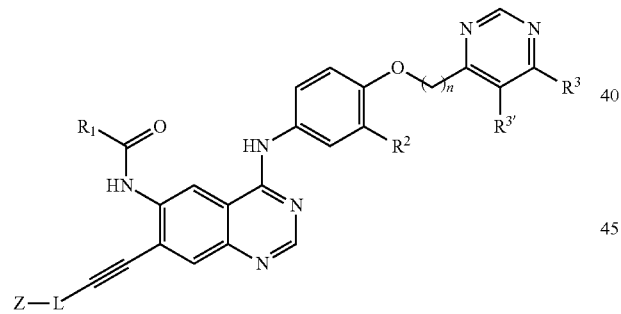

XIII-(ii)h-l-1

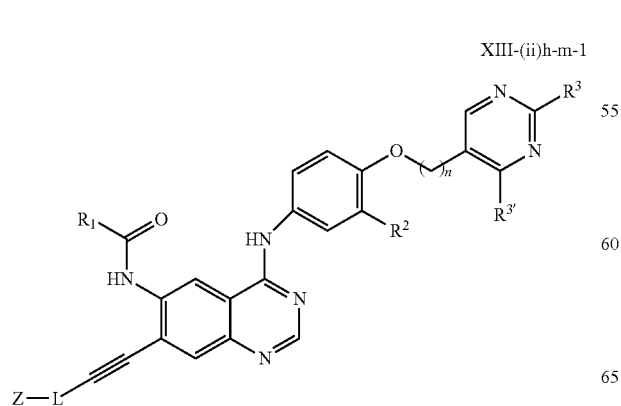

XIII-(ii)h-m-1

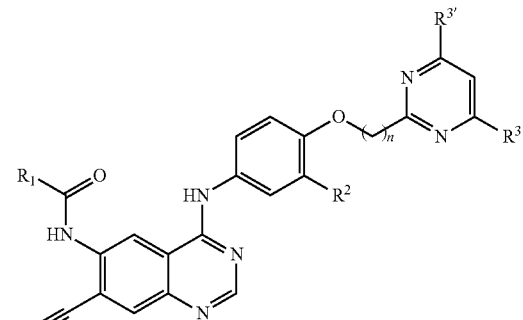

XIII-(ii)h-n-1

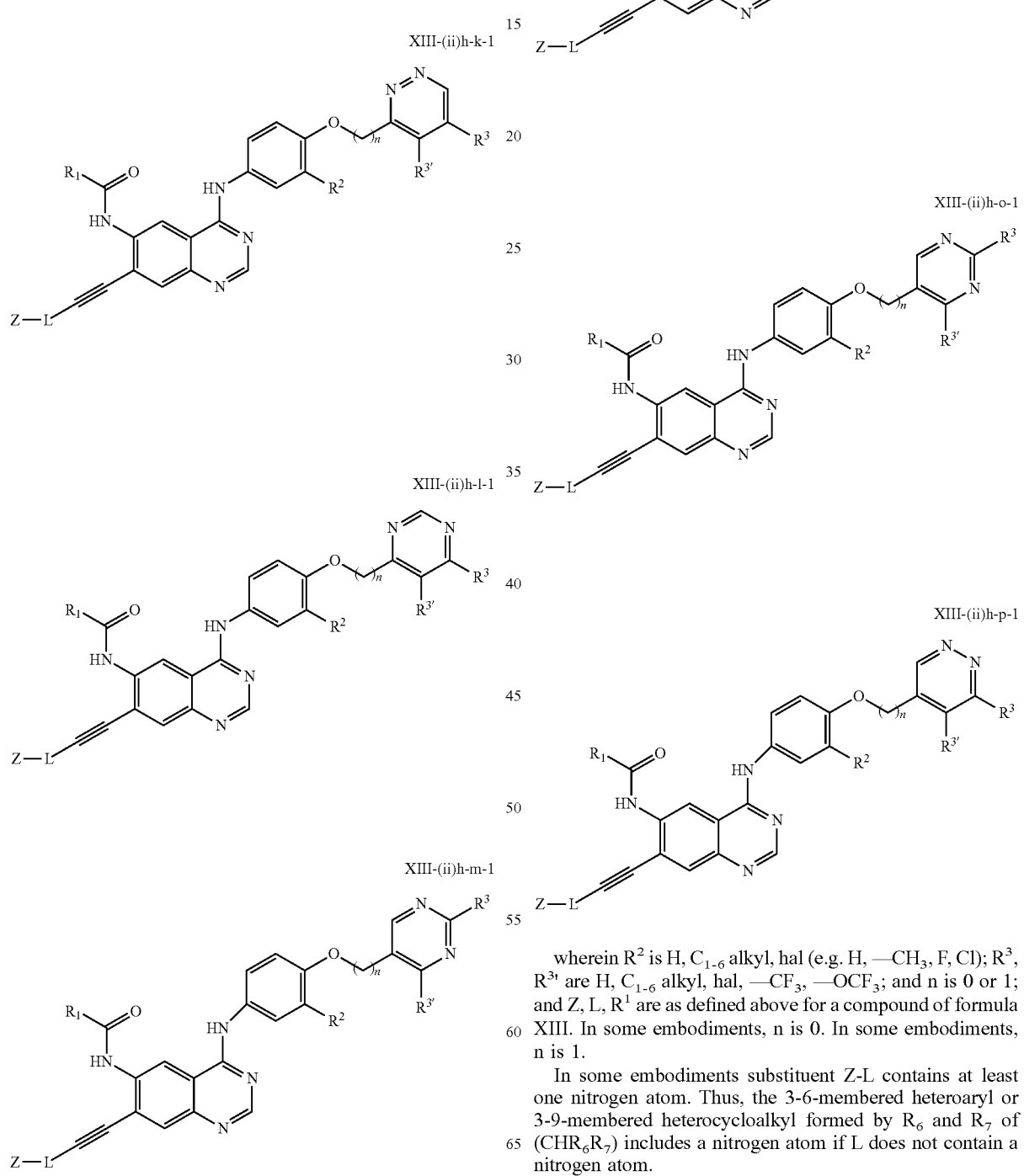

XIII-(ii)h-o-1

XIII-(ii)h-p-1 wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, R¹ are as defined above for a compound of formula XIII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments of a compound of formula XIII has the following formulas

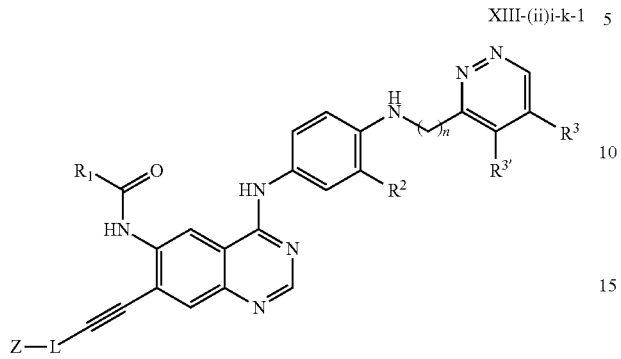

XIII-(ii)i-k-1

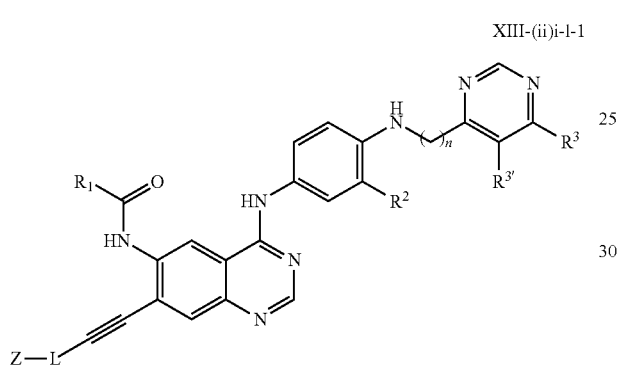

XIII-(ii)i-l-1

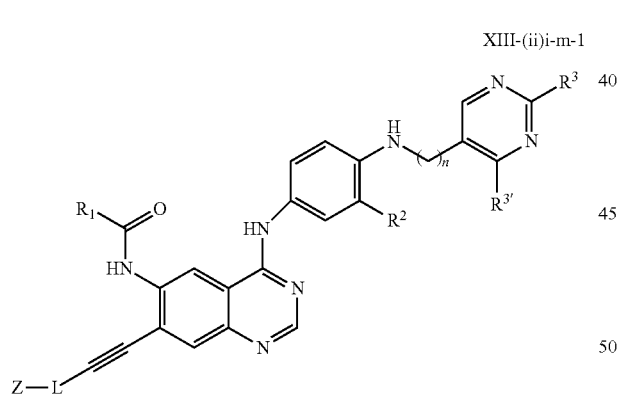

XIII-(ii)i-m-1

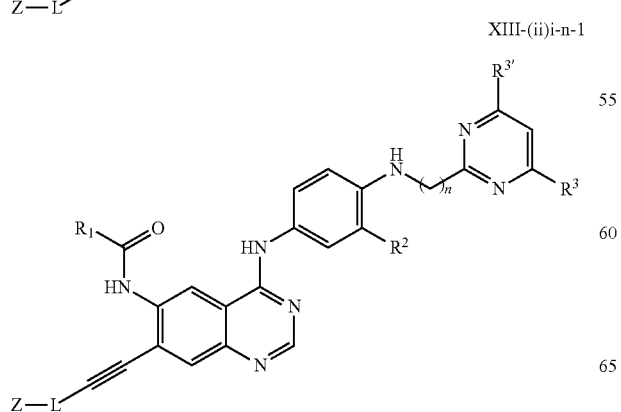

XIII-(ii)i-n-1

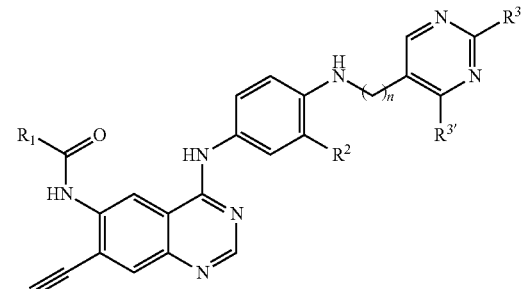

XIII-(ii)i-o-1

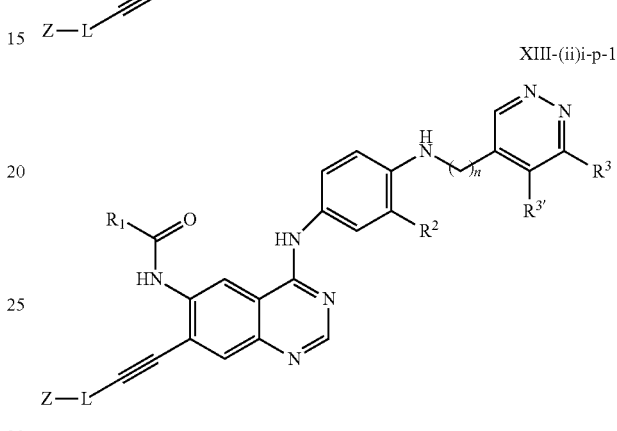

XIII-(ii)i-p-1 wherein $R^2$ is H, $C_{1-6}$ alkyl, hal (e.g. H, —CH$_3$, F, Cl); $R^3$, $R^{3'}$ are H, $C_{1-6}$ alkyl, hal, —CF$_3$, —OCF$_3$; and n is 0 or 1; and Z, L, $R^1$ are as defined above for a compound of formula XIII. In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R^6$ and $R^7$ of (CHR$_6$R$_7$) includes a nitrogen atom if L does not contain a nitrogen atom.

In some embodiments $R^a$ and $R^b$ are hydrogen.

In some embodiments, $R^4$ and $R^5$ are independently of each other H, $C_{1-4}$ alkyl, cyclopropyl, tetrahydrofuryl.

In some embodiments, L is a covalent bond or straight chain or branched $C_{1-4}$ alkyl (e.g. —CH$_2$—, —(CH$_2$)$_2$—, —(CH$_2$)$_3$—, —(CH$_2$)$_4$— or —C(CH$_3$)$_2$— or —CH$_2$—C(CH$_3$)$_2$—).

In some embodiments of a compound of formula XIII, a 3 to 6-membered heterocycloalkyl (in combination with —(NR$^4$R$^5$)) refers to a non-aromatic or partially aromatic ring system having 3, 4, 5, or 6 ring atoms selected from C, N, O, or S (e.g. C, N, or O), the number of N atoms being 0, 1, 2 and the number of O and S atoms each being 0, 1, 2. Examples of 3 to 6-membered heterocycloalkyl groups include oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl and the like. In some embodiments, 3 to 6-membered heterocycloalkyl include 5-membered heterocycloalkyl having 1 or 2 O-atoms, such as oxiranyl, oxetanyl, tetrahydrofuranyl, dioxanyl.

In some embodiments of a compound of formula XIII, a 3 to 6-membered heteroaryl (in combination with —(NR$^6$R$^7$) or —(CHR$^6$R$^7$)) refers to a (fully) aromatic ring system having 3, 4, 5, or 6 ring atoms (e.g. 5 ring atoms), selected from C, N, O, or S (e.g. C, N, or O, and C or N, with the number of N atoms being 0, 1, 2 or 3 and the number of O and S atoms each being 0, 1 or 2). Examples of "heteroaryl" include furyl, imidazolyl, isoxazolyl, oxazolyl, pyrazinyl, pyrazolyl (pyrazyl), pyridazinyl, pyridinyl, pyrimidinyl, pyrrolyl, thiazolyl, thienyl, and the like. In some embodiments, examples of "heteroaryl" include pyrrolyl, imidazolyl. Preferably, the aromatic ring system is a nitrogen containing heteroaryl.

In some embodiments of a compound of formula XIII, a 3 to 9-membered heterocycloalkyl (in combination with —(NR$^6$R$^7$) or —(CHR$^6$R$^7$)) refers to a non-aromatic or partially aromatic ring system having 3 to 9 ring atoms selected from C, N, O, or S (e.g. C, N, or O), the number of N atoms being 0, 1, 2 or 3 and the number of O and S atoms each being 0, 1 or 2. Examples of a 3 to 9-membered heterocycloalkyl (in combination with —(NR$^6$R$^7$) or —(CHR$^6$R$^7$)) include monocycles such as oxiranyl, thiaranyl, aziradinyl, oxetanyl, thiatanyl, azetidinyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxane, 1,3-dithianyl, piperazinyl, thiomorpholinyl, dioxothiomorpholinyl, piperidinyl, morpholinyl, oxepanyl, thiepanyl, azepanyl, diazepanyl, oxazepanyl (e.g. azetidinyl, pyrrolidinyl, piperidinyl, piperazinyl, morpholinyl, azepanyl); fused ring systems, such as 3-azabicyclo[3.1.0]hexyl, 3-azabicyclo[3.3.0]octyl, 3,7-diazabicyclo[3.3.0]octyl, 3-aza-7-oxabicyclo[3.3.0]octyl, 2,6-diazabicyclo[3.3.0]octyl, 2,7-diazabicyclo[3.3.0]octyl, 2,8-diazabicyclo[4.3.0]nonyl, 3-oxa-8-azabicyclo[4.3.0]nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4.3.0]nonyl, and the like; bridged ring systems such as bicyclo[3.3.1]nonanyl, bicyclo[3.2.1]octanyl, bicyclo[2.2.2]octanyl, bicyclo[3.1.1]heptanyl, bicyclo[2.2.1]heptanyl (e.g. bicyclo[3.2.1]octanyl, bicyclo[2.2.1]heptanyl), having one or two heteroatoms selected from N and O; spiro ring systems such as spiropentanyl, spiro[2.3]hexanyl spiro[3.3] heptanyl, spiro[3.4]octanyl, spiro[4.4]nonanyl, spiro[3.5] nonanyl, spiro[4.5]decanyl (e.g. spiro[3.3]heptanyl, spiro [4.4]nonanyl), having one or two heteroatoms selected from N and O (e.g. diazaspiro[3.3]heptanyl, oxa-azaspiro[3.3] heptanyl, diazaspiro[4.4]nonanyl, oxa-azaspiro[4.4] nonanyl). Preferably, the 3 to 9-membered heterocycloalkyl contains at least one nitrogen atom. In some embodiments, Z is —(NR$^4$R$^5$), wherein R$^4$ and R$^5$ are independently of each other H, C$_{1-6}$ alkyl, cyclopropyl, cylobutyl, 3 to 6-membered heterocycloalkyl containing 0, 1, or 2 N-atoms and 0, 1, or 2 O-atoms, or —(NR$^6$R$^7$), —(CHR$^6$R$^7$), wherein R$^6$ and R$^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with C$_{1-4}$ alkyl, hal, —OR', —NR'R", wherein R', R" are independently of each other H or -C$_{1-4}$ alkyl.

In some embodiments, —(NR$^6$R$^7$) ring systems include

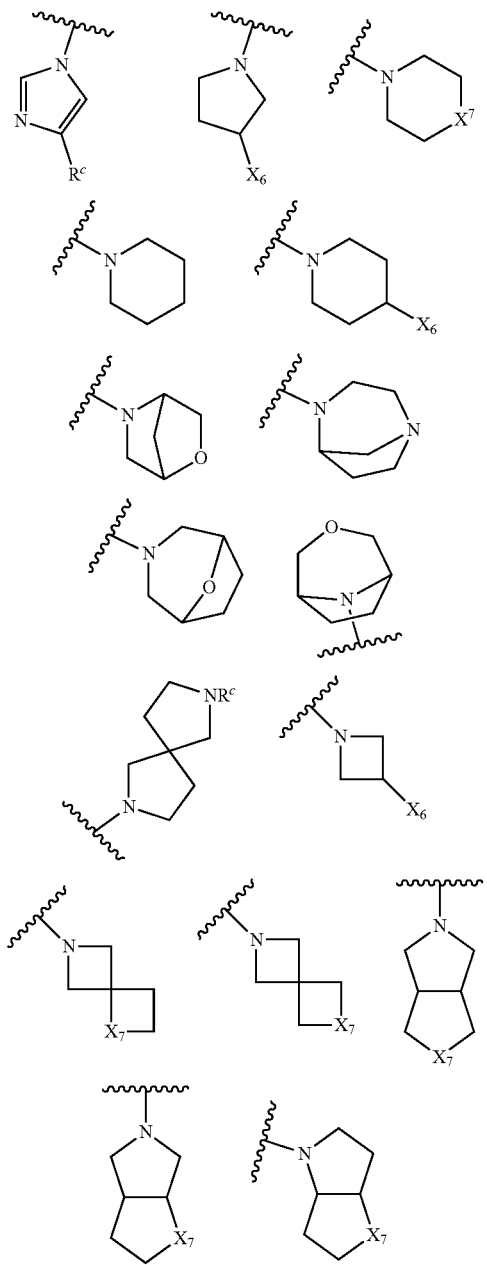

wherein R$^c$ is H, C$_{1-4}$ alkyl, oxetane; X$^6$ is H, —CH$_3$, —OH, —OCH$_3$, —OCF$_3$, —N(CH$_3$)$_2$, F, Cl; X$^7$ is —O—, —NH— or —N(CH$_3$)—, —SO$_2$.

In some embodiments, —(CHR$^6$R$^7$) ring systems include

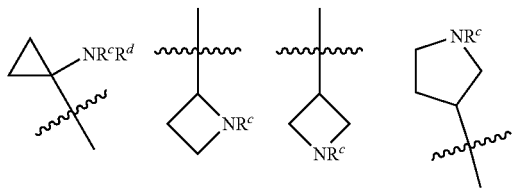

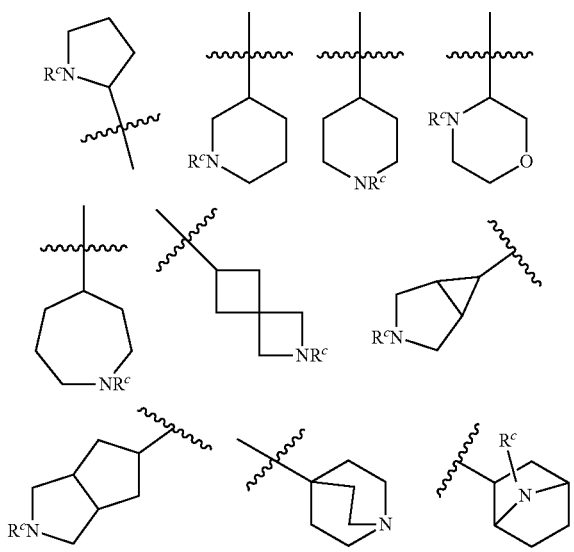

wherein $R^c$ is H, $C_{1-4}$ alkyl, oxetane, and $R^d$ is H, $C_{1-4}$ alkyl.

In some embodiments, —(NHR$^6$R$^7$) and —(CHR$^6$R$^7$) include

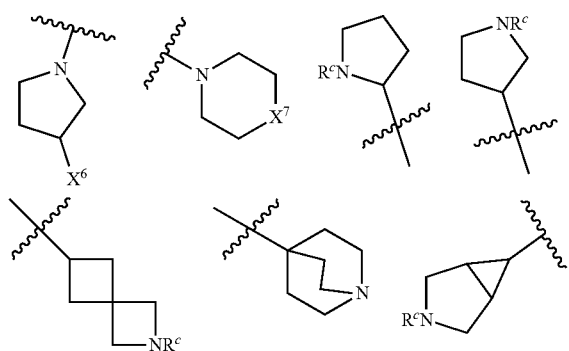

wherein $R^c$ is H, $C_{1-4}$ alkyl (e.g. H, —CH$_3$); $X^6$ is H, $C_{1-4}$ alkyl (e.g. H, —CH$_3$); $X^7$ is —O—, —NH— or —N(CH$_3$)—, (e.g. —N(CH$_3$)—).

In some embodiments, the compound of formula XIII has the formula XIV or XV

XIV

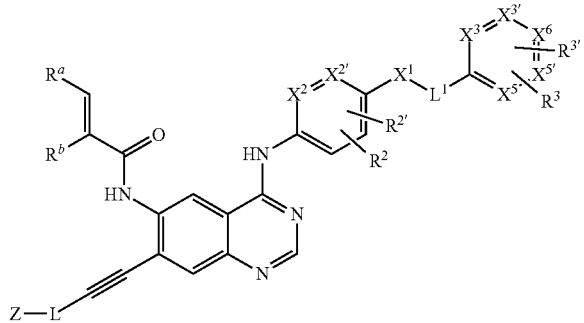

XV

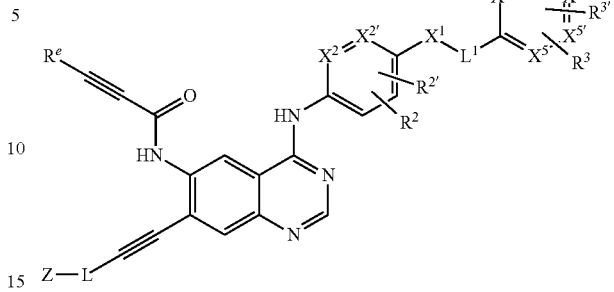

wherein $X^1$ is —O—, —CH$_2$—, —NH—, —S—; $X^2$, $X^{2'}$, $X^3$, $X^{3'}$, $X^5$, $X^{5'}$, $X^6$ are independently of each other —N═, —CH═;

$L^1$ is a covalent bond or straight chain or branched $C_{1-3}$alkyl, which is unsubstituted or substituted with hal, $R^2$, $R^{2'}$, $R^3$, $R^{3'}$ are independently of each other H, $C_{1-6}$ alkyl, hal, —CF$_3$, —OCF$_3$;

L is a covalent bond, straight chain or branched $C_{1-4}$ alkyl or

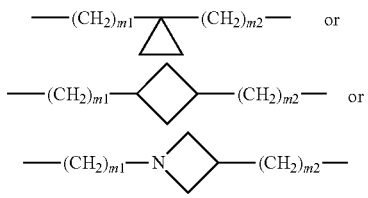

wherein m1, m2 are independently of each other 0, 1, 2, 3, or 4;

Z is —(NR$^4$R$^5$), wherein R$^4$ and R$^5$ are independently of each other H, $C_{1-6}$ alkyl, cyclopropyl, cylobutyl, 3 to 6-membered heterocycloalkyl, —(NR$^6$R$^7$), —(CHR$^6$R$^7$), wherein R$^6$ and R$^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

$R^a$, $R^b$ are independently of each other H, hal, or —CH$_2$—O—CH$_3$ (e.g. H), and R$_e$ is H or methyl.

In some embodiments substituent Z-L contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if L does not contain a nitrogen atom.

In some embodiments R$^a$ and R$^b$ are hydrogen.

In some embodiments, $L^1$ is straight chain or branched $C_{1-3}$alkyl, which is unsubstituted or substituted with hal. In some embodiments, $L^1$ is not a covalent bond.

In some embodiments, $X^3$, $X^{3'}$, $X^5$, $X^{5'}$, $X^6$ are —CH═ (i.e. a phenyl ring). In some embodiments, $X^3$ is —N═ and $X^{3'}$, $X^5$, $X^{5'}$, $X^6$ are —CH═ or $X^{3'}$ is —N═ and $X^3$, $X^5$, $X^{5'}$, $X^6$ are is —CH═ or $X^6$ is —N═ and $X^3$, $X^{3'}$, $X^5$, $X^{5'}$ are —CH═ (i.e. a pyridine ring).

In some embodiments, both $X^3$, $X^{3'}$ are —N═ and $X^5$, $X^{5'}$, $X^6$ are —CH═ or both $X^{3'}$, $X^6$ are —N═ and $X^3$, $X^5$, $X^{5'}$ are —CH═ (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring). In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= (i.e. a pyridine ring).

In some embodiments, $R^2$ and $R^{2'}$ are independently of each other H, $C_{1-6}$ alkyl, hal (e.g. H, —CH$_3$, F, Cl). In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —CF$_3$, —OCF$_3$. In some embodiments, $R^3$ is H, $C_{1-6}$ alkyl, hal, —CF$_3$, —OCF$_3$ and $R^{3'}$ is H, hal.

In some embodiments, $R^2$ and $R^{2'}$ are H and $R^3$ is H, $C_{1-6}$ alkyl, hal, —CF$_3$, —OCF$_3$ and $R^{3'}$ is H, hal; or $R^2$ and $R^{2'}$ are hal and $R^3$ is H, $C_{1-6}$ alkyl, hal, —CF$_3$, —OCF$_3$ and $R^{3'}$ is H, hal; or $R^2$ is hal or $C_{1-6}$ alkyl and $R^{2'}$ is H and $R^3$ is H, $C_{1-6}$ alkyl, hal, —CF$_3$, —OCF$_3$ and $R^{3'}$ is H; or $R^2$ is hal or $C_{1-6}$ alkyl and $R^{2'}$ is H and $R^{3'}$ is $C_{1-6}$ alkyl, hal and $R^3$ is H.

In some embodiments, $R^4$ and $R^5$ are independently of each other H, $C_{1-4}$ alkyl, cyclopropyl, tetrahydrofuryl (e.g. $C_{1-4}$ alkyl).

In some embodiments, L is a covalent bond or straight chain or branched $C_{1-4}$ alkyl (e.g. —CH$_2$—, —(CH$_2$)$_2$—, —(CH$_2$)$_3$—, —(CH$_2$)$_4$— or —C(CH$_3$)$_2$— or —CH$_2$—C(CH$_3$)$_2$—).

Group Z is as defined above. In some embodiments, Z is —(NR$^4$R$^5$), wherein $R^4$ and $R^5$ are independently of each other H, $C_{1-6}$ alkyl, cyclopropyl, cylobutyl, 3 to 6-membered heterocycloalkyl containing 0, 1, or 2 N-atoms and 0, 1, or 2 O-atoms, or —(NR$^6$R$^7$), —(CHR$^6$R$^7$), wherein $R^6$ and $R^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments, —(NR$^6$R$^7$) ring systems include

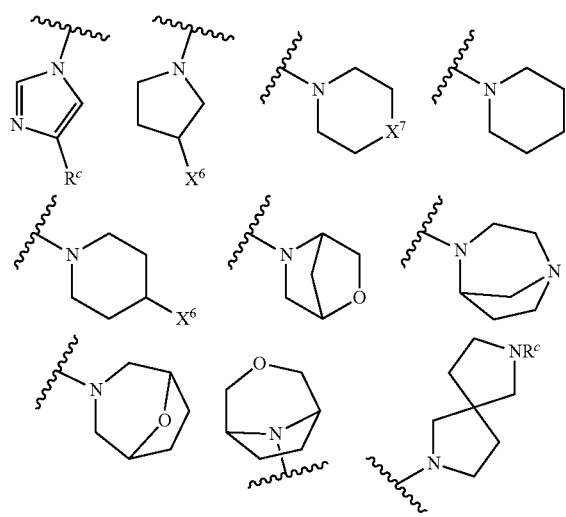

-continued

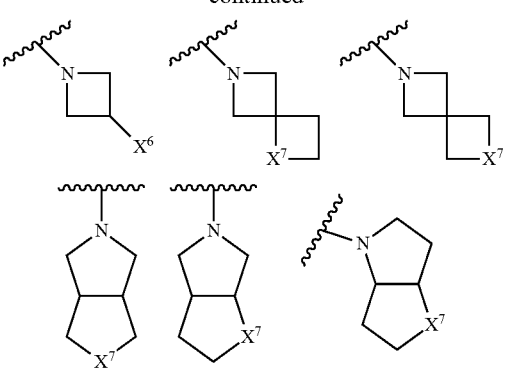

wherein $R^c$ is H, $C_{1-4}$ alkyl, oxetane; $X^6$ is H, —CH$_3$, —OH, —OCH$_3$, —OCF$_3$, —N(CH$_3$)$_2$, F, Cl; $X^7$ is —O—, —NH— or —N(CH$_3$)—, —SO$_2$.

In some embodiments, —(CR$^6$R$^7$) ring systems include

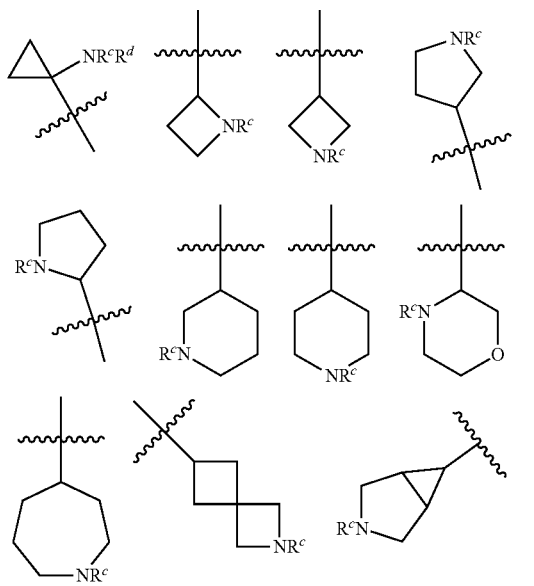

wherein W is H, $C_{1-4}$ alkyl, oxetane, and $R^d$ is H, $C_{1-4}$ alkyl.

In some embodiments, —(NHR$^6$R$^7$) and —(CHR$^6$R$^7$) include

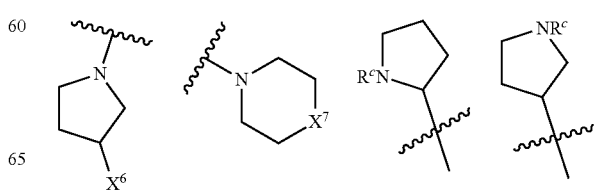

-continued

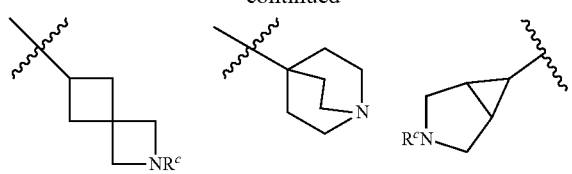

wherein $R^c$ is H, $C_{1-4}$ alkyl (e.g. H, —$CH_3$); $X^6$ is H, $C_{1-4}$ alkyl (e.g. H, —$CH_3$); $X^7$ is —O—, —NH— or —N($CH_3$)— (e.g. —N($CH_3$)—).

In some embodiments, L is a covalent bond. In some embodiments, L is straight chain or branched $C_{1-4}$ alkyl (e.g. —$CH_2$—, —($CH_2$)$_2$—, —($CH_2$)$_3$—, —($CH_2$)$_4$—, —C($CH_3$)$_2$— or —$CH_2$—C($CH_3$)$_2$—). In some embodiments, L is

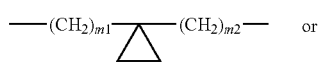

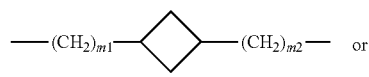

—($CH_2$)$_{m1}$—N⟨azetidine⟩—($CH_2$)$_{m2}$— wherein m1, m2 are independently of each other 0, 1 or 2.

In some embodiments, $X^1$ is —O—. In some embodiments, $X^1$ is —$CH_2$—. In some embodiments, $X^1$ is —NH—. In some embodiments, $X^1$ is —S—. In some embodiments, $L^1$ is a covalent bond. In some embodiments, $L^1$ is —$CH_2$— or —CH($CH_3$)— or —CH(hal)-. In some embodiments, $L^1$ is —$CH_2$—$CH_2$— or —$CH_2$CH($CH_3$)— or —$CH_2$—CH(hal)-.

In some embodiments, linker combinations -$X^1$-$L^1$- include —O—, —$CH_2$—, —O—$CH_2$—, —NH—$CH_2$—, —S—$CH_2$—, —$CH_2$—$CH_2$—, —O—CH($CH_3$)—, —$CH_2$—CH($CH_3$)—, —NH—CH($CH_3$)—, —S—CH($CH_3$)—, —O—CH(hal)-, $CH_2$—CH(hal)-, —NH—CH(hal)-, —S—CH(hal)- (e.g. —O—, —$CH_2$—, —O—$CH_2$—, —NH—$CH_2$—, —$CH_2$—$CH_2$—, —O—CH($CH_3$)—, —$CH_2$—CH($CH_3$)—, —O—CH(hal)-, —$CH_2$—CH(hal)- and —O—, —$CH_2$—, —O—$CH_2$—, —NH—$CH_2$—, —$CH_2$—$CH_2$—).

In some embodiments, -$X^1$-$L^1$- is —O—, In some embodiments, -$X^1$-$L^1$- is —O—$CH_2$—. In some embodiments, -$X^1$-$L^1$- is —NH—. In some embodiments, -$X^1$-$L^1$- is —NH—$CH_2$—.

In some embodiments, the compound of formula XIV and XV has the formula XIV-1, XV-1 and XIV-2, XV-2

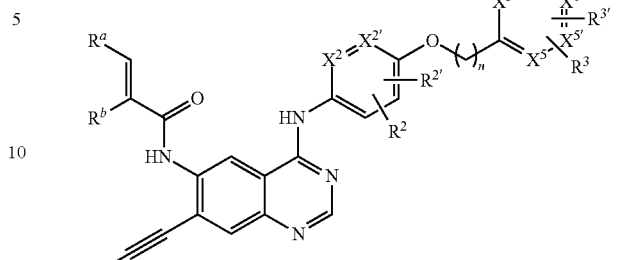
XIV-1

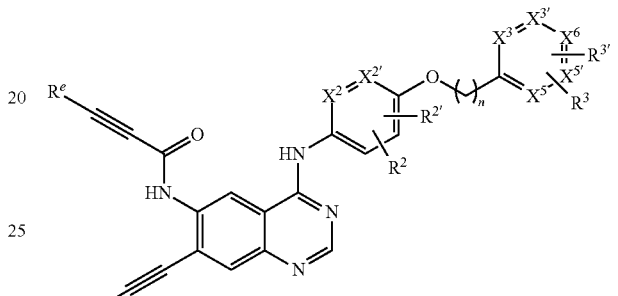
XV-1

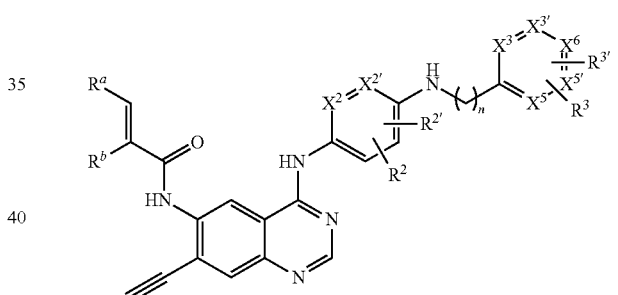
XIV-2

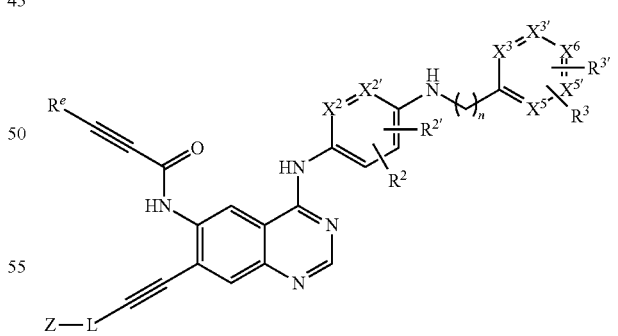
XV-2 wherein $X^2$, $X^{2'}$, $X^3$, $X^{3'}$, $X^5$, $X^{5'}$, $X^6$ are independently of each other —N=, —CH=;

$R^2$, $R^{2'}$, $R^3$, $R^{3'}$ are independently of each other H, $C_{1-6}$ alkyl, hal, —$CF_3$, —$OCF_3$;

L is a covalent bond, straight chain or branched $C_{1-4}$ alkyl or

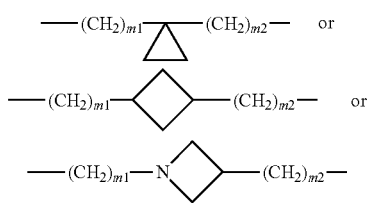

wherein m1, m2 are independently of each other 0, 1, 2, 3, or 4 (e.g. a covalent bond, straight chain or branched $C_{1-4}$ alkyl);

Z is —($NR^4R^5$), wherein $R^4$ and $R^5$ are independently of each other H, $C_{1-6}$ alkyl, cyclopropyl, cylobutyl, 3 to 6-membered heterocycloalkyl, or —($NR^6R^7$), —($CHR^6R^7$), wherein $R^6$ and $R^7$ form together with the atom to which they are attached to 3 to 6-membered heteroaryl or 3 to 9-membered heterocycloalkyl, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R'', wherein R', R'' are independently of each other H or -$C_{1-4}$ alkyl:

$R^a$, $R^b$ are independently of each other H, hal, or —$CH_2$—O—$CH_3$ (e.g. H), and $R_e$ is H or methyl.

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom, In some embodiments $R_a$ and $R^b$ are hydrogen.

In some embodiments, both $X^2$, $X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2$, $X^{2'}$ are —N= (i.e. a pyridazine ring).

In some embodiments, $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= or $X^6$ is —N= and $X^3$, $X^{3'}$, $X^5$, $X^{5'}$ are —CH= (i.e. a pyridine ring).

In some embodiments, both $X^3$, $X^{3'}$ are —N= and $X^5$, $X^{5'}$, $X^6$ are —CH= or both $X^{3'}$, $X^6$ are —N= and $X^3$, $X^5$, $X^{5'}$ are —CH= (i.e. a pyridazine ring). In some embodiments, both $X^3$, $X^5$ are —N= and $X^{3'}$, $X^{5'}$, $X^6$ are —CH= or both $X^{3'}$, $X^{5'}$ are —N= and $X^3$, $X^5$, $X^6$ are —CH= or both $X^3$, $X^6$ are —N= and $X^{3'}$, $X^5$, $X^{5'}$ are —CH= (i.e. a. pyrimidine ring). In some embodiments, both $X^3$, $X^{5'}$ are —N= and $X^{3'}$, $X^5$, $X^6$ are —CH= (i.e. a pyrazine ring).

In some embodiments, $X^2$, $X^{2'}$ are —CH= (i.e. a phenyl ring). $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= (i.e. a pyridine ring).

In some embodiments, $X^2$, $X^{2'}$ are —CH= (i.e. a phenyl ring). $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= (i.e. a pyridine ring).

In some embodiments, $X^2$, $X^{2'}$ are —CH= (i.e. a phenyl ring). $X^3$, $X^{3'}$, $X^5$, $X^{5'}$, $X^6$ are —CH= (i.e. a phenyl ring). In some embodiments, $X^3$ is —N= and $X^{3'}$, $X^5$, $X^{5'}$, $X^6$ are —CH= or $X^{3'}$ is —N= and $X^3$, $X^5$, $X^{5'}$, $X^6$ are —CH= (i.e. a pyridine ring).

$R^2$ and $R^{2'}$ are independently of each other H, $C_{1-6}$ alkyl, hal (e.g. H, —$CH_3$, F, Cl). In some embodiments, $R^2$ and $R^{2'}$ are H. In some embodiments, $R^2$ and $R^{2'}$ are hal. In some embodiments, $R^2$ is hal and $R^{2'}$ is H.

In some embodiments, $R^3$ and $R^{3'}$ are independently of each other H, $C_{1-6}$ alkyl, hal, —$CF_3$, —$OCF_3$. In some embodiments, $R^3$ is H, $C_{1-6}$ alkyl, hal, —$CF_3$, —$OCF_3$ and $R^{3'}$ is H, hal.

In some embodiments, $R^2$ and $R^{2'}$ are H and $R^3$ is H, $C_{1-6}$ alkyl, hal, —$CF_3$, —$OCF_3$ and $R^{3'}$ is H, hal; or $R^2$ and $R^{2'}$ are hal and $R^3$ is H, $C_{1-6}$ alkyl, hal, —$CF_3$, —$OCF_3$ and $R^{3'}$ is H, hal; or $R^2$ is hal or $C_{1-6}$ alkyl and $R^{2'}$ is H and $R^3$ is H, $C_{1-6}$ alkyl, hal, —$CF_3$, —$OCF_3$ and $R^{3'}$ is H; or $R^2$ is hal or $C_{1-6}$ alkyl and $R^{2'}$ is H and $R^{3'}$ is $C_{1-6}$ alkyl, hal and $R^3$ is H.

In some embodiments, the compound of XIV-1, XV-1 has one of the following formulas

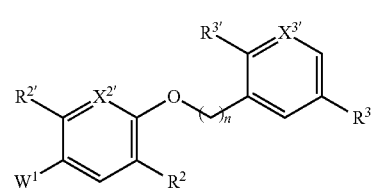

XIV-1-(ii)d-1

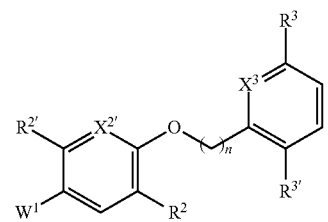

XIV-1-(ii)d-2

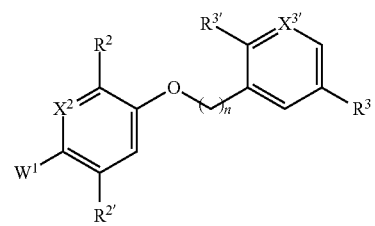

XIV-1-(ii)d-3

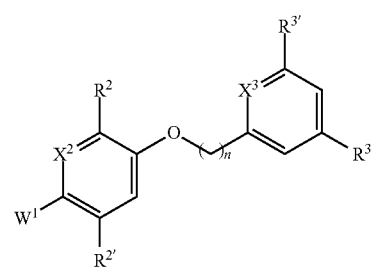

XIV-1-(ii)d-4

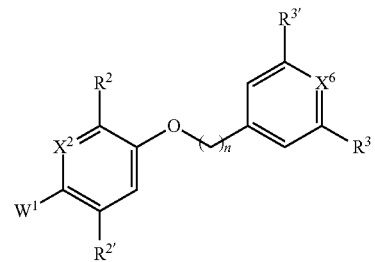

XIV-1-(ii)d-5

XIV-1-(ii)d-6

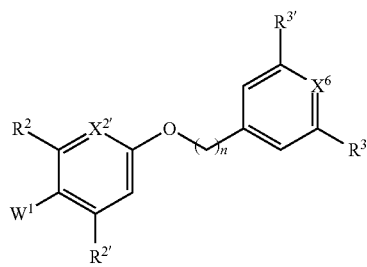

and W₁ is

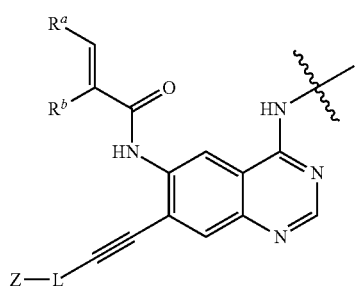

or

XV-1-(ii)d-1

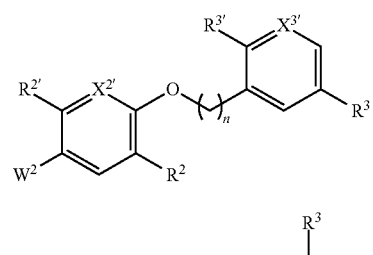

XV-1-(ii)d-2

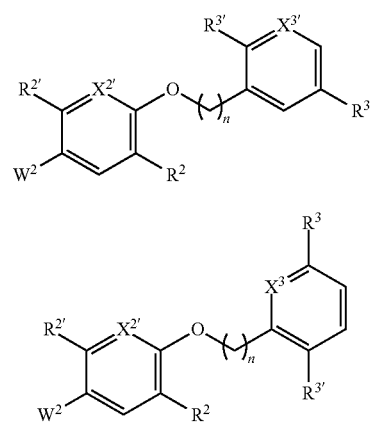

XV-1-(ii)d-3

XV-1-(ii)d-4

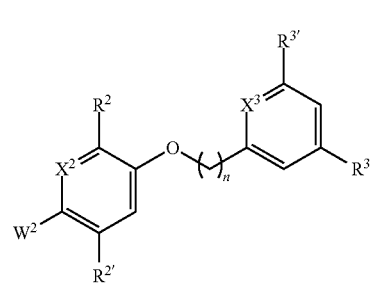

XV-1-(ii)d-5

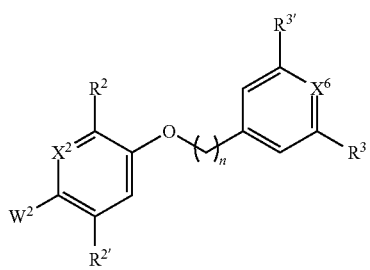

XV-1-(ii)d-6

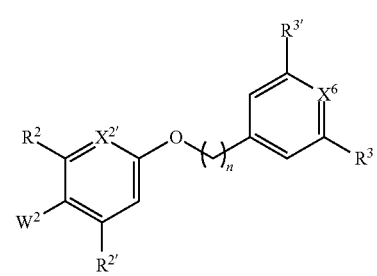

and W₂ is

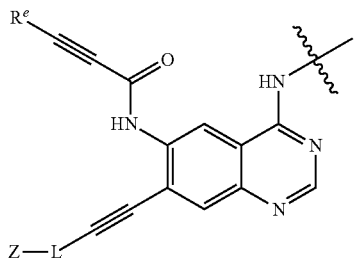

$X^2$, $X^{2'}$, $X^3$, $X^{3'}$, $X^5$, $X^{5'}$, $X^6$ are independently of each other —N= or —CH=; and $R^2$, $R^{2'}$, $R^3$, $R^{3'}$ are independently of each other H, $C_{1-6}$ alkyl, hal, —$CF_3$, or —$OCF_3$; and Z, L, $R^a$, $R^b$, $R^e$ are as defined above for a compound of formula XIV and XV (or XIV-1, XV-1).

In some embodiments substituent Z-L contains at least one nitrogen atom. Thus, the 3-6-membered heteroaryl or 3-9-membered heterocycloalkyl formed by $R_6$ and $R_7$ of (CHR₆R₇) includes a nitrogen atom if L does not contain a nitrogen atom.

In some embodiments $R^a$ and $R^b$ are hydrogen.

In some embodiments, $X^2$ and $X^{2'}$ are —CH= (i.e. a phenyl ring) and $X^3$, $X^{3'}$ and $X^6$ are —CH= (i.e. a phenyl ring).

In some embodiments, $X^2$ and $X^{2'}$ are —CH= (i.e. a phenyl ring) and $X^3$, $X^{3'}$ and $X^6$ are —N= (i.e. a pyridine ring).

In some embodiments, $X^2$ and $X^{2'}$ are —N= (i.e. a pyridine ring) and $X^3$, $X^{3'}$ and $X^6$ are —CH= (i.e. a phenyl ring).

In some embodiments, $X^2$ and $X^{2'}$ a —N= (i.e. a pyridine ring) and $X^3$, $X^{3'}$ and $X^6$ are —N= (i.e. a pyridine ring).

In some embodiments, a compound of formula XIV-1, XV-1 has one of the following formulas and $W_1$ is
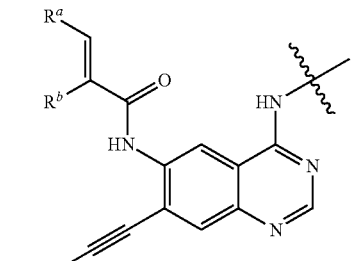
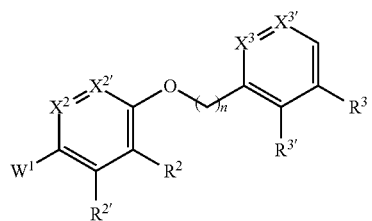 XIV-1-(ii)e-1
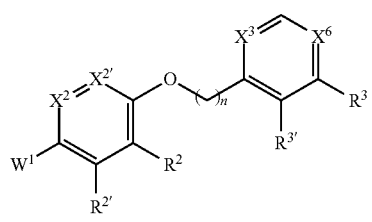 XIV-1-(ii)e-2
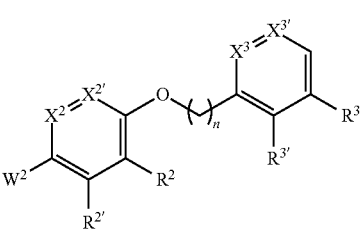 XV-1-(ii)e-1
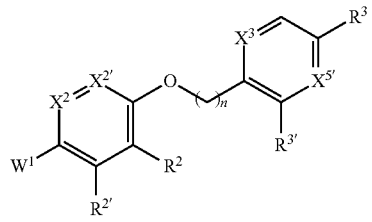 XIV-1-(ii)e-3
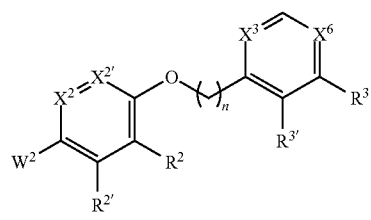 XV-1-(ii)e-2
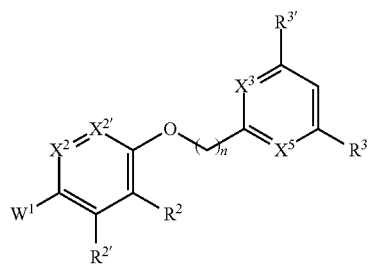 XIV-1-(ii)e-4
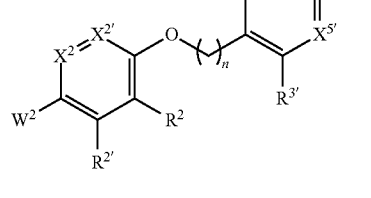 XV-1-(ii)e-3
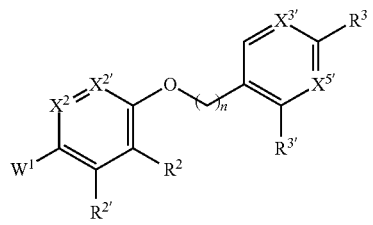 XIV-1-(ii)e-5
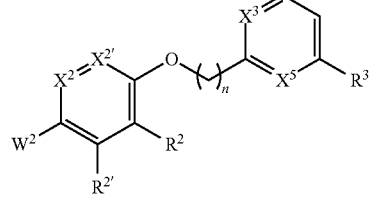 XV-1-(ii)e-4
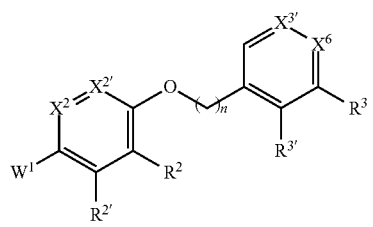 XIV-1-(ii)e-6
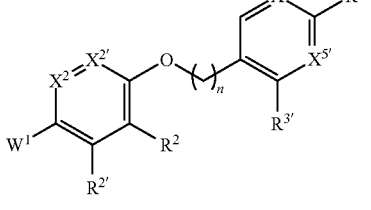 XIV-1-(ii)e-5

-continued

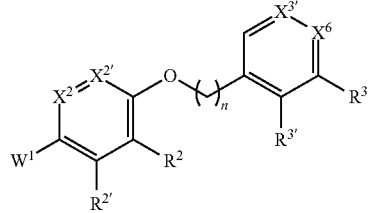
XIV-1-(ii)e-6 and W₂ is

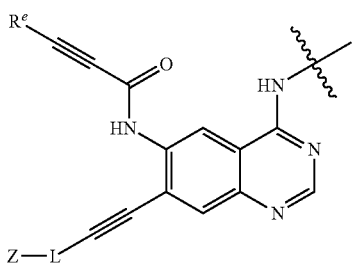

wherein $X^2, X^{2'}, X^3, X^{3'}, X^5, X^{5'}, X^6$ are independently of each other —N= or —CH=; and $R^2, R^{2'}, R^3, R^{3'}$ are independently of each other H, $C_{1-6}$ alkyl, hal, —CF₃, or —OCF₃, n is 0 or 1; and $Z, L, R^a, R^b, R^e$ are as defined above for a compound of formula XIV and XV (or XIV-1, XV-1).

In some embodiments substituent Z-L contains at least one nitrogen atom. Thus, the 3-6-membered heteroaryl or 3-9-membered heterocycloalkyl formed by $R_6$ and $R_7$ of (CHR₆R₇) includes a nitrogen atom if L does not contain a nitrogen atom.

In some embodiments $R^a$ and $R^b$ are hydrogen.

In some embodiments, both $X^2, X^{2'}$ are —CH= (i.e. a phenyl ring). In some embodiments, $X^2$ is —N= and $X^{2'}$ is —CH= or $X^{2'}$ is —N= and $X^2$ is —CH= (i.e. a pyridine ring). In some embodiments, both $X^2, X^{2'}$ are —N= (i.e. a pyridazine ring).

In some embodiments, $X^3, X^{3'}, X^5, X^{5'}, X^6$ are —CH= (i.e. a phenyl ring). In some embodiments, $X^3$ is —N= and $X^{3'}, X^5, X^{5'}, X^6$ are —CH= or $X^{3'}$ is —N= and $X^3, X^5, X^{5'}, X^6$ are —CH= or $X^6$ is —N= and $X^3, X^{3'}, X^5, X^{5'}$ are —CH= (i.e. a pyridine ring).

In some embodiments, both $X^3, X^{3'}$ are —N= and $X^5, X^{5'}, X^6$ are —CH= or both $X^{3'}, X^6$ are —N= and $X^3, X^5, X^{5'}$ are —CH= (i.e. a pyridazine ring). In some embodiments, both $X^3, X^5$ are —N= and $X^{3'}, X^{5'}, X^6$ are —CH= or both $X^{3'}, X^{5'}$ are —N= and $X^3, X^5, X^6$ are —CH= or both $X^3, X^6$ are —N= and $X^{3'}, X^5, X^{5'}$ are —CH= (i.e. a pyrimidine ring). In some embodiments, both $X^3, X^{5'}$ are —N= and $X^{3'}, X^5, X^6$ are —CH= (i.e. a pyrazine ring).

In some embodiments, $X^2, X^{2'}$ are —CH= (i.e. a phenyl ring). In some embodiments, $X^3, X^{3'}, X^5, X^{5'}, X^6$ are —CH= (i.e. a phenyl ring). In some embodiments, $X^3$ is —N= and $X^{3'}, X^5, X^{5'}, X^6$ are —CH= or $X^{3'}$ is —N= and $X^3, X^5, X^{5'}, X^6$ are —CH= (i.e. a pyridine ring). In some embodiments, a compound of formula XIV-2, XV-2 has one of the following formulas

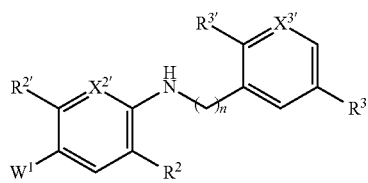
XIV-2-(ii)f-1

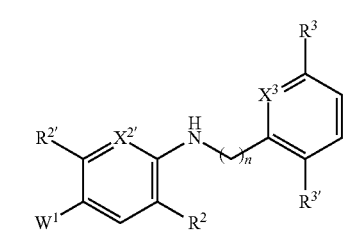
XIV-2-(ii)f-2

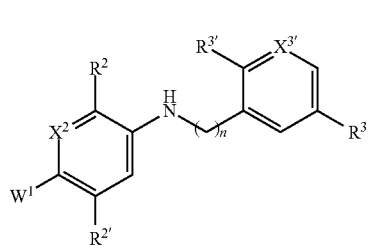
XIV-2-(ii)f-3

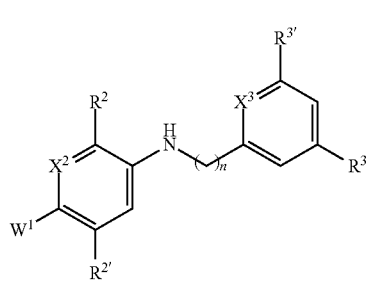
XIV-2-(ii)f-4

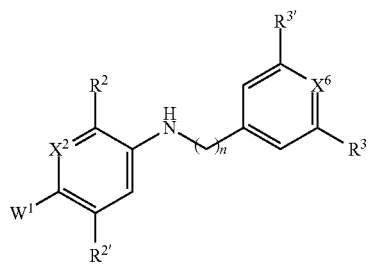
XIV-2-(ii)f-5

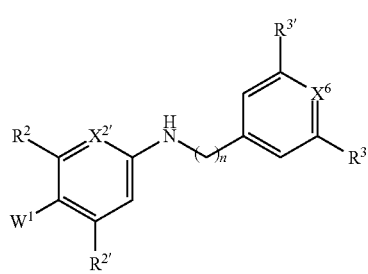
XIV-2-(ii)f-6 and $W_1$ is

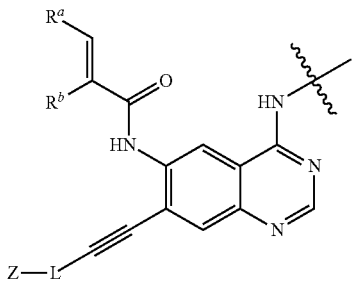

XV-2-(ii)f-1

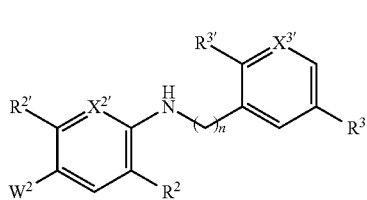

XV-2-(ii)f-2

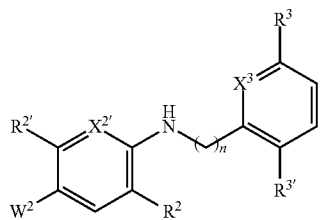

XV-2-(ii)f-3

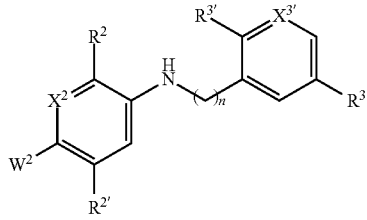

XV-2-(ii)f-4

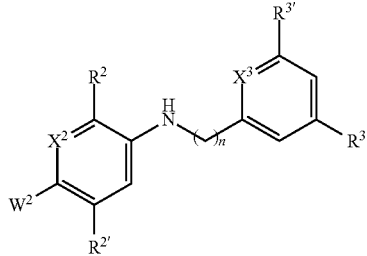

XV-2-(ii)f-5

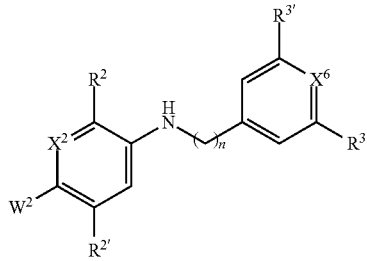

XV-2-(ii)f-6

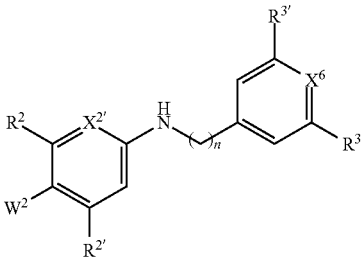

and $W_2$ is

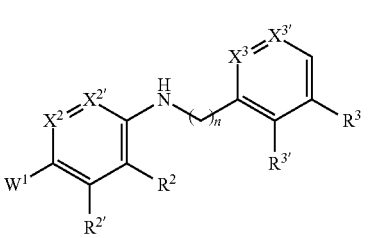

wherein $X^2, X^{2'}, X^3, X^{3'}, X^5, X^{5'}, X^6$ are independently of each other —N═ or —CH═; and $R^2, R^{2'}, R^3, R^{3'}$ are independently of each other H, $C_{1-6}$ alkyl, hal, —$CF_3$, or —$OCF_3$; and Z, L, $R^a$, $R^b$, $R^e$ are as defined above for a compound of formula XIV and XV (or XIV-2, XV-2).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, $X^2$ and $X^{2'}$ are —CH═ (i.e. a phenyl ring) and $X^3$, $X^{3'}$ and $X^6$ are —CH═ (i.e. a phenyl ring).

In some embodiments, $X^2$ and $X^{2'}$ are —CH═ (i.e. a phenyl ring) and $X^3$, $X^{3'}$ and $X^6$ are —N═ (i.e. a pyridine ring).

In some embodiments, $X^2$ and $X^{2'}$ are —N═ (i.e. a pyridine ring) and $X^3$, $X^{3'}$ and $X^6$ are —CH═ (i.e. a phenyl ring).

In some embodiments, $X^2$ and $X^{2'}$ a —N═ (i.e. a pyridine ring) and $X^3$, $X^{3'}$ and $X^6$ are —N═ (i.e. a pyridine ring).

In some embodiments, a compound of formula XI-2, XV-2 has one of the following formulas XIV-2-(ii)g-1

XIV-2-(ii)g-2
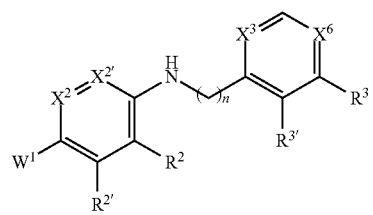
XIV-2-(ii)g-3
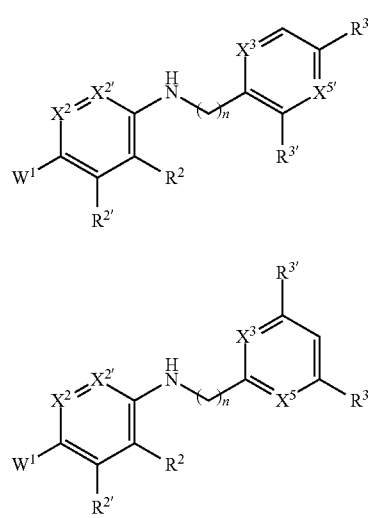
XIV-2-(ii)g-4
XIV-2-(ii)g-5
XIV-2-(ii)g-6
and $W_1$ is
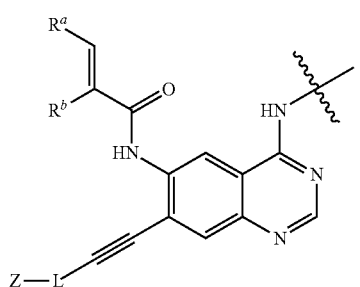
XV-2-(ii)g-1
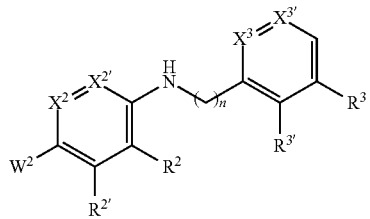
XV-2-(ii)g-2
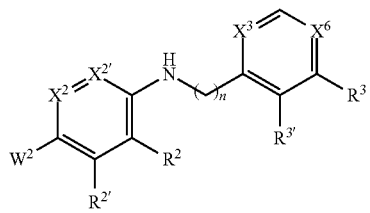
XV-2-(ii)g-3
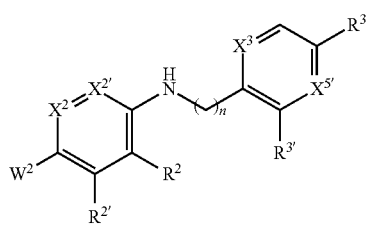
XV-2-(ii)g-4
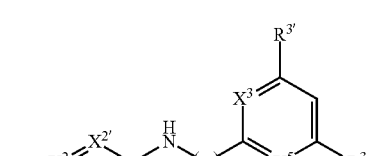
XV-2-(ii)g-5
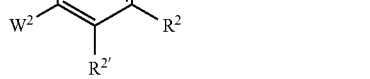
XV-2-(ii)g-6
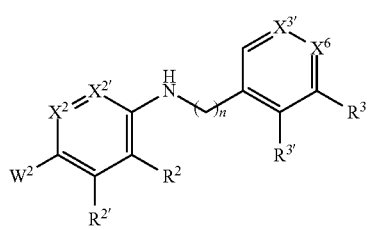

and W$_2$ is

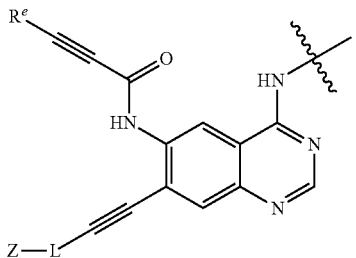

wherein X$^2$, X$^{2\prime}$, X$^3$, X$^{3\prime}$, X$^5$, X$^{5\prime}$, X$^6$ are independently of each other —N= or —CH=; and R$^2$, R$^{2\prime}$, R$^3$, R$^{3\prime}$ are independently of each other H, C$_{1-6}$ alkyl, hal, —CF$_3$, or —OCF$_3$, n is 0 or 1; and Z, L, R$^a$, R$^b$, R$^e$ are as defined above for a compound of formula XIV and XV (or XIV-1, XV-1).

In some embodiments substituent Z-L contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if L does not contain a nitrogen atom.

In some embodiments R$^a$ and R$^b$ are hydrogen.

In some embodiments, both X$^2$, X$^{2\prime}$ are —CH= (i.e. a phenyl ring). In some embodiments, X$^2$ is —N= and X$^{2\prime}$ is —CH= or X$^{2\prime}$ is —N= and X$^2$ is —CH= (i.e. a pyridine ring). In some embodiments, both X$^2$, X$^{2\prime}$ are —N= (i.e. a pyridazine ring).

In some embodiments, X$^3$, X$^{3\prime}$, X$^5$, X$^{5\prime}$, X$^6$ are —CH= (i.e. a phenyl ring). In some embodiments, X$^3$ is —N= and X$^{3\prime}$, X$^5$, X$^{5\prime}$, X$^6$ are —CH= or X$^{3\prime}$ is —N= and X$^3$, X$^5$, X$^{5\prime}$, X$^6$ are —CH= or X$^6$ is —N= and X$^3$, X$^{3\prime}$, X$^5$, X$^{5\prime}$ are —CH= (i.e. a pyridine ring).

In some embodiments, both X$^3$, X$^{3\prime}$ are —N= and X$^5$, X$^{5\prime}$, X$^6$ are —CH= or both X$^{3\prime}$, X$^6$ are —N= and X$^3$, X$^5$, X$^{5\prime}$ are —CH= (i.e. a pyridazine ring). In some embodiments, both X$^3$, X$^5$ are —N= and X$^{3\prime}$, X$^{5\prime}$, X$^6$ are —CH= or both X$^{3\prime}$, X$^{5\prime}$ are —N= and X$^3$, X$^5$, X$^6$ are —CH= or both X$^3$, X$^6$ are —N= and X$^{3\prime}$, X$^5$, X$^{5\prime}$ are —CH= (i.e. a pyrimidine ring). In some embodiments, both X$^3$, X$^{5\prime}$ are —N= and X$^{3\prime}$, X$^5$, X$^6$ are —CH= (i.e. a pyrazine ring).

In some embodiments, X$^2$, X$^{2\prime}$ are —CH= (i.e. a phenyl ring). In some embodiments, X$^3$, X$^{3\prime}$, X$^5$, X$^{5\prime}$, X$^6$ are —CH= (i.e. a phenyl ring). In some embodiments, X$^3$ is —N= and X$^{3\prime}$, X$^5$, X$^{5\prime}$, X$^6$ are —CH= or X$^{3\prime}$ is —N= and X$^3$, X$^5$, X$^{5\prime}$, X$^6$ are —CH= (i.e. a pyridine ring). R$^2$ and R$^{2\prime}$ are independently of each other H, hal or C$_{1-6}$ alkyl (e.g. H, hal or —CH$_3$).

In some embodiments, R$^2$ and R$^{2\prime}$ are H. In some embodiments, R$^2$ is hal or C$_{1-6}$ alkyl and R$^{2\prime}$ is H. In some embodiments, R$^2$ is H and R$^{2\prime}$ is hal. In some embodiments, R$^2$ and R$^{2\prime}$ are hal.

In some embodiments, R$^3$ is H, hal, —CF$_3$, or —OCF$_3$. In some embodiments, R$^{3\prime}$ is H, hal or C$_{1-6}$ alkyl (e.g. H, hal or —CH$_3$).

In some embodiments, R$^3$ and R$^{3\prime}$ are H. In some embodiments, R$^3$ is H and R$^{3\prime}$ is hal, or C$_{1-6}$ alkyl (e.g. C$_{1-6}$ alkyl). In some embodiments, R$^3$ is hal, —CF$_3$, or —OCF$_3$ and R$^{3\prime}$ is H.

In some embodiments, a compound of formula XIV-1, XV-1, or XIV-2, XV-2 has the formulas

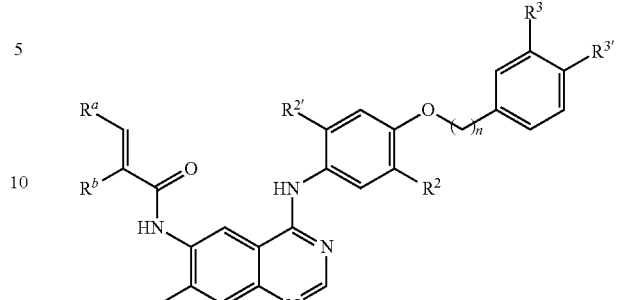

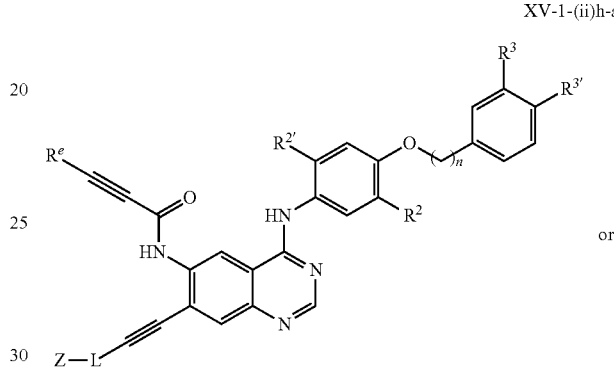

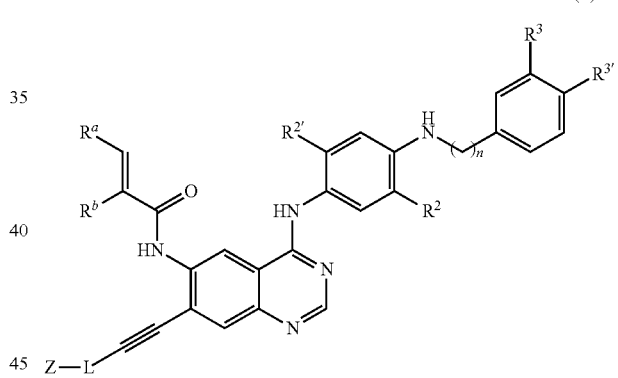

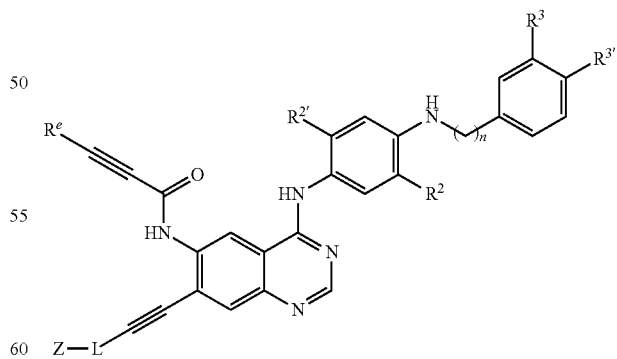

wherein R$^2$, R$^{2\prime}$ are independently of each other H, C$_{1-6}$ alkyl, hal (e.g. H, —CH$_3$, F, Cl); R$^3$, R$^{3\prime}$ are H, C$_{1-6}$ alkyl, hal, —CF$_3$, —OCF$_3$; and n is 0 or 1; and Z, L, R$^a$, R$^b$, R$^e$ are as defined above for a compound of formula XIV and XV (or XIV-1, XV-1, or XIV-2, XV-2).

In some embodiments substituent Z-L contains at least one nitrogen atom. Thus, the 3-6-membered heteroaryl or 3-9-membered heterocycloalkyl formed by $R_6$ and $R_7$ of $(CHR_6R_7)$ includes a nitrogen atom if L does not contain a nitrogen atom.

In some embodiments $R^a$ and $R^b$ are hydrogen.

In some embodiments, n is 0. In some embodiments, n is 1.

In some embodiments of a compound of formula XIV-1, XV-1 has the formula

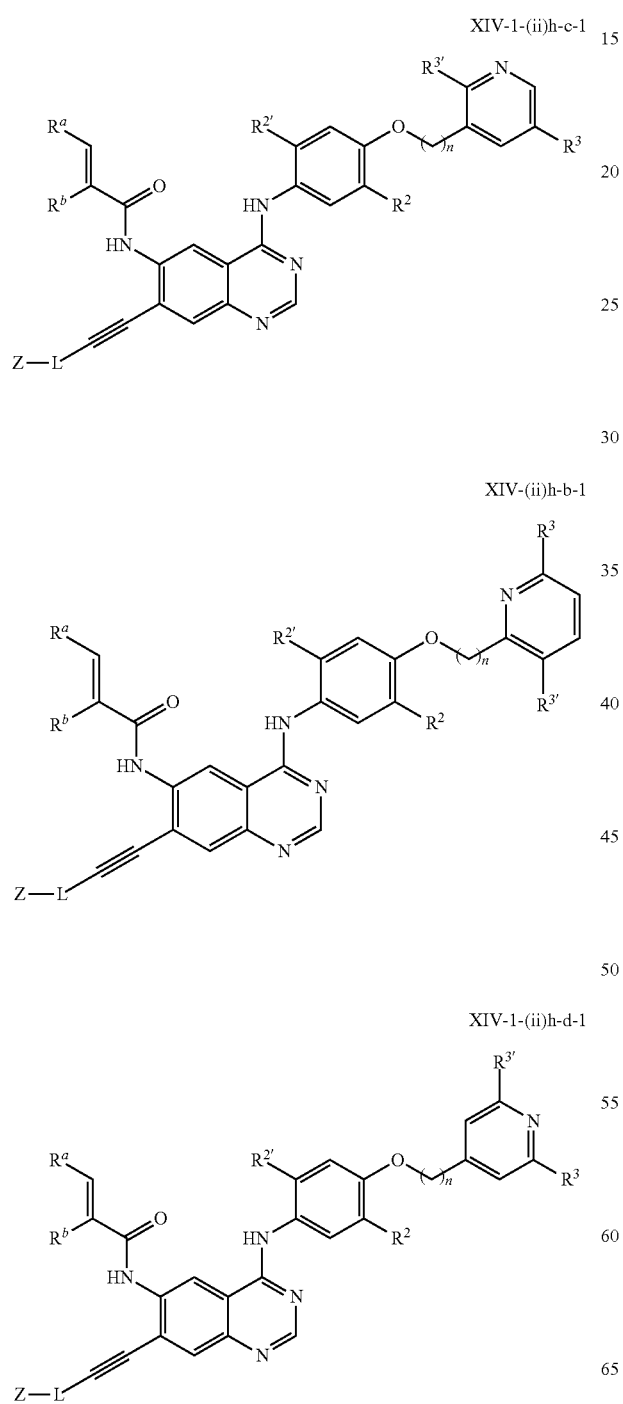

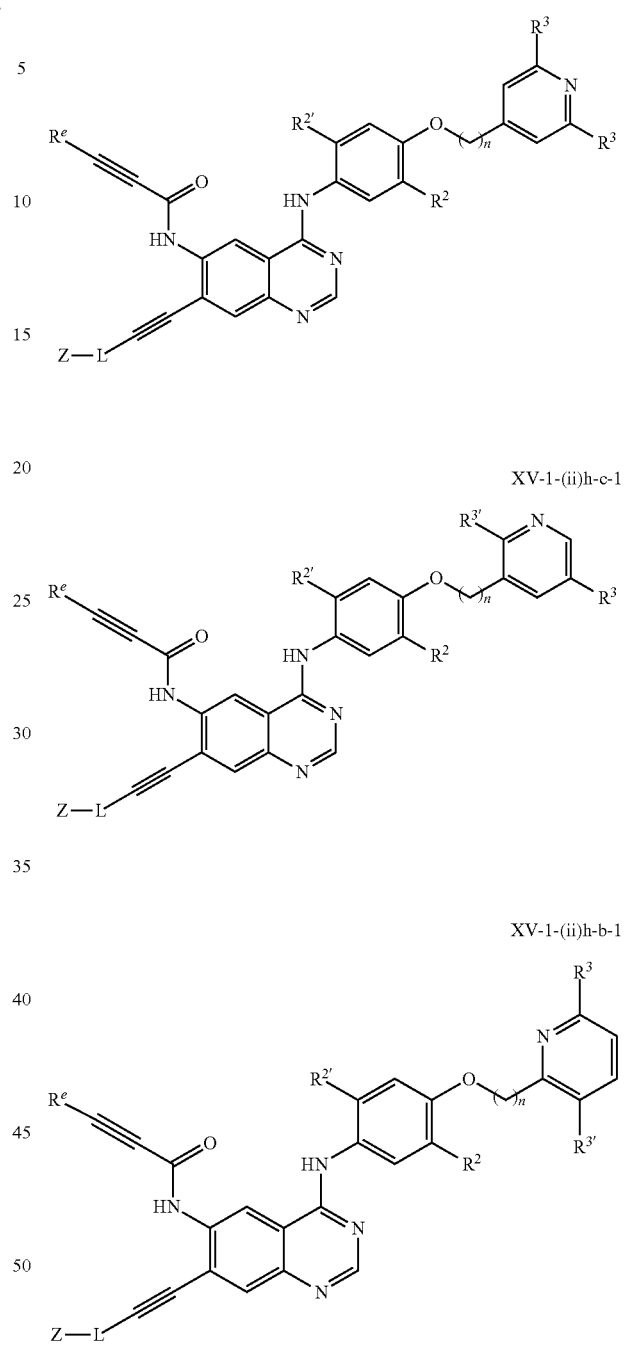

wherein $R^2$, $R^{2'}$ are independently of each other H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^a$, $R^b$, $R^e$ are as defined above for a compound of formula XIV and XV (or XIV-1, XV-1, or XIV-2, XV-2).

In some embodiments substituent Z-L contains at least one nitrogen atom. Thus, the 3-6-membered heteroaryl or 3-9-membered heterocycloalkyl formed by $R_6$ and $R_7$ of $(CHR_6R_7)$ includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula XIV-1 has the formula

XVI-1-(ii)h-b-2

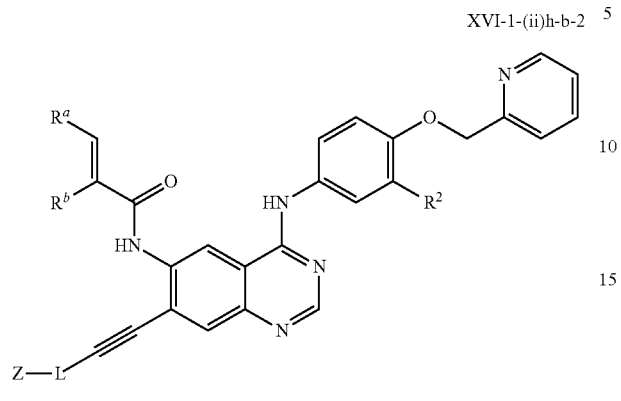

wherein $R^2$ is H, $C_{1-6}$ alkyl, hal (e.g. H, —CH$_3$, F, Cl); $R^3$, $R^{3'}$ are H, $C_{1-6}$ alkyl, alkyl, hal, —CF$_3$, –OCF$_3$; and n is 0 or 1; and Z, L, $R^a$, $R^b$, $R^e$ are as defined above for a compound of formula V and VI (or V-1, VI-1, or V-2, VI-2).

In some embodiments, $R^2$ is halogen, such as Cl.

In some embodiments, $R^a$ and $R^b$ are hydrogen.

In some embodiments, a compound of formula XIV-2, XV-2 has the formulas

XIV-1-(ii)i-c-1

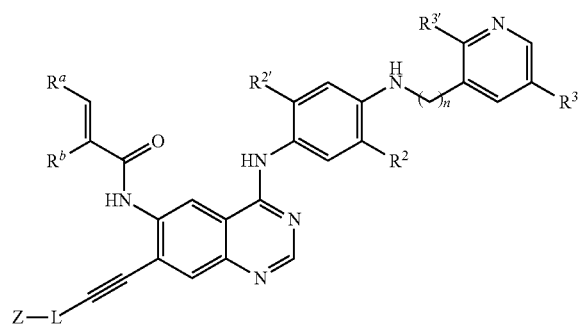

XIV-1-(ii)i-b-1

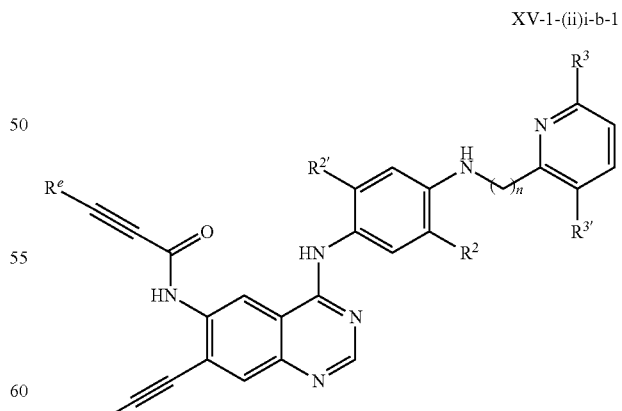

-continued

XIV-1-(ii)i-d-1

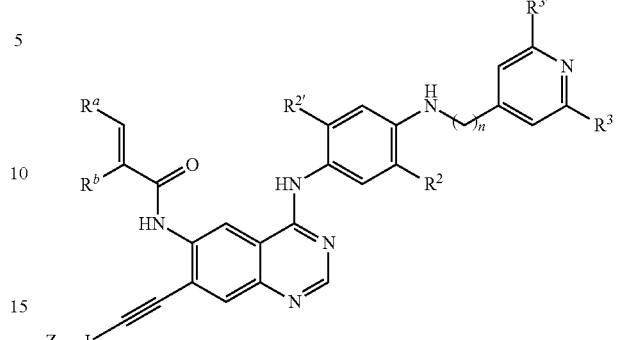

XV-1-(ii)i-d-1


XV-1-(ii)i-c-1

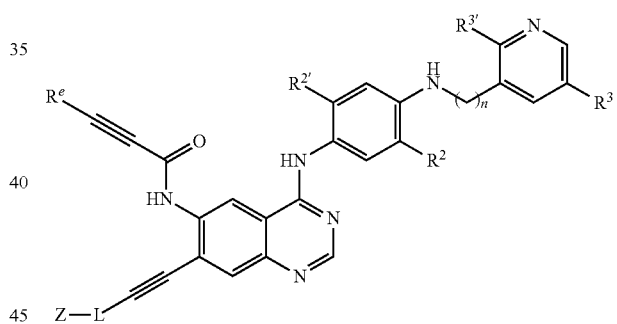

XV-1-(ii)i-b-1

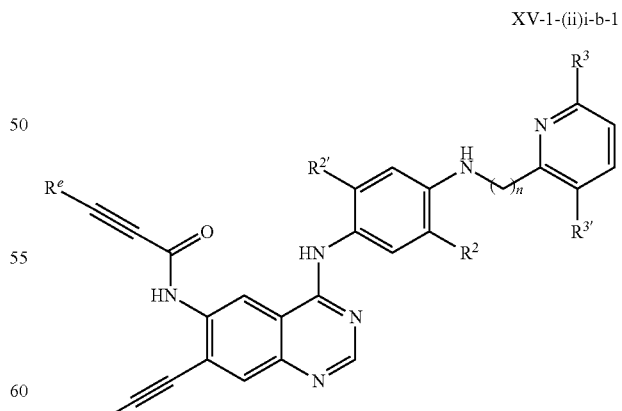

wherein $R^2$, $R^{2'}$ are independently of each other H, $C_{1-6}$ alkyl, hal (e.g. H, —CH$_3$, F, Cl); $R^3$, $R^{3'}$ are is H, $C_{1-6}$ alkyl, hal, —CF$_3$, —OCF$_3$; and n is 0 or 1; and Z, L, $R^a$, $R^b$, $R^e$ are as defined above for a compound of formula XIV, XV (or XIV-2, XV-2). In some embodiments, n is 0. In some embodiments, n is 1.

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments of a compound of formula XIV-1, XV-1 has the formulas

XIV-1-(ii)h-h-1

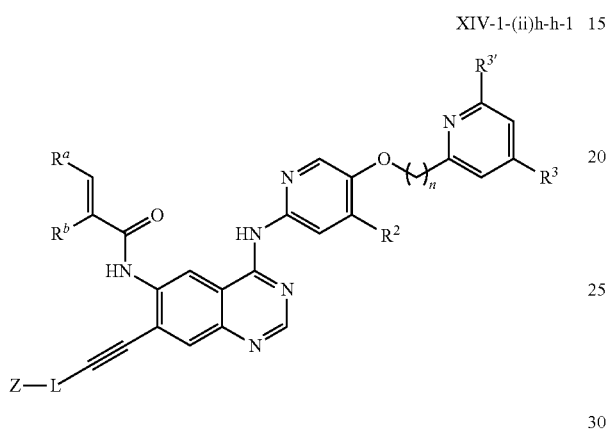

XIV-1-(ii)h-i-1

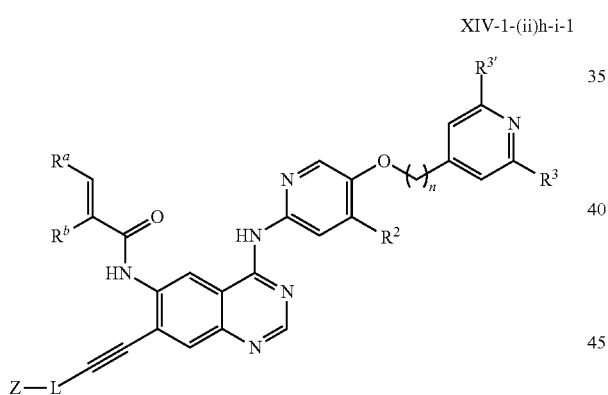

XIV-1-(ii)h-j-1

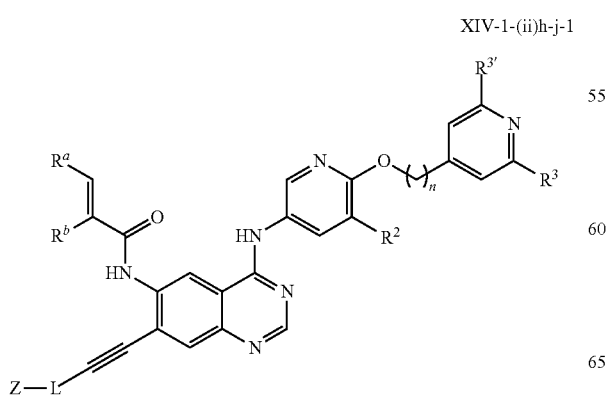

XIV-1-(ii)h-f-1

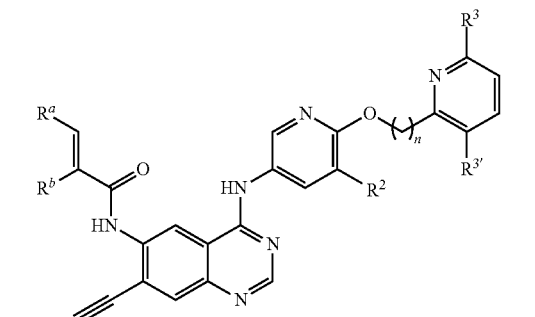

XIV-1-(ii)h-e-1

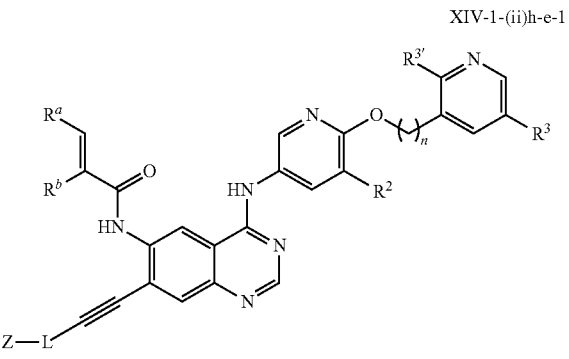

XIV-1-(ii)h-g-1

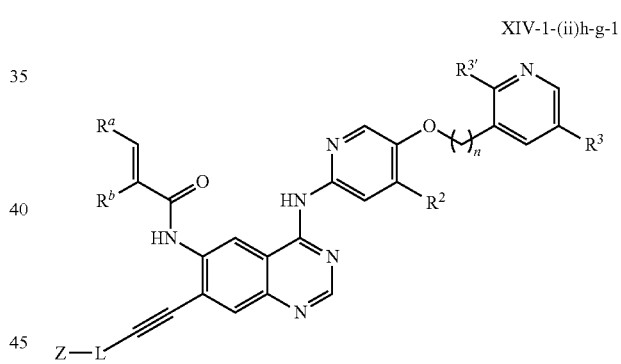

or

XV-1-(ii)h-h-1

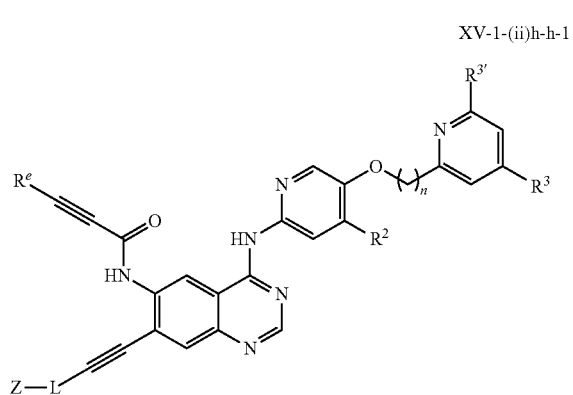

XV-1-(ii)h-i-1

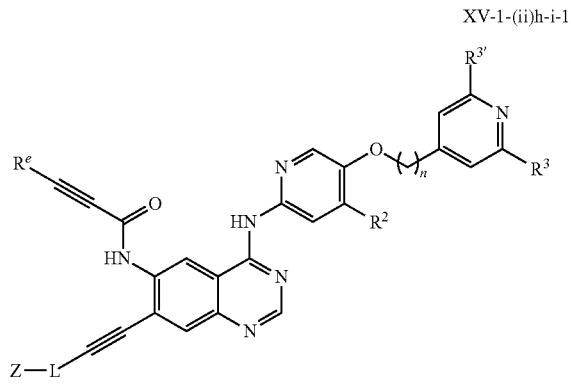

XV-1-(ii)h-j-1

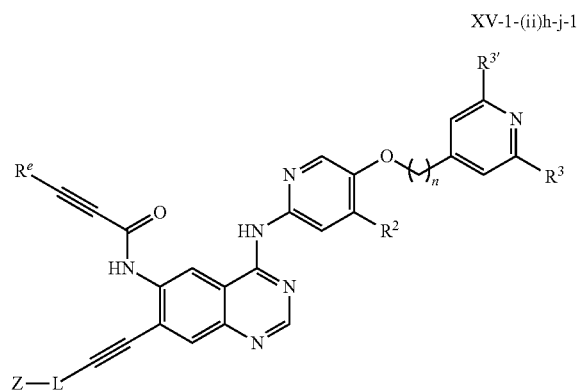

XV-1-(ii)h-f-1

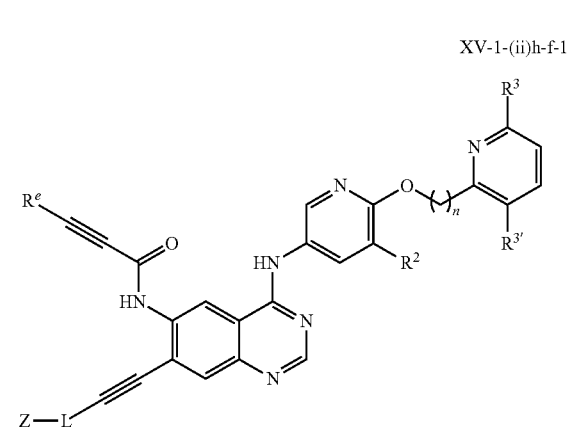

XV-1-(ii)h-e-1

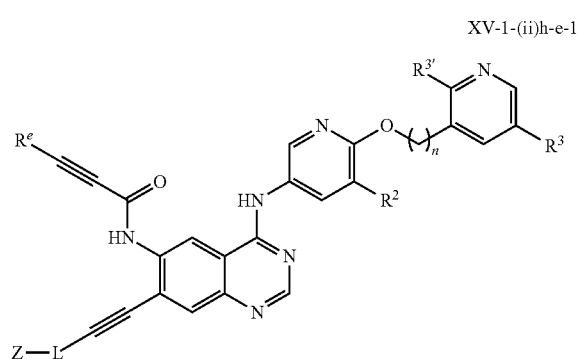

XV-1-(ii)h-g-1

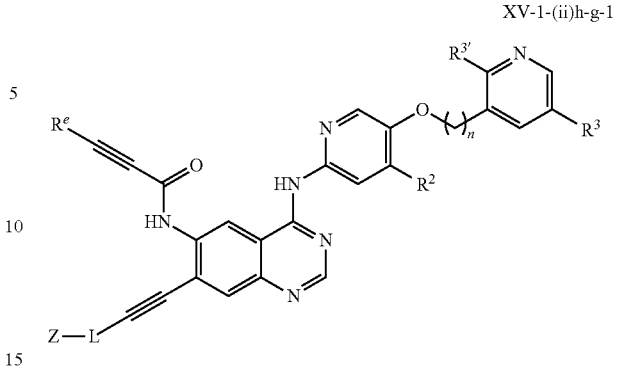

wherein $R^2$ is H, $C_{1-6}$ alkyl, hal (e.g. H, —CH$_3$, F, Cl); $R^3$, $R^{3\prime}$ are is H, $C_{1-6}$ alkyl, hal, —CF$_3$, —OCF$_3$; and n is 0 or 1; and Z, L, $R^a$, $R^b$, $R^e$ are as defined above for a compound of formula XIV, XV (or XIV-1, XV-1).

In some embodiments substituent Z-L contains at least one nitrogen atom. Thus, the 3-6-membered heteroaryl or 3-9-membered heterocycloalkyl formed by $R_6$ and $R_7$ of (CHR$_6$R$_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula XIV-2, XV-2 has the formulas

XIV-2-(ii)i-h-1

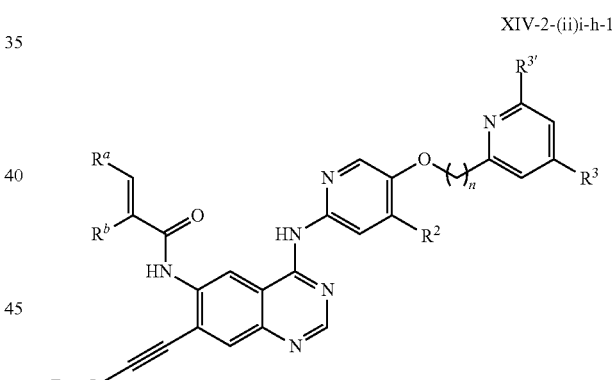

XIV-2-(ii)i-i-1

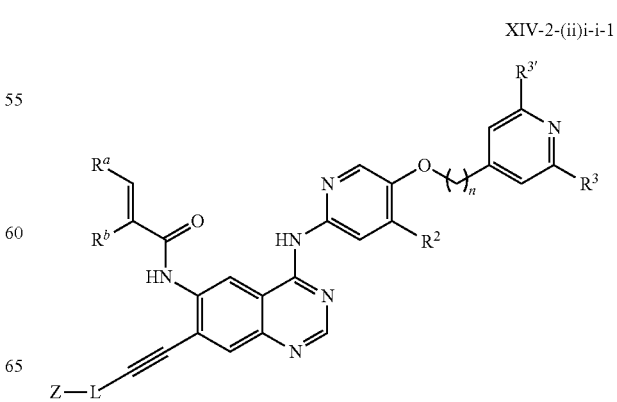

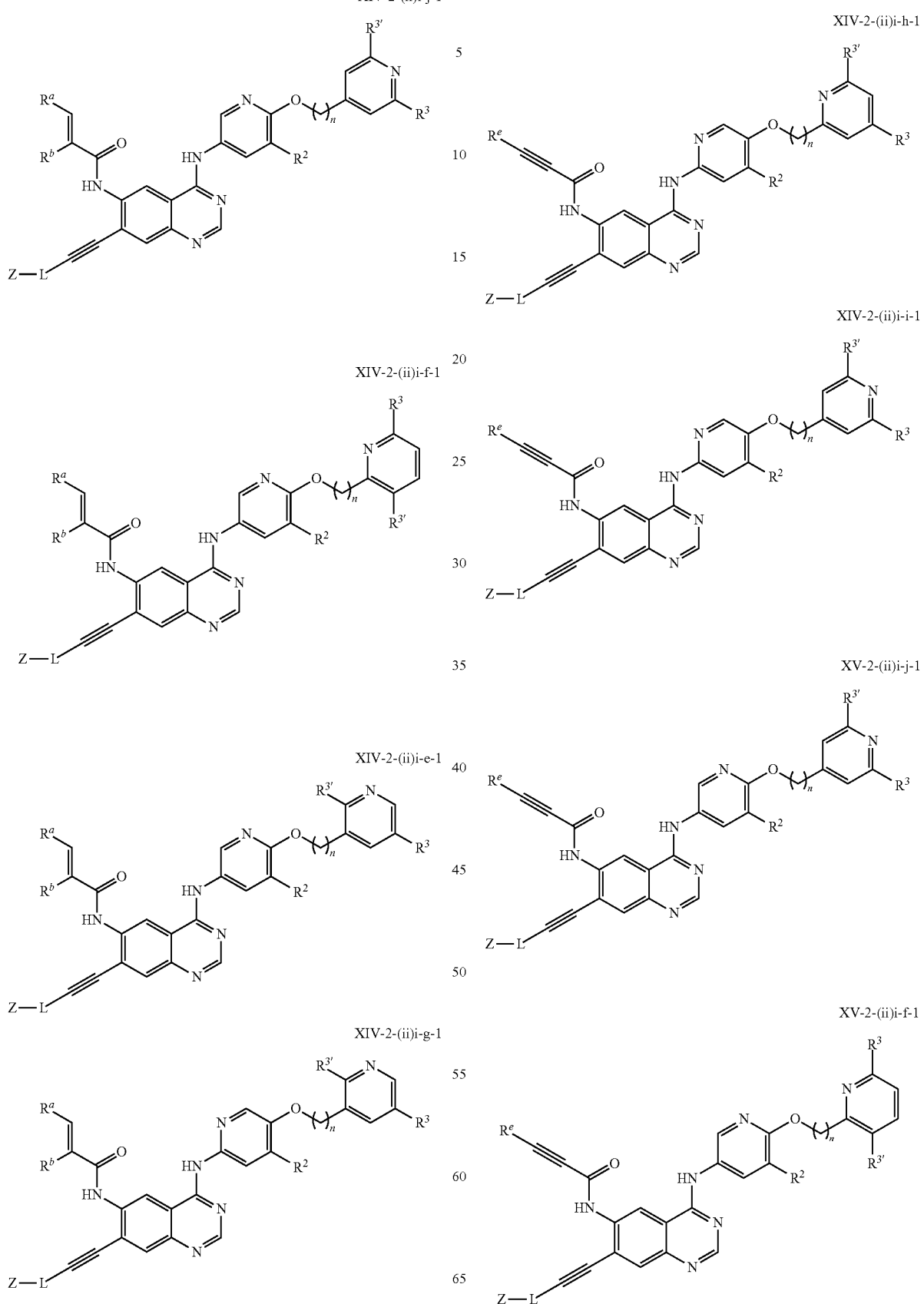

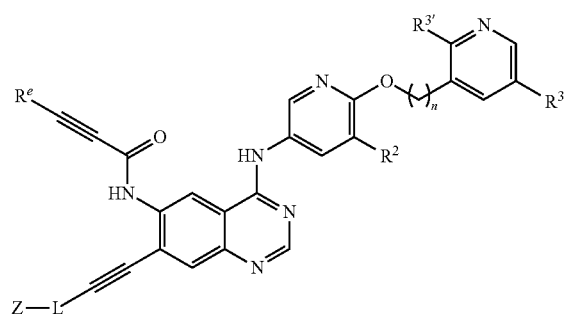

XV-2-(ii)i-e-1

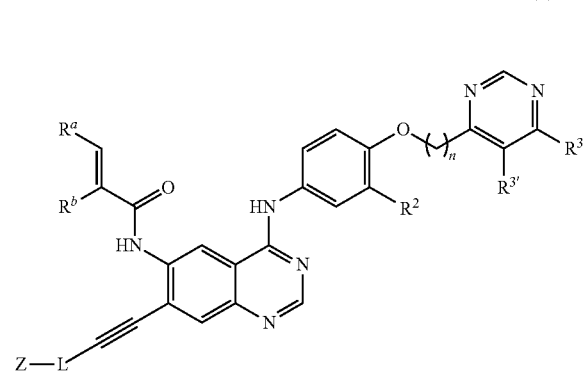

XIV-1-(ii)h-l-1

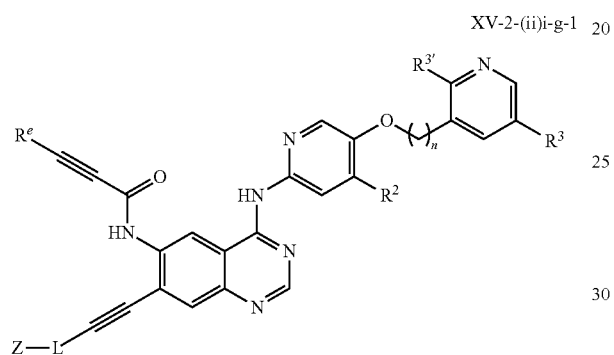

XV-2-(ii)i-g-1

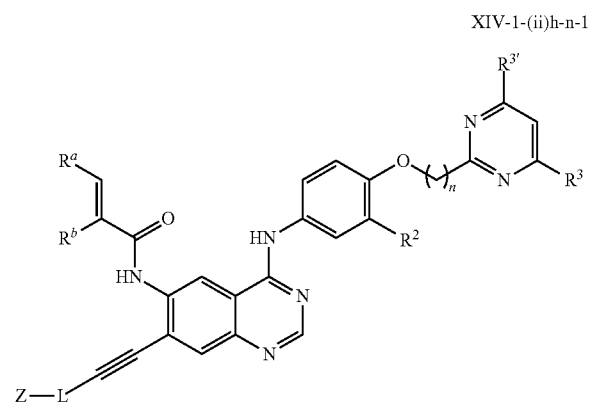

XIV-1-(ii)h-n-1 wherein $R^2$ is H, $C_{1-6}$ alkyl, hal (e.g. H, —$CH_3$, F, Cl); $R^3$, $R^{3'}$ are H, $C_{1-6}$ alkyl, hal, —$CF_3$, —$OCF_3$; and n is 0 or 1; and Z, L, $R^a$, $R^b$, $R^e$ are as defined above for a compound of formula XIV, XV (or XIV-2, XV-2).

In some embodiments substituent Z-L contains at least one nitrogen atom. Thus, the 3-6-membered heteroaryl or 3-9-membered heterocycloalkyl formed by $R_6$ and $R_7$ of (CH$R_6R_7$) includes a nitrogen atom if L does not contain a nitrogen atom.

In some embodiments $R^a$ and $R^b$ are hydrogen.

In some embodiments, a compound of formula XIV-1, XV-1 has the formulas

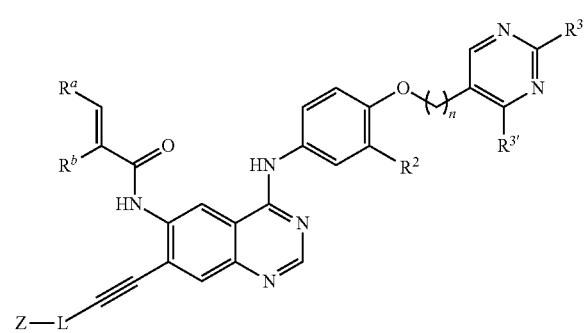

XIV-1-(ii)h-m-1

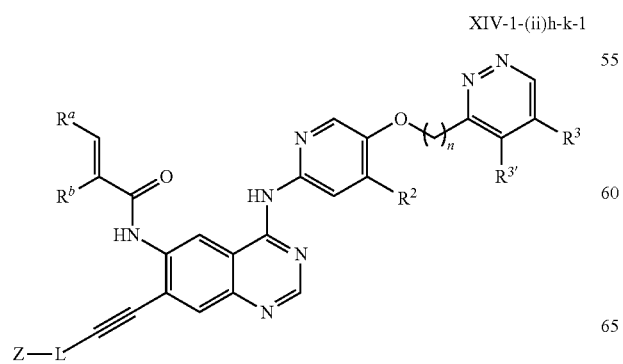

XIV-1-(ii)h-k-1

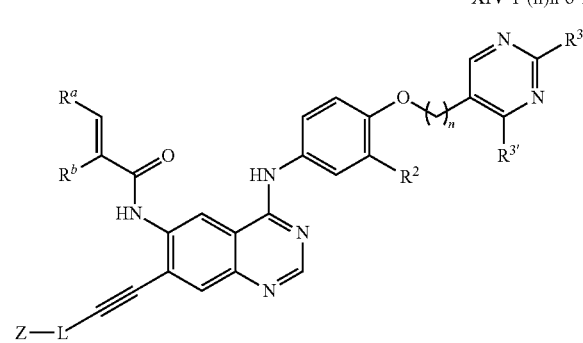

XIV-1-(ii)h-o-1

XIV-1-(ii)h-p-1

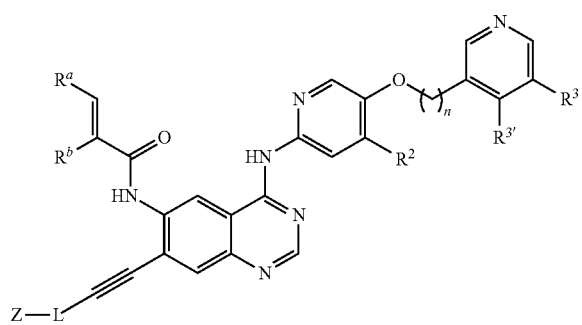

or

XV-1-(ii)h-k-1

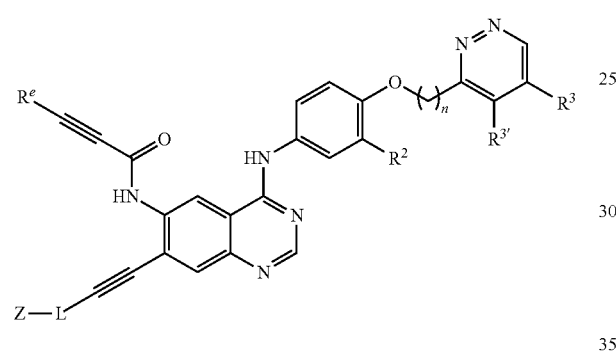

XV-1-(ii)h-l-1

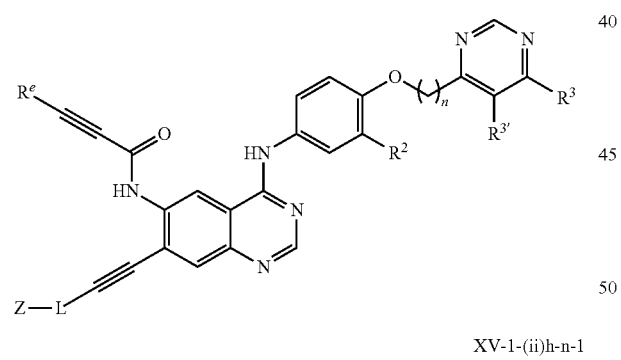

XV-1-(ii)h-n-1

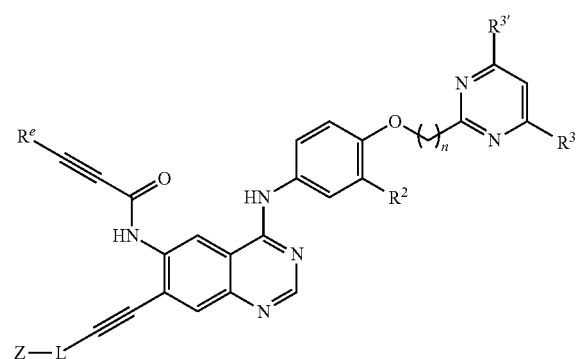

XV-1-(ii)h-m-1

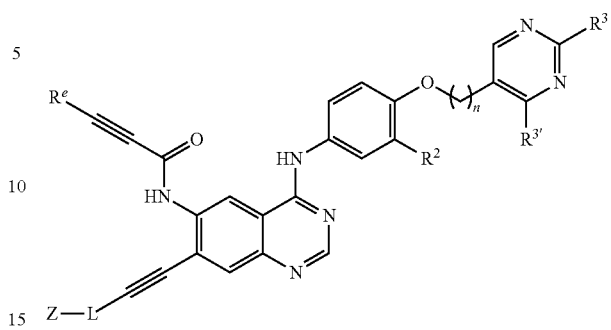

XV-1-(ii)h-o-1

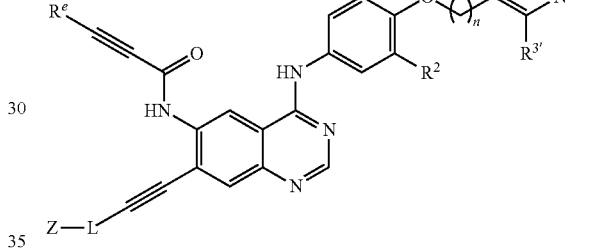

XV-1-(ii)h-p-1

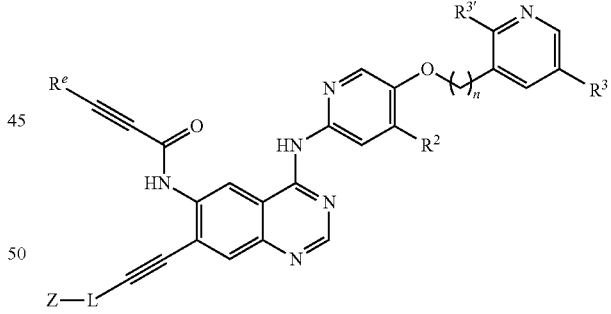

wherein $R^2$ is H, $C_{1-6}$ alkyl, hal (e.g. H, —$CH_3$, F, Cl); $R^3$, $R^{3'}$ are is H, $C_{1-6}$ alkyl, hal, —$CF_3$, —$OCF_3$; and n is 0 or 1; and Z, L, $R^a$, $R^b$, $R^e$ are as defined above for a compound of formula XIV, XV (or XIV-1, XV-1).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

In some embodiments, n is 0. In some embodiments, n is 1.

In some embodiments, a compound of formula XIV-2, XV-2 has the formulas
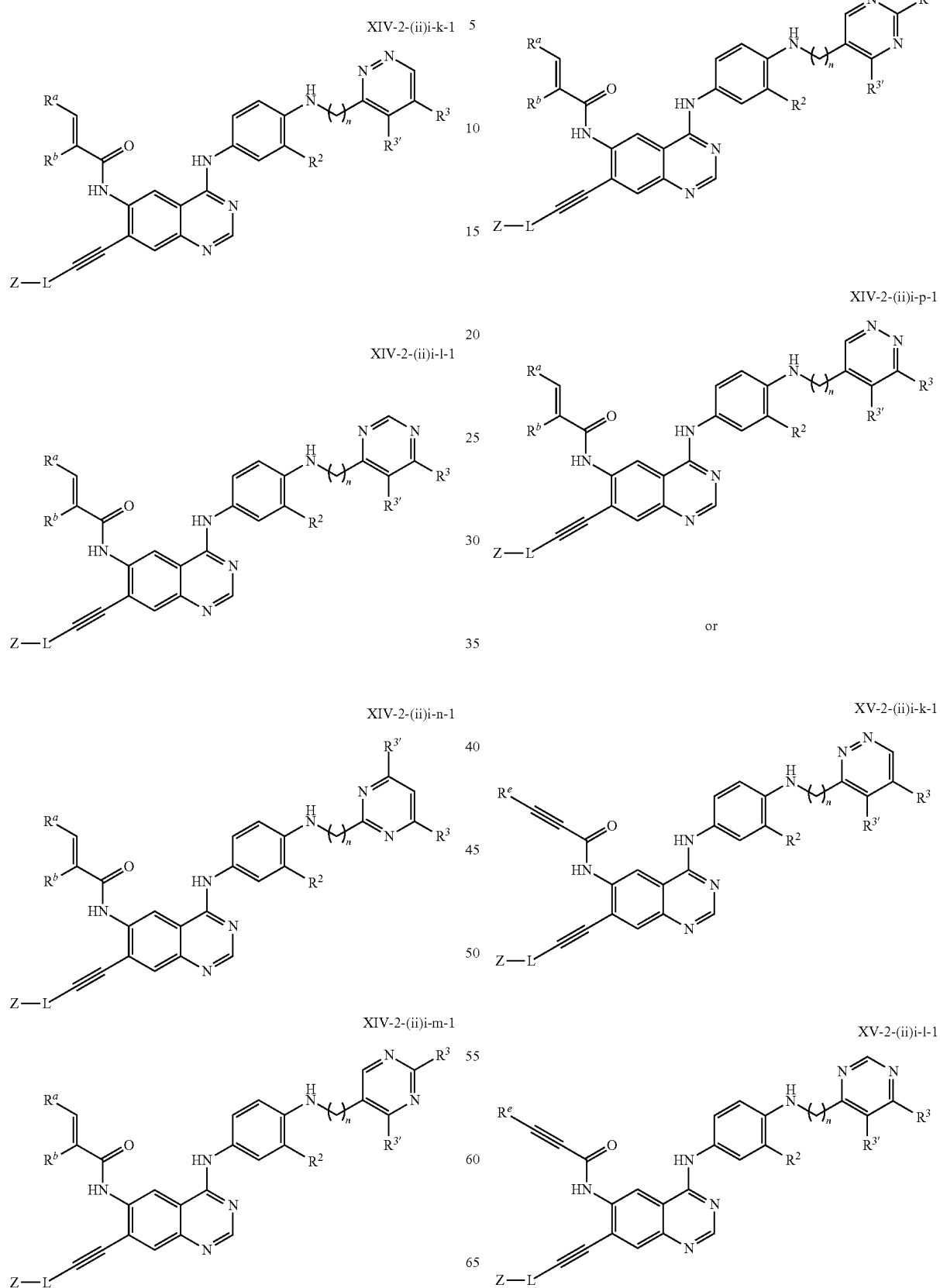

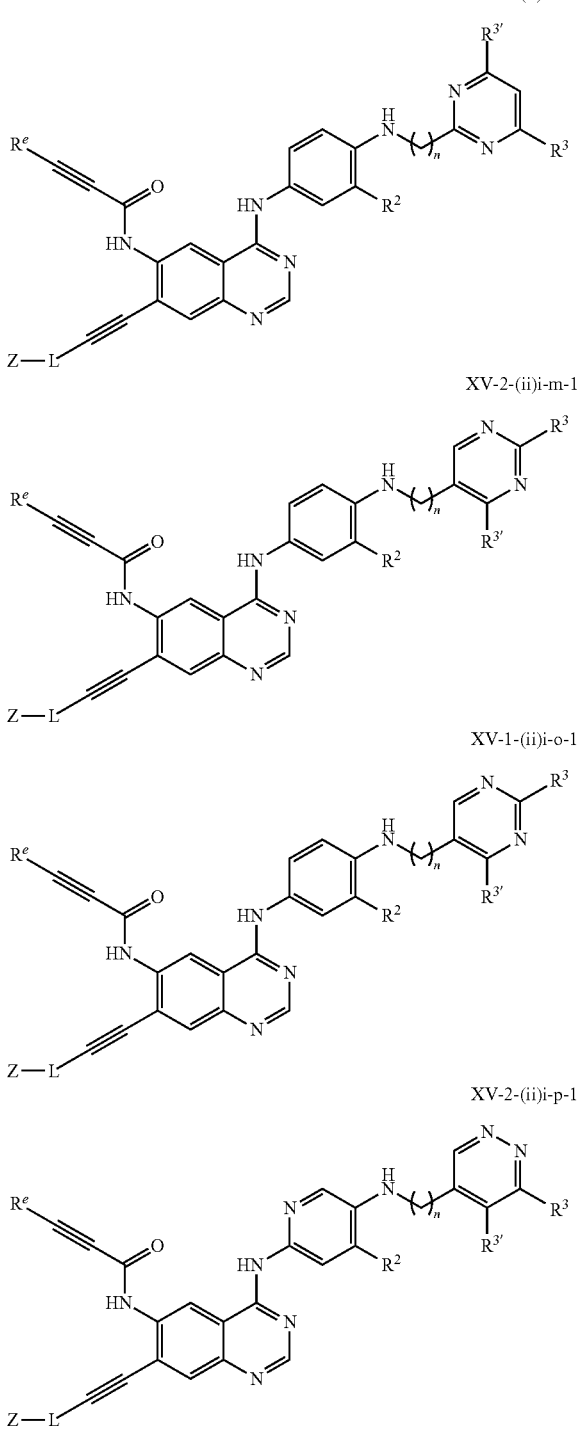

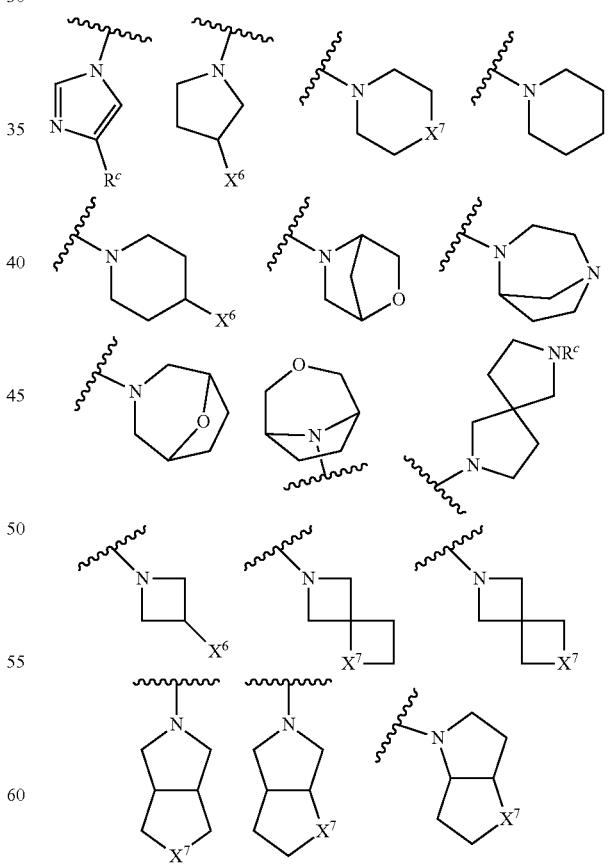

In some embodiments, n is 0. In some embodiments, n is 1.

In some embodiments, $R^4$ and $R^5$ are independently of each other H, $C_{1-4}$ alkyl, cyclopropyl, tetrahydrofuryl (e.g. $C_{1-4}$ alkyl).

In some embodiments, L is a covalent bond or straight chain or branched $C_{1-4}$ alkyl (e.g. —$CH_2$—, —$(CH_2)_2$—, —$(CH_2)_3$—, —$(CH_2)_4$— or —$C(CH_3)_2$— or —$CH_2$—$C(CH_3)_2$—).

In some embodiments, group Z is defined as specified above. in some embodiments, Z is —($NR^4R^5$), wherein $R^4$ and $R^5$ are independently of each other H, $C_{1-6}$ alkyl, cyclopropyl, cylobutyl, 3 to 6-membered heterocycloalkyl containing 0, 1, or 2 N-atoms and 0, 1, or 2 O-atoms, or —($NR^6R^7$), —($CHR^6R^7$), wherein $R^6$ and $R^7$ form together with the atom to which they are attached to 3 to 6-membered heteroaryl containing 0, 1, 2 or 3 N-atoms and 0, 1, or 2 O-atoms or 3 to 9-membered heterocycloalkyl containing 0, 1, 2 or 3 N-atoms and 0, 1, or 2 O-atoms, wherein the 3 to 9-membered heterocycloalkyl is a monocycle or a fused, bridged or spirobicycle or a combination thereof, and is unsubstituted or substituted with $C_{1-4}$ alkyl, hal, —OR', —NR'R", wherein R', R" are independently of each other H or -$C_{1-4}$ alkyl.

In some embodiments, —($CR^6R^7$) and —($NR^6R^7$) ring systems of Z are selected from wherein $R^2$ is H, $C_{1-6}$ alkyl, hal (e.g. H, —$CH_3$, F, Cl); $R^3$, $R^{3'}$ are is H, $C_{1-6}$ alkyl, hal, —$CF_3$, —$OCF_3$; and n is 0 or 1; and Z, L, $R^a$, $R^b$, $R^e$ are as defined above for a compound of formula XIV, XV (or XIV-2, XV-2).

In some embodiments substituent Z-L contains at least one nitrogen atom. Thus, the 3-6-membered heteroaryl or 3-9-membered heterocycloalkyl formed by $R_6$ and $R_7$ of ($CHR_6R_7$) includes a nitrogen atom if L does not contain a nitrogen atom.

In some embodiments $R^a$ and $R^b$ are hydrogen.

wherein $R^c$ is H, $C_{1-4}$ alkyl, oxetane; $X^6$ is H, —$CH_3$, —OH, —$OCH_3$, —$OCF_3$, —$N(CH_3)_2$, F, Cl; $X^7$ is —O—, —NH— or —$N(CH_3)$—, —$SO_2$, and

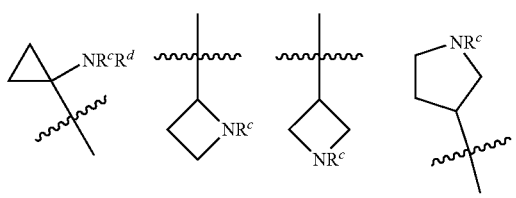

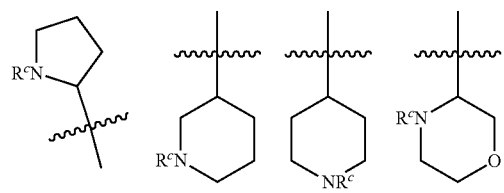

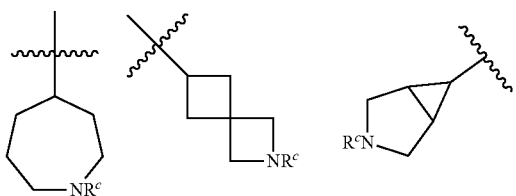

wherein $R^c$ is H, $C_{1-4}$ alkyl, oxetane, and $R^d$ is H, $C_{1-4}$ alkyl.

In some embodiments, —(CHR$^6$R$^7$)-, —(NR$^6$R$^7$) are selected from

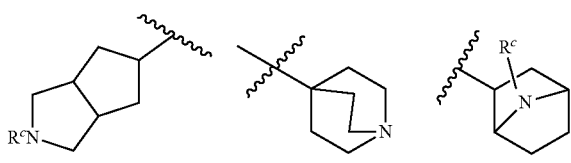

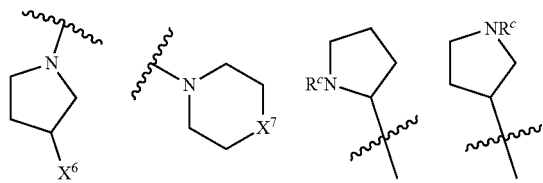

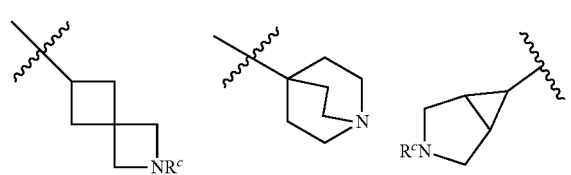

wherein $X^7$ is —O—, —NH— or —N(CH$_3$)—, —SO$_2$; $R^c$ is H, $C_{1-4}$ alkyl, oxetane, and $R^d$ is H, $C_{1-4}$ alkyl.

In some embodiments, compounds of XIII have formula XVI

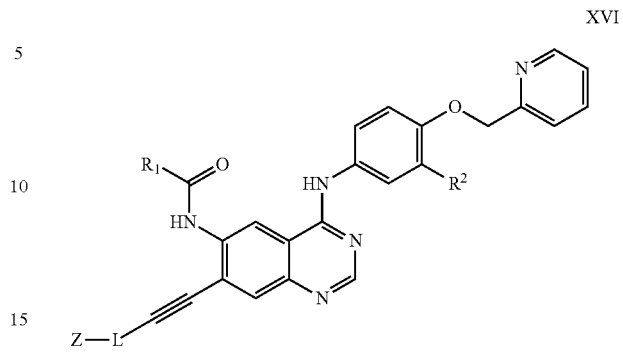

XVI wherein $R^1$ is —CH=CH$_2$, —C≡CH or —C≡C—CH$_3$; $R^2$ is H, $C_{1-4}$ alkyl (e.g. —CH$_3$, hal);

L is a covalent bond or straight chain or branched $C_{1-4}$ alkyl (e.g. —CH$_2$—, —(CH$_2$)$_2$—, —(CH$_2$)$_3$—, —(CH$_2$)$_4$— or —C(CH$_3$)$_2$—);

Z is —(NR$^4$R$^5$), wherein R$^4$ and R$^5$ are independently of each other H, $C_{1-6}$ alkyl, or —(CHR$^6$R$^7$)-, —(NR$^6$R$^7$) wherein R$^6$ and R$^7$ form together with the atom to which they are attached to 3 to 6-membered heteroaryl, or 3 to 9-membered heterocycloalkyl, wherein the 3 to 9-membered heterocycloalkyl is a monocycle or a fused bridged or spirobicycle or a combination thereof, which is unsubstituted or substituted with $C_{1-4}$ alkyl.

In some embodiments, Z is —(NR$^4$R$^5$), wherein R$^4$ and R$^5$ are independently of each other H, $C_{1-6}$ alkyl, or —(CHR$^6$R$^7$)-, —(NR$^6$R$^7$) wherein R$^6$ and R$^7$ form together with the atom to which they are attached to 3 to 9-membered heterocycloalkyl, wherein the 3 to 6-membered heterocycloalkyl is a monocycle, or fused bicycle, which is unsubstituted or substituted with $C_{1-4}$ alkyl.

In some embodiments, —(CHR$^6$R$^7$)-, —(NR$^6$R$^7$) are selected from

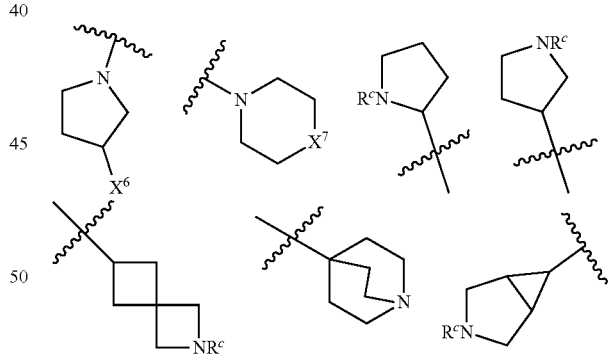

wherein $X^7$ is —O—, —NH— or —N(CH$_3$)—, —SO$_2$; $R^c$ is H, $C_{1-4}$ alkyl, oxetane, and $R^d$ is H, $C_{1-4}$ alkyl.

In some embodiments substituent Z-L contains at least one nitrogen atom. Thus, the 3-6-membered heteroaryl or 3-9-membered heterocycloalkyl formed by R$_6$ and R$_7$ of (CHR$_6$R$_7$) includes a nitrogen atom if L does not contain a nitrogen atom.

In some embodiments, the compound is selected from the compounds described in Table I, pharmaceutically acceptable salts thereof, and stereoisomers thereof.

In some embodiments, the compound is selected from the compounds described in Table I and pharmaceutically acceptable salts thereof.

In some embodiments, the compound is selected from the compounds described in Table I.

TABLE I

| Compound | No. |
|---|---|
| *structure* | 1 |
| *structure* | 2 |
| *structure* | 3 |
| *structure* | 4 |

TABLE I-continued

| Compound | No. |
|---|---|
| | 5 |
| | 6 |
| | 7 |
| | 8 |
| | 9 |

TABLE I-continued

| Compound | No. |
|---|---|
| | 10 |
| | 11 |
| | 12 |
| | 13 |

TABLE I-continued

| Compound | No. |
|---|---|
| | 14 |
| | 15 |
| | 16 |
| | 17 |
| | 18 |

TABLE I-continued

| Compound | No. |
|---|---|
| | 19 |
| | 20 |
| | 21 |
| | 22 |

TABLE I-continued

| Compound | No. |
|---|---|
| | 23 |
| | 24 |
| | 25 |
| | 26 |
| | 27 |

TABLE I-continued
| Compound | No. |
|---|---|
| 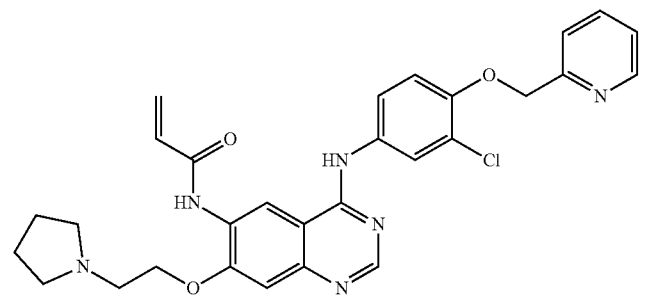 [SMILES: C=CC(=O)Nc1cc2c(Nc3ccc(OCc4ccccn4)c(Cl)c3)ncnc2cc1OCCN1CCCC1] | 28 |
| 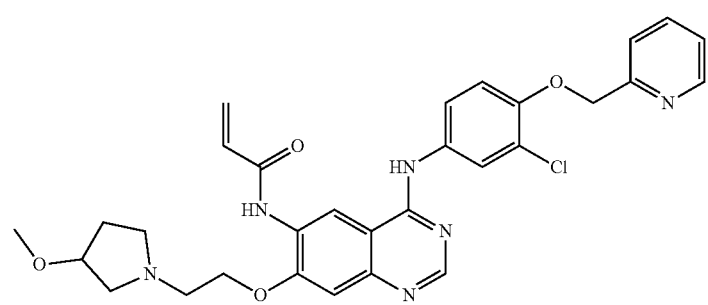 [SMILES: C=CC(=O)Nc1cc2c(Nc3ccc(OCc4ccccn4)c(Cl)c3)ncnc2cc1OCCN1CCC(OC)C1] | 29 |
| 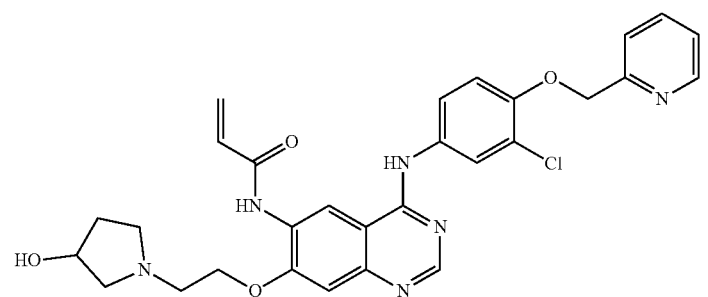 [SMILES: C=CC(=O)Nc1cc2c(Nc3ccc(OCc4ccccn4)c(Cl)c3)ncnc2cc1OCCN1CCC(O)C1] | 30 |
| 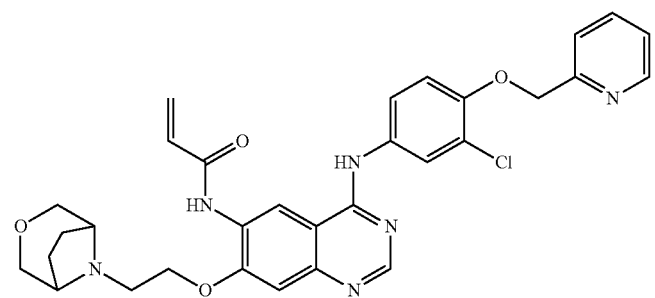 [SMILES: C=CC(=O)Nc1cc2c(Nc3ccc(OCc4ccccn4)c(Cl)c3)ncnc2cc1OCCN1C2CCC1COC2] | 31 |
| 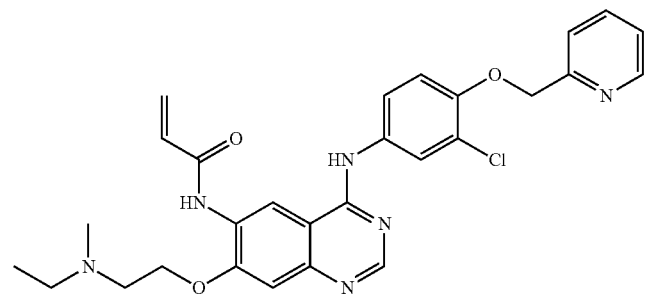 [SMILES: C=CC(=O)Nc1cc2c(Nc3ccc(OCc4ccccn4)c(Cl)c3)ncnc2cc1OCCN(C)CC] | 32 |

TABLE I-continued

| Compound | No. |
|---|---|
| | 33 |
| | 34 |
| | 35 |
| | 36 |
| | 37 |

TABLE I-continued

| Compound | No. |
|---|---|
| | 38 |
| | 39 |
| | 40 |
| | 41 |
| | 42 |

| Compound | No. |
|---|---|
| 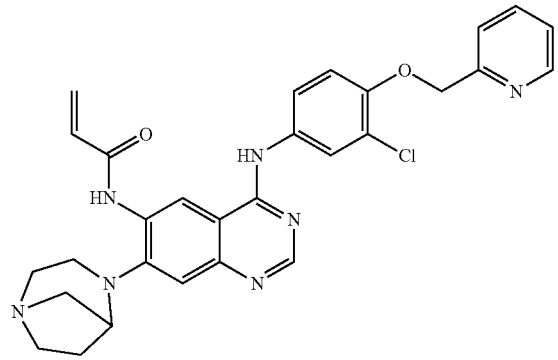 [SMILES: C=CC(=O)Nc1cc2c(Nc3ccc(OCc4ccccn4)c(Cl)c3)ncnc2cc1N1CCN2CCC1C2] | 43 |
| 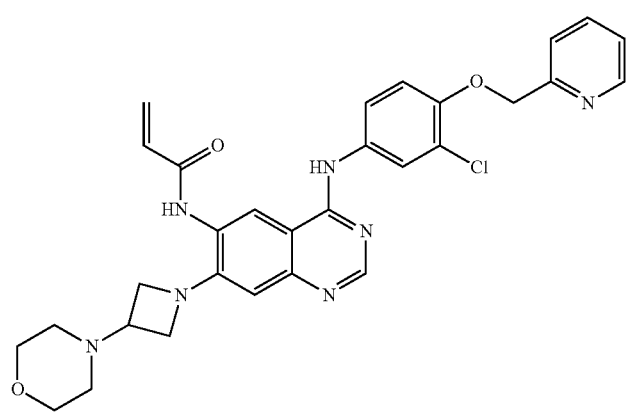 [SMILES: C=CC(=O)Nc1cc2c(Nc3ccc(OCc4ccccn4)c(Cl)c3)ncnc2cc1N1CC(N2CCOCC2)C1] | 44 |
| 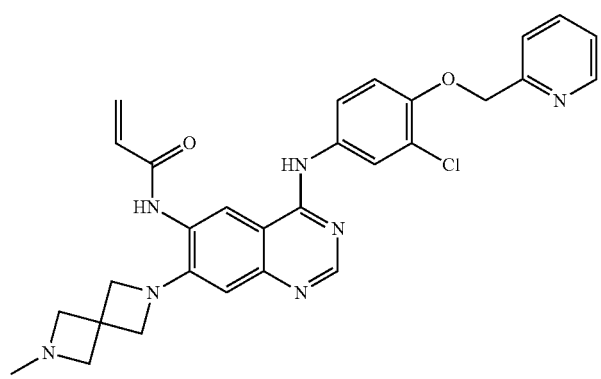 [SMILES: C=CC(=O)Nc1cc2c(Nc3ccc(OCc4ccccn4)c(Cl)c3)ncnc2cc1N1CC2(CN(C)C2)C1] | 45 |
| 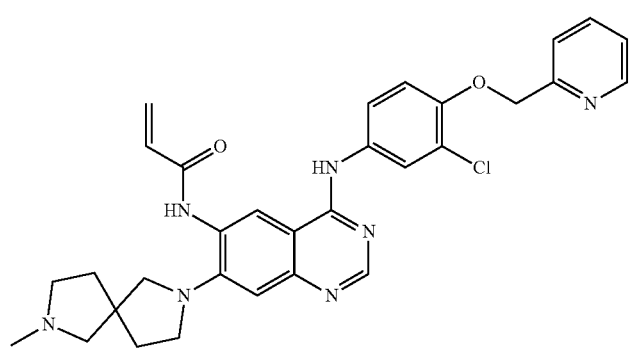 [SMILES: C=CC(=O)Nc1cc2c(Nc3ccc(OCc4ccccn4)c(Cl)c3)ncnc2cc1N1CCC2(CCN(C)C2)C1] | 46 |

TABLE I-continued
| Compound | No. |
|---|---|
| 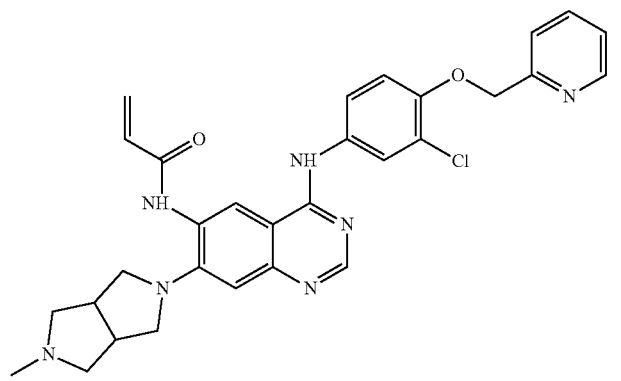 [SMILES: C=CC(=O)Nc1cc2c(Nc3ccc(OCc4ccccn4)c(Cl)c3)ncnc2cc1N1CC2CN(C)CC2C1] | 47 |
| 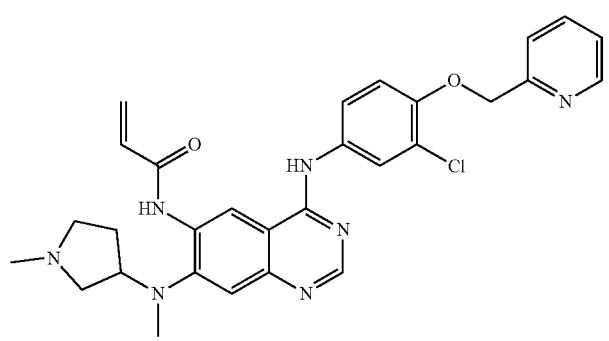 [SMILES: C=CC(=O)Nc1cc2c(Nc3ccc(OCc4ccccn4)c(Cl)c3)ncnc2cc1N(C)C1CCN(C)C1] | 48 |
| 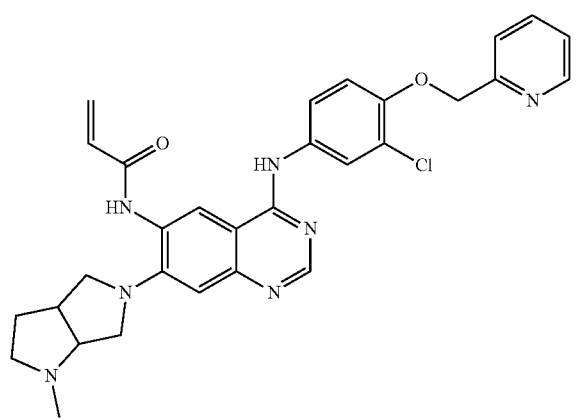 [SMILES: C=CC(=O)Nc1cc2c(Nc3ccc(OCc4ccccn4)c(Cl)c3)ncnc2cc1N1CC2CCN(C)C2C1] | 49 |
| 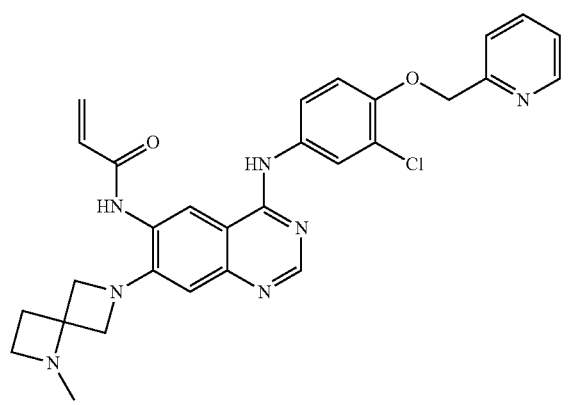 [SMILES: C=CC(=O)Nc1cc2c(Nc3ccc(OCc4ccccn4)c(Cl)c3)ncnc2cc1N1CC2(CCN2C)C1] | 50 |

TABLE I-continued

| Compound | No. |
|---|---|
| | 51 |
| | 52 |
| | 53 |
| | 54 |
| | 55 |

TABLE I-continued

| Compound | No. |
|---|---|
| | 56 |
| | 57 |
| | 58 |
| | 59 |
| | 60 |

TABLE I-continued

| Compound | No. |
|---|---|
| (structure) | 61 |
| (structure) | 62 |
| (structure) | 63 |
| (structure) | 64 |
| (structure) | 65 |

TABLE I-continued

| Compound | No. |
|---|---|
| | 66 |
| | 67 |
| | 68 |
| | 69 |
| | 70 |

TABLE I-continued
| Compound | No. |
|---|---|
| 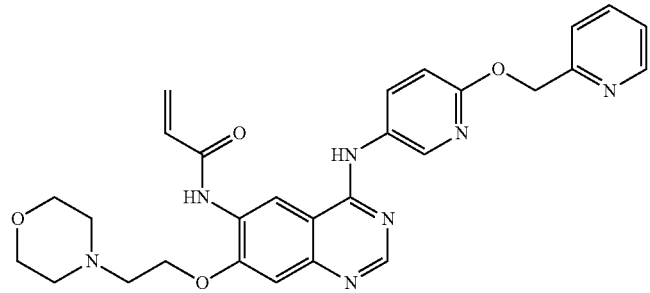 [SMILES: C=CC(=O)Nc1cc2c(Nc3ccc(OCc4ccccn4)nc3)ncnc2cc1OCCN1CCOCC1] | 71 |
| 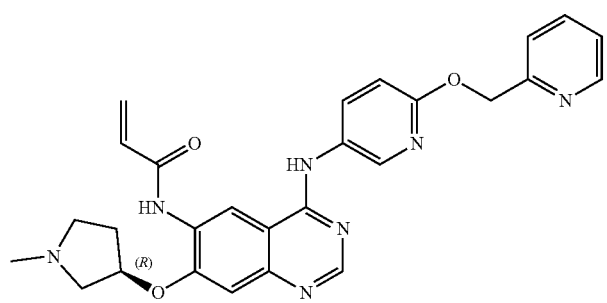 | 72 |
| 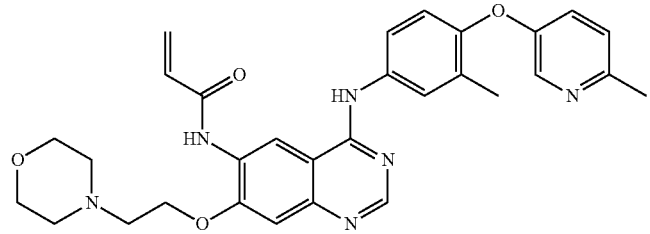 [SMILES: C=CC(=O)Nc1cc2c(Nc3ccc(Oc4ccc(C)nc4)c(C)c3)ncnc2cc1OCCN1CCOCC1] | 73 |
| 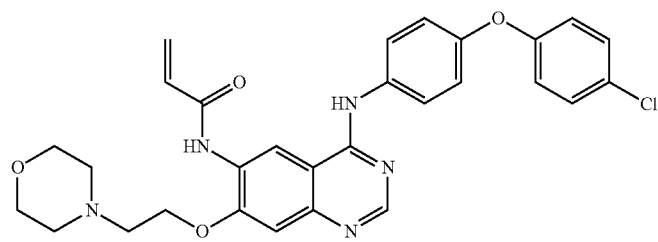 [SMILES: C=CC(=O)Nc1cc2c(Nc3ccc(Oc4ccc(Cl)cc4)cc3)ncnc2cc1OCCN1CCOCC1] | 74 |
| 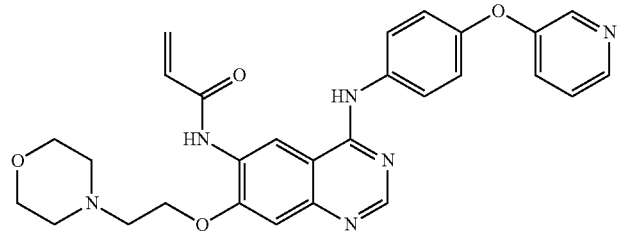 [SMILES: C=CC(=O)Nc1cc2c(Nc3ccc(Oc4cccnc4)cc3)ncnc2cc1OCCN1CCOCC1] | 75 |

TABLE I-continued

| Compound | No. |
|---|---|
| | 76 |
| | 77 |
| | 78 |
| | 79 |

TABLE I-continued

| Compound | No. |
|---|---|
| | 80 |
| | 81 |
| | 82 |
| | 83 |

TABLE I-continued

| Compound | No. |
|---|---|
| | 84 |
| | 85 |
| | 86 |
| | 87 |

TABLE I-continued

| Compound | No. |
|---|---|
| | 88 |
| | 89 |
| | 90 |
| | 91 |

TABLE I-continued
| Compound | No. |
|---|---|
| 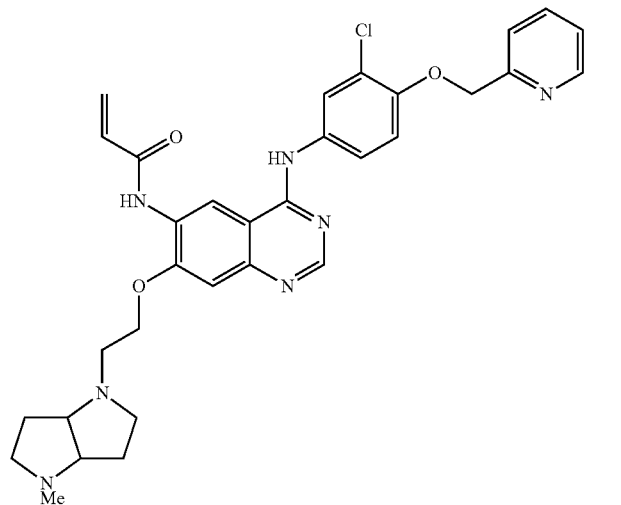 [SMILES: C=CC(=O)Nc1cc2c(Nc3ccc(OCc4ccccn4)c(Cl)c3)ncnc2cc1OCCN1CCC2C1CCN2C] | 92 |
| 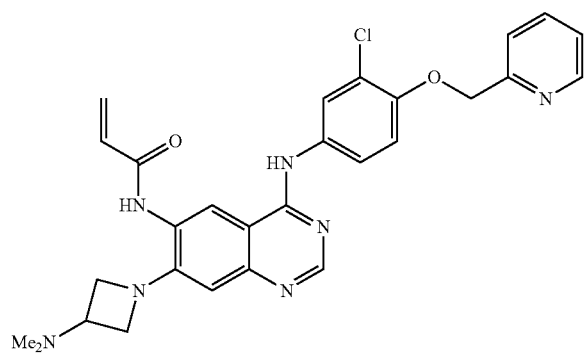 [SMILES: C=CC(=O)Nc1cc2c(Nc3ccc(OCc4ccccn4)c(Cl)c3)ncnc2cc1N1CC(N(C)C)C1] | 93 |
| 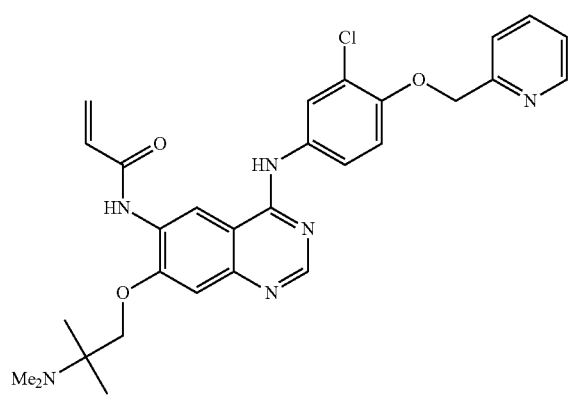 [SMILES: C=CC(=O)Nc1cc2c(Nc3ccc(OCc4ccccn4)c(Cl)c3)ncnc2cc1OCC(C)(C)N(C)C] | 94 |

TABLE I-continued
| Compound | No. |
|---|---|
| 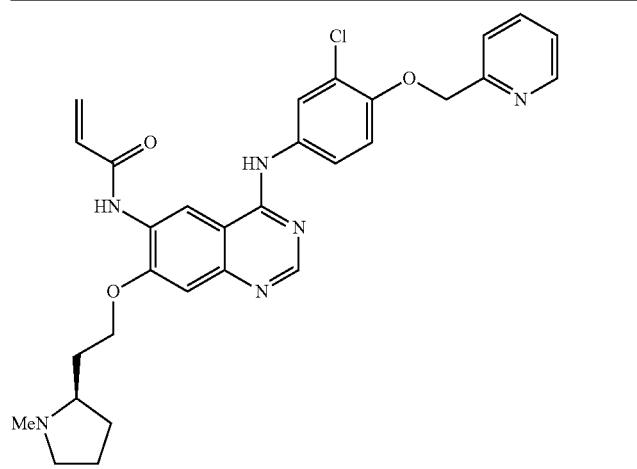 | 95 |
| 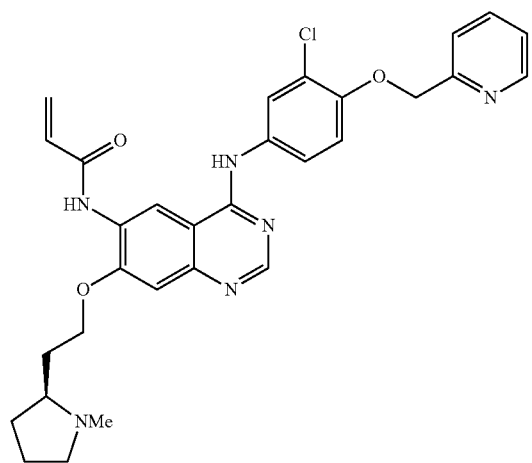 [SMILES: C=CC(=O)Nc1cc2c(Nc3ccc(OCc4ccccn4)c(Cl)c3)ncnc2cc1OCC[C@@H]1CCCN1C] | 96 |
| 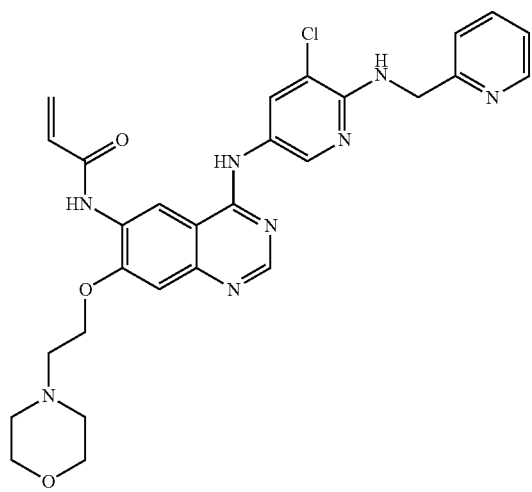 [SMILES: C=CC(=O)Nc1cc2c(Nc3cnc(NCc4ccccn4)c(Cl)c3)ncnc2cc1OCCN1CCOCC1] | 97 |

TABLE I-continued
| Compound | No. |
|---|---|
| 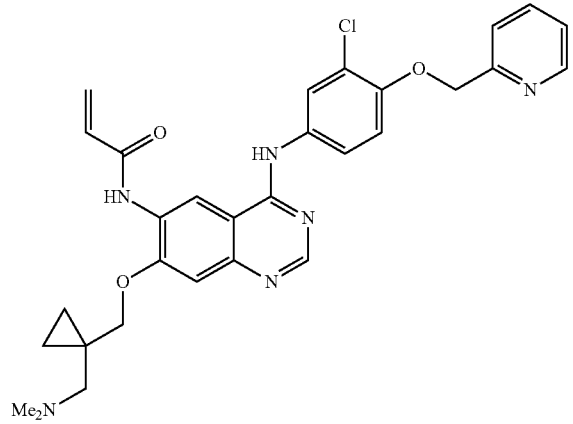 [SMILES: C=CC(=O)Nc1cc2c(Nc3ccc(OCc4ccccn4)c(Cl)c3)ncnc2cc1OCC1(CN(C)C)CC1] | 98 |
| 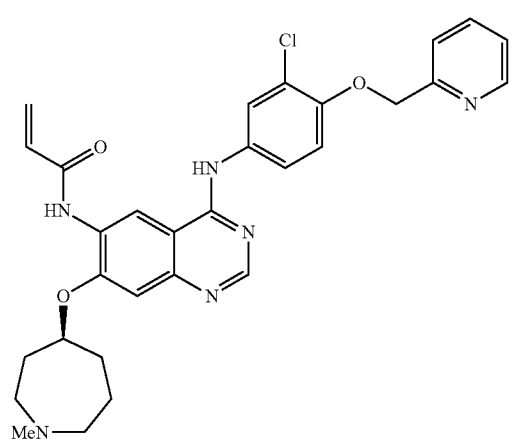 [SMILES: C=CC(=O)Nc1cc2c(Nc3ccc(OCc4ccccn4)c(Cl)c3)ncnc2cc1O[C@H]1CCCN(C)CC1] | 99 |
| 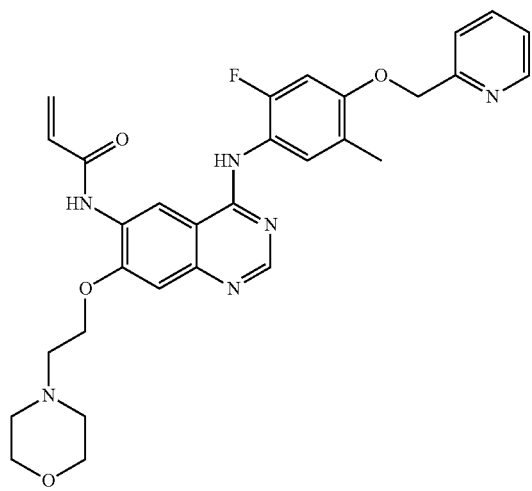 [SMILES: C=CC(=O)Nc1cc2c(Nc3cc(C)c(OCc4ccccn4)cc3F)ncnc2cc1OCCN1CCOCC1] | 100 |

TABLE I-continued
| Compound | No. |
|---|---|
| 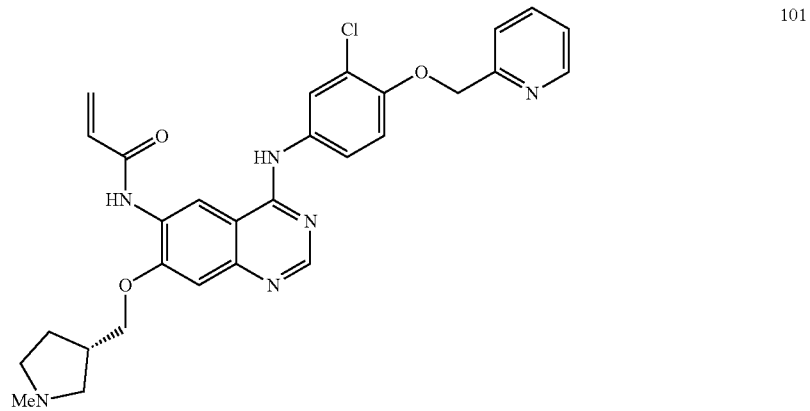 | 101 |
| 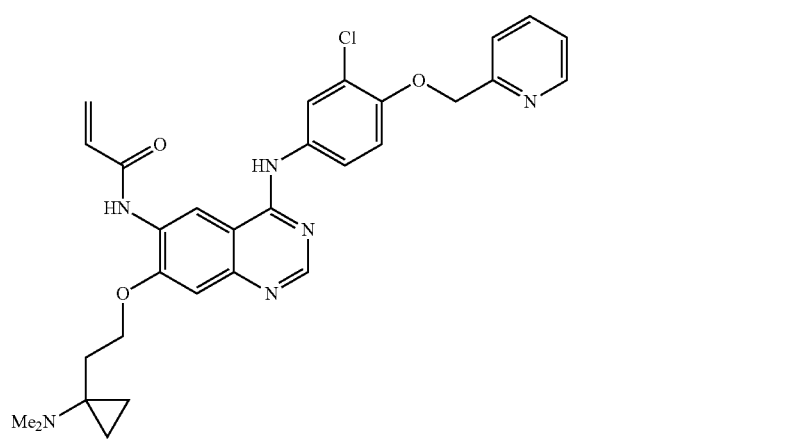 [SMILES: C=CC(=O)Nc1cc2c(Nc3ccc(OCc4ccccn4)c(Cl)c3)ncnc2cc1OCCC1(N(C)C)CC1] | 102 |
| 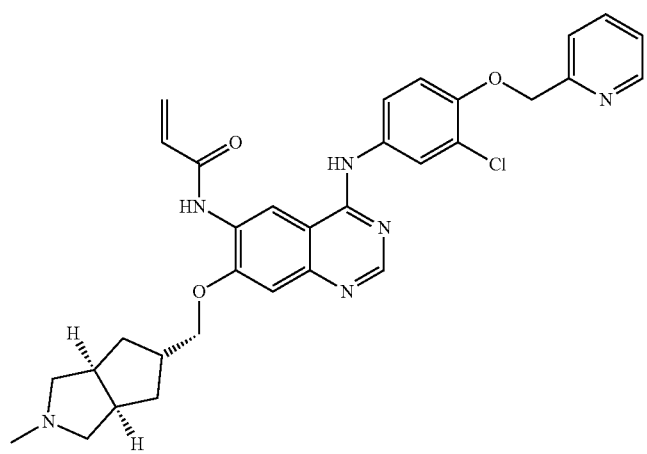 | 103 |

TABLE I-continued

| Compound | No. |
|---|---|
| | 104 |
| | 105 |
| | 106 |
| | 107 |

TABLE I-continued
| Compound | No. |
|---|---|
| 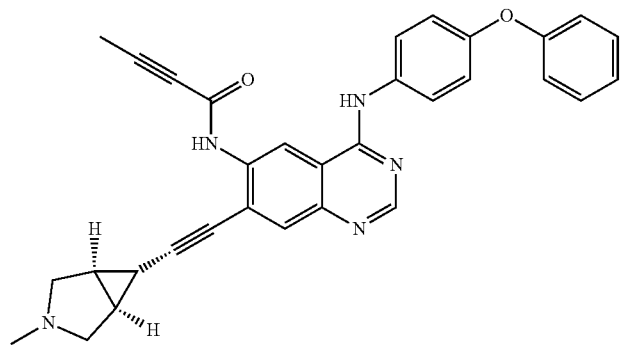 | 108 |
| 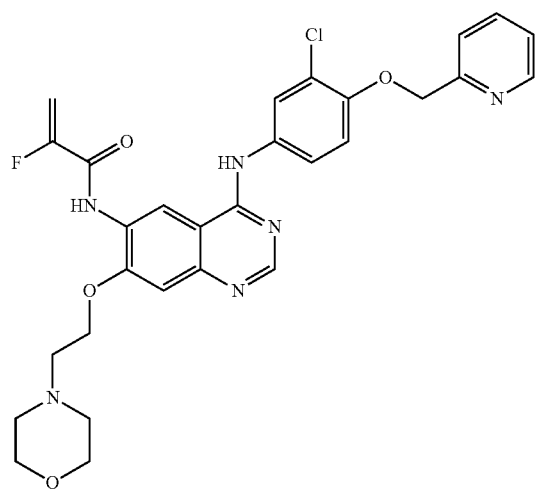 [SMILES: C=C(F)C(=O)Nc1cc2c(Nc3ccc(OCc4ccccn4)c(Cl)c3)ncnc2cc1OCCN1CCOCC1] | 109 |
| 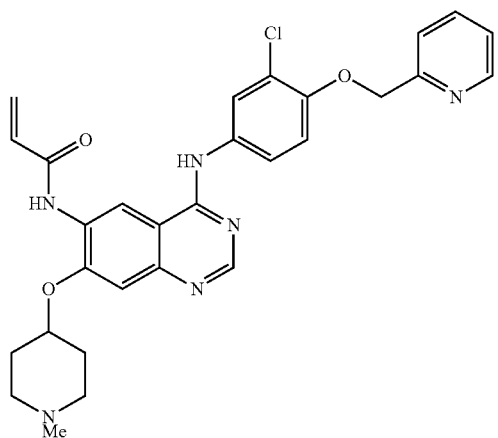 [SMILES: C=CC(=O)Nc1cc2c(Nc3ccc(OCc4ccccn4)c(Cl)c3)ncnc2cc1OC1CCN(C)CC1] | 110 |

TABLE I-continued
| Compound | No. |
|---|---|
| 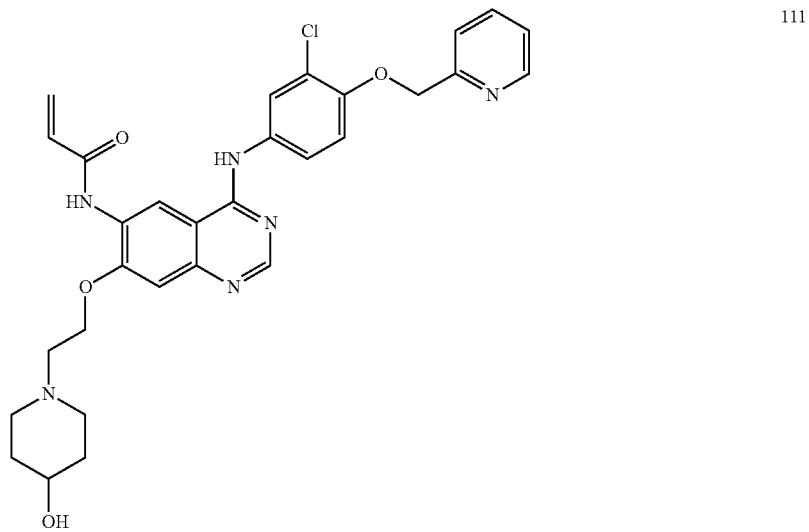 | 111 |
| 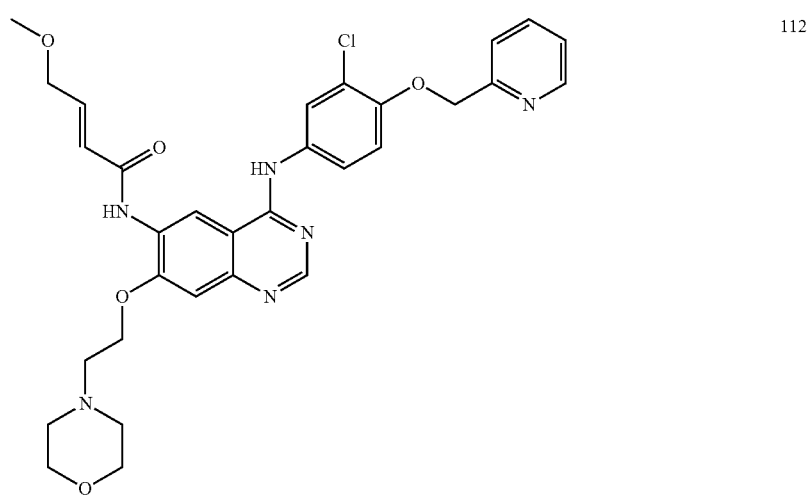 | 112 |
| 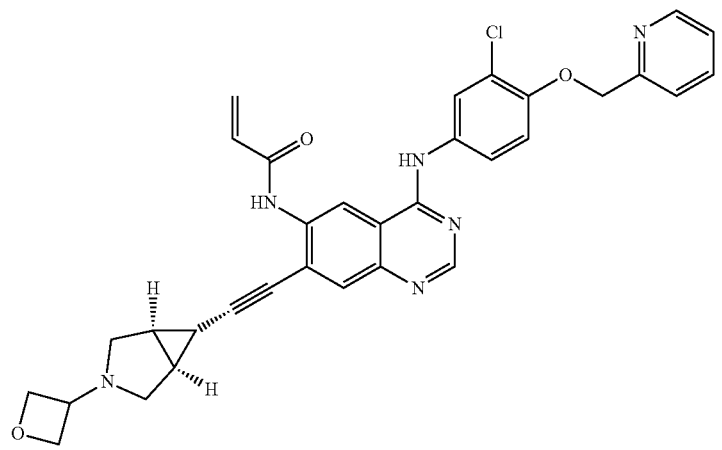 | 113 |

TABLE I-continued

| Compound | No. |
|---|---|
| | 114 |
| | 115 |
| | 116 |
| | 117 |

TABLE I-continued
| Compound | No. |
|---|---|
| 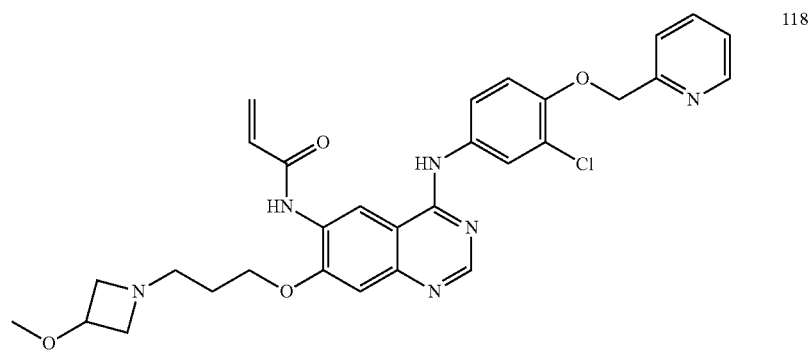 | 118 |
| 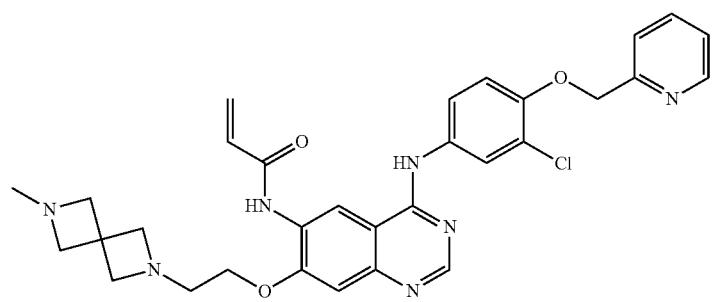 [SMILES: C=CC(=O)Nc1cc2c(Nc3ccc(OCc4ccccn4)c(Cl)c3)ncnc2cc1OCCN1CC2(CN(C)C2)C1] | 119 |
| 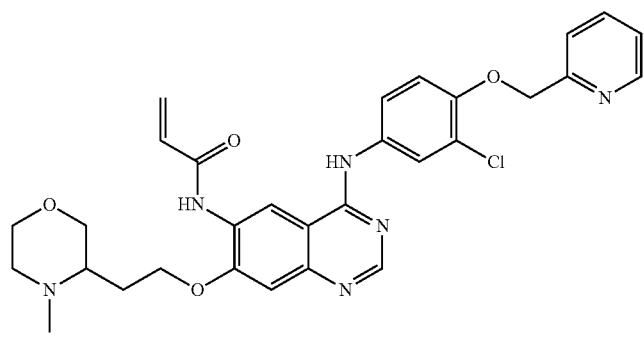 [SMILES: C=CC(=O)Nc1cc2c(Nc3ccc(OCc4ccccn4)c(Cl)c3)ncnc2cc1OCCC1COCCN1C] | 120 |
| 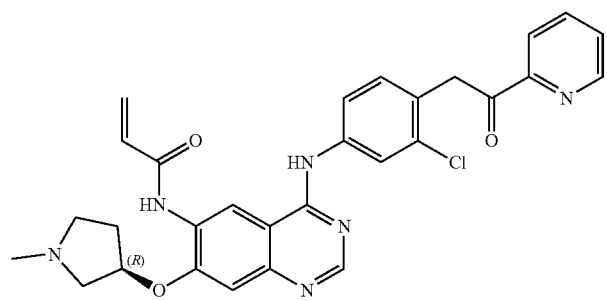 | 121 |

TABLE I-continued

| Compound | No. |
|---|---|
| | 122 |
| | 123 |
| | 124 |
| | 125 |

TABLE I-continued
| Compound | No. |
|---|---|
| 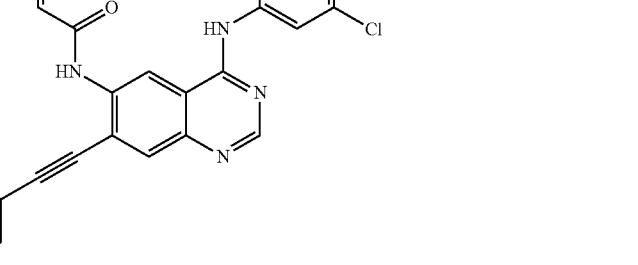 | 126 |
| 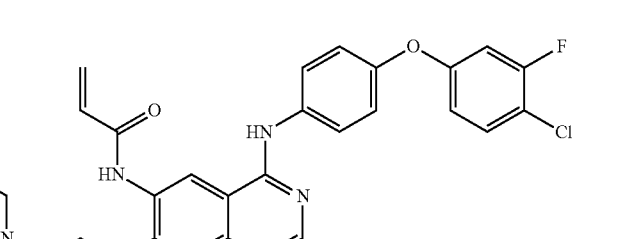 | 127 |
| 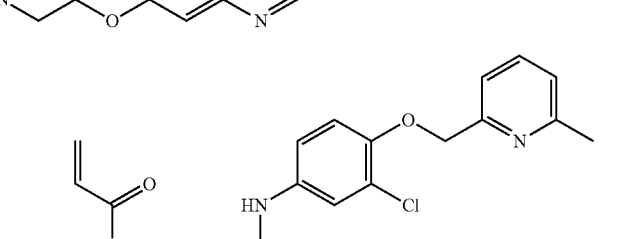 | 128 |
| 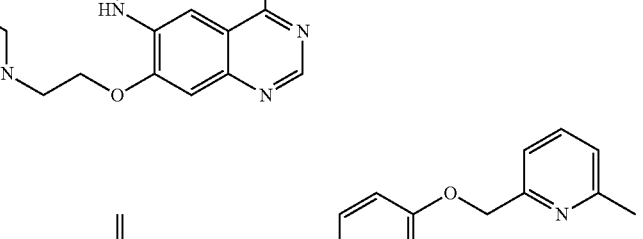 | 129 |
| 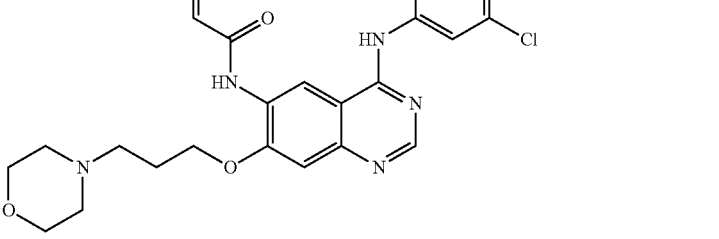 | 130 |

TABLE I-continued
| Compound | No. |
|---|---|
| 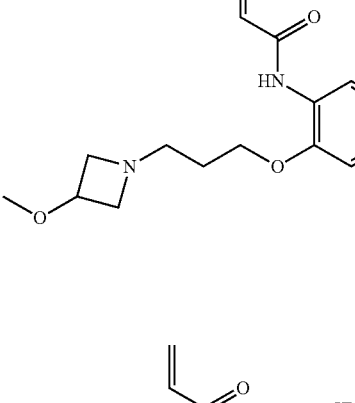 | 131 |
| 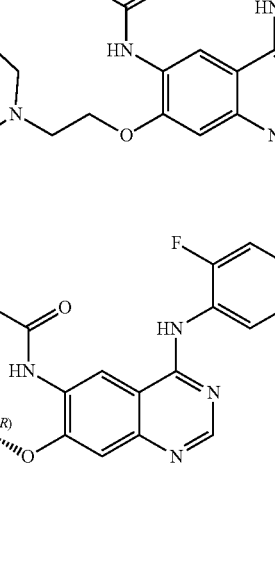 | 132 |
| 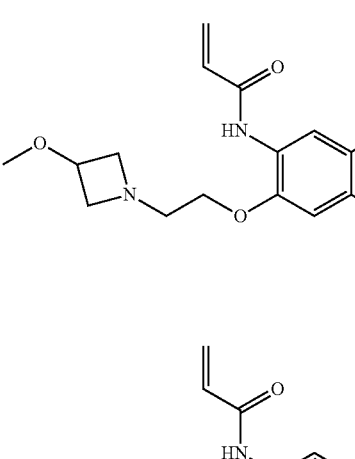 | 133 |
|  | 134 |
|  | 135 |

TABLE I-continued

| Compound | No. |
|---|---|
| | 136 |
| | 137 |
| | 138 |
| | 139 |
| | 140 |

TABLE I-continued
| Compound | No. |
|---|---|
| 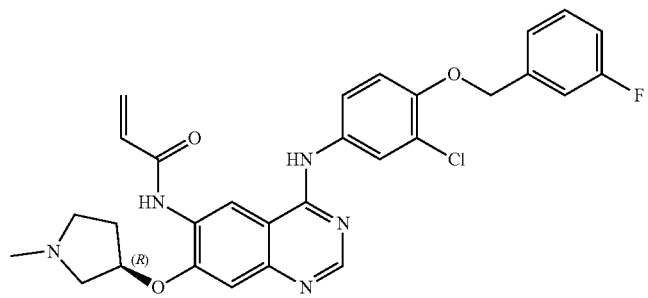 | 141 |
| 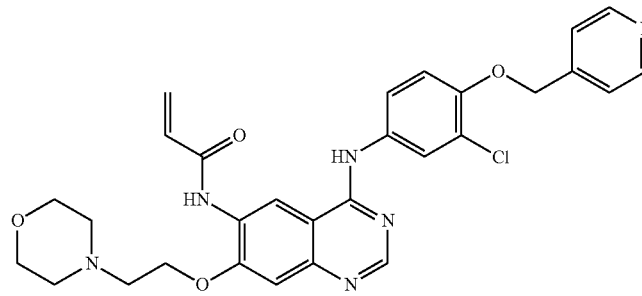 | 142 |
| 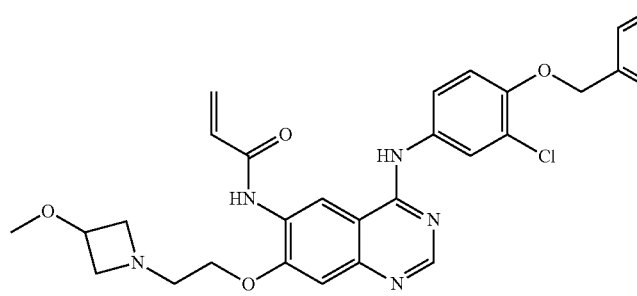 | 143 |
| 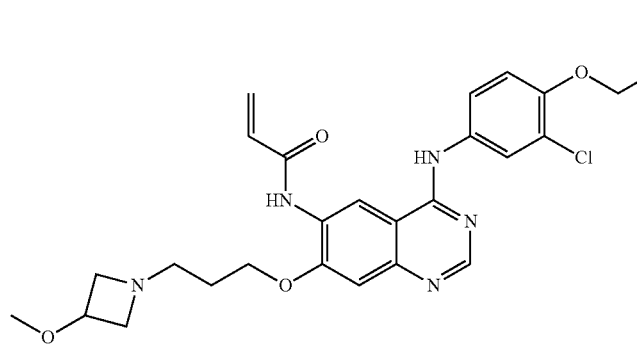 | 144 |
| 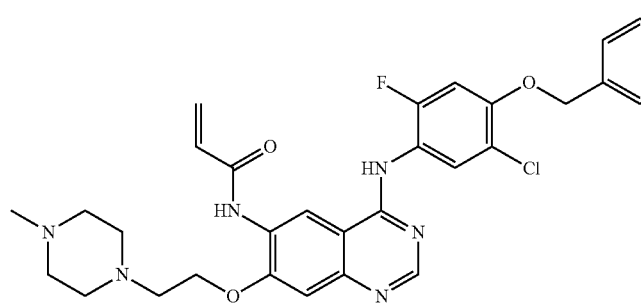 | 145 |

TABLE I-continued

| Compound | No. |
|---|---|
| (structure) | 146 |
| (structure) | 147 |
| (structure) | 148 |
| (structure) | 149 |
| (structure) | 150 |

TABLE I-continued
| Compound | No. |
|---|---|
| 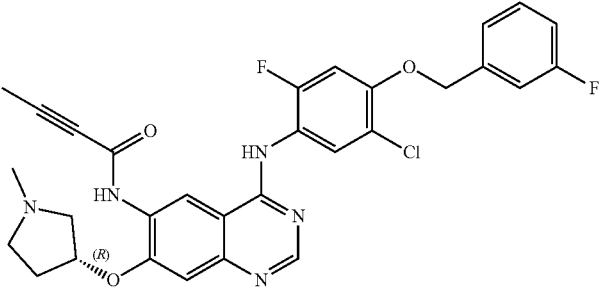 | 151 |
| 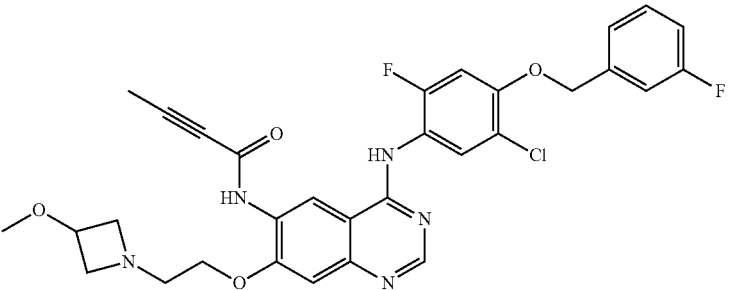 [SMILES: CC#CC(=O)Nc1cc2c(Nc3cc(Cl)c(OCc4cccc(F)c4)cc3F)ncnc2cc1OCCN1CC(OC)C1] | 152 |
| 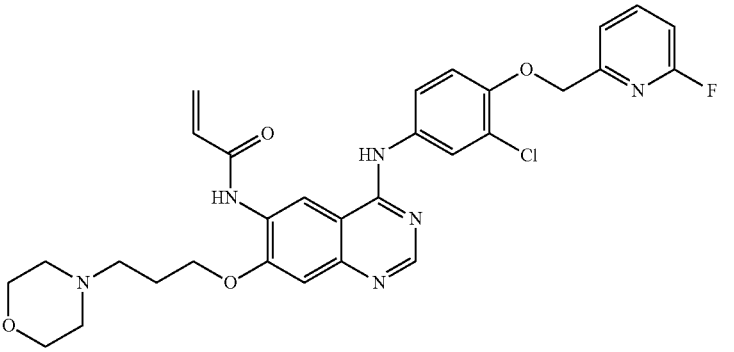 [SMILES: C=CC(=O)Nc1cc2c(Nc3ccc(OCc4cccc(F)n4)c(Cl)c3)ncnc2cc1OCCCN1CCOCC1] | 153 |
| 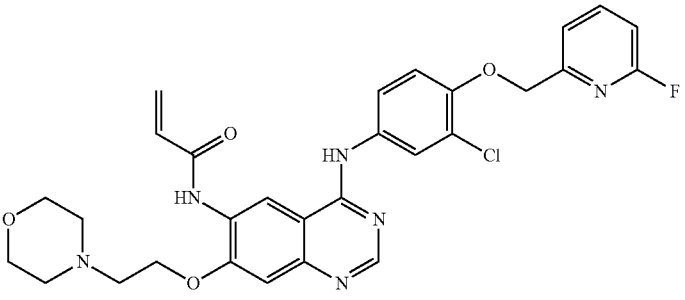 [SMILES: C=CC(=O)Nc1cc2c(Nc3ccc(OCc4cccc(F)n4)c(Cl)c3)ncnc2cc1OCCN1CCOCC1] | 154 |
| 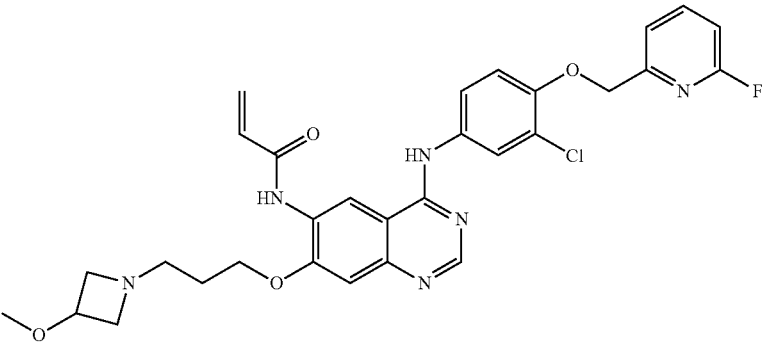 [SMILES: C=CC(=O)Nc1cc2c(Nc3ccc(OCc4cccc(F)n4)c(Cl)c3)ncnc2cc1OCCCN1CC(OC)C1] | 155 |

TABLE I-continued
| Compound | No. |
|---|---|
| 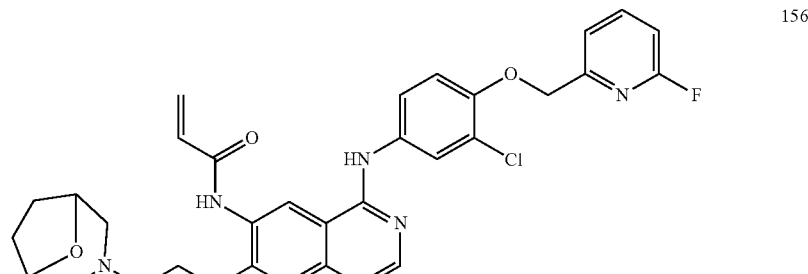 | 156 |
| 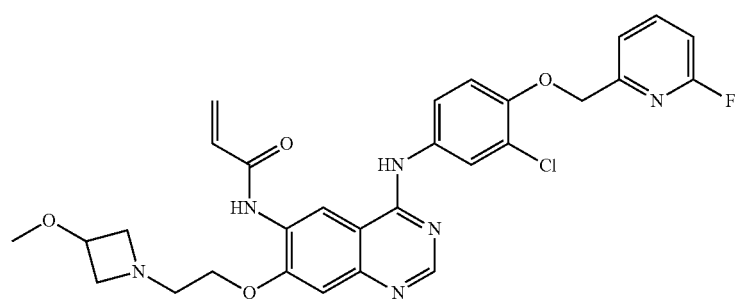 [SMILES: C=CC(=O)Nc1cc2c(Nc3ccc(OCc4cccc(F)n4)c(Cl)c3)ncnc2cc1OCCN1CC(OC)C1] | 157 |
| 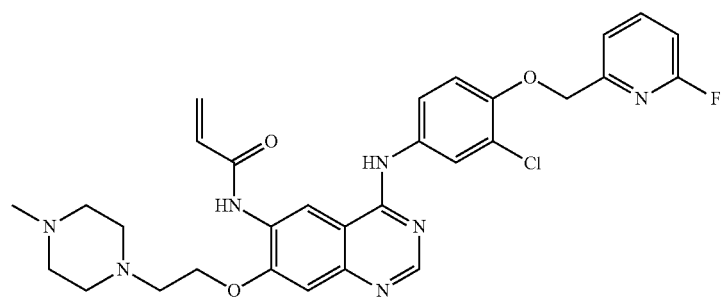 [SMILES: C=CC(=O)Nc1cc2c(Nc3ccc(OCc4cccc(F)n4)c(Cl)c3)ncnc2cc1OCCN1CCN(C)CC1] | 158 |
| 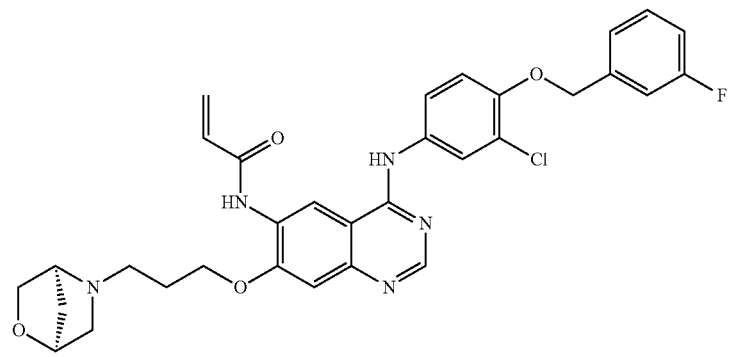 [SMILES: C=CC(=O)Nc1cc2c(Nc3ccc(OCc4cccc(F)c4)c(Cl)c3)ncnc2cc1OCCCN1C[C@@H]2C[C@H]1CO2] | 159 |

TABLE I-continued

| Compound | No. |
|---|---|
| | 160 |
| | 161 |
| | 162 |
| | 163 |

TABLE I-continued
| Compound | No. |
|---|---|
| 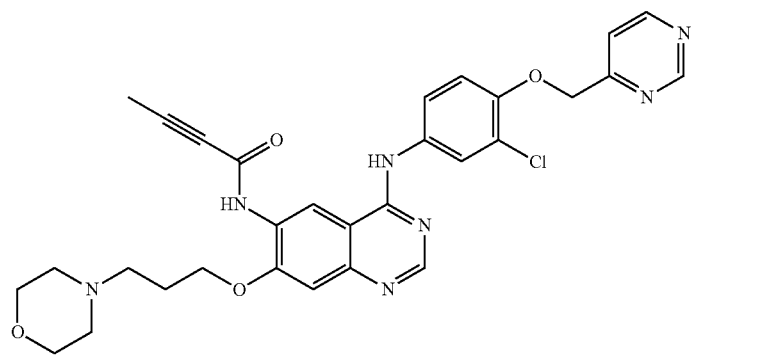 [SMILES: CC#CC(=O)Nc1cc2c(Nc3ccc(OCc4ccncn4)c(Cl)c3)ncnc2cc1OCCCN1CCOCC1] | 164 |
| 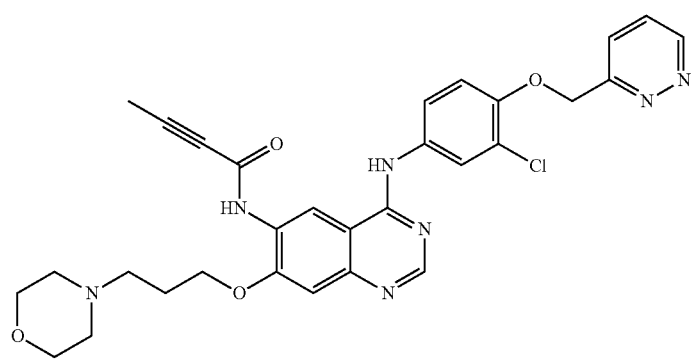 [SMILES: CC#CC(=O)Nc1cc2c(Nc3ccc(OCc4cccnn4)c(Cl)c3)ncnc2cc1OCCCN1CCOCC1] | 165 |
| 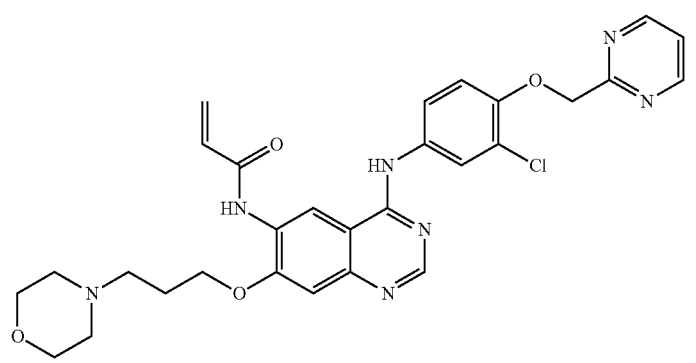 | 166 |
| 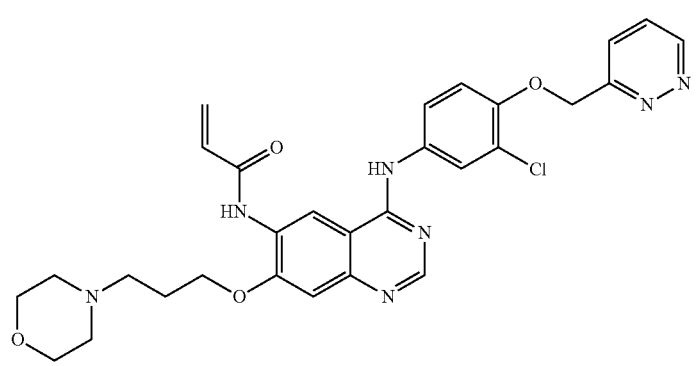 [SMILES: C=CC(=O)Nc1cc2c(Nc3ccc(OCc4cccnn4)c(Cl)c3)ncnc2cc1OCCCN1CCOCC1] | 167 |

TABLE I-continued
| Compound | No. |
|---|---|
| 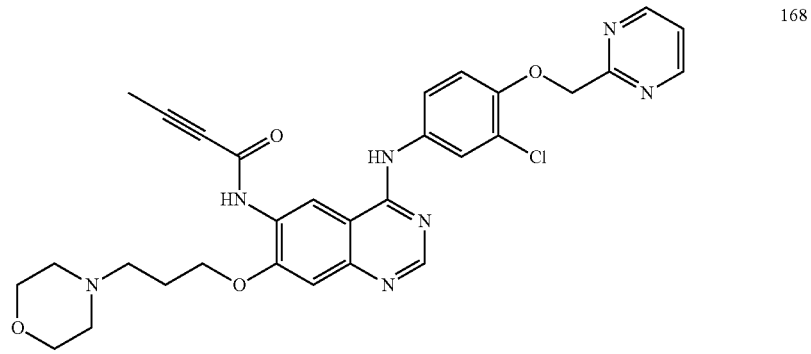 | 168 |
| 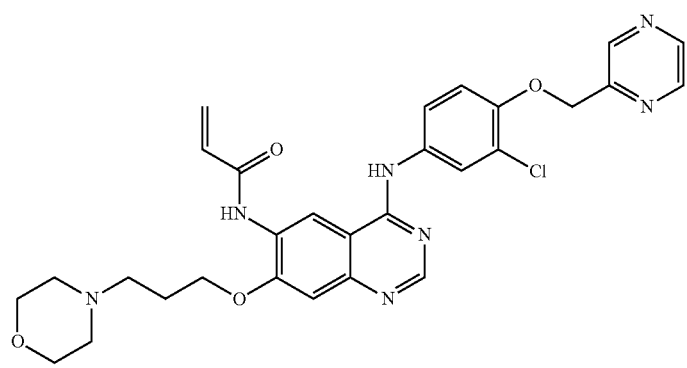 [SMILES: C=CC(=O)Nc1cc2c(Nc3ccc(OCc4cnccn4)c(Cl)c3)ncnc2cc1OCCCN1CCOCC1] | 169 |
| 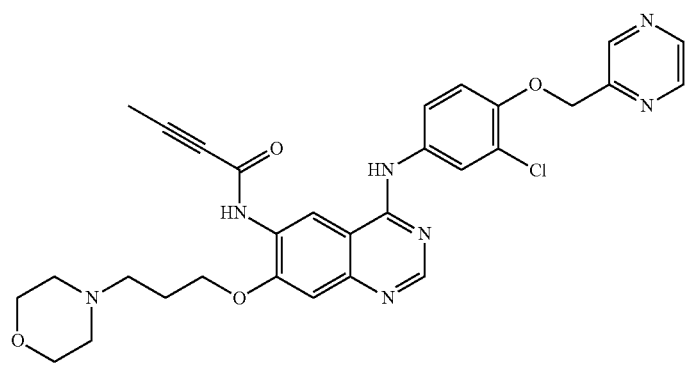 [SMILES: CC#CC(=O)Nc1cc2c(Nc3ccc(OCc4cnccn4)c(Cl)c3)ncnc2cc1OCCCN1CCOCC1] | 170 |
| 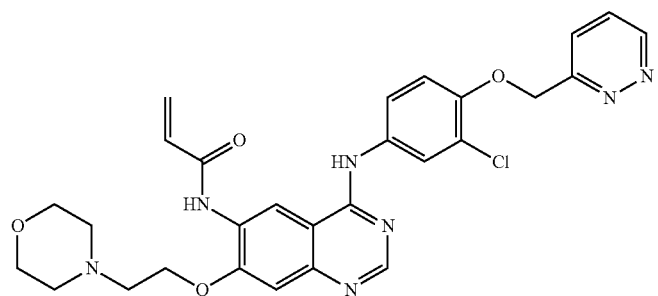 [SMILES: C=CC(=O)Nc1cc2c(Nc3ccc(OCc4cccnn4)c(Cl)c3)ncnc2cc1OCCN1CCOCC1] | 171 |

TABLE I-continued
| Compound | No. |
|---|---|
| 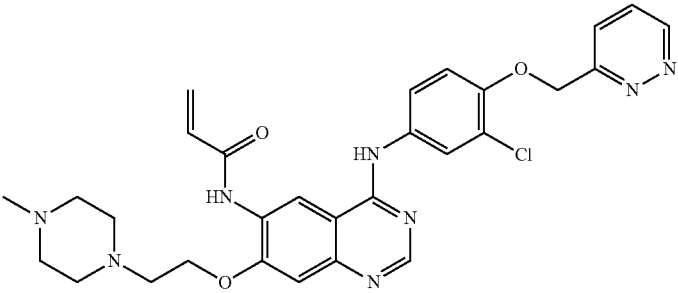 [SMILES: C=CC(=O)Nc1cc2c(Nc3ccc(OCc4cccnn4)c(Cl)c3)ncnc2cc1OCCN1CCN(C)CC1] | 172 |
| 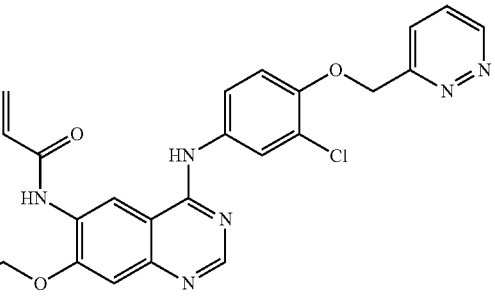 | 173 |
| 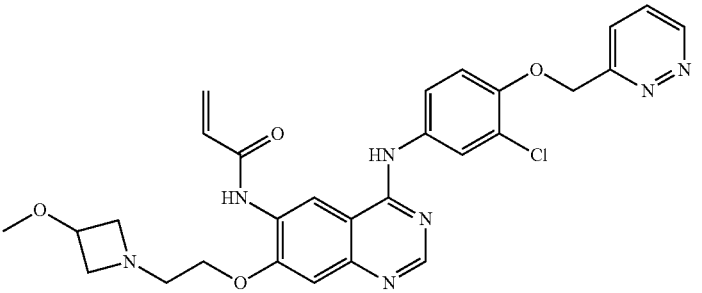 [SMILES: C=CC(=O)Nc1cc2c(Nc3ccc(OCc4cccnn4)c(Cl)c3)ncnc2cc1OCCN1CC(OC)C1] | 174 |
| 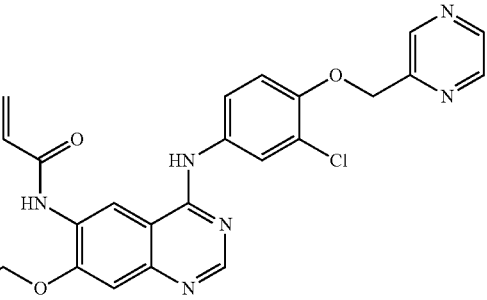 | 175 |
| 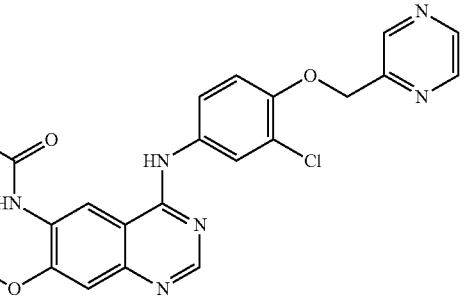 | 176 |

TABLE I-continued

| Compound | No. |
|---|---|
| (structure) | 177 |
| (structure) | 178 |
| (structure) | 179 |
| (structure) | 180 |

The compounds of the present disclosure can contain one or more asymmetric centers in the molecule. A compound without designation of the stereochemistry is to be understood to include all the optical isomers (e.g., diastereomers, enantiomers, etc) in pure or substantially pure form, as well as mixtures thereof (e.g. a racemic mixture, or an enantiomerically enriched mixture). It is well known in the art how to prepare such optically active forms (e.g. by resolution of the racemic form by recrystallization techniques, by synthesis from optically-active starting materials, by chiral synthesis, by chromatographic separation using a chiral stationary phase, and other methods).

The compounds can be isotopically-labeled compounds, for example, compounds including various isotopes of hydrogen, carbon, nitrogen, oxygen, phosphorous, fluorine, iodine, or chlorine. The disclosed compounds may exist in tautomeric forms and mixtures and separate individual tautomers are contemplated. In addition, some compounds may exhibit polymorphism.

The compounds of the present disclosure include the free form as well as the pharmaceutically acceptable salts and stereoisomers thereof. The pharmaceutically acceptable salts include all the typical pharmaceutically acceptable salts. The pharmaceutically acceptable salts of the present compounds can be synthesized from the compounds of the present disclosure which contain a basic or acidic moiety by conventional chemical methods, see e.g. Berge et al, "Pharmaceutical Salts," J. Pharm. ScL, 1977:66:1-19.

For example, conventional pharmaceutically acceptable salts for a basic compound include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Conventional pharmaceutically acceptable salts for an acidic compound include those derived from inorganic bases include aluminum, ammonium, calcium, copper, ferric, ferrous, lithium, magnesium, manganic salts, manganous, potassium, sodium, zinc and the like. Salts derived from pharmaceutically acceptable organic bases include salts of primary, secondary and tertiary amines, substituted amines including naturally occurring substituted amines, cyclic amines and basic ion exchange resins, such as arginine, betaine caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The compounds of the present disclosure may exist in solid, i.e. crystalline or noncrystalline form (optionally as solvates) or liquid form. In the solid state, it may exist in, or as a mixture thereof. In crystalline solvates, solvent molecules are incorporated into the crystalline lattice during crystallization. The formation of solvates may include non-aqueous solvents such as, but not limited to, ethanol, isopropanol, DMSO, acetic acid, ethanolamine, or ethyl acetate, or aqueous solvents such as water (also called "hydrates"). It is common knowledge that crystalline forms (and solvates thereof) may exhibit polymorphism, i.e. exist in different crystalline structures known as "polymorphs", that have the same chemical composition but differ in packing, geometrical arrangement, and other descriptive properties of the crystalline solid state. Polymorphs, therefore, may have different physical properties such as shape, density, hardness, deformability, stability, and dissolution properties, and may display different melting points, IR spectra, and X-ray powder diffraction patterns, which may be used for identification. Such different polymorphs may be produced, for example, by changing or adjusting the reaction conditions or reagents, during preparation of the compound of the present disclosure.

Syntheses of Compounds

In some embodiments, the present disclosure provides methods of preparation of the compounds of the present disclosure. In some embodiments, the compounds are prepared according to the syntheses shown in schemes A to D in the experimental section.

In some embodiments, the present disclosure provides a method of preparing a compound of the present disclosure.

In some embodiments, the present disclosure provides a method of a compound, comprising one or more steps as described herein.

In some embodiments, the present disclosure provides a compound obtainable by, or obtained by, or directly obtained by a method for preparing a compound as described herein.

In some embodiments, the present disclosure provides an intermediate as described herein, being suitable for use in a method for preparing a compound as described herein.

The compounds of the present disclosure can be prepared by any suitable technique known in the art. Processes for the preparation of these compounds are described in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilized.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

As will be understood by the person skilled in the art of organic synthesis, compounds of the present disclosure are readily accessible by various synthetic routes, some of which are exemplified in the accompanying examples. The skilled person will easily recognize which kind of reagents and reactions conditions are to be used and how they are to be applied and adapted in any particular instance—wherever necessary or useful—in order to obtain the compounds of the present disclosure. In some embodiments, some of the compounds of the present disclosure can readily be synthesised by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W.

Greene, "Greene's Protective Groups in Organic Synthesis", 4th edition (2006) (John Wiley & Sons).

General routes for the preparation of a compound of the application are described in the general procedures A-D:

General Procedure A:

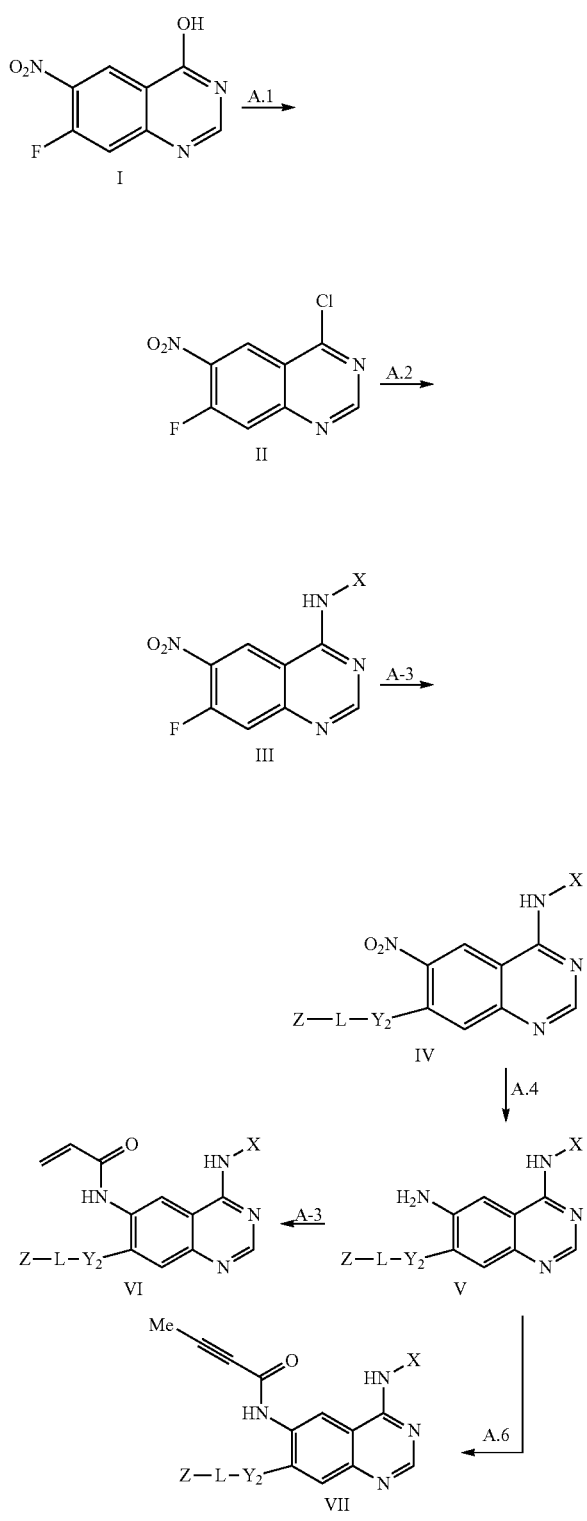

Step A.1:

A solution of 7-fluoro-6-nitro-quinazolin-4-ol (5.00 g, 23.9 mmol, 1.00 eq) in thionyl chloride (20.0 mL) was added dimethyl formamide (174 mg, 2.39 mmol, 183 uL, 0.10 eq). The reaction was stirred at 80° C. for 10 h. The reaction mixture was concentrated under reduced pressure to give 4-chloro-7-fluoro-6-nitroquinazoline (6.00 g, crude) as an off-white solid. The product was taken to next step without purification.

Step A.2:

A mixture of 4-chloro-7-fluoro-6-nitroquinazoline (2.4 g, 10.55 mmol, 1 eq) and the free amine $H_2N-X$ (1 eq) isopropyl alcohol was heated at 80° C. for 1 h. The reaction mixture was concentrated under reduced pressure to give a residue. The residue was triturated with ethyl acetate to give amine III.

Step A.3:

To a solution of amine III (1 eq) and the NH or OH nucleophile $Z-L-Y^2$—H (1.1 eq) in acetonitrile was added cesium carbonate (2 eq) or DBU (2 eq) and optionally potassium iodide (1 eq). Then the mixture was stirred at 80-110° C. for 12 h. The reaction mixture was quenched by addition of water and then extracted with ethyl acetate. The combined organic layers were washed with brine dried over sodium sulfate, filtered and concentrated under reduced pressure to give a residue. The residue was purified by flash silica gel chromatography to give IV.

Step A.4:

Variant i): A mixture of IV (1 eq) and nickel(ii) chloride hexahydrate (2 eq) in dichloromethane and methanol (1:1) was added sodium borohydride (4 eq) at 0° C. and then the mixture was stirred at 0° C. for 12 h. The reaction mixture was filtered and the filtrate was concentrated to give a residue. The residue was purified by reversed phase column chromatography to give amine V.

Variant ii): A mixture of IV (1 eq), iron (3 eq) and ammonium chloride (5 eq) in methanol and water (4:1) was stirred at 70° C. for 12 h. The reaction mixture was filtered and the filtrate was concentrated under reduced pressure to give a residue. The residue was purified by Reverse-MPLC to give amine V.

Step A.5:

Variant i): To a solution of V (1 eq), 4-dimethylamino-pyridine (1.5 eq) and acrylic acid (1.2 eq) in dimethyl formamide was added 1-(3-dimethylaminopropyl)-3-ethyl-carbodiimide (2 eq) and then the solution was stirred at 25° C. for 1 h. The reaction mixture was filtered. The filtrate was purified by prep-HPLC to give acrylamide VI.

Variant ii): To a solution of V (1 eq) and triethylamine (4 eq) in dimethyl formamide was added acrylic anhydride (1.2 eq) and then the solution was stirred at 25° C. for 0.5 h. The reaction mixture was filtered. The filtrate was purified by prep-HPLC to give acrylamide VI.

Variant iii): To a solution of V (1.0 eq) in dimethylformamide was added triethylamine (3.00 eq) and acryloyl chloride (1.20 eq) at 0° C. The reaction mixture was stirred at 0° C. for 1 h and subsequently filtered. The filtrate was purified by prep-HPLC to give acrylamide VI.

Step A.6:

To a solution of V (1.0 eq), 1-(3-dimethylaminopropyl)-3-ethylcarbodiimide hydrochloride (5.00 eq) and pyridine (5.00 eq) in N,N-dimethylformamide was added but-2-ynoic acid (10.0 eq). The mixture was stirred at 50° C. for 2 h and subsequently concentrated in vacuum. The mixture was purified by prep-HPLC to give ynamide VII.

General Procedure B:

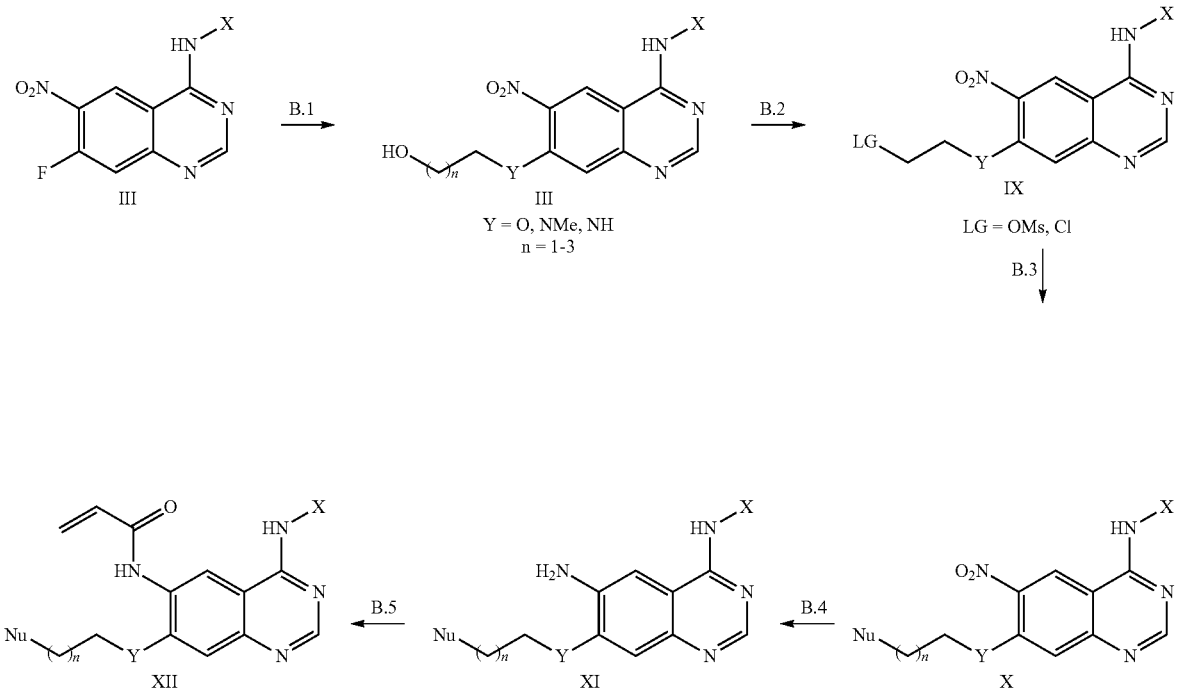

Step B.1:

To a solution of III, obtained in step A.2. (1.00 eq) and potassium tert-butoxide (4.00 eq) in dimethylsulfoxide (10.0 mL) was added the corresponding diol of aminoalcohol (6.00 eq) dropwise at 20° C. The mixture was stirred at 20° C. for 12 h. The mixture was diluted with water and extracted with ethyl acetate. The combined organic layer was washed with brine and dried over sodium sulfate, filtered and concentrated to give crude product. The crude product was purified by silica gel chromatography to give alcohol VIII.

Step B.2:

Variant i): To a solution of VIII (1 eq) and triethylamine (4.00 eq) in dichloromethane and dimethylsulfoxide (6:1) was added MsCl (4.00 eq) dropwise at 0° C. The mixture was stirred at 20° C. for 2 h. The mixture was diluted with water and extracted with dichloromethane. The combined organic layer was washed with brine and dried over sodium sulfate, filtered and concentrated to give Mesylate IX.

Variant ii): To a solution of VIII (1.0 eq) in thionyl chloride was added N,N-dimethylformamide (0.1 eq). The mixture was stirred at 90° C. for 3 h. The mixture was cooled to 25° C. and then concentrated in vacuum. The mixture was partitioned between and ethyl acetate. The organic phase was washed with brine, dried with anhydrous sodium sulfate, filtered and concentrated in vacuum. The residue was purified by silica gel chromatography to afford chloride IX.

Step B.3:

To a solution of IX (1.0 eq) and potassium carbonate (4.00 eq) in dimethylsulfoxide was the corresponding N—H nucleophile (2.0 eq) in one portion at 20° C. The mixture was stirred at 50° C. for 12 h. The mixture was diluted with water and extracted with ethyl acetate. The combined organic layer was washed with brine and dried over sodium sulfate, filtered and concentrated to give crude product. The crude product was purified by prep-HPLC to give X.

Step B.4:

Variant i): A mixture of X (1 eq) and nickel(ii) chloride hexahydrate (2 eq) in dichloromethane and methanol (1:1) was added sodium borohydride (4 eq) at 0° C. and then the mixture was stirred at 0° C. for 12 h. The reaction mixture was filtered and the filtrate was concentrated to give a residue. The residue was purified by reversed phase column chromatography to give amine XI.

Variant ii): A mixture of X (1 eq), iron (3 eq) and ammonium chloride (5 eq) in methanol and water (4:1) was stirred at 70° C. for 12 h. The reaction mixture was filtered and the filtrate was concentrated under reduced pressure to give a residue. The residue was purified by Reverse-MPLC to give amine XI.

Step B.5:

Variant i): To a solution of XI (1 eq), 4-dimethylamino-pyridine (1.5 eq) and acrylic acid (1.2 eq) in dimethyl formamide was added 1-(3-dimethylaminopropyl)-3-ethyl-carbodiimide (2 eq) and then the solution was stirred at 25° C. for 1 h. The reaction mixture was filtered. The filtrate was purified by prep-HPLC to give acrylamide XII.

Variant ii): To a solution of XI (1 eq) and triethylamine (4 eq) in dimethyl formamide was added acrylic anhydride (1.2 eq) and then the solution was stirred at 25° C. for 0.5 h. The reaction mixture was filtered. The filtrate was purified by prep-HPLC to give acrylamide XII.

Variant iii): To a solution of XI (1.0 eq) in dimethylformamide was added triethylamine (3.00 eq) and acryloyl chloride (1.20 eq) at 0° C. The reaction mixture was stirred at 0° C. for 1 h and subsequently filtered. The filtrate was purified by prep-HPLC to give acrylamide XII.

General Procedure C:

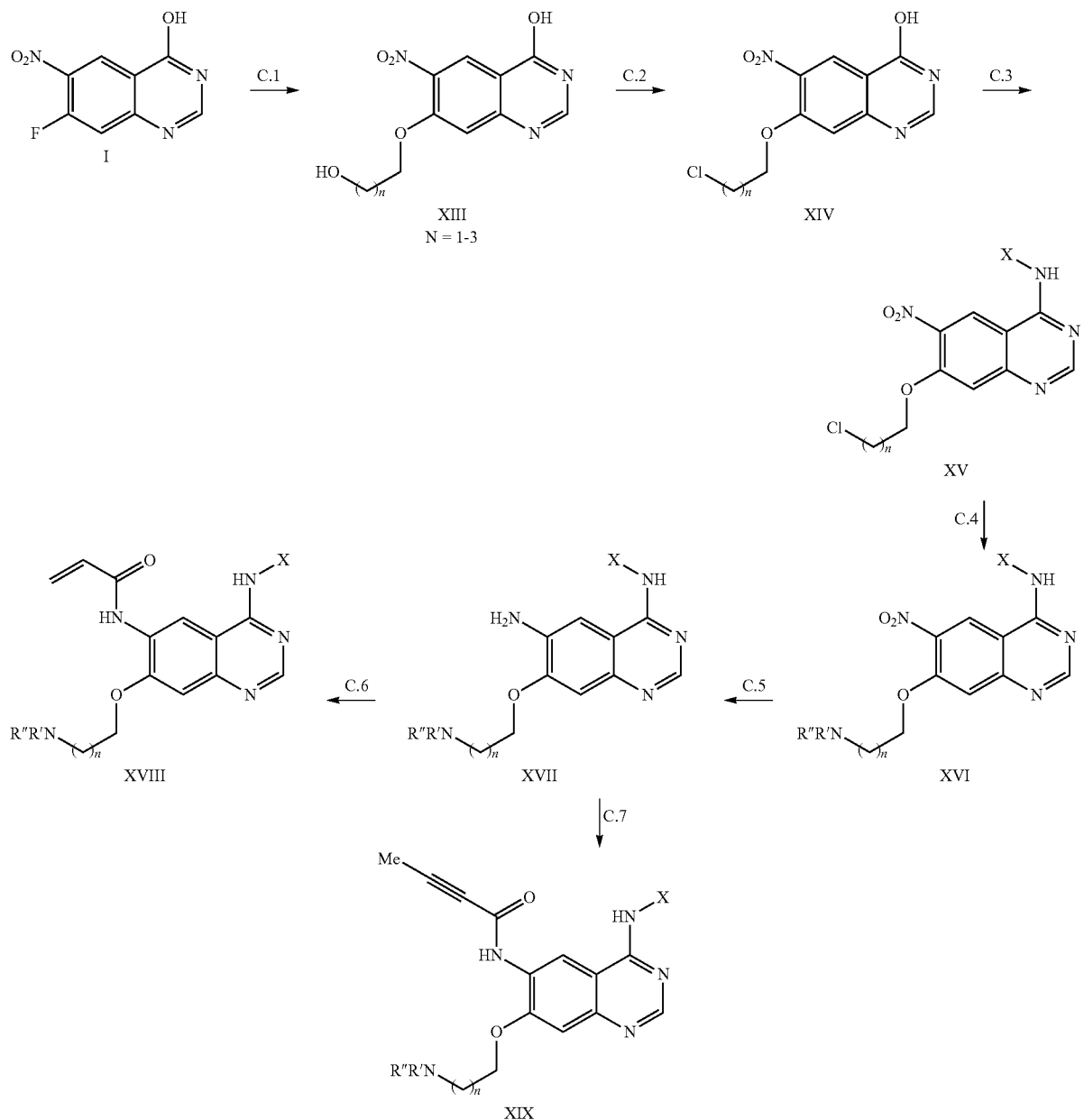

Step C.1:

Sodium (3.0 eq) was added to the corresponding diol (18.7 eq) at 25° C. The suspension was stirred at 25° C. for 0.5 h. Alcohol I (1.0 eq) was added to the above suspension. The mixture was heated to 70° C. and stirred at 70° C. for 1.5 h. The mixture was cooled to 25° C. and then adjusted to pH=7 with hydrochloric acid (3 M). After filtration, the filter cake was dried under reduced pressure to afford diol XIII.

Step C.2:

To a solution of diol XIII (1.00 eq) in thionyl chloride (10.0 mL) was added N,N-dimethylformamide (0.1 eq). The mixture was stirred at 90° C. for 3 h. The mixture was cooled to 25° C. and then concentrated in vacuum. The mixture was partitioned between water and ethyl acetate. The organic phase was washed with brine, dried with anhydrous sodium sulfate, filtered and concentrated in vacuum. The residue was purified by silica gel chromatography to afford dichloride XIV.

Step C.3:

A solution of dichloride XIV (1.0 eq) and $H_2N$-X (1.50 eq) in propan-2-ol was stirred at 90° C. for 12 h. The mixture was cooled to 25° C. and then concentrated in vacuum. The residue was triturated with methanol, then filtered and dried under reduced pressure to afford XV.

Step C.4:

To a solution of XV (1.0 eq), potassium iodide (0.1 eq) and tetrabutylammonium iodide (0.1 eq) in toluene was added HNR'R" (3.00 eq). The mixture was stirred at 110° C. for 12 h. The mixture was cooled to 25° C. and then concentrated in vacuum. The residue was triturated with water and filtered, the filter cake was dried in vacuum to afford XVI.

Step C.5:

Variant i): A mixture of XVI (1 eq) and nickel(ii) chloride hexahydrate (2 eq) in dichloromethane and methanol (1:1) was added sodium borohydride (4 eq) at 0° C. and then the mixture was stirred at 0° C. for 12 h. The reaction mixture was filtered and the filtrate was concentrated to give a residue. The residue was purified by reversed phase column chromatography to give amine XVII.

Variant ii): A mixture of XVI (1 eq), iron (3 eq) and ammonium chloride (5 eq) in methanol and water (4:1) was stirred at 70° C. for 12 h. The reaction mixture was filtered and the filtrate was concentrated under reduced pressure to give a residue. The residue was purified by Reverse-MPLC to give amine XVII.

Step C.6:

Variant i): To a solution of XVII (1 eq), 4-dimethylaminopyridine (1.5 eq) and acrylic acid (1.2 eq) in dimethyl formamide was added 1-(3-dimethylaminopropyl)-3-ethylcarbodiimide (2 eq) and then the solution was stirred at 25° C. for 1 h. The reaction mixture was filtered. The filtrate was purified by prep-HIPLC to give acrylamide Variant ii): To a solution of XVII (1 eq) and triethylamine (4 eq) in dimethyl formamide was added acrylic anhydride (1.2 eq) and then the solution was stirred at 25° C. for 0.5 h. The reaction mixture was filtered. The filtrate was purified by prep-HPLC to give acrylamide XVIII.

Variant iii): To a solution of XVII (1.0 eq) in dimethylformamide was added triethylamine (3.00 eq) and acryloyl chloride (1.20 eq) at 0° C. The reaction mixture was stirred at 0° C. for 1 h and subsequently filtered. The filtrate was purified by prep-HPLC to give acrylamide XVIII.

Steps C.7:

To a solution of XVII (1.0 eq), 1-(3-dimethylaminopropyl)-3-ethylcarbodiimide hydrochloride (5.00 eq) and pyridine (5.00 eq) in N,N-dimethylformamide was added but-2-ynoic acid (10.0 eq). The mixture was stirred at 50° C. for 2 h and subsequently concentrated in vacuum. The mixture was purified by prep-HPLC to give ynamide XIX.

General Procedure D:

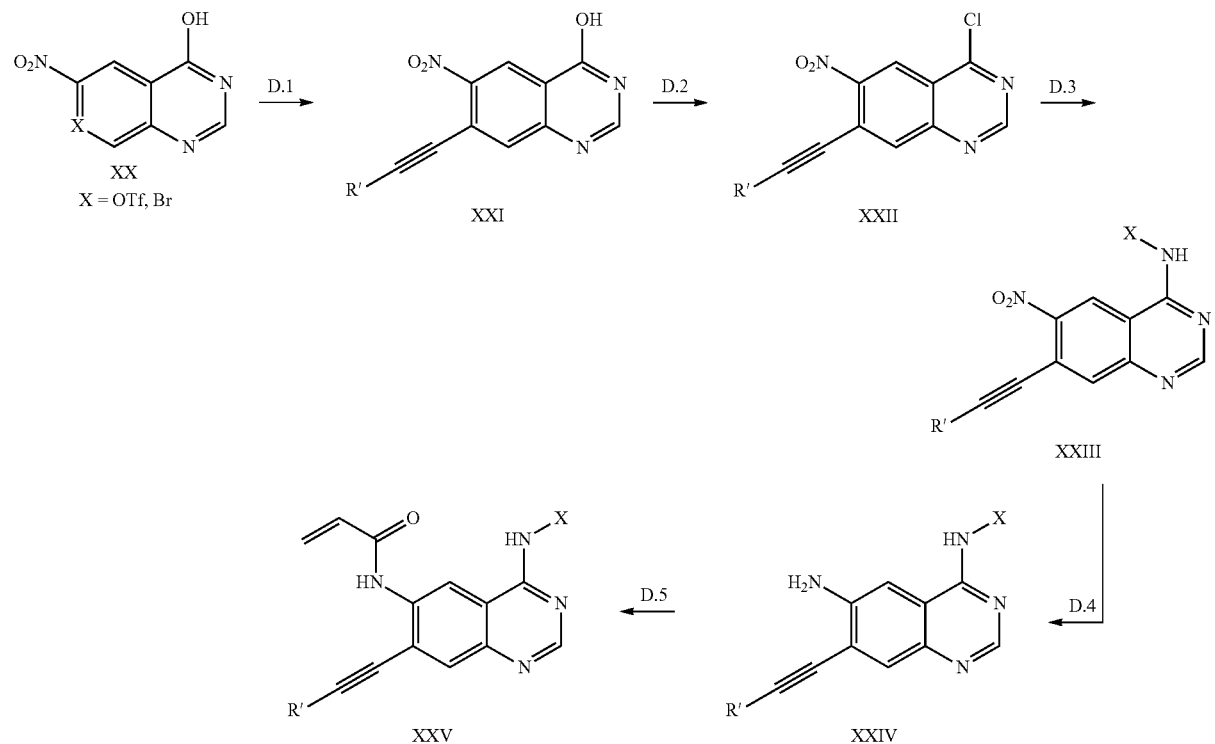

Step D.1:

To a solution of bromide or triflate XX (1.00 eq) in dimethylsulfoxide was added the corresponding alkyne (1.50 eq), triethylamine (3.00 eq), copper (I) iodide (0.5 eq), tetrakis(triphenylphosphine)palladium (0.05 eq) at 20° C. The mixture was degassed with nitrogen and stirred at 20° C. for 12 h under nitrogen. The mixture was added methanol and filtered, the filter cake was concentrated to give alkyne XXI.

Step D.2:

To a suspension of alkyne XXI (1.00 eq) in thionyl chloride was added N,N-dimethylformamide (2.0 eq) at 20° C. The mixture was stirred at 90° C. for 0.5 h until the suspension turned to homogenous solution. The solution was concentrated to give chloride XXII.

Step D.3

A suspension of chloride XXII (1.0 eq) and H$_2$N-X, in propan-2-ol was stirred at 80° C. for 12 h. The mixture was concentrated to give a residue. And the residue was purified by reverse phase chromatography to give XXIII.

Step D.4:

Variant i): A mixture of XXIII (1 eq) and nickel(ii) chloride hexahydrate (2 eq) in dichloromethane and methanol (1:1) was added sodium borohydride (4 eq) at 0° C. and then the mixture was stirred at 0° C. for 12 h. The reaction mixture was filtered and the filtrate was concentrated to give a residue. The residue was purified by reversed phase column chromatography to give amine XXIV.

Variant ii): A mixture of XXIII (1 eq), iron (3 eq) and ammonium chloride (5 eq) in methanol and water (4:1) was stirred at 70° C. for 12 h. The reaction mixture was filtered and the filtrate was concentrated under reduced pressure to give a residue. The residue was purified by Reverse-MPLC to give amine XXIV.

Step D.5:

Variant i): To a solution of XXIV (1 eq), 4-dimethylaminopyridine (1.5 eq) and acrylic acid (1.2 eq) in dimethyl formamide was added 1-(3-dimethylaminopropyl)-3-ethylcarbodiimide (2 eq) and then the solution was stirred at 25° C. for 1 h. The reaction mixture was filtered. The filtrate was purified by prep-HPLC to give acrylamide XXV.

Variant ii): To a solution of XXIV (1 eq) and triethylamine (4 eq) in dimethyl formamide was added acrylic anhydride (1.2 eq) and then the solution was stirred at 25° C. for 0.5 h. The reaction mixture was filtered. The filtrate was purified by prep-HPLC to give acrylamide XXV.

Variant iii): To a solution of XXIV (1.0 eq) in dimethylformamide was added triethylamine (3.00 eq) and acryloyl chloride (1.20 eq) at 0° C. The reaction mixture was stirred at 0° C. for 1 h and subsequently filtered. The filtrate was purified by prep-HPLC to give acrylamide XXV.

Pharmaceutical Compositions

In some embodiments, the present disclosure provides a pharmaceutical composition comprising a therapeutically-effective amount of one or more of the compounds of the present disclosure or pharmaceutically acceptable salt thereof and one or more pharmaceutically acceptable carriers and/or excipients (also referred to as diluents). The excipients are acceptable in the sense of being compatible with the other ingredients of the formulation and not deleterious to the recipient thereof (i.e., the patient). The term "therapeutically-effective amount" as used herein refers to the amount of a compound (as such or in form of a pharmaceutical composition) of the present disclosure which is effective for producing some desired therapeutic effect.

Pharmaceutical compositions may be in unit dose form containing a predetermined amount of a compound of the present disclosure per unit dose. Such a unit may contain a therapeutically effective dose of a compound of the present disclosure or salt thereof or a fraction of a therapeutically effective dose such that multiple unit dosage forms might be administered at a given time to achieve the desired therapeutically effective dose. In some embodiments, unit dosage formulations are those containing a daily dose or sub-dose, or an appropriate fraction thereof of a compound of the present disclosure or salt thereof.

The compounds of the present disclosure may be administered by any acceptable means in solid or liquid form, including (1) oral administration, for example, drenches (i.e. aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical compositions.

Such compositions may contain components conventional in pharmaceutical preparations, e.g. wetting agents, emulsifiers and lubricants, such as sodium lauryl sulfate and magnesium stearate, as well as coloring agents, release agents, coating agents, sweetening, flavoring and perfuming agents, preservatives and antioxidants, pH modifiers, bulking agents, and additional active agents. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Such compositions may be prepared by any method known in the art, for example, by bringing into association the active ingredient with one or more carriers and/or excipients. Different compositions and examples of carriers and/or excipients are well known to the skilled person and are described in detail in e.g., Remington: The Science and Practice of Pharmacy. Pharmaceutical Press, 2013; Rowe, Sheskey, Quinn: Handbook of Pharmaceutical Excipients. Pharmaceutical Press, 2009. Excipients that may be used in the preparation of the pharmaceutical compositions may include one or more of buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide a composition suitable for an administration of choice.

As indicated above, the compounds of the present disclosure may be in solid or liquid form and administered by various routes in any convenient administrative form, e.g., tablets, powders, capsules, solutions, dispersions, suspensions, syrups, sprays, suppositories, gels, emulsions, patches, etc.

In solid dosage forms of the present disclosure for oral administration (capsules, tablets, pills, dragees, powders, granules, trouches and the like), a compound is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders; such as, for example, carboxymethylcellulose, alginates, gelatin, polyvinyl pyrrolidone, sucrose and/or acacia; (3) hutnectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like. A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the present disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. An oral composition can also include adjuvants such as wetting agents, emulsifying and suspending agents, sweetening, flavoring, coloring, perfuming and preservative agents.

In form of suspensions, a compound may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for rectal or vaginal administration of a compound of the present disclosure include a suppository, which may be prepared by mixing one or more compounds of the present disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Other suitable forms include pessaries, tampons, creams, gels, pastes, foams or spray formulations containing such carriers as are known in the art to be appropriate.

Dosage forms for the topical or transdermal administration of a compound of the present disclosure include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required. Such ointments, pastes, creams and gels may contain, in addition to a compound of the present disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Dosage forms such as powders and sprays for administration of a compound of the present disclosure, may contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Dosage forms such as transdermal patches for administration of a compound of the present disclosure may include absorption enhancers or retarders to increase or decrease the flux of the compound across the skin. The rate of such flux can be controlled by either providing a rate controlling membrane or dispersing the compound in a polymer matrix or gel. Other dosage forms contemplated include ophthalmic formulations, eye ointments, powders, solutions and the like. It is understood that all contemplated compositions must be stable under the conditions of manufacture and storage, and preserved against the contaminating action of microorganisms, such as bacteria and fungi.

The dosage levels of a compound of the present disclosure in the pharmaceutical compositions of the present disclosure may be adjusted in order to obtain an amount of a compound of the present disclosure which is effective to achieve the desired therapeutic response for a particular patient, composition, and mode of administration, without being deleterious to the patient. The dosage of choice will depend upon a variety of factors including the nature of the particular compound of the present disclosure used, the route of administration, the time of administration, the rate of excretion or metabolism of the particular compound used, the rate and extent of absorption, the duration of the treatment, other drugs, compounds and/or materials used in combination with the particular compound, the age, sex, weight, condition, general health and prior medical history of the patient being treated, and like factors well known in the medical arts. A medical practitioner having ordinary skill in the art can readily determine and prescribe the effective amount of the pharmaceutical composition required.

In some embodiments, a suitable daily dose of a compound of the present disclosure will be that amount of the compound which is the lowest dose effective to produce a therapeutic effect. Such an effective dose will generally depend upon the factors described above. In some embodiments, oral, intravenous, intracerebroventricular and subcutaneous doses of the compounds of the present disclosure for a patient, when used for the indicated analgesic effects, will range from about 0.0001 to about 100 mg, more usual 0.1 to 100 mg/kg per kilogram of body weight of recipient (patient, mammal) per day. In some embodiments, daily dosages may be from about 1 to about 1000 mg/day, and for example, from about 1 to about 100 mg/day.

The effective dose of a compound of the present disclosure may be administered as two, three, four, five, six or more sub-doses administered separately at appropriate intervals throughout a specified period (per day or per week or per month), optionally, in unit dosage forms. In some embodiments, dosing also depends on factors as indicated above, e.g. on the administration, and can be readily arrived at by one skilled in medicine or the pharmacy art.

The compounds of the present disclosure inhibit or modulate the activity of a receptor tyrosine kinase, in particular extracellular mutants of ErbB-receptors, such as, but not limited to, EGFR-Viii (also EGFR-V3) and HER2-S310F. Thus, the compounds and compositions of the present disclosure can be useful as a medicament, i.e. as a medicament in therapy, for the treatment of cancer, as detailed below. In some embodiments, the present disclosure provides a method of treatment of a mammal, for example, a human, suffering from cancer, as detailed below. The term "treatment" is intended to encompass prophylaxis, therapy and cure. Such treatment comprises the step of administering a therapeutically effective amount of a compound of Formula I or salt thereof (or of a pharmaceutical composition containing a compound of Formula I or salt thereof) to said mammal, for example, a human.

Thus, the present disclosure is directed towards the use of the compounds of the present disclosure or pharmaceutically acceptable salts or stereoisomers thereof or a pharmaceutical composition thereof for the treatment of cancer, as detailed below, in a mammal, for example a human.

In some embodiments, a use (or method of treatment) of a subject comprises administering to a subject in need of such treatment a therapeutically effective amount of a compound of the present disclosure or pharmaceutically acceptable salts thereof or a pharmaceutical composition thereof by targeting allosteric and/or oncogenic variants of EGFR and HER-2 receptor.

The present disclosure contemplates administration of a compound of the present disclosure alone or in combination with one or more additional therapeutic agents, such as other Tyrosine kinase inhibitors: Erlotinib hydrochloride (e.g. Tarceva(R) by Genentech/Roche), Linifanib (or ABT 869, by Genentech), sunitinib malate (e.g. Sutent(R) by Pfizer), bosutinib (or SKI-606, described in U.S. Pat. No. 6,780, 996), dasatinib (e.g. Sprycel(R) by Bristol-Myers Squibb), armala (e.g. pazopanib, e.g. Votrient(R) by GlaxoSmithKline), imatinib and imatinib mesylate (e.g. Gilvec(R) and Gleevec(R) by Novartis); Vascular Endothelial Growth Factor (VEG) receptor inhibitors (Bevacizumab, or Avastin (R) by Genentech/Roche), axitinib, (or AG013736, described in WO 01/002369), Brivanib Alaninate (or BMS-582664), motesanib (or AMG-706, described in PCT WO 02/066470), pasireotide (e.g. SOM230, described in WO 02/010192), sorafenib (e.g. Nexavar(R)); HER2 receptor inhibitors: Trastuzumab (e.g. Herceptin(R) by Genentech/Roche), neratinib (or HKI-272, described WO 05/028443), lapatinib or lapatinib ditosylate (e.g. Tykerb(R) by GlaxoSmithKline); CD20 antibodies: Rituximab (e.g. Riuxan(R) and MabThera(R) by Genentech/Roche), tositumomab (e.g. Bexxar(R) by GlaxoSmithKline), of atutnumab (e.g. Arzerra (R) by GlaxoSmithKline); Bcr/Abl kinase inhibitors: nilotinib hydrochloride (e.g. Tasigna(R) by Novartis); DNA Synthesis inhibitors: Capecitabine (e.g. Xeloda(R) by Roche), gemcitabine hydrochloride (e.g. Gemzar(R) by Eli Lilly and Company), nelarabine (or Arranon(R) and Atriance(R) by GlaxoSmithKline); Antineoplastic agents: oxaliplatin (e.g. Eloxatin(R) ay Sanofi-Aventis described in U.S. Pat. No. 4,169,846); Epidermal growth factor receptor (EGFR) inhibitors: Gefitinib (or Iressa(R)), Matinib (or Tovok(R) by Boehringer Ingelheim), cetuximab (e.g. Erbitux(R) by Bristol-Myers Squibb), panitumumab (e.g. Vectibix(R) by Amgen); HER dimerization inhibitors: Pertuzumab (e.g. Omnitarg(R), by Genentech); Human Granulocyte colony-stimulating factor (G-CSF) modulators: Filgrastim (e.g. Neupogen(R) by Amgen); Immunomodulators: Afutuzumab (by Roche(R)), pegfilgrastim (e.g. Neulasta(R) by Amgen), lenalidomide (e.g. CC-5013, e.g. Revlimid(R)), thalidomide (e.g. Thalomid(R)); (m) CD40 inhibitors: Dacetuzumab (e.g. SGN-40 or huS2C6, by Seattle Genetics, Inc); Pro-apoptotic receptor agonists (PARAs): Dulanermin (e.g. AMG-951, by Amgen/Genentech); Hedgehog antagonists: Vismodegib (or GDC-0449, described in WO 06/028958); PI3K inhibitors: Pictilisib (or GDC-0941 described in WO 09/036082 and WO 09/055730), Dactolisib (or BEZ 235 or NVP-BEZ 235, described in WO 06/122806); Phospholipase A2 inhibitors: Anagrelide (e.g. Agrylin(R)); BCL-2 inhibitors: Navitoclax (or ABT-263, described in WO 09/155386); Mitogen-activated protein kinase kinase (MEK) inhibitors: XL-518 (Cas No. 1029872-29-4, by ACC Corp.); Aromatase inhibitors: Exemestane (e.g. Aromasin(R) by Pfizer), letrozole (e.g. Femara(R) by Novartis), anastrozole (e.g. Arimidex(R)); Topoisomerase I inhibitors: Irinotecan (e.g. Camptosar(R) by Pfizer), topotecan hydrochloride (e.g. Hycamtin(R) by GlaxoSmithKline); Topoisomerase II inhibitors: etoposide (e.g. VP-16 and Etoposide phosphate, e.g. Toposar(R), VePesid(R) and Etopophos(R)), teniposide (e.g. VM-26, e.g. Vumon(R)); mTOR inhibitors: Temsirolimus (e.g. Torisel(R) by Pfizer), ridaforolimus (formally known as deferolimus, (or AP23573 and MK8669, described in WO 03/064383), everolimus (e.g. Afinitor(R) by Novartis); Osteoclastic bone resorption inhibitors: zoledronic acid (or Zometa(R) by Novartis); CD33 Antibody Drug Conjugates: Gemtuzumab ozogamicin (e.g. Mylotarg(R) by Pfizer/Wyeth); CD22 Antibody Drug Conjugates: Inotuzumab ozogamicin (also referred to as CMC-544 and WAY-207294, by Hangzhou Sage Chemical Co., Ltd.); CD20 Antibody Drug Conjugates: Ibritumomab tiuxetan (e.g. Zevalin(R)); Somatostain analogs: octreotide (e.g. octreotide acetate, e.g. Sandostatin(R) and Sandostatin LAR(R)); Synthetic Interleukin-11 (IL-11): oprelvekin (e.g. Neumega(R) by Pfizer/Wyeth); Synthetic erythropoietin: Darbepoetin alfa (e.g. Aranesp(R) by Amgen); Receptor Activator for Nuclear Factor kappa B (RANK) inhibitors:

Denosumab (e.g. Prolia(R) by Amgen); Thrombopoietin mimetic peptibodies: Romiplostim (e.g. Nplate(R) by Amgen; Cell growth stimulators: Palifermin (e.g. Kepivance (R) by Amgen); Anti-Insulin-like Growth Factor-1 receptor (IGF-1R) antibodies: Figitumumab (e.g. CP-751,871, by ACC Corp), robatumumab (CAS No. 934235-44-6); Anti-CS1 antibodies: Elotuzumab (HuLuc63, CAS No. 915296-00-3); CD52 antibodies: Alemtuzumab (e.g. Campath(R)); CTLA-4 inhibitors: Tremelimumab (IgG2 monoclonal antibody by Pfizer, formerly known as ticilimumab, CP-675, 206), ipilimumab (CTLA-4 antibody, e.g. MDX-010, CAS No. 477202-00-9); Historic deacetylase inhibitors (HDI): Voninostat (e.g. Zolinza(R) by Merck); Alkylating agents: Temozolomide (e.g. Temodar(R) and Temodal(R) by Schering-Plough/Merck), dactinomycin (e.g. actinomycin-D and e.g. Cosmegen(R)), melphalan (e.g. L-PAM, L-sarcolysin, and phenylalanine mustard, e.g. Alkeran(R)), altretamine (e.g. hexamethylmelamine (HMM), e.g. Hexalen(R)), carmustine (e.g. BiCNU(R)), bendamustine (e.g. Treanda(R)), busulfan (e.g. Busulfex(R) and Myleran(R)), carboplatin Paraplatin(R)), lomustine (e.g. CCNU, e.g. CeeNU(R)), cisplatin (e.g. CDDP, e.g. Platinol(R) and Platinol(R)-AQ), chlorambucil (e.g. Leukeran(R)), cyclophosphamide (e.g. Cytoxan(R) and Neosar(R)), dacarbazine (e.g. DTIC, DIC and imidazole carboxamide, e.g. DTIC-Dome(R)), altretamine (e.g. hexamethylmelamine (HMM) e.g. Hexalen(R)), ifosfamide (e.g. Ifex(R)), procarbazine (e.g. Matulane(R)), mechlorethamine (e.g. nitrogen mustard, mustine and mechloroethamine hydrochloride, e.g. Mustargen(R)), streptozocin (e.g. Zanosar(R)), thiotepa (e.g. thiophosphoamide, TESPA and TSPA, e.g. Thioplex(R); Biologic response modifiers: bacillus calmette-guerin (e.g. theraCys(R) and TICE(R) BCG), denileukin diftitox (e.g. Ontak(R)); Anti-tumor antibiotics: doxorubicin (e.g. Adriamycin(R) and Rubex(R)), bleomycin (e.g. lenoxane(R)), daunorubicin (e.g. dauorubicin hydrochloride, daunomycin, and rubidomycin hydrochloride, e.g. Cerubidine(R)), daunorubicin liposomal (daunorubicin citrate liposome, e.g. DaunoXome(R)), mitoxantrone (e.g. DHAD, e.g. Novantrone(R)), epirubicin (e.g. Ellence™), idarubicin (e.g. Idamycin(R), Idamycin PFS(R)), mitomycin C (e.g. Mutamycin(R)); Anti-microtubule agents: Estramustine (e.g. Emcyl(R)); Cathepsin K inhibitors: Odanacatib (or MK-0822, by Lanzhou Chon Chemicals, ACC Corp., and ChemieTek, described in WO 03/075836); Epothilone B analogs: Ixabepilone (e.g. Lxempra(R) by Bristol-Myers Squibb); Heat Shock Protein (HSP) inhibitors: Tanespimycin (17-allylamino-17-demethoxygeldanamycin, e.g. KOS-953 and 17-AAG, by SIGMA, described in U.S. Pat. No. 4,261,989); TpoR agonists: Eltrombopag (e.g. Promacta(R) and Revolade(R) by GlaxoSmithKline); Anti-mitotic agents: Docetaxel (e.g. Taxotere(R) by Sanofi-Aventis); Adrenal steroid inhibitors: aminoglutethimide (e.g. Cytadren(R)); Anti-androgens: Nilutamide (e.g. Nilandron(R) and Anandron(R)), bicalutamide (sold under tradename Casodex(R)), flutamide (e.g. Fulexin™); Androgens: Fluoxymesterone (e.g. halotestin(R)); Proteasome inhibitors: Bortezomib Velcade(R)); CDK1 inhibitors: Alvocidib (e.g. flovopirdol or HMR-1275, described in U.S. Pat. No. 5,621,002); Gonadotropin-releasing hormone (GnRH) receptor agonists: Leuprolide or leuprolide acetate (e.g. Viadure(R) by Bayer A G, Eligard(R) by Sanofi-Aventis and Lupron(R) by Abbott Lab); Taxane anti-neoplastic agents: Cabazitaxel, larotaxel; 5HT1a receptor agonists: Xaliproden (or SR57746, described in U.S. Pat. No. 5,266,573); HPC vaccines: Cervarix(R) sold by GlaxoSmithKline, Gardasil(R) sold by Merck; Iron Chelating agents: Deferasinox (e.g. Exjade(R) by Novartis); Anti-metabolites: Claribine (2-chlorodeoxyadenosine, e.g. leustatin(R)), 5-fluorouracil (e.g. Adrucil (R)), 6-thioguanine (e.g. Purinethol(R)), pemetrexed (e.g. Alimta(R)), cytarabine (e.g. arabinosylcytosine (Ara-C), e.g. Cytosar-U(R)), cytarabine liposomal (e.g. Liposomal Ara-C, e.g. DepoCyt™), decitabine (e.g. Dacogen(R)), hydroxyurea (e.g. Hydrea(R), Droxia™ and Mylocel™), fludarabine (e.g. Fludara(R)), floxuridine (e.g. FUDR(R)), cladribine (e.g. 2-chlorodeoxyadenosine (2-CdA) e.g. Leustatin™) methotrexate (e.g. amethopterin, methotrexate sodim (MTX), e.g. Rheumatrex(R) and Trexall™), pentostatin (e.g. Nipent(R)); Bisphosphonates: Pamidronate (e.g. Aredia(R)), zoledronic acid (e.g. Zometa(R)); Demethylating agents: 5-azacitidine (e.g. Vidaza(R)), decitabine (e.g. Dacogen(R)); Plant Alkaloids: Paclitaxel protein-bound (e.g. Abraxane(R)), vinblastine (e.g. vinblastine sulfate, vincaleukoblastine and VLB, e.g. Alkaban-AQ(R) and Velban (R)), vincristine (e.g. vincristine sulfate, LCR, and VCR, e.g. Oncovin(R) and Vincasar Pfs(R)), vinorelbine (e.g. Navelbine(R)), paclitaxel (e.g. Taxol and Onxal™); Retinoids: Alitretinoin (e.g. Panretin(R)), tretinoin (all-trans retinoic acid, e.g. ATRA, e.g. Vesanoid(R)), Isotretinoin (13-cis-retinoic acid, e.g. Accutane(R), Amnesteem(R), Claravis(R), Clarus(R), Decutan(R), Isotane(R), Izotech(R), Oratane(R), Isotret(R), and Sotret(R)), bexarotene (e.g. Targretin(R)); Glucocorticosteroids: Hydrocortisone (e.g. cortisone, hydrocortisone sodium succinate, hydrocortisone sodium phosphate, and e.g. Ala-Cort(R), Hydrocortisone Phosphate, Solu-Cortef(R), Hydrocort Acetate(R) and Lanacort(R)), dexamethasone, prednisolone (e.g. Delta-Cortel (R), Orapred(R), Pediapred(R) and Prelone(R)), prednisone (e.g. Deltasone(R), Liquid Red(R), Meticorten(R) and Orasone(R)), methylprednisolone (e.g. 6-Methylprednisolone, Methylprednisolone Acetate, Methylprednisolone Sodium Succinate, e.g. Duralone(R), Medralone(R), Medrol(R), M-Prednisol(R) and Solu-Medrol(R)); Cytokines: interleukin-2 (e.g. aldesleukin and IL-2, e.g. Proleukin(R)), interleukin-11 (e.g. oprevelkin, e.g. Neumega(R)), alpha interferon alfa (e.g. IFN-alpha, e.g. Intron(R) A, and Roferon-A (R)); Lutinizing hormone releasing hormone (LHRH) agonists: Goserelin (e.g. Zoladex(R)); Progesterones: megestrol (e.g. megestrol acetate, e.g. Megace(R)); Miscellaneous cytotoxic agents: Arsenic trioxide (e.g. Trisenox(R)), asparaginase (e.g. L-asparaginase, Erwinia L-asparaginase, e.g. Elspar(R) and Kidrolase(R)); Anti-nausea drugs: NK-1 receptor antagonists: Casopitant (e.g. Rezonic(R) and Zunrisa(R) by GlaxoSmithKline); and Cytoprotective agents: Amifostine (e.g. Ethyol(R)), leucovorin (e.g. calcium leucovorin, citrovorum factor and folinic acid).

Biological Assays

Compounds designed, selected and/or optimised by methods described above, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

In some embodiments, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No.

5,763,263. High-throughput assays can use one or more different assay techniques including, but not limited to, those described below.

Various in vitro or in vivo biological assays may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

Potent Inhibition

Compounds and compositions of the disclosure are potent inhibitors of one or more oncogenic variants of an EGFR. In some embodiments, compounds and compositions of the disclosure are potent inhibitors of one or more of a wild type HER-2 receptor or an oncogenic variant of a HER-2 receptor. In some embodiments, the oncogenic variant of a HER-2 receptor is an allosteric variant of a HER-2 receptor.

Tables A and B assign each compound a potency code: A, B, C, D, E, F, G, H, I, J or K. According to the code, A represents an IC50 value ≤5 nM. B represents an IC50 value >5 nM and ≤10 nM. C represents an IC50 value >10 nM and ≤20 nM. D represents an IC50 value >20 nM and ≤30 nM. E represents an IC50 value >30 nM and ≤50 nM. F represents an IC50 value >50 nM and ≤100 nM. G represents an IC50 value >100 nM and ≤200 nM. H represents an IC50 value >200 nM and ≤300 nM. I represents an IC50 value >300 nM and ≤500 nM. J represents an IC50 value >500 nM and ≤1000 nM. K represents an IC50 value >1000 nM.

TABLE A

| | Activity for Inhibiting EGFR | | | |
|---|---|---|---|---|
| Compound No. | EGFR WT | EGFR V3 | EGFR NPH | EGFR SVD |
| 1 | K | G | | |
| 2 | K | F | | |
| 3 | I | E | | |
| 4 | H | F | | |
| 5 | E | C | E | C |
| 6 | H | D | | |
| 7 | K | G | | |
| 8 | I | D | E | D |
| 9 | J | F | | |
| 10 | K | F | | |
| 11 | I | F | I | I |
| 12 | J | G | | |
| 13 | I | F | I | H |
| 14 | I | E | | |
| 15 | I | H | | |
| 16 | H | D | | |
| 17 | H | C | D | C |
| 18 | I | D | | |
| 19 | H | D | G | G |
| 20 | H | D | C | C |
| 21 | J | D | C | C |
| 22 | F | D | D | C |
| 23 | K | G | | |
| 24 | K | H | | |
| 25 | J | H | D | E |
| 26 | I | E | E | E |
| 27 | I | E | | |
| 28 | H | C | F | E |
| 29 | I | D | | |
| 30 | 1 | E | | |
| 31 | J | E | F | F |
| 32 | I | D | | |
| 33 | I | D | F | F |
| 34 | J | E | | |
| 35 | I | D | F | D |
| 36 | K | E | F | F |
| 37 | K | G | | |
| 38 | I | E | | |
| 39 | J | D | F | E |
| 40 | H | C | C | C |

TABLE A-continued

| | Activity for Inhibiting EGFR | | | |
|---|---|---|---|---|
| Compound No. | EGFR WT | EGFR V3 | EGFR NPH | EGFR SVD |
| 41 | J | E | F | E |
| 42 | J | F | K | J |
| 43 | K | G | | |
| 44 | I | G | | |
| 45 | J | H | | |
| 46 | I | F | | |
| 47 | I | E | J | J |
| 48 | K | H | | |
| 49 | K | G | | |
| 50 | K | E | | |
| 51 | J | D | F | E |
| 52 | J | D | F | F |
| 53 | K | E | | |
| 54 | K | C | G | F |
| 55 | K | F | | |
| 56 | I | D | I | I |
| 57 | J | C | F | E |
| 58 | K | H | | |
| 59 | I | E | | |
| 60 | H | C | H | H |
| 61 | K | I | | |
| 62 | I | C | E | D |
| 63 | K | F | I | I |
| 64 | K | G | | |
| 65 | J | D | | |
| 66 | J | D | G | F |
| 67 | G | D | | |
| 68 | J | G | J | J |
| 69 | I | C | D | D |
| 70 | F | C | F | E |
| 71 | J | F | | |
| 72 | K | I | | |
| 73 | J | F | | |
| 74 | K | F | | |
| 75 | K | G | | |
| 76 | H | F | | |
| 77 | G | F | | |
| 78 | K | E | I | H |
| 79 | I | F | | |
| 80 | G | F | | |
| 81 | H | G | | |
| 82 | J | I | | |
| 83 | J | F | | |
| 84 | J | D | F | F |
| 85 | H | D | D | D |
| 86 | J | G | | |
| 87 | K | G | | |
| 88 | J | E | | |
| 89 | F | E | | |
| 90 | J | E | | |
| 91 | J | F | | |
| 92 | G | E | | |
| 93 | K | H | | |
| 94 | I | E | | |
| 95 | G | D | | |
| 96 | G | C | | |
| 97 | J | F | | |
| 98 | H | E | | |
| 99 | H | D | | |
| 100 | I | E | | |
| 101 | G | C | | |
| 102 | J | E | F | E |
| 103 | H | E | | |
| 104 | D | E | | |
| 105 | J | F | | |
| 106 | G | E | | |
| 107 | H | F | | |
| 108 | J | G | | |
| 109 | E | C | | |
| 110 | H | D | | |
| 111 | I | E | | |
| 112 | I | G | | |
| 113 | J | F | | |
| 114 | I | E | | |
| 115 | H | E | | |
| 116 | J | E | | |

TABLE A-continued

Activity for Inhibiting EGFR

| Compound No. | EGFR WT | EGFR V3 | EGFR NPH | EGFR SVD |
|---|---|---|---|---|
| 117 | J | G | | |
| 118 | H | D | | |
| 119 | I | F | | |
| 120 | K | E | | |
| 121 | K | G | | |
| 122 | J | F | | |
| 123 | H | E | | |
| 124 | J | E | | |
| 125 | J | G | | |
| 126 | I | E | | |
| 127 | J | F | | |
| 128 | J | G | | |
| 129 | J | G | | |
| 130 | H | G | | |
| 131 | H | H | | |
| 132 | K | I | | |
| 133 | H | G | | |
| 134 | H | F | | |
| 135 | I | F | | |
| 136 | G | G | | |
| 137 | H | F | | |
| 138 | G | F | | |
| 139 | J | G | | |
| 140 | I | G | | |
| 141 | G | G | | |
| 142 | J | G | | |
| 143 | H | F | | |
| 144 | G | G | | |
| 145 | G | F | | |
| 146 | F | F | | |
| 147 | J | F | | |
| 148 | H | G | | |
| 149 | G | F | | |
| 150 | H | F | | |
| 151 | G | F | | |
| 152 | G | E | | |
| 153 | J | E | | |
| 154 | J | E | | |
| 155 | I | E | | |
| 156 | K | F | | |
| 157 | J | E | | |
| 158 | G | E | | |
| 159 | I | G | | |
| 160 | I | G | | |
| 161 | H | E | | |
| 162 | I | E | | |
| 163 | K | F | | |
| 164 | I | F | | |
| 165 | G | E | | |
| 166 | K | E | | |
| 167 | K | E | | |
| 168 | H | E | | |
| 169 | K | E | | |
| 170 | H | E | | |
| 171 | K | F | | |
| 172 | J | G | | |
| 173 | K | F | | |
| 174 | K | F | | |
| 175 | K | E | | |
| 176 | K | E | | |
| 177 | J | E | | |
| 178 | K | E | | |
| 179 | J | E | | |
| 180 | J | E | | |

TABLE B

Activity for Inhibiting HER2

| Compound No. | HER2 WT | HER2 S310F | HER2 YVMA |
|---|---|---|---|
| 1 | | F | J |
| 2 | | G | I |
| 3 | C | D | |
| 4 | D | F | |
| 5 | A | A | B |
| 6 | B | C | F |
| 7 | G | H | |
| 8 | B | C | F |
| 9 | C | G | |
| 10 | C | D | H |
| 11 | E | F | |
| 12 | F | G | |
| 13 | B | E | I |
| 14 | C | F | |
| 15 | C | G | |
| 16 | A | D | E |
| 17 | A | B | E |
| 18 | B | D | F |
| 19 | B | D | G |
| 20 | A | C | C |
| 21 | A | B | D |
| 22 | A | B | E |
| 23 | G | G | |
| 24 | | H | I |
| 25 | C | C | F |
| 26 | B | B | E |
| 27 | C | D | E |
| 28 | B | C | E |
| 29 | A | C | F |
| 30 | A | C | G |
| 31 | B | E | G |
| 32 | A | C | F |
| 33 | B | C | G |
| 34 | C | C | F |
| 35 | A | C | E |
| 36 | C | D | E |
| 37 | F | F | |
| 38 | B | D | F |
| 39 | B | C | F |
| 40 | A | C | D |
| 41 | B | D | F |
| 42 | E | F | J |
| 43 | F | G | |
| 44 | F | I | |
| 45 | | I | K |
| 46 | D | G | |
| 47 | C | E | J |
| 48 | G | I | |
| 49 | F | G | |
| 50 | | H | K |
| 51 | B | C | F |
| 52 | B | D | G |
| 53 | | E | G |
| 54 | B | D | G |
| 55 | | F | H |
| 56 | D | F | H |
| 57 | B | C | F |
| 58 | G | I | |
| 59 | E | G | |
| 60 | B | D | I |
| 61 | | I | K |
| 62 | A | B | E |
| 63 | E | F | I |
| 64 | | I | K |
| 65 | C | C | F |
| 66 | F | C | F |
| 67 | B | C | F |
| 68 | C | E | I |
| 69 | | C | D |
| 70 | | B | B |
| 71 | | H | K |
| 72 | | I | K |
| 73 | | E | I |
| 74 | G | H | |
| 75 | | G | I |
| 76 | | E | G |
| 77 | | D | G |
| 78 | C | F | J |

TABLE B-continued

Activity for Inhibiting HER2

| Compound No. | HER2 WT | HER2 S310F | HER2 YVMA |
|---|---|---|---|
| 79 | | G | K |
| 80 | | F | J |
| 81 | | G | K |
| 82 | | F | J |
| 83 | | C | G |
| 84 | | B | E |
| 85 | | B | E |
| 86 | | D | G |
| 87 | | E | H |
| 88 | | C | G |
| 89 | | C | F |
| 90 | | D | G |
| 91 | | E | H |
| 92 | | D | G |
| 93 | | J | K |
| 94 | | E | I |
| 95 | | B | E |
| 96 | | C | H |
| 97 | | H | J |
| 98 | | D | H |
| 99 | | E | H |
| 100 | | F | I |
| 101 | | C | E |
| 102 | | D | F |
| 103 | | C | F |
| 104 | | E | E |
| 105 | | E | G |
| 106 | | E | G |
| 107 | | C | E |
| 108 | | F | J |
| 109 | | C | F |
| 110 | | E | H |
| 111 | | E | G |
| 112 | | I | K |
| 113 | | E | G |
| 114 | | E | G |
| 115 | | E | F |
| 116 | | E | H |
| 117 | | F | G |
| 118 | | C | D |
| 119 | | F | G |
| 120 | | C | F |
| 121 | | E | I |
| 122 | | G | J |
| 123 | | E | G |
| 124 | | E | G |
| 125 | | G | K |
| 126 | | E | F |
| 127 | | I | K |
| 128 | | G | I |
| 129 | | E | G |
| 130 | | E | I |
| 131 | | F | I |
| 132 | | I | J |
| 133 | | F | J |
| 134 | | E | I |
| 135 | | G | I |
| 136 | | E | G |
| 137 | | F | I |
| 138 | | E | F |
| 139 | | E | G |
| 140 | | G | I |
| 141 | | E | I |
| 142 | | I | K |
| 143 | | E | G |
| 144 | | E | G |
| 145 | | E | H |
| 146 | | D | F |
| 147 | | F | H |
| 148 | | D | F |
| 149 | | C | E |
| 150 | | C | E |
| 151 | | C | G |
| 152 | | B | F |
| 153 | | C | F |
| 154 | | E | G |
| 155 | | C | E |
| 156 | | E | H |
| 157 | | E | I |
| 158 | | E | G |
| 159 | | F | I |
| 160 | | G | I |
| 161 | | E | G |
| 162 | | E | G |
| 163 | | E | G |
| 164 | | E | G |
| 165 | | C | F |
| 166 | | E | G |
| 167 | | C | F |
| 168 | | D | F |
| 169 | | C | E |
| 170 | | B | C |
| 171 | | F | I |
| 172 | | F | I |
| 173 | | E | H |
| 174 | | F | I |
| 175 | | D | G |
| 176 | | D | G |
| 177 | | C | F |
| 178 | | E | G |
| 179 | | C | E |
| 180 | | D | G |

In some embodiments, the compound is capable of inhibiting a mutant EGFR (e.g., EGFR-Viii, EGFR-NPH, or EGFR-SVD).

In some embodiments, the compound exhibits an $IC_{50}$ value of 100 nM or less, 80 nM or less, 60 nM or less, 50 nM or less, 40 nM or less, 30 nM or less, 20 nM or less, 10 nM or less, or 5 nM or less for inhibiting a mutant EGFR (e.g., EGFR-Viii, EGFR-NPH, or EGFR-SVD).

In some embodiments, the compound exhibits an $IC_{50}$ value of 100 nM or less for inhibiting EGFR-Viii. In some embodiments, the compound is selected from the group consisting of 2, 3, 4, 5, 6, 8, 9, 10, 11, 13, 14, 16, 17, 18, 19, 20, 21, 22, 26 27, 28, 29, 30, 31, 32, 33, 34, 35, 36, 38, 39, 40, 41, 42, 46, 47, 50, 51, 52, 53, 54, 55, 56, 57, 59, 60, 62, 63, 65, 66, 67, 69, 70, 71, 73, 74, 76, 77, 78, 79, 80, 83, 84, 85, 88, 115, 116, 118, 119, 120, 122, 123, 124, 126, 127, 134, 135, 137, 138, 143, 145, 146, 147, 149, 150, 151, 152, 153, 154, 155, 156, 157, 158, 161, 162, 163, 164, 165, 166, 167, 168, 169, 170, 171, 173, 174, 175, 176, 177, 178, 179, 180, and pharmaceutically acceptable salts and stereoisomers thereof.

In some embodiments, the compound exhibits an $IC_{50}$ value of 50 nM or less for inhibiting EGFR-Viii. In some embodiments, the compound is selected from the group consisting of 3, 5, 6, 8, 14, 16, 17, 18, 19, 20, 21, 22, 26, 27, 28, 29, 30, 31, 32, 33, 34, 35, 36, 38, 39, 40, 41, 47, 50, 51, 52, 53, 54, 56, 57, 59, 60, 62, 65, 66, 67, 69, 70, 78, 84, 85, 88, 115, 116, 118, 120, 123, 124, 126, 152, 153, 154, 155, 157, 158, 161, 162, 165, 166, 167, 168, 169, 170, 175, 176, 177, 178, 179, 180, and pharmaceutically acceptable salts and stereoisomers thereof.

In some embodiments, the compound exhibits an $IC_{50}$ value of 30 nM or less for inhibiting EGFR-Viii. In some embodiments, the compound is selected from the group consisting of 5, 6, 8, 16, 17, 18, 19, 20, 22, 28, 29, 32, 33, 35, 39, 40, 51, 52, 54, 56, 57, 60, 62, 65, 66, 67, 69, 70, 84, 85, 118, and pharmaceutically acceptable salts and stereoisomers thereof.

In some embodiments, the compound exhibits an $IC_{50}$ value of 20 nM or less for inhibiting EGFR-Viii. In some embodiments, the compound is selected from the group consisting of 5, 17, 28, 40, 54, 57, 60, 62, 69, 70, and pharmaceutically acceptable salts and stereoisomers thereof.

In some embodiments, the compound exhibits greater inhibition of a mutant EGFR (e.g., EGFR-Viii, EGFR-NPH, or EGFR-SVD) relative to wild-type EGFR.

In some embodiments, the compound exhibits at least 2-fold, 3-fold, 5-fold, 10-fold, 20-fold, 30-fold, 50-fold, or 100-fold greater inhibition of a mutant EGFR (e.g., EGFR-Viii, EGFR-NPH, or EGFR-SVD) relative to wild-type EGFR.

In some embodiments, the compound exhibits at least 5-fold greater inhibition of EGFR-Viii relative to wild-type EGFR. In some embodiments, the compound is selected from the group consisting of 1, 2, 3, 6, 7, 8, 9, 10, 12, 14, 16, 17, 18, 19, 20, 21, 23, 26, 27, 28, 29, 30, 31, 32, 33, 34, 35, 36, 37, 38, 39, 40, 41, 42, 43, 47, 49, 50, 51, 52, 53, 54, 55, 56, 59, 60, 62, 63, 64, 65, 66, 68, 69, 70, 71, 73, 74, 75, 78, 79, 83, 84, 85, 86, 87, 88, 115, 116, 117, 118, 120, 121, 122, 123, 124, 125, 126, 127, 128, 129, 135, 139, 147, 153, 154, 155, 156, 157, 158, 161, 162, 163, 166, 167, 168, 169, 170, 171, 172, 173, 174, 175, 176, 177, 178, 179, 180, and pharmaceutically acceptable salts and stereoisomers thereof.

In some embodiments, the compound exhibits at least 10-fold greater inhibition of EGFR-Viii relative to wild-type EGFR. In some embodiments, the compound is selected from the group consisting of 2, 3, 6, 8, 10, 16, 17, 18, 21, 26, 27, 28, 29, 30, 31, 32, 33, 34, 35, 36, 38, 39, 40, 41, 42, 47, 50, 51, 52, 53, 54, 55, 56, 57, 59, 60, 62, 63, 65, 66, 69, 73, 74, 78, 83, 84, 85, 88, 116, 118, 120, 122, 124, 126, 147, 153, 154, 156, 157, 163, 167, 169, 171, 173, 174, 175, 176, 177, 178, 179, 180, and pharmaceutically acceptable salts and stereoisomers thereof.

In some embodiments, the compound exhibits at least 20-fold greater inhibition of EGFR-Viii relative to wild-type EGFR. In some embodiments, the compound is selected from the group consisting of 8, 34, 36, 39, 41, 50, 51, 52, 53, 54, 57, 65, 66, 69, 78, 84, 88, 120, 153, 169, 175, 176, 178, 179, and pharmaceutically acceptable salts and stereoisomers thereof.

In some embodiments, the compound exhibits at least 30-fold greater inhibition of EGFR-Viii relative to wild-type EGFR. In some embodiments, the compound is selected from the group consisting of 51, 53, 54, 65, 66, 78, 84, 120, and pharmaceutically acceptable salts and stereoisomers thereof.

In some embodiments, the compound is capable of inhibiting wild-type HER2 or a mutant HER2 (e.g., HER2-S310F or HER2-YVMA).

In some embodiments, the compound exhibits an $IC_{50}$ value of 100 nM or less, 80 nM or less, 60 nM or less, 50 nM or less, 40 nM or less, 30 nM or less, 20 nM or less, 10 nM or less, or 5 nM or less for inhibiting wild-type HER2 or a mutant HER2 (e.g., HER2-S310F or HER2-YVMA).

In some embodiments, the compound exhibits an $IC_{50}$ value of 100 nM or less, 80 nM or less, 60 nM or less, 50 nM or less, 40 nM or less, 30 nM or less, 20 nM or less, 10 nM or less, or 5 nM or less for inhibiting wild-type HER2.

In some embodiments, the compound exhibits an $IC_{50}$ value of 50 nM or less for inhibiting wild-type HER2. In some embodiments, the compound is selected from the group consisting of 3, 4, 5, 6, 8, 9, 10, 11, 13, 14, 15, 16, 17, 18, 19, 20, 21, 22, 25, 26, 27, 28, 29, 30, 31, 32, 33, 34, 35, 36, 38, 39, 40, 41, 42, 46, 47, 51, 52, 54, 56, 57, 59, 60, 62, 63, 65, 67, 68, 78, 81, and pharmaceutically acceptable salts and stereoisomers thereof.

In some embodiments, the compound exhibits an $IC_{50}$ value of 20 nM or less for inhibiting wild-type HER2. In some embodiments, the compound is selected from the group consisting of 3, 5, 6, 8, 9, 10, 13, 14, 15, 16, 17, 18, 19, 20, 21, 22, 25, 26, 27, 28, 29, 30, 31, 32, 33, 34, 35, 36, 38, 39, 40, 41, 47, 51, 52, 54, 57, 60, 62, 65, 67, 68, 78, and pharmaceutically acceptable salts and stereoisomers thereof.

In some embodiments, the compound exhibits an $IC_{50}$ value of 10 nM or less for inhibiting wild-type HER2. In some embodiments, the compound is selected from the group consisting of 5, 6, 8, 16, 17, 18, 19, 20, 21, 22, 26, 28, 29, 30, 31, 32, 33, 35, 38, 39, 40, 41, 51, 52, 54, 57, 60, 62, 67, and pharmaceutically acceptable salts and stereoisomers thereof.

In some embodiments, the compound exhibits an $IC_{50}$ value of 5 nM or less for inhibiting wild-type HER2. In some embodiments, the compound is selected from the group consisting of 5, 16, 17, 22, 29, 30, 32, 35, 62, and pharmaceutically acceptable salts and stereoisomers thereof.

In some embodiments, the compound exhibits an $IC_{50}$ value of 100 nM or less, 80 μM or less, 60 nM or less, 50 nM or less, 40 nM or less, 30 nM or less, 20 nM or less, 10 nM or less, or 5 nM or less for inhibiting a mutant HER2 (e g. HER2-S310F or HER2-YVMA).

In some embodiments, the compound exhibits an $IC_{50}$ value of 100 nM or less for inhibiting HER2-S310F. In some embodiments, the compound is selected from the group consisting of 3, 4, 5, 6, 8, 10, 11, 13, 14, 16, 17, 18, 19, 20, 22, 25, 26, 27, 28, 29, 30, 31, 32, 33, 34, 35, 36, 37, 38, 39, 40, 41, 42, 47, 51, 52, 53, 54, 56, 57, 60, 62, 63, 65, 66, 67, 68, 69, 70, 73, 76, 77, 78, 82, 83, 84, 85, 86, 87, 88, 115, 116, 117, 118, 119, 120, 121, 123, 124, 126, 129, 130, 131, 133, 134, 136, 137, 138, 139, 141, 143, 144, 145, 146, 147, 148, 149, 150, 151, 152, 153, 154, 155, 156, 157, 158, 159, 161, 162, 163, 164, 165, 166, 167, 168, 169, 170, 171, 172, 173, 174, 175, 176 177, 178, 179, 180, and pharmaceutically acceptable salts and stereoisomers thereof.

In some embodiments, the compound exhibits an $IC_{50}$ value of 50 mM or less for inhibiting HER2-S310F. In some embodiments, the compound is selected from the group consisting of 3, 4, 5, 6, 8, 10, 13, 16, 17, 18, 19, 20, 21, 22, 25, 26, 27, 28, 29, 30, 31, 32, 33, 34, 35, 36, 38, 39, 40, 41, 47, 51, 52, 53, 54, 57, 60, 62, 65, 66, 67, 68, 69, 70, 73, 76, 77, 83, 84, 85, 86, 87, 88, 115, 116, 118, 120, 121, 123, 124, 126, 129, 130, 134, 136, 138, 139, 141, 143, 144, 145, 146, 148, 149, 150, 151, 152, 153, 154, 155, 156, 157, 158, 161, 162, 163, 164, 165, 166, 167, 168, 169, 170, 173, 175, 176, 177, 178, 179, 180, and pharmaceutically acceptable salts and stereoisomers thereof.

In some embodiments, the compound exhibits an $IC_{50}$ value of 20 nM or less for inhibiting HER2-S310F. In some embodiments, the compound is selected from the group consisting of 5, 6, 8, 17, 20, 21, 22, 25, 26, 28, 29, 30, 32, 33, 34, 35, 39, 40, 51, 57, 62, 65, 66, 67, 69, 70, 83, 84, 85, 88, 118, 120, 149, 150, 151, 152, 153, 155, 165, 167, 169, 170, 177, 179, and pharmaceutically acceptable salts and stereoisomers thereof.

In some embodiments, the compound exhibits an $IC_{50}$ value of 10 nM or less for inhibiting HER2-S310F. In some embodiments, the compound is selected from the group consisting of 5, 17, 21, 22, 62, 70, 84, 85, 152, 170, and pharmaceutically acceptable salts and stereoisomers thereof.

In some embodiments, the compound exhibits an $IC_{50}$ value of 100 nM or less for inhibiting HER2-YVMA. In some embodiments, the compound is selected from the group consisting of 5, 6, 8, 16, 17, 18, 20, 21, 22, 25, 26, 27, 29, 32, 34, 35, 36, 38, 39, 40, 41, 57, 62, 65, 66, 67, 69, 70, 84, 85, 115, 118, 120, 126, 138, 146, 148, 149, 150, 152, 153, 155, 165, 167, 168, 169, 170, 177, 179, and pharmaceutically acceptable salts and stereoisomers thereof.

In some embodiments, the compound exhibits an $IC_{50}$ value of 50 nM or less for inhibiting HER2-YVMA. In some embodiments, the compound is selected from the group consisting of 5, 16, 17, 20, 21, 26, 27, 28, 35, 36, 40, 41, 62, 69, 70, 84, 85, 118, 149, 150, 155, 169, 170, 179, and pharmaceutically acceptable salts and stereoisomers thereof.

In some embodiments, the compound exhibits an $IC_{50}$ value of 30 nM or less for inhibiting HER2-YVMA. In some embodiments, the compound is selected from the group consisting of 5, 20, 21, 26, 40, 69, 70, 118, 170, and pharmaceutically acceptable salts and stereoisomers thereof.

Paradoxic ErbB Receptor Activation

Although the mechanisms described herein apply to any form of cancer in which these EGFR variants of the disclosure are expressed, the prevalence of these variants in glioblastoma (GBM) are provide by way of example. Other cancers expressing the EGFR variants of the disclosure include, but are not limited to, solid cancers, epithelial cancers and/or cancers of epithelial origin, bladder cancer, breast cancer, cervical cancer, colorectal cancer, endometrial cancer, gastric cancer, glioblastoma (GBM), head and neck cancer, lung cancer, and non-small cell lung cancer (NSCLC).

In GBM tumors EGFR is frequently the target of genomic mutations and alternative splicing events that result in alteration of the extracellular dimer interface. Many tumors express more than one aberrant isoform. The disclosure provides the mechanism of activation for the most commonly occurring variants, EGFR-Viii, EGFR-Vii, EGFR-Vvi, and EGFR-A289V. Although each isoform is the result of a distinct ectodomain alteration, all are activated by a common mechanism involving covalent ligand-independent dimerization.

AMG-595 (Amgen) is an EGFR-Viii isoform selective antibody that has no activity against wild type EGFR or other splice-activated variants. Rindopepimut (Celldex) is a vaccine the produces an immunological response selectively against tumor cells expressing EGFR-Viii but not wild type EGFR or other splice-activated isoforms. Other EGFR isoforms expressed in GBM tumors (EGFR-Vii and EGFR-Vvi) are constitutively active covalent receptors and their expression may limit the breadth and duration of treatment benefit for an ErbB inhibitor that is selective only for EGFR-Viii. Therefore, it may be useful to exclude patients whose tumors express EGFR-Vii, EGFR-Vvi, or EGFR ectodomain point mutants from treatment with an EGFR-Viii selective therapy.

The heterogenic expression pattern for multiple ectodomain variants of ErbB receptors in tumors indicates that a small molecule inhibitor that inhibits all variants is preferred. The family of covalently-activated EGFR isoforms responds very differently to small molecule ErbB inhibitors compared to EGFR catalytic domain mutations observed in NSCLC. Importantly, Type I inhibitors, including erlotinib, all induce the formation of covalent EGFR dimers and increase EGFR phosphorylation at sub-saturating concentrations, an activity that is further enhanced when ErbB inhibitor is washed away. This manifests in paradoxical activation of proliferation at sub-saturating concentrations.

The discovery of paradoxical activation of proliferation at sub-saturating concentrations of Type I ErbB inhibitors is further demonstrated for a series of extracellular variants of HER2, prevalent in a number of cancers including breast and bladder. All variants existed as covalently activated receptors, and levels of covalent dimers increased following treatment with Type I inhibitors including sapitinib and afatinib. As with covalently-activated EGFR variants, sub-saturating doses of Type I inhibitors increased phosphorylation of HER2 variants, increasing the proliferation of cells expressing them.

In contrast to Type I inhibitors, the disclosure demonstrates that Non-Type I (e.g. Type II) inhibitors, including neratinib, are devoid of paradoxical activation for cells expressing ErbB ectodomain variants. Neratinib is found to exemplify a molecule that is both potent and selective for each member of the covalently-activated EGFR family versus wild type EGFR.

In some embodiments, the disclosure provides a structure/functional relationship for predicting how structural variations affecting receptor regions distal to the active site can confer different responses to small molecule active site inhibitors. The disclosure described herein of paradoxical activation of covalently-activated ErbB receptor variants by Type I inhibitors has important clinical implications. The data of the disclosure provide a mechanistic explanation for the failed clinical studies for Type I inhibitors in tumor types where expression of covalently-activated ErbB receptors is prevalent. This includes erlotinib and gefitinib in GBM tumors, erlotinib in SCCHN tumors, and sapitinib in breast tumors. Thus, the disclosure provides methods of using tumor expression levels for covalently-activated ErbB receptors as exclusion criteria for treating patients with a Type I ErbB receptor inhibitor therapeutic.

Glioblastoma

Glioblastoma (GBM), grade IV astrocytoma, is the most common form of brain cancer. The outcome for this disease is dismal. Surgery followed by a therapeutic regimen of radiation and temozolomide is standard of care, however this produces a median overall survival (OS) of only 14.6 months and few patients survive for five years. There has been little progress made in extending survival for GBM patients over the past decade. Although bevacizumab showed an improved progression free survival benefit in the recurrent setting, the addition of bevacizumab to standard of care therapy in the front-line setting did not result in an OS benefit.

EGFR is the most frequently altered oncogene in GBM. In addition to EGFR gene amplification, many tumors express variants generated by aberrant splicing or genomic mutation. The first recognized variant is EGFR-Viii, resulting from truncation of exons 2-7 and expressed by approximately 30% of GBM tumors. EGFR-Viii is oncogenic. EGFR-Viii is constitutively activated in the absence of EGF ligand, exhibiting sustained signaling that is resistant to downregulation. Therefore, EGFR-Viii is both transforming and tumorigenic. Expression of EGFR-Viii is associated with poor long term overall survival in GBM.

RNA sequencing data has revealed that EGFR-Viii is just one of several aberrantly spliced variants of EGFR expressed in GBM tumors. Two others result in truncation of exons 12-13 and 14-15 (EGFR-Vii). Like EGFR-Viii, EGFR-Vii is both transforming and tumorigenic. In addition to splice variants, GBM tumors also express a collection of EGFR point mutations including C620Y and A289V, which are transforming and tumorigenic. The complex landscape of EGFR alterations in GBM is further compounded by the observation that many tumors express more than one receptor variant.

Because the expression of multiple EGFR variants in GBM gives rise to transforming and tumorigenic activity and because EGFR is the most frequently altered oncogene present in GBM tumors, EGFR is an especially attractive target for small molecule ErbB inhibitors. Following the success for small molecule EGFR therapeutics against NSCLC tumors harboring activating mutations in EGFR (erlotinib, gefitinib, and afatinib), these drugs were tested in GBM. Despite intense clinical investigation of this group of ErbB inhibitors in GBM, involving >30 clinical trials and >1500 patients, all failed to produce any benefit, even for those tumors that expressed EGFR-Viii. Some evidence suggests that erlotinib promoted disease progression. A phase II study evaluating erlotinib in combination with radiation and temozolomide showed median PFS (mPFS) and median OS (mOS) of 2.8 months and 8.6 months, as compared to 6.9 months and 14.6 months for patients receiving radiation and temozolomide alone. Another randomized phase II trial with erlotinib showed that patients who received erlotinib, including those whose tumors expressed EGFR-Viii, performed worse by a number of parameters than those patients who received standard of care therapy. The clinical failures for ErbB inhibitors such as erlotinib in GBM tumors has cast doubt on the role of EGFR as a driver of tumor growth in GBM and led to inquiry as to why ErbB inhibitors that were so effective in treating EGFR mutations in lung cancer were so ineffective in treating EGFR variants in GBM.

A feature for the EGFR variants expressed in GBM is their location within the extracellular domain. This is in contrast to activating mutations of EGFR found in lung cancer, which often reside in the intracellular catalytic domain. EGFR is composed of four extracellular domains (two ligand binding domains and two cysteine rich regions), a transmembrane domain, and an intracellular catalytic domain. Ligand binding promotes dimerization of the extracellular cysteine rich domains (CR1 and CR2), an event that confers dimerization of the intracellular domain and activation of receptor catalytic activity. Nearly all EGFR splicing events and mutations in GBM affect the extracellular region, including two cysteine rich regions (CR1 and CR2) that form the extracellular dimer interface. The CR regions contain >40 cysteine residues, all of which form intramolecular disulfide bonds. In EGFR-Viii, truncation of exons 2-7 results in partial loss of sequence encoding the CR1 region. A consequence is loss of one cysteine from the Cys295-Cys307 pair, leaving Cys307 as a free unpaired cysteine. For EGFR-Viii, this cysteine can form an intermolecular disulfide bond with another EGFR monomer to drive a covalently dimerized and constitutively activated receptor. Mutation of Cysteine 307 to a Serine (C307S) prevents the formation of covalently dimerized EGFR-Viii and is inactive.

Although several recent preclinical studies have suggested that EGFR kinase inhibitors such as erlotinib are ineffective at inhibiting EGFR-Viii, there has been no mechanism proposed for this effect. There is also a lack in current understanding for the mechanism responsible for activation of other ectodomain variants in GBM, including EGFR-Vii and EGFR-A289V. The disclosure provides a mechanism of receptor activation and impact on ErbB inhibitor activity for a group of four of the most common ectodomain variants in GBM, EGFR-Viii, EGFR-Vii, EGFR-delta 12-13, and EGFR-A289V.

The disclosure demonstrates that like EGFR-Viii, an additional group of commonly occurring EGFR variants in GBM (EGFR-Vii, EGFR-Vvi, and EGFR-A289V) all exist as constitutively active covalent dimers and together form a family of EGFR isoforms that are activated by this common mechanism. In some embodiments, the disclosure shows that the propensity of these variants to covalently dimerize is coupled to the conformation of the intracellular catalytic site, conferring distinct activity for classes of small molecules inhibitors binding to this distal site. Inhibitors that stabilize the active conformation of the kinase (Type I inhibitors, including erlotinib) induce the formation of covalent dimers for all covalently-activated EGFR isoforms. This is associated with the propensity of Type I inhibitors to increase EGFR phosphorylation at sub-saturating concentrations and to paradoxically stimulate the proliferation of cells expressing covalently-activated EGFR isoforms.

Neither enhanced dimerization nor paradoxical activation of EGFR is seen with small molecule inhibitors that stabilize the inactive kinase conformation (Type II inhibitors, including lapatinib and neratinib). Examples of Type II inhibitors were identified that were potent inhibitors of covalently-activated EGFR isoforms and which were selective for this family compared to WT-EGFR.

Similar to the mutations identified for EGFR, the disclosure identifies a group of splice events and mutations affecting the CR domains of HER2 and HER4. The disclosure demonstrates that this group of splice events and mutations affecting the CR domains of HER2 and HER4 exists as covalent dimers and are paradoxically activated by agents with a Type I binding mode. These data provide a mechanistic explanation for the failure of multiple clinical trials involving Type I inhibitors, including >30 clinical trials of Type I ErbB inhibitors in GBM. Collectively these data indicate that tumors expressing covalently-activated EGFR isoforms should be excluded from treatment with Type I ErbB inhibitors such as erlotinib because of paradoxical activation. These data further demonstrate the utility for optimizing Type II ErbB inhibitors against the covalently-activated ErbB family.

Clinical Trials using Type I ErbB Inhibitors

Methods of the disclosure identify subjects expressing ErbB family receptor variants in one or more cancer cells or cancer cell types of the subject. Identification of a subject as having a variant of the disclosure may be used as either inclusion or exclusion criteria for either a clinical trial to assess the efficacy of an existing or novel cancer treatment or for an approved treatment protocol.

In some embodiments, the methods of the disclosure may be used to exclude patients expressing one or more of the ErbB variants of the disclosure from a clinical trial assessing the safety and/or efficacy of a Type I inhibitor of the disclosure. The ErbB variants of the disclosure are paradoxically activated upon contact with a Type I inhibitor, leading to increased proliferation of the cancer cell. In past and ongoing clinical trials, the patient populations used for these studies had not been screened for expression of an ErbB variant of the disclosure. Consequently, a Type I inhibitor of the disclosure that "failed" a clinical trial by failing to show increased efficacy over a standard treatment or placebo for the treatment of cancer may, in fact, be effective but the results may have been confounded by the inclusion of patients who express an ErbB variant of the disclosure. Because patients who express an ErbB variant of the disclosure may demonstrate increased proliferation of cancer cells when treated with a Type I inhibitor, and, therefore, demonstrate a lack of improvement or even a further progression of the cancer, these patients may prevent approval of cancer therapeutics that could be life-saving for those patients who do not express an ErbB receptor variant of the disclosure. Thus, the methods of the disclosure include identifying a subject as expressing an ErbB receptor variant of the disclosure and excluding this patient from treatment with a Type I inhibitor. In some embodiments, a patient who expresses an ErbB receptor variant of the disclosure may be treated with a Non-Type I inhibitor, including a Type II inhibitor.

In some embodiments, when a patient who expresses an ErbB receptor variant of the disclosure is identified as expressing only the EGFR-Viii splice variant, the patient may be treated with an EGFR-Viii selective inhibitor or may be included in a clinical trial for an EGFR-Viii selective inhibitor. In some embodiment of the methods of the disclosure, the patient should express only the EGFR-Viii splice variant to be treated with an EGFR-Viii selective inhibitor. If the patient expresses multiple variants, including the EGFR-Viii variant, resulting in a combination of expressed variants, the patient should be excluded from treatment with an EGFR-Viii selective inhibitor, however, this patient may be successfully treated with a Non-Type I selective inhibitor (e.g. a Type II inhibitor).

By extension, should a selective inhibitor target any one or more of the ErbB receptor variants of the disclosure, the identification of expression of the splice variant in a patient may be used as an inclusion criterion for a clinical study or treatment regimen providing that selective inhibitor.

Table 1 provides a listing of exemplary clinical trials for Type I inhibitors that "failed" when in tumor types that express covalently activated ErbB receptors were included in the study. The disclosure provides a method of screening or re-screening participants in a clinical trial for expression of one or more covalently activated ErbB receptor variants of the disclosure. As a further step, the methods of the disclosure include treating those patients who do not express one or more covalently activated ErbB receptor variants of the disclosure for a first or subsequent attempt with a Type I inhibitor to determine efficacy of the Type I inhibitor in a tumor type or patient that does not express one or more covalently activated ErbB receptor variants of the disclosure. In some embodiments, those patients who are excluded from a first or subsequent treatment with a Type I inhibitor may be treated with a Non-Type I inhibitor of the disclosure, including a Type II inhibitor.

TABLE 1

Listing of clinical trials for Type I inhibitors that failed in tumor types where expression levels of covalently activated ErbB receptors is prevalent.

| Type 1 inhibitor | Tumor Setting | Study |
|---|---|---|
| erlotinib | GBM | Van den Bent et al. J Clin Oncol., 2009 |
| erlotinib | GBM | Peereboom et al. J Neuro-oncol., 2010 |
| afatiniB | GBM | Reardon et al. Neuro Oncol., 2014 |
| gefitinib | SCCHN | Argiris et al. J Clin Oncol., 2013 |
| erlotinib | SCCHN | Martins et al, J Clin Oncol. 2013 |
| gefitinib | bladder | Petrylak et al, BJU Int. 2010 |
| gefitinib | bladder | Philips et al. Ann Oncol. 2009 |
| sapitinib | breast | NCT00900627/THYME |
| sapitinib | breast | NCT01151215 |

Table 2 provides a listing of exemplary ErbB inhibitors of the disclosure. Methods of the disclosure may include the identification or determination of expression of an ErbB receptor of the disclosure as either an exclusion criteria for treatment or a clinical trial administering a Type I inhibitor or as inclusion criteria for treatment or a clinical trial administering a Non-Type I (e.g. Type II) inhibitor or the NT-113 Type I inhibitor.

TABLE 2

Exemplary ErbB inhibitors

| Inhibitor Name | CAS Number | Type I? |
|---|---|---|
| CUDC-101 | 1012054-59-9 | Yes |
| poziotinib (HM781-36B) | 1092364-38-9 | Yes |
| dacomitinib (PF-299804) | 1110813-31-4 | Yes |
| JNJ-26483327 | 1131863-89-2 | Yes |
| WZ 4002 | 1213269-23-8 | Yes |
| WZ 3146 | 1214265-56-1 | Yes |
| WZ8040 | 1214265-57-2 | Yes |
| AP-26113 | 1350848-43-9 | Yes |
| Rociletinib (CO 1686, AVL301) | 1374640-70-6 | Yes |
| NT-113 | 1398833-56-1 | Yes |
| AZD9291 | 1421373-65-0 | Yes |
| erlotinib (OSI-744) | 183319-69-9 | Yes |
| gefitinib (ZD1839) | 184475-35-2 | Yes |
| PKI 166 | 187724-61-4 | Yes |
| PD 168393 | 194423-15-9 | Yes |
| BIBX 1382 | 196612-93-8 | Yes |
| vatalanib (CGP79787) | 212141-54-3 | Yes |
| lapatinib | 231277-92-2 | No** |
| pelitinib (EKB-569) | 257933-82-7 | Yes |
| Canertinib (Cl-1033) | 267243-28-7 | Yes |
| afatinib (BIBW2992) | 439081-18-2 | Yes |
| vandetanib (ZD6474) | 443913-73-3 | Yes |
| AEE788 | 497839-62-0 | Yes |
| icotinib (BPI-2009H) | 610798-31-7 | Yes |
| dovitinib | 692737-80-7 | Yes |
| neratinib (HKI-272) | 698387-09-6 | No** |
| AC-480 (BMS-599626) | 714971-09-2 | Yes |
| XL-647 | 781613-23-8 | Yes |
| HKI-357 | 848133-17-5 | No** |
| Sapitinib (AZD8931) | 848942-61-0 | Yes |
| TAK 285 | 871026-44-7 | No** |
| AST 1306 | 897383-62-9 | No** |
| AV-412 | 451493-31-5 | Yes |

*Type I inhibitors of the disclosure are characterized by their mode of kinase inhibition which is described by their ability to target the ATP-binding site in an active conformation to competitively inhibit ATP-binding. Key structural elements have been described including an alignment of specific hydrophobic residues.
**Inhibitors of inactive kinases bind to target in such a manner as to disrupt key structural elements of the active conformation, including specific hydrophobic residues. These non-Type I inhibitors are differentiated from Type I inhibitors by their interaction with target in such a way as to prevent the target adopting an active ATP-binding conformation. Non-Type I inhibitors of the disclosure include, but are not limited to Type II inhibitors. Inhibitors that are not Type I inhibitors in this table are Type II inhibitors.

Paradoxical Stimulation of Proliferation by Type I Inhibitors in Cells Driven by Covalently-Activated ErbB Oncoproteins Although illustrated through the example of EGFR variants in the diagnosis and treatment of glioblastoma, the methods of the disclosure include ErbB receptor variants (e.g. EGFR, and HER2 variants) in any cancer in which these variants are expressed. An exemplary collection of these variants is provided in Table 3.

TABLE 3

Exemplary Covalent ErbB Oncoproteins

| Receptor | Event | Event Type | Region | Expression |
|---|---|---|---|---|
| EGFR | Viii | splicing | CR1 (deletion of exons 2-7) | GBM, NSCLC, SCCNHN |
| EGFR | Vii | splicing | CR (deletion of exons 14-15) | GBM |
| EGFR | Vvi | splicing | CR2 (deletion of exons 12-13) | GBM |
| EGFR | delta768 | splicing | CR1 (deletion of nucleotides 102-769) | neuroblastoma |

TABLE 3-continued

Exemplary Covalent ErbB Oncoproteins

| Receptor | Event | Event Type | Region | Expression |
|---|---|---|---|---|
| EGFR | delta660 | splicing | CR1 (deletion of nucleotide 237 of exon 2 to 896 of exon 8) | SCCHN |
| ErbB2 | delta16 | splicing | CR2 (deletion of exon 16) | GBM |
| ErbB2 | p95HER2 | splicing/ altered translation start/ proteolytic cleavage | AA 1-611 deletion | Breast |

With respect to EGFR and glioblastoma, RNA sequencing of 164 GBM tumors reveals heterogenous expression of multiple ectodomain variants of EGFR. Aberrant splicing, alone or coincident with genomic rearrangement, produces EGFR-Viii (loss of exons 2-7), EGFR-Vii (loss of exons 14-15), and EGFR-Vvi (loss of exons 12-13), Table 4.

TABLE 4

| Variant | Tumor expression (prevalence) | Exons spliced out | Position | Free Cys generated |
|---|---|---|---|---|
| EGFR-Vii | GBM (3%) | 14-15 | CR2 | Cys539, Cys628, Cys636 |
| EGFR-Viii | GBM (20%)/ SCCHN (36%)/ NSCLC (3%)/ BrCa (5%) | 2-7 | CR1 | Cys307 |
| EGFR-Vvi | GBM (32%) | 12-13 | CR2 | Cys555 |
| EGFR-A289V | GBM (16%) | NA | CR1 | ND |

Prevalence is based on expression levels >1% as reported by TCGA data sets (Brennan et al. (2013) Cell 155(2): 462-477).

All three ectodomain variants affect the CR1 or CR2 regions and result in loss of exons coding for sequence at the extracellular dimer interface. There is also a series of greater than 20 genomic mutations found in GBM tumors, which also map to the CR1 and CR2 regions at the dimer interface (see, for example, FIG. 1 and Table 5).

TABLE 5

| Mutation | Region |
|---|---|
| R222C | CR1 |
| R252C/P | CR1 |
| R256Y | CR1 |
| T263P | CR1 |
| Y270C | CR1 |
| A289T/V/D | CR1 |
| H304Y | CR1 |
| G331R | CR1 |
| P596S/L/R | CR2 |
| G598V/A | CR2 |
| G614D | CR2 |
| C628F/Y | CR2 |
| C636Y | CR2 |
| S645C | CR2 |

Figure 2:
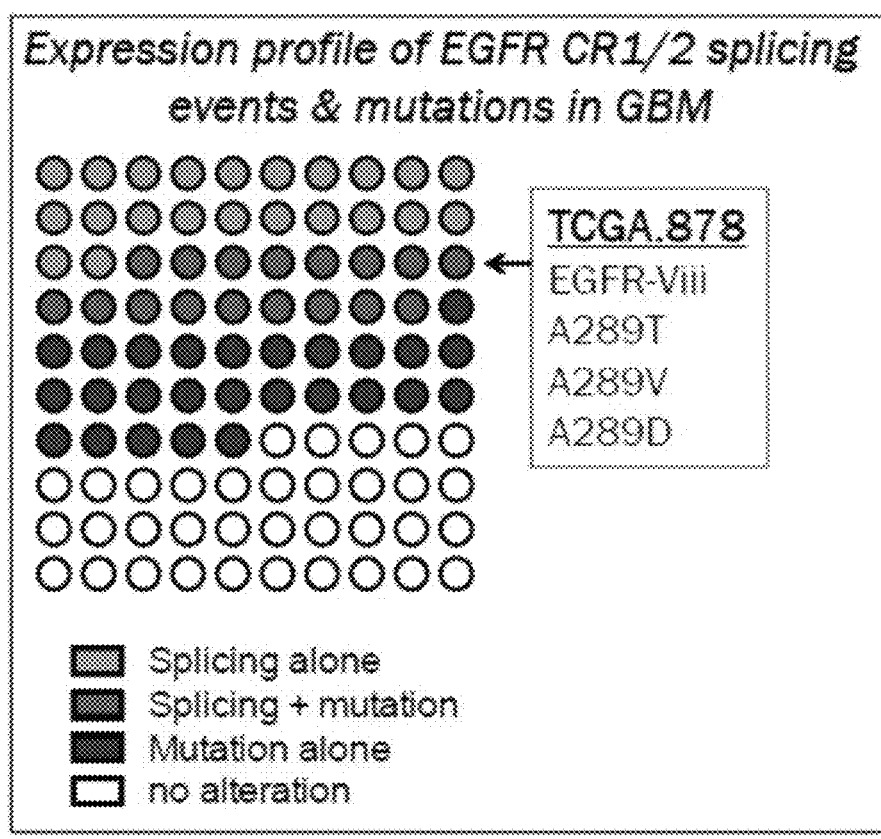
FIG. 2 is a schematic depiction of an expression pattern for EGFR splicing events and mutations in the CR1 and CR2 regions for a group of 164 GBM tumors. One tumor, TCGA.878, expressing four variants (EGFR-Viii, EGR-A289T, EGFR-A289V, and EGFR-A289D, is noted. More than 65% of GBM tumors express EGFR ectodomain variants affecting the CR1/2 regions.

The most common of these affect A289, with A289V being most prevalent. EGFR-Viii is expressed by 20%, Vii by 3% and Vvi by 32% of tumors. Mutations within the extracellular region are observed in 40% of tumors, and at position A289 by 16% of tumors. Expression of at least one variant is observed in 65% of GBM tumors (FIG. 2). Many tumors express multiple variants. This is exemplified by TCGA.878, a GBM tumor expressing EGFR-Viii, A289T, A289V, and A289D (FIG. 2). 69% of tumors expressing EGFR-Viii also co-express at least one other ectodomain variant of EGFR, and several tumors co-expressed all three ectodomain variants. Only 6% of GBM tumors express EGFR-Viii in isolation. Expression of EGFR in GBM may be mutually exclusive with expression of other RTK oncogenes, which are co-expressed with EGFR variants in only 7% of GBM tumors. These data demonstrate how EGFR alterations in GBM have a dominant and mutually exclusive expression pattern compared with other oncogenic drivers.

Figure 3:
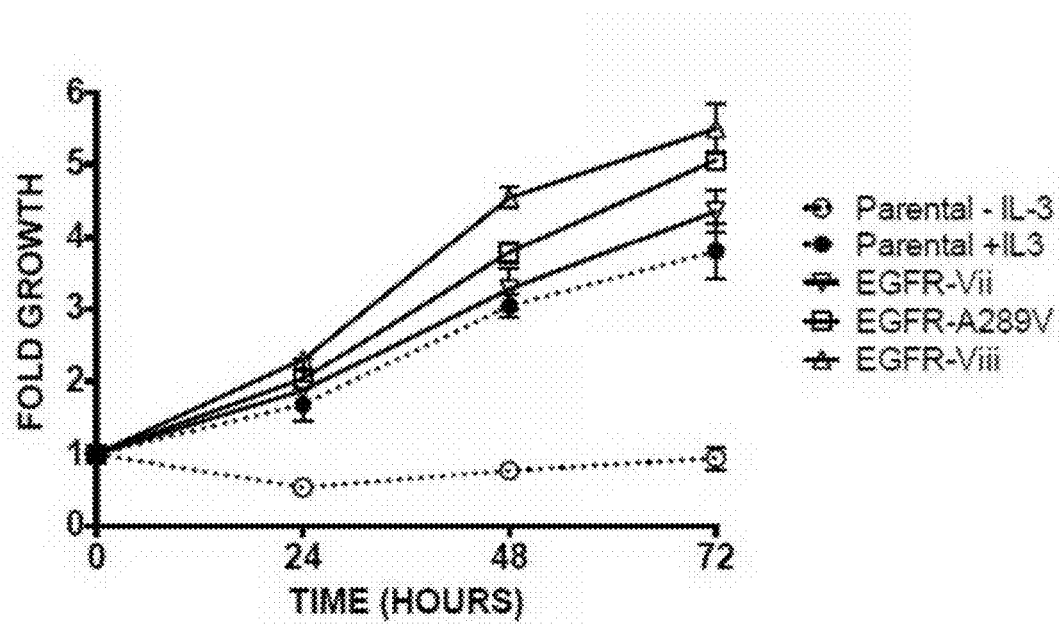
FIG. 3 is a graph depicting exemplary ectodomain variants of ErbB receptors that are transforming. The proliferation of BaF3 cells expressing EGFR-Viii, EGFR-Vii, or EGFR-A289V, or vector alone (parental), cultured in the absence of IL-3. The proliferation of parental BaF3 cells cultured in the presence of IL-3 is shown as a control.

Splicing events and mutations affecting the extracellular ligand binding domain have been shown to be both transforming and tumorigenic. The data of the disclosure confirmed the transforming properties for EGFR-Viii, EGFR-Vii, and EGFR-A289V. When expressed in BaF3 cells all transformed cells to proliferate in the absence of IL-3 (FIG. 3).

The x-ray structure for the ectodomain of wild type EGFR reveals 21 intramolecular disulfide bonds lining the dimer interface at the CR1 and CR2 regions. Exemplary disulfide bonds lining the dimer interface at the CR1 and CR2 regions may occur at one or more regions of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1. Similarly, exemplary disulfide bonds lining the dimer interface at the CR1 and CR2 regions of a HER-2 receptor may occur at one or more regions of C199-C212, C220-C227, C224-C235, C236-C244, C240-C252, C255-C264, C268-C295, C299-C311, C315-C331, C334-C338, C342-C367, C511-C520, C531-C540, C544-C560, C563-C576, C567-C584, C587-C596, C600-C623, C626-C634 and C630-C642.

Figure 4:
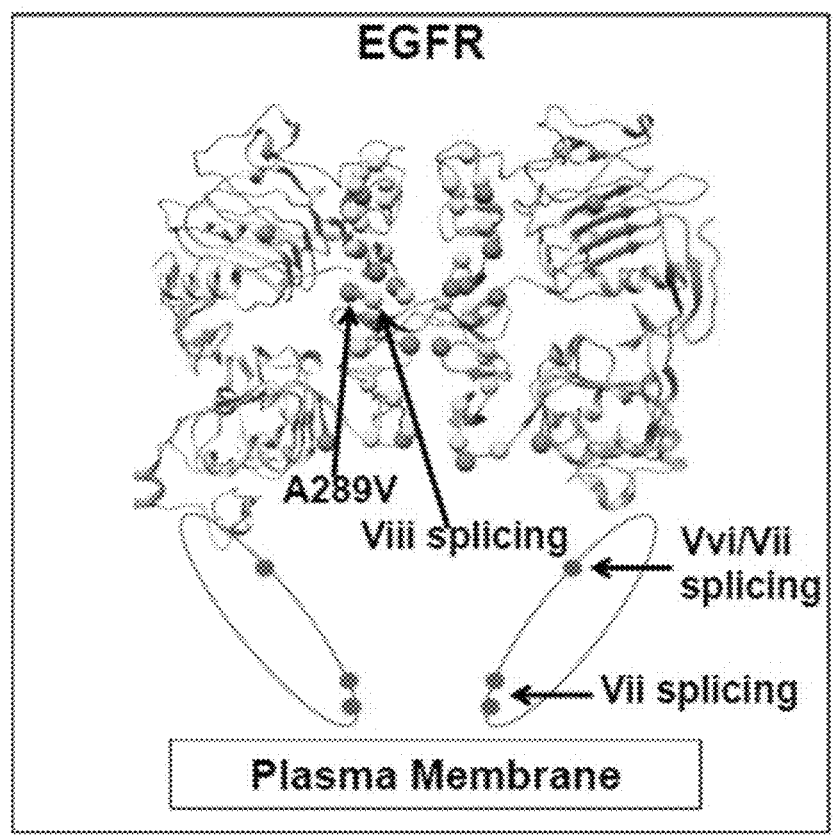
FIG. 4 is an illustration of the structure of EGFR and exemplary free cysteines that are formed at the extracellular dimer interface of EGFR as a result of genomic mutations and alternative splicing events in cancer. Arrows note the positions of free cysteines predicted to be generated as a result of the events EGFR-A289V, EGFR-Viii, EGFR-Vii, and EGFR-Vvi. Positions are mapped onto the crystal structure of the ectodomain of EGFR (1IVO). EGF ligand is shown in green, and EGFR protomers are shown in grey and orange.

This is a common feature for all ErbB receptors. One of the 11 intramolecular disulfide bonds in the CR1 region of EGFR is formed by Cys295-Cys307, which is disrupted in EGFR-Viii. Loss of sequence coding for part of the CR1 region eliminates Cys295, leaving Cys307 free to form an intermolecular disulfide bond with another EGFR-Viii monomer (FIG. 4). The mutation to Cys307-Ser prevents formation of covalent EGFR-Viii dimers and exhibits reduced tumorigenicity in vivo.

Inspection of sequences losses produced by truncations for both EGFR-Vvi and EGFR-Vii reveals that intramolecular disulfide bonds at the CR2 ectodomain dimer interface will be disrupted. Loss of exons 14-15 in EGFR-Vvi will result in disruption of the Cys539-Cys555 bond, leaving Cys555 as a free cysteine, and loss of exons 14-15 in EGFR-Vii will result in disruption of the Cys539-Cys555, Cys620-Cys628 and Cys624-Cys636 bonds, leaving Cys555, Cys628 and Cys636 as free cysteines. Cys555, Cys628, and Cys636 all reside in the CR2 region of the dimerization interface, FIG. 4. Free cysteines generated at these sites could confer the potential for receptors to form covalent dimers, as has been demonstrated for EGFR-Viii.

Point mutations may reside in cysteine rich regions CR1 and CR2 and could also affect disulfide bonds at the ectodomain dimer interface (FIG. 1). Some point mutations may introduce new cysteines into the CR1 region (e.g. R252C). Other mutations may directly affect cysteines that form intramolecular disulfide bonds in the CR2 region of wild type EGFR (e.g. C624F), and some of these have been shown to promote covalently dimerized receptors in the presence of EGF ligand. Many other mutations do not directly affect cysteine composition within the ectodomain but are situated in close proximity to native intramolecular disulfide bonds at the dimer interface, and offer the potential to disrupt these structures. Indeed mutations that are adjacent to a disulfide bond in the third Ig-like domain of FGFR2 have been shown to disrupt this bond and confer a covalently dimerized and activated receptor. A289, the most common site for mutation in GBM, is less than 10 angstroms from the Cys-295-Cys307 bond, and alterations at this site might disrupt this disulfide, resulting in presentation of free cysteines at the CR1 dimer interface region.

Figure 5A:
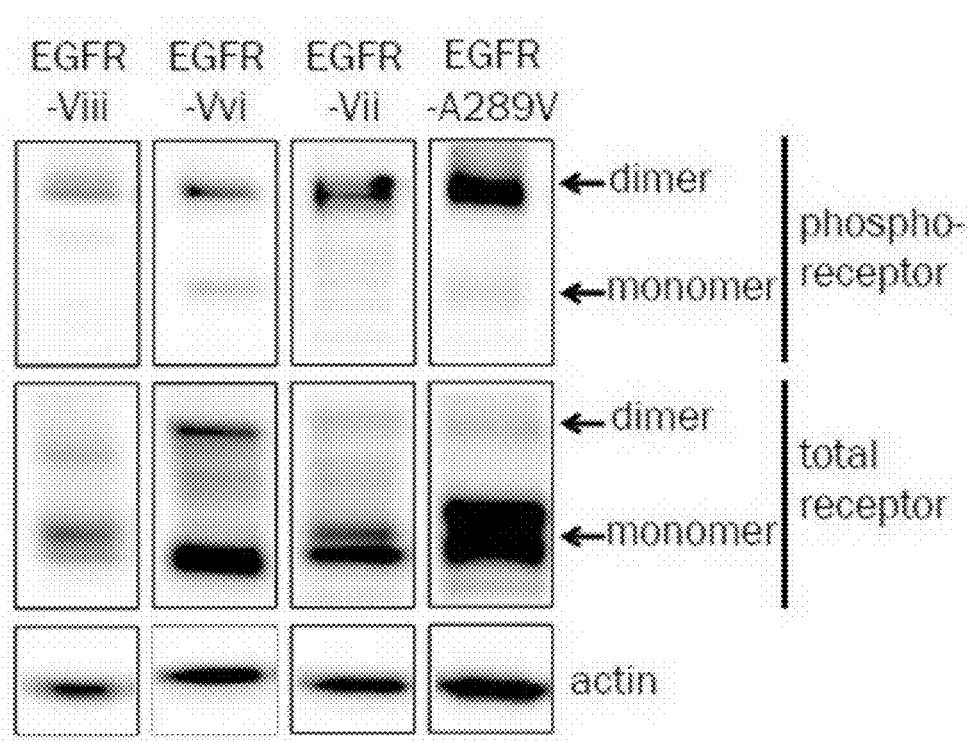
FIG. 5A is a series of photographs of Western blots depicting the expression of total and phosphorylated monomeric EGFR versus covalent EGFR dimers for EGFR-Viii, EGFR-Vii, EGFR-Vvi, and EGFR-A289V, detected by resolving proteins under non-reducing conditions. The data demonstrate that EGFR-Viii, EGFR-Vii, EGFR-Vvi, and EGFR-A289V exist as covalently activated dimers.
Figure 5B:
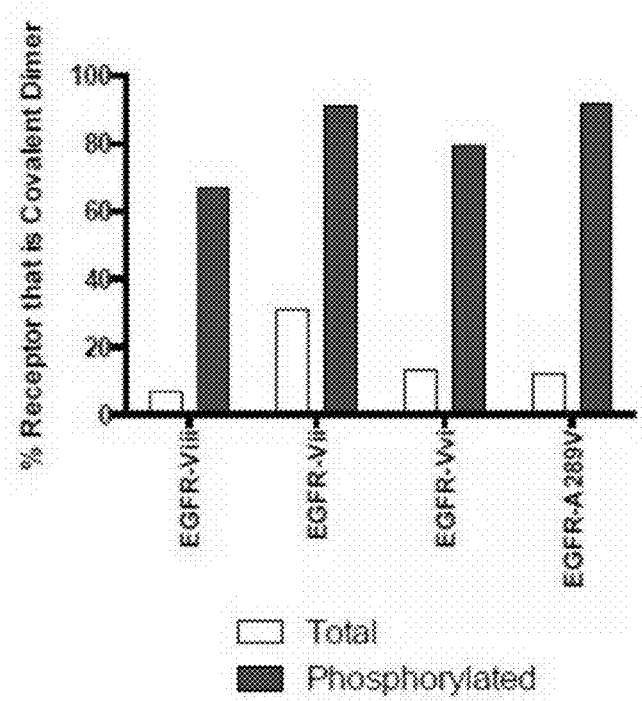
FIG. 5B is a graph depicting the quantitation of results from FIG. 5A, and the quantitation of percentage of receptor that exists as covalent dimer for total versus phosphorylated receptor.

The occurrence of free cysteines at the ectodomain dimer interface for EGFR-Vvi, EGFR-Vii, and EGFR-A289V could give rise to covalent and constitutively active dimers as has been demonstrated for EGFR-Viii. To test this hypothesis, each receptor isoform was expressed in U87-MG tumor cells, which endogenously express only a very low level of wild type EGFR, and evaluated for the phosphorylation of EGFR under non-reducing conditions to allow detection of covalently dimerized versus monomeric receptor. EGFR-Viii, EGFR-Vii, EGFR-Vvi, and EGFR-A289V were all present as covalent and active receptors (FIG. 5). Although covalent dimer represented only a minor fraction of total receptor levels, the majority of phosphorylated and activated receptors were present as covalent dimers. Therefore, distinct rearrangements within the ectodomain generated by genomic alterations and aberrant splicing all produce receptors activated by a common mechanism involving ligand independent covalent dimerization.

Figure 6:
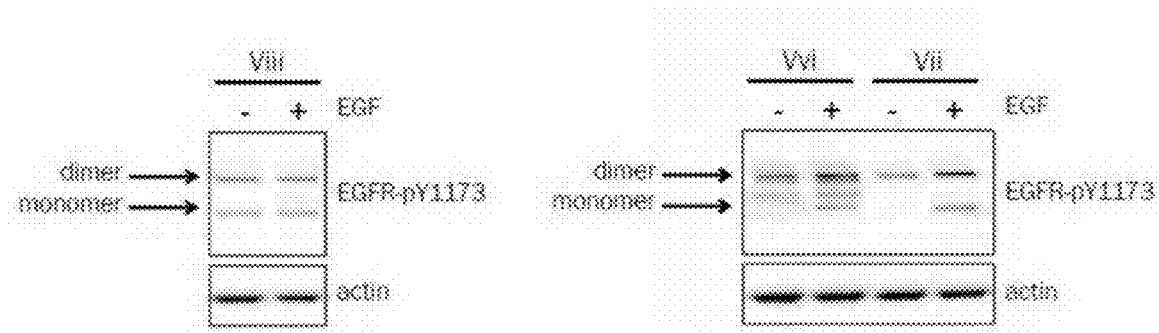
FIG. 6 is a pair of photographs of Western blots depicting the effect of EGF treatment on levels of monomeric and dimeric phosphorylated EGFR for EGFR-Vii and EGFR-Vvi. In contrast to EGFR-Viii, EGF further potentiates the formation of active covalent dimers for EGFR-Vii and EGFR-Vvi.

The ability of EGF ligand to modulate the activity for each member of the splice-activated EGFR family was assessed. In EGFR-Viii the ligand binding domain has been mostly truncated because of loss of sequence encoded by exons 2-7. The addition of EGF has no effect on the phosphorylation of monomeric or covalently dimerized EGFR-Viii expressed in U87-MG cells (FIG. 6). The ectodomain truncations for both EGFR-Vii and EGFR-Vvi occur downstream and affect sequence within the CR2 region more proximal to the transmembrane domain. The EGF binding site is intact for both of these variants. In contrast to EGFR-Viii, both EGFR-Vii and EGFR-Vvi have constitutive basal activity for covalent dimers, which can be further enhanced by EGF (FIG. 6).

Figure 7A:
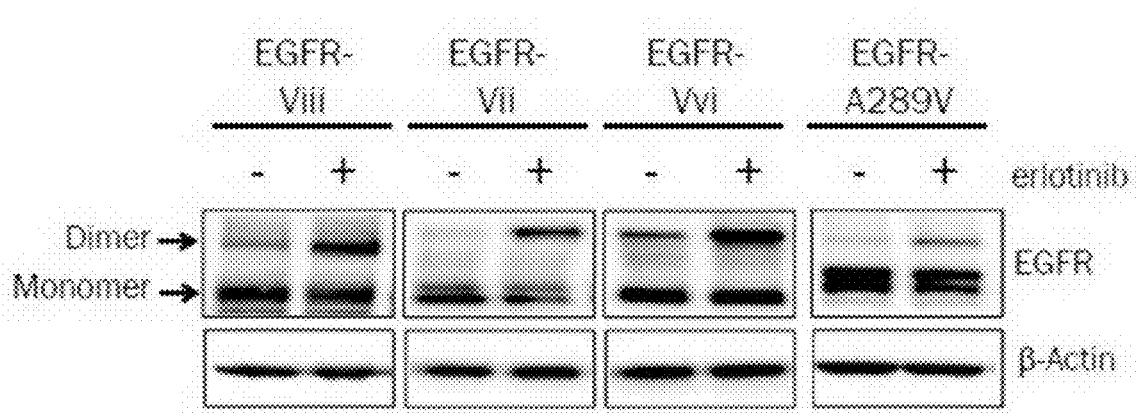
FIG. 7A is a series of photographs of Western blots depicting the effect of 100 nM erlotinib treatment on levels of monomeric and dimeric EGFR levels in cells expressing EGFR-Viii, EGFR-Vii, EGFR-Vvi, or EGFR-A289V. Monomeric and dimeric EGFR levels were detected by resolving proteins under non-reducing conditions. The data demonstrate that Type I inhibitors enhance the formation of covalent dimers for all covalently-activated EGFR variants.
Figure 7B:
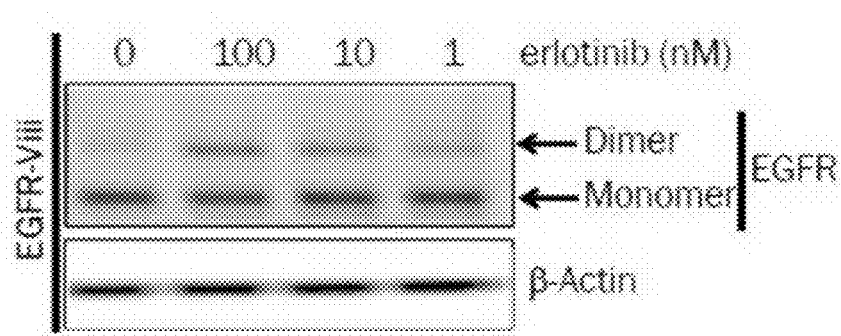
FIG. 7B is a pair of photographs of Western blots depicting the effect of varying concentrations of erlotinib on monomeric and dimeric EGFR levels in cells expressing EGFR-Vii. Monomeric and dimeric EGFR levels were detected by resolving proteins under non-reducing conditions.
Figure 7C:
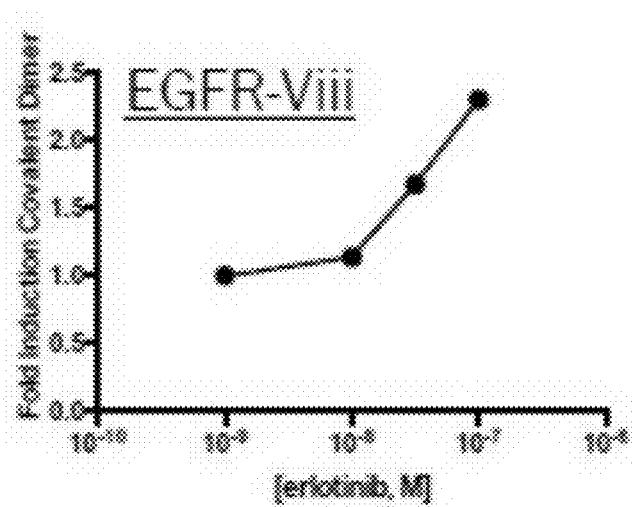
FIG. 7C is a graph quantifying the data presented in FIG. 7B. The data demonstrate that erlotinib induces a dose dependent increase in covalently dimerized receptor.
Figure 8:
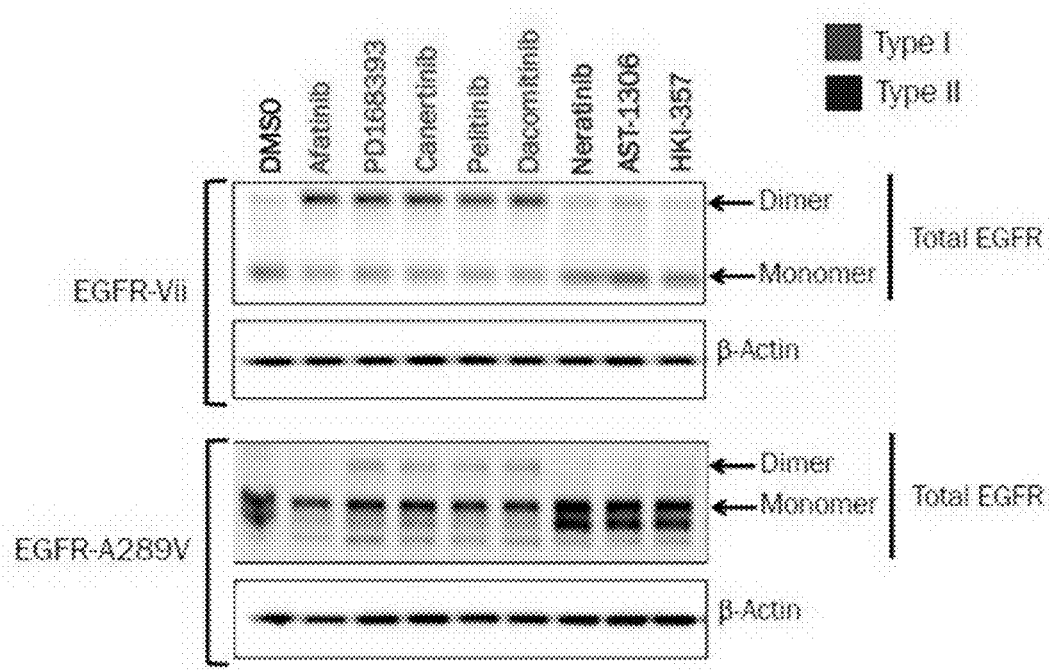
FIG. 8 is a series of photographs of Western blots depicting the effect of a panel of Type I and Type II inhibitors on dimeric and monomeric EGFR levels for cells expressing EGFR-Vii and EGFR-A289V. Monomeric and dimeric EGFR levels were detected by resolving proteins under non-reducing conditions. The data demonstrate that Type I, but not Type II, ErbB inhibitors enhance the formation of covalent dimers for covalently-activated EGFR variants.

The ability of multiple aberrations of EGFR in GBM to drive constitutive activation indicates that EGFR is an important therapeutic target. However, none of the ErbB inhibitors approved for treatment of EGFR catalytic site mutations in NSCLC proved effective in treating GBM. The experiments of the disclosure sought to establish whether small molecule ErbB inhibitors that have demonstrated clinical activity against oncogenic catalytic mutations expressed in NSCLC might have differential activity against each of the covalently-activated EGFR isoforms. Herein, the data demonstrate that erlotinib enhances the formation of covalent dimers for all three splice-activated EGFR isoforms and EGFR-A289V (FIG. 7A). These effects were dose-dependent (FIG. 7B). This ability of erlotinib to induce covalent dimers for covalently-activated EGFR variants was observed for all Type I ErbB inhibitors, but not Type II inhibitors, and includes molecules with either reversible or covalent binding modes (FIG. 8 and Table 6).

TABLE 6

| Molecule | Binding Mode | Class | Induced dimers |
| --- | --- | --- | --- |
| Erlotinib | reversible | Type I | Yes |
| Gefitinib | reversible | Type I | Yes |
| Lapatinib | reversible | Type II | No |
| Afatinib | covalent | Type I | Yes |
| CO-1686 | covalent | Type I | Yes |
| AZD9291 | covalent | Type I | Yes |
| WZ8040 | covalent | Type I | Yes |
| WZ3146 | covalent | Type I | Yes |
| WZ4002 | covalent | Type I | Yes |
| Neratinib | covalent | Type II | No |
| HKI-357 | covalent | Type II | No |
| PD168393 | covalent | Type I | Yes |
| Canertinib | covalent | Type I | Yes |
| Pelitinib | covalent | Type I | Yes |
| Dacomitinib | covalent | Type I | Yes |
| AST-1306 | covalent | Type II | No |

Figure 9:
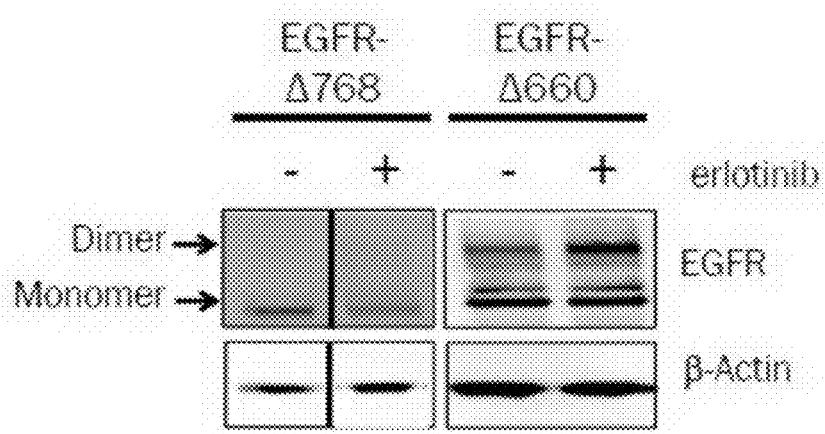
FIG. 9 is a series of photographs of Western blots depicting the effect of 100 nM erlotinib treatment on monomeric and dimeric EGFR levels for two EGFR variants. Monomeric and dimeric EGFR levels were detected by resolving proteins under non-reducing conditions. The data demonstrate that both EGFR-Δ660 and EGFR-Δ768 can exist as covalent dimers and covalent dimer is potentiated following treatment with erlotinib.

This discovery was extended to two other splice variants that were identified in glioblastoma and head and neck cancers, EGFR-Δ768 and EGFR-Δ660 (FIG. 9 and Table 7). Both receptor isoforms could exist as covalently activated receptors, and erlotinib induced covalent dimerization for both.

TABLE 7

| Variant | Tumor expression (prevalence) | Exons spliced out | Position | Free Cys generated |
| --- | --- | --- | --- | --- |
| EGFR-Δ768 | Neuroblastoma (NA) | 2-7 (partial) | CR1 | Cys291 |
| EGFR-Δ660 | SCCHN (NA) | 2-8 (partial) | CR1 | Cys 307 |

Figure 10A:
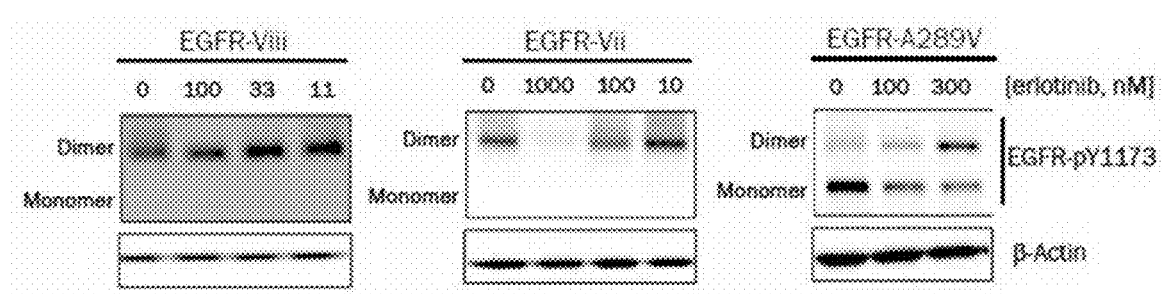
FIG. 10A is a series of photographs of Western blots depicting the effect of varying concentrations of erlotinib on monomeric and dimeric levels of phosphorylated EGFR in cells expressing EGFR-Viii, EGFR-Vii, and EGFR-A289V. Monomeric and dimeric EGFR levels were detected by resolving proteins under non-reducing conditions. The data demonstrate that sub-saturating concentrations of erlotinib stimulate the phosphorylation of covalently dimerized splice-activated EGFR isoforms.
Figure 10B:
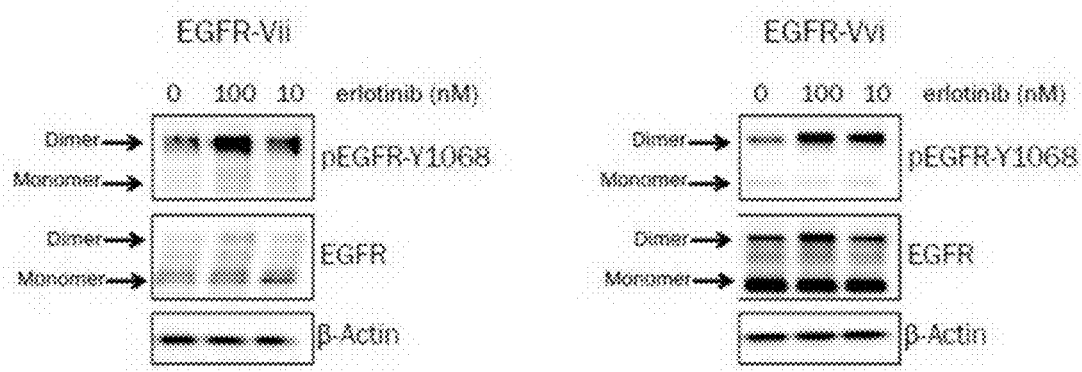
FIG. 10B is a series of photographs of Western blots depicting the effect of varying concentrations of erlotinib treatment, followed by a 30 minute washout, on total and phosphorylated EGFR levels in cells expressing EGFR-Vii or EGFR-Vvi. Proteins were resolved under non-reducing conditions. The data demonstrate that erlotinib paradoxically enhances the phosphorylation of covalent dimers for EGFR-Vii and EGFR-Vvi.

Treatment with sub-saturating concentrations of the Type I ErbB inhibitor erlotinib also results in enhanced phosphorylation of covalently-activated EGFR variants, shown for EGFR-Vii, EGFR-Viii, and EGFR-A289V (FIG. 10A). Further, when cells expressing either EGFR-Vii or EGFR-Vvi are treated with erlotinib, and then washed prior to collection of lysates, all show enhanced phosphorylation compared to untreated control cells, consistent with increased dimer formation in response to the Type I inhibitor (FIG. 10B).

Figure 11A:
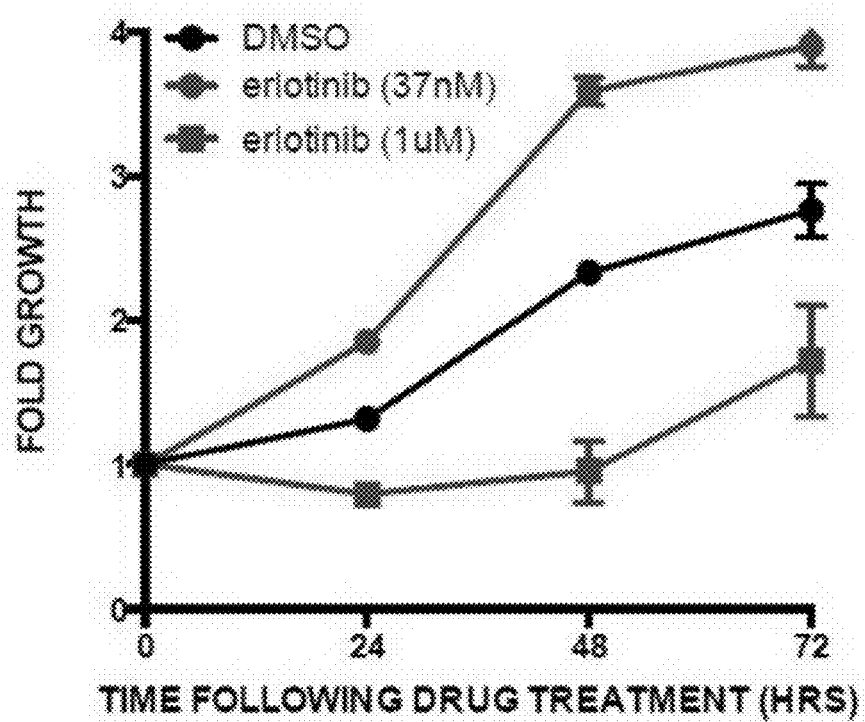
FIG. 11A is a graph depicting the effect of DMSO, 37 nM erlotinib, or 100 nM erlotinib on the proliferation of BaF3 cells expressing EGFR-Viii. Proliferation data were collected at multiple time points over a three day period. The data demonstrate that sub-saturating concentrations of erlotinib result in paradoxical stimulation of proliferation in cells expressing splice-activated EGFR.
Figure 11B:
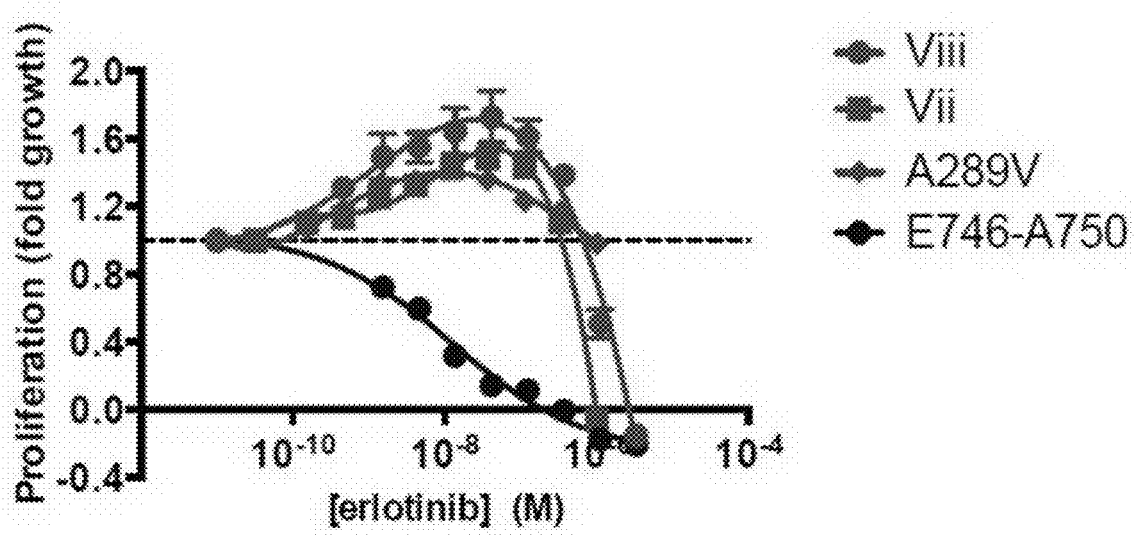
FIG. 11B is a graph depicting the effect of varying concentrations of erlotinib on the proliferation of BaF3 cells expressing EGFR-Viii, EGFR-Vii or EGFR-A289V. Proliferation was assessed at 72 hours after erlotinib dosing. The data demonstrate that sub-saturating concentrations of erlotinib paradoxically stimulate the growth of BaF3 cells driven by EGFR-Viii, EGFR-Vii, and EGFR-A289V.
Figure 12:
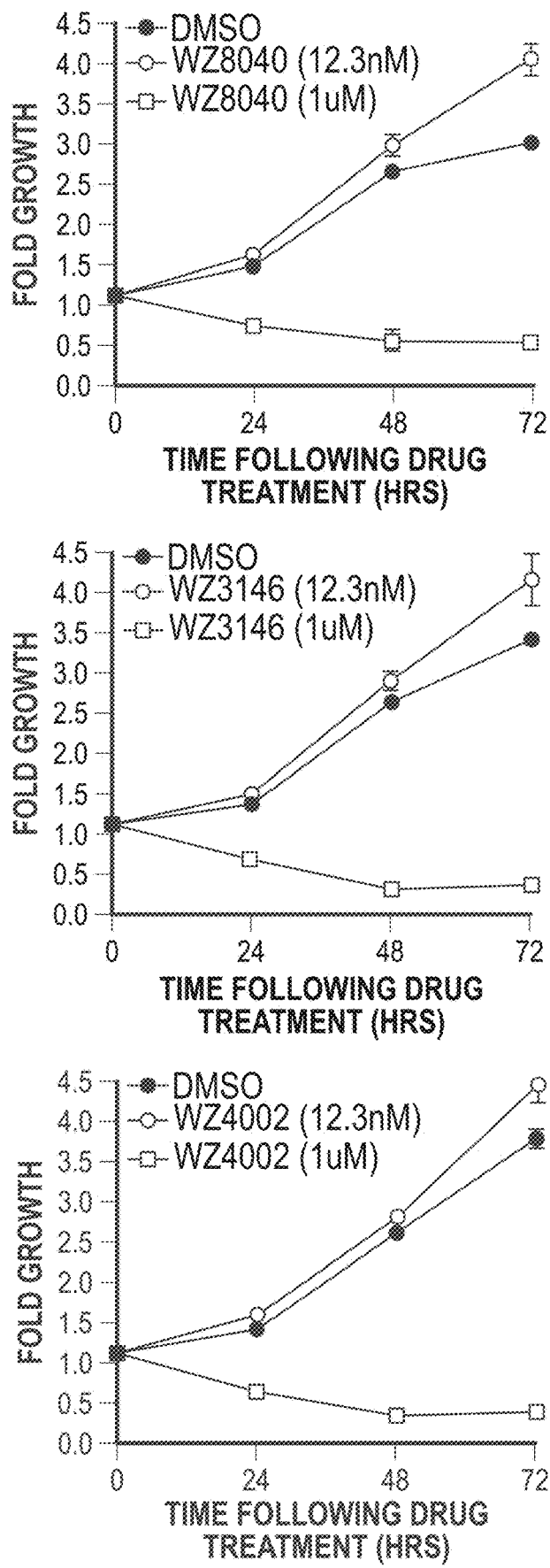
FIG. 12 is a series of graphs depicting the effect of 12.5 nM or 1 uM of WZ8040, WZ3146, or WZ4002 on the proliferation of BaF3 cells expressing EGFR-Viii. Proliferation data were collected at multiple time points over a three day period. The data demonstrate that sub-saturating concentrations of WZ8040, WZ3146 or WZ4002 result in paradoxical stimulation of proliferation in cells expressing EGFR-Viii.

To assess the impact of enhanced EGFR activity evoked by sub-saturating concentrations of erlotinib on cell proliferation, EGFR-Viii, EGFR-Vii, and EGFR-A289V were expressed in BaF3 cells to transform them to IL-3 independence. While high saturating concentrations of erlotinib (1 uM) inhibited proliferation of BaF3-EGFR-Viii cells, lower sub-saturating concentrations (37 nM) stimulated proliferation (FIG. 11A). The biphasic effect of erlotinib on the proliferation of cells expressing covalently-activated EGFR was similarly seen in BaF3 cells expressing EGFR-Vii or EGFR-A2989V, but was not seen in isogenic BaF3 cells expressing the oncogenic EGFR catalytic domain mutation E746-A750 (FIG. 11B), thus demonstrating that paradoxical activation is specific to covalently-activated EGFR isoforms. The biphasic effect on proliferation for cells expressing EGFR-Viii was also seen with the covalent inhibitors WZ8040, WZ4002, and WZ3146, indicating that this behavior exists for small molecules with both reversible and covalent binding modes (FIG. 12). The ability of Type I inhibitors to paradoxically enhance cell proliferation at sub-saturating drug concentrations is fully consistent with the ability of molecules with this type of mechanism to promote the formation of covalently activated dimers.

Mutations and splicing events affecting the CR1 and CR2 regions of the HER2 and HER4 ectodomains are also observed cancer (Table 8). The most common of these is HER2Δ16, expressed in approximately 50% of breast cancers, but not detected in any normal tissue. HER2Δ16 results from alternative splicing and loss of exon 16, encoding the extracellular juxtamembrane region, producing two free cysteine residues situated at the dimer interface in the CR2 region, Cys626 and Cys630 (Table 8). Compared to HER2-WT, HER2Δ16 is highly tumorigenic. In breast cancer patients, expression of HER2Δ16 is associated with greater incidence of lymph node involvement and metastatic disease.

TABLE 8

| Variant | Tumor expression (prevalence) | Exons spliced out | Position | Free Cys generated |
|---|---|---|---|---|
| HER2-Δ16 | BrCa (52% of HER2 +)/GaCa | 16 | CR2 | Cys626, Cys630 |
| HER2-C311R | GBM (<1%) | NA | CR1 | Cys299 |
| HER2-S310F/Y | Bladder (5%), Breast (2%), Cervical (1%), Stomach (1%), NSCLC (2% squamous) | NA | CR1 | ND |

Figure 13A:
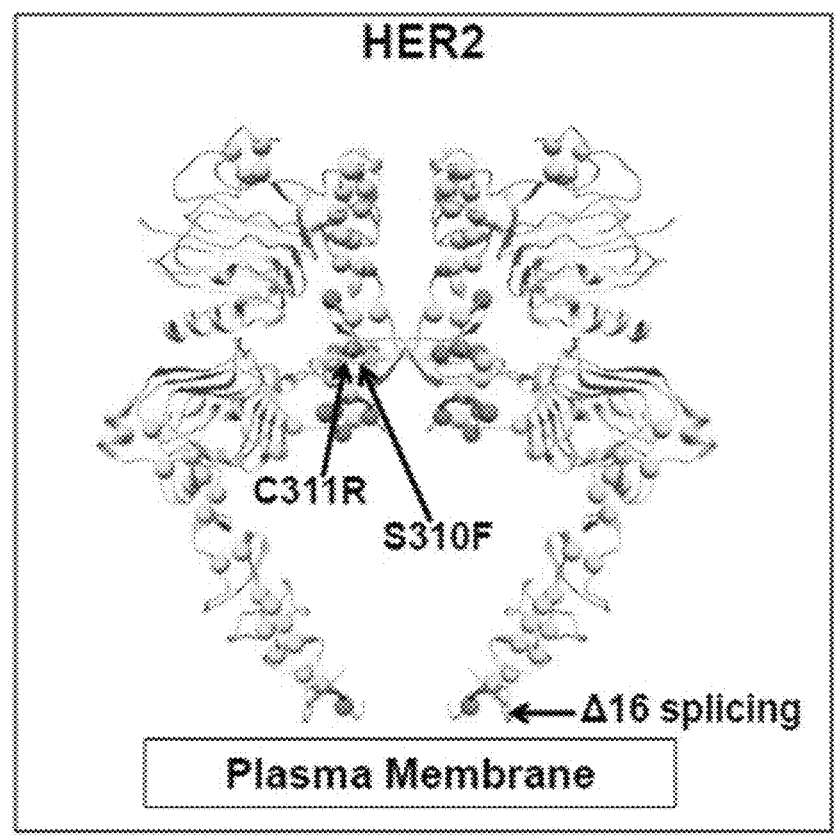
FIG. 13A is an illustration of the structure of EGFR and exemplary free cysteines are formed at the extracellular dimer interface of HER2 receptors as a result of genomic mutations and alternative splicing events in cancer. Arrows point to positions of free cysteines generated by the Δ16 splice event or C311R or S310F mutations.
Figure 13B:
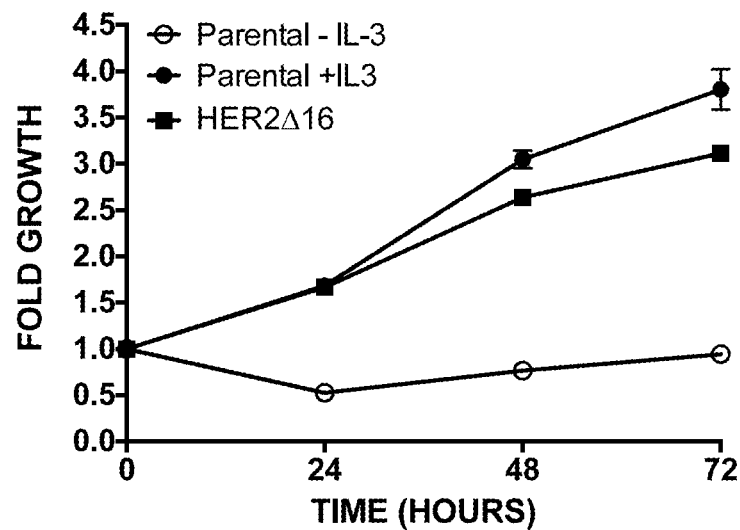
FIG. 13B is a pair of graphs demonstrating that HER2 and HER4 splice variants are transforming. The proliferation of BaF3 cells expressing HER4-WT (JMA), HER4Δ16 (JMC), and HER2Δ16, or vector alone (parental), cultured in the absence of IL-3. The proliferation of parental BaF3 cells cultured in the presence of IL-3 is shown as a control.
Figure 13B:
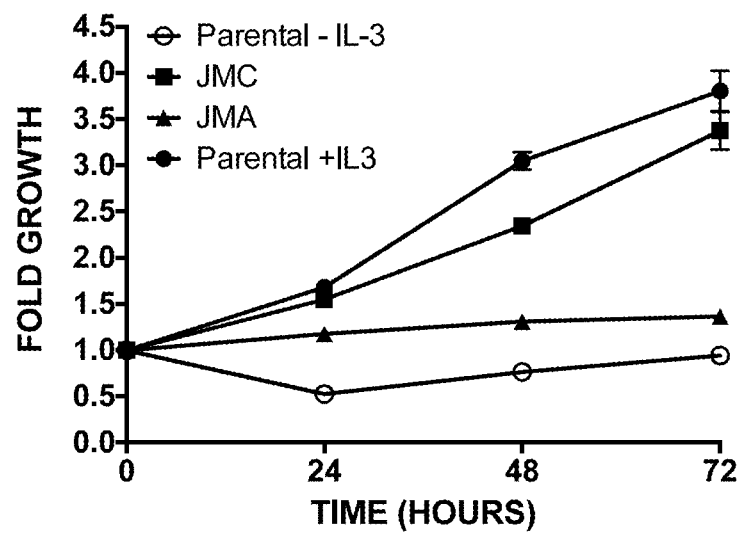

As observed with EGFR, point mutations also occur at the dimer interface of the HER2 CR1 region (Table 8 and FIG. 13). Some mutations introduce novel cysteines or remove one member of a pair of cysteines coordinating an intramolecular disulfide bond. Other mutations, including HER2-S310F/Y, are situated proximal to disulfide bonds and may allosterically disrupt them, as discovered for EGFR-A289V. HER2-S310F/Y mutations are the most frequently occurring HER2 mutations in cancer, expressed by >15% of bladder cancers.

Figure 14:
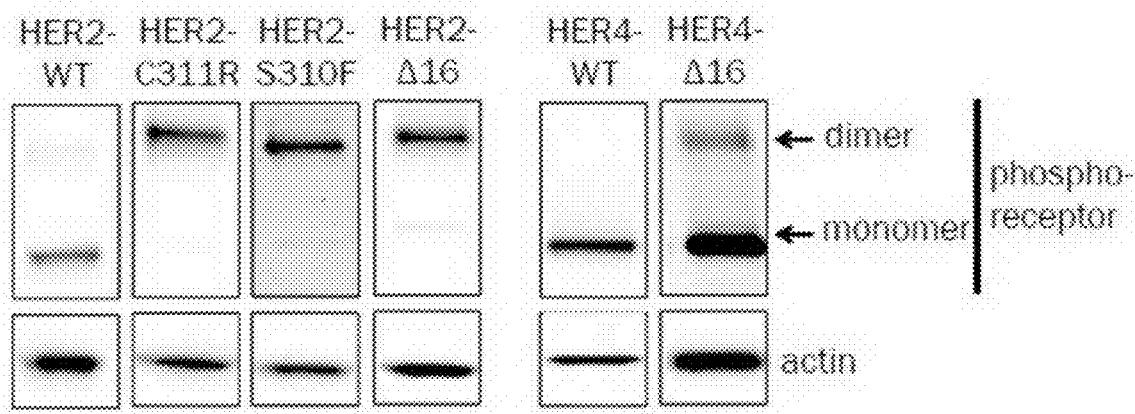
FIG. 14 is a series of photographs of Western blots depicting the expression of dimeric and monomeric levels of phosphorylated HER2 or HER4 receptors in cells expressing each variant. Monomeric and dimeric EGFR levels were detected by resolving proteins under non-reducing conditions. The data demonstrate that multiple HER2 and HER4 splicing events and mutations in the CR1 and CR2 regions result in covalently active dimers.

Select extracellular variants of HER2, including HER2-C311R and HER2Δ16, exist as covalently activated dimers. The data of the disclosure demonstrate that other commonly occurring extracellular variants including HER2-S310F also exist as covalently activated receptors (FIG. 14).

Figure 15A:
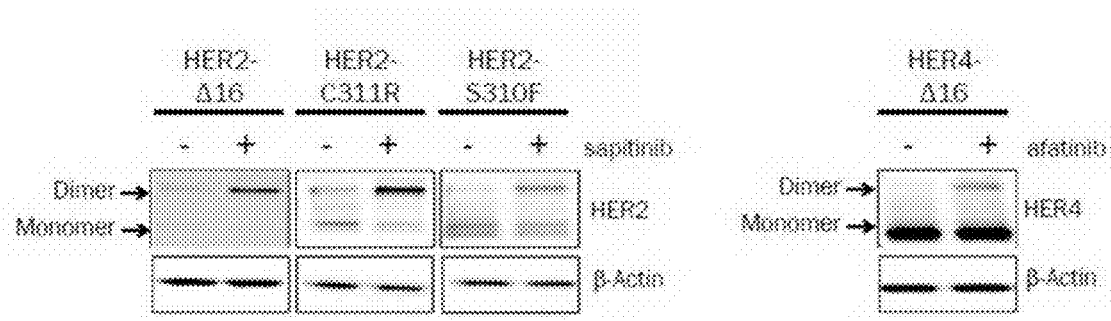
FIG. 15A is a series of photographs of Western blots depicting the effect of the Type I HER2 inhibitor sapitinib or the Type I HER4 inhibitor afatinib on levels of dimerized receptors for cells expressing HER2-Δ16, HER2-C311R, HER2-S310F, or HER4Δ16. Monomeric and dimeric HER2 and HER4 levels were detected by resolving proteins under non-reducing conditions. The data demonstrate that Type I inhibitors induce the formation of covalent dimers for covalently-activated HER2 and HER4 isoforms.
Figure 15B:
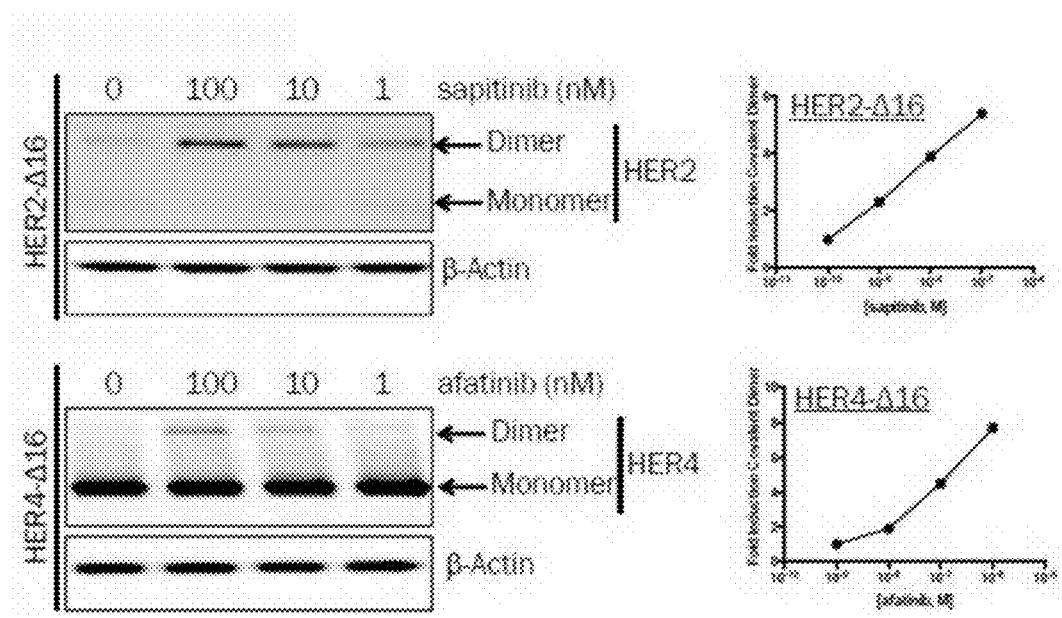
FIG. 15B a series of photographs of Western blots and corresponding graphs depicting the effect of varying concentrations of sapitinib or afatinib on the levels of dimerized HER2 or HER2 in cells expressing HER2-Δ16 or HER4-Δ16. Monomeric and dimeric HER2 and HRE4 levels were detected by resolving proteins under non-reducing conditions. The data demonstrate that Type I inhibitors induce a dose dependent increase in covalently dimerized receptors for HER2 and HER4 variants.
Figure 16:
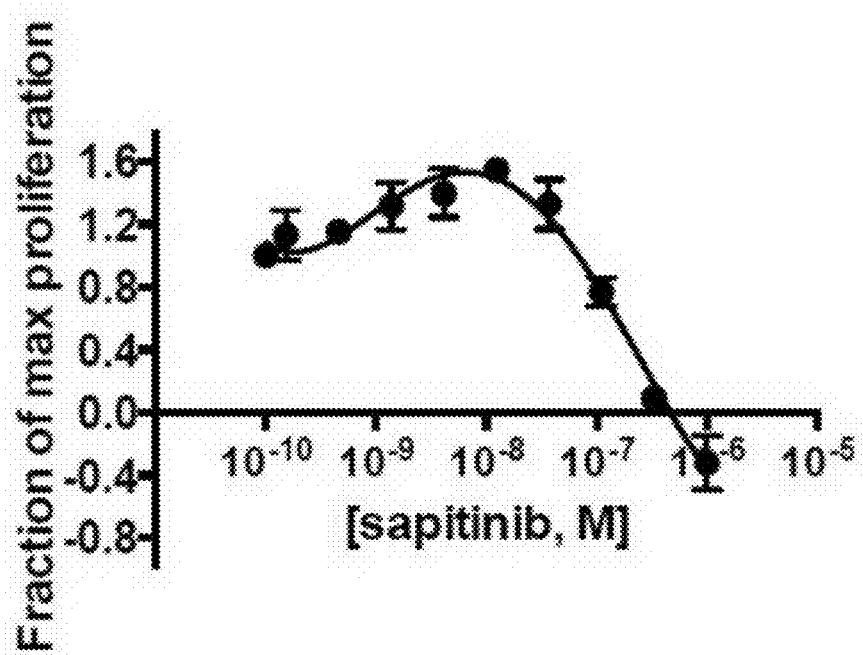
FIG. 16 is a graph depicting the effect of varying concentrations of sapitinib on the proliferation of BaF3-HER2-Δ16 cells. The data demonstrate that sub-saturating concentrations of the Type I inhibitor sapitinib paradoxically stimulate the proliferation of BaF3-HER2Δ16 cells.
Figure 17A:
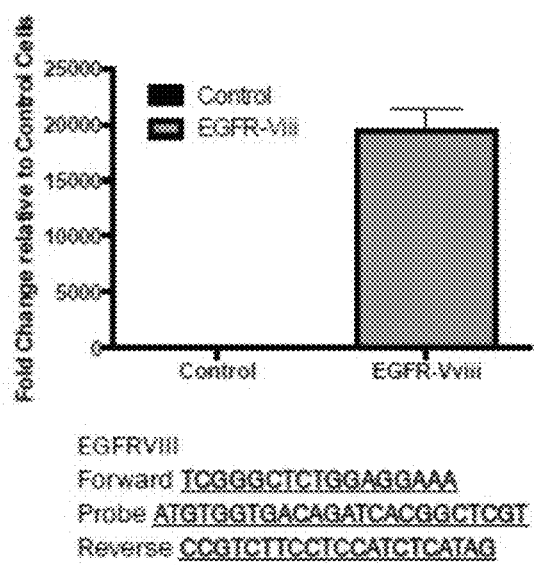
FIGS. 17A-C are a series of graphs demonstrating that expression levels of ErbB splice variants can be measured by isoform selective PCR. The expression levels of EGFR-Viii (A), EGFR-Vii (B), and EGFR-Vvi (C) in cells engineered to express the respective splice-variant as compared to cells that do not express the respective splice-variant. Primers and probes used to detect each variant are listed. Primers and probes used to detect EGFRVIII are identified as SEQ ID NO: 9 (forward), SEQ ID NO: 10 (probe) and SEQ ID NO: 11 (reverse). Primers and probes used to detect EGFRVii are identified as SEQ ID NO: 12 (forward), SEQ ID NO: 13 (probe) and SEQ ID NO: 14 (reverse). Primers and probes used to detect EGFRVvi are identified as SEQ ID NO: 15 (forward), SEQ ID NO: 16 (probe) and SEQ ID NO: 17 (reverse).
Figure 17B:
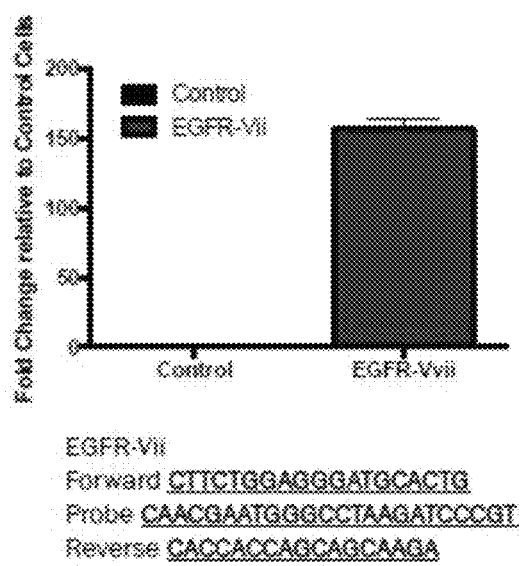
Figure 17C:
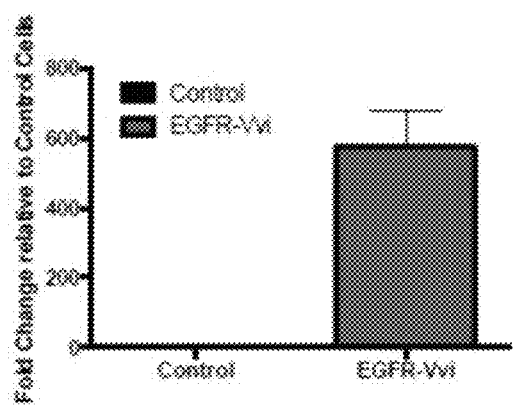
Figure 18:
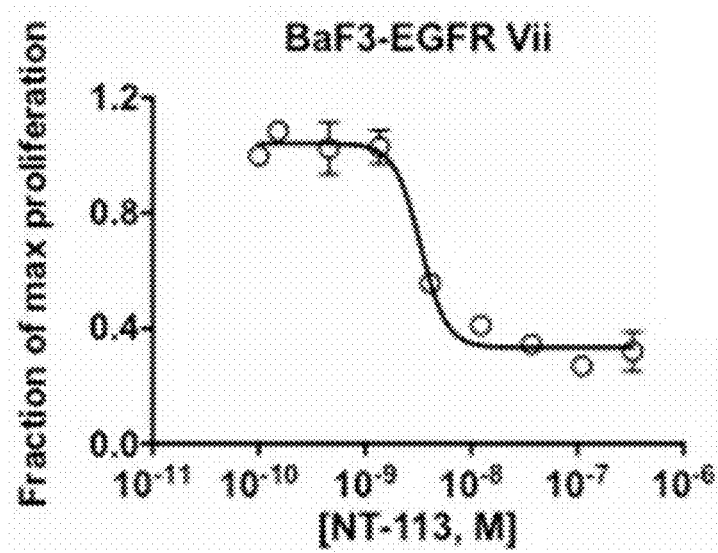
FIG. 18 is a graph showing the fraction of the maximum proliferation of cells having, for example, the EGFR-Vii mutation with NT-113, a potent Type I covalent inhibitor. NT-113 induces dimerization for covalently activated ErbB receptors. In contrast to reversible Type I inhibitors, and other covalent Type I inhibitors, there is no evidence for increased cellular proliferation in response to NT-113. Therefore, in contrast to reversible Type I inhibitors, and other covalent Type I inhibitors, NT-113 represents a potent Type I covalent molecule that could be used to treat tumors driven by covalently-activated ErbB receptors.

Similar to observations for covalently-activated EGFR variants, Type I inhibitors (sapitinib and afatinib) induce the expression of covalent dimers for HER2 extracellular variants (FIG. 15A). These effects were dose dependent (FIG. 15B). Finally, sapitinib can paradoxically stimulate the proliferation of BaF3 cells driven by HER2-Δ16 (FIG. 16). Collectively, these data provide instructive guidelines for the treatment of tumors expressing covalently activated ErbB receptors, including exclusion criteria for Type I inhibitors and preferred method of treatment for Type II pharmacophores in tumors expressing these variant receptors.

Methods

Retroviral Production: EGFR mutants were subcloned into pMXs-IRES-Blasticidin (RTV-016, Cell Biolabs, San Diego, Calif.). Retroviral expression vector retrovirus was produced by transient transfection of HEK 293T cells with the retroviral EGFR mutant expression vector pMXs-IRES-Blasticidin (RTV-016, Cell Biolabs), pCMV-Gag-Pol vector and pCMV-VSV-G-Envelope vector. Briefly, HEK 293T/17 cells were plated in 100 mm collagen coated plate (354450, Corning Life Sciences, Tewksbury, Mass.) ($4\times10^5$ per plate) and incubated overnight. The next day, retroviral plasmids (3 μg of EGFR mutant, 1.0 μg of pCMV-Gag-Pol and 0.5 μg pCMV-VSV-G) were mixed in 500 μl of Optimem (31985, Life Technologies). The mixture was incubated at room temperature for 5 min and then added to Optimem containing transfection reagent Lipofectamine (11668, Invitrogen) and incubated for 20 minutes. Mixture was then added dropwise to HEK 293T cells. The next day the medium was replaced with fresh culture to medium and retrovirus was harvested @ 24 and 48 hrs.

Generation of EGFR mutant stable cell lines: BaF3 cells (1.5E5 cells) were infected with 1 ml of viral supernatant supplemented with 8 μg/ml polybrene by centrifuging for 30 min at 1000 rpm. Cells were placed in a 37° C. incubator overnight. Cells were then spun for 5 minutes to pellet the cells. Supernatant was removed and cells re-infected a fresh 1 ml of viral supernatant supplemented with 8 μg/ml polybrene by centrifuging for 30 min at 1000 rpm. Cells were placed in 37° C. incubator overnight. Cells were then maintained in RPMI containing 10% Heat Inactivated FBS, 2% L-glutamine containing 10 ng/ml IL-3. After 48 hours cells were selected for retroviral infection in 10 μg/ml Blasticidin for one week. Blasticidin resistant populations were washed twice in phosphate buffered saline before plating in media lacking IL-3 to select for IL-3 independent growth.

Assay for cell proliferation: BaF3 cell lines were resuspended at 1.3E5 c/ml in RPMI containing 10% Heat Inactivated FBS, 2% L-glutamine and 1% Pen/Strep and dispensed in triplicate (17.5E4 c/well) into 96 well plates. To determine the effect of drug on cell proliferation, cells incubated for 3 days in the presence of vehicle control or test drug at varying concentrations. Inhibition of cell growth was determined by luminescent quantification of intracellular ATP content using CellTiterGlo (Promega), according to the protocol provided by the manufacturer. Comparison of cell number on day 0 versus 72 hours post drug treatment was used to plot dose-response curves. The number of viable cells was determined and normalized to vehicle-treated controls. Inhibition of proliferation, relative to vehicle-treated controls was expressed as a fraction of 1 and graphed using PRISM® software (Graphpad Software, San Diego, Calif.). $EC_{50}$ values were determined with the same application.

Cellular protein analysis: Cell extracts were prepared by detergent lysis (RIPA, R0278, Sigma, St Louis, Mo.) containing 10 mM Iodoacetamide (786-228, G-Biosciences, St, Louis, Mo.), protease inhibitor (P8340, Sigma, St. Louis, Mo.) and phosphatase inhibitors (P5726, P0044, Sigma, St. Louis, Mo.) cocktails. The soluble protein concentration was determined by micro-BSA assay (Pierce, Rockford Ill.). Protein immunodetection was performed by electrophoretic transfer of SDS-PAGE separated proteins to nitrocellulose, incubation with antibody, and chemiluminescent second step detection. Nitrocellulose membranes were blocked with 5% nonfat dry milk in TBS and incubated overnight with primary antibody in 5% bovine serum albumin. The following primary antibodies from Cell Signaling Technology were used at 1:1000 dilution: phospho-EGFR[Y1173] and total EGFR. β-Actin antibody, used as a control for protein loading, was purchased from Sigma Chemicals. Horseradish peroxidase-conjugated secondary antibodies were obtained from Cell Signaling Technology and used at 1:5000 dilution. Horseradish peroxidase-conjugated secondary antibodies were incubated in nonfat dry milk for 1 hour. SuperSignal chemiluminescent reagent (Pierce Biotechnology) was used according to the manufacturer's directions and blots were imaged using the Alpha Innotech image analyzer and Alpha-EaseFC software (Alpha Innotech, San Leandro Calif.).

Uses of the Compounds and Compositions

In some aspects, the present disclosure is directed to a method of inhibiting an oncogenic variant of an ErbB receptor (e.g., an oncogenic variant of an EGFR), comprising administering the subject in need thereof a therapeutically effective amount of a compound described herein.

In some aspects, the present disclosure is directed to a method of inhibiting an oncogenic variant of an ErbB receptor (e.g., an oncogenic variant of an EGFR), comprising administering the subject in need thereof a composition described herein.

In some aspects, the present disclosure is directed to a method of preventing or treating cancer, comprising administering the subject in need thereof a therapeutically effective amount of a compound described herein.

In some aspects, the present disclosure is directed to a method of preventing or treating cancer, comprising administering the subject in need thereof a composition described herein.

In some aspects, the present disclosure is directed to a method of preventing or treating cancer, comprising: i) identifying a subject candidate as the subject in need of the treatment when that at least one oncogenic variant of an ErbB receptor described herein is present in the subject; and ii) administering the subject in need of the treatment a therapeutically effective amount of a compound described herein.

In some aspects, the present disclosure is directed to a method of preventing or treating cancer, comprising: i) identifying a subject candidate as the subject in need of the treatment when that at least one oncogenic variant of an ErbB receptor described herein is present in the subject; and ii) administering the subject in need of the treatment a composition described herein.

In some aspects, the present disclosure is directed to a method of preventing or treating cancer, comprising: i) identifying a subject candidate as the subject in need of the treatment when that at least one oncogenic variant of an ErbB receptor described herein is present in a biological sample from the subject; and ii) administering the subject in need of the treatment a therapeutically effective amount of a compound described herein.

In some aspects, the present disclosure is directed to a method of preventing or treating cancer, comprising: i) identifying a subject candidate as the subject in need of the treatment when that at least one oncogenic variant of an ErbB receptor described herein is present in a biological sample from the subject; and ii) administering the subject in need of the treatment a composition described herein.

In some aspects, the present disclosure is directed to a method of preventing or treating cancer, comprising administering the subject in need thereof a therapeutically effective amount of a compound described herein when that at least one oncogenic variant of an ErbB receptor described herein is identified as being present in the subject.

In some aspects, the present disclosure is directed to a method of preventing or treating cancer, comprising administering the subject in need thereof a compound described herein when that at least one oncogenic variant of an ErbB receptor described herein is identified as being present in the subject.

In some aspects, the present disclosure is directed to a method of preventing or treating cancer, comprising administering the subject in need thereof a therapeutically effective amount of a compound described herein when that at least one oncogenic variant of an ErbB receptor described herein is identified as being present in a biological sample from the subject.

In some aspects, the present disclosure is directed to a method of preventing or treating cancer, comprising administering the subject in need thereof a composition described herein when that at least one oncogenic variant of an ErbB receptor described herein is identified as being present in a biological sample from the subject.

In some aspects, the present disclosure is directed to a compound described herein for use in the inhibition of an oncogenic variant of an ErbB receptor (e.g., an oncogenic variant of an EGFR).

In some aspects, the present disclosure is directed to a compound described herein for use in the prevention or treatment of cancer.

In some aspects, the present disclosure is directed to a composition described herein for use in the inhibition of an oncogenic variant of an ErbB receptor (e.g., an oncogenic variant of an EGFR).

In some aspects, the present disclosure is directed to a composition described herein for use in the prevention or treatment of cancer.

In some aspects, the present disclosure is directed to a compound described herein for use in the prevention or treatment of cancer in a subject, wherein at least one oncogenic variant of an ErbB receptor described herein is present in the subject.

In some aspects, the present disclosure is directed to a composition described herein for use in the prevention or treatment of cancer in a subject, wherein at least one oncogenic variant of an ErbB receptor described herein is present in the subject.

In some aspects, the present disclosure is directed to a compound described herein for use in the prevention or treatment of cancer in a subject, wherein at least one oncogenic variant of an ErbB receptor described herein is present in a biological sample from the subject.

In some aspects, the present disclosure is directed to a composition described herein for use in the prevention or treatment of cancer in a subject, wherein at least one oncogenic variant of an ErbB receptor described herein is present in a biological sample from the subject.

In some aspects, the present disclosure is directed to use of a compound described herein in the manufacture of a medicament for inhibiting an oncogenic variant of an ErbB receptor (e.g., an oncogenic variant of an EGFR).

In some aspects, the present disclosure is directed to use of a compound described herein in the manufacture of a medicament for preventing or treating cancer.

In some embodiments, the compound is selected from the compounds described in Table 1, pharmaceutically acceptable salts thereof, and stereoisomers thereof.

In some embodiments, the compound is selected from the compounds described in Table 1 and pharmaceutically acceptable salts thereof.

In some embodiments, the compound is selected from the compounds described in Table 1.

In some embodiments, cancer is a solid tumor.

In some embodiments, the cancer is a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC), or any subtype thereof.

In some embodiments, the cancer is glioblastoma (GBM) or any subtype thereof.

In some embodiments, the cancer is glioblastoma.

The disclosure provides a composition comprising a compound of the disclosure or pharmaceutically acceptable salts or stereoisomers thereof. In some embodiments, the composition comprises a pharmaceutically acceptable carrier. In some embodiments, the composition comprises a second therapeutically active agent. In some embodiments, the second therapeutically active agent comprises a second compound of the disclosure. In some embodiments, the second therapeutically active agent comprises a non-Type I inhibitor. In some embodiments, the non-Type I inhibitor comprises a Type II inhibitor. In some embodiments, the Type II inhibitor comprises a small molecule inhibitor.

The disclosure provides a composition of the disclosure for use in the treatment of cancer, wherein the cancer or a tumor or a cell thereof expresses an oncogenic variant of an epidermal growth factor receptor (EGFR).

In some embodiments of the compositions for use in the treatment of cancer of the disclosure, including those wherein the cancer or a tumor or a cell thereof expresses an oncogenic variant of an epidermal growth factor receptor (EGFR), the oncogenic variant of an EGFR is an allosteric variant of EGFR.

In some embodiments of the compositions for use in the treatment of cancer of the disclosure, cancer or a tumor or a cell thereof expresses an oncogenic variant of an epidermal growth factor receptor (EGFR) and wherein the oncogenic variant of an EGFR is an allosteric variant of EGFR, the oncogenic variant of an EGFR comprises an EGFR variant III (EGFR-Viii) mutation.

In some embodiments of the compositions for use in the treatment of cancer of the disclosure, cancer or a tumor or a cell thereof expresses an oncogenic variant of an epidermal growth factor receptor (EGFR) and wherein the oncogenic variant of an EGFR is an allosteric variant of EGFR, the oncogenic variant of an EGFR comprises a substitution of a valine (V) for an alanine (A) at position 289 of SEQ ID NO: 1.

In some embodiments of the compositions for use in the treatment of cancer of the disclosure, cancer or a tumor or a cell thereof expresses an oncogenic variant of an epidermal growth factor receptor (EGFR) and wherein the oncogenic variant of an EGFR is an allosteric variant of EGFR, the oncogenic variant of an EGFR comprises a modification of a structure of the EGFR, wherein the oncogenic variant of an EGFR is a capable of forming a covalently linked dimer, wherein the covalently linked dimer is constitutively active and wherein the covalently linked dimer enhances an activity of EGFR when contacted to a Type I ErbB inhibitor. In some embodiments, the modification of the structure of the EGFR comprises a modification of one or more of a nucleic acid sequence, an amino acid sequence, a secondary structure, a tertiary structure, and a quaternary structure. In some embodiments, the oncogenic variant comprises a mutation, a splicing event, a post-translational process, a conformational change or any combination thereof. In some embodiments, the modification of the structure of the EGFR occurs within a first cysteine rich (CR1) and/or second cysteine rich (CR2) region of EGFR. In some embodiments, the first cysteine rich (CR1) and/or second cysteine rich (CR2) region of EGFR comprises amino acid residues T211-R334 and/or C526-S645 of SEQ ID NO: 1, respectively. In some embodiments, the oncogenic variant of an EGFR generates a physical barrier to formation of a disulfide bond within the CR1 and/or the CR2 region. In some embodiments, the oncogenic variant of an EGFR removes a physical barrier to formation of a disulfide bond within the CR1 and/or the CR2 region. In some embodiments, the oncogenic variant of an EGFR comprises one or more free or unpaired. Cysteine (C) residues located at a dimer interface of the EGFR. In some embodiments, the oncogenic variant of an EGFR comprises one or more free or unpaired Cysteine (C) residues at a site selected from the group consisting of C190-C199, C194-C207, C215-C223, C219-C231, C232-C240, C236-C248, C251-C260, C264-C291, C295-C307, C311-C326, C329-C333, C506-C515, C510-0523, C526-C535, C539-C555, C558-C571, C562-C579, C582-C591, C595-C617, C620-C628 and C624-C636 according to SEQ ID NO: 1. In some embodiments, the modification occurs within 10 angstroms or less of an intramolecular disulfide bond at a site selected from the group consisting of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1.

In some embodiments of the compositions for use in the treatment of cancer of the disclosure, cancer or a tumor or a cell thereof expresses oncogenic variant of EGFR and the oncogenic variant of EGFR is a mutation of EGFR, a nucleotide sequence encoding the oncogenic variant of an EGFR comprises a deletion or a substitution of a sequence encoding exon 19 or a portion thereof. In some embodiments, the deletion or the substitution comprises one or more amino acids that encode an adenosine triphosphate (ATP) binding site. In some embodiments, the ATP binding site comprises amino acids E746 to A750 of SEQ ID NO: 1. In some embodiments, the ATP binding site or the deletion or substitution thereof comprises K858 of SEQ ID NO: 1. In some embodiments, the deletion comprises K858 of SEQ ID NO: 1. In some embodiments, an arginine (R) is substituted for the lysine (K) at position 858 (K858R) of SEQ ID NO: 1. In some embodiments, an arginine (R) is substituted for the leucine (L) at position 858 (L858R) of SEQ ID NO: 1.

In some embodiments of the compositions for use in the treatment of cancer of the disclosure, cancer or a tumor or a cell thereof expresses an oncogenic variant of an epidermal growth factor receptor (EGFR) and wherein the oncogenic variant of an EGFR is an allosteric variant of EGFR, a nucleotide sequence encoding the oncogenic variant of an EGFR comprises an insertion within a sequence encoding exon 20 or a portion thereof. In some embodiments, the sequence encoding exon 20 or a portion thereof comprises a sequence encoding KEILDEAYVMASVDNPHVCAR (SEQ ID NO: 7). In some embodiments, the sequence encoding exon 20 or a portion thereof comprises a sequence encoding a C-helix, a terminal end of the C-helix or a loop following the C-helix. In some embodiments, the insertion comprises the amino acid sequence of ASV, SVD, NPH, or FQEA. In some embodiments, the sequence encoding exon 20 or a portion thereof comprises one or more of: (a) an insertion of the amino acid sequence ASV between positions V769 and D770 of SEQ ID NO: 1; (b) an insertion of the amino acid sequence SVD between positions D770 and N771 of SEQ ID NO: 1; (c) an insertion of the amino acid sequence NPH between positions H773 and V774 of SEQ ID NO: 1; (d) an insertion of the amino acid sequence FQEA between positions A763 and Y764 of SEQ ID NO: 1; (e) an insertion of the amino acid sequence PH between positions H773 and V774 of SEQ ID NO: 1; (f) an insertion of the amino acid G between positions D770 and N771 of SEQ ID NO: 1; (g) an insertion of the amino acid H between positions H773 and V774 of SEQ ID NO: 1; (h) an insertion of the amino acid sequence HV between positions V774 and C775 of SEQ ID NO: 1; (i) an insertion of the amino acid sequence AH between positions H773 and V774 of SEQ ID NO: 1; (j) an insertion of the amino acid sequence SVA between positions A767 and S768 of SEQ ID NO: 1; (k) a substitution of the amino acid sequence GYN for the DN between positions 770 and 771 of SEQ ID NO: 1; (l) an insertion of the amino acid H between positions N771 and P772 of SEQ ID NO: 1; (m) an insertion of the amino acid Y between positions H773 and V774 of SEQ ID NO: 1; (n) an insertion of the amino acid sequence PHVC between positions C775 and R776 of SEQ ID NO: 1; (o) a substitution of the amino acid sequence YNPY for the H at position 773 of SEQ ID NO: 1; (p) an insertion of the amino acid sequence DNP between positions P772 and H773 of SEQ ID NO: 1; (q) an insertion of the amino acid sequence VDS between positions S768 and V769 of SEQ ID NO: 1; (r) an insertion of the amino acid H between positions D770 and N771 of SEQ ID NO: 1; (s) an insertion of the amino acid N between positions N771 and P772 of SEQ ID NO: 1; (t) an insertion of the amino acid sequence PNP between positions P772 and H773 of SEQ ID NO: 1; (u) a substitution of the amino acid sequence GSVDN for the DN between positions 770 and 771 of SEQ ID NO: 1; (v) a substitution of the amino acid sequence GYP for the NP between positions 771 and 772 of SEQ ID NO: 1; (w) an insertion of the amino acid G between positions N771 and P772 of SEQ ID NO: 1; (x) an insertion of the amino acid sequence GNP between positions P772 and H773 of SEQ ID NO: 1; (y) an insertion of the amino acid sequence GSV between positions V769 and D770 of SEQ ID NO: 1; (z) a substitution of the amino acid sequence GNPHVC for the VC between positions 774 and 775 of SEQ ID NO: 1; (aa) an insertion of the amino acid sequence LQEA between positions A763 and Y764 of SEQ ID NO: 1; (bb) an insertion of the amino acid sequence GL between positions D770 and N771 of SEQ ID NO: 1; (cc) an insertion of the amino acid Y between positions D770 and N771 of SEQ ID NO: 1; (dd) an insertion of the amino acid sequence NPY between positions H773 and V774 of SEQ ID NO: 1; (ee) an insertion of the amino acid sequence TH between positions H773 and V774 of SEQ ID NO: 1; (ff) a substitution of the amino acid sequence KGP for the NP between positions 771 and 772 of SEQ ID NO: 1; (gg) a substitution of the amino acid sequence SVDNP for the NP between positions 771 and 772 of SEQ ID NO: 1; (hh) an insertion of the amino acid sequence NN between positions N771 and P772 of SEQ ID NO: 1; (ii) an insertion of the amino acid T between positions N771 and P772 of SEQ ID NO: 1; and (jj) a substitution of the amino acid sequence STLASV for the SV between positions 768 and 769 of SEQ ID NO: 1.

In some embodiments of the compositions for use in the treatment of cancer of the disclosure, cancer or a tumor or a cell thereof expresses an oncogenic variant of an epidermal growth factor receptor (EGFR) and wherein the oncogenic variant of an EGFR is an allosteric variant of EGFR, the oncogenic variant of an EGFR comprises EGFR-Vii, EGFR-Vvi, EGFR-R222C, EGFR-R252C, EGFR-R252P, EGFR-R256Y, EGFR-T263P, EGFR-Y270C, EGFR-A289T, EGFR-A289V, EGFR-A289D, EGFR-H304Y, EGFR-G331R, EGFR-P596S, EGFR-P596L, EGFR-P596R, EGFR-G598V, EGFR-G598A, EGFR-G614D, EGFR-C620Y, EGFR-C614W, EGFR-C628F, EGFR-C628Y, EGFR-C636Y, EGFR-G645C, EGFR-Δ660, EGFR-Δ768 or any combination thereof.

The disclosure provides a composition of the disclosure for use in the treatment of cancer, wherein the cancer, a tumor or a cell thereof expresses one or more of: (a) a wild type human epidermal growth factor receptor 2 (HER2) receptor or (b) an oncogenic variant of a HER-2 receptor.

In some embodiments of the compositions for use in the treatment of cancer of the disclosure, including those wherein the cancer or a tumor or a cell thereof expresses a wild type HER-2 receptor, the wild type HER2 receptor comprises the amino acid sequence of SEQ ID NO: 2, 3, 4, 5, or 6.

In some embodiments of the compositions for use in the treatment of cancer of the disclosure, including those wherein the cancer or a tumor or a cell thereof expresses an oncogenic variant of a HER-2 receptor, the oncogenic variant of a HER2 receptor is an allosteric variant of the HER2 receptor.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, the oncogenic variant of a HER2 receptor comprises a substitution of a phenylalanine (F) for a serine (S) at position 310 of SEQ ID NO: 2 or 5.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, the oncogenic variant of a HER2 receptor comprises a substitution of a tyrosine (Y) for a serine (S) at position 310 of SEQ ID NO: 2 or 5.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, the oncogenic variant of a HER2 receptor comprises a substitution of a glutamine (Q) for an arginine (R) at position 678 of SEQ ID NO: 2 or 5.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, the oncogenic variant of a HER2 receptor comprises a substitution of a leucine (L) for a valine (V) at position 777 of SEQ ID NO: 2 or 5.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, the oncogenic variant of a HER2 receptor comprises a substitution of a methionine (M) for a valine (V) at position 777 of SEQ ID NO: 2 or 5.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, the oncogenic variant of a HER2 receptor comprises a substitution of an isoleucine (I) for a valine (V) at position 842 of SEQ ID NO: 2 or 5.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, the oncogenic variant of a HER2 receptor comprises a substitution of an alanine (A) for a leucine (L) at position 755 of SEQ ID NO: 2 or 5.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, the oncogenic variant of a HER2 receptor comprises a substitution of a proline (P) for a leucine (L) at position 755 of SEQ ID NO: 2 or 5.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, the oncogenic variant of a HER2 receptor comprises a substitution of a serine (S) for a leucine (L) at position 755 of SEQ ID NO: 2 or 5.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, a nucleotide sequence encoding the oncogenic variant of a HER2 receptor comprises an insertion within a sequence encoding exon 20 or a portion thereof. In some embodiments, the sequence encoding exon 20 or a portion thereof comprises a sequence encoding KEILDEAYVMAGVGSPYVSR (SEQ ID NO: 8). In some embodiments, the sequence encoding exon 20 or a portion thereof comprises a sequence encoding a C-helix, a terminal end of the C-helix or a loop following the C-helix. In some embodiments, the insertion comprises the amino acid sequence of GSP or YVMA. In some embodiments, the sequence encoding exon 20 or a portion thereof comprises one or more of: (a) an insertion of the amino acid sequence YVMA between positions A775 and G776 of SEQ ID NO: 2; (b) an insertion of the amino acid sequence GSP between positions P780 and Y781 of SEQ ID NO: 2; (c) an insertion of the amino acid sequence YVMA between positions A771 and Y772 of SEQ ID NO: 2; (d) an insertion of the amino acid sequence YVMA between positions A775 and G776 of SEQ ID NO: 2; (e) an insertion of the amino acid V between positions V777 and G778 of SEQ ID NO: 2; (f) an insertion of the amino acid V between positions V777 and G778 of SEQ ID NO: 2; (g) a substitution of the amino acid sequence AVGCV for the GV between positions 776 and 777 of SEQ ID NO: 2; (h) a substitution of the amino acid sequence LC for the G between position 776 of SEQ ID NO: 2; (i) a substitution of the amino acid sequence LCV for the G between position 776 of SEQ ID NO: 2; (j) an insertion of the amino acid sequence GSP between positions V777 and G778 of SEQ ID NO: 2; (k) a substitution of the amino acid sequence PS for the LRE between positions 755 and 757 of SEQ ID NO: 2; (l) a substitution of the amino acid sequence CPGSP for the SP between positions 779 and 780 of SEQ ID NO: 2; (m) an insertion of the amino acid C between positions V777 and G778 of SEQ ID NO: 2; (n) a substitution of the amino acid sequence VVMA for the AG between positions 775 and 776 of SEQ ID NO: 2; (o) a substitution of the amino acid sequence VV for the G at position 776 of SEQ ID NO: 2; (p) a substitution of the amino acid sequence AVCV for the GV between positions 776 and 777 of SEQ ID NO: 2; (q) a substitution of the amino acid sequence VCV for the GV between positions 776 and 777 of SEQ ID NO: 2; (r) an insertion of the amino acid G between positions G778 and S779 of SEQ ID NO: 2; (s) a substitution of the amino acid sequence PK for the LRE between positions 755 and 757 of SEQ ID NO: 2; (t) an insertion of the amino acid V between positions A775 and G776 of SEQ ID NO: 2; (u) an insertion of the amino acid sequence YAMA between positions A775 and G776 of SEQ ID NO: 2; (v) a substitution of the amino acid sequence CV for the G at position 776 of SEQ ID NO: 2; (w) a substitution of the amino acid sequence AVCGG for the GVG between positions 776 and 778 of SEQ ID NO: 2; (x) a substitution of the amino acid sequence CVCG for the GVG between positions 776 and 778 of SEQ ID NO: 2; (y) a substitution of the amino acid sequence VVVG for the GVG between positions 776 and 778 of SEQ ID NO: 2; (z) a substitution of the amino acid sequence SVGG for the GVGS between positions 776 and 779 of SEQ ID NO: 2; (aa) a substitution of the amino acid sequence VVGES for the GVGS between positions 776 and 779 of SEQ ID NO: 2; (bb) a substitution of the amino acid sequence AVGSGV for the GV between positions 776 and 777 of SEQ ID NO: 2; (cc) a substitution of the amino acid sequence CVC for the GV between positions 776 and 777 of SEQ ID NO: 2; (dd) a substitution of the amino acid sequence HVC for the GV between positions 776 and 777 of SEQ ID NO: 2; (ee) a substitution of the amino acid sequence VAAGV for the GV between positions 776 and 777 of SEQ ID NO: 2; (ff) a substitution of the amino acid sequence VAGV for the GV between positions 776 and 777 of SEQ ID NO: 2; (gg) a substitution of the amino acid sequence VVV for the GV between positions 776 and 777 of SEQ ID NO: 2; (hh) an insertion of the amino acid sequence FPG between positions G778 and S779 of SEQ ID NO: 2; (ii) an insertion of the amino acid sequence GS between positions S779 and P780 of SEQ ID NO: 2; (jj) a substitution of the amino acid sequence VPS for the VLRE between positions 754 and 757 of SEQ ID NO: 2; (kk) an insertion of the amino acid E between positions V777 and G778 of SEQ ID NO: 2; (ll) an insertion of the amino acid sequence MAGV between positions V777 and G778 of SEQ ID NO: 2; (mm) an insertion of the amino acid S between positions V777 and G778 of SEQ ID NO: 2; (nn) an insertion of the amino acid sequence SCV between positions V777 and G778 of SEQ ID NO: 2; and (oo) an insertion of the amino acid sequence LMAY between positions Y772 and V773 of SEQ ID NO: 2.

In some embodiments of the compositions for use in the treatment of cancer of the disclosure, including those wherein the cancer or a tumor or a cell thereof expresses an oncogenic variant of a HER-2 receptor and wherein the oncogenic variant of the HER-2 receptor is an allosteric variant of the HER-2 receptor, the oncogenic variant of a HER2 receptor comprises HER2-Δ16, HER2-C311R, HER2-S310F, p95-HER2-M611 or any combination thereof.

The disclosure provides a use of the composition of the disclosure for treating cancer, comprising administering to a subject a therapeutically-effective amount of the composition, wherein the cancer, a tumor or a cell thereof expresses an oncogenic variant of an epidermal growth factor receptor (EGFR).

In some embodiments of the uses of the compositions of the disclosure for the treatment of cancer, including those wherein the cancer or a tumor or a cell thereof expresses an oncogenic variant of an EGFR, the oncogenic variant of EGFR is an allosteric variant of EGFR.

In some embodiments of the uses of the compositions of the disclosure for the treatment of cancer, including those wherein the cancer or a tumor or a cell thereof expresses an oncogenic variant of an EGFR and wherein the oncogenic variant of EGFR is an allosteric variant of EGFR, the oncogenic variant of an EGFR comprises an EGFR variant III (EGFR-Viii) mutation.

In some embodiments of the uses of the compositions of the disclosure for the treatment of cancer, including those wherein the cancer or a tumor or a cell thereof expresses an oncogenic variant of an EGFR and wherein the oncogenic variant of EGFR is an allosteric variant of EGFR, the oncogenic variant of an EGFR comprises a substitution of a valine (V) for an alanine (A) at position 289 of SEQ ID NO: 1.

In some embodiments of the uses of the compositions of the disclosure for the treatment of cancer, including those wherein the cancer or a tumor or a cell thereof expresses an oncogenic variant of an EGFR and wherein the oncogenic variant of EGFR is an allosteric variant of EGFR, the oncogenic variant of an EGFR comprises a modification of a structure of the EGFR, wherein the oncogenic variant of an EGFR is a capable of forming a covalently linked dimer, wherein the covalently linked dimer is constitutively active and wherein the covalently linked dimer enhances an activity of EGFR when contacted to a Type I ErbB inhibitor. In some embodiments, the modification of the structure of the EGFR comprises a modification of one or more of a nucleic acid sequence, an amino acid sequence, a secondary structure, a tertiary structure, and a quaternary structure. In some embodiments, the oncogenic variant comprises a mutation, a splicing event, a post-translational process, a conformational change or any combination thereof. In some embodiments, the modification of the structure of the EGFR occurs within a first cysteine rich (CR1) and/or second cysteine rich (CR2) region of EGFR. In some embodiments, the first cysteine rich (CR1) and/or second cysteine rich (CR2) region of EGFR comprises amino acid residues T211-R334 and/or C526-S645 of SEQ ID NO: 1, respectively. In some embodiments, the oncogenic variant of an EGFR generates a physical barrier to formation of a disulfide bond within the CR1 and/or the CR2 region. In some embodiments, the oncogenic variant of an EGFR removes a physical barrier to formation of a disulfide bond within the CR1 and/or the CR2 region. In some embodiments, the oncogenic variant of an EGFR comprises one or more free or unpaired Cysteine (C) residues located at a dimer interface of the EGFR. In some embodiments, the oncogenic variant of an EGFR comprises one or more free or unpaired Cysteine (C) residues at a site selected from the group consisting of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1. In some embodiments, the modification occurs within 10 angstroms or less of an intramolecular disulfide bond at a site selected from the group consisting of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1.

In some embodiments of the uses of the compositions of the disclosure for the treatment of cancer, including those wherein the cancer or a tumor or a cell thereof expresses an oncogenic variant of EGFR and the oncogenic variant of EGFR is a mutation of EGFR, a nucleotide sequence encoding the oncogenic variant of an EGFR comprises a deletion or the substitution comprises one or more amino acids that encode an adenosine triphosphate (ATP) binding site. In some embodiments, the ATP binding site comprises amino acids E746 to A750 of SEQ ID NO: 1. In some embodiments, the ATP binding site or the deletion or substitution thereof comprises K858 of SEQ ID NO: 1. In some embodiments, the deletion comprises K858 of SEQ ID NO: 1. In some embodiments, an arginine (R) is substituted for the lysine (K) at position 858 (K858R) of SEQ ID NO: 1. In some embodiments, an arginine (R) is substituted for the leucine (L) at position 858 (L858R) of SEQ ID NO: 1.

In some embodiments of the uses of the compositions of the disclosure for the treatment of cancer, including those wherein the cancer or a tumor or a cell thereof expresses an oncogenic variant of an EGFR and wherein the oncogenic variant of EGFR is an allosteric variant of EGFR, a nucleotide sequence encoding the oncogenic variant of an EGFR comprises an insertion within a sequence encoding exon 20 or a portion thereof. In some embodiments, the sequence encoding exon 20 or a portion thereof comprises a sequence encoding KEILDEAYVMASVDNPHVCAR (SEQ ID NO: 7). In some embodiments, the sequence encoding exon 20 or a portion thereof comprises a sequence encoding a C-helix, a terminal end of the C-helix or a loop following the C-helix. In some embodiments, the insertion comprises the amino acid sequence of ASV, SVD, NPH, or FQEA. In some embodiments, the sequence encoding exon 20 or a portion thereof comprises one or more of: (a) an insertion of the amino acid sequence ASV between positions V769 and D770 of SEQ ID NO: 1; (b) an insertion of the amino acid sequence SVD between positions D770 and N771 of SEQ ID NO: 1; (c) an insertion of the amino acid sequence NPH between positions H773 and V774 of SEQ ID NO: 1; (d) an insertion of the amino acid sequence FQEA between positions A763 and Y764 of SEQ ID NO: 1; (e) an insertion of the amino acid sequence PH between positions H773 and V774 of SEQ ID NO: 1; (f) an insertion of the amino acid G between positions D770 and N771 of SEQ ID NO: 1; (g) an insertion of the amino acid H between positions H773 and V774 of SEQ ID NO: 1; (h) an insertion of the amino acid sequence HV between positions V774 and C775 of SEQ ID NO: 1; (i) an insertion of the amino acid sequence AH between positions H773 and V774 of SEQ ID NO: 1; (j) an insertion of the amino acid sequence SVA between positions A767 and S768 of SEQ ID NO: 1; (k) a substitution of the amino acid sequence GYN for the DN between positions 770 and 771 of SEQ ID NO: 1; (l) an insertion of the amino acid H between positions N771 and P772 of SEQ ID NO: 1; (m) an insertion of the amino acid Y between positions H773 and V774 of SEQ ID NO: 1; (n) an insertion of the amino acid sequence PHVC between positions C775 and R776 of SEQ ID NO: 1; (o) a substitution of the amino acid sequence YNPY for the H at position 773 of SEQ ID NO: 1; (p) an insertion of the amino acid sequence DNP between positions P772 and H773 of SEQ ID NO: 1; (q) an insertion of the amino acid sequence VDS between positions S768 and V769 of SEQ ID NO: 1; (r) an insertion of the amino acid H between positions D770 and N771 of SEQ ID NO: 1; (s) an insertion of the amino acid N between positions N771 and P772 of SEQ ID NO: 1; (t) an insertion of the amino acid sequence PNP between positions P772 and H773 of SEQ ID NO: 1; (u) a substitution of the amino acid sequence GSVDN for the DN between positions 770 and 771 of SEQ ID NO: 1; (v) a substitution of the amino acid sequence GYP for the NP between positions 771 and 772 of SEQ ID NO: 1; (w) an insertion of the amino acid G between positions N771 and P772 of SEQ ID NO: 1; (x) an insertion of the amino acid sequence GNP between positions P772 and H773 of SEQ ID NO: 1; (y) an insertion of the amino acid sequence GSV between positions V769 and D770 of SEQ ID NO: 1; (z) a substitution of the amino acid sequence GNPHVC for the VC between positions 774 and 775 of SEQ ID NO: 1; (aa) an insertion of the amino acid sequence LQEA between positions A763 and Y764 of SEQ ID NO: 1;

(bb) an insertion of the amino acid sequence GL between positions D770 and N771 of SEQ ID NO: 1; (cc) an insertion of the amino acid Y between positions D770 and N771 of SEQ ID NO: 1; (dd) an insertion of the amino acid sequence NPY between positions H773 and V774 of SEQ ID NO: 1; (ee) an insertion of the amino acid sequence TH between positions H773 and V774 of SEQ ID NO: 1; (ff) a substitution of the amino acid sequence KGP for the NP between positions 771 and 772 of SEQ ID NO: 1; (gg) a substitution of the amino acid sequence SVDNP for the NP between positions 771 and 772 of SEQ ID NO: 1; (hh) an insertion of the amino acid sequence NN between positions N771 and P772 of SEQ ID NO: 1; (ii) an insertion of the amino acid T between positions N771 and P772 of SEQ ID NO: 1; and (jj) a substitution of the amino acid sequence STLASV for the SV between positions 768 and 769 of SEQ ID NO: 1.

In some embodiments of the uses of the compositions of the disclosure for the treatment of cancer, including those wherein the cancer or a tumor or a cell thereof expresses an oncogenic variant of an EGFR and wherein the oncogenic variant of EGFR is an allosteric variant of EGFR, the oncogenic variant of an EGFR comprises EGFR-Vii, EGFR-Vvi, EGFR-R222C, EGFR-R252C, EGFR-R252P, EGFR-R256Y, EGFR-T263P, EGFR-Y270C, EGFR-A289T, EGFR-A289V, EGFR-A289D, EGFR-H304Y, EGFR-G331R, EGFR-P596S, EGFR-P596L, EGFR-P596R, EGFR-G598V, EGFR-G598A, EGFR-G614D, EGFR-C620Y, EGFR-C614W, EGFR-C628F, EGFR-C628Y, EGFR-C636Y, EGFR-G645C, EGFR-Δ60, EGFR-Δ768 or any combination thereof.

The disclosure provides a use of a composition of the disclosure for treating cancer, comprising administering to a subject a therapeutically-effective amount of the composition, wherein the cancer, a tumor or a cell thereof expresses one or more of: (a) a wild type human epidermal growth factor receptor 2 (HER2) receptor or an oncogenic variant of a HER-2 receptor.

In some embodiments of the uses of the compositions of the disclosure for the treatment of cancer, including those wherein the cancer, a tumor or a cell thereof expresses a wild type HER-2 receptor, the wild type HER2 receptor comprises the amino acid sequence of SEQ ID NO: 2, 4, 5, or 6.

In some embodiments of the uses of the compositions of the disclosure for the treatment of cancer, including those wherein the cancer, a tumor or a cell thereof expresses an oncogenic variant of a HER-2 receptor, the oncogenic variant of a HER2 receptor is an allosteric variant of the HER2 receptor.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, the oncogenic variant of a HER2 receptor comprises a substitution of a phenylalanine (F) for a serine (S) at position 310 of SEQ ID NO: 2 or 5.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, the oncogenic variant of a HER2 receptor comprises a substitution of a tyrosine (Y) for a serine (S) at position 310 of SEQ ID NO: 2 or 5.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, the oncogenic variant of a HER2 receptor comprises a substitution of a glutamine (Q) for an arginine (R) at position 678 of SEQ ID NO: 2 or 5.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, the oncogenic variant of a HER2 receptor comprises a substitution of a leucine (L) for a valine (V) at position 777 of SEQ ID NO: 2 or 5.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, the oncogenic variant of a HER2 receptor comprises a substitution of a methionine (M) for a valine (V) at position 777 of SEQ ID NO: 2 or 5.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, the oncogenic variant of a HER2 receptor comprises a substitution of an isoleucine (I) for a valine (V) at position 842 of SEQ ID NO: 2 or 5.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, the oncogenic variant of a HER2 receptor comprises a substitution of an Martine (A) for a leucine (L) at position 755 of SEQ ID NO: 2 or 5.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, the oncogenic variant of a receptor comprises a substitution of a proline (P) for a leucine (L) at position 755 of SEQ ID NO: 2 or 5.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, the oncogenic variant of a receptor comprises a substitution of a serine (S) for a leucine (L) at position 755 of SEQ ID NO: 2 or 5.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, a nucleotide sequence encoding the oncogenic variant of a HER2 receptor comprises an insertion within a sequence encoding exon 20 or a portion thereof. In some embodiments, the sequence encoding exon 20 or a portion thereof comprises a sequence encoding KEILDEAYVMAGVGSPYVSR (SEQ ID NO: 8). In some embodiments, the sequence encoding exon 20 or a portion thereof comprises a sequence encoding a C-helix, a terminal end of the C-helix or a loop following the C-helix. In some embodiments, the insertion comprises the amino acid sequence of GSP or YVMA. In some embodiments, the sequence encoding exon 20 or a portion thereof comprises one or more of: (a) an insertion of the amino acid sequence YVMA between positions A775 and G776 of SEQ ID NO: 2; (b) an insertion of the amino acid sequence GSP between positions P780 and Y781 of SEQ ID NO: 2; (c) an insertion of the amino acid sequence YVMA between positions A771 and Y772 of SEQ ID NO: 2; (d) an insertion of the amino acid sequence YVMA between positions A775 and G776 of SEQ ID NO: 2; (e) an insertion of the amino acid V between positions V777 and G778 of SEQ ID NO: 2; (f) an insertion of the amino acid V between positions V777 and G778 of SEQ ID NO: 2; (g) a substitution of the amino acid sequence AVGCV for the GV between positions 776 and 777 of SEQ ID NO: 2; (h) a substitution of the amino acid sequence LC for the G between position 776 of SEQ ID NO: 2; (i) a substitution of the amino acid sequence LCV for the G between position 776 of SEQ ID NO: 2; (j) an insertion of the amino acid sequence GSP between positions V777 and G778 of SEQ ID NO: 2; (k) a substitution of the amino acid sequence PS for the LRE between positions 755 and 757 of SEQ ID NO: 2; (l) a substitution of the amino acid sequence CPGSP for the SP between positions 779 and 780 of SEQ ID NO: 2; (m) an insertion of the amino acid C between positions V777 and G778 of SEQ ID NO: 2; (n) a substitution of the amino acid sequence VVMA for the AG between positions 775 and 776 of SEQ ID NO: 2; (o) a substitution of the amino acid sequence VV for the G at position 776 of SEQ ID NO: 2; (p) a substitution of the amino acid sequence AVCV for the GV between positions 776 and 777 of SEQ ID NO: 2; (q) a substitution of the amino acid sequence VCV for the GV between positions 776 and 777 of SEQ ID NO: 2; (r) an insertion of the amino acid G between positions G778 and S779 of SEQ ID NO: 2; (s) a substitution of the amino acid sequence PK for the LRE between positions 755 and 757 of SEQ ID NO: 2; (t) an insertion of the amino acid V between positions A775 and G776 of SEQ ID NO: 2; (u) an insertion of the amino acid sequence YAMA between positions A775 and G776 of SEQ ID NO: 2; (v) a substitution of the amino acid sequence CV for the G at position 776 of SEQ ID NO: 2; (w) a substitution of the amino acid sequence AVCGG for the GVG between positions 776 and 778 of SEQ ID NO: 2; (x) a substitution of the amino acid sequence CVCG for the GVG between positions 776 and 778 of SEQ ID NO: 2; (y) a substitution of the amino acid sequence VVVG for the GVG between positions 776 and 778 of SEQ ID NO: 2; (z) a substitution of the amino acid sequence SVGG for the GVGS between positions 776 and 779 of SEQ ID NO: 2; (aa) a substitution of the amino acid sequence VVGES for the GVGS between positions 776 and 779 of SEQ ID NO: 2; (bb) a substitution of the amino acid sequence AVGSGV for the GV between positions 776 and 777 of SEQ ID NO: 2; (cc) a substitution of the amino acid sequence CVC for the GV between positions 776 and 777 of SEQ ID NO: 2; (dd) a substitution of the amino acid sequence HVC for the GV between positions 776 and 777 of SEQ ID NO: 2; (ee) a substitution of the amino acid sequence VAAGV for the GV between positions 776 and 777 of SEQ ID NO: 2; (ff) a substitution of the amino acid sequence VAGV for the GV between positions 776 and 777 of SEQ ID NO: 2; (gg) a substitution of the amino acid sequence VVV for the GV between positions 776 and 777 of SEQ ID NO: 2; (hh) an insertion of the amino acid sequence FPG between positions G778 and S779 of SEQ ID NO: 2; (ii) an insertion of the amino acid sequence GS between positions S779 and P780 of SEQ ID NO: 2; (jj) a substitution of the amino acid sequence VPS for the VLRE between positions 754 and 757 of SEQ ID NO: 2; (kk) an insertion of the amino acid E between positions V777 and G778 of SEQ ID NO: 2; (ll) an insertion of the amino acid sequence MAGV between positions V777 and G778 of SEQ ID NO: 2; (mm) an insertion of the amino acid S between positions V777 and G778 of SEQ ID NO: 2; (nn) an insertion of the amino acid sequence SCV between positions V777 and G778 of SEQ ID NO: 2; and (oo) an insertion of the amino acid sequence LMAY between positions Y772 and V773 of SEQ ID NO: 2.

In some embodiments of the uses of the compositions of the disclosure for the treatment of cancer, including those wherein the cancer, a tumor or a cell thereof expresses an oncogenic variant of a HER-2 receptor and wherein the oncogenic variant of a HER2 receptor is an allosteric variant of the HER2 receptor, the oncogenic variant of a HER2 receptor comprises HER2-Δ16, HER2-C311R, HER2-S310F, p95-HER2-M611 or any combination thereof.

The disclosure provides a use of a composition of the disclosure the treatment of cancer, including those wherein the cancer, a tumor or a cell thereof expresses an oncogenic variant of a HER-4 receptor. In some embodiments, the oncogenic variant of the HER-4 receptor is an allosteric variant of the HER4 receptor. In some embodiments, the oncogenic variant of a HER4 receptor comprises deletion of exon 16 (HER4-Δ16).

In some embodiments of the uses of the compositions of the disclosure for the treatment of cancer, the composition is suitable for systemic administration. In some embodiments, the composition is suitable for oral administration. In some embodiments, the composition is suitable for intravenous administration In some embodiments of the uses of the compositions of the disclosure for the treatment of cancer, the composition is suitable for local administration. In some embodiments, the composition is suitable for intratumoral, intraocular, intraosseus, intraspinal or intracerebroventricular administration.

In some embodiments of the uses of the compositions of the disclosure for the treatment of cancer, the subject or the cancer is insensitive or resistant to treatment with one or more of gefinitinib, erlotinib, afatinib, osimertinib, and necitunumab. In some embodiments, the subject or the cancer is insensitive or resistant to treatment with one or more of crixotinib, alectinib, and ceritinib. In some embodiments, the subject or the cancer is insensitive or resistant to treatment with one or more of dabrafenib and trametinib. In some embodiments, the subject or the cancer is insensitive or resistant to treatment with crizotinib.

In some embodiments of the uses of the compositions of the disclosure for the treatment of cancer, the cancer, tumor or cell thereof expresses an oncogenic variant of an EGFR, wherein the sequence encoding the oncogenic variant of the EGFR comprises a deletion of exon 20 or a portion thereof and wherein the cancer, tumor or cell thereof does not comprise an oncogenic variation in a sequence encoding one or more of an EGFR kinase domain (KD), BRAF, NTRK, and KRAS or wherein.

In some embodiments of the uses of the compositions of the disclosure for the treatment of cancer, the cancer, tumor or cell thereof comprises an oncogenic variant of an EGFR, wherein the sequence encoding the oncogenic variant of the EGFR comprises a deletion of exon 20 or a portion thereof and wherein the cancer, tumor or cell thereof does not comprise a marker indicating responsiveness to immunotherapy.

In some embodiments, the oncogenic variant (e.g., allosteric variant) or the oncogenic mutation (e.g., allosteric mutation) is deflected by a Food and Drug Administration (FDA)-approved diagnosis.

In some embodiments, the subject has an adverse reaction to treatment with a therapeutic agent different from the compound of the present disclosure. In some embodiments, the subject has an adverse reaction to treatment with a Type I inhibitor. In some embodiments, the subject has an adverse reaction to treatment with one or more of gefinitinib, erlotinib, afatinib, osimertinib, necitunumab, crizotinib, alectinib, ceritinib, dabrafenib, trametinib, afatinib, sapitinib, dacomitinib, canertinib, pelitinib, WZ4002, WZ8040, WZ3146, CO-1686 and AZD9291. In some embodiments, the adverse reaction is an activation of the oncogenic variant of an EGFR and wherein the oncogenic variant comprises a mutation in an extracellular domain of the receptor. In some embodiments, the adverse reaction is an activation of the oncogenic variant of a HER-2 Receptor and wherein the oncogenic variant comprises a mutation in an extracellular domain of the receptor.

In some embodiments, the method comprises administering to the subject in need thereof a therapeutically effective amount of a non-Type I inhibitor. In some embodiments, the non-Type I inhibitor comprises a small molecule Type II inhibitor.

In some embodiments, the method comprises administering to the subject in need thereof a therapeutically effective amount of a non-Type I inhibitor. In some embodiments, the non-Type I inhibitor comprises a small molecule Type II inhibitor.

In some embodiments, the compound is used in combination with a therapeutically effective amount of a non-Type I inhibitor. In some embodiments, the non-Type I inhibitor comprises a small molecule Type II inhibitor.

In some embodiments, the composition comprises a non-Type I inhibitor. In some embodiments, the non-Type I inhibitor comprises a small molecule Type II inhibitor.

In some embodiments of the uses of the compositions of the disclosure for the treatment of cancer, the cancer comprises a solid tumor. In some embodiments, the cancer comprises a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC) or any subtype thereof. In some embodiments, the cancer comprises a glioblastoma (GBM). In some embodiments, the cancer comprises a breast cancer. In some embodiments, the cancer comprises a lung cancer.

In some embodiments of the uses of the compositions of the disclosure for the treatment of cancer, the therapeutically effective amount reduces a severity of a sign or symptom of the cancer. In some embodiments, the sign of the cancer comprises a tumor grade and wherein a reduction of the severity of the sign comprises a decrease of the tumor grade. In some embodiments, the sign of the cancer comprises a tumor metastasis and wherein a reduction of the severity of the sign comprises an elimination of the metastasis or a reduction in the rate or extent the metastasis. In some embodiments, the sign of the cancer comprises a tumor volume and wherein a reduction of the severity of the sign comprises an elimination of the tumor or a reduction in the volume. In some embodiments, the symptom of the cancer comprises pain and wherein a reduction of the severity of the sign comprises an elimination or a reduction in the pain.

In some embodiments of the uses of the compositions of the disclosure for the treatment of cancer, the therapeutically effective amount induces a period of remission.

In some embodiments of the uses of the compositions of the disclosure for the treatment of cancer, the therapeutically effective amount improves a prognosis of the subject.

In some embodiments of the uses of the compositions of the disclosure for the treatment of cancer, the subject is a participant or a candidate for participation in in a clinical trial or protocol thereof. In some embodiments, the subject is excluded from treatment with a Type I inhibitor. In some embodiments, the Type I inhibitor comprises gefinitinib, erlotinib, afatinib, osimertinib, necitunumab, crizotinib, alectinib, ceritinib, dabrafenib, trametinib, afatinib, sapitinib, dacomitinib, canertinib, pelitinib, WZ4002, WZ8040, WZ3146, CO-1686 or AZD9291.

In some embodiments of the uses of the compositions of the disclosure for the treatment of cancer, the use comprises treating the subject with a Non-Type I inhibitor.

In some embodiments of the uses of the compositions of the disclosure for the treatment of cancer, the composition comprises a Non-Type I inhibitor.

In some embodiments of the uses of the compositions of the disclosure for the treatment of cancer, the Non-Type I inhibitor comprises a Type II small molecule inhibitor. In some embodiments, the Type II small molecule inhibitor comprises neratinib, AST-1306, HKI-357, or lapatinib.

In some embodiments, the oncogenic variant is an oncogenic variant in an ErbB receptor.

In some embodiments, the oncogenic variant in the ErbB receptor is an allosteric variant.

In some embodiments, the ErbB receptor is an epidermal growth factor receptor (EGFR) or a human epidermal growth factor receptor 2 (HER2) receptor.

In some embodiments, the ErbB receptor is an epidermal growth factor receptor (EGFR).

In some embodiments, the ErbB receptor is a HER2 receptor.

In some embodiments, the oncogenic variant is an oncogenic variant in an epidermal growth factor receptor (EGFR).

In some embodiments, the oncogenic variant in the EGFR is an allosteric variant.

In some embodiments, the oncogenic variant is an oncogenic variant of a HER2 receptor.

In some embodiments, the oncogenic variant in the HER2 receptor is an allosteric variant.

In some embodiments, the oncogenic variant in the EGFR is an EGFR variant III (EGFR-Viii) variant.

In some embodiments, the oncogenic variant in the EGFR is a substitution of a valine (V) for an alanine (A) at position 289 of SEQ ID NO: 1.

In some embodiments, the oncogenic variant is an oncogenic variant in an EGFR and wherein the oncogenic variant in the EGFR is an allosteric variant in the EGFR, the oncogenic variant in the EGFR is a modification of a structure of the EGFR, wherein the oncogenic variant in the EGFR is capable of forming a covalently linked dimer, wherein the covalently linked dimer is constitutively active and wherein the covalently linked dimer enhances an activity of EGFR when contacted to a Type I ErbB inhibitor. In some embodiments, the modification of the structure of the EGFR comprises a modification of one or more of a nucleic acid sequence, an amino acid sequence, a secondary structure, a tertiary structure, and a quaternary structure. In some embodiments, the modification of the structure of the EGFR occurs within a first cysteine rich (CR1) and/or second cysteine rich (CR2) region of EGFR. In some embodiments, the first cysteine rich (CR1) and/or second cysteine rich (CR2) region of EGFR comprises amino acid residues T211-R334 and/or C526-S645 of SEQ ID NO: 1, respectively. In some embodiments, the oncogenic variant in the EGFR generates a physical barrier to formation of a disulfide bond within the CR1 and/or the CR2 region. In some embodiments, the oncogenic variant in the EGFR removes a physical barrier to formation of a disulfide bond within the CR1 and/or the CR2 region. In some embodiments, the oncogenic variant in the EGFR results into one or more free or unpaired Cysteine (C) residues located at a dimer interface of the EGFR. In some embodiments, the oncogenic variant in the EGFR results into one or more free or unpaired Cysteine (C) residues at a site selected from the group consisting of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1. In some embodiments, the modification occurs within 10 angstroms or less of an intramolecular disulfide bond at a site selected from the group consisting of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1.

In some embodiments, the oncogenic variant is an oncogenic variant in an EGFR and wherein the oncogenic variant in the EGFR is an allosteric variant in the EGFR, wherein a nucleotide sequence encoding the EGFR having the oncogenic variant comprises a deletion or the substitution comprises one or more amino acids that encode an adenosine triphosphate (ATP) binding site. In some embodiments, the ATP binding site comprises amino acids E746 to A750 of SEQ ID NO: 1. In some embodiments, the ATP binding site or the deletion or substitution thereof comprises K858 of SEQ ID NO: 1. In some embodiments, the deletion comprises K858 of SEQ ID NO: 1. In some embodiments, an arginine (R) is substituted for the lysine (K) at position 858 (K858R) of SEQ ID NO: 1. In some embodiments, an arginine (R) is substituted for the leucine (L) at position 858 (L858R) of SEQ ID NO: 1.

In some embodiments, the oncogenic variant is an oncogenic variant in an EGFR and wherein the oncogenic variant in the EGFR is an allosteric variant in the EGFR, wherein a nucleotide sequence encoding the EGFR having the oncogenic variant comprises an insertion within a sequence encoding exon 20 or a portion thereof. In some embodiments, the sequence encoding exon 20 or a portion thereof comprises a sequence encoding KEILDEAYVMASVDN-PEIVCAR (SEQ ID NO: 7). In some embodiments, the sequence encoding exon 20 or a portion thereof comprises a sequence encoding a C-helix, a terminal end of the C-helix or a loop following the C-helix. In some embodiments, the insertion comprises the amino acid sequence of ASV, SVD, NPH, or FQEA. In some embodiments, the sequence encoding exon 20 or a portion thereof comprises one or more of: (a) an insertion of the amino acid sequence ASV between positions V769 and D770 of SEQ ID NO: 1; (b) an insertion of the amino acid sequence SVD between positions D770 and N771 of SEQ ID NO: 1; (c) an insertion of the amino acid sequence NPH between positions H773 and V774 of SEQ ID NO: 1; (d) an insertion of the amino acid sequence FQEA between positions A763 and Y764 of SEQ ID NO: 1; (e) an insertion of the amino acid sequence PH between positions H773 and V774 of SEQ ID NO: 1; (f) an insertion of the amino acid G between positions D770 and N771 of SEQ ID NO: 1; (g) an insertion of the amino acid H between positions H773 and V774 of SEQ ID NO: 1; (h) an insertion of the amino acid sequence HV between positions V774 and C775 of SEQ ID NO: 1; (i) an insertion of the amino acid sequence AH between positions H773 and V774 of SEQ ID NO: 1; (j) an insertion of the amino acid sequence SVA between positions A767 and S768 of SEQ ID NO: 1; (k) a substitution of the amino acid sequence GYN for the DN between positions 770 and 771 of SEQ ID NO: 1; (l) an insertion of the amino acid H between positions N771 and P772 of SEQ ID NO: 1; (m) an insertion of the amino acid Y between positions H773 and V774 of SEQ ID NO: 1; (n) an insertion of the amino acid sequence PHVC between positions C775 and R776 of SEQ ID NO: 1; (o) a substitution of the amino acid sequence YNPY for the H at position 773 of SEQ ID NO: 1; (p) an insertion of the amino acid sequence DNP between positions P772 and H773 of SEQ ID NO: 1; (q) an insertion of the amino acid sequence VDS between positions S768 and V769 of SEQ ID NO: 1; (r) an insertion of the amino acid H between positions D770 and N771 of SEQ ID NO: 1; (s) an insertion of the amino acid N between positions N771 and P772 of SEQ ID NO: 1; (t) an insertion of the amino acid sequence PNP between positions P772 and H773 of SEQ ID NO: 1; (u) a substitution of the amino acid sequence GSVDN for the DN between positions 770 and 771 of SEQ ID NO: 1; (v) a substitution of the amino acid sequence GYP for the NP between positions 771 and 772 of SEQ ID NO: 1; (w) an insertion of the amino acid G between positions N771 and P772 of SEQ ID NO: 1; (x) an insertion of the amino acid sequence GNP between positions P772 and H773 of SEQ ID NO: 1; (y) an insertion of the amino acid sequence GSV between positions V769 and D770 of SEQ ID NO: 1; (z) a substitution of the amino acid sequence GNPHVC for the VC between positions 774 and 775 of SEQ ID NO: 1; (aa) an insertion of the amino acid sequence LQEA between positions A763 and Y764 of SEQ ID NO: 1; (bb) an insertion of the amino acid sequence GL between positions D770 and N771 of SEQ ID NO: 1; (cc) an insertion of the amino acid Y between positions D770 and N771 of SEQ ID NO: 1; (dd) an insertion of the amino acid sequence NPY between positions H773 and V774 of SEQ ID NO: 1; (ee) an insertion of the amino acid sequence TH between positions H773 and V774 of SEQ ID NO: 1; (ff) a substitution of the amino acid sequence KGP for the NP between positions 771 and 772 of SEQ ID NO: 1; (gg) a substitution of the amino acid sequence SVDNP for the NP between positions 771 and 772 of SEQ ID NO: 1; (hh) an insertion of the amino acid sequence NN between positions N771 and P772 of SEQ ID NO: 1; (ii) an insertion of the amino acid T between positions N771 and P772 of SEQ ID NO: 1; and (jj) a substitution of the amino acid sequence STLASV for the SV between positions 768 and 769 of SEQ ID NO: 1.

In some embodiments, the oncogenic variant is an oncogenic variant in an EGFR and wherein the oncogenic variant in the EGFR is an allosteric variant in the EGFR, the EGFR having the oncogenic variant comprises EGFR-Vii, EGFR-Vvi, EGFR-R222C, EGFR-R252C, EGFR-R252P, EGFR-R256Y, EGFR-T263P, EGFR-Y270C, EGFR-A289T, EGFR-A289V, EGFR-A289D, EGFR-H304Y, EGFR-G331R, EGFR-P596S, EGFR-P596L, EGFR-P596R, EGFR-G598V, EGFR-G598A, EGFR-G614D, EGFR- C620Y, EGFR-C614W, EGFR-C628F, EGFR-C628Y, EGFR-C636Y, EGFR-G645C, EGFR-A660, EGFR-A768 or any combination thereof.

In some embodiments, the oncogenic variant is an oncogenic variant in a HER-2 receptor.

In some embodiments, the oncogenic variant is an oncogenic variant in a HER-2 receptor, the oncogenic variant in the HER2 receptor is an allosteric variant in the HER2 receptor.

In some embodiments, the oncogenic variant is an oncogenic variant in a HER-2 receptor and wherein the oncogenic variant in the HER2 receptor is an allosteric variant in the HER2 receptor, the oncogenic mutatin in the HER2 receptor comprises a substitution of a phenylalanine (F) for a serine (S) at position 310 of SEQ ID NO: 2 or 5.

In some embodiments, the oncogenic variant is an oncogenic variant in a HER-2 receptor and wherein the oncogenic variant in the HER2 receptor is an allosteric variant in the HER2 receptor, the oncogenic mutatin in the HER2 receptor comprises a substitution of a tyrosine (Y) for a serine (S) at position 310 of SEQ ID NO: 2 or 5.

In some embodiments, the oncogenic variant is an oncogenic variant in a HER-2 receptor and wherein the oncogenic variant in the HER2 receptor is an allosteric variant in the HER2 receptor, the oncogenic mutatin in the HER2 receptor comprises a substitution of a glutamine (Q) for an arginine (R) at position 678 of SEQ ID NO: 2 or 5.

In some embodiments, the oncogenic variant is an oncogenic variant in a HER-2 receptor and wherein the oncogenic variant in the HER2 receptor is an allosteric variant in the HER2 receptor, the oncogenic mutatin in the HER2 receptor comprises a substitution of a leucine (L) for a valine (V) at position 777 of SEQ ID NO: 2 or 5.

In some embodiments, the oncogenic variant is an oncogenic variant in a HER-2 receptor and wherein the oncogenic variant in the HER2 receptor is an allosteric variant in the HER2 receptor, the oncogenic mutatin in the HER2 receptor comprises a substitution of a methionine (M) for a valine (V) at position 777 of SEQ ID NO: 2 or 5.

In some embodiments, the oncogenic variant is an oncogenic variant in a HER-2 receptor and wherein the oncogenic variant in the HER2 receptor is an allosteric variant in the HER2 receptor, the oncogenic mutatin in the HER2 receptor comprises a substitution of an isoleucine (I) for a valine (V) at position 842 of SEQ ID NO: 2 or 5.

In some embodiments, the oncogenic variant is an oncogenic variant in a HER-2 receptor and wherein the oncogenic variant in the HER2 receptor is an allosteric variant in the HER2 receptor, the oncogenic mutatin in the HER2 receptor comprises a substitution of an alanine (A) for a leucine (L) at position 755 of SEQ ID NO: 2 or 5.

In some embodiments, the oncogenic variant is an oncogenic variant in a HER-2 receptor and wherein the oncogenic variant in the HER2 receptor is an allosteric variant in the HER2 receptor, the oncogenic mutatin in the HER2 receptor comprises a substitution of a proline (P) for a leucine (L) at position 755 of SEQ ID NO: 2 or 5.

In some embodiments, the oncogenic variant is an oncogenic variant in a HER-2 receptor and wherein the oncogenic variant in the HER2 receptor is an allosteric variant in the HER2 receptor, the oncogenic mutatin in the HER2 receptor comprises a substitution of a serine (S) for a leucine (L) at position 755 of SEQ ID NO: 2 or 5.

In some embodiments, the oncogenic variant is an oncogenic variant in a HER-2 receptor and wherein the oncogenic variant in the HER2 receptor is an allosteric variant in the HER2 receptor, wherein a nucleotide sequence encoding the HER2 receptor having the oncogenic variant comprises an insertion within a sequence encoding exon 20 or a portion thereof. In some embodiments, the sequence encoding exon 20 or a portion thereof comprises a sequence encoding KEILDEAYVMAGVGSPYVSR (SEQ ID NO: 8). In some embodiments, the sequence encoding exon 20 or a portion thereof comprises a sequence encoding a C-helix, a terminal end of the C-helix or a loop following the C-helix. In some embodiments, the insertion comprises the amino acid sequence of GSP or YVMA. In some embodiments, the sequence encoding exon 20 or a portion thereof comprises one or more of: (a) an insertion of the amino acid sequence YVMA between positions A775 and G776 of SEQ ID NO: 2; (b) an insertion of the amino acid sequence GSP between positions P780 and Y781 of SEQ ID NO: 2; (c) an insertion of the amino acid sequence YVMA between positions A771 and Y772 of SEQ ID NO: 2; (d) an insertion of the amino acid sequence YVMA between positions A775 and G776 of SEQ ID NO: 2; (e) an insertion of the amino acid V between positions V777 and G778 of SEQ ID NO: 2; (f) an insertion of the amino acid V between positions V777 and G778 of SEQ ID NO: 2; (g) a substitution of the amino acid sequence AVGCV for the GV between positions 776 and 777 of SEQ ID NO: 2; (h) a substitution of the amino acid sequence LC for the G between position 776 of SEQ ID NO: 2; (i) a substitution of the amino acid sequence LCV for the G between position 776 of SEQ ID NO: 2; (j) an insertion of the amino acid sequence GSP between positions V777 and G778 of SEQ ID NO: 2; (k) a substitution of the amino acid sequence PS for the LRE between positions 755 and 757 of SEQ ID NO: 2; (l) a substitution of the amino acid sequence CPGSP for the SP between positions 779 and 780 of SEQ ID NO: 2; (m) an insertion of the amino acid C between positions V777 and G778 of SEQ ID NO: 2; (n) a substitution of the amino acid sequence VVMA for the AG between positions 775 and 776 of SEQ ID NO: 2; (o) a substitution of the amino acid sequence VV for the G at position 776 of SEQ ID NO: 2; (p) a substitution of the amino acid sequence AVCV for the GV between positions 776 and 777 of SEQ ID NO: 2; (q) a substitution of the amino acid sequence VCV for the GV between positions 776 and 777 of SEQ ID NO: 2; (r) an insertion of the amino acid G between positions G778 and S779 of SEQ ID NO: 2; (s) a substitution of the amino acid sequence PK for the LRE between positions 755 and 757 of SEQ ID NO: 2; (t) an insertion of the amino acid V between positions A775 and G776 of SEQ ID NO: 2; (u) an insertion of the amino acid sequence YAMA between positions A775 and G776 of SEQ ID NO: 2; (v) a substitution of the amino acid sequence CV for the G at position 776 of SEQ ID NO: 2; (w) a substitution of the amino acid sequence AVCGG for the GVG between positions 776 and 778 of SEQ ID NO: 2; (x) a substitution of the amino acid sequence CVCG for the GVG between positions 776 and 778 of SEQ ID NO: 2; (y) a substitution of the amino acid sequence VVVG for the GVG between positions 776 and 778 of SEQ ID NO: 2; (z) a substitution of the amino acid sequence SVGG for the GVGS between positions 776 and 779 of SEQ ID NO: 2; (aa) a substitution of the amino acid sequence VVGES for the GVGS between positions 776 and 779 of SEQ ID NO: 2; (bb) a substitution of the amino acid sequence AVGSGV for the GV between positions 776 and 777 of SEQ ID NO: 2; (cc) a substitution of the amino acid sequence CVC for the GV between positions 776 and 777 of SEQ ID NO: 2; (dd) a substitution of the amino acid sequence HVC for the GV between positions 776 and 777 of SEQ ID NO: 2; (ee) a substitution of the amino acid sequence VAAGV for the GV between positions 776 and 777 of SEQ ID NO: 2; (ff) a substitution of the amino acid sequence VAGV for the GV between positions 776 and 777 of SEQ ID NO: 2; (gg) a substitution of the amino acid sequence VVV for the GV between positions 776 and 777 of SEQ ID NO: 2; (hh) an insertion of the amino acid sequence FPG between positions G778 and S779 of SEQ ID NO: 2; (ii) an insertion of the amino acid sequence GS between positions S779 and P780 of SEQ ID NO: 2; (jj) a substitution of the amino acid sequence VPS for the VLRE between positions 754 and 757 of SEQ ID NO: 2; (kk) an insertion of the amino acid E between positions V777 and G778 of SEQ ID NO: 2; (ll) an insertion of the amino acid sequence MAGV between positions V777 and G778 of SEQ ID NO: 2; (mm) an insertion of the amino acid S between positions V777 and G778 of SEQ ID NO: 2; (nn) an insertion of the amino acid sequence SCV between positions V777 and G778 of SEQ ID NO: 2; and (oo) an insertion of the amino acid sequence LMAY between positions Y772 and V773 of SEQ ID NO: 2.

In some embodiments, the oncogenic variant is an oncogenic variant in a HER-2 receptor and wherein the oncogenic variant in the HER2 receptor is an allosteric variant in the HER2 receptor, the HER2 receptor having the oncogenic variant comprises HER2-Δ16, HER2-C311R, HER2-S310F, p95-HER2-M611 or any combination thereof.

In some embodiments, the oncogenic variant is an oncogenic variant in a HER-4 receptor. In some embodiments, the oncogenic variant in the HER-4 receptor is an allosteric variant in the HER4 receptor. In some embodiments, the oncogenic variant in the HER4 receptor results into the deletion of exon 16 (HER4-Δ16).

In some embodiments, the oncogenic variant is an oncogenic variant in an EGFR, wherein the sequence encoding the EGFR having the oncogenic variant comprises a deletion of exon 20 or a portion thereof and wherein the cancer, the tumor or the cell thereof does not comprise a second oncogenic variant in a sequence other than exon 20 of EGFR. In some embodiments, the second oncogenic variation comprises a sequence encoding one or more of an EGFR kinase domain (KD), BRAF, NTRK, and KRAS.

In some embodiments, the oncogenic variant is an oncogenic variant in an EGFR, wherein the sequence encoding the EGFR having the oncogenic variant comprises a deletion of exon 20 or a portion thereof and wherein the cancer, the tumor or the cell thereof does not comprise a marker indicating responsiveness to immunotherapy.

EXAMPLES

Example 1. Synthesis of Exemplary Compounds of the Present Disclosure

General Procedure A:

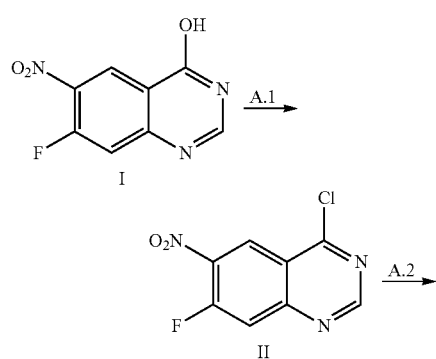

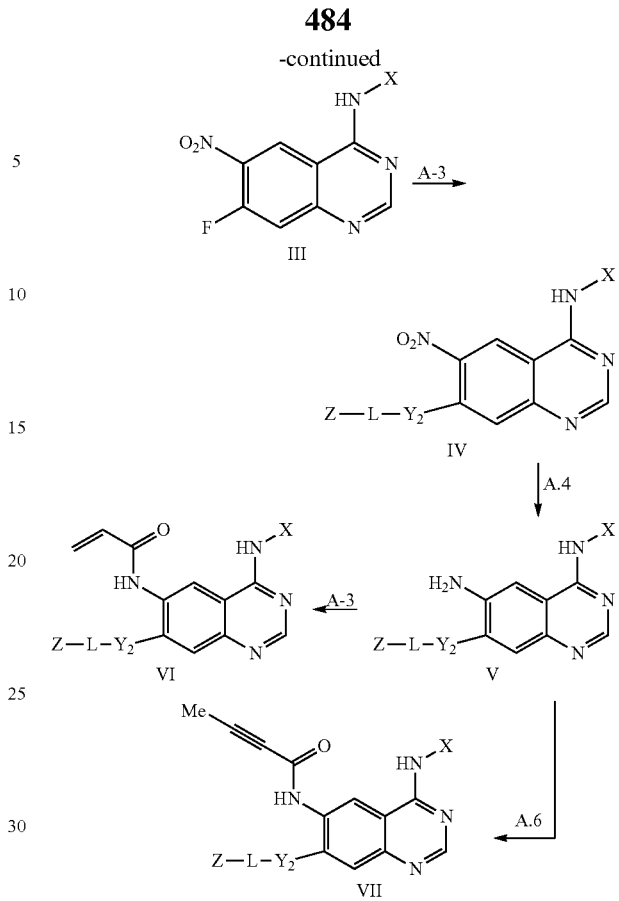

Step A.1:
A solution of 7-fluoro-6-nitro-quinazolin-4-ol (5.00 g, 23.9 mmol, 1.00 eq) in thionyl chloride (20.0 mL) was added dimethyl formamide (174 mg, 2.39 mmol, 183 uL, 0.10 eq). The reaction was stirred at 80° C. for 10 h. The reaction mixture was concentrated under reduced pressure to give 4-chloro-7-fluoro-6-nitroquinazoline (6.00 g, crude) as an off-white solid. The product was taken to next step without purification.

Step A.2:
A mixture of 4-chloro-7-fluoro-6-nitroquinazoline (2.4 g, 10.55 mmol, 1 eq) and the free amine $H_2N$-X (1 eq) in isopropyl alcohol was heated at 80° C. for 1 h. The reaction mixture was concentrated under reduced pressure to give a residue. The residue was triturated with ethyl acetate to give amine III.

Step A.3:
To a solution of amine III (1 eq) and the NH or OH nucleophile Z-L-$Y^2$—H (1.1 eq) in acetonitrile was added cesium carbonate (2 eq) or DBU (2 eq) and optionally potassium iodide (1 eq). Then the mixture was stirred at 80-110° C. for 12 h. The reaction mixture was quenched by addition of water and then extracted with ethyl acetate. The combined organic layers were washed with brine dried over sodium sulfate, filtered and concentrated under reduced pressure to give a residue. The residue was purified by flash silica gel chromatography to give IV.

Step A.4:
Variant i): A mixture of IV (1 eq) and nickel(ii) chloride hexahydrate (2 eq) in dichloromethane and methanol (1:1) was added sodium borohydride (4 eq) at 0° C. and then the mixture was stirred at 0° C. for 12 h. The reaction mixture was filtered and the filtrate was concentrated to give a residue. The residue was purified by reversed phase column chromatography to give amine V.

Variant ii): A mixture of IV (1 eq), iron (3 eq) and ammonium chloride (5 eq) in methanol and water (4:1) was stirred at 70° C. for 12 h. The reaction mixture was filtered and the filtrate was concentrated under reduced pressure to give a residue. The residue was purified by Reverse-MPLC to give amine V.

Step A.5:

Variant i): To a solution of V (1 eq), 4-dimethylaminopyridine (1.5 eq) and acrylic acid (1.2 eq) in dimethyl formamide was added 1-(3-dimethylaminopropyl)-3-ethylcarbodiimide (2 eq) and then the solution was stirred at 25° C. for 1 h. The reaction mixture was filtered. The filtrate was purified by prep-HPLC to give acrylamide VI.

Variant ii): To a solution of V (1 eq) and triethylamine (4 eq) in dimethyl formamide was added acrylic anhydride (1.2 eq) and then the solution was stirred at 25° C. for 0.5 h. The reaction mixture was filtered. The filtrate was purified by prep-HPLC to give acrylamide VI.

Variant iii): To a solution of V (1.0 eq) in dimethylformamide was added triethylamine (3.00 eq) and acryloyl chloride (1.20 eq) at 0° C. The reaction mixture was stirred at 0° C. for 1 h and subsequently filtered. The filtrate was purified by prep-HPLC to give acrylamide VI.

Step A.6:

To a solution of V (1.0 eq), 1-(3-dimethylaminopropyl)-3-ethylcarbodiimide hydrochloride (5.00 eq) and pyridine (5.00 eq) in N,N-dimethylformamide was added but-2-ynoic acid (10.0 eq). The mixture was stirred at 50° C. for 2 h and subsequently concentrated in vacuum. The mixture was purified by prep-HPLC to give ynamide VII.

General Procedure B:

Step B.2:

Variant i): To a solution of VIII (1 eq) and triethylamine (4.00 eq) in dichloromethane and dimethylsulfoxide (6:1) was added MsCl (4.00 eq) dropwise at 0° C. The mixture was stirred at 20° C. for 2 h. The mixture was diluted with water and extracted with dichloromethane. The combined organic layer was washed with brine and dried over sodium sulfate, filtered and concentrated to give Mesylate IX.

Variant ii): To a solution of VIII (1.0 eq) in thionyl chloride was added N,N-dimethylformamide (0.1 eq). The mixture was stirred at 90° C. for 3 h. The mixture was cooled to 25° C. and then concentrated in vacuum. The mixture was partitioned between and ethyl acetate. The organic phase was washed with brine, dried with anhydrous sodium sulfate, filtered and concentrated in vacuum. The residue was purified by silica gel chromatography to afford chloride IX.

Step B.3:

To a solution of IX (1.0 eq) and potassium carbonate (4.00 eq) in dimethylsulfoxide was the corresponding N—H nucleophile (2.0 eq) in one portion at 20° C. The mixture was stirred at 50° C. for 12 h. The mixture was diluted with water and extracted with ethyl acetate. The combined organic layer was washed with brine and dried over sodium sulfate, filtered and concentrated to give crude product. The crude product was purified by prep-HPLC to give X.

Step B.4:

Variant i): A mixture of X (1 eq) and nickel(ii) chloride hexahydrate (2 eq) in dichloromethane and methanol (1:1) was added sodium borohydride (4 eq) at 0° C. and then the mixture was stirred at 0° C. for 12 h. The reaction mixture was filtered and the filtrate was concentrated to give a residue. The residue was purified by reversed phase column chromatography to give amine XI.

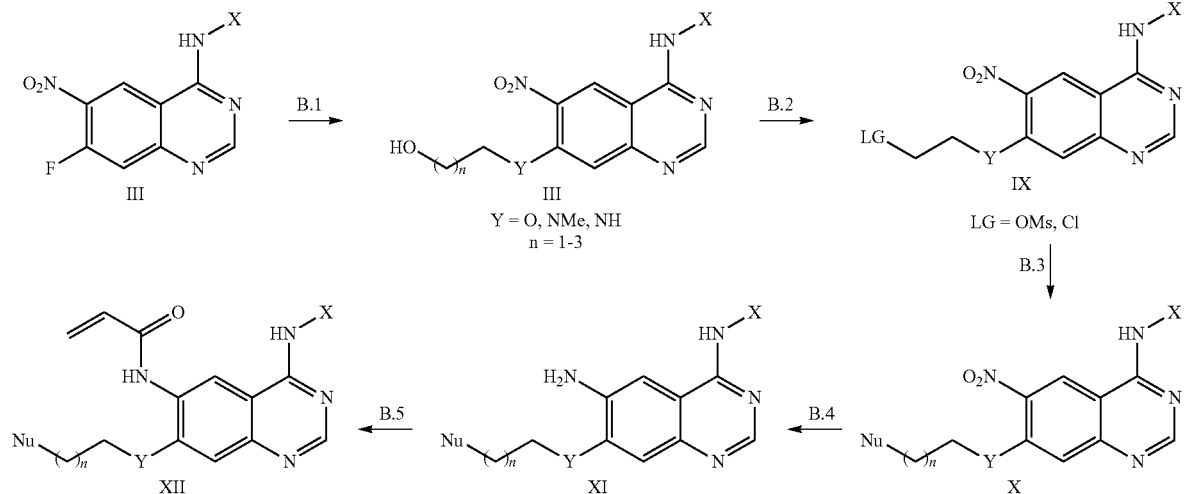

Step B.1:

To a solution of III, obtained in step A.2 (1.00 eq) and potassium tert-butoxide (4.00 eq) in dimethylsulfoxide (10.0 mL) was added the corresponding diol of aminoalcohol (6.00 eq) dropwise at 20° C. The mixture was stirred at 20° C. for 12 h. The mixture was diluted with water and extracted with ethyl acetate. The combined organic layer was washed with brine and dried over sodium sulfate, filtered and concentrated to give crude product. The crude product was purified by silica gel chromatography to give alcohol VIII.

Variant ii): A mixture of X (1 eq), iron (3 eq) and ammonium chloride (5 eq) in methanol and water (4:1) was stirred at 70° C. for 12 h. The reaction mixture was filtered and the filtrate was concentrated under reduced pressure to give a residue. The residue was purified by Reverse-HPLC to give amine XI.

Step B.5:

Variant i): To a solution of XI (1 eq), 4-dimethylaminopyridine (1.5 eq) and acrylic acid (1.2 eq) in dimethyl formamide was added 1-(3-dimethylaminopropyl)-3-ethylcarbodiimide (2 eq) and then the solution was stirred at 25°

C. for 1 h. The reaction mixture was filtered. The filtrate was purified by prep-HIPLC to give acrylamide Variant ii): To a solution of XI (1 eq) and triethylamine (4 eq) in dimethyl formamide was added acrylic anhydride (1.2 eq) and then the solution was stirred at 25° C. for 0.5 h. The reaction mixture was filtered. The filtrate was purified by prep-HPLC to give acrylamide XII.

Variant iii): To a solution of XI (1.0 eq) in dimethylformamide was added triethylamine (3.00 eq) and acryloyl chloride (1.20 eq) at 0° C. The reaction mixture was stirred at 0° C. for 1 h and subsequently filtered. The filtrate was purified by prep-HPLC to give acrylamide XII.

General Procedure C:

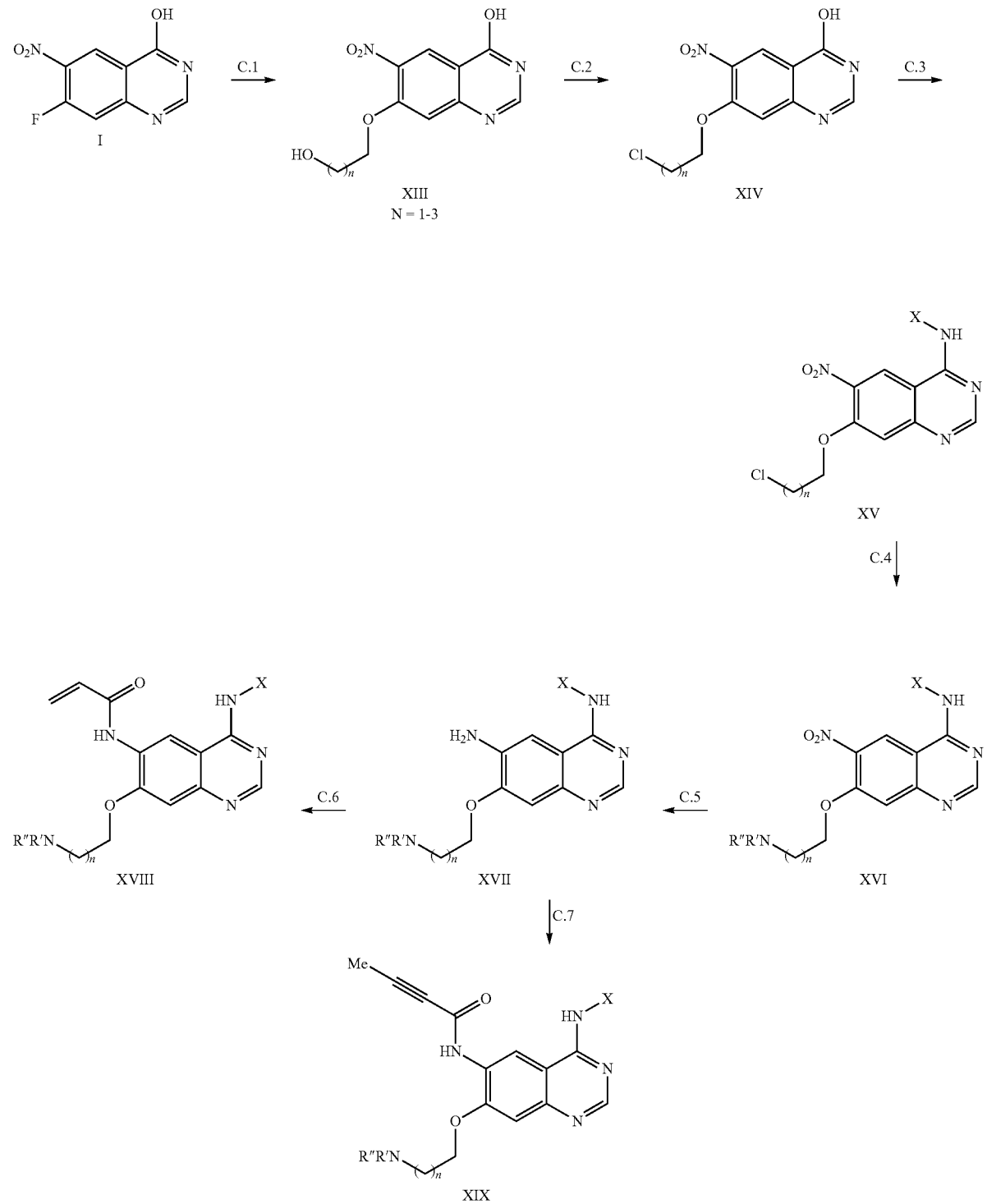

Step C.1:
Sodium (3.0 eq) was added to the corresponding diol (18.7 eq) at 25° C. The suspension was stirred at 25° C. for 0.5 h. Alcohol I (1.0 eq) was added to the above suspension. The mixture was heated to 70° C. and stirred at 70° C. for 1.5 h. The mixture was cooled to 25° C. and then adjusted to pH=7 with hydrochloric acid (3 M). After filtration, the filter cake was dried under reduced pressure to afford diol XIII.

Step C.2:
To a solution of diol XIII (1.00 eq) in thionyl chloride (10.0 mL) was added N,N-dimethylformamide (0.1 eq). The mixture was stirred at 90° C. for 3 h. The mixture was cooled to 25° C. and then concentrated in vacuum. The mixture was partitioned between water and ethyl acetate. The organic phase was washed with brine, dried with anhydrous sodium sulfate, filtered and concentrated in vacuum. The residue was purified by silica gel chromatography to afford dichloride XIV.

Step C.3:
A solution of dichloride XIV (1.0 eq) and $H_2N$-X (1.50 eq) in propan-2-ol was stirred at 90° C. for 12 h. The mixture was cooled to 25° C. and then concentrated in vacuum. The residue was triturated with methanol, then filtered and dried under reduced pressure to afford XV.

Step C.4:
To a solution of XV (1.0 eq), potassium iodide (0.1 eq) and tetrabutylammonium iodide (0.1 eq) in toluene was added HNR'R" (3.00 eq). The mixture was stirred at 110° C. for 12 h. The mixture was cooled to 25° C. and then concentrated in vacuum. The residue was triturated with water and filtered, the filter cake was dried in vacuum to afford XVI.

Step C.5:
Variant i): A mixture of XVI (1 eq) and nickel(ii) chloride hexahydrate (2 eq) in dichloromethane and methanol (1:1) was added sodium borohydride (4 eq) at 0° C. and then the mixture was stirred at 0° C. for 12 h. The reaction mixture was filtered and the filtrate was concentrated to give a residue. The residue was purified by reversed phase column chromatography to give amine XVII.

Variant ii): A mixture of XVI (1 eq), iron (3 eq) and ammonium chloride (5 eq) in methanol and water (4:1) was stirred at 70° C. for 12 h. The reaction mixture was filtered and the filtrate was concentrated under reduced pressure to give a residue. The residue was purified by Reverse-MPLC to give amine XVII.

Step C.6:
Variant i): To a solution of XVII (1 eq), 4-dimethylaminopyridine (1.5 eq) and acrylic acid (1.2 eq) in dimethyl formamide was added 1-(3-dimethylaminopropyl)-3-ethylcarbodiimide (2 eq) and then the solution was stirred at 25° C. for 1 h. The reaction mixture was filtered. The filtrate was purified by prep-HPLC to give acrylamide Variant ii): To a solution of XVII (1 eq) and triethylamine (4 eq) in dimethyl formamide was added acrylic anhydride (1.2 eq) and then the solution was stirred at 25° C. for 0.5 h. The reaction mixture was filtered. The filtrate was purified by prep-HPLC to give acrylamide XVIII.

Variant iii): To a solution of XVII (1.0 eq) in dimethylformamide was added triethylamine (3.00 eq) and acryloyl chloride (1.20 eq) at 0° C. The reaction mixture was stirred at 0° C. for 1 h and subsequently filtered. The filtrate was purified by prep-HPLC to give acrylamide XVIII.

Steps C.7:
To a solution of XVII (1.0 eq), 1-(3-dimethylaminopropyl)-3-ethylcarbodiimide hydrochloride (5.00 eq) and pyridine (5.00 eq) in N,N-dimethylformamide was added but-2-ynoic acid (10.0 eq). The mixture was stirred at 50° C. for 2 h and subsequently concentrated in vacuum. The mixture was purified by prep-HPLC to give ynamide XIX.

General Procedure D:

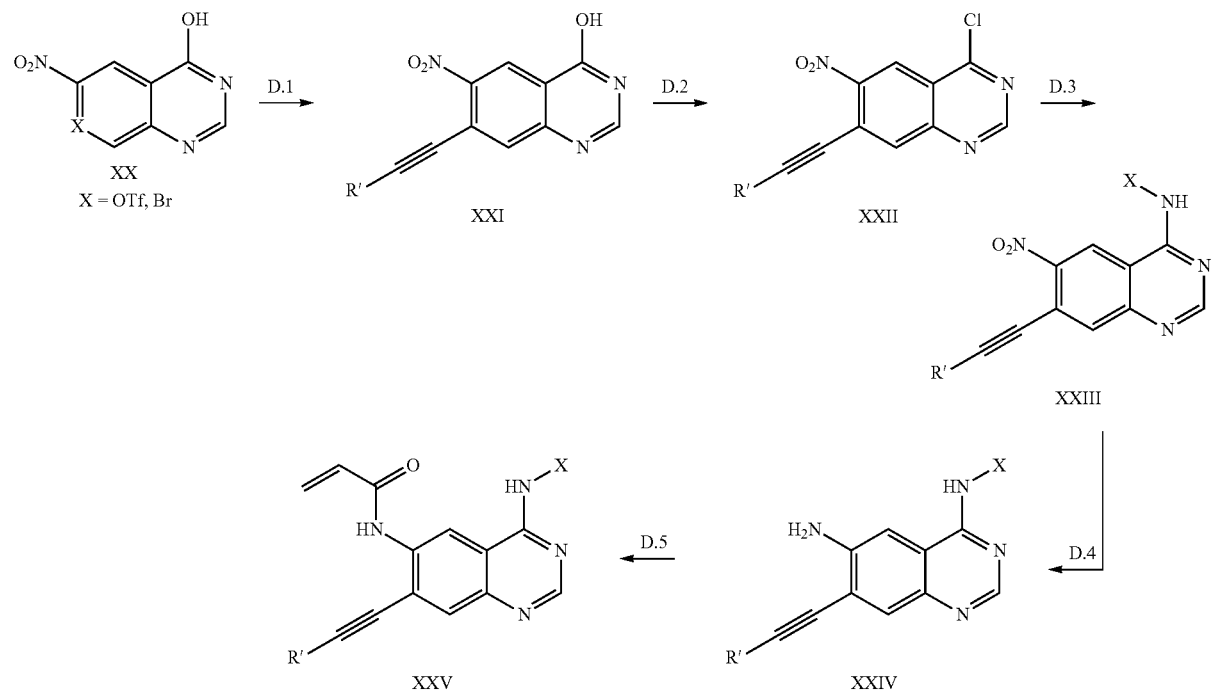

Step D.1:

To a solution of bromide or triflate XX (1.00 eq) in dimethylsulfoxide was added the corresponding alkyne (1.50 eq), triethylamine (3.00 eq), copper (I) iodide (0.5 eq), tetrakis(triphenylphosphine)palladium (0.05 eq) at 20° C. The mixture was degassed with nitrogen and stirred at 20° C. for 12 h under nitrogen. The mixture was added methanol and filtered, the filter cake was concentrated to give alkyne XXI.

Step D.2:

To a suspension of alkyne XXI (1.00 eq) in thionyl chloride was added N,N-dimethylformamide (2.0 eq) at 20° C. The mixture was stirred at 90° C. for 0.5 h until the suspension turned to homogenous solution. The solution was concentrated to give chloride XXII.

Step D.3:

A suspension of chloride XXII (1.0 eq) and $H_2$N-X in propan-2-ol was stirred at 80° C. for 12 h. The mixture was concentrated to give a residue. And the residue was purified by reverse phase chromatography to give XXIII.

Step D.4:

Variant i): A mixture of XXIII (1 eq) and nickel(ii) chloride hexahydrate (2 eq) in dichloromethane and methanol (1:1) was added sodium borohydride (4 eq) at 0° C. and then the mixture was stirred at 0° C. for 12 h. The reaction mixture was filtered and the filtrate was concentrated to give a residue. The residue was purified by reversed phase column chromatography to give amine XXIV.

Variant ii): A mixture of XXIII (1 eq), iron (3 eq) and ammonium chloride (5 eq) in methanol and water (4:1) was stirred at 70° C. for 12 h. The reaction mixture was filtered and the filtrate was concentrated under reduced pressure to give a residue. The residue was purified by Reverse-MPLC to give amine XXIV.

Step D.5:

Variant i): To a solution of XXIV (1 eq), 4-dimethylaminopyridine (1.5 eq) and acrylic acid (1.2 eq) in dimethyl formamide was added 1-(3-dimethylaminopropyl)-3-ethylcarbodiimide (2 eq) and then the solution was stirred at 25° C. for 1 h. The reaction mixture was filtered. The filtrate was purified by prep-HPLC to give acrylamide XXV.

Variant ii): To a solution of XXIV (1 eq) and triethylamine (4 eq) in dimethyl formamide was added acrylic anhydride (1.2 eq) and then the solution was stirred at 25° C. for 0.5 h. The reaction mixture was filtered. The filtrate was purified by prep-HPLC to give acrylamide XXV.

Variant iii): To a solution of XXIV (1.0 eq) in dimethylformamide was added triethylamine (3.00 eq) and acryloyl chloride (1.20 eq) at 0° C. The reaction mixture was stirred at 0° C. for 1 h and subsequently filtered. The filtrate was purified by prep-HPLC to give acrylamide XXV.

| Compound | No. |
|---|---|
| 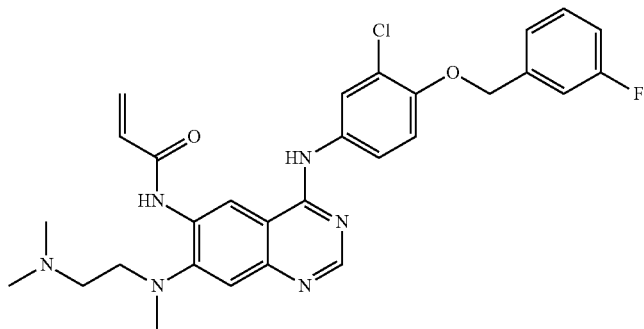 [SMILES: C=CC(=O)Nc1cc2c(Nc3ccc(OCc4cccc(F)c4)c(Cl)c3)ncnc2cc1N(C)CCN(C)C] | 1 |
| 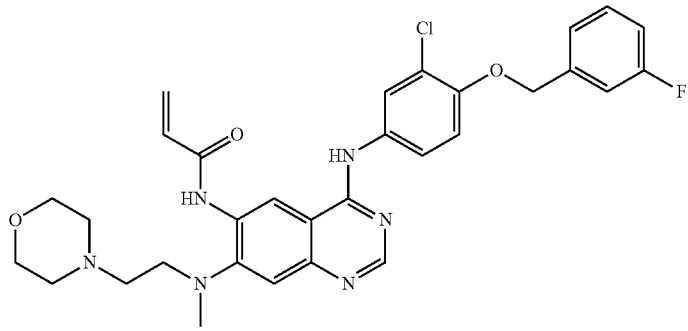 [SMILES: C=CC(=O)Nc1cc2c(Nc3ccc(OCc4cccc(F)c4)c(Cl)c3)ncnc2cc1N(C)CCN1CCOCC1] | 2 |

-continued

| Compound | No. |
|---|---|
| | 3 |
| | 4 |
| | 5 |
| | 6 |

| Compound | No. |
|---|---|
| 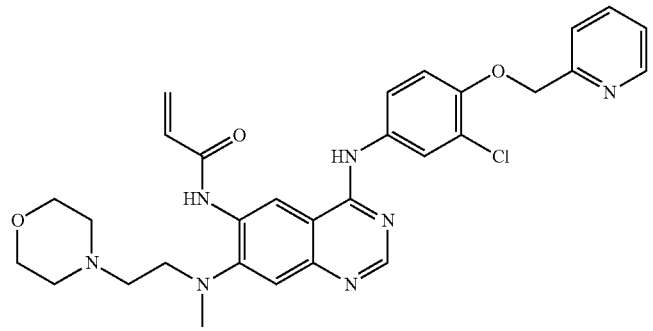 [SMILES: C=CC(=O)Nc1cc2c(Nc3ccc(OCc4ccccn4)c(Cl)c3)ncnc2cc1N(C)CCN1CCOCC1] | 7 |
| 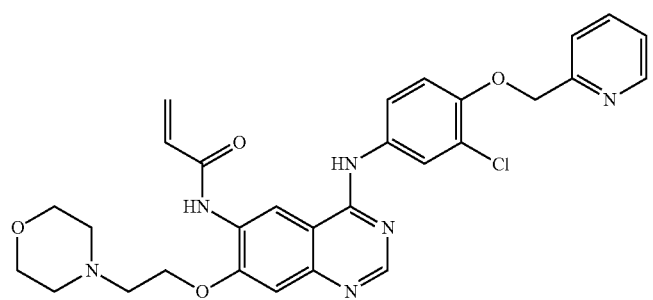 [SMILES: C=CC(=O)Nc1cc2c(Nc3ccc(OCc4ccccn4)c(Cl)c3)ncnc2cc1OCCN1CCOCC1] | 8 |
| 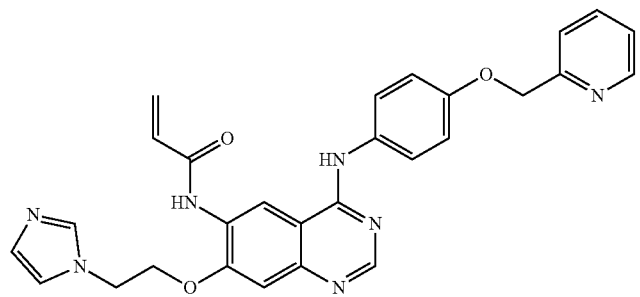 [SMILES: C=CC(=O)Nc1cc2c(Nc3ccc(OCc4ccccn4)cc3)ncnc2cc1OCCn1ccnc1] | 9 |
| 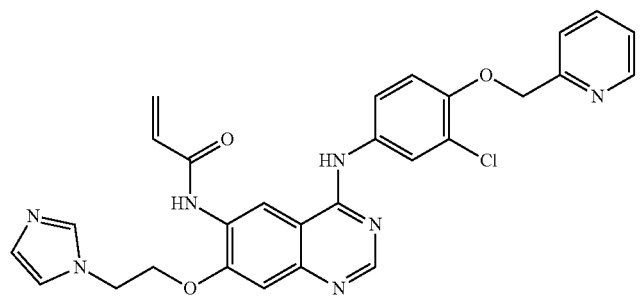 [SMILES: C=CC(=O)Nc1cc2c(Nc3ccc(OCc4ccccn4)c(Cl)c3)ncnc2cc1OCCn1ccnc1] | 10 |
| 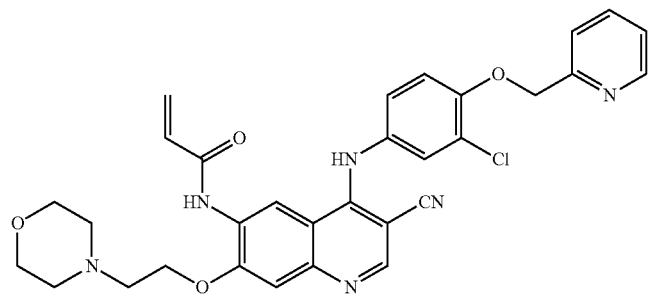 [SMILES: C=CC(=O)Nc1cc2c(Nc3ccc(OCc4ccccn4)c(Cl)c3)c(C#N)cnc2cc1OCCN1CCOCC1] | 11 |

| Compound | No. |
|---|---|
| 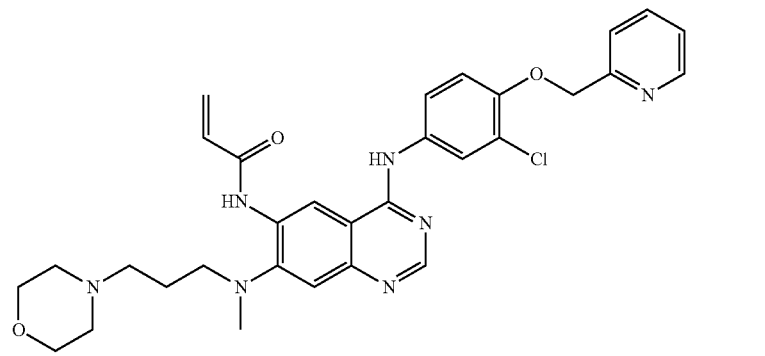 [SMILES: C=CC(=O)Nc1cc2c(Nc3ccc(OCc4ccccn4)c(Cl)c3)ncnc2cc1N(C)CCCN1CCOCC1] | 12 |
| 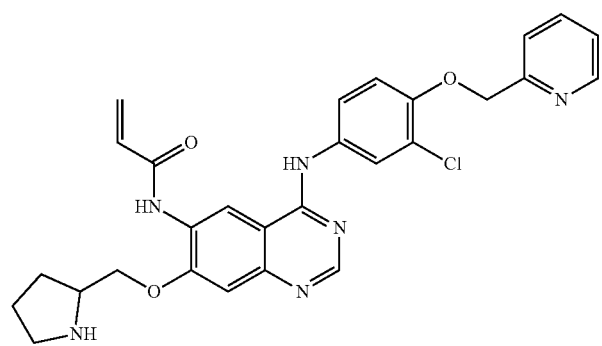 [SMILES: C=CC(=O)Nc1cc2c(Nc3ccc(OCc4ccccn4)c(Cl)c3)ncnc2cc1OCC1CCCN1] | 13 |
| 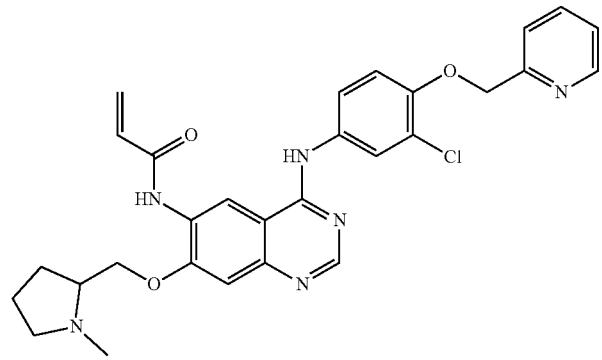 [SMILES: C=CC(=O)Nc1cc2c(Nc3ccc(OCc4ccccn4)c(Cl)c3)ncnc2cc1OCC1CCCN1C] | 14 |
| 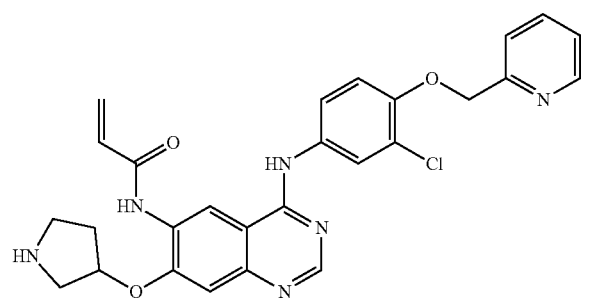 [SMILES: C=CC(=O)Nc1cc2c(Nc3ccc(OCc4ccccn4)c(Cl)c3)ncnc2cc1OC1CCNC1] | 15 |

| Compound | No. |
|---|---|
| 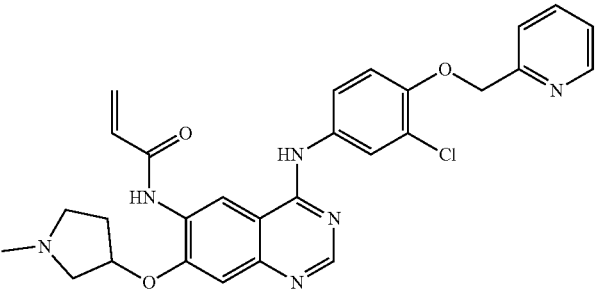 [SMILES: C=CC(=O)Nc1cc2c(Nc3ccc(OCc4ccccn4)c(Cl)c3)ncnc2cc1OC1CCN(C)C1] | 16 |
| 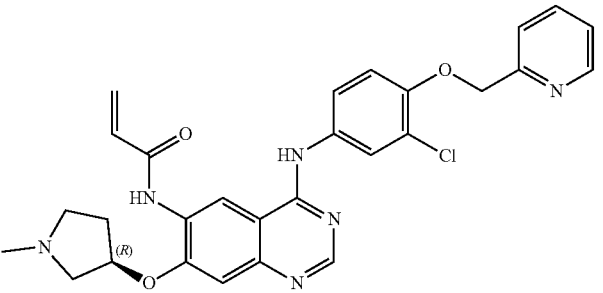 | 17 |
| 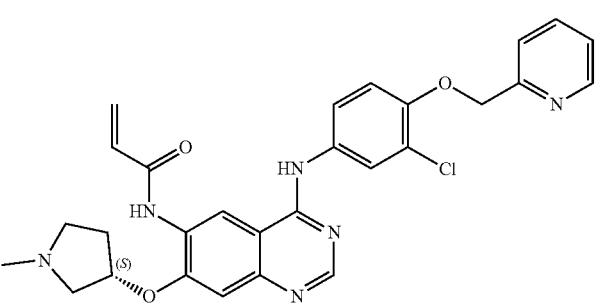 | 18 |
| 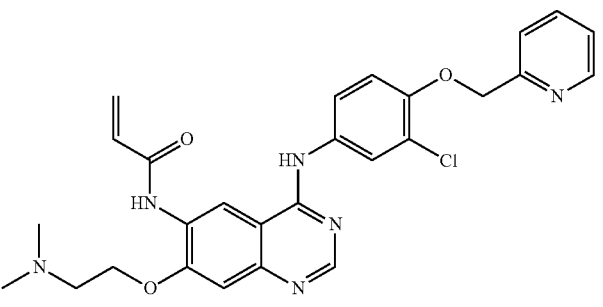 [SMILES: C=CC(=O)Nc1cc2c(Nc3ccc(OCc4ccccn4)c(Cl)c3)ncnc2cc1OCCN(C)C] | 19 |
| 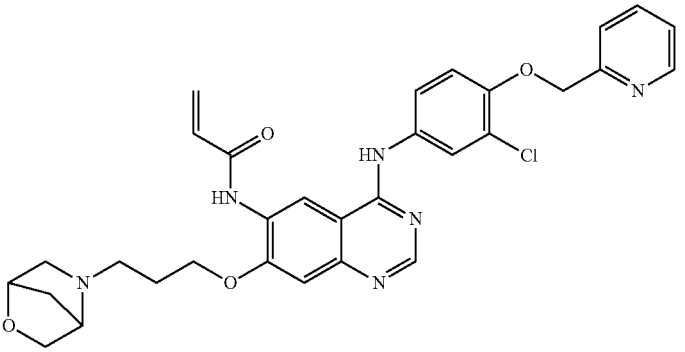 [SMILES: C=CC(=O)Nc1cc2c(Nc3ccc(OCc4ccccn4)c(Cl)c3)ncnc2cc1OCCCN1CC2CC1CO2] | 20 |

-continued
| Compound | No. |
|---|---|
| 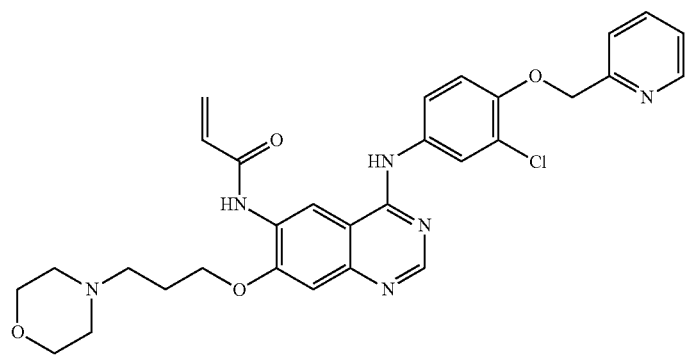 | 21 |
| 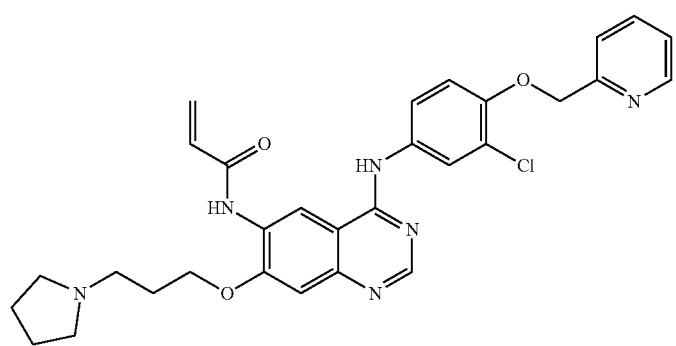 [SMILES: C=CC(=O)Nc1cc2c(Nc3ccc(OCc4ccccn4)c(Cl)c3)ncnc2cc1OCCCN1CCCC1] | 22 |
| 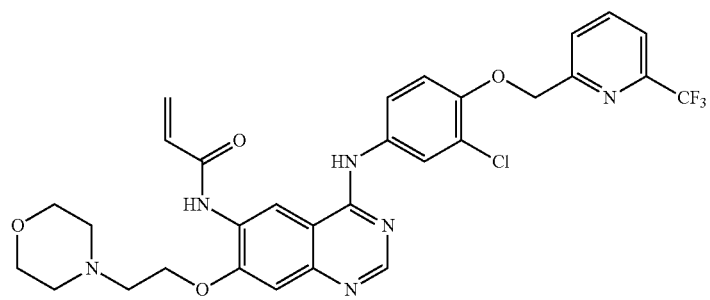 [SMILES: C=CC(=O)Nc1cc2c(Nc3ccc(OCc4cccc(C(F)(F)F)n4)c(Cl)c3)ncnc2cc1OCCN1CCOCC1] | 23 |
| 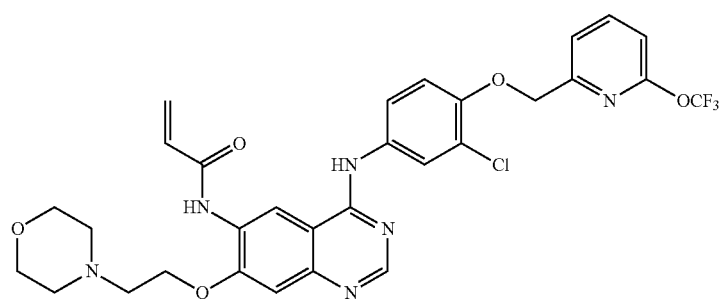 [SMILES: C=CC(=O)Nc1cc2c(Nc3ccc(OCc4cccc(OC(F)(F)F)n4)c(Cl)c3)ncnc2cc1OCCN1CCOCC1] | 24 |
| 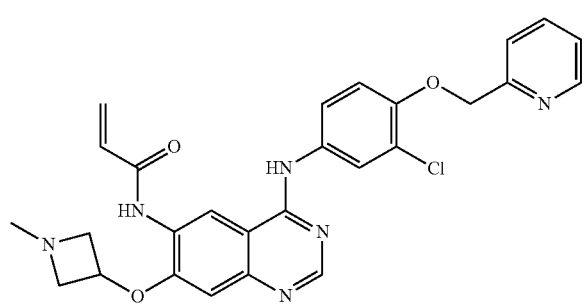 [SMILES: C=CC(=O)Nc1cc2c(Nc3ccc(OCc4ccccn4)c(Cl)c3)ncnc2cc1OC1CN(C)C1] | 25 |

-continued
| Compound | No. |
|---|---|
| 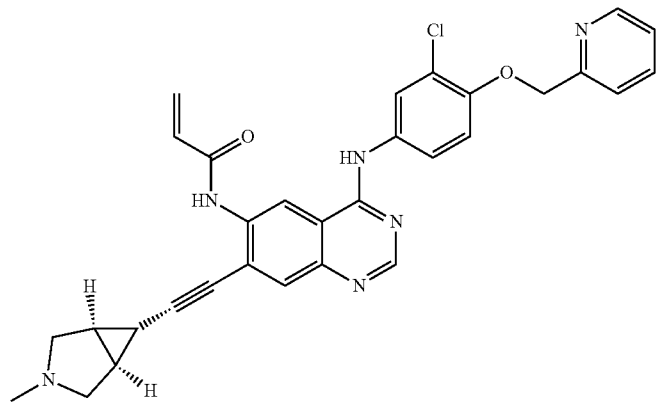 | 26 |
| 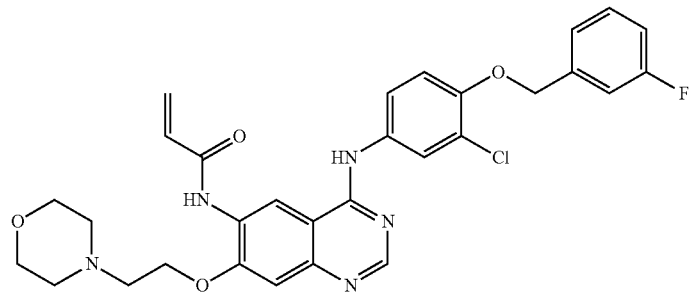 [SMILES: C=CC(=O)Nc1cc2c(Nc3ccc(OCc4cccc(F)c4)c(Cl)c3)ncnc2cc1OCCN1CCOCC1] | 27 |
| 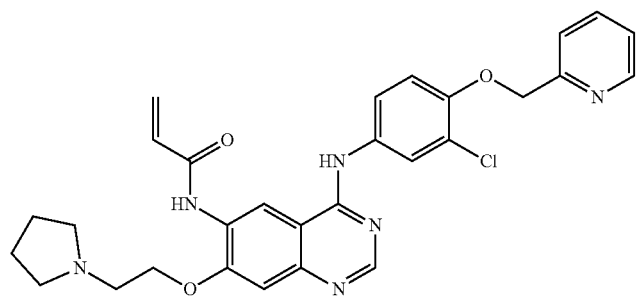 [SMILES: C=CC(=O)Nc1cc2c(Nc3ccc(OCc4ccccn4)c(Cl)c3)ncnc2cc1OCCN1CCCC1] | 28 |
| 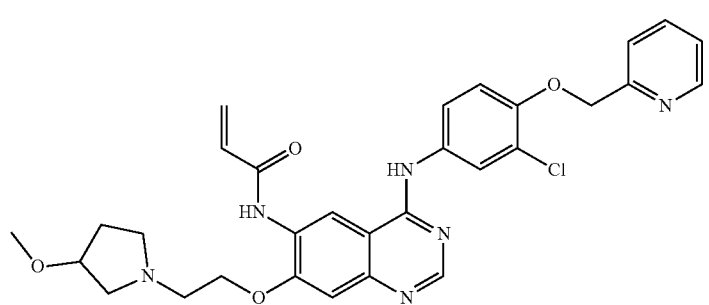 [SMILES: C=CC(=O)Nc1cc2c(Nc3ccc(OCc4ccccn4)c(Cl)c3)ncnc2cc1OCCN1CCC(OC)C1] | 29 |

-continued

| Compound | No. |
|---|---|
| | 30 |
| | 31 |
| | 32 |
| | 33 |
| | 34 |

| Compound | No. |
|---|---|
| 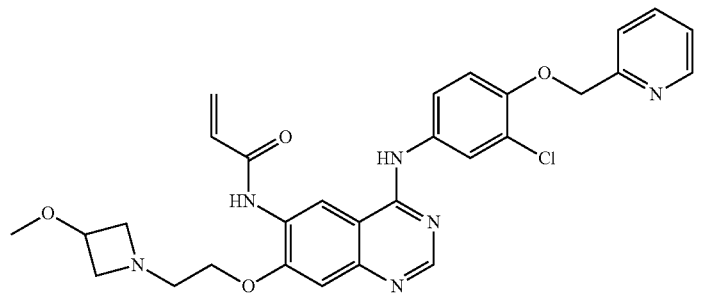 [SMILES: C=CC(=O)Nc1cc2c(Nc3ccc(OCc4ccccn4)c(Cl)c3)ncnc2cc1OCCN1CC(OC)C1] | 35 |
| 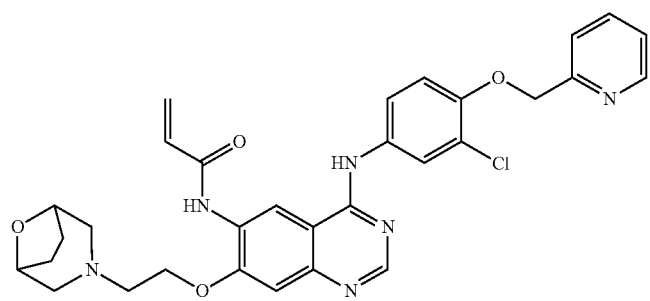 [SMILES: C=CC(=O)Nc1cc2c(Nc3ccc(OCc4ccccn4)c(Cl)c3)ncnc2cc1OCCN1CC2CCC(C1)O2] | 36 |
| 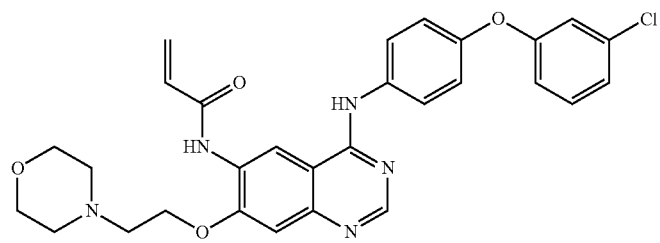 [SMILES: C=CC(=O)Nc1cc2c(Nc3ccc(Oc4cccc(Cl)c4)cc3)ncnc2cc1OCCN1CCOCC1] | 37 |
| 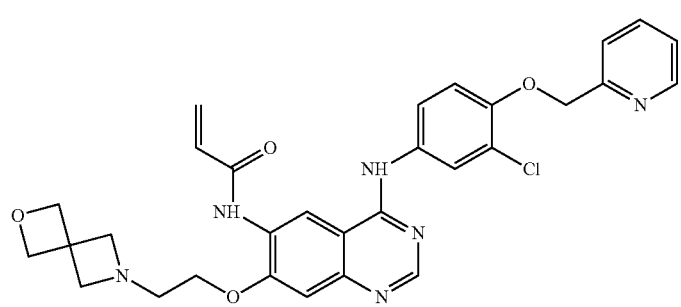 [SMILES: C=CC(=O)Nc1cc2c(Nc3ccc(OCc4ccccn4)c(Cl)c3)ncnc2cc1OCCN1CC2(COC2)C1] | 38 |
| 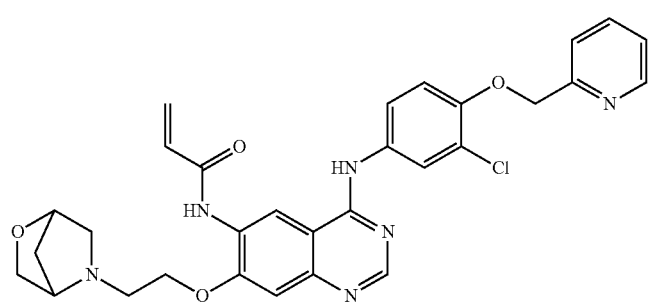 [SMILES: C=CC(=O)Nc1cc2c(Nc3ccc(OCc4ccccn4)c(Cl)c3)ncnc2cc1OCCN1CC2CC1CO2] | 39 |

| Compound | No. |
|---|---|
| 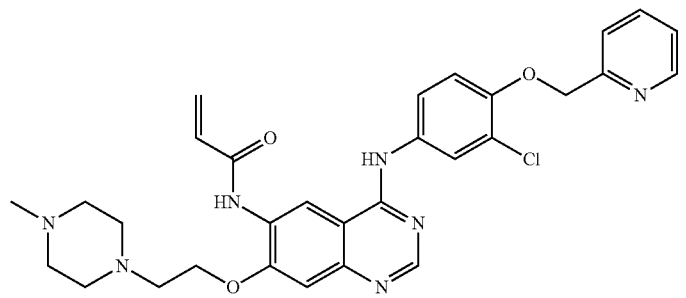 [SMILES: C=CC(=O)Nc1cc2c(Nc3ccc(OCc4ccccn4)c(Cl)c3)ncnc2cc1OCCN1CCN(C)CC1] | 40 |
| 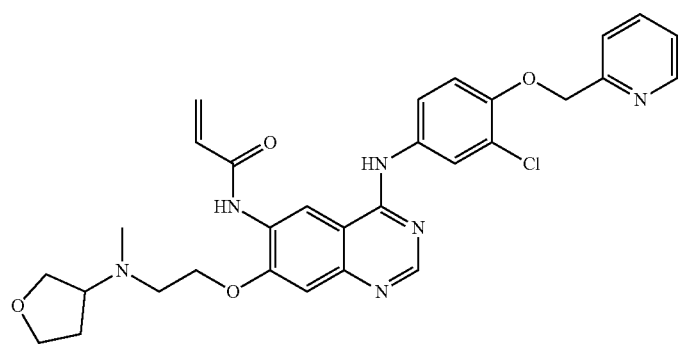 [SMILES: C=CC(=O)Nc1cc2c(Nc3ccc(OCc4ccccn4)c(Cl)c3)ncnc2cc1OCCN(C)C1CCOC1] | 41 |
| 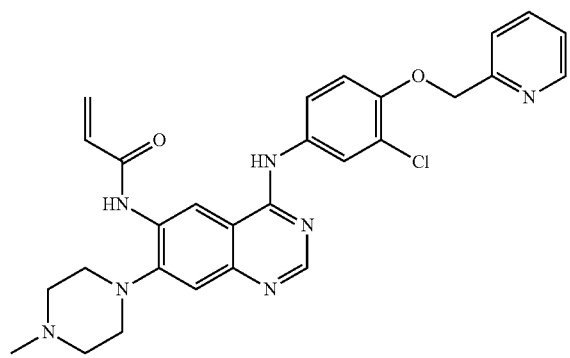 [SMILES: C=CC(=O)Nc1cc2c(Nc3ccc(OCc4ccccn4)c(Cl)c3)ncnc2cc1N1CCN(C)CC1] | 42 |
| 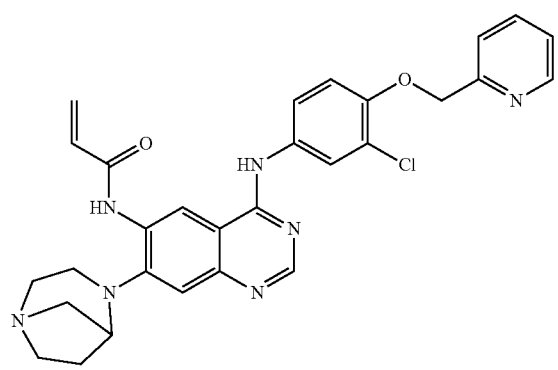 [SMILES: C=CC(=O)Nc1cc2c(Nc3ccc(OCc4ccccn4)c(Cl)c3)ncnc2cc1N1CCN2CCC1C2] | 43 |

| Compound | No. |
|---|---|
| 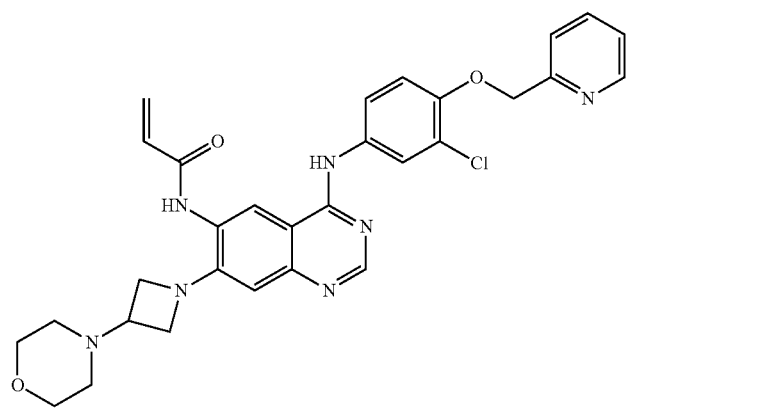 [SMILES: C=CC(=O)Nc1cc2c(Nc3ccc(OCc4ccccn4)c(Cl)c3)ncnc2cc1N1CC(N2CCOCC2)C1] | 44 |
| 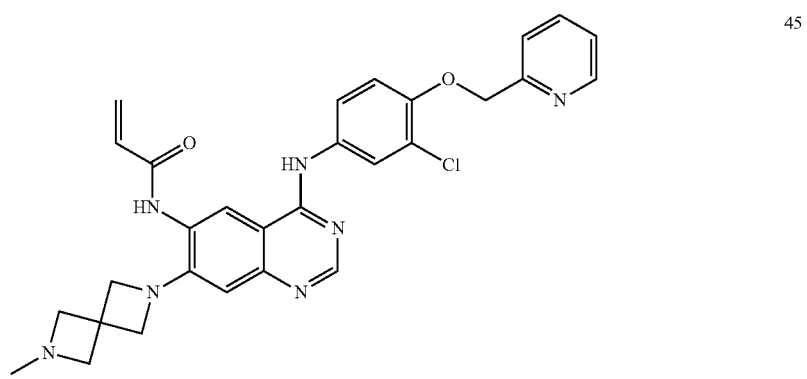 | 45 |
| 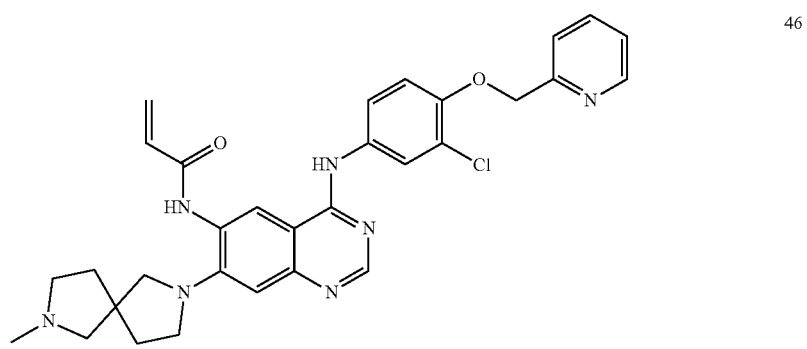 | 46 |
| 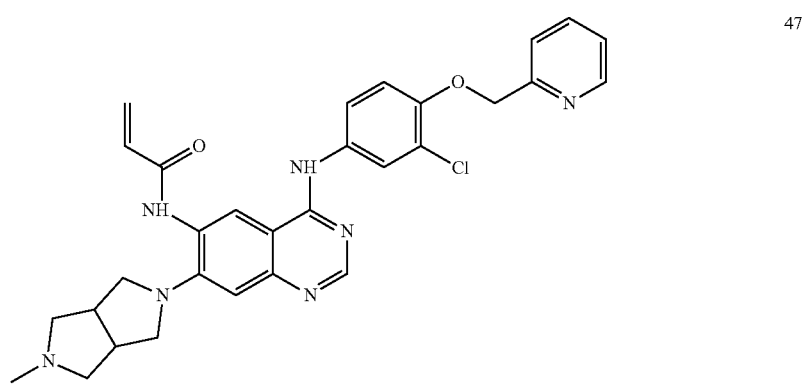 | 47 |

-continued
| Compound | No. |
|---|---|
| 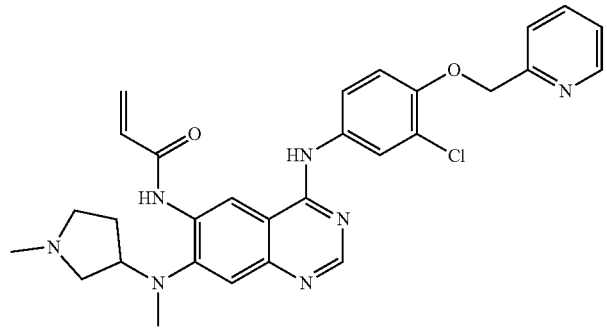 [SMILES: C=CC(=O)Nc1cc2c(Nc3ccc(OCc4ccccn4)c(Cl)c3)ncnc2cc1N(C)C1CCN(C)C1] | 48 |
| 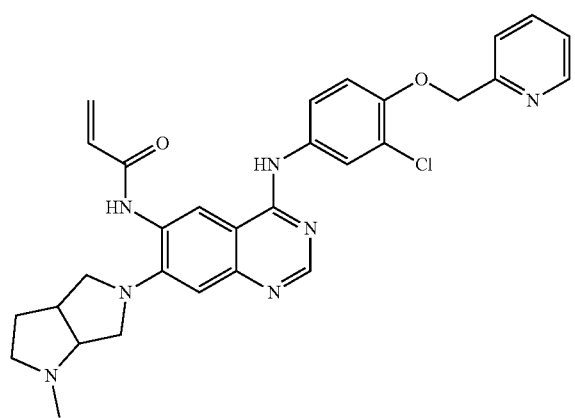 [SMILES: C=CC(=O)Nc1cc2c(Nc3ccc(OCc4ccccn4)c(Cl)c3)ncnc2cc1N1CC2CCN(C)C2C1] | 49 |
| 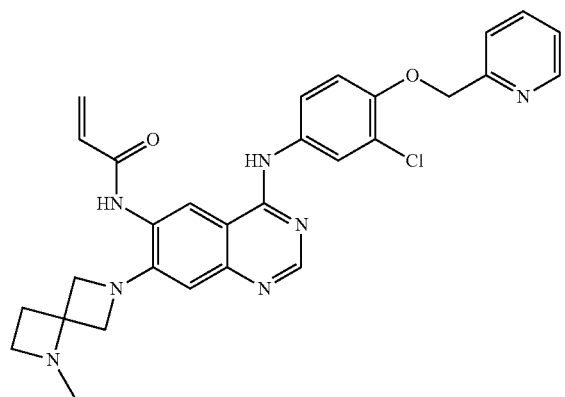 [SMILES: C=CC(=O)Nc1cc2c(Nc3ccc(OCc4ccccn4)c(Cl)c3)ncnc2cc1N1CC2(CCN2C)C1] | 50 |
| 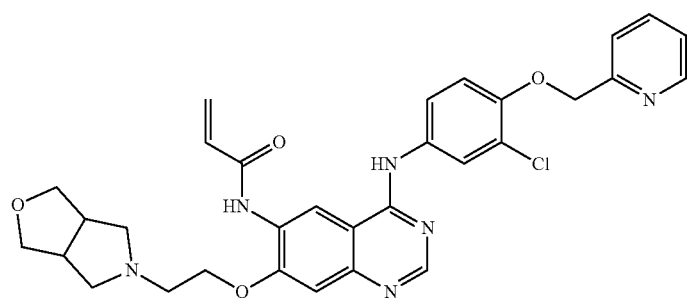 [SMILES: C=CC(=O)Nc1cc2c(Nc3ccc(OCc4ccccn4)c(Cl)c3)ncnc2cc1OCCN1CC2COCC2C1] | 51 |

-continued
| Compound | No. |
|---|---|
| 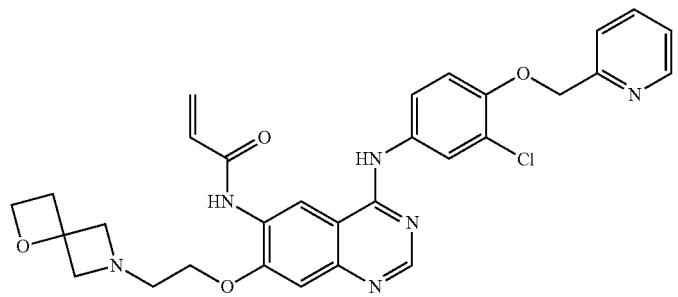 [SMILES: C=CC(=O)Nc1cc2c(Nc3ccc(OCc4ccccn4)c(Cl)c3)ncnc2cc1OCCN1CC2(CCO2)C1] | 52 |
| 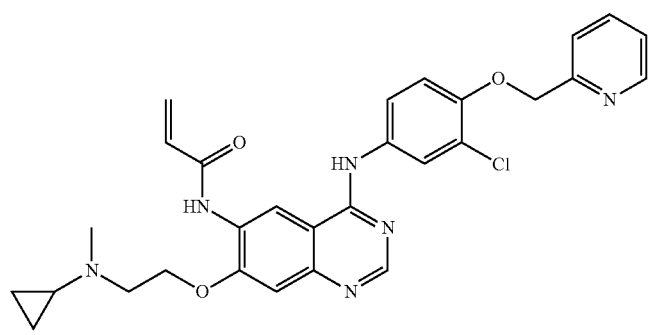 [SMILES: C=CC(=O)Nc1cc2c(Nc3ccc(OCc4ccccn4)c(Cl)c3)ncnc2cc1OCCN(C)C1CC1] | 53 |
| 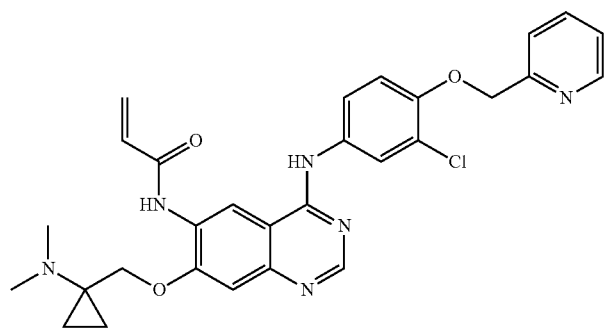 [SMILES: C=CC(=O)Nc1cc2c(Nc3ccc(OCc4ccccn4)c(Cl)c3)ncnc2cc1OCC1(N(C)C)CC1] | 54 |
| 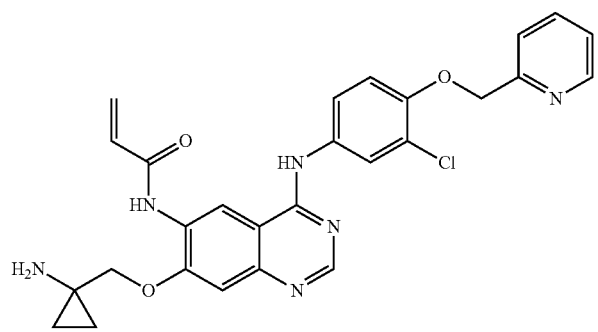 [SMILES: C=CC(=O)Nc1cc2c(Nc3ccc(OCc4ccccn4)c(Cl)c3)ncnc2cc1OCC1(N)CC1] | 55 |
| 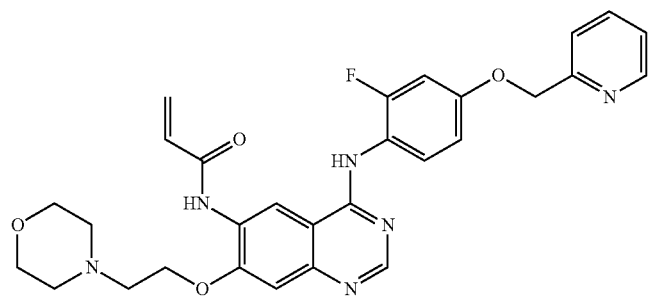 [SMILES: C=CC(=O)Nc1cc2c(Nc3ccc(OCc4ccccn4)cc3F)ncnc2cc1OCCN1CCOCC1] | 56 |

| Compound | No. |
|---|---|
| 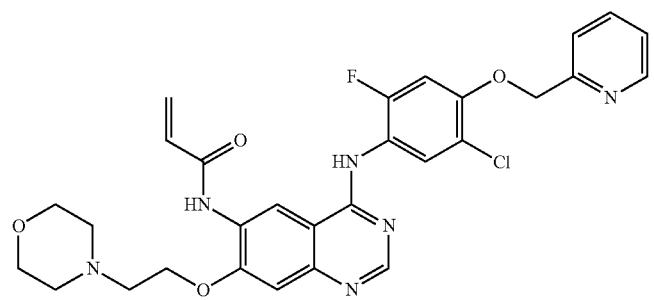 [SMILES: C=CC(=O)Nc1cc2c(Nc3cc(Cl)c(OCc4ccccn4)cc3F)ncnc2cc1OCCN1CCOCC1] | 57 |
| 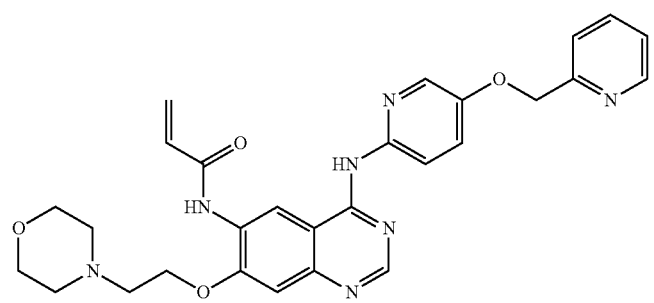 [SMILES: C=CC(=O)Nc1cc2c(Nc3ccc(OCc4ccccn4)cn3)ncnc2cc1OCCN1CCOCC1] | 58 |
| 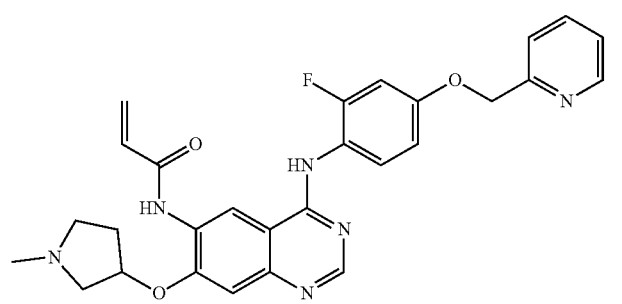 [SMILES: C=CC(=O)Nc1cc2c(Nc3ccc(OCc4ccccn4)cc3F)ncnc2cc1OC1CCN(C)C1] | 59 |
| 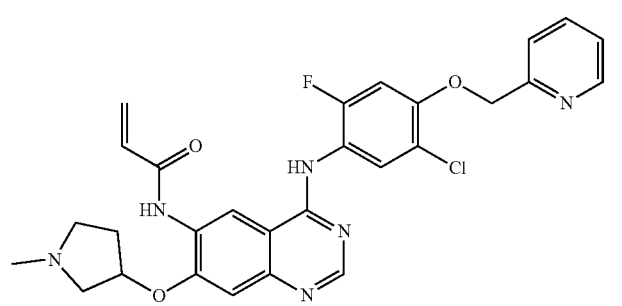 [SMILES: C=CC(=O)Nc1cc2c(Nc3cc(Cl)c(OCc4ccccn4)cc3F)ncnc2cc1OC1CCN(C)C1] | 60 |
| 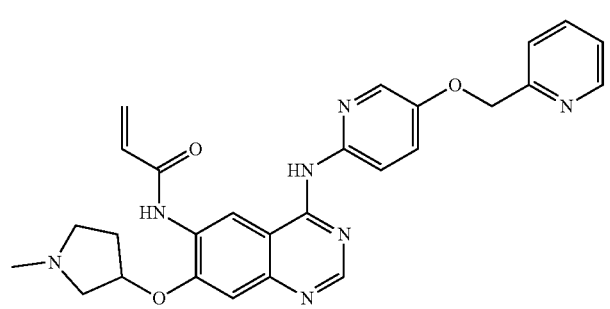 [SMILES: C=CC(=O)Nc1cc2c(Nc3ccc(OCc4ccccn4)cn3)ncnc2cc1OC1CCN(C)C1] | 61 |

| Compound | No. |
|---|---|
| 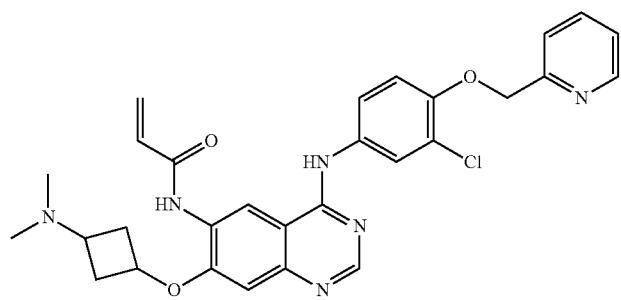 [SMILES: C=CC(=O)Nc1cc2c(Nc3ccc(OCc4ccccn4)c(Cl)c3)ncnc2cc1OC1CC(N(C)C)C1] | 62 |
| 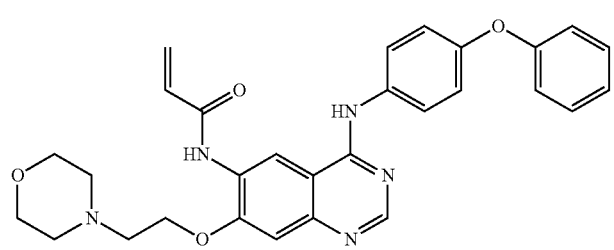 [SMILES: C=CC(=O)Nc1cc2c(Nc3ccc(Oc4ccccc4)cc3)ncnc2cc1OCCN1CCOCC1] | 63 |
| 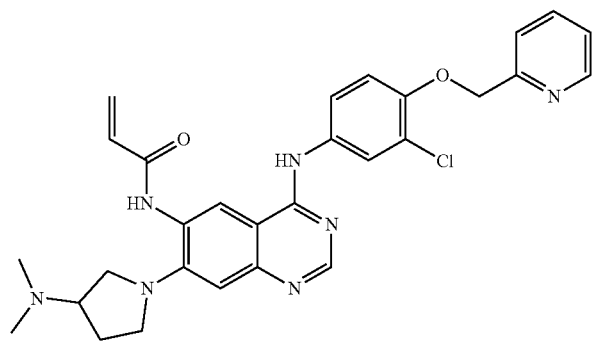 [SMILES: C=CC(=O)Nc1cc2c(Nc3ccc(OCc4ccccn4)c(Cl)c3)ncnc2cc1N1CCC(N(C)C)C1] | 64 |
| 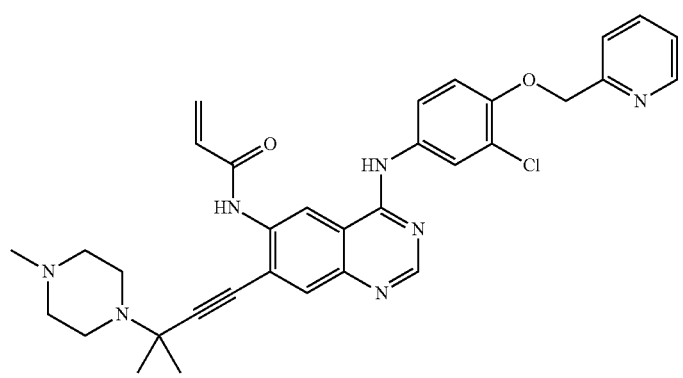 [SMILES: C=CC(=O)Nc1cc2c(Nc3ccc(OCc4ccccn4)c(Cl)c3)ncnc2cc1C#CC(C)(C)N1CCN(C)CC1] | 65 |

-continued

| Compound | No. |
|---|---|
| | 66 |
| | 67 |
| | 68 |
| | 69 |
| | 70 |

-continued
| Compound | No. |
|---|---|
| 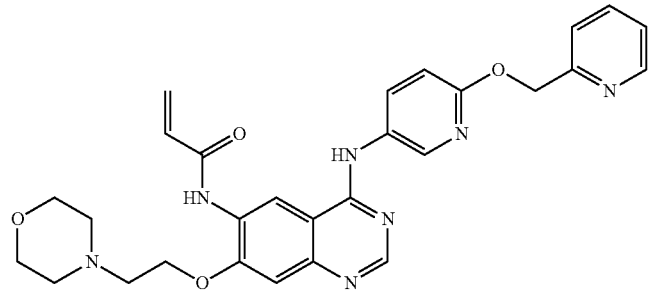 [SMILES: C=CC(=O)Nc1cc2c(Nc3ccc(OCc4ccccn4)nc3)ncnc2cc1OCCN1CCOCC1] | 71 |
| 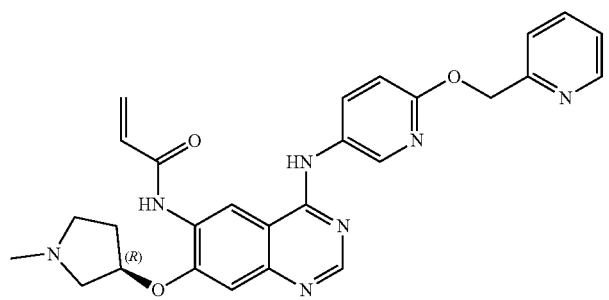 | 72 |
| 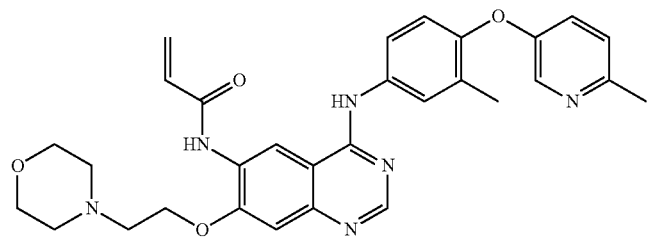 [SMILES: C=CC(=O)Nc1cc2c(Nc3ccc(Oc4ccc(C)nc4)c(C)c3)ncnc2cc1OCCN1CCOCC1] | 73 |
| 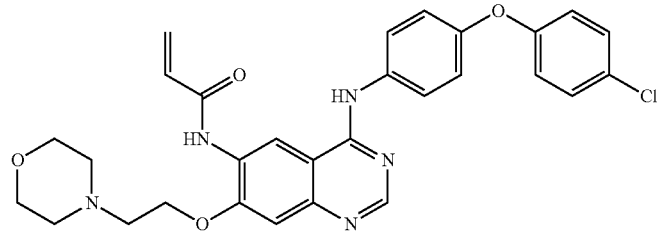 [SMILES: C=CC(=O)Nc1cc2c(Nc3ccc(Oc4ccc(Cl)cc4)cc3)ncnc2cc1OCCN1CCOCC1] | 74 |
| 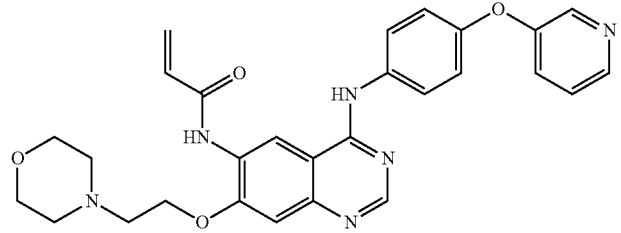 [SMILES: C=CC(=O)Nc1cc2c(Nc3ccc(Oc4cccnc4)cc3)ncnc2cc1OCCN1CCOCC1] | 75 |

| Compound | No. |
|---|---|
| | 76 |
| | 77 |
| | 78 |
| | 79 |

| Compound | No. |
|---|---|
| 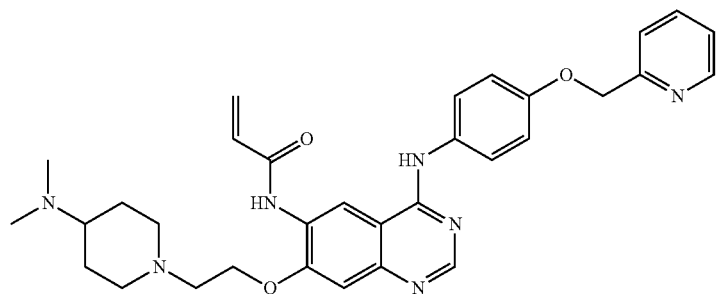 [SMILES: C=CC(=O)Nc1cc2c(Nc3ccc(OCc4ccccn4)cc3)ncnc2cc1OCCN1CCC(N(C)C)CC1] | 80 |
| 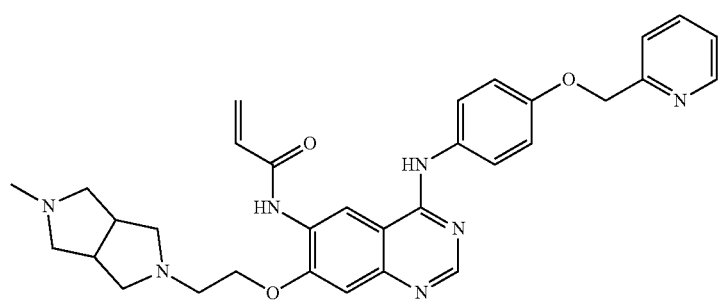 [SMILES: C=CC(=O)Nc1cc2c(Nc3ccc(OCc4ccccn4)cc3)ncnc2cc1OCCN1CC2CN(C)CC2C1] | 81 |
| 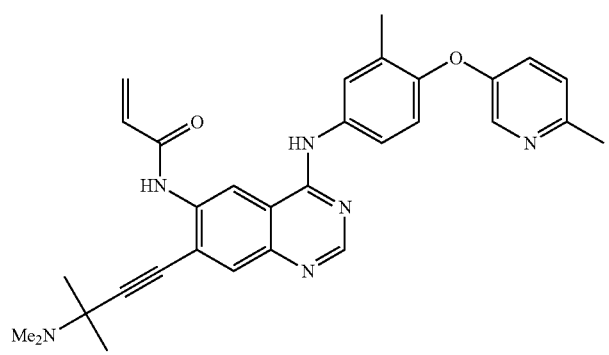 [SMILES: C=CC(=O)Nc1cc2c(Nc3ccc(Oc4ccc(C)nc4)c(C)c3)ncnc2cc1C#CC(C)(C)N(C)C] | 82 |
| 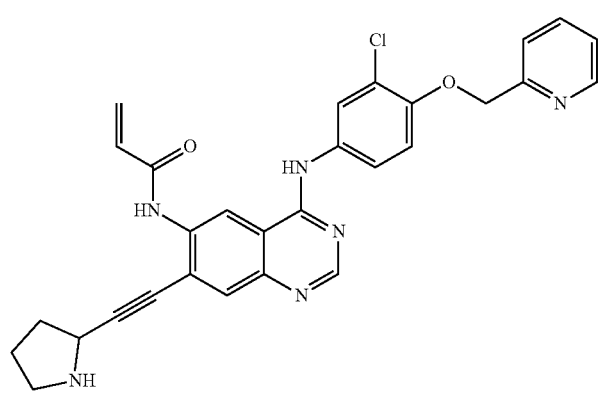 [SMILES: C=CC(=O)Nc1cc2c(Nc3ccc(OCc4ccccn4)c(Cl)c3)ncnc2cc1C#CC1CCCN1] | 83 |

-continued
| Compound | No. |
|---|---|
| 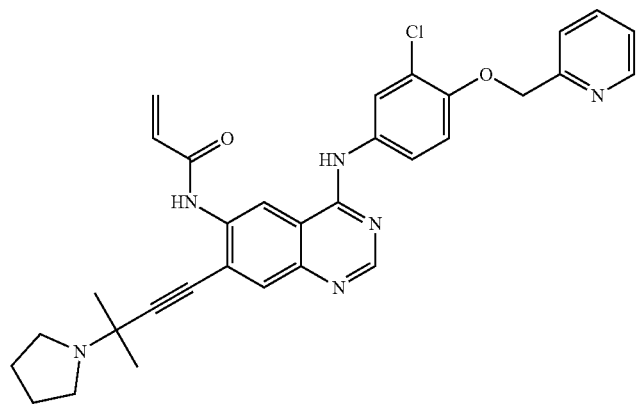 [SMILES: C=CC(=O)Nc1cc2c(Nc3ccc(OCc4ccccn4)c(Cl)c3)ncnc2cc1C#CC(C)(C)N1CCCC1] | 84 |
| 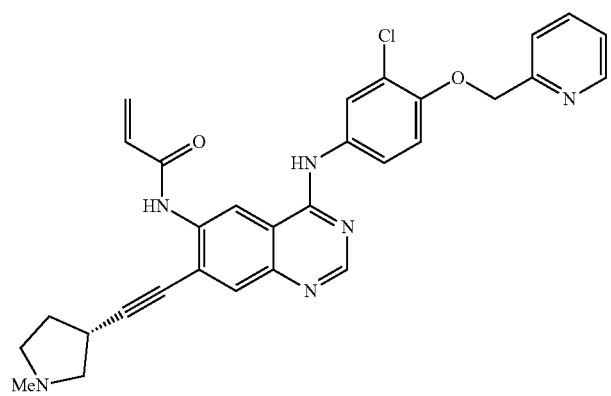 [SMILES: C=CC(=O)Nc1cc2c(Nc3ccc(OCc4ccccn4)c(Cl)c3)ncnc2cc1C#C[C@H]1CCN(C)C1] | 85 |
| 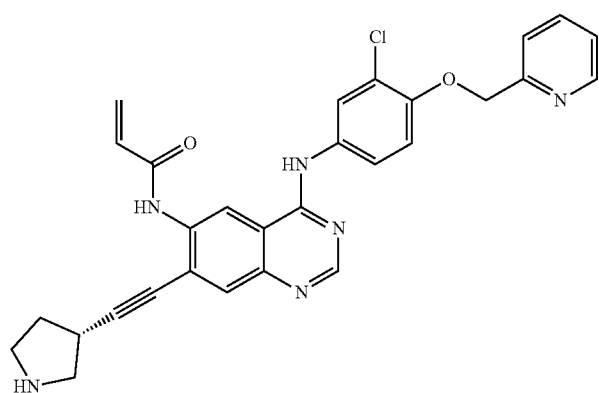 [SMILES: C=CC(=O)Nc1cc2c(Nc3ccc(OCc4ccccn4)c(Cl)c3)ncnc2cc1C#C[C@H]1CCNC1] | 86 |
| 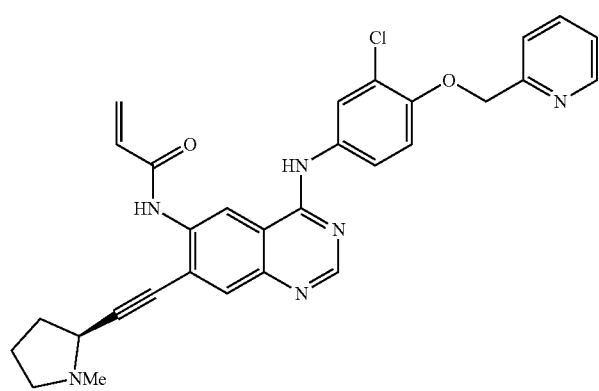 [SMILES: C=CC(=O)Nc1cc2c(Nc3ccc(OCc4ccccn4)c(Cl)c3)ncnc2cc1C#C[C@@H]1CCCN1C] | 87 |

| Compound | No. |
|---|---|
| 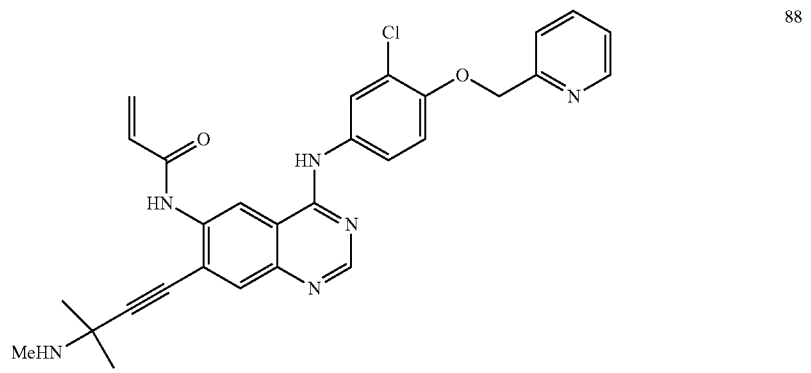 | 88 |
| 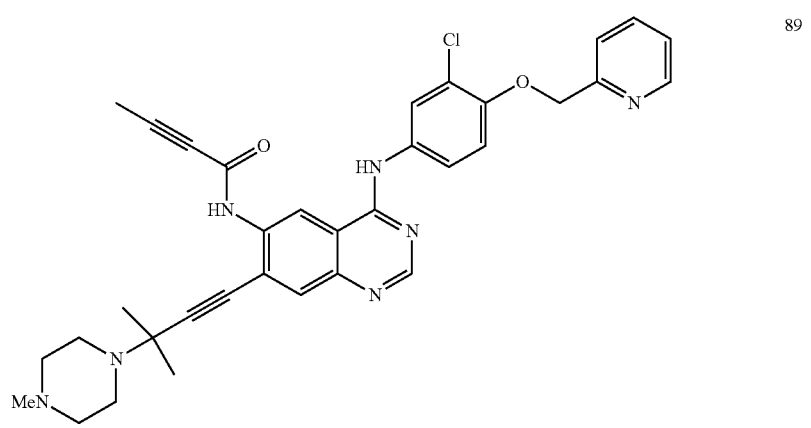 | 89 |
| 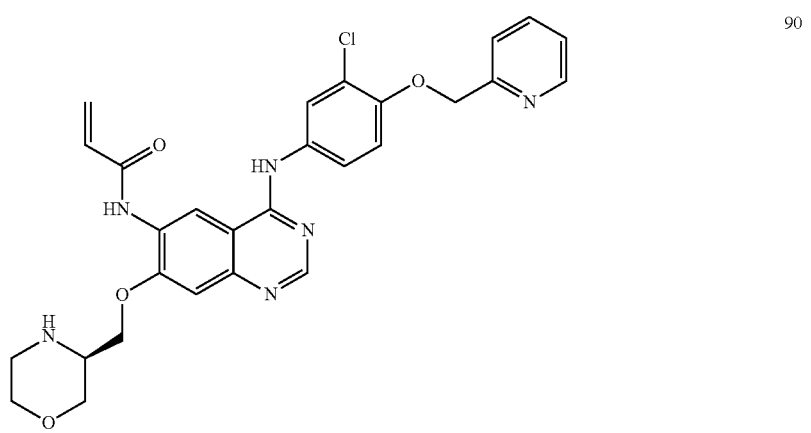 | 90 |
| 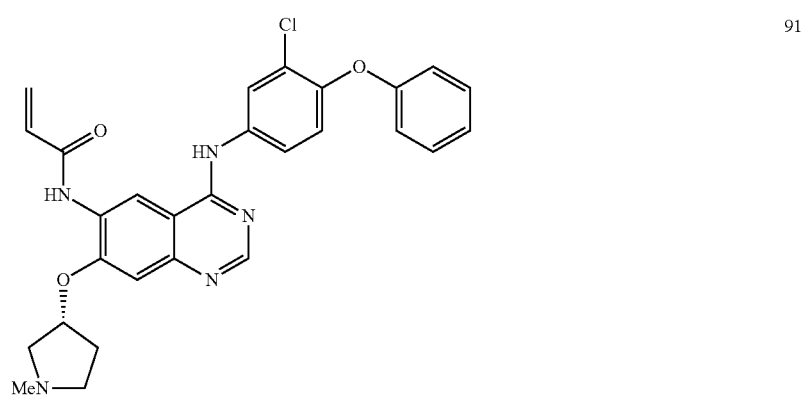 | 91 |

-continued
| Compound | No. |
|---|---|
| 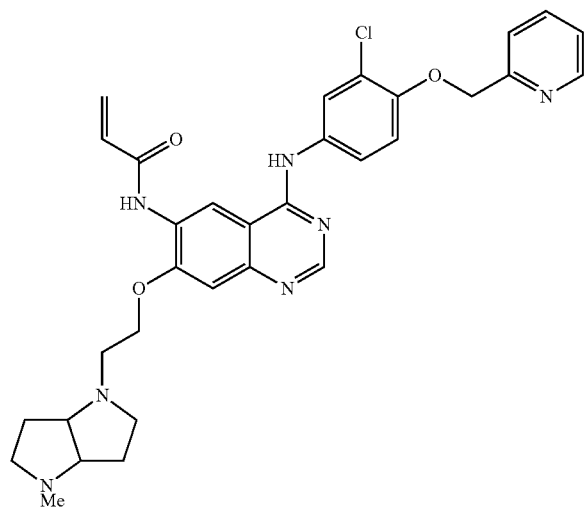 [SMILES: C=CC(=O)Nc1cc2c(Nc3ccc(OCc4ccccn4)c(Cl)c3)ncnc2cc1OCCN1CCC2C1CCN2C] | 92 |
| 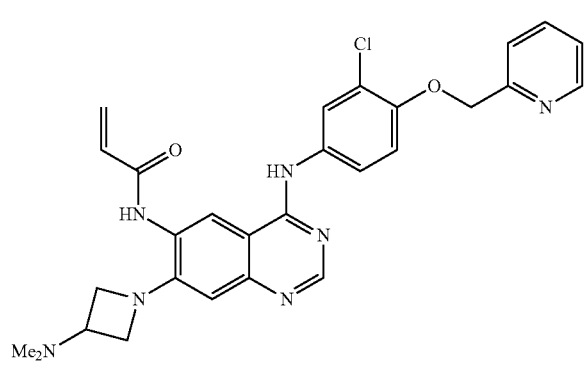 [SMILES: C=CC(=O)Nc1cc2c(Nc3ccc(OCc4ccccn4)c(Cl)c3)ncnc2cc1N1CC(N(C)C)C1] | 93 |
| 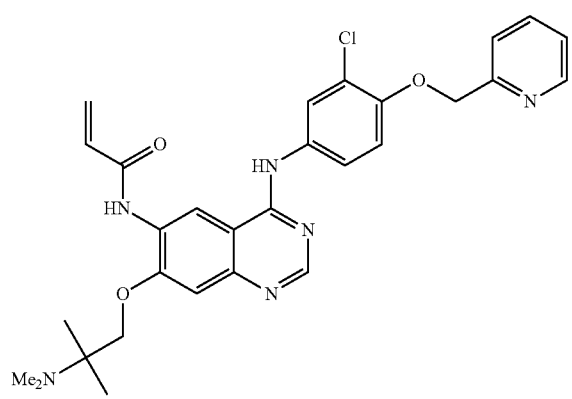 [SMILES: C=CC(=O)Nc1cc2c(Nc3ccc(OCc4ccccn4)c(Cl)c3)ncnc2cc1OCC(C)(C)N(C)C] | 94 |

| Compound | No. |
|---|---|
| 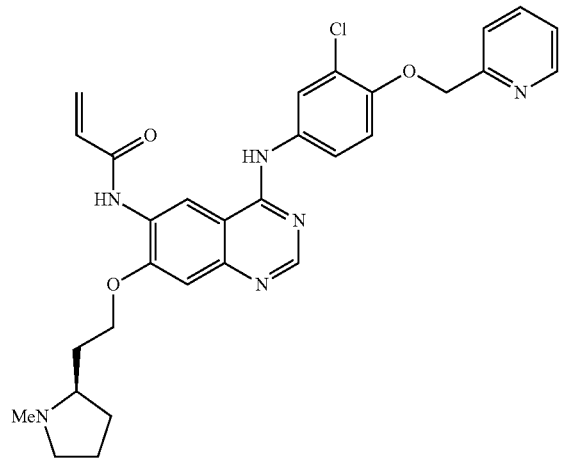 [SMILES: C=CC(=O)Nc1cc2c(Nc3ccc(OCc4ccccn4)c(Cl)c3)ncnc2cc1OCC[C@H]1CCCN1C] | 95 |
| 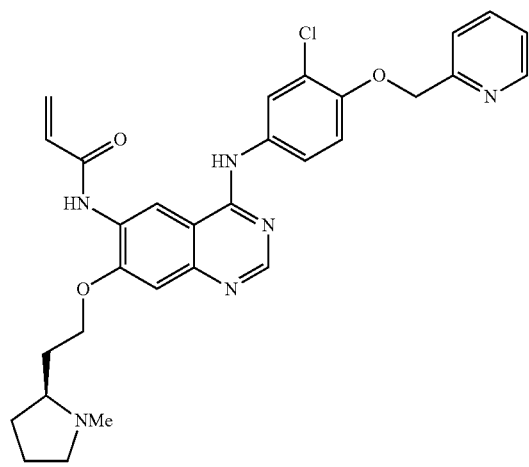 [SMILES: C=CC(=O)Nc1cc2c(Nc3ccc(OCc4ccccn4)c(Cl)c3)ncnc2cc1OCC[C@@H]1CCCN1C] | 96 |
| 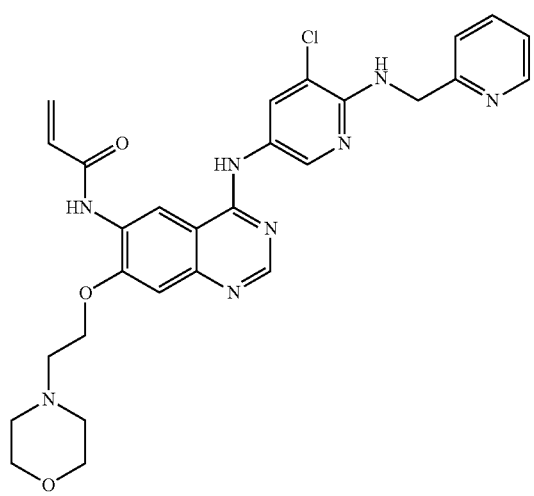 [SMILES: C=CC(=O)Nc1cc2c(Nc3cnc(NCc4ccccn4)c(Cl)c3)ncnc2cc1OCCN1CCOCC1] | 97 |

-continued
| Compound | No. |
|---|---|
| 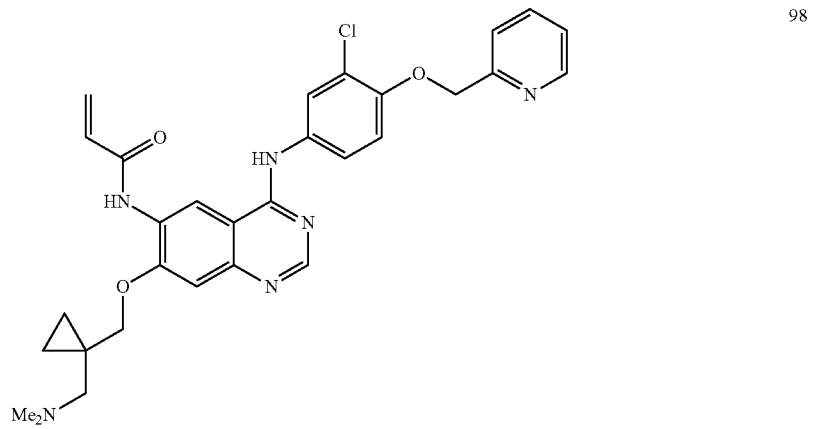 | 98 |
| 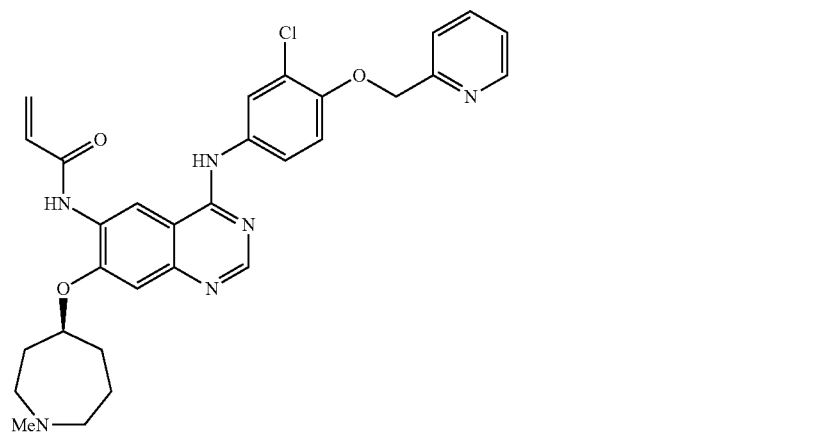 [SMILES: C=CC(=O)Nc1cc2c(Nc3ccc(OCc4ccccn4)c(Cl)c3)ncnc2cc1O[C@H]1CCCN(C)CC1] | 99 |
| 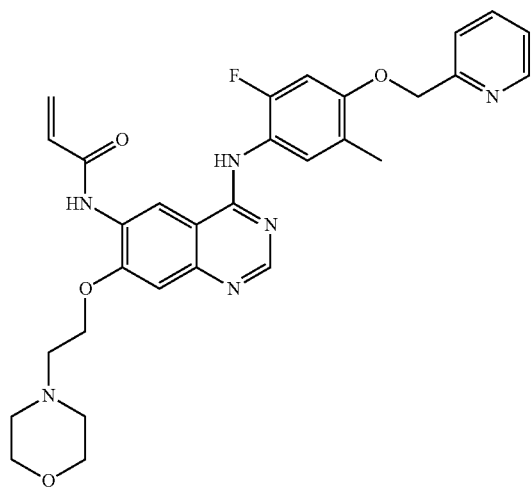 [SMILES: C=CC(=O)Nc1cc2c(Nc3cc(C)c(OCc4ccccn4)cc3F)ncnc2cc1OCCN1CCOCC1] | 100 |

-continued
| Compound | No. |
|---|---|
| 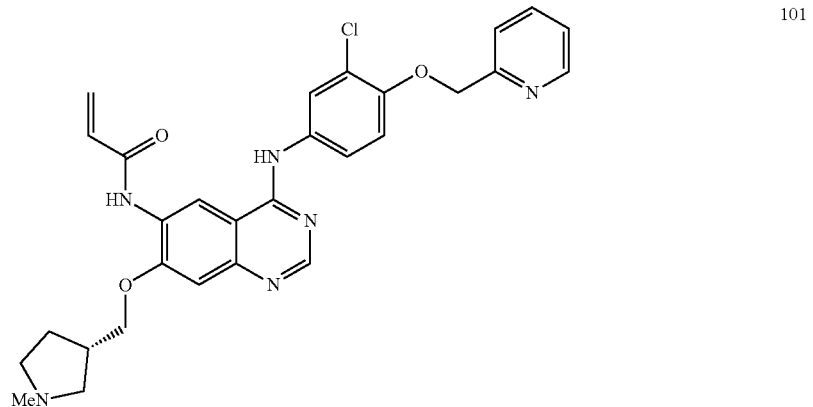 | 101 |
| 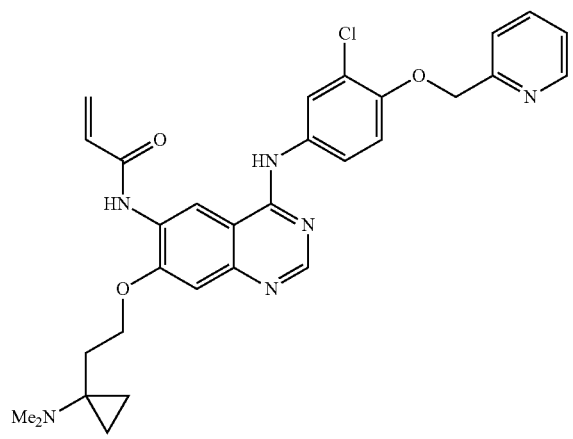 [SMILES: C=CC(=O)Nc1cc2c(Nc3ccc(OCc4ccccn4)c(Cl)c3)ncnc2cc1OCCC1(N(C)C)CC1] | 102 |
| 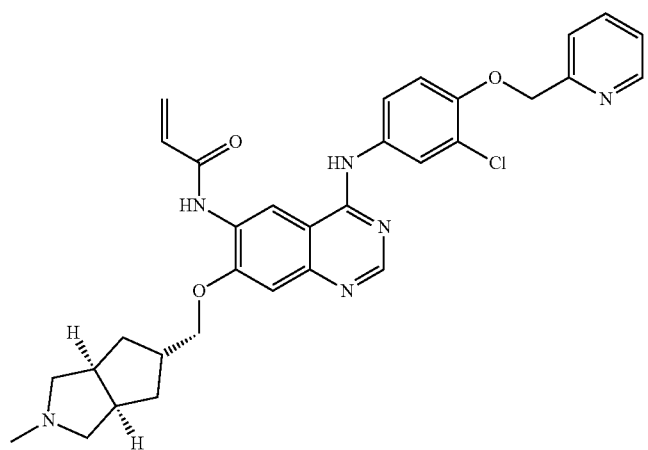 | 103 |

| Compound | No. |
|---|---|
| 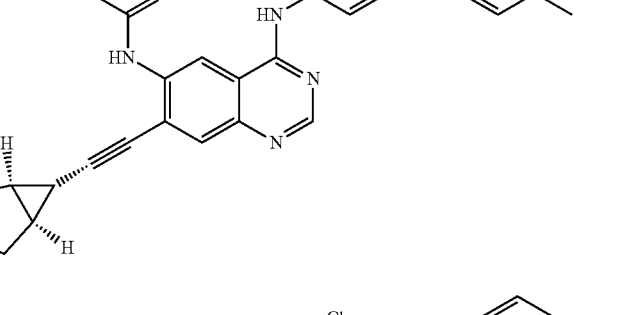 | 104 |
| 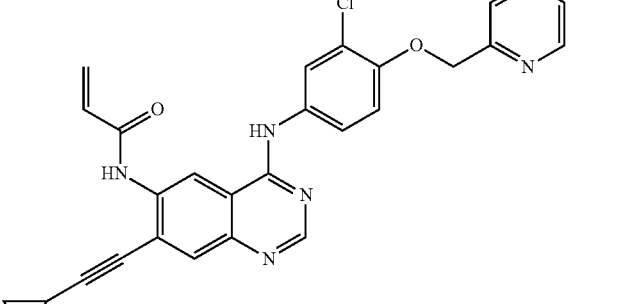 | 105 |
| 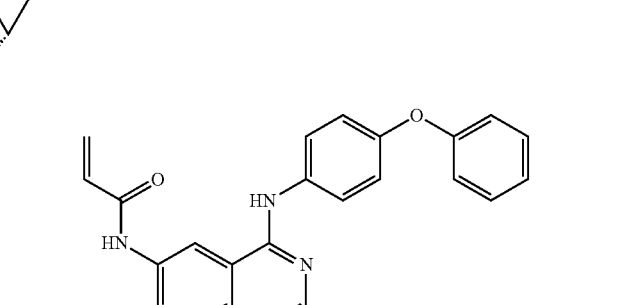 | 106 |
| 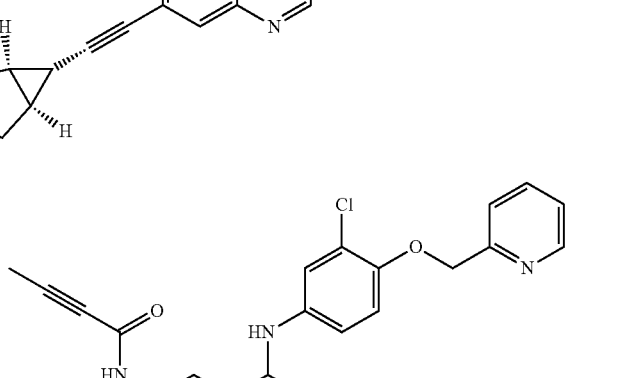 | 107 |

| Compound | No. |
|---|---|
| | 108 |
| | 109 |
| | 110 |

| Compound | No. |
|---|---|
| 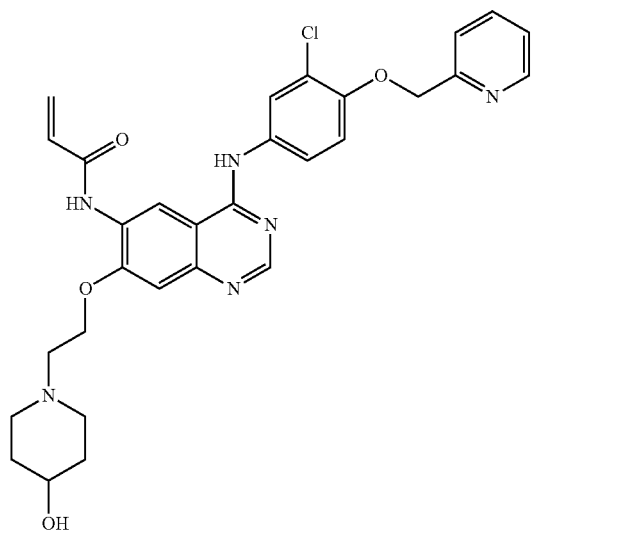 [SMILES: C=CC(=O)Nc1cc2c(Nc3ccc(OCc4ccccn4)c(Cl)c3)ncnc2cc1OCCN1CCC(O)CC1] | 111 |
| 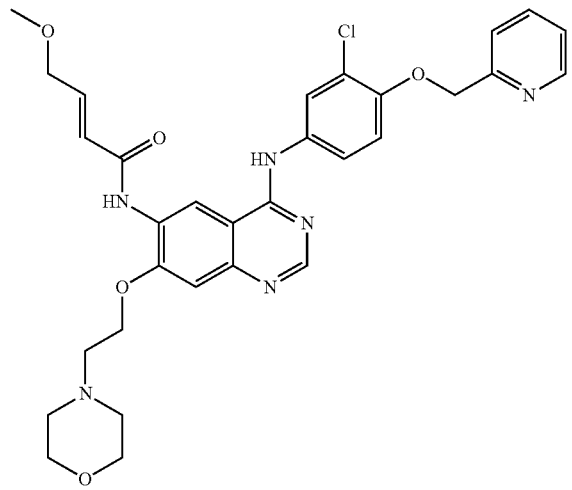 [SMILES: COC/C=C/C(=O)Nc1cc2c(Nc3ccc(OCc4ccccn4)c(Cl)c3)ncnc2cc1OCCN1CCOCC1] | 112 |
| 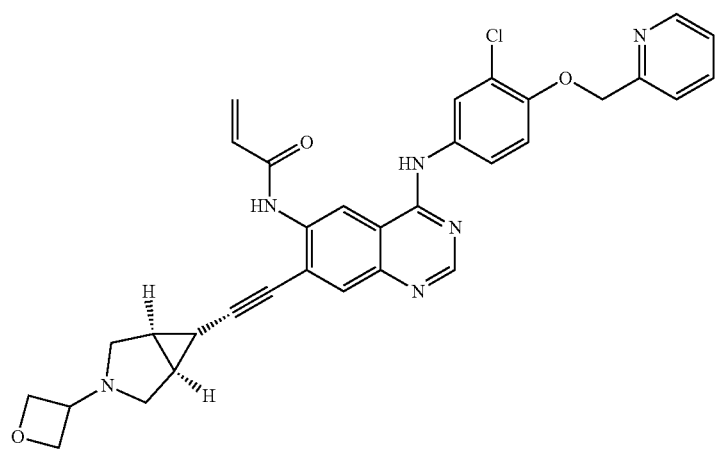 | 113 |

| Compound | No. |
|---|---|
| 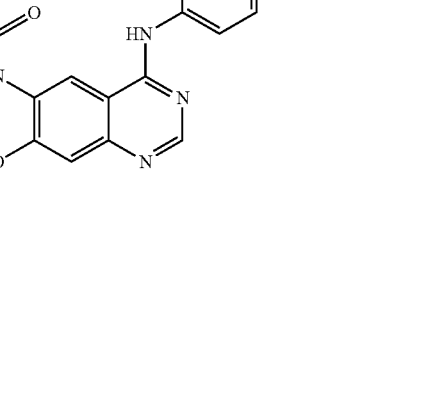 | 114 |
| 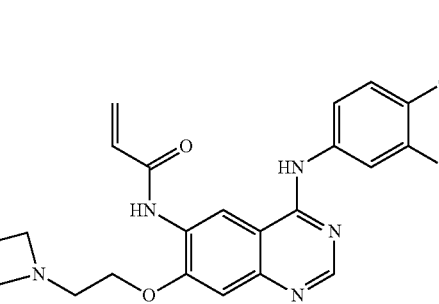 | 115 |
| 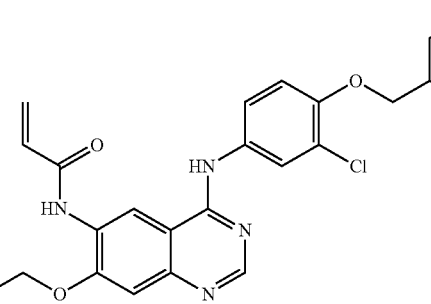 | 116 |
| 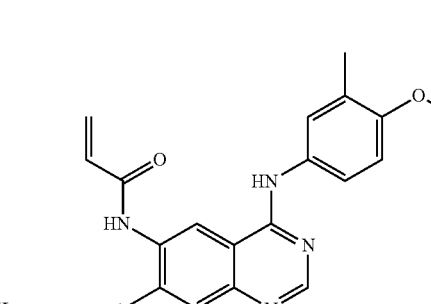 | 117 |

-continued

| Compound | No. |
|---|---|
| | 118 |
| | 119 |
| | 120 |
| | 121 |

-continued
| Compound | No. |
|---|---|
| 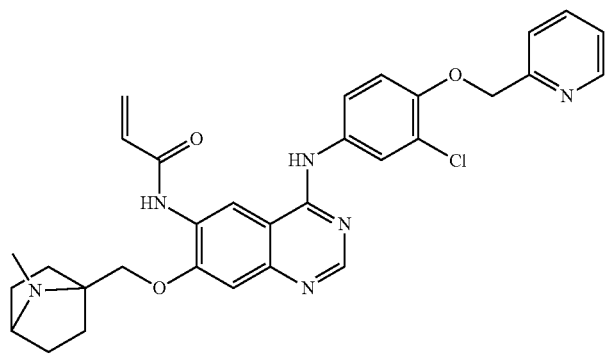 [SMILES: C=CC(=O)Nc1cc2c(Nc3ccc(OCc4ccccn4)c(Cl)c3)ncnc2cc1OCC12CCC(CC1)N2C] | 122 |
| 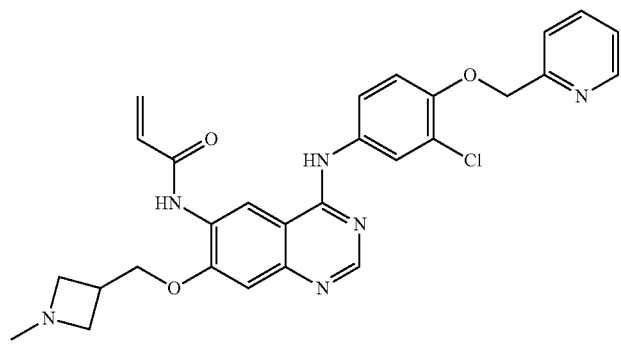 [SMILES: C=CC(=O)Nc1cc2c(Nc3ccc(OCc4ccccn4)c(Cl)c3)ncnc2cc1OCC1CN(C)C1] | 123 |
| 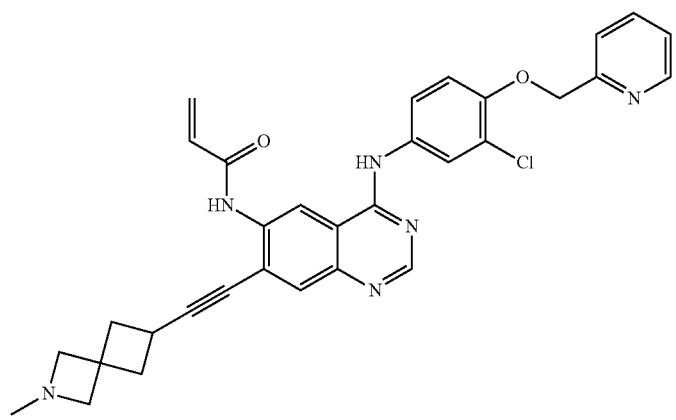 [SMILES: C=CC(=O)Nc1cc2c(Nc3ccc(OCc4ccccn4)c(Cl)c3)ncnc2cc1C#CC1CC2(C1)CN(C)C2] | 124 |
| 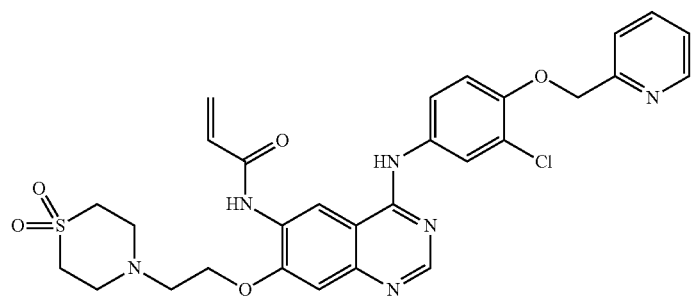 [SMILES: C=CC(=O)Nc1cc2c(Nc3ccc(OCc4ccccn4)c(Cl)c3)ncnc2cc1OCCN1CCS(=O)(=O)CC1] | 125 |

-continued
| Compound | No. |
|---|---|
| 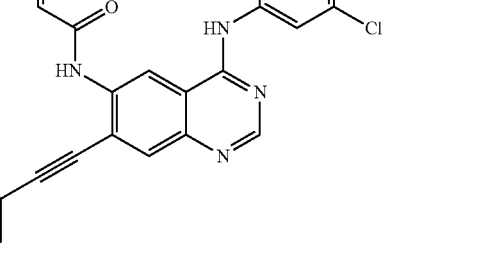 | 126 |
| 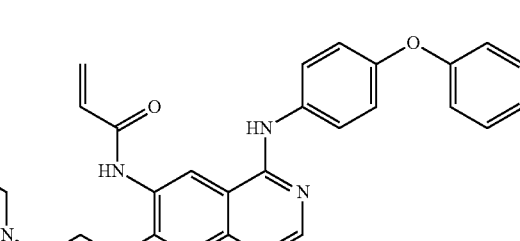 | 127 |
| 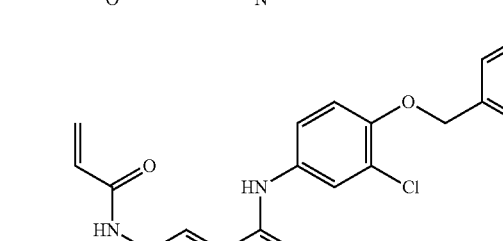 | 128 |
| 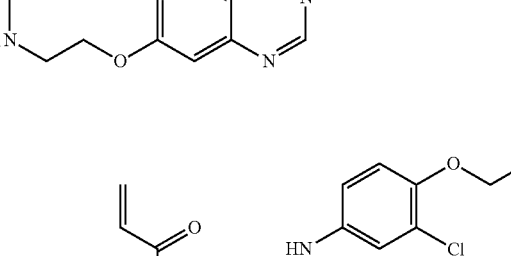 | 129 |
| 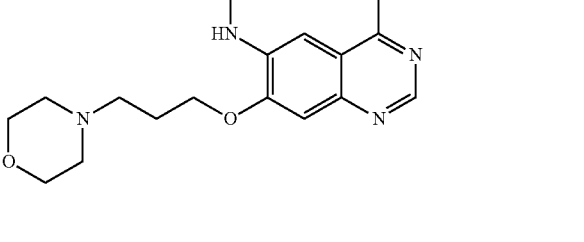 | 130 |

-continued
| Compound | No. |
|---|---|
| 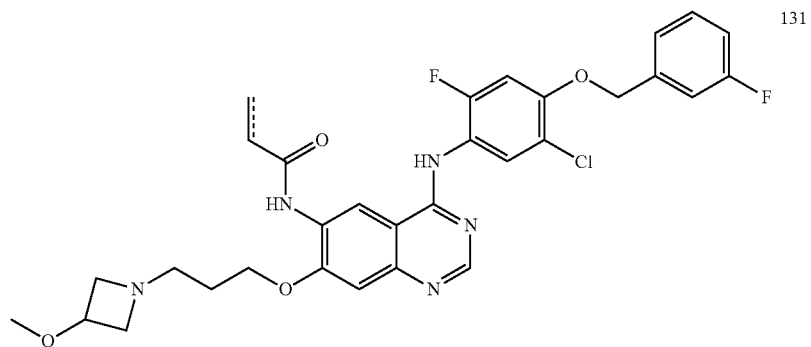 | 131 |
| 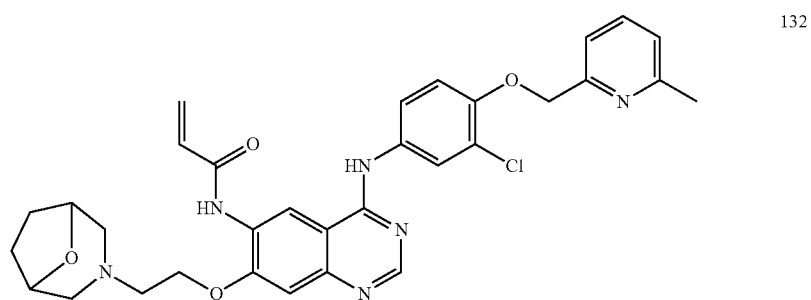 | 132 |
| 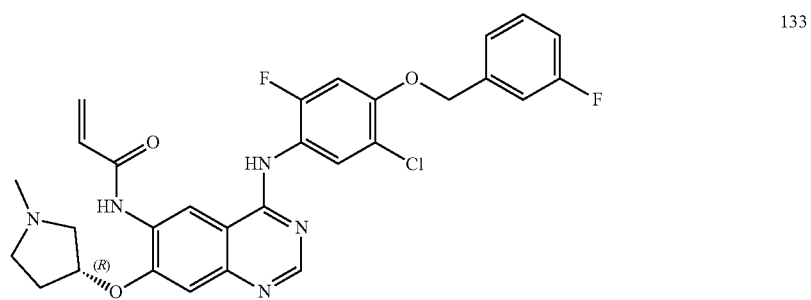 | 133 |
| 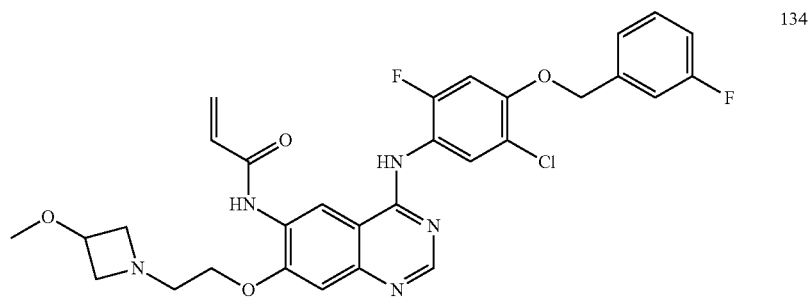 | 134 |
| 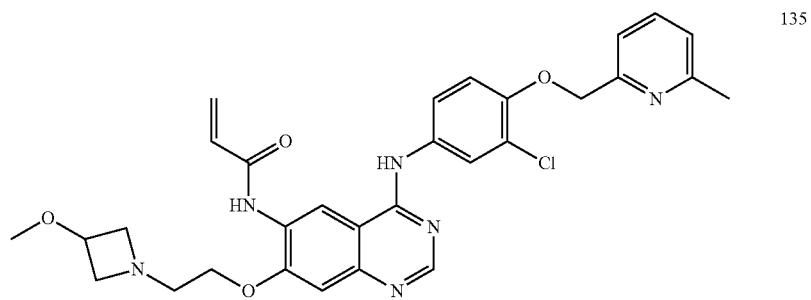 | 135 |

| Compound | No. |
|---|---|
| | 136 |
| | 137 |
| | 138 |
| | 139 |
| | 140 |

| Compound | No. |
|---|---|
| | 141 |
| | 142 |
| | 143 |
| | 144 |
| | 145 |

| Compound | No. |
|---|---|
| | 146 |
| | 147 |
| | 148 |
| | 149 |
| | 150 |

-continued
| Compound | No. |
|---|---|
| 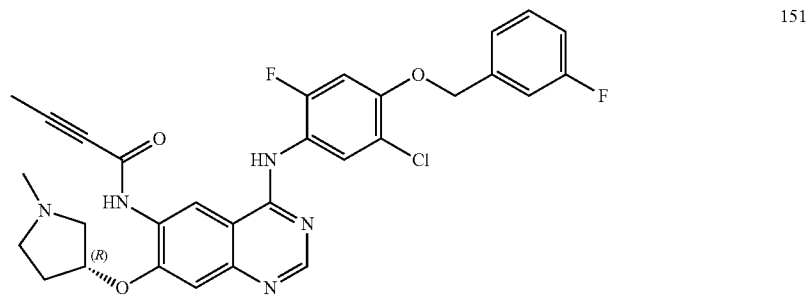 | 151 |
| 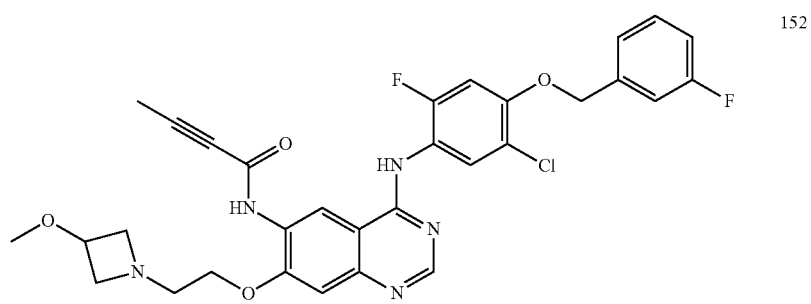 | 152 |
| 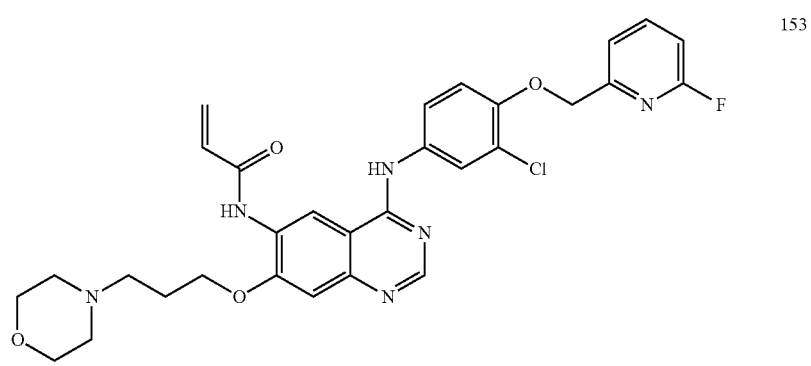 | 153 |
| 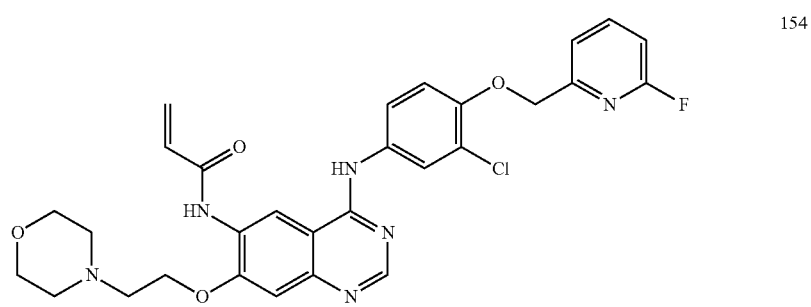 | 154 |
| 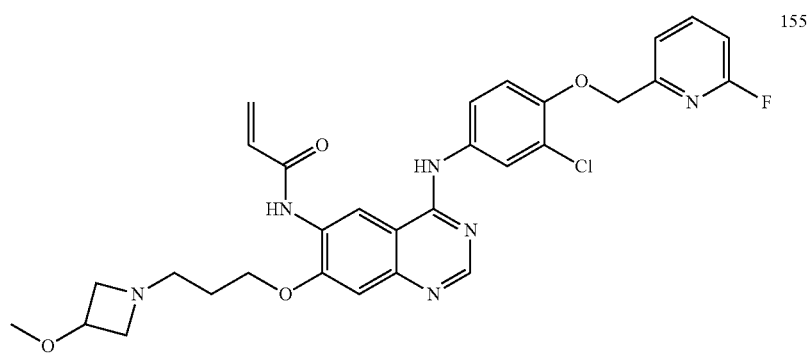 | 155 |

| Compound | No. |
|---|---|
| 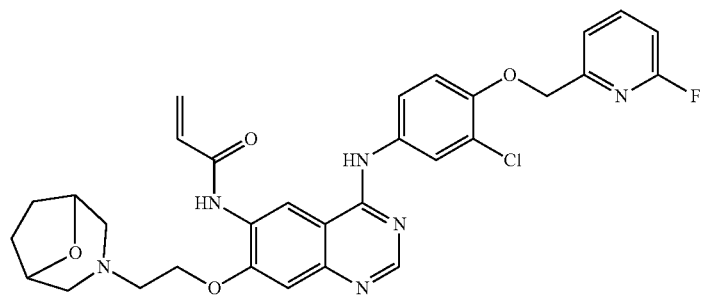 [SMILES: C=CC(=O)Nc1cc2c(Nc3ccc(OCc4cccc(F)n4)c(Cl)c3)ncnc2cc1OCCN1CC2CCC(C1)O2] | 156 |
| 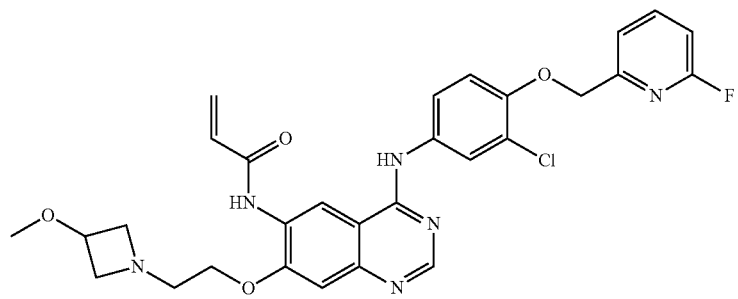 [SMILES: C=CC(=O)Nc1cc2c(Nc3ccc(OCc4cccc(F)n4)c(Cl)c3)ncnc2cc1OCCN1CC(OC)C1] | 157 |
| 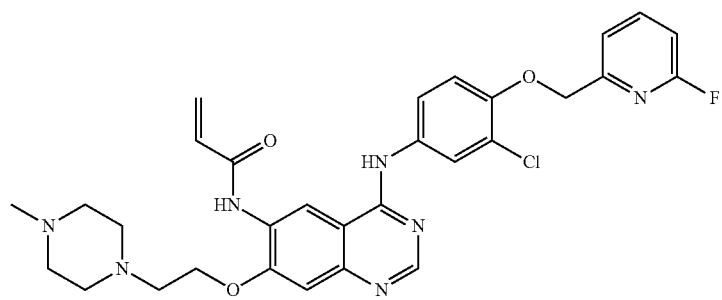 [SMILES: C=CC(=O)Nc1cc2c(Nc3ccc(OCc4cccc(F)n4)c(Cl)c3)ncnc2cc1OCCN1CCN(C)CC1] | 158 |
| 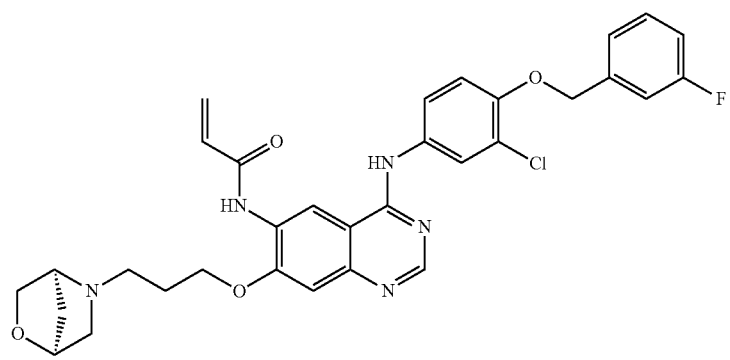 [SMILES: C=CC(=O)Nc1cc2c(Nc3ccc(OCc4cccc(F)c4)c(Cl)c3)ncnc2cc1OCCCN1C[C@@H]2C[C@H]1CO2] | 159 |

-continued
| Compound | No. |
|---|---|
| 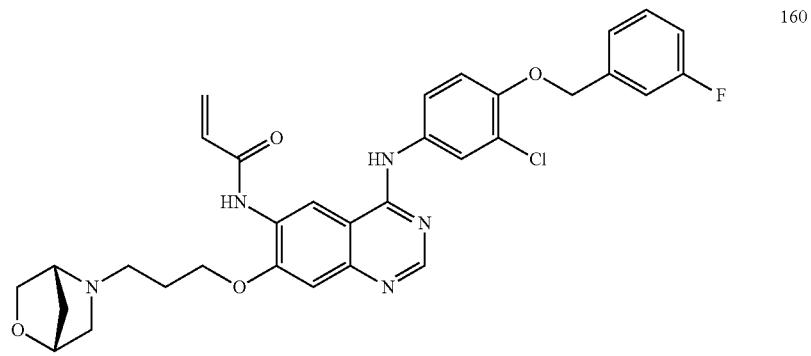 | 160 |
| 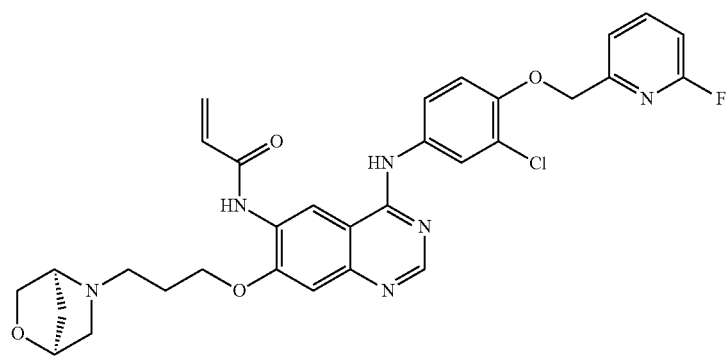 [SMILES: C=CC(=O)Nc1cc2c(Nc3ccc(OCc4cccc(F)n4)c(Cl)c3)ncnc2cc1OCCCN1C[C@@H]2C[C@H]1CO2] | 161 |
| 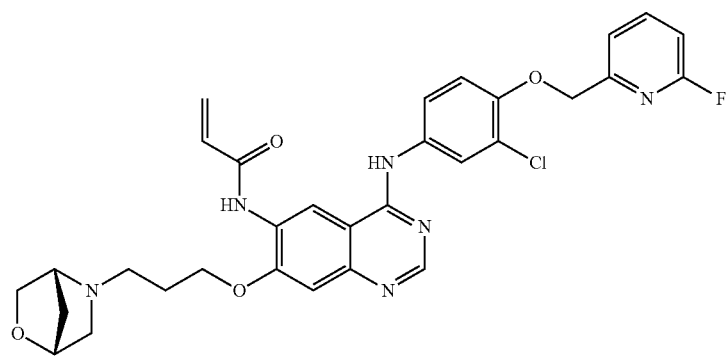 | 162 |
| 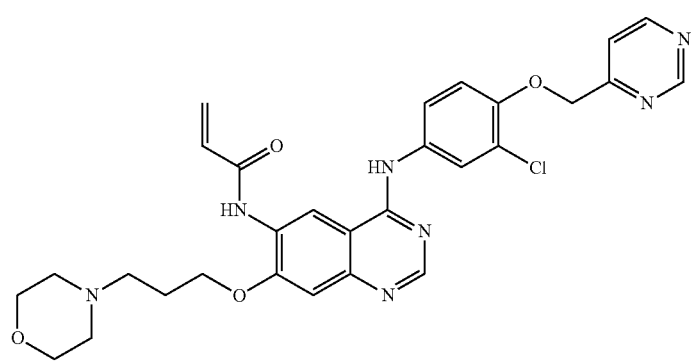 | 163 |

-continued

| Compound | No. |
|---|---|
| | 164 |
| | 165 |
| | 166 |
| | 167 |

-continued
| Compound | No. |
|---|---|
| 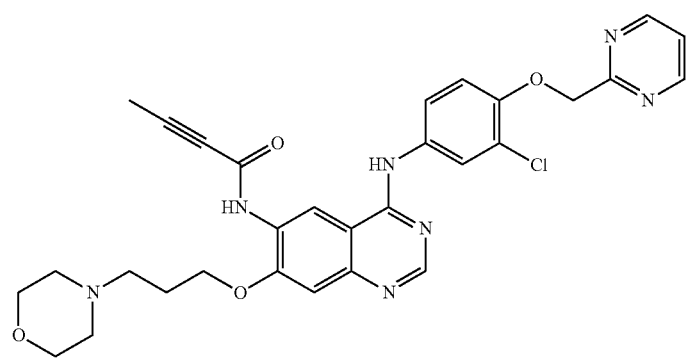 [SMILES: CC#CC(=O)Nc1cc2c(Nc3ccc(OCc4ncccn4)c(Cl)c3)ncnc2cc1OCCCN1CCOCC1] | 168 |
| 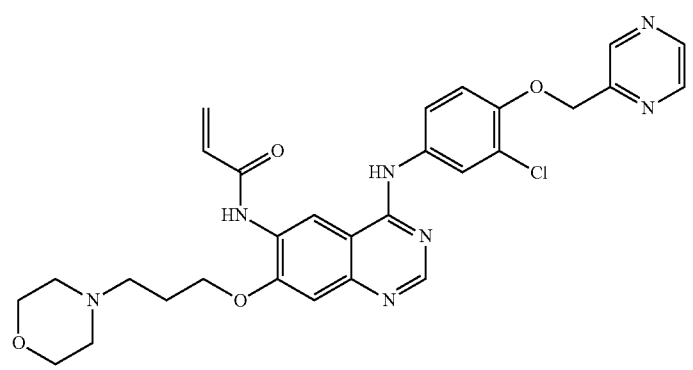 [SMILES: C=CC(=O)Nc1cc2c(Nc3ccc(OCc4cnccn4)c(Cl)c3)ncnc2cc1OCCCN1CCOCC1] | 169 |
| 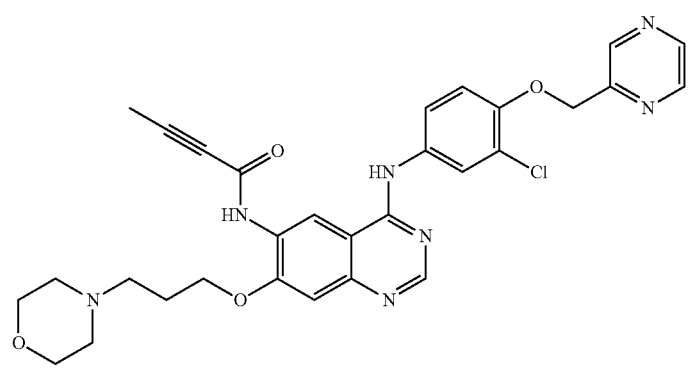 [SMILES: CC#CC(=O)Nc1cc2c(Nc3ccc(OCc4cnccn4)c(Cl)c3)ncnc2cc1OCCCN1CCOCC1] | 170 |
| 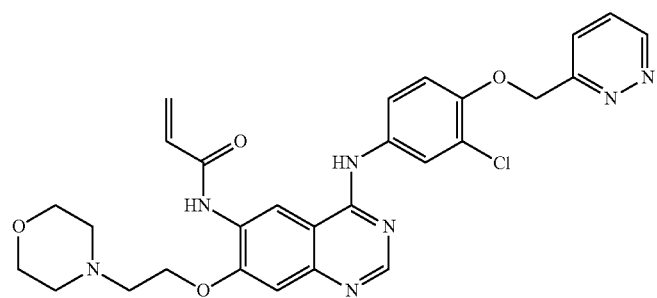 [SMILES: C=CC(=O)Nc1cc2c(Nc3ccc(OCc4cccnn4)c(Cl)c3)ncnc2cc1OCCN1CCOCC1] | 171 |

| Compound | No. |
|---|---|
| 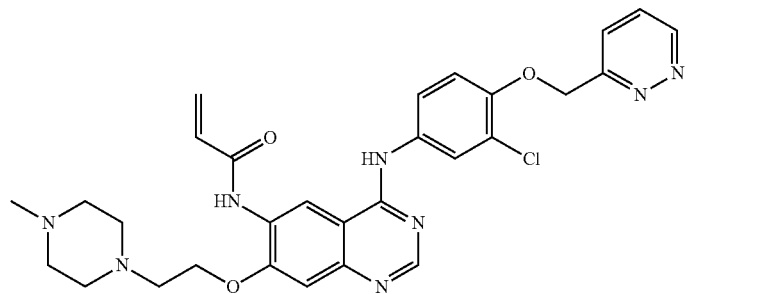 [SMILES: C=CC(=O)Nc1cc2c(Nc3ccc(OCc4cccnn4)c(Cl)c3)ncnc2cc1OCCN1CCN(C)CC1] | 172 |
| 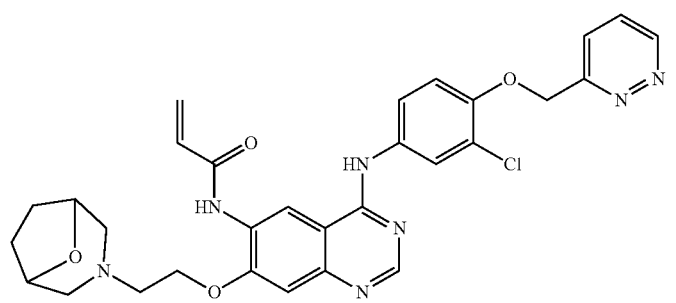 [SMILES: C=CC(=O)Nc1cc2c(Nc3ccc(OCc4cccnn4)c(Cl)c3)ncnc2cc1OCCN1CC2CCC(C1)O2] | 173 |
| 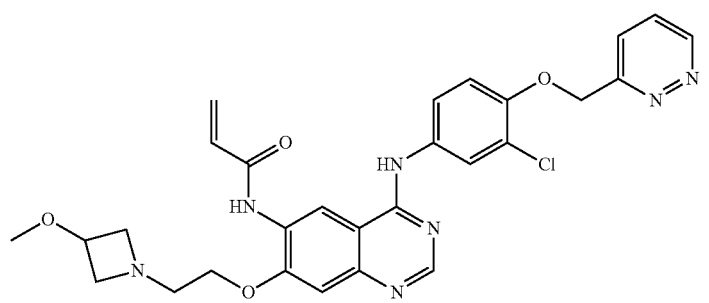 [SMILES: C=CC(=O)Nc1cc2c(Nc3ccc(OCc4cccnn4)c(Cl)c3)ncnc2cc1OCCN1CC(OC)C1] | 174 |
| 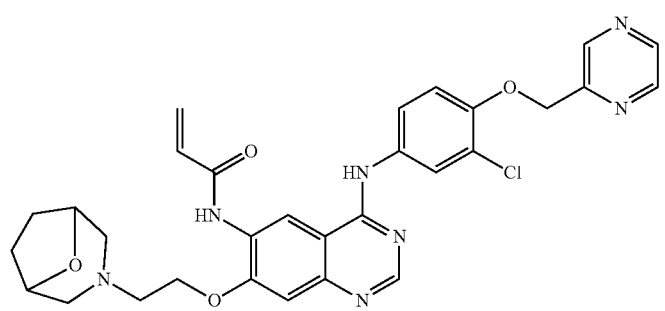 [SMILES: C=CC(=O)Nc1cc2c(Nc3ccc(OCc4cnccn4)c(Cl)c3)ncnc2cc1OCCN1CC2CCC(C1)O2] | 175 |
| 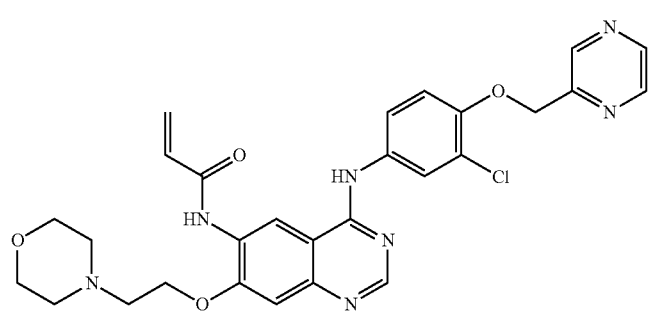 [SMILES: C=CC(=O)Nc1cc2c(Nc3ccc(OCc4cnccn4)c(Cl)c3)ncnc2cc1OCCN1CCOCC1] | 176 |

-continued

| Compound | No. |
|---|---|

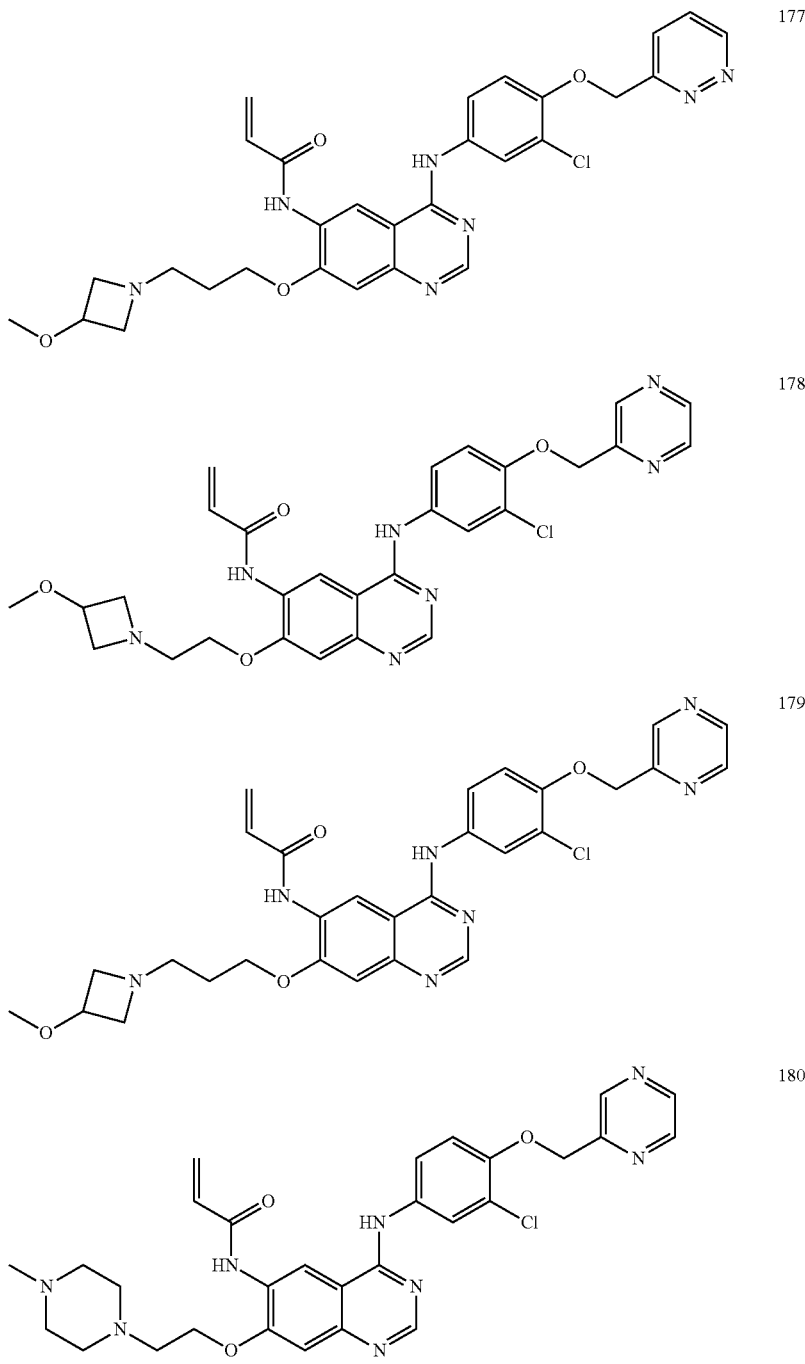

177

178

179

180

1: Synthesized according to general procedure A, wherein in step A.2 H$_2$N-X is 3-chloro-4-((3-fluorobenzyl)oxy)aniline (995 mg, 3.95 mmol); in step A.3 the NH nucleophile is N$^1$,N$^1$,N$^2$-trimethylethane-1,2-diamine (254 mg, 2.48 mmol); variant i) was used in step A.4; and variant ii) was used in step A.5; and 8% overall yield from II. $^1$H NMR (400 MHz, DMSO-d$_6$) δ=10.14 (br s, 1H), 9.69 (s, 1H), 8.84 (s, 1H), 8.47 (s, 1H), 7.98 (s, 1H), 7.71 (br d, J=8.8 Hz, 1H), 7.53-7.42 (m, 1H), 7.37 (s, 1H), 7.36-7.30 (m, 2H), 7.25 (br d, J=9.0 Hz, 1H), 7.19 (br t, J=8.6 Hz, 1H), 6.57 (br dd, J=10.0, 16.8 Hz, 1H), 6.34 (br d, J=16.8 Hz, 1H), 5.85 (br d, J=10.6 Hz, 1H), 5.25 (s, 2H), 2.99 (br d, J=5.8 Hz, 2H), 2.86 (s, 3H), 2.48-2.46 (m, 2H), 2.19 (s, 6H). MS (ESI) m/z 549.1 [M+H]$^+$ 2: Synthesized according to general procedure A, wherein in step A.2 H$_2$N-X is 3-chloro-4-((3-fluorobenzyl)oxy)aniline (995 mg, 3.95 mmol); in step A.3 the NH nucleophile is N-methyl-2-morpholino-ethanamine (234.49 mg, 1.63 mmol); variant i) was used in step A.4; and variant i) was used in step A.5; and 16% overall yield from II. $^1$H NMR (400 MHz, CDCl$_3$) δ=8.53 (s, 1H), 8.38 (s, 1H), 7.71 (br d, J=2.0 Hz, 1H), 7.43 (br dd, J=2.0, 8.8 Hz, 1H), 7.31-7.24 (m, 1H), 7.21-7.19 (m, 1H), 7.18-7.10 (m, 2H), 6.94 (br t, J=7.2 Hz, 1H), 6.85 (d, J=9.0 Hz, 1H), 5.05 (s, 2H), 3.59-3.44 (m, 4H), 3.26 (br t, J=6.6 Hz, 2H), 2.87 (s, 3H), 2.53 (br t, J=6.6 Hz, 2H), 2.41-2 28 (m, 4H), 1.97 (s, 2H). MS (ESI) m/z 567.1 [M+H]$^+$ 3: Synthesized according to general procedure A, wherein in step A.2 H$_2$N-X is 3-chloro-4-((3-fluorobenzyl)oxy)aniline (995 mg, 3.95 mmol); in step A.3 the OH nucleophile is 3-morpholinopropan-1-ol (275 mg, 1.90 mmol); variant ii) was used in step A.4; and variant i) was used in step A.5; and 2% overall yield from II. $^1$H NMR (400 MHz, DMSO-d$_6$) δ=9.69 (s, 1H), 9.61 (s, 1H), 8.84 (s, 1H), 8.49 (s, 1H), 7.99 (d, J=2.5 Hz, 1H), 7.70 (dd, J=2.5, 8.9 Hz, 1H), 7.53-7.42 (m, 1H), 7.37-7.29 (m, 2H), 7.28-7.22 (m, 2H), 7.22-7.14 (m, 1H), 6.71 (br dd, J=10.3, 17.2 Hz, 1H), 6.32 (dd, J=1.8, 17.2 Hz, 1H), 5.94-5.74 (m, 1H), 5.25 (s, 2H), 4.26 (t, J=6.4 Hz, 2H), 3.58 (t, J=4.6 Hz, 4H), 2.49-2.45 (m, 2H), 2.38 (br s, 4H), 1.99 (quin, J=6.6 Hz, 2H). MS (ESI) m/z 592.0 [M+H]$^+$ 4: Synthesized according to general procedure A, wherein in step A.2 H$_2$N-X is 3-chloro-4-(pyridin-2-ylmethoxy)aniline (3.50 g, 14.9 mmol); in step A.3 the OH nucleophile is 3-morpholinopropan-1-ol (275 mg, 1.90 mmol); variant ii) was used in step A.4; and variant i) was used in step A.5; and 2% overall yield from II. $^1$H NMR (400 MHz, CDCl$_3$) δ=9.05 (s, 1H), 8.89 (s, 1H), 8.63-8.58 (m, 2H), 7.92 (s, 1H), 7.88 (d, J=2.4 Hz, 1H), 7.79-7.73 (m, 1H), 7.67 (d, J=7.6 Hz, 1H), 7.50 (dd, J=8.8, 2.8 Hz, 1H), 7.26-7.23 (m, 1H), 7.00 (d, J=5.2 Hz, 1H), 5.30 (s, 2H), 4.35 (t, J=5.6 Hz, 2H), 3.82-3.78 (m, 4H), 2.90 (t, J=5.6 Hz, 2H), 2.63-2.59 (m, 4H), 2.08 (s, 3H). MS (ESI) m/z 573.4 [M+H]$^+$ 5: Synthesized according to general procedure A, wherein in step A.2 H$_2$N-X is 3-chloro-4-(pyridin-2-ylmethoxy)aniline (3.50 g, 14.9 mmol); in step A.3 the NH nucleophile is N-methyl-2-morpholinoethanamine (508 mg, 3.52 mmol); variant i) was used in step A.4; and variant ii) was used in step A.5; and 4% overall yield from II. $^1$H NMR (400 MHz, CDCl$_3$) δ=9.05 (s, 1H), 8.89 (s, 1H), 8.63-8.58 (m, 2H), 7.92 (5, 1H), 7.88 (d, J=2.4 Hz, 1H), 7.79-7.73 (m, 1H), 7.67 (d, J=7.6 Hz, 1H), 7.50 (dd, J=8.8, 2.8 Hz, 1H), 7.26-7.23 (m, 1H), 7.00 (d, J=5.2 Hz, 1H), 5.30 (s, 2H), 4.35 (t, J=5.6 Hz, 2H), 3.82-3.78 (m, 4H), 2.90 (t, J=5.6 Hz, 2H), 2.63-2.59 (m, 4H), 2.08 (s, 3H). MS (ESI) m/z 573.4 [M+H]$^+$ 6: Synthesized according to general procedure A, wherein in step A.2 H$_2$N-X is 5-chloro-2-fluoro-4-((3-fluorobenzyl)oxy)aniline (700 mg, 2.60 mmol); in step A.3 the OH nucleophile is 2-morpholinoethanol (569 mg, 4.34 mmol, 532 uL); variant i) was used in step A.4; and variant ii) was used in step A.5; and 1% overall yield from II. $^1$H NMR (400 MHz, DMSO-d$_6$) δ=9.67 (br d, J=9.0 Hz, 2H), 8.86 (s, 1H), 8.38 (s, 1H), 7.60 (d, J=8.0 Hz, 1H) 7.54-7.46 (m, 1H) 7.40-7.29 (m, 4H) 7.26-7.15 (m, 1H) 6.71 (dd, J=17.0, 10.2 Hz, 1H), 6.38-6.25 (m, 1H), 5.87-5.78 (m, 1H), 5.30 (s, 2H), 4.35 (t, J=5.8 Hz, 2H) 3.63-3.53 (m, 4 H) 2.84 (t, J=5.6 Hz, 2H) 2.52-2.53 (m, 4H). MS (ESI) m/z 596.3 [M+]$^+$ 7: Synthesized according to general procedure A starting from intermediate V (300 mg, 530 umol) obtained in 5, variant ii) was used in step A.5; and 16% overall yield from V. $^1$H NMR (400 MHz, DMSO-d$_6$) δ=9.75 (br s, 1H), 9.67 (br s, 1H), 8.69-8.55 (m, 2H), 8.47 (s, 1H), 8.00 (d, J=2.4 Hz, 1H), 7.89 (dt, J=7.6, 1.6 Hz, 1H), 7.70 (dd, J=8.8, 2.2 Hz, 1H), 7.59 (d, J=7.8 Hz, 1H), 7.38 (dt, J=6.2, 1.0 Hz, 1H), 7.29 (s, 1H), 7.25 (d, J=9.2 Hz, 1H), 6.68 (br dd, J=16.8, 10.0 Hz, 1H), 6.33 (dd, J=17.0, 2.0 Hz, 1H), 5.87-5.79 (m, 1H), 5.29 (s, 2H), 3.57-3.44 (m, 4H), 3.14 (br t, J=7.0 Hz, 2H), 2.88 (s, 3H), 2.53 (br s, 2H), 2.31 (br s, 4H). MS (ESI) m/z 574.1 [M+H]$^+$ 8: Synthesized according to general procedure A, wherein in step A.2 H$_2$N-X is 3-chloro-4-(pyridin-2-ylmethoxy)aniline (3.50 g, 14.9 mmol); in step A.3 the OH nucleophile is 2-morpholinoethanol (179 mg, 1.37 mmol); variant i) was used in step A.4; and variant i) was used in step A.5; and 21% overall yield from II. $^1$H NMR (400 MHz, DMSO-d$_6$) δ=9.69 (s, 1H), 9.62 (s, 1H), 8.83 (s, 1H), 8.60 (d, J=4.8 Hz, 1H), 8.49 (s, 1H), 7.99 (d, J=2.4 Hz, 1H), 7.88 (dt, J=1.2, 7.6 Hz, 1H), 7.69 (dd, J=2.4, 9.0 Hz, 1H), 7.59 (d, J=8.0 Hz, 1H), 7.41-7.34 (m, 1H), 7.31 (s, 1H), 7.25 (d, J=9.2 Hz, 1H), 6.68 (br dd, J=10.8, 17.2 Hz, 1H), 6.31 (dd, J=16.8, 1.2 Hz, 1H), 5.82 (br d, J=11.6 Hz, 1H), 5.29 (s, 2H), 4.34 (t, J=5.6 Hz, 2H), 3.57 (t, J=4.4 Hz, 4H), 3.32 (br s, 4H), 2.82 (t, J=5.6 Hz, 2H). MS (ESI) m/z 561.4 [M+H]$^+$ 9: Synthesized according to general procedure A, wherein in step A.2 H$_2$N-X is 4-(2-pyridylmethoxy)aniline (3.00 g, 14.9 mmol); in step A.3 the OH nucleophile is 2-imidazol-1-ylethanol (137 mg, 1.23 mmol); variant i) was used in step A.4; and variant ii) was used in step A.5; and 1% overall yield from II. $^1$H NMR (400 MHz, DMSO-d$_6$) δ=9.63 (s, 1H), 9.55 (s, 1H), 8.84 (s, 1H), 8.59 (d, J=3.6 Hz, 1H), 8.41 (s, 1H), 7.85 (dt, J=1.6, 7.6 Hz, 1H), 7.77 (s, 1H), 7.63 (d, J=9.2 Hz, 2H), 7.54 (d, J=7.6 Hz, 1H), 7.37-7.33 (m, 1H), 7.32 (s, 1H), 7.23 (s, 1H), 7.03 (d, J=8.8 Hz, 2H), 6.86 (s, 1H), 6.72 (dd, J=10.8, 17.2 Hz, 1H), 6.33 (dd, J=2.0, 17.2 Hz, 1H), 5.86 (d, J=11.6 Hz, 1H), 5.19 (s, 2H), 4.47 (br dd, J=3.6, 10.4 Hz, 4H). MS (ESI) m/z 508.3 [M+H]30

10: Synthesized according to general procedure A starting from intermediate III (800 mg, 1.88 mmol) obtained in 5, wherein in step A.3 the OH nucleophile is 2-(1H-imidazol-1-yl)ethanol (632 mg, 5.64 mmol); variant i) was used in step A.4; and variant ii) was used in step A.5; and 1.5% overall yield from III. $^1$H NMR (400 MHz, DMSO-d$_6$) δ=9.71 (s, 1H), 9.55 (br s, 1H), 8.87 (s, 1H), 8.60 (br d, J=4.4 Hz, 1H), 8.49 (s, 1H), 7.99 (s, 1H), 7.89 (t, J=7.8 Hz, 1H), 7.78 (s, 1H), 7.69 (br d, J=7.2 Hz, 1H), 7.59 (d, J=7.8 Hz, 1H), 7.40-7.35 (m, 1H), 7.33 (s, 1H), 7.29-7.17 (m, 2H), 6.87 (s, 1H), 6.73 (dd, J=10.2, 17.0 Hz, 1H), 6.35 (br d, J=16.8 Hz, 1H), 5.88 (br d, J=11.2 Hz, 1H), 5.29 (s, 2H), 4.49 (br s, 4H). MS (ESI) m/z 542.4 [M+H]$^+$ 12: Synthesized according to general procedure A starting from intermediate III (800 mg, 1.88 mmol) obtained in 4, wherein in step A.3 the NH nucleophile is N-methyl-3-morpholinopropan-1-amine (595 mg, 3.76 mmol); variant i) was used in step A.4; and variant i) was used in step A.5; and 40% overall yield from III. $^1$H NMR (400 MHz, CDCl$_3$) δ=9.07 (s, 1H), 8.84 (s, 1H), 8.67 (s, 1H), 8.64-8.58 (m, 1H), 7.92 (d, J=2.6 Hz, 1H), 7.81-7.73 (m, 2H), 7.71-7.66 (m, 1H), 7.63 (s, 1H), 7.54 (dd, J=8.8, 2.6 Hz, 1H), 7.28-7.23 (m, 1H), 7.03 (d, J=8.8 Hz, 1H), 6.57-6.49 (m, 1H), 6.42-6.33 (m, 1H), 5.90 (dd, J=10.2, 1.0 Hz, 1H), 5.32 (s, 2H), 3.70 (t, J=4.6 Hz, 4H), 3.09-3.02 (m, 2H), 2.79 (s, 3H), 2.47-2.36 (m, 6H), 1.75 (br t, J=7.4 Hz, 2H). MS (ESI) m/z 588.4 [M+H]$^+$ 13: To a solution from intermediate III (600 mg, 1.41 mmol, 1.00 eq) obtained in 4 in dimethysulfoxide (20.0 mL) was added tert-butyl 2-(hydroxymethyl)pyrrolidine-1-carboxylate (369 mg. 1.83 mmol, 1.30 eq) and potassium tert-butoxide (316 mg, 2.82 mmol, 2.00 eq). The mixture was stirred at 25° C. for 12 h. The reaction mixture was diluted with water (100 mL), filtered and the filter cake was concentrated under reduced pressure to give tert-butyl 2-(((4-(3-chloro-4-(pyridin-2-ylmethoxy)phenyl)amino)-6- nitroquinazolin-7-yl)oxy)methyl)pyrrolidine-1-carboxylate (660 mg, crude) as a yellow solid, which was used into the next step without further purification. To a solution of tert-butyl 2-(((4-(3-chloro-4-(pyridin-2-ylmethoxy)phenyl)amino)-6-nitroquinazolin-7-yl)oxy)methyl)pyrrolidine-1-carboxylate (660 mg, 1.09 mmol, 1.00 eq) in dichloromethane (40.0 mL) and methanol (10.0 mL) was added nickel(ii) chloride hexahydrate (517 mg, 2.17 mmol, 2.00 eq) and sodium borohydride (165 mg, 4.35 mmol, 4.00 eq). The mixture was stirred at 0° C. for 0.5 h. The reaction mixture was concentrated under reduced pressure to give a residue. To the residue was added dichloromethane (20.0 mL) and the mixture was filtered. The filtrate was concentrated under reduced pressure to give tert-butyl 2-(((6-amino-4-((3-chloro-4-(pyridin-2-ylmethoxy)phenyl)amino)quinazolin-7-yl)oxy)methyl)pyrrolidine-1-carboxylate (500 mg, crude) as a yellow solid, which was used into the next step without further purification. To a solution of tert-butyl 2-(((6-amino-4-((3-chloro-4-(pyridin-2-ylmethoxy)phenyl)amino)quinazolin-7-yl)oxy)methyl)pyrrolidine-1-carboxylate (300 mg, 520 umol, 1.00 eq) in dimethyl formamide (5.00 mL) was added triethylamine (105 mg, 1.04 mmol, 145 uL, 2.00 eq) and acrylic anhydride (98.3 mg, 780 umol, 1.50 eq). The mixture was stirred at 25° C. for 0.5 h. The reaction mixture was filtered and the filtrate was concentrated under reduced pressure to give a residue. The residue was purified by prep-HPLC to give tert-butyl 2-(((6-acrylamido-4-((3-chloro-4-(pyridin-2-ylmethoxy)phenyl)amino)quinazolin-7-yl)oxy)methyl)pyrrolidine-1-carboxylate (140 mg, 222 umol, 43% yield) as a yellow solid. $^1$H NMR (400 MHz, CDCl$_3$) δ=9.62 (br s, 1H), 9.19 (s, 1H), 8.70-8.57 (m, 2H), 7.91 (d, J=2.6 Hz, 1H), 7.82-7.74 (m, 1H), 7.71-7.66 (m, 1H), 7.62 (br s, 1H), 7.52 (dd, J=8.8, 2.6 Hz, 1H), 7.26 (br d, J=7.2 Hz, 1H), 7.14 (s, 1H), 7.02 (d, J=9.0 Hz, 1H), 6.88 (br dd, J=16.8, 10.2 Hz, 1H), 6.54 (d, J=16.0 Hz, 1H), 5.83 (br d, J=10.4 Hz, 1H), 5.32 (s, 2H), 4.56 (br s, 1H), 4.15-3.96 (m, 2H), 3.63-3.39 (m, 2H), 2.15-1.87 (m, 4H), 1.49 (s, 9H). MS (ESI) m/z 631.4 [M+H]$^+$ To a solution of tert-butyl 2-(((6-acrylamido-4-((3-chloro-4-(pyridin-2-ylmethoxy)phenyl)amino)quinazolin-7-yl)oxy)methyl)pyrrolidine-1-carboxylate (70.0 mg, 111 umol, 1.00 eq) in dichloromethane (1.0 mL) was added the mixed solution of trifluoroacetic acid (152 mg, 1.33 mmol, 98.6 uL, 12.0 eq) and dichloromethane (9.0 mL) dropwise. After addition, the mixture was stirred at 25° C. for 1 h. The reaction mixture was concentrated under reduced pressure to give a residue. The residue was purified by prep-HPLC to give 15 (24.36 mg, 38.3 umol, 35% yield) as a yellow solid. $^1$H NMR (400 MHz, CDCl$_3$) δ=9.38 (br s, 1H), 9.01 (br s, 1H), 8.58 (br d, J=4.6 Hz, 1H), 8.36 (s, 2H), 7.77 (td, J=7.6, 1.4 Hz, 1H), 7.72-7.61 (m, 2H), 7.42 (br d, J=8.4 Hz, 1H), 7.29-7.23 (m, 2H), 6.98 (s, 1H), 6.89 (d, J=9.0 Hz, 1H), 6.49 (br dd, J=16.6, 10.2 Hz, 1H), 6.37-6.22 (m, 1H), 5.52 (br d, J=10.4 Hz, 1H), 5.21 (s, 2H), 4.35-4.15 (m, 2H), 3.87 (br d, J=7.2 Hz, 1H), 3.37 (br d, J=7.4 Hz, 2H), 2.13 (br s, 2H), 2.06 (br d, J=7.4 Hz, 1H), 1.87-1.72 (m, 1H). MS (ESI) m/z 531.4 [M+H]$^+$ 14: Synthesized according to general procedure A starting from intermediate III (800 mg, 1.88 mmol) obtained in 4, wherein in step A.3 the OH nucleophile is 1-methylpyrrolidin-2-yl)methanol (216 mg, 1.88 mmol); variant i) was used in step A.4; and variant i) was used in step A.5; and 7% overall yield from III. $^1$H NMR (400 MHz, DMSO-d$_6$) δ=9.68 (s, 1H), 9.59 (s, 1H), 8.77 (s, 1H), 8.60 (d, J=4.4 Hz, 1H), 8.49 (s, 1H), 8.00 (d, J=2.4 Hz, 1H), 7.88 (dt, J=7.6, 2.0 Hz, 1H), 7,70 (dd, J=8.8, 2.8 Hz, 1H), 7.59 (d, J=8.0 Hz, 1H), 7.37 (dd, J=7.6, 5.6 Hz, 1H), 7.29 (s, 1H), 7.25 (d, J=9.2 Hz, 1H), 6.63 (dd, J=17.2, 10.4 Hz, 1H), 6.30 (dd, J=16.8, 1.6 Hz, 1H), 5.83-5.78 (m, 1H), 5.29 (s, 2H), 4.21-4.15 (m, 1H), 4.12-4.06 (m, 1H), 2.99-2.94 (m, 1H), 2.71 (br dd, J=8.8, 6.0 Hz, 1H), 2.38 (s, 3 H), 2.25-2.18 (m, 1H), 2.03-1.95 (m, 1H), 1.73-1.65 (m, 3H). MS (ESI) m/z 545.5 [M+H]$^+$ 15: A mixture of III (600 mg, 1.41 mmol, 1.00 eq) obtained in 4 tert-butyl 3-hydroxypyrrolidine-1-carboxylate (396 mg, 2.11 mmol, 1.50 eq) and potassium tert-butoxide (316 mg, 2.82 mmol, 2.00 eq) in dimethylsulfoxide (4.00 mL) was stirred at 25° C. for 1 h. The reaction mixture was quenched by addition of water (50.0 mL) and extracted with ethyl acetate (3×100 mL). The combined organic layers were washed with brine (3×50.0 mL), dried over sodium sulfate, filtered and concentrated under reduced pressure to give tert-butyl 3-(((4-(3-chloro-4-(pyridin-2-ylmethoxy)phenyl)amino)-6-nitroquinazolin-7-yl)oxy)pyrrolidine-1-carboxylate (900 mg, crude) as a yellow solid. To a mixture of tert-butyl 3-((4-((3-chloro-4-(pyridin-2-ylmethoxy)phenyl)amino)-6-nitroquinazolin-7-yl)oxy)pyrrolidine-1-carboxylate (900 mg, 1.52 mmol, 1.00 eq) and nickel(ii) chloride hexahydrate (361 mg, 1.52 mmol, 1.00 eq) in dichloromethane (10.0 mL) and methanol (10.0 mL) was added sodium borohydride (115 mg, 3.04 mmol, 2.00 eq) at 25° C. The mixture was stirred at 25° C. for 0.5 h. The reaction mixture was concentrated to give a residue. The residue was dissolved in dichloromethane (200 mL) and filtered. The filtrate was concentrated to give tert-butyl 3-((6-amino-4-((3-chloro-4-(pyridin-2-ylmethoxy)phenyl)amino)quinazolin-7-yl)oxy)pyrrolidine-1-carboxylate (700 mg, crude) as yellow oil. To a solution of tert-butyl 3-((6-amino-4-((3-chloro-4-(pyridin-2-ylmethoxy)phenyl)amino)quinazolin-7-yl)oxy)pyrrolidine-1-carboxylate (300 mg, 533 umol, 1.00 eq) and triethylamine (107 mg, 1.07 mmol, 2.00 eq) in dimethyl formamide (3.00 mL) was added acrylic anhydride (67.2 mg, 533 umol, 1.00 eq) at 25° C. The mixture was stirred at 25° C. for 0.5 h. The reaction mixture was filtered. The filtrate was purified by prep-HPLC and lyophilized to give tert-butyl 3-((6-acrylamido-4-((3-chloro-4-(pyridin-2-ylmethoxy)phenyl)amino)quinazolin-7-yl)oxy)pyrrofidine-1-carboxylate (150 mg, 243 umol, 46% yield) as a yellow solid. $^1$H NMR (400 MHz, CDCl$_3$) δ=9.15 (s, 1H), 8.73-8.56 (m, 2H), 8.08 (br s, 1H), 7.90 (d, J=2.6 Hz, 1H), 7.81-7.75 (m, 1H), 7.69 (d, J=7.8 Hz, 1H), 7.57 (br s, 1H), 7.53 (dd, J=8.8, 2.6 Hz, 1H), 7.27 (br s, 1H), 7.04 (d, J=8.8 Hz, 1H), 6.60-6.44 (m, 1H), 6.42-6.23 (m, 1H), 5.90 (d, J=10.2 Hz, 1H), 5.33 (s, 2H), 5.20 (br s, 1H), 4.02-3.46 (m, 4H), 2.46-2.23 (m, 2H), 1.50 (br s, 9H). MS (ESI) m/z 617.4 [M+H]$^+$ A mixture of teat-butyl 3-((6-amino-4-(3-chloro-4-(pyridin-2-ylmethoxy)phenyl)amino)quinazolin-7-yl)oxy)pyrrolidine-1-carboxylate (70 mg, 113 umol, 1.00 eq), trifluoroacetic acid (308 mg, 2.70 mmol, 23.8 eq) in dichloromethane (2.00 mL) was stirred at 25° C. for 2 h. The reaction mixture was concentrated to give residue. The residue was purified by prep-HPLC and lyophilized to give crude product. The crude product was prep-HPLC and lyophilized to give 15 (2.91 mg, 5.63 umol, 5% yield, 100% purity) as a yellow solid. $^1$H NMR (400 MHz, DMSO-d$_6$) δ=9.73 (s, 1H), 9.57 (s, 1H), 8.99 (s, 1H), 8.61 (d, J=4.2 Hz, 1H), 8.50 (s, 1H), 8.29 (br s, 1H), 7.99 (d, J=2.4 Hz, 1H), 7.90 (dt, J=7.8, 1.8 Hz, 1H), 7.70 (dd, J=9.0, 2.6 Hz, 1H), 7.60 (d, J=7.8 Hz, 1H), 7.39 (dd, J=6.6, 4.8 Hz, 1H), 7.32. (s, 1H), 7.26 (d, J=9.2 Hz, 1H), 6.78 (dd, J=16.8, 10.2 Hz, 1H), 6.35 (dd, J=16.8, 2.0 Hz, 1H), 5.89-5.82 (m, 1H), 5.38 (br s, 1H), 5.30 (s, 2H), 3.37 (br s, 4H), 2.31-2.16 (m, 2H). $^1$H NMR (400 MHz, CDCl$_3$) δ=9.17 (s, 1H), 8.99 (s, 1H), 8.61 (s, 2H), 7.86 (s, 1H), 7.83-7.75 (m, 1H), 7.68 (d, J=7.8 Hz, 1H), 7.57-7.43 (m, 1H), 7.28-7.26 (m, 1H), 7.01 (br d, J=9.2 Hz, 1H), 6.86-6.70 (m, 1H), 6.51 (br d, J=16.4 Hz, 1H), 5.82 (br d, J=10.8 Hz, 1H), 5.37 (br s, 1H), 5.30 (s, 2H), 3.86 (br d, J=13.2 Hz, 1H), 3.60 (br s, 1H), 3.48 (br d, J=10.8 Hz, 2H), 2.51 (br s, 2H). MS (ESI) m/z 517.3 [M+H]$^+$ 16: Synthesized according to general procedure A starting from intermediate III (700 mg, 1.64 mmol) obtained in 4, wherein in step A.3 the OH nucleophile is 1-methylpyrrolidin-3-ol (332 mg, 3.29 mmol); variant i) was used in step A.4; and variant ii) was used in step A.5; and 6% overall yield from III. $^1$H NMR (400 MHz, CDCl$_3$) δ=9.13 (s, 1H), 8.81 (s, 1H), 8.64 (s, 1H), 8.62 (dd, J=4.2, 0.8 Hz, 1H), 7.90 (d, J=2.6 Hz, 1H), 7.81-7.75 (m, 1H), 7.73 (s, 1H), 7.71-7.66 (m, 1H), 7.52 (dd, J=8.8, 2.6 Hz, 1H), 7.28-7.23 (m, 1H), 7.16 (s, 1H), 7.01 (d, J=8.8 Hz, 1H), 6.58-6.38 (m, 2H), 5.89-5.76 (m, 1H), 5.31 (s, 2H), 5.07 (br s, 1H), 3.18 (d, J=11.2 Hz, 1H), 3.11 (dt, J=8.4, 3.4 Hz, 1H), 2.66 (dd, J=11.2, 5.2 Hz, 1H), 2.60-2.48 (m, 1H), 2.46 (s, 3H), 2.37 (q, J=8.4 Hz, 1H), 2.19-2.12 (m, 1H). MS (ESI) m/z 531.4 [M+H]$^+$ 17: Synthesized according to general procedure A starting from intermediate III (600 mg, 1.41 mmol) obtained in 4, wherein in step A.3 the OH nucleophile is (R)-1-methylpyrrolidin-3-ol (285 mg, 2.82 mmol); variant i) was used in step A.4; and variant ii) was used in step A.5; and 9% overall yield from III. $^1$H NMR (400 MHz, CDCl$_3$) δ=9.14 (s, 1H), 8.64 (s, 1H), 8.61 (d, J=4.9 Hz, 1H), 8.52 (s, 1H), 7.89 (d, J=2.6 Hz, 1H), 7.80-7.72 (m, 1H), 7.70-7.63 (m, 1H), 7.50 (dd, J=2.6, 8.9 Hz, 1H), 7.42 (s, 1H), 7.24 (br d, J=6.4 Hz, 1H), 7.17 (s, 1H), 7.02 (d, J=8.9 Hz, 1H), 6.54-6.45 (m, 1H), 6.43-6.33 (m, 1H), 5.89-5.82 (m, 1H), 5.31 (s, 2H), 5.10-5.01 (m, 1H), 3.15-2.99 (m, 2H), 2.72 (dd, J=5.5, 11.0 Hz, 1H), 2.58-2.47 (m, 1H), 2.45 (s, 3H), 2.43-2.32 (m, 1H), 2.19-2.07 (m, 1H). MS (ESI) m/z 531.2 [M+H]$^+$ 18: Synthesized according to general procedure A starting from intermediate III (500 mg, 1.17 mmol) obtained in 4, wherein in step A.3 the OH nucleophile is (3S)-1-methylpyrrolidin-3-ol (237 mg, 2.34 mmol); variant i) was used in step A.4; and variant ii) was used in step A.5; and 33% overall yield from III. $^1$H NMR (400 MHz, CDCl$_3$) δ=9.14 (s, 1H), 8.64 (s, 1H), 8.61 (d, J=4.0 Hz, 1H), 8.55 (br s, 1H), 7.89 (d, J=2.8 Hz, 1H), 7.80-7.74 (m, 1H), 7.70-7.65 (m, 1H), 7.52-7.48 (m, 1H), 7.42 (s, 1H), 7.26-7.23 (m, 1H), 7.18 (s, 1H), 7.02 (d, J=8.8 Hz, 1H), 6.56-6.46 (m, 1H), 6.44-6.34 (m, 1H), 5.89-5.82 (m, 1H), 5.31 (s, 2H), 5.09-5.02 (m, 1H), 3.14-3.01 (m, 2H), 2.70-2.68 (m, 1H), 2.57-2.49 (m, 1H), 2.45 (s, 3H), 2.40-2.37 (m, 1H), 2.17-2.11 (m, 1H). MS (ESI) m/z 531.4 [M+H]$^+$ 19: Synthesized according to general procedure A starting from intermediate III (1.00 g, 2.35 mmol) obtained in 4, wherein in step A.3 the OH nucleophile is 2-(dimethylamino)ethanol (251 mg, 2.82 mmol); variant i) was used in step A.4; and variant i) was used in step A.5; and 21% overall yield from III. $^1$H NMR (400 MHz, DMSO-d$_6$) δ=9.67 (br d, J=10.4 Hz, 2 H), 8.86 (s, 1H), 8.60 (d, J=4.8 Hz, 1H), 8.48 (s, 1H), 7.98 (d, J=2.8 Hz, 1H), 7.88 (dt, J=7.6, 1.6 Hz, 1H), 7.69 (dd, J=8.8, 2.4 Hz, 1H), 7.59 (d, J=7.6 Hz, 1H), 7.37 (dd, J=7.2, 4.8 Hz, 1H), 7.31 (s, 1H), 7.25 (d, J=9.2 Hz, 1H), 6.67 (dd, J=17.2, 10.4 Hz, 1H), 6.31 (dd, J=17.2, 2.0 Hz, 1H), 5.84-5.79 (m, 1H), 5.29 (s, 2H), 4.30 (t, J=5.6 Hz, 2H), 2.75 (t, J=5.6 Hz, 2H), s, 6H). MS (ESI) m/z 519.4 [M+H]$^+$ 20: Synthesized according to general procedure B, wherein in step B.1 propane-1,3-diol (894 mg, 11.7 mmol) was used; in step B.2 variant i) was used, in step B.3 the nucleophile is 2-oxa-5-azabicyclo[2.2.1]heptane hydrochloride (1.11 g, 8.21 mmol), in step B.4 variant i) was used and variant i) was used in step 13.5; and 2% overall yield from III. $^1$H NMR (400 MHz, CDCl$_3$) δ=9.20-9.09 (m, 2H), 8.57-8.51 (m, 2H), 8.42 (br s, 1H), 7.80 (d, J=2.6 Hz, 1H), 7.72-7.67 (m, 1H), 7.63 (br s, 1H), 7.61-7.56 (m, 1H), 7.42 (dd, J:=8.8, 2.6 Hz, 1H), 7.17 (br s, 1H), 6.93 (d, J=9.0 Hz, 1H), 6.87 (dd, J=17.0, 10.2 Hz, 1H), 6.44 (dd, J=16.8, 1.2 Hz, 1H), 5.79-5.72 (m, 1H), 5.23 (s, 2H), 4.50 (s, 1H), 4.19-4.13 (m, 3H), 3.95 (s, 1H), 3.74-3.68 (m, 1H), 3.33-3.23 (m, 1H), 3.21-3.13 (m, 2H), 2.83 (br d, J=10.2 Hz, 1H), 2.19 (br s, 2H), 2.07 (br d, J=10.8 Hz, 1H), 1.95 (br d, J=10.8 Hz, 1H). MS (ESI) m/z 587.4 [M+H]$^+$ 21: Synthesized according to general procedure A starting from intermediate III (700 mg, 1.64 mmol) obtained in 4, wherein in step A.3 the OH nucleophile is 3-morpholinopropan-1-ol (716 mg, 4.93 mmol); variant i) was used in step A.4; and variant i) was used in step A.5; and 18% overall yield from III. $^1$H NMR (400 MHz, DMSO-d$_6$) δ=9.67 (br s, 1H), 9.59 (br s, 1H), 8.83 (s, 1H), 8.60 (d, J=4.0 Hz, 1H), 8.48 (s, 1H), 7.99 (d, J=2.4 Hz, 1H), 7.88 (dt, J=8.0, 2.0 Hz, 1H), 7.69 (dd, J=8.8, 2.0 Hz, 1H), 7.59 (d, J=8.0 Hz, 1H), 7.37 (dd, J=7.2, 5.2 Hz, 1H), 7.27-7.23 (m, 2H), 6.71 (dd, J=17.2, 10.4 Hz, 1H), 6.31 (dd, J=17.2, 2.0 Hz, 1H), 5.84-5.79 (m, 1H), 5.28 (s, 2H), 4.26 (t, J=6.0 Hz, 2H), 3.58 (t, J=4.4 Hz, 4H), 2.48-2.45 (m, 2H), 2.38 (br s, 4H), 1.99 (quin, J=6.4 Hz, 2H). MS (ESI) m/z 575.4 [M+H]$^+$ 22: Synthesized according to general procedure A starting from intermediate III (500 mg, 1.17 mmol) obtained in 4, wherein in step A.3 the OH nucleophile is 3-pyrrolidin-1-ylpropan-1-ol (455 mg, 3.52 mmol); variant i) was used in step A.4; and variant i) was used in step A.5; and 15% overall yield from III. $^1$H NMR (400 MHz, DMSO-d$_6$) δ=9.68 (s, 1H), 9.60 (br s, 1H), 8.84 (s, 1H), 8.60 (d, J=4.0 Hz, 1H), 8.48 (s, 1H), 8.22 (br s, 1H), 7.99 (d, J=2.4 Hz, 1H), 7.88 (dt, J=7.6, 1.6 Hz, 1H), 7.69 (dd, J=8.8, 2.4 Hz, 1H), 7.59 (d, J=7.6 Hz, 1H), 7.40-7.34 (m, 1H), 7.28-7.22 (m, 2H), 6.72 (br dd, J=10.0, 15.6 Hz, 1H), 6.31 (dd, J=17.2, 2.0 Hz, 1H), 5.85-5.78 (m, 1H), 5.28 (s, 2H), 4.26 (t, J=6.0 Hz, 2H), 2.67-2.62 (m, 2H), 2.52 (br s, 4H), 2.05-1.99 (m, 2H), 1.71 (br s, 4H). MS (EST) m/z 559.4 [M+H]$^+$ 23: Synthesized according to general procedure A, wherein in step A.2 H$_2$N-X is 3-chloro-4-((6-(trifluoromethyl)pyridin-2-yl)methoxy)aniline (731 mg, 2.42 mmol); in step A.3 the OH nucleophile is 2-morpholinoethanol (956 mg, 7.29 mmol); variant i) was used in step A.4; and variant i) was used in step A.5; and 21% overall yield from II. $^1$H NMR (400 MHz, CDCl$_3$) δ=9.16 (s, 1H), 8.75 (s, 1H), 8.65 (s, 1H), 8.40-8.30 (m, 1H), 8.01-7.92 (m, 2H), 7.90 (d, J=2.6 Hz, 1H), 7.67 (d, J=7.2 Hz, 1H), 7.63 (br s, 1H), 7.54 (dd, J=2.6, 8.8 Hz, 1H), 7.34 (s, 1H), 7.01 (d, J=8.9 Hz, 1H), 6.61-6.39 (m, 2H), 6.02-5.81 (m, 1H), 5.37 (s, 2H), 4.38 (t, J=5.5 Hz, 2H), 3.87-3.72 (m, 4H), 3.00 (t, J=5.5 Hz, 2H), 2.76-2.62 (m, 4H). MS (ESI) m/z 629.3 [M+H]$^+$ 24: Synthesized according to general procedure A, wherein in step A.2 H$_2$N-X is 3-chloro-4-((6-(trifluoromethoxy)pyridin-2-yl)methoxy)aniline (400 mg, 1.26 mmol); in step A.3 the OH nucleophile 2-morpholinoethanol (324 mg, 2.47 mmol); variant ii) was used in step A.4; and variant i) was used in step A.5; and 33% overall yield from II. $^1$H NMR (400 MHz, DMSO-d$_6$) δ=9.69 (s, 1H), 9.60 (s, 1H), 8.83 (s, 1H), 8.50 (s, 1H), 8.22 (s, 1H), 8.12 (t, J=8.0 Hz, 1H), 8.01 (d, J=2.8 Hz, 1H), 7.71 (dd, J=2.4, 9.2 Hz, 1H), 7.63 (d, J=7.6 Hz, 1H), 7.34-7.24 (m, 3H), 6.68 (dd, J=10.4, 17.2 Hz, 1H), 6.31 (dd, J=1.6, 17.2 Hz, 1H), 5.87-5.77 (m, 1H), 5.28 (s, 2H), 4.34 (t, J=5.6 Hz, 2H), 3.60-3.53 (m, 4H), 2.82 (t, J=5.6 Hz, 2H). MS (ESI) m/z 645.2 [M+H]$^+$ 25: Synthesized according to general procedure A starting from intermediate III (500 mg, 1.17 mmol) obtained in 4, wherein in step A.3 the OH nucleophile is 1-methylazetidin-3-ol (580 mg, 4.70 mmol); variant i) was used in step A.4; and variant i) was used in step A.5; and 17% overall yield from III. $^1$H NMR (400 MHz, CDCl$_3$) δ=9.05 (s, 1H), 8.56 (s, 1H), 8.53 (d, J=4.9 Hz, 1H), 7.86 (s, 1H), 7.77 (d, J=2.6 Hz, 1H), 7.72-7.66 (m, 1H), 7.59 (d, J=7.8 Hz, 1H), 7.52 (s, 1H), 7.42 (dd, J=2.7, 8.8 Hz, 1H), 7.18 (br d, J=7.7 Hz, 1H), 6.93 (d, J=8.8 Hz, 1H), 6.87 (s, 1H), 6.52-6.40 (m, 1H), 6.34-6.24 (m, 1H), 5.89-5.79 (m, 1H), 5.22 (s, 3H), 4.58-4.09 (m, 2H), 3.85-3.42 (m, 2H), 2.84 (s, 3H). MS (ESI) m/z 517.4 [M+H]$^+$ 26: To a mixture of tert-butyl 2,5-dihydropyrrole-1-carboxylate (10.0 g, 59.1 mmol, 1.00 eq) and rhodium acetate dimer (261 mg, 591 umol, 0.0100 eq) in dichloromethane (100 mL) was added dropwise a solution of ethyl 2-diazoacetate (10.1 g, 70.9 mmol, 1.20 eq) in dichloromethane (50.0 mL) within 1 h at 35° C. After addition, the mixture was stirred at 35° C. for 12 h. The mixture was concentrated to afford a residue. The residue was distilled to remove the remained reactant under vacuum at 120° C. The distilled residue was purified by silica gel chromatography (petroleum ether/ethyl acetate=1/0-10/1) to afford (1R,5S,6s)-3-tert-butyl 6-ethyl 3-azabicyclo[3.1.0]hexane-3,6-dicarboxylate (3.60 g, 14.1 mmol, 24% yield) as a colorless oil and (1R,5S,6r)-3-tert-butyl 6-ethyl 3-azabicyclo[3.1.0]hexane-3,6-dicarboxylate (1.90 g, 7.44 mmol, 13% yield) as a colorless oil. $^1$H NMR (400 MHz, Chloroform-d) δ=4.12 (q, J=7.2 Hz, 2H), 3.73-3.53 (m, 2H), 3.46-3.35 (m, 2H), 2.05 (br s, 2H), 1.47 (t, J=3.2 Hz, 1H), 1.44-1.39 (m, 9H), 1.25 (t, J=7.2 Hz, 3H). $^1$H NMR (400 MHz, Chloroform-d) δ=4.09 (q, J=7.2 Hz, 2H), 3.84-3.69 (m, 2H), 3.41 (br t, J=10.8 Hz, 2H), 1.86 (s, 1H), 1.84 (d, J=2.6 Hz, 1H), 1.79-1.72 (m, 1H), 1.42 (s, 9H), 1.24 (t, J=7.1 Hz, 3H).

To a mixture of (1R,5S,6s)-3-tert-butyl 6-ethyl 3-azabicyclo[3.1.0]hexane-3,6-dicarboxylate (3.10 g, 12.1 mmol, 1.00 eq) in methanol (20.0 mL) and water (20.0 mL) was added sodium hydroxide (1.46 g, 36.4 mmol, 3.00 eq) at 25° C. The mixture was stirred at 25° C. for 12 h. The mixture was concentrated to remove methanol, diluted with water (50.0 mL), acidified with conc. hydrochloric to pH=4~5. The mixture was extracted with ethyl acetate (3×50.0 mL). The combined organic layers were washed with water (50.0 mL), dried over anhydrous sodium sulfate, filtered and the filtrate was concentrated to afford (1R,5S,6s)-3-(tert-butoxycarbonyl)-3-azabicyclo[3.1.0]hexane-6-carboxylic acid (2.40 g, 10.6 mmol, 87% yield) as a white solid. $^1$H NMR (400 MHz, Chloroform-d) δ=3.76-3.57 (m, 2H), 3.43 (br d, J=3.3 Hz, 2H), 2.13 (br s, 2H), 1.49 (t, J=3.0 Hz, 1H), 1.43 (s, 9H).

To a solution of (1R,5S,6s)-3-(tert-butoxycarbonyl)-3-azabicyclo[3.1.0]hexane-6-carboxylic acid (2.40 g, 9.50 mmol, 1.00 eq) in tetrahydrofuran (30.0 mL) was added dropwise borane tetrahydrofuran complex (1.00 M, 19.0 mL, 2.00 eq) at 0° C. The mixture was stirred at 0° C. for 2 h. The reaction was quenched with methanol (5.00 mL) and concentrated to afford a residue. The residue was diluted sodium carbonate (10.0 mL), extracted with ethyl acetate (2×20.0 mL). The combined organic layers were washed with water, dried over anhydrous sodium sulfate, filtered and the filtrate was concentrated to afford (1R,5S,6s)-tert-butyl 6-(hydroxymethyl)-3-azabicyclo[3.1.0]hexane-3-carboxylate (2.00 g, 9.38 mmol, 98% yield) as a colorless oil. H NMR (400 MHz, Chloroform-d) δ=3.71-3.51 (m, 3H), 3.47 (br d, J=6.4 Hz, 2H), 3.35 (br t, J=8.3 Hz, 2H), 1.49-1.29 (m, 12H), 0.95 (tt, J=3.4, 6.9 Hz, 1H).

To a solution of (1R,5S,6s)-tert-butyl 6-formyl-3-azabicyclo[3.1.0]hexane-3-carboxylate (2.00 g, 9.38 mmol, 1.00 eq) in dichloromethane (50.0 mL) was added Dess-Martin periodinane (4.38 g, 10.3 mmol, 3.19 mL, 1.10 eq) at 0° C. The mixture was stirred at 0° C. for 1 h. The mixture was diluted with water (5.00 mL) and saturated sodium carbonate (5.00 mL), extracted with dichloromethane (2×20.0 mL). The combined organic layers were washed with water (20.0 mL), dried over anhydrous sodium sulfate, filtered. The filtrate was concentrated to afford a residue. The residue was purified by silica gel chromatography (petroleum ether/ethyl acetate=1/0-4/1) to afford (1R,5S,6s)-tert-butyl 6-formyl-3-azabicyclo[3.1.0] hexane-3-carboxylate (1.90 g, 8.99 mmol, 96% yield) as a colorless oil. $^1$H NMR (400 MHz, Chloroform-d) δ=9.43 (d, J=4.0 Hz, 1H), 3.75-3.59 (m, 2H), 3.46 (br d, J=10.5 Hz, 2H), 2.21 (t, J=2.3 Hz, 2H), 1.82 (q, J=3.2 Hz, 1H), 1.44 (s, 9H).

To a solution of (1R,5S,6s)-tert-butyl 6-formyl-3-azabicyclo[3.1.0]hexane-3-carboxylate (1.90 g, 8.99 mmol, 1.00 eq) and potassium carbonate (2.49 g, 18.0 mmol, 2.00 eq) in methanol (40.0 mL) was added dimethyl (1-diazo-2-oxopropyl)phosphonate (2.07 g, 10.8 mmol, 1.20 eq) at 20° C. The mixture was stirred at 20° C. for 12 h. The mixture was concentrated to dryness and diluted with ethyl acetate (20.0 mL). After filtration, the filtrate was concentrated to afford a residue. The residue was purified by silica gel chromatography (petroleum ether/ethyl acetate=5/1) to afford (1R,5S,6r)-tert-butyl 6-ethynyl-3- azabicyclo[3.1.0]hexane-3-carboxylate (1.20 g, 5.79 mmol, 64% yield) as a white solid. $^1$H NMR (400 MHz, Chloroform-d) δ=3.72-3.53 (m, 2H), 3.34 (br t, J=7.6 Hz, 2H), 1.88 (d, J=2.1 Hz, 1H), 1.82 (t, J=2.8 Hz, 2H), 1.43 (s, 9H), 1.14-1.06 (m, 1H).

To a solution of N-(3-chloro-4-(pyridin-2-ylmethoxy)phenyl)-7-fluoro-6-nitroquinazolin-4-amine (2.20 g, 4.76 mmol, 1.00 eq, hydrochloride) in dimethylformamide (25.0 mL) was added potassium acetate (2.34 g, 23.8 mmol, 5.00 eq) at 15° C. The mixture was stirred at 100° C. for 1 h. The mixture was concentrated to afford a residue. The residue was diluted with water (30.0 mL). After filtration, the filter cake was washed with water (10.0 mL), dried in vacuum to afford 4-((3-chloro-4-(pyridin-2-ylmethoxy)phenyl)amino)-6-nitroquinazolin-7-ol (2.00 g, 4.72 mmol, 99% yield) as a yellow solid. $^1$H NMR (400 MHz, DMSO-d$_6$) δ=10.06 (br s, 1H), 9.18 (s, 1H), 8.60 (br d, J=4.3 Hz, 1H), 8.52 (s, 1H), 8.00 (d, J=2.1 Hz, 1H), 7.88 (dt, J=1.5, 7.6 Hz, 1H), 7.68 (br dd, J=2.0, 8.9 Hz, 1H), 7.58 (br d, J=7.8 Hz, 1H), 7.37 (br dd, J=5.3, 6.7 Hz, 1H), 7.27 (d, J=8.9 Hz, 1H), 7.17 (s, 1H), 5.29 (s, 2H).

To a solution of 4-((3-chloro-4-(pyridin-2-ylmethoxy)phenyl)amino-6-nitroquinazolin-7-ol (2.00 g, 4.72 mmol, 1.00 eq) and pyridine (1.87 g, 23.6 mmol, 1.90 mL, 5.00 eq) in dichloromethane (60.0 mL) was added triflic anhydride (2.66 g, 9.44 mmol, 1.56 mL, 2.00 eq) at 0° C. The mixture was stirred at 20° C. for 12 h. The mixture was concentrated to afford a residue. The residue was purified by silica gel chromatography (petroleum ether/ethyl acetate=1/1-0/1) to afford 4-((3-chloro-4-(pyridin-2-ylmethoxy)phenyl)amino)-6-nitroquinazolin-7-trifluoromethanesulfonate (2.10 g, 3.78 mmol, 80% yield) as a yellow solid.

To a solution of (1R,5S,6r)-tert-butyl 6-ethynyl-3-azabicyclo[3.1.0]hexane-3-carboxylate (250 mg, 1.21 mmol, 1.34 eq), 4-((3-chloro-4-(pyridin-2-ylmethoxy)phenyl)amino)-6-nitroquinazolin-7-yltrifluoro-methanesulfonate (500 mg, 899 umol, 1.00 eq), copper iodide (34.3 mg, 180 umol, 0.200 eq) and triethylamine (6.06 g, 59.9 mmol, 8.33 mL, 66.6 eq) in dimethylformamide (10.0 mL) was added tetrakis[triphenylphosphine]palladium(0) (104 mg, 90.0 umol, 0.100 eq)

at 15° C. The mixture was stirred at 15° C. for 12 h. The reaction was concentrated to afford a residue. The residue was triturated with ethyl acetate (5.00 mL). After filtration, the filter cake was dried in vacuum to afford crude product. The crude product was purified by silica gel chromatography (petroleum ether/ethyl acetate=1/1-0/1) to afford (1R,5S,6r)-tert-butyl 6-((4-((3-chloro-4-(pyridin-2-ylmethoxy)phenyl)amino)-6-nitroquinazolin-7-yl)ethynyl)-3-azabicyclo[3.1.0]hexane-3-carboxylate (450 mg, 587 umol, 65% yield, 80% purity) as a yellow solid. $^1$H NMR (400 MHz, DMSO-$d_6$) δ=10.31 (s, 1H), 9.39 (s, 1H), 8.67 (s, 1H), 8.60 (br, d, J=4.3 Hz, 1H), 8.00 (d, J=2.6 Hz, 1H), 7.93-7.81 (m, 2H), 7.70 (dd, J=2.5, 9.0 Hz, 1H), 7.60-7.57 (m, 1H), 7.37 (dd, J=5.1, 7.0 Hz, 1H), 7.29 (d, J=9.0 Hz, 1H), 5.30 (s, 2H), 3.56 (br d, J=10.9 Hz, 2H), 3.46-3.35 (m, 2H), 2.09 (br s, 2H), 1.47 (br t, J=3.3 Hz, 1H), 1.39 (s, 9H). MS (ESI) m/z 613.4 [M+H]$^+$ A mixture of (1R,5S,6r)-tert-butyl 6-((4-((3-chloro-4-(pyridin-2-ylmethoxy)phenyl)amino)-6-nitroquinazolin-7-yl)ethynyl)-3-azabicyclo[3.1.0]hexane-3-carboxylate (400 mg, 522 umol, 1.00 eq) in 4 M hydrochloride/ethyl acetate (3.00 mL) was stirred at 15° C. for 0.5 h. The mixture was concentrated to afford crude product. The crude product was freed with saturated sodium carbonate (5.00 mL) and extracted with ethyl acetate (2×30 mL). The combined organic layers were washed with water (10.0 mL), dried over anhydrous sodium sulfate, filtered and concentrated to afford 7-((1R,5S,6r)-3-azabicyclo[3.1.0]hexan-6-ylethynyl)-N-(3-chloro-4-(pyridin-2-ylmethoxy)phenyl)-6-nitroquinazolin-4-amine (200 mg, 390 umol, 75% yield) as a yellow solid. MS (ESI) m/z 513.3 [M+H]$^+$ To a solution of 7-((1R,5S,6r)-3-azabicyclo[3.1.0]hexane-6-ylethynyl)-N-(3-chloro-4-(pyridin-2-ylmethoxy)phenyl)-6-nitroquinazolin-4-amine (180 mg, 351 umol, 1.00 eq) and paraformaldehyde (52.7 mg, 1.75 mmol, 5.00 eq) in trifluoroethanol (5.00 mL) was added sodium borohydride (26.6 mg, 702 umol, 2.00 eq) at 60° C. The mixture was stirred at 60° C. for 12 h. The mixture was concentrated to afford a residue. The residue was diluted with saturated sodium carbonate (1.00 mL) and water (5.00 mL), extracted with ethyl acetate (3×20 mL). The combined organic layer was washed with water (20.0 mL), dried over anhydrous sodium sulfate, filtered and the filtrate was concentrated to afford N-(3-chloro-4-(pyridin-2-ylmethoxy)phenyl)-7-((1R,5S,6r)-3-methyl-3-azabicyclo[3.1.0]hexan-6-yl)ethynyl)-6-nitroquinazolin-4-amine (180 mg, 342 umol, 97% yield) as a yellow solid. $^1$H NMR (400 MHz, DMSO-$d_6$) δ=10.47 (s, 1H), 9.48 (s, 1H), 8.68 (s, 1H), 8.60 (br d, J=4.3 Hz, 1H), 8.02 (d, J=2.2 Hz, 1H), 7.95 (s, 1H), 7.88 (dt, J=1.5, 7.7 Hz, 1H), 7.72 (br dd, J=2.1, 9.0 Hz, 1H), 7.58 (d, J=7.7 Hz, 1H), 7.41-7.34 (m, 1H), 7.29 (d, J=9.0 Hz, 1H), 5.30 (s, 2H), 3.69 (br d, J=11.2 Hz, 2H), 3.40-3.36 (m, 2H), 2.76 (br s, 3H), 2.59 (br s, 1H), 2.31 (br s, 2H). MS (ESI) m/z 527.4 [M+H]$^+$ To a solution of N-(3-chloro-4-(pyridin-2-ylmethoxy)phenyl)-7-(((1R,5S,6r)-3-methyl-3-azabicyclo[3.1.0]hexan-6-yl)ethynyl)-6-nitroquinazolin-4-amine (180 mg, 342 umol, 1 eq) and ammonium chloride (205 mg, 3.84 mmol, 134 uL, 11.3 eq) in methanol (10.0 mL) and water (10.0 mL) was added iron powder (167 mg, 2.99 mmol, 8.75 eq) at 20° C. The mixture was heated to 80° C. and stirred at 80° C. for 1 h. The mixture was concentrated to afford a residue. The residue was diluted with water (10.0 mL), saturated sodium carbonate (5.00 mL), ethyl acetate (30.0 mL). The mixture was extracted with ethyl acetate (2×30 mL) and the combined organic layer was washed with water (20.0 mL), dried over anhydrous sodium sulfate, filtered. The filtrate was concentrated to afford N$^4$-(3-chloro-4-(pyridin-2-ylmethoxy)phenyl)-7-(((1R,5S,6r)-3-methyl-3-azabicyclo[3.1.0]hexan-6-yl)ethynyl)quinazoline-4,6-diamine (110 mg, 221 umol, 65% yield) as a brown solid.

To a solution of N$^4$-(3-chloro-4-(pyridin-2-ylmethoxy)phenyl)-7-(((1R,5S,6r)-3-methyl-3-azabicyclo[3.1.0]hexan-6-yl)ethynyl)quinazoline-4,6-diamine (100 mg, 201 umol, 1.00 eq) and pyridine (0.500 M, 1.21 mL, 3.00 eq) in dimethylformamide (4.00 mL) was added 1-(3-dimethylaminopropyl)-3-ethylcarbodiimide hydrochloride (77.2 mg, 402 umol, 2.00 eq) and acrylic acid (0.100 M, 2.41 mL, 1.2 eq) at 0° C. The mixture was stirred at 15° C. for 5 h. The mixture was filtered to afford a solution. The solution was purified by prep-HPLC and lyophilized to afford 26 (35.5 mg, 63.8 umol, 32% yield) as a white solid. $^1$H NMR (400 MHz, DMSO-$d_6$) δ=9.83 (br d, J=3.5 Hz, 2H), 8.70 (s, 1H), 8.60 (d, J=4.8 Hz, 1H), 8.53 (s, 1H), 8,24 (s, 1H), 8.00 (d, J=2.4 Hz, 1H), 7.88 (dt, J=1.7, 7.7 Hz, 1H), 7.76 (s, 1H), 7.70 (dd, J=2.4, 8.9 Hz, 1H), 7.59 (d, J=7.8 Hz, 1H), 7.37 (dd, J=5.2, 7.3 Hz, 1H), 7.26 (d, J=9.0 Hz, 1H), 6.63 (dd, J=10.3, 17.0 Hz, 1H), 6.33 (dd, J=1.8, 17.0 Hz, 1H), 5.85 (dd, J=1.7, 10.1 Hz, 1H), 5.29 (s, 2H), 3.01 (d, J=9.2 Hz, 2H), 2.29 (br d, J=8.7 Hz, 2H), 2.23 (s, 3H), 1.95-1.86 (m, 3H). MS (ESI) m/z 551.0 [M+H]

27: Synthesized according to general procedure A starting from intermediate III (600 mg, 1.36 mmol) obtained in 1, wherein in step A.3 the OH nucleophile is 2-morpholinoethanol (213 mg, 1.63 mmol); variant i) was used in step A.4; and variant ii) was used in step A.5; and 14% overall yield from III. $^1$H NMR (400 MHz, CDCl$_3$) δ=9.08 (s, 1H), 8.65 (s, 1H), 8.62 (s, 1H), 7.81 (d, J=2.6 Hz, 1H), 7.73 (s, 1H), 7.48 (dd, J=8.8, 2.6 Hz, 1H), 7.36 (td, J=7.8, 6.2 Hz, 1H), 7.26-7.19 (m, 3H), 7.08-6.99 (m, 1H), 6.91 (d, J=9.0 Hz, 1H), 6.52-6.31 (m, 2H), 5.84 (dd, J=9.8, 1.6 Hz, 1H), 5.22-5.05 (m, 2H), 4.31 (t, J=5.6 Hz, 2H), 3.83-3.70 (m, 4H), 2.89 (t, J=5.6 Hz, 2H), 2.63-2.54 (m, 4 H). MS (ESI) m/z 578.4 [M+H]

28: Synthesized according to general procedure C, wherein in step C.1 the diol is ethylene glycol (5.55 g, 89.4 mmol); in step C.3 H$_2$N-X is 3-chloro-4-(2-pyridylmethoxy)aniline (842 mg, 3.59 mmol); in step C.4 HNR'R" is pyrrolidine (395 mg, 5.55 mmol); variant ii) was used in step C.5; and variant i) was used in step C.6; and 7% overall yield from I. $^1$H NMR (400 MHz, DMSO-$d_6$) δ=9.70 (s, 1H), 9.64 (s, 1H), 8.85 (s, 1H), 8.60 (d, J=4.0 Hz, 1H), 8.49 (s, 1H), 7.99 (d, J=2.6 Hz, 1H), 7.88 (dt, J=1.8, 7.7 Hz, 1H), 7.69 (dd, J=2.6, 9.0 Hz, 1H), 7.59 (d, J=7.8 Hz, 1H), 7.37 (dd, J=5.0, 6.7 Hz, 1H), 7.30 (s, 1H), 7.25 (d, J=9.0 Hz, 1H), 6.68 (dd, J=10.1, 17.1Hz, 1H), 6.31 (dd, J=1.9, 17.1 Hz, 1H), 5.85-5.78 (m, 1H), 5.29 (s, 2H), 4.32 (t, J=5.9 Hz, 2H), 2.92 (br t, J=5.6 Hz, 2H), 2.57 (br s, 4H), 1.69 (br s, 4H). MS (ESI) m/z 545.4 [M+1]$^+$ 29: Synthesized according to general procedure C starting from intermediate XV (400 mg, 765 umol) obtained in 28, wherein in step C.4 HNR'R" is 3-methoxypyrrolidine (211 mg, 1.53 mmol); variant ii) was used in step C.5; and variant iii) was used in step C.6; and 6% overall yield from XV. $^1$H NMR (400 MHz, MeOD-$d_4$) δ=8.89 (s, 1H), 8.56 (d, J=5.0 Hz, 1H), 8.44 (s, 1H), 8.36 (br s, 1H), 7.95-7.87 (m, 2H), 7.72 (d, J=7.9 Hz, 1H), 7.57 (dd, J=2.6, 8.8 Hz, 1H), 7.39 (dd, J=5.2, 7.2 Hz, 1H), 7.23 (s, 1H), 7.15 (d, J=8.9 Hz, 1H), 6.75-6.61 (m, 1H), 6.54-6.43 (m, 1H), 5.87 (dd, J=1.6, 10.1 Hz, 1H), 5.27 (s, 2H), 4.47 (t, J=4.8 Hz, 2H), 4.14 (br t, J=5.4 Hz, 1H), 3.55-3.39 (m, 2H), 3.33 (s, 3H), 3.30-3.22 (m, 3H), 3.20-3.13 (m, 1H), 2.32-2.17 (m, 1H), 2.15-2.03 (m, 1H). MS (ESI) m/z 575.1 [M+H]$^+$ 30: Synthesized according to general procedure C starting from intermediate XV (413 mg, 3.35 mmol) obtained in 28, wherein in step C.4 HNR'R" is pyrrolidin-3-ol hydrochloride (13 mg, 3.35 mmol); variant ii) was used in step C.5; and variant i) was used in step C.6; and 20% overall yield from XV. $^1$H NMR (400 MHz, DMSO-$d_6$) δ=9.68 (s, 1H), 9.63 (s, 1H), 8.86 (s, 1H), 8.60 (d, J=4.4 Hz, 1H), 8.48 (s, 1H), 7.98 (d, J=2.6 Hz, 1H), 7.91-7.85 (m, 1H), 7.69 (dd, J=2.4, 8.9 Hz, 1H), 7.59 (d, J=7.8 Hz, 1H), 7.40-7.33 (m, 1H), 7.30 (s, 1H), 7.25 (d, J=9.0 Hz, 1H), 6.69 (dd, J=10.5, 17.2 Hz, 1H), 6.31 (dd, J=1.8, 17.0 Hz, 1H), 5.81 (d, J=11.9 Hz, 1H), 5.29 (s, 2H), 4.69 (d, J=4.4 Hz, 1H), 4.30 (t, J=5.9 Hz, 2H), 4.19 (br s, 1H), 2.93-2.88 (m, 2H), 2.82 (dd, J=6.1, 9.6 Hz, 1H), 2.74-2.68 (m, 1H), 2.59-2.56 (m, 1H), 2.45-2.42 (m, 1H), 2.01-1.95 (m, 1H), 1.59-1.48 (m, 1H). MS (ESI) m/z 561.0 [M+H]$^+$ 31: Synthesized according to general procedure C starting from intermediate XV (800 mg, 1.53 mmol) obtained in 28, wherein in step C.4 HNR'R" is 3-oxa-8-azabicyclo[3.2.1]octane hydrochloride (458 mg, 3.06 mmol); variant ii) was used in step C.5; and variant ii) was used in step C.6; and 9% overall yield from XV. $^1$H NMR (400 MHz, CDCl$_3$) δ=9.29 (s, 1H), 9.19 (s, 1H), 8.66-8.58 (m, 2H), 8.51 (br s, 1H), 7.88 (d, J=2.6 Hz, 2H), 7.81-7.74 (m, 1H), 7.69 (d, J=7.8 Hz, 1H), 7.52 (dd, J=8.8, 2.6 Hz, 1H), 7.32 (s, 1H), 7.27 (br d, J=7.0 Hz, 1H), 7.01 (d, J=9.0 Hz, 1H), 6.76-6.65 (m, 1H), 6.57-6.46 (m, 1H), 5.92-5.83 (m, 1H), 5.31 (s, 2H), 4.34 (t, J=5.4 Hz, 2H), 3.95 (d, J=11.2 Hz, 2H), 3.62 (br d, J=9.8 Hz, 2H), 3.42 (br s, 2H), 3.13-3.10 (m, 2H), 2.17-1.99 (m, 4 H). MS (ESI) m/z 587.4 [M+H]$^+$ 32: Synthesized according to general procedure C starting from intermediate XV (1.00 g, 1.91 mmol) obtained in 28, wherein in step C.4 HNR'R" is N-methylethanamine (565 mg, 9.56 mmol); variant ii) was used in step C.5; and variant i) was used in step C.6; and 4% overall yield from XV. $^1$H NMR (400 MHz, DMSO-$d_6$) δ=9.69 (s, 2H), 8.86 (s, 1H), 8.60 (d, J=4.0 Hz, 1H), 8.49 (s, 1H), 8.23 (s, 1H), 7.98 (d, J=2.6 Hz, 1H), 7.88 (dt, J=1.7, 7.7 Hz, 1H), 7.69 (dd, J=2.6, 8.9 Hz, 1H), 7.59 (d, J=7.8 Hz, 1H), 7.37 (dd, J=5.0, 6.7 Hz, 1H), 7.30 (s, 1H), 7.25 (d, J=9.0 Hz, 1H), 6.68 (dd, J=10.3, 17.1 Hz, 1H), 6.31 (dd, J=1.8, 17.0 Hz, 1H), 5.86-5.77 (m, 1H), 5.29 (s, 2H), 4.31 (t, J=5.7 Hz, 2H), 2.86 (t, J=5.7 Hz, 2H), 2.54-2.52 (m, 2H), 2.29 (s, 3H), 1.01 (t, J=7.2 Hz, 3H). MS (ESI) m/z 533.4 [M+1]$^+$ 33: Synthesized according to general procedure C starting from intermediate XV (150 mg, 308 umol) obtained in 28, wherein in step C.4 HNR'R" is azetidine (144 mg, 1.54 mmol) and the mixture was stirred at 120° C. under microwave; variant ii) was used in step C.5; and variant ii) was used in step C.6; and 49% overall yield from XV. $^1$H NMR (400 MHz, DMSO-$d_6$) δ=9.73-6.93 (m, 2H), 8.87 (s, 1H), 8.62-8.58 (m, 1H), 8.49 (s, 1H), 8.18-8.13 (m, 1H), 7.98 (d, J=2.4 Hz, 1H), 7.93-7.85 (m, 1H), 7.72-7.66 (m, 1H), 7.59 (d, J=7.6 Hz, 1H), 7.40-7.34 (m, 1H), 7.29-7.21 (m, 2H), 6.67 (br d, J=9.6 Hz, 1H), 6.38-6.28 (m, 1H), 5.88-5.80 (m, 1H), 5.29 (s, 2H), 4.30-4.20 (m, 2H), 3.60-3.50 (m, 4H), 3.15-3.10 (m, 1H), 3.09-3.06 (m, 1H), 2.15-2.07 (m, 2H). MS (ESI) m/z 531.4 [M+H]$^+$ 34: Synthesized according to general procedure C starting from intermediate XV (800 mg, 1.53 mmol) obtained in 28, wherein in step C.4 HNR'R" is 3-fluoroazetidine hydrochloride (453 mg, 3.06 mmol); variant ii) was used in step C.5; and variant iii) was used in step C.6; and 3% overall yield from XV. $^1$H NMR (400 MHz, DMSO-$_6$) δ=9.68 (s, 1H), 9.61 (s, 1H), 8.81 (s, 1H), 8.60 (d, J=4.6 Hz, 1H), 8.49 (s, 1H), 8.23 (s, 1H), 7.99 (d, J=2.6 Hz, 1H), 7.88 (dt, J=1.7, 7.7 Hz, 1H), 7.69 (dd, J=2.6, 8.9 Hz, 1H), 7.59 (d, J=7.8 Hz, 1H), 7.37 (dd, J=5.1, 6.8 Hz, 1H), 7.27-7.23 (m, 2H), 6.66 (dd, J=10.3, 16.9 Hz, 1H), 6.31 (dd, J=1.7, 17.0 Hz, 1H), 5.84-5.79 (m, 1H), 5.29 (s, 2H), 5.23-5.05 (m, 1H), 4.21 (br t, J=5.1 Hz, 2H), 3.69-3.60 (m, 2H), 3.31-3.19 (m, 2H), 2.93 (br t, J=5.1 Hz, 2H). MS (ESI) m/z 549.4 [M+H]$^+$ 35: Synthesized according to general procedure C starting from intermediate XV (500 mg, 956 umol) obtained in 28, wherein in step C.4 HNR'R" is 3-methoxyazetidine hydrochloride (306 mg, 1.91 mmol); variant ii) was used in step C.5; and variant i) was used in step C.6; and 6% overall yield from XV. $^1$H NMR (400 MHz, CDCl$_3$) δ=9.13 (s, 1H), 8.93 (s, 1H), 8.65 (s, 1H), 8.62 (d, J=4.2 Hz, 1H), 7.90 (d, J=2.6 Hz, 1H), 7.82-7.74 (m, 1H), 7.71-7.66 (m, 1H), 7.56-7.48 (m, 2H), 7.28-7.24 (m, 1H), 7.03 (d, J=8.8 Hz, 1H), 6.63-6.33 (m, 2H), 5.99-5.77 (m, 1H), 5.32 (s, 2H), 4.24 (t, J=5.1 Hz, 2H), 4.11 (t, J=5.6 Hz, 1H), 3.74 (dd, J=6.2, 8.1 Hz, 2H), 3.31 (s, 3H), 3.14 (dd, J=5.6, 8.4 Hz, 2H), 3.01 (t, J=5.1 Hz, 2H). MS (ESI) m/z 561.1 [M+H]$^+$ 36: Synthesized according to general procedure C starting from intermediate XV (800 mg, 1.53 mmol) obtained in 28, wherein in step C.4 HNR'R" is 8-oxa-3-azabicyclo[3.2.1]octane hydrochloride (458 mg, 3.06 mmol); variant ii) was used in step C.5; and variant i) was used in step C.6; and 16% overall yield from XV. $^1$H NMR (400 MHz, CDCl$_3$) δ=9.13 (s, 1H), 8.66 (s, 1H), 8.62 (d, J=4.2 Hz, 1H), 8.28 (s, 1H), 7.90 (d, J=2.6 Hz, 1H), 7.81-7.74 (m, 1H), 7.71-7.66 (m, 1H), 7.52 (dd, J=8.8, 2.6 Hz, 1H), 7.43 (s, 1H), 7.28-7.24 (m, 2H), 7.03 (d, J=9.0 Hz, 1H), 6.56-6.48 (m, 1H), 6.40-6.30 (m, 1H), 5.94-5.86 (m, 1H), 5.32 (s, 2H), 4.38-4.30 (m, 4H), 2.90 (t, J=5.6 Hz, 2H), 2.68 (d, J=10.6 Hz, 2H), 2.53 (dd, J=10.8, 1.8 Hz, 2H), 1.97-1.88 (m, 4 H). MS (ESI) m/z 587.3 [M+H]$^+$ 37: Synthesized according to general procedure A, wherein in step A.2 H$_2$N-X is 4-(3-chlorophenoxy)aniline (965 mg, 4.39 mmol); in step A.3 the OH nucleophile 2-morpholinoethanol (703 mg, 5.36 mmol); variant i) was used in step A.4; and variant i) was used in step A.5; and 26% overall yield from II. $^1$H NMR (400 MHz, DMSO-$d_6$) δ=9.00 (s, 1H), 8.45 (s, 1H), 8.23 (br s, 1H), 7.74 (d, J=8.8 Hz, 2H), 7.38-7.32 (m, 1H), 7.25 (s, 1H), 7.14-7.08 (m, 3H), 7.03 (t, J=2.0 Hz, 1H), 6.98 (dd, J=8.2, 2.2 Hz, 1H), 6.72 (dd, J=17.0, 10.2 Hz, 1H), 6.51 (dd, J=17.0, 1.4 Hz, 1H), 5.89 (dd, J=10.2, 1.6 Hz, 1H), 4.43 (t, J=5.0 Hz, 2H), 3.85-3.80 (m, 4H), 3.06 (t, J=5.0 Hz, 2H), 2.75 (br s, 4H). MS (ESI) m/z 546.2 [M+H]$^+$ 38: Synthesized according to general procedure C starting from intermediate XV (800 mg, 1.53 mmol) obtained in 28, wherein in step C.4 HNR'R" is 2-oxa-6-azaspiro[3.3]heptane (607 mg, 6.12 mmol); variant ii) was used in step C.5; and variant i) was used in step C.6; and 18% overall yield from XV. $^1$H NMR (400 MHz, DMSO-$d_6$) δ=9.69 (s, 1H), 9.64 (s, 1H), 8.82 (s, 1H), 8.60 (d, J=4.8 Hz, 1H), 8.49 (s, 1H), 8.24 (s, 1H), 7.99 (d, J=2.6 Hz, 1H), 7.88 (dt, J=1.7, 7.7 Hz, 1H), 7.69 (dd, J=2.6, 9.0 Hz, 1H), 7.59 (d, J=7.9 Hz, 1H), 7.37 (dd, J=5.3, 7.1 Hz, 1Hz), 7.27-7.23 (m, 2H), 6.68 (dd, J=10.1, 17.0 Hz, 1H), 6.33 (dd, J=1.8, 17.1 Hz, 1H), 5.86-5.80 (m, 1H), 5.29 (s, 2H), 4.58 (5, 4H), 4.17 (br t, J=5.3 Hz, 2H), 3.41 (s, 4H), 2.82 (br t, J=5.2 Hz, 2H). MS (ESI) m/z 573.5 [M+H]$^+$ 39: Synthesized according to general procedure C starting from intermediate XV (0.400 g, 765 umol) obtained in 28, wherein in step C.4 HNR'R" is 2-oxa-5-azabicyclo[2.2.1]heptane (279 mg, 2.06 mmol); variant ii) was used in step C.5; and variant i) was used in step C.6; and 7% overall yield from XV. $^1$H NMR (400 MHz, MeOD-$d_4$) δ=8.93 (s, 1H), 8.56 (d, J=4.6 Hz, 1H), 8.42 (s, 1H), 7.95-7.86 (m, 2H), 7.72 (d, J=7.8 Hz, 1H), 7.57 (dd, J=2.6, 8.8 Hz, 1H), 7.45-7.36 (m, 1H), 7.20 (s, 1H), 7.15 (d, J=8.9 Hz, 1H), 6.71-6.62 (m, 1H), 6.52-6.43 (m, 1H), 5.86 (dd, J=1.6, 10.3 Hz, 1H), 5.27

(s, 2H), 4.47 (s, 4.37-4.27 (m, 2H), 4.11 (d, J=8.1 Hz, 1H), 3.72 (s, 1H), 3.68 (dd, J=1.5, 8.2 Hz, 1H), 3.25-3.16 (m, 1H), 3.15-3.06 (m, 1H), 3.01 (d, J=9.3 Hz, 1H), 2.74 (d, J=10.5 Hz, 1H), 1.98 (br d, J=9.4 Hz, 1H), 1.83 (br d, J=10.1 Hz, 1H). MS (ESI) m/z 573.4 [M+H]$^+$

40: Synthesized according to general procedure C starting from intermediate XV (600 mg, 1.15 mmol) obtained in 28, wherein in step C.4 HNR'R'' is N-methyltetrahydrofuran-3-amine (316 mg, 2.30 mmol); variant ii) was used in step C.5; and variant ii) was used in step C.6; and 22% overall yield from XV. $^1$H NMR (400 MHz, CDCl$_3$) δ=9.10 (d, J=1.8 Hz, 1H), 8.90 (br s, 1H), 8.67-8.57 (m, 2H), 7.87-7.83 (m, 1H), 7.83-7.74 (m, 2H), 7.67 (d, J=7.8 Hz, 1H), 7.52-7.44 (m, 1H), 7.24 (br s, 2H), 6.97 (br s, 1H), 6.54-6.38 (m, 2H), 5.88-5.79 (m, 1H), 5.28 (d, J=2.6 Hz, 2H), 4.32 (br d, J=4.0 Hz, 2H), 2.92 (br t, J=4.2 Hz, 2H), 3.11-2.74 (m, 1H), 2.71-2.40 (m, 7H), 2.32 (s, 3H). MS (ESI) m/z 574.4 [M+H]$^+$ 41: Synthesized according to general procedure C starting from intermediate XV (600 mg, 1.15 mmol) obtained in 28, wherein in step C.4 HNR'R'' is 1-methylpiperazine (230 mg, 2.30 mmol); variant ii) was used in step C.5; and variant ii) was used in step C.6; and 22% overall yield from XV. $^1$H NMR (400 MHz, CDCl$_3$) δ=9.12 (s, 1H), 8.65 (s, 2H), 8.62 (d, J=4.4 Hz, 1H), 7.90 (d, J=2.6 Hz, 1H), 7.82-7.74 (m, 1H), 7.72-7.65 (m, 1H), 7.58 (s, 1H), 7.52 (dd, J=8.8, 2.6 Hz, 1H), 7.26 (br d, J=7.0 Hz, 1H), 7.03 (d, J=9.0 Hz, 1H), 6.58-6.37 (m, 2H), 5.87 (dd, J=9.8, 1.4 Hz, 1H), 5.32 (s, 2H), 4.31 (t, J=5.4 Hz, 2H), 4.03 (td, J=8.6, 4.4 Hz, 1H), 3.93-3.85 (m, 1H), 3.84-3.71 (m, 2H), 3.33 (quin, J=6.6 Hz, 1H), 3.04-2.84 (m, 2H), 2.40 (s, 3H), 2.20-2.06 (m, 1H), 1.99-1.88 (m, 1H). MS (ESI) m/z 575.4 [M+H]$^+$ 42: Synthesized according to general procedure A starting from intermediate III (500 mg, 1.17 mmol) obtained in 4, wherein in step A.3 the NH nucleophile is 1-methylpiperazine (153 mg, 1.53 mmol); variant i) was used in step A.4; and variant ii) was used in step A.5; and 11% overall yield from III. $^1$H NMR (400 MHz, CDCl$_3$) δ=9.06 (s, 1H), 8.75 (s, 1H), 8.68 (s, 1H), 8.62 (d, J=4.2 Hz, 1H), 7.92 (d, J=2.6 Hz, 1H), 7.77 (dd, J=7.6, 1.6 Hz, 1H), 7.71-7.66 (m, 1H), 7.63 (s, 1H), 7.59-7.49 (m, 2H), 7.27 (br s, 1H), 7.03 (d, J=9.0 Hz, 1H), 6.55-6.47 (m, 1H), 6.41-6.29 (m, 1H), 5.91 (d, J=10.8 Hz, 1H), 5.32 (s, 2H), 3.08 (t, J=4.8 Hz, 4H), 2.69 (br s, 4H), 2.44 (s, 3H). MS (ESI) m/z 530.4 [M+H]$^+$ 43: Synthesized according to general procedure A starting from intermediate III (500 mg, 1.17 mmol) obtained in 4, wherein in step A.3 the NH nucleophile is 1,4-diazabicyclo[3.2.1]octane hydrochloride (241 mg, 1.62 mmol); variant i) was used in step A.4; and variant i) was used in step A.5; and 1% overall yield from III. $^1$H NMR (400 MHz, CD$_3$OD) δ=8.65 (s, 1H), 8.58 (d, J=5.0 Hz, 1H), 8.48 (s, 1H), 8.44 (br s, 2H), 7.96-7.90 (m, 2H), 7.74 (d, J=8.0 Hz, 1H), 7.61 (dd, J=8.8, 2.4 Hz, 1H), 7.44-7.40 (m, 1H), 7.38 (s, 1H), 7.18 (d, J=9.0 Hz, 1H), 6.69-6.59 (m, 1H), 6.56-6.48 (m, 1H), 5.92 (d, J=11.4 Hz, 1H), 5.30 (s, 2H), 3.99 (br s, 1H), 3.63-3.53 (m, 1H), 3.39 (br d, J=11.00 Hz, 1H), 3.29-3.19 (m, 3H), 3.19-3.14 (m, 1H), 3.12-3.00 (m, 2H), 2.24-2.05 (m, 2H). MS (ESI) m/z 542.4 [M+H]$^+$ 44: Synthesized according to general procedure A starting from intermediate III (500 mg, 1.17 mmol) obtained in 4, wherein in step A.3 the NH nucleophile is 4-(azetidin-3-yl)morpholine (327 mg, 1.52 mmol); variant i) was used in step A.4; and variant ii) was used in step A.5; and 20% overall yield from III. $^1$H NMR (400 MHz, CDCl$_3$) δ=8.65-8.56 (m, 2H), 8.47 (br s, 1H), 7.82-7.74 (m, 2H), 7.67 (br d, J=7.8 Hz, 2H), 7.48 (br dd, J=8.8, 2.0 Hz, 2H), 7.26 (br d, J=6.8 Hz, 1H), 7.01-6.90 (m, 2H), 6.57-6.47 (m, 1H), 6.34 (br dd, J=16.8, 10.2 Hz, 1H), 5.89 (br d, J=10.0 Hz, 1H), 5.30 (s, 2H), 4.06-3.97 (m, 2H), 3.84 (br s, 2H), 3.76 (br t, J=4.2 Hz, 4H), 3.31-3.22 (m, 1H), 2.42 (br s, 4H). MS (ESI) m/z 572.5 [M+H]$^+$ 45: A mixture of intermediate III obtained in 4 (1.00 g, 2.35 mmol, 1.00 eq), tert-butyl 2,6-diazaspiro[3.3]heptane-2-carboxylate (880 mg, 3.05 mmol, 1.30 eq, oxalic acid salt) and potassium carbonate (974 mg, 7.05 mmol, 3.00 eq) in dimethylsulfoxide (10.0 mL) was stirred at 25° C. for 3 h. The reaction mixture was added water (20.0 mL). The mixture was filtered. The filter cake was dried to give tert-butyl6-(4-((3-chloro-4-(pyridin-2-ylmethoxy)phenyl)amino)-6-nitroquinazolin-7-yl)-2,6-diazaspiro[3.3]heptane-2-carboxylate (1.5 g, crude) as a yellow solid. $^1$H NMR (400 MHz, DMSO-d$_6$) δ=10.02 (br s, 1H), 9.10 (s, 1H), 8.60 (br d, J=4.4 Hz, 1H), 8.46 (s, 1H), 8.00 (br d, J=1.8 Hz, 1H), 7.89 (br t, J=7.6 Hz, 1H), 7.68 (br d, J=8.8 Hz, 1H), 7.59 (br d, J=7.8 Hz, 1H), 7.43-7.32 (m, 1H), 7.26 (br d, J=9.0 Hz, 1H), 6.72 (s, 1H), 5.29 (s, 2H), 4.15 (s, 4H), 4.04 (br s, 4H), 1.39 (s, 9H). MS (ESI) m/z 604.2 [M+H]$^+$ A mixture of tert-butyl6-(4-((3-chloro-4-(pyridin-2-ylmethoxy)phenyl)amino)-6-nitroquinazolin-7-yl)-2,6-diazaspiro[3.3]heptane-2-carboxylate (1.40 g, 2.32 mmol, 1.00 eq) and trifluoroacetic acid (4.31 g, 37.8 mmol, 2.80 mL, 16.3 eq) in dichloromethane (20.0 mL) was stirred at 25° C. for 4 h. The reaction mixture was concentrated to give a residue. The residue was triturated with ethyl acetate (10.0 mL) and petroleum ether (20.0 mL) to give N-(3-chloro-4-(pyridin-2-ylmethoxy)phenyl)-6-nitro-7-(2,6-diazaspiro[3.3]heptan-2-yl)quinazolin-4-amine (1.4 g, crude) as a yellow solid. $^1$H NMR (400 MHz, DMSO-d$_6$) δ=9.24 (s, 1H), 8.80 (s, 1H), 8.62 (br d, J=4.3 Hz, 2H), 7.97-7.86 (m, 2H), 7.64-7.55 (m, 2H), 7.41 (dd, J=5.1, 7.0 Hz, 1H), 7.36 (d, J=9.0 Hz, 1H), 6.82 (s, 1H), 5.35 (s, 2H), 4.30 (s, 4H), 4.20 (br t, J=5.9 Hz, 4H). MS (ESI) m/z 504.1 [M+H]$^+$ A mixture of N-(3-chloro-4-(pyridin-2-ylmethoxy)phenyl)-6-nitro-7-(2,6-diazaspiro[3.3]heptan-2-yl)quinazolin-4-amine (1.40 g, 2.78 mmol, 1.00 eq), formaldehyde (834 mg, 27.8 mmol, 765 uL, 10.0 eq) and sodium borohydride (126 mg, 3.33 mmol, 1.20 eq) in 1,1,1-trifluoroethane (10.0 mL) was stirred at 40° C. for 4 h. The reaction mixture was concentrated to give a residue. The residue was purified by Reverse-MPLC and concentrated under reduced pressure to give N-(3-chloro-4-(pyridin-2-ylmethoxy)phenyl)-7-(6-methyl-2,6-diazaspiro[3.3]heptan-2-yl)-6-nitroquinazolin-4-amine (600 mg, 1.16 mmol, 42% yield) as a yellow solid. $^1$H NMR (400 MHz, DMSO-d$_6$) δ=9.12 (s, 1H), 8.60 (d, J=4.3 Hz, 1H), 8.50 (s, 1H), 8.18 (s, 2H), 8.02 (d, J=2.3 Hz, 1H), 7.89 (dt, J=1.7, 7.7 Hz, 1H), 7.71 (dd, J=2.3, 9.0 Hz, 1H), 7.59 (d, J=7.8 Hz, 1H), 7.38 (dd, J=5.0, 7.0 Hz, 1H), 7.28 (d, J=9.0 Hz, 1H), 6.77 (s, 1H), 5.30 (s, 2H), 4.15 (s, 4H), 3.85 (s, 4H), 2.53 (br s, 3H). MS (ESI) m/z 518.5 [M+H]$^+$ A mixture of N-(3-chloro-4-(pyridin-2-ylmethoxy)phenyl)-7-(6-methyl-2,6-diazaspiro[3.3]heptan-2-yl)-6-nitroquinazolin-4-amine (600 mg, 1.16 mmol, 1.00 eq), iron (323 mg, 5.79 mmol, 5.00 eq) and ammonium chloride (558 mg, 10.43 mmol, 364 uL, 9.00 eq) in methanol (15.0 mL) and water (2.00 mL) was stirred at 80° C. for 4 h. The reaction mixture was added of methanol (100 mL). The mixture was filtered. The filtrate was concentrated to give a residue. The residue was purified by prep-HPLC to give the mixture was filtered. The filter cake was dried to give N$^4$-(3-chloro-4-(pyridin-2-ylmethoxy)phenyl)-7-(6-methyl-2,6-diazaspiro[3.3]heptan-2-yl)quinazoline-4,6-diamine (200 mg, 409 umol, 35% yield) as a yellow solid. $^1$H NMR (400 MHz, CDCl$_3$) δ=8.61 (d, J=4.8 Hz, 1H), 8.55 (s, 1H), 7.84 (d, J=2.3 Hz, 1H), 7.82-7.71 (m, 1H), 7.68 (d, J=7.7 Hz, 1H), 7.48 (dd, J=2.6, 8.8 Hz, 1H), 7.26 (br d, J=6.8 Hz, 1H), 7.01 (d, J=8.9 Hz, 1H), 6.93-6.81 (m, 3H), 5.31 (s, 2H), 4.11 (s, 4H), 3.81 (br s, 2H), 3.43 (s, 4H), 2.36 (s, 3H). MS (ESI) m/z 488.3 [M+H]$^+$ To a solution of N$^4$-(3-chloro-4-(pyridin-2-ylmethoxy) phenyl)-7-(6-methyl-2,6-diazaspiro[3.3]heptan-2-yl)quinazoline-4,6-diamine (80.0 mg, 164 umol, 1.00 eq), triethylamine (49.8 mg, 492 umol, 68.5 uL, 3.00 eq) in dimethyl formamide (2.00 mL) was added acrylic anhydride (20.7 mg, 164 umol, 1.41 uL, 1.00 eq) at 25° C. The mixture was stirred at 25° C. for 0.5 h. The reaction mixture was filtered. The filtrate was purified by prep-HPLC and lyophilized to give 45 (4.15 mg, 7.50 umol, 4.58% yield, 98% purity) as a yellow solid. $^1$H NMR (400 MHz, CDCl$_3$) δ=8.64-8.59 (m, 2H), 8.47 (s, 1H), 7.85 (d, J=2.3 Hz, 1H), 7.82-7.75 (m, 2H), 7.68 (d, J=8.1 Hz, 1H) 7.50 (dd, J=2.5, 8.7 Hz, 1H) 7.40 (br s, 1H), 7.26 (br d, J=7.2 Hz, 1H), 7.07-6.93 (m, 2H), 6.59-6.49 (m, 1H), 6.45-6.27 (m, 1H), 5.91 (br d, J=10.1 Hz, 1H), 5.30 (s, 2H), 4.07 (s, 4H), 3.41 (s, 4H), 2.34 (s, 3H). MS (ESI) m/z 542.3 [M+H]$^+$ 46: Synthesized according to general procedure A starting from intermediate III (400 mg, 939 umol) obtained in 4, wherein in step A.3 the NH nucleophile is 2-methyl-2,7-diazaspiro[4.4]nonane (240 mg, 1.13 mmol); variant ii) was used in step A.4; and variant ii) was used in step A.5; and 4% overall yield from III. $^1$H NMR (400 MHz, CDCl$_3$) δ=9.00 (br s, 1H), 8.60 (d, J=4.6 Hz, 1H), 8.46 (br s, 3H), 8.26 (br s, 1H), 7.81-7.71 (m, 2H), 7.65 (d, J=7.8 Hz, 1H), 7.59 (br d, J=8.3 Hz, 1H), 7.24 (br s, 1H), 7.01-6.96 (m, 1H), 6.94 (br s, 1H), 6.50 (br s, 2H), 5.86 (br s, 1H), 5.28 (s, 2H), 3.62 (br d, J=8.8 Hz, 1H), 3.26-3.20 (m, 4H), 3.11 (br d, J=7.1 Hz, 2H), 2.88 (br d, J=10.3 Hz, 1H), 2.70 (s, 3H), 2.11-2.02 (m, 2H), 2.01-1.88 (m, 2H). MS (ESI) m/z 570.1 [M+H]$^+$ 47: Synthesized according to general procedure A starting from intermediate III (400 mg, 939 umol) obtained in 4, wherein in step A.3 the NH nucleophile is 2-methyloctahydropyrrolo[3,4-c]pyrrole (243 mg, 1.22 mmol); variant i) was used in step A.4; and variant ii) was used in step A.5; and 5% overall yield from III. $^1$H NMR (400 MHz, DMSO-d$_6$) δ=9.74 (s, 1H), 9.59 (s, 1H), 8.60 (d, J=4.4 Hz, 1H), 8.49-8.42 (m, 2H), 8.01 (d, J=2.4 Hz, 1H), 7.92-7.85 (m, 1H), 7.71 (dd, J=2.4, 9.2 Hz, 1H), 7.58 (d, J=8.0 Hz, 1H), 7.40-7.34 (m, 1H), 7.24 (d, J=9.2 Hz, 1H), 7.07 (s, 1H), 6.65-6.53 (m, 1H), 6.36-6.28 (m, 1H), 5.87-5.77 (m, 1H), 5.28 (s, 2H), 3.47-3.38 (m, 2H), 3.07-2.99 (m, 2H), 2.86-2.81 (m, 2H), 2.24 (s, 3H). MS (ESI) m/z 556.4 [M+H]$^+$ 48: Synthesized according to general procedure A starting from intermediate III (600 mg, 1.41 mmol) obtained in 4, wherein in step A.3 the NH nucleophile is N,1-dimethylpyrrolidin-3-amine (241 mg, 2.11 mmol); variant ii) was used in step A.4; and variant ii) was used in step A.5; and 19% overall yield from III. $^1$H NMR (400 MHz, DMSO-d$_6$) δ=9.66 (br d, J=7.1 Hz, 2H), 8.70 (s, 1H), 8.60 (d, J=4.6 Hz, 1H), 8.47 (s, 1H), 7.99 (d, J=2.6 Hz, 1H), 7.88 (dt, J=1.5, 7.7 Hz, 1H), 7.70 (dd, J=2.4, 8.9 Hz, 1H), 7.59 (d, J=7.7 Hz, 1H), 7.37 (dd, J=5.3, 7.0 Hz, 1H), 7.33 (s, 1H), 7.25 (d, J=9.0 Hz, 1H), 6.69 (br dd, J=10.3, 16.9 Hz, 1H), 6.33 (dd, J=1.7, 16.9 Hz, 1H), 5.82 (br d, J=11.7 Hz, 1H), 5.28 (s, 2H), 3.90 (br s, 1H), 2.72 (s, 3H), 2.63 (br dd, J=4.2, 9.5 Hz, 2H), 2.44 (br s, 1H), 2.31-2.26 (m, 1H), 2.23 (s, 3H), 1.99-1.79 (m, 2H). MS (ESI) m/z 544.4 [M+H]$^+$ 566.4 [M+Na]$^+$ 49: Synthesized according to general procedure A starting from intermediate III (500 mg, 1.17 mmol) obtained in 4, wherein in step A.3 the NH nucleophile is 1-methyloctahydropyrrolo[3,4-b]pyrrole (178 mg, 1.41 mmol); variant i) was used in step A.4; and variant ii) was used in step A.5; and 23% overall yield from III. $^1$H NMR (400 MHz, CD$_3$OD) δ=8.58 (br s, 2H), 8.44 (s, 1H), 7.97-7.90 (m, 2H), 7.74 (d, J=7.8 Hz, 1H), 7.60 (dd, J=9.0, 2.2 Hz, 1H), 7.45-7.37 (m. 1H), 7.29 (s, 1H), 7.18 (d, J=9.0 Hz, 1H), 6.73-6.62 (m, 1H), 6.58-6.49 (m, 1H) 5.91 (d, J=10.0 Hz, 1H), 5.30 (s, 2H), 3.58 (d, J=10.4 Hz, 1H), 3.28 (br d, J=9.0 Hz, 1H) 3.18-3.12 (m, 1H), 3.07-2.96 (m, 3H), 2.88 (br dd, J=10.0, 4.0 Hz, 1H), 2.50 (s, 3H), 2.44-2.36 (m, 1H), 2.34-2.24 (m, 1H), 1.82-1.70 (m, 1H). MS (ESI) m/z 556.4 [M+H]$^+$ 50: To a mixture of intermediate III obtained in 4 (400 mg, 939 umol, 1.00 eq) and tert-butyl 1,6-diazaspiro[3.3]heptane-1-carboxylate (205 mg, 1.03 mmol, 1.10 eq, 0.5 oxalic acid) in acetonitrile (10.0 mL) was added potassium carbonate (260 mg, 1.88 mmol, 2.00 eq) The mixture was stirred at 80° C. for 2 h. After the reaction was completed, the mixture was filtered. The filter cake was washed with ethyl acetate (50 mL). The filtrate was combined and concentrated to give tert-butyl6-(4-((3-chloro-4-(pyridin-2-ylmethoxy)phenyl)amino)-6-nitroquinazolin-7-yl)-1,6-diazaspiro[3.3]heptane-1-carboxylate (511 mg, crude) as a yellow solid. $^1$H NMR (400 MHz, CDCl$_3$) δ=8.75-8.60 (m, 2H), 8.54 (s, 1H), 8.41 (s, 1H), 7.85-7.70 (m, 5H), 7.11 (d, J=8.4 Hz, 1H), 6.68 (s, 1H), 5.33 (s, 2H), 4.55-4.50 (m, 2H), 4.43-4.42 (m, 2H), 3.95-3.85 (m, 2H), 2.65-2.50 (m, 2H), 1.40 (s, 9H).

A solution of tert-butyl 6-(4-((3-chloro-4-(pyridin-2-ylmethoxy)phenyl)amino)-6-nitroquinazolin-7-yl)-1,6-diazaspiro[3.3]heptane-1-carboxylate (490 mg, 811 umol, 1.00 eq) in a mixture solvent of trifluoroacetic acid (0.500 mL) and dichloromethane (5.00 mL) was stirred at 10° C. for 1 h. Then the mixture was stirred at 20° C. for 2 h. To the mixture was added trifluoroacetic acid (0.500 mL) and the mixture was stirred at 20° C. for 4 h. After the reaction was completed, the mixture was concentrated to give N-(3-chloro-4-(pyridin-2-ylmethoxy)phenyl)-6-nitro-7-(1,6-diazaspiro[3.3]heptan-6-yl)quinazolin-4-amine (510 mg, crude, trifluoroacetate) as a yellow oil.

A mixture of N-(3-chloro-4-(pyridin-2-ylmethoxy)phenyl)-6-nitro-7-(1,6-diazaspiro[3.3]heptan-6-yl)quinazoline-4-amine (500 mg, 809 umol, 1.00 eq, trifluoroacetate), sodium borohydride acetate (343 mg, 1.62 mmol, 2.00 eq) and formalin solution (98.5 mg, 1.21 mmol, 28% purity, 1.50 eq) acetonitrile (5.00 mL) was stirred at 25° C. for 10 h. After the reaction was completed, the mixture was concentrated to give N-(3-chloro-4-(pyridin-2-ylmethoxy)phenyl)-7-(1-methyl-1,6-diazaspiro[3.3]heptan-6-yl)-6-nitroquinazolin-4-amine (821 mg, crude) as a yellow oil.

A mixture of N-(3-chloro-4-(pyridin-2-ylmethoxy)phenyl)-7-(1-methyl-1,6-diazaspiro[3.3]heptan-6-yl)-6-nitroquinazolin-4-amine (815 mg, crude), iron powder (308 mg, 5.51 mmol, 3.50 eq) and ammonium chloride (295 mg, 5.51 mmol, 3.50 eq) in a mixture solvent of methanol (5.00 mL) and water (3.00 mL) was stirred at 80° C. for 1 h. After the reaction was completed, the mixture was concentrated to remove water and give a residue. The residue was triturated with methanol (30.0 mL) and filtered. The pH of the filtrate was adjusted to around 11 and solid precipitated in the mixture. The volume of the mixture was concentrated to about 5.00 mL. The mixture was filtered and the filtrate was purified by prep-HPLC to give N$^4$-(3-chloro-4-(pyridin-2-ylmethoxy)phenyl)-7-(1-methyl-1,6-diazaspiro[3.3]heptan-6-yl)quinazoline-4,6-diamine (46.0 mg, 94.3 umol, 6% yield) as a yellow solid.

$^1$H NMR (400 MHz, CDCl$_3$) δ=8.60 (d, J=4.8 Hz, 1H), 8.55 (s, 1H), 7.83 (d, J=2.4 Hz, 1H), 7.79-7.72 (m, 1H), 7.66 (d, J=8.0 Hz, 1H), 7.47 (dd, J=2.4, 8.8 Hz, 1H), 7.26-7.21

(m, 1H), 7.00 (d, J=8.8 Hz, 1H), 6.95 (s, 1H), 6.91 (br s, 1H), 6.87 (s, 1H), 5.29 (s, 2H), 4.18-4.10 (m, 2H), 4.06-4.00 (m, 2H), 3.84 (br s, 2H), 3.21 (t, J=6.8 Hz, 2H), 2.45 (t, J=6.8 Hz, 2H), 2.37 (s, 3H).

A mixture of $N^4$-(3-chloro-4-(pyridin-2-ylmethoxy)phenyl)-7-(1-methyl-1,6-diazaspiro[3.3]heptan-6-yl)quinazoline-4,6-diamine (29.0 mg, 59.4 umol, 1.00 eq), acrylic acid (5.14 mg, 71.3 umol, 1.20 eq), pyridine (14.1 mg, 178 umol, 3.00 eq) and carbon diylamine hydrochloride (17.1 mg, 89.1 umol, 1.50 eq) in dimethyl formamide (0.500 mL) was stirred at 15° C. for 1 h. After the reaction was completed, the mixture was filtered and the filtrate was purified by prep-HPLC to give 50 (19.03 mg, 34.76 umol, 58% yield, 99% purity) as a yellow solid. $^1$H NMR (400 MHz, CDCl$_3$) δ=8.62 (s, 1H), 8.61 (br d, J=4.4 Hz, 1H), 8.57 (br s, 1H), 7.87 (d, J=2.8 Hz, 1H), 7.80-7.72 (m, 1H), 7.70-7.64 (m, 1H), 7.49 (dd, J=2.4, 8.8 Hz, 1H), 7.46-7.35 (m, 2H), 7.26-7.22 (m, 1H), 7.08 (s, 1H), 7.01 (d, J=8.8 Hz, 1H), 6.57-6.48 (m, 1H), 6.40-6.27 (m, 1H), 5.90 (br d, J=10.0 Hz, 1H), 5.30 (s, 2H), 4.17-4.10 (m, 2H), 4.02-3.94 (m, 2H), 3.21 (t, J=6.8 Hz, 2H), 2.45 (t, J=6.8 Hz, 2H), 2.37 (s, 3H). MS (ESI) m/z 542.4 [M+H]$^+$ 51: Synthesized according to general procedure C starting from intermediate XV (430 mg, 822 umol) obtained in 28, wherein in step C.4 HNR'R" is hexahydro-1H-furo[3,4-c]pyrrole (0.100 g, 884 umol); variant ii) was used in step C.5; and variant i) was used in step C.6; and 47% overall yield from XV. $^1$H NMR (400 MHz, DMSO-d$_6$) δ=8.92 (s, 1H), 8.56 (d, J=4.5 Hz, 1H), 8.45 (s, 1H), 8.28 (br s, 1H), 7.95-7.87 (m, 2H), 7.72 (d, J=7.9 Hz, 1H), 7.59 (dd, J=2.6, 8.8 Hz, 1H), 7.44-7.36 (m, 1H), 7.24 (s, 1H), 7.17 (d, J=8.9 Hz, 1H), 6.72-6.63 (m, 1H), 6.54-6.44 (m, 1H), 5.88 (dd, J=1.6, 10.1 Hz, 1H), 5.28 (s, 2H), 4.43 (t, J=4.8 Hz, 2H), 3.78 (d, J=9.2 Hz, 2H), 3.69-3.60 (m, 2H), 3.46-3.38 (m, 2H), 3.25 (br d, J=4.8 Hz, 1H), 3.03 (br s, 2H), 2.55 (br dd, J=5.7, 10.2 Hz, 2H). MS (ESI) m/z 587.3 [M+H]$^+$ 52: Synthesized according to general procedure C starting from intermediate XV (500 mg, 956 umol) obtained in 28, wherein in step C.4 HNR'R" is 1-oxa-6-azaspiro[3.3]heptane oxalate (235 mg, 1.24 mmol); variant ii) was used in step C.5; and variant i) was used in step C.6; and 7% overall yield from XV. $^1$H NMR (400 MHz, DMSO-d$_6$) δ=9.69 (s, 1H), 9.63 (s, 1H), 8.84 (s, 1H), 8.61 (d, J=4.2 Hz. 1H), 8.50 (s, 1H), 8.34 (s, 1H), 8.00 (d, J=2.6 Hz, 1H), 7.89 (dt, J=1.7, 7.7 Hz, 1H), 7.70 (dd, J=2.5, 9.0 Hz, 1H), 7.60 (d, J=7.8 Hz, 1H), 7.38 (dd, J=5.2, 6.8 Hz, 1H), 7.26 (t, J=4.5 Hz, 2H), 6.70 (dd, J=10.1, 17.0 Hz, 1H), 6.34 (dd, J=1.8, 16.9 Hz, 1H), 5.96-5.72 (m, 1H), 5.29 (s, 2H), 4.36 (t, J32 7.5 Hz, 2H), 4,19 (br t, J=5.3 Hz, 2H), 3.64-3.55 (m, 2H), 3.26-3.17 (m, 2H), 2.85 (br t, J=5.3 Hz, 2H), 2.73 (t, J=7.5 Hz, 2H). MS (ESI) m/z 573.1.1 [M+H]$^+$ 53: Synthesized according to general procedure C starting from intermediate XV (600 mg, 1.15 mmol) obtained in 28, wherein in step C.4 HNR'R" is N-methylcyclopropanamine (247 mg, 2.30 mmol); variant ii) was used in step C.5; and variant was used in step C.6; and 19% overall yield from XV. $^1$H NMR (400 MHz, DMSO-d$_6$) δ=9.68 (s, 1H), 9.56 (s, 1H), 8.83 (s, 1H) 8.60 (d, J=4.6 Hz, 1H), 8.63-8.58 (m, 1H), 8.49 (s, 1H), 7.99 (d, J=2.6 Hz, 1H), 7.88 (dt, J=1.7, 7.7 Hz, 1H), 7.69 (dd, J=2.5, 9.0 Hz, 1H), 7.59 (d, J=7.8 Hz, 1H), 7,37 (dd, J=5.1, 7.1 Hz, 1H), 7.29 (s, 1H), 7.25 (d, J=9.0 Hz, 1H), 6.66 (dd, J=10.3, 17.0 Hz, 1H), 6.30 (dd, J=1.7, 17.0 Hz, 1H), 5.81 (dd, J=1.7, 10.1 Hz, 1H), 5.29 (s, 2H), 4.31 (t, J=5.9 Hz, 2H), 3.00 (t, J=5.8 Hz, 2H), 2.37 (s, 3H), 1.81 (tt, J=3.4, 6.5 Hz, 1H), 0.46-0.40 (m, 2H), 0.36-0.30 (m, 2H). MS (ESI) m/z 545.4 [M+H]$^+$ 54: A solution of tert-butyl (1-(((4-((3-chloro-4-(pyridin-2-ylmethoxy)phenyl)amino)-6-nitroquinazolin-7-yl)oxy)methyl)cyclopropyl)carbamate (1.40 g, 2.36 mmol, 1.00 eq) in hydrochloric acid/ethyl acetate (4M, 20.0 mL) was stirred at 15° C. for 2 h under nitrogen atmosphere. The mixture was filtered. The filter cake was washed ethyl acetate (3×3.00 mL) and dried under reduced pressure to afford 7-((1-aminocyclopropyl)methoxy)-N-(3-chloro-4-(pyridin-2-ylmethoxy)phenyl)-6-nitroquinazolin-4-amine (1.00 g, 1.89 mmol, 80% yield, hydrochloride) as a yellow solid. $^1$H NMR (400 MHz, DMSO-d$_6$) δ=12.09 (br s, 1H), 9.97-9.73 (m, 1H), 8.94 (br d, J=1.5 Hz, 1H), 8.86 (br s, 2H), 8.73 (br d, J=4.6 Hz, 1H), 8.27-8.09 (m, 1H), 7.96 (d, J=2.4 Hz, 1H), 7.78 (br d, J=7.3 Hz, 1H), 7.75-7.68 (m, 2H), 7.60 (br d, J=4.9 Hz, 1H), 7.38 (d, J=9.0 Hz, 1H), 5.55-5.40 (m, 2H), 4.53 (s, 2H), 1.32-1.17 (m, 2H), 1.13-1.04 (m, 2H).

To a solution of 7-((1-aminocyclopropyl)methoxy)-N-(3-chloro-4-(pyridin-2-ylmethoxy)phenyl)-6-nitroquinazolin-4-amine (1.00 g, 1.89 mmol, 1.00 eq, hydrochloride) in acetonitrile (25.0 mL) was added 37% formalin (460 mg, 5.67 mmol, 422 uL, 3.00 eq), sodium triacetoxy borohydride (1.28 g, 6.04 mmol, 3.20 eq). The mixture was stirred at 25° C. for 12 h. The mixture was concentrated under reduced pressure to give a residue. The residue was triturated with water (10.0 mL) and dried under reduced pressure to give N-(3-chloro-4-(pyridin-2-ylmethoxy)phenyl)-7-((1-(dimethylamino)cyclopropyl)methoxy)-6-nitroquinazolin-4-amine (650 mg, 998 nmol, 52% yield, 80% purity) as a yellow solid. $^1$H NMR (400 MHz, CD$_3$OD) δ=9.05 (br s, 1H), 8.56 (br s, 2H), 7.98-7.86 (m, 3H), 7.71 (br d, J=7.8 Hz, 1H), 7.60 (br d, J=7.8 Hz, 1H), 7.40 (br d, J=6.4 Hz, 1H), 7.33 (s, 1H), 7.16 (br d, J=8.6 Hz, 1H), 5.27 (s, 2H), 4.52 (br s, 2H), 2.96-2.80 (m, 6H), 1.17 (br d, J=13.2 Hz, 4H).

To a solution of N-(3-chloro-4-(pyridin-2-ylmethoxy)phenyl)-7-((1-(dimethylamino)cyclopropyl)methoxy)-6-nitroquinazolin-4-amine (650 mg, 998 umol, 80% purity, 1.00 eq) in a mixture solvent of methanol (18.0 mL) and water (9.00 mL) was added iron powder (502 mg, 8.98 mmol, 9.00 eq) and ammonium chloride (374 mg, 6.99 mmol, 7.00 eq). The mixture was stirred at 60° C. for 12 h. The mixture was filtered and concentrated under reduced pressure to give a residue. The residue was purified by reversed phase chromatography and lyophilized to give $N^4$-(3-chloro-4-(pyridin-2-ylmethoxy)phenyl)-7-((1-(dimethylamino)cyclopropyl)methoxy)quinazoline-4,6-diamine (180 mg, 319 umol, 31% yield, 87% purity) as a yellow solid. $^1$H NMR (400 MHz, CD$_3$OD) δ=8.56 (d, J=4.9 Hz, 1H), 8.29 (s, 1H), 7.92 (dt, J=1.7, 7.8 Hz, 1H), 7.86 (d, J=2.4 Hz, 1H), 7.73 (d, J=7.8 Hz, 1H), 7.54 (dd, J=2.4, 8.8 Hz, 1H), 7.44-7.38 (m, 1H), 7.36 (s, 1H), 7.16 (d, J=8.8 Hz, 1H), 7.06 (s, 1H), 5.28 (s, 2H), 4.26 (s, 2H), 2.56 (s, 6H), 0.92-0.82 (m, 4H).

To a solution of $N^4$-(3-chloro-4-(pyridin-2-ylmethoxy)phenyl)-7-((1-(dimethylamino)cyclopropyl)methoxy)quinazoline-4,6-diamine (160 mg, 284 umol, 87% purity, 0.87 eq) in dimethylformamide (0.400 mL) was added acrylic acid (0.500 M in dimethylformamide, 977 uL, 1.50 eq), carbodiimide hydrochloride (125 mg, 652 umol, 2.00 eq) and pyridine (0.500 M in dimethylformamide, 1.30 mL, 2 eq). The mixture was stirred at 25° C. for 2 h. After the reaction was completed, the mixture was filtered. The filtrate was purified by prep-HPLC and lyophilized to afford 54 (85.18 mg, 148.16 umol, 45% yield, 94% purity) as a yellow solid. $^1$H NMR (400 MHz, CDCl$_3$) δ=9.09 (s, 1H), 8.64 (s, 1H), 8.61 (br d, J=3.4 Hz, 1H), 8.28 (s, 1H), 7.89 (d, J=2.4 Hz, 1H), 7.81-7.73 (m, 1H), 7.67 (d, J=7.8 Hz, 1H), 7.54-7.47 (m, 2H), 7.25 (br d, J=7.3 Hz, 1H), 7.21 (s, 1H), 7.06-6.99 (m, 1H), 6.49 (d, J=16.9 Hz, 1H), 6.34-6.21 (m, 1H), 5.96-5.84 (m, 1H), 5,31 (s, 2H), 4.22 (s, 2H), 2.57 (s, 6H), 0.98-0.86 (m, 2H), 0.83-0.74 (m, 2H). MS (ESI) m/z 545.5 [M+H]$^+$ 55: To a solution of tert-butyl (1-(hydroxymethyl)cyclopropyl)carbamate (1.00 g, 5.34 mmol, 3.00 eq) in tetrahydrofuran (30.0 mL) was added sodium hydride (427 mg, 10.7 mmol, 60% purity, 6.00 eq) at 0° C. and the mixture was stirred at 0° C. for 0.5 h. N-(3-chloro-4-(pyridin-2-ylmethoxy)phenyl)-7-fluoro-6-nitroquinazolin-4-amine (758 mg, 1.78 mmol, 1.00 eq) was added to the reaction mixture. The result solution was stirred at 50° C. for 2.5 h. The mixture was diluted with ethyl acetate (180 mL). The combined organic layers were washed with brine (6×15.0 mL), dried over anhydrous sodium sulfate, filtered and concentrated under reduced pressure to afford tert-butyl (1-(((4-((3-chloro-4-(pyridin-2-ylmethoxy)phenyl)amino)-6-nitroquinazolin-7-yl)oxy)methyl)cyclopropyl)carbamate (1.40 g, crude) as a yellow solid, $^1$H NMR (400 MHz, DMSO-d$_6$) δ=10.14 (br s, 1H), 9.31-9.13 (m, 1H), 8.60 (br d, J=4.6 Hz, 1H), 8.56 (s, 1H), 7.98 (br d, J=2.4 Hz, 1H), 7.88 (dt, J=1.7, 7.7 Hz, 1H), 7.80-7.62 (m, 3H), 7.58 (br d, J=7.8 Hz, 1H), 7.43-7.33 (m, 2H), 7.26 (br d, J=9.0 Hz, 2H), 5.29 (s, 2H), 4.26 (s, 2H), 1.36 (br d, J=2.0 Hz, 9H), 0.76 (br s, 2H), 0.71-0.68 (m, 2H).

To a solution of tert-butyl (1-(((4-(3-chloro-4-(pyridin-2-ylmethoxy)phenyl)amino)-6-nitroquinazolin-7-yl)oxy)methyl)cyclopropyl)carbamate (1.00 g, 1.69 mmol, 1.00 eq) in methanol (44.0 mL) was added iron powder (848 mg, 15.1 mmol, 9.00 eq), ammonium chloride (631 mg, 11.8 mmol, 7.00 eq) and water (11.0 mL). The mixture was stirred at 60° C. for 12 h. The mixture was filtered and concentrated under reduced pressure to give a residue. The residue was purified by reversed phase chromatography and lyophilized to give tert-butyl (1-(((6-amino-4-((3-chloro-4-(pyridin-2-ylmethoxy)phenyl)amino)quinazolin-7-yl)oxy)methyl)cyclopropyl)carbamate (300 mg, 533 mmol, 31% yield) as a white solid. $^1$H NMR (400 MHz, DMSO-d$_6$) δ=9.23 (s, 1H), 8.68-8.53 (m, 1H), 8.30 (s, 1H), 8.05 (d, J=2.4 Hz, 1H), 7.88 (dt, J=1.7, 7.7 Hz, 1H), 7.70 (dd, J=2.6, 8.9 Hz, 1H), 7.58 (d, J=7.8 Hz, 1H), 7.52 (br s, 1H), 7.39-7.36 (m, 1H), 7.35 (s, 1H), 7.22 (d, J=9.0 Hz, 1H), 6.95 (s, 1H), 5.51 (br s, 2H), 5.27 (s, 2H), 4.02 (s, 2H), 1.37 (s, 9H), 0.89-0.82 (m, 2H), 0.82-0.77 (m, 2H)

To a solution of tert-butyl (1-(((6-amino-4-((3-chloro-4-(pyridin-2-ylmethoxy)phenyl)amino)quinazolin-7-yl)oxy)methyl)cyclopropyl)carbamate (280 mg, 497 umol, 1.00 eq) in dimethylformamide (0.500 mL) was added carbodiimide hydrochloride (191 mg, 995 umol, 2.00 eq), acrylic acid (0.500 M in dimethylformamide, 1.49 mL, 1.50 eq) and pyridine (0.500 M in dimethylformamide, 1.99 mL, 2.00 eq). The mixture was stirred at 25° C. for 12 h. After the reaction was completed, the mixture was filtered. The filtrate was purified by prep-HPLC and lyophilized to afford tert-butyl (1-(((6-acrylamido-4-((3-chloro-4-(pyridin-2-ylmethoxy)phenyl)amino)quinazolin-7-yl)oxy)methyl)cyclopropyl)carbamate (150 mg, 243 umol, 48% yield) as a yellow solid. $^1$H NMR (400 MHz, DMSO-d$_6$) δ=9.70 (s, 1H), 9.46 (br s, 1H), 9.12 (br s, 1H), 8.60 (d, J=3.9 Hz, 1H), 8.46 (s, 1H), 7.96 (d, J=2.7 Hz, 1H), 7.88 (dt, J=1.7, 7.7 Hz, 1H), 7.67 (dd, J=2.6, 8.9 Hz, 1H), 7.59 (d, J=7.8 Hz, 1H), 7.55 (br s, 1H), 7.37 (dd, J=5.5, 7.2 Hz, 1H), 7.24 (d, J=9.0 Hz, 1H), 7.17 (s, 1H), 6.81 (br dd, J=10.0, 16.9 Hz, 1H), 6.39 (br d, J=16.6 Hz, 1H), 5.93-5.83 (m, 1H), 5.29 (s, 2H), 4.15 (s, 2H), 1.37 (s, 9H), 0.95-0.87 (m, 2H), 0.84 (br s, 2H).

To a solution of tert-butyl (1-(((6-acrylamido-4-((3-chloro-4-(pyridin-2-ylmethoxy)phenyl)amino)quinazolin-7-yl)oxy)methyl)cyclopropyl)carbamate (10.0 mg, 16.2 umol, 1.00 eq) in dichloromethane (1.00 mL) was added trifluoroacetic acid (154 mg, 1.35 mmol, 0.100 mL, 83.3 eq). The mixture was stirred at 25° C. for 2 h. The mixture was concentrated under reduced pressure to give a residue. The residue was combined with the residue of EW8418-290 and purified by prep-HPLC and lyophilized to afford 55 (5.74 mg, 4.37 umol, 26% yield, 96% purity, trifluoroacetate) as a yellow solid. $^1$H NMR (400 MHz, DMSO-d$_6$) δ=10.85 (br s, 1H), 9.76 (s, 1H), 9.20 (s, 1H), 8.75 (s, 1H), 8.67 (br s, 3H), 8.61 (br d, J=3.7 Hz, 1H), 7.94-7.85 (m, 2H), 7.60 (br d, J=7.8 Hz, 2H), 7.43-7.36 (m, 1H), 7.36-7.29 (m, 2H), 6.79 (dd, J=10.3, 16.9 Hz, 1H), 6.40 (d, J=17.1 Hz, 1H), 5.97-5.87 (m, 1H), 5.35-5.30 (m, 2H), 4.38 (s, 2H), 1.14 (s, 2H), 1.10-1.03 (m, 2H). MS (ESI) m/z 517.2 [M+H]$^+$ 56: Synthesized according to general procedure A, wherein in step A.2 H$_2$N-X is 2-fluoro-4-(pyridin-2-ylmethoxy)aniline (1.44 g, 6.59 mmol); in step A.3 the OH nucleophile 2-morpholinoethanol (250 mg, 1.91 mmol); variant ii) was used in step A.4; and variant ii) was used in step A.5; and 24% overall yield from II. $^1$H NMR (400 MHz, CDCl$_3$) δ=9.17 (s, 1H), 8.69-8.58 (m, 3H), 8.09-7.96 (m, 1H), 7.76 (td, J=7.8, 1.8 Hz, 1H), 7.54 (d, J=7.8 Hz, 1H), 7.43 (s, 1H), 7.29 (s, 1H), 7.28-7.24 (m, 1H), 6.94-6.83 (m, 2H), 6.58-6.35 (m, 2H), 5.87 (dd, J=10.0, 1.4 Hz, 1H), 5.24 (s, 2H), 4.37 (t, J=5.6 Hz, 2H), 3.85-3.72 (m, 4H), 2.93 (t, J=5.6 Hz, 2H), 2.68-2.58 (m, 4H). MS (ESI) m/z 545.3 [M+H]$^+$ 57: Synthesized according to general procedure A, wherein in step A.2 H$_2$N-X is 5-chloro-2-fluoro-4-(pyridin-2-ylmethoxy)aniline (1.11 g, 4.39 mmol); in step A.3 the OH nucleophile 2-morpholinoethanol (399 mg, 3.04 mmol); variant ii) was used in step A.4; and variant i) was used in step A.5; and 9% overall yield from II. $^1$H NMR (400 MHz, DMSO-d$_6$) δ=9.66 (br s, 1H), 9.59 (s, 1H), 8.85 (s, 1H), 8.66-8.58 (m, 1H), 8.39 (s, 1H), 7.91 (td, J=7.6, 1.8 Hz, 1H), 7.61 (dd, J=8.0, 3.6 Hz, 2H), 7.40 (dd, J=7.4, 5.8 Hz, 1H), 7.36 (d, J=11.8 Hz, 1H), 7.32 (s, 1H), 6.70 (dd, J=17.0, 10.2 Hz, 1H), 6.31 (dd, J=17.0, 1.8 Hz, 1H), 5.82 (dd, J=10.2, 1.8 Hz, 1H), 5.34 (s, 2H), 4.35 (t, J=5.8 Hz, 2H), 3.65-3.51 (m, 4H), 2.84 (t, J=5.8 Hz, 2H), 2.56-2.52 (m, 4H). MS (ESI) m/z 579.3 [M+H]$^+$ 58: Synthesized according to general procedure A, wherein in step A.2 H$_2$N-X is 5-(pyridin-2-ylmethoxy)pyridin-2-amine (305 mg, 1.52 mmol); in step A.3 the OH nucleophile 2-morpholinoethanol (241 mg, 1.84 mmol); variant i) was used in step A.4; and variant i) was used in step A.5; and 1% overall yield from II. $^1$H NMR (400 MHz, CD$_3$OD) δ=8.99 (s, 1H), 8.58 (br d, J=4.2 Hz, 1H), 8.48 (s, 1H), 8.44 (br s, 2H) 8.24-8.13 (m, 2H), 7.91 (td, J=7.8, 1.8 Hz, 1H), 7.65 (d, J=7.8 Hz, 1H), 7.54 (dd, J=9.0, 2.8 Hz, 1H), 7.41 (dd, J=6.8, 5.0 Hz, 1H), 7.22 (s, 1H), 6.70 (dd, J=17.0, 10.2 Hz, 1H), 6.48 (dd, J=17.0, 1.6 Hz, 1H), 5.90-5.82 (m, 1H), 5.27 (s, 2H), 4.39 (br t, J=5.0 Hz, 2H), 3.84-3.76 (m, 4H), 3.00 (t, J=5.0 Hz, 2H), 2.69 (br s, 4H). MS (ESI) m/z 528.4 [M+H]$^+$ 59: Synthesized according to general procedure A starting from intermediate III (600 mg, 1.47 mmol) obtained in 56, wherein in step A.3 the NH nucleophile is 1-methylpyrrolidin-3-ol (297 mg, 2.93 mmol); variant ii) was used in step A.4; and variant iii) was used in step A.5; and 19% overall yield from III. $^1$H NMR (400 MHz, DMSO-d$_6$) δ=9.54 (br d, J=13.7 Hz, 2H), 8.86 (s, 1H), 8.60 (d, J=4.8 Hz, 1H), 8.32 (s, 1H), 7.86 (dt, J=1.8, 7.7 Hz, 1H), 7.56 (d, J=7.8 Hz, 1H), 7.40-7.29 (m, 2H), 7.12 (s, 1H), 7.04 (dd, J=2.4, 12.0 Hz, 1H), 6.90 (dd, J=2.0, 8.7 Hz, 1H), 6.74 (dd, J=10.2, 17.1 Hz, 1H), 6.30 (dd, J=1.9, 17.1 Hz, 1H), 5.86-5.74 (m, 1H), 5.22

(s, 2H), 5.10 (br s, 1H), 2.82 (br d, J=3.7 Hz, 2H), 2.78-2.72 (m, 1H), 2.42-2.34 (m, 2H), 2.28 (s, 3H), 2.04-1.95 (m, 1H). MS (ESI) m/z 515.4 [M+H]$^+$

60: Synthesized according to general procedure A starting from intermediate III (900 mg, 2.03 mmol) obtained in 57, wherein in step A.3 the NH nucleophile is 1-methylpyrrolidin-3-ol (444 mg, 4.26 mmol); variant ii) was used in step A.4; and variant iii) was used in step A.5; and 13% overall yield from III. $^1$H NMR (400 MHz, DMSO-d$_6$) δ=9.63 (br s, 1H), 9.51 (br s, 1H), 8.89 (s, 1H), 8.61 (d, J=4.8 Hz, 1H), 8.36 (br s, 1H), 7.90 (dt, J=1.7, 7.7 Hz, 1H), 7.64-7.55 (m, 2H), 7.42-7.30 (m, 2H), 7.14 (s, 1H), 6.76 (dd, J=10.1, 17.0 Hz, 1H), 6.31 (dd, J=1.8, 17.1 Hz, 1H), 5.84-5.78 (m, 1H), 5.33 (s, 2H), 5.10 (br s, 1H), 2.83 (br d, J=4.5 Hz, 2H), 2.79-2.71 (m, 1H), 2.42-2.35 (m, 2H), 2.29 (s, 3H), 2.08-1.97 (m, 1H). MS (ESI) m/z 549.3 [M+H]$^+$, 571.3 [M+Na]$^+$ 61: Synthesized according to general procedure A starting from intermediate III (600 mg, 1.53 mmol) obtained in 58, wherein in step A.3 the NH nucleophile is 1-methylpyrrolidin-3-ol (309 mg, 3.06 mmol); variant ii) was used in step A.4; and variant ii) was used in step A.5; and 7% overall yield from III. $^1$H NMR (400 MHz, DMSO-d$_6$) δ=10.05 (s, 1H), 9.53 (s, 1H), 9.05 (s, 1H), 8.61 (br d, J=4.6 Hz, 1H), 8.53 (s, 1H), 8.24-8.15 (m, 2H), 7.87 (t, J=7.6 Hz, 1H), 7.64-7.51 (m, 2H), 7.43-7.33 (m, 1H), 7.16 (s, 1H), 6.75 (br dd, J=10.5, 16.9 Hz, 1H), 6.32 (br d, J=17.2 Hz, 1H), 5.82 (br d, J=10.9 Hz, 1H), 5.29 (s, 2H), 5.11 (br s, 1H), 2.83 (br d, J=3.9 Hz, 2H), 2.79-2.72 (m, 1H), 2.39-2.34 (m, 2H), 2.29 (s, 3H), 2.05-1.95 (m, 1H). MS (ESI) m/z 498.4 [M+H]$^+$ 62: Synthesized according to general procedure A starting from intermediate III (820 mg, 1.93 mmol) obtained in 4, wherein in step A.3 the OH nucleophile is 3-(dimethylamino)cyclobutanol (444 mg, 3.85 mmol); variant i) was used in step A.4; and variant ii) was used in step A.5; and 12% overall yield from III. $^1$H NMR (400 MHz, DMSO-d$_6$) δ=9.66 (s, 1H), 9.60 (s, 1H), 8.90 (s, 1H), 8.59 (d, J=4.3 Hz, 1H), 8.47 (s, 1H), 7.97 (d, J=2.6 Hz, 1H), 7.88 (dt, J=1.7, 7.7 Hz, 1H), 7.68 (dd, J=2.5, 9.0 Hz, 1H), 7.58 (d, J=7.8 Hz, 1H), 7.36 (dd, J=5.3, 7.0 Hz, 1H), 7.24 (d, J=9.0 Hz, 1H), 7.09 (s, 1H), 6.75 (dd, J=10.2, 17.1 Hz, 1H), 6.32 (dd, J=1.9, 16.9 Hz, 1H), 5.84-5.78 (m, 1H), 5.28 (s, 2H), 4.73 (quin, J=7.0 Hz, 1H), 2.78-2.68 (m, 2H), 2.40 (t, J=7.1 Hz, 1H), 2.07 (s, 6H), 2.03-1.94 (m, 2H). MS (ESI) 545.3 [M+H]$^+$, 567.3 [M+Na]$^+$ 63: Synthesized according to general procedure A, wherein in step A.2 H$_2$N-X is 4-phenoxyaniline (370 mg, 2.00 mmol); in step A.3 the OH nucleophile 2-morpholinoethanol (453 mg, 3.45 mmol); variant i) was used in step A.4; and variant i) was used in step A.5; and 6% overall yield from II. $^1$H NMR (400 MHz, DMSO-d$_6$) δ=9.71 (s, 1H), 9.58 (s, 1H), 8.86 (s, 1H), 8.48 (s, 1H), 8.2.9 (s, 1H), 7.81 (d, J=9.0 Hz, 2H), 7.43-7.37 (m, 2H), 7.31 (s, 1H), 7.13 (t, J=7.40 Hz, 1H), 7.04 (dd, J=11.8, 8.8 Hz, 4H), 6.68 (dd, J=17.0, 10.0 Hz, 1H), 6.31 (dd, J=17.0, 1.8 Hz, 1H), 5.85-5.79 (m, 1H), 4.35 (t, J=5.8 Hz, 2H), 3.62-3.55 (m, 4H), 2.83 (t, J=5.6 Hz, 2H), 2.56-2.53 (m, 4H). MS (ESI) m/z 512.3 [M+H]$^+$ 64: To a solution of intermediate III (800 mg, 1.88 mmol) obtained in 4 and potassium carbonate (779 mg, 5.64 mmol, 3.00 eq) in dimethylsulfoxide (10.0 mL) was added tert-butyl N-pyrrolidin-3-ylcarbamate (700 mg, 3.76 mmol, 2.00 eq). The mixture was stirred at 25° C. for 1 h. The residue was triturated with water (30.0 mL) and filtered, the filter cake was dried under reduced pressure to afford tert-butyl (1-(4-((3-chloro-4-(pyridin-2-ylmethoxy)phenyl)amino)-6-nitroquinazolin-7-yl)pyrrolidin-3-yl)carbamate (970 mg, 1.64 mmol, 87% yield) as a yellow solid. $^1$H NMR (400 MHz, DMSO-d$_6$) δ=9.90 (br s, 1H), 9.03 (s, 1H), 8.60 (br d, J=4.5 Hz, 1H), 8.49 (s, 1H), 8.02 (d, J=2.1 Hz, 1H), 7.88 (dt, J=1.5, 7.7 Hz, 1H), 7.71 (br dd, J=2.0, 8.9 Hz, 1H), 7.58 (d, J=7.8 Hz, 1H), 7.37 (dd, J=5.1, 7.0 Hz, 1H), 7.26 (br d, J=9.0 Hz, 2H), 7.00 (s, 1H), 5.29 (s, 2H), 4.11 (br s, 1H), 3.51-3.42 (m, 1H), 3.42-3.35 (m, 2H), 2.99 (br dd, J=4.5, 10.1 Hz, 1H), 2.54 (s, 1H), 2.19-2.08 (m, 1H), 1.97-1.89 (m, 1H), 1.38 (s, 9H).

A mixture of tert-butyl (1-(4-((3-chloro-4-(pyridin-2-ylmethoxy)phenyl)amino)-6-nitroquinazolin-7-yl)pyrrolidin-3-yl)carbamate (770 mg, 1.30 mmol, 1.00 eq) in hydrochloric acid/ethyl acetate (10.0 mL). The mixture was stirred at 25° C. for 2 h. The mixture was concentrated in vacuum. The residue was triturated with water (30.0 mL) and saturated sodium carbonate (5.00 mL). After filtration, the filter cake was dried in vacuum to afford 7-(3-aminopyrrolidin-1-yl)-N-(3-chloro-4-(pyridin-2-ylmethoxy)phenyl)-6-nitroquinazolin-4-amine (570 mg, 1.16 mmol, 89% yield) as a yellow solid. $^1$H NMR (400 MHz, DMSO-d$_6$) δ=9.95 (br s, 1H), 9.01 (br s, 1H), 8.60 (br s, 1H), 8.42 (br s, 1H), 8.00 (br s, 1H), 7.87 (br d, J=6.8 Hz, 1H), 7.67 (br d, J=7.6 Hz, 1H), 7.58 (br d, J=7.2 Hz, 1H), 7.36 (br s, 1H), 7.24 (br d, J=8.3 Hz, 1H), 6.95 (br s, 1H), 5.28 (br s, 2H), 3.57-3.39 (m, 2H), 3.27-3.22 (m, 1H), 2.83 (br s, 1H), 2.03 (br s, 1H), 198-1.63 (m, 2H).

To a solution of 7-(3-aminopyrrolidin-1-yl)-N-(3-chloro-4-(pyridin-2-ylmethoxy)phenyl)-6-nitroquinazolin-4-amine (570 mg, 1.16 mmol, 1.00 eq) in acetonitrile (20.0 mL) was added formaldehyde (940 mg, 11.6 mmol, 0.863 mL, 10.0 eq), sodium triacetoxy borohydride (786 mg, 3.71 mmol, 3.20 eq). The mixture was stirred at 25° C. for 12 h. The residue was triturated with water (30 mL) and filtered, the filter cake was dried under reduced pressure to afford N-(3-chloro-4-(pyridin-2-ylmethoxy)phenyl)-7-(3-(dimethylamino)pyrrolidin-1-yl)-6-nitroquinazolin-4-amine (500 mg, 0.962 mmol, 82% yield) as a yellow solid. $^1$H NMR (400 MHz, DMSO-d$_6$) δ=9.93 (br s, 1H), 9.04 (br s, 1H), 8.59 (br s, 1H), 8.48 (br s, 1H), 8.02 (br s, 1H), 7.88 (br s, 1H), 7.70 (br s, 1H), 7.59 (br s, 1H), 7.37 (br s, 1H), 7.26 (br d, J=6.7 Hz, 1H), 7.04 (br s, 1H), 5.28 (br s, 2H), 3.16 (br s, 4H), 2.77 (br s, 1H), 2.19 (br s, 6H), 2.14-2.02 (m, 1H), 1.85 (br s, 1H).

To a solution of N-(3-chloro-4-(pyridin-2-ylmethoxy)phenyl)-7-(3-(dimethylamino)pyrrolidin-1-yl)-6-nitroquinazolin-4-amine (500 mg, 0.962 mmol, 1.00 eq) and iron powder (376 mg, 6.73 mmol, 7.00 eq) in methanol (25.0 mL) was added a solution of ammonium chloride (463 mg, 8.65 mmol, 0.303 mL, 9.00 eq) in water (5.00 mL). The mixture was stirred at 80° C. for 3 h. The mixture was cooled to 25° C. and then concentrated in vacuum. The residue was triturated with methanol (100 mL) and filtered. The filtrate was concentrated to afford a residue. The residue was triturated with water (30.0 mL) and saturated sodium carbonate (2.00 mL). After filtration, the filter cake was washed with methanol (100 mL). The filtrate was concentrated in vacuum to afford N$^4$-(3-chloro-4-(pyridin-2-ylmethoxy)phenyl)-7-(3-(dimethylamino)pyrrolidin-1-yl)quinazoline-4,6-diamine (570 mg, crude) as a brown solid. $^1$H NMR (400 MHz, DMSO-d$_6$) δ=9.24 (s, 1H), 8.59 (br d, J=4.6 Hz, 1H), 8.34-8.28 (m, 1H), 8.09-7.99 (m, 1H), 7.90-7.85 (m, 1H), 7.71 (dd, J=2.1, 9.0 Hz, 1H), 7.61-7.56 (m, 1H), 7.42-7.38 (m, 1H), 7.36 (br d, J=5.0 Hz, 1H), 7.22 (d, J=9.0 Hz, 1H), 7.03 (s, 1H), 5.32-5.25 (m, 2H), 5.09 (br s, 2H), 3.18 (br d, J=8.7 Hz, 4H), 2.41 (br s, 6H), 2.18-2.09 (m, 1H), 2.04-1.87 (m, 1H), 1.35 (s, 1H).

To a solution of N$^4$-(3-chloro-4-(pyridin-2-ylmethoxy)phenyl)-7-(3-(dimethylamino)pyrrolidin-1-yl)quinazoline- 4,6-diamine (250 mg, 0.510 mmol, 1.00 eq), 1-(3-dimethylaminopropyl)-3-ethylcarbodiimide hydrochloride (196 mg, 1.02 mmol, 2.00 eq) and pyridine (80.7 mg, 1.02 mmol, 0.0824 mL, 2.00 eq) in N,N-dimethylformamide (3.00 mL) was added a solution of acrylic acid (0.500 M, 1.53 mL, 1.50 eq) in N,N-dimethylformamide. The mixture was stirred at 20° C. for 1 h. The mixture was concentrated in vacuum. The residue was purified by prep-HPLC and lyophilized to afford 64 (70.49 mg, 118 umol, 23% yield, 99% purity, formic acid) as a yellow solid. $^1$H NMR (400 MHz, DMSO-d$_6$) δ=9.92 (br s, 1H), 9.50 (br s, 1H), 8.62-8.57 (m, 1H), 8.42 (s, 1H), 8.23 (d, J=15.0 Hz, 1H), 8.20-8.19 (m, 1H), 8.04 (d, J=2.6 Hz, 1H), 7.88 (dt, J=1.8, 7.7 Hz, 1H), 7.76-7.68 (m, 1H), 7.58 (d, J=7.8 Hz, 1H), 7.39-7.34 (m, 1H), 7.26-7.20 (m, 1H), 6.86 (s, 1H), 6.59-6.47 (m, 1H), 6.29 (dd, J=1.7, 17.1 Hz, 1H), 5.80 (dd, J=1.6, 10.3 Hz, 1H), 5.27 (s, 2H), 3.48-3.34 (m, 4H), 2.82-2.68 (m, 1H), 2.19 (br s, 6H), 2.15-2.07 (m, 1H), 1.86-1.68 (m, 1H). MS (ESI) m/z 544.4 [M+H]$^+$ 65: To a stirred suspension of 1-methylpiperazine (2.50 g, 25.0 mmol, 1.00 eq), 3-chloro-3-methylbut-1-yne (3.07 g, 30.0 mmol, 1.20 eq), triethylamine (2.53 g, 25.0 mmol, 1.00 eq) in tetrahydrofuran (10.0 mL) was added copper (I) chloride (336 mg, 3.39 mmol, 0.136 eq) at 0° C. under nitrogen. The mixture was purged by nitrogen for 0.1 h and stirred at 20° C. for 0.5 h. Water (80.0 mL) and 1 N aqueous hydrochloric acid (20.0 mL) were added and the mixture was concentrated under reduced pressure. The mixture was washed with ethyl acetate (2×20.0 mL) and basified by addition of potassium carbonate (approx. 10.0 g). The mixture was extracted with ethyl acetate (3×20.0 mL), washed with brine (30.0 mL), drying with magnesium sulphate, and concentration to give 1-methyl-4-(2-methylbut-3-yn-2-yl)piperazine (2.00 g, 12.0 mmol, 48% yield) as a brown solid. $^1$H NMR (400 Hz, DMSO-d$_6$) δ=3.14 (s, 1H), 2.57-2.51 (m, 2H), 2.31 (br s, 3H), 2.13 (s, 3H), 1.35-1.20 (m, 6H).

To a solution of 4-((3-chloro-4-(pyridin-2-ylmethoxy)phenyl)amino)-6-nitroquinazolin-7-yl trifluoromethanesulfonate (0.400 g, 720 umol, 1.00 eq), 1-methyl-4-(2-methylbut-3-yn-2-yl)piperazine (144 mg, 864 umol, 1.20 eq), copper (I) iodide (27.4 mg, 144 umol, 0.200 eq) in N,N-dimethylformamide (5.00 mL) and triethylamine (2.00 mL) was added tetrakis(triphenylphosphine)palladium (14.4 ug, 72.0 umol, 0.100 eq) at 20° C. The mixture was stirred at 20° C. for 3 h. The mixture was concentrated in vacuum to give a residue. The residue was purified by silica gel chromatography (petroleum ether/ethyl acetate=1/1 to ethyl acetate/methanol/triethylamine=5/1/0.001) to give N-(3-chloro-4-(pyridin-2-ylmethoxy)phenyl)-7-(3-methyl-3-(4-methylpiperazin-1-yl)but-1-yn-1-yl)-6-nitroquinazolin-4-amine (0.250 g, 437 umol, 60% yield) as a yellow solid.

MS (ESI) m/z 572.1 [M+H]$^+$. $^1$H NMR (400 Hz, DMSO-d$_6$) δ=9.46 (s, 1H), 8.72 (s, 1H), 8.60 (br d, J=4.8 Hz, 1H), 8.03 (s, 1H), 7.96 (s, 1H), 7.89 (br t, J=7.6 Hz, 1H), 7.72 (br d, J=7.6 Hz, 1H), 7.59 (d, J=7.9 Hz, 1H), 7.42-7.34 (m, 1H), 7.31 (d, J=8.7 Hz, 1H), 5.31 (s, 2H), 3.40-3.36 (m, 2H), 2.71 (br s, 3H), 2.26 (br s, 3H), 1.45 (s, 6H).

To a suspension of N-(3-chloro-4-(pyridin-2-ylmethoxy)phenyl)-7-(3-methyl-3-(4-methylpiperazin-1-yl)but-1-yn-1-yl)-6-nitroquinazolin-4-amine (0.250 g, 437 umol, 1.00 eq), ammonium chloride (117 mg, 2.19 mmol, 5.00 eq) in methanol (10.0 mL) and water (5.00 mL) was added iron powder (122 mg, 2.19 mmol, 5.00 eq) at 20° C. The mixture was stirred at 80° C. for 1 h. The mixture was filtered, and the filtrate was concentrated in vacuum to give a residue. The residue was triturated with water (3.00 mL) to give N$^4$-(3-chloro-4-(pyridin-2-ylmethoxy)phenyl)-7-(3-methyl-3-(4-methylpiperazin-1-yl)but-1-yn-1-yl)quinazoline-4,6-diamine (0.180 g, crude) as a yellow solid. MS (ESI) m/z 542.3 [M+H]$^+$ To a solution of N$^4$-(3-chloro-4-(pyridin-2-ylmethoxy)phenyl)-7-(3-methyl-3-(4-methylpiperazin-1-yl)but-1-yn-1-yl)quinazoline-4,6-diamine (0.100 g, 185 umol, 1.00 eq) in N,N-dimethylformamide (2.00 mL) was added 1-(3-dimethylaminopropyl)-3-ethylcarbodiimide hydrochloride (106 mg, 553 umol, 3.00 eq), pyridine (0.500 M, 740 umol, 4.00 eq), acrylic acid (0.500 M, 222 umol, 1.20 eq) at 20° C. And the mixture was stirred at 20° C. for 12 h. The mixture was filtered. The filtrate was purified by prep-HPLC to give a crude product (30 mg), the crude product was repurified by prep-HPLC to give 65 (13.67 mg, 22.7 umol, 12% yield, 99% purity) as a yellow solid. $^1$H NMR (400 Hz, DMSO-d$_6$) δ=9.87 (br s, 1H), 9.82 (br s, 1H), 8.65 (s, 1H), 8.60 (br d, J=4.0 Hz, 1H), 8.57 (br s, 1H), 8.03 (br s, 1H), 7.88 (dt, J=1.7, 7.7 Hz, 1H), 7.79 (s, 1H), 7.72 (br d, J=9.2 Hz, 1H), 7.59 (d, J=7.8 Hz, 1H), 7.37 (dd, J=5.1, 6.5 Hz, 1H), 7.27 (d, J=8.8 Hz, 1H), 6.56 (br dd, J=9.7, 16.8 Hz, 1H), 6.32 (dd, J=1.8, 17.0 Hz, 1H), 5.87-5.79 (m, 1H), 5.29 (s, 2H), 2.65-2.60 (m, 4H), 2.36-2.28 (m, 4H), 2.14 (s, 3H), 1.42 (s, 6H). MS (ESI) m/z 596.5, [M+H]$^+$, 618.5 [M+Na]$^+$ 66: To a stirred suspension of 3-chloro-3-methylbut-1-yne (1.00 g, 9.75 mmol, 1.10 mL, 1.00 eq), dimethylamine (1.03 g, 12.7 mmol, 1.16 mL, 1.30 eq, HCl) and triethylamine (2.96 g, 29.2 mmol, 4.07 mL, 3.00 eq) in tetrahydrofuran (15.0 mL) was added cuprous chloride (193 mg, 1.95 mmol, 46.6 uL, 0.200 eq) under nitrogen atmosphere at 0° C. The mixture was purged by nitrogen for 0.1 h, and stirred at 20° C. for 0.5 h. The mixture was added water (20.0 mL), hydrochloric acid (1.00 M, 10.0 mL) and concentrated under reduced pressure. After that the mixture was washed with tert-butyl methyl ether (2×40.0 mL) and made basic by addition of potassium carbonate (5.00 g). The residue was extracted with tert-butyl methyl ether (3×60.0 mL), washing with brine (30.0 mL), dried over magnesium sulphate, filtered and concentrated to give N,N,2-trimethylbut-3-yn-2-amine (200 mg, 1.80 mmol, 18% yield) as light brown solid. $^1$H NMR (400 MHz, DMSO-d$_6$) δ=3.12 (s, 1H), 2.16 (s, 6H), 1.28 (s, 6H).

To a solution of N-(3-chloro-4-(pyridin-2-ylmethoxy)phenyl)-7-fluoro-6-nitroquinazolin-4-amine (4.00 g, 9.39 mmol, 1.00 eq) in dimethyl formamide (20.0 mL) was added potassium acetate (4.61 g, 47.0 mmol, 5.00 eq) at 15° C. The mixture was stirred at 100° C. for 1 h. The mixture was concentrated to afford a residue. The residue was diluted with water (50.0 mL). After filtration, the filter cake was washed with water (20.0 mL), dried in vacuum to give 4-((3-chloro-4-(pyridin-2-ylmethoxy)phenyl)amino)-6-nitroquinazolin-7-ol (4.0 g, crude) as yellow solid. $^1$H NMR (400 MHz, DMSO-d$_6$) δ=10.07 (s, 1H), 9.19 (br s, 1H), 8.68-8.52 (m, 2H), 8.00 (br s, 1H), 7.88 (br d, J=6.8 Hz, 1H), 7.69 (br d, J=7.6 Hz, 1H), 7.59 (br d, J=7.21 Hz, 1H), 7.37 (br s, 1H), 7.28 (br d, J=8.6 Hz, 1H), 7.20 (br s, 1H), 5.30 (s, 2H).

To a solution of 4-((3-chloro-4-(pyridin-2-ylmethoxy)phenyl)amino)-6-nitroquinazolin-7-ol (4.00 g, 9.44 mmol, 1.00 eq) and pyridine (3.73 g, 47.2 mmol, 3.81 mL, 5.00 eq) in dichloromethane (100 mL) was added trifluoromethanesulfonic anhydride (5.33 g, 18.9 mmol, 3.11 mL, 2.00 eq) at 0° C. The mixture was stirred at 20° C. for 12 h. The mixture was concentrated to afford a residue. The residue was purified by silica gel chromatography (silica gel column: 80 g; petroleum ether/ethyl acetate=1/1-0/1) to give 4-((3-chloro-4-(pyridin-2-ylmethoxy)phenyl)amino)-6-nitroquinazolin-7-yl trifluoromethanesulfonate (2.00 g, 3.60 mmol, 38% yield) as a yellow solid. $^1$H NMR (400 MHz, DMSO-$d_6$) δ=9.72 (s, 1H), 8.77 (s, 1H), 8.64-8.58 (m, 1H), 8.04 (s, 1H), 7.99 (d, J=2.6 Hz, 1H), 7.92-7.87 (m, 1H), 7.70 (dd, J=8.9, 2.6 Hz, 1H), 7.61-7.58 (m, 1H) 7.40-7.36 (m, 1H), 7.32 (d, J=9.0 Hz, 1H), 5.32 (s, 2H). MS (ESI) m/z 556.2 [M+H]$^+$ To a solution of 4-((3-chloro-4-(pyridin-2-ylmethoxy)phenyl)amino)-6-nitroquinazolin-7-yl trifluoromethanesulfonate (500 mg, 900 umol, 1.00 eq) in dimethyl formamide (10.0 mL) was added N,N,2-trimethylbut-3-yn-2-amine (150 mg, 1.35 mmol, 1.50 eq), copper iodide (85.7 mg, 450 umol, 0.500 eq), triethylamine (273 mg, 2.70 mmol, 376 uL, 3.00 eq), tetrakis(triphenylphosphine)palladium (104 mg, 90.0 umol, 0.100 eq) at 20° C. The mixture was de-gassed with nitrogen and stirred at 20° C. for 12 h under nitrogen. The mixture was concentrated under vacuum to give the residue. The residue was purified by flash chromatography [silica gel column: 12 g; petroleum ether/ethyl acetate=10/1-0/1; dichloromethane/methanol=10/1] to give N-(3-chloro-4-(pyridin-2-ylmethoxy)phenyl)-7-(3-(dimethylamino)-3-methylbut-1-yn-1-yl)-6-nitroquinazolin-4-amine (460 mg, crude) as light brown solid. $^1$H NMR (400 MHz, DMSO-$d_6$) δ=10.40 (br s, 1H), 9.47 (br s, 1H), 8.83 (br s, 1H), 8.73 (s, 1H), 8.61 (br d, J=4.8 Hz, 1H), 8.03 (br d, J=2.32 Hz, 2H), 7.89 (br d, J=1.6 Hz, 1H), 7.76-7.71 (m, 1H), 7.58-7.53 (m, 2H), 5.32 (s, 2H), 2.52 (s, 6H), 1.53 (s, 6H). MS (ESI) m/z 517.4 [M+H]$^+$ To a solution of N-(3-chloro-4-(pyridin-2-ylmethoxy)phenyl)-7-(3-(dimethylamino)-3-methylbut-1-yn-1-yl)-6-nitroquinazolin-4-amine (400 mg, 774 umol, 1.00 eq) in methanol (20.0 mL) and water (4.00 mL) was added iron (216 mg, 3.87 mmol, 5.00 eq) and ammonium chloride (207 mg, 3.87 mmol, 135 uL, 5.00 eq) at 20° C. The mixture was de-gassed with nitrogen and stirred at 70° C. for 1 h under nitrogen. The mixture was filtered to give the filtrate. The filtrate was purified by reverse-phase chromatography N$^4$-(3-chloro-4-(pyridin-2-ylmethoxy)phenyl)-7-(3-(dimethylamino)-3-methylbut-1-yn-1-yl)quinazoline-4,6-diamine (280 mg, 575 umol, 74% yield). $^1$H NMR (400 MHz, DMSO-$d_6$) δ=11.10 (br s, 1H), 10.70 (br s, 1H), 8.74 (s, 1H), 8.62 (d, J=4.2 Hz, 1H), 7.95-7.89 (m, 2H), 7.81 (s, 1H), 7.73 (s, 1H), 7.65-7.59 (m, 2H), 7.41 (dd, J=7.0, 5.3 Hz, 1H), 7.36 (d, J=9.0 Hz, 1H), 5.35 (s, 2H) 2.94 (s, 6H), 1.78 (s, 6H).

To the solution of N$^4$-(3-chloro-4-(pyridin-2-ylmethoxy)phenyl)-7-(3-(dimethylamino)-3-methylbut-1-yn-1-yl)quinazoline-4,6-diamine (220 mg, 451.75 umol, 1 eq) and acrylic acid (65.1 mg, 904 umol, 62.0 uL, 2.00 eq) in dimethyl formamide (5.00 mL) was added pyridine (71.5 mg, 904 umol, 72.9 uL, 2.00 eq) and 1-(3-dimethylaminopropyl)-3-ethylcarbodiimide hydrochloride (173 mg, 904 umol, 2.00 eq) at 20° C. The mixture was stirred at 20° C. for 1 h. The mixture was filtered to give the filtrate. The filtrate was purified by prep-HPLC to give 66 (30.38 mg, 55.03 umol, 12.18% yield, 98% purity) as yellow solid. $^1$H NMR (400 MHz, CD$_3$OD) δ=8.66 (s, 1H), 8.58 (d, J=4.52 Hz, 1H), 8.53 (s, 1H), 7.95 (d, J=2.4 Hz, 1H), 7.94-7.90 (m, 1H), 7.89 (s, 1H), 7.74 (d, J=7.8 Hz, 1H), 7.63 (dd, J=8.86, 2.63 Hz, 1H), 7.41 (dd, J=6.9, 5.32 Hz, 1H), 7,19 (d, J=8.9 Hz, 1H), 6.63-6.53 (m, 1H), 6.53-6.45 (m, 1H), 5.92 (dd, J=9.8, 2.0 Hz, 1H), 5.30 (s, 2H), 2.44 (s, 6H), 1.56 (s, 6H). MS (ESI) m/z 541.4 [M+H]$^+$ 67: Synthesized according to general procedure A starting from intermediate III (800 mg, 1.88 mmol) obtained in 4, wherein in step A.3 the OH nucleophile is 1-methylpyrrolidin-3-ol (380 mg, 3.76 mmol); variant ii) was used in step A.4; and 24% overall yield from III. $^1$H NMR (400 MHz, DMSO-$d_6$) δ=10.14 (br s, 1H), 9.68 (br s, 1H), 8.69 (br s, 1H), 8.60 (dd, J=0.7, 4.8 Hz, 1H), 8.48 (s, 1H), 8.22 (s, 2H), 8.01-7.95 (m, 1H), 7.88 (dt, J=1.7, 7.7 Hz, 1H), 7.67 (dd, J=2.3, 9.0 Hz, 1H), 7.58 (d, J=7.8 Hz, 1H), 7.37 (dd, J=4.9, 6.6 Hz, 1H), 7.25 (d, J=9.2 Hz, 1H), 7.18 (s, 1H), 5.28 (s, 2H), 5.16 (br s, 1H), 3.03-2.79 (m, 3H), 2.57-2.51 (m, 1H), 2.42-2.37 (m, 4H), 2.07 (br s, 3H), 2.00-1.94 (m, 1H). MS (ESI) m/z 543.4 [M+H]$^+$ 68: Synthesized according to general procedure A, wherein in step A.2 H$_2$N-X is 3-methyl-4-((6-methylpyridin-3-yl)oxy)aniline (500 mg, 2.33 mmol); in step A.3 the OH nucleophile 1-methylpyrrolidin-3-ol (414 mg, 4.09 mmol); variant ii) was used in step A.4; and variant v was used in step A.5; and 27% overall yield from II. $^1$H NMR (400 MHz, DMSO-$d_6$) δ=9.75-9.54 (m, 2H), 8.94 (br s, 1H), 8.48 (s, 1H), 8.23 (br d, J=4.8 Hz, 1H), 8.18 (d, J=2.2 Hz, 1H), 7.74 (d, J=2.3 Hz, 1H), 7.67 (dd, J=2.6, 8.7 Hz, 1H), 7.26-7.22 (m, 1H), 7.22-7.18 (m, 1H), 7.17 (br s, 1H), 6.94 (d, J=8.7 Hz, 1H), 6.82-6.70 (m, 1H), 6.32 (br d, J=17.0 Hz, 1H), 5.86-5.79 (m, 1H), 5.16 (br s, 1H), 3.05-2.82 (m, 3H), 2.52 (br d, J=1.8 Hz, 1H), 2.44 (s, 3H), 2.42-2.36 (m, 3H), 2.35-2.30 (m, 1H), 2.20 (s, 3H), 2.03 (br d, J=4.0 Hz, 1H). MS (ESI) m/z 511.4 [M+H]$^+$ 69: Synthesized according to general procedure A starting from intermediate III (400 mg, 939 umol) obtained in 4, wherein in step A.3 the OH nucleophile is 3-(4-methylpiperazin-1-yl)propan-1-ol (193 mg, 1.22 mmol); variant i) was used in step A.4; and variant ii) was used in step A.5; and 64% overall yield from III. $_1$H NMR (400 MHz, CDCl$_3$) δ=9.10 (s, 1H), 8.64 (s, 1H), 8.61 (d, J=4.8 Hz, 1H), 8.20 (s, 1H), 7.89 (d, J=2.6 Hz, 1H), 7.81-7.73 (m, 1H), 7.68 (d, J=7.8 Hz, 1H), 7.63 (s, 1H), 7.51 (dd, J=8.8, 2.6 Hz, 1H), 7.54 (br s, 1H), 7.28-7.23 (m, 2H), 7.01 (d, J=8.8 Hz, 1H), 6.55-6.45 (m, 1H), 6.42-6.30 (m, 1H), 5.88 (dd, J=10.2, 1.0 Hz, 1H), 5.31 (s, 2 H), 4.30 (t, J=6.4 Hz, 2H), 2.66-2.55 (m, 4H), 2.51 (br s, 4H), 2.32 (s, 3H), 2.19-2.09 (m, 4H). MS (ESI) m/z 588.4 [M+H]$^+$ 70: Synthesized according to general procedure C starting from intermediate XV (600 mg, 1.15 mmol) obtained in 28, wherein in step C.4 HNR'R" is 1-methylpiperazine (412 mg, 4.11 mmol); variant ii) was used in step C.5; and 17% overall yield from XV. $^1$H NMR (400 MHz, CDCl$_3$) δ=8.90 (s, 1H), 8.68 (s, 1H), 8.63 (s, 1H), 8.60 (d, J=4.8 Hz, 1H), 7.88 (d, J=2.8 Hz, 1H), 7.79-7.73 (m, 1H), 7.69-7.64 (m, 1H), 7.51-7.44 (m, 2H), 7.26-7.22 (m, 1H), 7.02 (d, J=9.2 Hz, 2H), 5.31 (s, 2H), 4.36 (t, J=5.6 Hz, 2H), 2.92 (t, J=5.6 Hz, 2H), 2.75-2.39 (m, 8H), 2.32 (s, 3H), 2.08 (s, 3H). MS (ESI) m/z 586.3 [M+H]$^+$ 71: Synthesized according to general procedure A, wherein in step A.2 H$_2$N-X is 6-(2-pyridylmethoxy)pyridin-3-amine (961 mg); in step A.3 the OH nucleophile is 2-morpholinoethanol (304 mg, 2.32 mmol); variant i) was used in step A.4; and variant i) was used in step A.5; and 7% overall yield from II. $^1$H NMR (400 MHz, CDCl$_3$) δ=9.14 (s, 1H), 8.67-8.58 (m, 2H), 8.45 (s, 1H), 8.38 (d, J=2.4 Hz, 1H), 8.03 (dd, J=2.8, 8.8 Hz, 1H), 7.71 (dt, J=1.6, 7.6 Hz, 1H), 7.49 (d, J=7.6 Hz, 1H), 7.37 (s, 1H), 7.29 (s, 1H), 7.26-7.20 (m, 1H), 6.96 (d, J=8.8 Hz, 1H), 6.53-6.45 (m, 1H), 6.43-6.32 (m, 1H), 5.88 (dd, J=1.2, 10.0 Hz, 1H), 5.55 (s, 2H), 4.37 (t, J=5.6 Hz, 2H), 3.80-3.71 (m, 4H), 2.92 (t, J=5.6 Hz, 2H), 2.64-2.55 (m, 4H). MS (ESI) m/z 528.4 [M+H]$^+$ 72: Synthesized according to general procedure A starting from intermediate III (400 mg, 939 umol) obtained in 71, wherein in step A.3 the OH nucleophile is (3R)-1-methylpyrrolidin-3-ol (247 mg, 2.45 mmol); variant ii) was used in step A.4; and variant ii) was used in step A.5; and 5% overall yield from III. $^1$H NMR (400 MHz, CDCl$_3$) δ=9.15 (s, 1H), 8.99 (br s, 1H), 8.63 (d, J=4.4 Hz, 1H), 8.59 (s, 1H), 8.39 (d, J=2.4 Hz, 1H), 8.03 (dd, J=2.8, 8.8 Hz, 1H), 7.74-7.67 (m, 2H), 7.49 (d, J=8.0 Hz, 1H), 7.25-7.20 (m, 1H), 7.15 (s, 1H), 6.94 (d, J=8.8 Hz, 1H), 6.61 (br s, 1H), 6.53-6.46 (m, 1H), 5.86-5.80 (m, 1H), 5.54 (s, 2H), 5.17-5.08 (m, 1H), 3.49-3.17 (m, 2H), 2.87-2.73 (m, 1H), 2.65-2.50 (m, 5H), 2.30-2.20 (m, 1H). MS (ESI) m/z 498.4 [M+H]$^+$ 73: Synthesized according to general procedure A starting from intermediate III (700 mg, 1.73 mmol) obtained in 68, wherein in step A.3 the OH nucleophile is 2-morpholinoethanol (453 mg, 3.45 mmol); variant ii) was used in step A.4; and variant i) was used in step A.5; and 39% overall yield from III. $^1$H NMR (400 MHz, DMSO-d$_6$) δ=9.68 (br s, 1H), 9.59 (s, 1H), 8.86 (s, 1H), 8.49 (s, 1H), 8.20 (s, 1H), 8.18 (d, J=2.7 Hz, 1H), 7.75 (d, J=2.3 Hz, 1H), 7.67 (dd, J=2.4, 8.7 Hz, 1H), 7.31 (s, 1H), 7.26-7.22 (m, 1H), 7.22-7.18 (m, 1H), 6.95 (d, J=8.7 Hz, 1H), 6.68 (dd, J=10.3, 17.0 Hz, 1H), 6.31 (dd, J=1.9, 17.1 Hz, 1H), 5.85-5.79 (m, 1H), 4.34 (t, J=5.7 Hz, 2H), 3.59-3.55 (m, 4H), 2.82 (t, J=5.7 Hz, 2H), 2.55-2.51 (m, 4H), 2.51-2.48 (m, 1H), 2.44 (s, 3H), 2.20 (s, 3H). MS (ESI) m/z 541.2 [M+H]$^+$ 74: Synthesized according to general procedure A, wherein in step A.2 H$_2$N-X is 4-(4-chlorophenoxy)aniline (579 mg, 2.64 mmol); in step A.3 the OH nucleophile is 2-morpholinoethanol (166 mg, 1.27 mmol); variant was used in step A.4; and variant ii) was used in step A.5; and 17% overall yield from II. $^1$H NMR (400 MHz, CDCl$_3$) δ=9.24 (s, 1H), 8.97 (s, 1H), 8.64 (s, 1H), 8.34 (s, 1H), 7.70 (d, J=9.0 Hz, 2H), 7.51 (s, 1H), 7.35-7.30 (m, 2H), 7.07 (d, J=9.0 Hz, 2H), 7.03-6.99 (m, 2H) 6.66-6.58 (m, 1H), 6.55-6.50 (m, 1H), 5.90 (dd, J=9.8, 1.6 Hz, 1H), 4.42 (t, J=5.4 Hz, 2H), 3.89-3.81 (m, 4H), 3.12 (t, J=5.4 Hz, 2H), 2.83 (br d, J=4.2 Hz, 4H). MS (ESI) m/z 546.3 [M+H]$^+$ 75: Synthesized according to general procedure A, wherein in step A.2 H$_2$N-X is 4-(pyridin-3-yloxy)aniline (409 mg, 2.20 mmol); in step A.3 the OH nucleophile is 2-morpholinoethanol (939 mg, 7.16 mmol); variant ii) was used in step A.4; and variant i) was used in step A.5; and 4% overall yield from II. $^1$H NMR (400 MHz, DMSO-d$_6$) δ=9.75 (s, 1H), 9.61 (s, 1H), 8.87 (s, 1H), 8.49 (s, 1H), 8.40 (s, 1H), 8.36 (t, J=2.8 Hz, 1H), 7.85 (d, J=8.8 Hz, 2H), 7.44 (br s, 2H), 7.32 (s, 1H), 7.12 (d, J=8.7 Hz, 2H), 6.69 (br dd, J=10.6, 16.7 Hz, 1H), 6.31 (d, J =16.9 Hz, 1H), 5.83 (d, J=10.6 Hz, 1H), 4.35 (t, J=5.7 Hz, 2H), 3.58 (t, J=4.4 Hz, 4H), 2.83 (t, J=5.6 Hz, 2H), 2.56-2.52 (m, 4H). MS (ESI) m/z 513.4 [M+H]$^+$ 76: Synthesized according to general procedure C starting from intermediate XV (2.00 g, 6.94 mmol) obtained in 28, wherein in step C.4 HNR'R" is N,N-dimethylpiperidin-4-amine (609 mg, 3.70 mmol, HCl); variant ii) was used in step C.5; variant i) was used in step C.6; and 6% overall yield from XV. $^1$H NMR (400 MHz, DMSO-d$_6$) δ=9.68 (s, 1H), 9.59 (s, 1H), 8.85 (s, 1H), 8.61 (d, J=4.6 Hz, 1H), 8.49 (s, 1H), 8.00 (d, J=2.6 Hz, 1H), 7.89 (dt, J=1.7, 7.6 Hz, 1H), 7.70 (dd, J=2.6, 8.9 Hz, 1H), 7.60 (d, J=7.9 Hz, 1H), 7.41-7.35 (m, 1H), 7.31 (s, 1H), 7.26 (d, J=9.2 Hz, 1H), 6.69 (dd, J=10.2, 17.2 Hz, 1H), 6.32 (dd, J=1.8, 17.1 Hz, 1H), 5.91-5.74 (m, 1H), 5.29 (s, 2H), 4.32 (t, J=5.7 Hz, 2H), 2.99 (br d, J=11.7 Hz, 2H), 2.80 (t, J=5.7 Hz, 2H), 2.15 (s, 6H), 2.10-1.96 (m, 3H), 1.69 (br d, J=11.9 Hz, 2H), 1.43-1.30 (m, 2H). MS (ESI) m/z 602.5 [M+H]$^+$ 77: Synthesized according to general procedure C starting from intermediate XV (100 mg, 206 umol) obtained in 28, wherein in step C.4 HNR'R" is 2-methyloctahydropyrrolo[3,4-c]pyrrole (66.9 mg, 411 umol, HCl); variant ii) was used in step C.5; variant i) was used in step C.6; and 10% overall yield from XV. $^1$H NMR (400 MHz, DMSO-d$_6$) δ=9.68 (s, 1H), 9.60 (s, 1H), 8.85 (s, 1H), 8.61 (d, J=4.8 Hz, 1H), 8.50 (s, 1H), 8.00 (d, J=2.6 Hz, 1H), 7.89 (dt, J=1.7, 7.7 Hz, 1H), 7.70 (dd, J=2.5, 9.0 Hz, 1H), 7.60 (d, J=7.8 Hz, 1H), 7.41-7.34 (m, 1H), 7.30 (s, 1H), 7.26 (d, J=9.0 Hz, 1H), 6.68 (dd, J=10.1, 17.1 Hz, 1H), 6.31 (dd, J=1.7, 17.1 Hz, 1H), 5.88-5.75 (m, 1H), 5.29 (s, 2H), 4.32 (br t, J=5.6 Hz, 2H), 2.86 (br t, J=5.6 Hz, 2H), 2.80-2.71 (m, 2H), 2.57 (br s, 2H), 2.43-2.35 (m, 2H), 2.31 (br dd, J=4.1, 8.7 Hz, 2H), 2.24 (dd, J=2.8, 8.8 Hz, 2H), 2.17 (s, 3H). MS (ESI) m/z 600.1 [M+H]$^+$ 78: Synthesized according to general procedure A starting from intermediate III (400 mg, 939 umol) obtained in 4, wherein in step A.3 the NH nucleophile is N,N-dimethylpiperidin-4-amine (168 mg, 1.32 mmol); variant ii) was used in step A.4; variant i) was used in step A.5; and 45% overall yield from III. $^1$H NMR (400 MHz, CDCl$_3$) δ=9.00 (s, 1H), 8.73 (s, 1H), 8.61 (br s, 1 H), 8.60 (s, 1H), 8.45 (br s, 1H), 7.88 (d, J=2.6 Hz, 1H), 7.80-7.76 (m, 1H), 7.67 (d, J=7.8 Hz, 1H), 7.54 (d, J=2.6 Hz, 1H), 7.52 (s, 1H), 7.28-7.23 (m, 1H), 6.99 (d, J=9.0 Hz, 1H), 6.54-6.48 (m, 2H), 5.88 (dd, J=7.0, 4.4 Hz, 1H), 5.29 (s, 2H), 3.28 (br d, J=12.0 Hz, 2H), 2.89-2.82 (m, 1H), 2.77 (br t, J=11.6 Hz, 2H), 2.70 (s, 6H), 2.28-2.09 (m, 4H). MS (ESI) m/z 558.4 [M+H]$^+$ 79: The reaction mixture of 4-chloro-7-fluoro-6-nitroquinazoline (800 mg, 3.52 mmol, 1.00 eq) and 4-(pyridin-2-ylmethoxy)aniline (704 mg, 3.52 mmol, 1.00 eq) in acetonitrile (20.0 was stirred for 2 h at 25° C. The mixture was concentrated under vacuum to give 7-fluoro-6-nitro-N-(4-(pyridin-2-ylmethoxy)phenyl)quinazolin-4-amine (1.5 g, crude) as yellow solid. $^1$H NMR (400 MHz, DMSO-d$_6$) δ=11.69 (br s, 1H), 9.93 (d, J=7.70 Hz, 1H), 8.92 (s, 1H), 8.83 (br d, J=4.77 Hz, 1H), 8.29-8.2.2 (m, 1H), 8.04 (d, J=11.86 Hz, 1H), 7.89 (d, J=7.83 Hz, 1H), 7.78 (d, J=8.93 Hz, 2H), 7.75-7.70 (m, 1H), 7.26 (d, J=9.05 Hz, 2H), 5.47 (s, 2H).

A mixture of 7-fluoro-6-nitro-N-(4-(pyridin-2-ylmethoxy)phenyl)quinazolin-4-amine (400 mg, 1.02 mmol, 1.00 eq), tert-butyl 3-(hydroxymethyl)morpholine-4-carboxylate (444 mg, 2.04 mmol, 2.00 eq) and potassium tert-butoxide (344.07 mg, 3.07 mmol, 3.00 eq) in dimethylsulfoxide (10.0 mL) was stirred for 1 h at 20° C. The mixture was filtered to give the filtrate. The filtrate was purified by reverse-phase chromatography [column: 80 g, CH$_3$CN/H$_2$O (FA: 0.1%)=0/1-1/1] to give tert-butyl 3-(((6-nitro-4-((4-(pyridin-2-ylmethoxy)phenyl)amino)quinazolin-7-yl)oxy)methyl)morpholine-4-carboxylate (340 mg, 578 nmol, 57% yield) as a yellow solid.

$^1$H NMR (400 MHz, DMSO-d$_6$) δ=10.06 (s, 1H), 9.24 (s, 1H), 8.66-8.57 (m, 2H), 7.86 (br t, J=7.58 Hz, 1H), 7.69 (br d, J=8.93 Hz, 2H), 7.61 (s, 1H), 7.55 (br d, J=7.95 Hz, 1H), 7.41-7.34 (m, 1H), 7.13-7.07 (m, 2H), 5.21 (s, 2H), 4.59 (br t, J=8.74 Hz, 1H), 4.48 (br d, J=13.57 Hz, 1H), 4.28 (br s, 1H), 3.97 (br d, J=11.37 Hz, 1H), 3.83 (br d, J=8.80 Hz, 1H), 3.72 (br s, 1H), 3.55 (br d, J=9.17 Hz, 1H), 3.47-3.41 (m, 2H), 1.35 (br s, 9H).

The mixture of tert-butyl 3-(((6-nitro-4-((4-(pyridin-2-ylmethoxy)phenyl)amino)quinazolin-7-yl)oxy)methyl)morpholine-4-carboxylate (0.450 g, 764.51 umol, 1.00 eq), iron (213 mg, 3.82 mmol, 5.00 eq), and ammonium chloride (204 mg, 3.82 mmol, 134 uL, 5.00 eq) in methanol (10.0 mL) and water (2.00 mL) was stirred for 1 h at 70° C. The mixture was filtered to give the filtrate. The filtrate was purified by reverse-phase chromatography to give tert-butyl 3-(((6-amino-4-((4-(pyridin-2-ylmethoxy)phenyl)-amino)quinazolin-7-yl)oxy)methyl)morpholine-4-carboxylate (200 mg, 358 umol, 47% yield) as a yellow solid. $^1$H NMR (400 MHz, DMSO-d$_6$) δ=10.07 (br s, 1H), 8.60 (d, J=4.16 Hz, 1H), 8.48

(s, 1H), 7.86 (td, J=7.70, 1.71 Hz, 1H), 7.64-7.58 (m, 2H), 7.55 (d, J=7.82 Hz, 1H), 7.49 (s, 1H), 7.37 (dd, J=7.09, 5.14 Hz, 1H), 7.17 (br s, 1H), 7.08 (d, J=9.05 Hz, 2H), 5.62 (br s, 2H), 5.21 (5, 2H), 4.47-4.31 (m, 3H), 4.05 (br d, J=11.86 Hz, 1H), 3.84 (br d, J=8.68 Hz, 1H), 3.68 (br s, 1H), 3.57 (br d, J=11.74 Hz, 1H), 3.46-3.41 (m, 2H), 1.42 (br s, 9H).

To a solution of teat-butyl 3-(((6-amino-4-((4-(pyridin-2-ylmethoxy)phenyl)amino)quinazolin-7-yl)oxy)methyl)morpholine-4-carboxylate (200 mg, 358 umol, 1.00 eq) and acrylic acid (38.7 mg, 537 umol, 36.9 uL, 1.50 eq) in dimethyl formamid (5.00 mL) was added 1-(3-dimethylaminopropyl)-3-ethylcarbodiimide hydrochloride (137 mg, 716 umol, 2.00 eq) and pyridine (56.6 mg, 716 umol, 57.8 uL, 2.00 eq) at 25° C. The reaction mixture was stirred for 1 h at 25° C. Acrylic acid (51.6 mg, 716 umol, 49.1 uL, 2.00 eq), 1-(3-dimethylaminopropyl)-3-ethylcarbodiimide hydrochloride (137 mg, 716 umol, 2.00 eq) and pyridine (56.6 mg, 716 umol, 57.8 uL, 2.00 eq) were added to the mixture. The resulting mixture was stirred for 6 h at 25° C. The mixture was filtered to give the filtrate. The filtrate was purified by prep-HPLC to give tert-butyl 3-(((6-acrylamido-4-((4-(pyridin-2-ylmethoxy)phenyl)amino)quinazolin-7-yl)oxy) methyl)morpholine-4-carboxylate (50.0 mg, 81.6 umol, 23% yield) as a light yellow solid. $^1$H NMR (400 MHz, DMSO-$d_6$) δ=9.64 (s, 1H), 8.96 (br s, 1H), 8.60 (br d, J=4.04 Hz, 1H), 8.43 (s, 1H), 7.86 (br t, J=7.40 Hz, 1H), 7.65 (br d, J=8.68 Hz, 2H), 7.55 (d, J=7.58 Hz, 1H), 7.40-7.34 (m, 2H), 7.05 (br d, J=9.05 Hz, 2H), 6.71 (br dd, J=16.81, 10.33 Hz, 1H), 6.33 (br d, J=16.02 Hz, 1H), 5.84 (br d, J=10.51 Hz, 1H), 5.20 (s, 2H), 4.48 (br s, 1H), 4.33 (br s, 2H), 4.08 (br d, J=11.74 Hz, 1H), 3.85 (br d, J=10.15 Hz, 1H), 3.69 (br d, J=11.86 Hz, 1H), 3.54 (br d, J=10.88 Hz, 1H), 3.46-3.38 (m, 2H), 1.40 (br s, 9H).

The reaction mixture of tert-butyl 3-(((6-acrylamido-4-((4-(pyridin-2-ylmethoxy)phenyl)-amino)quinazolin-7-yl) oxy)methyl)morpholine-4-carboxylate (45.0 mg, 73.5 umol, 1.00 eq) and trifluoroacetic acid (3.08 g, 27.0 mmol, 2.00 mL, 368 eq) in dichloromethane (10.0 mL) was stirred for 2 h at 0° C. The mixture was concentrated under vacuum to give the crude product. The crude product was purified by prep-HPLC to give 79 (30 mg, 58.53 umol, 79.69% yield, 100% purity) as a yellow solid. $^1$H NMR (400 MHz, DMSO-$d_6$) δ=9.67 (s, 1H), 9.62 (s, 1H), 8.85 (s, 1H), 8.60 (d, J=4.03 Hz, 1H), 8.43 (s, 1H), 7.86 (td, J=7.70, 1.83 Hz, 1H), 7.69-7.63 (m, 2H), 7.55 (d, J=7.82 Hz, 1H), 7.36 (dd, J=6.97, 5.38 Hz, 1H), 7.24 (s, 1H), 7.08-7.02 (m, 2H), 6.71 (dd, J=16.93, 10.33 Hz, 1H), 6.33 (dd, J=17.00, 1.96 Hz, 1H), 5.88-5.82 (m, 1H), 5.20 (s, 2H), 4.15-4.10 (m, 1H), 4.07-4.01 (m, 1H), 3.88 (dd, J=10.70, 2.75 Hz, 1H), 3.70 (br d, J=10.76 Hz, 1H), 3.46-3.39 (m, 1H), 3.29-3.26 (m, 2H), 3.18 (br s, 1H), 2.89-2.76 (m, 2H). MS (ESI) m/z 513.5 [M+H]$^+$ 80: Synthesized according to general procedure C, wherein in step C.1 the ethane-1,2-diol (22.2 g, 358 mmol); in step C.3 H$_2$NR-X is 4-(pyridin-2-ylmethoxy)aniline (1.39 g, 6.94 mmol); in step C.4 HNR'R" is N,N-dimethylpiperidin-4-amine (454 mg, 3.54 mmol); variant ii) was used in step C.5; and variant i) was used in step C.6; and 31% overall yield from I. $^1$H NMR (400 MHz, DMSO-$d_6$) δ=9.62 (br d, J=3.6 Hz, 2H), 8.84 (s, 1H), 8.60 (br d, J=3.8 Hz, 1H), 8.42 (s, 1H), 7.85 (br t, J=6.8 Hz, 1H), 7.66 (br d, J=8.8 Hz, 2H), 7.55 (br d, J=7.4 Hz, 1H), 7.40-7.33 (m, 1H), 7.28 (s, 1H), 7.05 (br d, J=9.0 Hz, 2H), 6.68 (br dd, J=17.0, 10.0 Hz, 1H), 6.31 (br d, J=17.2 Hz, 1H), 5.81 (br d, J=10.0 Hz, 1H), 5.20 (s, 2H), 4.31 (br s, 2H), 2.98 (br d, J=11.4 Hz, 2H), 2.79 (br s, 2H), 2.14 (s, 6H), 2.09 (br d, J=4.8 Hz, 2H), 2.02 (br d, J=8.6 Hz, 1H), 1.68 (br d, J=11.2 Hz, 2H), 1.45-1.30 (m, 2H). MS (ESI) m/z 568.6 [M+H]$^+$ 81: Synthesized according to general procedure C starting from intermediate XV (800 mg, 1.77 mmol) obtained in 80, wherein in step C.4 HNR'R" is 2-methyloctahydropyrrolo[3,4-c]pyrrole (881 mg, 4.43 mmol, 2 HCl); variant ii) was used in step C.5; variant i) was used in step C.6; and 8% overall yield from XV. $^1$H NMR (400 MHz, DMSO-$d_6$) δ=9.74 (s, 1H), 9.70-9.55 (m, 1H), 8.85 (s, 1H), 8.60 (br d, J=4.8 Hz, 1H), 8.43 (s, 1H), 8.28 (s, 3H), 7.85 (td, J=7.6, 1.6 Hz, 1H), 7.66 (br d, J=9.0 Hz, 2H), 7.55 (br d, J=7.8 Hz, 1H), 7.36 (dd, J=7.0, 5.0 Hz, 1H), 7.29 (s, 1H), 7.05 (br d, J=9.0 Hz, 2H), 6.72 (br dd, J=17.0, 10.2 Hz, 1H), 6.32 (br dd, J=17.0, 1.6 Hz, 1H), 5.87-5.76 (m, 1H), 5.20 (s, 2H), 4.35 (br t, J=5.2 Hz, 2H), 2.98 (br t, J=5.2 Hz, 2H), 2.90-2.82 (m, 2H), 2.77-2.67 (m, 4H), 2.63-2.54 (m, 4H), 2.44 (s, 3 H). MS (ESI) m/z 566.6 [M+H]$^+$.

82: A mixture of 4-chloro-7-fluoro-6-nitro-quinazoline (2.10 g, 9.24 mmol, 1.10 eq) and 3-methyl-4(((6-methylpyridin-3-yl)oxy)aniline (1.80 g, 8.40 mmol, 1.00 eq) in propan-2-ol (30.0 mL) was stirred at 90° C. for 2 h. The mixture was cooled to 25° C. and concentrated in vacuum. The residue was triturated with ethyl acetate (20.0 mL) and filtered, the filter cake was dried under reduced pressure to afford 7-fluoro-N-(3-methyl-4-((6-methylpyridin-3-yl)oxy) phenyl)-6-nitroquinazolin-4-amine (3.70 g, crude) as a yellow solid. $^1$H NMR (400 MHz, DMSO-6) δ=11.29 (br s, 1H), 9.83 (d, J=7.8 Hz, 1H), 8.81 (s, 1H), 8.44 (d, J=2.8 Hz, 1H), 7.92 (d, J=12.1 Hz, 1H), 7.88 (dd, J=2.8, 8.7 Hz, 1H), 7.80 (d, J=2.2 Hz, 1H), 7.76-7.70 (m, 1H), 7.14 (d, J=8.7 Hz, 1H), 2.65 (s, 3H), 2.25 (s, 3H).

To a solution of 7-fluoro-N-(3-methyl-4-((6-methylpyridin-3-yl)oxy)phenyl)-6-nitroquinazolin-4-amine (3.70 g, 9.13 mmol, 1.00 eq) in N,N-dimethylformamide (40.0 mL) was added potassium acetate (4.48 g, 45.6 mmol, 5.00 eq). The mixture was stirred at 100° C. for 2 h. The mixture was concentrated in vacuum. The mixture was partitioned between ethyl acetate (100 mL) and water (30.0 mL). The aqueous phase was extracted with ethyl acetate (2×100 mL). The combined organic phase was washed with brine (2×30.0 mL), dried with anhydrous sodium sulfate, filtered and concentrated in vacuum to afford 4-((3-methyl-4-((6-methylpyridin-3-yl)oxy)phenyl)amino)-6-nitroquinazolin-7-ol (2.40 g, 5.95 mmol, 65% yield) as a brown solid. 1H NMR (400 MHz, DMSO-d6) δ=9.97 (br s, 1H), 9.15 (s, 1H), 8.46 (s, 1H), 8.24-8.14 (m, 1H), 7.74 (s, 1H), 7.68 (br d, J=8.8 Hz, 1H), 7.25-7.23 (m, 1H), 7.22-7.19 (m, 1H), 7.08 (s, 1H), 6.95 (d, J=8.8 Hz, 1H), 2.44 (s, 3H), 2.21 (s, 3H).

To a solution of 4-((3-methyl-4-((6-methylpyridin-3-yl) oxy)phenyl)amino-6-nitroquinazolin-7-ol (1.90 g, 4.71 mmol, 1.00 eq) and pyridine (1.86 g, 23.6 mmol, 1.90 mL, 5.00 eq) in dichloromethane (30.0 mL) was added trifluoromethanesulfonic anhydride (2.66 g, 9.42 mmol, 1.55 mL, 2.00 eq) at 0° C. The mixture was stirred at 25° C. for 2 h. The mixture was concentrated in vacuum. The residue was purified by silica gel chromatography to afford 4-((3-methyl-4-((6-methylpyridin-3-yl)oxy)phenyl)amino)-6-nitroquinazolin-7-yl trifluoromethanesulfonate (700 mg, 1.31 mmol, 27% yield) as a yellow solid. 1H NMR (400 MHz, DMSO-d6) δ=10.61 (s, 1H), 9.76 (s, 1H), 9.15 (s, 1H), 8.51 (s, 1H), 8.24-8.17 (m, 2H), 8.04 (s, 1H), 7.69-7.63 (m, 1H), 6.99 (d, J=8.7 Hz, 1H), 6.90 (d, J=8.7 Hz, 1H), 2.45 (s, 3H), 1.98 (s, 3H).

To a solution of 4-((3-methyl-4-((6-methylpyridin-3-yl) oxy)phenyl)amino)-6-nitroquinazolin-7-yl trifluoromethanesulfonate (600 mg, 1.12 mmol, 1.00 eq) in N,N-dimethylformamide (10.0 mL) was added N,N,2-trimethylbut-3- yn-2-amine (187 mg, 1.68 mmol, 1.50 q), copper (I) iodide (107 mg, 0.560 mmol, 0.500 eq), triethylamine (340 mg, 3.36 mmol, 0.468 mL, 3.00 eq), tetrakis[triphenylphosphine]palladium(0) (129 mg, 0.112 mmol, 0.100 eq) at 25° C. The mixture was stirred at 25° C. for 12 h. The mixture was concentrated in vacuum. The residue was purified by silica gel chromatography (petroleum ether/ethyl acetate=1/0 to 0/1) to afford 7-(3-(dimethylamino)-3-methylbut-1-yn-1-yl)-N-(3-methyl-4-((6-methylpyridin-3-yl)oxy)phenyl)-6-nitroquinazolin-4-amine (360 mg, 0.725 mmol, 64% yield) as a yellow solid. 1H NMR (400 MHz, DMSO-d6) δ=10.35 (s, 1H), 9.47 (s, 1H), 8.77-8.63 (m, 1H), 8.19 (s, 1H), 7.96 (s, 1H), 7.77 (br d, J=2.1 Hz, 1H), 7.69 (dd, J=2.4, 8.9 Hz, 1H), 7.27-7.23 (m, 2H), 6.97 (d, J=8.8 Hz, 1H), 2.44 (s, 3H), 2.35 (br s, 6H), 2.23 (s, 3H), 1.46 (s, 6H).

To a solution of 7-(3-(dimethylamino)-3-methylbut-1-yn-1-yl)-N-(3-methyl-4-((6-methylpyridin-3-yl)oxy)phenyl)-6-nitroquinazolin-4-amine (310 mg, 0.624 mmol, 1.00 eq) and iron powder (244 mg, 4.37 mmol, 7.00 eq) in methanol (15.0 mL) was added a solution of ammonium chloride (301 mg, 5.62 mmol, 0.196 mL, 9.00 eq) in water (3.00 mL). The mixture was stirred at 80° C. for 2 h. The residue was added methanol (100 mL) and stirred at 55° C. for 0.5 h. After filtration, the filtrate was concentrated to afford a residue. The residue was triturated with water (30.0 mL) and saturated sodium carbonate (2.00 mL). After filtration, the filter cake was washed with methanol (100 mL). The filtrate was concentrated in vacuo to afford 7-(3-(dimethylamino)-3-methylbut-1-yn-1-yl)-N4-(3-methyl-4-((6-methylpyridin-3-yl)oxy)phenyl)quinazoline-4,6-diamine (230 mg, 0.493 mmol, 78% yield) as a brown solid. 1H NMR (400 MHz, DMSO-d6) δ=9.47 (s, 1H), 8.33 (s, 1H), 8.18-8.16 (m, 1H), 7.80 (d, J=2.4 Hz, 1H), 7.75 (d, J=4.5 Hz, 1H), 7.73 (s, 1H), 7.71 (s, 1H), 7.68 (d, J=2.4 Hz, 1H), 7.62 (s, 1H), 7.55 (s, 1H), 5.47 (s, 2H), 2.43 (s, 3H), 2.29 (s, 6H), 2.19 (s, 3H), 1.46 (s, 6H).

To a solution of 7-(3-(dimethylamino)-3-methylbut-1-yn-1-yl)-N4-(3-methyl-4-((6-methylpyridin-3-yl)oxy)phenyl) quinazoline-4,6-diamine (2.10 mg, 0.450 mmol, 1.00 eq), pyridine (178 mg, 2.25 mmol, 0.182 mL, 5.00 eq) and 1-(3-dimethylaminopropyl)-3-ethylcarbodiimide hydrochloride (431 mg, 2.25 mmol, 5.00 eq) in N,N-dimethylformamide (3.00 mL) was added a solution of acrylic acid (0.500 M, 3.60 mL, 4.00 eq) in N,N-dimethylformamide. The mixture was stirred at 25° C. for 2 h. The mixture was quenched by methanol (2.00 mL) and concentrated in vacuum. The residue was purified by prep-HPLC and lyophilized to afford N-(7-(3-(dimethylamino)-3-methylbut-1-yn-1yl)-((3-methyl-4-((6-methylpyridin-3-yl)oxy)phenyl) amino)quinazolin-6-yl)acrylamide (82) (24.35 mg, 46.3 umol, 10% yield, 99% purity) as yellow solid. 1H NMR (400 MHz, DMSO-d6) δ=9.87 (d, J=4.5 Hz, 2H), 8.69 (s, 1H), 8.58 (s, 1H), 8.19 (d, J=2.0 Hz, 1H), 7.83 (s, 1H), 7.80 (d, J=2.3 Hz, 1H), 7.71 (dd, J=2.6, 8.7 Hz, 1H), 7.28-7.22 (m, 2H), 6.97 (d, J=8.8 Hz, 1H), 6.60-6.51 (m, 1H), 6.33 (dd, J=1.8, 17.1 Hz, 1H), 5.84 (dd, J=1.8, 10.2 Hz, 1H), 2.45 (s, 3H), 2.26 (s, 6H), 2.22 (s, 3H), 1.42 (s, 6H). MS (ESI) m/z 521.5 [M+H]+

83: To a solution of dimethyl (1-diazo-2-oxopropyl) phosphonate (1.16 g, 6.02 mmol, 1.20 eq) and potassium carbonate (1.39 g, 10.0 mmol, 2.00 eq) in methanol (20.0 mL) was added tert-butyl 2-formylpyrrolidine-1-carboxylate (1.00 g, 5.02 mmol, 1.00 eq) at 20° C. The mixture was stirred at 20° C. for 12 h. The mixture was concentrated to dryness and diluted with ethyl acetate (20.0 mL). After filtration, the filtrate was concentrated to afford a residue. The residue was purified by silica gel chromatography (petroleum ether/ethyl acetate=5/1) to give tert-butyl 2-ethynylpyrrolidine-1-carboxylate (800 mg, 4.10 mmol, 81% yield) as a white solid. 1H NMR (400 MHz, Chloroform-d) δ=4.56-4.29 (m, 1H), 3.46 (br d, J=9.40 Hz, 1H), 3.30 (br s, 1H), 2.34-2.14 (m, 1H), 2.12-1.96 (m, 3H), 1.89 (br s, 1H), 1.47 (s, 9H).

To a solution of tert-butyl 2-ethynylpyrrolidine-1-carboxylate (386 mg, 1.98 mmol, 1.10 eq), 4-((3-chloro-4-(pyridin-2-ylmethoxy)phenyl)amino)-6-nitroquinazolin-7-yltrifluoromethane-sulfonate (1.00 g, 1.80 mmol, 1.00 eq), copper iodide (68.5 mg, 360 umol, 0.200 eq) and triethylamine (12.1 g, 120 mmol, 16.7 mL, 66.6 eq) in dimethylformamide (10.0 mL) was added tetrakis[triphenylphosphine]palladium(0) (208 mg, 180 umol, 0.100 eq) at 15° C. The mixture was stirred at 15° C. for 12 h. The reaction was concentrated to afford a residue. The residue was purified by silica gel chromatography (petroleum ether/ethyl acetate=1/1-0/1) to give tert-butyl 2-((4-((3-chloro-4-(pyridin-2-ylmethoxy)phenyl)amino)-6-nitroquinazolin-7-yl)ethynyl) pyrrolidine-1-carboxylate (1.00 g, 1.66 mmol, 92% yield) as a yellow solid. 1H NMR (400 MHz, DMSO-d6) δ=10.4 (s, 1H), 9.4 (s, 1H), 8.7 (s, 1H), 8.6 (br d, J=4.28 Hz, 1H), 8.0 (d, J=2.57 Hz, 1H), 8.0 (s, 1H), 7.9 (s, 1H), 7.9 (td, J=7.70, 1.83 Hz, 1H), 7.7 (dd, J=9.05, 2.57 Hz, 1H), 7.4 (dd, J=6.60, 4.89 Hz, 1H), 7.3 (d, J=9.05 Hz, 1H), 5.3 (s, 2 H), 4.7 (br s, 1H), 3.4-3.5 (m, 2 H), 2.2 (br s, 1H), 2.0-2.1 (m, 2 H), 1.9 (br s, 1H), 1.4 (s, 9H).

To a solution of tert-butyl 2-((4-((3-chloro-4-(pyridin-2-ylmethoxy)phenyl)amino)-6-nitroquinazolin-7-yl)ethynyl) pyrrolidine-1-carboxylate (400 mg, 666 umol, 1.00 eq) and ammonium chloride (400 mg, 7.48 mmol, 262 uL, 11.3 eq) in methanol (13.0 mL) and water (13.0 mL) was added iron (325 mg, 5.82 mmol, 8.75 eq) at 20° C. The mixture was heated to 80° C. and stirred at 80° C. for 1 h. The combined mixture was concentrated to afford a residue. The residue was diluted with water (10.0 mL), saturated sodium carbonate (5.00 mL) and the mixture was stirred for 30 min. After filtration, the filtrate was extracted with ethyl acetate (2×30.0 mL) to recover the product. The combined organic layer were concentrated to afford crude product to give tert-butyl 2-((6-amino-4-((3-chloro-4-(pyridin-2-ylmethoxy)phenyl)amino)quinazolin-7-yl)ethynyl)pyrrolidine-1-carboxylate (300 mg, crude) as a brown oil. 1H NMR (400 MHz, DMSO-d6) δ=9.5 (s, 1H), 8.6-8.6 (m, 1H), 8.3 (s, 1H), 8.0 (d, J=2.57 Hz, 1H), 7.9 (td, J=7.70, 1.71 Hz, 1H), 7.7 (dd, J=9.05, 2.57 Hz, 1H), 7.5-7.7 (m, 2H), 7.5 (br s, 1H), 7.4 (dd, J=6.97, 5.38 Hz, 1H), 7.2 (d, J=9.05 Hz, 1H), 5.3 (s, 2H), 4.7 (dd, J=7.64, 3.36 Hz, 1H), 3.4-3.5 (m, 2H), 2.2 (br d, J=7.46 Hz, 1H), 2.0-2.2 (m, 2H), 1.8-1.9 (m, 1H), 1.8-1.9 (m, 1H), 1.5 (s, 7H), 1.4-1.5 (m, 1H).

To a solution of tert-butyl 2-((6-amino-4-((3-chloro-4-(pyridin-2-ylmethoxy)phenyl)amino)quinazolin-7-yl)ethynyl)pyrrolidine-1-carboxylate (270 mg, 473 umol, 1.00 eq) and pyridine (748 mg, 9.46 mmol, 20.0 eq) in dioxane (5.00 mL) was added 1-(3-dimethylaminopropyl)-3-ethylcarbodiimide hydrochloride (906 mg, 4.73 mmol, 10.0 eq) and acrylic acid (341 mg, 4.73 mmol, 10.0 eq) at 0° C. The mixture was stirred at 15° C. for 5 h. The mixture was filtered to afford a solution. The solution was purified by prep-HPLC and lyophilized to give tert-butyl 2-((6-acrylamide-4-((3-chloro-4-(pyridin-2-ylmethoxy)phenyl)amino) quinazolin-7-yl)ethynyl)pyrrolidine-1-carboxylate (200 mg, crude) as an orange solid. MS (ESI) m/z 625.3 [M+H]+

A mixture of tert-butyl 2-((6-acrylamido-4-((3-chloro-4-(pyridin-2-ylmethoxy)phenyl)amino)quinazolin-7-yl)ethynyl)pyrrolidine-1-carboxylate (100 mg, 160 umol, 1.00 eq)

4 M hydrochloride/ethyl acetate (3.00 mL) was stirred at 25° C. for 30 min. The mixture was concentrated to dryness. The solution was purified by prep-HPLC and lyophilized to afford crude product which was re-purified by prep-HPLC (column: Phenomenex Synergi C18 150*30 mm*4 um; mobile phase: [water(0.225%FA)-ACN]; B%: 5%-35%, 10 min) and lyophilized to afford N-(4-((3-chloro-4-(pyridin-2-ylmethoxy)phenyl)amino)-7-(pyrrolidin-2-ylethynyl)quinazolin-6-yl)acrylamide (83) (22.23 mg, 3'7.4 nmol, 12% yield, 96% purity, formate) as a yellow solid. $^1$H NMR (400 MHz, DMSO-d6) δ32 9.9 (br s, 2H), 8.7 (s, 1H), 8.6-8.6 (m, 1H), 8.5 (s, 1H), 8.3 (s, 2H), 8.0 (d, J=2.57 Hz, 1H), 7.9 (td, J=7.70, 1.71 Hz, 1H), 7.8 (s, 1H), 7.7 (dd, J=8.93, 2.57 Hz, 1H), 7.6 (d, J=7.82. Hz, 1H), 7.4 (dd, J=6.97, 5.38 Hz, 1H), 7.3 (d, J=9.05 Hz, 1H), 6.6 (dd, J=17.06, 10.09 Hz, 1H), 6.3 (dd, J=16.99, 1.83 Hz, 1H), 5.8-5.9 (m, 1H), 5.3 (s, 2H), 4.1 (br dd, J=7.27, 4.83 Hz, 1H), 3.0-3.0 (m, 1H), 2.8 (br dd, J=7.64, 5.07 Hz, 1H), 2.0-2.1 (m, 1H), 1.8-1.9 (m, 2 H), 1.7-1.7 (m, 1H). MS (ESI) m/z 525.3 [M+H]+

84: A mixture of 3-chloro-3-methylbut-1-yne (2.00 g, 19.5 mmol, 2.19 mL, 1.00 eq) and pyrrolidine (4.85 g, 68.3 mmol, 5.70 mL, 3.50 eq) in water (10.0 mL) was stirred for 24 h at 15° C. The mixture was filtered to give the filter cake. The filter cake was dissolved in tert-Butyl methyl ether (40.0 mL), and washed with brine (35.0 mL). The organic layer was dried over sodium sulfate, filtered and concentrated under vacuum to give 1-(2-methylbut-3-yn-2-yl)pyrrolidine (0.400 g, 2.91 mmol, 15% yield) as a light brown solid. 1H NMR (400 MHz, DMSO-d6) δ=3.09 (s, 1H) 2 59 (br s, 4H) 1.68 (br s, 4H) 1.30 (s, 6H).

A mixture of N-(3-chloro-4-(pyridin-2-ylmethoxy)phenyl)-7-fluoro-6-nitroquinazolin-4-amine (6.00 g, 14.1 mmol, 1.00 eq) and potassium acetate (6.91 g, 70.46 mmol, 5.00 eq) in dimethyl formamide (20.0 mL) was stirred for 2 h at 100° C. The mixture was concentrated under vacuum to give the residue. Water (50.0 mL) was added to the residue, and the mixture was stirred for 0.5 h at room temperature. The mixture was filtered to give the filter cake, which was concentrated under vacuum to give 4-((3-chloro-4-(pyridin-2-ylmethoxy)phenyl)amino)-6-nitroquinazolin-7-ol (5.60 g, 13.2 mmol, 94% yield) as a brown solid. 1H NMR (400 MHz, DMSO-d6) δ=9.03 (br s, 1H), 8.60 (br s, 1H), 8.39 (br s, 1H), 8.04 (br s, 1H), 7.88 (br s, 1H), 7.72 (br s, 1H), 7.59 (br s, 1H), 7.37 (br s, 1H), 7.25 (br s, 1H), 6.96 (br s, 1H), 5.29 (br s, 2H).

A mixture of 4-[3-chloro-4-(2-pyridylmethoxy)anilino]-6-nitro-quinazolin-7-ol (6.00 g, 14.16 mmol, 1.00 eq), trifluoromethanesulfonic anhydride (7.99 g, 28.31 mmol, 4.67 mL, 2.00 eq) and pyridine (5.60 g, 70.8 mmol, 5.71 mL, 5.00 eq) in dichloromethane (50.0 mL) was stirred for 12 h at 25° C. The mixture was concentrated under vacuum to the residue. The residue was purified by flash to give 4-((3-chloro-4-(pyridin-2-ylmethoxy)phenyl)amino-6-nitroquinazolin-7-yl trifluoromethanesulfonate (1.80 g, 3.24 mmol, 23% yield) as a yellow solid. 1H NMR (400 MHz, DMSO-d6) δ=10.60 (s, 1H), 9.72 (s, 1H), 8.78 (s, 1H), 8.61 (d, J=4.77 Hz, 1H), 8.04 (s, 1H), 7.99 (d, J=2.57 Hz, 1H), 7.92-7.87 (m, 1H), 7.70 (dd, J=8.93, 2.57 Hz, 1H), 7.62-7.58 (m, 1H), 7.38 (dd, J=6.66, 4.95 Hz, 1H), 7.33 (d, J=9.05 Hz, 1H), 5.32 (s, 2H).

A mixture of 4-((3-chloro-4-(pyridin-2-ylmethoxy)phenyl)amino)-6-nitroquinazolin-7-yl trifluoromethanesulfonate (0.800 g, 1.44 mmol, 1.00 eq), 1-(2-methylbut-3-yn-2-yl)pyrrolidine (296 mg, 2.16 mmol, 1.50 eq), copper iodide (137 mg, 720 umol, 0.500 eq), triethylamine (437 mg, 4.32 mmol, 601 uL, 3.00 eq) and bis(triphenylphosphine) palladium(II) dichloride (505 mg, 720 umol, 0.500 eq) in dimethyl formamide (8.00 mL) was stirred for 12 h at 25° C. under nitrogen atmosphere. The mixture was filtered to give the filtrate, which was concentrated under vacuum to give the residue. The residue was purified by flash chromatography [silica gel column:12 g, petroleum ether/ethyl acetate=1/0-1/1, dichloromethane/methanol=10/1] to give N-(3-chloro-4-(pyridin-2-ylmethoxy)phenyl)-7-(3-methyl-3-(pyrrolidin-1-yl)but-1-yn-1-yl)-6-nitroquinazolin-4-amine (0.600 g, 1.10 mmol, 77% yield) as a yellow solid, which was used to next step directly. MS (ESI) m/z 543.4 [M+H]+

A mixture of N-(3-chloro-4-(pyridin-2-ylmethoxy)phenyl)-7-(3-methyl-3-(pyrrolidin-1-yl)but-1-yn-1-yl)-6-nitroquinazolin-4-amin (570 mg, 1.05 mmol, 1.00 eq), iron (293 mg, 5.25 mmol, 5.00 eq), ammonium chloride (281 mg, 5.25 mmol, 184 uL, 5.00 eq) in methanol (20.0 mL) and water (4.00 mL) was stirred for 1 h at 70° C. The mixture was filtered to give the filtrate, which was concentrated under vacuum to give the residue. The residue was purified by reverse-phase chromatography to give N4-(3-chloro-4-(pyridin-2-ylmethoxy)phenyl)-7-(3-methyl-3-(pyrrolidin-1-yl)but-1-yn-1-yl)quinazoline-4,6-diamine (150 mg, 292 umol, 28% yield) as a yellow solid. 1H NMR (400 MHz, DMSO-d6) δ=9.48 (s, 1H), 8.60 (br d, J=4.52 Hz, 1H), 8.34 (s, 1H), 8.05 (d, J=2.45 Hz, 1H), 7.92-7.87 (m, 1H), 7.72 (dd, J=8.99, 2.51 Hz, 1H), 7.63-7.57 (m, 2H), 7.51 (s, 1H), 7.37 (dd, J=6.85. 5.26 Hz, 1H), 7.25 (d, J=9.05 Hz, 1H), 5.46 (s, 2H), 5.29 (s, 2H), 2.73 (br s, 4H), 1.76-1.72 (m, 4H) 1.48 (s, 6H).

A mixture of N4-(3-chloro-4-(pyridin-2-ylmethoxy)phenyl)-7-(3-methyl-3-(pyrrolidin-1-yl)but-1-yn-1-yl)quinazoline-4,6-diamine (120 mg, 234 umol, 1.00 eq), acrylic acid (33.7 mg, 468 umol, 32.1 uL, 2.00 eq) and 1-(3-dimethylaminopropyl)-3-ethylcarbodiimide hydrochloride (89.7 mg, 468 umol, 2.00 eq), pyridine (37.0 mg, 468 umol, 37.8 uL, 2.00 eq) in dimethyl formamide (5.00 mL) was stirred for 1 h at 20° C. The mixture was filtered to give the filtrate. The filtrate was purified by prep-HPLC to give N-(4-((3-chloro-4-(pyridin-2-ylmethoxy)phenyl)amino)-7-(3-methyl-3-(pyrrolidin-1-yl)but-1-yn-1-yl)quinazolin-6-yl)acrylamide (84) (35 mg, 57.09 umol, 24.41% yield, 100% purity, FA) as a yellow solid. 1H NMR (400 MHz, DMSO-d6) δ=9.95-9.79 (m, 2H), 8.67-8.55 (m, 3H), 8.21 (s, 1H), 8.04 (d, J=2.45 Hz, 1H), 7.89 (td, J=7.70, 1.71 Hz, 1H), 7.82 (s, 1H), 7.73 (dd, J=8.99, 2.38 Hz, 1H) 7.59 (d, J=7.83 Hz, 1H), 7.38 (dd, J=7.03, 5.20 Hz, 1H), 7.28 (d, J=9.17 Hz, 1H), 6.59-6.48 (m, 1H), 6.33 (dd, J=17.12, 1.71 Hz, 1H), 5.85 (dd, J=10.27, 1.59 Hz, 1H), 5.30 (s, 2H), 2.69 (br s, 4H), 1.69 (br s, 4H), 1.44 (s, 6H). MS (ESI) m/z 567.4 [M+H]+

85: To a solution of tert-butyl 3-formylpyrrolidine-1-carboxylate (2.00 g, 10.0 mmol. 1.00 eq) and potassium carbonate (2.77 g, 20.1 mmol, 2.00 eq) in methanol (50.0 mL) was added 1-diazo-1-dimethoxyphosphoryl-propan-2-one (2.31 g, 12.1 mmol, 1.20 eq) at 25° C. The mixture was stirred at 25° C. for 12 h. The mixture was partitioned between ethyl acetate (30.0 mL) and water (20.0 mL). The aqueous phase was extracted with ethyl acetate (2×20.0 mL). The combined organic phase was washed with brine (2×10.0 mL), dried with anhydrous sodium sulfate, filtered and concentrated in vacuum. The residue was purified by silica gel chromatography to afford tert-butyl 3-ethynylpyrrolidine-1-carboxylate (1.80 g, 9.22 mmol, 91% yield) as a colorless oil. 1H NMR (400 MHz, CDCl3) δ=3.71-3.56 (m, 1H), 3.55-3.41 (m, 1H), 3.37-3.23 (m, 2H), 2.93 (br s, 1H), 2.20-2.11 (m, 1H), 2.19-2.11 (m, 1H), 2.10 (d, J=2.4 Hz, 1H), 1.94 (br d, J=7.0 Hz, 1H), 1.45 (s, 9H).

To a solution of 4-((3-chloro-4-(pyridin-2-ylmethoxy)phenyl)amino)-6-nitroquinazolin-7-yl trifluoromethanesulfonate (2.36 g, 4.25 mmol, 1.00 eq) in N,N-dimethylformamide (30.0 mL) was added tert-butyl 3-ethynylpyrrolidine-1-carboxylate (1.24 g, 6.37 mmol, 1.50 eq), copper(I) iodide (404 mg, 2.12 mmol, 0.500 eq), triethylamine (1.29 g, 12.7 mmol, 1.77 mL, 3.00 eq) and tetrakis[triphenylphosphine]palladium(0) (491 mg, 0.425 mmol, 0.100 eq) at 25° C. under nitrogen. The mixture was stirred at 25° C. for 12 h. The mixture was concentrated in vacuum. The residue was purified by silica gel chromatography to afford tert-butyl 3-((4-((3-chloro-4-(pyridin-2-ylmethoxy)phenyl)amino)-6-nitroquinazolin-7-yl)ethynyl)pyrrolidine-1-carboxylate (720 mg, 1.20 mmol, 28% yield) as a yellow solid. 1H NMR (400 MHz, DMSO-d6) δ=10.35 (br s, 1H), 9.42 (s, 1H), 8.70 (s, 1H), 8.60 (d, J=4.0 Hz, 1H), 8.00 (d, J=2.4 Hz, 1H), 7.95 (s, 1H), 7.88 (dt, J=1.7, 7.7 Hz, 1H), 7.70 (dd, J=2.4, 9.0 Hz, 1H), 7.59 (d, J=7.8 Hz, 1H), 7.37 (dd, J=5.0, 6.5 Hz, 1H), 7.30 (d, J=9.0 Hz, 1H), 5.30 (s, 2H), 3.62 (br d, J=7.3 Hz, 1H), 3.49-3.40 (m, 2H), 3.36 (br s, 2H), 2.23 (br s, 1H), 2.01 (br d, J=7.9 Hz, 1H), 1.42 (s, 9H).

A mixture of tert-butyl 3-((4-((3-chloro-4-(pyridin-2-ylmethoxy)phenyl)amino)-6-nitroquinazolin-7-yl)ethynyl)pyrrolidine-1-carboxylate (620 mg, 1.03 mmol, 1.00 eq) in hydrochloric acid/ethyl acetate (4.00 M, 2.00 mL) was stirred at 25° C. for 2 h. The mixture was concentrated in vacuum to afford N-(3-chloro-4-(pyridin-2-ylmethoxy)phenyl)-6-nitro-7-(pyrrolidin-3-ylethynyl)quinazolin-4-amine (600 mg, crude, hydrochloric acid) as a yellow solid. 1H NMR (400 MHz, DMSO-d6) δ=11.94 (br s, 1H), 9.82 (s, 1H), 9.63 (br s, 2H), 8.94 (s, 1H), 8.75 (d, J=4.5 Hz, 1H), 8.24-8.15 (m, 2H), 7.98 (d, J=2.4 Hz, 1H), 7.81 (d, J=7.8 Hz, 1H), 7.73 (dd, J=2.6, 8.9 Hz, 1H), 7.67-7.61 (m, 1H), 7.38 (d, J=9.0 Hz, 1H), 5.47 (s, 2H), 3.67-3.52 (m, 2H), 3.41-3.31 (m, 1H), 3.30-3.18 (m, 2H), 2.42-2.31 (m, 1H), 2.14-2.02 (m, 1H), 1.91 (s, 1H).

To a solution of N-(3-chloro-4-(pyridin-2-ylmethoxy)phenyl)-6-nitro-7-(pyrrolidin-3-ylethynyl)quinazolin-4-amine (650 mg, 1.21 mmol, 1.00 eq, hydrochloric acid) in acetonitrile (20.0 mL) was added formaldehyde (982 mg, 12.1 mmol, 0.901 mL, 10.0 eq), sodium triacetoxy borohydride (820 mg, 3.87 mmol, 3.20 eq). The mixture was stirred at 25° C. for 12 h. The residue was triturated with water (30.0 mL) and filtered, the filter cake was dried under reduced pressure to afford N-(3-chloro-4-(pyridin-2-ylmethoxy)phenyl)-7-((1-methylpyrrolidin-3-yl)ethynyl)-6-nitroquinazolin-4-amine (540 mg, 1.05 mmol, 86% yield) as a yellow solid. 1H NMR (400 MHz, DMSO-d6) δ=10.48-10.36 (m, 1H), 9.50-9.45 (m, 1H), 8.71 (s, 1H), 8.60 (d, J=4.3 Hz, 1H), 8.06-7.99 (m, 2H), 7.89 (dt, J=1.7, 7.7 Hz, 1H), 7.72 (dd, J=2.3, 8.9 Hz, 1H), 7.59 (d, J=7.8 Hz, 1H), 7.37 (dd, J=5.1, 7.0 Hz, 1H), 7.30 (d, J=9.0 Hz, 1H), 5.32-5.29 (m, 2H), 3.60-3.51 (m, 1H), 3.40 (br d, J=8.7 Hz, 1H), 3.29-3.26 (m, 1H), 3.15-3.09 (m, 2H), 2.69 (s, 3H), 2.45-2.34 (m, 1H), 2.15-2.04 (m, 1H).

To a solution of N-(3-chloro-4-(pyridin-2-ylmethoxy)phenyl)-7-((1-methylpyrrolidin-3-yl)ethynyl)-6-nitroquinazolin-4-amine (490 mg, 0.952 mmol, 1.00 eq) and iron powder (372 mg, 6.66 mmol, 7.00 eq) in methanol (25.0 mL) was added a solution of ammonium chloride (458 mg, 8.56 mmol, 0.299 mL, 9.00 eq) in water (5.00 mL). The mixture was stirred at 80° C. for 2 h. The residue was added methanol (50.0 mL) and stirred at 55° C. for 0.5 h. After filtration, the filtrate was concentrated to afford a residue. The residue was triturated with water (20.0 mL) and saturated sodium carbonate (2.00 mL). After filtration, the filter cake was washed with methanol (50.0 mL). The filtrate was concentrated in vacuum to afford N4-(3-chloro-4-(pyridin-2-ylmethoxy)phenyl)-7-((1-methylpyrrolidin-3-yl)ethynyl)quinazoline-4,6-diamine (420 mg, 0.866 mmol, 91% yield) as a yellow solid. 1H NMR (400 MHz, DMSO-d6) δ=9.46 (br s, 1H), 8.59 (br d, J=4.4 Hz, 1H), 8.32 (s, 1H), 8.04 (d, J=2.3 Hz, 1H), 7.93-7.84 (m, 1H), 7.70 (dd, J=2.2, 8.8 Hz, 1H), 7.63-7.55 (m, 2H), 7.47 (s, 1H), 7.41-7.33 (m, 1H), 7.24 (d, J=9.0 Hz, 1H), 5.67-5.50 (m, 1H), 5.60 (br s, 1H), 5.28 (s, 2H), 3.47-3.35 (m, 2H), 3.05 (br t, J=8.6 Hz, 1H), 2.76 (br t, J=7.2 Hz, 2H), 2.43 (s, 3H), 2.32-2.24 (m, 1H), 2.09-1.94 (m, 1H).

To a solution of N4-(3-chloro-4-(pyridin-2-ylmethoxy)phenyl)-7-((1-methylpyrrolidin-3-yl)ethynyl)quinazoline-4,6-diamine (370 mg, 0.763 mmol, 1.00 eq), pyridine (121 mg, 1.53 mmol, 0.123 mL, 2.00 eq) and 1-(3-dimethylaminopropyl)-3-ethylcarbodiimide hydrochloride (293 mg, 1.53 mmol, 2.00 eq) in N,N-dimethylformamide (5.00 mL) was added a solution of acrylic acid (0.500 M, 2.29 mL, 1.50 eq) in N,N-dimethylformamide. The mixture was stirred at 25° C. for 2 h. The mixture was quenched by methanol (2.00 mL) and concentrated in vacuum. The residue was purified by prep-HPLC and lyophilized to afford N-(4-((3-chloro-4-(pyridin-2-ylmethoxy)phenyl)amino)-7-((1-methylpyrrolidin-3-yl)ethynyl)quinazolin-6-yl)acrylamide (85) (176.4 mg, 324 umol, 42% yield, 99% purity) as a yellow solid. 1H NMR (400 MHz, DMSO-d6) δ=9.85 (br s, 2H), 8.70 (s, 1H), 8.62-8.58 (m, 1H), 8.54 (s, 1H), 8.01 (d, J=2.4 Hz, 1H), 7.88 (dt, J=1.8, 7.7 Hz, 1H), 7.78 (s, 1H), 7.71 (dd, J=2.4, 9.0 Hz, 1H), 7.59 (d, J=7.8 Hz, 1H), 7.39-7.34 (m, 1H), 7.26 (d, J=9.0 Hz, 1H), 6.60 (dd, J=10.2, 17.1 Hz, 1H), 6.33 (dd, J=1.8, 17.1 Hz, 1H), 5.89-5.80 (m, 1H), 5.29 (s, 2H), 3.27-3.21 (m, 2H), 2.87 (t, J=8.3 Hz, 1H), 2.60-2.54 (m, 1H), 2.48 (br d, J=3.5 Hz, 1H), 2.27 (s, 3H), 2.23 (tdd, J=1.8, 4.0, 10.3 Hz, 1H), 1.97-1.86 (m, 1H). MS (ESI) m/z 539.4 [M+H]+

86: To a solution of tert-butyl 3-((4-((3-chloro-4-(pyridin-2-ylmethoxy)phenyl)amino)-6-nitroquinazolin-7-yl)ethynyl)pyrrolidine-1-carboxylate (700 mg, 1.16 mmol, 1.00 eq) and iron powder (455 mg, 8.15 mmol, 7.00 eq) in methanol (35.0 mL) was added a solution of ammonium chloride (561 mg, 10.5 mmol, 0.366 mL, 9.00 eq) in water (7.00 mL). The mixture was stirred at 80° C. for 2 h. The residue was added methanol (100 mL) and stirred at 55° C. for 0.5 h. After filtration, the filtrate was concentrated to afford a residue. The residue was triturated with water (30.0 mL) and saturated sodium carbonate (2.00 mL). After filtration, the filter cake was washed with methanol (100 mL). The filtrate was concentrated in vacuum to afford crude product which was purified by prep-HPLC (Phenomenex Synergi C18 150*25*10 um, water(0.1%HCl)-ACN) to afford tort-butyl 3-((6-amino-4-((3-chloro-4-(pyridin-2-ylmethoxy)phenyl)amino)quinazolin-7-yl)ethynyl)pyrrolidine-1-carboxylate (280 mg, 0.490 mmol, 42% yield) as a brown solid. 1H NMR (400 MHz, DMSO-d6) δ=11.30-11.24 (m, 1H), 8.73-8.67 (m, 2H), 8.08 (dt, J=1.4, 7.7 Hz, 1H), 7.89 (d, J=2.6 Hz, 1H), 7.87-7.79 (m, 1H), 7.76-7.71 (m, 2H), 7.62 (dd, J=2.5, 9.0 Hz, 1H), 7.55 (dd, J=5.5, 7.0 Hz, 1H), 7.35 (d, J=9.0 Hz, 1H), 5.42 (s, 2H), 3.70-3.62 (m, 1H), 3.58-3.41 (m, 2H), 3.36-3.21 (m, 2H), 2.24 (br d, J=5.1 Hz, 1H), 2.19-2.04 (m, 1H), 1.64-1.33 (m, 9H).

To a solution of tert-butyl 3-((6-amino-4-((3-chloro-4-(pyridin-2-ylmethoxy)phenyl)amino)quinazolin-7-yl)ethynyl)pyrrolidine-1-carboxylate (270 mg, 0.473 mmol, 1.00 eq), pyridine (374 mg, 4.73 mmol, 0.382 mL, 10.0 eq) and 1-(3-dimethylaminopropyl)-3-ethylcarbodiimide hydrochloride (906 mg, 4.73 mmol, 10.0 eq) in tetrahydrofuran (10.0 mL) was added acrylic acid (341 mg, 4.73 mmol, 0.324 mL, 10.0 eq). The mixture was stirred at 25° C. for 2 h. The mixture was partitioned between ethyl acetate (20.0 mL) and water (10.0 mL). The aqueous phase was extracted with ethyl acetate (2×20.0 mL). The combined organic phase was washed with brine (2×10.0 mL), dried with anhydrous sodium sulfate, filtered and concentrated in vacuum to afford tert-butyl 3-((6-acrylamido-4-((3-chloro-4-(pyridin-2-ylmethoxy)phenyl)amino)quinazolin-7-yl)ethynyl)pyrrolidine-1-carboxylate (450 mg, crude) as a brown oil.

A mixture of tort-butyl 3-((6-acrylamido-4-((3-chloro-4-(pyridin-2-ylmethoxy)phenyl)amino)quinazolin-7-yl)ethynyl)pyrrolidine-1-carboxylate (420 mg, 0.672 mmol, 1.00 eq) in dichloromethane (10.0 mL) was added trifluoroacetic acid (3.08 g, 27.0 mmol, 2.00 mL, 40.2 eq). The mixture was stirred at 25° C. for 0.5 h. The mixture was quenched by methanol (2.00 mL) and concentrated in vacuum. The residue was purified by prep-HPLC and lyophilized to afford N-(4-((3-chloro-4-(pyridin-2-ylmethoxy)phenyl)amino)-7-(pyrrolidin-3-ylethynyl)quinazolin-6-yl)acrylamide (86) (16.46 mg, 26.8 umol, 3% yield, 93% purity, formic acid) as a yellow solid. 1H NMR (400 MHz, DMSO-d6) δ=10.07 (br s, 1H), 9.89 (br s, 1H), 8.74 (s, 1H), 8.61-8.58 (m, 1H), 8.54 (s, 1H), 8.34 (s, 1H), 8.01 (d, J=2.4 Hz, 1H), 7.88 (dt, J=1.8, 7.7 Hz, 1H), 7.82 (s, 1H), 7.71 (dd, J=2.2, 8.8 Hz, 1H), 7.59 (d, J=7.8 Hz, 1H), 7.39-7.35 (m, 1H), 7.27 (d, J=9.0 Hz, 1H), 6.66 (br dd, J=10.2, 17.1 Hz, 1H), 6.34 (dd, J=1.8, 17.1 Hz, 1H), 5.85 (dd, J=1.8, 10.2 Hz, 1H), 5.29 (s, 2H), 3.30 (br d, J=6.0 Hz, 2H), 3.16-3.10 (m, 1H), 3.06 (br s, 2H), 2.18 (br dd, J=6.7, 12.6 Hz, 1H), 2.05-1.91 (m, 1H). MS (ESI) m/z 525.3 [M+H]+

87: To a solution of tert-butyl 2-((4-((3-chloro-4-(pyridin-2-ylmethoxy)phenyl)amino)-6-nitroquinazolin-7-yl)ethynyl)pyrrolidine-1-carboxylate (500 mg, 831 umol, 1.00 eq) in 4 M hydrochloric acid in ethyl acetate (20.0 mL) was stirred for 0.5 h at 25° C. The mixture was concentrated to afford a residue. The residue was purified by reversed phase (C18, 0.1% HCl in water-MeCN) to give N-(3-chloro-4-(pyridin-2-ylmethoxy)phenyl)-6-nitro-7-(pyrrolidin-2-ylethynyl)quinazolin-4-amine (300 mg, 558 umol, 67% yield, hydrochloride) as a yellow solid. 1H NMR (400 MHz, DMSO-d6) δ=12.0 (br s, 1H), 10.2 (br s, 1H), 10.0 (br s, 1H), 9.9 (s, 1H), 8.9 (s, 1H), 8.8 (br d, J=4.52 Hz, 1H), 8.3 (s, 1H), 8.2 (br t, J=7.70 Hz, 1H), 8.0 (d, J=2.57 Hz, 1H), 7.8 (d, J=7.82 Hz, 1H), 7.7 (dd, J=8.93, 2.45 Hz, 1H), 7.6-7.7 (m, 1H), 7.4 (d, J=9.05 Hz, 1H), 5.5 (s, 2H), 4.6-4.9 (m, 1H), 3.2-3.4 (m, 2 H), 2.4-2.4 (m, 1H), 2.0-2.1 (m, 3H).

To a solution of N-(3-chloro-4-(pyridin-2-ylmethoxy)phenyl)-6-nitro-7-(pyrrolidin-2-ylethynyl)quinazolin-4-amine (280 mg, 521 umol, 1.00 eq, hydrochloride) and formaldehyde (0.100 M, 10.4 mL, 2.00 eq) in acetonitrile (15.0 mL) was added sodium triacetoxyhydroborate (220 mg, 1.04 mmol, 2.00 eq) at 20° C. The mixture was stirred at 20° C. for 1 h. The mixture was concentrated to afford a residue. The residue was diluted with water (10.0 mL), extracted with ethyl acetate (2×20.0 mL). The combined organic layers were washed with water (10.0 mL), dried over sodium sulfate, filtered and concentrated to afford a residue. The residue was purified by reversed-phase (C18, 0.1%HCl in water-MeCN) to gived N-(3-chloro-4-(pyridin-2-ylmethoxy)phenyl)-7-((1-methylpyrrolidin-2-yl)ethynyl)-6-nitroquinazolin-4-amine (200 mg, 388 umol, 74% yield) as a yellow solid. 1H NMR (400 MHz, DMSO-d6) δ=10.6 (br s, 1H), 9.6 (s, 1H), 8.7 (s, 1H), 8.6 (br d, J=4.03 Hz, 1H), 8.2 (s, 1H), 8.0 (br d, J=2.08 Hz, 1H), 7.9 (td, J=7.67, 1.53 Hz, 1H), 7.7-7.8 (m, 1H), 7.6 (br d, J=7.70 Hz, 1H), 7.4 (dd, J=6.85, 5.01 Hz, 1H), 7.3 (d, J=9.05 Hz, 1H), 5.3 (s, 2H), 4.7 (br s, 1H), 3.4-3.6 (m, 2 H), 2.9 (s, 3H), 2.0-2.3 (m, 4H).

To a solution of N-(3-chloro-4-(pyridin-2-ylmethoxy)phenyl)-7-((1-methylpyrrolidin-2-yl)ethynyl)-6-nitroquinazolin-4-amine (190 mg, 344 umol, 1.00 eq, hydrochloric acid) and ammonium chloridel (207 mg, 3.87 mmol, 135 uL, 11.2 eq) in methanol (6.00 mL) and water (6.00 mL) was added powder iron (168 mg, 3.02 mmol, 8.75 eq) at 20° C. The mixture was heated to 80° C. and stirred at 80° C. for 1 h. The combined mixture was concentrated to afford a residue. The residue was diluted with water (10.0 mL), saturated sodium carbonate (5.00 mL) and the mixture was stirred for 30 min. After filtration, the filtrate was extracted with ethyl acetate (2×30.0 mL) to recover the product. The combined organic layer were concentrated to afford N4-(3-chloro-4-(pyridin-2-ylmethoxy)phenyl)-7-((1-methylpyrrolidin-2-yl)ethynyl)quinazoline-4,6-diamine (120 mg, crude) as a brown oil. MS (ESI) m/z 485.3 [M+H]+

To a solution of N4-(3-chloro-4-(pyridin-2-ylmethoxy)phenyl)-7-((1-methylpyrrolidin-2-yl)ethynyl)quinazoline-4,6-diamine (110 mg, 227 umol, 1.00 eq) and pyridine (0.500 M, 907 uL, 2.00 eq) in dimethylformamide (2.00 mL) was added 1-(3-dimethylaminopropyl)-3-ethylcarbodiimide hydrochloride (87.0 mg, 454 umol, 2.00 eq) and acrylic acid (0.500 M, 680 uL, 1.50 eq) at 20° C. The mixture was stirred at 20° C. for 2 h. The mixture was purified by prep-HPLC and lyophilized to afford N-(4-((3-chloro-4-(pyridin-2-ylmethoxy)phenyl)amino)-7-((1-methylpyrrolidin-2-yl)ethynyl)quinazolin-6-yl)acrylamide (87) (25.02 mg, 46.0 umol, 20% yield, 99% purity) as a yellow solid. 1H NMR (400 MHz, DMSO-d6) δ=12.0 (br s, 1H), 11.8 (br s, 1H), 10.5 (s, 1H), 9.2 (s, 1H), 8.9 (s, 1H), 8.8 (d, J=4.77 Hz, 1H), 8.2 (s, 1H), 8.2-8.2 (m, 1H), 7.9 (d, J=2.08 Hz, 1H), 7.8 (d, J=7.95 Hz, 1H), 7.7 (br t, J=6.42 Hz, 2H), 7.4 (d, J=9.05 Hz, 1H), 7.2 (br dd, J=16.93, 10.21 Hz, 1H), 6.4 (br d, J=17.12 Hz, 1H), 5.9-5.9 (m, 1H), 5.9-5.9 (m, 1H), 5.5 (s, 2 H), 4.6-4.7 (m, 1H), 3.1-3.3 (m, 2H), 2.9-3.0 (m, 3H), 2.0-2.3 (m, 4H). MS (ESI) m/z 539.3 [M+H]+

88: A reaction mixture of tert-butyl (2-methylbut-3-yn-2-yl)carbamate (2.50 g, 13.6 mmol, 1.00 eq), iodomethane (3.87 g, 27.3 mmol, 1.70 mL, 2.00 eq) and sodium hydride (1.09 g, 27.3 mmol, 60% purity, 2.00 eq) in dimethyl formamide (10.0 mL) was stirred for 2 h at 0° C. Water (20.0 mL) was added to the mixture and extracted with ethyl acetate (3×50.0 mL). The organic layers were washed with brine (3×20.0 mL), dried over sodium sulfate, filtered and concentrated under vacuum to give the crude product. The crude product was purified by flash chromatography [silica gel column: 40 g, petroleum ether/ethyl acetate=10/1] to give tert-butyl methyl(2-methylbut-3-yn-2-yl)carbamate (1.30 g, 6.59 mmol, 48% yield) as colorless oil. 1H NMR (400 MHz, CDCl3) δ=2.92 (s, 3.H), 2.30 (s, 1H), 1.59 (s, 6H), 1.41 (s, 9H).

A reaction mixture of 4-((3-chloro-4-(pyridin-2-ylmethoxy)phenyl)amino)-6-nitroquinazolin-7-yl trifluoromethanesulfonate (900 mg, 1.62 mmol, 1.00 eq), tert-butyl methyl(2-methylbut-3-yn-2-yl)carbamate (639 mg, 3.24 mmol, 2.00 eq), copper iodide (154 mg, 809 umol, 0.500 eq), tetrakis(triphenylphosphine)palladium (374 mg, 324 umol, 0.200 eq) and triethylamine (328 mg, 3.24 mmol, 451 uL, 2.00 eq) in dimethyl formamide (15.0 mL) was stirred for 12 h at 25° C. The mixture was concentrated under vacuum to give the residue. The residue was purified by flash chromatography [silica gel column: 20 g; petroleum ether/ethyl acetate 32 10/1-1/1] to give tert-butyl (4-(4-((3-chloro-4-(pyridin-2-ylmethoxy)phenyl)amino)-6-nitroquinazolin-7-yl)-2-methylbut-3-yn-2-yl)(methyl)carbamate (580 mg, 962 umol, 59% yield) as a yellow solid. 1H NMR (400 MHz, DMSO-d6) δ=10.36 (s, 1H), 9.45 (s, 1H), 8.71 (s, 1H), 8.61 (br d, J=4.03 Hz, 1H), 8.01 (d, J=2.57 Hz, 1H), 7.92 (s, 1H), 7.90-7.86 (m, 1H), 7.71 (dd, J=8.99, 2.51 Hz, 1H), 7.61-7.59 (m, 1H), 7.38 (dd, J=7.15, 5.07 Hz, 1H), 7.31 (d, J=9.05 Hz, 1H), 5.31 (s, 2H), 2.74 (s, 3H), 1.73 (s, 6H), 1.43 (s, 9H).

A reaction mixture of tert-butyl (4-(4-((3-chloro-4-(pyridin-2-ylmethoxy)phenyl)amino)-6-nitroquinazolin-7-yl)-2-methylbut-3-yn-2-yl)(methyl)carbamate (600 mg, 995 umol, 1.00 eq), iron power (278 mg, 4.97 mmol, 5.00 eq) and ammonium chloride (266 mg, 4.97 mmol, 5.00 eq) in methanol (20.0 mL) and water (4.00 mL) was stirred for 1 h at 70° C. The mixture was filtered to give the filtrate, which was concentrated under vacuum to give the residue. The residue was purified by prep-HPLC to give tert-butyl (4-(6-amino-4-((3-chloro-4-(pyridin-2-ylmethoxy)phenyl)amino)quinazolin-7-yl)-2-methylbut-3-yn-2-yl)(methyl)carbamate (160 mg, 279 umol, 28% yield) as a yellow solid. 1H NMR (400 MHz, DMSO-d6) δ=9.46 (s, 1H), 8.60 (br d, J=4.40 Hz, 1H), 8.32 (s, 1H), 8.04 (d, J=2.08 Hz, 1H), 7.94-7.86 (m, 1H), 7.70 (dd, J=8.93, 1.96 Hz, 1H), 7.59 (br d, J=8.07 Hz, 1H), 7.55 (s, 1H), 7.44 (s, 1H), 7.40-7.36 (m, 1H), 7.25 (d, J=9.17 Hz, 1H), 5.80 (br s, 2H), 5.29 (s, 2H), 2.94 (s, 3H), 1.71 (s, 6H), 1.46 (s, 9H).

A mixture of tert-butyl (4-(6-amino-4-((3-chloro-4-(pyridin-2-ylmethoxy)phenyl)-amino)quinazolin-7-yl)-2-methylbut-3-yn-2-yl)(methyl)carbamate (170 mg, 297 umol, 1.00 eq), acrylic anhydride (44.9 mg, 356 umol, 4.79 uL, 1.20 eq), and triethylamine (60.0 mg, 593 umol, 82.6 uL, 2.00 eq) in dimethyl formamide (4.00 mL) was stirred for 1 h at 22° C. The mixture was filtered to give the filtrate. The filtrate was purified by prep-HPLC to give tert-butyl (4-(6-acrylamido-4-((3-chloro-4-(pyridin-2-ylmethoxy)phenyl)amino)quinazolin-7-yl)-2-methylbut-3-yn-2-yl)(methyl)carbamate (62 mg, 98.86 umol, 33.33% yield) as a yellow solid. 1H NMR (400 MHz, CDCl3) δ=9.68 (s, 1H), 9.25 (s, 1H), 8.67 (s, 1H), 8.62 (br d, J=4.28 Hz, 1H), 8.03 (s, 1H), 7.93 (d, J=2.57 Hz, 1H), 7.89 (s, 1H), 7.80-7.74 (m, 1H), 7.69 (d, J=7.82 Hz, 1H), 7.56 (dd, J=8.86, 2.63 Hz, 1H), 7.31-7.23 (m, 3H), 7.13 (dd, J=16.93, 10.21 Hz, 1H), 7.03 (d, J=8.80 Hz, 1H), 6.56 (dd, J=16.93, 1.53 Hz, 1H), 5.87-5.76 (m, 1H), 5.32 (s, 2H), 2.97 (s, 3H), 1.75 (s, 6H), 1.50 (s, 9H).

A reaction mixture of tert-butyl (4-(6-acrylamido-4-((3-chloro-4-(pyridin-2-ylmethoxy)phenyl)amino)quinazolin-7-yl)-2-methylbut-3-yn-2-yl)(methyl)carbamate (57.0 mg, 90.9 umol, 1.00 eq) and trifluoroacetic acid (1.54 g, 13.5 mmol, 1.00 mL, 149 eq) in dichloromethane (5.00 mL) was stirred for 1 h at 0° C. The mixture was concentrated under vacuum to give the residue. The residue was purified by prep-HPLC to give N-(4-((3-chloro-4-(pyridin-2-ylmethoxy)phenyl)amino)-7-(3-methyl-3-(methylamino)but-1-yn-1-yl)quinazolin-6-yl)acrylamide 88 (16.73 mg, 29.20 umol, 32.12% yield, 100% purity, FA) as a yellow solid. 1H NMR (400 MHz, DMSO-d6) δ=9.88 (s, 1H), 9.80 (s, 1H), 8.71 (s, 1H), 8.61 (br d, J=4.77 Hz, 1H), 8.57 (s, 1H), 8.25 (s, 1H), 8.03 (s, 1H), 7.89 (t, J=7.58 Hz, 1H), 7.78 (s, 1H), 7.72 (br d, J=9.17 Hz, 1H), 7.59 (d, J=7.82 Hz, 1H), 7.41-7.36 (m, 1H), 7.28 (d, J=8.68 Hz, 1H), 6.59 (br dd, J=16.63, 10.15 Hz, 1H), 6.34 (br d, J=17.12 Hz, 1H), 5.85 (br d, J=10.03 Hz, 1H), 5.30 (s, 2H), 2.36 (s, 3H), 1.38 (s, 6 H). MS (ESI) m/z 527.3 [M+H]+

89: To a solution of N4-(3-chloro-4-(pyridin-2-ylmethoxy)phenyl)-7-(3-methyl-3-(4-methylpiperazin-1-yl)but-1-yn-1-yl)quinazoline-4,6-diamine (50.0 mg, 92.2 umol, 1.00 eq) and but-2-ynoic acid (15.5 mg, 184 umol, 2.00 eq) in pyridine (3.00 mL) was added 1-(3-dimethylaminopropyl)-3-ethylcarbodiimide hydrochloride (70.7 mg, 369 umol, 4.00 eq) at 25° C. The mixture was stirred at 25° C. for 0.5 h. The reaction mixture was filtered. The filtrate was purified by prep-HPLC (column: X timate C18 150*25 mm*5 um; mobile phase: [water (0.05% ammonia hydroxide v/v)-ACN]; B%: 51%-81%, 10 min) to give N-(4-((3-chloro-4-(pyridin-2-ylmethoxy)phenyl)amino)-7-(3-methyl-3-(4-methylpiperazin-1-yl)but-1-yn-1-yl)quinazolin-6-yl)but-2-ynamide 89 (4.91 mg, 8.07 umol, 9% yield, 100% purity) as a white solid. 1H NMR (400 MHz, CDCl3) δ=8.88 (s, 1H), 8.68 (s, 1H), 8.62 (d, J=4.2 Hz, 1H), 8.48 (s, 1H), 7.95 (s, 1H), 7.92 (d, J=2.6 Hz, 1H), 7.87 (s, 1H), 7.78 (d, J=1.8 Hz, 1H), 7.72-7.66 (m, 1H), 7.54 (dd, J=8.9, 2.6 Hz, 1H), 7.26 (br d, J=6.6 Hz, 1H), 7.04 (d, J=9.0 Hz, 1H), 5.32 (s, 2H), 2.84 (br s, 4H), 2.57 (br s, 4H), 2.33 (s, 3H), 2.07 (s, 3H), 1.61 (s, 6H). MS (ESI) m/z 608.4 [M+H]+

90: The reaction mixture of N-(3-chloro-4-(pyridin-2-ylmethoxy)phenyl)-7-fluoro-6-nitroquinazolin-4-amine (0.800 g, 1.88 mmol, 1.00 eq), tert-butyl 3-(hydroxymethyl)morpholine-4-carboxylate (816 mg, 3.76 mmol, 2.00 eq) and potassium tert-butoxide (632 mg, 5.64 mmol, 3.00 eq) in dimethylsulfoxide (10.0 mL) was stirred for 1 h at 25° C. The mixture was filtered to give the filtrate. The filtrate was purified by reverse-phase chromatography [column: 80 g; CH3CN/H2O (FA:0.1%)=0/1-1/2] to give tert-butyl 3-(((4-((3-chloro-4-(pyridin-2-ylmethoxy)phenyl)amino)-6-nitroquinazolin-7-yl)oxy)methyl)morpholine-4-carboxylate (900 mg, 1.44 mmol, 77% yield) as a yellow solid. 1H NMR (400 MHz, CDCl3) δ=9.03 (br s, 1H), 8.60 (br d, J=4.65 Hz, 1H), 8.53 (s, 2H), 7.91-7.86 (m, 1H), 7.84 (br s, 1H), 7.59 (d, J=7.70 Hz, 1H), 7.44 (br s, 1H), 7.39-7.35 (m, 1H), 7.31 (br s, 1H), 7.16 (br d, J=8.93 Hz, 1H), 5.25 (s, 2H), 4.56-4.47 (m, 1H), 4.43-4.29 (m, 1H), 4.24 (br s, 1H), 3.99 (br d, J=11.62 Hz, 1H), 3.83 (br d, J=10.88 Hz, 1H), 3.68 (br s, 1H), 3.53 (br d, J32 9.29 Hz, 1H), 3.41 (br s, 2H), 1.36 (br s, 9H).

A reaction mixture of tert-butyl 3-(((4-((3-chloro-4-(pyridin-2-ylmethoxy)phenyl)amino-6-nitroquinazolin-7-yl)oxy)methyl)morpholine-4-carboxylate (1.00 g, 1.60 mmol, 1.00 eq), ammonium chloride (429 mg, 8.02 mmol, 281 uL, 5.00 eq) and iron (448 mg, 8.02 mmol, 5.00 eq) in methanol (15.0 mL) and water (4.00 mL) was stirred for 1 h at 70° C. The mixture was filtered to give the filtrate. The filtrate was purified by reverse-phase chromatography [column:80 g; CH3CN/H2O(NH3.H2O:0.1%)=0/1-1/1] to give tert-butyl3-(((6-amino-4-((3-chloro-4-(pyridin-2-ylmethoxy)phenyl)amino)quinazolin-7-yl)oxy)methyl)morpholine-4-carboxylate (150 mg, 253 umol, 16% yield) as a yellow solid. 1H NMR (400 MHz, DMSO-d6) δ=9.26 (s, 1H), 8.60 (d, J=4.63 Hz, 1H), 8.33 (s, 1H), 8.05 (d, J=2.50 Hz, 1H), 7.89 (td, J=7.69, 1.75 Hz, 1H), 7.71 (dd, J=9.01, 2.50 Hz, 1H), 7.59 (d, J=7.75 Hz, 1H), 7.42-7.34 (m, 2H), 7.23 (d, J=9.13 Hz, 1.H), 7.17 (br s, 1H), 5.33 (s, 2H), 5.28 (s, 2H), 4.44-4.26 (m, 3H), 4.05 (d, J=11.88 Hz, 1H), 3.84 (br d, J=9.38 Hz, 1H), 3.68 (br s, 1H), 3.55 (br d, J=10.63 Hz, 1H), 3.45-3.37 (m, 1H), 3.22 (br s, 1H), 1.41 (br s, 9H).

A reaction mixture of tert-butyl 3-(((6-amino-4-((3-chloro-4-(pyridin-2-ylmethoxy)phenyl)amino)quinazolin-7-yl)oxy)methyl)morpholine-4-carboxylate (100 mg, 169 umol, 1.00 eq), acrylic acid (24.3 mg, 337 umol, 23.1 uL, 2.00 eq), 1-(3-dimethylaminopropyl)-3-ethylcarbodiimide hydrochloride (64.7 mg, 337 umol, 2.00 eq) and pyridine (40.0 mg, 506 umol, 40.8 uL, 3.00 eq) in dimethyl formamide (5.00 mL) was stirred for 1 h at 20° C. The mixture was filtered to give the filtrate. The filtrate was purified by prep-HPLC {column: Waters Xbridge 150*25 5 um; mobile phase: [water (0.05% ammonia hydroxide v/v)-ACN]; B%:

48%-78%, 10 min.} to give tert-butyl 3-(((6-acrylamido-4-((3-chloro 4-(pyridin-2-ylmethoxy)phenyl)amino)quinazolin-7-yl)oxy)methyl)morpholine-4-carboxylate (40.0 mg, 61.8 umol, 37% yield) as a yellow solid. 1H NMR (400 MHz, DMSO-d6) δ=9.71 (s, 1H), 9.43 (s, 1H), 8.98 (br s, 1H), 8.61 (d, J=4.77 Hz, 1H), 8.50 (s, 1H), 7.99 (d, J=2.57 Hz, 1H), 7.89 (td, J=7.70, 1.71 Hz, 1H), 7.70 (dd, J=8.99, 2.38 Hz, 1H), 7.60 (d, J=7.82 Hz, 1H), 7.43-7.35 (m, 2H), 7.26 (d, J=9.05 Hz, 1H), 6.72 (dd, J=16.93, 10.21 Hz, 1H), 6.34 (br d, J=16.63 Hz, 1H), 5.85 (br d, J=9.90 Hz, 1H), 5.29 (s, 2H), 4.51 (br s, 1H), 4.35 (br s, 2H), 4.08 (d, J=11.98 Hz, 1H), 3.85 (br d, J=8.93 Hz, 1H), 3.70 (br d, J=11.49 Hz, 1H), 3.55 (br d, J=10.88 Hz, 1H), 3.46-3.35 (m, 2H), 1.39 (br s, 9H).

A reaction mixture of tert-butyl 3-(((6-acrylamido-4-((3-chloro-4-(pyridin-2-ylmethoxy)phenyl)amino)quinazolin-7-yl)oxy)methyl)morpholine-4-carboxylate (30.0 mg, 46.4 umol, 1.00 eq) and trifluoroacetic acid (308 mg, 2.70 mmol, 0.200 mL, 58.3 eq) in dichloromethane (1.00 mL) was stirred for 1 h at 0° C. and then stirred for 0.5 h at 20° C. The mixture was concentrated under vacuum to give the residue. The residue was purified by prep-HPLC {column: Xtimate C18 150*25 mm*5 um; mobile phase: [water (0.05% ammonia v/v)-ACN]; B%: 21%-51%, 10 min.} to give N-(4-((3-chloro-4-(pyridin-2-ylmethoxy)phenyl) amino)-7-(morpholin-3-ylmethoxy)quinazolin-6-yl)acrylamide 90 (11 mg, 19.71 umol, 42.51% yield, 98% purity) as an off-white solid. 1H NMR (400 MHz, DMSO-d6) δ=9.71 (br d, J=5.99 Hz, 2H), 8.89 (s, 1H), 8.61 (d, J=4.16 Hz, 1H), 8.50 (s, 1H), 8.00 (d, J=2.57 Hz, 1H), 7.89 (td, J=7.70, 1.71 Hz, 1H), 7.70 (dd, J=8.99, 2.51 Hz, 1H), 7.60 (d, J=7.83 Hz, 1H), 7.38 (dd, J=6.91, 4.95 Hz, 1H), 7.29-7.24 (m, 2H), 6.76 (dd, J=16.99, 10.27 Hz, 1H), 6.34 (dd, J=16.99, 1.83 Hz, 1H), 5.89-5.82 (m, 1H), 5.29 (s, 2H), 4.20-4.14 (m, 1H), 4.12-4.05 (m, 1H), 3.90 (dd, J=10.70, 2.38 Hz, 1H), 3.74 (br d, J=11.37 Hz, 1H), 3.51-3.42 (m, 1H), 3.28-3.20 (m, 2H), 2.95-2.80 (m, 2H). MS (ESI) m/z 547.4 [M+H]+

91: To a solution of 7-fluoro-6-nitroquinazolin-4-ol (5.00 g, 23.9 mmol, 1.00 eq) in thienyl chloride (80.0 mL) was added dimethyl formamide (175 mg, 2.39 mmol, 184 uL, 0.100 eq) at 25° C. The mixture was stirred at 90° C. for 12 h. The reaction mixture was concentrated under reduced pressure to give 4-chloro-7-fluoro-6-nitroquinazoline (5.00 g, crude) as a light yellow solid.

To a solution of 2-chloro-1-fluoro-4-nitrobenzene (3.00 g, 17.1 mmol, 1.00 eq) in dimethylsulfoxide (40.0 mL) was added potassium carbonate (4.72 g, 34.2 mmol, 2.00 eq) and phenol (1.77 g, 18.8 mmol, 1.65 mL, 1.10 eq). The mixture was stirred at 80° C. for 2 h. The reaction mixture was added water (100 mL) and extracted with ethyl acetate (3×100 mL). The combined organic layers were washed with brine (50 mL), dried over sodium sulfate, filtered and concentrated under reduced pressure to give 2-chloro-4-nitro-1-phenoxybenzene (5.00 g, crude) as yellow oil. 1H NMR (400 MHz, CDCl3) δ=8.34-8.25 (m, 1H), 8.01-7.90 (m, 1H), 7.42-7.33 (m, 2H), 7.25-7.17 (m, 1H), 7.04-6.96 (m, 2H), 6.80 (d, J=9.0 Hz, 1H).

To a solution of 2-chloro-4-nitro-1-phenoxybenzene (5.00 g, 20.0 mmol, 1.00 eq) in water (30.0 mL) and methanol (150 mL) was added ammonium chloride (9.64 g, 180 mmol, 6.30 mL, 9.00 eq) and iron powder (5.59 g, 100 mmol, 5.00 eq) in portions. The mixture was stirred at 80° C. for 2 h. The reaction mixture was added methanol (200 mL) and filtered. The filtrate was concentrated to give crude product. The crude product was diluted with water (100 mL) and extracted with ethyl acetate (3×100 mL). The combined organic layer was washed with brine (50 mL) and dried over sodium sulfate, filtered and concentrated to give 3-chloro-4-phenoxyaniline (4.70 g, crude) as yellow oil. 1H NMR (400 MHz, CDCl3) δ=7.25-7.18 (m, 2H), 6.99-6.91 (m, 1H), 6.86-6.78 (m, 3H), 6.70 (d, J=2.8 Hz, 1H), 6.48 (dd, J=2.8, 8.6 Hz, 1H), 3.95-3.11 (m, 2H).

To a solution of 4-chloro-7-fluoro-6-nitroquinazoline (3.00 g, 13.2 mmol, 1.00 eq) in isopropyl alcohol (50.0 mL) was added 3-chloro-4-phenoxyaniline (3.19 g, 14.5 mmol, 1.10 eq) in one portion at 20° C. The mixture was stirred at 80° C. for 2 h. The reaction mixture was concentrated under reduced pressure to give N-(3-chloro-4-phenoxyphenyl)-7-fluoro-6-nitroquinazolin-4-amine (4.70 g, 11.4 mmol, 87% yield) as a white solid. MS (ESI) m/z 410.9 [M+H]+; 1H NMR (400 MHz, DMSO-d6) δ=9.66 (br d, J=7.2 Hz, 1H), 8.87-8.79 (m, 1H), 8,18 (br s, 1H), 7.89 (br d, J=12.4 Hz, 1H), 7.85-7.77 (m, 1H), 7.42 (t, J=8.0 Hz, 2H), 7.23 (d, J=9.0 Hz, 1H), 7.16 (t, J=7.4 Hz, 1H), 7.00 (d, J=8.6 Hz, 2H).

To a solution of N-(3-chloro-4-phenoxyphenyl)-7-fluoro-6-nitroquinazolin-4-amine (2.00 g, 4.87 mmol, 1.00 eq), (R)-1-methylpyrrolidin-3-ol (985 mg, 9.74 mmol, 1.07 mL, 2.00 eq) in dimethylsulfoxide (25.0 mL) was added potassium tert-butoxide (1.64 g, 14.6 mmol, 3.00 eq). The mixture was stirred at 20° C. for 12 h. The reaction mixture was diluted with water (50 mL) and extracted with ethyl acetate (2×50 mL). The combined organic layers were washed with brine (50 mL), dried over sodium sulfate, filtered and concentrated under reduced pressure to give (R)-N-(3-chloro-4-phenoxyphenyl)-7-((1-methylpyrrolidin-3-yl) oxy)-6-nitroquinazolin-4-amine (2.00 g, crude) as a yellow solid. MS (ESI) m/z 492.1 [M+H]+

To a solution of (R)-N-(3-chloro-4-phenoxyphenyl)-7-((1-methylpyrrolidin-3-yl)oxy)-6-nitroquinazolin-4-amine (2.00 g, 4.07 mmol, 1.00 eq) and ammonium chloride (1.96 g, 36.6 mmol, 1.28 mL, 9.00 eq) in water (4.00 mL) and methanol (20.0 mL) was added iron powder (1.59 g, 28.5 mmol, 7.00 eq) in one portion. The mixture was stirred at 80° C. for 1 h. The mixture was added methanol (50 mL) and filtered. The filtrate was concentrated to give a residue. The residue was purified by prep-HPLC (column: Phenomenex luna C18 150*25 10 u; mobile phase: [water (0.225%FA)-ACN]; B%: 16%-36%, 7.8 min) to give (R)-N4-(3-chloro-4-phenoxyphenyl)-7-((1-methylpyrrolidin-3-yl)oxy)quinazoline-4,6-diamine (1.00 g, crude) as a yellow solid. 1H NMR (400 MHz, DMSO-d6) δ=9.42 (br s, 1H), 8.39 (s, 1H), 8.24 (d, J=2.6 Hz, 1H), 8.15 (s, 1H), 7.85 (dd, J=2.6, 9.0 Hz, 1H), 7.43 (s, 1H), 7.41-7.35 (m, 2H), 7.18 (d, J=9.0 Hz, 1H), 7.11 (t, J=7.4 Hz, 1H), 7.05 (s, 1H), 6.98-6.87 (m, 2H), 5.43 (br s, 2H), 5.20 (br d, J=3.8 Hz, 1H), 3.13 (br d, J=3.0 Hz, 2H), 3.10-2.99 (m, 2H), 2.79-2.69 (m, 1H), 2.53 (s, 3H), 2.09-2.01 (m, 1H). MS (ESI) m/z 462.1 [M+H]+

To a solution of (R)-N4-(3-chloro-4-phenoxyphenyl)-7-((1-methylpyrrolidin-3-yl)oxy)quinazoline-4,6-diamine (0.300 g, 649 nmol, 1.00 eq) and acrylic anhydride (123 mg, 974 umol, 6.69 uL, 1.50 eq) in dimethyl formamide (2.00 mL) was added triethylamine (131 mg, 1.30 mmol, 181 uL, 2.00 eq) dropwise at 25° C. The mixture was stirred at 25° C. for 0.5 h. The reaction mixture was filtered. The filtrate was purified by prep-HPLC (column: Xtimate C18 150*25 mm*5 um; mobile phase: [water (0.05% ammonia hydroxide v/v)-ACN]; B%: 50%-80%, 10 min) and prep-HPLC (column: Xtimate C18 150*25 mm*5 um; mobile phase: [water (0.05% ammonia hydroxide v/v)-ACN]; B%: 50%-80%, 10 min) and lyophilized to give (R)-N-(4-((3-chloro-4-phenoxyphenyl)amino)-7-((1-methylpyrrolidin-3-yl)oxy) quinazolin-6-yl)acrylamide 91 (69.38 mg, 133 umol, 21% yield, 99% purity, 99% ee) as a white solid. 1H NMR (400

MHz, CDCl3) δ=9.15 (s, 1H), 8.86 (s, 1H), 8.69 (s, 1H), 8.07 (d, J=2.6 Hz, 1H), 7.90 (s, 1H), 7.60 (dd, J=8.8, 2.6 Hz, 1H), 7.39-7.33 (m, 2H), 7.19 (s, 1H), 7.14-7.09 (m, 1H), 7.05 (d, J=8.8 Hz, 1H), 7.01 (dd, J=8.6, 1.0 Hz, 2H), 6.55-6.40 (m, 2H), 5.87-5.80 (m, 1H), 5.09 (br t, J=6.0 Hz, 1H), 3.19 (d, J=11.0 Hz, 1H), 3.11 (td, J=8.8, 3.4 Hz, 1H), 2.67 (dd, J=11.0, 5.2 Hz, 1H), 2.60-2.50 (m, 1H), 2.47 (s, 3H), 2.37 (q, J=8.4 Hz, 1H), 2.22-2.10 (m, 1H). MS (ESI) m/z 516.1 [M+H]+

92: A mixture of N-(3-chloro-4-(pyridin-2-ylmethoxy)phenyl)-7-(2-chloroethoxy)-6-nitroquinazolin-4-amine (1.00 g, 2.06 mmol, 1.00 eq), tert-butyl hexahydropyrrolo[3,2-b]pyrrole-1(2H)-carboxylate (654 mg, 3.08 mmol, 1.50 eq), potassium carbonate (1.14 g, 8.23 mmol, 4.00 eq) and potassium iodide (341 mg, 2.06 mmol, 1.00 eq) in acetonitrile (10.0 mL) was stirred at 110° C. for 12 h. The reaction mixture was concentrated to give a residue. The residue was triturated with water (20.0 mL) to give tert-butyl 4-(2-((4-((3-chloro-4-(pyridin-2-ylmethoxy)phenyl)amino)-6-nitroquinazolin-7-yl)oxy)ethyl)hexahydropyrrolo[3,2-b] pyrrole-1(2H)-carboxylate (1.20 g, 1.81 mmol, 88% yield) as a yellow solid. MS (ESI) m/z 662.4 [M+H]+

A mixture of tert-butyl 4-(2-((4-((3-chloro-4-(pyridin-2-ylmethoxy)phenyl)amino)-6-nitroquinazolin-7-yl)oxy)ethyl)hexahydropyrrolo[3,2-b]pyrrole-1(2H)- carboxylate (1.00 g, 1.51 mmol, 1.00 eq), 2,2,2-trifluoroacetic acid (3.08 g, 27.0 mmol, 17.9 eq) in dichloromethane (10.0 mL) was stirred at 25° C. for 12 h. The reaction mixture was concentrated to give a residue. The residue was purified by prep-HPLC {column: Phenomenex Synergi Max-RP 250*50 mm*10 um; mobile phase: [water(0.225%FA)-ACN]; B%: 10%-40%, 18 min, 50% min} and lyophilized to give N-(3-chloro-4-(pyridin-2-ylmethoxy)phenyl)-7-(2-(hexahydropyrrolo[3,2-b]pyrrol-1(2H)-yl)ethoxy)-6-nitroquinazolin-4-amine (700 mg, 1.25 mmol, 82% yield) as a yellow solid. 1H NMR (400 MHz, DMSO-d6) δ=10.10 (br s, 1H), 9.22 (s, 1H), 8.64 (s, 1H), 8.62-8.59 (m, 1H), 8.19 (s, 1H), 8.02 (d, J=2.4 Hz, 1H), 7.89 (dt, J=1.7, 7.7 Hz, 1H), 7.70 (dd, J=2.5, 9.0 Hz, 1H), 7.59 (d, J=7.8 Hz, 1H), 7.49 (s, 1H), 7.38 (dd, J=5.3, 7.0 Hz, 1H), 7.29 (d, J=9.0 Hz, 1H), 5.31 (s, 2H), 4.48-4.33 (m, 2H), 4.14-4.07 (m, 1H), 3.26-3.20 (m, 2H), 3.15-3.06 (m, 2H), 2.80 (td, J=4.6, 13.8 Hz, 1H), 2.53 (br s, 1H), 2.38-2.26 (m, 1H), 2.2.6-2.14 (m, 1H), 1.92 (br dd, J=5.5, 13.3 Hz, 1H), 1.85-1.69 (m, 2H). MS (ESI) m/z 562.1 [M+H]+

A mixture of N-(3-chloro-4-(pyridin-2-ylmethoxy)phenyl)-7-(2-(hexahydropyrrolo[3,2-b]pyrrol-1(2H)-yl)ethoxy)-6-nitroquinazolin-4-amine (500 mg, 889 umol, 1.00 eq) and formaldehyde (285 mg, 8.90 mmol, 360 uL, 10.0 eq) and sodium borohydride (33.7 mg, 889 umol, 1.00 eq) in 2,2,2-trifluoroethanol (6.00 mL) was stirred at 40° C. for 12 h. The reaction mixture was concentrated to give a residue. The residue was purified by Reverse-MPLC on Xtimate C-18(20/40 um, 120A) gel eluted with H2O (0.1%FA:): MeCN (20/1 to 1/5) and lyophilized to give N-(3-chloro-4-(pyridin-2-ylmethoxy)phenyl)-7-(2-(4-methylhexahydropyrrolo[3,2-b]pyrrol-1(2H)-yl)ethoxy)-6-nitroquinazolin-4-amine (500 mg, 868 umol, 97% yield) as a yellow solid. 1H NMR (400 MHz, DMSO-d6) δ=10.07 (br s, 1H), 9.23-9.17 (m, 1H), 8.66-8.55 (m, 2H), 8.19 (s, 2H), 8.01 (d, J=2.4 Hz, 1H), 7.89 (dt, J=1.7, 7.7 Hz, 1H), 7.70 (dd, J=2.4, 8.9 Hz, 1H), 7.59 (d, J=7.8 Hz, 1H), 7.48 (s, 1H), 7.37 (dd, J=5.1, 7.0 Hz, 1H), 7.29 (d, J=9.0 Hz, 1H), 5.30 (s, 2H), 4.41-4.33 (m, 2H), 3,50-3.19 (m, 2H), 3.09-2.95 (m, 2H), 2.51 (br s, 3H), 2.45 (br d, J=17.4 Hz, 4H), 1.96-1.79 (m, 1H), 1.77-1.49 (m, 2H). MS (ESI) m/z 576.2 [M+H]+

A mixture of N-(3-chloro-4-(pyridin-2-ylmethoxy)phenyl)-7-(2-(4-methylhexahydropyrrolo[3,2-b]pyrrol-1(2H)-yl)ethoxy)-6-nitroquinazolin-4-amine (500 mg, 867 umol, 1.00 eq), iron (242 mg, 4.34 mmol, 5.00 eq) and ammonium chloride (417 mg, 7.81 mmol, 9.00 eq) in methanol (5.00 mL) and water (1.00 mL) was stirred at 80° C. for 12 h. To the mixture was added methanol (50.0 mL). The mixture was filtered. The filtrate was concentrated to give a residue. The residue was purified by prep-HPLC {column: Phenomenex Gemini 150*25 mm*10 um; mobile phase: [water (0.04%NH3H2O+10 mM NH4HCO3)-ACN]; B%: 36%-66%, 43 min} and lyophilized to give N4-(3-chloro-4-(pyridin-2-ylmethoxy)phenyl)-7-(2-(4-methylhexahydropyrrolo[3,2-b]pyrrol-1(2H)-yl)ethoxy) quinazoline-4,6-diamine (70.0 mg, 128 umol, 15% yield) as a yellow solid. 1H NMR (400 MHz, CDCl3) δ=8.52 (br d, J=4.3 Hz, 1H), 8.47 (s, 1H), 7.76 (d, J=2.4 Hz, 1H), 7.68 (br t, J=6.9 Hz, 1H), 7.62-7.57 (m, 1H), 7.40 (dd, J=2.4, 8.8 Hz, 1H), 7.18-7.15 (m, 1H), 7.08 (s, 1H), 6.96-6.92 (m, 1H), 6.88 (br s, 1H), 6.84 (s, 1H), 5.22 (s, 2H), 4.20 (br t, J=5.6 Hz, 2H), 3.16-3.08 (m, 2H), 3.05-2.94 (m, 2H), 2.87-2.75 (m, 2H), 2.46 (q, J=8.0 Hz, 1H), 2.33-2.32 (m, 1H), 2.23 (s, 3H), 1.79 (br s, 4H).

To a solution of N4-(3-chloro-4-(pyridin-2-ylmethoxy)phenyl)-7-(2-(4-methylhexahydropyrrolo[3,2-b]pyrrol-1(2H)-yl)ethoxy)quinazoline-4,6-diamine (60.0 mg, 109 umol, 1.00 eq), pyridine (34.7 mg, 439 umol, 4.00 eq) and 1-(3-dimethylaminopropyl)-3-ethylcarbodiimide (84.3 mg, 439 umol, 4.00 eq) in dimethyl formamide (1.00 mL) was added acrylic acid (11.9 mg, 164 umol, 1.50 eq) at 25° C. The mixture was stirred at 25° C. for 0.5 h. The reaction mixture was filtered. The filtrate was purified by prep-HPLC {column: Xtimate C18 150*25 mm*5 um; mobile phase: [water (0.05% ammonia hydroxide v/v)-ACN]; B%: 51%-81%, 10min} and lyophilized to give N-(4-((3-chloro-4-(pyridin-2-ylmethoxy)phenyl)amino)-7-(2-(4-methylhexahydropyrrolo[3,2-b]pyrrol-1(2H)-yl)ethoxy)quinazolin-6-yl)acrylamide 92 (25.96 mg, 42.3 umol, 38% yield, 98% purity) as a white solid. 1H NMR (400 MHz, CDCl3) δ=9.20 (s, 1H), 9.11 (s, 1H), 8.65 (s, 1H), 8.62 (d, J=4.3 Hz, 1H), 7.91 (d, J=2.6 Hz, 1H), 7.81-7.74 (m, 1H), 7.68 (br d, J=10.5 Hz, 2H), 7.53 (dd, J=2.6, 8.9 Hz, 1H), 7.26 (s, 2H), 7.02 (d, J=8.8 Hz, 1H), 6.69-6.43 (m, 2H), 5.97-5.76 (m, 1H), 5.32 (s, 2H), 4.37-4.27 (m, 2H), 3.27-3.16 (m, 2H), 3.15-3.04 (m, 2H), 2.93-2.83 (m, 2H), 2.59-2.49 (m, 1H), 2.36 (dt, J=7.0, 9.5 Hz, 1H), (s, 3H), 1.92-1.87 (m, 2H), 1.87-1.77 (m, 2H). MS (ESI) m/z 600.3 [M+H]+

93: A mixture of N-(3-chloro-4-(pyridin-2-ylmethoxy)phenyl)-7-fluoro-6-nitroquinazolin-4-amine (1.00 g, 2.35 mmol, 1.00 eq), N,N-dimethylazetidin-3-amine (481 mg, 3.52 mmol, 1.50 eq, HCl) and potassium carbonate (1.30 g, 9.39 mmol, 4.00 eq) in dimethylsulfoxide (20.0 mL) was stirred at 25° C. for 12 h. To the reaction mixture was added of water (20.0 mL). The mixture was filtered. The filter cake was dried to give N-(3-chloro-4-(pyridin-2-ylmethoxy)phenyl)-7-(3-(dimethylamino)azetidin-1-yl)-6-nitroquinazolin-4-amine (1.00 g, 1.98 mmol, 84% yield) as a yellow solid. 1H NMR (400 MHz, DMSO-d6) δ=9.98 (br s, 1H), 9.12 (s, 1H), 8.60 (br d, J=4.4 Hz, 1H), 8.49 (s, 1H), 8.02 (br s, 1H), 7.89 (t, J=7.6 Hz, 1H), 7.70 (br d, J=8.8 Hz, 1H), 7.59 (d, J=7.8 Hz, 1H), 7.43-7.33 (m, 1H), 7.27 (d, J=9.0 Hz, 1H), 6.78 (s, 1H), 5.30 (s, 2H), 4.04 (br t, J=7.9 Hz, 2H), 3.79 (br dd, J=5.0, 8.8 Hz, 2H), 3.23-3.12 (m, 1H), 2 13 (s, 6H). MS (ESI) m/z 506.1 [M+H]+

A mixture of N-(3-chloro-4-(pyridin-2-ylmethoxy)phenyl)-7-(3-(dimethylamino)azetidin-1-yl)-6-nitroquinazolin-4-amine (900 mg, 1.78 mmol, 1.00 eq), iron (496 mg, 8.89 mmol, 5.00 eq), ammonium chloride (856 mg, 16.0 mmol, 9.00 eq) in methanol (20.0 mL) and water (5.00 mL) was stirred at 80° C. for 1 h. To the mixture was added methanol (50.0 mL). The reaction mixture was filtered. The filtrate was concentrated to give a residue. The residue was triturated with saturated sodium carbonate (10.0 mL) to give N4-(3-chloro-4-(pyridin-2-ylmethoxy)phenyl)-7-(3-(dimethylamino)azetidin-1-yl)quinazoline-4,6-diamine (600 mg, 1.26 mmol, 71% yield) as a yellow solid. 1H NMR (400 MHz, DMSO-d6) δ=9.09 (s, 1H), 8.53 (br d, J=4.3 Hz, 1H), 8.21 (s, 1H), 7.97 (br d, J=2.3 Hz, 1H), 7.85-7.76 (m, 1H), 7.62 (br dd, J=2.1, 8.9 Hz, 1H), 7.52 (br d, J=7.7 Hz, 1H), 7.35-7.22 (m, 2H), 7.14 (br d, J=8.9 Hz, 1H), 6.55 (s, 1H), 5.20 (s, 2H), 4.80 (br s, 2H), 4.08 (br t, J=7.2 Hz, 2H), 3.61 (br t, J=6.7 Hz, 2H), 3.07-2.99 (m, 1H), 2.05 (s, 6H). MS (ESI) m/z 476.3 [M+H]+

To a solution of N4-(3-chloro-4-(pyridin-2-ylmethoxy)phenyl)-7-(3-(dimethylamino)azetidin-1-yl)quinazoline-4,6-diamine (300 mg, 630 umol, 1.00 eq), pyridine (199 mg, 2.52 mmol, 4.00 eq) and acrylic acid (54.5 mg, 756 umol, 51.9 uL, 1.20 eq) in dimethyl formamide (2.00 mL) was added 1-(3-dimethylaminopropyl)-3-ethylcarbodiimide (362 mg, 1.89 mmol, 3.00 eq) at 25° C. The mixture was stirred at 25° C. for 0.5 h. The reaction mixture was filtered. The filtrate was purified by prep-HPLC {column: Xtimate C18 150*25 mm*5 um; mobile phase: [water (0.05% ammonia hydroxide v/v)-ACN]; B%: 20%-50%, 10min} and lyophilized to give N-(4-((3-chloro-4-(pyridin-2-ylmethoxy)phenyl)amino)-7-(3-(dimethylamino)azetidin-1-yl)quinazolin-6-yl)acrylamide 93 (84.35 mg, 159 umol, 25% yield, 100% purity) as a yellow solid. 1H NMR (400 MHz, DMSO-d6) δ=9.76 (s, 1H), 9.49 (s, 1H), 8.76-8,54 (m, 1H), 8.43 (s, 1H), 8.26 (s, 1H), 8.03 (d, J=2.6 Hz, 1H), 7.89 (dt, J=1.8, 7.7 Hz, 1H), 7.72 (dd, J=2.6, 9.0 Hz, 1H), 7.59 (d, J=7.8 Hz, 1H), 7.37 (ddd, J=1.0, 4.9, 7.5 Hz, 1H), 7.24 (d, J=9.2 Hz, 1H), 6.63 (s, 1H), 6.53 (dd, J=10.3, 17.1 Hz, 1H), 6.30 (dd, J=1.9, 17.1 Hz, 1H), 5.81 (dd, J=1.7, 10.3 Hz, 1H), 5.28 (s, 2H), 4.09 (t, J=7.5 Hz, 2H), 3.77 (dd, J=5.6, 7.9 Hz, 2H), 3.14 (quin, J=6.2 Hz, 1H), 2.10 (s, 6H). MS (ESI) m/z 530.1 [M+H]+

94: To a solution of N-(3-chloro-4-(pyridin-2-ylmethoxy)phenyl)-7-fluoro-6-nitroquinazolin-4-amine (1.00 g, 2.35 mmol, 1.00 eq) and potassium tert-butoxide (791 mg, 7.05 mmol, 3.00 eq) in dimethylsulfoxide (10.0 mL) was added 2-(dimethylamino)-2-methyl-propan-1-ol (551 mg, 4.70 mmol, 2.00 eq) at 25° C. The mixture was stirred at 25° C. for 2 h. The reaction was quenched by water (30.0 mL). The mixture was partitioned between ethyl acetate (50.0 mL) and water (30.0 mL). The aqueous phase was extracted with ethyl acetate (2×20.0 mL). The combined organic phase was washed with brine (2×20.0 mL), dried over anhydrous sodium sulfate, filtered and concentrated in vacuum to afford N-(3-chloro-4-(pyridin-2-ylmethoxy)phenyl)-7-(2-(dimethylamino)-2-methylpropoxy)-6-nitroquinazolin-4-amine (950 mg, 1.82 mmol, 77% yield) as a brown solid. 1H NMR (400 MHz, DMSO-d6) δ=10.06 (s, 1H), 9.21 (s, 1H), 8.62 (s, 1H), 8.61-8.59 (m, 1H), 8.01 (d, J=2.6 Hz, 1H), 7.89-7.86 (m, 1H), 7.70 (dd, J=2.6, 8.9 Hz, 1H), 7.58 (d, J=7.8 Hz, 1H), 7.50 (s, 1H), 7.38-7.35 (m, 1H), 7.28 (d, J=9.0 Hz, 1H), 5.30 (s, 2H), 2.25 (s, 6H), 1.51-1.46 (m, 2H), 1.13 (s, 6H).

To a solution of N-(3-chloro-4-(pyridin-2-ylmethoxy)phenyl)-7-(2-(dimethylamino)-2-methylpropoxy)-6-nitroquinazolin-4-amine (950 mg, 1.82 mmol, 1.00 eq) and iron powder (710 mg, 12.7 mmol, 7.00 eq) in methanol (50.0 mL) was added a solution of ammonium chloride (875 mg, 16.4 mmol, 0.572 mL, 9.00 eq) in water (10.0 mL). The mixture was stirred at 80° C. for 2 h. The residue was added methanol (100 mL) and stirred at 55° C. for 0.5 h. After filtration, the filtrate was concentrated to afford a residue. The residue was triturated with water (30.0 mL) and saturated sodium carbonate (3.00 mL). After filtration, the filter cake was washed with methanol (100 mL). The filtrate was concentrated in vacuum to afford N4-(3-chloro-4-(pyridin-2-ylmethoxy)phenyl)-7-(2-(dimethylamino)-2-methylpropoxy)quinazoline-4,6-diamine (800 mg, 1.62 mmol, 89% yield) as a brown solid. 1H NMR (400 MHz, DMSO-d6) δ=10.77 (br s, 1H), 9.50 (br s, 1H), 8.59 (br d, J=4.4 Hz, 1H), 8.37 (s, 1H), 8.04 (d, J=2.2 Hz, 1H), 7.91-7.87 (m, 1H), 7.70 (br dd, J=2.3, 8.9 Hz, 1H), 7.58 (br d, J=7.8 Hz, 1H), 7.42 (5, 1H), 7.23 (br d, J=8.9 Hz, 1H), 7.14 (s, 1H), 5.28 (s, 2H), 4.33 (s, 2H), 2.73 (s, 6H), 1.47 (s, 6H).

To a solution of N4-(3-chloro-4-(pyridin-2-ylmethoxy)phenyl)-7-(2-(dimethylamino)-2-methylpropoxy)quinazoline-4,6-diamine (300 mg, 0.609 mmol, 1.00 eq), pyridine (96.3 mg, 1.22 mmol, 0.0982 mL, 2.00 eq) and 1-(3-dimethylaminopropyl)-3-ethylcarbodiimide hydrochloride (233 mg, 1.22 mmol, 2.00 eq) in N,N-dimethylformamide (3.00 mL) was added a solution of acrylic acid (0.500 M, 1.83 mL, 1.50 eq) in N,N-dimethylformamide. The mixture was stirred at 25° C. for 2 h. The mixture was quenched by methanol (2.00 mL) and concentrated in vacuum. The residue was purified by prep-HPLC (column: Xtimate C18 150*25 mm*5 um; mobile phase: [water (0.05% ammonia hydroxide v/v)-ACN]; B%: 38%-68%, 10 min) and lyophilized to afford N-(4-((3-chloro-4-(pyridin-2-ylmethoxy)phenyl)amino)-7-(2-(dimethylamino)-2-methylpropoxy)quinazolin-6-yl)acrylamide 94 (19.51 mg, 87.8 umol, 14% yield, 97% purity) as a yellow solid. 1H NMR (400 MHz, DMSO-d6) δ=9.67 (s, 1H), 9.62 (s, 1H), 8.70 (s, 1H), 8.62-8.58 (m, 1H), 8.51 (s, 1H), 8.01 (d, J=2.6 Hz, 1H), 7.88 (dt, J=1.7, 7.7 Hz, 1H), 7.71 (dd, J=2.6, 9.0 Hz, 1H), 7.59 (d, J=7.8 Hz, 1H), 7.37 (dd, J=4.9, 6.5 Hz, 1H), 7.32 (s, 1H), 7.25 (d, J=9.0 Hz, 1H), 6.57 (dd, J=10.2, 16.9 Hz, 1H), 6.30 (dd, J=1.9, 17.1 Hz, 1H), 5.86-5.76 (m, 1H), 5.29 (s, 2H), 4.06 (s, 2H), 2.25 (s, 6H), 1.13 (s, 6H). MS (ESI) m/z 547.4 [M +1]+

95: To a solution of N-(3-chloro-4-(pyridin-2-ylmethoxy)phenyl)-7-fluoro-6-nitroquinazolin-4-amine (1.30 g, 3.05 mmol, 1.00 eq) and 2-(1-methylpyrrolidin-2-yl)ethanol (789 mg, 6.11 mmol, 830 uL, 2.00 eq) in dimethylsulfoxide (5.00 mL) was added potassium tert-butoxide (1.03 g, 9.16 mmol, 3.00 eq) in portions at 20° C. The mixture was stirred at 20° C. for 12 h. The reaction mixture was added water (200 mL) and filtered. The filter cake was dried to give N-(3-chloro-4-(pyridin-2-ylmethoxy)phenyl)-7-(2-(1-methylpyrrolidin-2-yl)ethoxy)-6-nitroquinazolin-4-amine (1.40 g, crude) as a yellow solid. 1H NMR (400 MHz, DMSO-d6) δ=10.06 (br s, 1H), 9.20 (s, 1H), 8.64-8.58 (m, 2H), 8.02 (d, J=2.4 Hz, 1H), 7.89 (td, J=7.6, 1.6 Hz, 1H), 7.70 (dd, J=9.0, 2.4 Hz, 1H), 7.59 (d, J=7.8 Hz, 1H), 7.46 (s, 1H), 7.38 (dd, J=7.0, 5.0 Hz, 1H), 7.29 (d, J=9.0 Hz, 1H), 5.30 (s, 2 H), 4.34 (br t, J=5.8 Hz, 2H), 3.01-2.92 (m, 1H), 2.24 (s, 3H), 2.23-2.18 (m, 1H), 2.17-2.04 (m, 2H), 1.99-1.86 (m, 1H), 1.77-1.44 (m, 4H). MS (ESI) m/z 535.3 [M+H]+

To a solution of N-(3-chloro-4-(pyridin-2-ylmethoxy)phenyl)-7-(2-(1-methylpyrrolidin-2-yl)ethoxy)-6-nitroquinazolin-4-amine (1.40 g, 2.62 mmol, 1.00 eq) and ammonium chloride (1.26 g, 23.6 mmol, 823 uL, 9.00 eq) in methanol (40.0 mL) and water (10.0 mL) was added iron powder (1.02 g, 18.3 mmol, 7.00 eq) in portions. The mixture was stirred at 80° C. for 2 h. The mixture was added methanol (200 mL) and filtered. The filtrate was concentrated to give crude product. The crude product was purified by reverse-phase chromatography (FA-MeCN) and lyophilized to give N4-(3-chloro-4-(pyridin-2-ylmethoxy)phenyl)-7-(2-(1-methylpyrrolidin-2-yl)ethoxy)quinazoline-4,6-diamine (1.00 g, 1.98 mmol, 76% yield) as a yellow solid. 1H NMR (400 MHz, DMSO-d6) δ=9.48 (br s, 1H), 8.62-8.57 (m, 1H), 8.38 (s, 1H), 8.15 (s, 1H), 8.03 (d, J=2.6 Hz, 1H), 7.89 (td, J=7.8, 1.8 Hz, 1H), 7.69 (dd, J=9.0, 2.6 Hz, 1H), 7.59 (d, J=7.8 Hz, 1H), 7.44 (s, 1H), 7.40-7.34 (m, 1H), 7.24 (d, J=9.2 Hz, 1H), 7.13 (s, 1H), 5.48 (br s, 2H), 5.28 (s, 2H), 4.34 (dt, J=10.2, 5.2 Hz, 1H), 4.26-4.18 (m, 1H), 3.59 (br s, 2H), 3.07 (br s, 2H), 2.84 (s, 3H), 2.35-2.23 (m, 1H), 2.15 (br s, 1H), 2.07-1.91 (m, 2H), 1.80 (br s, 1H). MS (ESI) m/z 505.3 [M+H]+

To a solution of N4-(3-chloro-4-(pyridin-2-ylmethoxy)phenyl)-7-(2-(1-methylpyrrolidin-2-yl)ethoxy)quinazoline-4,6-diamine (300 mg, 594 umol, 1.00 eq), acrylic acid (64.2 mg, 891 umol, 61.2 uL, 1.50 eq) and pyridine (141 mg, 1.78 mmol, 144 uL, 3.00 eq) in dimethyl formamide (3.00 mL) was added 1-(3-dimethylaminopropyl)-3-ethylcarbodiimide hydrochloride (456 mg, 2.38 mmol, 4.00 eq) in portions at 20° C. The mixture was stirred at 20° C. for 1 h. The mixture was filtered. The filtrate was purified by prep-HPLC (column: Phenomenex Gemini 150*25 mm*10 um; mobile phase: [water(10 mM NH4HCO3)-ACN]; B%: 40%-70%, 10 min) and lyophilized to give N-(4-((3-chloro-4-(pyridin-2-ylmethoxy)phenyl)amino)-7-(2-(1-methylpyrrolidin-2-yl)ethoxy)quinazolin-6-yl)acrylamide 95 (100.54 mg, 178 umol, 30% yield, 99% purity) as a yellow solid. 1H NMR (400 MHz, DMSO-d6) δ=9.01 (s, 1H), 8.56 (s, 1H), 8.53 (d, J=4.8 Hz, 1H), 8.27 (s, 1H), 7.82 (d, J=2.6 Hz, 1H), 7.72-7.66 (m, 1H), 7.64-7.58 (m, 2H), 7.45 (dd, J=9.0, 2.6 Hz, 1H), 7.19-7.14 (m, 2H), 6.94 (d, J=9.0 Hz, 1H), 6.47-6.39 (m, 1H), 6.32-6.22 (m, 1H), 5.80 (d, J=11.0 Hz, 1H), 5.23 (s, 2H), 4.23 (t, J=6.4 Hz, 2H), 3.13-3.03 (m, 1H), 2.33 (s, 3H), 2.31-2.10 (m, 4H), 2.04-1.95 (m, 1H), 1.94-1.81 (m, 2H), 1.59-1.52 (m, 1H), MS (ESI) m/z 559.3 [M+H]+

96: To a solution of N-(3-chloro-4-(pyridin-2-ylmethoxy)phenyl)-7-fluoro-6-nitroquinazolin-4-amine (800 mg, 1.88 mmol, 1.00 eq) and (S)-(1-methylpyrrolidin-2-yl)methanol (325 mg, 2.82 mmol, 339 uL, 1.50 eq) in dimethyl sulfoxide (15.0 mL) was added potassium tert-butoxide (632 mg, 5.64 mmol, 3.00 eq) in portions at 0° C. The mixture was stirred at 25° C. for 2 h. The reaction mixture was diluted with water (50 mL) and filtered. The filter cake was dried to give (S)-N-(3-chloro-4-(pyridin-2-ylmethoxy)phenyl)-7-((1-methylpyrrolidin-2-yl)methoxy)-6-nitroquinazolin-4-amine (800 mg, crude) as a yellow solid. 1H NMR (400 MHz, CDCl3) δ=8.74 (s, 1H), 8.62 (br d, J=4.2 Hz, 1H), 8.53 (s, 1H), 7.88 (d, J=2.4 Hz, 1H), 7.83-7.73 (m, 1H), 7.68 (br d, J=7.8 Hz, 1H), 7.54 (br s, 1H), 7.48 (dd, J=8.8, 2.6 Hz, 1H), 7.41 (s, 1H), 7.26 (br s, 1H), 7.05 (d, J=9.0 Hz, 1H), 5.47-5.16 (m, 2H), 4.29-4.09 (m, 2H), 3.15 (br t, J=8.0 Hz, 1H), 2.92-2.76 (m, 1H), 2.53 (s, 3H), 2.44-2.30 (m, 1H), 1.98-1.66 (m, 4H).

A mixture of (S)-N-(3-chloro-4-(pyridin-2-ylmethoxy)phenyl)-7-((1-methylpyrrolidin-2-yl)methoxy)-6-nitroquinazolin-4-amine (400 mg, 768 umol, 1.00 eq), iron powder (214 mg, 3.84 mmol, 5.00 eq), ammonium chloride (205 mg, 3.84 mmol, 134 uL, 5.00 eq) in methanol (20.0 mL) and water (10.0 mL) was stirred at 80° C. for 1.5 h under nitrogen atmosphere. The reaction mixture was concentrated under reduced pressure to remove solvent. The residue was triturated with water (50 mL) and filtered. The filter cake was washed with methanol. The filtrate was concentrated under reduced pressure to give (S)-N4-(3-chloro-4-(pyridin-2-ylmethoxy)phenyl)-7-((1-methylpyrrolidin-2-yl)methoxy)quinazoline-4,6-diamine (200 mg, crude) as a yellow solid. MS (ESI) m/z 491.4 [M+H]+

To a solution of (S)-N4-(3-chloro-4-(pyridin-2-ylmethoxy)phenyl)-7-((1-methylpyrrolidin-2-yl)methoxy)quinazoline-4,6-diamine (170 mg, 346 umol, 1.00 eq) and triethylamine (70.1 mg, 692 umol, 96.4 uL, 2.00 eq) in dimethyl formamide (4.00 mL) was added acrylic anhydride (56.8 mg, 450 umol, 1.30 eq) dropwise at 25° C. The mixture was stirred at 25° C. for 0.5 h. The reaction mixture was filtered. The filtrate was purified by prep-HPLC (column: Xtimate C18 150*25 mm*5 um; mobile phase: [water (0.05% ammonia hydroxide v/v)-ACN]; B%: 37%-67%, 10 min) to give (S)-N-(4-((3-chloro-4-(pyridin-2-ylmethoxy)phenyl)amino)-7-((1-methylpyrrolidin-2-ylmethoxy)quinazolin-6-yl)acrylamide 96 (124.49 mg, 228 umol, 65% yield, 100% purity, 99% ee) as a yellow solid. 1H NMR (400 MHz, CDCl3) δ=9.11 (s, 1H), 8.86 (br s, 1H), 8.65 (s, 1H), 8.62 (d, J=5.0 Hz, 1H), 7.90 (d, J=2.8 Hz, 1H), 7.82-7.74 (m, 1H), 7.71-7.65 (m, 1H), 7.58 (s, 1H), 7.52 (dd, J=8.8, 2.6 Hz, 1H), 7.31 (s, 1H), 7.26 (br d, J=6.8 Hz, 1H), 7.02 (d, J=9.0 Hz, 1H), 6.56-6.45 (m, 1H), 6.44-6.31 (m, 1H), 5.86 (d, J=11.2 Hz, 1H), 5.32 (s, 2H), 4.50-4.39 (m, 2H), 3.19 (br d, J=7.4 Hz, 1H), 2.79 (br s, 1H), 2.51 (s, 3H), 2.46-2.36 (m, 1H), 2.16-2.02. (m, 1H), 1.98-1.92 (m, 3H). MS (ESI) m/z 545.4 [M+H]+

97: A mixture of 2,3-dichloro-5-nitropyridine (1.50 g, 7.77 mmol, 1.00 eq), pyridin-2-ylmethanamine (1.01 g, 9.33 mmol, 951 uL, 1.20 eq) in acetonitrile (30.0 mL) was stirred at 25° C. for 4 h under nitrogen atmosphere. The reaction mixture was concentrated under reduced pressure to give a residue. The residue was purified by flash silica gel chromatography (ISCO®; 20 g SepaFlash Silica Flash Column, Eluent of 0~1% Ethyl acetate/Petroleum ether gradient @ 60 mL/min) to give 3-chloro-5-nitro-N-(pyridin-2-ylmethyl)pyridin-2-amine (1.50 g, 5.67 mmol, 73% yield) as a white solid. 1H NMR (400 MHz, DMSO-d6) δ=8.87 (d, J=2.2 Hz, 1H), 8.52 (br d, J=4.8 Hz, 2H), 8.43 (d, J=2.4 Hz, 1H), 7.74 (td, J=7.6, 1.6 Hz, 1H), 7.40-7.14 (m, 2H), 4.82 (d, J=6.0 Hz, 2H).

A mixture of 3-chloro-5-nitro-N-(pyridin-2-ylmethyl)pyridin-2-amine (1.20 g, 4.53 mmol, 1.00 eq), iron powder (1.27 g, 22.7 mmol, 5.00 eq) and ammonium chloride (1.21 g, 22.7 mmol, 793 uL, 5.00 eq) in methanol (10.0 mL) and water (5.00 mL) was stirred at 80° C. for 2 h under nitrogen atmosphere. The reaction mixture was concentrated under reduced pressure to remove solvent to give a residue. The residue was purified by flash silica gel chromatography (ISCO®; 12 g SepaFlash® Silica Flash Column, Eluent of 40~100% Ethyl acetate/Petroleum ether gradient @ 50 mL/min) to give 3-chloro-N2-(pyridin-2-ylmethyl)pyridine-2,5-diamine (500 mg, 2.13 mmol, 47% yield) as an off-white solid. 1H NMR (400 MHz, DMSO-d6) δ=8.50 (d, J=4.2 Hz, 1H), 7.70 (td, J=7.8, 1.8 Hz, 1H), 7.43 (d, J=2.4 Hz, 1H), 7.32-7.18 (m, 2 H), 7.05 (d, J=2.4 Hz, 1H), 6.22 (t, J=5.8 Hz, 1H), 4.59 (br s, 2H), 4.55 (d, J=5.8 Hz, 2H).

A mixture of 4-chloro-7-fluoro-6-nitroquinazoline (400 mg, 1.76 mmol, 1.00 eq), 3-chloro-N2-(pyridin-2-ylmethyl)pyridine-2,5-diamine (495 mg, 2.11 mmol, 1.20 eq) in isopropanol (30.0 mL) was stirred at 80° C. for 2 h under nitrogen atmosphere. The reaction mixture was concentrated under reduced pressure to remove solvent to give 3-chloro-N5-(7-fluoro-6-nitroquinazolin-4-yl)-N2-(pyridin-2-ylmethyl)pyridine-2,5-diamine (750 mg, crude) as a yellow solid. MS (ESI) m/z 426.0 [M+H]+

To a solution of 2-morpholinoethanol (555 mg, 4.23 mmol, 518 uL, 3.00 eq) in tetrahydrofuran (15.0 mL) was added sodium hydrogen (338 mg, 8.45 mmol, 60% purity, 6.00 eq) at 0° C. and the mixture was stirred for 0.5 h. Then The mixture was added 3-chloro-N5-(7-fluoro-6-nitroquinazolin-4-yl)-N2-(pyridin-2-ylmethyl)pyridine-2,5-diamine (600 mg, 1.41 mmol, 1.00 eq) in tetrahydrofuran (5.00 mL) dropwise at 0° C. The mixture was stirred at 0° C. for 2 h. The reaction mixture was quenched by water (5.0 mL) at 0° C., then diluted with water (40 mL) and extracted with ethyl acetate (3×20 mL). The combined organic layers were washed with brine (3×20 mL), dried over sodium sulfate, filtered and concentrated under reduced pressure to give 3-chloro-N5-(7-(2-morpholinoethoxy)-6-nitroquinazolin-4-yl)-N2-(pyridin-2-ylmethyl)pyridine-2,5-diamine (750 mg, crude) as a yellow solid. 1H NMR (400 MHz, CDCl3) δ=8.84 (s, 1H), 8.78-8.70 (m, 1H), 8.68-8.64 (m, 1H), 8.56 (br d, J=4.4 Hz, 1H), 8.08 (d, J=2.0 Hz, 1H), 8.01 (d, J=2.2 Hz, 1H), 7.72-7.66 (m, 1H), 7.38-7.32 (m, 2H), 7.24-7.18 (m, 1H), 6.22 (br t, J=5.2 Hz, 1H), 4.89-4.77 (m, 1H), 4.89-4.77 (m, 1H), 4.36 (t, J=5.4 Hz, 2H) 3.78-3.72 (m, 4H), 2.99-2.85 (m, 2H), 2.70-2.59 (m, 4H).

A mixture of 3-chloro-N5-(7-(2-morpholinoethoxy)-6-nitroquinazolin-4-yl)-N2-(pyridin-2-ylmethyl)pyridine-2,5-diamine (400 mg, 745 umol, 1.00 eq), iron powder (208 mg, 3.72 mmol, 5.00 eq), ammonium chloride (199 mg, 3.72 mmol, 130 uL, 5.00 eq) in methanol (20.0 mL) and water (5.00 mL) was stirred at 80° C. for 2 h under nitrogen atmosphere. The reaction mixture was concentrated under reduced pressure to remove solvent. The residue was triturated with water (50 mL) and filtered. The filter cake was dissolved in methanol (100 mL) and filtered. The filtrate was concentrated under reduced pressure to give N4-(5-chloro-6-((pyridin-2-ylmethyl)amino)pyridin-3-yl)-7-(2-morpholinoethoxy)quinazoline-4,6-diamine (200 mg, crude) as a brown solid. MS (ESI) m/z 507.4 [M+H]+

To a solution of N4-(5-chloro-6-((pyridin-2-ylmethyl)amino)pyridin-3-yl)-7-(2-morpholinoethoxy)quinazoline-4,6-diamine (200 mg, 395 umol, 1.00 eq) and triethylamine (79.8 mg, 789 umol, 109 uL, 2.00 eq) in dimethyl formamide (3.00 mL) was added acrylic anhydride (64.7 mg, 512 umol, 1.30 eq) dropwise at 25° C. Then the mixture was stirred at 25° C. for 0.5 h. The reaction mixture was filtered. The filtrate was purified by prep-HPLC (column: Xtimate C18 50*25 mm*5 um; mobile phase: [water (0.05% ammonia hydroxide v/v)-ACN]; B%: 27%-57%, 10 min) and lyophilized to give N-(4-((5-chloro-6-((pyridin-2-ylmethyl)amino)pyridin-3-yl)amino)-7-(2-morpholinoethoxy)quinazolin-6-yl)acrylamide 97 (49.00 mg, 82.1 umol, 2.1% yield, 94% purity) as a yellow solid. 1H NMR (400 MHz, CDCl3) δ=9.11 (s, 1H), 8.84 (s, 1H), 8.62 (br d, J=4.2 Hz, 1H), 8.59 (s, 1H), 8.23 (d, J=2.4 Hz, 1H), 8.01 (d, J=2.4 Hz, 1H), 7.83 (s, 1H), 7.68 (td, J=7.8, 1.8 Hz, 1H), 7.36 (d, J=8.0 Hz, 1H), 7.26 (s, 1H), 7.22 (dd, J=6.8, 5.2 Hz, 1H), 6.59-6.35 (m, 2H), 6.23 (t, J=5.0 Hz, 1H), 6.07-5.79 (m, 1H), 4.82 (d, J=5.2 Hz, 2 H), 4.35 (t, J=5.4 Hz, 2H), 3.84-3.72 (m, 4H), 2.93 (t, J=5.4 Hz, 2H), 2.65-2.54 (m, 4H). MS (ESI) m/z 561.4 [M+H]+

98: A mixture of N-(3-chloro-4-(pyridin-2-ylmethoxy)phenyl)-7-fluoro-6-nitroquinazolin-4-amine (2.00 g, 4.70 mmol, 1.00 eq), cyclopropane-1,1-diyldimethanol (959 mg, 9.39 mmol, 2.00 eq) and potassium tert-butoxide (2.11 g, 18.8 mmol, 4.00 eq) in dimethylsulfoxide (20.0 mL) was stirred at 25° C. for 1 h. To the mixture was added water (20.0 mL). The mixture was filtered. The filter cake was dried to give (1-(((4-((3-chloro-4-(pyridin-2-ylmethoxy)phenyl)amino)-6-nitroquinazolin-7-yl)oxy)methyl)cyclopropyl)methanol (2.10 g, 4.13 mmol, 88% yield) as a yellow solid. 1H NMR (400 MHz, DMSO-d6) δ=10.07 (br s, 1H), 9.21 (s, 1H), 8.61 (br s, 2H), 8.08-7.97 (m, 1H), 7.89 (br t, J=7.3 Hz, 1H), 7.70 (br d, J=8.7 Hz, 1H), 7.59 (br d, J=7.6 Hz, 1H), 7.45-7.35 (m, 2H), 7.29 (br d, J=8.9 Hz, 1H), 5.30 (s, 2H), 4.78-4.57 (m, 1H), 4.21 (s, 2H), 3.44 (br d, J=5.0 Hz, 2H), 0.57 (br d, J=3.4 Hz, 4H). MS (ESI) m/z 508.0 [M+H]+

The mixture of (1-(((4-((3-chloro-4-(pyridin-2-ylmethoxy)phenyl)amino)-6-nitroquinazolin-7-yl)oxy)methyl)cyclopropyl)methanol (2.00 g, 3.94 mmol, 1.00 eq) and sulfurous dichloride (3.28 g, 27.6 mmol, 2.00 mL, 7.00 eq) in tetrahydrofuran (20.0 mL) and dichloromethane (20.0 mL) was stirred at 50° C. for 2 h. The reaction mixture was concentrated to give a residue. The residue was triturated with ethyl acetate (20.0 mL) to give N-(3-chloro-4-(pyridin-2-ylmethoxy)phenyl)-7-((1-(chloromethyl)cyclopropyl)methoxy)-6-nitroquinazolin-4-amine (2.00 g, 3.80 mmol, 96% yield) as a yellow solid. 1H NMR (400 MHz, DMSO-d6) δ=9.61 (s, 1H), 8.92 (s, 1H), 8.70 (d, J=4.4 Hz, 1H), 8.10-8.05 (m, 1H), 7.95 (d, J=2.6 Hz, 1H), 7.73 (d, J=7.9 Hz, 1H), 7.67 (br dd, J=2.5, 8.9 Hz, 1H), 7.62 (s, 1H), 7.55 (dd, J=5.4, 7.0 Hz, 1H), 7.38 (d, J=9.2 Hz, 1H), 5.42 (s, 2H), 4.31 (s, 2H), 3.86-3.64 (m, 2H), 0.94-0.76 (m, 4H). MS (ESI) m/z 526.0 [M+H]+

A mixture of N-(3-chloro-4-(pyridin-2-ylmethoxy)phenyl)-7-((1-(chloromethyl)cyclopropyl)methoxy)-6-nitroquinazolin-4-amine (1.00 g, 1.90 mmol, 1.00 eq), dimethylamine (171 mg, 3.80 mmol, 2.00 eq), potassium carbonate (1.05 g, 7.60 mmol, 4.00 eq) and potassium iodide (315 mg, 1.90 mmol, 1.00 eq) in acetonitrile (20.0 mL) was stirred at 110° C. for 12 h. The reaction mixture was concentrated to give a residue. The residue was triturated with water (20.0 mL) to give N-(3-chloro-4-(pyridin-2-ylmethoxy)phenyl)-7-((1-((dimethylamino)methyl)cyclopropyl)methoxy)-6-nitroquinazolin-4-amine (950 mg, 1.78 mmol, 93% yield) as a yellow solid. 1H NMR (400 MHz, DMSO-d6) δ=9.04 (s, 1H), 8.53 (br d, J=4.3 Hz, 1H), 8.40 (s, 1H), 7.86 (d, J=2.2 Hz, 1H), 7.83-7.79 (m, 1H), 7.52 (br d, J=7.6 Hz, 2H), 7.29 (br d, J=7.0 Hz, 1H), 7.22 (s, 1H), 7.16 (br d, J=8.9 Hz, 1H), 5.21 (s, 2H), 4.07 (s, 2H), 2.18 (s, 2H), 2.09 (s, 6H), 0.58 (s, 2H), 0.42-0.31 (m, 2H). MS (ESI) m/z 535.2 [M+H]+

A mixture of N-(3-chloro-4-(pyridin-2-ylmethoxy)phenyl)-7-((1-((dimethylamino)methyl)cyclopropyl)methoxy)-6-nitroquinazolin-4-amine (800 mg, 1.50 mmol, 1.00 eq), iron (417 mg, 7.48 mmol, 5.00 eq) and ammonium chloride (399 mg, 7.48 mmol, 5.00 eq) in methanol (10.0 mL) and water (10.0 mL) was stirred at 80° C. for 2 h. To the mixture was added methanol (40.0 mL). The mixture was filtered. The filtrate was concentrated to give a residue. The residue was triturated with saturated sodium carbonate (20.0 mL) to give N4-(3-chloro-4-(pyridin-2-ylmethoxy)phenyl)-7-((1-((dimethylamino)methyl)cyclopropyl)methoxy)quinazoline-4,6-diamine (600 mg, crude) as a yellow solid. MS (ESI) m/z 505.2 [M+H]+

To a solution of N4-(3-chloro-4-(pyridin-2-ylmethoxy)phenyl)-7-((1-((dimethylamino)methyl)cyclopropyl)methoxy)quinazoline-4,6-diamine (300 mg, 594 umol, 1.00 eq), pyridine (188 mg, 2.38 mmol, 4.00 eq) and acrylic acid (51.4 mg, 713 umol, 1.20 eq) in dimethyl formamide (3.00 mL) was added 1-(3-dimethylaminopropyl)-3-ethylcarbodiimide (455 mg, 2.38 mmol, 4.00 eq) at 25° C. The mixture was stirred at 25° C. for 0.5 h. The reaction mixture was filtered. The filtrate was purified by prep-HPLC {column: Xtimate C18 150*25 mm*5 um; mobile phase: [water (0.05% ammonia hydroxide v/v)-ACN]; B%: 43%-73%, 10 min} and lyophilized to give N-(4-((3-chloro-4-(pyridin-2-ylmethoxy)phenyl)amino)-7-((1-((dimethylamino)methyl)cyclopropyl)methoxy)quinazolin-6-yl)acrylamide 98 (82.51 mg, 144 umol, 24% yield, 98% purity) as a green solid. 1H NMR (400 MHz, DMSO-d6) δ=9.67 (s, 1H), 9.52 (s, 1H), 8.77 (s, 1H), 8.67-8.56 (m, 1H), 8.50 (s, 1H), 8.01 (d, J=2.6 Hz, 1H), 7.89 (dt, J=1.8, 7.7 Hz, 1H), 7.71 (dd, J=2.6, 9.0

Hz, 1H), 7.60 (d, J=7.8 Hz, 1H), 7.38 (dd, J=5.4, 7.0 Hz, 1H), 7.31-7.21 (m, 2H), 6.66 (br dd, J=10.3, 16.9 Hz, 1H), 6.32 (dd, J=2.0, 17.0 Hz, 1H), 5.83 (dd, J=1.9, 10.2 Hz, 1H), 5.29 (s, 2H), 4.10 (s, 2H), 2.29 (s, 2H), 2.18 (s, 6H), 0.74-0.62 (m, 2H), 0.52-0.36 (m, 2H). MS (ESI) m/z 559.4 [M+H]+

99: To a solution of N-(3-chloro-4-(pyridin-2-ylmethoxy)phenyl)-7-fluoro-6-nitroquinazolin-4-amine (1.30 g, 3.05 mmol, 1.00 eq) and 1-methylazepan-4-ol (789 mg, 6.11 mmol, 2.00 eq) in dimethylsulfoxide (10.0 mL) was added potassium tert-butoxide (1.03 g, 9.16 mmol, 3.00 eq) in portions at 20° C. The mixture was stirred at 20° C. for 12 h. The reaction mixture was added water (50 mL) and filtered. The filter cake was dried to give N-(3-chloro-4-(pyridin-2-ylmethoxy)phenyl)-7-((1-methylazepan-4-yl)oxy)-6-nitroquinazolin-4-amine (1.60 g, crude) as a yellow solid. MS (EST) m/z 535.3 [M+H]+

To a solution of N-(3-chloro-4-(pyridin-2-ylmethoxy)phenyl)-7-((1-methylazepan-4-yl)oxy)-6-nitroquinazolin-4-amine (1.60 g, 2.99 mmol, 1.00 eq) and ammonium chloride (1.44 g, 26.9 mmol, 941 uL, 9.00 eq) in methanol (40.0 mL) and water (10.0 mL) was added iron powder (1.17 g, 20.9 mmol, 7.00 eq) in portions. The mixture was stirred at 80° C. for 2 h. The mixture was added methanol (50 mL) and filtered. The filtrate was concentrated to give the residue. The residue was purified by prep-HPLC (column: Kromasil 250*50 mm*10 um; mobile phase: [water(0.1%TFA)-ACN]; B%: 12 ACN %-42 ACN %,25 min, 45% min) and lyophilized to give N4-(3-chloro-4-(pyridin-2-ylmethoxy)phenyl)-7-((1-methylazepan-4-yl)oxy)quinazoline-4,6-diamine (350 mg, 693 umol, 23% yield) as a yellow solid. 1H NMR (400 MHz, MeOD) δ=8.71 (br s, 1H), 8.57 (s, 1H), 8.28-8.14 (m, 1H), 7.98-7.90 (m, 1H), 7.89 (d, J=2.6 Hz, 1H), 7.73-7.58 (m, 2H), 7.52 (s, 1H), 7.29-7.23 (m, 2H), 5.42 (s, 2H), 5.10 (br s, 1H), 3.79-3.59 (m, 2H), 3.56-3.44 (m, 1H), 3.25 (br d, J=7.1 Hz, 1H), 2.99 (s, 3H), 2.53-2.37 (m, 2H), 2.35-2.08 (m, 3H), 1.98 (br s, 1H). MS (ESI) m/z 505.4 [M+H]+

To a solution of N4-(3-chloro-4-(pyridin-2-ylmethoxy)phenyl)-7-((1-methylazepan-4-yl)oxy)quinazoline-4,6-diamine (300 mg, 594 umol, 1.00 eq) and triethylamine (180 mg, 1.78 mmol, 248 uL, 3.00 eq) in dimethyl formamide (3.00 mL) was added acrylic anhydride (97.4 mg, 772 umol, 1.30 eq) dropwise at 20° C. The mixture was stirred at 20° C. for 1 h. The mixture was filtered and the filtrate was purified by prep-HPLC (column: Phenomenex Synergi C18 150*30 mm*4 um; mobile phase: [water(0.225%FA)-ACN]; B%: 5%-35%, 10 min) and lyophilized to give N-(4-((3-chloro-4-(pyridin-2-ylmethoxy)phenyl)amino)-7-((1-methylazepan-4-yl)oxy)quinazolin-6-yl)acrylamide 99 (17.34 mg, 28.4 umol, 5% yield, 99% purity, as a yellow solid. 1H NMR (400 MHz, MeOD) δ=8.79 (s, 1H), 8.58 (br d, J=4.2 Hz, 2H), 8.45 (s, 1H), 7.97-7.87 (m, 2H), 7.74 (d, J=8.0 Hz, 1H), 7.58 (dd, J=8.8, 2.6 Hz, 1H), 7.41 (dd, J=6.8, 5.2 Hz, 1H), 7.19 (s, 1H), 7.16 (d, J=9.0 Hz, 1H), 6.72-6.62 (m, 1H), 6.53-6.43 (m, 1H), 5.95-5.85 (m, 1H), 5.28 (s, 2H), 5.04-4.96 (m, 1H), 3.28-3.20 (m, 1H), 3.17-2.96 (m, 3H), 2.69 (s, 3H), 2.45-2.34 (m, 1H), 2.33-2.21 (m, 2H), 2.19-2.11 (m, 1H) 2.09-1.98 (m, 1H), 1.92-1.79 (m, 1H). MS (ESI) m/z 559.3 [M+H]+

100: To a solution of tert-butyl nitrite (10.0 g, 79.3 mmol, 11.5 mL, 1.00 eq) in acetonitrile (100 mL) was added 5-fluoro-2-methylphenol (9.81 g, 95.1 mmol, 1.20 eq) at 25° C. The mixture was stirred at 25° C. for 12 h. The mixture was quenched with 5% aqueous solution of sodium thiosulfate (50.0 mL) and extracted with ethyl acetate (200 mL). The organic layer was washed with water (200 mL), dried over sodium sulfate, filtered and the filtrate was concentrated to afford a residue. The residue was purified by silica gel chromatography (petroleum ether/ethyl acetate=1/0 to 3/1) to give 5-fluoro-2-methyl-4-nitrophenol (4.00 g, crude) as a brown solid. 1H NMR (400 MHz, CDCl3) δ=7.94 (d, J=8.4 Hz, 1H), 6.66 (d, J=11.6 Hz, 1H), 5.63 (s, 1H), 2.27 (s, 3H).

A mixture of 5-fluoro-2-methyl-4-nitrophenol (4.00 g, 23.4 mmol, 1.00 eq), 2-(chloromethyl)pyridine (7.67 g, 46.8 mmol, 2.00 eq, HCl) and potassium carbonate (25.8 g, 187 mmol, 8.00 eq) in acetonitrile (100 mL) was stirred at 90° C. for 1 h. The reaction was filtered and the filter cake was washed with ethyl acetate (100 mL). The filtrate was concentrated to afford a residue. The residue was purified by silica gel chromatography (petroleum ether/ethyl acetate=1/0 to 3/1) to give 2-((5-fluoro-2-methyl-4-nitrophenoxy)methyl)pyridine (1.20 g, 4.58 mmol, 20% yield) as a yellow solid. 1H NMR (400 MHz, CDCl3) δ=8.67-8.60 (m, 1H), 7.95 (dd, J=0.7, 8.4 Hz, 1H), 7.76 (dt, J=1.8, 7.7 Hz, 1H), 7.47 (d, J=7.8 Hz, 1H), 7.31-7.27 (m, 1H), 6.76 (d, J=12.7 Hz, 1H), 5.27 (s, 2H), 2.32 (s, 3H).

To a solution of 2-((5-fluoro-2-methyl-4-nitrophenoxy)methyl)pyridine (1.10 g, 4.19 mmol, 1.00 eq) in ethanol (10.0 mL) was added water (3.00 mL), ammonium chloride (1.12 g, 21.0 mmol, 5.00 eq) and iron powder (703 mg, 12.6 mmol, 3.00 eq). The reaction mixture was stirred at 80° C. for 1 h. The reaction mixture was filtered. The filtrate was concentrated in vacuo. To the residue was added water (30.0 mL) and extracted with ethyl acetate (3×50.0 mL). The combined organic layer was washed with brine (30.0 mL), dried over sodium sulfate, filtered and concentrated in vacuo to give 2-fluoro-5-methyl-4-(pyridin-2-ylmethoxy)aniline (900 mg, 3.88 mmol, 92% yield) as a yellow solid. 1H NMR (400 MHz, DMSO) δ=8.57 (dd, J=0.8, 4.0 Hz, 1H), 7.86-7.79 (m, 1H), 7.52 (d, J=7.8 Hz, 1H), 7.37-7.27 (m, 1H), 6.77 (d, J=12.8 Hz, 1H), 6.61 (d, J=10.3 Hz, 1H), 5.04 (s, 2H), 4.56 (s, 2H), 2.10 (s, 3H).

To a solution of 4-chloro-7-fluoro-6-nitroquinazoline (490 mg, 2.15 mmol, 1.00 eq) in isopropanol (10.0 mL) was added 2-fluoro-5-methyl-4-(pyridin-2-ylmethoxy)aniline (500 mg, 2.15 mmol, 1.00 eq). The reaction mixture was stirred at 90° C. for 1 h. The reaction mixture was concentrated in vacuo to give 7-fluoro-N-(2-fluoro-5-methyl-4-(pyridin-2-ylmethoxy)phenyl)-6-nitroquinazolin-4-amine (600 mg, crude) as a yellow solid. MS (ESI) m/z 424.3 [M+H]+

To a solution of 2-morpholinoethanol (310 mg, 2.36 mmol, 2.00 eq) in tetrahydrofuran (0.500 mL) was added sodium hydride (189 mg, 4.72 mmol, 60% purity, 4.00 eq). The reaction mixture was stirred at 0° C. for 0.5 h. Then 7-fluoro-N-(2-fluoro-5-methyl-4-(pyridin-2-ylmethoxy)phenyl)-6-nitroquinazolin-4-amine (500 mg, 1.18 mmol, 1.00 eq) was added. The reaction mixture was stirred at 0° C. for 1 h. The reaction mixture was quenched with water (10.0 mL), extracted with ethyl acetate (3×10.0 mL). The combined organic layer was washed with brine (3×10 mL), dried over sodium sulfate, filtered and concentrated to give N-(2-fluoro-5-methyl-4-(pyridin-2-ylmethoxy)phenyl)-7-(2-morpholinoethoxy)-6-nitroquinazolin-4-amine (200 mg, 374 umol, 32% yield) as a pink oil. 1H NMR (400 MHz, DMSO) δ=10.00 (s, 1H), 9.15 (s, 1H), 8.63-8.57 (m, 1H), 8.49 (s, 1H), 7.89 (dt, J=1.8, 7.7 Hz, 1H), 7.60 (d, J=7.9 Hz, 1H), 7.50 (s, 1H), 7.38 (dt, J=0.9, 6.2 Hz, 1H), 7.2.9 (d, J=8.8 Hz, 1H), 7.08 (d, J=12.1 Hz, 1H), 5.26 (s, 2H), 4.43 (t, J=5.5 Hz, 2H), 3.62-3.51 (m, 4H), 3.31 (br s, 4H), 2.78 (t, J=5.5 Hz, 2H), 2.24 (s, 3H). MS (ESI) m/z 535.4 [M+H]+

To a solution of N-(2-fluoro-5-methyl-4-(pyridin-2-ylmethoxy)phenyl)-7-(2-morpholinoethoxy)-6-nitroquinazolin-4-amine (160 mg, 299 umol, 1.00 eq) in ethanol (6.00 mL) was added water (3.00 mL), iron powder (50.2 mg, 898 umol, 3.00 eq) and ammonium chloride (80.1 mg, 1.50 mmol, 5.00 eq). The reaction mixture was stirred at 80° C. for 1 h. The reaction mixture was filtered and the filtrate was concentrated in vacuo. The residue was dissolved in water (10.0 mL), extracted with ethyl acetate (2×10 mL). The combined organic layer was washed with brine (3×10 mL), dried over sodium sulfate, filtered and concentrated to give N4-(2-fluoro-5-methyl-4-(pyridin-2-ylmethoxy)phenyl)-7-(2-morpholinoethoxy)quinazoline-4,6-diamine (130 mg, 258 umol, 86% yield) as a yellow oil. 1H NMR (400 MHz, CDCl3) δ=8.61 (br d, J=4.4 Hz, 1H), 8.55 (s, 1H), 8.07 (d, J=9.2 Hz, 1H), 7.74 (dt, J=1.6, 7.7 Hz, 1H), 7.54 (d, J=7.8 Hz, 1H), 7.26-7.20 (m, 1H), 7.17 (s, 1H), 7.01 (br s, 1H), 6.95 (s, 1H), 6.73 (d, J=12.3 Hz, 1H), 5.19 (s, 2H), 4.48-4.18 (m, 4H), 3.80-3.68 (m, 4H), 2.90 (t, J=5.6 Hz, 2H), 2.66-2.55 (m, 4H), 2.34 (s, 3H).

To a solution of N4-(2-fluoro-5-methyl-4-(pyridin-2-ylmethoxy)phenyl)-7-(2-morpholinoethoxy)quinazoline-4,6-diamine (100 mg, 198 umol, 1.00 eq) in dimethyformamide (0.500 mL) was added acrylic acid (0.500 M solution in dimethyformamide, 595 uL, 1.50 eq), 1-(3-dimethylaminopropyl)-3-ethylcarbodiimide hydrochloride (57.0 mg, 297 umol, 1.50 eq) and pyridine (47.0 mg, 595 umol, 3.00 eq). The reaction mixture was stirred at 20° C. for 1 h. The reaction mixture was filtered. The filtrate was purified by Prep-HPLC (column: Phenomenex Synergi C18 150*25*10 um; mobile phase: [water(0.225%FA)-ACN]; B%: 6%-30%, 8 min) and lyophilized to give N-(4-((2-fluoro-5-methyl-4-(pyridin-2-ylmethoxy)phenyl)amino)-7-(2-morpholinoethoxy)quinazolin-6-yl)acrylamide 100 (68.86 mg, 123.27 umol, 62% yield, 100% purity) as a yellow solid. 1H NMR (400 MHz, DMSO-d6) δ=9.61 (s, 1H), 9.53 (s, 1H), 8.82 (s, 1H), 8.61 (dd, J=0.7, 4.8 Hz, 1H), 8.33 (s, 1H), 7.89 (dt, J=1.8, 7.7 Hz, 1H), 7.59 (d, J=7.8 Hz, 1H), 7.41-7.35 (m, 1H), 7.29 (s, 1H), 7.23 (d, J=8.8 Hz, 1H), 7.04 (d, J=12.2 Hz, 1H), 6.69 (dd, J=10.1, 17.0 Hz, 1H), 6.30 (dd, J=1.8, 17.0 Hz, 1H), 5.86-5.72 (m, 1H), 5.24 (s, 2H), 4.34 (t, J=5.7 Hz, 2H), 3.61-3.52 (m, 4H), 2.83 (t, J=5.7 Hz, 2H), 2.54-2.51 (m, 4H), 2.23 (s, 3H). MS (ESI) m/z 559.4 [M+H]+.

101: To a solution of 1-methylpyrrolidine-3-carboxylic acid (1.00 g, 6.04 mmol, 1.00 eq, hydrochloride) in tetrahydrofuran (10.0 mL) was added borane dimethyl sulfide complex (10.0 M, 15.1 mmol, 2.50 eq) at 0° C. The mixture was stirred at 20° C. for 12 h. Saturated sodium bicarbonate (5.00 mL) was added and the resulting mixture was stirred for 0.5 h. The mixture was extracted with ethyl acetate (3×20.0 mL). The organic was washed with brine (3×20.0 mL), and dried over anhydrous sodium sulfate, filtered and concentrated to give (1-methylpyrrolidin-3-yl)methanol (0.600 g, crude) as yellow oil. 1H NMR (400 MHz, DMSO-d6) δ=4.71 (t, J=5.1 Hz, 1H), 3.44-3.33 (m, 2H), 3.15-3.06 (m, 1H), 3.04-2.94 (m, 1H), 2.83-2.73 (m, 1H), 2.59 (s, 3H), 2.57-2.52 (m, 2H), 2.11-2.00 (m, 1H), 1.67-1.60 (m, 1H).

To a solution of N-(3-chloro-4-(pyridin-2-ylmethoxy)phenyl)-7-fluoro-6-nitroquinazolin-4-amine (1.06 g, 2.48 mmol, 1.00 eq), (1-methylpyrrolidin-3-yl)methanol (0.400 g, 3.47 mmol, 1.40 eq) in dimethylsulfoxide (13.0 mL) was added potassium tert-butoxide (835 mg, 7.44 mmol, 3.00 eq). The mixture was stirred at 20° C. for 12 h. The mixture was added ice-water (30.0 mL) and stirred for 0.5 h. After filtration, the filter cake was triturated with petroleum ether (5.00 mL) to give N-(3-chloro-4-(pyridin-2-ylmethoxy)phenyl)-7-((1-methylpyrrolidin-3-yl)methoxy)-6-nitroquinazolin-4-amine (1.00 g, 1.92 mmol, 77% yield) as a yellow solid. 1H NMR (400 MHz, DMSO-d6) δ=10.10 (s, 1H), 9.29-9.22 (m, 1H), 8.64 (s, 1H), 8.61 (br d, J=4.6 Hz, 1H), 8.02 (d, J=2.6 Hz, 1H), 7.89 (dt, J=1.5, 7.7 Hz, 1H), 7.71 (dd, J=2.5, 9.0 Hz, 1H), 7.59 (d, J=7.8 Hz, 1H), 7.50-7.45 (m, 1H), 7.41-7.35 (m, 1H), 7.30 (d, J=9.0 Hz, 1H), 5.31 (s, 2H), 4.40-4.28 (m, 2H), 3.14-3.06 (m, 1H), 2.96 (br s, 1H), 2.93-2.85 (m, 1H), 2.80-2.73 (m, 1H), 2.67 (s, 3H), 2.31-2.23 (m, 1H), 1.85 (br dd, J=8.2, 13.3 Hz, 1H).

To a solution of N-(3-chloro-4-(pyridin-2-ylmethoxy)phenyl)-7-((1-methylpyrrolidin-3-yl)methoxy)-6-nitroquinazolin-4-amine (0.800 g, 1.54 mmol, 1.00 eq) in methanol (40.0 mL) were added ammonium chloride (411 mg, 7.68 mmol, 5.00 eq), iron powder (429 mg, 7.68 mmol, 5.00 eq) and water (10.0 mL). The mixture was stirred at 80° C. for 12 h. The mixture was added methanol (50.0 mL) and stirred at 55° C. for 0.5 h, then filtered. The filtrate was concentrated to afford a residue. The residue was diluted with saturated sodium bicarbonate (5.00 mL), extracted with dichloromethane/methanol (10/1, 2×20.0 mL). The organic layer was washed with water (3×20.0 mL), dried over anhydrous sodium sulfate, filtered and concentrated to give N4-(3-chloro-4-(pyridin-2-ylmethoxy)phenyl)-7-((1-methylpyrrolidin-3-yl)methoxy)quinazoline-4,6-diamine (0.600 g, 1.22 mmol, 79% yield) as a yellow solid. 1H NMR (400 MHz, DMSO-d6) δ=9.24 (s, 1H), 8.60 (dd, J=0.9, 4.0 Hz, 1H), 8.37-8.29 (m, 1H), 8.04 (d, J=2.6 Hz, 1H), 7.89 (dt, J=1.8, 7.7 Hz, 1H), 7.70 (dd, J=2.6, 9.0 Hz, 1H), 7.59 (d, J=7.8 Hz, 1H), 7.38 (s, 1H), 7.38-7.35 (m, 1H), 7.23 (d, J=9.0 Hz, 1H), 7.07 (s, 1H), 5.27 (s, 4H), 4,10-4.00 (m, 2H), 2.70-2.62 (m, 2H), 2.56-2.54 (m, 1H), 2.47-2.38 (m, 2H), 2.26 (s, 3H), 2.08-1.96 (m, 1H), 1.63-1.53 (m, 1H). MS (ESI) m/z 491.3, [M+H]+

To a solution of N4-(3-chloro-4-(pyridin-2-ylmethoxy)phenyl)-7-((1-methylpyrrolidin-3-yl)methoxy)quinazoline-4,6-diamine (0.300 g, 611 umol, 1.00 eq), 1-(3-dimethylaminopropyl)-3-ethylcarbodiimide hydrochloride (234 mg, 1.22 mmol, 2.00 eq) and pyridine (145 mg, 1.83 mmol, 3.00 eq) in N,N-dimethylformamide (1.00 mL) was added acrylic acid (0.500 M, 1.59 mL, 794 mmol, 1.30 eq). The mixture was stirred at 20° C. for 1 h. The mixture was filtered and the filtrate was purified by prep-HPLC (column: Waters Xbridge 150*25 5 u; mobile phase: [water (0.05% ammonia hydroxide v/v)-acetonitrile]; B%: 52%-82%, 10 min) to give N-(4-((3-chloro-4-(pyridin-2-ylmethoxy)phenyl)amino)-7-((1-methylpyrrolidin-3-yl)methoxy)quinazolin-6-yl)acrylamide 101 (150 mg, 276 umol, 45% yield) as a yellow solid. 1H NMR (400 MHz, DMSO-d6) δ=9.68 (s, 1H), 9.54 (s, 1H), 8.84 (s, 1H), 8.60 (d, J=4.2 Hz, 1H), 8.49 (s, 1H), 7.99 (d, J=2.6 Hz, 1H), 7.88 (dt, J=1.7, 7.7 Hz, 1H), 7.69 (dd, J=2.6, 8.9 Hz, 1H), 7.59 (d, J=7.8 Hz, 1H), 7.37 (dd, J=5.1, 6.8 Hz, 1H), 7.28-7.22 (m, 2H), 6.67 (dd, J=10.3, 17.0 Hz, 1H), 6.32 (dd, J=1.8, 17.0 Hz, 1H), 5.83 (dd, J=1.8, 10.2 Hz, 1H), 5.29 (s, 2H), 4.16-4.05 (m, 2H), 2.71-2.63 (m, 1H), 2.60-2.53 (m, 2H), 2.45-2.35 (m, 2H), 2.25 (s, 2.03-1.91 (m, 1H), 1.59 (dt, J=7.0, 12.7 Hz, 1H). MS (ESI) m/z 545.4, [M+H]+

102: A mixture of 3-hydroxypropanenitrile (10.0 g, 141 mmol, 9.52 mL, 1.00 eq), (bromomethyl)benzene (24.1 g, 141 mmol, 16.7 mL, 1.00 eq) and N,N-diisopropylethylamine (21.8 g, 169 mmol, 29.4 mL, 1.20 eq) was heated to 150° C. and stirred at 150° C. for 2 h. The mixture was cooled to room temperature and diluted with sulfuric acid (1 M, 100 mL) and ethyl acetate (100 mL). The organic layer was washed with water (100 mL), dried over sodium sulfate, filtered and the filtrate was concentrated to afford a brown oil. The brown oil was distilled under vacuum (~5 torr) and collected the distillate between 140 to 150° C. to give 3-(benzyloxy)propanenitrile (10.0 g, 62.0 mmol, 44% yield) as colorless oil. 1H NMR (400 MHz, CDCl3) δ=7.43-7.28 (m, 5H), 4.58 (s, 2H), 3.68 (t, J=6.4 Hz, 2H), 2.62 (t, J=6.4 Hz, 2H).

To a solution of 3-(benzyloxy)propanenitrile (9.00 g, 55.8 mmol, 1.00 eq) in dry tetrahydrofuran (180 mL) was added tetraisopropoxytitanium (17.5 g, 61.4 mmol, 18.1 mL, 1.10 eq) and ethylmagnesium bromide (3 M, 37.2 mL, 2.00 eq) in turn at 20° C. The mixture was stirred at 20° C. for 0.5 h before a mixture of boron trifluoride in diethyl ether (15.9 g, 112 mmol, 13.8 mL, 2.00 eq) was added in one portion. The mixture was added water (100 mL) and adjusted pH>10 with sodium hydroxide. The mixture was extracted with ethyl acetate (2×100 mL). The combined organic layers were washed with water (2×100 mL) and then added hydrochloric acid (1 M, 200 mL) in water. After separation, the aqueous phase was washed with ethyl acetate (2×100 mL) and then basified with sodium hydroxide to pH>10. The product was extracted with ethyl acetate (2×100 mL) and the combined organic phase was washed with water (100 mL), dried over sodium sulfate, filtered and concentrated to afford 1-(2-(benzyloxy)ethyl)cyclopropanamine (4.40 g, 23.0 mmol, 41% yield) as colorless oil. 1H NMR (400 MHz, CDCl3) δ=7.37-7.30 (m, 5H), 4.53 (s, 2H), 3.68 (t, J=6.3 Hz, 2H), 1.73 (t, J=6.3 Hz, 2H), 0.59-0.52 (m, 2H), 0.46-0.40 (m, 2H).

To a solution of 1-(enzyloxy)ethyl)cyclopropanamine (4.40 g, 23.0 mmol, 1.00 eq) in acetonitrile (50.0 mL) was added formaldehyde (37%, 7.47 g, 92.0 mmol, 6.85 mL, 4.00 eq) and sodium triacetoxyhydroborate (29.3 g, 138 mmol, 6.00 eq). The reaction mixture was stirred at 20° C. for 12 h. The reaction mixture was concentrated in vacuo. The residue was added sat. sodium bicarbonate (100 mL) and extracted with ethyl acetate (3×100 mL). The organic layer was washed with water (100 mL), dried over sodium sulfate, filtered and concentrated in vacuo to give 1-(2-(benzyloxy)ethyl)-N,N-dimethylcyclopropanamine (3.50 g, 16.0 mmol, 69% yield) as a yellow solid. 1H NMR (400 MHz, DMSO) δ=7.10-7.03 (m, 5H), 4.18 (s, 2H), 3.18 (t, J=7.1 Hz, 2H), 1.96 (s, 6H), 1.56-1.50 (m, 2H), 0.23-0.15 (m, 4H). MS (ESI) m/z 220.4 [M+H]+.

To a solution of 1-(2-benzyloxy)ethyl)-N,N-dimethylcyclopropanamine (1.50 g, 6.84 mmol, 1.00 eq) in methanol (20.0 mL) was added hydrochloric acid (12 M, 2.28 mL, 4.00 eq) and palladium on carbon (150 mg, 10% purity). The reaction mixture was stirred at 20° C. for 12 h under hydrogen atmosphere (15 psi). The reaction mixture was filtered and concentrated in vacuo to give 2-(1-(dimethylamino)cyclopropyl)ethanol (800 mg, 4.83 mmol, 71% yield, HCl) as yellow oil. 1H NMR (400 MHz, CD3OD) δ=3.65 (t, J=5.9 Hz, 2H), 2.97-2.86 (m, 6H), 2.07 (t, J=5.9 Hz, 2H), 1.22-1.16 (m, 2H), 1.09-1.04 (m, 2H).

To a solution of N-(3-chloro-4-(pyridin-2-ylmethoxy)phenyl)-7-fluoro-6-nitroquinazolin-4-amine (1.00 g, 2.35 mmol, 1.00 eq) in dimethylsulfoxide (20.0 mL) was added 2-(1-(dimethylamino)cyclopropyl)ethanol (778 mg, 4.70 mmol, 2.00 eq, HCl) and potassium tert-butoxide (791 mg, 7.05 mmol, 3.00 eq). The reaction mixture was stirred at 20° C. for 12 h. The reaction mixture was added water (30 mL) and filtered. The filter cake was dried in vacuo to give N-(3-chloro-4-(pyridin-2-ylmethoxy)phenyl)-7-(2-(1-(dimethylamino)cyclopropyl)ethoxy)-6-nitroquinazolin-4-amine (1.20 g, 2.24 mmol, 96% yield) as a yellow solid. 1H NMR (400 MHz, DMSO) δ=10.02 (br s, 1H), 9.16 (s, 1H), 8.63-8.54 (m, 1H), 7.99 (br d, J=2.1 Hz, 1H), 7.92-7.81 (m, 1H), 7.67 (br d, J=8.8 Hz, 1H), 7.58 (br d, J=7.7 Hz, 1H), 7.42 (br s, 1H), 7.39-7.33 (m, 1H), 7.27 (br d, J=8.9 Hz, 1H), 5.29 (s, 2H), 4.28 (br d, J=5.9 Hz, 2H), 2.26 (s, 6H), 2.00 (br t, J=6.4 Hz, 2H), 0.59-0.53 (m, 2H), 0.52-0.44 (m, 2H).

To a solution of N-(3-chloro-4-(pyridin-2-ylmethoxy)phenyl)-7-(2-(1-(dimethylamino)cyclopropyl)ethoxy)-6-nitroquinazolin-4-amine (1.10 g, 2.06 mmol, 1.00 eq) in ethanol (20.0 mL) was added water (10.0 mL), ammonium chloride (550 mg, 10.3 mmol, 5.00 eq) and iron powder (344 mg, 6.17 mmol, 3.00 eq). The reaction mixture was stirred at 80° C. for 2 h. The reaction mixture was filtered and concentrated in vacuo. To the residue was added water (50 mL) and extracted with ethyl acetate (2×100 mL). The combined organic layer was washed with brine (50 mL), dried over sodium sulfate, filtered and concentrated in vacuo to give N4-(3-chloro-4-(pyridin-2-ylmethoxy)phenyl)-7-(2-(1-(dimethylamino)cyclopropyl)ethoxy)quinazoline-4,6-diamine (700 mg, 1.39 mmol, 67% yield) as a yellow oil. 1H NMR (400 MHz, CDCl3) δ=8.52 (br d, J=4.8 Hz, 1H), 8.47 (s, 1H), 7.76 (d, J=2.3 Hz, 1H), 7.71-7.63 (m, 1H), 7.58 (d, J=7.7 Hz, 1H), 7.39 (dd, J=2.4, 8.7 Hz, 1H), 7.16 (br d, J=6.1 Hz, 1H), 7.08 (s, 1H), 6.92 (d, J=9.0 Hz, 2H), 6.85 (s, 1H), 5.21 (s, 2H), 4.18 (br s, 2H), 4.11 (t, J=7.2 Hz, 2H), 2.31 (s, 6H), 2.05 (t, J=7.1 Hz, 2H), 0.64-0.59 (m, 2H), 0.51-0.44 (m, 2H). MS (ESI) m/z 505.4 [M+H]+

To a solution of N4-(3-chloro-4-(pyridin-2-ylmethoxy)phenyl)-7-(2-(1-(dimethylamino)cyclopropyl)ethoxy)quinazoline-4,6-diamine (200 mg, 396 umol, 1.00 eq) in dimethyformamide (4.00 mL) was added acrylic acid (0.5 M in dimethyformamide, 1.19 mL, 1.50 eq), pyridine (94.0 mg, 1.19 mmol, 3.00 eq) and 1-(3-dimethylaminopropyl)-3-ethylcarbodiimide hydrochloride (114 mg, 594 umol, 1.50 eq). The reaction mixture was stirred at 20° C. for 30 min. The reaction mixture was filtered. The filtrate was purified by prep-HPLC (column: Phenomenex Synergi C18 150*30 mm*4 um; mobile phase: [water(0.225%FA)-ACN]; B%: 8%-35%, 10 min) and lyophilized to give N-(4-((3-chloro-4-(pyridin-2-ylmethoxy)phenyl)amino)-7-(2-(1-(dimethylamino)cyclopropyl)ethoxy)quinazolin-6-yl)acrylamide 102 (98.87 mg, 133 umol, 34% yield, 100% purity, 4 FA) as a yellow gum. 1H NMR (400 MHz, DMSO-d6) δ=9.67 (br s, 1H), 9.56 (s, 1H), 8.83 (s, 1H), 8.64-8.57 (m, 1H), 8.49 (s, 1H), 8.17 (s, 4H), 7.98 (d, J=2.6 Hz, 1H), 7.88 (dt, J=1.7, 7.7 Hz, 1H), 7.69 (dd, J=2.5, 9.0 Hz, 1H), 7.59 (d, J=7.8 Hz, 1H), 7.37 (dd, J=5.3, 7.1 Hz, 1H), 7.29-7.21 (m, 2H), 6.69 (dd, J=10.2, 16.9 Hz, 1H), 6.32 (dd, J=1.9, 16.9 Hz, 1H), 5.85-5.75 (m, 1H), 5.28 (s, 2H), 4.22 (t, J=7.0 Hz, 2H), 2.30 (s, 6H), 2.08 (t, J=6.9 Hz, 2H), 0.63-0.47 (m, 4H). MS (ESI) m/z 559.3 [M+H]+.

103: To a solution of tert-butyl 5-oxohexahydrocyclopenta[c]pyrrole-2(1H)-carboxylate (4.50 g, 20.0 mmol, 1.00 eq) and methoxymethyl(triphenyl)phosphonium; chloride (13.7 g, 40.0 mmol, 2.00 eq) in tetrahydrofuran (100 mL) was added potassium tert-butoxide (4.48 g, 40.0 mmol, 2.00 eq) at 0° C. The mixture was allowed to warm to 25° C. and stirred at 25° C. for 12 h. The mixture was diluted with water (100 mL), extracted with ethyl acetate (2×200 mL). The combined organic layers were washed with water, dried over anhydrous sodium sulfate, filtered and the filtrate was concentrated to afford a residue. The residue was purified by silica gel chromatography (petroleum ether/ethyl acetate=1/0-3/1) to afford tert-butyl 5-(methoxymethylene)hexahydrocyclopenta[c]pyrrole-2(1H)-carboxylate (5.00 g, 17.4 mmol, 87% yield) as a colorless oil. 1H NMR (400 MHz, CDCl3-d) δ=5.9 (t, J=2.08 Hz, 1H), 3.6 (s, 3H), 3.5 (br s, 2H), 3.0-3.2 (m, 2 H), 2.6 (br d, J=4.89 Hz, 2H), 2.4-2.6 (m, 2H), 2.1-2.2 (m, 2 H), 1.4 (s, 9H).

A mixture of solution of tert-butyl 5-(methoxymethylene) hexahydrocyclopenta[c]pyrrole-2(1H)-carboxylate (5.00 g, 17.4 mmol, 1.00 eq) in tetrahydrofuran (50.0 mL) and 1 M hydrochloric acid (50.0 mL) was stirred at 100° C. for 2 h. TLC showed the reaction was completed. The mixture was basified with 15% sodium hydroxide to PH=9-10 and added another sodium hydroxide (9.28 g, 34.8 mmol, 15% purity, 2.00 eq). Then di-tert-butyldicarbonate (6.25 g, 28.6 mmol, 1.65 eq) was added and the mixture was stirred at 25° C. for another 1 h. The mixture was extracted with ethyl acetate (3×20.0 mL). The combined organic layers were washed with water (20.0 mL), dried over anhydrous sodium sulfate, filtered and the filtrate was concentrated to afford a residue. The residue was purified by silica gel chromatography (petroleum ether/ethyl acetate=1/0-5/1) to afford (3aR,5s, 6aS)-tert-butyl 5-formylhexahydrocyclopenta[c]pyrrole-2 (1H)-carboxylate (1.30 g, 5.43 mmol, 31% yield) as a colorless oil and (3aR,5r,6aS)-tert-butyl 5-formylhexahydrocyclopenta[c]pyrrole-2(1H)-carboxylate (450 mg, 1.88 mmol, 11% yield) as a colorless oil. 1H NMR (400 MHz, Chloroform-d) δ=9.6-9.7 (m, 1H), 3.6 (br s, 2H), 3.2 (br s, 2H), 3.0-3.1 (m, 1H), 2.6-2.8 (m, 2H), 2.1-2.2 (m, 2H), 1.7 (br s, 2H), 1.5 (s, 9H).

To a solution of (3aR,5s,6aS)-tert-butyl 5-formylhexahydrocyclopenta[c]pyrrole-2(1H)-carboxylate (1.30 g, 5.43 mmol, 1.00 eq) in methanol (20.0 mL) was added sodium borohydride (206 mg, 5.43 mmol, 1.00 eq) at 25° C. The mixture was stirred at 25° C. for 10 min. The mixture was quenched with saturated ammonium chloride (3.00 mL) and concentrated to afford a residue. The residue was extracted with ethyl acetate (2×20.0 mL). The combined organic layers were washed with water (20.0 mL), dried over anhydrous sodium sulfate, filtered and the filtrate was concentrated to afford (3aR,5s,6aS)-tert-butyl 5-(hydroxymethyl)hexahydrocyclopenta[c]pyrrole-2(1H)-carboxylate (1.10 g, 4.56 mmol, 84% yield) as a colorless oil. 1H NMR (400 MHz, Chloroform-d) δ=3.4-3.5 (m, 4H), 3.0-3.1 (m, 2H), 2.6-2.7 (m, 2H), 2.3 (dquin, J=14.79, 7.40, 7.40, 7.40, 7.40 Hz, 1H), 1.5-1.7 (m, 4H), 1.4 (s, 9H).

To a solution of (3aR,5s,6aS)-tert-butyl 5-(hydroxymethyl)hexahydrocyclopenta[c]pyrrole-2(1H)-carboxylate (600 mg, 2.18 mmol, 1.50 eq) and N-(3-chloro-4-(pyridin-2-ylmethoxy)phenyl)-7-fluoro-6-nitroquinazolin-4-amine (619 mg, 1.45 mmol, 1.00 eq) in dimethylsulfoxide (6.00 mL) was added potassium tert-butoxide (489 mg, 4.36 mmol, 3.00 eq). The mixture was stirred at 25° C. for 12 h. The mixture was diluted with water (10.0 mL) and then filtered. The filter cake was washed with water (10.0 mL), dried in vacuum to afford crude product. The crude product was purified by reversed phase (C18, 0.1% hydrochloric acid in water-acetonitrile) to afford (3aR,5s,6aS)-tert-butyl 5-(((4-((3-chloro-4-(pyridin-2-ylmethoxy)phenyl)amino)-6-nitroquinazolin-7-yl)oxy)methyl)hexahydrocyclopenta[c] pyrrole-2(1H)-carboxylate (500 mg, 773 umol, 53% yield) as a yellow solid. 1H NMR (400 MHz, DMSO-d6) δ=11.6 (br s, 1H), 9.5 (s, 1H), 8.9 (s, 1H), 8.7 (br d, J=4.40 Hz, 1H), 8.0 (br t, J=7.15 Hz, 1H), 7.9 (d, J=2.45 Hz, 1H), 7.6-7.7 (m, 2H), 7.6 (s, 1H), 7.4-7.5 (m, 1H), 7.3-7.4 (m, 1H), 5.4 (s, 2H), 4.2 (br d, J=6.24 Hz, 2H), 3.4-3.5 (m, 2H), 3.0 (br dd, J=11.07, 3.61 Hz, 2H), 2.7-2.8 (m, 2H), 2.6-2.6 (m, 1H), 1.6-1.7 (m, 4H), 1.4 (s, 9H).

A mixture of (3aR,5s,6aS)-tert-butyl 5-(((4-((3-chloro-4-(pyridin-2-ylmethoxy)phenyl)amino)-6-nitroquinazolin-7-yl)oxy)methyl)hexahydrocyclopenta[c]pyrrole-2(1H)-carboxylate (500 mg, 772 umol, 1.00 eq) in hydrochloric acid (4 M in ethyl acetate, 15.0 mL) was stirred at 25° C. for 1 h. The mixture was concentrated to afford N-(3-chloro-4-(pyridin-2-ylmethoxy)phenyl)-6-nitro-7-(((3aR,5s,6aS)-octahydrocyclopenta[c]pyrrol-5-yl)methoxy)quinazolin-4-amine (500 mg, crude, hydrochloride) as a yellow solid. 1H NMR (400 MHz, DMSO-d6) δ=12.1 (br s, 1H), 9.8 (s, 1H), 9.3 (br s, 2H), 8.9 (s, 1H), 8.7 (d, J=4.40 Hz, 1H), 8.2 (td, J=7.73, 1.41 Hz, 1H), 8.0 (d, J=2.57 Hz, 1H), 7.8 (d, J=7.82 Hz, 1H), 7.7 (s, 1H), 7.7 (dd, J=8.93, 2.57 Hz, 1H), 7.6-7.7 (m 1H), 7.4 (d, J=9.05 Hz, 1H), 5.5 (s, 2H), 4.3 (d, J=6.36 Hz, 2H), 3.3-3.5 (m, 2H), 2.8-2.9 (m, 4H), 2.6-2.7 (m, 1H), 1.6-1.8 (m, 4H) MS (ESI) m/z 547.4 [M+H]+

To a solution of N-(3-chloro-4-(pyridin-2-ylmethoxy) phenyl)-6-nitro-7-(((3aR,5s,6aS)-octahydrocyclopenta[c] pyrrol-5-yl)methoxy)quinazolin-4-amine (500 mg, 857 umol, 1.00 eq, hydrochloride) and formaldehyde (37% in water, 938 mg, 11.6 mmol, 861 uL, 13.5 eq) in acetonitrile (35.5 mL) was added sodium triacetoxyhydroborate (785 mg, 3.70 mmol, 4.32 eq) at 20° C. The mixture was stirred at 20° C. for 12 h. The mixture was concentrated to afford a residue. The residue was diluted with water and stirred for 30 min. After filtration, the filter cake was washed with methanol, dried under vacuum to afford N-(3-chloro-4-(pyridin-2-ylmethoxy)phenyl)-7-(((3aR,5s,6aS)-2-methyloctahydrocyclopenta[c]pyrrol-5-yl)methoxy)-6-nitroquinazolin-4-amine (370 mg, crude) as a yellow solid. 1H NMR (400 MHz, DMSO-d6) δ=10.1 (s, 1H), 9.2 (s, 1H), 8.6-8.6 (m, 2H), 8.0 (d, J=2.45 Hz, 1H), 7.9 (td, J=7.64, 1.71 Hz, 1H), 7.7 (dd, J=8.93, 2.45 Hz, 1H), 7.6 (d, J=7.82 Hz, 1H), 7.4 (s, 1H), 7.4 (dd, J=6.97, 5.26 Hz, 1H), 7.3 (d, J=9.05 Hz, 1H), 5.3 (s, H), 4.2 (d, J=6.48 Hz, 2H), 2.6-2.7 (m, 2H), 2.5-2.6 (m, 4H), 2.2 (s, 3H), 2.1-2.2 (m, 1H), 1.5-1.7 (m, 4H). MS (ESI) m/z 561.3 [M+H]+

To a solution of N-(3-chloro-4-(pyridin-2-ylmethoxy) phenyl)-7-(((3aR,5s,6aS)-2-methyloctahydrocyclopenta[c] pyrrol-5-yl)methoxy)-6-nitroquinazolin-4-amine (270 mg, 481 umol, 1.00 eq) and ammonium chloride (318 mg, 5.95 mmol, 208 uL, 12.4 eq) in methanol (15.0 mL) and water (15.0 mL) was added powder iron (259 mg, 4.63 mmol, 9.63 eq) at 20° C. The mixture was heated to 80° C. and stirred at 80° C. for 1 h. The mixture was concentrated to afford a residue. The residue was diluted with methanol (30.0 mL) and stirred for 20 min. After filtration, the filtrate was concentrated to afford crude product. The crude product was triturated with water (5.00 mL), saturated aqueous sodium carbonate solution (1.00 mL) to afford N4-(3-chloro-4-(pyridin-2-ylmethoxy)phenyl)-7-(((3aR,5s,6aS)-2-methyloctahydrocyclopenta[c]pyrrol-5-yl)methoxy)quinazoline-4, 6-diamine (210 mg, 395 umol, 82% yield) as a yellow solid. 1H NMR (400 MHz, DMSO-d6) δ=9.2 (s, 1H), 8.6-8.6 (m, 1H), 8.3 (s, 1H), 8.0 (d, J=2.57 Hz, 1H), 7.9-7.9 (m, 1H), 7.7 (dd, J=8.99, 2.63 Hz, 1H), 7.6-7.6 (m, 1H), 7.4-7.4 (m, 2H), 7.2 (d, J=9.05 Hz, 1H), 7.1 (s, 1H), 5.3 (s, 2H), 4.1 (br d, J=6.48 Hz, 2H), 2.5-3.0 (m, 6H), 2.3-2.4 (m, 4H), 1.5-1.8 (m, 4H). MS (ESI) m/z 531.4 [M+H]+

To a solution of N4-(3-chloro-4-(pyridin-2-ylmethoxy) phenyl)-7-(((3aR,5s,6aS)-2-methyloctahydrocyclopenta[c] pyrrol-5-yl)methoxy)quinazoline-4,6-diamine (250 mg, 471 umol, 1.00 eq) and pyridine (149 mg, 1.88 mmol, 4.00 eq) and acrylic acid (0.500 M in dimethylformamide, 1.13 mL, 1.20 eq) in dimethylformamide (2.00 mL) was added 1-(3-dimethylaminopropyl)-3-ethylcarbodiimide hydrochloride (271 mg, 1.41 mmol, 3.00 eq) in dimethylformamide at 0° C. The mixture was stirred at 25° C. for 5 h. The mixture was purified by prep-HPLC (column: Phenomenex Synergi C18 150*30 mm*4 um; mobile phase: [water(0.225%FA)-ACN]; B%: 1%-30%, 10 min) to afford crude product (7.7% purity by HPLC). The crude product was re-purified by prep-HPLC (column: Phenomenex Synergi C18 150*25*10 um; mobile phase: [water(0.05%HCl)-ACN]; B%: 10%-30%, 9 min) and lyophilized to afford N-(4-((3-chloro-4-(pyridin-2-ylmethoxy)phenyl)amino)-7-(((3aR,5s,6aS)-2-methyloctahydrocyclopenta[c]pyrrol-5-yl)methoxy)quinazolin-6-yl)acrylamide 103 (25.43 mg, 40.1 umol, 9% yield, 98% purity, hydrochloride) as a yellow solid. 1H NMR (400 MHz, D2O-d2) δ=8.8 (d, J=5.75 Hz, 1H), 8.8-8.8 (m, 1H), 8.7-8.7 (m, 1H), 8.6-8.7 (m, 2H), 8.2 (d, J=8.07 Hz, 1H), 8.1 (t, J=6.91 Hz, 1H), 7.7-7.8 (m, 1H), 7.5-7.6 (m, 1H), 7.3-7.4 (m, 2H), 6.5-6.7 (m, 1H), 6.4-6.5 (m, 1H), 6.0-6.1 (m, 1H), 5.7 (s, 2 H), 4.2-4.4 (m, 2 H), 3.8-4.0 (m, 2H), 3.3-3.5 (m, 1H), 3.2 (br s, 1H), 3.0-3.1 (m, 2H), 2.9-3.0 (m, 3H), 2.7-2.8 (m, 3H), 1.6-2.0 (m, 4H). MS (ESI) m/z 585.1 [M+H]+

104: A mixture of 7-fluoro-6-nitroquinazolin-4-ol (30.0 g, 143 mmol, 1.00 eq) and dimethyl formamide (1.05 g, 14.3 mmol, 1.10 mL, 0.100 eq) in sulfurous dichloride (30.0 mL) was stirred at 90° C. for 12 h. The mixture was concentrated to give a 4-chloro-7-fluoro-6-nitroquinazoline (35.0 g, crude) as a yellow solid. MS (ESI) m/z 228.0 [M+H]+

A mixture of 4-chloro-7-fluoro-6-nitro-quinazoline (5.00 g, 21.9 mmol, 1.00 eq) and 3-methyl-4-((6-methylpyridin-3-yl)oxy)aniline (5.18 g, 24.2 mmol, 1.10 eq) in isopropyl alcohol (50.0 mL) was stirred at 80° C. for 1 h. The reaction mixture was concentrated to give a residue. The residue was triturated with ethyl acetate (20.0 mL) to give 7-fluoro-N-(3-methyl-4-((6-methylpyridin-3-yl)oxy)phenyl)-6-nitroquinazolin-4-amine (8.00 g, 19.7 mmol, 89% yield) as a yellow solid. 1H NMR (400 MHz, DMSO-d6) δ=11.04 (br s, 1H), 9.77 (d, J=7.8 Hz, 1H), 8.79 (s, 1H), 8.44 (d, J=2.8 Hz, 1H), 7.90 (d, J=12.2 Hz, 1H), 7.85-7.77 (m, 2H), 7.76-7.64 (m, 2H), 7.13 (d, J=8.7 Hz, 1H), 2.63 (s, 3H), 2.26 (s, 3H). MS (ESI) m/z 406.1 [M+H]+

A mixture of 7-fluoro-N-(3-methyl-4-((6-methylpyridin-3-yl)oxy)phenyl)-6-nitroquinazolin-4-amine (4.00 g, 9.87 mmol, 1.00 eq) and potassium acetate (4.84 g, 49.3 mmol, 5.00 eq) in dimethyl formamide (40.0 mL) was stirred at 100° C. for 1 h. The reaction mixture was concentrated to give a residue. The residue was triturated with water (20.0 mL) to give 4-((3-methyl-4-((6-methylpyridin-3-yl)oxy)phenyl)amino)-6-nitroquinazolin-7-ol (3.20 g, 7.93 mmol, 80% yield) as a yellow solid. 1H NMR (400 MHz, DMSO-d6) δ=10.01 (br s, 1H), 9.19 (s, 1H), 8.49 (s, 1H), 8.19 (d, J=2.1 Hz, 1H), 7.75 (br s, 1H), 7.68 (br d, J=8.6 Hz, 1H), 7.31-7.18 (m, 2H), 7.13 (s, 1H), 6.96 (d, J=8.7 Hz, 1H), 2.44 (s, 3H), 2.21 (s, 3H). MS (ESI) m/z 404.1 [M+H]+

To a solution of 4-((3-methyl-4-((6-methylpyridin-3-yl)oxy)phenyl)amino)-6-nitroquinazolin-7-ol (2.50 g, 6.20 mmol, 1.00 eq) and pyridine (2.45 g, 30.99 mmol, 2.50 mL, 5.00 eq) in dichloromethane (30.0 mL) was added trifluoromethanesulfonic anhydride (3.50 g, 12.4 mmol, 2.05 mL, 2.00 eq) at 0° C. The mixture was stirred at 20° C. for 1 h. The reaction mixture was concentrated to give a residue. The residue was purified by column chromatography (SiO2, petroleum ether/ethyl acetate=1.0/1 to 0/1) to give 4-((3-methyl-4-((6-methylpyridin-3-yl)oxy)phenyl)amino)-6-nitroquinazolin-7-yl trifluoromethanesulfonate (2.00 g, 3.74 mmol, 60% yield) as a yellow solid. 1H NMR (400 MHz, CDCl3) δ=8.98 (s, 1H), 8.80-8.70 (m, 1H), 8.15 (d, J=2.8 Hz, 1H), 7.80 (s, 1H), 7.54 (br s, 1H), 7.41 (br d, J=7.2 Hz, 1H), 7.24 (br d, J=7.3 Hz, 1H), 7.17-7.11 (m, 1H), 6.84 (d, J=8.8 Hz, 1H), 2.50 (s, 3H), 2.22 (s, 3H). MS (ESI) m/z 536.1 [M+H]+

To a solution of 4-((3-methyl-4-((6-methylpyridin-3-yl)oxy)phenyl)amino)-6-nitroquinazolin-7-yl trifluoromethanesulfonate (1.00 g, 1.87 mmol, 1.00 eq), (1R,5S,6s)-tert-butyl 6-ethynyl-3-azabicyclo[3.1.0]hexane-3-carboxylate (503 mg, 2.43 mmol, 1.30 eq), copper(I) iodide (71.1 mg, 373 umol, 0.200 eq) and triethylamine (567 mg, 5.60 mmol, 779 uL, 3.00 eq) in dimethyl formamide (10.0 mL) was added tetrakis[triphenylphosphine]palladium(0) (216 mg, 186 umol, 0.100 eq) at 15° C. The mixture was stirred at 15° C. for 12 h. The reaction was concentrated to afford a residue. The residue was triturated with ethyl acetate (200 mL). After filtration, the filtrate was dried in vacuum to afford crude product. The crude product was purified by silica gel chromatography (petroleum ether/ethyl acetate=1/1 to 0/1) to afford (1R,5S,6s)-tert-butyl 6-((4-((3-methyl-4-((6-methylpyridin-3-yl)oxy)phenyl)amino)-6-nitroquinazolin-7-yl)ethynyl)-3-azabicyclo[3.1.0]hexane-3-carboxylate (700 mg, 1.18 mmol, 63% yield) as a yellow oil, 1H NMR (400 MHz, CDCl3) δ=8.94 (s, 1H), 8.79 (s, 1H), 8.56 (br s, 1H), 8.27 (d, J=2.4 Hz, 1H), 8.00 (s, 1H), 7.57-7.54 (m, 1H), 7.20-7.08 (m, 2H), 6.90 (d, J=8.7 Hz, 1H), 3.85-3.65 (m, 2H), 3.45 (br d, J=11.1 Hz, 2H), 2.56 (s, 3H), 2.29 (s, 3H), 2.09 (br s, 2H), 1.54-1.49 (m, 1H), 1.48 (s, 9H). MS (ESI) m/z 593.6 [M+H]+

A mixture of (1R,5S,6s)-tert-butyl 6-((4-((3-methyl-4-((6-methylpyridin-3-yl)oxy)phenyl)amino)-6-nitroquinazolin-7-yl)ethynyl)-3-azabicyclo[3.1.0]hexane-3-carboxylate (700 mg, 1.18 mmol, 1.00 eq) in hydrochloric acid/ethyl acetate (4.00 M, 10.0 mL, 33.8 eq) was stirred at 25° C. for 0.5 h. The reaction mixture was concentrated to give a residue. The residue was triturated with ethyl acetate (10.0 mL) to give 7-(((1R,5S,6s)-3-azabicyclo[3.1.0]hexan-6-yl)ethynyl)-N-(3-methyl-4-((6-methylpyridin-3-yl)oxy)phenyl)-6-nitroquinazolin-4-amine (800 mg, crude) as a yellow solid. MS (ESI) m/z 493.4 [M+H]+

A mixture of 7-((1R,5S,6s)-3-azabicyclo[3.1.0]hexan-6-ylethynyl)-N-(3-methyl-4-((6-methylpyridin-3-yl)oxy)phenyl)-6-nitroquinazolin-4-amine (600 mg, 1.22 mmol, 1.00 eq), sodium borohydride (55.3 mg, 1.46 mmol, 1.20 eq) and formaldehyde (195 mg, 6.09 mmol, 246, 5.00 eq) in 2,2,2-trifluoroethanol (3.00 mL) was stirred at 60° C. for 2 h. The mixture was concentrated to afford a residue. The residue was diluted with saturated sodium carbonate (30.0 mL) and water (10.0 mL), extracted with ethyl acetate 80.0 mL). The combined organic layer was washed with water (20.0 mL), dried over anhydrous sodium sulfate, filtered and the filtrate was concentrated to afford 7-(((1R,5S,6s)-3-methyl-3-azabicyclo[3.1.0]hexan-6-yl)ethynyl)-N-(3-methyl-4-((6-methylpyridin-3-yl)oxy)phenyl)-6-nitroquinazolin-4-amine (350 mg, 690 umol, 57% yield) as a yellow solid. 1H NMR (400 MHz, DMSO-d6) δ=9.44 (s, 1H), 8.67 (s, 1H), 8.20 (d, J=1.5 Hz, 1H), 7.89 (s, 1H), 7.76 (br s, 1H), 7.71-7.65 (m, 1H), 7.65-7.60 (m, 1H), 7.60-7.54 (m, 1H), 7.25 (s, 1H), 6.98 (d, J=8.8 Hz, 1H), 3.03 (d, J=9.2 Hz, 2H), 2.45 (s, 3H), 2.30 (br d, J=8.3 Hz, 2H), 2.24 (d, J=3.2 Hz, 6H), 1.98-1.86 (m, 3H). MS (ESI) m/z 507.5 [M+H]+

A mixture of 7-(((1R,5S,6s)-3-methyl-3-azabicyclo [3.1.0]hexan-6-yl)ethynyl)-N-(3-methyl-4-((6-methylpyridin-3-yl)oxy)phenyl)-6-nitroquinazolin-4-amine (300 mg, 592 umol, 1.00 eq), iron powder (165 mg, 2.96 mmol, 5.00 eq) and ammonium chloride (158 mg, 2.96 mmol, 5.00 eq) in methanol (10.0 mL) and water (2.00 mL) was stirred at 70° C. for 12 h. The reaction mixture was added methanol (20.0 mL). The mixture was filtered. The filtrate was concentrated to give a residue. The residue was purified by prep-HPLC {column: Phenomenex Synergi C18 150*30 mm*4 um; mobile phase: [water(0.225%FA)-ACN]; B%: 1%-30%, 10 min} and lyophilized to give 7-(((1R,5S,6s)-3-methyl-3-azabicyclo[3.1.0]hexan-6-yl)ethynyl)-N4-(3-methyl-4-((6-methylpyridin-3-yl)oxy)phenyl)quinazoline-4,6-diamine (130 mg, 272 umol, 46% yield) as a yellow solid. 1H NMR (400 MHz, CDCl3) δ=8.55 (s, 1H), 8.27 (d, J=2.6 Hz, 1H), 7.78 (s, 1H), 7.63 (br d, J=2.2 Hz, 1H), 7.52 (dd, J=2.6, 8.4 Hz, 1H), 7.15-7.10 (m, 2H), 7.01 (s, 1H), 6.92 (d, J=8.7 Hz, 1H), 3.33 (d, J=9.8 Hz, 2H), 2.58 (br s, 2H), 2.55 (s, 3H), 2.44 (s, 3H), 2.29 (s, 3H), 2.08 (br d, J=2.9 Hz, 1H), 1.98 (br s, 2H). MS (ESI) m/z 477.4 [M+H]+

To a solution of 7-(((1R,5S,6s)-3-methyl-3-azabicyclo[3.1.0]hexan-6-yl)ethynyl)-N4-(3-methyl-4-((6-methylpyridin-3-yl)oxy)phenyl)quinazoline-4,6-diamine (120 mg, 252 umol, 1.00 eq), triethylamine (50.9 mg, 503 umol, 70.1 uL, 2.00 eq) in dimethyl formamide (1.00 mL) was added prop-2-enoyl prop-2-enoate (31.7 mg, 251 umol, 3.46 uL, 1.00 eq) at 25° C. The mixture was stirred at 25° C. for 2 h. The reaction mixture was filtered. The filtrate was purified by prep-HPLC {column: Phenomenex Gemini 150*25 mm*10 um; mobile phase: [water(10 mM NH4HCO3)-ACN]; B%: 35%-65%, 10 min} and lyophilized to give N-(7-(((1R,5S,6s)-3-methyl-3-azabicyclo[3.1.0]hexan-6-yl)ethynyl)-4-((3-methyl-4-((6-methylpyridin-3-yl)oxy)phenyl)amino)quinazolin-6-yl)acrylamide 104 (33.6 mg, 63.3 umol, 25% yield, 100% purity) as an orange solid. 1H NMR (400 MHz, CDCl3) δ=9.03 (s, 1H), 8.60 (s, 1H), 8.27 (s, 1H), 8.21 (d, J=2.7 Hz, 1H), 7.82 (s, 1H), 7.72 (s, 1H), 7.56 (d, J=2.3 Hz, 1H), 7.50 (dd, J=2.7, 8.7 Hz, 1H), 7.10-6.97 (m, 2H), 6.84 (d, J=8.7 Hz, 1H), 6.55-6.38 (m, 1H), 6.35-6.19 (m, 1H), 5.91-5.75 (m, 1H), 3.09 (d, J=9.3 Hz, 2H), 2.46 (s, 3H), 2.35 (br d, J=8.9 Hz, 2H), 2.28 (s, 3H), 2.22 (s, 3H), 2.02 (br s, 1H), 1.87 (br s, 2H). MS (ESI) m/z 531.5 [M+H]+

105: A mixture of (1R,5S,6s)-tert-butyl 6-((4-((3-chloro-4-(pyridin-2-ylmethoxy)phenyl)amino)-6-nitroquinazolin-7-yl)ethynyl)-3-azabicyclo[3.1.0]hexane-3-carboxylate (450 mg, 734 umol, 1.00 eq), iron (205 mg, 3.67 mmol, 5.00 eq) and ammonium chloride (353 mg, 6.61 mmol, 9.00 eq) in methanol (2.00 mL) and water (2.00 mL) was stirred at 80° C. for 2 h. The reaction mixture was concentrated to give a residue. The residue was added ethyl acetate (50.0 mL). The mixture was filtered. The filtrate was concentrated to give tert-butyl (1R,5S,6s)-tert-but 6-((6-amino-4-((3-chloro-4-(pyridin-2-ylmethoxy)phenyl)amino)quinazolin-7-yl)ethynyl)-3-azabicyclo[3.1.0]hexane-3-carboxylate (450 mg, crude) as a yellow solid. MS (ESI) m/z 583.5 [M+H]+

To a solution of (1R,5S,6s)-tert-butyl 6-((6-amino-4-((3-chloro-4-(pyridin-2-ylmethoxy)phenyl)amino)quinazolin-7-yl)ethynyl)-3-azabicyclo[3.1.0]hexane-3-carboxylate (200 mg, 343 umol, 1.00 eq), triethylamine (69.4 mg, 686 umol, 2.00 eq) in dimethyl formamide (1.00 mL) was added prop-2-enoyl prop-2-enoate (47.5 mg, 377 umol, 1.10 eq) at 25° C. The mixture was stirred at 25° C. for 2 h. The mixture was filtered. The filtrate was purified by reversed-phase chromatography (0.1% FA condition) and lyophilized to give (1R,5S,6s)-tert-butyl 6-((6-acrylamido-4-((3-chloro-4-(pyridin-2-ylmethoxy)phenyl)amino)quinazolin-7-yl)ethynyl)-3-azabicyclo[3.1.0]hexane-3-carboxylate (90.0 mg, 141 umol, 41.2% yield) as a yellow solid. 1H NMR (400 MHz, CDCl3) δ=9.11 (br s, 1H), 8.69 (d, J=2.8 Hz, 1H), 8.62 (br s, 1H), 8.28 (br s, 1H), 7.91 (br s, 2H), 7.77 (br d, J=7.2 Hz, 1H), 7.68 (br d, J=10.1 Hz, 2H), 7.54 (br d, J=8.6 Hz, 1H), 7.13-6.94 (m, 1H), 6.61-6.48 (m, 1H), 6.46-6.26 (m, 1H), 5.94 (br d, J=10.0 Hz, 1H), 5.32 (s, 2H), 3.92-3.66 (m, 2H), 3.48 (br d, J=10.0 Hz, 2H), 2.08 (br s, 2H), 1.52 (br d, J=3.4 Hz, 1H), 1.49 (d, J=2.7 Hz, 9H). MS (ESI) m/z 637.4 [M+H]+

A mixture of (1R,5S,6s)-tert-butyl 6-((6-acrylamido-4-((3-chloro-4-(pyridin-2-ylmethoxy)phenyl)amino)quinazolin-7-yl(ethynyl)-3-azabicyclo[3.1.0]hexane-3-carboxylate (70.0 mg, 109 umol, 1.00 eq) and trifluoroacetic acid (2.16 g, 18.9 mmol, 1.40 mL, 172 eq) in dichloromethane (3.00 mL) was stirred at 25° C. for 1 h. The reaction mixture was concentrated to give a residue. The residue was purified by prep-HPLC (column: Phenomex luna C18 150*25 10 u; mobile phase: [water(0.225%FA)-ACN]: B%: 14%-34%, 7.8 min) and lyophilized to give N-(7-(((1R,5S,6s)-3-azabicyclo[3.1.0]hexan-6-ylethynyl)-4-((3-chloro-4-(pyridin-2-ylmethoxy)phenyl)amino)quinazolin-6-yl)acrylamide 105 (54.94 mg, 94.2 umol, 85% yield, 100% purity, FA) as a yellow solid. 1H NMR (400 MHz, MeOD) δ=8.66 (s, 1H), 8.56 (br d, J=3.5 Hz, 1H), 8.50 (s, 1H), 8.13 (br d, J=11.5 Hz, 1H), 7.98-7.87 (m, 2H), 7.79 (s, 1H), 7.72 (d, J=7.9 Hz, 1H), 7.59 (dd, J=2.6, 8.9 Hz, 1H), 7.40 (dd, J=5.1, 6.9 Hz, 1H), 7.16 (d, J32 9.0 Hz, 1H), 6.63-6.53 (m, 1H), 6.52-6.44 (m, 1H), 5.95-5.83 (m, 1H), 5.27 (s, 2H), 3.63-3.50 (m, 4H), 2.37 (br s, 2H), 1.78 (t, J=3.7 Hz, 1H). MS (ESI) m/z 537.3 [M+H]+

106: To a solution of 4-phenoxyaniline (5.00 g, 27.0 mmol, 1.00 eq) in propan-2-ol (100 mL) was added 4-chloro-7-fluoro-6-nitro-quinazoline (6.76 g, 29.7 mmol, 1.10 eq). The mixture was stirred at 90° C. for 12 h. The mixture was concentrated in vacuum to afford crude product. The residue was triturated with petroleum ether/ethyl acetate=5/1 (50.0 mL), filtered and dried under reduced pressure to afford 7-fluoro-6-nitro-N-(4-phenoxyphenyl)quinazolin-4-amine (11.0 g, crude) as a yellow solid. 1H NMR (400 MHz, DMSO-d6) δ=11.65 (br s, 1H), 9.84 (d, J=7.7 Hz, 1H), 8.87 (s, 1H), 7.96 (d, J=11.9 Hz, 1H), 7.79-7.76 (m, 1H), 7.76-7.73 (m, 1H), 7.46-7.40 (m, 2H), 7.21-7.15 (m, 1H), 7.15-7.13 (m, 1H), 7.12-7.10 (m, 1H), 7.08 (d, J=1.0 Hz, 1H), 7.06 (d, J=0.9 Hz, 1H). MS (ESI) m/z 376.9 [M+H]+

To a solution of 7-fluoro-6-nitro-N-(4-phenoxyphenyl)quinazolin-4-amine (10.0 g, 26.6 mmol, 1.00 eq) in N,N-dimethylformamide (100 mL) was added potassium acetate (13.0 g, 133 mmol, 5.00 eq). The mixture was stirred at 100° C. for 2 h. The mixture was concentrated in vacuum. The residue was triturated with water (200 mL). After filtration, the filter cake was washed with water (100 mL) and dried in vacuum to afford 6-nitro-4-((4-phenoxyphenyl)amino)quinazolin-7-ol (11.0 g, crude) as a red solid. 1H NMR (400 MHz, DMSO-d6) δ=8.87 (s, 1H), 8,24 (s, 1H), 7.81 (s, 1H), 7.79 (s, 1H), 7.40-7.36 (m, 2H), 7.18-7.06 (m, 2H), 7.06-6.97 (m, 5H), 6.65 (s, 1H).

To a solution of 6-nitro-4-(4-phenoxyanilino)quinazolin-7-ol (10.0 g, 26.7 mmol, 1.00 eq) and pyridine (10.6 g, 134 mmol, 10.8 mL, 5.00 eq) in dichloromethane (200 mL) was added trifluoromethanesulfonic anhydride (15.1 g, 53.4 mmol, 8.81 mL, 2.00 eq) at 0° C. The mixture was stirred at 25° C. for 2 h. The mixture was partitioned between dichloromethane (200 mL) and water (100 mL). The aqueous phase was extracted with dichloromethane (2×100 mL). The combined organic phase was dried over anhydrous sodium sulfate, filtered and concentrated in vacuum. The residue was purified by silica gel chromatography (petroleum ether/ethyl acetate=1/0 to 8/1) to afford 6-nitro-4-((4-phenoxyphenyl)amino)quinazolin-7-yl trifluoromethanesulfonate (3.10 g, 6.12 mmol, 22% yield) as a brown solid. 1H NMR (400 MHz, DMSO-d6) δ=10.64 (s, 1H), 9.75 (s, 1H), 8.75 (s, 1H), 8.03 (s, 1H), 7.83-7.80 (m, 1H), 7.80-7.77 (m, 1H), 7.44-7.39 (m, 2H), 7.19-7.13 (m, 1H), 7.13-7.08 (m, 2H), 7.07-7.03 (m, 2H). MS (ESI) m/z 507.1 [M+H]+

To a solution of 6-nitro-4-((4-phenoxyphenyl)amino)quinazolin-7-yl trifluoromethanesulfonate (1.50 g, 2.96 mmol, 1.00 eq) in N,N-dimethylformamide (15.0 mL) was added tert-butyl 6-ethynyl-3-azabicyclo[3.1.0] hexane-3-carboxylate (920 mg, 4.44 mmol, 1.50 eq), copper(i) iodide (282 mg, 1.48 mmol, 0.500 eq), triethylamine (899 mg, 8.88 mmol, 1.24 mL, 3.00 eq) and tetrakis[triphenylphosphine]palladium(0) (342 mg, 0.296 mmol, 0.100 eq) at 25° C. under nitrogen. The mixture was stirred at 25° C. for 12 h. The mixture was concentrated in vacuum. The residue was purified by silica gel chromatography (petroleum ether/ethyl acetate=1/0 to 1/1) to afford (1R,5S,6s)-tert-butyl 6-((6-nitro-4-((4-phenoxyphenyl)amino)quinazolin-7-yl)ethynyl)-3-azabicyclo[3.1.0]hexane-3-carboxylate (1.43 g, 2.54 mmol, 85% yield) as a brown solid. 1H NMR (400 MHz, DMSO-d6) δ=10.37 (br s, 1H), 9.43 (s, 1H), 8.66 (br s, 1H), 7.90 (br s, 1H), 7.80 (br d, J=8.7 Hz, 2H), 7.40 (br t, J=7.8 Hz, 2H), 7.14 (br t, J=7.3 Hz, 1H), 7.08 (br d, J=8.8 Hz, 2H), 7.04 (br d, J=8.2 Hz, 2H), 3.56 (br d, J=11.0 Hz, 2H), 3.37 (br s, 2H), 2.09 (br s, 2H), 1.47 (br s, 1H), 1.39 (s, 9H). MS (ESI) m/z 564.3 [M+H]+

A mixture of (1R,5S,6s)-tert-butyl 6-((6-nitro-4-((4-phenoxyphenyl)amino)quinazolin-7-yl)ethynyl)-3-azabicyclo[3.1.0]hexane-3-carboxylate (1.33 g, 2.36 mmol, 1.00 eq) in 4.00 M hydrochloric acid/ethyl acetate (15.0 mL) was stirred at 25° C. for 1 h. The mixture was concentrated in vacuum. The residue was triturated with ethyl acetate (30.0 mL). After filtration, the filter cake was dried in vacuum to afford 7-((1R,5S,6s)-3-azabicyclo[3.1.0]hexan-6-ylethynyl)-6-nitro-N-(4-phenoxyphenyl)quinazolin-4-amine (1.00 g, 2.00 mmol, 84% yield, hydrochloric acid) as a yellow solid. 1H NMR (400 MHz, DMSO-d6) δ=11.14 (br s, 1H), 9.59 (s, 1H), 9.48 (br s, 1H), 9.30 (br s, 1H), 8.80 (s, 1H), 8.02 (s, 1H), 7.79 (s, 1H), 7.76 (s, 1H), 7.45-7.39 (m, 2H), 7.17 (t, J=7.4 Hz, 1H), 7.13-7.09 (m, 2H), 7.06 (dd, J=1.0, 8.6 Hz, 2H), 3.47 (dd, J=6.1, 11.8 Hz, 2H), 3.42-3.34 (m, 2H), 2.31 (br s, 2H), 2.15 (t, J=3.6 Hz, 1H).

To a solution of 7-((1R,5S,6s)-3-azabicyclo[3.1.0]hexan-6-ylethynyl)-6-nitro-N-(4-phenoxyphenyl)quinazolin-4-amine (1.00 g, 2.00 mmol, 1.00 eq, hydrochloric acid) and paraformaldehyde (300 mg, 9.99 mmol, 5.00 eq) in trifluoroethanol (15.0 mL) was added sodium borohydride (151 mg, 4.00 mmol, 2.00 eq). The mixture was stirred at 60° C. for 12 h. The mixture was concentrated in vacuum. The reaction mixture was partitioned between ethyl acetate (50.0 mL) and water (30.0 mL). The organic phase was separated, washed with water (2×20.0 mL), dried over anhydrous sodium sulfate, filtered and concentrated under reduced pressure to give a residue to afford 7-(((1R,5S,6s)-3-methyl-3-azabicyclo[3.1.0]hexan-6-yl)ethynyl)-6-nitro-N-(4-phenoxyphenyl)quinazolin-4-amine (1.00 g, crude) as a brown solid. 1H NMR (400 MHz, DMSO-d6) δ=10.36 (s, 1H), 9.42 (s, 1H), 8.70-8.58 (m, 1H), 7.90-7.85 (m, 1H), 7.82 (s, 1H), 7.80 (s, 1H), 7.41-7.38 (m, 2H), 7.17-7.13 (m, 1H), 7.10-7.07 (m, 2H), 7.04 (br d, J=7.6 Hz, 2H), 3.02 (d, J=9.2 Hz, 2H), 2.31-2.27 (m, 2H), 2.23 (s, 3H), 1.96-1.88 (m, 3H).

To a solution of 7-(((1R,5S,6s)-3-methyl-3-azabicyclo[3.1.0]hexan-6-yl)ethynyl)-6-nitro-N-(4-phenoxyphenyl)quinazolin-4-amine (900 mg, 1.88 mmol, 1.00 eq) and iron powder (737 mg, 13.2 mmol, 7.00 eq) in methanol (45.0 mL) was added a solution of ammonium chloride (907 mg, 17.0 mmol, 9.00 eq) in water (9.00 mL). The mixture was stirred at 80° C. for 2 h. The residue was added methanol (100 mL) and stirred at 55° C. for 0.5 h, then filtered. The filtrate was concentrated to afford a residue. The residue was triturated with water (30.0 mL) and saturated sodium carbonate (2.00 mL). After filtration the filter cake was washed with methanol (100 mL). The filtrate was concentrated in vacuum. The solid was purified by prep-HPLC (Phenomenex Synergi C18 150*25*10 um, water(0.1%FA)-ACN) to afford 7-(((1R,5S,6s)-3-methyl-3-azabicyclo[3.1.0]hexan-6-yl)ethynyl)-N4-(4-phenoxyphenyl)quinazoline-4,6-diamine (360 mg, 0.804 mmol, 42% yield) as a brown solid. 1H NMR (400 MHz, DMSO-d6) δ=9.45 (s, 1H), 8.28 (s, 1H), 7.84-7.83 (m, 1H), 7.82-7.80 (m, 1H), 7.54 (s, 1H), 7.45 (s, 1R), 7.41-7.36 (m, 2H), 7.14-7.09 (m, 1H), 7.06-7.03 (m, 2H), 7.02-6.99 (m, 2H), 5.53 (s, 2H), 3.01 (d, J=9.1 Hz, 2H), 2.28 (br d, J=8.8 Hz, 2H), 2.23 (s, 3H), 1.98-1.95 (m, 2H), 1.94-1.90 (m, 1H). MS (ESI) m/z 448.3 [M+H]+

To a solution of 7-(((1R,5S,6s)-3-methyl-3-azabicyclo[3.1.0]hexan-6-yl)ethynyl)-N4-(4-phenoxyphenyl)quinazoline-4,6-diamine (150 mg, 0.335 mmol, 1.00 eq), 1-(3-dimethylaminopropyl)-3-ethylcarbodiimide hydrochloride (643 mg, 3.35 mmol, 10.0 eq) and pyridine (265 mg, 3.35 mmol, 0.271 mL, 10.0 eq) in N,N-dimethylformamide (3.00 mL) was added acrylic acid (242 mg, 3.35 mmol, 10.0 eq) at 0° C. The mixture was stirred at 25° C. for 1 h. The mixture was quenched by methanol (2.00 mL) and concentrated in vacuum. The residue was purified by prep-HPLC (column: Xtimate C18 150*25 mm*5 um; mobile phase: [water (0.05% ammonia hydroxide v/v)-ACN]; B%: 58%-88%, 1 min) and lyophilized to afford N-(7-(((1R,5S,6s)-3-methyl-3-azabicyclo[3.1.0]hexan-6-yl)ethynyl)-4-((4-phenoxyphenyl)amino)quinazolin-6-yl)acrylamide 106 (21.18 mg, 41.8 umol, 99% purity, 12% yield) as a yellow solid. 1H NMR (400 MHz, DMSO-d6) δ=9.88 (s, 1H), 9.85 (s, 1H), 8.73 (s, 1H), 8.51 (s, 1H), 7.81 (d, J=9.0 Hz, 2H), 7.76 (s, 1H), 7.40 (t, J=7.9 Hz, 2H), 7.13 (t, J=7.3 Hz, 1H), 7.06 (d, J=8.9 Hz, 2H), 7.02 (d, J=7.7 Hz, 2H), 6.63 (dd, J=10.2, 17.1 Hz, 1H), 6.33 (dd, J=1.8, 17.1 Hz, 1H), 5.85 (dd, J=1.8, 10.2 Hz, 1H), 3.00 (d, J=9.2 Hz, 2H), 2.28 (br d, J=8.8 Hz, 2H), 2.23 (s, 3H), 1.92 (br s, 2H), 1.90 (br d, J=3.2 Hz, 1H). MS (ESI) m/z 502.3 [M+H]+

107: A mixture of N4-(3-chloro-4-(pyridin-2-ylmethoxy)phenyl)-7-(((1R,5S,6s)-3-methyl-3-azabicyclo[3.1.0]hexan-6-yl)ethynyl)quinazoline-4,6-diamine (70.0 mg, 140 umol, 1.00 eq), but-2-ynoic acid (118 mg, 1.41 mmol, 10.0 eq) and 1-(3-dimethylaminopropyl)-3-ethylcarbodiimide (270 mg, 1.41 mmol, 10.0 eq) in pyridine (1.00 mL) was stirred at 25° C. for 0.5 h. The reaction mixture was filtered. The filtrate was purified by prep-HPLC (column: Waters Xbridge 150*25 5 u; mobile phase: [water(10 mM NH4HCO3)-ACN]; B%: 35%-68%, 10 min) and lyophilized to give N-(4-((3-chloro-4-(pyridin-2-ylmethoxy)phenyl)amino)-7-(((1R,5S,6s)-3-methyl-3-azabicyclo[3.1.0]hexan-6-yl)ethynyl)quinazolin-6-yl)but-2-ynamide 107 (5.37 mg, 9.54 umol, 6.7% yield, 100% purity) as a yellow solid. 1H NMR (400 MHz, DMSO-d6) δ=10.26 (br s, 1H), 9.82 (s, 1H), 8.60 (d, J=4.1 Hz, 1H), 8.53 (d, J=14.1 Hz, 1H), 8.01 (d, J=2.5 Hz, 1H), 7.89 (dt, J=1.8, 7.7 Hz, 1H), 7.75 (s, 1H), 7.71 (dd, J=2.6, 8.9 Hz, 1H), 7.59 (d, J=7.9 Hz, 1H), 7.38 (dd, J=4.9, 6.6 Hz, 1H), 7.27 (d, J=9.0 Hz, 1H), 5.30 (s, 2H), 3.03 (d, J=9.1 Hz, 2H), 2.31 (br d, J=8.8 Hz, 2H), 2.24 (s, 3H), 2.09 (br s, 3H), 1.94 (br s, 2H), 1.90-1.86 (m, 1H). MS (ESI) m/z 563.5 [M+H]+

108: To a solution of 7-(((1R,5S,6s)-3-methyl-3-azabicyclo[3.1.0]hexan-6-yl)ethynyl)-N4-(4-phenoxyphenyl)quinazoline-4,6-diamine (140 mg, 0.313 mmol, 1.00 eq), 1-(3-dimethylaminopropyl)-3-ethylcarbodiimide hydrochloride (600 mg, 3.13 mmol, 10.0 eq) and pyridine (247 mg, 3.13 mmol, 0.253 mL, 10.0 eq) in N,N-dimethylformamide (3.00 mL) was added but-2-ynoic acid (263 mg, 3.13 mmol, 10.0 eq). The mixture was stirred at 25° C. for 2 h. The mixture was quenched by methanol (2.00 mL) and concentrated in vacuum. The residue was purified by prep-HPLC (column: Shim-pack C18 150*25*10 um; mobile phase: [water (0.225%FA)-ACN]; B%: 13%-43%, 10 min 1 min) and lyophilized to afford N-(7-(((1R,5S,6s)-3-methyl-3-azabicyclo[3.1.0]hexan-6-yl)ethynyl)-4-((4-phenoxyphenyl)amino)quinazolin-6-yl)but-2-ynamide 108 (20.39 mg, 36.07 umol, 11% yield, 99% purity, formic acid) as a yellow solid. 1H NMR (400 MHz, DMSO-d6) δ=10.26 (br s, 1H), 9.85 (s, 1H), 8.54 (s, 1H), 8.53 (s, 1H), 8.22 (s, 1H), 7.82 (s, 1H), 7.80 (s, 1H), 7.74 (s, 1H), 7.43-7.36 (m, 2H), 7.13 (t, J=7.4 Hz, 1H), 7.09-7.04 (m, 2H), 7.02 (dd, J=1.0, 8.7 Hz, 2H), 3.02 (d, J=9.2 Hz, 2H), 2.31 (br d, J=9.4 Hz, 2H), 2.24 (s, 3H), 2.08 (br s, 3H), 1.93 (br s, 2H), 1.90-1.86 (m, 1H). MS (ESI) m/z 514.3 [M+H]+

109: To a solution of N4-(3-chloro-4-(pyridin-2-ylmethoxy)phenyl)-7-(2-morpholinoethoxy)quinazoline-4,6-diamine (200 mg, 394 umol, 1.00 eq), pyridine (62.4 mg, 789 umol, 63.7 uL, 2.00 eq) and 2-fluoroacrylic acid (107 mg, 1.18 mmol, 3.00 eq) in dimethyl formamide (3.00 mL) was added 1-(3-dimethylaminopropyl)-3-ethylcarbodiimide hydrochloride (454 mg, 2.37 mmol, 6.00 eq) at 25° C. in portions. The mixture was stirred at 25° C. for 12 h. The reaction mixture was filtered. The filtrate was purified by prep-HPLC (column: Xtimate C18 150*25 mm*5 um; mobile phase: [water (0.05% ammonia hydroxide v/v)-ACN]; B%: 37%-67%, 1 min) to give N-(4-((3-chloro-4-(pyridin-2-ylmethoxy)phenyl)amino)-7-(2-morpholinoethoxy)quinazolin-6-yl)-2-fluoroacrylamide 109 (32.12 mg, 54.9 umol, 14% yield, 99% purity) as an off-white solid. 1H NMR (400 MHz, CDCl3) δ=9.10 (br d, J=4.4 Hz, 1H), 9.03 (s, 1H), 8.67 (s, 1H), 8.62 (d, J=4.4 Hz, 1H), 7.90 (d, J=2.6 Hz, 1H), 7.83-7.74 (m, 1H), 7.69 (br d, J=7.6 Hz, 2H), 7.54 (dd, J=8.8, 2.6 Hz, 1H), 7.30 (s, 1H), 7.26 (br d, J=6.2 Hz, 1H), 7.04 (d, J=8.8 Hz, 1H), 5.99-5.80 (m, 1H), 5.37 (dd, J=15.2, 3.8 Hz, 1H), 5.32 (s, 2H), 4.38 (t, J=5.4 Hz, 2H), 3.80-3.73 (m, 4H), 2.94 (t, J=5.4 Hz, 2H), 2.66-2.60 (m, 4H). MS (ESI) m/z 579.4 [M+H]+

110: A mixture of N-(3-chloro-4-(pyridin-2-ylmethoxy) phenyl)-7-fluoro-6-nitroquinazolin-4-amine (2.00 g, 4.70 mmol, 1.00 eq), 1-methylpiperidin-4-ol (1.08 g, 9.39 mmol, 1.10 mL, 2.00 eq) and potassium tert-butoxide (2.11 g, 18.7 mmol, 4.00 eq) in dimethylsulfoxide (20.0 mL) was stirred at 25° C. for 1 h. To the mixture was added water (20 mL). The mixture was filtered. The filter cake was dried to give N-(3-chloro-4-(pyridin-2-ylmethoxy)phenyl)-7-((1-methylpiperidin-4-yl)oxy)-6-nitroquinazolin-4-amine (2.00 g, 3.84 mmol, 81% yield) as a yellow solid. 1H NMR (400 MHz, DMSO-d6) δ=10.02 (br s, 1H), 9.16 (s, 1H), 8.61 (br s, 2H), 8.01 (br s, 1H), 7.89 (br t, J=7.4 Hz, 1H), 7.69 (br d, J=8.2 Hz, 1H), 7.59 (br d, J=7.7 Hz, 1H), 7.50 (s, 1H), 7.42-7.33 (m, 1H), 7.28 (br d, J=8.9 Hz, 1H), 5.30 (s, 2H), 4.89 (br s, 1H), 2.55 (br s, 2H), 2.32 (br d, J=7.7 Hz, 2H), 2.18 (s, 3H), 1.97 (br s, 2H), 1.77 (br s, 2H). MS (ESI) m/z 521.3 [M+H]+

A mixture of N-(3-chloro-4-(pyridin-2-ylmethoxy)phenyl)-7-((1-methylpiperidin-4-yl)oxy)-6-nitroquinazolin-4-amine (1.60 g, 3.07 mmol, 1.00 eq), iron (857 mg, 15.3 mmol, 5.00 eq) and ammonium chloride (1.48 g, 27.6 mmol, 9.00 eq) in methanol (5.00 mL) and water (5.00 mL) was stirred at 80° C. for 2 h. The reaction mixture was concentrated to give a residue. The residue was added ethyl acetate (500 mL). The reaction mixture was filtered. The filtrate was concentrated to give N4-(3-chloro-4-(pyridin-2-ylmethoxy)phenyl)-7-((1-methylpiperidin-4-yl)oxy)quinazoline-4,6-diamine (1.50 g, crude) as a yellow solid. MS (ESI) m/z 491.3 [M+H]+

To a solution of N4-(3-chloro-4-(pyridin-2-ylmethoxy)phenyl)-7-((1-methylpiperidin-4-yl)oxy)quinazoline-4,6-diamine (500 mg, 1.02 mmol, 1 eq), pyridine (241 mg, 3.06 mmol, 3.00 eq) and acrylic acid (88.1 mg, 1.22 mmol, 1.20 eq) in dimethyl formamide (3.00 mL) was added 1-(3-dimethylaminopropyl)-3-ethylcarbodiimide hydrochloride (585 mg, 3.06 mmol, 3.00 eq) at 25° C. The reaction mixture was stirred at 25° C. for 1 h. The reaction mixture was filtered. The filtrate was purified by prep-HPLC (column: Phenomenex Synergi C18 150*30 mm*4 um; mobile phase: [water(0.225%FA)-ACN]; B%: 10%-40%, 10 min) and lyophilized to give N-(4-((3-chloro-4-(pyridin-2-ylmethoxy)phenyl)amino)-7-((1-methylpiperidin-4-yl)oxy)quinazolin-6-yl)acrylamide 110 (190.01 mg, 321 umol, 31% yield, 100% purity, FA) as a yellow solid. 1H NMR (400 MHz, DMSO-d6) δ=9.68 (br s, 1H), 9.53 (s, 1H), 8.83 (s, 1H), 8.60 (d, J=4.8 Hz, 1H), 8.49 (s, 1H), 8.21 (s, 1H), 8.00 (d, J=2.6 Hz, 1H), 7.89 (dt, J=1.7, 7.7 Hz, 1H), 7.70 (dd, J=2.6, 8.9 Hz, 1H), 7.59 (d, J=7.8 Hz, 1H), 7.37 (dd, J=5.1, 7.3 Hz, 1H), 7.32 (s, 1H), 7.25 (d, J=9.0 Hz, 1H), 6.71 (dd, J=10.3, 17.0 Hz, 1H), 6.33 (dd, J=1.8, 17.0 Hz, 1H), 5.83 (dd, J=1.8, 10.1 Hz, 1H), 5.29 (s, 2H), 4.80-4.67 (m, 1H), 2.76-2.64 (m, 2H), 2.34 (br dd, J=2.1, 4.0 Hz, 2H), 2.25 (s, 3H), 2.10-1.97 (m, 2H), 1.91-1.77 (m, 2H). MS (ESI) m/z 545.3 [M+H]+

111: A mixture of N-(3-chloro-4-(pyridin-2-ylmethoxy) phenyl)-7-(2-chloroethoxy)-6-nitroquinazolin-4-amine (1.00 g, 2.06 mmol, 1.00 eq), piperidin-4-ol (416 mg, 4.11 mmol, 2.00 eq), potassium carbonate (853 mg, 6.17 mmol, 3.00 eq) in dimethyl formamide (20.0 mL) was stirred at 80° C. for 5 h under nitrogen atmosphere. The reaction mixture was diluted with water (50 mL) and filtered. The filter cake was dried to give 1-(2-((4-((3-chloro-4-(pyridin-2-ylmethoxy)phenyl)amino)-6-nitroquinazolin-7-yl)oxy)ethyl) piperidin-4-ol (800 mg, crude) as a yellow solid. 1H NMR (400 MHz, CDCl3) δ=8.74 (s, 1H), 8.62 (d, J=4.8 Hz, 1H), 8.55 (s, 1H), 7.88 (d, J=2.6 Hz, 1H), 7.83-7.75 (m, 1H), 7.71-7.52 (m, 2H), 7.49 (dd, J=8.8, 2.6 Hz, 1H), 7.41 (s, 1H), 7.27 (br s, 1H), 7.05 (d, J=9.0 Hz, 1H), 5.33 (s, 2H), 4.49-4.33 (m, 2H), 3.75 (br s, 1H), 2.99-2.90 (m, 3H), 2.45-2.33 (m, 2H) 1.94 (br d, J=9.6 Hz, 1H), 1.56 (br s, 2H). MS (EST) m/z 551.2 [M+H]+

A mixture of 1-(2-((4-((3-chloro-4-(pyridin-2-ylmethoxy) phenyl)amino)-6-nitroquinazolin-7-yl)oxy)ethyl)piperidin-4-ol (400 mg, 726 umol, 1.00 eq), iron powder (202 mg, 3.63 mmol, 5.00 eq), ammonium chloride (194 mg, 3.63 mmol, 5.00 eq) in methanol (20.0 mL) and water (10.0 mL) was stirred at 80° C. for 2 h under nitrogen atmosphere. The reaction mixture was filtered and washed with methanol. The combined filtrate was concentrated under reduced pressure to give a residue. The residue was triturated with water (20 mL) and filtered. The filter cake was dried to give 1-(2-((6-amino-4-((3-chloro-4-(pyridin-2-ylmethoxy)phenyl)amino)quinazolin-7-yl)oxy)ethyl)piperidin-4-ol (300 mg, crude) as a yellow solid. MS (ESI) m/z 521.4 [M+H]+

To a solution of 1-(2-((6-amino-4-((3-chloro-4-(pyridin-2-ylmethoxy)phenyl)amino)quinazolin-7-yl)oxy)ethyl)piperidin-4-ol (200 mg, 384 umol, 1.00 eq), acrylic acid (41.5 mg, 576 umol, 39.5 uL, 1.50 eq) and pyridine (60.7 mg, 768 umol, 62.0 uL, 2.00 eq) in dimethyl formamide (3.00 mL) was added 1-(3-dimethylaminopropyl)-3-ethylcarbodiimide hydrochloride (368 mg, 1.92 mmol, 5.00 eq) at 25° C. in portions. The mixture was stirred at 25° C. for 1 h. The reaction mixture was filtered. The filtrate was purified by prep-HPLC (column: Xtimate C18 150*25 mm*5 um; mobile phase: [water (0.05% ammonia hydroxide v/v)-ACN]; B%: 29%-59%, 1 min) to afforded N-(4-((3-chloro-4-(pyridin-2-ylmethoxy)phenyl)amino)-7-(2-(4-hydroxypiperidin-1-yl)ethoxy)quinazolin-6-yl)acrylamide 111 (52.83 mg, 91.9 umol, 24% yield, 100% purity) as an off-white solid. 1H NMR (400 MHz, CDCl3) δ=9.15 (s, 1H), 9.11 (s, 1H), 8.64 (s, 1H), 8.62 (br d, J=4.8 Hz, 1H), 7.92 (d, J=2.6 Hz, 1H), 7.89 (s, 1H), 7.82-7.74 (m, 1H), 7.71-7.65 (m, 1H), 7.54 (dd, J=8.8, 2.8 Hz, 1H), 7.23-7.28 (m, 2H), 7.01 (d, J=8.8 Hz, 1H), 6.51 (d, J=6.2 Hz, 2H), 5.87-5.81 (m, 1H), 5.31 (s, 2H), 4.33 (t, J=5.3 Hz, 2H), 3.82 (br d, J=4.8 Hz, 1H), 2.92 (br t, J=5.2 Hz, 4H), 2.35 (br t, J=9.6 Hz, 2H), 1.97 (br d, J=9.4 Hz, 2H), 1.73-1.57 (m, 2H). MS (ESI) m/z 575.4 [M+H]+

112: Sodium (139 mg, 6.06 mmol, 144 uL, 5.00 eq) was dissolved in methanol (5.00 mL) at 0° C. and the mixture was stirred at 25° C. for 0.5 h. Then to the mixture was added (E)-4-bromobut-2-enoic acid (200 mg, 1.21 mmol, 1.00 eq) in portions. The mixture was stirred at 70° C. for 2 h. The mixture was concentrated to give residue. The residue was diluted with water (20 mL) and added 1 M hydrochloric acid to adjust pH=1. The mixture was extracted with ethyl acetate (3×20.0 mL). The combined organic layer was washed with brine (20 mL) and dried over sodium sulfate, filtered and concentrated to give (E)-4-methoxybut-2-enoic acid (90.0 mg, 775 umol, 64% yield) as a white solid. 1H NMR (400 MHz, DMSO-d6) δ=12.31 (br s, 1H), 6.81 (dt, J=15.8, 4.2 Hz, 1H), 5.91 (dt, J=15.8, 2.0 Hz, 1H), 4.06 (dd, J=4.2, 2.0 Hz, 2H), 3.29 (s, 3H).

To a solution of N4-(3-chloro-4-(pyridin-2-ylmethoxy)phenyl)-7-(2-morpholinoethoxy)quinazoline-4,6-diamine (200 mg, 394 umol, 1.00 eq), (E)-4-methoxybut-2-enoic acid (68.7 mg, 592 umol, 1.50 eq) and pyridine (93.6 mg, 1.18 mmol, 95.5 uL, 3.00 eq) in dimethyl formamide (3.00 mL) was added 1-(3-dimethyl aminopropyl)-3-ethylcarbodiimide hydrochloride (303 mg, 1.58 mmol, 4.00 eq) in portions. The mixture was stirred at 25° C. for 1 h. The mixture was filtered and the filtrate was purified by prep-HPLC (column: Phenomenex Synergi C18 150*30 mm*4 um; mobile phase: [water(0.225%FA)-ACN]; B%: 7%-37%, 10 min) and lyophilized to give (E)-N-(4-((3-chloro-4-(pyridin-2-ylmethoxy)phenyl)amino)-7-(2-morpholinoethoxy)quinazolin-6-yl)-4-methoxybut-2-enamide 112 (21.50 mg, 32.7 umol, 8% yield, 99% purity, FA) as a yellow solid. 1H NMR (400 MHz, DMSO-d6) δ=9.68 (s, 1H), 9.55 (s, 1H), 8.85 (s, 1H), 8.63-8.59 (m, 1H), 8.49 (s, 1H), 8.38 (s, 1H), 7.99 (d, J=2.6 Hz, 1H), 7.89 (td, J=7.8, 1.8 Hz, 1H), 7.70 (dd, J=9.0, 2.6 Hz, 1H), 7.59 (d, J=7.8 Hz, 1H), 7.38 (dd, J=7.0, 5.4 Hz, 1H), 7.30 (s, 1H), 7.25 (d, J=9.0 Hz, 1H), 6.90-6.81 (m, 1H), 6.57 (br d, J=15.6 Hz, 1H), 5.29 (s, 2H), 4.34 (t, J=5.8 Hz, 2H), 4.14 (dd, J=4.2, 1.8 Hz, 2H), 3.61-3.56 (m, 4H), 3.35 (br s, 3H), 2.84 (t, J=5.8 Hz, 2H), 2.53-2.52 (m, 4H). MS (ESI) m/z 605.4 [M+H]+

113: To a solution of 7-(((1R,5S,6s)-3-azabicyclo[3.1.0]hexan-6-ylethynyl)-N-(3-chloro-4-(pyridin-2-ylmethoxy)phenyl)-6-nitroquinazolin-4-amine (400 mg, 800 umol, 1.00 eq), oxetan-3-one (281 mg, 3.90 mmol, 5.00 eq) in methanol (10.0 mL) and tetrahydrofuran (10.0 mL) was added triethylamine (499 mg, 4.93 mmol, 6.32 eq), acetic acid (720 mg, 12.0 mmol, 15.4 eq) at 20° C. The mixture was stirred at 60° C. for 0.5 h. Sodium cyanoborohydride (245 mg, 3.90 mmol, 5.00 eq) was added at 20° C. The mixture was stirred at 60° C. for 1 h. The mixture was concentrated in vacuo to give a residue. The residue was extracted with ethyl acetate/methanol (5/1, 3×20.0 mL), washed with brine (3×20.0 mL), and dried over anhydrous sodium sulfate, filtered and concentrated to give N-(3-chloro-4-(pyridin-2-ylmethoxy)phenyl)-6-nitro-7-(((1R,5S,6s)-3-(oxetan-3-yl)-3-azabicyclo[3.1.0]hexan-6-yl)ethynyl)quinazolin-4-amine (0.350 g, 615 umol, 78% yield) as a brown solid. 1H NMR (400 MHz, DMSO-d6) δ=10.32 (s, 1H), 9.40 (s, 1H), 8.68 (s, 1H), 8.60 (br d, J=4.8 Hz, 1H), 8.00 (d, J=2.6 Hz, 1H), 7.91 (s, 1H), 7.89-7.84 (m, 1H), 7.70 (dd, J=2.5, 9.0 Hz, 1H), 7.58 (d, J=7.7 Hz, 1H), 7.37 (dd, J=5.1, 7.0 Hz, 1H), 7.30 (d, J=9.2 Hz, 1H), 5.30 (s, 2H), 4.53 (t, J=6.6 Hz, 2H), 4.43 (t, J=6.0 Hz, 2H), 3.72 (quip, J=6.3 Hz, 1H), 3.06 (d, J=9.2 Hz, 2H), 2.39 (br d, J=8.4 Hz, 2H), 2.00 (br s, 2H), 1.93 (br d, J=2.9 Hz, 1H). MS (ESI) m/z 569.4 [M+H]+

To a suspension of N-(3-chloro-4-(pyridin-2-ylmethoxy)phenyl)-6-nitro-7-(((1R,5S,6s)-3-(oxetan-3-yl)-3-azabicyclo[3.1.0]hexan-6-yl)quinazolin-4-amine (0.320 g, 562 umol, 1.00 eq), iron powder (220 mg, 3.94 mmol, 7.00 eq) in tetrahydrofuran (10.0 mL), methanol (10.0 mL) was added ammonium chloride (211 mg, 3.94 mmol, 7.00 eq) in water (5.00 mL). The mixture was stirred at 80° C. for 2 h. The mixture was added methanol (50.0 mL) and stirred at 55° C. for 0.5 h. After filtration, the filtrate was concentrated to afford a residue. The residue was triturated with water (10.0 mL), saturated sodium carbonate (5.00 mL) to give N4-(3-chloro-4-(pyridin-2-ylmethoxy)phenyl)-7-(((1R,5S,6s)-3-(oxetan-3-yl)-3-azabicyclo[3.1.0]hexan-6-yl)ethynyl)quinazoline-4,6-diamine (0.300 g, crude) as a yellow solid. MS (ESI) m/z 539.1 [M+H]+

To a solution of N4-(3-chloro-4-(pyridin-2-ylmethoxy)phenyl)-7-(((1R,5S,6s)-3-(oxetan-3-yl)-3-azabicyclo[3.1.0]hexan-6-yl)ethynyl)quinazoline-4,6-diamine (150 mg, 278 umol, 1.00 eq), acrylic acid (40.1 mg, 557 umol, 2.00 eq) and pyridine (44.0 mg, 557 umol, 2.00 eq) in dimethylformamide (3.00 mL) was added 1-(3-dimethylaminopropyl)-3-ethylcarbodiimide hydrochloride (267 mg, 1.39 mmol, 5.00 eq) at 25° C. in portions. The mixture was stirred at 25° C. for 0.5 h. The reaction mixture was filtered. The filtrate was purified by prep-HPLC (column: Xtimate C18 150*25 mm*5 um; mobile phase: [water (0.05% ammonia hydroxide v/v)-acetonitrile]; B%: 38%-68%, 1 min) to give N-(4-((3-chloro-4-(pyridin-2-ylmethoxy)phenyl)amino)-7-(((1R,5S,6s)-3-(oxetan-3-yl)-3-azabicyclo[3.1.0]hexan-6-yl)ethynyl)quinazolin-6-yl)acrylamide 113 (63.06 mg, 105 umol, 38% yield, 99% purity) as a yellow solid. 1H NMR (400 MHz, CDCl3) δ=9.07 (s, 1H), 8.66 (s, 1H), 8.61 (d, J=4.5 Hz, 1H), 8.33 (s, 1H), 8.03 (br s, 1H), 7.92-7.85 (m, 2H), 7.82-7.74 (m, 1H), 7.72-7.63 (m, 1H), 7.54 (dd, J=2.6, 8.8 Hz, 1H), 7.26 (br d, J=6.7 Hz, 1H), 7.00 (d, J=8.9 Hz, 1H), 6.56-6.47 (m, 1H), 6.38 (d, J=10.3 Hz, 1H), 5.93 (d, J=10.5 Hz, 1H), 5.30 (s, 2H), 4.75-4.66 (m, 2H), 4.60 (t, J=6.1 Hz, 2H), 3.79 (t, J=6.3 Hz, 1H), 3.15 (d, J=8.9 Hz, 2H), 2.47 (br d, J=8.4 Hz, 2H), 2.14 (t, J=3.1 Hz, 1H), 1.99 (br s, 2H). MS (ESI) m/z 593.4 [M+H]+

114: To a solution of N-(3-chloro-4-(pyridin-2-ylmethoxy)phenyl)-7-(2-chloroethoxy)-6-nitroquinazolin-4-amine (600 mg, 1.23 mmol, 1.00 eq) in dimethyl formamide (6.00 mL) was added potassium carbonate (511 mg, 3.70 mmol, 3.00 eq) and 4-methoxypiperidine (284 mg, 2.47 mmol, 2.00 eq), then the mixture was stirred at 80° C. for 8 h. The mixture was poured into water (30.0 mL) to give some precipitate. Then the precipitate was washed with water (5.00 mL) and dried under vacuum to give the crude product N-(3-chloro-4-(pyridin-2-ylmethoxy)phenyl)-7-(2-(4-methoxypiperidin-1-yl)ethoxy)-6-nitroquinazolin-4-amine (660 mg, 1.17 mmol, 94% yield) as a yellow solid was used into the next step directly without further purification. MS (ESI) m/z 565.3 [M+H]+

To a solution of N-(3-chloro-4-(pyridin-2-ylmethoxy)phenyl)-7-(2-(4-methoxypiperidin-1-yl)ethoxy)-6-nitroquinazolin-4-amine (560 mg, 991 umol, 1.00 eq) in methanol (6.00 mL) and water (1.50 mL) was added iron powder (276 mg, 4.96 mmol, 5.00 eq) and ammonium chloride (159 mg, 2.97 mmol, 3.00 eq). Then the mixture was stirred at 80° C. for 2 h. The mixture was filtered and the filtrate was extracted with ethyl acetate (4×5.00 mL). All organic phases were combined, washed with brine (5.0o mL), dried over anhydrous sodium sulfate and concentrated under vacuum to give the crude product N4-(3-chloro-4-(pyridin-2-ylmethoxy)phenyl)-7-(2-(4-methoxypiperidin-1-yl)ethoxy) quinazoline-4,6-diamine (270 mg, 388 umol, 39% yield, 77% purity) as a yellow solid was used into next step without further purification. MS (ESI) m/z 535.3 [M+H]+

To a solution of N4-(3-chloro-4-(pyridin-2-ylmethoxy) phenyl)-7-(2-(4-methoxypiperidin-1-yl)ethoxy)quinazoline-4,6-diamine (250 mg, 467 umol, 1.00 eq) in dimethyl formamide (2.00 mL) was added 1-(3-dimethylaminopropyl)-3-ethylcarbodiimide hydrochloride (358 mg, 1.87 mmol, 4.00 eq), acrylic acid (101 mg, 1.40 mmol, 96.2 uL, 3.00 eq) and pyridine (110 mg, 1.40 mmol, 113 uL, 3.00 eq) at 30° C. and the mixture was stirred at 30° C. for 1 h. The mixture was diluted with methanol (1.00 mL) and sent for purification. The mixture was purified by prep-HPLC (column: Xtimate C18 150*25 mm*5 um; mobile phase: [water (0.05% ammonia hydroxide v/v)-ACN]; B%: 43%-73%, 1 min) and prep-HPLC (column: Phenomenex Synergi C18 150*25*10 um; mobile phase: [water(0.225%FA)-ACN]; B%: 23%-53%, 9 min) again to give N-(4-((3-chloro-4-(pyridin-2-ylmethoxy)phenyl)amino)-7-(2-(4-methoxypiperidin-1-yl)ethoxy)quinazolin-6-yl)acrylamide 114 (27.56 mg, 43.39 umol, 9% yield, 100% purity, FA) as a yellow solid. 1H NMR (400 MHz, DMSO-d6) δ=9.68 (s, 1H), 9.61 (s, 1H), 8.85 (s, 1H), 8.61 (br d, J=4.2 Hz, 1H), 8.49 (s, 1H), 8.20 (s, 1H), 8.00 (d, J=2.6 Hz, 1H), 7.89 (dt, J=1.6, 7.6 Hz, 1H), 7.70 (dd, J=2.6, 8.8 Hz, 1H), 7.60 (d, J=7.8 Hz, 1H), 7.41-7.35 (m, 1H), 7.31 (s, 1H), 7.26 (d, J=9.0 Hz, 1H), 6.69 (dd, J=10.4, 16.8 Hz, 1H), 6.32 (dd, J=1.8. 17.2 Hz, 1H), 5.89-5.76 (m, 1H), 5.29 (s, 2H), 4.32 (br t, J=5.6 Hz, 2H), 3.22 (s, 3H), 3.17-3.15 (m, 1H), 2.82 (br t, J=5.6 Hz, 4H), 2.25 (br t, J=10.0 Hz, 2H), 1.82 (br d, J=9.8 Hz, 2H), 1.48-1.34 (m, 2H). MS (ESI) m/z 589.4 [M+H]+

115: Synthesized according to general procedure B, wherein in step B.1 ethane-1,2-diol was used; in step B.2 variant ii) was used, in step B.3 the nucleophile is 1-methyl-1,6-diazaspiro[3.3]heptane, in step B.4 variant ii) was used and variant i) was used in step B.5; and 29% overall yield from IX. $^1$H NMR (400 MHz, DMSO-d$_6$) δ=9.69 (s, 1H), 9.63 (s, 1H), 8.82 (s, 1H), 8.68-8.56 (m, 1H), 8.50 (s, 1H), 8.00 (d, J=2.6 Hz, 1H), 7.89 (br d, J=1.7 Hz, 1H), 7.70 (dd, J=2.6, 9.0 Hz, 1H), 7.60 (d, J=7.8 Hz, 1H), 7.42-7.33 (m, 1H), 7.26 (t, J=4.5 Hz, 2H), 6.68 (dd, J=10.3, 17.0 Hz, 1H), 6.33 (dd, J=1.8, 17.1 Hz, 1H), 5.88-5.77 (m, 1H), 5.29 (s, 2H), 4.19 (br t, J=5.3 Hz, 2H), 3.36-3.34 (m, 2H), 3.22 (br d, J=8.7 Hz, 2H), 2.96 (t, J=6.7 Hz, 2H), 2.82 (br t, J=5.3 Hz, 2H), 2.19 (s, 3H), 2.15 (t, J=6.7 Hz, 2H). MS (ESI) m/z 586.3 [M+H]$^+$ 116: To the mixture of N-(3-chloro-4-(pyridin-2-ylmethoxy)phenyl)-7-fluoro-6-nitroquinazolin-4-amine (1.00 g, 2.35 mmol, 1.00 eq), obtained by general procedure A (in step A.2 the free amine is 3-chloro-4-(pyridin-2-ylmethoxy) aniline) and tert-butyl 2-(hydroxymethyl)azetidin-1-carboxylate (660 mg, 3.52 mmol, 1.50 eq) in dimethylsulfoxide (15.0 mL) was added potassium 2-methylpropan-2-olate (1.05 g, 9.39 mmol, 4.00 eq) in several portions at 25° C. The mixture was stirred at 25° C. for 2 h. The reaction mixture was concentrated to dryness to give a residue. The residue was triturated with water (70.0 mL). After filtration, the filter cake was washed with water (20.0 mL), dried under vacuum to afford tert-butyl 2-(((4-((3-chloro-4-(pyridin-2-ylmethoxy)phenyl)amino)-6-nitroquinazolin-7-yl)oxy) methyl)azetidine-1-carboxylate (1.10 g, 1.85 mmol, 79% yield) as a yellow solid. $^1$H NMR (400 MHz, DMSO-d$_6$) δ=10.10 (br s, 1H), 9.25 (s, 1H), 8.65-8.57 (m, 1H), 8.01 (d, J=2.0 Hz, 1H), 7.89 (br t, J=7.2 Hz, 1H), 7.70 (dd, J=2.0, 8.9 Hz, 1H), 7.59 (br d, J=7.8 Hz, 1H), 7.52 (s, 1H), 7.43-7.35 (m, 1H), 7.29 (d, J=8.8 Hz, 1H), 5.30 (s, 2H), 4.65 (br d, J=9.0 Hz, 1H), 4.53 (br s, 1H), 4.36 (br d, J=9.4 Hz, 1H), 3.76 (br s, 2H), 2.35 (br d, J=10.5 Hz, 1H), 2.23 (br s, 1H), 1.30 (s, 10H). MS (ESI) m/z 615.2 [M+H]+

To the solution of tert-butyl 2-(((4-((3-chloro-4-(pyridin-2-ylmethoxy)phenyl)amino)-6-nitroquinazolin-7-yl)oxy) methyl)azetidine-1-carboxylate (1.10 g, 1.85 mmol, 1.00 eq) in dichloromethane (10.0 mL) was added hydrochloride/ ethyl acetate (4 M, 10.00 mL, 21.6 eq) at 25° C. The mixture was stirred at 25° C. for 2 h. The reaction mixture was concentrated to dryness to give a residue. The residue was triturated with saturated solution of sodium bicarbonate (30.0 mL). After filtration, the filter cake was washed with water (30.0 mL), dried in vacuum to give 7-(azetidin-2-ylmethoxy)-N-(3-chloro-4-(pyridin-2-ylmethoxy)phenyl)-6-nitroquinazolin-4-amine (880 mg, 1.79 mmol, 96% yield) as a yellow solid. $^1$H NMR (400 MHz, DMSO-d$_6$) δ=9.19 (br s, 1H), 8.60 (br d, J=4.4 Hz, 1H), 8.50 (br s, 1H), 7.98 (br d, J=3.8 Hz, 1H), 7.88 (br t, J=7.8 Hz, 1H), 7.69-7.56 (m, 2H), 7.42-7.33 (m, 2H), 7.22 (br d, J=8.8 Hz, 1H), 5.28 (s, 2H), 4.49-4.31 (m, 1H), 4.48-4.23 (m, 1H), 4.28-4.08 (m, 1H), 3.65-3.46 (m, 1H), 3.43-3.41 (m, 1H), 2.32-2.01 (m, 2H). MS (ESI) m/z 493.0 [M+H]$^+$ To the mixture of 7-(azetidin-2-ylmethoxy)-N-(3-chloro-4-(pyridin-2-ylmethoxy)phenyl)-6-nitroquinazolin-4-amine (500 mg, 1.01 mmol, 1.00 eq) and paraformaldehyde (153 mg, 5.10 mmol, 5.02 eq) in trifluoroethanol (6.00 mL) was added sodium borohydride (80.0 mg, 2.11 mmol, 2.08 eq) at 25° C. The mixture was stirred at 60° C. for 2 h. The mixture was concentrated to give a residue. The residue was triturated with water (15.0 mL). After filtration, the filter cake was washed with water (10.0 mL), dried under vacuum to afford N-(3-chloro-4-(pyridin-2-ylmethoxy)phenyl)-7-((1-methylazetidin-2-yl)methoxy)-6-nitroquinazolin-4-amine (500 mg, 986 umol, 97% yield) as a yellow solid. $^1$H NMR (400 MHz, DMSO-d6) δ=10.07 (s, 1H), 9.21 (s, 1H), 8.64-8.59 (m, 2H), 8.02 (d, J=2.4 Hz, 1H), 7.89 (dt, J=1.7, 7.7 Hz, 1H), 7.70 (dd, J=2.4, 9.0 Hz, 1H), 7.59 (d, J=7.8 Hz, 1H), 7.46 (s, 1H), 7.38 (dd, J=5.2, 6.6 Hz, 1H), 7.29 (d, J=9.2 Hz, 1H), 5.30 (s, 2H), 4.35-4.30 (m, 1H), 4.27-4.21 (m, 1H), 3.93-3.84 (m, 1H), 3.41-3.36 (m, 1H), 3.30-3.26 (m, 1H), 2.83-2.74 (m, 1H), 2.28 (s, 3H), 2.05-1.97 (m, 2H). MS (ESI) m/z 507.1 [M+H]$^+$ The mixture of N-(3-chloro-4-(pyridin-2-ylmethoxy)phenyl)-7-((1-methylazetidin-2-yl)methoxy)-6-nitroquinazolin-4-amine (600 mg, 1.18 mmol, 1.00 eq), iron powder (200 mg, 3.58 mmol, 3.03 eq) and ammonium chloride (320 mg, 5.98 mmol, 5.05 eq) in methnol (10.0 mL) and water (5.00 mL) was stirred at 80° C. for 2 h. The mixture was filtered, the filtrate was concentrated to afford a residue. The residue was triturated with water (20.0 mL). After filtration, the filter cake was washed with water (10.0 mL), dried in vacuum to give N4-(3-chloro-4-(pyridin-2-ylmethoxy)phenyl)-7-((1-methylazetidin-2-yl)methoxy)quinazoline-4,6-diamine (530 mg, 1.11 mmol, 93% yield) as a yellow solid.

1H NMR (400 MHz, DMSO-d6) δ=9.28 (br s, 1H), 8.60 (br s, 1H), 8.33 (s, 1H), 8.06 (br s, 1H), 7.89 (br t, J=7.2 Hz, 1H), 7.71 (br d, J=8.4 Hz, 1H), 7.59 (br d, J=7.6 Hz, 1H), 7.43 (br s, 1H), 7.38 (br s, 1H), 7.23 (br d, J=8.6 Hz, 1H), 7.09 (s, 1H), 5.30-5.21 (m, 4H), 4.16 (br d, J=3.6 Hz, 2H), 3.49-3.40 (m, 2H), 2.84-2.75 (m, 1H), 2.32 (s, 3H), 2.11-2.01 (m, 2H). MS (ESI) m/z 477.2 [M+H]$^+$

To the mixture of N4-(3-chloro-4-(pyridin-2-ylmethoxy) phenyl)-7-((1-methylazetidin-2-yl)methoxy)quinazoline-4, 6-diamine (200 mg, 419 umol, 1.00 eq) and triethylamine (128 mg, 1.26 mmol, 176 uL, 3.02 eq) in dimethylformamide (4.00 mL) was added prop-2-enoyl chloride (44.0 mg, 486 umol, 40.0 uL, 1.16 eq) at 0° C. The mixture was stirred at 25° C. for 1 h. The mixture was filtered. The filtrate was purified by pre-HPLC (column: Phenomenex Synergi C18 150*30 mm*4 um; mobile phase: [water(0.225%FA)-ACN]; B%: 5%-35%, 10 min) and (column: Waters Xbridge 150*25 5 u; mobile phase: [water (0.05% ammonia hydroxide v/v)-ACN]; B%: 35%-65%, 10 min) to give N-(4-((3-chloro-4-(pyridin-2-ylmethoxy)phenyl)amino)-7-((1-methylazetidin-2-yl)methoxy)quinazolin-6-yl)acrylamide 116 (25.7 mg, 48.5 umol, 11% yield) as a yellow solid.

1H NMR (400 MHz, DMSO-d6) δ=9.68 (br d, J=2.0 Hz, 2H), 8.79 (s, 1H), 8.64-8.57 (m, 1H), 8.50 (s, 1H), 8.00 (d, J=2.4 Hz, 1H), 7.89 (dt, J=1.6, 7.6 Hz, 1H), 7.71 (dd, J=2.4, 9.2 Hz, 1H), 7.60 (d, J=7.8 Hz, 1H), 7.38 (dd, J=5.2, 6.5 Hz, 1H), 7.30-7.23 (m, 2H), 6.64 (br dd, J=10.0, 17.2 Hz, 1H), 6.31 (dd, J=1.8, 17.2 Hz, 1H), 5.81 (dd, J=1.8, 10.2. Hz, 1H), 5.29 (s, 2H), 4.27-4.14 (m, 2H), 3.47-3.39 (m, 1H), 3.29 (br d, J=3.2 Hz, 1H), 2.81-2.73 (m, 1H), 2.28 (s, 3H), 2.08-1.97 (m, 2H). MS (ESI) m/z 531.1 [M+H]$^+$

Synthesis of tert-butyl 2-(hydroxymethyl)azetidine-1-carboxylate

To the mixture of 1-(tert-butoxycarbonyl)azetidine-2-carboxylic acid (1.00 g, 4.97 mmol, 1.00 eq) in tetrahydrofuran (10.0 mL) was added borane dimethyl sulfide complex (10.0 M, 1.99 mL, 4.00 eq) at 0° C. The mixture was stirred at 25° C. for 3 h. The reaction was quenched by methanol (20.0 mL) and the mixture was concentrated to dryness to give a residue. The residue was poured into water (40.0 mL) and extracted with ethyl acetate (3×20.0 mL). The combined organic layers were washed with brine (30.0 mL), dried over anhydrous sodium sulfate, filtered and concentrated to afford tert-butyl 2-(hydroxymethyl)azetidine-1-carboxylate (910 mg, 4.86 mmol, 98% yield) as a light brown oil. 1H NMR (400 MHz, CDCl3) δ=4.45 s, 1H), 3.94-3.85 (m, 1H), 3.84-3.69 (m, 4H), 2.24-2.13 (m, 1H), 2.01-1.89 (m, 1H), 1.47 (s, 9H).

117: To a suspension of 1-fluoro-2-methyl-4-nitro-benzene (5.00 g, 32.2 mmol, 1.00 eq), phenol (3.34 g, 35.5 mmol, 3.12 mL, 1.10 eq) in acetonitrile (50.0 mL) was added potassium carbonate (13.4 g, 96.7 mmol, 3.00 eq). The mixture was stirred at 80° C. for 12 h. The mixture was concentrated, diluted with water (50.0 mL), extracted with ethyl acetate (3×50.0 mL), washed with saturated sodium carbonate (3×20.0 mL), dried over anhydrous sodium sulfate, filtered and concentrated to afford 2-methyl-4-nitro-1-phenoxy-benzene (7.00 g, 30.5 mmol, 95% yield) as a yellow solid.

$^1$H NMR (400 MHz, DMSO-d$_6$) δ=8.23 (br d, J=2.1 Hz, 1H), 8.05 (dd, J=2.4, 9.0 Hz, 1H), 7.54-7.43 (m, 2H), 7.32-7.22 (m, 1H), 7.18-7.07 (m, 2H), 6.84 (d, J=9.0 Hz, 1H), 2.37 (s, 3H).

To a suspension of 2-methyl-4-nitro-1-phenoxy-benzene (4.00 g, 17.5 mmol, 1.00 eq) in methanol (30.0 mL) was added Pd/C (400 mg, 17.5 mmol, 10% purity). The mixture was degassed under vacuum and then stirred at 20° C. for 24 h under hydrogen (15 psi, balloon). The mixture was filtered, concentrated to afford 3-methyl-4-phenoxy-aniline (3.30 g, 16.6 mmol, 95% yield) as brown oil.

$^1$H NMR (400 MHz, DMSO-d$_6$) δ=7.30-7.23 (m, 2H), 6.98-6.92 (m, 1H), 6.80-6.73 (m, 2H), 6.67 (d, J=8.4 Hz, 1H), 6.49 (d, J=2.6 Hz, 1H), 6.42 (dd, J=2.7, 8.4 Hz, 1H), 4.91 (s, 2H), 1.96 (s, 3H).

To a suspension of 4-chloro-7-fluoro-6-nitro-quinazoline (3.43 g, 15.1 mmol, 1.00 eq) in iso-propanol (30.0 mL) was added 3-methyl-4-phenoxy-aniline (3.00 g, 15.1 mmol, 1.00 eq). The mixture was stirred at 80° C. for 2 h. The mixture was triturated with ethyl acetate (10.0 mL) to give a crude product. The crude product was diluted with saturated potassium carbonate (30.0 mL), extracted with ethyl acetate (3×30.0 mL), washed with brine (3×20.0 mL), dried over anhydrous sodium sulfate, filtered and concentrated to afford 7-fluoro-N-(3-methyl-4-phenoxy-phenyl)-6-nitro-quinazolin-4-amine (3.00 g, 7.69 mmol, 51% yield) as a red solid.

$^1$H NMR (400 MHz, DMSO-d$_6$) δ=10.45 (br s, 1H), 9.60 (d, J=8.1 Hz, 1H), 8.66 (s, 1H), 7.80 (d, J=12.6 Hz, 1H), 7.72 (d, J=2.3 Hz, 1H), 7.66 (dd, J=2.5, 8.7 Hz, 1H), 7.41-7.34 (m, 2H), 7.13-7.05 (m, 1H), 6.99 (d, J=8.7 Hz, 1H), 6.95-6.88 (m, 2H), 2.20 (s, 3H)

To a solution of 7-fluoro-N-(3-methyl-4-phenoxyphenyl)-6-nitroquinazolin-4-amine (3.00 g, 7.69 mmol, 1.00 eq) in dimethylformamide (30.0 mL) was added potassium acetate (3.77 g, 38.4 mmol, 5.00 eq) at 15° C. The mixture was stirred at 100° C. for 3 h. The mixture was concentrated to afford a residue. The residue was diluted with water (30.0 mL). After filtration, the filter cake was washed with water (10.0 mL), dried in vacuum to afford 4-((3-methyl-4-phenoxyphenyl)amino-6-nitroquinazolin-7-ol (2.80 g, crude) as a yellow solid. MS (ESI) m/z 389.2 [M+H]$^+$ To a solution of 4-((3-methyl-4-phenoxyphenyl)amino)-6-nitroquinazolin-7-ol (2.80 g, 7.20 mmol, 1.00 eq) and pyridine (2.85 g, 36.0 mmol, 2.90 mL, 5.00 eq) in dichloromethane (90.0 mL) was added triflic anhydride (4.06 g, 14.4 mmol, 2.37 mL, 2.00 eq) slowly at 0° C. The mixture was stirred at 25° C. for 2 h. The mixture was concentrated to afford a residue. The residue was purified by silica gel chromatography (petroleum ether/ethyl acetate=1/0-8/1) to afford 4-((3-methyl-4-phenoxyphenyl)amino)-6-nitroquinazolin-7-yl trifluoromethanesulfonate (1.23 g, crude) as a yellow solid.

$^1$H NMR (400 MHz, DMSO-d$_6$)δ=9.76 (d, J=2.6 Hz, 1H), 8.76 (d, J=3.2 Hz, 1H), 8.02 (br d, J=7.0 Hz, 1H), 7.73 (s, 1H), 7.67 (dd, J=2.3, 8.7 Hz, 1H), 7.45-7.32 (m, 2H), 7.13-7.05 (m, 1H), 7.00 (dd, J=2.1, 8.7 Hz, 1H) 6.94 (br d, J=8.6 Hz, 2H), 2.22 (s, 3H).

To a solution of tert-butyl 6-ethynyl-3-azabicyclo[3.1.0]hexane-3-carboxylate (438 mg, 2.11 mmol, 1.10 eq), 4-((3-methyl-4-phenoxyphenyl)amino)-6-nitroquinazolin-7-yl trifluoromethanesulfonate (1.00 g, 1.92 mmol, 1.00 eq), copper iodide (73.2 mg, 384 umol, 0.200 eq) and triethylamine (13.0 g, 128 mmol, 17.8 mL, 66.6 eq) in dimethylformamide (20.0 mL) was added tetrakis[triphenylphosphine]palladium (0) (222 mg, 192 umol, 0.100 eq) at 25° C. The mixture was stirred at 25° C. for 3 h. The reaction was concentrated to afford a residue. The residue was triturated with ethyl acetate (10.0 mL). After filtration, the filter cake was dried in vacuum to afford crude product. The crude product was purified by silica gel chromatography (petroleum ether/ethyl acetate=5/1 to 2/1) to afford (1R,5S,6s)-tert-butyl 6-((4-((3-methyl-4-phenoxyphenyl)amino)-6-nitroquinazolin-7-yl)ethynyl)-3-azabicyclo[3.1.0]hexane-3-carboxylate (950 mg, crude) as a yellow solid.

$^1$H NMR (400 MHz, DMSO-d$_6$) δ=10.29 (br s, 1H), 9.40 (s, 1H), 8.63 (s, 1H), 7.85 (s, 1H), 7.77-7.44 (m, 2H), 7.33 (br t, J=7.4 Hz, 2H), 7.07-7.00 (m, 1H), 6.94 (br d, J=8.6 Hz, 1H), 6.88 (br d, J=8.1 Hz, 2H), 3.53 (br d, J=10.6 Hz, 2H), 3.40-3.33 (m, 2H), 2.16 (s, 3H), 2.06 (br s, 2H), 1.44 (br s, 1H), 1.36 (s, 9H).

A mixture of (1R,5S,6s)-tert-butyl 6-((4-((3-methyl-4-phenoxyphenyl)amino)-6-nitroquinazolin-7-yl)ethynyl)-3-azabicyclo[3.1.0]hexane-3-carboxylate (890 mg, 1.54 mmol, 1.00 eq) in 4 M hydrochloride/ethyl acetate (7.00 mL) was stirred at 25° C. for 0.5 h. The mixture was concentrated to afford crude product. The crude product was purified by reversed phase (C18, 0.1% hydrochloric acid in water-acetonitrile) and lyophilized to afford 7-((1R,5S,6s)-3-azabicyclo[3.1.0]hexan-6-ylethynyl)-N-(3-methyl-4-phenoxyphenyl)-6-nitroquinazolin-4-amine (600 mg, crude) as a yellow solid.

$^1$H NMR (400 MHz, DMSO-$d_6$) δ=10.27 (br s, 1H), 9.37 (s, 1H), 8.61 (s, 1H), 8.16 (s, 1H), 7.83 (s, 1H), 7.68 (d, J=2.3 Hz, 1H), 7.62 (dd, J=2.3, 8.6 Hz, 1H), 7.34-7.26 (m, 2H), 7.02 (t, J=7.3 Hz, 1H), 6.92 (d, J=8.7 Hz, 1H), 6.86 (dd, J=0.9, 8.6 Hz, 2H), 2.92 (d, J=11.7 Hz, 2H), 2.68 (br d, J=11.2 Hz, 2H), 2.13 (s, 3H), 1.86 (br s, 2H), 1.56 (t, J=3.3 Hz, 1H).

To a solution of 7-((1R,5S,6s)-3-azabicyclo[3.1.0]hexan-6-ylethynyl)-N-(3-methyl-4-phenoxyphenyl)-6-nitroquinazolin-4-amine (400 mg, 837 umol, 1.00 eq) and paraformaldehyde (126 mg, 4.19 mmol, 115 uL, 5.00 eq) in trifluoroethanol (11.0 mL) was added sodium borohydride (63.4 mg, 1.68 mmol, 2.00 eq) at 60° C. The mixture was stirred at 60° C. for 12 h. The mixture was concentrated to afford a residue. The residue was diluted with saturated sodium carbonate (3.00 mL) and water (10.0 mL), extracted with ethyl acetate (3×20.0 mL). The combined organic layer was washed with water (20.0 mL), dried over anhydrous sodium sulfate, filtered and the filtrate was concentrated to afford 7-(((1R,5S,6s)-3-methyl-3-azabicyclo[3.1.0]hexan-6-yl)ethynyl)-N-(3-methyl-4-phenoxyphenyl)-6-nitroquinazolin-4-amine (400 mg, crude) as a yellow solid.

$^1$H NMR (400 MHz, DMSO-$d_6$) δ=10.33 (br s, 1H), 9.44 (s, 1H), 8.68 (s, 1H), 7.90 (s, 1H), 7.74 (s, 1H), 7.68 (dd, J=2.2, 8.6 Hz, 1H), 7.43-7.36 (m, 2H), 7.13-7.07 (m, 1H), 6.99 (d, J=8.8 Hz, 1H), 6.93 (d, J=7.8 Hz, 2H), 3.03 (d, J=9.2 Hz, 2H), 2.34-2.29 (m, 2H), 2.24 (s, 3H), 2.21 (s, 3H), 2.00-1.90 (m, 3H).

To a solution of 7-(((1R,5S,6s)-3-methyl-3-azabicyclo[3.1.0]hexan-6-yl)ethynyl)-N-(3-methyl-4-phenoxyphenyl)-6-nitroquinazolin-4-amine (350 mg, 712 umol, 1.00 eq) and ammonium chloride (430 mg, 8.05 mmol, 134 uL, 11.3 eq) in methanol (20.0 mL) and water (20.0 mL) was added iron powder (537 mg, 9.61 mmol, 13.5 eq) at 25° C. The mixture was heated to 80° C. and stirred at 80° C. for 1 h. The mixture was concentrated to afford a residue. The residue was diluted with water (20.0 mL), saturated sodium carbonate (1.00 mL), ethyl acetate (50.0 mL). The mixture was extracted with ethyl acetate (2×30.0 mL) and the combined organic layer was washed with water (10.0 mL), dried over anhydrous sodium sulfate, filtered. The filtrate was concentrated to afford 7-(((1R,5S,6s)-3-methyl-3-azabicyclo[3.1.0]hexan-6-yl)ethynyl)-N$^4$-(3-methyl-4-phenoxyphenyl)quinazoline-4,6-diamine (200 mg, crude) as a brown solid.

MS (ESI) m/z 462.3 [M+H]$^+$

To a solution of 7-(((1R,5S,6s)-3-methyl-3-azabicyclo[3.1.0]hexan-6-yl)ethynyl)-N$^4$-(3-methyl-4-phenoxyphenyl)quinazoline-4,6-diamine (200 mg, 433 nmol, 1.00 eq) and pyridine (0.500 M in dimethylformamide, 4.33 mL, 5.00 eq) in dimethylformamide (4.00 mL) was added 1-(3-dimethylaminopropyl)-3-ethylcarbodiimide hydrochloride (831 mg, 4.33 mmol, 10.0 eq) and acrylic acid (0.500 M in dimethylformamide, 4.33 mL, 5.00 eq, 2.41 mL, 1.20 eq) at 0° C. The mixture was stirred at 25° C. for 1 h. The mixture was filtered to afford a solution. The solution was purified by prep-HPLC (column: Waters Xbridge 150*25 5 u; mobile phase: [water (0.05% ammonia hydroxide v/v)-acetonitrile]; 62%-82%, 10 min) and lyophilized to afford N-(7-(((1R,5S,6s)-3-methyl-3-azabicyclo[3.1.0]hexan-6-yl)ethynyl)-4-((3-methyl-4-phenoxyphenyl)amino)quinazolin-6-yl)acrylamide (25.6 mg, 49.7 umol, 11% yield) as a white solid.

$^1$H NMR (400 MHz, DMSO-$d_6$) δ=9.85 (d, J=3.9 Hz, 2H), 8.74 (s, 1H), 8.54 (s, 1H), 7.81-7.73 (m, 2H), 7.69 (dd, J=2.5, 8.5 Hz, 1H), 7.40-7.33 (m, 2H), 7.07 (t, J=7.3 Hz, 1H), 6.97 (d, J=8.7 Hz, 1H), 6.94-6.89 (m, 2H), 6.64 (dd, J=10.2, 16.9 Hz, 1H), 6.34 (dd, J=1.8, 17.0 Hz, 1H), 5.86 (dd, J=1.8, 10.2 Hz, 1H), 3.02 (d, J=9.2 Hz, 2H), 2.31 (br d, J=8.6 Hz, 2H), 2.25 (s, 3H), 2.19 (s, 3H), 1.94 (br s, 2H), 1.92-1.89 (m, 1H). MS (ESI) m/z 516.3 [M+H]$^+$

118: Synthesized according to general procedure B, wherein in step B.1 propane-1,3-diol was used; in step B.2 variant ii) was used, in step B.3 the nucleophile is 3-methoxyazetidine, in step B.4 variant ii) was used and variant i) was used in step B.5; and 6% overall yield from III. $^1$H NMR (400 MHz, DMSO-$d_6$) δ=9.67 (s, 1H), 9.58 (s, 1H), 8.84 (s, 1H), 8.60 (d, J=4.5 Hz, 1H), 8.48 (s, 1H), 7.98 (d, J=2.4 Hz, 1H), 7.88 (dt, J=1.8, 7.7 Hz, 1H), 7.69 (dd, J=2.6, 8.9 Hz, 1H), 7.59 (d, J=7.8 Hz, 1H), 7.37 (dd, J=5.1, 7.1 Hz, 1H), 7.26 (s, 1H), 7.23 (s, 1H), 6.71 (br dd, J=10.2, 16.9 Hz, 1H), 6.31 (dd, J=1.8, 17.1 Hz, 1H), 5.88-5.75 (m, 1H), 5.28 (s, 2H), 4.21 (br t, J=6.3 Hz, 2H), 4.01-3.87 (m, 1H), 3.94 (quin, J=5.8 Hz, 1H), 3.51 (br dd, J=6.1, 7.9 Hz, 2H), 3.14 (s, 3H), 2.77 (dd, J=5.9, 7.8 Hz, 3H), 2.60-2.55 (m, 1H), 2.60-2.55 1H), 2.60-2.55 (m, 4H), 1.83 (quin, J=6.5 Hz, 2H). MS (ESI) m/z 575.4 [M+H]$^+$ 119: A mixture of N-(3-chloro-4-(pyridin-2-ylmethoxy)phenyl)-7-(2-chloroethoxy)-6-nitroquinazolin-4-amine (1.00 g, 2.06 mmol, 1.00 eq) (obtained from general procedure B [IX]), tert-butyl 2,6-diazaspiro[3.3]heptane-2-carboxylate (652 mg, 2.26 mmol, 1.10 eq, oxalic acid), potassium carbonate (1.14 g, 8.23 mmol, 4.00 eq) and potassium iodide (341 mg, 2.06 mmol, 1.00 eq) in acetonitrile (10.0 mL) was stirred at 110° C. for 12 h. The reaction was concentrated to give a residue. The residue was triturated with water (50.0 mL) to give tert-butyl 6-(2-((4-((3-chloro-4-(pyridin-2-ylmethoxy)phenyl)amino)-6-nitroquinazolin-7-yl)oxy)ethyl)-2,6-diazaspiro[3.3]heptane-2-carboxylate (1.20 g, crude) as a yellow solid. MS (ESI) m/z 648.3 [M+H]$^+$ A mixture of tert-butyl-(4-(4-((3-chloro-2-fluorophenyl)amino)-6-nitroquinazolin-7-yl)-2-methylbut-3-yn-2-yl)-2,6-diazaspiro[3.3]heptane-2-carboxylate (1.00 g, 1.54 mmol, 1.00 eq), iron (861 mg, 15.4 mmol, 10.0 eq) and ammonium chloride (825 mg, 15.4 mmol, 10.0 eq) in methanol (10.0 mL) and water (10.0 mL) was stirred at 80° C. for 1 h. The reaction mixture was concentrated to give a residue. The residue was purified by reversed-phase HPLC (0.1% NH$_3$.H$_2$O) and lyophilized to give tert-butyl 6-(4-(6-amino-4-((3-chloro-2-fluorophenyl)amino)quinazolin-7-yl)-2-methylbut-3-yn-2-yl)-2,6-diazaspiro[3.3]heptane-2-carboxylate (500 mg, 808 umol, 52% yield) as a yellow solid. $^1$H NMR (400 MHz, CDCl$_3$) δ=8.61 (d, J=4.6 Hz, 1H), 8.57 (s, 1H), 7.85 (d, J=2.4 Hz, 1H), 7.80-7.73 (m, 1H), 7.71-7.64 (m, 1H), 7.49 (dd, J=2.5, 8.9 Hz, 1H), 7.26 (br d, J=7.0 Hz, 1H), 7.16 (s, 1H), 7.07-6.98 (m, 2H), 6.94 (s, 1H), 5.31 (s, 2H), 4.18 (t, J=5.3 Hz, 2H), 4.02 (s, 4H), 3.48 (s, 4H), 2.93 (t, J=5.2 Hz, 2H), 1.45 (s, 9H).

To a solution of tert-butyl 6-(4-(6-amino-4-((3-chloro-2-fluorophenyl)amino)quinazolin-7-yl)-2-methylbut-3-yn-2-yl)-2,6-diazaspiro[3.3]heptane-2-carboxylate (200 mg, 323 umol, 1.00 eq) and triethylamine (65.5 mg, 647 umol, 2.00 eq) in dimethyl formamide (2.00 mL) was added acrylic anhydride (40.8 mg, 323 umol, 1.00 eq) at 25° C. The mixture was stirred at 25° C. for 0.5 h. The reaction mixture was quenched by addition water (10.0 mL) and extracted with ethyl acetate (3×30.0 mL). The combined organic layers were washed with brine (3×10.0 mL), dried over sodium sulfate, filtered and concentrated under reduced pressure to give tert-butyl 6-(2-((6-acrylamido-4-((3-chloro-4-(pyridine-2-ylmethoxy)phenyl)amino)quinazolin-7-yl)

oxy)ethyl)-2,6-diazaspiro[3.3]heptane-2-carboxylate (210 mg, crude) as a yellow solid. MS (ESI) m/z 672.3 [M+H]+

A mixture of tert-butyl 6-(2-(((6-acrylamido-4-((3-chloro-4-(pyridine-2-ylmethoxy)phenyl)amino)quinazolin-7-yl)oxy)ethyl)-2,6-diazaspiro[3.3]heptane-2-carboxylate (200 mg, 297 umol, 1.00 eq) and trifluoroacetic acid (616 mg, 5.40 mmol, 400 uL, 18.2 eq) in dichloromethane (2.00 mL) was stirred at 25° C. for 0.5 h. The residue was triturated with ethyl acetate (5.00 mL) and ethyl acetate (20.0 mL) to give N-(7-(2-(2,6-diazaspiro[3.3]heptan-2-yl)ethoxy)-4-((3-chloro-4-(pyridin-2-ylmethoxy)phenyl)amino)quinazolin-6-yl)acrylamide (200 mg, crude) as a yellow solid.

MS (ESI) m/z 572.3 [M+H]+

To a mixture of N-(7-(2-(2,6-diazaspiro[3.3]heptan-2-yl)ethoxy)-4-((3-chloro-4-(pyridine-2-ylmethoxy)phenyl)amino)quinazolin-6-yl)acrylamide (100 mg, 174 umol, 1.00 eq) and formaldehyde (26.2 mg, 874 umol, 5.00 eq) in 2,2,2-trifluoroethanol (1.00 mL) was added sodium borohydride (13.2 mg, 349 umol, 2.00 eq) at 40° C. The mixture was stirred at 40° C. for 0.5 h. The reaction mixture was concentrated to give a residue. The residue was purified by prep-HPLC (column: Xtimate C18 150*25 mm*5 um; mobile phase: [water (0.05% ammonia hydroxide v/v)-ACN]; B%: 50%-83%, 10 min) and lyophilized to give N-(4-((3-chloro-4-(pyridin-2-ylmethoxy)phenyl)amino)-7-(2-(6-methyl-2,6-diazaspiro[3.3]heptan-2-yl)ethoxy)quinazolin-6-yl)acrylamide 119 (5.95 mg, 10.2 umol, 5.8% yield, 100% purity) as a white solid. $^1$H NMR (400 MHz, CDCl$_3$) δ=9.12 (s, 1H), 9.06 (s, 1H), 8.64 (s, 1H), 8.62 (br d, J=4.8 Hz, 1H), 7.91 (d, J=2.6 Hz, 1H), 7.80-7.75 (m, 1H), 7.70-7.64 (m, 2H), 7.53 (dd, J=2.6, 8.9 Hz, 1H), 7.26 (s, 2H), 7.02 (d, J=8.8 Hz, 1H), 6.58-6.37 (m, 2H), 5.86 (dd, J=2.5, 9.0 Hz, 1H), 5.32 (s, 2H), 4.19 (t, J=5.1 Hz, 2H), 3.44 (s, 4H), 3.32 (s, 4H), 2.93 (t, J=5.1Hz, 2H), 2.30 (s, 3H). MS (ESI) m/z 586.3 [M+H]+

120: To a solution of N-(3-chloro-4-(pyridin-2-ylmethoxy)phenyl)-7-fluoro-6-nitroquinazolin-4-amine (1.00 g, 2.35 mmol, 1.00 eq) (obtained from general procedure A [III]) in dimethylsulfoxide (10.0 mL) was added tert-butyl 3-(2-hydroxyethyl)morpholine-4-carboxylate (815 mg, 3.52 mmol, 1.50 eq) and potassium tert-butoxide (790 mg, 7.05 mmol, 3.00 eq) at 30° C. The mixture was stirred at 30° C. for 3 h. The mixture was diluted with water (90.0 mL) and some solid was precipitated out. Filtered and the filter cake was dried to give tert-butyl 3-(2-((4-((3-chloro-4-(pyridin-2-ylmethoxy)phenyl)amino)-6-nitroquinazolin-7-yl)oxy)ethyl)morpholine-4-carboxylate (1.20 g, 1.80 mmol, 76% yield, 95% purity) as a yellow solid. $^1$H NMR (400 MHz, DMSO-d$_6$) δ=10.06 (br s, 1H), 9.20 (br s, 1H), 8.60 (br s, 2H), 8.08-7.82 (m, 2H), 7.76-7.51 (m, 2H), 7.38 (br s, 2H), 7.27 (br d, J=8.4 Hz, 1H), 5.29 (br s, 2H), 4.30 (br s, 2H), 4.10 (br d, J=4.0 Hz, 5H), 3.77 (br d, J=9.2 Hz, 2H), 3.62 (br s, 1H), 3.48 (br d, J=11.2 Hz, 2H), 2.36-2.20 (m, 1H), 2.08 (br s, 1H), 1.23 (br s, 9H). MS (ESI) m/z 637.0 [M+H]+

A solution of tert-butyl 3-(2-((4-((3-chloro-4-(pyridin-2-ylmethoxy)phenyl)amino)-6-nitroquinazolin-7-yl)oxy)ethyl)morpholine-4-carboxylate (1.20 g, 1.80 mmol, 1.00 eq) in dioxane hydrochloride (4.00 M, 450 uL, 1.00 eq) was stirred at 30° C. for 1 h. The mixture was concentrated in vacuo to give N$^4$-(3-chloro-4-(pyridin-2-ylmethoxy)phenyl)-7-(2-(morpholin-3-yl)ethoxy)quinazoline-4,6-diamine (1.00 g, 1.67 mmol, 92% yield, 95% purity, hydrochloride) as a white solid. MS (ESI) m/z 537.0 [M+H]+

To a solution of N$^4$-(3-chloro-4-(pyridin-2-ylmethoxy)phenyl)-7-(2-(morpholin-3-yl)ethoxy)quinazoline-4,6-diamine (1.00 g, 1.74 mmol, 1.00 eq, hydrochloride) in dichloromethane (10.0 mL) and methanol (10.0 mL) was added formaldehyde (184 mg, 2.27 mmol, 3.27 uL, 37% purity, 1.30 eq) and sodium borohydride acetate (554 mg, 2.62 mmol, 1.50 eq) at 30° C. The mixture was stirred at 30° C. for 18 h. The mixture was diluted with saturated sodium bicarbonate (30.0 mL), and then extracted with dichloromethane (3×50.0 mL). The combined organic phase was washed with brine (30.0 mL), dried over anhydrous sodium sulfate, filtered and concentrated in vacuum to give N-(3-chloro-4-(pyridin-2-ylmethoxy)phenyl)-7-(2-(4-methylmorpholin-3-yl)ethoxy)-6-nitroquinazolin-4-amine (900 mg, 1.62 mmol, 92% yield, 99% purity) as a yellow solid. $^1$H NMR (400 MHz, DMSO-d$_6$) δ=10.22 (br s, 1H), 9.29 (s, 1H), 8.66-8.55 (m, 2H), 8.03 (d, J=2.4 Hz, 1H), 7.89 (dt, J=1.6, 7.7 Hz, 1H), 7.71 (dd, J=2.4, 9.1 Hz, 1H), 7.59 (d, J=7.6 Hz, 1H), 7.43 (s, 1H), 7.38 (dd, J=5.2, 6.8 Hz, 1H), 7.28 (d, J=8.8 Hz, 1H), 5.30 (s, 2H), 4.38-4.30 (m, 2H), 4.23 (d, J=9.2 Hz, 1H), 4.12 (q, J=5.2 Hz, 1H), 4.02 (d, J=9.2 Hz, 1H), 3.78-3.70 (m, 1H), 3.70-3.60 (m, 1H), 3.55-3.44 (m, 1H), 3.20-3.15 (m, 4H), 2.96-2.70 (m, 2H). MS (ESI) m/z 550.1 [M+H]+

To a solution of N-(3-chloro-4-(pyridin-2-ylmethoxy)phenyl)-7-(2-(4-methylmorpholin-3-yl)ethoxy)-6-nitroquinazolin-4-amine (900 mg, 1.63 mmol, 1.00 eq) in methanol (1.00 mL) and water (1.00 mL) was added iron powder (456 mg, 8.17 mmol, 5.00 eq) and ammonium chloride (437 mg, 8.17 mmol, 5.00 eq) at 30° C. The mixture was stirred at 80° C. for 5 h. The mixture was diluted with saturated sodium bicarbonate solution (50.0 mL), and then extracted with ethyl acetate (2×50.0 mL). The combined organic phase was washed with brine (50.0 mL), dried over anhydrous sodium sulfate, filtered and concentrated in vacuum to give N$^4$-(3-chloro-4-(pyridin-2-ylmethoxy)phenyl)-7-(2-(4-methylmorpholin-3-yl)ethoxy)quinazoline-4,6-diamine (600 mg, 1.15 mmol, 70% yield, 100% purity) as a yellow solid. MS (ESI) m/z 521.3 [M+H]+

To a solution of acrylic acid (49.8 mg, 691 umol, 47.4 uL, 1.20 eq) in dimethyl formamide (2.00 mL) was added N$^4$-(3-chloro-4-(pyridin-2-ylmethoxy)phenyl)-7-(2-(4-methylmorpholin-3-yl)ethoxy)quinazoline-4,6-diamine (300 mg, 575 umol, 1.00 eq), 1-(3-dimethylaminopropyl)-3-ethylcarbodiimide hydrochloride (441 mg, 2.30 mmol, 4.00 eq) and pyridine (182 mg, 2.30 mmol, 186 uL, 4.00 eq) at 30° C. The mixture was stirred at 30° C. for 1 h. The mixture was concentrated in vacuo to give the crude product. The crude product was purified by prep-HPLC (water (10 mM ammonium bicarbonate)-acetonitrile]; B%: 37%-57%, 10 min) to give a yellow solid which was further purified by prep-HPLC (0.05% ammonia hydroxide v/v)-acetonitrile]; B%: 30%-60%, 10 min) to give N-(4-((3-chloro-4-(pyridin-2-ylmethoxy)phenyl)amino)-7-(2-(4-methylmorpholin-3-yl)ethoxy)quinazolin-6-yl)acrylamide 120 (36.52 mg, 63.51 umol, 11% yield, 100% purity) as a white solid. $^1$H NMR (400 MHz, CDCl$_3$) δ=9.10 (s, 1H), 8.64 (s, 1H), 8.61 (d, J=5.2 Hz, 1H), 8.34 (s, 1H), 7.90 (d, J=2.4 Hz, 1H), 7.80-7.73 (m, 2H), 7.70-7.65 (m, 1H), 7.56-7.51 (m, 1H), 7.26-7.23 (m, 2H), 7.02 (d, J=8.8 Hz, 1H), 6.55-6.47 (m, 1H), 6.39-6.28 (m, 1H), 5.88 (d, J=11.2 Hz, 1H), 5.31 (s, 2H), 4.39-4.20 (m, 2H), 3.88-3.79 (m, 2H), 3.76-3.66 (m, 1H), 3.53 (dd, J=8.8, 11.2 Hz, 1H), 2.78 (td, J=3.2, 11.9 Hz, 1H), 2.49-2.40 (m, 2H), 2.39 (s, 3H), 2.21-2.06 (m, 2H). MS (ESI) m/z 575.3 [M+H]+

121: Synthesized according to general procedure A, wherein in step A.2 H$_2$N-X is 2-(4-amino-2-chlorophenyl)-1-(pyridin-2-yl)ethanone; in step A.3 the NH nucleophile is (R)-1-methylpyrrolidin-3-ol; variant ii) was used in step A.4; and variant iii) was used in step A.5; and 3% overall yield from II. $^1$H NMR (400 MHz, CDCl$_3$) δ=9.15 (s, 1H), 8.87 (br s, 1H), 8.77 (br d, J=4.8 Hz, 1H), 8.68 (s, 1H), 8.15-8.09 (m, 1H), 8.06 (d, J=2.0 Hz, 1H), 7.91-7.85 (m, 2H), 7.64 (dd, J=8.4, 2.2 Hz, 1H), 7.54 (dd, J=7.0, 5.4 Hz, 1H), 7.32 (d, J=8.3 Hz, 1H), 7.18 (s, 1H), 6.51 (br d, J=4.6 Hz, 2H), 5.90-5.81 (m, 1H), 5.10 (br s, 1H), 4.74 (s, 2H), 3.29-3.09 (m, 2H), 2.70 (br d, J=6.4 Hz, 1H), 2.60-2.52 (m, 1H), 2.50 (s, 3H), 2.45-2.37 (m, 1H), 2.24-2.12 (m, 1H). MS (ESI) m/z 543.2 [M+H]$^+$ Synthesis of 2-(4-amino-2-chlorophenyl)-1-(pyridin-2-yl)ethanone To a solution of 1-(pyridin-2-yl)ethanone (5.00 g, 41.3 mmol, 1.00 eq) and 1-chloro-3-nitrobenzene (13.0 g, 82.5 mmol, 2.00 eq) in dimethylsulfoxide (100 mL) was added sodium tert-butoxide (4.76 g, 49.5 mmol, 1.20 eq) at 25° C. The mixture was stirred at 25° C. for 1 h.

The reaction mixture was diluted with water (50.0 mL) and extracted with ethyl acetate (3×50.0 mL). The combined organic layers were washed with brine (50.0 mL), dried over sodium sulfate, filtered and concentrated under reduced pressure to give a residue. The residue was purified by column chromatography (SiO$_2$, Petroleum ether/Ethyl acetate=1/0 to 3/1) to give 2-(2-chloro-4-nitrophenyl)-1-(pyridin-2-yl)ethanone (3.50 g, 10.5 mmol, 25% yield, 83% purity) as a yellow solid. $^1$H NMR (400 MHz, CDCl$_3$) δ=8.71-8.64 (m, 1H), 8.23 (d, J=2.4 Hz, 1H), 8.07-7.99 (m, 2H), 7.82 (dt, J=1.6, 7.6 Hz, 1H), 7.48 (ddd, J=1.0, 4.8, 7.6 Hz, 1H), 7.41 (d, J=8.4 Hz, 1H). MS (ESI) m/z 277.1 [M+H]$^+$ To a solution of 2-(2-chloro-4-nitrophenyl)-1-(pyridin-2-yl)ethanone (500 mg, 1.50 mmol, 1.00 eq) in ethyl alcohol (10.0 mL) and hydrochloric acid (10.0 mL) was added dihydrate tin chloride (1.35 g, 6.00 mmol, 4.00 eq) at 25° C. The mixture was stirred at 50° C. for 1 h. The reaction mixture was diluted with water (20.0 mL) and to the mixture was added sodium carbonate to pH=8~9. Then it was extracted with ethyl acetate (3×50.0 mL). The combined organic layers were concentrated under reduced pressure to give a residue. The residue was purified by column chromatography (SiO$_2$, Petroleum ether/Ethyl acetate=10/1 to 1/1) to give 2-(4-amino-2-chlorophenyl)-1-(pyridin-2-yl)ethanone (200 mg, 405 umol, 27% yield) as a yellow solid. $^1$H NMR (400 MHz, CDCl$_3$) δ=8.87-8.64 (m, 1H), 8.20-8.00 (m, 1H), 7.87 (dt, J=1.6, 7.6 Hz, 1H), 7.51 (ddd, J=1.2, 4.8, 7.6 Hz, 1H), 7.07 (d, J=8.2 Hz, 1H), 6.78 (d, J=2.4 Hz, 1H), 6.59 (dd, J=2.4, 8.0 Hz, 1H), 4.62 (s, 2H). MS (ESI) m/z 247.1 [M+H]$^+$ 122: A mixture of N-(3-chloro-4-(pyridin-2-ylmethoxy)phenyl)-7-fluoro-6-nitroquinazolin-4-amine (230 mg, 1.01 mmol, 1.00 eq) (obtained via general procedure A [III]), tert-butyl 1-(hydroxymethyl)-7-azabicyclo[2.2.1]heptane-7-carboxylate (0.430 g, 1.01 mmol, 1.00 eq) and potassium tert-butoxide (227 mg, 2.02 mmol, 2.00 eq) in dimethylsulfoxide (10.0 mL) was stirred at 25° C. for 2 h. The reaction mixture was diluted with water (15.0 mL) and extracted with ethyl acetate (3×50.0 mL). The combined organic layers were washed with brine (20.0 mL), dried over anhydrous sodium sulfate, filtered and concentrated under reduced pressure to afford tert-butyl 1-(((4-((3-chloro-4-(pyridin-2-ylmethoxy)phenyl)amino)-6-nitroquinazolin-7-yl)oxy)methyl)-7-azabicyclo[2.2.1]heptane-7-carboxylate (0.600 g, crude) as a yellow solid. $^1$H NMR (400 MHz, CDCl$_3$) δ=9.41 (br s, 1H), 9.25 (s, 1H), 8.78 (s, 1H), 8.66 (s, 1H), 8.59 (s, 1H), 7.78-7.77 (m, 1H), 7.69 (d, J=1.6 Hz, 1H), 7.56 (s, 1H), 7.53-7.51 (m, 1H), 7.18 (br s, 1H), 6.93-6.90 (m, 1H), 5.22 (s, 2H), 4.73 (s, 2H), 3.84 (br d, J=5.0 Hz, 1H), 1.77 (br d, J=3.9 Hz, 4H), 1.71-1.65 (m, 4H), 1.38 (s, 9H).

A mixture of tert-butyl 1-(((4-((3-chloro-4-(pyridin-2-ylmethoxy)phenyl)amino)-6-nitroquinazolin-7-yl oxy)methyl)-7-azabicyclo[2.2.1]heptane-7-carboxylate (0.700 g, 1.11 mmol, 1.00 eq) in hydrochloric acid/ethyl acetate (10.0 mL) was stirred at 25° C. for 0.5 h. The reaction mixture was concentrated under reduced pressure to afford 7-(7-azabicyclo[2.2.1]heptan-1-ylmethoxy)-N-(3-chloro-4-(pyridin-2-ylmethoxy)phenyl)-6-nitroquinazolin-4-amine (0.7 g, crude, hydrochloride) as a yellow solid. MS (ESI) m/z 533.3 [M+H]$^+$ To a solution of 7-(7-azabicyclo[2.2.1]heptan-1-ylmethoxy)-N-(3-chloro-4-(pyridin-2-ylmethoxy)phenyl)-6-nitroquinazolin-4-amine (0.700 g, 1.23 mmol, 1.00 eq, hydrochloride) and paraformaldehyde (185 mg, 6.15 mmol, 169 uL, 5.00 eq) in trifluoroethanol (10.0 mL) was added sodium borohydride (93.0 mg, 2.46 mmol, 2.00 eq). The mixture was stirred at 60° C. for 12 h. The reaction mixture was concentrated under reduced pressure to give a residue. The residue was purified by reversed phase chromatography (column: C18, 80 g; condition: H$_2$O-0.1% NH$_3$.H$_2$O—CH$_3$CN) and lyophilized to afford N-(3-chloro-4-(pyridin-2-ylmethoxy)phenyl)-7-((7-methyl-7-azabicyclo[2.2.1]heptan-1-yl)methoxy)-6-nitroquinazolin-4-amine (0.200 g, 366 umol, 30% yield) as a yellow solid. $^1$H NMR (400 MHz, CDCl$_3$) δ=8.60 (s, 1H), 8.50-8.46 (m, 1H), 8.43 (s, 1H), 7.73 (d, J=2.6 Hz, 1H), 7.68-7.62 (m, 1H), 7.56-7.46 (m, 2H), 7.34 (dd, J=2.7, 8.8 Hz, 1H), 7.29 (s, 1H), 7.12 (br s, 1H), 6.90 (d, J=8.9 Hz, 1H), 5.18 (s, 2H), 4.27 (s, 2H), 3.20-3.13 (m, 1H), 2.16 (s, 3H), 1.87-1.71 (m, 4H), 1.46-1.41 (m, 2H), 1.37-1.29 (m, 2H).

A mixture of N-(3-chloro-4-(pyridin-2-ylmethoxy)phenyl)-7-((7-methyl-7-azabicyclo[2.2.1]heptan-1-yl)methoxy)-6-nitroquinazolin-4-amine (0.200 g, 366 umol, 1.00 eq), ammonium chloride (58.7 mg, 1.10 mmol, 3.00 eq) and ferrous powder (61.3 mg, 1.10 mmol, 3.00 eq) in a mixture solvent of methanol (3.00 mL) and water (3.00 mL) was stirred at 80° C. for 5 h. The reaction mixture was filtered and concentrated under reduced pressure to give a residue. The residue was purified was by reversed phase chromatography (column: C18, 80 g; condition: H$_2$O-0.1% NH$_3$.H$_2$O—CH$_3$CN) and lyophilized to afford N$^4$-(3-chloro-4-(pyridin-2-ylmethoxy)phenyl)-7-((7-methyl-7-azabicyclo[2.2.1]heptan-1-yl)methoxy)quinazoline-4,6-diamine (150 mg, 290 umol, 79% yield) as a yellow solid.

$^1$H NMR (400 MHz, CDCl$_3$) δ=8.47 (d, J=4.5 Hz, 1H), 8.43 (s, 1H), 7.72 (d, J=2.7 Hz, 1H), 7.66-7.59 (m, 1H), 7.56-7.51 (m, 1H), 7.35 (dd, J=2.6, 8.9 Hz, 1H), 7.12-7.09 (m, 1H), 7.08 (s, 1H), 6.88 (d, J=8.9 Hz, 1H), 6.78 (s, 1H), 6.76 (s, 1H), 5.17 (s, 2H), 4.35 (br s, 2H), 4.17 (s, 2H), 3.24-3.19 (m, 1H), 2.14 (s, 3H), 1.86-1.73 (m, 4H), 1.44-1.32 (m, 4H).

A mixture of N$^4$-(3-chloro-4-(pyridin-2-ylmethoxy)phenyl)-7-((7-methyl-7-azabicyclo[2.2.1]heptan-1-yl)methoxy)quinazoline-4,6-diamine (0.150 g, 290 umol, 1.00 eq), acrylic acid (41.8 mg, 580 umol, 39.8 uL, 2.00 eq), 1-ethyl-3-(3-dimethylamino-propyl)-carbodiimide hydrochloride (167 mg, 870 umol, 3.00 eq) and pyridine (68.9 mg, 870 umol, 70.3 uL, 3.00 eq) in dimethylformamide (2.00 mL) was stirred at 25° C. for 10 h. The reaction mixture was extracted with ethyl acetate (3×35.0 mL). The combined organic layers were washed with brine (15.0 mL), dried over anhydrous sodium sulfate, filtered and concentrated under reduced pressure to give a residue. The residue was purified by prep-HPLC (column: Xtimate C18 150×25 mm×5 um; mobile phase: [water (0.05% ammonia hydroxide v/v)-ACN]; B%: 47%-77%, 10 min) and lyophilized to afford N-(4-(((3-chloro-4-(pyridin-2-ylmethoxy)phenyl)amino)-7-

((7-methyl-7-azabicyclo[2.2.1]heptan-1-yl)methoxy)quinazolin-6-yl)acrylamide 122 (37.02 mg, 64.2 umol, 31% yield, 99% purity) as a yellow solid. $^1$H NMR (400 MHz, CDCl$_3$) δ=9.82 (s, 1H), 9.17 (s, 1H), 8.63 (s, 1H), 8.61 (br d, J=4.8 Hz, 1H), 7.96-7.82 (m, 2H), 7.81-7.73 (m, 1H), 7.68 (d, J=7.8 Hz, 1H), 7.53 (dd, J=2.6, 8.9 Hz, 1H), 7.28-7.24 (m, 1H), 6.99 (d, J=8.9 Hz, 1H), 6.74-6.62 (m, 1H), 6.53-6.42 (m, 1H), 5.76 (dd, J=1.4, 10.2 Hz, 1H), 5.30 (s, 2H), 4.29 (s, 2H), 3.46-3.32 (m, 1H), 2.24 (s, 3H), 1.99 (br s, 4H), 1.53 (br d, J=7.3 Hz, 4H). MS (ESI) m/z 571.4 [M+H]$^+$ Synthesis of tert-butyl 1-(hydroxymethyl)-7-azabicyclo[2.2.1]heptane-7-carboxylate To a solution of text-butyl 1-formyl-7-azabicyclo[2.2.1]heptane-7-carboxylate (0.300 g, 1.33 mmol, 1.00 eq) in methanol (2.00 mL) was added sodium borohydride (60.5 mg, 1.60 mmol, 1.20 eq) slowly. The mixture was stirred at 0° C. for 1 h. The reaction mixture was quenched by saturated aqueous solution of sodium bicarbonate (5.00 mL) and extracted with ethyl acetate (3×30.0 mL). The combined organic layers were washed with brine (10 mL), dried over anhydrous sodium sulfate, filtered and concentrated under reduced pressure to afford tert-butyl 1-(hydroxymethyl)-7-azabicyclo[2.2.1]heptane-7-carboxylate (290 mg, 1.28 mmol, 96% yield) as a yellow oil. $^1$H NMR (400 MHz, CDCl$_3$) δ=4.17 (t, J=4.7 Hz, 1H), 3.84 (d, J=7.1 Hz, 2H), 1.84-1.75 (m, 2H), 1.74-1.67 (m, 2H), 1.43-1.39 (m, 1H), 1.38 (s, 9H), 1.36-1.28 (m, 3H).

123: To a solution of 3-chloro-4-(pyridin-2-ylmethoxy)phenyl)-7-fluoro-6-nitroquinazolin-4-amine (0.500 g, 1.17 mmol, 1.00 eq) (obtained via general procedure A [III]) and tert-butyl 3-(hydroxymethyl)azetidine-1-carboxylate (263 mg, 1.41 mmol, 1.20 eq) in dimethyl sulfoxide (10.0 mL) was added potassium tert-butoxide (527 mg, 4.70 mmol, 4.00 eq) in portions at 25° C. The mixture was stirred at 25° C. for 2 h. The reaction mixture was diluted with water (100 mL) and filtered. Then the filter cake was dried to give tert-butyl 3-(((4-((3-chloro-4-(pyridin-2-ylmethoxy)phenyl)amino)-6-nitroquinazolin-7-yl)oxy)methyl)azetidine-1-carboxylate (480 mg, crude) as a yellow solid. $^1$H NMR (400 MHz, DMSO-d$_6$) δ=10.09 (br s, 1H), 9.22 (s, 1H), 8.68-8.51 (m, 2H), 8.01 (d, J=2.0 Hz, 1H), 7.94-7.84 (m, 1H), 7.70 (dd, J=2.0, 9.0 Hz, 1H), 7.59 (d, J=7.8 Hz, 1H), 7.48 (s, 1H), 7.38 (dd, J=5.2, 6.8 Hz, 1H), 7.29 (d, J=9.2 Hz, 1H), 5.30 (s, 2H), 4.43 (br d, J=6.0 Hz, 2H), 3.96 (br s, 2H), 3.77 (br s, 2H), 3.11-2.97 (m, 1H), 1.40 (s, 9H). MS (ESI) m/z 593.2 [M+H]$^+$ The mixture of tert-butyl 3-(((4-((3-chloro-4-(pyridin-2-ylmethoxy)phenyl)amino)-6-nitroquinazolin-7-yl)oxy)methyl)azetidine-1-carboxylate (300 mg, 506 umol, 1.00 eq), iron powder (113 mg, 2.02 mmol, 4.00 eq) and ammonium chloride (140 mg, 2.62 mmol, 5.17 eq) in methanol (10.0 mL) and water (5.00 mL) was stirred at 80° C. for 2 h. The mixture was filtered, the filtrate was concentrated to afford a residue. The residue was triturated with water (20.0 mL). After filtration, the filter cake was washed with water (10.0 mL), dried in vacuum to give tert-butyl 3-(((6-amino-4-((3-chloro-4-(pyridin-2-ylmethoxy)phenyl)amino)quinazolin-7-yl)oxy)methyl)azetidine-1-carboxylate (280 mg, 497 umol, 98% yield) as a brown solid. MS (ESI) m/z 563.4 [M+H]$^+$ To the mixture of tert-butyl 3-(((6-amino-4-((3-chloro-4-(pyridin-2-ylmethoxy)phenyl)amino)quinazolin-7-yl)oxy)methyl)azetidine-1-carboxylate (200 mg, 355 umol, 1.00 eq) and triethylamine (109 mg, 1.08 mmol, 150 uL, 3.04 eq) in tetrahydrofuran (3.00 mL) was added acrylic anhydride (90.0 mg, 714 umol, 2.01 eq) at 25° C. The mixture was stirred at 25° C. for 2 h. The reaction mixture was poured into water (20.0 mL) and extracted with ethyl acetate (3×10.0 mL). The combined organic layers were washed with brine (10.0 mL), dried over anhydrous sodium sulfate, filtered and concentrated to afford a residue. The residue was purified by prep-TLC (methanol/dichloromethane=10/1) to afford tert-butyl 3-(((6-acrylamido-4-((3-chloro-4-(pyridin-2-ylmethoxy)phenyl)amino)quinazolin-7-yl)oxy)methyl)azetidine-1-carboxylate (85.0 mg, 138 umol, 39% yield) as a brown solid. $^1$H NMR (400 MHz, DMSO-d$_6$) δ=9.70 (s, 1H), 9.55 (s, 1H), 8.83 (s, 1H), 8.61 (d, J=4.4 Hz, 1H), 8.50 (s, 1H), 8.00 (d, J=2.4 Hz, 1H), 7.89 (dt, J=1.6, 7.6 Hz, 1H), 7.70 (dd, J=2.4, 9.2 Hz, 1H), 7.59 (d, J=7.6 Hz, 1H), 7.38 (dd, J=5.2, 7.2 Hz, 1H), 7.32 (s, 1H), 7.26 (d, J=9.2 Hz, 1H), 6.66 (dd, J=10.4, 17.2 Hz, 1H), 6.31 (dd, J=1.6, 17.2 Hz, 1H), 5.85-5.77 (m, 1H), 5.29 (s, 2H), 4.37 (d, J=6.4 Hz, 2H), 3.98 (br s, 2H), 3.77 (br s, 2H), 3.10-3.02 (m, 1H), 1.39 (s, 9H). MS (ESI) m/z 617.3 [M+H]$^+$ To the mixture of tert-butyl 3-(((6-acrylamido-4-((3-chloro-4-(pyridin-2-ylmethoxy)phenyl)amino)quinazolin-7-yl)oxy)methyl)azetidine-1-carboxylate (50.0 mg, 81.0 umol, 1.00 eq) in dichloromethane (1.00 mL) was added trifluoroacetic acid (508 mg, 4.46 mmol, 330 uL, 55.0 eq) at 25° C. The mixture was stirred at 25° C. for 0.5 h. The mixture was concentrated to dryness to give N-(7-(azetidin-3-ylmethoxy)-4-((3-chloro-4-(pyridin-2-ylmethoxy)phenyl)amino)quinazolin-6-yl)acrylamide (50.0 mg, crude) as a brown solid which was used to next step without purification. MS (ESI) m/z 517.3 [M+H]

To the mixture of N-(7-(azetidin-3-ylmethoxy)-4-((3-chloro-4-(pyridin-2-ylmethoxy)phenyl)amino)quinazolin-6-yl)acrylamide (50.0 mg, 96.7 umol, 1.00 eq) and paraformaldehyde (15.0 mg, 500 umol, 13.8 uL, 5.17 eq) in trifluoroethanol (1.00 mL) was added sodium borohydride (8.00 mg, 211 umol, 2.19 eq) at 25° C. The mixture was stirred at 60° C. for 1 h and quenched by saturated ammonium chloride solution (1.00 mL). The mixture was purified by prep-HPLC (column: Xtimate C18 150*25 mm*5 um; mobile phase: [water (0.05% ammonia hydroxide v/v)-ACN]; B%: 50%-80%, 10 min) to give N-(4-((3-chloro-4-(pyridin-2-ylmethoxy)phenyl)amino)-7-((1-methylazetidin-3-yl)methoxy)quinazolin-6-yl) Acrylamide 123 (14.9 mg, 27.8 umol, 29% yield, 99% purity) as a white solid.

$^1$H NMR (400 MHz, DMSO-d$_6$) δ=9.67 (br d, J=15.2 Hz, 2H), 8.84 (s, 1H), 8.60 (d, J=4.0 Hz, 1H), 8.48 (br s, 1H), 7.99 (br d, J=2.0 Hz, 1H), 7.89 (dt, J=1.6, 7.6 Hz, 1H), 7.69 (br d, J=8.0 Hz, 1H), 7.60 (d, J=7.6 Hz, 1H), 7.38 (dd, J=5.2, 6.5 Hz, 1H), 7.29-7.22 (m, 2H), 6.65 (br dd, J=10.4, 17.1 Hz, 1H), 6.32 (dd, J=1.6, 17.0 Hz, 1H), 5.86-5.79 (m, 1H), 5.29 (s, 2H), 4.32 (d, J=6.0 Hz, 2H), 3.30-3.27 (m, 2H), 3.07 (t, J=6.4 Hz, 2H), 2.89-2.82 (m, 1H), 2.22 (s, 3H). MS (ESI) m/z 531.3 [M+H]

124: To a solution of (4-(3-chloro-4-(2-pyridylmethoxy)aniline)-6-nitro-quinazolin-7-yl) trifluoromethanesulfonate (2.00 g, 3.60 mmol, 1.00 eq) (obtained by trifiation of the corresponding alcohol), tert-butyl 6-ethynyl-2-azaspiro[3.3]heptanes-2-carboxylate (876 mg, 3.96 mmol, 1.10 eq), copper(I) iodide (137 mg, 719 umol, 0.200 eq) and triethylamine (2.91 g, 28.8 mmol, 4.00 mL, 7.99 eq) in dimethyl formamide (4.00 mL) was added tetrakis(triphenylphosphine)palladium(0) (420 mg, 363 umol, 0.370 eq) at 25° C. under nitrogen atmosphere, the mixture was stirred at 25° C. for 2 h. The reaction mixture was concentrated to give a residue. The residue was purified by silica gel chromatography (petroleum ether/ethyl acetate=1/1-0/1) to afford tert-butyl-6-((4-((3-chloro-4-(pyridin-2-ylmethoxy)phenyl)amino)-6-nitroquinazolin-7-yl)ethynyl)-2-azaspiro[3.3]heptane-2-carboxylate (1.20 g, 1.91 mmol, 53% yield) as a yellow solid. $^1$H NMR (400 MHz, DMSO-d$_6$) δ=10.35 (s, 1H), 9.42 (s, 1H), 8.71 (s, 1H), 8.61 (br d, J=5.2 Hz, 1H), 8.02 (d, J=2.6 Hz, 1H), 7.95 (s, 1H), 7.91-7.84 (m, 1H), 7.72 (dd, J=2.2, 9.0 Hz, 1H), 7.59 (d, J=7.8 Hz, 1H), 7.31 (d, J=8.8 Hz, 1H), 5.32 (s, 2H), 3.88 (br d, J=9.2 Hz, 4H), 3.17 (d, J=5.2 Hz, 1H), 2.33 (br s, 4H), 1.38 (s, 9H). MS (ESI) m/z 627.5 [M+H]

The mixture of tert-butyl 6-((4-((3-chloro-4-(pyridin-2-ylmethoxy)phenyl)amino)-6-nitroquinazolin-7-yl)ethynyl)-2-azaspiro[3.3]heptane-2-carboxylate (1.00 g, 1.59 mmol, 1.00 eq), iron powder (267 mg, 4.78 mmol, 3.00 eq), saturated ammonium chloride (426 mg, 7.97 mmol, 5.00 eq) in methanol (20.0 mL) and water (10.0 mL) was stirred at 80° C. for 1 h. The reaction mixture was filtrated to give the filtrate, the filtrated was poured into water (50.0 mL) and the aqueous phase was extracted with ethyl acetate (4×50.0 mL). The combined organic phase was washed with brine (30.0 mL), dried with anhydrous sodium sulfate, filtered and concentrated in vacuum to give a residue, the residue was purified by silica gel chromatography (petroleum ether/ethyl acetate=1/1-0/1) to afford tert-butyl 6-((6-amino-4-((3-chloro-4-(pyridin-2-ylmethoxy)phenyl)amino)quinazolin-7-yl)ethynyl)-2-azaspiro[3.3]heptane-2-carboxylate (800 mg, 1.34 mmol, 84% yield) as a yellow solid.

$^1$H NMR (400 MHz, DMSO-d$_6$) δ=9.52 (s, 1H), 8.68-8.63 (m, 1H), 8.38 (s, 1H), 8.10 (d, J=2.6 1H), 7.94 (dt, J=1.8, 7.8 Hz, 1H), 7.76 (dd, J=2.6, 8.8 Hz, 1H), 7.67-7.61 (m, 2H), 7.51 (s, 1H), 7.43 (dd, J=5.2, 7.0 Hz, 1H), 7.30 (d, J=9.2 Hz, 1H), 5.64 (s, 2H), 5.34 (s, 2H), 4.01-3.88 (m, 4H), 3.31 (br d, J=8.4 Hz, 1H), 2.68-2.59 (m, 4H), 1.43 (s, 9H). MS (ESI) m/z 597.5 [M+H]

To a solution of tert-butyl 6-((6-amino-4-((3-chloro-4-(pyridin-2-ylmethoxy)phenyl)amino)quinazolin-7-yl)ethynyl)-2-azaspiro[3.3]heptane-2-carboxylate (500 mg, 837 umol, 1.00 eq), triethylamine (424 mg, 4.19 mmol, 583 uL, 5.00 eq) in dimethyl formamide (5.00 mL) was added prop-2-enoyl prop-2-enoate (316 mg, 2.51 mmol, 3.00 eq) at 25° C., the mixture was stirred at 25° C. for 1 h. The reaction mixture was poured into water (50.0 mL) and extracted with ethyl acetate (3×40.0 mL). The combined organic phase was washed with brine (30.0 mL), dried with anhydrous sodium sulfate, filtered and concentrated in vacuum to give a residue, the residue was purified by silica gel chromatography (petroleum ether/ethyl acetate=2/1-0/1) to afford tert-butyl 6-((6-acrylamido-4-((3-chloro-4-(pyridin-2-ylmethoxy)phenyl)amino)quinazolin-7-yl)ethynyl)-2-azaspiro[3.3]heptane-2-carboxylate (200 mg, 307 umol, 37% yield) as a yellow solid. $^1$H NMR (400 MHz, DMSO-d$_6$) δ=9.88 (d, J=13.6 Hz, 2H), 8.73-8.69 (m, 1H), 8.03-8.01 (m, 1H), 7.92-7.87 (m, 1H), 7.79 (s, 1H), 7.72 (dd, J=2.6, 9.0 Hz, 1H), 7.59 (d, J=7.8 Hz, 1H), 7.40-7.35 (m, 1H), 7.30-7.26 (m, 1H), 6.68-6.59 (m, 1H), 6.38-6.32 (m, 1H), 5.88-5.84 (m, 1H), 5.32-5.29 (m, 2H), 3.8 7 (br d, J=19.8 Hz, 4H), 3.28-3.21 (m, 1H), 2.63-2.57 (m, 2H), 2.40-2.34 (m, 2H), 1,38 (s, 9H). MS (ESI) m/z 651.4 [M+H]

To a solution of tert-butyl 6-((6-acrylamido-4-((3-chloro-4-(pyridin-2-ylmethoxy)phenyl)amino)quinazolin-7-yl)ethynyl)-2-azaspiro[3.3]heptane-2-carboxylate (40.0 mg, 61.4 umol, 1.00 eq) in dichloromethane (2.00 mL) was added trifluoroacetic acid (693 mg, 6.08 mmol, 450 uL, 99.0 eq) at 25° C., the mixture was stirred at 25° C. for 0.5 h. The reaction mixture was concentrated to give a residue, the residue was poured into methanol (10.0 mL) and stirred, concentrated in vacuum to give crude product N-(7-(2-azaspiro[3.3]heptan-6-ylethynyl)-4-((3-chloro-4-(pyridin-2-ylmethoxy)phenyl)amino)quinazolin-6-yl)acrylamide (40.0 mg, crude) as a yellow solid which was used into next step without further purification. MS (ESI) m/z 551.3 [M+H].

To a solution of N-(7-(2-azaspiro[3.3]heptan-6-ylethynyl)-4-((3-chloro-4-(pyridin-2-ylmethoxy)phenyl)amino)quinazolin-6-yl)acrylamide (40.0 mg, 72.6 umol, 1.00 eq), paraformaldehyde (12.0 mg, 399 umol, 11.0 uL, 5.51 eq) in trifluoroethanol (1.00 mL) was added sodium borohydride (6.00 mg, 158 umol, 2.18 eq), the mixture was stirred at 60° C. for 2 h. The reaction was concentrated to give a residue, the residue was purified by pre-HPLC (column: Phenomenex luna C18 150×25 10 u; mobile phase: [water (0.1%TFA)-ACN]; B%: 1%-31%, 12 min) to afford N-(4-((3-chloro-4-(pyridin-2-ylmethoxy)phenyl)amino)-7-((2-methyl-2-azaspiro[3.3]heptan-6-yl)ethynyl)quinazolin-6-yl)acrylamide 124 (10.6 mg, 17.7 umol, 25% yield) as a yellow solid. $^1$H NMR (400 MHz, DMSO-d$_6$) δ=11.22-10.85 (m, 1H), 10.10 (s, 2H), 8.89 (s, 1H), 8.81 (s, 1H), 8.64-8.59 (m, 1H), 7.95-7.89 (m, 2H), 7.86 (s, 1H), 7.67-7.59 (m, 2H), 7.44-7.38 (m, 1H), 7.34 (d, J=9.0 Hz, 1H), 6.66 (br dd, J=10.2, 17.0 Hz, 1H), 6.38 (br d, J=17.2 Hz, 1H), 5.96-5.81 (m, 1H), 5.37-5.33 (m, 2H), 4.27 (br d, J=5.4 Hz, 2H), 4.01 (td, J=5.8, 12.0 Hz, 4H), 3.39-3.29 (m, 1H), 2.79 (br d, J=4.6 Hz, 3H), 2.72-2.62 (m, 2H). MS (ESI) m/z 565.5 [M+H]

Synthesis of tert-butyl 6-ethynyl-2-azaspiro[3.3]heptane-2-carboxylate

To a solution of methoxymethyl(triphenyl)phosphonium; chloride (2.21 g, 6.44 mmol, 1.36 eq) in tetrahydrofuran (10.0 mL) was added lithium bis(trimethylsilyl)amide (1.00 M, 6.44 mL, 1.36 eq) dropwise at −78° C. The mixture was stirred at −78° C. for 0.5 h, then tert-butyl 6-oxo-2-azaspiro[3.3]heptane-2-carboxylate (1.00 g, 4.73 mmol, 1.00 eq) in tetrahydrofuran (10.0 mL) was added dropwise at −78° C. The mixture was raised to 25° C. slowly and stirred for 12 h. The mixture was diluted with water (30.0 mL) and extracted with ethyl acetate (3×20.0 mL). The combined organic layers were washed with water, dried over anhydrous sodium sulfate, filtered and the filtrate was concentrated to afford a residue. The residue was purified by silica gel chromatography (petroleum ether/ethyl acetate=20/1-10/1) to afford tert-butyl 6-(methoxymethylene)-2-azaspiro[3.3]heptane-2-carboxylate (760 mg, 3.18 mmol, 67% yield) as a colorless oil. $^1$H NMR (400 MHz, CDCl$_3$) δ=5.64 (q, J=2.4 Hz, 1H), 3.76 (s, 4H), 3.40 (s, 3H), 2.70 (d, J=2.4 Hz, 2H), 2.63 (d, J=2.0 Hz, 2H), 1.28 (s, 9H).

To a solution of tert-butyl 6-(methoxymethylene)-2-azaspiro[3.3]heptane-2-carboxylate (2.50 g, 10.5 mmol, 1.00 eq) in tetrahydrofuran (30.0 mL) was addled 1 M hydrochloric acid (30.0 mL) at 25° C. The mixture was stirred at 100° C. for 2 h. The mixture was basified with 4 M sodium hydroxide to PH=10-11, and added another sodium hydroxide (4.00 M, 5.75 mL, 2.2 eq) and di-tert-butyldicarbonate (3.50 g, 16.04 mmol, 1.54 eq) at 25° C. The mixture was stirred at 25° C. for another 1 h. The mixture was extracted with ethyl acetate (3×20.0 mL). The combined organic layers were washed with water (20.0 mL), dried over anhydrous sodium sulfate, filtered and the filtrate was concentrated to afford a residue. The residue was purified by silica gel chromatography (petroleum ether/ethyl acetate=10/1-3/1) to afford tert-butyl 6-formyl-2-azaspiro[3.3]heptane-2-carboxylate (2.30 g, 10.2 mmol, 97% yield) as a colorless oil. $^1$H NMR (400 MHz, CDCl$_3$) δ=9.65 (d, J=1.6 Hz, 1H), 3.87 (s, 2H), 3.76 (s, 2H), 2.38-2.26 (m, 4H), 1.36 (s, 9H).

To a solution of tert-butyl 6-formyl-2-azaspiro[3.3]heptane-2-carboxylate tert-butyl 6-formyl-2-azaspiro[3.3]heptanes-2-carboxylate (2.70 g, 12.0 mmol, 1.00 eq) and potassium carbonate (3.32 g, 24.0 mmol, 2.01 eq) in methanol (20.0 mL) was added dimethyl (1-diazo-2-oxopropyl)phosphonate (2.76 g, 14.4 mmol, 1.20 eq) dropwise at 25° C. The mixture was stirred at 25° C. for 2 h. The reaction mixture was concentrated under reduced pressure to give a residue. The residue was purified by silica gel chromatography (petroleum ether/ethyl acetate=10/1) to afford tert-butyl 6-ethynyl-2-azaspiro[3.3]heptane-2-carboxylate (2.00 g, 9.04 mmol, 75% yield) as a white solid. $^1$H NMR (400 MHz, CDCl$_3$) δ=3.83 (d, J=4.4 Hz, 4H), 2.80 (dq, J=2.4, 8.0 Hz, 1H), 2.46-2.38 (m, 2H), 2.26-2.17 (m, 2H), 2.08 (d, J=2.4 Hz, 1H), 1.36 (s, 9H).

125: Synthesized according to general procedure A, wherein in step A.2 H$_2$N-X is 3-chloro-4-(pyridin-2-ylmethoxy)aniline; in step A.3 the OH nucleophile is 4-(2-hydroxyethyl)thiomorpholine 1,1-dioxide; variant ii) was used in step A.4; and variant i) was used in step A.5; and 44% overall yield from III. $^1$H NMR (400 MHz, DMSO-d$_6$) δ=9.69 (s, 1H), 9.58 (s, 1H), 8.84 (s, 1H), 8.61-8.60 (m, 1H), 8.61 (d, J=4.3 Hz, 1H), 8.50 (s, 1H), 8.22 (s, 1H), 8.00 (d, J=2.6 Hz, 1H), 7.89 (dt, J=1.7, 7.7 Hz, 1H), 7.70 (dd, J=2.6, 8.9 Hz, 1H), 7.60 (d, J=7.8 Hz, 1H), 7.38 (dd, J=5.1, 6.8 Hz, 1H), 7.32 (s, 1H), 7.26 (d, J=9.0 Hz, 1H), 6.68 (dd, J=10.4, 17.0 Hz, 1H), 6.32 (dd, J=1.8, 17.0 Hz, 1H), 5.90-5.79 (m, 1H), 5.29 (s, 2H), 4.34 (t, J=5.4 Hz, 2H), 3.08 (s, 8H), 3.07-3.03 (m, 2H). MS (ESI) m/z 609.2 [M+H]$^+$ 126: To a solution of 4-((3-chloro-4-(pyridin-2-ylmethoxy)phenyl)amino)-6-nitroquinazolin-7-yl trifluoromethanesulfonate (800 mg, 1.44 mmol, 1.00 eq) (obtained by triflation of the corresponding alcohol) and 4-ethynyiquinuclidine (253 mg, 1.87 mmol, 1.30 eq) in dimethyl formamide (10.0 mL) was added copper(I) iodide (54.8 mg, 288 umol, 0.20 eq), tetrakis(triphenylphosphine)palladium (166 mg, 144 umol, 0.100 eq) and triethylamine (1.46 g, 14.4 mmol, 2.00 mL, 10.0 eq) at 25° C. under nitrogen atmosphere. Then the mixture was stirred at 25° C. for 6 h. The mixture was poured into ammonium hydroxide aqueous solution (100 mL) and extracted with ethyl acetate (3×100 mL). All organic phases were combined, washed with brine (100 mL), dried over anhydrous sodium sulfate and concentrated under vacuum to give a residue. The residue was purified by column chromatography on silica gel (ethyl acetate methanol=1/0 to 1/1) to give N-(3-chloro-4-(pyridin-2-ylmethoxy)phenyl)-6-nitro-7-(quinuclidin-4-ylethynyl)quinazolin-4-amine (300 mg, 310 umol, 21% yield, 55% purity) as a yellow solid. MS (ESI) m/z 541.3 [M+H]$^+$ To a solution of N-(3-chloro-4-(pyridin-2-ylmethoxy)phenyl)-6-nitro-7-(quinuclidin-4-ylethynyl)quinazolin-4-amine (300 mg, 555 umol, 1.00 eq) in methanol (4.00 mL) was added a solution of saturated ammonium chloride (89.0 mg, 1.66 mmol, 3.00 eq) in water (1.00 mL) and iron powder (155 mg, 2.77 mmol, 5.00 eq). The mixture was stirred at 80° C. for 20 h. The mixture was diluted with methanol (50.0 mL) and filtered to give a filtrate which was concentrated to give a residue. The residue was washed with a solution of dimethylsulfoxide (3.00 mL) and methanol (1.00 mL). Then the mixture was filtered to give a filtrate which was purified by prep-HPLC (column: Phenomenex Synergi Max-RP 150*50 mm*10 um; mobile phase: [water(0.225%FA)-ACN]; B%: 4%-34%, 10 min) and lyophilized to give 20 mg of product. The filter cake was dried under vacuum to give 230 mg of product. Total 250 mg of N$^4$-(3-chloro-4-(pyridin-2-ylmethoxy)phenyl)-7-(quinuclidin-4-ylethynyl)quinazoline-4,6-diamine (250 mg, 489 umol, 88% yield) was obtained as a yellow solid. $^1$H NMR (400 MHz, DMSO-d$_6$) δ=9.53 (br s, 1H), 8.59 (d, J=4.6 Hz, 1H), 8.32 (s, 1H), 8.05 (d, J=2.4 Hz, 1H), 7.88 (br d, J=1.7 Hz, 1H), 7.70 (br d, J=2.4 Hz, 1H), 7.59 (s, 1H), 7.57 (s, 1H), 7.51 (s, 1H), 7.37 (dd, J=5.1, 6.8 Hz, 1H), 7.24 (d, J=9.2 Hz, 1H), 5.59 (br s, 2H), 5.28 (s, 2H), 3.28 (m, 6H), 2.22-2.09 (m, 6H). MS (ESI) m/z 511.4 [M+H]

To a solution of 4-(3-chloro-4-(pyridin-2-yl)methoxy) phenyl)-7-(quinuclidin-4-ylethynyl)quinazoline-4,6-diamine (190 mg, 372 umol, 1.00 eq) in dimethyl formamide (2.00 mL) was added triethylamine (113 mg, 1.12 mmol, 3.00 eq), followed by a solution of prop-2-enoyl prop-2-enoate (46.9 mg, 372 umol, 1.00 eq) in dimethyl formamide (0.500 mL) dropwise at 0° C. The mixture was stirred at 0° C. for 10 min. The mixture was diluted with dimethyl formamide (2.00 mL) to give a solution. The solution was purified by prep-HPLC (column: Xtimate C18 150*25 mm*5 um; mobile phase: [water (0.05% ammonia hydroxide v/v)-ACN]; B%: 56%-86%, 10 min) and lyophilized to give a crude product. Then the crude product was purified again by prep-HPLC (column: Xtimate C18 150*25 mm*5 um; mobile phase: [water (0.05% ammonia hydroxide v/v)-ACN]; B%: 56%-86%, 10 min). But no desired mass was detected and the sample on preparative column was rinsed by 0.1% trifluoroacetic acid in acetonitrile to give desired fraction. The desired fraction was lyophilized to give a product of the second purification, which was purified again by prep-HPLC (column: Phenomenex luna C18 150*25 10 u; mobile phase: [water(0.1%TFA)-ACN]; B%: 5%-35%, 10 min) and lyophilized to give N-(4-((3-chloro-4-(pyridin-2-ylmethoxy)phenyl)amino)-7-(quinuclidin-4-ylethynyl) quinazolin-6-yl)acrylamide 126 (5.68 mg, 8.36 umol, 2.25% yield, 99% purity, trifluoroacetic acid salt) as a yellow solid.

$^1$H NMR (400 MHz, DMSO-d$_6$) δ=11.25-10.69 (m, 1H), 10.19-10.04 (m, 1H), 9.91-9.57 (m, 1H), 8.90-8.70 (m, 2H), 8.65-8.58 (m, 1H), 7.95-7.90 (m, 2H), 7.87-7.82 (m, 1H), 7.67-7.56 (m, 2H), 7.45-7.37 (m, 1H), 7.36-7.29 (m, 1H), 6.66-6.52 (m, 1H), 6.42-6.31 (m, 1H), 5.94-5.83 (m, 1H), 5.41-5.26 (s, 2H), 3.36-3.25 (m, 6H), 2.22-1.98 (m, 6H). MS (ESI) m/z 565.3 [M+H]$^+$

Synthesis of 4-ethynylquinuclidine

To a solution of quinuclidine-4-carbonitrile (900 mg, 6.61 mmol, 1.00 eq) in toluene (10.0 mL) was added Diisobutylaluminium Hydride (1 M in toluene, 13.2 mL, 2.00 eq) at −78° C. Then the mixture was stirred at −78° C. for 1 h. The reaction mixture was quenched by addition sodium sulfate decahydrate (15.0 g), and then filtered and the filtrate was concentrated under reduced pressure to give quinuclidine-4-carbaldehyde (1 g, crude) as a white solid. $^1$H NMR (400 MHz, DMSO-d$_6$) δ=9.34 (s, 1H), 2.77-2.75 (m, 6H), 1.48 (br d, J=2.4 Hz, 6H).

To a solution of quinuclidine-4-carbaldehyde (540 mg, 3.88 mmol, 1.00 eq) and potassium carbonate (1.07 g, 7.76 mmol, 2.00 eq) in methanol (10.0 mL) was added dimethyl (1-diazo-2-oxopropyl)phosphonate (894 mg, 4.66 mmol, 1.20 eq) at 0° C. Then the mixture was stirred at 25° C. for 2 h. The reaction mixture was concentrated under reduced pressure to give a residue. The residue was purified by column chromatography (Silica, dichloromethane/methanol=10/1) to afford 4-ethynylquinuclidine (600 mg, crude) as colorless oil.

$^1$H NMR (400 MHz, DMSO-d$_6$) δ=2.98 (s, 1H), 2.87-2.81 (m, 6H), 1.69-1.64 (m, 6H).

127: Synthesized according to general procedure A, wherein in step A.2 H$_2$N-X is 4-(4-chloro-3-fluoro-phenoxy)aniline, in step A.3 the OH nucleophile is 2-morpholinoethanol; variant ii) was used in step A.4; and variant i) was used in step A.5; and 14% overall yield from III. $^1$H NMR (400 MHz, CDCl$_3$) δ=9.16 (s, 1H), 8.85 (s, 1H), 8.66 (s, 1H), 7.84 (s, 1H), 7.81-7.71 (m, 2H), 7.34 (t, J=8.6 Hz, 1H), 7.13-7.04 (m, 2H), 6.88-6.73 (m, 2H), 6.55-6.42 (m, 2H), 5.87 (dd, J=9.2 Hz, 1H), 4.36 (t, J=5.4 Hz, 2H), 3.84-3.73 (m, 4H), 2.94 (t, J=5.4 Hz, 2H), 2.63 (br d, J=4.4 Hz, 3H), 2.61 (br s, 2H). MS (ESI) m/z 564.0 [M +H]

Synthesis of 4-(4-chloro-3-fluoro-phenoxy)aniline

To a solution of 1-fluoro-4-nitrobenzene (1.00 g, 7.09 mmol, 751 uL, 1.00 eq) in dimethyl formamide (10.0 mL) was added 4-chloro-3-fluoro-phenol (1.25 g, 8.50 mmol, 1.20 eq) and cesium carbonate (4.62 g, 14.1 mmol, 2.00 eq) at 25° C., the mixture was stirred at 80° C. for 12 h. The reaction mixture was poured into water (60.0 mL) and the aqueous phase was extracted with ethyl acetate (3×40.0 mL). The combined organic phase was washed with brine (30.0 mL), dried over anhydrous sodium sulfate, filtered and concentrated in vacuum to give a residue. The residue was purified by silica gel chromatography (Petroleum ether/Ethyl acetate=10/1) to afford 1-chloro-2-fluoro-4-(4-nitrophenoxy)benzene (1.80 g, 6.73 mmol, 95% yield) as a yellow solid. $^1$H NMR (400 MHz, DMSO-$d_6$) δ=8.31-8.23 (m, 2H), 7.71 (t, J=8.8 Hz, 1H), 7.43 (dd, J=2.8, 10.2 Hz, 1H), 7.28-7.22 (m, 2H), 7.12-7.06 (m, 1H).

A mixture of 1-chloro-2-fluoro-4-(4-nitrophenoxy)benzene (1.80 g, 6.73 mmol, 1.00 eq), iron powder (1.13 g, 20.2 mmol, 3.00 eq), ammonium chloride (1.80 g, 33.6 mmol, 5.00 eq) in methanol (20.0 mL) and water (10.0 mL) was stirred at 80° C. for 1 h. The reaction mixture was poured into methanol (50.0 mL) and stirred for 10 min, filter and the filtrate was concentrate to give a residue. The residue was poured into water (50.0 mL) and the aqueous phase was extracted with ethyl acetate (3×50.0 mL). The combined organic phase was washed with brine (30.0 mL), dried over anhydrous sodium sulfate, filtered and concentrated in vacuum to give 4-(4-chloro-3-fluoro-phenoxy)aniline (1.20 g, 5.05 mmol, 75% yield) as a yellow oil. $^1$H NMR (400 MHz, DMSO-$d_6$) δ=7.54-7.45 (m, 1H), 6.89 (dd, J=2.8, 11.0 Hz, 1H), 6.84-6.78 (m, 2H), 6.72-6.67 (m, 1H), 6.66-6.58 (m, 2H), 5.07 (s, 2H).

128: Synthesized according to general procedure A, wherein in step A.2 H$_2$N-X 3-chloro-4-((6-methylpyridin-2-yl)methoxy)aniline; in step A.3 the OH nucleophile is 2-morpholinoethanol; variant ii) was used in step A.4; and variant i) was used in step A.5; and 14% overall yield from I. $^1$H NMR (400 MHz, CDCl$_3$) δ=9.10 (s, 1H), 8.74 (s, 1H), 8.63 (s, 1H), 7.88 (d, J=2.6 Hz, 1H), 7.69 (s, 1H), 7.64 (t, J=7.7 Hz, 1H), 7.54-7.44 (m, 2H), 7.10 (d, J=7.6 Hz, 1H), 6.99 (d, J=8.9 Hz, 1H), 6.54-6.38 (m, 2H), 5.86 (dd, J=1.7, 9.6 Hz, 1H), 5.26 (s, 2H), 4.35 (t, J=5.5 Hz, 2H), 3.79-3.74 (m, 4H), 2.92 (t, J=5.4 Hz, 2H), 2.61 (br d, J=4.6 Hz, 4H), 2.59 (s, 3H). MS (ESI) m/z 575.5 [M+H]$^+$ Synthesis of 3-chloro-4-((6-methylpyridin-2-yl)methoxy)aniline To a solution 2-chloro-1-fluoro-4-nitrobenzene (1.00 g, 5.70 mmol, 1.00 eq) and (6-methyl-2-pyridyl) methanol (842 mg, 6.84 mmol, 1.20 eq) in dimethyl formamide (10.0 mL) was added potassium carbonate (1.57 g, 11.4 mmol, 2.00 eq), then the mixture was stirred at 25° C. for 3 h under nitrogen. The reaction mixture was added water (50.0 mL) and extracted with ethyl acetate (3×50.0 mL). The combined organic layers were dried over sodium sulfate, filtered and concentrated under reduced pressure to give 2-((2-chloro-4-nitrophenoxy)methyl)-6-methylpyridine (1.86 g, crude) as a white solid. $^1$H NMR (400 MHz, DMSO-$d_6$) δ=8.34 (d, J=2.8 1H), 8.23 (dd, J=2.8, 9.2 Hz, 1H), 7.76 (t, J=7.7 Hz, 1H), 7.46 (d, J=9.2 Hz, 1H), 7.35 (d, J=7.6 Hz, 1H), 7.24 (d, J=7.7 Hz, 1H), 5.40 (s, 2H), 2.49 (s, 3H).

To a solution of 2-((2-chloro-4-nitrophenoxy)methyl)-6-methylpyridine (1.86 g, 6.67 mmol, 1.00 eq) in dichloromethane (10.0 mL) and methanol (20.0 mL) was added nickel(ii) chloride hexahydrate (1.58 g, 6.67 mmol, 1.00 eq). Then sodium borohydride (504 mg, 13.3 mmol, 2.00 eq) was added to the reaction mixture at 25° C., the reaction mixture was stirred at 25° C. for 1 h. The reaction mixture was filtered and the filter cake was washed with dichloromethane (40.0 mL). The combined organic layers were concentrated under reduced pressure to give a black solid, the black solid was added water (40.0 mL) and extracted with ethyl acetate (3×40.0 mL). The combined organic layers were dried over sodium sulfate, filtered and concentrated under reduced pressure to give 3-chloro-4-((6-methylpyridin-2-yl)methoxy)aniline (1.27 g, 5.11 mmol, 76.6% yield) as a yellow solid. $^1$H NMR (400 MHz, DMSO-$d_6$) δ=7.71 (t, J=7.7 Hz, 1H), 7.33 (d, J=7.7 Hz, 1H), 7.18 (d, J=7.7 Hz, 1H), 6.90 (d, J=8.7 Hz, 1H), 6.67 (d, J=2.6 Hz, 1H), 6.50-6.44 (m, 1H), 5.02 (s, 2H), 4.93 2H), 2.47 (s, 3H).

129: Synthesized according to general procedure A, wherein in step A.2 H$_2$N-X 3-chloro-4-((6-methylpyridin-2-yl)methoxy)aniline; in step A.3 the OH nucleophile is 3-morpholinopropan-1-ol; variant ii) was used in step A.4; and variant i) was used in step A.5; and 42% overall yield from III. $^1$H NMR (400 MHz, DMSO-$d_6$) δ=9.68 (br s, 1H), 9.59 (br s, 1H), 8.84 (s, 1H), 8.49 (s, 1H), 7.99 (d, J=2.2 Hz, 1H), 7.77 (t, J=7.6 Hz, 1H), 7.70 (dd, J=2.3, 8.9 Hz, 1H), 7.38 (d, J=7.8 Hz, 1H), 7.27 (s, 1H), 7,23 (dd, J=3.9, 8.3 Hz, 2H), 6.71 (br dd, J=10.0, 17.1 Hz, 1H), 6.32 (dd, J=1.5, 17.0 Hz, 1H), 5.82 (br d, J=11.2 Hz, 1H), 5.24 (s, 2H), 4.27 (br t, J=6.1 Hz, 2H), 3.59 (br t, J=4.3 Hz, 4H), 2.50-2.45 (m, 5H), 2.39 (br s, 4H), 2.00 (quin, J=6.5 Hz, 2H). MS (ESI) m/z 589.5 [M+H]$^+$ 130: Synthesized according to general procedure A, wherein in step A.2 H$_2$N-X 3-chloro-4-((3-fluorobenzyl)oxy)aniline; in step A.3 the OH nucleophile is 2-(4-methylpiperazin-1-yl)ethanol; variant ii) was used in step A.4; and variant i) was used in step A.5; and 18% overall yield from III. $^1$H NMR (400 MHz, CDCl$_3$) δ=9.11 (s, 1H), 8.73 (s, 1H), 8.64 (s, 1H), 7.85 (d, J=2.4 Hz, 1H), 7.64 (s, 1H), 7.51 (dd, J=2.4, 8.8 Hz, 1H), 7.38 (dt, J=6.4, 7.8 Hz, 1H), 7.28-7.20 (m, 3H), 7.04 (dt, J=1.6, 8.4 Hz, 1H), 6.95 (d, J=8.8 Hz, 1H), 6.55-6.37 (m, 2H), 5.85 (dd, J=1.8, 9.4 Hz, 1H), 5.15 (s, 2H), 4.34 (t, J=5.4 Hz, 2H), 2.93 (t, J=5.4 Hz, 2H), 2.73-2.61 (m, 4H), 2.52 (br s, 4H), 2.32 (s, 3H). MS (ESI) m/z 591.4 [M+H]

131: Synthesized according to general procedure C starting from intermediate XIV obtained in analogy to the respective intermediate in 28, wherein in step C.3 H$_2$NX is 5-chloro-2-fluoro-4-((3-fluorobenzyl)oxy)aniline C.4 HNR'R" is 3-methoxyazetidine hydrochloride; variant ii) was used in step C.5; and variant ii) was used in step C.6; and 18% overall yield from XIV. $^1$H NMR (400 MHz, CDCl$_3$) δ=9.16 (s, 1H), 8.70 (s, 1H), 8.44 (d, J=8.3 Hz, 1H), 8.30 (s, 1H), 7.44-7.37 (m, 1H), 7.34 (s, 1H), 7.30 (s, 1H), 7.28-7.21 (m, 2H), 7.08-7.08 (m, 1H), 7.06 (dt, J=2.0, 8.4 Hz, 1H), 6.86 (d, J=11.8 Hz, 1H), 6.57-6.46 (m, 1H), 6.45-6.28 (m, 1H), 5.89 (dd, J=1.2, 10.0 Hz, 1H), 5.16 (s, 2H), 4.31 (t, J=6.4 Hz, 2H), 4.08 (quin, J=5.8 Hz, 1H), 3.72-3.61 (m, 2H), 3.30 (s, 3H), 3.01-2.88 (m, 2H), 2.71 (t, J=6.8 Hz, 2H), 2.01 (t, J=6.6 Hz, 2H). MS (ESI) m/z 610.5 [M+H]$^+$ 132: Synthesized according to general procedure C starting from intermediate XIV obtained in analogy to the respective intermediate in 28, wherein in step C.3 H$_2$NX is 3-chloro-4-((6-methylpyridin-2-yl)methoxy)aniline C.4 HNR'R" is 8-oxa-3-azabicyclo[3.2.1]octane; variant ii) was used in step C.5; and variant ii) was used in step C.6; and 4% overall yield from XIV. $^1$H NMR (400 MHz, DMSO-$d_6$) δ=9.67 (s, 1H), 9.54 (s, 1H), 8.84 (s, 1H), 8.49 (s, 1H), 8.27

(s, 1H), 7.98 (d, J=2.5 Hz, 1H), 7.76 (t, J=7.7 Hz, 1H), 7.70 (dd, J=2.6, 9.0 Hz, 1H), 7.37 (d, J=7.9 Hz, 1H), 7.31 (s, 1H), 7.23 (dd, J=4.2, 8.3 Hz, 2H), 6.69 (dd, J=10.2, 17.1 Hz, 1H), 6.31 (dd, J=1.8, 17.0 Hz, 1H), 5.85-5.78 (m, 1H), 5.23 (s, 2H), 4.31 (t, J=5.7 Hz, 2H), 4.19-4.15 (m, 2H), 2.78 (s, 2H), 2.64 (s, 2H), 2.52 (br s, 3H), 2.30 (br d, J=1.8 Hz, 2H), 1.82-1.76 (m, 2H), 1.67-1.61 (m, 2H). MS (EST) m/z 601.3 [M+H]$^+$

133: Synthesized according to general procedure A, wherein in step A.2 H$_2$N-X 5-chloro-2-fluoro-4-((3-fluorobenzyl)oxy)aniline; in step A.3 the OH nucleophile is R)-1-methylpyrrolidin-3-ol; variant ii) was used in step A.4; and variant i) was used in step A.5; and 1% overall yield from II. $^1$H NMR (400 MHz, DMSO-d$_6$) δ=9.65 (s, 1H), 9.61 (s, 1H) 8.91 (s, 1H), 8.37 (s, 1H), 7.59 (d, J=7.9 Hz, 1H), 7.49 (dt, J=6.1, 8.0 Hz, 1H), 7.37-7.33 (m, 2H), 7.31 (s, 1H), 7.21 (dt, J=2.3, 8.7 Hz, 1H), 7.16 (s, 1H), 6.76 (dd, J=10.3, 17.0 Hz, 1H), 6.32 (dd, J=1.8, 16.9 Hz, 1H), 5.89-5.76 (m, 1H), 5.29 (s, 2H), 5.17-5.07 (m, 1H), 2.91-2.83 (m, 1H), 2.82-2.74 (m, 2H), 2.43-2.34 (m, 2H), 2.29 (s, 3H), 2.06-1.96 (m, 1H). MS (ESI) m/z 566.4 [M+H]$^+$ 134: Synthesized according to general procedure C starting from intermediate XIV obtained in analogy to the respective intermediate in 28, wherein in step C.3 H$_2$NX is 5-chloro-2-fluoro-4-((3-fluorobenzyl)oxy)aniline C.4 HNR'R" is 3-methoxyazetidine; variant ii) was used in step C.5; and variant ii) was used in step C.6; and 14% overall yield from XIV. $^1$H NMR (400 MHz, DMSO-d$_6$) δ=9.64 (br s, 1H), 9.59 (s, 1H), 8.80 (s, 1H), 8.37 (s, 1H), 7.59 (d, J=8.0 Hz, 1H), 7.49 (d, J=6.1 Hz, 1H), 7.36-7.32 (m, 2H), 7.31 (s, 1H), 7.25 (s, 1H), 7.23-7.17 (m, 1H), 6.68 (dd, J=10.2, 17.0 Hz, 1H), 6.31 (dd, J=1.8, 17.0 Hz, 1H), 5.88-5.75 (m, 1H), 5.29 (s, 2H), 4.20 (t, J=5.2 Hz, 2H), 3.94 (quin, J=5.8 Hz, 1H), 3.61-3.55 (m, 2H), 3.13 (s, 3H), 2.96 (dd, J=5.8, 8.2 Hz, 2H), 2.88 (t, J=5.3 Hz, 2H). MS (ESI) m/z 596.2 [M+H]$^+$ 135: Synthesized according to general procedure C starting from intermediate XIV obtained in analogy to the respective intermediate in 28, wherein in step C.3 H$_2$NX is 3-chloro-4-((6-methylpyridin-2-yl)methoxy)aniline C.4 HNR'R" is 3-methoxyazetidine; variant ii) was used in step C.5; and variant ii) was used in step C.6; and 3% overall yield from XIV. $^1$H NMR (400 MHz, DMSO-d$_6$) δ=9.66 (br d, J=17.7 Hz, 2H), 8.81 (s, 1H), 8.49 (s, 1H), 8.26 (s, 1H), 7.99 (d, J=2.6 Hz, 1H), 7.76 (t, J=7.7 Hz, 1H), 7.70 (dd, J=2.6, 9.0 Hz, 1H), 7.37 (d, J=7.6 Hz, 1H), 7.25 (s, 1H), 7.24 (d, J=6.0 Hz, 1H), 7.22 (d, J=4.5 Hz, 1H), 6.67 (dd, J=10.2, 17.1 Hz, 1H), 6.31 (dd, J=1.9, 17.1 Hz, 1H), 5.84-5.78 (m, 1H), 5.23 (s, 2H), 4.20 (t, J=5.2 Hz, 2H), 3.94 (quin, J=5.7 Hz, 1H), 3.60-3.57 (m, 2H), 3.13 (s, 3H), 2.99-2.96 (m, 2H), 2.88 (t, J=5.2 Hz, 2H), 2.52 (br d, J=2.0 Hz, 3H). MS (ESI) m/z 575.3 [M+H]$^+$ 136: To a solution of N$^4$-(5-chloro-2-fluoro-4-((3-fluorobenzyl)oxy)phenyl)-7-(3-(3-methoxyazetidin-1-yl) propoxy)quinazoline-4,6-diamine (120 mg, 216 nmol, 1.00 eq) and but-2-ynoic acid (127 mg, 1.51 mmol, 7.00 eq) in pyridine (3.00 mL) was added propylphosphonic anhydride (961 mg, 1.51 mmol, 899 uL, 50% purity, 7.00 eq) dropwise at 0° C. After addition, the mixture was stirred for 1 h at 0° C. The reaction mixture was filtered and the filtrate was purified by prep-HPLC (column: Waters Xbridge 150*25 5 u; mobile phase: [water(10 mM NH$_4$HCO$_3$)-ACN]; B%: 40%-70%, 10 min) and lyophilized to give N-(4-((5-chloro-2-fluoro-4-((3-fluorobenzyl)oxy)phenyl)amino)-7-(3-(3-methoxyazetidin-1-yl)propoxy)quinazolin-6-yl)but-2-ynamide (7.86 mg, 12.4 umol, 5% yield, 98% purity) as an off-white solid. $^1$H NMR (400 MHz, CDCl$_3$) δ=8.96 (s, 1H), 8.69 (s, 1H), 8.40 (d, J=8.2 Hz, 2H), 7.43-7.38 (m, 1H), 7.35 (br s, 1H), 7.28-7.21 (m, 3H), 7.13-7.01 (m, 1H), 6.85 (d, J=11.8 Hz, 1H), 5.16 (s, 2H), 4.30 (t, J=6.2 Hz, 2H), 4.09 (quin, J=5.8 Hz, 1H), 3.74-3.65 (m, 2H), 3.30 (s, 3H), 3.01-2.90 (m, 2H), 2.72 (t, J=6.8 Hz, 2H), 2.10 (s, 3H), 2.01 (t, J=6.8 Hz, 2H). MS (ESI) m/z 622.4 [M+H]$^+$ Synthesis of N$^4$-(5-chloro-2-fluoro-4-((3-fluorobenzyl)oxy) phenyl)-7-(3-(3-methoxyazetidin-1-yl)propoxy)quinazoline-4,6-diamine Synthesized according to general procedure C starting from intermediate XIV wherein in step C.3 H$_2$NX is 3-chloro-4-((6-methylpyridin-2-yl)methoxy)aniline C.4 HNR'R" is 3-methoxyazetidine; variant ii) was used in step C.5; and variant ii) was used in step C.6 to give N4-(5-chloro-2-fluoro-4-((3-fluorobenzyl)oxy)phenyl)-7-(3-(3-methoxyazetidin-1-yl)propoxy)quinazoline-4,6-diamine. MS (ESI) m/z 535.3 [M+H]$^+$. Intermediate XIV was obtained by adding sodium (659 mg, 28.7 mmol, 679 uL, 3.00 eq) to propane-1,3-diol (20.0 mL) in portions at 25° C. After the reaction turned clear, 7-fluoro-6-nitroquinazolin-4-ol (2.00 g, 9.56 mmol, 1.00 eq) was added to the mixture in portions and the reaction mixture was stirred at 25° C. for 4 h. To the reaction mixture was added hydrogen chloride (1.00 M) till pH to 3~4. Then the mixture was filtered and washed with water. The filter cake was dried to give 7-(3-hydroxypropoxy)-6-nitroquinazolin-4-ol (1.50 g, crude) as a white solid.

$^1$H NMR (400 MHz, DMSO-d$_6$) δ=12.57 (br s, 1H), 8.60 (s, 1H), 8.31 (s, 1H), 7.51 (s, 1H), 4.68 (t, J=5.2 Hz, 1H), 4.43 (t, J=6.0 Hz, 2H), 3.66 (q, J=6.0 Hz, 2H), 1.99 (quin, J=6.0 Hz, 2H).

137: Synthesized according to general procedure A, wherein in step A.2 H$_2$N-X 3-chloro-4-((6-methylpyridin-2-yl)methoxy)aniline; in step A.3 the OH nucleophile is 2-(4-methylpiperazin-1-yl)ethanol; variant ii) was used in step A.4; and variant i) was used in step A.5; and 18% overall yield from III. $^1$H NMR (400 MHz, DMSO-d$_6$) δ=9.67 (br s, 1H), 9.58 (br s, 1H), 8.84 (s, 1H), 8.49 (s, 1H), 7.98 (d, J=2.1 Hz, 1H), 7.75 (t, J=7.7 Hz, 1H), 7.72-7.66 (m, 1H), 7.37 (br d, J=7.6 Hz, 1H), 7.30 (s, 1H), 7.22 (dd, J=5.1, 8.1 Hz, 2H), 6.68 (br dd, J=10.2, 16.9 Hz, 1H), 6.31 (dd, J=1.6, 17.0 Hz, 1H), 5.81 (br d, J=10.4 Hz, 1H), 5.23 (s, 2H), 4.32 (br t, J=5.5 Hz, 2H), 3.33-3.31 (m, 3H), 2.79 (br s, 2H), 2.52-2.51 (m, 4H), 2.30 (br s, 4H), 2.13 (s, 3H). MS (ESI) m/z 588.4 [M+H]$^+$ 138: Synthesized according to general procedure C starting from intermediate XIV wherein in step C.3 H$_2$NX is 3-chloro-4-((6-methylpyridin-2-yl)methoxy)aniline C.4 HNR'R" is 3-methoxyazetidine; variant ii) was used in step C.5; and variant i) was used in step C.6. $^1$H NMR (400 MHz, DMSO-d$_6$) δ=9.68 (br s, 1H), 9.61-9.49 (m, 1H), 8.84 (s, 1H), 8.47 (s, 1H), 7.98 (d, J=1.8 Hz, 1H), 7.76 (t, J=7.8 Hz, 1H), 7.69 (br d, J=7.6 Hz, 1H), 7.38 (d, J=7.6 Hz, 1H), 7.30-7.13 (m, 3H), 6.71 (br dd, J=10.2, 16.8 Hz, 1H), 6.32 (dd, J=1.8, 17.0 Hz, 1H), 5.88-5.75 (m, 1H), 5.24 (s, 2H), 4.22 (br t, J=6.2 Hz, 2H), 3.95 (t, J=5.8 Hz, 1H), 3.57-3.45 (m, 2H), 3.15 (s, 3H), 2.77 (dd, J=5.8, 7.8 Hz, 2H), 2.60-2.57 (m, 2H), 2.53 (br s, 3H), 1.93-1.77 (m, 2H). MS (ESI) m/z 589.5 [M+H]$^+$ Intermediate XIV was obtained by adding sodium (659 mg, 28.7 mmol, 679 uL, 3.00 eq) to propane-1,3-diol (20.0 mL) in portions at 25° C. After the reaction turned clear, 7-fluoro-6-nitroquinazolin-4-ol (2.00 g, 9.56 mmol, 1.00 eq) was added to the mixture in portions and the reaction mixture was stirred at 25° C. for 4 h. To the reaction mixture was added hydrogen chloride (1.00 M) till pH to 3~4. Then the mixture was filtered and washed with water. The filter cake was dried to give 7-(3-hydroxypropoxy)-6-nitroquinazolin-4-ol (1.50 g, crude) as a white solid.

139: Synthesized according to general procedure C starting from intermediate XIII wherein in step C.3 $H_2NX$ is 3-chloro-4-((3-fluorobenzyl)oxy)aniline C.4 HNR'R" is 8-oxa-3-azabicyclo[3.2.1]octane; variant ii) was used in step C.5; and variant i) was used in step C.6; and 29% overall yield from XIII. $^1$H NMR (400 MHz, CDCl$_3$) δ=9.11 (s, 1H), 8.65 (s, 1H), 8.27 (s, 1H), 7.89 (d, J=2.5 Hz, 1H), 7.51 (dd, J=2.6, 8.8 Hz, 1H), 7.41-7.34 (m, 2H), 7.26-7.21 (m, 1H), 7.07-7.01 (m, 1H), 7.01-6.96 (m, 1H), 6.58-6.45 (m, 1H), 6.41-6.28 (m, 1H), 5.89 (dd, J=1.0, 10.2 Hz, 1H), 5.17 (s, 2H), 4.36-4.30 (m, 4H), 2.89 (t, J=5.6 Hz, 2H), 2.67 (br d, J=10.5 Hz, 2H), 2.52 (dd, J=1.9, 11.0 Hz, 2H), 1.94-1.87 (m, 4H). MS (ESI) m/z 604.4 [M+H]$^+$ 140: Synthesized according to general procedure A, wherein in step A.2 $H_2N$-X 3-chloro-4-((6-methylpyridin-2-yl)methoxy)aniline; in step A.3 the OH nucleophile is (R)-1-methylpyrrolidin-3-ol; variant ii) was used in step A.4; and variant i) was used in step A.5; and 18% overall yield from III. $^1$H NMR (400 MHz, CDCl$_3$) δ=9.13 (s, 1H), 8.63 (s, 1H), 8.58 (5, 1H), 7.87 (d, J=2.6 Hz, 1H), 7.68-7.61 (m, 1H), 7.52-7.48 (m, 2H), 7.46 (d, J=7.9 Hz, 1H), 7.16 (s, 1H), 7.10 (d, J=7.8 Hz, 1H), 6.99 (d, J=8.9 Hz, 1H), 6.53-6.45 (m, 1H), 6.44-6.35 (m, 1H), 5.88-5.80 (m, 1H), 5.27 (s, 2H), 5.05 (br t, J=6.4 Hz, 1H), 3.11 (d, J=11.0 Hz, 1H), 3.05 (dt, J=3.9, 8.7 Hz, 1H), 2.69 (dd, J=5.4, 11.1 Hz, 1H), 2.59 (s, 3H), 2.56-2.47 (m, 1H), 2.44 (s, 3H), 2.37 (q, J=8.2 Hz, 1H), 2.19-2.10 (m, 1H). MS (ESI) m/z 545.4 [M+H]$^+$ 141: Synthesized according to general procedure A, wherein in step A.2 $H_2N$-X 3-chloro-4-((2-methylpyridin-4-yl)methoxy)aniline; in step A.3 the NH nucleophile is morpholine; variant ii) was used in step A.4; and variant i) was used in step A.5; and 24% overall yield from III. $^1$H NMR (400 MHz, CDCl$_3$) δ=9.15 (s, 1H), 8.65 (s, 1H), 8.61-8.52 (m, 1H), 7.93-7.85 (m, 7.59-7.43 (m, 2H), 7.42-7.35 (m, 1H), 7.28-7.22 (m, 2H), 7.18 (br s, 1H), 7.04 (dt, J=2.4, 8.4 Hz, 1H), 7.01-6.96 (m, 1H), 6.56-6.47 (m, 1H), 6.45-6.35 (m, 1H), 5.90-5.81 (m, 1H), 5.17 (s, 2H), 5.06 (br s, 1H), 3.16-3.00 (m, 2H), 2.76-2.66 (m, 1H), 2.60-2.49 (m, 1H), 2.46 (s, 3H), 2.43-2.34 (m, 1H), 2.23-2.08 (m, 2H). MS (ESI) m/z 545.5 [M+H]$^+$ 142: Synthesized according to general procedure C starting from intermediate XIII obtained in analogy to 28 wherein in step C.3 $H_2NX$ is 3-chloro-4-((3-fluorobenzyl)oxy)aniline C.4 HNR'R" is 8-oxa-3-azabicyclo[3.2.1]octane; variant ii) was used in step C.5; and variant i) was used in step C.6; and 15% overall yield from XIV. $^1$H NMR (400 MHz, CDCl$_3$) δ=9.12 (s, 1H), 8.65 (s, 1H), 8.53 (d, J=5.1 Hz, 1H), 8.48 (s, 1H), 7.91 (d, J=2.6 Hz, 1H), 7.51 (dd, J=2.6, 8.9 Hz, 1H), 7.41 (s, 1H), 7.29 (s, 2H), 7.22 (d, J=4.9 Hz, 1H), 6.95 (d, J=8.9 Hz, 1H), 6.54-6.47 (m, 1H), 6.43-6.32 (m, 1H), 5.88 (dd, J=1.0, 10.2 Hz, 1H), 5.15 (s, 2H), 4.37 (t, J=5.6 Hz, 2H), 3.78-3.74 (m, 4H), 2.92 (t, J=5.5 Hz, 2H), 2.62-2.59 (m, 7H). MS (ESI) m/z 575.4 [M+H]$^+$ Synthesis of 3-chloro-4-((2-methylpyridin-4-yl)methoxy)aniline To a solution of 2-methylisonicotinic acid (1.00 g, 7.29 mmol, 1.00 eq) in tetrahydrofuran (10.0 mL) was added borane-dimethyl sulfide complex (10 M, 1.82 mL, 2.50 eq) dropwise at 0° C. The mixture was stirred at 20° C. for 12 h, quenched with methanol (40.0 mL) and hydrochloric acid (1 M, 60.0 mL). The resulting mixture was basified with saturated sodium bicarbonate (75.0 mL) and extracted with ethyl acetate (3×25.0 mL). The combined organic layers were dried over anhydrous sodium sulfate and concentrated to afford (2-methylpyridin-4-yl)methanol (600 mg, 4.87 mmol, 67% yield) as a white solid. $^1$H NMR (400 MHz, DMSO-d$_6$) δ=8.58 (d, J=6.1 Hz, 1H), 7.54 (s, 1H), 7.41 (d, J=6.0 Hz, 1H), 5.64 (br t, J=5.1 Hz, 1H), 4.65-4.58 (m, 2H), 2.61 (s, 3H).

To a solution of (2-methylpyridin-4-yl)methanol (500 mg, 4.06 mmol, 1.00 eq) and potassium carbonate (1.12 g, 8.12 mmol, 2.00 eq) in acetonitrile (5.00 mL) was added 2-chloro-1-fluoro-4-nitrobenzene (713 mg, 4.06 mmol, 1.00 eq). The mixture was stirred at 80° C. for 12 h. The mixture was filtered and concentrated to afford a residue. The residue was purified by silica gel chromatography (petroleum ether/ethyl acetate=5/1 to 1/1) to afford 4-((2-chloro-4-nitrophenoxy)methyl)-2-methylpyridine (830 mg, 2.98 mmol, 73% yield) as a brown solid. $^1$H NMR (400 MHz, CDCl$_3$) δ=8.55 (d, J=5.11 Hz, 1H), 8.36 (d, J=2.8 Hz, 1H), 8.16 (dd, J=2.8, 9.1 Hz, 1H), 7.25 (s, 1H), 7.20 (d, J=5.1 Hz, 1H), 6.99 (d, J=9.1 Hz, 1H), 5.25 (s, 2H), 2.61 (s, 3H).

To a solution of 4-((2-chloro-4-nitrophenoxy)methyl)-2-ethylpyridine (730 mg, 2.62 mmol, 1.00 eq) in methanol (3.00 mL) and water (3.00 mL) was added iron powder (1.17 g, 21.0 mmol, 8.00 eq) and ammonium chloride (1.40 g, 26.2 mmol, 10.0 eq). The mixture was stirred at 80° C. for 2 h. The mixture was cooled to 25° C. and then concentrated in vacuum to give a residue. The residue was diluted with water (20.0 mL) and extracted with ethyl acetate (3×60.0 mL). The combined organic layers were washed with water (20.0 mL), dried over anhydrous sodium sulfate, filtered and concentrated under reduced pressure to give 3-chloro-4-((2-methylpyridin-4-yl)methoxy)aniline (550 mg, 2.21 mmol, 84% yield) as a brown oil. MS (ESI) m/z 249.8 [M+H]$^+$ 143: Synthesized according to general procedure C starting from intermediate XIII obtained in analogy to 28 wherein in step C.3 $H_2NX$ is 3-chloro-4-((3-fluorobenzyl)oxy)aniline C.4 HNR'R" 3-methoxyazetidine; variant ii) was used in step C.5; and variant i) was used in step C.6; and 11% overall yield from XV. $^1$H NMR (400 MHz, CDCl$_3$) δ=9.11 (s, 1H), 8.97 (br s, 1H), 8.64 (s, 1H), 7.88 (d, J=2.6 Hz, 1H), 7.57 (s, 1H), 7.50 (dd, J=2.6, 8.9 Hz, 1H), 7.41-7.33 (m, 1H), 7.27-7.21 (m, 3H), 7.07-7.00 (m, 1H), 6.97 (d, J=8.8 Hz, 1H), 6.56-6.42 (m, 2H), 5.89-5.80 (m, 1H), 5.16 (s, 2H), 4.22 (t, J=5.1 Hz, 2H), 4.10 (t, J=5.7 Hz, 1H), 3.74 (br t, J=6.9 Hz, 2H), 3.29 (s, 3H), 3.13 (dd, J=6.4, 7.3 Hz, 2H), 3.00 (t, J=5.0 Hz, 2H). MS (ESI) m/z 578.3 [M+H]$^+$ 144: Synthesized according to general procedure C starting from intermediate XIII obtained in analogy to 28 wherein in step C.3 $H_2NX$ is 3-chloro-4-((3-fluorobenzyl)oxy)aniline C.4 HNR'R" 3-methoxyazetidine; variant ii) was used in step C.5; and variant i) was used in step C.6; and 16% overall yield from XIV. $^1$H NMR (400 MHz, CDCl$_3$) δ=9.12 (s, 1H), 8.66 (s, 1H), 8.31 (s, 1H), 7.92-7.86 (m, 1H), 7.55-7.48 (m, 1H), 7.45 (s, 1H), 7.42-7.35 (m, 1H), 7.28-7.22 (m, 3H), 7.05 (dt, J=2.8, 8.6 Hz, 1H), 7.00 (d, J=8.8 Hz, 1H), 6.57 (s, 1H), 6.46-6.29 (m, 1H), 5.97-5.83 (m, 1H), 5.18 (s, 2H), 4.30 (t, J=6.4 Hz, 2H), 4.08 (quin, J=5.8 Hz, 1H), 3.71-3.62 (m, 2H), 3.30 (s, 3H), 3.00-2.91 (m, 2H), 2.71 (t, J=6.8 Hz, 2H), 2.00 (quin, J=6.6 Hz, 2H). MS (ESI) m/z 592.4 [M+H]$^+$ 145: Synthesized according to general procedure C starting from intermediate XIII obtained in analogy to 28 wherein in step C.3 $H_2NX$ is 5-chloro-2-fluoro-4-((3-fluorobenzyl)oxy)aniline C.4 HNR'R" 1-methylpiperazine; variant ii) was used in step C.5; and variant i) was used in step C.6; and 9% overall yield from XV. 1H NMR (400 MHz, DMSO-d6) δ=9.63 (s, 1H), 9.56 (s, 1H), 8.84 (s, 1H), 8.38 (s, 1H), 8.19 (s, 1H), 7.59 (d, J=7.9 Hz, 1H), 7.49 (dt, J=6.0, 8.1 Hz, 1H), 7.36-7.33 (m, 2H), 7.31 (d, J=2.0 Hz, 2H), 7.20

(dt, J=2.3, 8.4 Hz, 1H), 6.69 (dd, J=10.3, 17.0 Hz, 1H), 6.31 (dd, J=1.8, 17.0 Hz, 1H), 5.85-5.78 (m, 1H), 5.29 (s, 2H), 4.33 (t, J=5.8 Hz, 2H), 2.82 (t, J=5.8 Hz, 2H), 2.52-2.51 (m, 4H), 2.37-2.29 (m, 4H), 2.15 (s, 3H). MS (ESI) m/z 609.3 [M+H]+

146: To a suspension of N4-(5-chloro-2-fluoro-4-((3-fluorobenzyl)oxy)phenyl)-7-(2-(4-methylpiperazin-1-yl)ethoxy)quinazoline-4,6-diamine (180 mg, 324 umol, 1.00 eq), but-2-ynoic acid (273 mg, 3.24 mmol, 10.0 eq) (obtained as intermediate during the synthesis of 145, after step C.5) in pyridine (0.900 mL) and tetrahydrofuran (2.70 mL) was added 2,4,6-tripropyl-1,3,5,2,4,6-trioxatriphosphinane 2,4,6-trioxide (1.44 g, 2.27 mmol, 1.35 mL, 50% purity, 7.00 eq) at 0° C. The mixture was stirred at 20° C. for 1 h. The mixture was diluted with saturated sodium carbonate (2.00 mL), water (3.00 mL) and extracted with ethyl acetate (3×10.0 mL). The combined organic layers were dried over anhydrous sodium sulfate, filtered and concentrated to afford a residue. The residue was purified by prep-HPLC (column: Waters Xbridge 150*50 10 u; mobile phase: [water (0.05% ammonia hydroxide v/v)-acetonitrile]; B%: 40%-70%, 10 min) and lyophilized to afford N-(4-((5-chloro-2-fluoro-4-((3-fluorobenzyl)oxy)phenyl)amino)-7-(2-(4-methylpiperazin-1-yl)ethoxy)quinazolin-6-yl)but-2-ynamide (7.55 mg, 12.0 nmol, 4% yield, 99% purity) as a yellow solid. 1H NMR (400 MHz, DMSO-d6) δ=10.09-9.41 (m, 2H), 8.56 (br d, J=9.3 Hz, 1H), 8,30 (br d, J=4.5 Hz, 1H), 7.59 (br d, J 32 8.1 Hz, 1H), 7.52-7.44 (m, 1H), 7.38-7.27 (m, 3H), 7.25-7.14 (m, 2H), 5.27 (s, 2H), 4.28 (br t, J=5.4 Hz, 2H), 2.76 (br t, J=5.7 Hz, 2H), 2.52-2.52 (m, 4H), 2.38-2.30 (m, 4H), 2.16 (s, 3H), 2.06 (br s, 3H). MS (ESI) m/z 621.3 [M+H]+

147: Synthesized according to general procedure C starting from intermediate XIII obtained in analogy to 28 wherein in step C.3 H2NX is 5-chloro-2-fluoro-4-((3-fluorobenzyl)oxy)aniline C.4 HNR'R" 8-oxa-3-azabicyclo[3.2.1]octane; variant ii) was used in step C.5; and variant i) was used in step C.6; and 6% overall yield from XIV. 1H NMR (400 MHz, CDCl3) δ=9.15 (s, 1H), 8.68 (s, 1H), 8.41 (d, J=8.2 Hz, 1H), 8.29 (br s, 1H), 7.43-7.33 (m, 2H), 7.29 (s, 1H), 7.25 (br d, J=7.9 Hz, 2H), 7.05 (dt, J=2.4, 8.3 Hz, 1H), 6.85 (d, J=11.9 Hz, 1H), 6.55-6.46 (m, 1H), 6.37 (d, J=10.1 Hz, 1H), 5.89 (dd, J=1.0, 10.1 Hz, 1H), 5.15 (s, 2H), 4.36-4.30 (m, 4H), 2.90 (t, J=5.6 Hz, 2H), 2.68 (br d, J=10.6 Hz, 2H), 2.52 (dd, J=1.7, 10.8 Hz, 2H), 1.94-1.88 (m, 4H). MS (ESI) m/z 622.2 [M+H]+

148: To a suspension of but-2-ynoic acid (178 mg, 2.11 mmol, 10.0 eq) and 7-(2-(8-oxa-3-azabicyclo[3.2.1]octan-3-yl)ethoxy)-N4-(5-chloro-2-fluoro-4-((3-fluorobenzyl)oxy)phenyl)quinazoline-4,6-diamine (120 mg, 211 umol, 1.00 eq) (obtained as intermediate during the synthesis of 147, after step C.5) in pyridine (0.600 mL) was added 2,4,6-tripropyl-1,3,5,2,4,6-trioxatriphosphinane 2,4,6-trioxide (941 mg, 1.48 mmol, 880 uL, 50% purity, 7.00 eq) at 0° C. The mixture was stirred at 20° C. for 1 h. The mixture was diluted with saturated sodium carbonate (1.50 mL), water (10.0 mL) and extracted with ethyl acetate (3×25.0 mL). The combined organic layers were dried over anhydrous sodium sulfate, filtered and concentrated to afford a residue. The residue was purified by prep-HPLC (column: Phenomenex Synergi C18 150*25*10 um; mobile phase: [water (0.225% formic acid)-acetonitrile]; B%: 28%-58%, 9 min) and lyophilized to afford N-(7-(2-(8-oxa-3-azabicyclo[3.2.1]octan-3-yl)ethoxy)-4-((5-chloro-2-fluoro-4-((3-fluorobenzyl)oxy)phenyl)amino)quinazolin-6-yl)but-2-ynamide (3.65 mg, 5.26 umol, 2% yield, 98% purity, formic acid) as a yellow solid. 1H NMR (400 MHz, CDCl3) δ=8.95 (s, 1H), 8.67 (s, 1H), 8.40 (br s, 1H), 8.34 (d, J=8.2 Hz, 1H), 7.46 (br s, 1H), 7.42-7.35 (m, 1H), 7.27-7.19 (m, 3H), 7.12-6.99 (m, 1H), 6.84 (d, J=11.6 Hz, 1H), 5.15 (s, 2H), 4.37-4.27 (m, 4H), 2.89 (t, J=5.4 Hz, 2H), 2.67 (br d, J=10.4 Hz, 2H), 2.52 (br d, J=10.9 Hz, 2H), 2.07 (s, 3H), 2.01-1.95 (m, 2H), 1.94-1.87 (m, 2H). MS (EST) m/z 634.2 [M+H]+.

149: To a solution of N4-(5-chloro-2-fluoro-4-((3-fluorobenzyl)oxy)phenyl)-7-(2-morpholinoethoxy)quinazoline-4,6-diamine (150 mg, 277 umol, 1.00 eq) and but-2-ynoic acid (93.1 mg, 1.11 mmol, 4.00 eq) in dimethyl formamide (1.00 mL) was added 1-(3-dimethylaminopropyl)-3-ethylcarbodiimide hydrochloride (212 mg, 1.11 mmol, 4.00 eq) and pyridine (131 mg, 1.66 mmol, 134 uL, 6.00 eq) and the mixture was stirred at 25° C. for 3 h. The mixture was diluted with dimethyl formamide (1.00 mL) to give a solution. The solution was purified by prep-HPLC (column: Waters Xbridge 150*25 5 u; mobile phase: [water(10 mM NH4HCO3)-ACN]; B%: 40%-70%, 10 min) and lyophilized to give N-(4-((5-chloro-2-fluoro-4-((3-fluorobenzyl)oxy)phenyl)amino)-7-(2-morpholinoethoxy)quinazolin-6-yl)but-2-ynamide (34.07 mg, 55.5 umol, 20% yield, 99% purity) as a yellow solid. 1H NMR (400 MHz, DMSO-d6) δ=9.91 (s, 1H), 9.64 (s, 1H), 8.59 (br s, 1H), 8.38 (s, 1H), 7.60 (d, J=7.9 Hz, 1H), 7.49 (dt, J=6.2., 8.0 Hz, 1H), 7.34 (br d, J=7.6 Hz, 2H), 7.31 (s, 2H), 7.20 (dt, J=2.3, 8.6 Hz, 1H), 5.29 (s, 2H), 4.32 (t, J=5.7 Hz, 2H), 3.66-3.55 (m, 4H), 2.79 (t, J=5.7 Hz, 2H), 2.52 (m, 4H), 2.07 (br s, 3H). MS (ESI) m/z 608.4 [M+H]+

Synthesis of N4-(5-chloro-2-fluoro-4-((3-fluorobenzyl)oxy)phenyl)-7-(2-morpholinoethoxy)quinazoline-4,6-diamine Synthesized according to general procedure A, wherein in step A.2 H2N-X 5-chloro-2-fluoro-4-((3-fluorobenzyl)oxy)aniline; in step A,3 the NH nucleophile is 2-morpholinoethanol; variant i) was used in step A.4 to give N4-(5-chloro-2-fluoro-4-((3-fluorobenzyl)oxy)phenyl)-7-(2-morpholinoethoxy)quinazoline-4,6-diamine. 1H NMR (400 MHz, DMSO-d6) δ=9.09 (br s, 1H), 8.32-8.08 (m, 2 H), 7.64 (d, J=8.0 Hz, 1H), 7.54-7.45 (m, 1H), 7.37-7.32 (m, 2H), 7.30 (s, 1H), 7.25-7.17 (m, 1H), 7.11 (s, 1H) 5.50-5.12 (m, 3H), 4.28 (br t, J=5.6 Hz, 2H), 3.74-3.51 (m, 5H), 2.83 (t, J=5.6 Hz, 2H) 2.56-2.53 (m, 4H). MS (ESI) m/z 542.3 [M+H]+

150: To a solution N4-(5-chloro-2-fluoro-4-((3-fluorobenzyl)oxy)phenyl)-7-(3-morpholinopropoxy)quinazoline-4,6-diamine (200 mg, 359 umol, 1.00 eq) and but-2-ynoic acid (211 mg, 2.52 mmol, 7.00 eq) in pyridine (3.00 mL) was added propylphosphonic anhydride (2.29 g, 3.60 mmol, 2.14 mL, 50% purity, 10.0 eq) dropwise at 0° C. After addition, the mixture was stirred at 0° C. for 1 h. The reaction mixture was filtered. The filtrate was purified by prep-HPLC (column: Waters X bridge 150*25 5 u; mobile phase: [water (10 mM NH4HCO3)-ACN]; B%: 35%-65%, 10 min) and lyophilized to give N-(4-((5-chloro-2-fluoro-4-((3-fluorobenzyl)oxy)phenyl)amino)-7-(3-morpholinopropoxy)quinazolin-6-yl)but-2-ynamide (10.68 mg, 16.4 umol, 5% yield, 95% purity) as a white solid.

1H NMR (400 MHz, CDCl3) δ=8.97 (s, 1H), 8.69 (s, 1H), 8.43 (d, J=8.2 Hz, 1H), 8.24 (s, 1H), 7.43-7.36 (m, 1H), 7.31 (s, 1H), 7.28-7.21 (m, 3H), 7.11-6.99 (m, 1H), 6.86 (d, J=11.8 Hz, 1H), 5.16 (s, 2H), 4.34 (t, J=6.4 Hz, 2H), 3.83-3.74 (m, 4H), 2.64-2.57 (m, 2H), 2.56-2.46 (m, 4H), 2.17 (br t, J=6.8 Hz, 2H), 2.10 (s, 3H). MS (ESI) m/z 622.4 [M+H]+

Synthesis of N4-(5-chloro-2-fluoro-4-((3-fluorobenzyl)oxy)phenyl)-7-(3-morpholinopropoxy)quinazoline-4,6-diamine Synthesized according to general procedure C starting from intermediate XIII obtained in analogy to 28 wherein in step C.3 H₂NX is 5-chloro-2-fluoro-4-((3-fluorobenzyl)oxy)aniline C.4 HNR'R" morpholine; variant ii) was used in step C.5 to give N⁴-(5-chloro-2-fluoro-4-((3-fluorobenzyl)oxy)phenyl)-7-(3-morpholinopropoxy)quinazoline-4,6-diamine MS (ESI) m/z 556.3 [M+H]⁺

151: To a solution of (R)-N⁴-(5-chloro-2-fluoro-4-((3-fluorobenzyl)oxy)phenyl)-7-((1-methylpyrrolidin-3-yl)oxy)quinazoline-4,6-diamine (200 mg, 391 umol, 1.00 eq) (obtained as intermediate in the synthesis of 133 [V]) in dimethyl formamide (2.00 mL) was added but-2-ynoic acid (49.3 mg, 586 umol, 1.50 eq), 1-(3-dimethylaminopropyl)-3-ethylcarbodiimide hydrochloride (150 mg, 781 umol, 2.00 eq) and pyridine (92.7 mg, 1.17 mmol, 94.6 uL, 3.00 eq). Then the mixture was stirred at 25° C. for 1 h. The mixture was diluted with dimethyl formamide (1.00 mL) to give a solution. The solution was purified by prep-HPLC (column: Waters Xbridge 150*25 5 u, mobile phase: [water(10 mM NH₄HCO)-ACN]; B%: 42%-72%, 10 min) and lyophilized to give (R)-N-(4-((5-chloro-2-fluoro-4-((3-fluorobenzyl)oxy)phenyl)amino)-7-((1-methylpyrrolidin-3-yl)oxy)quinazolin-6-yl)but-2-ynamide (51.17 mg, 84.9 umol, 22% yield, 96% purity) as a white solid. ¹H NMR (400 MHz, DMSO-d₆) δ=9.98 (br s, 1H), 9.63 (s, 1H), 8.63 (br s, 1H), 8.37 (s, 1H), 7.59 (d, J=7.9 Hz, 1H), 7.53-7.44 (m, 1H), 7.38-728 (m, 3H), 7.24-7.17 (m, 1H), 7.15 (s, 1H), 5.29 (s, 2H), 5.08 (br d, J=3.1 Hz, 1H), 2.79 (br s, 2H), 2.77-2.70 (m, 1H), 2.42-2.35 (m, 2H), 2.29 (s, 3H), 2.07 (br s, 3H), 1.98-1.87 (m, 1H). MS (ESI) m/z 578.3 [M+H]⁺

152: To the suspension of N⁴-(5-chloro-2-fluoro-4-((3-fluorobenzyl)oxy)phenyl)-7-(2-(3-methoxyazetidin-1-yl)ethoxy)quinazoline-4,6-diamine (0.150 g, 277umol, 1.00 eq)) (obtained as intermediate in the synthesis of 134 [XVII]) in pyridine (15.0 mL) was added but-2-ynoic acid (0.116 g, 1.38 mmol, 5.00 eq) and propylphosphonic anhydride (1.23 g, 194 mmol, 7.00 eq, 50% in ethyl acetate) at 25° C. The mixture was stirred at 30° C. for 2 h. The residue was added saturated sodium carbonate (50.0 mL). The aqueous phase was extracted with ethyl acetate/methanol (8/1, 3×100 mL). The combined organic phase was washed with sodium carbonate (3×100 mL), concentrated under vacuum to afford a residue. The residue was purified by prep-HPLC (column: Waters Xbridge 150*25 5 u; mobile phase: [water(10 mM NH₄HCO₃)-ACN]; B%: 42%-72%, 14 min) and lyophilized to afford N-(4-((5-chloro-2-fluoro-4-((3-fluorobenzyl)oxy)phenyl)amino)-7-(2-(3-methoxyazetidin-1-yl)ethoxy)quinazolin-6-yl)but-2-ynamide (68.38 mg, 111 umol, 40% yield, 99% purity) as a yellow solid. ¹H NMR (400 MHz, DMSO-d₆) δ=10.01 (br s, 1H), 9.64 (s, 1H), 8.57 (br s, 1H), 8.37 (s, 1H), 7.60 (br d, J=7.9 Hz, 1H), 7.49 (dt, J=6.0, 8.1 Hz, 1H), 7.34 (br d, J=7.3 Hz, 2H), 7.31 (br s, 1H), 7.25-7.18 (m, 2H), 5.29 (s, 2H), 4.16 (br t, J=5.1 Hz, 2H), 3.98 (quin, J=5.8 Hz, 1H), 3.62 (dd, J=6.1, 7.9 Hz, 2H), 3.16 (s, 3H), 2.98 (br t, J=6.9 Hz, 2H), 2.85 (br t, J=5.1 Hz, 2H), 2.06 (br s, 3H). MS (ESI) m/z 608.4 [M+H]⁺

153: Synthesized according to general procedure C starting from intermediate XIII obtained in analogy to 28 wherein in step C.3 H₂NX is 3-chloro-4-(6-fluoropyridin-2-yl)methoxy)aniline C.4 HNR'R" morpholine; variant ii) was used in step C.5; and variant i) was used in step C.6; and 5% overall yield from XIV. ¹H NMR (400 MHz, CDCl₃) δ=9.10 (s, 1H), 8.65 (s, 1H), 8.20 (br s, 1H), 8.00-7.80 (m, 2H), 7.75 (s, 1H), 7.65-7.46 (m, 2H), 6.98 (br d, J=8.8 Hz, 1H), 6.90 (br d, J=6.4 Hz, 1H), 6.57-6.43 (m, 1H), 6.43-6.28 (m, 1H), 5.89 (br d, J=10.2 Hz, 1H), 5.22 (s, 2H), 4.33 (br t, J=6.4 Hz, 2H), 3.76 (br s, J=4.2 Hz, 4H), 2.68-2.45 (m, 6H), 2.14 (br t, 6.8 Hz, 2H). MS (ESI) m/z 593.3 [M+H].

154: Synthesized according to general procedure C starting from intermediate XIII obtained in analogy to 28 wherein in step C.3 H₂NX is 3-chloro-4-((6-fluoropyridin-2-yl)methoxy)aniline C.4 HNR'R" morpholine; variant ii) was used in step C.5; and variant i) was used in step C.6; and 8% overall yield from XIV. ¹H NMR (400 MHz, CDCl₃) δ=9.15 (s, 1H), 8.74-8.60 (m, 2H), 8.37-8.21 (m, 1H), 7.94-7.80 (m, 2H), 7.64-7.48 (m, 3H), 7.33 (s, 1H), 7.02-6.95 (m, 1H), 6.90 (dd, J=2.6, 8.1 Hz, 1H), 6.56-6.41 (m, 2H), 5.89 (br dd, J=2.3, 9.0 Hz, 1H), 5.22 (d, J=3.8 Hz, 2H), 4.42-4.33 (m, 2H), 3.83-3.75 (m, 4H), 2.99 (t, J=5.4 Hz, 2H), 2.68 (br s, 4H). MS (ESI) m/z 579.2 [M+H]⁺

Synthesis of 3-chloro-4-((6-fluoropyridin-2-yl)methoxy)aniline

To a solution of 2-fluoro-6-methylpyridine (8.00 g, 72.0 mmol, 7.41 mL, 1.00 eq) in acetonitrile (200 mL) was added 1-chloropyrrolidine-2,5-dione (24.0 g, 180 mmol, 2.50. eq), benzoic peroxyanhydride (2.09 g, 8.64 mmol, 0.120 eq) and acetic acid (0.400 mL). The mixture was stirred at 85° C. for 12 h. The mixture was concentrated to afford a residue. The residue was diluted with water (50.0 mL) and extracted with ethyl acetate (3×100 mL). The combined organic layers were dried over anhydrous sodium sulfate, filtered and concentrated to afford a residue. The residue was purified by silica gel chromatography (petroleum ether/ethyl acetate=1/0-10/1) to afford 2-(chloromethyl)-6-fluoropyridine (4.50 g, 30.9 mmol, 43% yield) as a colorless oil. MS (ESI) m/z 145.9 [M+H]⁺

To a solution of 2-(chloromethyl)-6-fluoropyridine (2.00 g, 13.7 mmol, 0.750 eq) in acetonitrile (40.0 mL) was added potassium carbonate (2.53 g, 18.3 mmol, 1.00 eq), followed by the addition of 4-amino-2-chlorophenol (2.63 g, 18.3 mmol, 1.00 eq), potassium iodide (304 mg, 1.83 mmol, 0.100 eq) and potassium hydroxide (1.03 g, 18.3 mmol, 1.00 eq). The mixture was stirred at 90° C. for 12 h. The mixture was concentrated to afford a residue. The residue was diluted with water (100 mL) and extracted with ethyl acetate (3×200 mL). The combined organic layers were dried over anhydrous sodium sulfate, filtered and concentrated to afford a residue. The residue was purified by silica gel chromatography (petroleum ether/ethyl acetate=1/1) to afford 3-chloro-4-((6-fluoropyridin-2-yl)methoxy)aniline (1.10 g, 4.35 mmol, 24% yield) as a yellow solid. ¹H NMR (400 MHz, CDCl₃) δ=7.83 (q, J=7.9 Hz, 1H), 7.60-7.50 (m, 1H), 6.86 (dd, J=2.1, 8.2 Hz, 1H), 6.81-6.75 (m, 2H), 6.52 (dd, J=2.8, 8.6 Hz, 1H), 5.10 (s, 2H), 3.54 (br s, 2H).

155: Synthesized according to general procedure C starting from intermediate XIII obtained in analogy to 28 wherein in step C.3 H₂NX is 3-chloro-4-((6-fluoropyridin-2-yl)methoxy)aniline C.4 HNR'R" 3-methoxyazetidine; variant ii) was used in step C.5; and variant i) was used in step C.6; and 11% overall yield from XIV. ¹H NMR (400 MHz, CDCl₃) δ=9.11 (s, 1H), 8.65 (s, 1H), 8.30 (s, 1H), 7.93-7.84 (m, 2H), 7.58 (dd, J=1.6, 7.6 Hz, 1H), 7.52 (dd, J=2.6, 8.9 Hz, 1H), 7.42 (s, 1H), 7.27-7.26 (m, 1H), 6.99 (d, J=9.0 Hz, 1H), 6.90 (dd, J=2.1, 8.2 Hz, 1H), 6.55-6.48 (m, 1H), 6.43-6.34 (m, 1H), 5.89 (dd, J=1.2, 10.1 Hz, 1H), 5.23 (s, 2H), 4.29 (t, J=6.3 Hz, 2H), 4.06 (t, J=5.8 Hz, 1H), 3.66 (dd, J=6.1, 8.3 Hz, 2H), 3.28 (s, 3H), 2.97-2.92 (m, 2H), 2.70 (t, J=6.8 Hz, 2H), 1.99 (quit, J=6.71, 2H). MS (ESI) m/z 593.2 [M+H]⁺

156: Synthesized according to general procedure C starting from intermediate XIII obtained in analogy to 28 wherein in step C.3 H₂NX is 3-chloro-4-((6-fluoropyridin-2-yl)methoxy)aniline C.4 HNR'R" 8-oxa-3-azabicyclo[3.2.1]octane; variant ii) was used in step C.5; and variant i) was used in step C.6; and 11% overall yield from XIV. ¹H NMR (400 MHz, DMSO-d$_6$) δ=9.69 (s, 1H), 9.55 (s, 1H), 8.86 (s, 1H), 8.50 (s, 1H), 8.28 (s, 1H), 8.09 (q, J=8.4 Hz, 1H), 8.01 (d, J=2.4 Hz, 1H), 7.72 (dd, J=2.4, 9.0 Hz, 1H), 7.54 (dd, J=2.4, 7.4 Hz, 1H), 7.32 (s, 1H), 7.25 (d, J=9.0 Hz, 1H), 7.17 (dd, J=2.4, 8.0 Hz, 1H), 6.70 (dd, J=10.2, 17.2 Hz, 1H), 6.32 (dd, J=2.0, 17.0 Hz, 1H), 5.87-5.77 (m, 1H), 5.26 (s, 2H), 4.32 (t, J=5.6 Hz, 2H), 4.18 (dd, J=2.0, 4.2 Hz, 2H), 2.79 (t, J=5.6 Hz, 2H), 2.66 (d, J=10.8 Hz, 2H), 2.32 (dd, J=1.8, 11.1 Hz, 2H), 1.85-1.77 (m, 2H), 1.69-1.60 (m, 2H). MS (ESI) m/z 605.5 [M+H]

157: Synthesized according to general procedure C starting from intermediate XIII obtained in analogy to 28 wherein in step C.3 H$_2$NX is 3-chloro-4-((6-fluoropyridin-2-yl)methoxy)aniline C.4 HNR'R" 3-methoxyazetidine; variant ii) was used in step C.5; and variant i) was used in step C.6; and 8% overall yield from XV. $^1$H NMR (400 MHz, DMSO-d$_6$) δ=11.76-11.52 (m, 1H), 11.11 (br s, 1H), 10.44 (s, 1H), 9.19 (s, 1H), 8.82 (s, 1H), 8.10 (q, J=8.2 Hz, 1H), 7.89 (d, J=2.4 Hz, 1H), 7.61 (dd, J=2.4, 8.8 Hz, 1H), 7.55 (dd, J=2.4, 7.2 Hz, 1H), 7.42 (s, 1H), 7.34 (d, J=9.0 Hz, 1H), 7.26 (br dd, J=10.0, 17.0 Hz, 1H), 7.18 (dd, J=2.4, 8.2 Hz, 1H), 6.36 (dd, J=1.6, 17.2 Hz, 1H), 5.89-5.81 (m, 1H), 5.31 (s, 2H), 4.57-4.44 (m, 3H), 4.40-4.31 (m, 1H), 4.29-4.21 (m, 1H), 4.20-4.01 (m, 2H), 3.84-3.73 (m, 2H), 3.29-3.26 (m, 3H). MS (ESI) m/z 579.3 [M+H]

158: Synthesized according to general procedure C starting from intermediate XIII obtained in analogy to 28 wherein in step C.3 H$_2$NX is (3-chloro-4-((3-fluorobenzyl)oxy)aniline C.4 HNR'R" 1-methylpiperazine; variant ii) was used in step C.5; and variant i) was used in step C.6; and 22% overall yield from XV. $^1$H NMR (400 MHz, DMSO-d$_6$) δ=9.75-9.66 (m, 1H), 9.58 (s, 1H), 8.85 (s, 1H), 8.50 (s, 1H), 8.09 (q, J=8.4 Hz, 1H), 8.01 (d, J=2.6 Hz, 1H), 7.71 (dd, J=2.6, 8.8 Hz, 1H), 7.54 (dd, J=2.2, 7.6 Hz, 1H), 7.31 (s, 1H), 7.25 (d, J=9.0 Hz, 1H), 7.17 (dd, J=2.4, 8.2 Hz, 1H), 6.69 (dd, J=10.2, 17.0 Hz, 1H), 6.32 (dd, J=1.8, 17.2 Hz, 1H), 5.86-5.79 (m, 1H), 5.26 (s, 2H), 4.33 (t, J=5.6 Hz, 2H), 2.82 (t, J=5.8 Hz, 2H), 2.57-2.51 (m, 4H), 2.37-2.23 (m, 4H), 2.14 (s, 3H). MS (ESI) m/z 592.5 [M+H]

159: Synthesized according to general procedure C starting from intermediate XIII obtained in analogy to 28 wherein in step C.3 H$_2$NX is (3-chloro-4-((6-fluoropyridin-2-yl)methoxy)aniline C.4 HNR'R" (1S,4S)-2-oxa-5-azabicyclo[2.2.1]heptane; variant ii) was used in step C.5; and variant i) was used in step C.6; and 52% overall yield from XV. $^1$H NMR (400 MHz, DMSO-d$_6$) δ=9.67 (s, 1H), 9.59 (s, 1H), 8.84 (s, 1H), 8.49 (s, 1H), 7.99 (d, J=2.6 Hz, 1H), 7.71 (dd, J=2.6, 8.8 Hz, 1H), 7.53-7.45 (m, 1H), 7.36-7.30 (m, 2H), 7.28-7.23 (m, 2H), 7.22-7.16 (m, 1H), 6.72 (dd, J=10.2, 17.0 Hz, 1H), 6.32 (dd, J=2.0, 17.0 Hz, 1H), 5.86-5.79 (m, 1H), 5.25 (s, 2H), 4.33 (s, 1H), 4.28 (t, J=6.4 Hz, 2H), 3.85 (d, J=7.6 Hz, 1H), 3.50 (dd, J=1.8, 7.4 Hz, 1H), 3.47 (s, 1H), 2.84-2.78 (m, 1H), 2.78-2.64 (m, 2H), 2.42 (d, J=9.6 Hz, 1H), 1.93 (quin, J=6.8 Hz, 2H), 1.77-1.70 (m, 1H), 1.61-1.54 (m, 1H). MS (ESI) m/z 604.2 [M+H]

160: Synthesized according to general procedure C starting from intermediate XIII obtained in analogy to 28 wherein in step C.3 H$_2$NX is 3-chloro-4-((3-fluorobenzyl)oxy)aniline C.4 HNR'R" (1R,4R)-2-oxa-5-azabicyclo[2.2.1]heptane; variant ii) was used in step C.5; and variant i) was used in step C.6; and 41% overall yield from XIV. $^1$H NMR (400 MHz, CDCl$_3$) δ=9.00 (s, 1H), 8.54 (s, 1H), 8.12 (s, 1H), 7.74 (d, J=2.8 Hz, 1H), 7.67 (s, 1H), 7.41 (dd, J=2.6, 8.8 Hz, 1H), 7.29 (dt, J=5.8, 8.0 Hz, 1H), 7.18-7.12 (m, 3H), 6.99-6.92 (m, 1H), 6.84 (d, J=8.8 Hz, 1H), 6.45-6.37 (m, 1H), 6.33-6.23 (m, 1H), 5.83-5.76 (m, 1H), 5.06 (s, 2H), 4.35 (s, 1H), 4.21 (t, J=6.4 Hz, 2H), 3.97 (d, J=7.6 Hz, 1H), 3.57 (dd, J=1.6, 7.8 Hz, 1H), 3.41 (s, 1H), 2.89 (dd, J=1.6, 9.8 Hz, 1H), 2.80-2.72 (m, 1H), 2.71-2.60 (m, 1H), 2.47 (d, J=10.0 Hz, 1H), 2.04-1.94 (m, 2H), 1.80 (dd, J=1.8, 9.8 Hz, 1H), 1.73-1.64 (m, 1H). MS (ESI) m/z 604.5 [M+H]

161: Synthesized according to general procedure C starting from intermediate XIII obtained in analogy to 28 wherein in step C.3 H$_2$NX is 3-chloro-4-((6-fluoropyridin-2-yl)methoxy)aniline C.4 HNR'R" (1S,4S)-2-oxa-5-azabicyclo[2.2.1]heptane; variant ii) was used in step C.5; and variant i) was used in step C.6; and 3% overall yield from XV. $^1$H NMR (400 MHz, DMSO-d$_6$) δ=9.68 (s, 1H), 9.60 (s, 1H), 8.85 (s, 1H), 8.50 (s, 1H), 8.20 (s, 1H), 8.09 (q, J=8.2 Hz, 1H), 8.01 (d, J=2.6 Hz, 1H), 7.71 (dd, J=2.6, 8.8 Hz, 1H), 7.54 (dd, J=2.0, 7.4 Hz, 1H), 7.30-7.23 (m, 2H), 7.17 (dd, J=2.4, 8.2 Hz, 1H), 6.72 (dd, J=10.2, 17.0 Hz, 1H), 6.32 (dd, J=17.2 Hz, 1H), 5.89-5.77 (m, 1H), 5.26 (s, 2H), 4.34 (s, 1H), 4.28 (t, J=6.2 Hz, 2H), 3.85 (d, J=7.2 Hz, 1H), 3.51 (br d, J=1.6 Hz, 1H), 3.49 (br s, 1H), 2.82 (dd, J=1.6, 9.6 Hz, 1H), 2.77-2.66 (m, 2H), 2.44 (d, J=9.8 Hz, 1H), 1.94 (quin, J=6.8 Hz, 2H), 1.74 (dd, J=1.6, 9.4 Hz, 1H), 1.62-1.52 (m, 1H). MS (ESI) m/z 605.5 [M+H]

162: Synthesized according to general procedure C starting from intermediate XIII obtained in analogy to 28 wherein in step C.3 H$_2$NX is 3-chloro-4-((6-fluoropyridin-2-yl)methoxy)aniline C.4 HNR'R" (1R,4R)-2-oxa-5-azabicyclo[2.2.1]heptane; variant ii) was used in step C.5; and variant i) was used in step C.6; and 55% overall yield from XV. $^1$H NMR (400 MHz, DMSO-d$_6$) δ=9.69 (br s, 1H), 9.62 (s, 1H), 8.85 (s, 1H), 8.50 (s, 1H), 8.18 (s, 1H), 8.09 (q, J=8.2 Hz, 1H), 8.01 (d, J=2.4 Hz, 1H), 7.71 (dd, J=2.4, 9.0 Hz, 1H), 7.54 (dd, J=2.4, 7.4 Hz, 1H), 7.28-7.23 (m, 2H), 7.17 (dd, J=2.4, 8.2 Hz, 1H), 6.73 (dd, J=10.2, 16.9 Hz, 1H), 6.32 (dd, J=1.8, 17.0 Hz, 1H), 5.86-5.79 (m, 1H), 5.26 (s, 2H), 4.36 (s, 1H), 4.28 (br t, J=6.2 Hz, 2H), 3.87 (d, J=7.8 Hz, 1H), 3.57 (br s, 1H), 3.52 (br d, J=7.8 Hz, 1H), 2.88-2.78 (m, 2H), 2.77-2.69 (m, 1H), 2.49-2.47 (m, 1H), 1.96 (quin, J=6.6 Hz, 2H), 1.78 (br d, J=9.4 Hz, 1H), 1.61 (br d, J=9.0 Hz, 1H). MS (ESI) m/z 605.3 [M+H]

163: Synthesized according to general procedure C starting from intermediate XIII obtained in analogy to 28 wherein in step C.3 H$_2$NX is 3-chloro-4-(pyrimidin-4-ylmethoxy)aniline C.4 HNR'R" morpholine; variant ii) was used in step C.5; and variant i) was used in step C.6; and 22% overall yield from XIV. $^1$H NMR (400 MHz, DMSO-d$_6$) δ=9.22 (d, J=1.2 Hz, 1H), 9.10 (s, 1H), 8.82 (d, J=5.2 Hz, 1H), 8.64 (s, 1H), 8.32 (s, 1H), 7.98 (br s, 1H), 7.95 (d, J=2.4 Hz, 1H), 7.77 (d, J=5.2 Hz, 1H), 7.59 (dd, J=2.4, 8.8 Hz, 1H), 6.98 (d, J=8.8 Hz, 1H), 6.55-6.39 (m, 2H), 5.89 (dd, J=1.6, 9.8 Hz, 1H), 5.25 (s, 2H), 4.32 (t, J=6.4 Hz, 2H), 3.82-3.74 (m, 4H), 2.63 (t, J=7.2 Hz, 2H), 2.56 (br d, J=4.0 Hz, 4H), 2.19-2.16 (m, 2H). MS (ESI) m/z 576.2 [M+H]

Synthesis of 3-chloro-4-(pyrimidin-4-ylmethoxy)aniline

To a solution of 2-chloro-1-fluoro-4-nitro-benzene (1.59 g, 9.08 mmol, 1.00 eq) in dimethyl formamide (10.0 mL) was added potassium carbonate (2.51 g, 18.2 mmol, 2.00 eq) and pyrimidin-4-ylmethanol (1.00 g, 9.08 mmol, 1.05 eq). The mixture was stirred at 60° C. for 24 h. The reaction mixture was added water (100 mL), filtered and the filter cake was concentrated under reduced pressure to give 4-((2-chloro-4-nitrophenoxy)methyl)pyrimidine (1.50 g, 5.65 mmol, 62% yield) as a yellow solid.

MS (ESI) m/z 265.9 [M+H]

A mixture of 4-((2-chloro-4-nitrophenoxy)methyl)pyrimidine (1.50 g, 5.65 mmol, 1.00 eq), iron powder (1.58 g, 28.2 mmol, 5.00 eq) and ammonium chloride (2.42 g, 45.2 mmol, 8.00 eq) in methanol (15.0 mL) and water (8.00 mL) was stirred at 80° C. for 2 h. The mixture was filtered and the filtrate was concentrated to give a residue. The residue was poured into water (30.0 mL) and stirred for 10 min. The aqueous phase was extracted with ethyl acetate (3×20.0 mL). The combined organic phase was washed with brine (30.0 mL), dried over anhydrous sodium sulfate, filtered and concentrated in vacuum to give 3-chloro-4-(pyrimidin-4-ylmethoxy)aniline (1.10 g, 4.67 mmol, 83% yield) as a yellow solid.

164: To a solution of $N^4$-(3-chloro-4-(pyrimidin-4-ylmethoxy)phenyl)-7-(3-morpholinopropoxy)quinazoline-4,6-diamine (60.0 mg, 115 umol, 1.00 eq) (obtained as intermediate XVII during the synthesis of 163) and but-2-ynoic acid (29.0 mg, 345 umol, 3.00 eq) in pyridine (0.500 mL) was added 1-(3-dimethylaminopropyl)-3-ethylcarbodiimide hydrochloride (220 mg, 1.15 mmol, 10.0 eq) at 25° C. The mixture was stirred at 20° C. for 2 h. The mixture was poured into water (20.0 mL) and extracted with ethyl acetate (3×20.0 mL). The combined organic phase was washed with brine (30.0 mL), dried over anhydrous sodium sulfate, filtered, and concentrated to dryness to give a residue. The residue was purified by prep-HPLC (column: Waters Xbridge 150*25 mm* 5 um; mobile phase: [water(10 mM NH4HCO3)-ACN]; B%: 20%-50%, 10 min) to give N-(4-((3-chloro-4-(pyrimidin-4-ylmethoxy)phenyl)amino)-7-(3-morpholinopropoxy)quinazolin-6-yl)but-2-ynamide (35.58 mg, 60.5 umol, 52% yield) as a light yellow solid. $^1$H NMR (400 MHz, DMSO-$d_6$) δ=9.98 (br s, 1H), 9.67 (s, 1H), 9.21 (d, J=1.4 Hz, 1H), 8.89 (d, J=5.2 Hz, 1H), 8.59 (br s, 1H), 8.51 (s, 1H), 8.03 (d, J=2.0 Hz, 1H), 7.74-7.67 (m, 2H), 7.28-7.23 (m, 2H), 5.34 (s, 2H), 4.23 (t, J=6.2 Hz, 2H), 3.60 (t, J=4.6 Hz, 4H), 2.49-2.46 (m, 2H), 2.40 (br s, 4H), 2.07 (br s, 3H), 2.01-1.94 (m, 2H), MS (ESI) m/z 588.3 [M+H]

165: To a solution of $N^4$-(3-chloro-4-(pyridazin-3-ylmethoxy)phenyl)-7-(3-morpholinopropoxy)quinazoline-4,6-diamine (200 mg, 383 umol, 1.00 eq) (obtained as intermediate & XVII for 167) and but-2-ynoic acid (96.6 mg, 1.15 mmol, 3.00 eq) in pyridine (2.00 mL) was added 1-(3-dimethylaminopropyl)-3-ethylcarbodiimide hydrochloride (734 mg, 3.83 mmol, 10.0 eq) at 25° C. The mixture was stirred at 25° C. for 2 h. The mixture was poured into water (20.0 mL) and extracted with ethyl acetate (3×20.0 mL). The combined organic phase was washed with brine (30.0 mL), dried over anhydrous sodium sulfate, filtered, and concentrated to dryness to give a residue. The residue was purified by prep-HPLC (column: Waters Xbridge 150*25 mm* 5 um; mobile phase: [water(10 mM NH4HCO3)-ACN]; B%: 19%-49%, 10 min) to give N-(4-((3-chloro-4-(pyridazin-3-ylmethoxy)phenyl)amino)-7-(3-morpholinopropoxy)quinazolin-6-yl)but-2-ynamide (62.5 mg, 106 mmol, 28% yield) as a yellow solid. $^1$H NMR (400 MHz, CDCl$_3$) δ=9.23-9.13 (m, 1H), 8.91 (s, 1H), 8.64 (s, 1H), 8.28 (s, 1H), 7.97-7.86 (m, 2H), 7.82 (s, 1H), 7.63-7.49 (m, 2H), 7.08 (d, J=8.8 Hz, 1H), 5.54 (s, 2H), 4.33 (t, J=6.4 Hz, 2H), 3.81-3.71 (m, 4H), 2.59 (t, J=7.2 Hz, 2H), 2.52 (br s, 4H), 2.16 (br t, J=6.6 Hz, 2H), 2.09 (s, 3H). MS (ESI) m/z 588.1 [M+H]

166: Synthesized according to general procedure C starting from intermediate XIII obtained in analogy to 28 wherein in step C.3 H$_2$NX is 3-chloro-4-(pyrimidin-2-ylmethoxy)aniline C.4 HNR'R" morpholine; variant ii) was used in step C.5; and variant i) was used in step C.6; and 10% overall yield from XV. $^1$H NMR (400 MHz, DMSO-$d_6$) δ=9.66 (s, 1H), 9.60 (s, 1H), 8.87 (d, J=4.9 Hz, 2H), 8.83 (s, 1H), 8.48 (s, 1H), 8.17 (s, 1H), 7.95 (d, J=2.5 Hz, 1H), 7.63 (dd, J=2.5, 9.0 Hz, 1H), 7.50 (t, J=4.9 Hz, 1H), 7.27 (s, 1H), 7.11 (d, J=9.1 Hz, 1H), 6.71 (dd, J=10.2, 16.9 Hz, 1H), 6.32 (dd, J=1.9, 17.0 Hz, 1H), 5.88-5.77 (m, 1H), 5.40 (s, 2H), 4.26 (t, J=6.3 Hz, 2H), 3.59 (t, J=4.5 Hz, 4H), 2.49-2.46 (m, 2H), 2.39 (br s, 4H), 1.99 (quin, J=6.7 Hz, 2H). MS (ESI) m/z 576.1 [M+H]$^+$ Synthesis of 3-chloro-4-(pyrimidin-2-ylmethoxy)aniline To a solution of 2-chloro-1-fluoro-4-nitrobenzene (1.00 g, 5.70 mmol, 1.00 eq) and pyrimidin-2-ylmethanol (627 mg, 5.70 mmol, 1.00 eq) in dimethyl formamide (8.00 mL) was added potassium carbonate (1.57 g, 11.4 mmol, 2.00 eq) and the mixture was stirred at 60° C. for 16 h. The mixture was poured into water (25.0 mL) and some precipitate was separated out. Then the mixture was filtered and the filter cake was collected. The filter cake was washed with petroleum ether and ethyl acetate (5.00 mL, 5/1) and the mixture was filtered to give 2-((2-chloro-4-nitrophenoxy)methyl)pyrimidine (1.00 g, 3.69 mmol, 64% yield, 98% purity) as a yellow solid. $^1$H NMR (400 MHz, CDCl$_3$) δ=8.80 (d, J=4.9 Hz, 2H), 8.33 (d, J=2.7 Hz, 1H), 8.09 (dd, J=2.7, 9.2 Hz, 1H), 7.31 (t, J=4.9 Hz, 1H), 7.03 (d, J=9.2 Hz, 1H), 5.51 (s, 2H).

To a solution of 2-((2-chloro-4-nitrophenoxy)methyl)pyrimidine (1.00 g, 3.76 mmol, 1.00 eq) in methanol (10.0 mL) was added a solution of ammonium chloride (604 mg, 11.3 mmol, 3.00 eq) in water (2.50 mL) and iron powder (1.05 g, 18.8 mmol, 5.00 eq). Then the mixture was stirred at 80° C. for 2 h. To the mixture was added methanol (10.0 mL) and the mixture was filtered to give a filtrate, which was concentrated under vacuum to give a residue. To the residue was added ethyl acetate (15.0 mL) and saturated sodium bicarbonate (5.00 mL). And the mixture was extracted with ethyl acetate (2×15.0 mL). All organic phases were combined, dried over anhydrous sodium sulfate, filtered and concentrated under vacuum to give 3-chloro-4-(pyrimidin-2-ylmethoxy)aniline (880 mg, 3.47 mmol, 92% yield, 93% purity) as a brown solid was used into next step without further purification. $^1$H NMR (400 MHz, CDCl$_3$) δ=8.79 (d, J=4.9 Hz, 2H), 7.25 (t, J=4.9 Hz, 1H), 6.85 (d, J=8.6 Hz, 1H), 6.76 (d, J=2.8 Hz, 1H), 6.49 (dd, J=2.8, 8.7 Hz, 1H), 5.27 (s, 2H), 3.50 (br s, 2H).

167: Synthesized according to general procedure C starting from intermediate XIII obtained in analogy to 28 wherein in step C.3 H$_2$NX is 3-chloro-4-(pyridazin-3-ylmethoxy)aniline C.4 HNR'R" morpholine; variant ii) was used in step C.5; and variant i) was used in step C.6; and 21% overall yield from XIV. 1H NMR (400 MHz, CDCl3) δ=9.19 (dd, J=1.6, 5.0 Hz, 1H), 9.11 (s, 1H), 8.66 H), 8.21 (s, 1H), 7.99-7.88 (m, 2H), 7.78 (s, 1H), 7.62-7.53 (m, 2H), 7.30 (s, 1H), 7.09 (d, J=8.8 Hz, 1H), 6.55-6.47 (m, 1H), 6.42-6.32 (m, 1H), 5.90 (dd, J=1.0, 10.2 Hz, 1H), 5.55 (s, 2H), 4.34 (t, J=6.4 Hz, 2H), 3.82-3.73 (m, 4H), 2.58 (t, J=7.2 Hz, 2H), 2.52 (br d, J=4.4 Hz, 4H), 2.15 (quin, J=6.8 Hz, 2H). MS (ESI) m/z 576.2 [M+H].

Synthesis of 3-chloro-4-(pyridazin-3-ylmethoxy)aniline

To a solution of pyridazin-3-ylmethanol (1.00 g, 9.08 mmol, 1.00 eq) and 2-chloro-1-fluoro-4-nitro-benzene (1.59 g, 9.08 mmol, 1.00 eq) in dimethyl formamide (10.0 mL) was added potassium carbonate (2.51 g, 18.2 mmol, 2.00 eq). The mixture was stirred at 60° C. for 12 h. The mixture was concentrated to dryness to give a residue. The residue was triturated with water (100 mL), filtered and the filter cake was wash with water (30.0 mL). The filter cake was dried to give 3-((2-chloro-4-nitrophenoxy)methyl)pyridazine (2.30 g, 8.66 mmol, 95% yield) as a brown solid. $^1$H NMR (400 MHz, CDCl$_3$) δ=9.25-9.23 (m, 1H), 8.36 (d, J=2.8 Hz, 1H), 8.22-8.18 (m, 1H), 7.89-7.85 (m, 1H), 7.65-7.60 (m, 1H), 7.21 (d, J=9.2 Hz, 1H), 5.64 (s, 2H). MS (ESI) m/z 266.0 [M+H]

A mixture of 3-((2-chloro-4-nitrophenoxy)methyl) pyridazine (2.30 g, 8.66 mmol, 1.00 eq), iron powder (2.42 g, 43.3 mmol, 5.00 eq) and ammonium chloride (2.32 g, 43.3 mmol, 5.00 eq) in methanol (20.0 mL) and water (5.00 mL) was stirred at 80° C. for 1 h. To the mixture was added methanol (100 ml) and filtered, the filtrate was concentrated to give a residue. The residue was poured into water (30.0 mL) and stirred for 10 min. The aqueous phase was extracted with ethyl acetate (3×20.0 mL). The combined organic phase was washed with brine (30.0 mL), dried over anhydrous sodium sulfate, filtered and concentrated in vacuum to give 3-chloro-4-(pyridazin-3-ylmethoxy)aniline (1.77 g, 7.51 mmol, 87% yield) as a brown solid.

168: To a solution of $N^4$-(3-chloro-4-(pyrimidin-2-ylmethoxy)phenyl)-7-(3-morpholinopropoxy)quinazoline-4,6-diamine (70.0 mg, 134 umol, 1.00 eq) (obtained as intermediate XVII during the synthesis of 166) and but-2-ynoic acid (33.8 mg, 402 umol, 3.00 eq) in pyridine (1.00 mL) was added 1-(3-dimethylaminopropyl)-3-ethylcarbodiimide hydrochloride (257 mg, 1.34 mmol, 10.0 eq) at 25° C. The mixture was stirred at 25° C. for 2 h. The mixture was poured into water (20.0 mL) and extracted with ethyl acetate (3×20.0 mL). The combined organic phase was washed with brine (30.0 mL), dried over anhydrous sodium sulfate, filtered, and concentrated to give a residue. The residue was purified by prep-HPLC (column: Xtimate C18 150*40 mm*10 um; mobile phase: [water (0.05% ammonia hydroxide v/v)-ACN]; B%: 23%-53%, 10 min) to give N-(4-((3-chloro-4-(pyrimidin-2-ylmethoxy)phenyl)amino)-7-(3-morpholinopropoxy)quinazolin-6-yl)but-2-ynamide (62.5 mg, 106 mmol, 28% yield) as a yellow solid. $^1$H NMR (400 MHz, CDCl$_3$) δ=8.91 (s, 1H), 8.83 (s, 1H), 8.81 (s, 1H), 8.64 (s, 1H), 8.26 (s, 1H), 7.88 (d, J=2.6 Hz, 1H), 7.54-7.45 (m, 2H), 7.30 (s, 1H), 7.03 (d, J=8.8 Hz, 1H), 5.42 (s, 2H), 4.33 (t, J=6.6 Hz, 2H), 3.80-3.73 (m, 4H), 2.59 (t, J=7.2 Hz, 2H), 2.53 (br d, J=4.4 Hz, 4H), 2.16 (quin, J=6.8 Hz, 2H), 2.09 (s, 3H). MS (ESI) m/z 588.2 [M+H].

169: Synthesized according to general procedure A, wherein in step A.2 H$_2$N-X 3-chloro-4-(pyrazin-2-ylmethoxy) aniline; in step A.3 the OH nucleophile is 3-morpholinopropan-1-ol; variant i) was used in step A.4 to give $N^4$-(5-chloro-2-fluoro-4-((3-fluorobenzyl)oxy)phenyl)-7-(2-morpholinoethoxy)quinazoline-4,6-diamine. $^1$H NMR (400 MHz, DMSO-d$_6$) δ=9.70 (s, 1H), 9.61 (s, 1H), 8.90-8.80 (m, 2H), 8.74-8.64 (m, 2H), 8.50 (s, 1H), 8.01 (d, J=2.6 Hz, 1H), 7.73 (dd, J=2.6, 8.9 Hz, 1H), 7.32 (d, J=9.0 Hz, 1H), 7.28 (s, 1H), 6.72 (dd, J=10.3, 17.0 Hz, 1H), 6.32 (dd, J=1.9, 17.1 Hz, 1H), 5.89-5.73 (m, 1H), 5.38 (s, 2H), 4.27 (t, J=6.2 Hz, 2H), 3.58 (t, J=4.5 Hz, 4H), 2.48-2.46 (m, 2H), 2.38 (br s, 4H), 2.00 (quin, J=6.6 Hz, 2H). MS (ESI) m/z 576.3 [M+H]$^+$ Synthesis of 3-chloro-4-(pyrazin-2-ylmethoxy) aniline To a solution of 2-chloro-1-fluoro-4-nitro-benzene (3.00 g, 17.0 mmol, 1.00 eq) and pyrazin-2-ylmethanol (2.00 g, 18.1 mmol, 1.06 eq) in dimethyl formamide (20.0 mL) was added potassium carbonate (3.78 g, 27.3 mmol, 1.60 eq) and the reaction mixture was stirred at 60° C. for 12 h.

The reaction mixture was diluted with water (30.0 mL), filtered and the filter cake was concentrated under reduced pressure to give 2-((2-chloro-4-nitrophenoxy)methyl)pyrazine (4.00 g, 15.0 mmol, 88% yield) as a yellow solid. $^1$H NMR (400 MHz, DMSO-d$_6$) δ=8.88 (d, J=1.3 Hz, 1H), 8.76-8.65 (m, 2H), 8.36 (d, J=2.1 Hz, 1H), 8.26 (dd, J=2.8, 9.2 Hz, 1H), 7.54 (d, J=9.2 Hz, 1H), 5.56 (s, 2H).

To a solution of 2-((2-chloro-4-nitrophenoxy)methyl)pyrazine (4.00 g, 15.0 mmol, 1.00 eq) and iron powder (4.20 g, 75.2 mmol, 5.00 eq) in methanol (60.0 mL) and water (10.0 mL) was added saturated ammonium chloride (6.44 g, 120 mmol, 8.00 eq) and the mixture was stirred at 80° C. for 6 h. The reaction mixture was filtered and concentrated under reduced pressure to give a residue. The residue was diluted with water (50.0 mL) and extracted with ethyl acetate (2×200 mL). The combined organic layers were washed with brine (50.0 mL), dried over sodium sulfate, filtered and concentrated under reduced pressure to give 3-chloro-4-(pyrazin-2-ylmethoxy)aniline (3.5 g, 14.8 mmol, 98% yield) as a yellow solid.

170: To a solution of but-2-ynoic acid (20.0 mg, 237 umol, 9.86 uL, 3.10 eq) and N4-(3-chloro-4-(pyrazin-2-ylmethoxy)phenyl)-7-(3-morpholinopropoxy)quinazoline-4,6-diamine (40.0 mg, 76.6 umol, 1.00 eq) (obtained as intermediate V during the synthesis of 169) in pyridine (2.00 mL) was added 1-(3-dimethylaminopropyl)-3-ethylcarbodiimide hydrochloride (117 mg, 613 umol, 8.00 eq) and the mixture was stirred at 25° C. for 1 h. The residue was purified by prep-HPLC (column: Waters Xbridge 150*25 mm*5 um; mobile phase: [water (0.05% ammonia hydroxide v/v)-ACN]; B%: 38%-58%, 10 min) to give N-(4-((3-chloro-4-(pyrazin-2-ylmethoxy)phenyl)amino)-7-(3-morpholinopropoxy)quinazolin-6-yl)but-2-ynamide (10.11 mg, 17.19 umol, 22.44% yield, 100% purity) as an off-white solid. MS (ESI) m/z 588.1 [M+H]$^+$ $^1$H NMR (400 MHz, DMSO-d$_6$) δ=9.98 (br s, 1H), 9.67 (s, 1H), 8.87 (d, J=1.1 Hz, 1H), 8.73-8.64 (m, 2H), 8.60 (br s, 1H), 8.51 (s, 1H), 8.01 (d, J=2.2 Hz, 1H), 7.73 (dd, J=2.4, 8.9 Hz, 1H), 7.33 (d, J=9.0 Hz, 1H), 7.25 (s, 1H), 5.38 (s, 2H), 4.23 (t, J=6.1 Hz, 2H), 3.60 (t, J=4.5 Hz, 4H), 2.47 (br s, 2H), 2.40 (br s, 4H), 2.07 (br s, 3H), 2.01-1.94 (m, 2H).

171: Synthesized according to general procedure C starting from intermediate XIII obtained in analogy to 28 wherein in step C.3 H$_2$NX is 3-chloro-4-(pyridazin-3-ylmethoxy)aniline C.4 HNR'R" morpholine; variant ii) was used in step C.5; and variant i) was used in step C.6; and 11% overall yield from XIV. $^1$H NMR (400 MHz, CDCl$_3$) δ=9.20-9.17 (m, 1H), 9.11 (s, 1H), 8.94 (s, 1H), 8.64 (s, 1H), 7.94 (d, J=2.4 Hz, 1H), 7.92-7.87 (m, 2H), 7.60-7.53 (m, 2H), 7.07 (d, J=8.8 Hz, 1H), 6.51-6.46 (m, 2H), 5.89-5.83 (m, 1H), 5.53 (s, 2H), 4.35 (t, J=5.6 Hz, 2H), 3.80-3.75 (m, 4H), 2.93 (t, J=5.6 Hz, 2H), 2.65-2.58 (m, 4H). MS (ESI) m/z 562.0 [M+H]$^+$ 172: Synthesized according to general procedure C starting from intermediate XIII obtained in analogy to 28 wherein in step C.3 H$_2$NX is 3-chloro-4-(pyridazin-3-ylmethoxy)aniline C.4 NR'R" 1-methylpiperazine variant ii) was used in step C.5; and variant i) was used in step C.6; and 17% overall yield from XV. $^1$H NMR (400 MHz, CDCl$_3$) δ=9.23-9.17 (m, 1H), 9.14 (s, 1H), 8.91 (br s, 1H), 8.66 (s, 1H), 7.98-7.89 (m, 2H), 7.67 (br s, 1H), 7.63-7.52 (m, 2H), 7.12-7.07 (m, 1H), 6.52 (br d, J=4.4 Hz, 2H), 5.91-5.84 (m, 1H), 5.56 (s, 2H), 4.37 (t, J=5.6 Hz, 2H), 3.02-2.94 (m, 2H), 2.79-2.65 (m, 4H), 2.64-2.54 (m, 3H). MS (ESI) m/z 575.0 [M+H]

173: Synthesized according to general procedure C starting from intermediate XIII obtained in analogy to 28 wherein in step C.3 H$_2$NX is 3-chloro-4-(pyridazin-3-ylmethoxy) anilline C.4 HNR'R" 8-oxa-3-azabicyclo[3.2.1]octane; hydrochloride variant ii) was used in step C.5; and variant i) was used in step C.6 and 6% overall yield from XV. $^1$H NMR (400 MHz, DMSO-d$_6$) δ=9.71 (s, 1H), 9.58 (s, 1H), 9.25 (dd, J=1.8, 4.9 Hz, 1H), 8.86 (s, 1H), 8.50 (s, 1H), 8.02 (d, J=2.6 Hz, 1H), 7.91-7.86 (m, 1H), 7.84-7.79 (m, 1H), 7.72 (dd, J=2.6, 9.0 Hz, 1H), 7.36-7.30 (m, 2H), 6.70 (dd, J=10.2, 17.1 Hz, 1H), 6.31 (dd, J=1.8, 17.0 Hz, 1H), 5.87-5.79 (m, 1H), 5.53 (s, 2H), 4.32 (t, J=5.6 Hz, 2H), 4.18

(br d, J=2.1 Hz, 2H), 2.79 (t, J=5.6 Hz, 2H), 2.67 (d, J=1.5 Hz, 1H), 2.65 (s, 1H), 2.33 (d, J=1.8 Hz, 1H), 2.30 (d, J=1.8 Hz, 1H), 1.85-1.76 (m, 2H), 1.65 (br dd, J=3.8, 7.4 Hz, 2H). MS (ESI) m/z 588.2 [M+H]$^+$

174: Synthesized according to general procedure C starting from intermediate XIII obtained in analogy to 28 wherein in step C.3 H$_2$NX is 3-chloro-4-(pyrazin-2-ylmethoxy)aniline C.4 HNR'R" 3-methoxyazetidine variant ii) was used in step C.5 and variant i) was used in step C.6; and 1% overall yield from XIV. $^1$H NMR (400 MHz, CDCl$_3$) δ=9.17-9.07 (m, 2H), 9.01 (s, 1H), 8.54 (s, 1H), 7.84-7.80 (m, 2H), 7.50 (dd, J=5.0, 8.4 Hz, 1H), 7.44 (dd, J=2.6, 8.8 Hz, 1H), 7.17 (s, 1H), 6.97 (d, J=8.9 Hz, 1H), 6.54-6.39 (m, 2H), 5.81-5.71 (m, 1H), 5.44 (s, 2H), 4.16 (t, J=5.0 Hz, 2H), 4.08 (t, J=5.6 Hz, 1H), 3.89-3.79 (m, 2H), 3.23 (s, 3H), 3.21-3.14 (m, 2H), 3,06 (br t, J=4.3 Hz, 2H). MS (ESI) m/z 562.2 [M+H]$^+$ 175: Synthesized according to general procedure C starting from intermediate XIII obtained in analogy to 28 wherein in step C.3 H$_2$NX is 3-chloro-4-(pyrazin-2-ylmethoxy) anilline C.4 HNR'R" 8-oxa-3-azabicyclo[3.2.1]octane variant ii) was used in step C.5; and variant i) was used in step C.6; and 19% overall yield from XIV. $^1$H NMR (400 MHz, DMSO-d$_6$) δ=9.70 (s, 1H), 9.56 (s, 1H), 8.92-8.81 (m, 2H), 8.75-8.64 (m, 2H), 8.50 (s, 1H), 8.01 (d, J=2.5 Hz, 1H), 7.73 (dd, J=2.6, 8.9 Hz, 1H), 7.32 (t, J=4.5 Hz, 2H), 6.70 (dd, J=10.3, 16.9 Hz, 1H), 6.32 (dd, J=1.9, 17.0 Hz, 1H), 5.86-5.77 (m, 1H), 5.38 (s, 2H), 4.32 (t, J=5.6 Hz, 2H), 4.18 (br d, J=2.0 Hz, 2H), 2.79 (t, J=5.6 Hz, 2H), 2.66 (br d, J=10.4 Hz, 2H), 2.32 (dd, J=1.4, 10.8 Hz, 2H), 1.86-1.75 (m, 2H), 1.71-1.61 (m, 2H). MS (ESI) m/z 588.2 [M+H]$^+$ 176: Synthesized according to general procedure C starting from intermediate XIII obtained in analogy to 28 wherein in step C.3 H$_2$NX is 3-chloro-4-(pyrazin-3-ylmethoxy) anilline C.4 HNR'R" morpholine variant ii) was used in step C.5; and variant i) was used in step C.6; and 6% overall yield from XIV. $^1$H NMR (400 MHz, CDCl$_3$) δ=9.13 (s, 1H), 9.01 (s, 1H), 8.78 (br s, 1H), 8.66 (s, H), 8.60 (s, 2H), 7.93 (d, J=2.4 Hz, 1H), 7.74 (s, 1H), 7.61-7.56 (m, 1H), 7.06 (d, J=8.8 Hz, 1H), 6.50 (d, J=1.6 Hz, 2H), 5.92-5.84 (m, 1H), 5.34 (s, 2H), 4.37 (t, J=5.6 Hz, 2H), 3.83-3.74 (m, 4H), 2.94 (t, J=5.2 Hz, 2H), 2.68-2.56 (m, 4H). MS (ESI) m/z 562.2 [M+H]$^+$ 177: Synthesized according to general procedure C starting from intermediate XIII obtained in analogy to 28 wherein in step C.3 H$_2$NX is 3-chloro-4-(pyridazin-3-ylmethoxy) aniline C.4 HNR'R" 3-methoxyazetidine variant ii) was used in step C.5; and variant i) was used in step C.6; and 6% overall yield from XIV. $^1$H NMR (400 MHz, CDCl$_3$) δ=9.10 (dd, J=1.7, 5.0 Hz, 1H), 9.02 (s, 1H), 8.56 (s, 1H), 8.25 (s, 1H), 7.85 (d, J=2.6 Hz, 1H), 7.83 (dd, J=1.7, 8.5 Hz, 1H), 7.60 (s, 1H), 7.54-7.43 (m, 2H), 7.18 (s, 1H), 6.99 (d, J=8.9 Hz, 1H), 6.49-6.39 (m, 1H), 6.36-6.27 (m, 1H), 5.84-5.76 (m, 1H), 5.46 (s, 2H), 4.21 (t, J=6.2 Hz, 2H), 3.98 (quin, J=5.8 Hz, 1H), 3.63-3.53 (m, 2H), 3.20 (s, 3H), 2.91-2.80 (m, 2H), 2.62 (t, J=6.8 Hz, 2H), 1.95-1.86 (m, 2H). MS (ESI) m/z 576.5 [M+H]$^+$ 178: Synthesized according to general procedure C starting from intermediate XIII obtained in analogy to 28 wherein in step C.3 H$_2$NX is 3-chloro-4-(pyrazin-3-ylmethoxy) anilline C.4 HNR'R" 3-methoxyazetidine variant ii) was used in step C.5; and variant i) was used in step C.6; and 9% overall yield from XIV. $^1$H NMR (400 MHz, DMSO-d6) δ=9.70 (s, 1H), 9.65 (s, 1H), 8.87 (d, J=1.2 Hz, 1H), 8.81 (s, 1H), 8.71-8.68 (m, 1H), 8.66 (d, J=2.6 Hz, 1H), 8.50 (s, 1H), 8.00 (d, J=2.6 Hz, 1H), 7.73 (dd, J=2.6, 9.0 Hz, 1H), 7.32 (d, J=9.0 Hz, 1H), 7.26 (s, 1H), 6.67 (dd, J=10.4, 17.1 Hz, 1H), 6.31 (dd, J=1.8, 17.0 Hz, 1H), 5.82 (dd, J=1.8, 10.2 Hz, 1H), 5.37 (s, 2H), 4.20 (br t, J=5.1 Hz, 2H), 3.95 (quin, J=5.8 Hz, 1H), 3.60 (br t, J=6.8 Hz, 2H), 3.13 (s, 3H), 2.99 (br s, 2H), 2.90 (br s, 2H). MS (ESI) m/z 562.4 [M+H]$^+$ 179: Synthesized according to general procedure C starting from intermediate XIII obtained in analogy to 28 wherein in step C.3 H$_2$NX is 3-chloro-4-(pyrazin-3-ylmethoxy) aniline C.4 HNR'R" 1-methylpiperazine variant ii) was used in step C.5; and variant i) was used in step C.6; and 5% overall yield from XIV. $^1$H NMR (400 MHz, CDCl$_3$) δ=9.70 (s, 1H), 9.59 (s, 1H), 8.87 (d, J=1.2 Hz, 1H), 8.86 (s, 1H), 8.71 (dd, J=1.5, 2.4 Hz, 1H), 8.67 (d, J=2.6 Hz, 1H), 8.50 (s, 1H), 8.01 (d, J=2.6 Hz, 1H), 7.73 (dd, J=2.6, 9.0 Hz, 1H), 7.32 (d, J=9.0 Hz, 1H), 7.25 (s, 1H), 6.72 (dd, J=10.2, 16.9 Hz, 1H), 6.32 (dd, J=1.9, 16.9 Hz, 1H), 5.85-5.78 (m, 1H), 5.38 (s, 2H), 4.23 (t, J=6.4 Hz, 2H), 3.95 (t, J=5.7 Hz, 1H), 3.54-3.49 (m, 2H), 3.15 (s, 3H), 2.80-2.75 (m, 2H), 2.60-2.56 (m, 2H), 1.87-1.80 (m, 2H). MS (ESI) m/z 576.5 [M+H]$^+$ 180: Synthesized according to general procedure C starting from intermediate XIII obtained in analogy to 28 wherein in step C.3 H$_2$NX 3-chloro-4-(pyrazin-3-ylmethoxy) aniline C.4 HNR'R" 3-methoxyazetidine variant ii) was used in step C.5; and variant i) was used in step C.6; and 12% overall yield from XIV. $^1$H NMR (400 MHz, DMSO-d$_6$) δ=9.69 (s, 1H), 9.60 (s, 1H), 8.92-8.81 (m, 2H), 8.72-8.63 (m, 2H), 8.49 (s, 1H), 7.99 (d, J=2.5 Hz, 1H), 7.72. (dd, J=2.6, 8.9 Hz, 1H), 7.38-7.24 (m, 2H), 6.68 (dd, J=10.3, 17.0 Hz, 1H), 6.30 (dd, J=1.9, 17.0 Hz, 1H), 5.88-5.76 (m, 1H), 5.36 (s, 2H), 4.31 (t, J=5.7 Hz, 2H), 2.81 (br t, J=5.7 Hz, 2H), 2.61-2.53 (m, 3H), 2.41-2.28 (m, 4H), 2.16 (s, 4H). MS (ESI) m/z 575.4 [M+H]$^+$ Example 2. Inhibition Activity of Exemplary Compounds of the Present Disclosure Retroviral Production: EGFR mutants were subcloned into pMXs-IRES-Blasticidin (RTV-016, Cell Biolabs, San Diego, Calif.). Retroviral expression vector retrovirus was produced by transient transfection of HEK 293T cells with the retroviral EGFR mutant expression vector pMXs-IRES-Blasticidin (RTV-016, Cell Biolabs), pCMV-Gag-Pol vector and pCMV-VSV-G-Envelope vector. Briefly, HEK 293T/17 cells were plated in 100 mm collagen coated plate (354450, Corning Life Sciences, Tewksbury, Mass.) (4×10$^5$ per plate) and incubated overnight. The next day, retroviral plasmids (3 μg of EGFR mutant, 1.0 μg of pCMV-Gag-Pol and 0.5 μg pCMV-VSV-G) were mixed in 500 μl of Optimem (31985, Life Technologies). The mixture was incubated at room temperature for 5 min and then added to Optimem containing transfection reagent Lipofectamine (11668, Invitrogen) and incubated for 20 minutes. Mixture was then added dropwise to HEK 293T cells. The next day the medium was replaced with fresh culture medium and retrovirus was harvested @ 24 and 48 hrs.

Generation of EGFR mutant stable cell lines: BaF3 cells (1.5E5 cells) were infected with 1 ml of viral supernatant supplemented with 8 μg/ml polybrene by centrifuging for 30 min at 1000 rpm. Cells were placed in a 37° C. incubator overnight. Cells were then spun for 5 minutes to pellet the cells. Supernatant was removed and cells re-infected a fresh 1 ml of viral supernatant supplemented with 8 μg/ml polybrene by centrifuging for 30 min at 1000 rpm. Cells were placed in 37° C. incubator overnight. Cells were then maintained in RPMI containing 10% Heat Inactivated FBS, 2% L-glutamine containing 10 ng/ml IL-3. After 48 hours cells were selected for retroviral infection in 10 μg/ml Blasticidin for one week. Blasticidin resistant populations were washed twice in phosphate buffered saline before plating in media lacking IL-3 to select for IL-3 independent growth.

Assay for cell proliferation: BaF3 cell lines were resuspended at 1.3E5 c/ml in RPMI containing 10% Heat Inactivated FBS, 2% L-glutamine and 1% Pen/Strep and dispensed in triplicate (17.5E4 c/well) into 96 well plates. To determine the effect of drug on cell proliferation, cells incubated for 3 days in the presence of vehicle control or test drug at varying concentrations. Inhibition of cell growth was determined by luminescent quantification of intracellular ATP content using CellTiterGlo (Promega), according to the protocol provided by the manufacturer. Comparison of cell number on day 0 versus 72 hours post drug treatment was used to plot dose-response curves. The number of viable cells was determined and normalized to vehicle-treated controls. Inhibition of proliferation, relative to vehicle-treated controls was expressed as a fraction of 1 and graphed using PRISM® software (Graphpad Software, San Diego, Calif.). $EC_{50}$ values were determined with the same application.

Cellular protein analysis: Cell extracts were prepared by detergent lysis (RIPA, R0278, Sigma, St Louis, Mo.) containing 10 mM Iodoacetamide (786-228, G-Biosciences, St, Louis, Mo.), protease inhibitor (P8340, Sigma, St. Louis, Mo.) and phosphatase inhibitors (P5726, P0044, Sigma, St. Louis, MO) cocktails. The soluble protein concentration was determined by micro-BSA assay (Pierce, Rockford Ill.). Protein immunodetection was performed by electrophoretic transfer of SDS-PAGE separated proteins to nitrocellulose, incubation with antibody, and chemiluminescent second step detection. Nitrocellulose membranes were blocked with 5% nonfat dry milk in TBS and incubated overnight with primary antibody in 5% bovine serum albumin. The following primary antibodies from Cell Signaling Technology were used at 1:1000 dilution: phospho-EGFR[Y1173] and total EGFR. β-Actin antibody, used as a control for protein loading, was purchased from Sigma Chemicals. Horseradish peroxidase-conjugated secondary antibodies were obtained from Cell Signaling Technology and used at 1:5000 dilution.

Horseradish peroxidase-conjugated secondary antibodies were incubated in nonfat dry milk for 1 hour. SuperSignal chemiluminescent reagent (Pierce Biotechnology) was used according to the manufacturer's directions and blots were imaged using the Alpha Innotech image analyzer and AlphaEaseFC software (Alpha Innotech, San Leandro Calif.).

Tables A and B assign each compound a potency code: A, B, C, D, E, F, G, H, I, J or K.

According to the code, A represents an IC50 value ≤5 nM. B represents an IC50 value >5 nM and ≤10 nM. C represents an IC50 value >10 nM and ≤20 nM. D represents an IC50 value >20 nM and ≤30 nM. E represents an IC50 value >30 nM and ≤50 nM. F represents an IC50 value >50 nM and ≤100 nM. G represents an IC50 value >100 nM and ≤200 nM. H represents an IC50 value >200 nM and ≤300 nM. I represents an IC50 value >300 nM and ≤500 nM. J represents an IC50 value >500 nM and ≤1000 nM. K represents an IC50 value >1000 nM.

TABLE A

Activity for Inhibiting EGFR

| Compound No. | EGFR WT | EGFR V3 | EGFR NPH | EGFR SVD |
|---|---|---|---|---|
| 1 | K | G | | |
| 2 | K | F | | |
| 3 | I | E | | |
| 4 | H | F | | |
| 5 | E | C | E | C |
| 6 | H | D | | |
| 7 | K | G | | |
| 8 | I | D | E | D |
| 9 | J | F | | |
| 10 | K | F | | |
| 11 | I | F | I | I |
| 12 | J | G | | |
| 13 | I | F | I | H |
| 14 | I | E | | |
| 15 | I | H | | |
| 16 | H | D | | |
| 17 | H | C | D | C |
| 18 | I | D | | |
| 19 | H | D | G | G |
| 20 | H | D | C | C |
| 21 | J | D | C | C |
| 22 | F | D | D | C |
| 23 | K | G | | |
| 24 | K | H | | |
| 25 | J | H | D | E |
| 26 | I | E | E | E |
| 27 | I | E | | |
| 28 | H | C | F | E |
| 29 | I | D | | |
| 30 | I | E | | |
| 31 | J | E | F | F |
| 32 | I | D | | |
| 33 | I | D | F | F |
| 34 | J | E | | |
| 35 | I | D | F | D |
| 36 | K | E | F | F |
| 37 | K | G | | |
| 38 | I | E | | |
| 39 | J | D | F | E |
| 40 | H | C | C | C |
| 41 | J | E | F | E |
| 42 | J | F | K | J |
| 43 | K | G | | |
| 44 | I | G | | |
| 45 | J | H | | |
| 46 | I | F | | |
| 47 | I | E | J | J |
| 48 | K | H | | |
| 49 | K | G | | |
| 50 | K | E | | |
| 51 | J | D | F | E |
| 52 | J | D | F | F |
| 53 | K | E | | |
| 54 | K | C | G | F |
| 55 | K | F | | |
| 56 | I | D | I | I |
| 57 | J | C | F | E |
| 58 | K | H | | |
| 59 | I | E | | |
| 60 | H | C | H | H |
| 61 | K | I | | |
| 62 | I | C | E | D |
| 63 | K | F | I | I |
| 64 | K | G | | |
| 65 | J | D | | |
| 66 | J | D | G | F |
| 67 | G | D | | |
| 68 | J | G | J | J |
| 69 | I | C | D | D |
| 70 | F | C | F | E |
| 71 | J | F | | |
| 72 | K | I | | |
| 73 | J | F | | |
| 74 | K | F | | |
| 75 | K | G | | |
| 76 | H | F | | |
| 77 | G | F | | |

TABLE A-continued

Activity for Inhibiting EGFR

| Compound No. | EGFR WT | EGFR V3 | EGFR NPH | EGFR SVD |
|---|---|---|---|---|
| 78 | K | E | I | H |
| 79 | I | F | | |
| 80 | G | F | | |
| 81 | H | G | | |
| 82 | J | I | | |
| 83 | J | F | | |
| 84 | J | D | F | F |
| 85 | H | D | D | D |
| 86 | J | G | | |
| 87 | K | G | | |
| 88 | J | E | | |
| 89 | F | E | | |
| 90 | J | E | | |
| 91 | J | F | | |
| 92 | G | E | | |
| 93 | K | H | | |
| 94 | I | E | | |
| 95 | G | D | | |
| 96 | G | C | | |
| 97 | J | F | | |
| 98 | H | E | | |
| 99 | H | D | | |
| 100 | I | E | | |
| 101 | G | C | | |
| 102 | J | E | F | E |
| 103 | H | E | | |
| 104 | D | E | | |
| 105 | J | F | | |
| 106 | G | E | | |
| 107 | H | F | | |
| 108 | J | G | | |
| 109 | E | C | | |
| 110 | H | D | | |
| 111 | I | E | | |
| 112 | I | G | | |
| 113 | J | F | | |
| 114 | I | E | | |
| 115 | H | E | | |
| 116 | J | E | | |
| 117 | J | G | | |
| 118 | H | D | | |
| 119 | I | F | | |
| 120 | K | E | | |
| 121 | K | G | | |
| 122 | J | F | | |
| 123 | H | E | | |
| 124 | J | E | | |
| 125 | J | G | | |
| 126 | I | E | | |
| 127 | J | F | | |
| 128 | J | G | | |
| 129 | J | G | | |
| 130 | H | G | | |
| 131 | H | G | | |
| 132 | K | I | | |
| 133 | H | G | | |
| 134 | H | F | | |
| 135 | I | F | | |
| 136 | G | G | | |
| 137 | H | F | | |
| 138 | G | F | | |
| 139 | J | G | | |
| 140 | I | G | | |
| 141 | G | G | | |
| 142 | J | G | | |
| 143 | H | F | | |
| 144 | G | G | | |
| 145 | G | F | | |
| 146 | F | F | | |
| 147 | J | F | | |
| 148 | H | G | | |
| 149 | G | F | | |
| 150 | H | F | | |
| 151 | G | F | | |
| 152 | G | E | | |
| 153 | J | E | | |
| 154 | J | E | | |
| 155 | I | E | | |
| 156 | K | F | | |
| 157 | J | E | | |
| 158 | G | E | | |
| 159 | I | G | | |
| 160 | I | G | | |
| 161 | H | E | | |
| 162 | I | E | | |
| 163 | K | F | | |
| 164 | I | F | | |
| 165 | G | E | | |
| 166 | K | E | | |
| 167 | K | E | | |
| 168 | H | E | | |
| 169 | K | E | | |
| 170 | H | E | | |
| 171 | K | F | | |
| 172 | J | G | | |
| 173 | K | F | | |
| 174 | K | F | | |
| 175 | K | E | | |
| 176 | K | E | | |
| 177 | J | E | | |
| 178 | K | E | | |
| 179 | J | E | | |
| 180 | J | E | | |

TABLE B

Activity for Inhibiting HER2

| Compound No. | HER2 WT | HER2 S310F | HER2 YVMA |
|---|---|---|---|
| 1 | F | J | |
| 2 | G | I | |
| 3 | C | D | |
| 4 | D | F | |
| 5 | A | A | B |
| 6 | B | C | F |
| 7 | G | H | |
| 8 | B | C | F |
| 9 | C | G | |
| 10 | C | D | H |
| 11 | E | F | |
| 12 | F | G | |
| 13 | B | E | I |
| 14 | C | F | |
| 15 | C | G | |
| 16 | A | D | E |
| 17 | A | B | E |
| 18 | B | D | F |
| 19 | B | D | G |
| 20 | A | C | C |
| 21 | A | B | D |
| 22 | A | B | E |
| 23 | G | G | |
| 24 | | H | I |
| 25 | C | C | F |
| 26 | B | B | E |
| 27 | C | D | E |
| 28 | B | C | E |
| 29 | A | C | F |
| 30 | A | C | G |
| 31 | B | E | G |
| 32 | A | C | F |
| 33 | B | C | G |
| 34 | C | C | F |
| 35 | A | C | E |
| 36 | C | D | E |
| 37 | F | F | |
| 38 | B | D | F |
| 39 | B | C | F |

TABLE B-continued

Activity for Inhibiting HER2

| Compound No. | HER2 WT | HER2 S310F | HER2 YVMA |
|---|---|---|---|
| 40 | A | C | D |
| 41 | B | D | F |
| 42 | E | F | J |
| 43 | F | G | |
| 44 | F | I | |
| 45 | | I | K |
| 46 | D | G | |
| 47 | C | E | J |
| 48 | G | I | |
| 49 | F | G | |
| 50 | | H | K |
| 51 | B | C | F |
| 52 | B | D | G |
| 53 | | E | G |
| 54 | B | D | G |
| 55 | | F | H |
| 56 | D | F | H |
| 57 | B | C | F |
| 58 | G | I | |
| 59 | E | G | |
| 60 | B | D | I |
| 61 | | I | K |
| 62 | A | B | E |
| 63 | E | F | I |
| 64 | | I | K |
| 65 | C | C | F |
| 66 | F | C | F |
| 67 | B | C | F |
| 68 | C | E | I |
| 69 | | C | D |
| 70 | | B | B |
| 71 | | H | K |
| 72 | | I | K |
| 73 | | E | I |
| 74 | G | H | |
| 75 | | G | I |
| 76 | | E | G |
| 77 | | D | G |
| 78 | C | F | J |
| 79 | | G | K |
| 80 | | F | J |
| 81 | | G | K |
| 82 | | F | J |
| 83 | | C | G |
| 84 | | B | E |
| 85 | | B | E |
| 86 | | D | G |
| 87 | | E | H |
| 88 | | C | G |
| 89 | | C | F |
| 90 | | D | G |
| 91 | | E | H |
| 92 | | D | G |
| 93 | | J | K |
| 94 | | E | I |
| 95 | | B | E |
| 96 | | C | H |
| 97 | | H | J |
| 98 | | D | H |
| 99 | | E | H |
| 100 | | F | I |
| 101 | | C | E |
| 102 | | D | F |
| 103 | | C | F |
| 104 | | E | E |
| 105 | | E | G |
| 106 | | E | G |
| 107 | | C | E |
| 108 | | F | J |
| 109 | | C | F |
| 110 | | E | H |
| 111 | | E | G |
| 112 | | I | K |
| 113 | | E | G |
| 114 | | E | G |
| 115 | | E | F |
| 116 | | E | H |
| 117 | | F | G |
| 118 | | C | D |
| 119 | | F | G |
| 120 | | C | F |
| 121 | | E | I |
| 122 | | G | J |
| 123 | | E | G |
| 124 | | E | G |
| 125 | | G | K |
| 126 | | E | F |
| 127 | | I | K |
| 128 | | G | I |
| 129 | | E | G |
| 130 | | E | I |
| 131 | | F | I |
| 137 | | I | J |
| 133 | | F | J |
| 134 | | E | I |
| 135 | | G | I |
| 136 | | E | G |
| 137 | | F | I |
| 138 | | E | F |
| 139 | | E | G |
| 140 | | G | I |
| 141 | | E | I |
| 142 | | I | K |
| 143 | | E | G |
| 144 | | E | G |
| 145 | | E | H |
| 146 | | D | F |
| 147 | | F | H |
| 148 | | D | F |
| 149 | | C | E |
| 150 | | C | E |
| 151 | | C | G |
| 152 | | B | F |
| 153 | | C | F |
| 154 | | E | G |
| 155 | | C | E |
| 156 | | E | H |
| 157 | | E | I |
| 158 | | E | G |
| 159 | | F | I |
| 160 | | G | I |
| 161 | | E | G |
| 162 | | E | G |
| 163 | | E | G |
| 164 | | E | G |
| 165 | | C | F |
| 166 | | E | G |
| 167 | | C | F |
| 168 | | D | F |
| 169 | | C | E |
| 170 | | B | C |
| 171 | | F | I |
| 172 | | F | I |
| 173 | | E | H |
| 174 | | F | I |
| 175 | | D | G |
| 176 | | D | G |
| 177 | | C | F |
| 178 | | E | G |
| 179 | | C | E |
| 180 | | D | G |

Example 3. Selective Targeting of Various HER and EGFR Mutants

Figure 21:
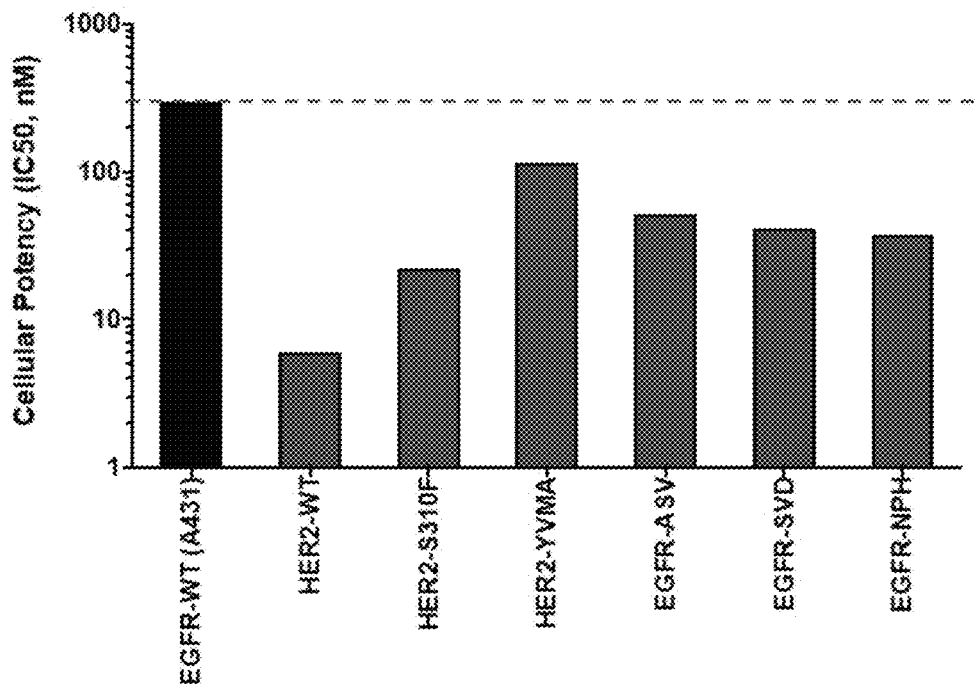
FIG. 21 is a graph showing the effect of Compound No. 6 on growth inhibition in a panel of cell lines harboring HER and EGFR variants.

To determine the ability of Compound No. 6 to target wild type HER2, wild type EGFR, and relevant mutants of each, a panel of BaF3 cell lines and the A431 cell line were dosed and assessed in cell proliferation assays. The BaF3 parental cell line is normally dependent on IL-3 for proliferation, but when transformed with active tyrosine kinase can grow in the absence of IL-3. However, when transformed kinase activity is inhibited by a targeted small molecule the associated proliferation is reduced in proportion to the extent of inhibition. A panel of BaF3 cell lines were generated by transforming the parental BaF3 cell line with wild type HER2 (HER2-WT), HER2 S310F (HER2-S310F), HER2 Exon 20 insertion YVMA (HER2-YVMA), EGFR-Exon 20 insertion ASV (EGFR-ASV), EGFR-Exon 20 insertion SVD (EGFR-SVD), or EGFR-Exon 20 insertion NPH (EGFR-NPH). The A431 lung cancer cell line, which natively expresses WT-EGFR, was used to assess WT-EGFR inhibition. To perform the proliferation assays, cells were plated in 96-well plates and subjected to various doses of Compound No. 6 to generate a dose-response curve for each cell line. Proliferation was assessed using the Cell Titer Glo cell proliferation kit (Promega # G7573). Briefly, Cell Titer Glo reagent was thawed and allowed to equilibrate at room temperature for 30 minutes. Plated and dosed cells were also allowed to equilibrate at Room Temperature for 30 minutes. Cell Titer Glo was added to plated cells at 15 ul per well, the plate was shaken for 20 minutes at room temperature, and luminescence was measured using Victor X3 Multimode plate reader (Perkin Elmer), Cell Titer Glo readings were taken following 72 hours (T72) after addition of Compound No. 6. Dose-response curves were generated for each cell line and IC50 values generated (FIG. 21). As shown in FIG. 21, compound No. 6 has the highest potency for HER-WT with an IC50 value <10 nM. Compound No. 6 has relatively high potency against HER2-S10F, HER2-ASV, EGFR-SVD, and EGFR-NPH, with IC50 values <100 nM. Compound No. 6 showed reduced potency against EGFR-WT, with an IC50 value >100 nM. These results indicate that Compound No. 6 targets and inhibits wild type HER2 and a variety of clinically relevant HER2 and EGFR mutants, but largely spares wild type EGFR in a cellular model.

Example 4. Inhibition of Proliferation in Patient-Derived Cell Lines

Figure 22:
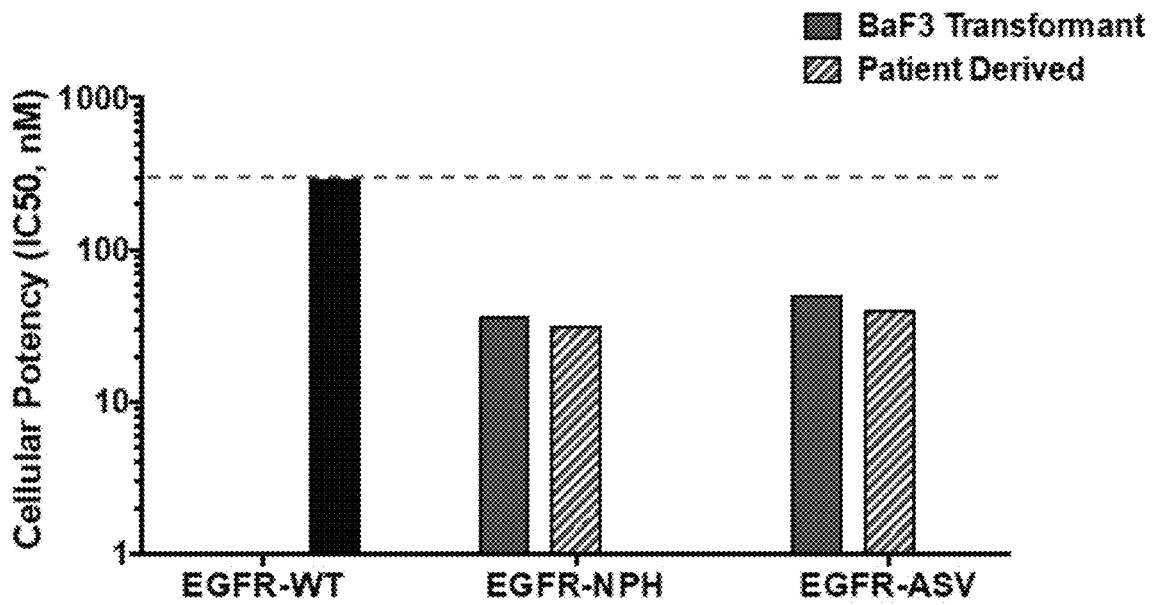
FIG. 22 is a graph showing the effect of Compound No. 6 on growth inhibition in patient-derived cell lines harboring EGFR mutants.

Compound No. 6 inhibition of EGFR-NPH and EGFR-ASV mutants in patient-derived cell lines was assessed using cell proliferation assays. The CUTO-14 and CUTO-17 cellular models are patient-derived cell lines that natively express the EGFR-ASV and EGFR-NPH mutants, respectively. The EGFR-WT expressing A431 cell line was used as a reference in the assessment. To perform the proliferation assays, cells were plated in 96-well plates and subject dose-response curves using Compound No. 6. Proliferation was assessed using the Cell Titer Glo cell proliferation kit (Promega # G7573). Briefly, Cell Titer Glo reagent was thawed and allowed to equilibrate at room temperature for 30 minutes. Plated and dosed cells were also allowed to equilibrate at Room Temperature for 30 minutes. Cell Titer Glo was added to plated cells at 15 ul per well, the plate was shaken for 20 minutes at room temperature, and luminescence was measured using Victor X3 Multimode plate reader (Perkin Elmer). Cell Titer Glo readings were taken following 72 hours (T72) after addition of Compound No. 6. The CUTO-14 (EGFR-ASV) and CUTO-17 (EGFR-NPH) cell lines responded comparably to Compound No. 6 as the BaF3 transformants, showing similar IC50 values (FIG. 22), indicating that Compound No. 6 selectively inhibits particular EGFR mutants, including EGFR-NPH and EGFR-ASV.

Example 5. Selective Inhibition of EGFR Mutants

Figure 23:
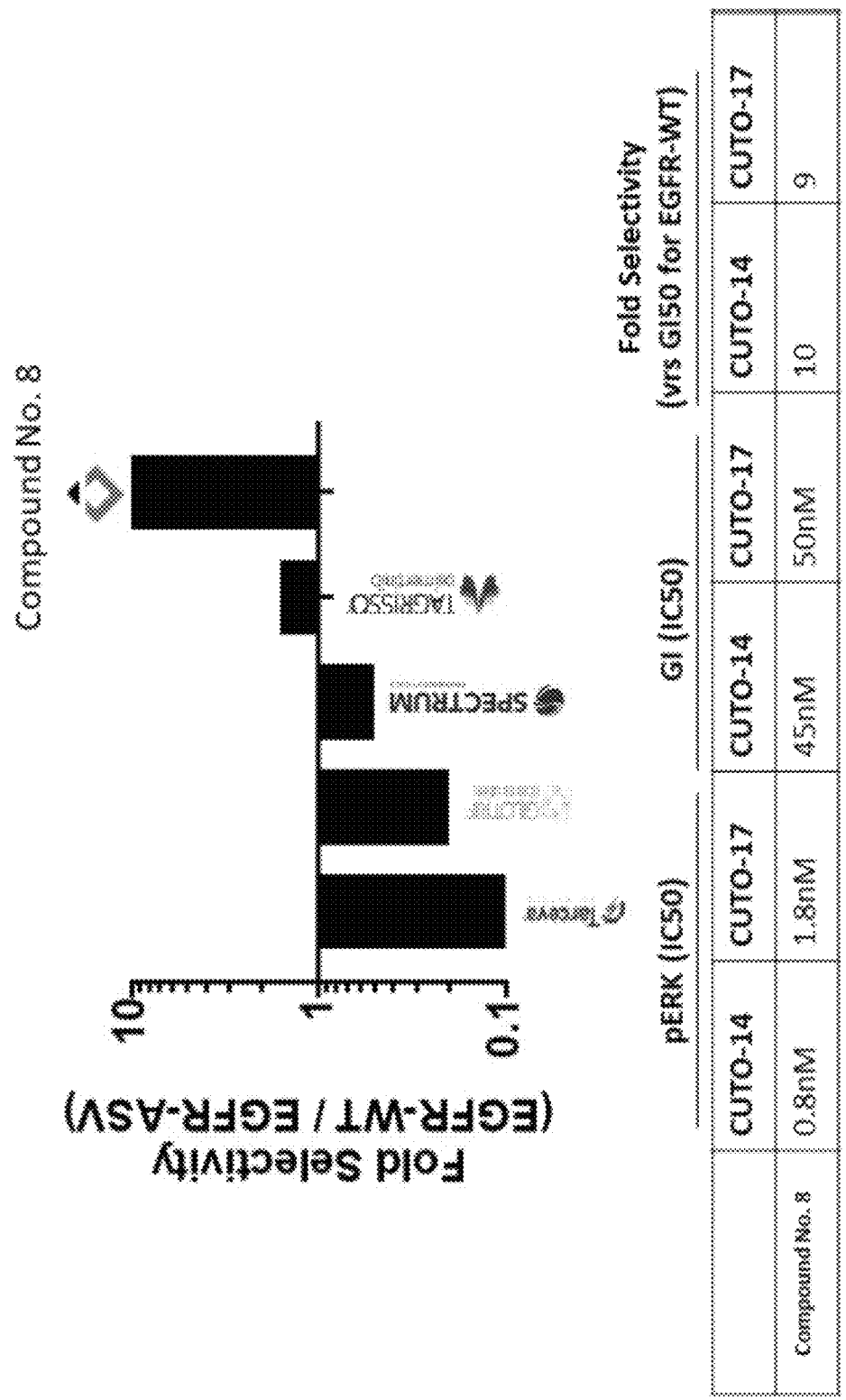
FIG. 23 is a graph comparing the selectivity of Compound No. 8 and a table summarizing representative selectivity data.

A shown in the top panel of FIG. 23, marketed compounds that target EGFR mutants show off-target binding to wild type EGFR, resulting in toxicities and reduced efficacy (FIG. 23, top panel). To determine the relative selectivity of Compound No. 8 for targeting EGFR mutants over wild type EGFR, the patient-derived CUTO-14 and CUTO-17 cellular models that natively express EGFR-ASV and EGFR-NPH mutants, respectively, were dosed with Compound No. 8 over a range of concentrations. Following dosing, the cells were assessed for EGFR mutant signaling and cell proliferation. To measure signaling, the pERK AlphaLisa (Perkin Elmer # ALSU-PERK-A10K) was used to quantify phosphorylation of ERK1/2 (Thr202/Tyr204) in all treated cells. Cell proliferation was determined using the Cell Titer Glo assay (Promega G7573) at 72 hours following treatment. IC50 values for both pERK and growth inhibition (GI50) were determined (FIG. 23, bottom table). The GI50 values calculated for Compound No. 8 in CUTO-14 and CUTO-17 cells were used to assess relative selectivity with reference to the GI50 value generated in Compound No. 8 treated A431 cells for EGFR-WT (FIG. 23, bottom table). The ratio of the GI50 value in A431 cells to the GI50 in CUTO-14 and the ratio of the GI50 value in A431 cells to the GI50 in CUTO-17 was calculated (FIG. 23, bottom table). Higher ratios represent higher selectivity for the EGFR mutants compared to EGFR-WT. The ratios were compared to reference values for marketed EGFR inhibitors, and the results indicate that Compound No. 8 has reduced off-target binding to EGFR-WT relative to the marketed inhibitors.

Example 6. Selective Targeting of Various HER and EGFR Mutants

Figure 24:
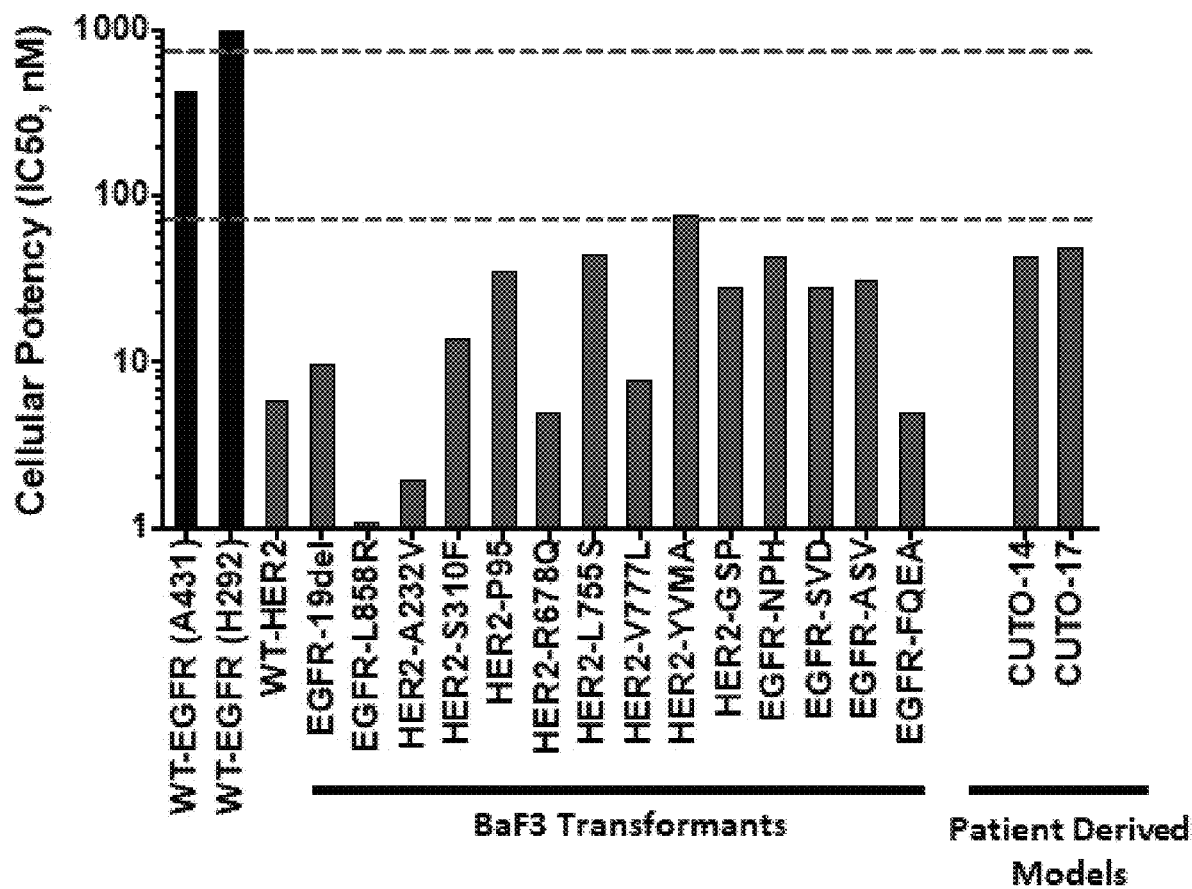
FIG. 24 is a graph showing the effect of Compound No. 8 on growth inhibition in a panel of cell lines harboring HER and EGFR mutants.

To determine the ability of Compound No. 8 to target wild type HER2, wild type EGFR, and clinically relevant mutants of each, a panel of BaF3 cell lines and the A431 cell line were dosed and assessed in cell proliferation assays. The BaF3 parental cell line is normally dependent on IL-3 for proliferation, but when transformed with active tyrosine kinase can grow in the absence of IL-3. However, when transformed kinase activity is inhibited by a targeted small molecule the associated proliferation is reduced in proportion to the extent of inhibition. A panel of BaF3 cell lines were generated by transforming the parental BaF3 cell line with wild type HER2, EGFR-19DEL, EGFR-L858R, HER2-A232V, HER2-S310F, HER2-P95, HER2-R678Q, HER2-L755S, HER2-V777L, HER2-YVMA, HER2-GSP, EGFR-NPH, EGFR-SVD, EGFR-ASV, EGFR-FQEA. The A431 and H292 cell lines, which natively express WT-EGFR, were used to assess WT-EGFR inhibition. The CUTO-14 and CUTO-17 patient-derived cellular models that natively express the EGFR-ASV and EGFR-NPH mutants, respectively, were also included in the panel. To perform the proliferation assays, cells were plated in 96-well plates and subjected to various doses of Compound No. 8 to generate a dose-response curve for each cell line. Proliferation was assessed using the Cell Titer Glo cell proliferation kit (Promegaf# G7573). Briefly, Cell Titer Glo reagent was thawed and allowed to equilibrate at room temperature for 30 minutes. Plated and dosed cells were also allowed to equilibrate at Room Temperature for 30 minutes. Cell Titer Glo was added to plated cells at 15 ul per well, the plate was shaken for 20 minutes at room temperature, and luminescence was measured using Victor X3 Multimode plate reader (Perkin Elmer). Cell Titer Glo readings were taken following 72 hours (T72) after addition of Compound No. 8. Dose-response curves were generated for each cell line and IC50 values generated (FIG. 24). The results show that Compound No. 8 has the high potency for HER-WT and all mutants, with IC50 values <100 nM. In contrast, Compound No. 8 showed reduced potency against EGFR-WT, with an IC50 value >100 nM in A431 and H292 cells. These results indicate that Compound No. 8 targets and inhibits wild type HER2 and a variety of clinically relevant HER2 and EGFR mutants, but largely spares wild type EGFR in a cellular model.

Figure 25:
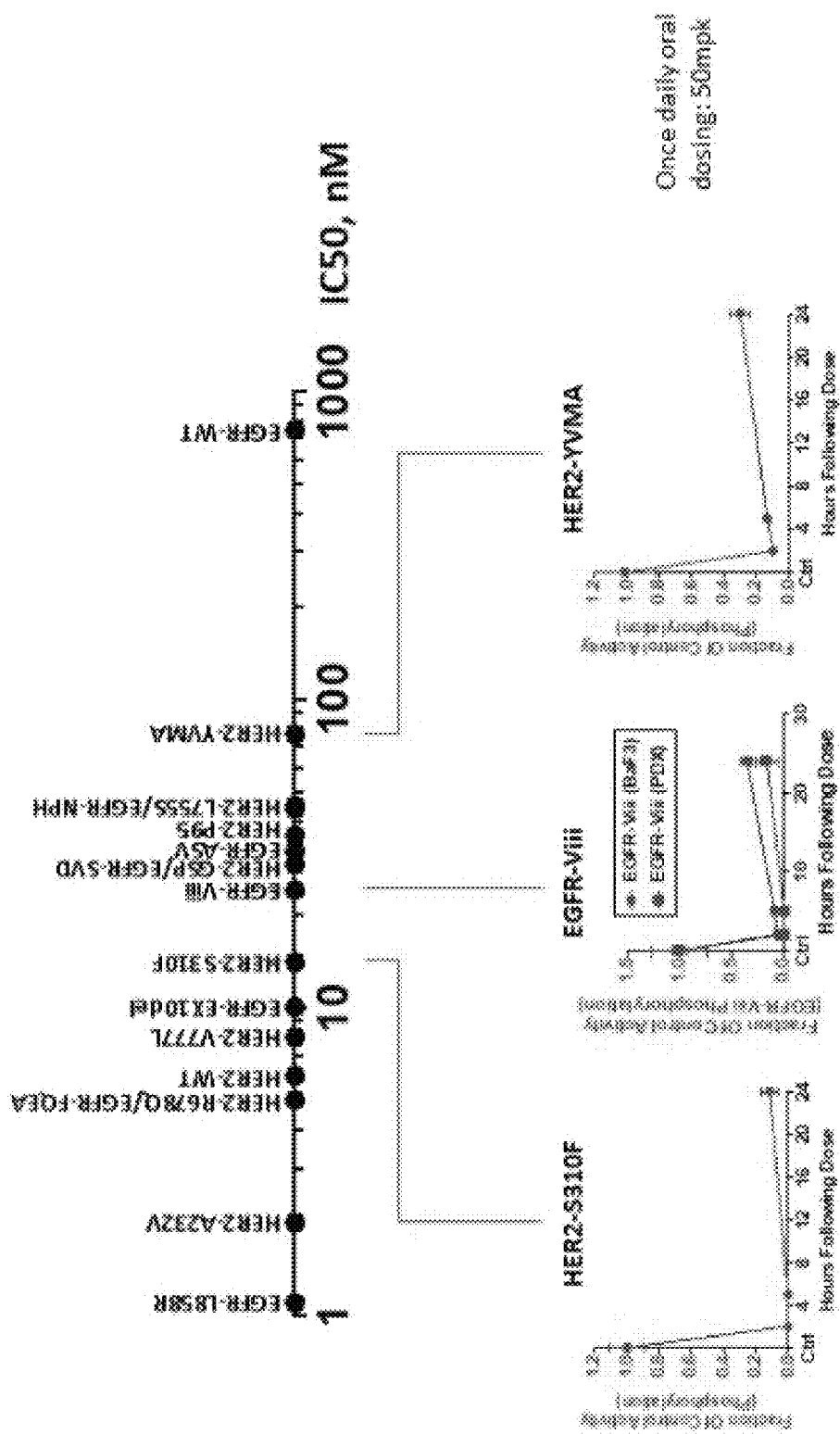
FIG. 25 is a diagram of the in vivo potency of Compound No. 8 on various HER and EGFR mutants.

Example 7. Inhibition of Kinase Targets In Vivo in Allo-ErbB Mutant Tumor Models The ability of Compound No. 8 to target and inhibit HER2 and EGFR mutant activity in vivo was tested using mouse models containing relevant tumor xenotransplantations. The xenotransplant mice were administered Compound No. 8 and tumors were collected and analyzed for phosphosites representative of Her2 or EGFR signaling. Athymic nude mice from Charles River Labs bearing either Her2 Exon 20-YVMA A775, or Her2 S310F, or EGFR-Viii BaF3 tumors were treated with two day acute oral dosing of Compound No. 8 at 50 mg/kg. Following the second dose, tumors were collected at 2 hours, 5 hours, and 24 hours. The tumor tissue was cut and homogenized using the Precellys Soft Tissue Homogenizing kit (KT03961-1-00.3.2) containing T-PER tissue protein extraction reagent (Thermo Scientific #78510), supplemented with Protease Inhibitor (Sigma P8340), and Phosphatase Inhibitors II and III (Sigma P5726 and P0044). Tissue samples were homogenized in the Precellys machine by spinning two times for one minute each. Sample tubes were centrifuged for 5 min at 15,000 rpm at 4° C. The supernatant was transferred to a fresh microtube and spun again for 5 minutes at 15,000 rpm at 4° C. Supernatant was then transferred to a fresh microtube and placed on ice. The protein concentration of the supernatant was measured using the BCA reagent Kit (Thermo Scientific #23225). Tumor tissue-derived lysates were analyzed for either HER2 activity or EGFR activity by detection of pErbB2 (Tyr1221/1222) or pERK (Thr202/Tyr204) phosphosites, respectively, via AlphaLisa. Briefly, tumor Lysates were diluted to 0.5 ug/ul in 1× diluted SureFire Ultra Kit Lysis Buffer (5× supplied stock) supplemented with Protease inhibitor (Sigma P8340) and Phosphatase Inhibitor II and III (Sigma P5726 and P0044). 10 ul of total tumor lysate was added per well in triplicate to a 384-well Opti-plate (Perkin Elmer #6007290). Activation Buffer was diluted 25-fold in combined Reaction Buffer 1 and Reaction Buffer 2, and acceptor beads were diluted 50-fold in the combined Reaction Buffers. 5 ul/well of the Acceptor bead:Reaction buffer mixture was added to each well. The plate was covered and shaken for 5 minutes on a plate shaker and then incubated at room temperature in the dark for 90 minutes before reading. As shown in FIG. 25, a significant reduction in the abundance of phosphorylation of both the HER2 and ERK-related phosphosites occurred following the treatment protocol indicating that Compound No. 8 inhibits HER2 and EGFR activity in vivo.

Example 8. Tumor Growth Inhibition in Mice Bearing Her2 Mutant Tumors

Figure 26:
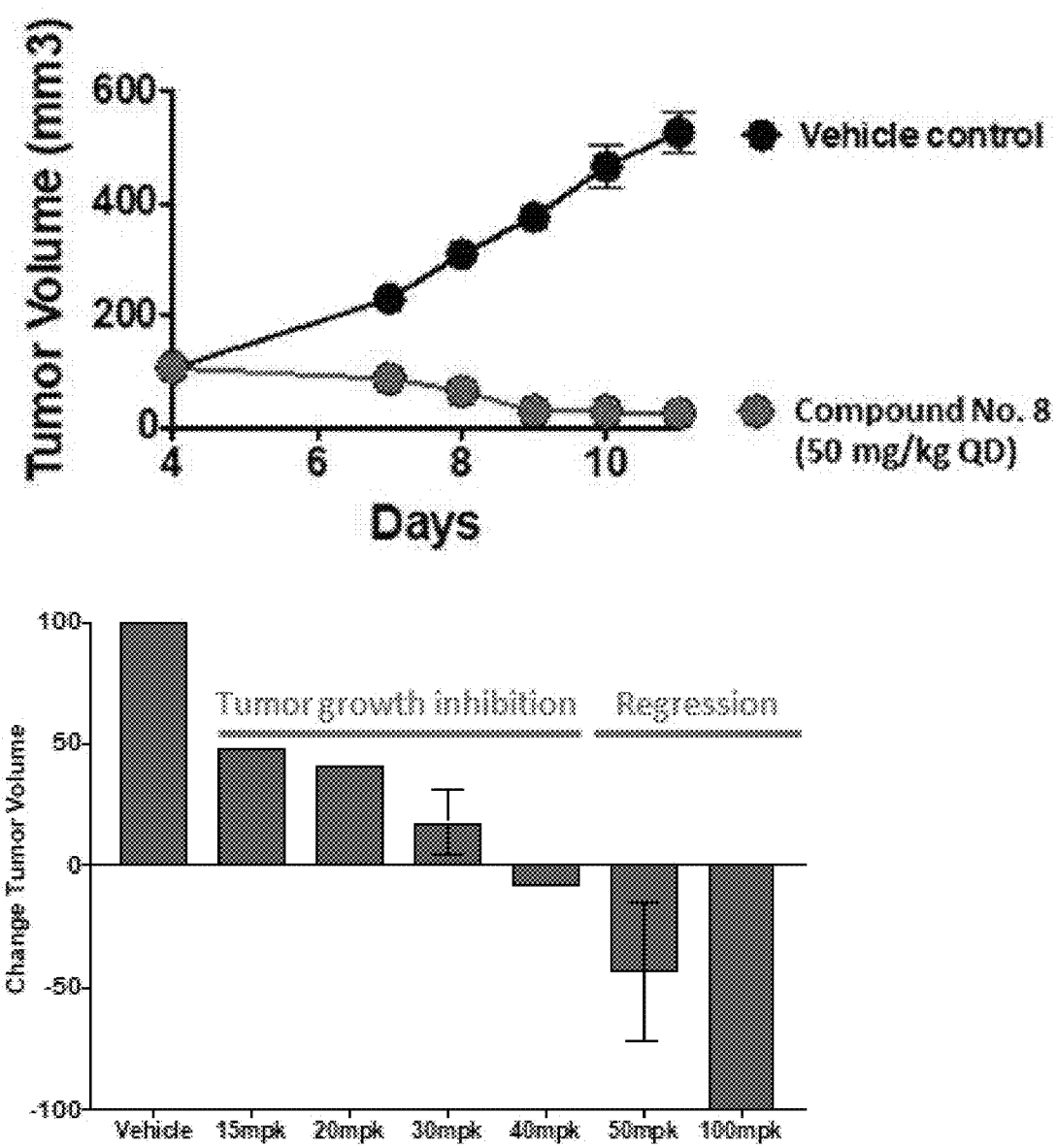
FIG. 26 is a graph showing the effect of Compound No. 8 on HER mutant tumor volume in vivo.

A mouse tumor model containing mutant Her2 was used to test Compound No. 8's ability to inhibit tumor growth and induce tumor regression in vivo. Athymic nude mice from Charles River Labs bearing Her2 S310F BaF3 tumors were treated with Compound No. 8 either at 50 mg/kg once per day for 10 days or in a dose-dependent manner ranging from 15 mg/kg to 100 mg/kg once per day (QD) for 10 days. Tumor size was measured for each dosing schedule, and analyzed to assess regression. For the 50 mg/kg Compound No. 8 10-day dosing, tumor size was observed over the 10-day time course as shown in the left panel of FIG. 26. Tumor volume in the vehicle control increased over the 10 days whereas the tumor volume in mice dosed with Compound No. 8 decreased over the same timeframe, indicating that Compound No. 8 induces regression in tumors harboring the Her2 S310F mutation. The effect was further confirmed in the dose-dependent experiment. The tumor regressed in a Compound No. 8 dose-dependent manner as shown in the right panel of FIG. 26. These results demonstrate that Compound No. 8 induces tumor growth inhibition and tumor regression in vivo, including in tumors harboring the Her2 S310F mutation.

Example 9. Tumor Growth Inhibition in Mice Bearing HER2 Mutant Tumors

Figure 27:
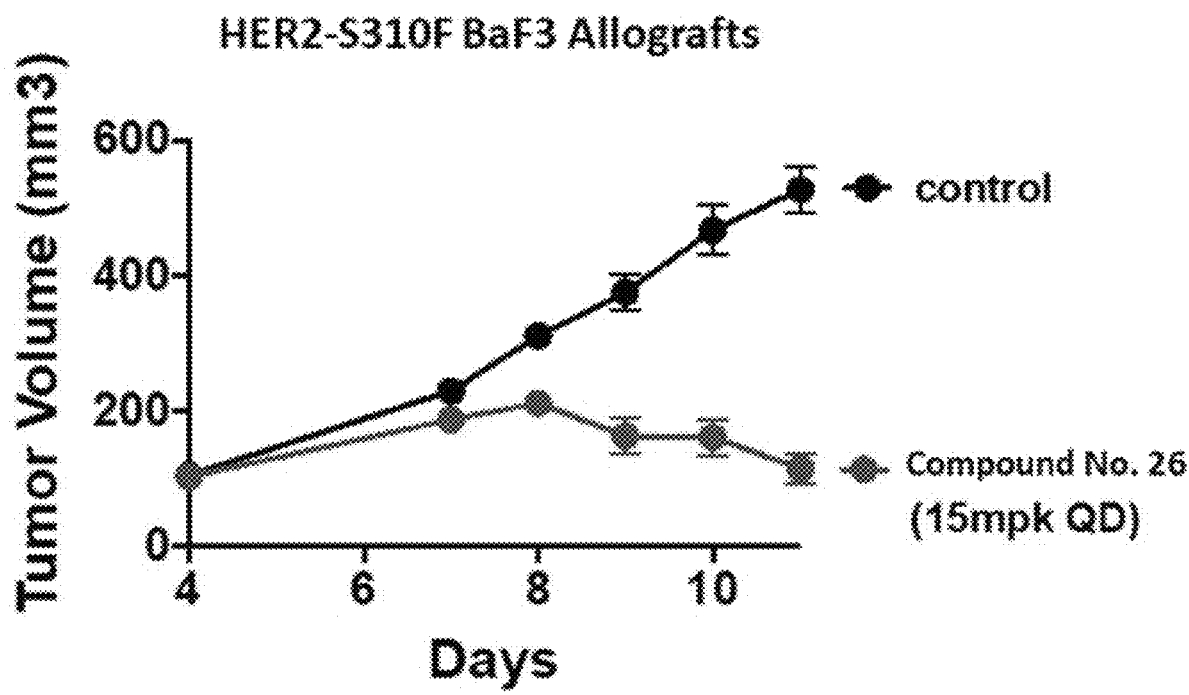
FIG. 27 is a graph showing the effect of Compound No. 26 on HER mutant tumor volume in vivo.
Figure 28:
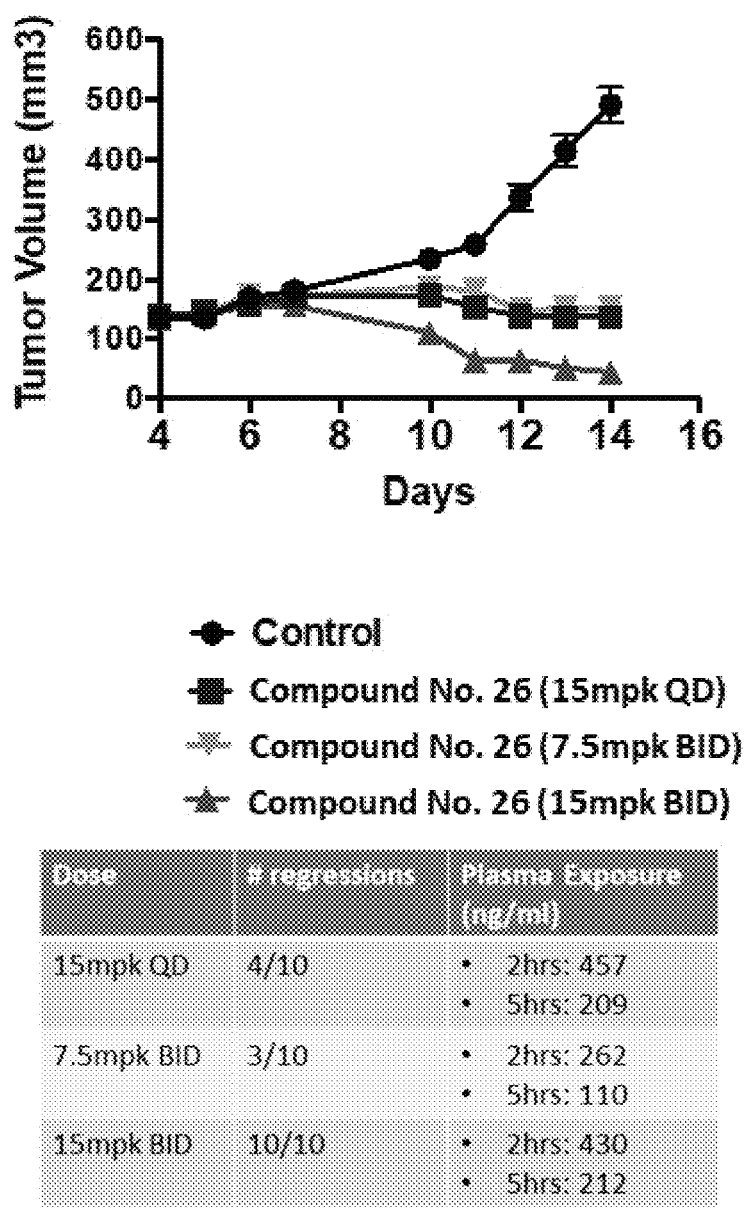
FIG. 28 is a graph showing the effect of Compound No. 26 on HER mutant tumor volume in vivo under several dosing regimens.

A mouse tumor model containing mutant Her2 was used to test the ability of Compound No. 26 to inhibit tumor growth and induce tumor regression in vivo. Athymic nude mice from Charles River Labs bearing Her2 S310F BaF3 tumors were treated with Compound No. 26 either at 15 mg/kg once per day (QD), 7.5 mg/kg twice per day (BID), and 15 mg/kg twice per day (BID). Tumor size was measured for each dosing condition and analyzed to assess regression. As shown in FIG. 27, tumor volume in the vehicle control increased over the time course, whereas the tumor volume in mice dosed with Compound No. 26 did not increase over the same timeframe, indicating that Compound No. 26 prevents growth in tumors harboring the Her2 S310F mutation. The effect was further confirmed in mice dosed at 15 mg/kg once per day (QD), 7.5 mg/kg twice per day (BID), and 15 mg/kg twice per day (BID). In addition to assessing tumor size in these groups, plasma was collected from dosed individuals at 2 and 5 hours following each treatment. Compound No. 26 levels were measured in the plasma samples to determine pharmacokinetic profiles that may influence tumor response. As shown in the right panel of FIG. 28, peak plasma levels were found in mice dosed with 15 mg/kg BID, which was the group with the highest number of individuals in which tumor regressions were observed. As shown in the left panel of FIG. 28, the 15 mg/kg once per day (QD) and 7.5 mg/kg twice per day (BID) dosing groups showed definite tumor growth inhibition properties, while the 15 mg/kg BID dosing group showed definite tumor regressive properties. These results demonstrate that Compound No. 26 prevents tumor growth and induces tumor regression in vivo, including in tumors harboring the Her2 S310F mutation.

Example 10. Tumor Growth Inhibition in Mice Bearing HER2 Mutant Tumors

Figure 29:
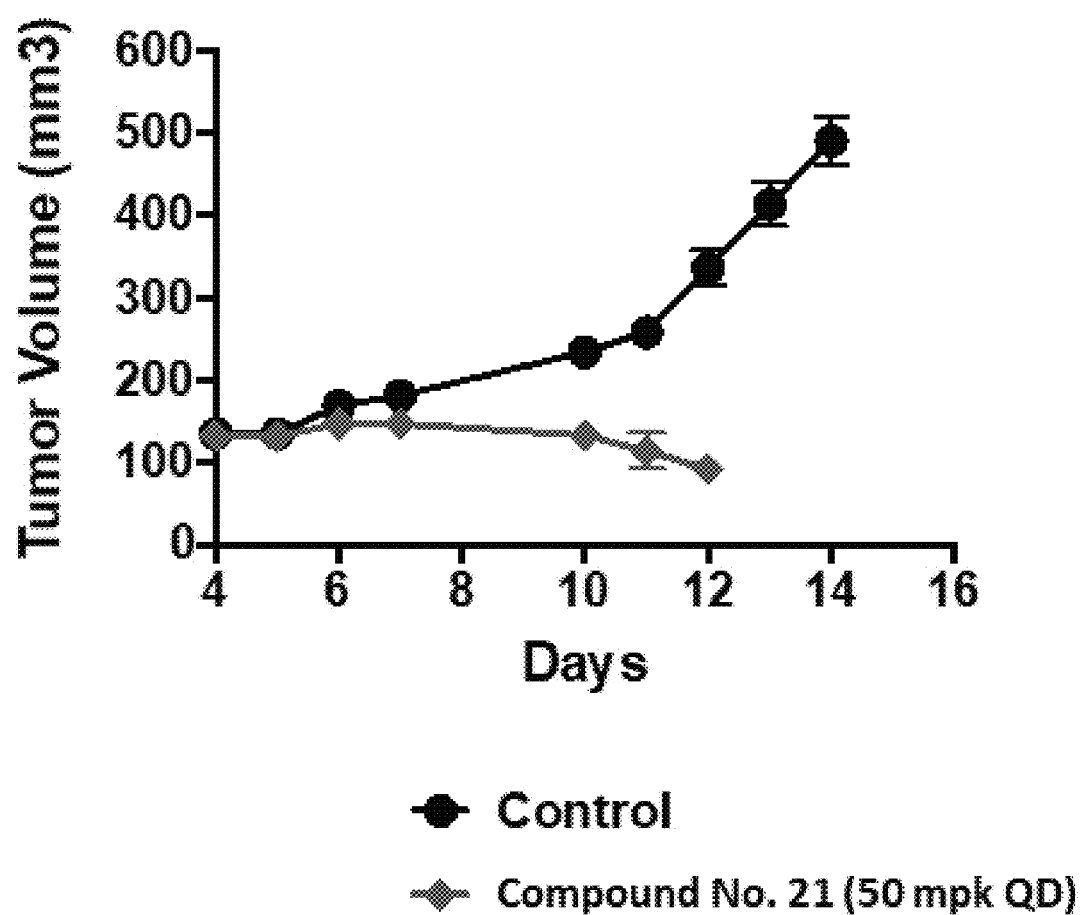
FIG. 29 is a graph showing the effect of Compound No. 21 on HER mutant tumor volume in vivo.

A mouse tumor model containing mutant Her2 was used to test the ability of Compound No. 21 to inhibit tumor growth and induce tumor regression in vivo. Athymic nude mice from Charles River Labs bearing Her2 S310F BaF3 tumors were treated with Compound No. 21 at 50 mg/kg once per day (QD) for 10 days. Tumor size was measured and analyzed to assess the effect on tumor growth and regression. As shown in FIG. 29, tumor volume in the vehicle control experiments increased over the 10-day time course, whereas the tumor volume in mice dosed with Compound No. 21 did not increase over the same timeframe and showed moderate reduction in volume, indicating that Compound No. 21 prevents growth and induces moderate regression in tumors harboring the Her2 S310F mutation. These results demonstrate that Compound No. 21 prevents tumor growth and induces tumor regression in vivo, including in tumors harboring the Her2 S310F mutation.

Example 11. Tumor Growth Inhibition in Mice Bearing HER2 Mutant Tumors

Figure 30:
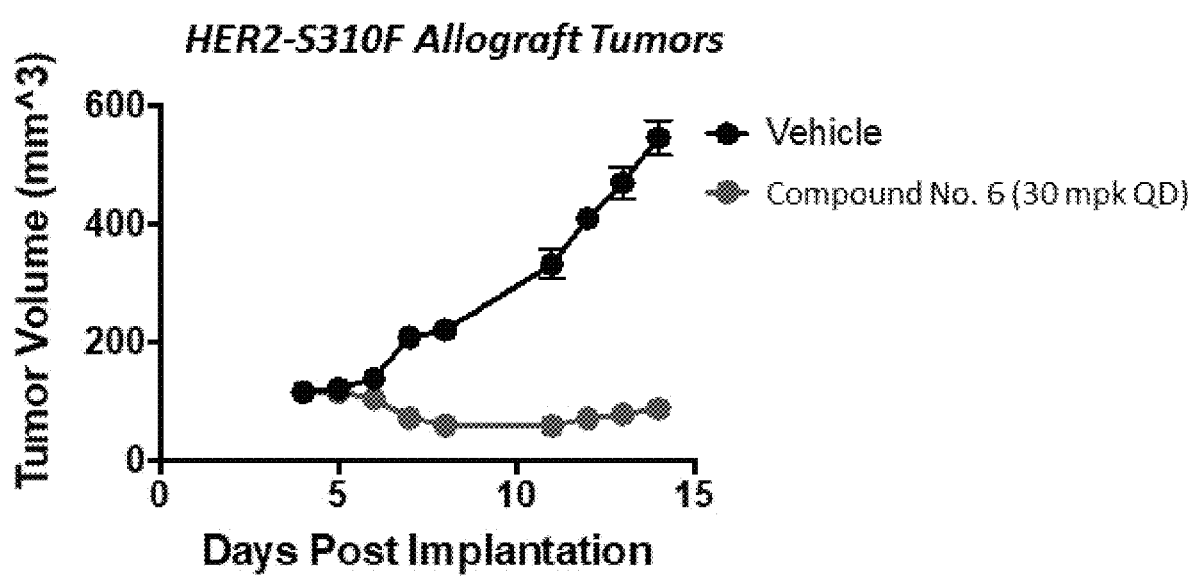
FIG. 30 is a graph showing the effect of Compound No. 6 on HER mutant tumor volume in vivo.

A mouse tumor model containing mutant Her2 was used to test the ability of Compound No. 6 to inhibit tumor growth and induce tumor regression in vivo. Athymic nude mice from Charles River Labs bearing Her2 S310F BaF3 tumors were treated with Compound No. 6 at 30 mg/kg once per day (QD) for 10 days. Tumor size was measured and analyzed to assess the effect on tumor growth and regression. As shown in FIG. 30, tumor volume in the vehicle control experiments increased over the 10-day time course, whereas the tumor volume in mice dosed with Compound No. 6 decreased over the same time, indicating that Compound No. 6 induces regression in tumors harboring the Her2 S310F mutation. These results demonstrate that Compound No. 6 prevents tumor growth and induces tumor regression in vivo, including in tumors harboring the Her2 S310F mutation.

Example 12. Tumor Growth Inhibition in Mice Bearing EGFR Mutant Tumors

Figure 31:
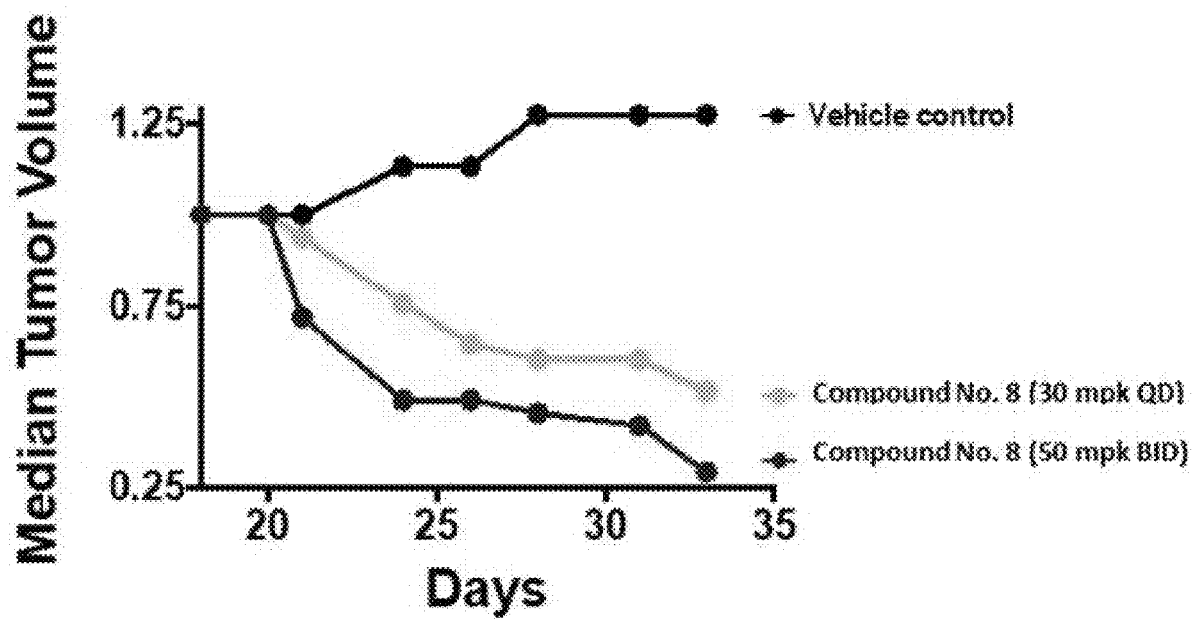
FIG. 31 is a graph showing the effect of Compound No. 8 on HER mutant tumor volume in vivo under several dosing regimens.

To determine the ability of Compound No. 8 to inhibit tumor growth and induce tumor regression in vivo, a mouse tumor model containing the EGFR-Exon 20 insertion ASV (CUTO-14) mutation was used. Athymic nude mice from Charles River Labs bearing CUTO-14 tumors were treated with Compound No. 8 at either 30 mg/kg once per day (QD) or 50 mg/kg twice per day (BID) over the indicated time course, and tumor volume was measured. Tumor volume was analyzed to assess the effect of Compound No. 8 on tumor growth and regression. As shown in FIG. 31, tumor volume in the vehicle control experiments increased over the time course, whereas the tumor volume in mice dosed with either the 30 mg/kg QD Compound No. 8 or the 50 mg/kg BID Compound No. 8 dosing schemes decreased over the same time. These results demonstrate that Compound No. 8 induces tumor growth inhibition and tumor growth regression in vivo, including in tumors harboring the EGFR-Exon 20 insertion ASV mutation.

Example 13. Tumor Growth Inhibition in Mice Bearing EGFR Mutant Tumors

Figure 32:
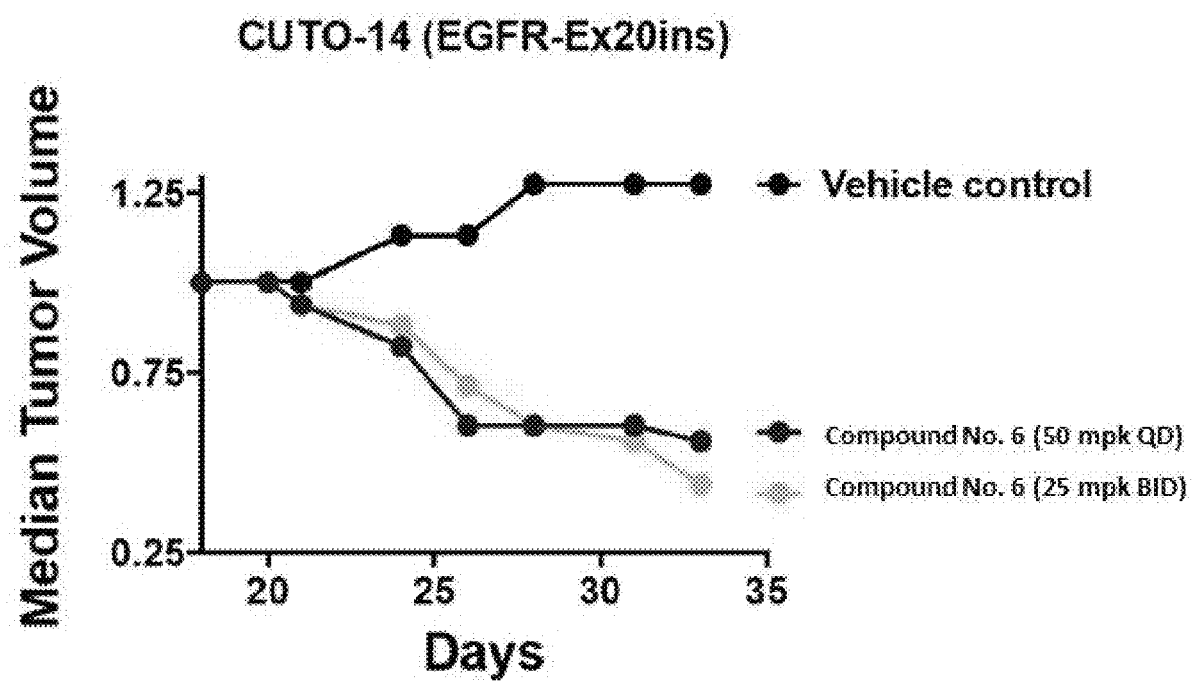
FIG. 32 is a graph showing the effect of Compound No. 6 on EGFR mutant tumor volume in vivo under several dosing regimens.

To determine the ability of Compound No. 6 to inhibit tumor growth and induce tumor regression in vivo, a mouse tumor model containing the EGFR-Exon 20 insertion ASV (CUTO-14) mutation was used. Athymic nude mice from Charles River Labs bearing CUTO-14 tumors were treated with Compound No. 6 at either 50 mg/kg once per day (QD) or 25 mg/kg twice per day (BID) over the indicated time course, and tumor volume was measured. Tumor volume was analyzed to assess the effect of Compound No. 6 on tumor growth and regression. As shown in FIG. 32, tumor volume in the vehicle control experiments increased over the time course, whereas the tumor volume in mice dosed with either the 50 mg/kg QD Compound No. 6 or the 25 mg/kg BID Compound No. 6 dosing schemes decreased over the same time. These results demonstrate that Compound No. 6 induces tumor growth inhibition and tumor regression in vivo, including in tumors harboring the EGFR-Exon 20 insertion ASV mutation.

Example 14. Inhibition of HER2 Activity in Mice Bearing Her2 Mutant Tumors

Figure 33:
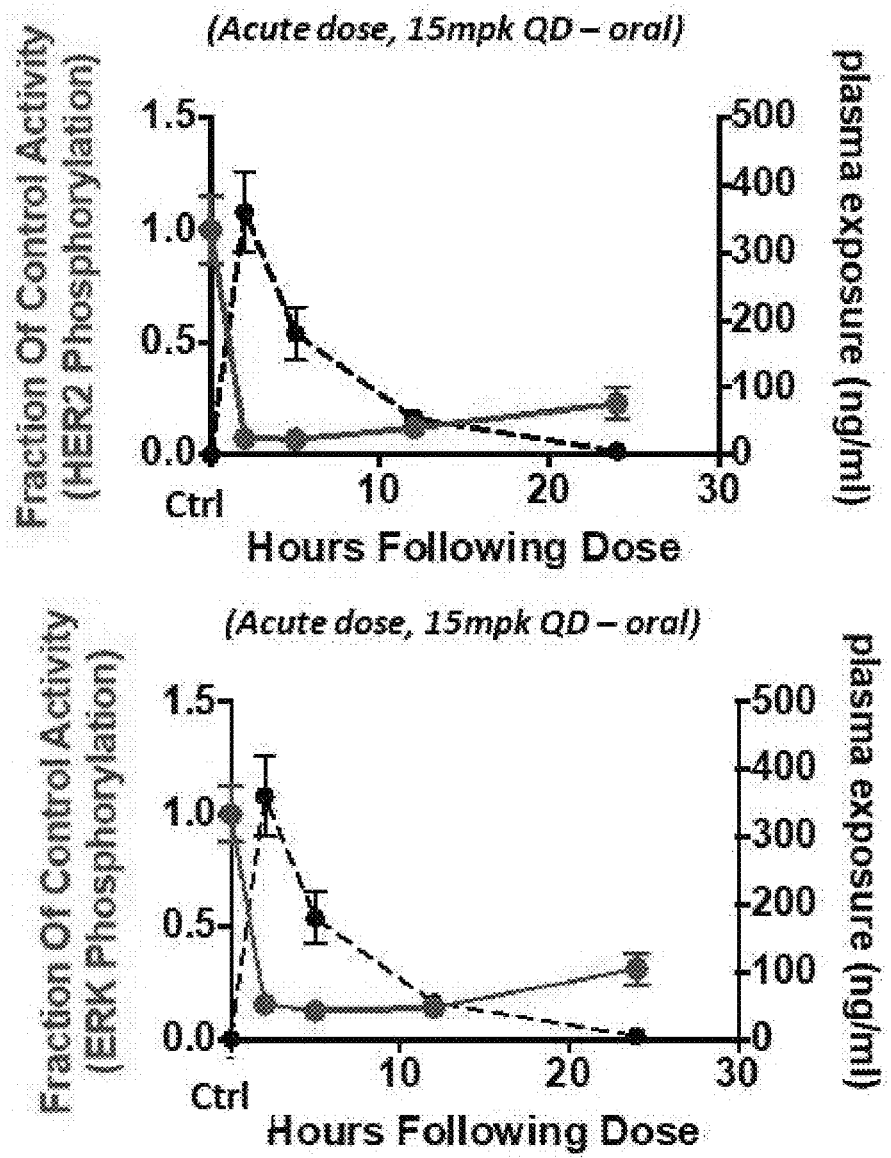
FIG. 33 is a graph showing the effect of Compound No. 26 on tumors with HER mutant signaling and corresponding Compound No. 26 plasma levels in vivo.

To determine the ability of Compound No. 21 to inhibit tumor growth and induce tumor regression in vivo, a mouse tumor model containing the HER2 Exon 20-YVMA A775 mutation was used. Athymic nude mice from Charles River Labs bearing Her2 Exon 20-YVMA A775 BaF3 tumors were treated with two day acute oral dosing of Compound No. 26 at 15 mg/kg. Following the second dose, tumors were collected at 2 hours, 5 hours, 12 hours and 24 hours, and analyzed for both pHER2 activity and pERK activity via AlphaLisa. Plasma was also collected at these time points and analayzed for the presence of Compound No. 26 to determine pharmacokinetic profile. The tumor tissue was cut and homogenized using the Precellys Soft Tissue Homogenizing kit (KT03961-1-00.3.2) containing T-PER tissue protein extraction reagent (Thermo Scientific #78510), supplemented with Protease Inhibitor (Sigma P8340), and Phosphatase Inhibitors II and III (Sigma P5726 and P0044). Tissue samples were homogenized in the Precellys machine by spinning two times for one minute each. Sample tubes were centrifuged for 5 min at 15,000 rpm at 4° C. The supernatant was transferred to a fresh microtube and spun again for 5 minutes at 15,000 rpm at 4° C. Supernatant was then transferred to a fresh microtube and placed on ice. The protein concentration of the supernatant was measured using the BCA reagent Kit (Thermo Scientific #23225). Tumor tissue-derived lysates were analyzed for either HER2 activity or EGFR activity by detection of pHER2 (Tyr1221/1222) or pERK (Thr202/Tyr204) phosphosites, respectively, via AlphaLisa. Briefly, tumor Lysates were diluted to 0.5 ug/ul in 1× diluted SureFire Ultra Kit Lysis Buffer (5× supplied stock) supplemented with Protease Inhibitor (Sigma P8340) and Phosphatase inhibitor II and III (Sigma P5726 and P0044). 10 ul of total tumor lysate was added per well in triplicate to a 384-well Opti-plate (Perkin Elmer #6007290). Activation Buffer was diluted 25-fold in combined Reaction Buffer 1 and Reaction Buffer 2, and acceptor beads were diluted 50-fold in the combined Reaction Buffers. 5 ul/well of the Acceptor bead:Reaction buffer mixture was added to each well. The plate was covered and shaken for 5 minutes on a plate shaker and then incubated at room temperature in the dark for 90 minutes before reading. pHer2 AlphaLisa (Perkin Elmer # ALSU-PEB2-A10K) was used to quantify phosphorylation of Her2 (Tyr1221/1222) or pERK AlphLisA (Perkin Elmer # ALSUPERK-A10K) was used to quantify phosphorylation of ERK1/2 (Thr202/Tyr204) in the control and Compound No. 26 treated tumor samples. As shown in FIG. 33, Compound No. 26 induced a near complete reduction of pHER2 and pERK1/2 at peak plasma levels, indicating that Compound No. 26 inhibits target mutant Her2 Exon 20-YVMA A775 kinase activity.

Example 15. Treatment of Mice Bearing HER2 Mutant Tumors

Figure 34:
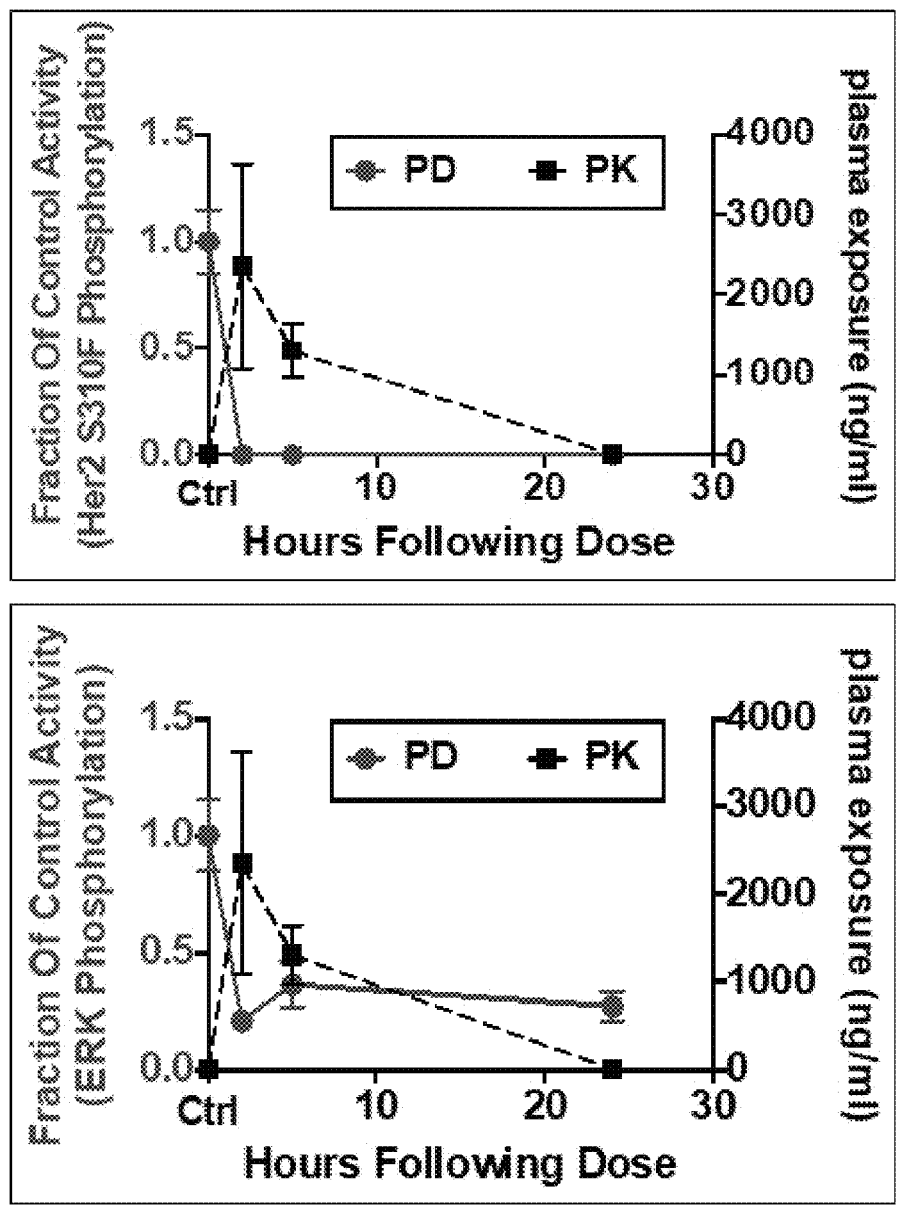
FIG. 34 is a graph showing the effect of Compound No. 21 on tumors with HER mutant signaling and corresponding Compound No. 21 plasma levels in vivo.

To determine the ability of Compound No. 21 to inhibit tumor growth and induce tumor regression in vivo, a mouse tumor model containing the HER2 S310F mutation was used to determine whether Compound No. 21. Athymic nude mice from Charles River Labs bearing HER2 S310F BaF3 tumors were treated with two day acute oral dosing of Compound No. 21 at 15 mg/kg. Following the second dose, tumors were collected at 2 hours, 5 hours, 12 hours and 24 hours, and analyzed for both pHER2 activity and pERK activity via AlphaLisa. Plasma was also collected at these time points and analayzed for the presence of Compound No. 21 to determine pharmacokinetic profile. The tumor tissue was cut and homogenized using the Precellys Soft Tissue Homogenizing kit (KT03961-1-00.3.2) containing T-PER tissue protein extraction reagent (Thermo Scientific #78510), supplemented with Protease Inhibitor (Sigma P8340), and Phosphatase Inhibitors II and III (Sigma P5726 and P0044). Tissue samples were homogenized in the Precellys machine by spinning two times for one minute each. Sample tubes were centrifuged for 5 min at 15,000 rpm at 4° C. The supernatant was transferred to a fresh microtube and spun again for 5 minutes at 15,000 rpm at 4° C. Supernatant was then transferred to a fresh microtube and placed on ice. The protein concentration of the supernatant was measured using the BCA reagent Kit (Thermo Scientific #23225). Tumor tissue-derived lysates were analyzed for either HER2 activity or EGFR activity by detection of pHER2 (Tyr1221/1222) or pERK (Thr202/Tyr204) phosphosites, respectively, via AlphaLisa. Briefly, tumor Lysates were diluted to 0.5 ug/ul in 1× diluted SureFire Ultra Kit Lysis Buffer (5× supplied stock) supplemented with Protease Inhibitor (Sigma P8340) and Phosphatase Inhibitor II and III (Sigma P5726 and P0044). 10 ul of total tumor lysate was added per well in triplicate to a 384-well Opti-plate (Perkin Elmer #6007290). Activation Buffer was diluted 25-fold in combined Reaction Buffer 1 and Reaction Buffer 2, and acceptor beads were diluted 50-fold in the combined Reaction Buffers. 5 ul/well of the Acceptor bead:Reaction buffer mixture was added to each well. The plate was covered and shaken for 5 minutes on a plate shaker and then incubated at room temperature in the dark for 90 minutes before reading. pHer2 AlphaLisa (Perkin Elmer # ALSU-PEB2-A10K) was used to quantify phosphorylation of Her2 (Tyr1221/1222) or pERK AlphLisA (Perkin Elmer # ALSUPERK-A10K) was used to quantify phosphorylation of ERK1/2 (Thr202/Tyr204) in the control and Compound No. 21 treated tumor samples. As shown in FIG. 34, Compound No. 21 induced a near complete reduction of pHER2 and pERK1/2 at peak plasma levels, indicating that Compound No. 21 inhibits target HER2 S310F mutant kinase activity.

Example 16. Treatment of Mice Bearing HER2 Mutant Tumors

Figure 35:
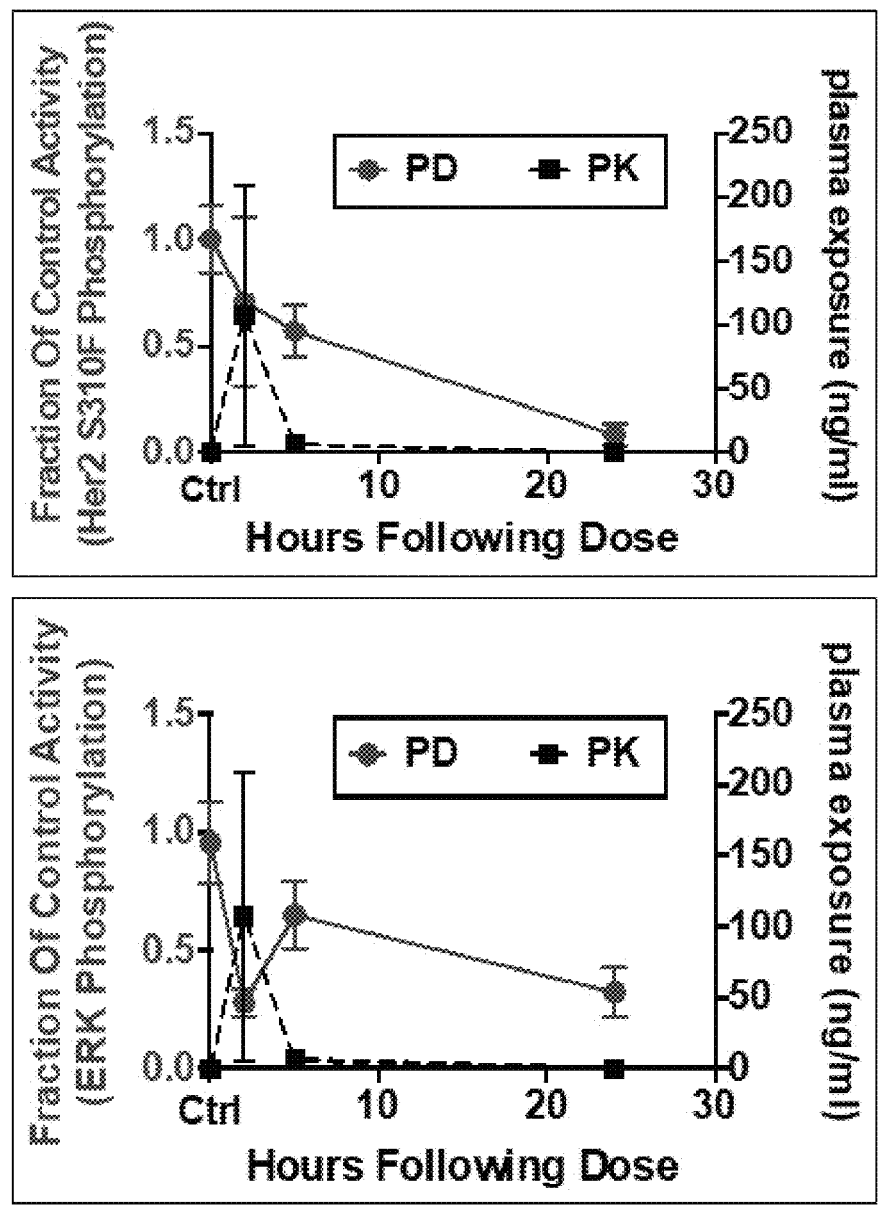
FIG. 35 is a graph showing the effect of Compound No. 5 on tumors with HER mutant signaling and corresponding Compound No. 5 plasma levels in vivo.

To determine the ability of Compound No. 5 to inhibit tumor growth and induce tumor regression in vivo, a mouse tumor model containing the HER2 S310F mutation was used to determine whether Compound No. 5 inhibits tumor growth and induces tumor regression in vivo. Athymic nude mice from Charles River Labs bearing HER2 S310F BaF3 tumors were treated with two day acute oral dosing of Compound No. 5 at 15 mg/kg. Following the second dose, tumors were collected at 2 hours, 5 hours, 12 hours and 24 hours, and analyzed for both pHER2 activity and pERK activity via AlphaLisa. Plasma was also collected at these time points and analayzed for the presence of Compound No. 5 to determine pharmacokinetic profile. The tumor tissue was cut and homogenized using the Precellys Soft Tissue Homogenizing kit (KT03961-1-00.3.2) containing T-PER tissue protein extraction reagent (Thermo Scientific #78510), supplemented with Protease Inhibitor (Sigma P8340), and Phosphatase Inhibitors II and III (Sigma P5726 and P0044). Tissue samples were homogenized in the Precellys machine by spinning two times for one minute each. Sample tubes were centrifuged for 5 min at 15,000 rpm at 4° C. The supernatant was transferred to a fresh microtube and spun again for 5 minutes at 15,000 rpm at 4° C. Supernatant was then transferred to a fresh microtube and placed on ice. The protein concentration of the supernatant was measured using the BCA reagent Kit (Thermo Scientific #23225). Tumor tissue-derived lysates were analyzed for either HER2 activity or EGFR activity by detection of pHER2 (Tyr1221/1222) or pERK (Thr202/Tyr204) phosphosites, respectively, via AlphaLisa. Briefly, tumor Lysates were diluted to 0.5 ug/ul in 1× diluted SureFire Ultra Kit Lysis Buffer (X supplied stock) supplemented with Protease Inhibitor (Sigma P8340) and Phosphatase Inhibitor II and III (Sigma P5726 and P0044). 10 ul of total tumor lysate was added per well in triplicate to a 384-well Opti-plate (Perkin Elmer #6007290). Activation Buffer was diluted 25-fold in combined Reaction Buffer 1 and Reaction Buffer 2, and acceptor beads were diluted 50-fold in the combined Reaction Buffers. 5 ul/well of the Acceptor bead:Reaction buffer mixture was added to each well. The plate was covered and shaken for 5 minutes on a plate shaker and then incubated at room temperature in the dark for 90 minutes before reading. pHer2 AlphaLisa (Perkin Elmer # ALSU-PEB2-A10K) was used to quantify phosphorylation of Her2 (Tyr1221/1222) or pERK AlphaLisA (Perkin Elmer # ALSUPERK-A10K) was used to quantify phosphorylation of ERK1/2 (Thr202/Tyr204) in the control and Compound No. 5 treated tumor samples. As shown in FIG. 35, Compound No. 5 induced The a reduction of pHER2 and pERK1/2 at peak plasma levels, indicating that Compound No. 5 inhibits target HER2 S310F mutant kinase activity.

Example 17. Treatment of Mice Bearing HER2 Mutant Tumors

Figure 36:
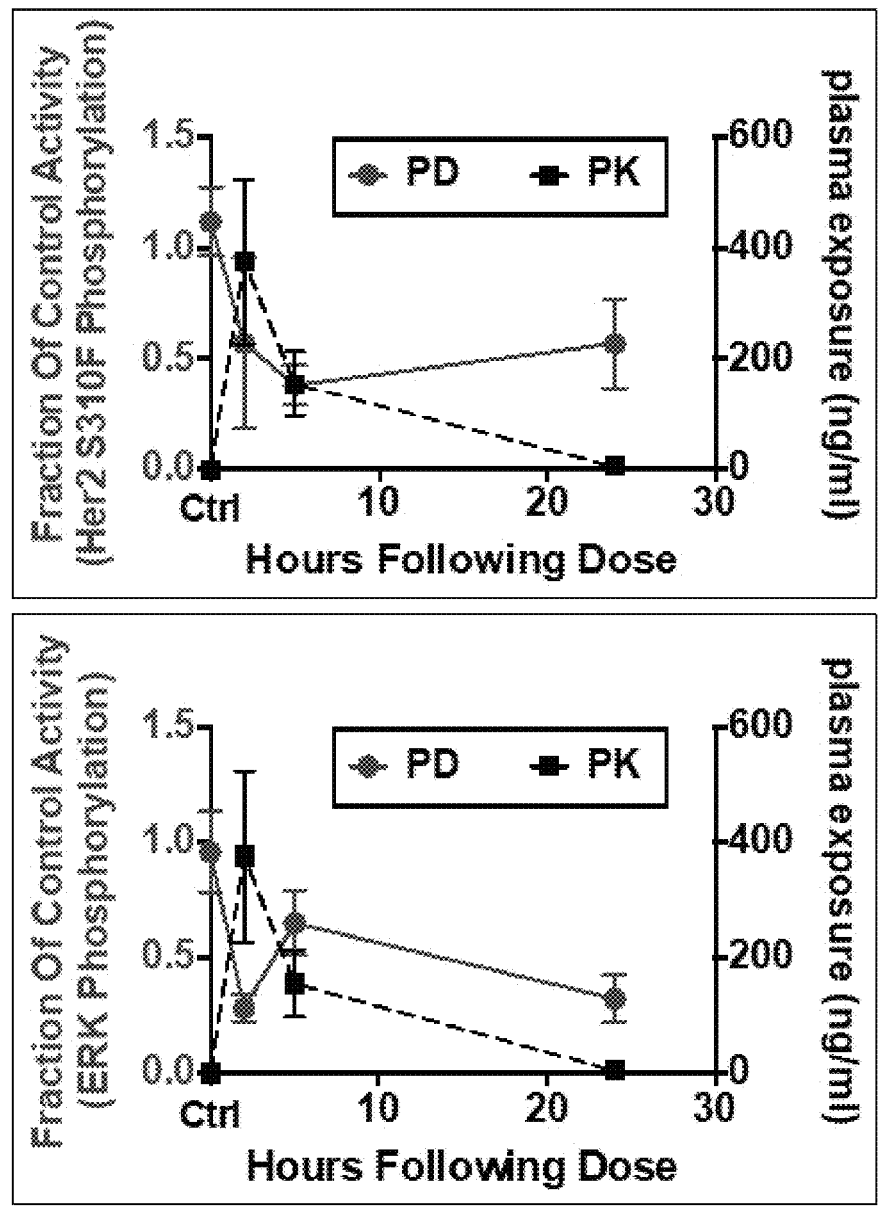
FIG. 36 is a graph showing the effect of Compound No. 118 on tumors with HER mutant signaling and corresponding Compound No. 118 plasma levels in vivo.

To determine the ability of Compound No. 118 to inhibit tumor growth and induce tumor regression in vivo, a mouse tumor model containing the HER2 S310F mutation was used. Athymic nude mice from Charles River Labs bearing HER2 S310F BaF3 tumors were treated with two day acute oral dosing of Compound No. 118 at 15 mg/kg. Following the second dose, tumors were collected at 2 hours, 5 hours, 12 hours and 24 hours, and analyzed for both pHER2 activity and pERK activity via AlphaLisa. Plasma was also collected at these time points and analayzed for the presence of Compound No. 118 to determine pharmacokinetic profile. The tumor tissue was cut and homogenized using the Precellys Soft Tissue Homogenizing kit (KT03961-1-00.3.2) containing T-PER tissue protein extraction reagent (Thermo Scientific #78510), supplemented with Protease Inhibitor (Sigma P8340), and Phosphatase Inhibitors II and III (Sigma P5726 and P0044). Tissue samples were homogenized in the Precellys machine by spinning two times for one minute each. Sample tubes were centrifuged for 5 min at 15,000 rpm at 4° C. The supernatant was transferred to a fresh microtube and spun again for 5 minutes at 15,000 rpm at 4° C. Supernatant was then transferred to a fresh microtube and placed on ice. The protein concentration of the supernatant was measured using the BCA reagent Kit (Thermo Scientific #23225). Tumor tissue-derived lysates were analyzed for either HER2 activity or EGFR activity by detection of pHER2 (Tyr1221/1222) or pERK (Thr202/Tyr204) phosphosites, respectively, via AlphaLisa. Briefly, tumor Lysates were diluted to 0.5 ug/ul in 1× diluted SureFire Ultra Kit Lysis Buffer (5× supplied stock) supplemented with Protease Inhibitor (Sigma P8340) and Phosphatase Inhibitor II and III (Sigma P5726 and P0044). 10 ul of total tumor lysate was added per well in triplicate to a 384-well Opti-plate (Perkin Elmer #6007290). Activation Buffer was diluted 25-fold in combined Reaction Buffer 1 and Reaction Buffer 2, and acceptor beads were diluted 50-fold in the combined Reaction Buffers. 5 ul/well of the Acceptor bead:Reaction buffer mixture was added to each well. The plate was covered and shaken for 5 minutes on a plate shaker and then incubated at room temperature in the dark for 90 minutes before reading. pHer2 AlphaLisa (Perkin Elmer # ALSU-PEB2-A10K) was used to quantify phosphorylation of Her2 (Tyr1221/1222) or pERK AlphLisA (Perkin Elmer # ALSUPERK-A10K) was used to quantify phosphorylation of ERK1/2 (Thr202/Tyr204) in the control and Compound No. 118 treated tumor samples. As shown in FIG. 36, Compound No. 118 induced a reduction of pHER2 and pERK1/2 at peak plasma levels, indicating that Compound No. 118 inhibits target HER2 S310F mutant kinase activity.

Example 18. Treatment of Mice Bearing HER2 Mutant Tumors

To determine the ability of Compound No. 27 to inhibit tumor growth and induce tumor regression in vivo, a mouse tumor model containing the HER2S310F mutation was used.

Figure 37:
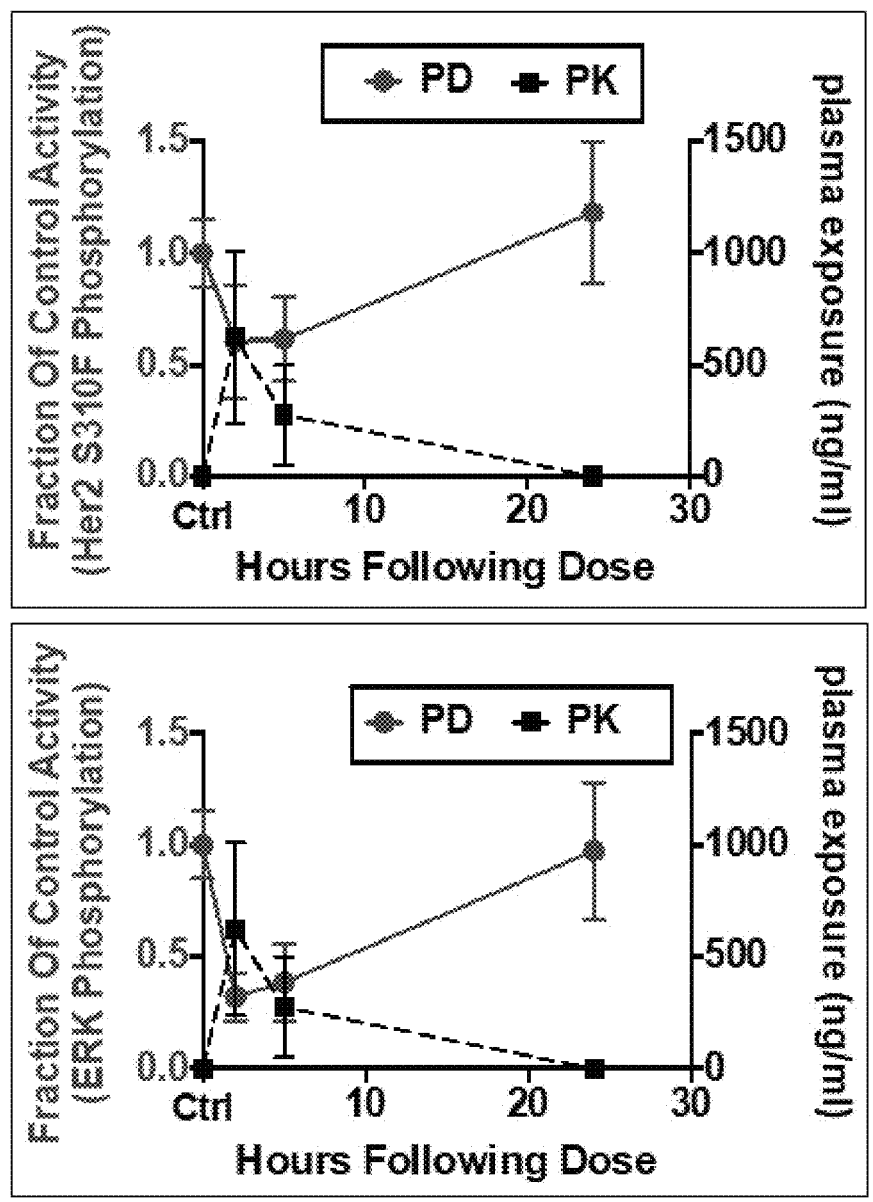
FIG. 37 is a graph showing the effect of Compound No. 27 on tumors with HER mutant signaling and corresponding Compound No. 27 plasma levels in vivo.

Athymic nude mice from Charles River Labs bearing HER2 S310F BaF3 tumors were treated with two day acute oral dosing of Compound No. 27 at 15 mg/kg. Following the second dose, tumors were collected at 2 hours, 5 hours, 12 hours and 24 hours, and analyzed for both pHER2 activity and pERK activity via AlphaLisa. Plasma was also collected at these time points and analyzed for the presence of Compound No. 27 to determine a pharmacokinetic profile of the compound. The tumor tissue was cut and homogenized using the Precellys Soft Tissue Homogenizing kit (KT03961-1-00.3.2) containing T-PER tissue protein extraction reagent (Thermo Scientific #78510), supplemented with Protease Inhibitor (Sigma P8340), and Phosphatase Inhibitors II and III (Sigma P5726 and P0044). Tissue samples were homogenized in the Precellys machine by spinning two times for one minute each. Sample tubes were centrifuged for 5 min at 15,000 rpm at 4° C. The supernatant was transferred to a fresh microtube and spun again for 5 minutes at 15,000 rpm at 4° C. Supernatant was then transferred to a fresh microtube and placed on ice. The protein concentration of the supernatant was measured using the BCA reagent Kit (Thermo Scientific #23225). Tumor tissue-derived lysates were analyzed for either HER2 activity or EGFR activity by detection of pHER2 (Tyr1221/1222) or pERK (Thr202/Tyr204) phosphosites, respectively, via AlphaLisa. Briefly, tumor Lysates were diluted to 0.5 ug/ul in 1× diluted SureFire Ultra Kit Lysis Buffer (5× supplied stock) supplemented with Protease Inhibitor (Sigma P8340) and Phosphatase Inhibitor II and III (Sigma P5726 and P0044). 10 ul of total tumor lysate was added per well in triplicate to a 384-well Opti-plate (Perkin Elmer #6007290). Activation Buffer was diluted 25-fold in combined Reaction Buffer 1 and Reaction Buffer 2, and acceptor beads were diluted 50-fold in the combined Reaction Buffers. 5 ul/well of the Acceptor bead:Reaction buffer mixture was added to each well. The plate was covered and shaken for 5 minutes on a plate shaker and then incubated at room temperature in the dark for 90 minutes before reading. pHer2 AlphaLisa (Perkin Elmer # ALSU-PEB2-A10K) was used to quantify phosphorylation of Her2 (Tyr1221/1222) or pERK AlphLisA (Perkin Elmer # ALSUPERK-A10K) was used to quantify phosphorylation of ERK1/2 (Thr202/Tyr204) in the control and Compound No. 27 treated tumor samples. As shown in FIG. 37, treatment with Compound No. 27 induced a reduction of pHER2 and pERK1/2 at peak plasma levels, indicating that Compound No. 27 inhibits target HER2 S310F mutant kinase activity.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of formula II:

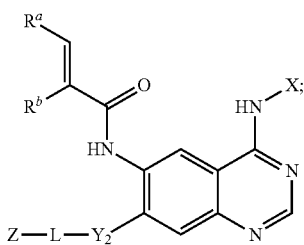

or a pharmaceutically acceptable salt or stereoisomer thereof, wherein:

$Y^2$ is —O—;

L is a covalent bond or straight chain or branched $C_{1-4}$ alkyl;

Z is —($NR^4R^5$), wherein $R^4$ and $R^5$ each independently are $C_{1-6}$ alkyl or 3-6-membered heterocycloalkyl; or Z is —($NR^6R^7$) or —($CHR^6R^7$), wherein $R^6$ and $R^7$, together with the atom to which they are attached, form 3-9-membered heterocycloalkyl, wherein the 3-9-membered heterocycloalkyl contains at least one nitrogen atom wherein the 3-9-membered heterocycloalkyl is unsubstituted or substituted with one or more $C_{1-4}$ alkyl or —OR', wherein R' is $C_{1-4}$ alkyl;

$R^a$ and $R^b$ each is H; and

X is

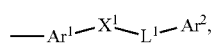

wherein $Ar^1$ is 6 membered aryl which is unsubstituted or substituted with one or more hal; $X^1$ is —O—; $L^1$ is straight or branched $C_{1-3}$alkyl; and $Ar^2$ is 6-membered N-heteroaryl.

2. The compound of claim 1, wherein -$X^1$-$L^1$- is —O—$CH_2$—.

3. The compound of claim 1, wherein X is

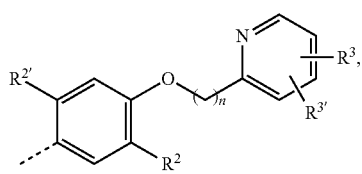

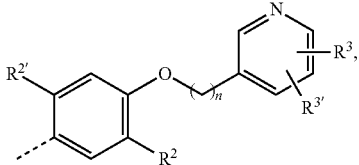

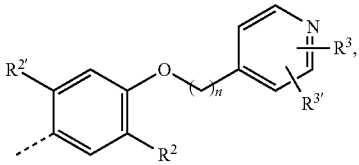

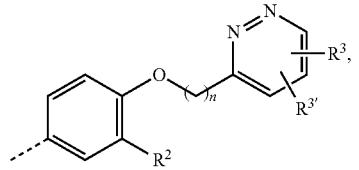

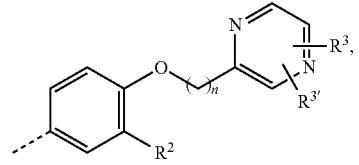

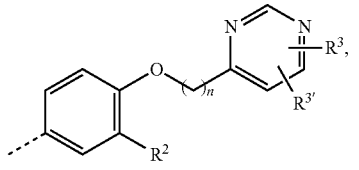

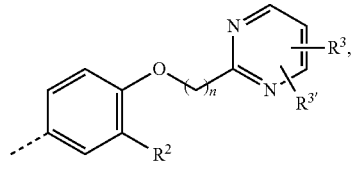

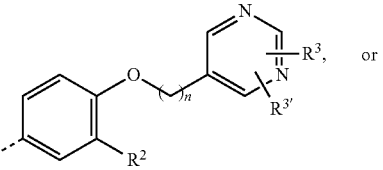

-continued

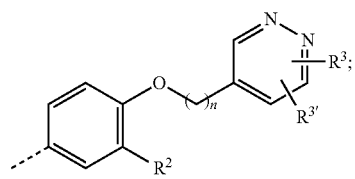
(ii)h-p wherein:
R² and R²' each independently are H or hal;
R³ and R³' each are H; and
n is 1.

4. The compound of claim 3, wherein R² and R²' each independently are H or Cl.

5. The compound of claim 4, wherein X is

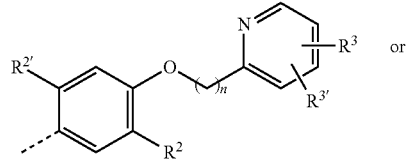
(ii)h-b

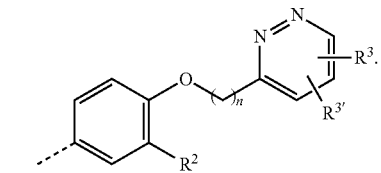
(ii)h-k

6. The compound of claim 1, wherein L is a covalent bond.

7. The compound of claim 1, wherein L is straight chain or branched C₁₋₄ alkyl.

8. The compound of claim 7, wherein L is —(CH₂)₂— or —(CH₂)₃—.

9. The compound of claim 1, wherein Z is —(NR⁴R⁵).

10. The compound of claim 1, wherein Z is —(NR⁶R⁷) or —(CHR⁶R⁷).

11. The compound of claim 10, wherein Z is —(NR⁶R⁷).

12. The compound of claim 11, wherein —(NR⁶R⁷) is

-continued

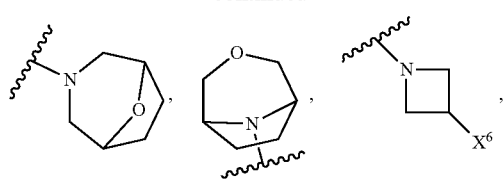

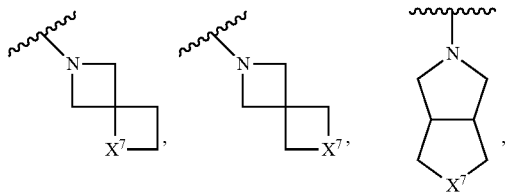

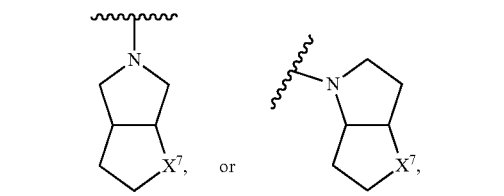

wherein:
X⁶ is —CH₃ or —OCH₃; and
X⁷ is —O—, —NH—, or —N(CH₃)—.

13. The compound of claim 12, wherein —(NR⁶R⁷) is

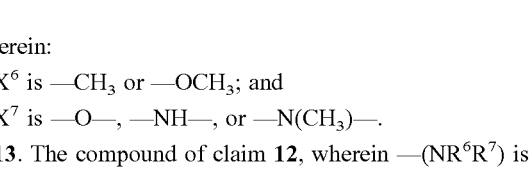

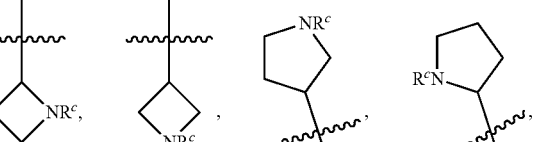

14. The compound of claim 10, wherein Z is —(CHR⁶R⁷).

15. The compound of claim 14, wherein —(CHR⁶R⁷) is

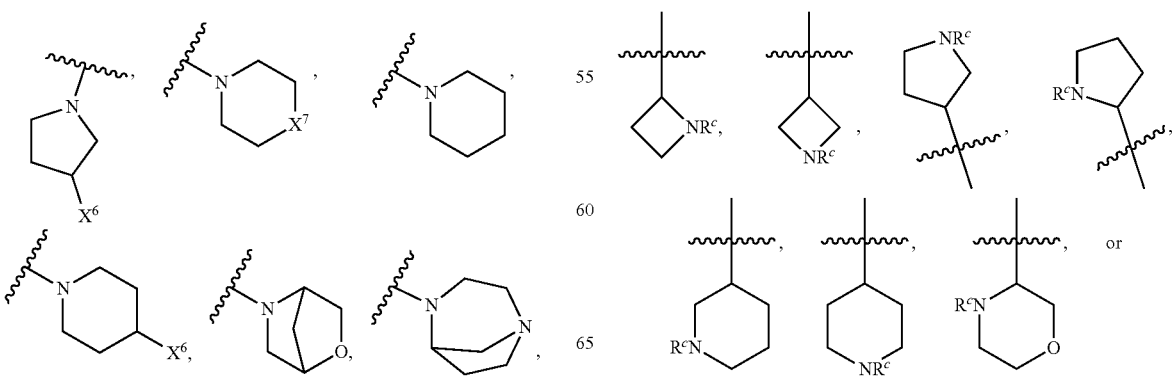

-continued

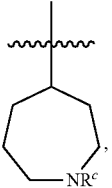

wherein $R^c$ is H or $C_{1-4}$ alkyl.

16. The compound of claim 15, wherein —(CHR⁶R⁷) is

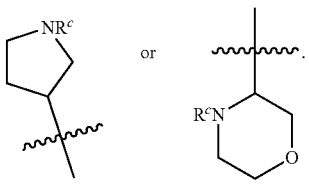

17. A compound of formula II:

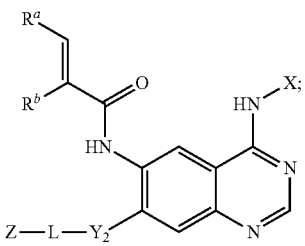

or a pharmaceutically acceptable salt or stereoisomer thereof, wherein:
 $Y^2$ is —O—;
 L is straight chain or branched $C_{1-4}$ alkyl;
 Z is —(NR⁶R⁷), wherein R⁶ and R⁷, together with the atom to which they are attached, form 3-9-membered heterocycloalkyl, wherein the 3-9-membered heterocycloalkyl is unsubstituted or substituted with one or more $C_{1-4}$ alkyl or —OR', wherein R' is $C_{1-4}$ alkyl;
 $R^a$ and $R^b$ each is H; and
 X is

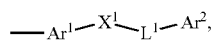

wherein Ar¹ is 6 membered aryl which is unsubstituted or substituted with one or more hal; X¹ is —O—; L¹ is straight or branched $C_{1-3}$alkyl; and Ar² is 6-membered N-heteroaryl.

18. The compound of claim 17, wherein X is

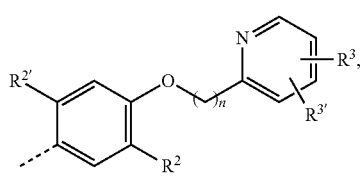
(ii)h-b

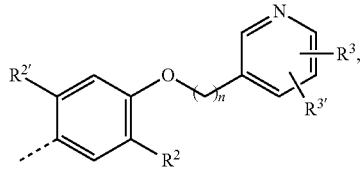
(ii)h-c

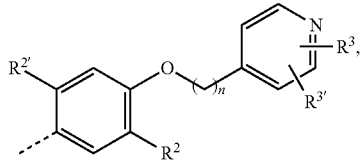
(ii)h-d

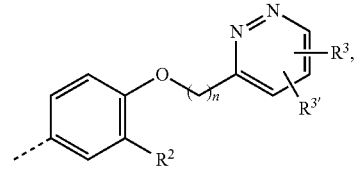
(ii)h-k

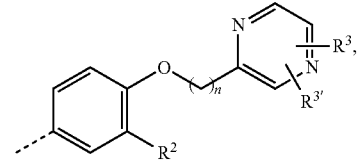
(ii)h-l

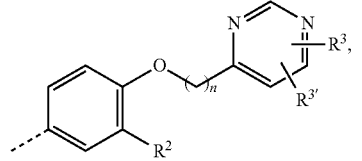
(ii)h-m

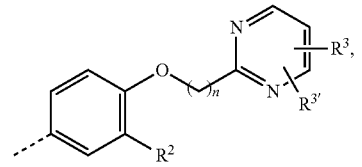
(ii)h-n

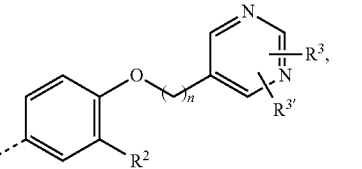
(ii)h-o or

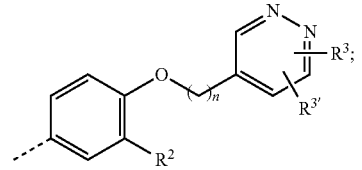
(ii)h-p wherein:
 R² and R²' each independently are H or hal;
 R³ and R³' each are H; and
 n is 1.

19. The compound of claim 18, wherein R² and R²' each independently are H or Cl.

20. The compound of claim 19, wherein X is

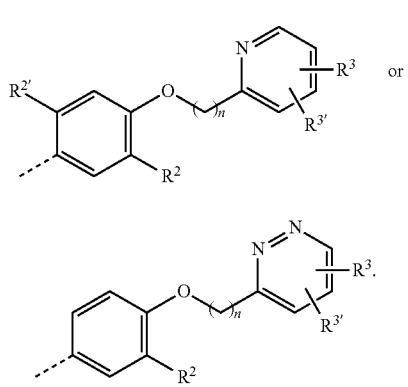

or

21. The compound of claim 17, wherein L is —(CH₂)₂— or —(CH₂)₃—.

22. The compound of claim 17, wherein —(NR⁶R⁷) is

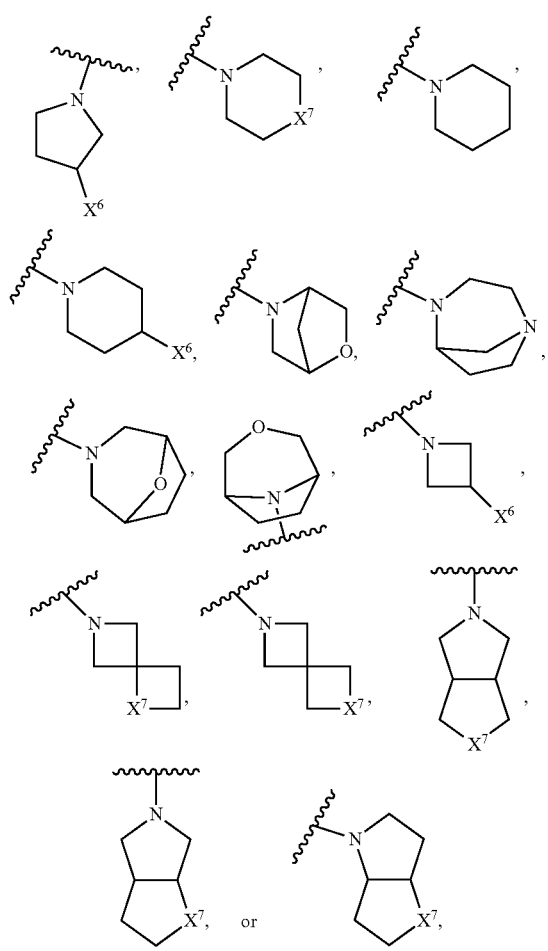

wherein:
X⁶ is —CH₃ or —OCH₃; and
X⁷ is —O—, —NH—, or —N(CH₃)—.

23. The compound of claim 22, wherein —(NR⁶R⁷) is

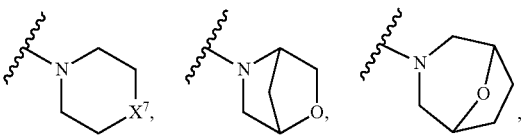

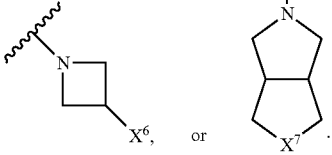

24. A compound of formula II:

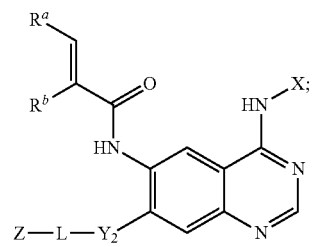

II or a pharmaceutically acceptable salt or stereoisomer thereof, wherein:

Y² is —O—;

L is —(CH₂)₂— or —(CH₂)₃—;

Z is —(NR⁶R⁷), wherein R⁶ and R⁷, together with the atom to which they are attached, form 3-9-membered heterocycloalkyl, wherein the 3-9-membered heterocycloalkyl is unsubstituted or substituted with one or more C₁₋₄ alkyl or —OR', wherein R' is C₁₋₄ alkyl;

Rᵃ and Rᵇ each is H; and

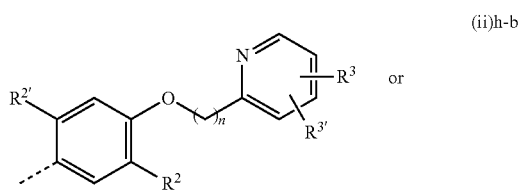

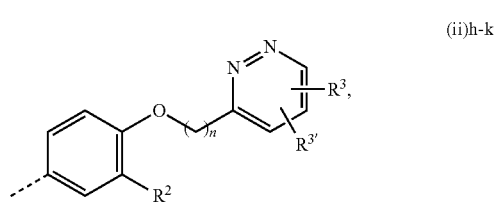

wherein R² and R²' each independently are H or Cl; R³ and R³' each are H; and n is 1.

25. A compound being selected from
| Compound | No. |
|---|---|
| 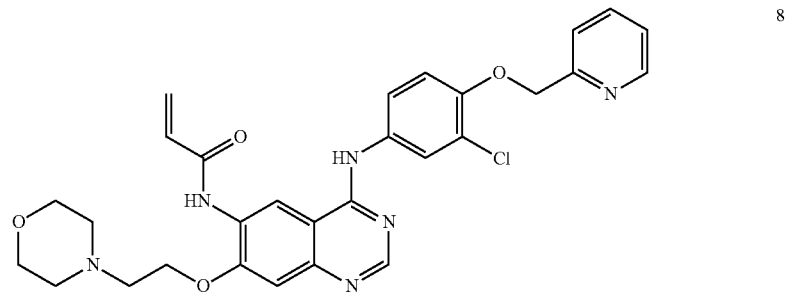 | 8 |
| 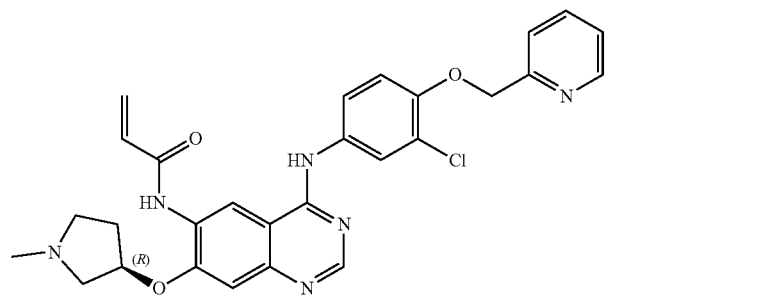 | 17 |
| 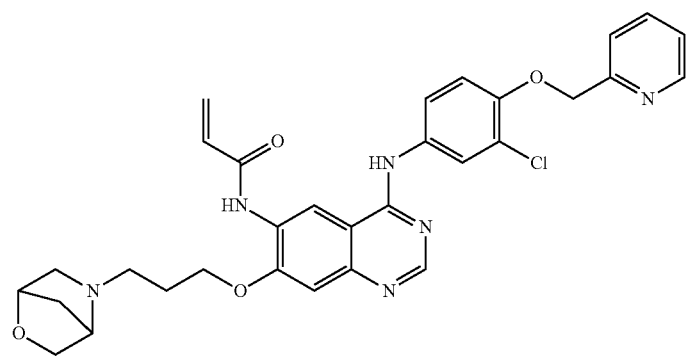 [SMILES: C=CC(=O)Nc1cc2c(Nc3ccc(OCc4ccccn4)c(Cl)c3)ncnc2cc1OCCCN1CC2CC1CO2] | 20 |
| 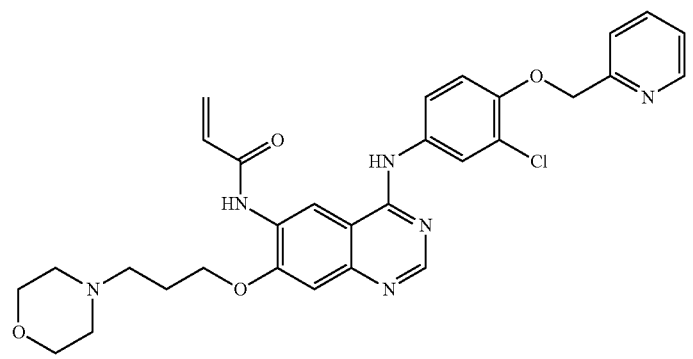 | 21 |

-continued

| Compound | No. |
|---|---|
| | 36 |
| | 40 |
| | 41 |
| | 51 |
| | 69 |

| Compound | No. |
|---|---|

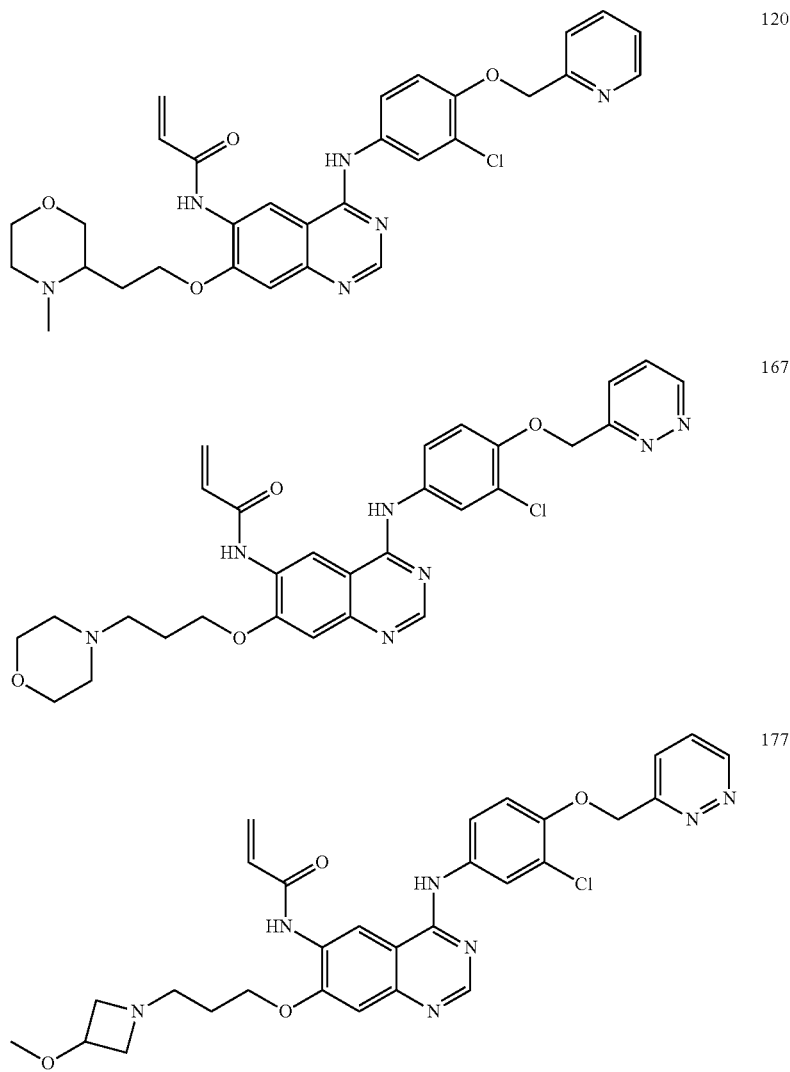

and pharmaceutically acceptable salts thereof.

26. A pharmaceutical composition comprising the compound of claim 1 and one or more pharmaceutically acceptable carriers or excipients.

27. A method of inhibiting an oncogenic variant of an ErbB receptor, comprising administering the subject in need thereof a therapeutically effective amount of the compound of claim 1.

28. A pharmaceutical composition comprising the compound of claim 25 and one or more pharmaceutically acceptable carriers or excipients.

29. A method of inhibiting an oncogenic variant of an ErbB receptor, comprising administering the subject in need thereof a therapeutically effective amount of the compound of claim 25.

* * * * *